United States Patent
Roberts et al.

(10) Patent No.: US 10,392,422 B2
(45) Date of Patent: Aug. 27, 2019

(54) MACROCYCLIC BROAD SPECTRUM ANTIBIOTICS

(71) Applicants: RQX PHARMACEUTICALS, INC., La Jolla, CA (US); GENENTECH, INC., San Francisco, CA (US)

(72) Inventors: Tucker Curran Roberts, San Diego, CA (US); Peter Andrew Smith, San Francisco, CA (US); Robert I. Higuchi, Solana Beach, CA (US); Prasuna Paraselli, San Diego, CA (US); Philippe Bergeron, Redwood City, CA (US); Michael F. T. Koehler, Palo Alto, CA (US); Huiyong Hu, Fremont, CA (US); Jacob Bradley Schwarz, San Ramon, CA (US); Cuong Ly, Burlingame, CA (US); James John Crawford, San Francisco, CA (US)

(73) Assignees: RQX PHARMACEUTICALS, INC., La Jolla, CA (US); GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/312,614

(22) PCT Filed: May 19, 2015

(86) PCT No.: PCT/US2015/031631
§ 371 (c)(1),
(2) Date: Nov. 18, 2016

(87) PCT Pub. No.: WO2015/179441
PCT Pub. Date: Nov. 26, 2015

(65) Prior Publication Data
US 2017/0088582 A1    Mar. 30, 2017

Related U.S. Application Data

(60) Provisional application No. 62/142,404, filed on Apr. 2, 2015, provisional application No. 62/000,980, filed on May 20, 2014.

(51) Int. Cl.
| | | |
|---|---|---|
| *A61K 38/00* | (2006.01) |
| *C07K 5/103* | (2006.01) |
| *C07K 7/06* | (2006.01) |
| *C07K 7/08* | (2006.01) |
| *C07K 5/02* | (2006.01) |
| *C07K 5/087* | (2006.01) |
| *C07K 5/09* | (2006.01) |
| *C07K 5/11* | (2006.01) |
| *A61K 45/06* | (2006.01) |
| *A61K 31/395* | (2006.01) |
| *A61K 31/407* | (2006.01) |
| *A61K 31/4196* | (2006.01) |
| *A61K 31/43* | (2006.01) |
| *A61K 31/431* | (2006.01) |
| *A61K 31/496* | (2006.01) |
| *A61K 31/545* | (2006.01) |

(Continued)

(52) U.S. Cl.
CPC ............ *C07K 5/101* (2013.01); *A61K 31/395* (2013.01); *A61K 31/407* (2013.01); *A61K 31/4196* (2013.01); *A61K 31/43* (2013.01); *A61K 31/431* (2013.01); *A61K 31/496* (2013.01); *A61K 31/545* (2013.01); *A61K 31/546* (2013.01); *A61K 38/06* (2013.01); *A61K 38/07* (2013.01); *A61K 38/08* (2013.01); *A61K 45/06* (2013.01); *C07K 5/0202* (2013.01); *C07K 5/0808* (2013.01); *C07K 5/0812* (2013.01); *C07K 5/0815* (2013.01); *C07K 5/1008* (2013.01); *C07K 5/1013* (2013.01); *C07K 5/1019* (2013.01); *C07K 7/06* (2013.01); *C07K 7/08* (2013.01); *A61K 38/00* (2013.01); *A61K 38/12* (2013.01); *Y02A 50/401* (2018.01); *Y02A 50/47* (2018.01); *Y02A 50/471* (2018.01); *Y02A 50/473* (2018.01); *Y02A 50/475* (2018.01); *Y02A 50/478* (2018.01); *Y02A 50/483* (2018.01)

(58) Field of Classification Search
None
See application file for complete search history.

(56) References Cited

U.S. PATENT DOCUMENTS

| 3,128,280 A | 4/1964 | Rorig |
| 5,204,328 A | 4/1993 | Nutt et al. |

(Continued)

FOREIGN PATENT DOCUMENTS

| CN | 1675236 A | 9/2005 |
| CN | 103788176 A | 5/2014 |

(Continued)

OTHER PUBLICATIONS

Bruton et al. Lipopeptide substrates for SpsB, the *Staphylococcus aureus* type I signal peptidase: design, conformation and conversion to α-ketoamide inhibitors. European Journal of Medicinal Chemistry 38:351-356. (2003) .

(Continued)

*Primary Examiner* — Thomas S Heard
(74) *Attorney, Agent, or Firm* — Wilson Sonsini Goodrich & Rosati

(57) ABSTRACT

Provided herein are antibacterial compounds, wherein the compounds in some embodiments have broad spectrum bioactivity. In various embodiments, the compounds act by inhibition of bacterial type 1 signal peptidase (SpsB), an essential protein in bacteria. Pharmaceutical compositions and methods for treatment using the compounds described herein are also provided.

19 Claims, 3 Drawing Sheets

(51) Int. Cl.
    A61K 31/546    (2006.01)
    A61K 38/06     (2006.01)
    A61K 38/07     (2006.01)
    A61K 38/08     (2019.01)
    C07K 5/083     (2006.01)
    A61K 38/12     (2006.01)

(56) References Cited

U.S. PATENT DOCUMENTS

| | | |
|---|---|---|
| 6,025,350 A | 2/2000 | Masamune et al. |
| 9,187,524 B2 | 11/2015 | Romesberg et al. |
| 9,309,285 B2 | 4/2016 | Roberts et al. |
| 2003/0130172 A1 | 7/2003 | Belvo et al. |
| 2004/0024178 A1 | 2/2004 | Ashman et al. |
| 2005/0153876 A1 | 7/2005 | Cameron et al. |
| 2007/0099885 A1 | 5/2007 | Endermann et al. |
| 2008/0275018 A1 | 11/2008 | Endermann et al. |
| 2008/0300231 A1 | 12/2008 | Endermann et al. |
| 2013/0130985 A1 | 5/2013 | Alewood et al. |
| 2013/0244929 A1 | 9/2013 | Gallant et al. |
| 2013/0281360 A1 | 10/2013 | Romesberg et al. |
| 2014/0249073 A1 | 9/2014 | Roberts et al. |
| 2017/0073370 A1 | 3/2017 | Roberts et al. |

FOREIGN PATENT DOCUMENTS

| | | |
|---|---|---|
| WO | WO-0114346 A1 | 3/2001 |
| WO | WO-03106480 A1 | 12/2003 |
| WO | WO-2011109441 A1 | 9/2011 |
| WO | WO-2011112441 A1 | 9/2011 |
| WO | WO-2012036907 A2 | 3/2012 |
| WO | WO-2012166665 A2 | 12/2012 |
| WO | WO-2013138187 A1 | 9/2013 |
| WO | WO-2014081886 A1 | 5/2014 |
| WO | WO-2015179441 A2 | 11/2015 |
| WO | WO-2017064629 A1 | 4/2017 |
| WO | WO-2017084629 A1 | 5/2017 |
| WO | WO-2017084630 A1 | 5/2017 |

OTHER PUBLICATIONS

Butler et al. Natural Products—The Future Scaffold for Novel Antibiotics. Biochemical Pharmacology 71:919-929 (2006).
Dufour et al. Total Synthesis of Arlomycin A2, a Signal Peptidase I (SPaseI) Inhibitor. J. P. Synlett 15:2355-2359 (2008).
Holtzel et al. Arylomycins A and B, new biaryl-bridged lipopeptide antibiotics produced by Streptomyces sp. Tu 6075. Antibot (Tokyo) 55(6):571-577 (2002).
Liu et al. Efforts toward broadening the spectrum of arylomycin antibiotic activity. Bioorg Med Chem Lett 23:5654-5659 (2013).
Liu et al. Synthesis and Characterization of the Arylomycin Lipoglycopeptide Antibiotics and the Crystallographic Analysis of Their Complex with Signal Peptidase. J Am Chem Soc 133:17869-17877 (2011).
PCT/CN2016/106598 International Preliminary Report on Patentability dated May 31, 2018.
Paetzel et al. Crystallographic and biophysical analysis of a bacterial signal peptidase in complex with a lipopeptide-based inhibitor. J Biol Chem 279(29):30781-30790 (2004).
PCT/CN2016/106597 International Preliminary Report on Patentability dated May 31, 2018.
PCT/CN2016/106597 International Search Report and Written Opinion dated Mar. 8, 2017.
PCT/CN2016/106597 Supplementary International Search Report dated Jul. 5, 2017.
PCT/CN2016/106598 International Search Report and Written Opinion dated Mar. 2, 2017.
PCT/CN2016/106598 Supplementary International Search Report dated Jun. 12, 2017.
PCT/CN2018/076957 International Search Report and Written Opinion dated Jun. 8, 2018.
PCT/US2012/39727 International Preliminary Report on Patentability dated Dec. 2, 2013.
PCT/US2012/39727 International Search Report and Written Opinion dated Jan. 3, 2013.
PCT/US2013/071093 International Preliminary Report on Patentability dated Jun. 4, 2015.
PCT/US2013/071093 International Search Report and Written Opinion dated Apr. 1, 2014.
PCT/US2014/051151 International Preliminary Report on Patentability dated Feb. 25, 2016.
Roberts et al. Initial efforts toward the optimization of arylomycins for antibiotic activity. J Am Chem Soc 129:15830-15838 (2007).
Roberts et al. Initial efforts toward the optimization of arylomycins for antibiotic activity. J Med Chem. 54(14):4954-4963 (2011).
Roberts et al. Synthesis and Biological Characterization of Arylomycin B Antibiotics. J. Nat. Prod. 74:956-961 (2011).
Schimana et al. Arylomycins A and B, new biaryl-bridged lipopeptide antibiotics produced by Streptomyces sp. Tü 6075. I. Taxonomy, fermentation, isolation and biological activities. J Antibiot (Tokyo) 55(6):565-570 (2002).
Smith et al. Broad Spectrum Antibiotic Activity of the Arylomycin Natural Products Is Masked by Natural Target Mutations. Chem Biol 17:1223-1231 (2010).
Therien et al. Broadening the Spectrum of β-Lactam Antibiotics through Inhibition of Signal Peptidase Type 1. Antimicrobial Agents and Chemotherapy. 56:4662-4670 (2012).
U.S. Appl. No. 14/086,908 Office Action dated Jan. 5, 2015.
U.S. Appl. No. 14/086,908 Office Action dated May 29, 2015.
U.S. Appl. No. 14/123,024 Office Action dated May 1, 2015.
U.S. Appl. No. 14/123,024 Office Action dated May 19, 2016.
U.S. Appl. No. 14/123,024 Office Action dated Oct. 15, 2015.
U.S. Appl. No. 15/358,100 Office Action dated Aug. 3, 2018.
Braun et al. Imp/OstA is required for cell envelope biogenesis in Escherichia coli. Molecular Microbiology 45(5):1289-1302 (2002).
Bundgaard et al. Design of Prodrugs pp. 7-9, 21-24 (1985).
Gould et al. Salt Selection for Basic Drugs. Int J. Pharm. 33:201-217. (1986).
Hallander et al Synergism Between Aminoglycosides and Cephalosporins with Antipseudomonal Activity: Interaction Index and Killing Curve Method Antimicrob. Agents Chemother. 22:743-752 (1982).
PCT/US2015/031631 International Preliminary Report on Patentability dated Dec. 1, 2016.
PCT/US2015/031631 International Search Report and Written Opinion dated Nov. 3, 2015.
Banker et al. Modern Pharmaceutices. 3rd ed. ( pp. 451 & 596) (1996).
Silverman. The Organic Chemistry of Drug Design and Drug Action, published 1992 by Academic Press, pp. 19-21.
U.S. Appl. No. 15/777,499 Office Action dated Mar. 20, 2019.
West. Solid State Chemistry and its Applications. Wiley, New York. pp. 358 & 365 (1988).
Wolff. Burger's Medicinal Chemistry and Drug Discovery. 5th Ed. Part 1, pp. 975-977 (1995).
JP2017-513597 Office Action dated May 15, 2019 (w/English translation).

MACROCYCLIC BROAD SPECTRUM ANTIBIOTICS

CROSS-REFERENCE

This application is a National Stage Entry of PCT/US2015/031631, filed on May 19, 2015 which claims the benefit of U.S. provisional application Ser. No. 62/000,980, filed May 20, 2014, and U.S. provisional application Ser. No. 62/142,404, filed Apr. 2, 2015, all of which are incorporated by reference in their entirety.

BACKGROUND OF THE INVENTION

Antibiotic resistance is a serious and growing phenomenon in contemporary medicine and has emerged as a major public health concern of the 21st century. Therefore, novel classes of broad-spectrum antibiotics, especially those that target novel mechanisms of action, are needed to treat multidrug-resistant pathogens.

SUMMARY OF THE INVENTION

Described herein are novel macrocyclic compounds for the treatment of microbial infections, such as for the treatment of bacterial infections. In various embodiments, the present disclosure provides lipopeptide macrocyclic compounds for the treatment of bacterial infections. In various embodiments, the present disclosure provides classes and subclasses of chemical compounds structurally related to arylomycin for the treatment of bacterial infections. In various embodiments, the macrocyclic compounds act by inhibition of bacterial type 1 signal peptidase (SpsB), an essential protein in bacteria.

In one aspect described herein are compounds of Formula (I):

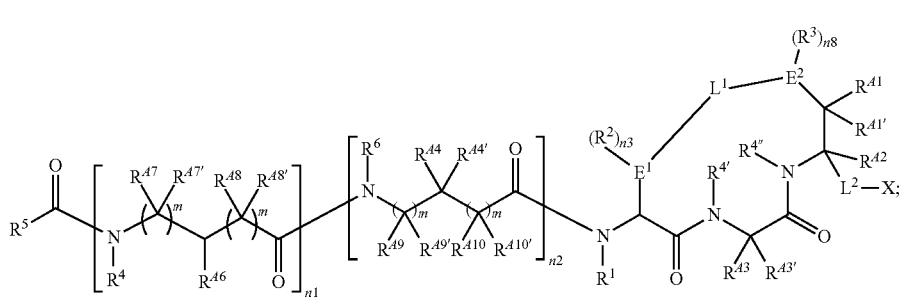

Formula (I)

wherein:

$E^1$ is $(C_1\text{-}C_6)$alkyl, $(C_2\text{-}C_7)$alkenyl, $(C_2\text{-}C_7)$alkynyl, $(C_3\text{-}C_7)$cycloalkyl, heterocyclyl, heteroaryl, or aryl;

$E^2$ is $(C_2\text{-}C_7)$alkenyl, $(C_2\text{-}C_7)$alkynyl, $(C_3\text{-}C_7)$cycloalkyl, heterocyclyl, heteroaryl, or aryl;

$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1\text{-}C_4)$alkylene optionally substituted with OH, CN, NO$_2$, halogen, $(C_1\text{-}C_6)$alkyl;

$L^2$ is a bond, or optionally substituted $(C_1\text{-}C_6)$alkylene;

X is —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH═CHS(O)$_2$CH$_3$, —NHCH(R$^{24}$)CH═CHS(O)$_2$NH$_2$,

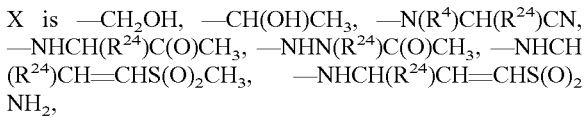

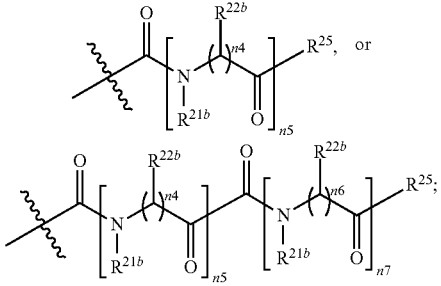

wherein n4, n5, and n6 are each independently 1, 2 or 3; n7 is 0, 1 or 2; R$^{21b}$ and R$^{22b}$ are independently at each occurrence hydrogen, hydroxy, $(C_1\text{-}C_6)$alkyl, $(C_3\text{-}C_7)$cycloalkyl, 5- to 7-membered heteroaryl, 5- to 7-membered heterocyclyl, or $(C_6\text{-}C_{10})$ aryl, wherein any alkyl, cycloalkyl, heterocyclyl, aryl or heteroaryl is optionally substituted with 1 to 3 J; R$^{24}$ is H or $(C_1\text{-}C_6)$alkyl; R$^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$—CH$_2$CH$_2$R$^{30}$, —N(H)CH$_2$(R$^{30}$), —CH═CHR$^{30}$, —CH═CHSO$_2$R$^{25b}$,

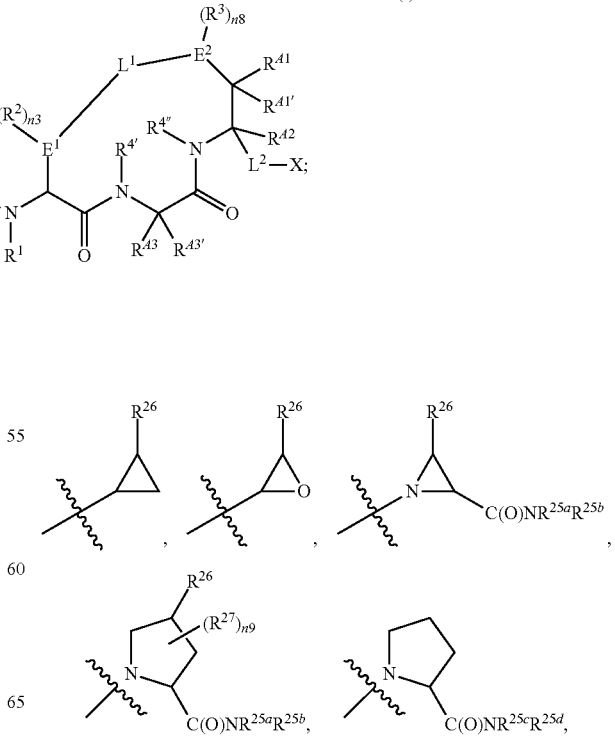

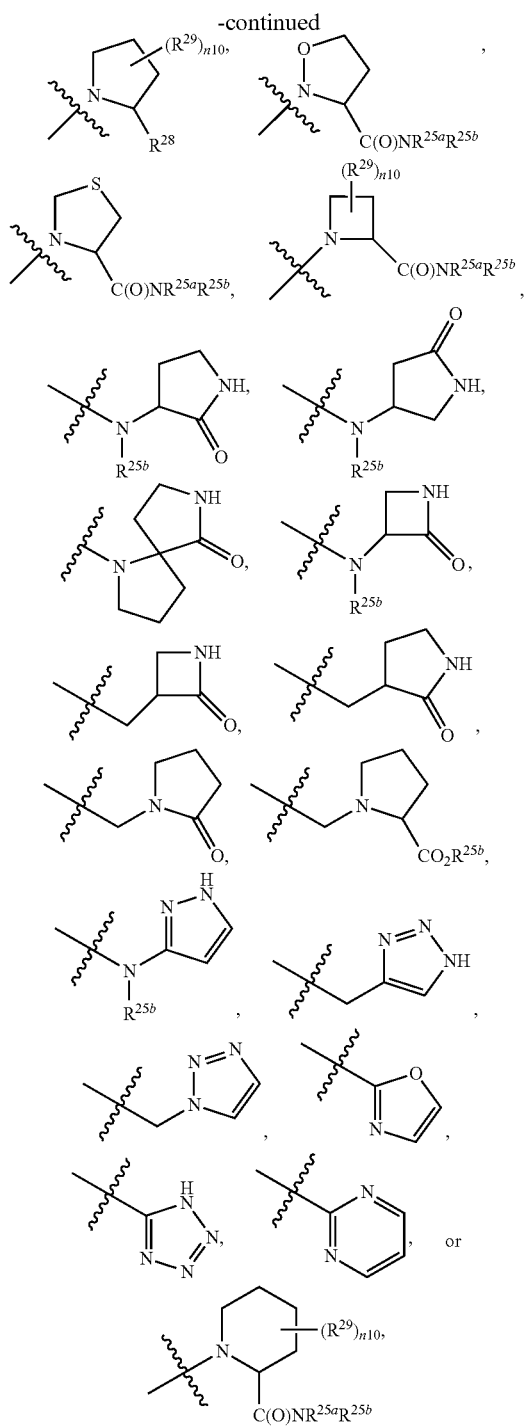

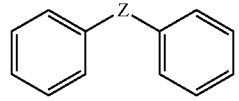

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; n10 is 0, 1, 2, 3 or 4; $R^5$ is aryl, heteroaryl, or a linear or branched alkyl chain of about 1-22 carbon atoms, wherein $R^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted wherein Z is a bond, O, S, NH, CH$_2$ or C≡C; or $R^5$ is a linear or branched alkyl chain of about 1-22 carbon atoms, comprising within the chain at least one —O— or —N(R$^4$)—; each $R^2$ and $R^3$ are each independently hydroxy, nitro, halo, cyano, glycosyloxy, amino, (C$_1$-C$_4$)alkyl, OR$^{40}$, or a group cleavable under physiological conditions to provide a compound of formula (I) wherein $R^2$ or $R^3$ respectively is hydroxy, wherein any carbon atom is optionally substituted with J;

each $R^{40}$ is independently —(C$_1$-C$_6$)alkyl, or —(C$_1$-C$_6$)alkyl-NR$^{41}$R$^{42}$;

each $R^{41}$ and $R^{42}$ is hydrogen, —(C$_1$-C$_6$)alkyl, —(C$_1$-C$_6$)heteroalkyl, —C(O)(C$_1$-C$_6$)alkyl, —C(O)N(R$^{43}$)$_2$, —SO$_2$N(R$^{43}$)$_2$; or $R^{41}$ and $R^{42}$ and the nitrogen atom to which that are attached form a heterocycloalkyl ring;

each $R^{43}$ is independently hydrogen or —(C$_1$-C$_6$)alkyl; or two $R^{43}$ and the nitrogen atom to which that are attached form a heterocycloalkyl ring;

n1 and n2 are independently 0 or 1;
n3 and n8 are independently 0, 1, or 2;
each m is independently 0 or 1;
$R^1$ is hydrogen or (C$_1$-C$_6$)alkyl optionally substituted with 1 to 3 J; or $R^1$ together with $E^1$ form a ring;
$R^4$, $R^{4'}$, and $R^{4''}$ are each independently at each occurrence hydrogen, or (C$_1$-C$_6$)alkyl optionally substituted with 1 to 3 J;
$R^6$ is hydrogen, or (C$_1$-C$_6$)alkyl optionally substituted with 1 to 3 J; or $R^6$ together with $R^{44}$ form a ring;
$R^{41}$, $R^{41'}$, $R^{42}$, $R^{43}$, $R^{43'}$, $R^{44}$, $R^{44'}$, $R^{47}$, $R^{48}$, $R^{48'}$, $R^{48''}$, $R^{49}$, $R^{49'}$, $R^{410}$, and $R^{410'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

$R^{46}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In another embodiment described herein are compounds of Formula (I) having the structure of Formula (Ia):

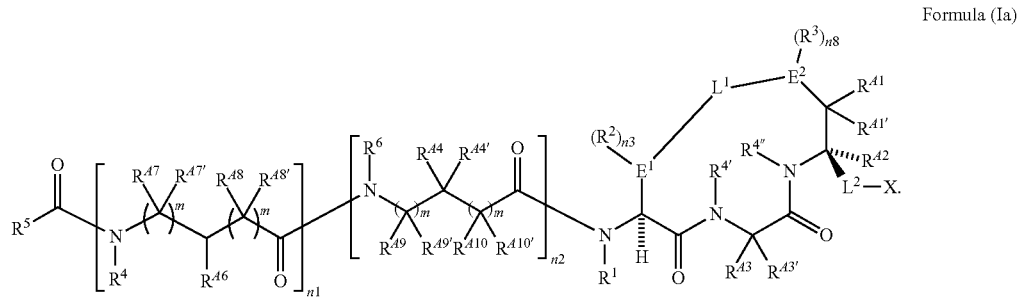
Formula (Ia)
In another embodiment described herein are compounds of Formula (I) having the structure of Formula (Ib):
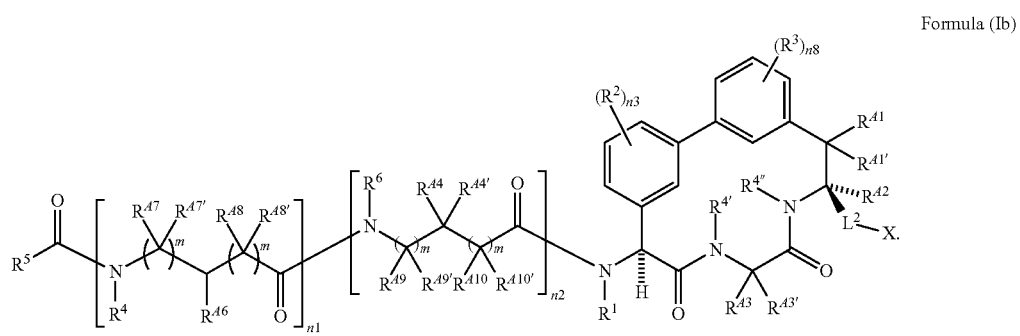
Formula (Ib)
In another embodiment described herein are compounds of Formula (I) having the structure of Formula (Ic):
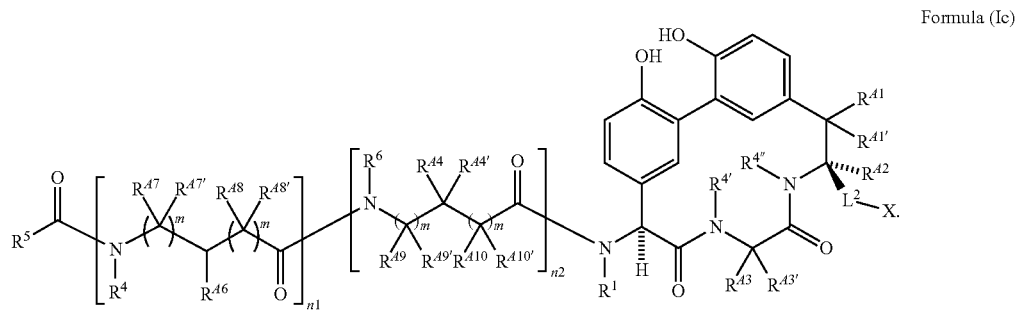
Formula (Ic)
In another embodiment described herein are compounds of Formula (I) having the structure of Formula (Id):
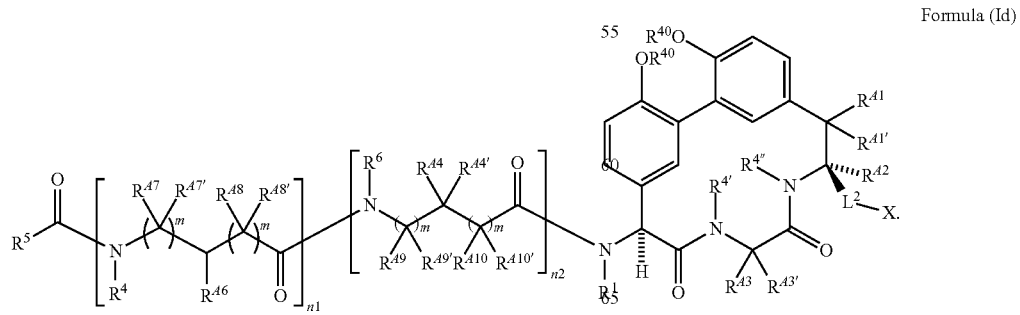
Formula (Id)

In some embodiments is a compound of Formula (I), (Ia), (Ib), (Ic), or (Id) wherein $R^{41}$, $R^{41'}$, $R^{4'}$, and $R^{4''}$ are H. In further embodiments is a compound of Formula (I), (Ia), (Ib), (Ic), or (Id) wherein $L^2$ is a bond. In further embodiments is a compound of Formula (I), (Ia), (Ib), (Ic), or (Id) wherein $R^1$ is $CH_3$. In further embodiments is a compound of Formula (I), (Ia), (Ib), (Ic), or (Id) wherein $L^2$ is a bond and $R^1$ is $CH_3$. In further embodiments is a compound of Formula (I), (Ia), (Ib), (Ic), or (Id) wherein n1 is 1 and n2 is 1. In further embodiments is a compound of Formula (I), (Ia), (Ib), (Ic), or (Id) wherein $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are each independently hydrogen, or $(C_1-C_6)$alkyl optionally substituted with 1 to 3 J. In further embodiments is a compound of Formula (I), (Ia), (Ib), (Ic), or (Id) wherein $R^{46}$ is $(C_1-C_6)$alkyl optionally substituted with 1 to 3 J. In further embodiments is a compound of Formula (I), (Ia), (Ib), (Ic), or (Id) wherein each m is 0. In another embodiment is a compound of Formula (I), (Ia), (Ib), (Ic), or (Id) wherein n1 is 0 and n2 is 1. In further embodiments is a compound of Formula (I), (Ia), (Ib), (Ic), or (Id) wherein $R^{42}$, $R^{43}$, $R^{43'}$, $R^{44}$, $R^{44'}$, $R^{49}$, $R^{49'}$, $R^{410}$, and $R^{410'}$ are each independently hydrogen, or $(C_1-C_6)$alkyl optionally substituted with 1 to 3 J. In a further embodiment is a compound of Formula (I), (Ia), (Ib), (Ic), or (Id) wherein $R^4$ is hydrogen. In another embodiment is a compound of Formula (I), (Ia), (Ib), (Ic), or (Id) wherein n1 is 0 and n2 is 0.

In another embodiment of the aforementioned embodiments is a compound of Formula (I), (Ia), (Ib), (Ic), or (Id) wherein X is

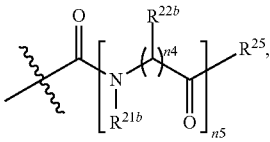

and $R^{25}$ is

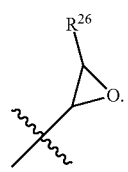

In another embodiment of the aforementioned embodiments is a compound of Formula (I), (Ia), (Ib), (Ic), or (Id) wherein X is

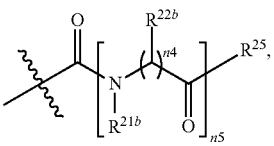

$R^{25}$ is

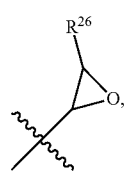

and $R^{26}$ is hydrogen or —$CH_3$. In another embodiment of the aforementioned embodiments is a compound of Formula (I), (Ia), (Ib), (Ic), or (Id) wherein X is

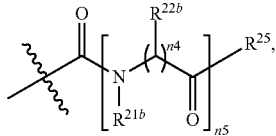

and $R^{25}$ is

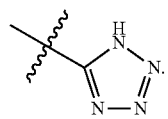 [SMILES: *c1nnn[nH]1]

In another embodiment of the aforementioned embodiments is a compound of Formula (I), (Ia), (Ib), (Ic), or (Id) wherein X is

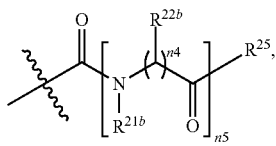

and $R^{25}$ is —$CH_3$. In another embodiment of the aforementioned embodiments is a compound of Formula (I), (Ia), (Ib), (Ic), or (Id) wherein X is

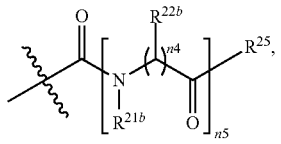

and $R^{25}$ is

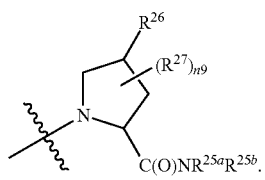

In another embodiment of the aforementioned embodiments is a compound of Formula (I), (Ia), (Ib), (Ic), or (Id) wherein X is

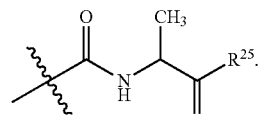

In another embodiment of the aforementioned embodiments is a compound of Formula (I), (Ia), (Ib), (Ic), or (Id) wherein $R^5$ is a linear or branched alkyl chain of about 1-22 carbon atoms, comprising within the chain at least one —$N(R^4)$—. In another embodiment of the aforementioned embodiments is a compound of Formula (I), (Ia), (Ib), (Ic), or (Id) wherein $R^5$ is a linear or branched alkyl chain of about 1-22 carbon atoms, comprising within the chain at least one —N(H)—. In another embodiment of the aforementioned embodiments is a compound of Formula (I), (Ia), (Ib), (Ic), or (Id) wherein $R^5$ is —$CH_2CH_2N(H)(CH_2)_9CH_3$.

In another embodiment of the aforementioned embodiments is a compound of Formula (I), (Ia), (Ib), (Ic), or (Id) wherein $R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

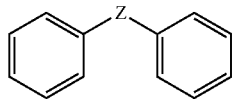

wherein Z is a bond, O, S, NH, $CH_2$ or C≡C. In another embodiment of the aforementioned embodiments is a compound of Formula (I), (Ia), (Ib), (Ic), or (Id) wherein $R^5$ is

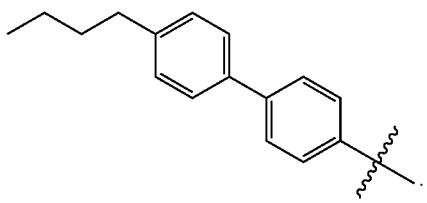 [SMILES: *c1ccc(-c2ccc(CCCC)cc2)cc1]

In another embodiment of the aforementioned embodiments is a compound of Formula (I), (Ia), (Ib), (Ic), or (Id) wherein $R^5$ is

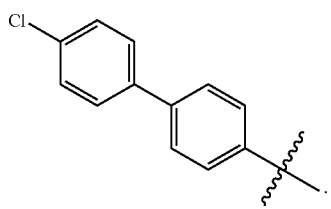 [SMILES: *c1ccc(-c2ccc(Cl)cc2)cc1]

In another aspect described herein are compounds of Formula (II):

wherein:
$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;
$E^2$ is $(C_2-C_7)$alkenyl, $(C_2-C_7)$alkynyl, $(C_3-C_7)$cycloalkyl, heterocyclyl, heteroaryl, or aryl;
$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;
$L^2$ is a bond, or optionally substituted $(C_1-C_6)$alkylene;
X is a group of formula

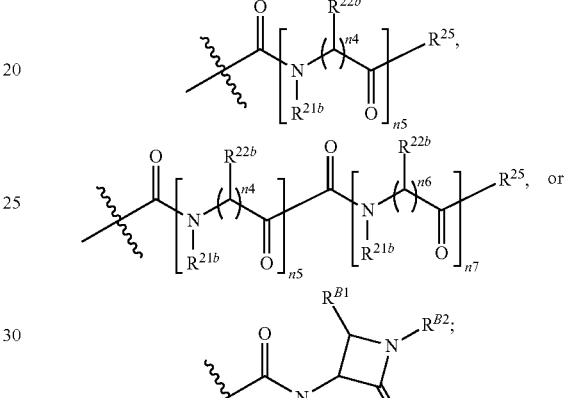

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

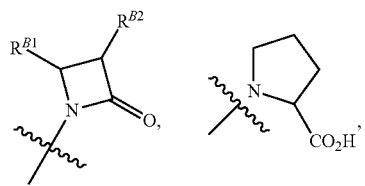

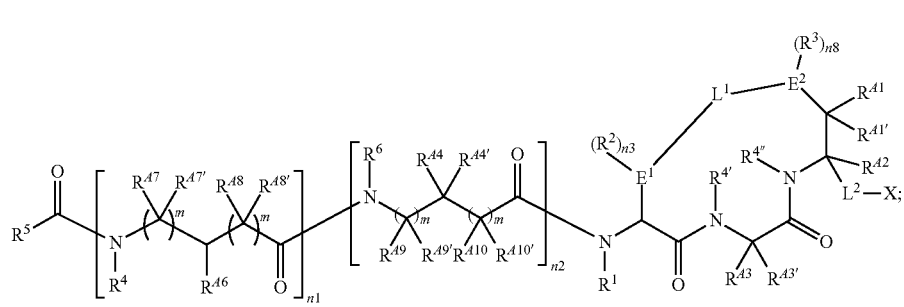

Formula (II)

-continued

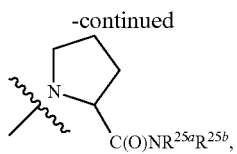

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl; or X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

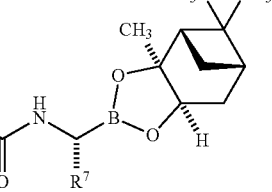

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, —CH$_2$CH$_2$CO$_2$H; or R$^{B3}$ and R$^{B4}$ together with the boron atom form an optionally substituted 5- or 6-membered boron containing ring;

R$^5$ is a linear or branched alkyl chain of about 1-22 carbon atoms, comprising within the chain at least one —O— or —N(R$^4$)—;

each R$^2$ and R$^3$ are each independently hydroxy, nitro, halo, cyano, glycosyloxy, amino, (C$_1$-C$_4$)alkyl, OR$^{40}$, or a group cleavable under physiological conditions to provide a compound of formula (II) wherein R$^2$ or R$^3$ respectively is hydroxy, wherein any carbon atom is optionally substituted with J;

each R$^{40}$ is independently —(C$_1$-C$_6$)alkyl, or —(C$_1$-C$_6$)alkyl-NR$^{41}$R$^{42}$;

each R$^{41}$ and R$^{42}$ is hydrogen, —(C$_1$-C$_6$)alkyl, —(C$_1$-C$_6$) heteroalkyl, —C(O)(C$_1$-C$_6$)alkyl, —C(O)N(R$^{43}$)$_2$, —SO$_2$N(R$^{43}$)$_2$; or R$^{41}$ and R$^{42}$ and the nitrogen atom to which that are attached form a heterocycloalkyl ring;

each R$^{43}$ is independently hydrogen or —(C$_1$-C$_6$)alkyl; or two R$^{43}$ and the nitrogen atom to which that are attached form a heterocycloalkyl ring;

n1 and n2 are independently 0 or 1;
n3 and n8 are independently 0, 1, or 2;
each m is independently 0 or 1;

R$^1$ is hydrogen or (C$_1$-C$_6$)alkyl optionally substituted with 1 to 3 J; or R$^1$ together with E$^1$ form a ring;

R$^4$, R$^{4'}$, and R$^{4''}$ are each independently at each occurrence hydrogen, or (C$_1$-C$_6$)alkyl optionally substituted with 1 to 3 J;

R$^6$ is hydrogen, or (C$_1$-C$_6$)alkyl optionally substituted with 1 to 3 J; or R$^6$ together with R$^{44}$ form a ring;

R$^{A1}$, R$^{A1'}$, R$^{A2}$, R$^{A3}$, R$^{A3'}$, R$^{A4}$, R$^{A4'}$, R$^{A7}$, R$^{A7'}$, R$^{A8}$, R$^{A8'}$, R$^{A9}$, R$^{A9'}$, R$^{A10}$, and R$^{A10'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

R$^{A6}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In another embodiment described herein are compounds of Formula (II) having the structure of Formula (IIa):

Formula (IIa)

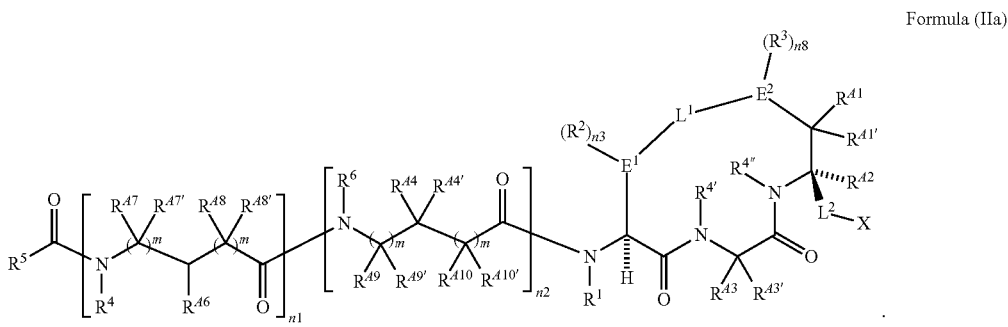

In another embodiment described herein are compounds of Formula (II) having the structure of Formula (IIb):

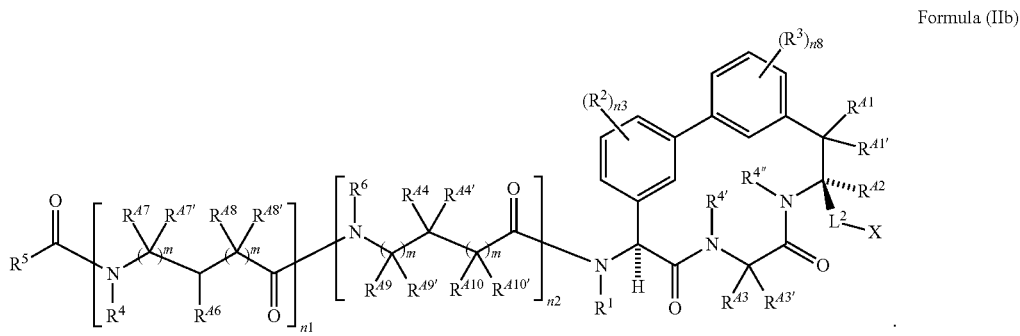

Formula (IIb)

In another embodiment described herein are compounds of Formula (II) having the structure of Formula (IIc):

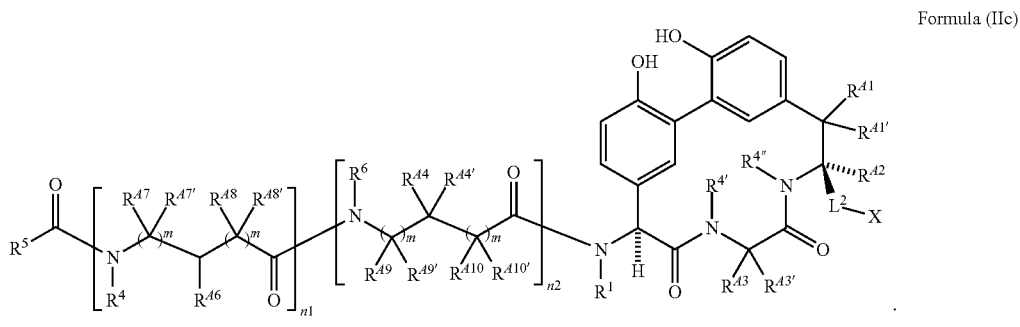

Formula (IIc)

In another embodiment described herein are compounds of Formula (II) having the structure of Formula (IId):

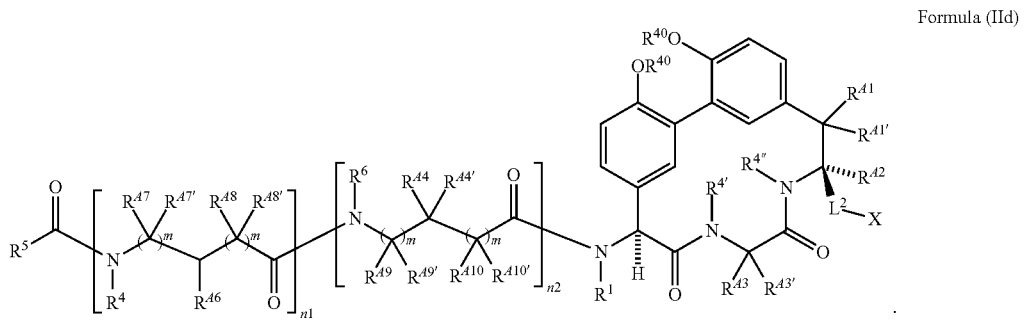

Formula (IId)

In some embodiments is a compound of Formula (II), (IIa), (IIb), (IIc), or (IId) wherein $R^{A1}$, $R^{A1'}$, $R^{4'}$, and $R^{4''}$ are H. In further embodiments is a compound of Formula (II), (IIa), (IIb), (IIc), or (IId) wherein $L^2$ is a bond. In further embodiments is a compound of Formula (II), (IIa), (IIb), (IIc), or (IId) wherein $R^1$ is $CH_3$. In further embodiments is a compound of Formula (II), (IIa), (IIb), (IIc), or (IId) wherein $L^2$ is a bond and $R^1$ is $CH_3$. In further embodiments is a compound of Formula (II), (IIa), (IIb), (IIc), or (IId) wherein n1 is 1 and n2 is 1. In further embodiments is a compound of Formula (II), (IIa), (IIb), (IIc), or (IId) wherein $R^{A2}$, $R^{A3}$, $R^{A3'}$, $R^{A4}$, $R^{A4'}$, $R^{A6}$, $R^{A7}$, $R^{A7'}$, $R^{A8}$, $R^{A8'}$, $R^{A9}$, $R^{A9'}$, $R^{A10}$, and $R^{A10'}$ are each independently hydrogen, or ($C_1$-$C_6$)alkyl optionally substituted with 1 to 3 J. In further embodiments is a compound of Formula (II), (IIa), (IIb), (IIc), or (IId) wherein $R^{A6}$ is hydrogen. In further embodiments is a compound of Formula (II), (IIa), (IIb), (IIc), or (IId) wherein each m is 0. In another embodiment is a compound of Formula (II), (IIa), (IIb), (IIc), or (IId) wherein n1 is 0 and n2 is 1. In further embodiments is a compound of Formula (II), (IIa), (IIb), (IIc), or (IId) wherein $R^{A2}$, $R^{A3}$, $R^{A3'}$, $R^{A4}$, $R^{A4'}$, $R^{A9}$, $R^{A9'}$, $R^{A10}$, and $R^{A10'}$ are each independently hydrogen, or ($C_1$-$C_6$)alkyl optionally substituted with 1 to 3 J. In a further embodiment is a compound of Formula (II), (IIa), (IIb), (IIc), or (IId) wherein $R^4$ is hydrogen. In another embodiment is a compound of Formula (II), (IIa), (IIb), (IIc), or (IId) wherein n1 is 0 and n2 is 0.

In another embodiment of the aforementioned embodiments is a compound of Formula (II), (IIa), (IIb), (IIc), or (IId) wherein X is $CO_2H$. In another embodiment of the aforementioned embodiments is a compound of Formula (II), (IIa), (IIb), (IIc), or (IId) wherein X is $C(=O)NHCH_2B$ (OH)$_2$. In another embodiment of the aforementioned embodiments is a compound of Formula (II), (IIa), (IIb), (IIc), or (IId) wherein X is C(=O)NHCH(CH$_3$)B(OH)$_2$. In another embodiment of the aforementioned embodiments is a compound of Formula (II), (IIa), (IIb), (IIc), or (IId) wherein X is

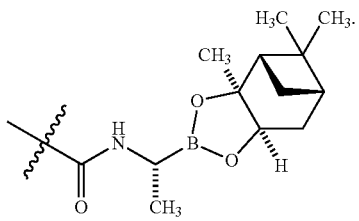 [SMILES: *C(=O)N[C@@H](C)B1O[C@@H]2C[C@@H]3C[C@@H](C3(C)C)[C@]2(C)O1]

In another aspect described herein are compounds of Formula (IV):

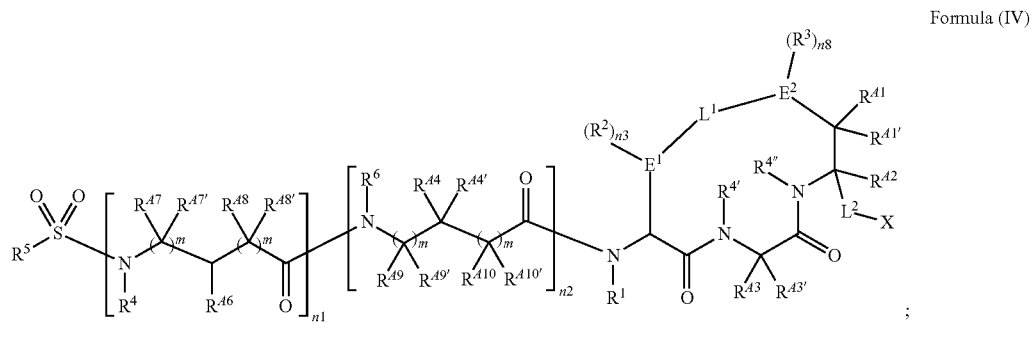

wherein:

E$^1$ is (C$_1$-C$_6$)alkyl, (C$_2$-C$_7$)alkenyl, (C$_2$-C$_7$)alkynyl, (C$_3$-C$_7$) cycloalkyl, heterocyclyl, heteroaryl, or aryl;

E$^2$ is (C$_2$-C$_7$)alkenyl, (C$_2$-C$_7$)alkynyl, (C$_3$-C$_7$)cycloalkyl, heterocyclyl, heteroaryl, or aryl;

L$^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O) NR$^4$—, —NR$^4$S(O)$_2$—, —S(O)$_2$NR$^4$—, —NR$^4$C(O) NR$^4$—, —NR$^4$C(O)O—, —OC(O)NR$^4$—, or (C$_1$-C$_4$)alkylene optionally substituted with OH, CN, NO$_2$, halogen, (C$_1$-C$_6$)alkyl;

L$^2$ is a bond, or optionally substituted (C$_1$-C$_6$)alkylene;

X is —CO$_2$H, —CH$_2$CO$_2$H, —C(=O)NHCH$_2$C(=O)H, —CH$_2$C(=O)H, —C(=O)N(H)CH(R$^7$)B(OR$^{B3}$)(OR$^{B4}$), —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH=CHS(O)$_2$CH$_3$, —NHCH(R$^{24}$)CH=CHS(O)$_2$NH$_2$,

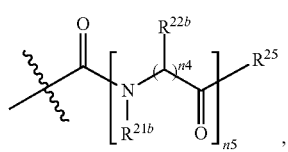

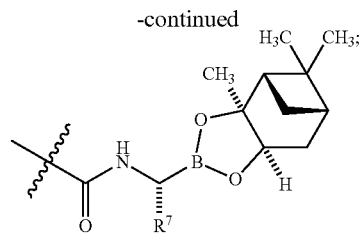

, or wherein n4, n5, and n6 are each independently 1, 2 or 3; n7 is 0, 1 or 2; R is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, —CH$_2$CH$_2$CO$_2$H; or R$^{B3}$ and R$^{B4}$ together with the boron atom form an optionally substituted 5- or 6-membered boron containing ring; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{24}$ is H or (C$_1$-C$_6$)alkyl; R$^{25}$ is H, OH, OR$^C$, NR$^{25a}$R$^{25b}$, —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$CH$_2$N(H)CH(R$^{26}$)C (O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

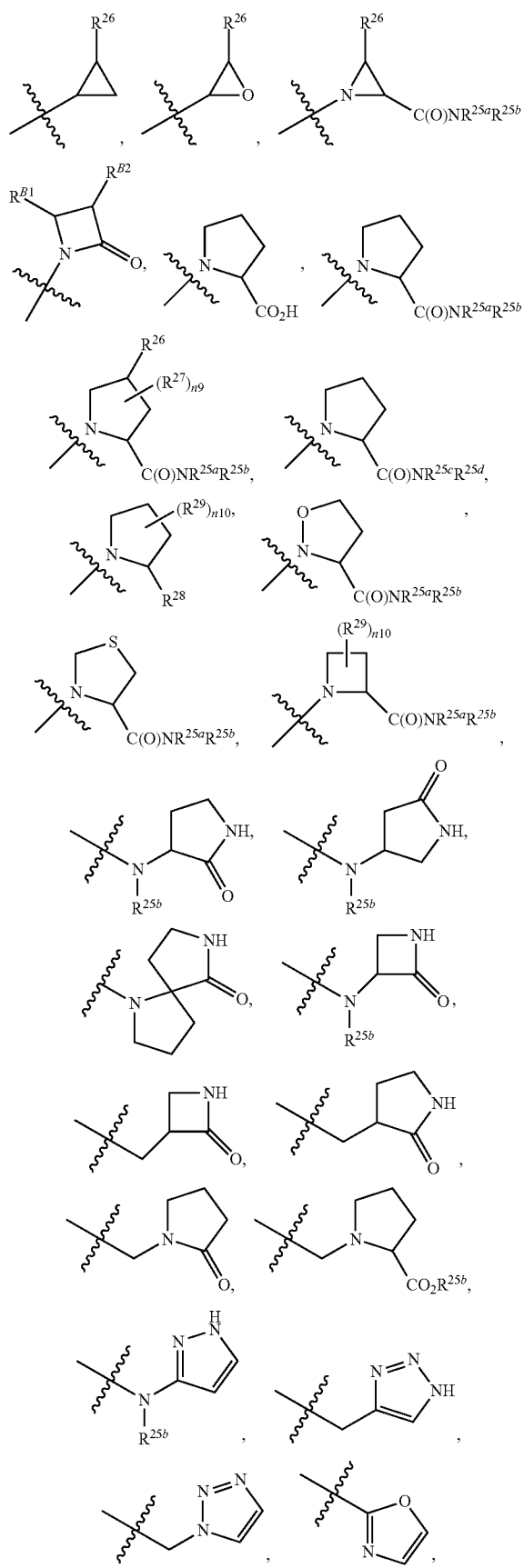

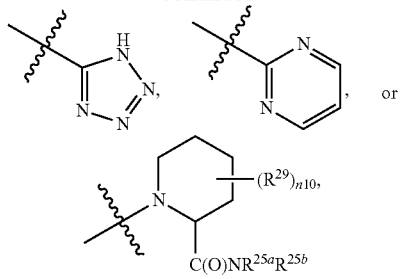

where $R^{B1}$ and $R^{B2}$ each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl; $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or $(C_1-C_6)$alkyl; each $R^{27}$ is independently —OH, halo, $(C_1-C_6)$alkyl, or $R^{26}$ and $R^{27}$ are joined to form a cycloalkyl ring; $R^{28}$ is H, —CH$_2$OH, —CH$_2$NH$_2$, —C(O)CH$_3$, or $(C_1-C_6)$alkyl; each $R^{29}$ is independently —OH, halo, or $(C_1-C_6)$alkyl; $R^{30}$ is heterocyclyl, heteroaryl, or aryl; n9 is 1, 2 or 3; n10 is 0, 1, 2, 3 or 4;

$R^5$ is aryl, heteroaryl, or a linear or branched alkyl chain of about 1-22 carbon atoms optionally comprising within the chain or at a chain terminus optionally substituted aryl, optionally substituted heteroaryl, or optionally substituted

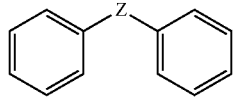

wherein Z is a bond, O, S, NH, CH$_2$ or C≡C; or $R^5$ is a linear or branched alkyl chain of about 1-22 carbon atoms, comprising within the chain at least one —O— or —N(R$^4$)—;

each $R^2$ and $R^3$ are each independently hydroxy, nitro, halo, cyano, glycosyloxy, amino, $(C_1-C_4)$alkyl, $OR^{40}$, or a group cleavable under physiological conditions to provide a compound of formula (IV) wherein $R^2$ or $R^3$ respectively is hydroxy, wherein any carbon atom is optionally substituted with J;

each $R^{40}$ is independently —$(C_1-C_6)$alkyl, or —$(C_1-C_6)$alkyl-NR$^{41}$R$^{42}$;

each $R^{41}$ and $R^{42}$ is hydrogen, —$(C_1-C_6)$alkyl, —$(C_1-C_6)$heteroalkyl, —C(O)(C$_1$-C$_6$)alkyl, —C(O)N(R$^{43}$)$_2$, —SO$_2$N(R$^{43}$)$_2$; or $R^{41}$ and $R^{42}$ and the nitrogen atom to which that are attached form a heterocycloalkyl ring;

each $R^{43}$ is independently hydrogen or —$(C_1-C_6)$alkyl; or two $R^{43}$ and the nitrogen atom to which that are attached form a heterocycloalkyl ring;

n1 and n2 are independently 0 or 1;
n3 and n8 are independently 0, 1, or 2;
each m is independently 0 or 1;
$R^1$ is hydrogen or $(C_1-C_6)$alkyl optionally substituted with 1 to 3 J; or $R^1$ together with $E^1$ form a ring;
$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{A4}$ form a ring;

$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J;

$R^{A6}$ is H, amino, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J;

each J is independently halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In another embodiment described herein are compounds of Formula (IV) having the structure of Formula (IVa):

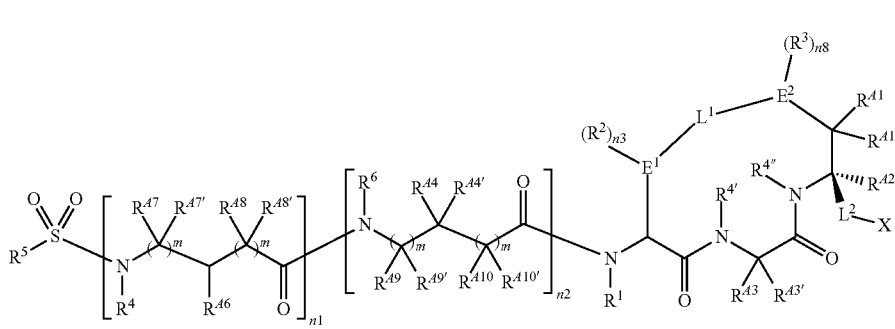

Formula (IVa)

In another embodiment described herein are compounds of Formula (IV) having the structure of Formula (IVb):

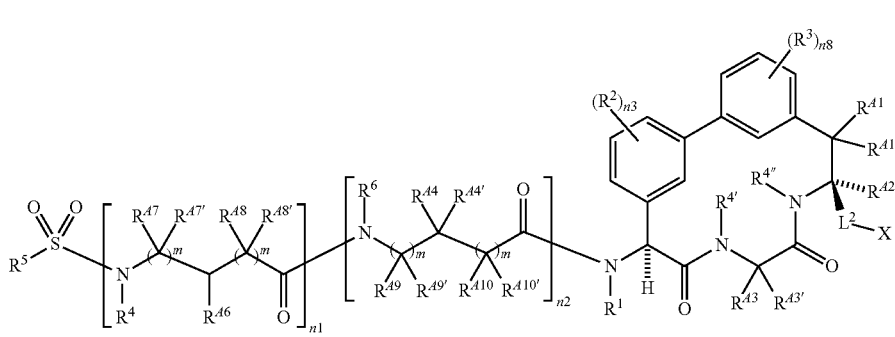

Formula (IVb)

In another embodiment described herein are compounds of Formula (IV) having the structure of Formula (IVc):

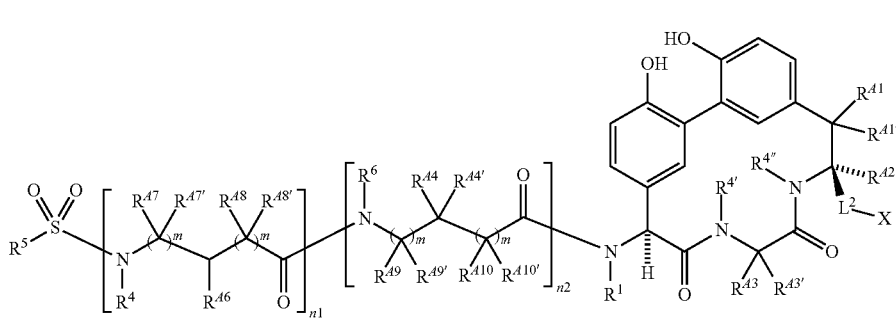

Formula (IVc)

In another embodiment described herein are compounds of Formula (IV) having the structure of Formula (IVd):

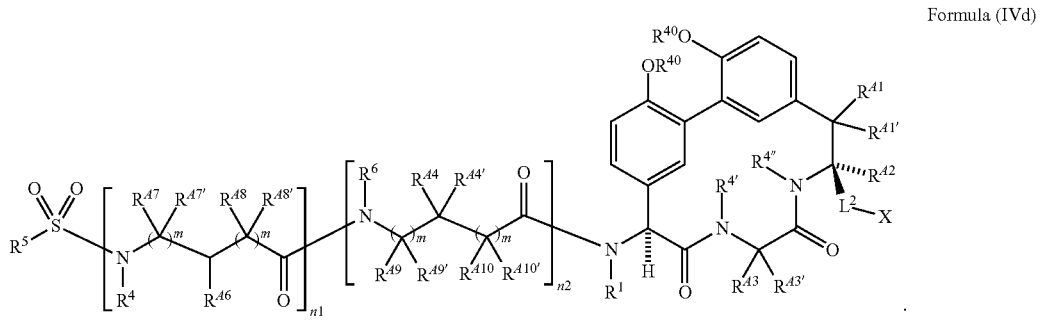

Formula (IVd)

In some embodiments is a compound of Formula (IV), (IVa), (IVb), (IVc), or (IVd) wherein $R^{A1}$, $R^{A1'}$, $R^{4'}$, and $R^{4''}$ are H. In further embodiments is a compound of Formula (IV), (IVa), (IVb), (IVc), or (IVd) wherein $L^2$ is a bond. In further embodiments is a compound of (IV), (IVa), (IVb), (IVc), or (IVd) wherein $R^1$ is $CH_3$. In further embodiments is a compound of Formula (IV), (IVa), (IVb), (IVc), or (IVd) wherein $L^2$ is a bond and $R^1$ is $CH_3$. In another embodiment is a compound of Formula (IV), (IVa), (IVb), (IVc), or (IVd) wherein n1 is 0 and n2 is 1. In further embodiments is a compound of Formula (IV), (IVa), (IVb), (IVc), or (IVd) wherein $R^{A2}$, $R^{A3}$, $R^{A3'}$, $R^{A4}$, $R^{A4'}$, $R^{A9}$, $R^{A9'}$, $R^{A10}$, and $R^{A10'}$ are each independently hydrogen, or $(C_1-C_6)$alkyl optionally substituted with 1 to 3 J. In another embodiment of the aforementioned embodiments is a compound of Formula (IV), (IVa), (IVb), (IVc), or (IVd) wherein X is

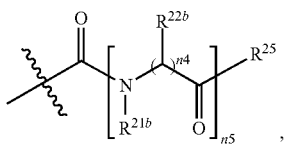

and $R^{25}$ is —$CH_3$. In another embodiment of the aforementioned embodiments is a compound of Formula (IV), (IVa), (IVb), (IVc), or (IVd) wherein X is

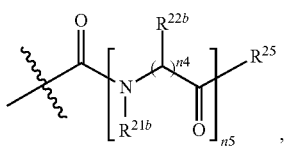

and $R^{25}$ is

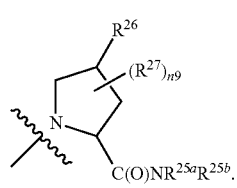

In another embodiment of the aforementioned embodiments is a compound of Formula (IV), (IVa), (IVb), (IVc), or (IVd) wherein X is

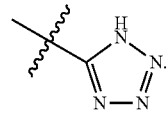

and $R^{25}$ is

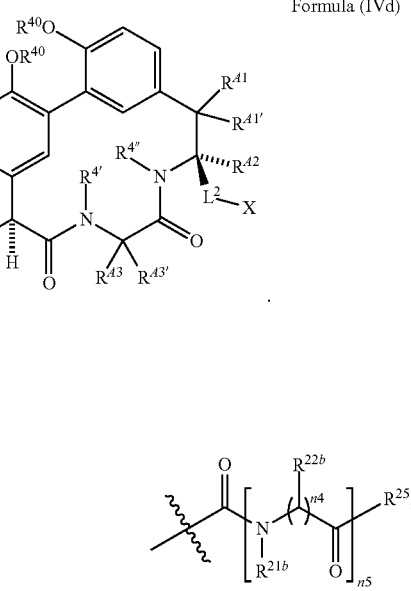

In another embodiment of the aforementioned embodiments is a compound of Formula (IV), (IVa), (IVb), (IVc), or (IVd) wherein X is

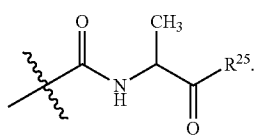

In another embodiment of the aforementioned embodiments is a compound of Formula (IV), (IVa), (IVb), (IVc), or (IVd) wherein $R^5$ is

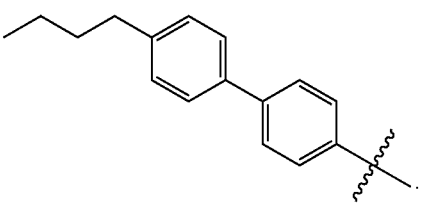 [SMILES: *c1ccc(-c2ccc(CCCC)cc2)cc1]

In another embodiment of the aforementioned embodiments is a compound of Formula (IV), (IVa), (IVb), (IVc), or (IVd) wherein $R^5$ is

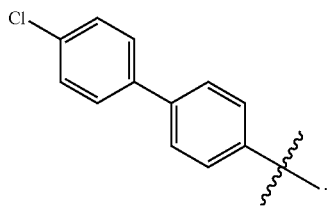 [SMILES: *c1ccc(-c2ccc(Cl)cc2)cc1]

In another embodiment of the aforementioned embodiments is a compound of Formula (IV), (IVa), (IVb), (IVc), or (IVd) wherein X is $CO_2H$. In another embodiment of the aforementioned embodiments is a compound of Formula (IV), (IVa), (IVb), (IVc), or (IVd) wherein X is $C(=O)NHCH(CH_3)B(OH)_2$. In another embodiment of the aforementioned embodiments is a compound of Formula (IV), (IVa), (IVb), (IVc), or (IVd) wherein X is

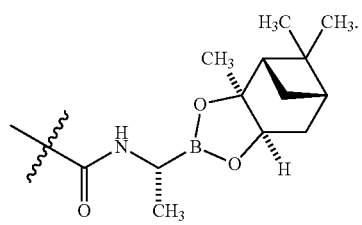 [SMILES: *C(=O)N[C@@H](C)B1O[C@@H]2C[C@@H]3C[C@@H](C3(C)C)[C@]2(C)O1]

In another embodiment of the aforementioned embodiments is a compound of Formula (I), (Ia), (Ib), (Ic), (Id), (II), (IIa), (IIb), (IIc), (IId), (IV), (IVa), (IVb), (IVc) or (IVd) wherein each m is 0. In another embodiment of the aforementioned embodiments is a compound of Formula (I), (Ia), (Ib), (Ic), (Id), (II), (IIa), (IIb), (IIc), (IId), (IV), (IVa), (IVb), (IVc) or (IVd) wherein $R^{A4}$ is $-CH_2CH_2CH_2CH_2NH_2$ and $R^{A4'}$ is H. In another embodiment of the aforementioned embodiments is a compound of Formula (I), (Ia), (Ib), (Ic), (Id), (II), (IIa), (IIb), (IIc), (IId), (IV), (IVa), (IVb), (IVc) or (IVd) wherein $R^5$ is a linear or branched alkyl chain of about 1-22 carbon atoms, comprising within the chain at least one $-N(R^4)-$. In another embodiment of the aforementioned embodiments is a compound of Formula (I), (Ia), (Ib), (Ic), (Id), (II), (IIa), (IIb), (IIc), (IId), (IV), (IVa), (IVb), (IVc) or (IVd) wherein $R^5$ is a linear or branched alkyl chain of about 1-22 carbon atoms, comprising within the chain at least one $-N(H)-$. In another embodiment of the aforementioned embodiments is a compound of Formula (I), (Ia), (Ib), (Ic), (Id), (II), (IIa), (IIb), (IIc), (IId), (IV), (IVa), (IVb), (IVc) or (IVd) wherein $R^5$ is $-CH_2CH_2N(H)(CH_2)_9CH_3$.

In another aspect described herein are compounds of Formula (III):

wherein:
$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

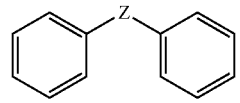

wherein Z is a bond, O, S, NH, $CH_2$ or $C\equiv C$;
n1 and n2 are independently 0 or 1;
each m is independently 0 or 1;
$R^1$ is hydrogen or $(C_1-C_6)$alkyl optionally substituted with 1 to 3 J;
each $R^4$ is independently hydrogen, or $(C_1-C_6)$alkyl optionally substituted with 1 to 3 J;
$R^6$ is hydrogen, or $(C_1-C_6)$alkyl optionally substituted with 1 to 3 J; or $R^6$ together with $R^{A4}$ form a ring;
$R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
$R^{A6}$ is H, amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
each J is independently halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;
each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalk- Formula (III)

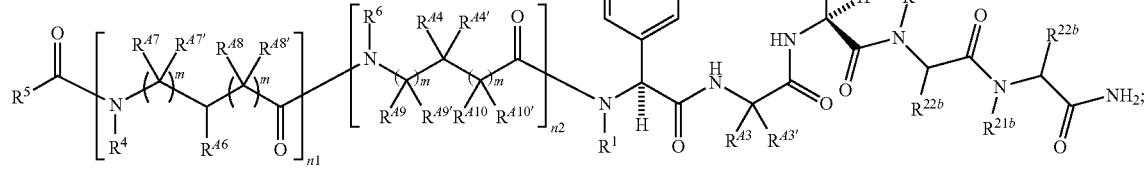

enyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In another aspect is a hydrate or metabolite of a compound of Formula (I), (Ia), (Ib), (Ic), (II), (IIa), (IIb), (IIc), (III), or (IV).

In another aspect is a pharmaceutical composition comprising a compound of Formula (I), (Ia), (Ib), (Ic), (II), (IIa), (IIb), (IIc), (III), (IV), (IVa), (IVb), or (IVc) and a pharmaceutically acceptable excipient thereof.

another aspect is the use of a compound of Formula (I), (Ia), (Ib), (Ic), (II), (IIa), (IIb), (IIc), (III), (IV), (IVa), (IVb), or (IVc) or a pharmaceutically acceptable salt, pharmaceutically acceptable solvate, or pharmaceutically acceptable prodrug thereof, for the preparation of a medicament for the treatment of a bacterial infection in a patient.

In another embodiment is a method for treating a bacterial infection in a mammal comprising administering to the mammal a compound of Formula (I), (Ia), (Ib), (Ic), (II), (IIa), (IIb), (IIc), (III), (IV), (IVa), (IVb), or (IVc) or a pharmaceutically acceptable salt or prodrug thereof at a frequency and for a duration sufficient to provide a beneficial effect to the mammal. In another embodiment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In another embodiment the bacterial infection is an infection involving a Gram-negative bacteria. In another embodiment, administering comprises a topical administration.

In a further embodiment are methods of treating a mammal in need of such treatment comprising administering to the mammal a second therapeutic agent. In another embodiment, the second therapeutic agent is not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In another embodiment, the second therapeutic agent is a β-lactam antibiotic. In another embodiment, the β-lactam antibiotic is selected from penicillins, monobactams, cephalosporins, cephamycins, and carbapenems. In another embodiment, the β-lactam antibiotic is selected from Azlocillin, Amoxicillin, Ampicillin, Doripenem, Meropenem, Biapenem, Cefamandole, Imipenem, Mezlocillin, Cefmetazole, Cefprozil, Piperacillin/tazobactam, Carbenicillin, Cefaclor, Cephalothin, Ertapenem, Cefazolin, Cefepime, Cefonicid, Cefoxitin, Ceftazidime, Oxacillin, Cefdinir, Cefixime, Cefotaxime, Cefotetan, Cefpodoxime, Ceftizoxime, Ceftriaxone, Faropenem, Mecillinam, Methicillin, Moxalactam, Ticarcillin, Tomopenem, Ceftobiprole, Ceftaroline, Flomoxef, Cefiprome, and Cefozopran. A further embodiment comprises administering a β-lactamase inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

Figure 1:
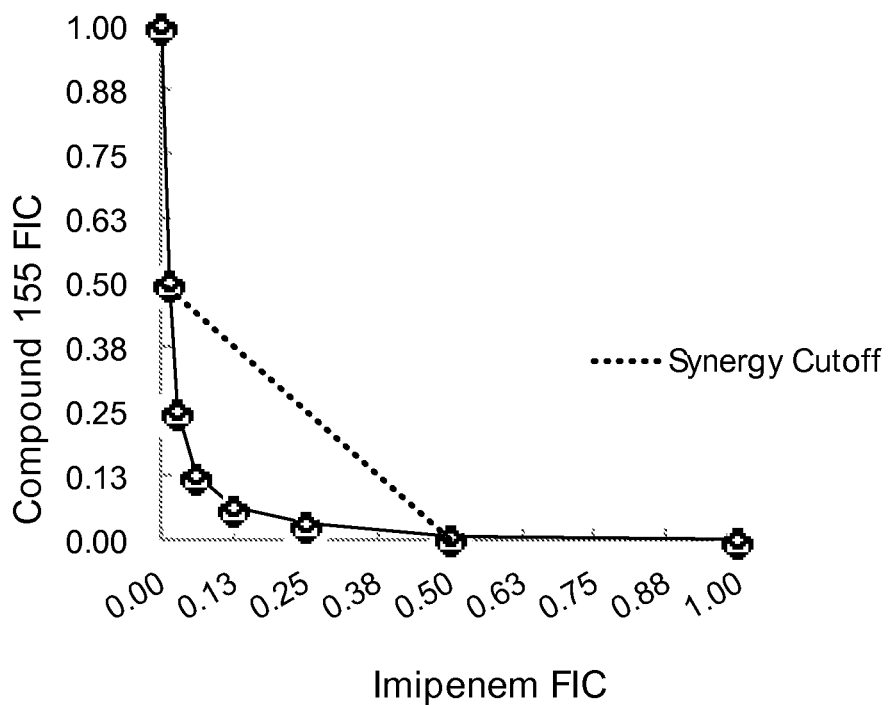
FIG. 1 depicts an isobologram of the fractional inhibitor concentration (FIC) of Compound 155 and imipenem.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound described herein that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds described herein are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. A description herein that a group is alkyl chain "optionally comprising within the chain or at a chain terminus" a moiety, the term signifies that the moiety can be disposed between two subunits of the alkyl chain, or can be disposed at an unsubstituted end of the chain, or can be disposed between the chain and a point of attachment of the chain, for example to a carbonyl, NR, or O group. For example, an alkylbenzoyl group is an alkyl chain with a phenyl group disposed between the alkyl and a carbonyl, fitting the above description; an N-alkylphenyl-carboxamido is an alkyl chain with a phenyl group disposed between the alkyl and the aminocarbonyl group, filling within the above description.

The term "alkylene" means a linear saturated divalent hydrocarbon radical of one to six carbon atoms or a branched saturated divalent hydrocarbon radical of one to six carbon atoms unless otherwise stated, such as methylene, ethylene, propylene, 1-methylpropylene, 2-methylpropylene, butylene, pentylene, and the like.

The term "carbonyl" means C=O.

The terms "carboxy" and "hydroxycarbonyl" mean COOH.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "heterocycloalkyl" ring is a cycloalkyl ring containing at least one heteroatom. A heterocycloalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a heterocycloalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzodioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "thioalkoxy" refers to an alkyl group previously defined attached to the parent molecular moiety through a sulfur atom.

The term "glycosyloxyoxy" refers to a glycoside attached to the parent molecular moiety through an oxygen atom.

The term "alkoxycarbonyl" represents as ester group; i.e. an alkoxy group, attached to the parent molecular moiety through a carbonyl group such as methoxycarbonyl, ethoxycarbonyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x\text{-}C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkyl, more preferred is —$(C_1\text{-}C_3)$perfluoroalkyl, most preferred is —$CF_3$.

The term "$(C_x\text{-}C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkylene, more preferred is —$(C_1\text{-}C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" or "aminocarbonyl" group is a group of the formula C(O)NR$_2$, wherein R can be H, alkyl, aryl, etc.

The term "azido" refers to an N$_3$ group. An "azide" can be an organic azide or can be a salt of the azide (N$_3$—) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O) (NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

The term "ring derived from a sugar" refers to a compound that forms a ring by removing the hydrogen atoms from two hydroxyl groups of any sugar.

The term "boronate ester" refers to an ester of a boronic acid, for example —B(OR$^{B3}$)(OR$^{B4}$) wherein at least one of R$^{B3}$ and R$^{B4}$ are not hydrogen.

The term "boronic acid" refers to a chemical compound containing a —B(OH)$_2$. In some embodiments, boronic acid compounds can form oligomeric anhydrides by dehydration of the boronic acid moiety.

The term "boronic acid anhydride" refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of Formula YY are illustrated below:

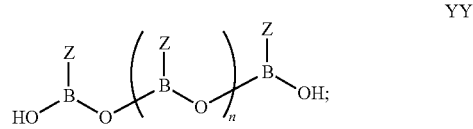

YY wherein n is an integer from 0 to about 10, preferably 0, 1, 2, 3, or 4, and Z is a macrocyclic compound of Formula (I), (Ia), (Ib), (Ic), (II), (IIa), (IIb), (IIc), (III), or (IV).

In some embodiments, the boronic acid anhydride compound comprises a cyclic trimer ("boroxine") of formula XX,

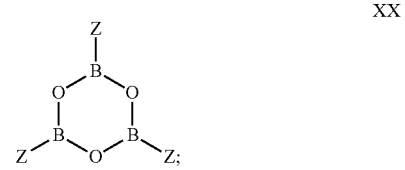

XX wherein Z is a macrocyclic compound of Formula (I), (Ia), (Ib), (Ic), (II), (IIa), (IIb), (IIc), (III), or (IV).

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds described herein may take the form of salts. The term "salts" embraces addition salts of free acids or free bases which are compounds described herein. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the present disclosure.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the present disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I), (Ia), (Ib), (Ic), (II), (IIa), (IIb), (IIc), (III), or (IV) compounds, for example in their purification by recrystallization. All of these salts may be prepared by conventional means from the corresponding compound according to Formula (I), (Ia), (Ib), (Ic), (II), (IIa), (IIb), (IIc), (III), or (IV) by reacting, for example, the appropriate acid or base with the compound according to Formula (I), (Ia), (Ib), (Ic), (II), (IIa), (IIb), (IIc), (III), or (IV). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Further examples of prodrugs include boronate esters which can be hydrolyzed under physiological conditions to afford the corresponding boronic acid. Conventional procedures for the selection and preparation of suitable prodrug derivatives are described, for example, in "Design of Prodrugs", ed. H. Bundgaard, Elsevier, 1985.

In addition, where features or aspects of the present disclosure are described in terms of Markush groups, those skilled in the art will recognize that the presently described compounds is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the present disclosure are described in terms of Markush groups, those skilled in the art will recognize that the present disclosure is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present disclosure further embraces isolated compounds according to Formula (I), (Ia), (Ib), (Ic), (II), (IIa), (IIb), (IIc), (III), or (IV). The expression "isolated compound" refers to a preparation of a compound of Formula (I), (Ia), (Ib), (Ic), (II), (IIa), (IIb), (IIc), (III), or (IV), or a mixture of compounds according to Formula (I), (Ia), (Ib), (Ic), (II), (IIa), (IIb), (IIc), (III), or (IV), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of Formula (I), (Ia), (Ib), (Ic), (II), (IIa), (IIb), (IIc), (III), or (IV) or a mixture of compounds according to Formula (I), (Ia), (Ib), (Ic), (II), (IIa), (IIb), (IIc), (III), or (IV), which contains the named compound or mixture of compounds according to Formula (I), (Ia), (Ib), (Ic), (II), (IIa), (IIb), (IIc), (III), or (IV) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds Described Herein

Tautomerism

Within the present disclosure it is to be understood that a compound of Formula (I), (Ia), (Ib), (Ic), (II), (IIa), (IIb), (IIc), (III), or (IV) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

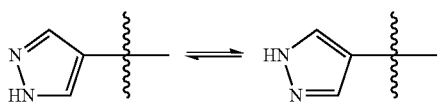 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

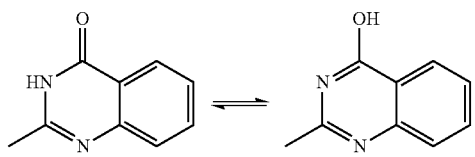

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

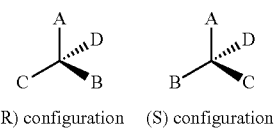

(R) configuration    (S) configuration

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of formula (I) which are biologically active in the treatment of cancer or other proliferative disease states.

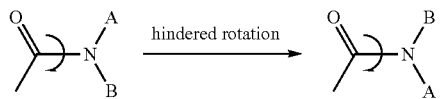

Regioisomerism

In some embodiments, the compounds described herein have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

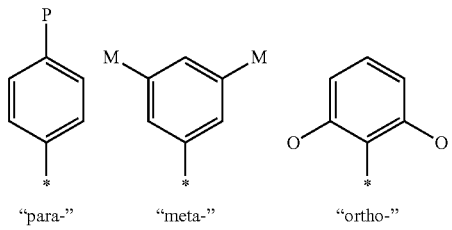

In various embodiments, the compound or set of compounds, such as are among the inventive compounds or are used in the inventive methods, can be any one of any of the combinations and/or sub-combinations of the above-listed embodiments.

Compounds

In one aspect described herein are compounds of Formula (I):

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1-C_4)$alkylene optionally substituted with OH, CN, NO$_2$, halogen, $(C_1-C_6)$alkyl;

$L^2$ is a bond, or optionally substituted $(C_1-C_6)$alkylene;

X is —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH=CHS(O)$_2$CH$_3$, —NHCH(R$^{24}$)CH=CHS(O)$_2$NH$_2$,

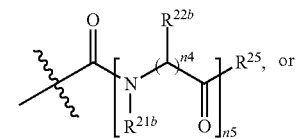

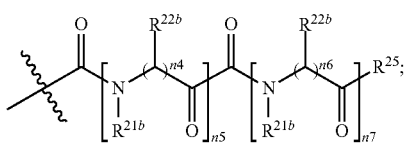

wherein n4, n5, and n6 are each independently 1, 2 or 3; n7 is 0, 1 or 2; R$^{21b}$ and R$^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; R$^{24}$ is H or $(C_1-C_6)$alkyl; R$^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$, Formula (I)

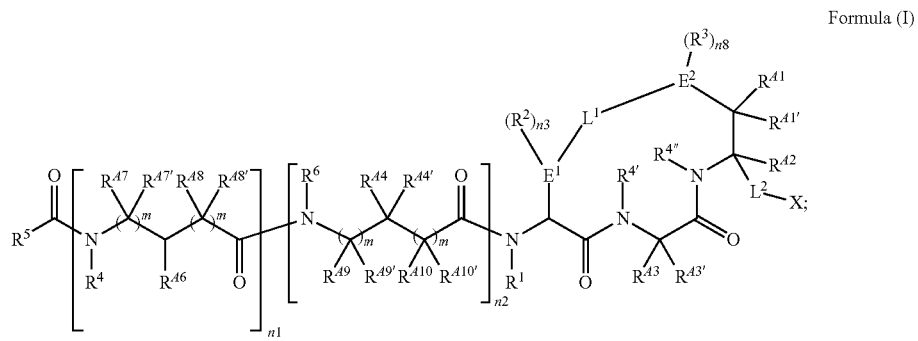

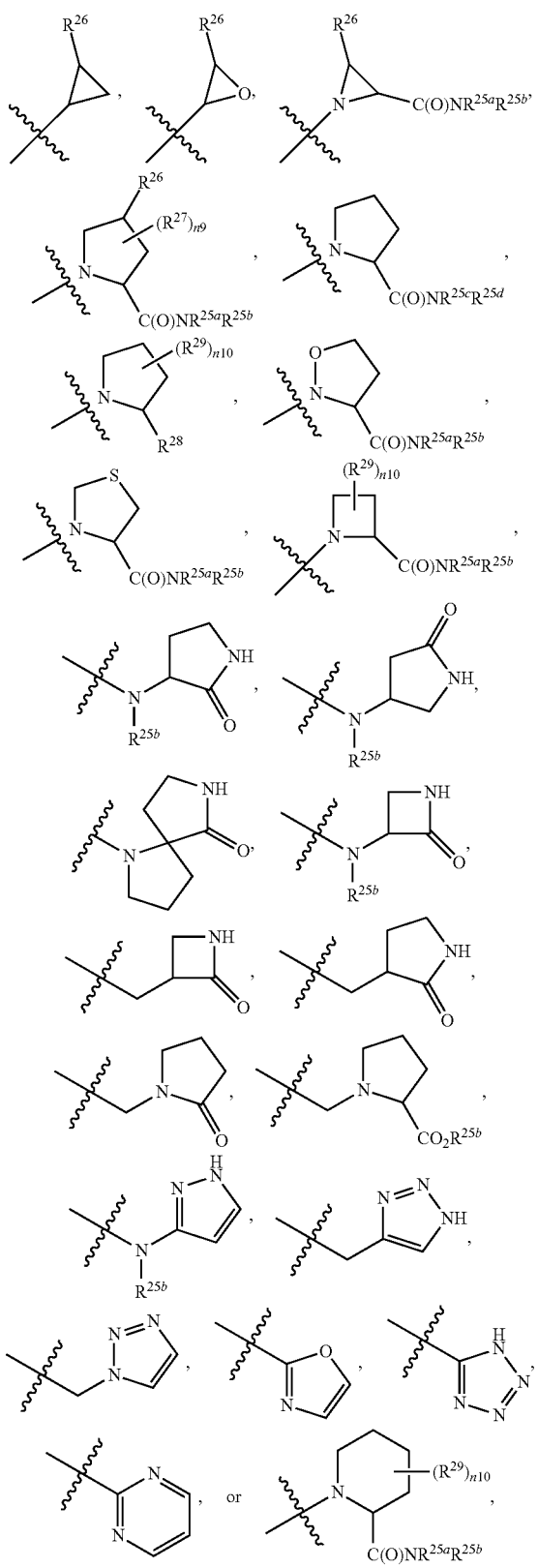

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; n10 is 0, 1, 2, 3 or 4; $R^5$ is aryl, heteroaryl, or a linear or branched alkyl chain of about 1-22 carbon atoms, wherein $R^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

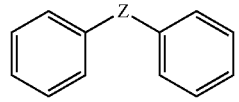

wherein Z is a bond, O, S, NH, CH$_2$ or C≡C; or $R^5$ is a linear or branched alkyl chain of about 1-22 carbon atoms, comprising within the chain at least one —O— or —N(R$^4$)—;
each $R^2$ and $R^3$ are each independently hydroxy, nitro, halo, cyano, glycosyloxy, amino, (C$_1$-C$_4$)alkyl, OR$^{40}$, or a group cleavable under physiological conditions to provide a compound of formula (I) wherein $R^2$ or $R^3$ respectively is hydroxy, wherein any carbon atom is optionally substituted with J;
each $R^{40}$ is independently —(C$_1$-C$_6$)alkyl, or —(C$_1$-C$_6$)alkyl-NR$^{41}$R$^{42}$;
each $R^{41}$ and $R^{42}$ is hydrogen, —(C$_1$-C$_6$)alkyl, —(C$_1$-C$_6$)heteroalkyl, —C(O)(C$_1$-C$_6$)alkyl, —C(O)N(R$^{43}$)$_2$, —SO$_2$N(R$^{43}$)$_2$; or $R^{41}$ and $R^{42}$ and the nitrogen atom to which that are attached form a heterocycloalkyl ring;
each $R^{43}$ is independently hydrogen or —(C$_1$-C$_6$)alkyl; or two $R^{43}$ and the nitrogen atom to which that are attached form a heterocycloalkyl ring;
n1 and n2 are independently 0 or 1;
n3 and n8 are independently 0, 1, or 2;
each m is independently 0 or 1;
$R^1$ is hydrogen or (C$_1$-C$_6$)alkyl optionally substituted with 1 to 3 J; or $R^1$ together with E$^1$ form a ring;
$R^4$, $R^{4'}$, and $R^{4''}$ are each independently at each occurrence hydrogen, or (C$_1$-C$_6$)alkyl optionally substituted with 1 to 3 J;
$R^6$ is hydrogen, or (C$_1$-C$_6$)alkyl optionally substituted with 1 to 3 J; or $R^6$ together with $R^{44}$ form a ring;
$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
$R^{46}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In one embodiment is a compound of Formula (I) wherein $E^1$ and $E^2$ are each independently aryl or heteroaryl. In another embodiment is a compound of Formula (I) wherein $E^1$ and $E^2$ are each independently aryl. In another embodiment is a compound of Formula (I) wherein $E^1$ and $E^2$ are each phenyl. In another embodiment is a compound of Formula (I) wherein $E^1$ is aryl and $E^2$ is heteroaryl. In another embodiment is a compound of Formula (I) wherein $E^1$ and $E^2$ are each heteroaryl.

In another embodiment is a compound of Formula (I) wherein $L^1$ is a bond, —O—, —OCH$_2$—, or —CH$_2$O—. In some embodiments is a compound of Formula (I) wherein $L^1$ is a bond. In some embodiments is a compound of Formula (I) wherein $L^1$ is —O—. In some embodiments is a compound of Formula (I) wherein $L^1$ is —OCH$_2$—. In some embodiments is a compound of Formula (I) wherein $L^1$ is —CH$_2$O—.

In another embodiment is a compound of Formula (I) wherein $E^1$ and $E^2$ are each phenyl and $L^1$ is a bond. In another embodiment is a compound of Formula (I) wherein $E^1$ and $E^2$ are each phenyl and $L^1$ is —O—. In another embodiment is a compound of Formula (I) wherein $E^1$ and $E^2$ are each phenyl and $L^1$ is —OCH$_2$—. In another embodiment is a compound of Formula (I) wherein $E^1$ and $E^2$ are each phenyl and $L^1$ is —CH$_2$O—.

In another embodiment is a compound of Formula (I) wherein $L^2$ is a bond. In another embodiment is a compound of Formula (I) wherein $L^2$ is optionally substituted $(C_1-C_6)$ alkylene. In a further embodiment, $L^2$ is methylene, ethylene, n-propylene, iso-propylene, n-butylene, iso-butylene, or tert-butylene.

In another embodiment is a compound of Formula (I) wherein X is —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH═CHS(O)$_2$CH$_3$, or —NHCH(R$^{24}$)CH═CHS(O)$_2$NH$_2$; and R$^{24}$ is H or (C$_1$-C$_6$)alkyl. In some embodiments is a compound of Formula (I) wherein X is —CH$_2$OH. In some embodiments is a compound of Formula (I) wherein X is —CH(OH)CH$_3$. In some embodiments is a compound of Formula (I) wherein X is —NHCH(R$^{24}$)C(O)CH$_3$. In some embodiments is a compound of Formula (I) wherein X is —NHN(R$^{24}$)C(O)CH$_3$. In some embodiments is a compound of Formula (I) wherein X is —NHCH(R$^{24}$)CH═CHS(O)$_2$CH$_3$. In some embodiments is a compound of Formula (I) wherein X is —NHCH(R$^{24}$)CH═CHS(O)$_2$NH$_2$.

In some embodiments is a compound of Formula (I) wherein X is wherein n4 and n5 are each independently 1, 2 or 3; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; and $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH═CHR$^{30}$, —CH═CHSO$_2$R$^{25b}$,

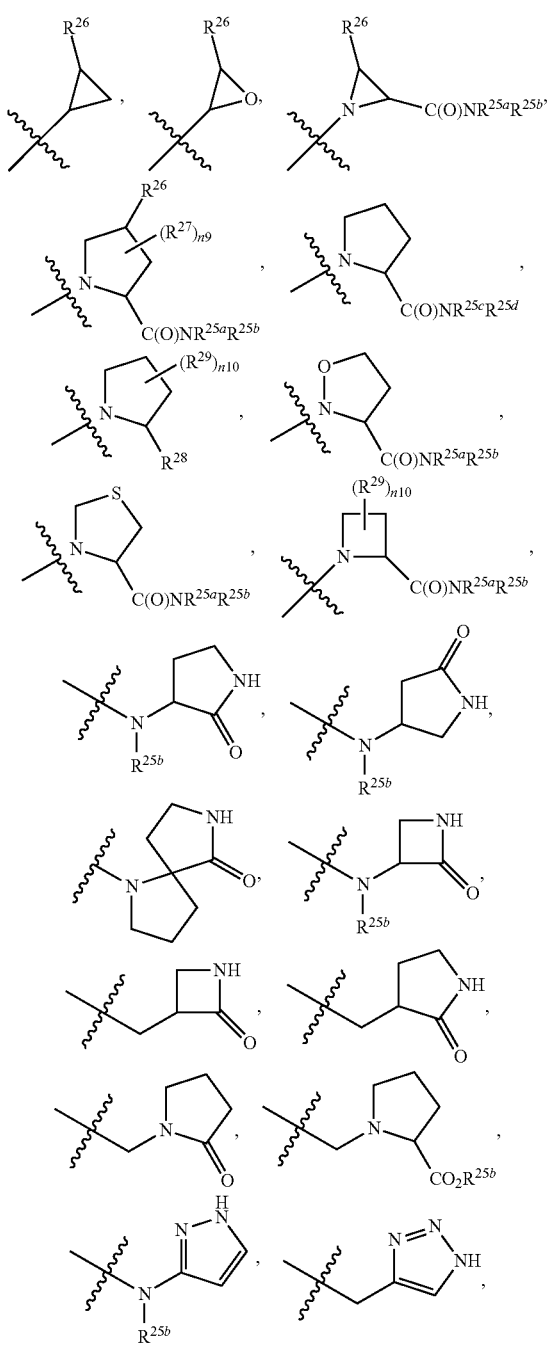

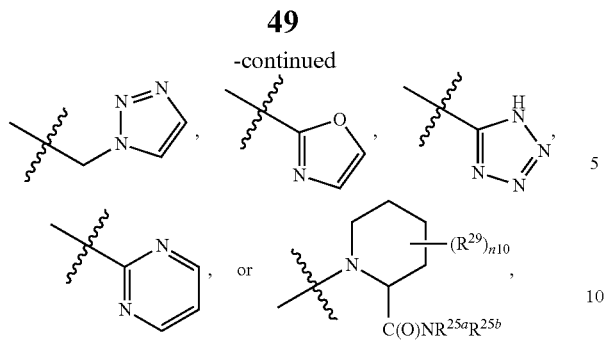

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In another embodiment is a compound of Formula (I) wherein X is

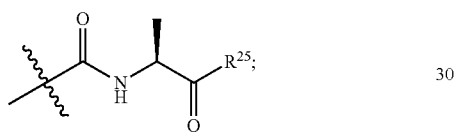

wherein $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

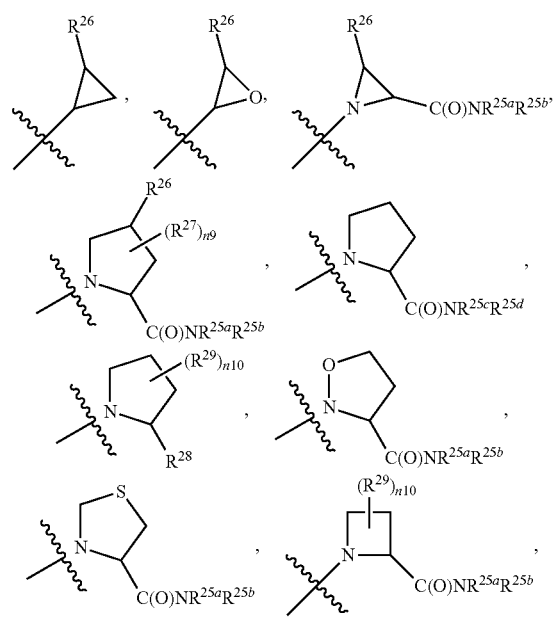

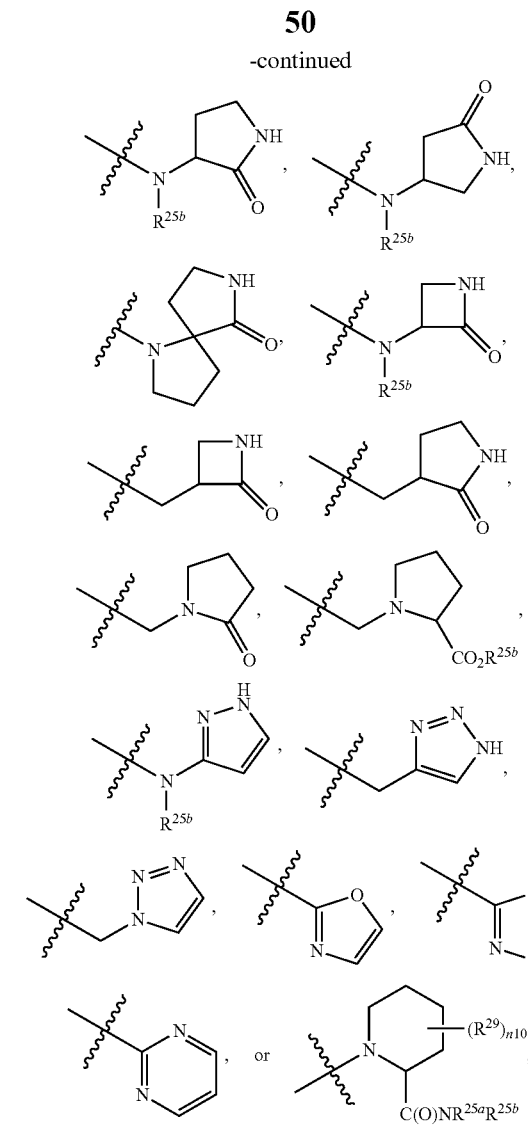

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4. In some embodiments is a compound of Formula (I) wherein X is

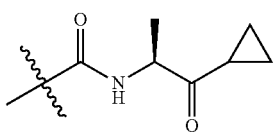

In some embodiments is a compound of Formula (I) wherein X is

51

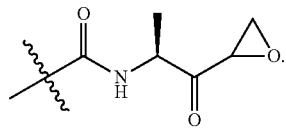 [SMILES: *C(=O)N[C@@H](C)C(=O)C1CO1]

In some embodiments is a compound of Formula (I) wherein X is

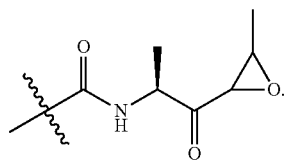 [SMILES: *C(=O)N[C@@H](C)C(=O)C1OC1C]

In some embodiments is a compound of Formula (I) wherein X is

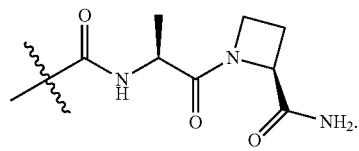 [SMILES: *C(=O)N[C@@H](C)C(=O)N1CC[C@H]1C(N)=O]

In some embodiments is a compound of Formula (I) wherein X is

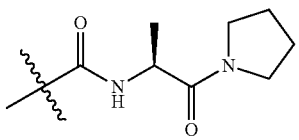

In some embodiments is a compound of Formula (I) wherein X is

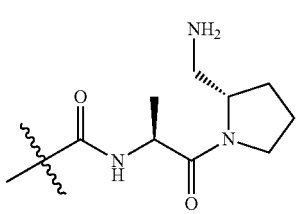

In some embodiments is a compound of Formula (I) wherein X is

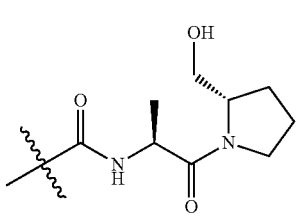

In some embodiments is a compound of Formula (I) wherein X is

52

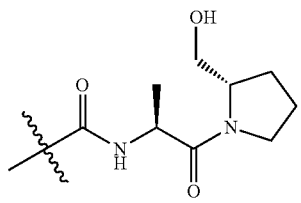

In some embodiments is a compound of Formula (I) wherein X is

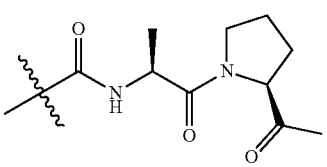

In some embodiments is a compound of Formula (I) wherein X is

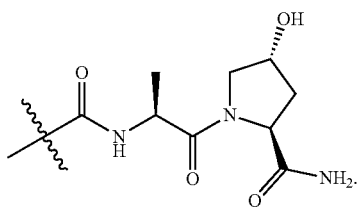 [SMILES: *C(=O)N[C@@H](C)C(=O)N1C[C@H](O)C[C@H]1C(N)=O]

In some embodiments is a compound of Formula (I) wherein X is

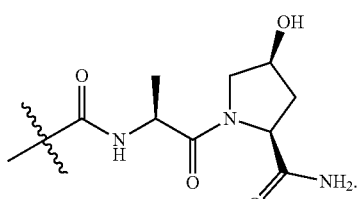

In some embodiments is a compound of Formula (I) wherein X is

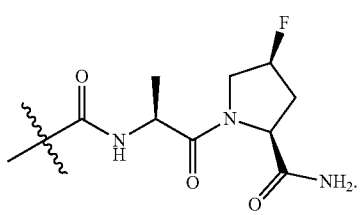 [SMILES: *C(=O)N[C@@H](C)C(=O)N1C[C@@H](F)C[C@H]1C(N)=O]

In some embodiments is a compound of Formula (I) wherein X is

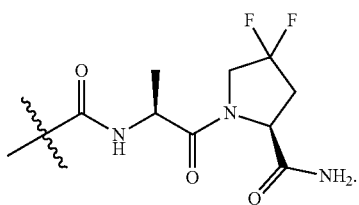 [SMILES: *C(=O)N[C@@H](C)C(=O)N1CC(F)(F)C[C@H]1C(N)=O]

In some embodiments is a compound of Formula (I) wherein X is

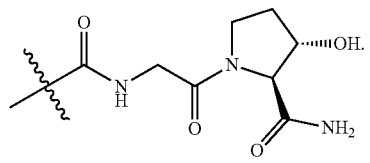 [SMILES: *C(=O)NCC(=O)N1CC[C@H](O)[C@H]1C(N)=O]

In some embodiments is a compound of Formula (I) wherein X is

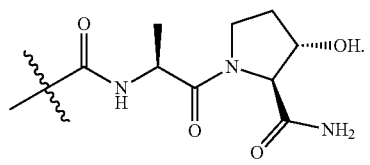 [SMILES: *C(=O)N[C@@H](C)C(=O)N1CC[C@H](O)[C@H]1C(N)=O]

In some embodiments is a compound of Formula (I) wherein X is

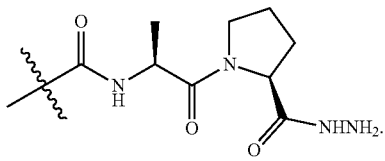 [SMILES: *C(=O)N[C@@H](C)C(=O)N1CCC[C@H]1C(=O)NN]

In some embodiments is a compound of Formula (I) wherein X is

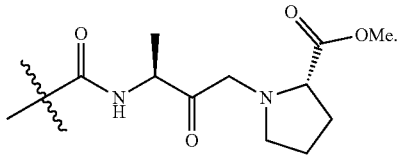 [SMILES: *C(=O)N[C@@H](C)C(=O)CN1CCC[C@H]1C(=O)OC]

In some embodiments is a compound of Formula (I) wherein X is

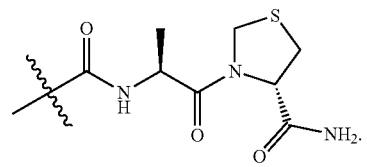 [SMILES: *C(=O)N[C@@H](C)C(=O)N1CSC[C@@H]1C(N)=O]

In some embodiments is a compound of Formula (I) wherein X is

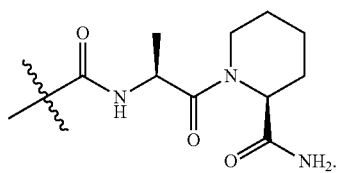

In some embodiments is a compound of Formula (I) wherein X is

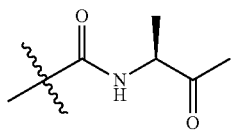

In some embodiments is a compound of Formula (I) wherein X is

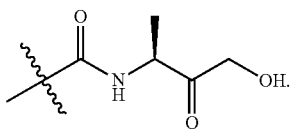 [SMILES: *C(=O)N[C@@H](C)C(=O)CO]

In some embodiments is a compound of Formula (I) wherein X is

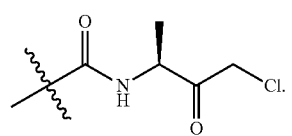 [SMILES: *C(=O)N[C@@H](C)C(=O)CCl]

In some embodiments is a compound of Formula (I) wherein X is

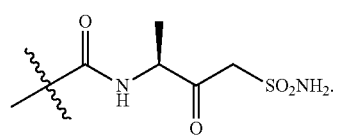 [SMILES: *C(=O)N[C@@H](C)C(=O)CS(N)(=O)=O]

In some embodiments is a compound of Formula (I) wherein X is

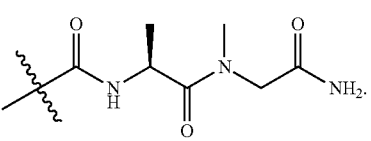 [SMILES: *C(=O)N[C@@H](C)C(=O)N(C)CC(N)=O]

In some embodiments is a compound of Formula (I) wherein X is

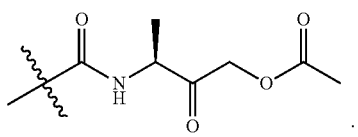 [SMILES: *C(=O)N[C@@H](C)C(=O)COC(C)=O]

In some embodiments is a compound of Formula (I) wherein X is

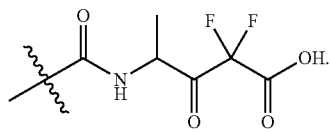 [SMILES: *C(=O)NC(C)C(=O)C(F)(F)C(=O)O]

In some embodiments is a compound of Formula (I) wherein X is

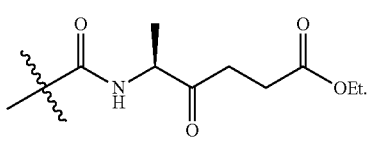 [SMILES: *C(=O)N[C@@H](C)C(=O)CCC(=O)OCC]

In some embodiments is a compound of Formula (I) wherein X is

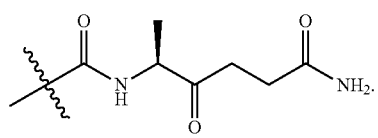 [SMILES: *C(=O)N[C@@H](C)C(=O)CCC(N)=O]

In some embodiments is a compound of Formula (I) wherein X is

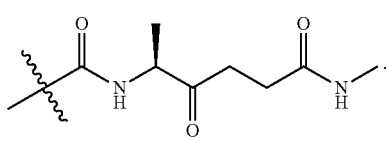 [SMILES: *C(=O)N[C@@H](C)C(=O)CCC(=O)NC]

In some embodiments is a compound of Formula (I) wherein X is

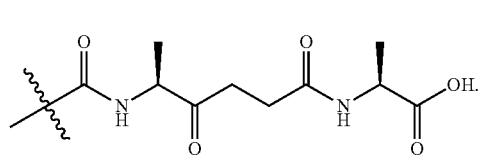 [SMILES: *C(=O)N[C@@H](C)C(=O)CCC(=O)N[C@@H](C)C(=O)O]

In some embodiments is a compound of Formula (I) wherein X is

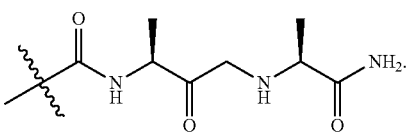 [SMILES: *C(=O)N[C@@H](C)C(=O)CN[C@@H](C)C(N)=O]

In some embodiments is a compound of Formula (I) wherein X is

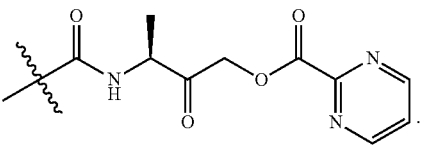 [SMILES: *C(=O)N[C@@H](C)C(=O)COC(=O)c1ncccn1]

In some embodiments is a compound of Formula (I) wherein X is

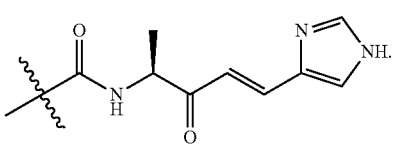 [SMILES: *C(=O)N[C@@H](C)C(=O)/C=C/c1c[nH]cn1]

In some embodiments is a compound of Formula (I) wherein X is

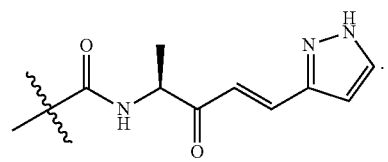 [SMILES: *C(=O)N[C@@H](C)C(=O)/C=C/c1cc[nH]n1]

In some embodiments is a compound of Formula (I) wherein X is

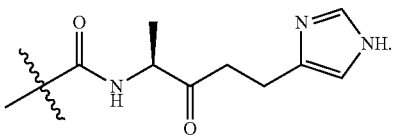 [SMILES: *C(=O)N[C@@H](C)C(=O)CCc1c[nH]cn1]

In some embodiments is a compound of Formula (I) wherein X is

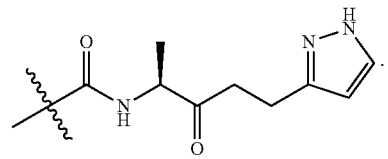 [SMILES: *C(=O)N[C@@H](C)C(=O)CCc1cc[nH]n1]

In some embodiments is a compound of Formula (I) wherein X is

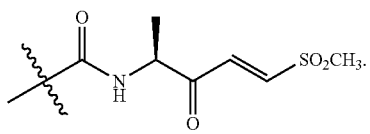 [SMILES: *C(=O)N[C@@H](C)C(=O)/C=C/S(C)(=O)=O]

In some embodiments is a compound of Formula (I) wherein X is

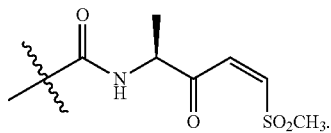

In some embodiments is a compound of Formula (I) wherein X is

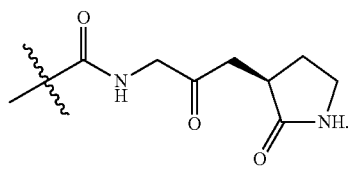 [SMILES: *C(=O)NCC(=O)C[C@H]1CCNC1=O]

In some embodiments is a compound of Formula (I) wherein X is

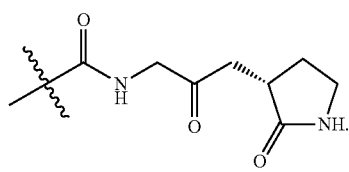 [SMILES: *C(=O)NCC(=O)C[C@@H]1CCNC1=O]

In some embodiments is a compound of Formula (I) wherein X is

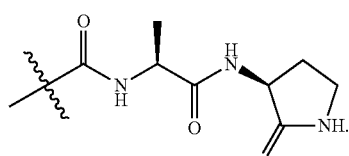

In some embodiments is a compound of Formula (I) wherein X is

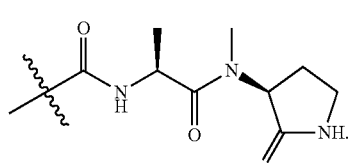

In some embodiments is a compound of Formula (I) wherein X is

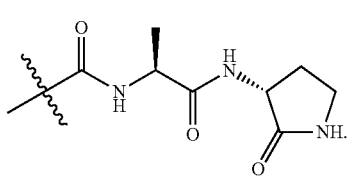

In some embodiments is a compound of Formula (I) wherein X is

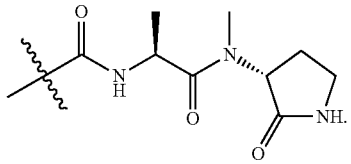

In some embodiments is a compound of Formula (I) wherein X is

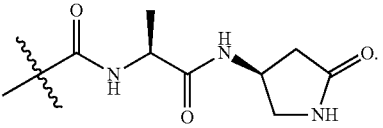

In some embodiments is a compound of Formula (I) wherein X is

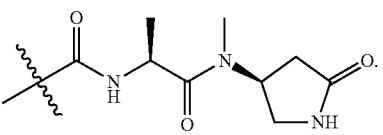

In some embodiments is a compound of Formula (I) wherein X is

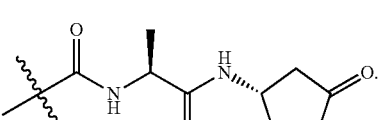

In some embodiments is a compound of Formula (I) wherein X is

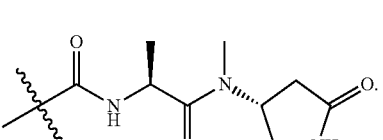

In some embodiments is a compound of Formula (I) wherein X is

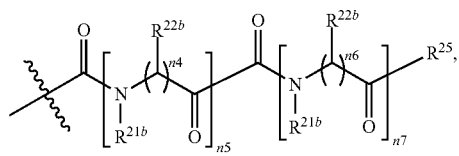

wherein n4 and n5 are each independently 1, 2 or 3; $R^{21b}$ and $R^{22b}$ are independently at each occurrence hydrogen, hydroxy, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; and $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1$-$C_6$alkyl), —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH(R^{26})CO_2R^{25b}$, —$CH_2N(H)CH(R^{26})C(O)N(H)R^{25b}$, —$CH_2CH_2R^{30}$, —$N(H)CH_2(R^{30})$, —CH=$CHR^{30}$, —CH=$CHSO_2R^{25b}$,

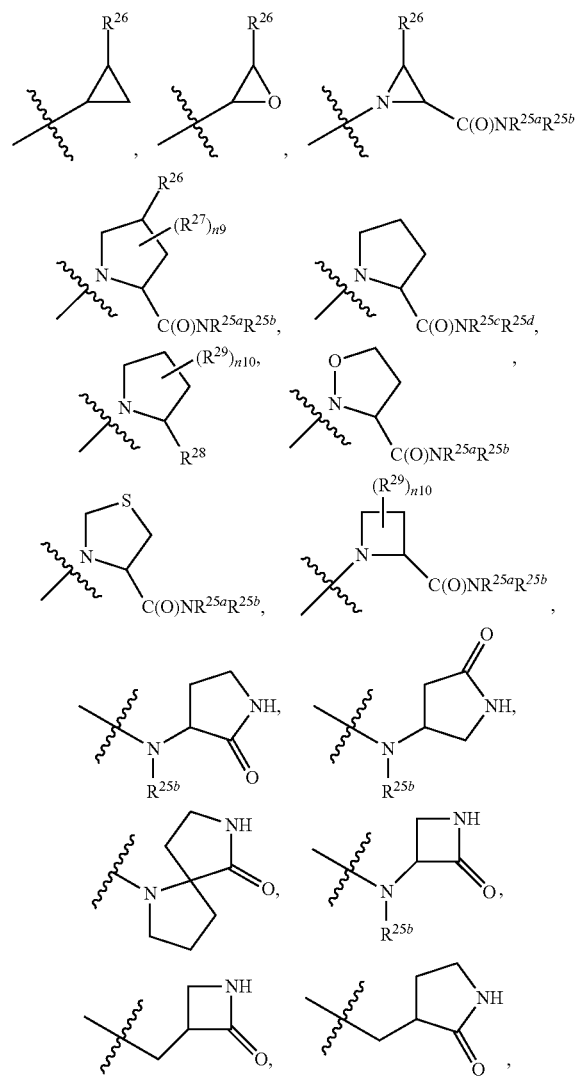

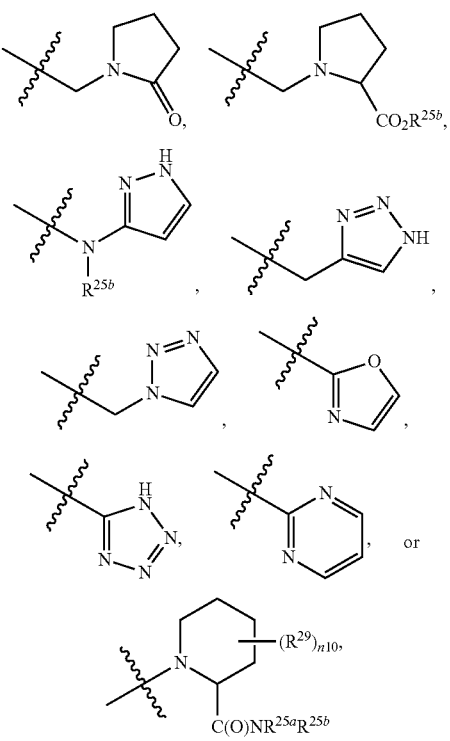

where $R^{25a}$ is H, —OH, —$OCH_3$, $NH_2$, $SO_2(C_1$-$C_6$)alkyl, or optionally substituted alkyl; each $R^{25b}$ is independently H, or optionally substituted alkyl; $R^{25c}$ is H or optionally substituted alkyl; $R^{25d}$ is —OH, —$OCH_3$, or $NH_2$; each $R^{26}$ is independently H, halo or ($C_1$-$C_6$)alkyl; each $R^{27}$ is independently —OH, halo, ($C_1$-$C_6$)alkyl, or $R^{26}$ and $R^{27}$ are joined to form a cycloalkyl ring; $R^{28}$ is H, —$CH_2OH$, —$CH_2NH_2$, —$C(O)CH_3$, or ($C_1$-$C_6$)alkyl; each $R^{29}$ is independently —OH, halo, or ($C_1$-$C_6$)alkyl; $R^{30}$ is heterocyclyl, heteroaryl, or aryl; n9 is 1, 2 or 3; and n10 is 0, 1, 2, 3 or 4.

In some embodiments is a compound of Formula (I) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

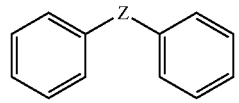

wherein Z is a bond, O, S, NH, $CH_2$ or C≡C. In some embodiments is a compound of Formula (I) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

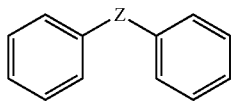

wherein Z is a bond, O, S, NH, CH$_2$ or C≡C. In some embodiments is a compound of Formula (I) wherein R$^5$ is a linear alkyl chain of about 1-22 carbon atoms, wherein R$^5$ is bonded to the carbonyl carbon to which it is attached directly to provide an amide linkage, comprising within the chain or at a chain terminus

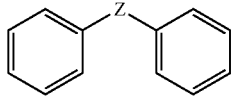

wherein Z is a bond. In some embodiments is a compound of Formula (I) wherein R$^5$ is a linear alkyl chain of about 4-22 carbon atoms, wherein R$^5$ is bonded to the carbonyl carbon to which it is attached directly to provide an amide linkage, comprising at a chain terminus

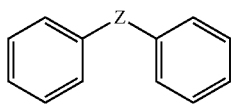

wherein Z is a bond. In some embodiments is a compound of Formula (I) wherein R$^5$ is a linear alkyl chain of about 4-22 carbon atoms, wherein R$^5$ is bonded to the carbonyl carbon to which it is attached directly to provide an amide linkage, comprising within the chain

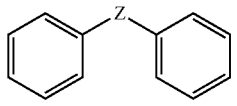

wherein Z is a bond. In some embodiments is a compound of Formula (I) wherein R$^5$ is a linear or branched alkyl chain of about 1-22 carbon atoms, wherein R$^5$ is bonded to the carbonyl carbon to which it is attached directly or by an NR$^4$, to provide an amide or urea linkage, respectively; optionally comprising within the chain or at a chain terminus optionally substituted aryl. In some embodiments is a compound of Formula (I) wherein R$^5$ is a linear or branched alkyl chain of about 2-22 carbon atoms, wherein R$^5$ is bonded to the carbonyl carbon to which it is attached directly to provide an amide linkage, comprising at a chain terminus optionally substituted aryl. In some embodiments is a compound of Formula (I) wherein R$^5$ is a linear or branched alkyl chain of about 2-22 carbon atoms, wherein R$^5$ is bonded to the carbonyl carbon to which it is attached directly to provide an amide linkage, comprising within the chain optionally substituted aryl. In some embodiments is a compound of Formula (I) wherein R$^5$ is a linear or branched alkyl chain of about 1-22 carbon atoms, wherein R$^5$ is bonded to the carbonyl carbon to which it is attached directly to provide an amide or urea linkage. In some embodiments is a compound of Formula (I) wherein R$^5$ is a linear or branched alkyl chain of about 4-18 carbon atoms, wherein R$^5$ is bonded to the carbonyl carbon to which it is attached directly to provide an amide or urea linkage. In some embodiments is a compound of Formula (I) wherein R$^5$ is a linear or branched alkyl chain of about 6-16 carbon atoms, wherein R$^5$ is bonded to the carbonyl carbon to which it is attached directly to provide an amide or urea linkage. In some embodiments is a compound of Formula (I) wherein R$^5$ is

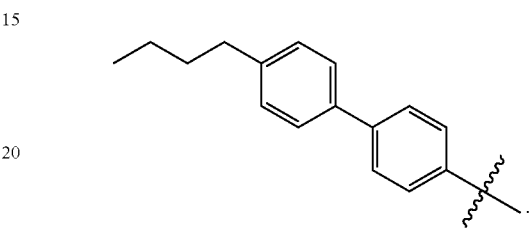

In some embodiments is a compound of Formula (I) wherein R$^5$ is

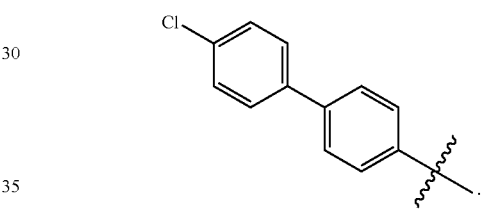

In some embodiments is a compound of Formula (I) wherein R$^5$ is a linear or branched alkyl chain of about 1-22 carbon atoms, comprising within the chain at least one —O— or —N(R$^4$)—. In some embodiments is a compound of Formula (I) wherein R$^5$ is a linear or branched alkyl chain of about 1-22 carbon atoms, comprising within the chain at least one —O—. In some embodiments is a compound of Formula (I) wherein R$^5$ is a linear or branched alkyl chain of about 1-22 carbon atoms, comprising within the chain at least one —N(R$^4$)—. In some embodiments is a compound of Formula (I) wherein R$^5$ is a linear or branched alkyl chain of about 1-22 carbon atoms, comprising within the chain at least one —N(H)—. In some embodiments is a compound of Formula (I) wherein R$^5$ is —CH$_2$CH$_2$N(H)(CH$_2$)$_9$CH$_3$.

In another embodiment is a compound of Formula (I) wherein n1 is 0 and n2 is 1. In another embodiment is a compound of Formula (I) wherein n1 is 0, n2 is 1, and R$^{44}$ is H. In another embodiment is a compound of Formula (I) wherein n1 is 0, n2 is 1, and R$^{44}$ is (C$_1$-C$_6$)alkyl optionally substituted with 1 to 3 J. In another embodiment is a compound of Formula (I) wherein n1 is 0, n2 is 1, and R$^{44}$ is CH$_3$. In another embodiment is a compound of Formula (I) wherein n1 is 0, n2 is 1, and R$^{44}$ is CH$_2$CH$_3$. In another embodiment is a compound of Formula (I) wherein n1 is 0, n2 is 1, and R$^{44}$ is CH$_2$CH(CH$_3$)$_2$. In another embodiment is a compound of Formula (I) wherein n1 is 0, n2 is 1, and R$^{44}$ is CH$_2$OH. In another embodiment is a compound of Formula (I) wherein n1 is 0, n2 is 1, and R$^{44}$ is CH(OH)CH$_3$. In another embodiment is a compound of Formula (I) wherein n1 is 0, n2 is 1, and R$^{44}$ is CH$_2$C(O)NH$_2$. In another embodiment is a compound of Formula (I) wherein n1 is 0, n2 is 1, and $R^{44}$ is $CH_2CH_2CH_2CH_2NH_2$.

In another embodiment is a compound of Formula (I) wherein n1 is 1 and n2 is 1. In another embodiment is a compound of Formula (I) wherein n1 is 1, n2 is 1, $R^{46}$ is $CH_3$, and $R^{44}$ is $(C_1-C_6)$alkyl optionally substituted with 1 to 3 J. In another embodiment is a compound of Formula (I) wherein n1 is 1, n2 is 1, $R^{46}$ is $CH_3$, and $R^{44}$ is $CH_3$. In another embodiment is a compound of Formula (I) wherein n1 is 1, n2 is 1, $R^{46}$ is $CH_3$, and $R^{44}$ is $CH_2CH_3$. In another embodiment is a compound of Formula (I) wherein n1 is 1, n2 is 1, $R^{46}$ is $CH_3$, and $R^{44}$ is $CH_2CH(CH_3)_2$. In another embodiment is a compound of Formula (I) wherein n1 is 1, n2 is 1, $R^{46}$ is $CH_3$, and $R^{44}$ is $CH_2OH$. In another embodiment is a compound of Formula (I) wherein n1 is 1, n2 is 1, $R^{46}$ is $CH_3$, and $R^{44}$ is $CH(OH)CH_3$. In another embodiment is a compound of Formula (I) wherein n1 is 1, n2 is 1, $R^{46}$ is $CH_3$, and $R^{44}$ is $CH_2C(O)NH_2$. In another embodiment is a compound of Formula (I) wherein n1 is 1, n2 is 1, $R^{46}$ is $CH_3$, and $R^{44}$ is $CH_2CH_2CH_2CH_2NH_2$. In another embodiment is a compound of Formula (I) wherein n1 is 1, n2 is 1, $R^{46}$ is H, and $R^{44}$ is $CH_2CH_2CH_2CH_2NH_2$.

In another embodiment of the aforementioned embodiments is a compound of Formula (I) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (I) wherein each m is 0. In another embodiment of the aforementioned embodiments is a compound of Formula (I) wherein $R^{41}$, $R^{41'}$, $R^{42}$, $R^{4'}$, and $R^{4''}$ are each independently H.

In another embodiment of the aforementioned embodiments is a compound of Formula (I) wherein n3 is 1 and n8 is 1. In another embodiment of the aforementioned embodiments is a compound of Formula (I) wherein n3 is 1, n8 is 1, and $R^2$ and $R^3$ are each hydroxy. In another embodiment of the aforementioned embodiments is a compound of Formula (I) wherein n3 is 1, n8 is 1, $R^2$ is hydroxy, and $R^3$ is $-OR^{40}$. In another embodiment of the aforementioned embodiments is a compound of Formula (I) wherein n3 is 1, n8 is 1, $R^2$ is hydroxy, $R^3$ is $-OR^{40}$, and $R^{40}$ is $-(C_1-C_6)$alkyl. In another embodiment of the aforementioned embodiments is a compound of Formula (I) wherein n3 is 1, n8 is 1, $R^2$ is hydroxy, $R^3$ is $-OR^{40}$, and $R^{40}$ is $-(C_1-C_6)$alkyl-$NR^{41}R^{42}$. In another embodiment of the aforementioned embodiments is a compound of Formula (I) wherein n3 is 1, n8 is 1, $R^2$ is $-OH$, $R^3$ is $-OR^{40}$, and $R^{40}$ is $-(C_1-C_6)$alkyl-$NH_2$. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (I) wherein n3 is 1, n8 is 1, $R^3$ is hydroxy, and $R^2$ is $-OR^{40}$. In another embodiment of the aforementioned embodiments is a compound of Formula (I) wherein n3 is 1, n8 is 1, $R^3$ is hydroxy, $R^2$ is $-OR^{40}$, and $R^{40}$ is $-(C_1-C_6)$alkyl. In another embodiment of the aforementioned embodiments is a compound of Formula (I) wherein n3 is 1, n8 is 1, $R^3$ is hydroxy, $R^2$ is $-OR^{40}$, and $R^{40}$ is $-(C_1-C_6)$alkyl-$NR^{41}R^{42}$. In another embodiment of the aforementioned embodiments is a compound of Formula (I) wherein n3 is 1, n8 is 1, $R^3$ is hydroxy, $R^2$ is $-OR^{40}$, and $R^{40}$ is $-(C_1-C_6)$alkyl-$NH_2$. In another embodiment of the aforementioned embodiments is a compound of Formula (I) wherein n3 is 1, n8 is 1, $R^3$ is hydroxy, $R^2$ is $-OR^{40}$, $R^{40}$ is $-(C_1-C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (I) wherein n3 is 1, n8 is 1, $R^3$ is hydroxy, $R^2$ is $-OR^{40}$, $R^{40}$ is $-(C_1-C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (I) wherein n3 is 1, n8 is 1, $R^2$ is hydroxy, $R^3$ is $-OR^{40}$, and any carbon atom of $R^3$ is substituted with J. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl, and any carbon atom of $R^3$ is substituted with J. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl, and any carbon atom of $R^3$ is substituted with J wherein J is $CO_2H$. In another embodiment of the aforementioned embodiments is a compound of Formula (I) wherein n3 is 1, n8 is 1, $R^2$ is hydroxy, $R^3$ is $-O-(C_1-C_6)$alkyl-$CO_2H$. In another embodiment of the aforementioned embodiments is a compound of Formula (I) wherein n3 is 1, n8 is 1, $R^2$ is hydroxy, $R^3$ is $-OCH_2CO_2H$. In another embodiment of the aforementioned embodiments is a compound of Formula (I) wherein n3 is 1, n8 is 1, $R^2$ is $-OCH_2CH_2NH_2$, $R^3$ is $-OCH_2CO_2H$. In another embodiment of the aforementioned embodiments is a compound of Formula (I) wherein n3 is 1, n8 is 1, $R^2$ is hydroxy, $R^3$ is $-OR^{40}$, $R^{40}$ is $R^{40}$ is $-(C_1-C_6)$alkyl-$NR^{41}R^{42}$, and any carbon atom of $R^3$ is substituted with J. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl-$NR^{41}R^{42}$, $R^{41}$ is hydrogen, $R^{42}$ is $-(C_1-C_6)$alkyl, and any carbon atom of $R^3$ is substituted with J. In another embodiment of the aforementioned embodiments is a compound of Formula (I) wherein n3 is 1, n8 is 1, $R^2$ is hydroxy, $R^3$ is $-OR^{40}$, $R^{40}$ is $-(C_1-C_6)$alkyl-$NR^{41}R^{42}$, $R^{41}$ is hydrogen, $R^{42}$ is $-(C_1-C_6)$alkyl, and any carbon atom of $R^3$ is substituted with J wherein J is $-NHCH_3$. In another embodiment of the aforementioned embodiments is a compound of Formula (I) wherein n3 is 1, n8 is 1, $R^2$ is hydroxy, $R^3$ is $-O-(C_1-C_6)$alkyl-$N(H)-(C_1-C_6)$alkyl-$N(H)CH_3$. In another embodiment of the aforementioned embodiments is a compound of Formula (I) wherein n3 is 1, n8 is 1, $R^2$ is hydroxy, $R^3$ is $-OCH_2CH_2N(H)CH_2CH_2N(H)CH_3$. In another embodiment of the aforementioned embodiments is a compound of Formula (I) wherein n3 is 1, n8 is 1, $R^2$ is hydroxy, $R^3$ is $-OCH_2CH_2N(H)CH_2CH_2CH_2N(H)CH_3$.

In another embodiment of the aforementioned embodiments is a compound of Formula (I) wherein n3 is 1, n8 is 1, $R^3$ is hydroxy, $R^2$ is $-OR^{40}$, and any carbon atom of $R^2$ is substituted with J. In another embodiment of the aforementioned embodiments is a compound of Formula (I) wherein n3 is 1, n8 is 1, $R^3$ is hydroxy, $R^2$ is $-OR^{40}$, $R^{40}$ is $-(C_1-C_6)$alkyl, and any carbon atom of $R^2$ is substituted with J. In another embodiment of the aforementioned embodiments is a compound of Formula (I) wherein n3 is 1, n8 is 1, $R^3$ is hydroxy, $R^2$ is $-OR^{40}$, $R^{40}$ is $-(C_1-C_6)$alkyl, and any carbon atom of $R^2$ is substituted with J wherein J is $CO_2H$. In another embodiment of the aforementioned embodiments is a compound of Formula (I) wherein n3 is 1, n8 is 1, $R^3$ is hydroxy, $R^2$ is $-O-(C_1-C_6)$alkyl-$CO_2H$. In another embodiment of the aforementioned embodiments is a compound of Formula (I) wherein n3 is 1, n8 is 1, R³ is hydroxy, R² is —OCH₂CO₂H. In another embodiment of the aforementioned embodiments is a compound of Formula (I) wherein n3 is 1, n8 is 1, R³ is —OCH₂CH₂NH₂, R² is —OCH₂CO₂H. In another embodiment of the aforementioned embodiments is a compound of Formula (I) wherein n3 is 1, n8 is 1, R³ is hydroxy, R² is —OR⁴⁰, R⁴⁰ is R⁴⁰ is —(C₁-C₆)alkyl-NR⁴¹R⁴², and any carbon atom of R² is substituted with J. In another embodiment of the aforementioned embodiments is a compound of Formula (I) wherein n3 is 1, n8 is 1, R³ is hydroxy, R² is —OR⁴⁰, R⁴⁰ is —(C₁-C₆)alkyl-NR⁴¹R⁴², R⁴¹ is hydrogen, R⁴² is —(C₁-C₆)alkyl, and any carbon atom of R² is substituted with J. In another embodiment of the aforementioned embodiments is a compound of Formula (I) wherein n3 is 1, n8 is 1, R³ is hydroxy, R² is —OR⁴⁰, R⁴⁰ is —(C₁-C₆)alkyl-NR⁴¹R⁴², R⁴¹ is hydrogen, R⁴² is —(C₁-C₆)alkyl, and any carbon atom of R² is substituted with J wherein J is —NHCH₃. In another embodiment of the aforementioned embodiments is a compound of Formula (I) wherein n3 is 1, n8 is 1, R³ is hydroxy, R² is —O—(C₁-C₆)alkyl-N(H)—(C₁-C₆)alkyl-N(H)CH₃. In another embodiment of the aforementioned embodiments is a compound of Formula (I) wherein n3 is 1, n8 is 1, R³ is hydroxy, R² is —OCH₂CH₂N(H)CH₂CH₂N(H)CH₃. In another embodiment of the aforementioned embodiments is a compound of Formula (I) wherein n3 is 1, n8 is 1, R³ is hydroxy, R² is —OCH₂CH₂N(H)CH₂CH₂CH₂N(H)CH₃.

In another embodiment is a compound of Formula (I) having the structure of Formula (Ia):

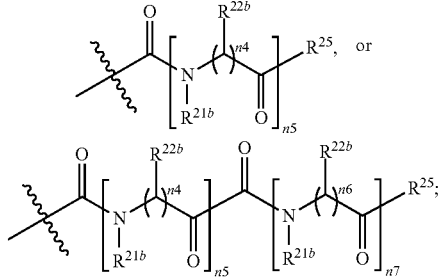

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{24}$ is H or $(C_1-C_6)$alkyl; $R^{25}$ is —CH₃, —CH₂Cl, —CH₂OR$^{25b}$, —CH₂R³⁰, —C(R²⁶)₂C(O)NH₂, —CH₂SO₂N(R$^{25b}$)₂, —CH₂N(R$^{25b}$)SO₂(C₁-C₆alkyl), —CH₂PO₃H, —CH₂P(O)(OH)OCH₃, —CH₂OC(O)CH₃, —CH₂OC(O)R³⁰, —CH₂CO₂R$^{25b}$, —CF₂CO₂R$^{25b}$, —CH₂CH₂CO₂R$^{25b}$, —CH₂CH₂C(O)N(R$^{25b}$)₂, —CH₂CH₂C(O)N(H)CH(R²⁶)CO₂R$^{25b}$, —CH₂N(H)CH(R²⁶)C(O)N(H)R$^{25b}$, —CH₂CH₂R³⁰, —N(H)CH₂(R³⁰), —CH=CHR³⁰, —CH=CHSO₂R$^{25b}$, Formula (Ia)

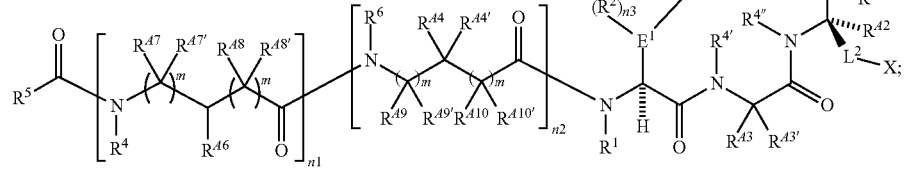

wherein:

E¹ is (C₁-C₆)alkyl, (C₂-C₇)alkenyl, (C₂-C₇)alkynyl, (C₃-C₇)cycloalkyl, heterocyclyl, heteroaryl, or aryl;

E² is (C₂-C₇)alkenyl, (C₂-C₇)alkynyl, (C₃-C₇)cycloalkyl, heterocyclyl, heteroaryl, or aryl;

L¹ is a bond, —O—, —S—, —NR⁴—, —C(O)—, —CH₂O—, —OCH₂—, —CH₂S—, —SCH₂—, —CH₂NR⁴—, —NR⁴CH₂—, —NR⁴C(O)—, —C(O)NR⁴—, —NR⁴S(O)₂—, —S(O)₂NR⁴—, —NR⁴C(O)NR⁴—, —NR⁴C(O)O—, —OC(O)NR⁴—, or (C₁-C₄)alkylene optionally substituted with OH, CN, NO₂, halogen, (C₁-C₆)alkyl;

L² is a bond, or optionally substituted (C₁-C₆)alkylene;

X is —CH₂OH, —CH(OH)CH₃, —N(R⁴)CH(R²⁴)CN, —NHCH(R²⁴)C(O)CH₃, —NHN(R²⁴)C(O)CH₃, —NHCH(R²⁴)CH=CHS(O)₂CH₃, —NHCH(R²⁴)CH=CHS(O)₂NH₂,

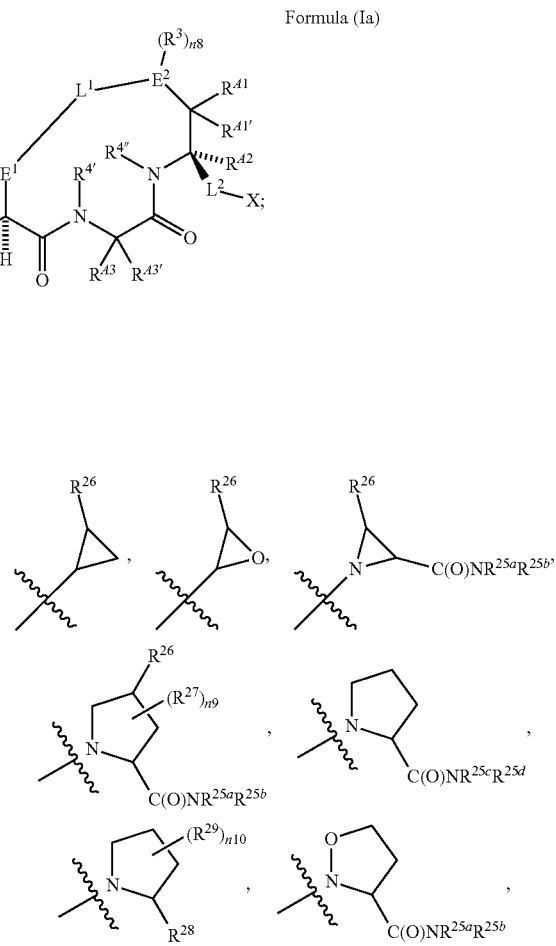

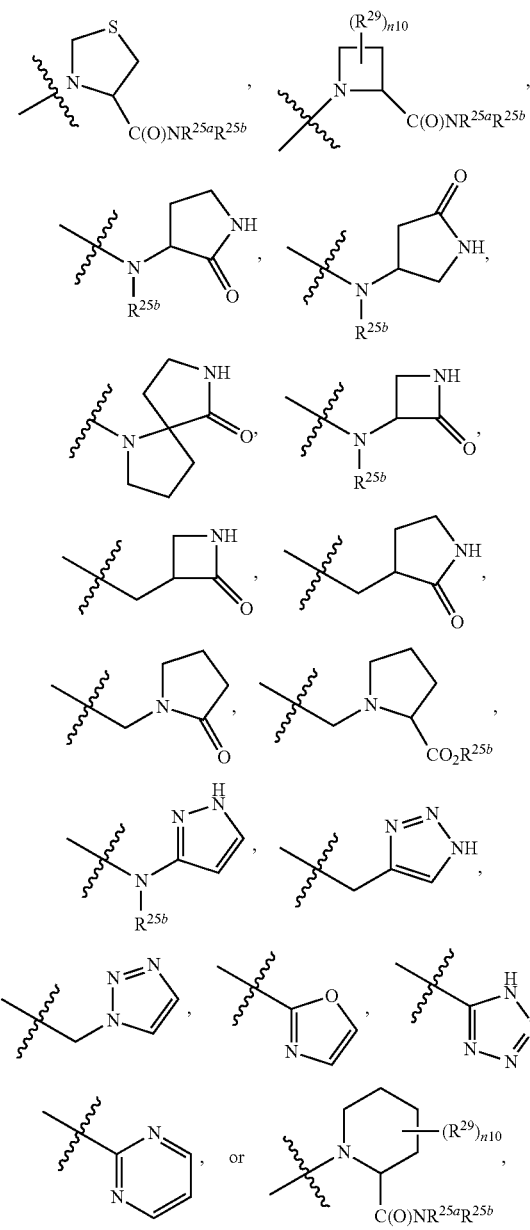

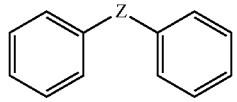

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; n10 is 0, 1, 2, 3 or 4; $R^5$ is aryl, heteroaryl, or a linear or branched alkyl chain of about 1-22 carbon atoms, wherein $R^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted wherein Z is a bond, O, S, NH, CH$_2$ or C≡C; or $R^5$ is a linear or branched alkyl chain of about 1-22 carbon atoms, comprising within the chain at least one —O— or —N(R$^4$)—;

each $R^2$ and $R^3$ are each independently hydroxy, nitro, halo, cyano, glycosyloxy, amino, (C$_1$-C$_4$)alkyl, OR$^{40}$, or a group cleavable under physiological conditions to provide a compound of formula (Ia) wherein $R^2$ or $R^3$ respectively is hydroxy, wherein any carbon atom is optionally substituted with J;

each $R^{40}$ is independently —(C$_1$-C$_6$)alkyl, or —(C$_1$-C$_6$)alkyl-NR$^{41}$R$^{42}$;

each $R^{41}$ and $R^{42}$ is hydrogen, —(C$_1$-C$_6$)alkyl, —(C$_1$-C$_6$) heteroalkyl, —C(O)(C$_1$-C$_6$)alkyl, —C(O)N(R$^{43}$)$_2$, —SO$_2$N(R$^{43}$)$_2$; or $R^{41}$ and $R^{42}$ and the nitrogen atom to which that are attached form a heterocycloalkyl ring;

each $R^{43}$ is independently hydrogen or —(C$_1$-C$_6$)alkyl; or two $R^{43}$ and the nitrogen atom to which that are attached form a heterocycloalkyl ring;

n1 and n2 are independently 0 or 1;
n3 and n8 are independently 0, 1, or 2;
each m is independently 0 or 1;
$R^1$ is hydrogen or (C$_1$-C$_6$)alkyl optionally substituted with 1 to 3 J; or $R^1$ together with $E^1$ form a ring;
$R^4$, $R^{4'}$, and $R^{4''}$ are each independently at each occurrence hydrogen, or (C$_1$-C$_6$)alkyl optionally substituted with 1 to 3 J;
$R^6$ is hydrogen, or (C$_1$-C$_6$)alkyl optionally substituted with 1 to 3 J; or $R^6$ together with $R^{44}$ form a ring;
$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
$R^{A6}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;
each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In one embodiment is a compound of Formula (Ia) wherein $E^1$ and $E^2$ are each independently aryl or heteroaryl. In another embodiment is a compound of Formula (Ia) wherein $E^1$ and $E^2$ are each independently aryl. In another embodiment is a compound of Formula (Ia) wherein $E^1$ and $E^2$ are each phenyl. In another embodiment is a compound of Formula (Ia) wherein $E^1$ is aryl and $E^2$ is heteroaryl. In another embodiment is a compound of Formula (Ia) wherein $E^1$ and $E^2$ are each heteroaryl.

In another embodiment is a compound of Formula (Ia) wherein $L^1$ is a bond, —O—, —OCH$_2$—, or —CH$_2$O—. In some embodiments is a compound of Formula (Ia) wherein $L^1$ is a bond. In some embodiments is a compound of Formula (Ia) wherein $L^1$ is —O—. In some embodiments is a compound of Formula (Ia) wherein $L^1$ is —OCH$_2$—. In some embodiments is a compound of Formula (Ia) wherein $L^1$ is —CH$_2$O—.

In another embodiment is a compound of Formula (Ia) wherein $E^1$ and $E^2$ are each phenyl and $L^1$ is a bond. In another embodiment is a compound of Formula (Ia) wherein $E^1$ and $E^2$ are each phenyl and $L^1$ is —O—. In another embodiment is a compound of Formula (Ia) wherein $E^1$ and $E^2$ are each phenyl and $L^1$ is —OCH$_2$—. In another embodiment is a compound of Formula (Ia) wherein $E^1$ and $E^2$ are each phenyl and $L^1$ is —CH$_2$O—.

In another embodiment is a compound of Formula (Ia) wherein $L^2$ is a bond. In another embodiment is a compound of Formula (Ia) wherein $L^2$ is optionally substituted (C$_1$—C$_6$)alkylene. In a further embodiment, $L^2$ is methylene, ethylene, n-propylene, iso-propylene, n-butylene, iso-butylene, or tert-butylene.

In one embodiment is a compound of Formula (Ia) wherein X is —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH=CHS(O)$_2$CH$_3$, or —NHCH(R$^{24}$)CH=CHS(O)$_2$NH$_2$; and R$^{24}$ is H or (C$_1$-C$_6$)alkyl. In some embodiments is a compound of Formula (Ia) wherein X is —CH$_2$OH. In some embodiments is a compound of Formula (Ia) wherein X is —CH(OH)CH$_3$. In some embodiments is a compound of Formula (Ia) wherein X is —NHCH(R$^{24}$)C(O)CH$_3$. In some embodiments is a compound of Formula (Ia) wherein X is —NHN(R$^{24}$)C(O)CH$_3$. In some embodiments is a compound of Formula (Ia) wherein X is —NHCH(R$^{24}$)CH=CHS(O)$_2$CH$_3$. In some embodiments is a compound of Formula (Ia) wherein X is —NHCH(R$^{24}$)CH=CHS(O)$_2$NH$_2$.

In some embodiments is a compound of Formula (Ia) wherein X is

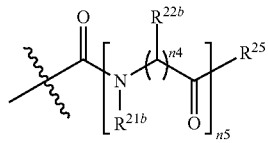

wherein n4 and n5 are each independently 1, 2 or 3; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; and R$^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

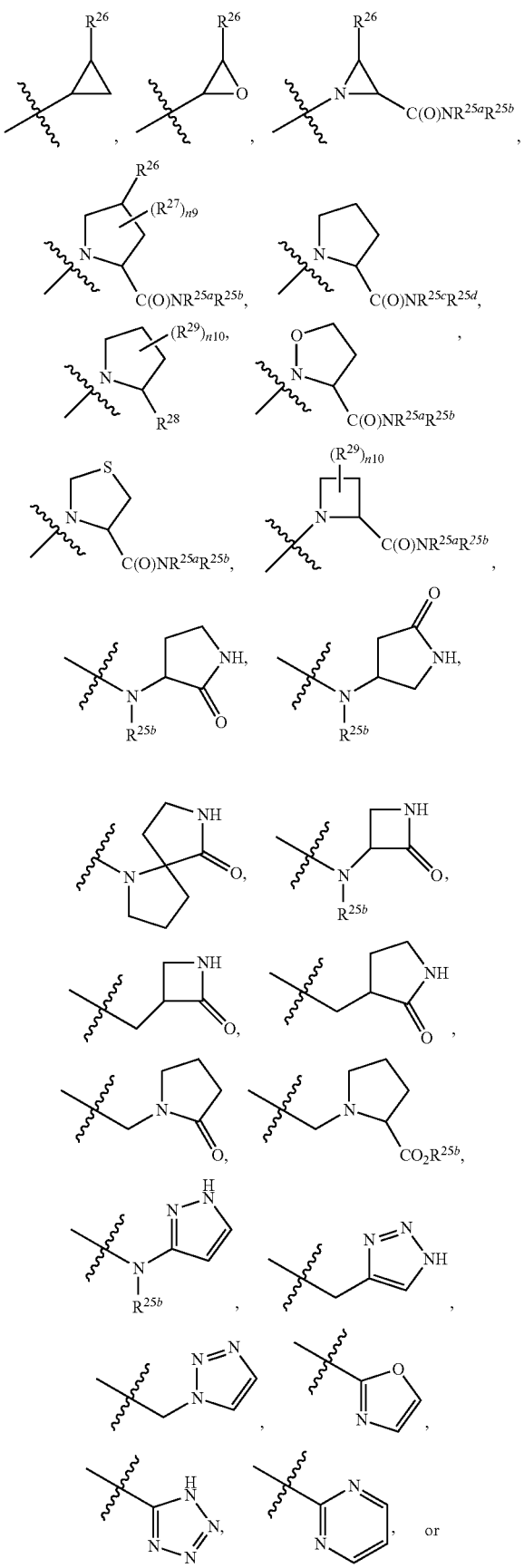

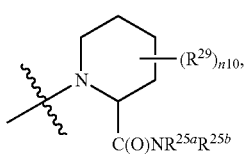

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In another embodiment is a compound of Formula (Ia) wherein X is

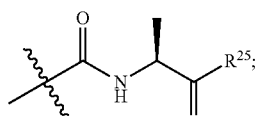

wherein $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

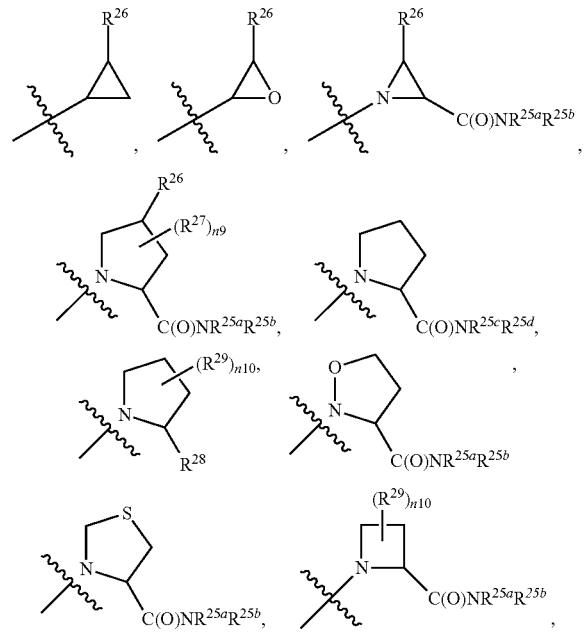

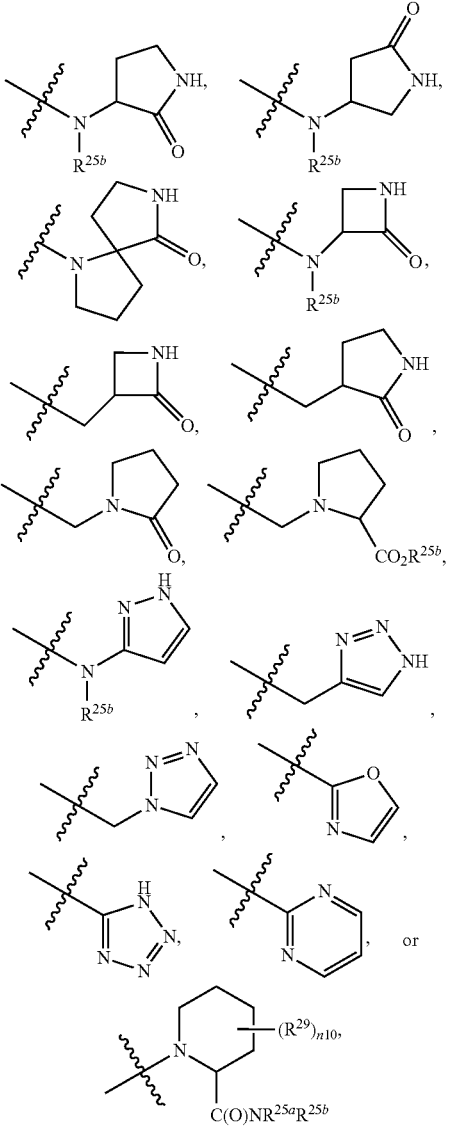

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4. In some embodiments is a compound of Formula (Ia) wherein X is

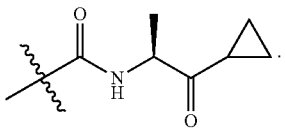 [SMILES: *C(=O)N[C@@H](C)C(=O)C1CC1]

In some embodiments is a compound of Formula (Ia) wherein X is

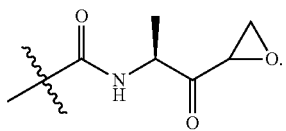 [SMILES: *C(=O)N[C@@H](C)C(=O)C1CO1]

In some embodiments is a compound of Formula (Ia) wherein X is

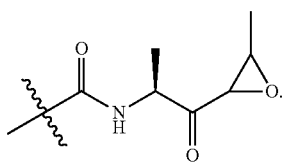 [SMILES: *C(=O)N[C@@H](C)C(=O)C1OC1C]

In some embodiments is a compound of Formula (Ia) wherein X is

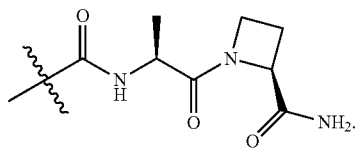 [SMILES: *C(=O)N[C@@H](C)C(=O)N1CC[C@H]1C(N)=O]

In some embodiments is a compound of Formula (Ia) wherein X is

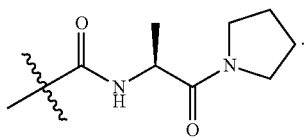 [SMILES: *C(=O)N[C@@H](C)C(=O)N1CCCC1]

In some embodiments is a compound of Formula (Ia) wherein X is

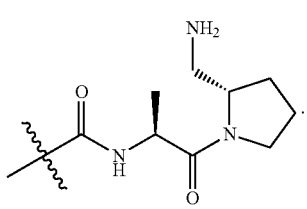 [SMILES: *C(=O)N[C@@H](C)C(=O)N1CCC[C@H]1CN]

In some embodiments is a compound of Formula (Ia) wherein X is

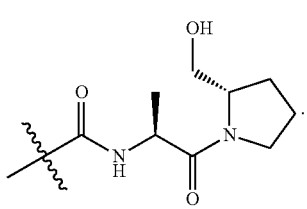 [SMILES: *C(=O)N[C@@H](C)C(=O)N1CCC[C@H]1CO]

In some embodiments is a compound of Formula (Ia) wherein X is

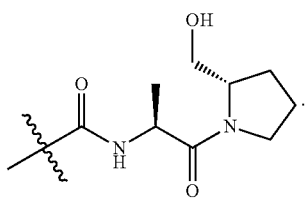 [SMILES: *C(=O)N[C@@H](C)C(=O)N1CCC[C@H]1CO]

In some embodiments is a compound of Formula (Ia) wherein X is

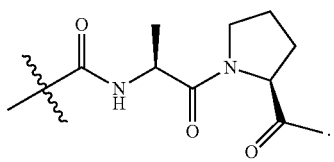 [SMILES: *C(=O)N[C@@H](C)C(=O)N1CCC[C@H]1C(C)=O]

In some embodiments is a compound of Formula (Ia) wherein X is

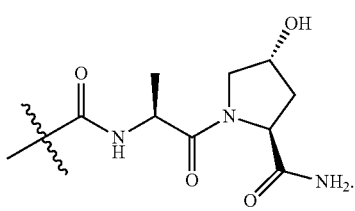 [SMILES: *C(=O)N[C@@H](C)C(=O)N1C[C@H](O)C[C@H]1C(N)=O]

In some embodiments is a compound of Formula (Ia) wherein X is

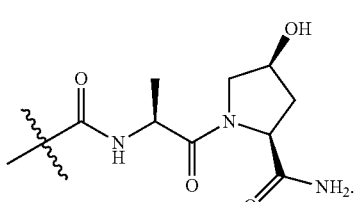

In some embodiments is a compound of Formula (Ia) wherein X is

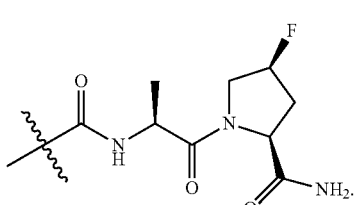

In some embodiments is a compound of Formula (Ia) wherein X is

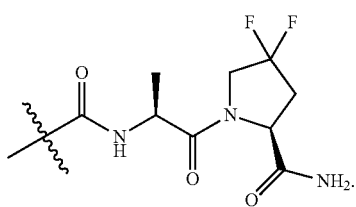 [SMILES: *C(=O)N[C@@H](C)C(=O)N1CC(F)(F)C[C@H]1C(N)=O]

In some embodiments is a compound of Formula (Ia) wherein X is


In some embodiments is a compound of Formula (Ia) wherein X is


In some embodiments is a compound of Formula (Ia) wherein X is

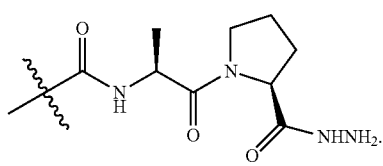 [SMILES: *C(=O)N[C@@H](C)C(=O)N1CCC[C@H]1C(=O)NN]

In some embodiments is a compound of Formula (Ia) wherein X is

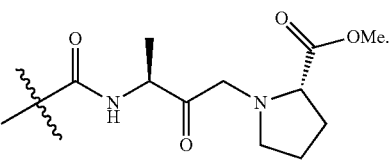 [SMILES: *C(=O)N[C@@H](C)C(=O)CN1CCC[C@H]1C(=O)OC]

In some embodiments is a compound of Formula (Ia) wherein X is

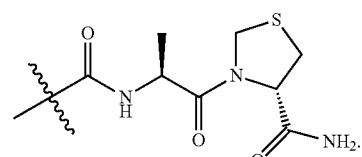

In some embodiments is a compound of Formula (Ia) wherein X is

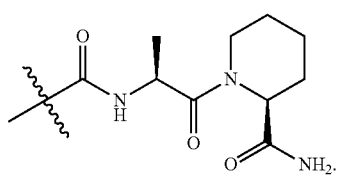 [SMILES: *C(=O)N[C@@H](C)C(=O)N1CCCC[C@H]1C(N)=O]

In some embodiments is a compound of Formula (Ia) wherein X is

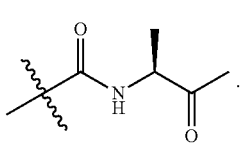 [SMILES: *C(=O)N[C@@H](C)C(C)=O]

In some embodiments is a compound of Formula (Ia) wherein X is

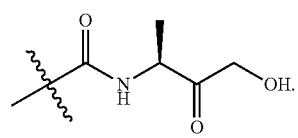 [SMILES: *C(=O)N[C@@H](C)C(=O)CO]

In some embodiments is a compound of Formula (Ia) wherein X is

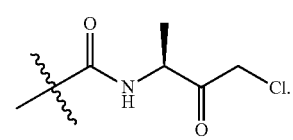 [SMILES: *C(=O)N[C@@H](C)C(=O)CCl]

In some embodiments is a compound of Formula (Ia) wherein X is

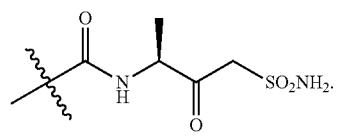 [SMILES: *C(=O)N[C@@H](C)C(=O)CS(N)(=O)=O]

In some embodiments is a compound of Formula (Ia) wherein X is

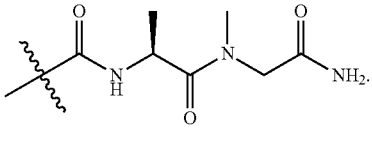 [SMILES: *C(=O)N[C@@H](C)C(=O)N(C)CC(N)=O]

In some embodiments is a compound of Formula (Ia) wherein X is

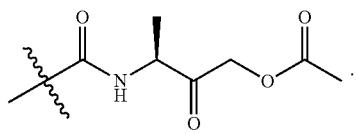 [SMILES: *C(=O)N[C@@H](C)C(=O)COC(C)=O]

In some embodiments is a compound of Formula (Ia) wherein X is

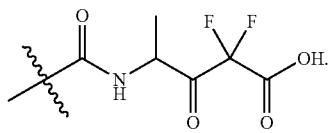 [SMILES: *C(=O)NC(C)C(=O)C(F)(F)C(=O)O]

In some embodiments is a compound of Formula (Ia) wherein X is

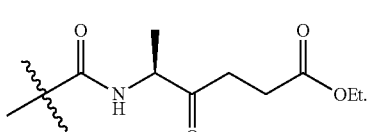

In some embodiments is a compound of Formula (Ia) wherein X is

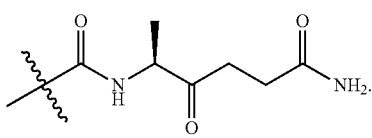 [SMILES: *C(=O)N[C@@H](C)C(=O)CCC(N)=O]

In some embodiments is a compound of Formula (Ia) wherein X is

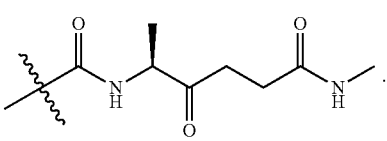 [SMILES: *C(=O)N[C@@H](C)C(=O)CCC(=O)NC]

In some embodiments is a compound of Formula (Ia) wherein X is

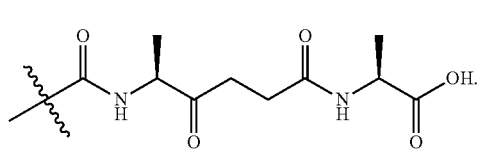

In some embodiments is a compound of Formula (Ia) wherein X is

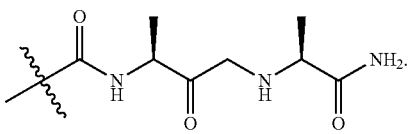 [SMILES: *C(=O)N[C@@H](C)C(=O)CN[C@@H](C)C(N)=O]

In some embodiments is a compound of Formula (Ia) wherein X is

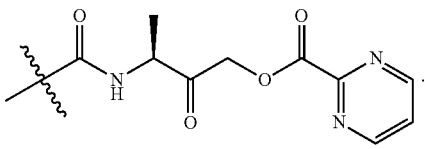 [SMILES: *C(=O)N[C@@H](C)C(=O)COC(=O)c1ncccn1]

In some embodiments is a compound of Formula (Ia) wherein X is

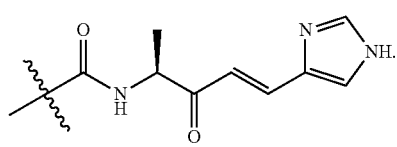 [SMILES: *C(=O)N[C@@H](C)C(=O)/C=C/c1c[nH]cn1]

In some embodiments is a compound of Formula (Ia) wherein X is

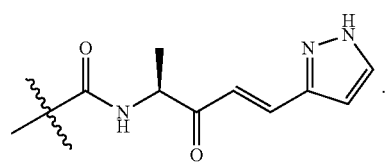 [SMILES: *C(=O)N[C@@H](C)C(=O)/C=C/c1cc[nH]n1]

In some embodiments is a compound of Formula (Ia) wherein X is

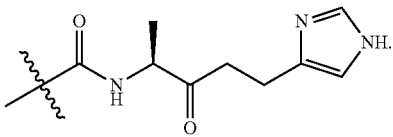 [SMILES: *C(=O)N[C@@H](C)C(=O)CCc1c[nH]cn1]

In some embodiments is a compound of Formula (Ia) wherein X is

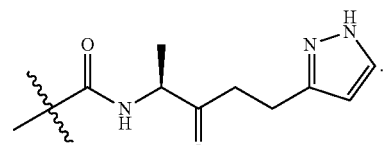

In some embodiments is a compound of Formula (Ia) wherein X is

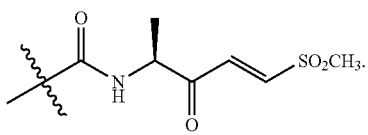 [SMILES: *C(=O)N[C@@H](C)C(=O)/C=C/S(C)(=O)=O]

In some embodiments is a compound of Formula (Ia) wherein X is

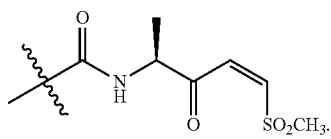 [SMILES: *C(=O)N[C@@H](C)C(=O)/C=C\S(C)(=O)=O]

In some embodiments is a compound of Formula (Ia) wherein X is

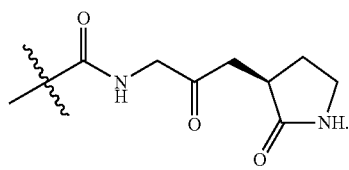 [SMILES: *C(=O)NCC(=O)C[C@H]1CCNC1=O]

In some embodiments is a compound of Formula (Ia) wherein X is

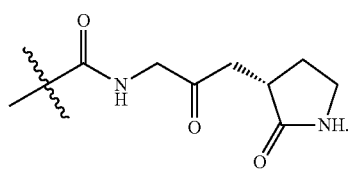 [SMILES: *C(=O)NCC(=O)C[C@@H]1CCNC1=O]

In some embodiments is a compound of Formula (Ia) wherein X is

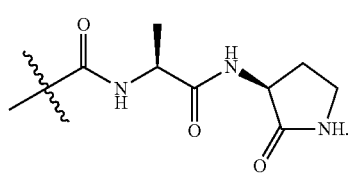

In some embodiments is a compound of Formula (Ia) wherein X is

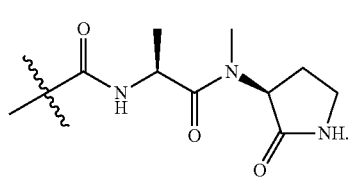

In some embodiments is a compound of Formula (Ia) wherein X is

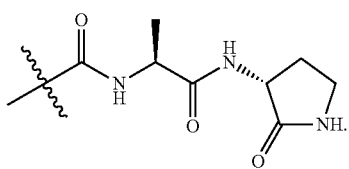 [SMILES: *C(=O)N[C@@H](C)C(=O)N[C@@H]1CCNC1=O]

In some embodiments is a compound of Formula (Ia) wherein X is

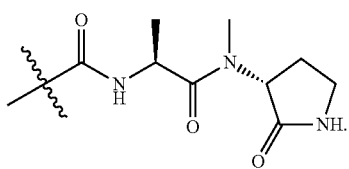 [SMILES: *C(=O)N[C@@H](C)C(=O)N(C)[C@@H]1CCNC1=O]

In some embodiments is a compound of Formula (Ia) wherein X is

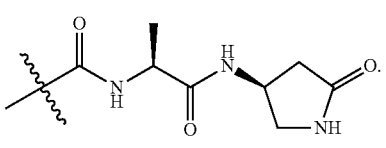 [SMILES: *C(=O)N[C@@H](C)C(=O)N[C@@H]1CNC(=O)C1]

In some embodiments is a compound of Formula (Ia) wherein X is

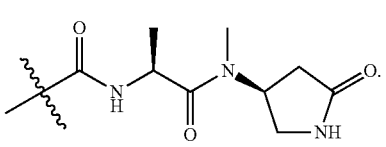 [SMILES: *C(=O)N[C@@H](C)C(=O)N(C)[C@@H]1CNC(=O)C1]

In some embodiments is a compound of Formula (Ia) wherein X is

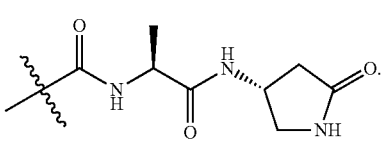

In some embodiments is a compound of Formula (Ia) wherein X is

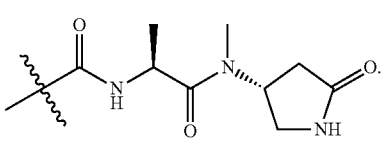 [SMILES: *C(=O)N[C@@H](C)C(=O)N(C)[C@H]1CNC(=O)C1]

In some embodiments is a compound of Formula (Ia) wherein X is wherein n4 and n5 are each independently 1, 2 or 3; $R^{21b}$ and $R^{22b}$ are independently at each occurrence hydrogen, hydroxy, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; and $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1$-$C_6$alkyl), —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH(R^{26})CO_2R^{25b}$, —$CH_2N(H)CH(R^{26})C(O)N(H)R^{25b}$, —$CH_2CH_2R^{30}$, —$N(H)CH_2(R^{30})$, —CH=CHR^{30}, —CH=CHSO_2R^{25b}, where $R^{25a}$ is H, —OH, —$OCH_3$, $NH_2$, $SO_2(C_1$-$C_6$)alkyl, or optionally substituted alkyl; each $R^{25b}$ is independently H, or optionally substituted alkyl; $R^{25c}$ is H or optionally substituted alkyl; $R^{25d}$ is —OH, —$OCH_3$, or $NH_2$; each $R^{26}$ is independently H, halo or ($C_1$-$C_6$)alkyl; each $R^{27}$ is independently —OH, halo, ($C_1$-$C_6$)alkyl, or $R^{26}$ and $R^{27}$ are joined to form a cycloalkyl ring; $R^{28}$ is H, —$CH_2OH$, —$CH_2NH_2$, —$C(O)CH_3$, or ($C_1$-$C_6$)alkyl; each $R^{29}$ is independently —OH, halo, or ($C_1$-$C_6$)alkyl; $R^{30}$ is heterocyclyl, heteroaryl, or aryl; n9 is 1, 2 or 3; and n10 is 0, 1, 2, 3 or 4.

In some embodiments is a compound of Formula (Ia) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted wherein Z is a bond, O, S, NH, $CH_2$ or C≡C. In some embodiments is a compound of Formula (Ia) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted wherein Z is a bond, O, S, NH, CH$_2$ or C≡C. In some embodiments is a compound of Formula (Ia) wherein R$^5$ is a linear alkyl chain of about 1-22 carbon atoms, wherein R$^5$ is bonded to the carbonyl carbon to which it is attached directly to provide an amide linkage, comprising within the chain or at a chain terminus

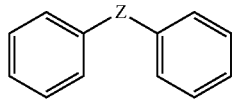

wherein Z is a bond. In some embodiments is a compound of Formula (Ia) wherein R$^5$ is a linear alkyl chain of about 4-22 carbon atoms, wherein R$^5$ is bonded to the carbonyl carbon to which it is attached directly to provide an amide linkage, comprising at a chain terminus

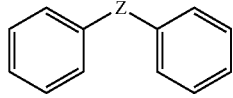

wherein Z is a bond. In some embodiments is a compound of Formula (Ia) wherein R$^5$ is a linear alkyl chain of about 4-22 carbon atoms, wherein R$^5$ is bonded to the carbonyl carbon to which it is attached directly to provide an amide linkage, comprising within the chain

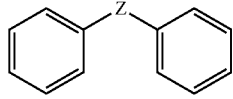

wherein Z is a bond. In some embodiments is a compound of Formula (Ia) wherein R$^5$ is a linear or branched alkyl chain of about 1-22 carbon atoms, wherein R$^5$ is bonded to the carbonyl carbon to which it is attached directly or by an NR$^4$, to provide an amide or urea linkage, respectively; optionally comprising within the chain or at a chain terminus optionally substituted aryl. In some embodiments is a compound of Formula (Ia) wherein R$^5$ is a linear or branched alkyl chain of about 2-22 carbon atoms, wherein R$^5$ is bonded to the carbonyl carbon to which it is attached directly to provide an amide linkage, comprising within the chain or at a chain terminus optionally substituted aryl. In some embodiments is a compound of Formula (Ia) wherein R$^5$ is a linear or branched alkyl chain of about 2-22 carbon atoms, wherein R$^5$ is bonded to the carbonyl carbon to which it is attached directly to provide an amide linkage, comprising at a chain terminus optionally substituted aryl. In some embodiments is a compound of Formula (Ia) wherein R$^5$ is a linear or branched alkyl chain of about 2-22 carbon atoms, wherein R$^5$ is bonded to the carbonyl carbon to which it is attached directly to provide an amide linkage, comprising within the chain optionally substituted aryl. In some embodiments is a compound of Formula (Ia) wherein R$^5$ is a linear or branched alkyl chain of about 1-22 carbon atoms, wherein R$^5$ is bonded to the carbonyl carbon to which it is attached directly to provide an amide or urea linkage. In some embodiments is a compound of Formula (Ia) wherein R$^5$ is a linear or branched alkyl chain of about 4-18 carbon atoms, wherein R$^5$ is bonded to the carbonyl carbon to which it is attached directly to provide an amide or urea linkage. In some embodiments is a compound of Formula (Ia) wherein R$^5$ is a linear or branched alkyl chain of about 6-16 carbon atoms, wherein R$^5$ is bonded to the carbonyl carbon to which it is attached directly to provide an amide or urea linkage. In some embodiments is a compound of Formula (Ia) wherein R$^5$ is

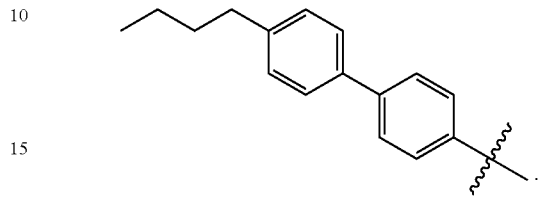

In some embodiments is a compound of Formula (Ia) wherein R$^5$ is

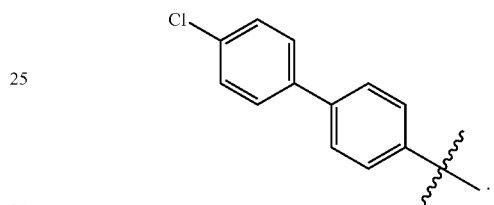

In some embodiments is a compound of Formula (Ia) wherein R$^5$ is a linear or branched alkyl chain of about 1-22 carbon atoms, comprising within the chain at least one —O— or —N(R$^4$)—. In some embodiments is a compound of Formula (Ia) wherein R$^5$ is a linear or branched alkyl chain of about 1-22 carbon atoms, comprising within the chain at least one —O—. In some embodiments is a compound of Formula (Ia) wherein R$^5$ is a linear or branched alkyl chain of about 1-22 carbon atoms, comprising within the chain at least one —N(R$^4$)—. In some embodiments is a compound of Formula (Ia) wherein R$^5$ is a linear or branched alkyl chain of about 1-22 carbon atoms, comprising within the chain at least one —N(H)—. In some embodiments is a compound of Formula (Ia) wherein R$^5$ is —CH$_2$CH$_2$N(H)(CH$_2$)$_9$CH$_3$.

In another embodiment is a compound of Formula (Ia) wherein n1 is 0 and n2 is 1. In another embodiment is a compound of Formula (Ia) wherein n1 is 0, n2 is 1, and R$^{44}$ is H. In another embodiment is a compound of Formula (Ia) wherein n1 is 0, n2 is 1, and R$^{44}$ is (C$_1$-C$_6$)alkyl optionally substituted with 1 to 3 J. In another embodiment is a compound of Formula (Ia) wherein n1 is 0, n2 is 1, and R$^{44}$ is CH$_3$. In another embodiment is a compound of Formula (Ia) wherein n1 is 0, n2 is 1, and R$^{44}$ is CH$_2$CH$_3$. In another embodiment is a compound of Formula (Ia) wherein n1 is 0, n2 is 1, and R$^{44}$ is CH$_2$CH(CH$_3$)$_2$. In another embodiment is a compound of Formula (Ia) wherein n1 is 0, n2 is 1, and R$^{44}$ is CH$_2$OH. In another embodiment is a compound of Formula (Ia) wherein n1 is 0, n2 is 1, and R$^{44}$ is CH(OH)CH$_3$. In another embodiment is a compound of Formula (Ia) wherein n1 is 0, n2 is 1, and R$^{44}$ is CH$_2$C(O)NH$_2$. In another embodiment is a compound of Formula (Ia) wherein n1 is 0, n2 is 1, and R$^{44}$ is CH$_2$CH$_2$CH$_2$CH$_2$NH$_2$.

In another embodiment is a compound of Formula (Ia) wherein n1 is 1 and n2 is 1. In another embodiment is a compound of Formula (Ia) wherein n1 is 1, n2 is 1, R$^{46}$ is $CH_3$, and $R^{44}$ is $(C_1-C_6)$alkyl optionally substituted with 1 to 3 J. In another embodiment is a compound of Formula (Ia) wherein n1 is 1, n2 is 1, $R^{46}$ is $CH_3$, and $R^{44}$ is $CH_3$. In another embodiment is a compound of Formula (Ia) wherein n1 is 1, n2 is 1, $R^{46}$ is $CH_3$, and $R^{44}$ is $CH_2CH_3$. In another embodiment is a compound of Formula (Ia) wherein n1 is 1, n2 is 1, $R^{46}$ is $CH_3$, and $R^{44}$ is $CH_2CH(CH_3)_2$. In another embodiment is a compound of Formula (Ia) wherein n1 is 1, n2 is 1, $R^{46}$ is $CH_3$, and $R^{44}$ is $CH_2OH$. In another embodiment is a compound of Formula (Ia) wherein n1 is 1, n2 is 1, $R^{46}$ is $CH_3$, and $R^{44}$ is $CH(OH)CH_3$. In another embodiment is a compound of Formula (Ia) wherein n1 is 1, n2 is 1, $R^{46}$ is $CH_3$, and $R^{44}$ is $CH_2C(O)NH_2$. In another embodiment is a compound of Formula (Ia) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (Ia) wherein $R^{47}$, $R^{47'}$, $R^{48}$, $R^{48'}$, $R^{49}$, $R^{49'}$, $R^{44}$, $R^{410}$, and $R^{410'}$ are each independently H. In another embodiment of the aforementioned embodiments is a compound of Formula (Ia) wherein each m is 0. In another embodiment of the aforementioned embodiments is a compound of Formula (Ia) wherein $R^{41}$, $R^{41'}$, $R^{42}$, $R^{4'}$, and $R^{4''}$ are each independently H.

In another embodiment of the aforementioned embodiments is a compound of Formula (Ia) wherein n3 is 1 and n8 is 1. In another embodiment of the aforementioned embodiments is a compound of Formula (Ia) wherein n3 is 1, n8 is 1, and $R^2$ and $R^3$ are each hydroxy. In another embodiment of the aforementioned embodiments is a compound of Formula (Ia) wherein n3 is 1, n8 is 1, $R^2$ is hydroxy, and $R^3$ is $—OR^{40}$. In another embodiment of the aforementioned embodiments is a compound of Formula (Ia) wherein n3 is 1, n8 is 1, $R^2$ is hydroxy, $R^3$ is $—OR^{40}$, and $R^{40}$ is $—(C_1-C_6)$alkyl. In another embodiment of the aforementioned embodiments is a compound of Formula (Ia) wherein n3 is 1, n8 is 1, $R^2$ is hydroxy, $R^3$ is $—OR^{40}$, and $R^{40}$ is $—(C_1-C_6)$alkyl-$NR^{41}R^{42}$. In another embodiment of the aforementioned embodiments is a compound of Formula (Ia) wherein n3 is 1, n8 is 1, $R^2$ is $—OH$, $R^3$ is $—OR^{40}$, and $R^{40}$ is $—(C_1-C_6)$alkyl-$NH_2$. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (Ia) wherein n3 is 1, n8 is 1, $R^3$ is hydroxy, and $R^2$ is $—OR^{40}$. In another embodiment of the aforementioned embodiments is a compound of Formula (Ia) wherein n3 is 1, n8 is 1, $R^3$ is hydroxy, $R^2$ is $—OR^{40}$, and $R^{40}$ is $—(C_1-C_6)$alkyl. In another embodiment of the aforementioned embodiments is a compound of Formula (Ia) wherein n3 is 1, n8 is 1, $R^3$ is hydroxy, $R^2$ is $—OR^{40}$, and $R^{40}$ is $—(C_1-C_6)$alkyl-$NR^{41}R^{42}$. In another embodiment of the aforementioned embodiments is a compound of Formula (Ia) wherein n3 is 1, n8 is 1, $R^3$ is $—OH$, $R^2$ is $—OR^{40}$, and $R^{40}$ is $—(C_1-C_6)$alkyl-$NH_2$. In another embodiment of the aforementioned embodiments is a compound of Formula (Ia) wherein n3 is 1, n8 is 1, $R^3$ is hydroxy, $R^2$ is $—OR^{40}$, $R^{40}$ is $—(C_1-C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (Ia) wherein n3 is 1, n8 is 1, $R^3$ is hydroxy, $R^2$ is $—OR^{40}$, $R^{40}$ is $—(C_1-C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (Ia) wherein n3 is 1, n8 is 1, $R^2$ is hydroxy, $R^3$ is $—OR^{40}$, and any carbon atom of $R^3$ is substituted with J. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl, and any carbon atom of $R^3$ is substituted with J. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl, and any carbon atom of $R^3$ is substituted with J wherein J is $CO_2H$. In another embodiment of the aforementioned embodiments is a compound of Formula (Ia) wherein n3 is 1, n8 is 1, $R^2$ is hydroxy, $R^3$ is $—O—(C_1-C_6)$alkyl-$CO_2H$. In another embodiment of the aforementioned embodiments is a compound of Formula (Ia) wherein n3 is 1, n8 is 1, $R^2$ is hydroxy, $R^3$ is $—OCH_2CO_2H$. In another embodiment of the aforementioned embodiments is a compound of Formula (Ia) wherein n3 is 1, n8 is 1, $R^2$ is $—OCH_2CH_2NH_2$, $R^3$ is $—OCH_2CO_2H$. In another embodiment of the aforementioned embodiments is a compound of Formula (Ia) wherein n3 is 1, n8 is 1, $R^2$ is hydroxy, $R^3$ is $—OR^{40}$, $R^{40}$ is $R^{40}$ is $—(C_1-C_6)$alkyl-$NR^{41}R^{42}$, and any carbon atom of $R^3$ is substituted with J. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl-$NR^{41}R^{42}$, $R^{41}$ is hydrogen, $R^{42}$ is $—(C_1-C_6)$alkyl, and any carbon atom of $R^3$ is substituted with J. In another embodiment of the aforementioned embodiments is a compound of Formula (Ia) wherein n3 is 1, n8 is 1, $R^2$ is hydroxy, $R^3$ is $—OR^{40}$, $R^{40}$ is $—(C_1-C_6)$alkyl-$NR^{41}R^{42}$, $R^{41}$ is hydrogen, $R^{42}$ is $—(C_1-C_6)$alkyl, and any carbon atom of $R^3$ is substituted with J wherein J is $—NHCH_3$. In another embodiment of the aforementioned embodiments is a compound of Formula (Ia) wherein n3 is 1, n8 is 1, $R^2$ is hydroxy, $R^3$ is $—O—(C_1-C_6)$alkyl-$N(H)—(C_1-C_6)$alkyl-$N(H)CH_3$. In another embodiment of the aforementioned embodiments is a compound of Formula (Ia) wherein n3 is 1, n8 is 1, $R^2$ is hydroxy, $R^3$ is $—OCH_2CH_2N(H)CH_2CH_2N(H)CH_3$. In another embodiment of the aforementioned embodiments is a compound of Formula (Ia) wherein n3 is 1, n8 is 1, $R^2$ is hydroxy, $R^3$ is $—OCH_2CH_2N(H)CH_2CH_2CH_2N(H)CH_3$.

In another embodiment of the aforementioned embodiments is a compound of Formula (Ia) wherein n3 is 1, n8 is 1, $R^3$ is hydroxy, $R^2$ is $—OR^{40}$, and any carbon atom of $R^2$ is substituted with J. In another embodiment of the aforementioned embodiments is a compound of Formula (Ia) wherein n3 is 1, n8 is 1, $R^3$ is hydroxy, $R^2$ is $—OR^{40}$, $R^{40}$ is $—(C_1-C_6)$alkyl, and any carbon atom of $R^2$ is substituted with J. In another embodiment of the aforementioned embodiments is a compound of Formula (Ia) wherein n3 is 1, n8 is 1, $R^3$ is hydroxy, $R^2$ is $—OR^{40}$, $R^{40}$ is $—(C_1-C_6)$alkyl, and any carbon atom of $R^2$ is substituted with J wherein J is $CO_2H$. In another embodiment of the aforementioned embodiments is a compound of Formula (Ia) wherein n3 is 1, n8 is 1, $R^3$ is hydroxy, $R^2$ is $—O—(C_1-C_6)$alkyl-$CO_2H$. In another embodiment of the aforementioned embodiments is a compound of Formula (Ia) wherein n3 is 1, n8 is 1, $R^3$ is hydroxy, $R^2$ is $—OCH_2CO_2H$. In another embodiment of the aforementioned embodiments is a compound of Formula (Ia) wherein n3 is 1, n8 is 1, $R^3$ is $—OCH_2CH_2NH_2$, $R^2$ is $—OCH_2CO_2H$. In another embodiment of the aforementioned embodiments is a compound of Formula (Ia) wherein n3 is 1, n8 is 1, $R^3$ is hydroxy, $R^2$ is —$OR^{40}$, $R^{40}$ is $R^{40}$ is —$(C_1-C_6)$alkyl-$NR^{41}R^{42}$, and any carbon atom of $R^2$ is substituted with J. In another embodiment of the aforementioned embodiments is a compound of Formula (Ia) wherein n3 is 1, n8 is 1, $R^3$ is hydroxy, $R^2$ is —$OR^{40}$, $R^{40}$ is —$(C_1-C_6)$alkyl-$NR^{41}R^{42}$, $R^{41}$ is hydrogen, $R^{42}$ is —$(C_1-C_6)$alkyl, and any carbon atom of $R^2$ is substituted with J. In another embodiment of the aforementioned embodiments is a compound of Formula (Ia) wherein n3 is 1, n8 is 1, $R^3$ is hydroxy, $R^2$ is —$OR^{40}$, $R^{40}$ is —$(C_1-C_6)$alkyl-$NR^{41}R^{42}$, $R^{41}$ is hydrogen, $R^{42}$ is —$(C_1-C_6)$alkyl, and any carbon atom of $R^2$ is substituted with J wherein J is —$NHCH_3$. In another embodiment of the aforementioned embodiments is a compound of Formula (Ia) wherein n3 is 1, n8 is 1, $R^3$ is hydroxy, $R^2$ is —O—$(C_1-C_6)$alkyl-N(H)—$(C_1-C_6)$alkyl-N(H)$CH_3$. In another embodiment of the aforementioned embodiments is a compound of Formula (Ia) wherein n3 is 1, n8 is 1, $R^3$ is hydroxy, $R^2$ is —$OCH_2CH_2N(H)CH_2CH_2N(H)CH_3$. In another embodiment of the aforementioned embodiments is a compound of Formula (Ia) wherein n3 is 1, n8 is 1, $R^3$ is hydroxy, $R^2$ is —$OCH_2CH_2N(H)CH_2CH_2CH_2N(H)CH_3$.

In another embodiment is a compound of Formula (I) having the structure of Formula (Ib):

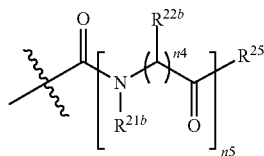

wherein n4 and n5 are each independently 1, 2 or 3; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J; and $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1-C_6alkyl)$, —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH(R^{26})CO_2R^{25b}$, —$CH_2N(H)CH(R^{26})C(O)N(H)R^{25b}$, —$CH_2CH_2R^{30}$, —N(H)$CH_2(R^{30})$, —CH=$CHR^{30}$, —CH=$CHSO_2R^{25b}$,

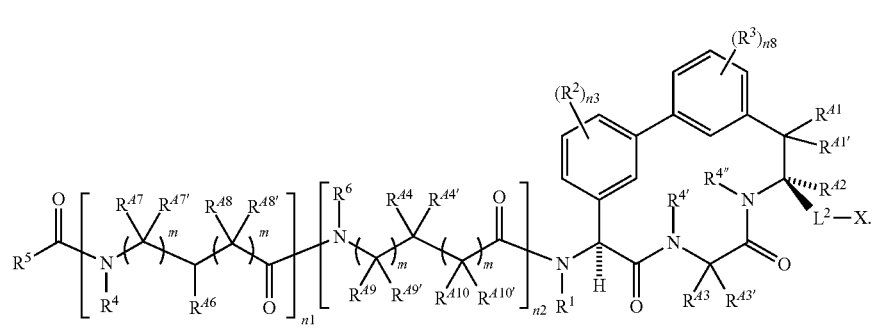

Formula (Ib)

In another embodiment is a compound of Formula (Ib) wherein $L^2$ is a bond. In another embodiment is a compound of Formula (Ib) wherein $L^2$ is optionally substituted $(C_1-C_6)$alkylene. In a further embodiment, $L^2$ is methylene, ethylene, n-propylene, iso-propylene, n-butylene, iso-butylene, or tert-butylene.

In one embodiment is a compound of Formula (Ib) wherein X is —$CH_2OH$, —$CH(OH)CH_3$, —$N(R^4)CH(R^{24})CN$, —$NHCH(R^{24})C(O)CH_3$, —$NHN(R^{24})C(O)CH_3$, —$NHCH(R^{24})CH=CHS(O)_2CH_3$, or —$NHCH(R^{24})CH=CHS(O)_2NH_2$; and $R^{24}$ is H or $(C_1-C_6)$alkyl. In some embodiments is a compound of Formula (Ib) wherein X is —$CH_2OH$. In some embodiments is a compound of Formula (Ib) wherein X is —$CH(OH)CH_3$. In some embodiments is a compound of Formula (Ib) wherein X is —$NHCH(R^{24})C(O)CH_3$. In some embodiments is a compound of Formula (Ib) wherein X is —$NHN(R^{24})C(O)CH_3$. In some embodiments is a compound of Formula (Ib) wherein X is —$NHCH(R^{24})CH=CHS(O)_2CH_3$. In some embodiments is a compound of Formula (Ib) wherein X is —$NHCH(R^{24})CH=CHS(O)_2NH_2$.

In some embodiments is a compound of Formula (Ib) wherein X is

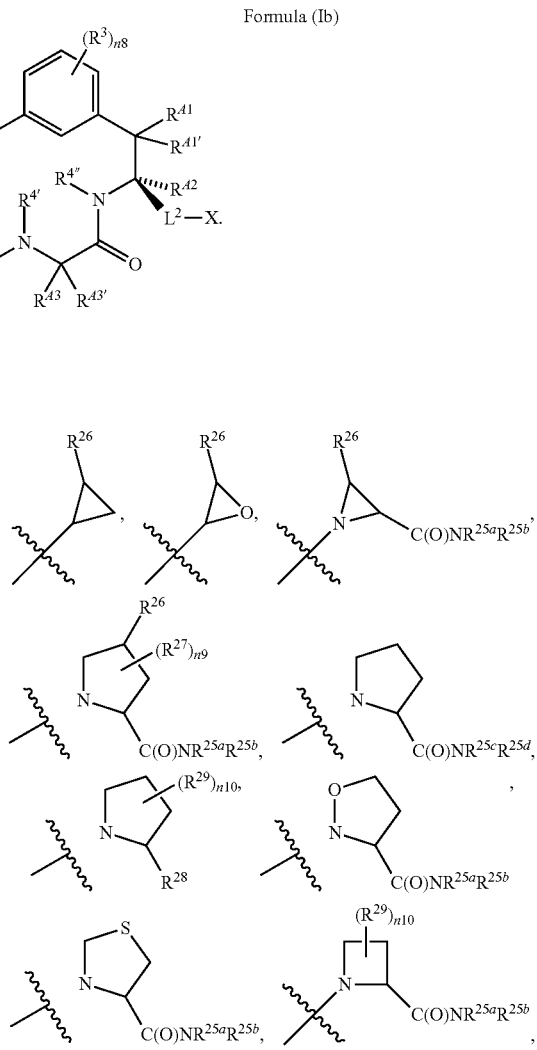

-continued

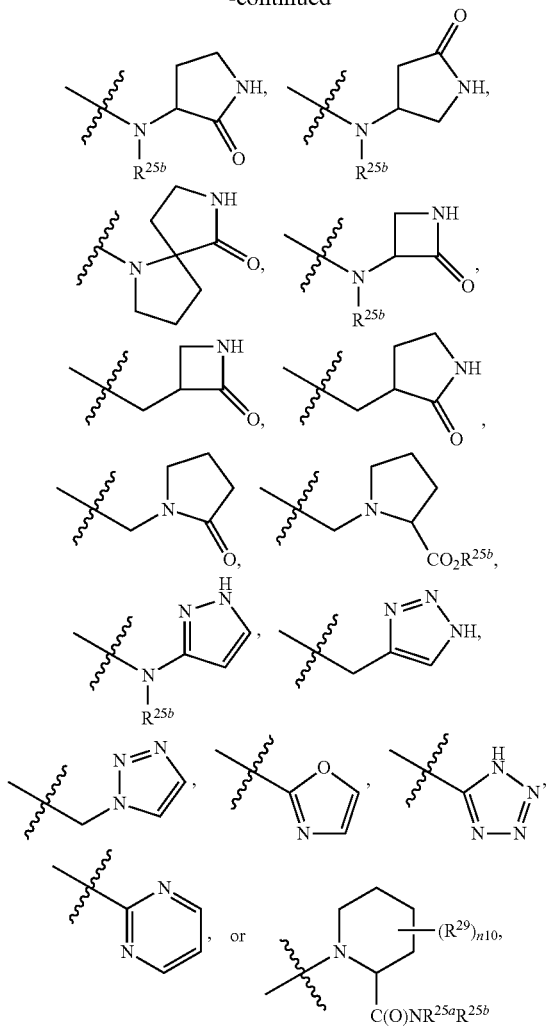

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In another embodiment is a compound of Formula (Ib) wherein X is

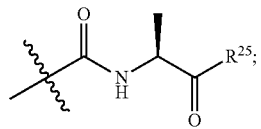

wherein $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

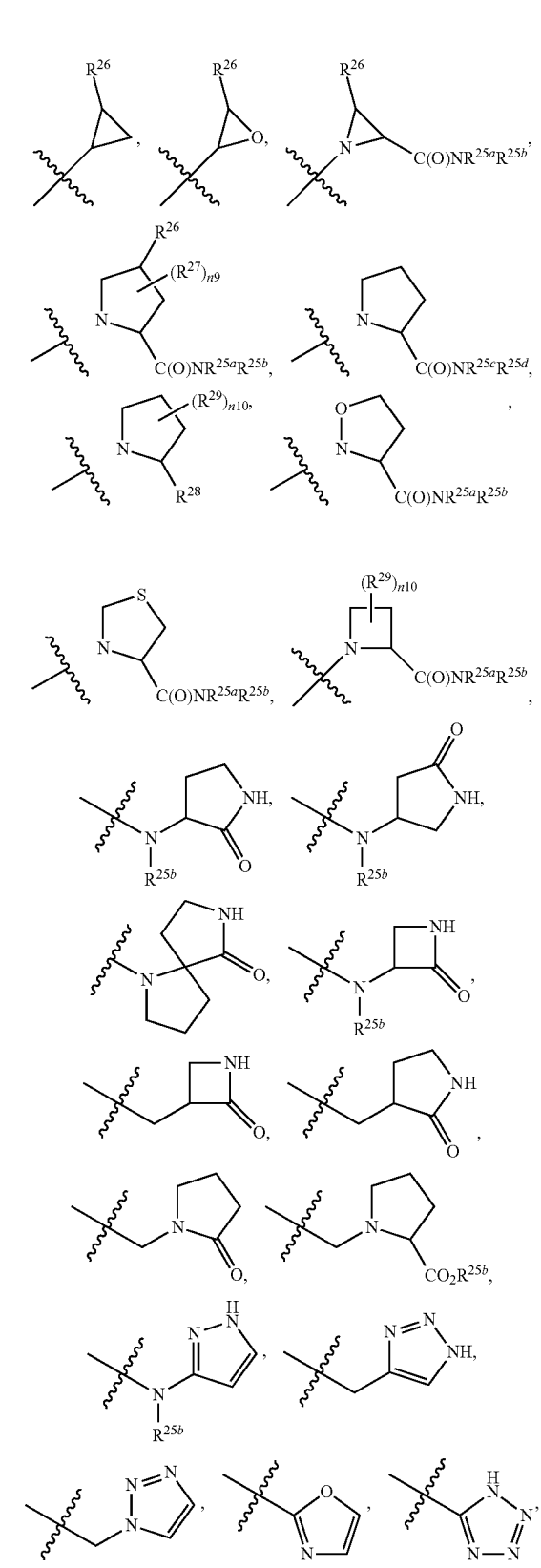

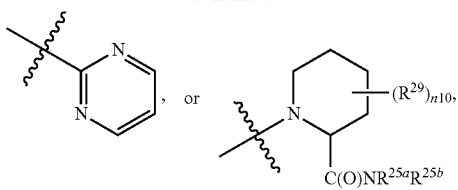

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4. In some embodiments is a compound of Formula (Ib) wherein X is

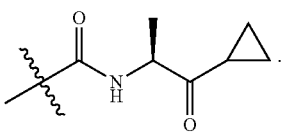 [SMILES: *C(=O)N[C@@H](C)C(=O)C1CC1]

In some embodiments is a compound of Formula (Ib) wherein X is

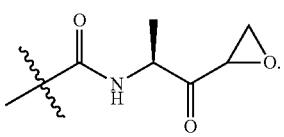 [SMILES: *C(=O)N[C@@H](C)C(=O)C1CO1]

In some embodiments is a compound of Formula (Ib) wherein X is

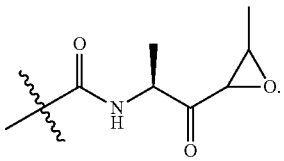 [SMILES: *C(=O)N[C@@H](C)C(=O)C1OC1C]

In some embodiments is a compound of Formula (Ib) wherein X is

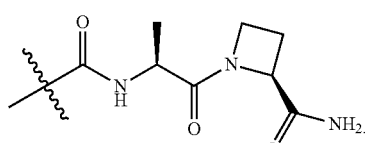

In some embodiments is a compound of Formula (Ib) wherein X is

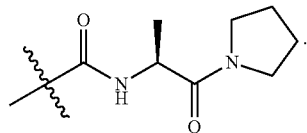 [SMILES: *C(=O)N[C@@H](C)C(=O)N1CCCC1]

In some embodiments is a compound of Formula (Ib) wherein X is

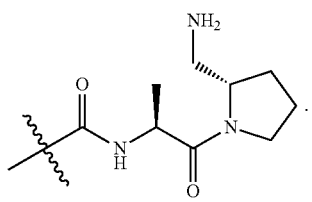 [SMILES: *C(=O)N[C@@H](C)C(=O)N1CCC[C@H]1CN]

In some embodiments is a compound of Formula (Ib) wherein X is

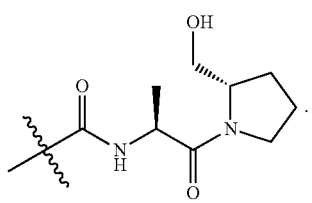 [SMILES: *C(=O)N[C@@H](C)C(=O)N1CCC[C@H]1CO]

In some embodiments is a compound of Formula (Ib) wherein X is

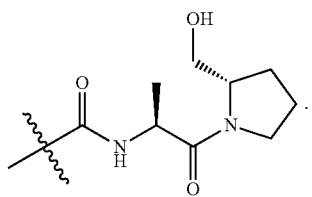 [SMILES: *C(=O)N[C@@H](C)C(=O)N1CCC[C@H]1CO]

In some embodiments is a compound of Formula (Ib) wherein X is

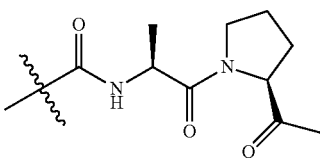

In some embodiments is a compound of Formula (Ib) wherein X is

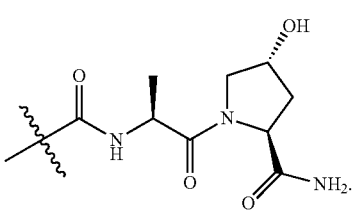 [SMILES: *C(=O)N[C@@H](C)C(=O)N1C[C@H](O)C[C@H]1C(N)=O]

In some embodiments is a compound of Formula (Ib) wherein X is

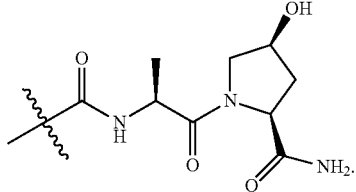 [SMILES: *C(=O)N[C@@H](C)C(=O)N1C[C@@H](O)C[C@H]1C(N)=O]

In some embodiments is a compound of Formula (Ib) wherein X is

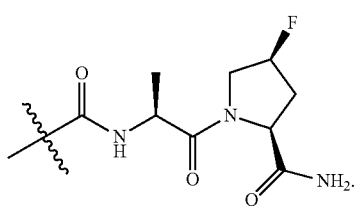 [SMILES: *C(=O)N[C@@H](C)C(=O)N1C[C@@H](F)C[C@H]1C(N)=O]

In some embodiments is a compound of Formula (Ib) wherein X is

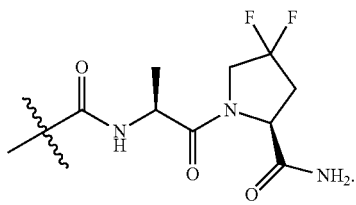 [SMILES: *C(=O)N[C@@H](C)C(=O)N1CC(F)(F)C[C@H]1C(N)=O]

In some embodiments is a compound of Formula (Ib) wherein X is

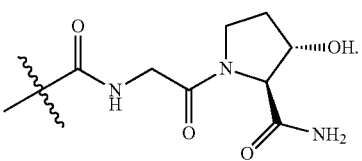 [SMILES: *C(=O)NCC(=O)N1CC[C@H](O)[C@H]1C(N)=O]

In some embodiments is a compound of Formula (Ib) wherein X is

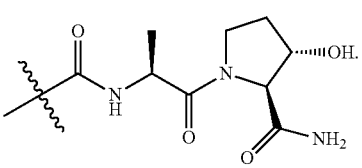 [SMILES: *C(=O)N[C@@H](C)C(=O)N1CC[C@H](O)[C@H]1C(N)=O]

In some embodiments is a compound of Formula (Ib) wherein X is

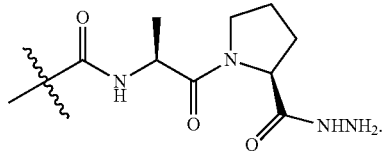 [SMILES: *C(=O)N[C@@H](C)C(=O)N1CCC[C@H]1C(=O)NN]

In some embodiments is a compound of Formula (Ib) wherein X is

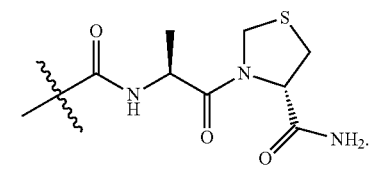 [SMILES: *C(=O)N[C@@H](C)C(=O)N1CSC[C@@H]1C(N)=O]

In some embodiments is a compound of Formula (Ib) wherein X is

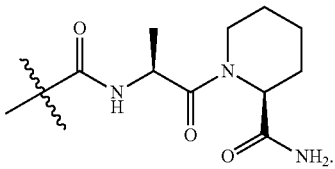 [SMILES: *C(=O)N[C@@H](C)C(=O)N1CCCC[C@H]1C(N)=O]

In some embodiments is a compound of Formula (Ib) wherein X is

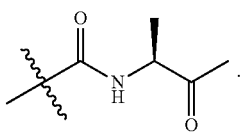 [SMILES: *C(=O)N[C@@H](C)C(C)=O]

In some embodiments is a compound of Formula (Ib) wherein X is

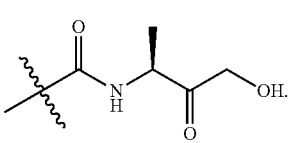 [SMILES: *C(=O)N[C@@H](C)C(=O)CO]

In some embodiments is a compound of Formula (Ib) wherein X is

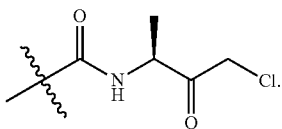 [SMILES: *C(=O)N[C@@H](C)C(=O)CCl]

In some embodiments is a compound of Formula (Ib) wherein X is

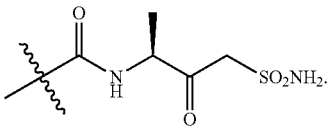 [SMILES: *C(=O)N[C@@H](C)C(=O)CS(N)(=O)=O]

In some embodiments is a compound of Formula (Ib) wherein X is

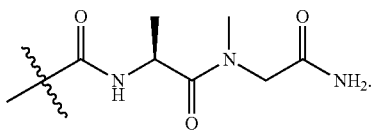 [SMILES: *C(=O)N[C@@H](C)C(=O)N(C)CC(N)=O]

In some embodiments is a compound of Formula (Ib) wherein X is

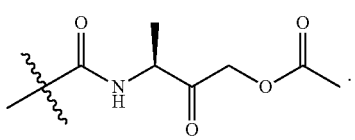 [SMILES: *C(=O)N[C@@H](C)C(=O)COC(C)=O]

In some embodiments is a compound of Formula (Ib) wherein X is

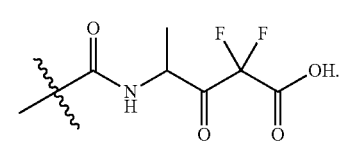 [SMILES: *C(=O)NC(C)C(=O)C(F)(F)C(=O)O]

In some embodiments is a compound of Formula (Ib) wherein X is

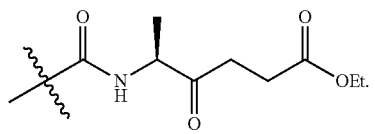 [SMILES: *C(=O)N[C@@H](C)C(=O)CCC(=O)OCC]

In some embodiments is a compound of Formula (Ib) wherein X is

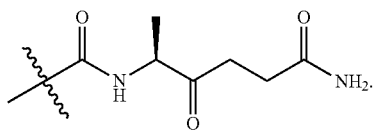 [SMILES: *C(=O)N[C@@H](C)C(=O)CCC(N)=O]

In some embodiments is a compound of Formula (Ib) wherein X is

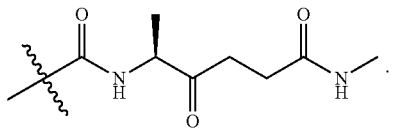 [SMILES: *C(=O)N[C@@H](C)C(=O)CCC(=O)NC]

In some embodiments is a compound of Formula (Ib) wherein X is

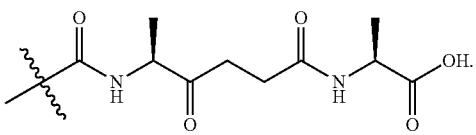 [SMILES: *C(=O)N[C@@H](C)C(=O)CCC(=O)N[C@@H](C)C(=O)O]

In some embodiments is a compound of Formula (Ib) wherein X is

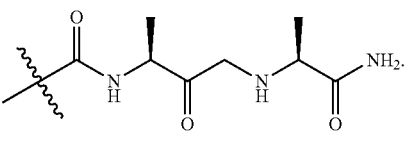 [SMILES: *C(=O)N[C@@H](C)C(=O)CN[C@@H](C)C(N)=O]

In some embodiments is a compound of Formula (Ib) wherein X is

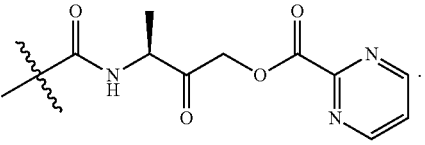

In some embodiments is a compound of Formula (Ib) wherein X is

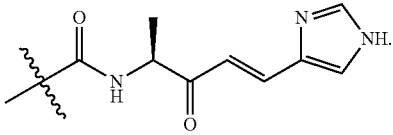 [SMILES: *C(=O)N[C@@H](C)C(=O)/C=C/c1c[nH]cn1]

In some embodiments is a compound of Formula (Ib) wherein X is

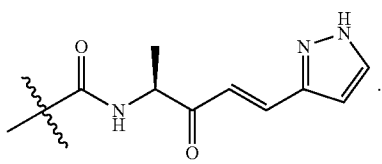 [SMILES: *C(=O)N[C@@H](C)C(=O)/C=C/c1cc[nH]n1]

In some embodiments is a compound of Formula (Ib) wherein X is

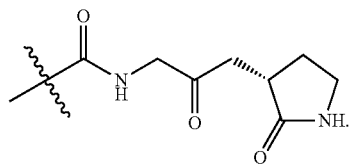

In some embodiments is a compound of Formula (Ib) wherein X is

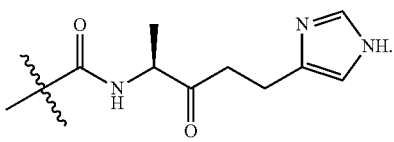 [SMILES: *C(=O)N[C@@H](C)C(=O)CCc1c[nH]cn1]

In some embodiments is a compound of Formula (Ib) wherein X is

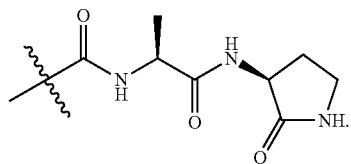

In some embodiments is a compound of Formula (Ib) wherein X is

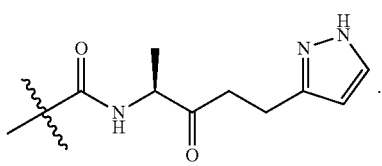 [SMILES: *C(=O)N[C@@H](C)C(=O)CCc1cc[nH]n1]

In some embodiments is a compound of Formula (Ib) wherein X is

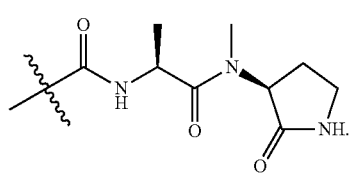

In some embodiments is a compound of Formula (Ib) wherein X is

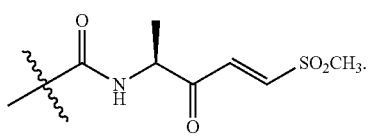 [SMILES: *C(=O)N[C@@H](C)C(=O)/C=C/S(C)(=O)=O]

In some embodiments is a compound of Formula (Ib) wherein X is

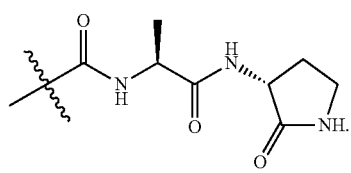

In some embodiments is a compound of Formula (Ib) wherein X is

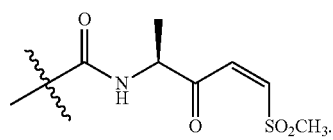 [SMILES: *C(=O)N[C@@H](C)C(=O)/C=C\S(C)(=O)=O]

In some embodiments is a compound of Formula (Ib) wherein X is

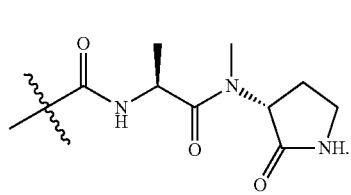

In some embodiments is a compound of Formula (Ib) wherein X is

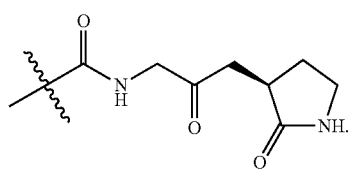 [SMILES: *C(=O)NCC(=O)C[C@H]1CCNC1=O]

In some embodiments is a compound of Formula (Ib) wherein X is

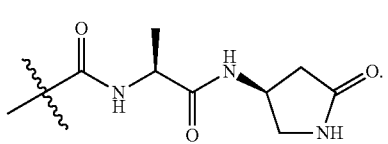 [SMILES: *C(=O)N[C@@H](C)C(=O)N[C@@H]1CNC(=O)C1]

In some embodiments is a compound of Formula (Ib) wherein X is

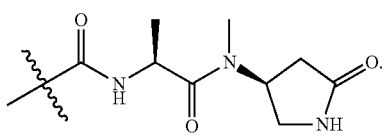 [SMILES: *C(=O)N[C@@H](C)C(=O)N(C)[C@@H]1CNC(=O)C1]

In some embodiments is a compound of Formula (Ib) wherein X is

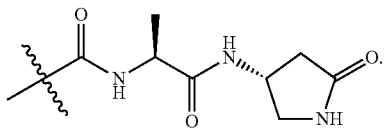 [SMILES: *C(=O)N[C@@H](C)C(=O)N[C@H]1CNC(=O)C1]

In some embodiments is a compound of Formula (Ib) wherein X is

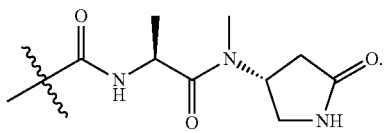 [SMILES: *C(=O)N[C@@H](C)C(=O)N(C)[C@H]1CNC(=O)C1]

In some embodiments is a compound of Formula (Ib) wherein X is

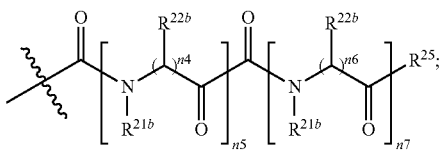

wherein n4 and n5 are each independently 1, 2 or 3; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J; and $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

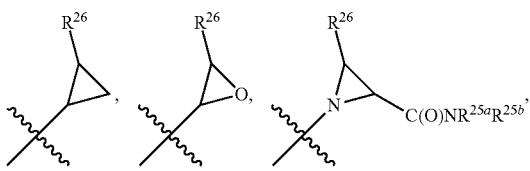

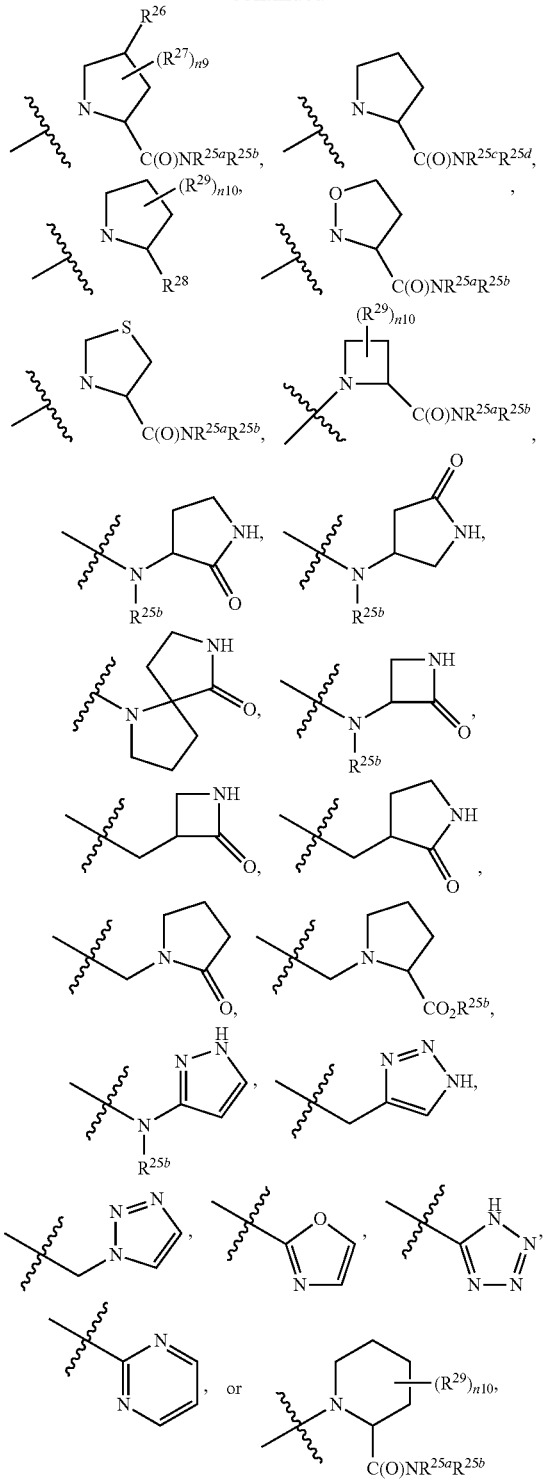

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or $(C_1-C_6)$alkyl; $R^{30}$ is heterocyclyl, heteroaryl, or aryl; n9 is 1, 2 or 3; and n10 is 0, 1, 2, 3 or 4.

In some embodiments is a compound of Formula (Ib) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

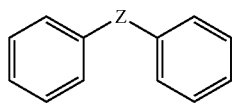

wherein Z is a bond, O, S, NH, CH$_2$ or C≡C. In some embodiments is a compound of Formula (Ib) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

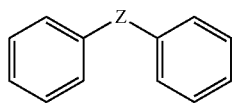

wherein Z is a bond, O, S, NH, CH$_2$ or C≡C. In some embodiments is a compound of Formula (Ib) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

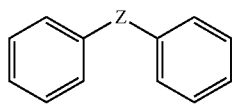

wherein Z is a bond. In some embodiments is a compound of Formula (Ib) wherein $R^5$ is a linear alkyl chain of about 4-22 carbon atoms, wherein $R^5$ is bonded to the carbonyl carbon to which it is attached directly to provide an amide linkage, comprising at a chain terminus

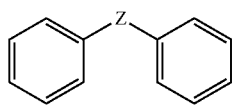

wherein Z is a bond. In some embodiments is a compound of Formula (Ib) wherein $R^5$ is a linear alkyl chain of about 4-22 carbon atoms, wherein $R^5$ is bonded to the carbonyl carbon to which it is attached directly to provide an amide linkage, comprising within the chain

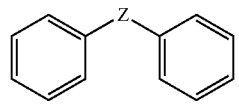

wherein Z is a bond. In some embodiments is a compound of Formula (Ib) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Ib) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Ib) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Ib) wherein $R^5$ is a linear or branched alkyl chain of about 6-16 carbon atoms, wherein $R^5$ is bonded to the carbonyl carbon to which it is attached directly to provide an amide or urea linkage. In some embodiments is a compound of Formula (Ib) wherein $R^5$ is

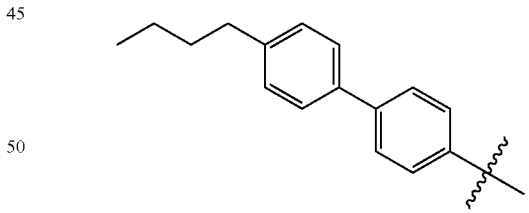

In some embodiments is a compound of Formula (Ib) wherein $R^5$ is

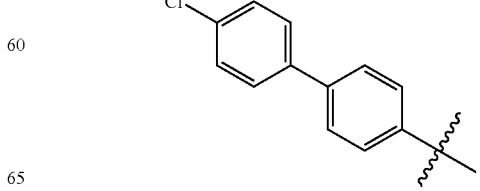

In some embodiments is a compound of Formula (Ib) wherein $R^5$ is a linear or branched alkyl chain of about 1-22 carbon atoms, comprising within the chain at least one —O— or —N($R^4$)—. In some embodiments is a compound of Formula (Ib) wherein $R^5$ is a linear or branched alkyl chain of about 1-22 carbon atoms, comprising within the chain at least one —O—. In some embodiments is a compound of Formula (Ib) wherein $R^5$ is a linear or branched alkyl chain of about 1-22 carbon atoms, comprising within the chain at least one —N($R^4$)—. In some embodiments is a compound of Formula (Ib) wherein $R^5$ is a linear or branched alkyl chain of about 1-22 carbon atoms, comprising within the chain at least one —N(H)—. In some embodiments is a compound of Formula (Ib) wherein $R^5$ is —CH$_2$CH$_2$N(H)(CH$_2$)$_9$CH$_3$.

In another embodiment is a compound of Formula (Ib) wherein n1 is 0 and n2 is 1. In another embodiment is a compound of Formula (Ib) wherein n1 is 0, n2 is 1, and $R^{44}$ is H. In another embodiment is a compound of Formula (Ib) wherein n1 is 0, n2 is 1, and $R^{44}$ is (C$_1$-C$_6$)alkyl optionally substituted with 1 to 3 J. In another embodiment is a compound of Formula (Ib) wherein n1 is 0, n2 is 1, and $R^{44}$ is CH$_3$. In another embodiment is a compound of Formula (Ib) wherein n1 is 0, n2 is 1, and $R^{44}$ is CH$_2$CH$_3$. In another embodiment is a compound of Formula (Ib) wherein n1 is 0, n2 is 1, and $R^{44}$ is CH$_2$CH(CH$_3$)$_2$. In another embodiment is a compound of Formula (Ib) wherein n1 is 0, n2 is 1, and $R^{44}$ is CH$_2$OH. In another embodiment is a compound of Formula (Ib) wherein n1 is 0, n2 is 1, and $R^{44}$ is CH(OH)CH$_3$. In another embodiment is a compound of Formula (Ib) wherein n1 is 0, n2 is 1, and $R^{44}$ is CH$_2$C(O)NH$_2$. In another embodiment is a compound of Formula (Ib) wherein n1 is 0, n2 is 1, and $R^{44}$ is CH$_2$CH$_2$CH$_2$CH$_2$NH$_2$.

In another embodiment is a compound of Formula (Ib) wherein n1 is 1 and n2 is 1. In another embodiment is a compound of Formula (Ib) wherein n1 is 1, n2 is 1, $R^{46}$ is CH$_3$, and $R^{44}$ is (C$_1$-C$_6$)alkyl optionally substituted with 1 to 3 J. In another embodiment is a compound of Formula (Ib) wherein n1 is 1, n2 is 1, $R^{46}$ is CH$_3$, and $R^{44}$ is CH$_3$. In another embodiment is a compound of Formula (Ib) wherein n1 is 1, n2 is 1, $R^{46}$ is CH$_3$, and $R^{44}$ is CH$_2$CH$_3$. In another embodiment is a compound of Formula (Ib) wherein n1 is 1, n2 is 1, $R^{46}$ is CH$_3$, and $R^{44}$ is CH$_2$CH(CH$_3$)$_2$. In another embodiment is a compound of Formula (Ib) wherein n1 is 1, n2 is 1, $R^{46}$ is CH$_3$, and $R^{44}$ is CH$_2$OH. In another embodiment is a compound of Formula (Ib) wherein n1 is 1, n2 is 1, $R^{46}$ is CH$_3$, and $R^{44}$ is CH(OH)CH$_3$. In another embodiment is a compound of Formula (Ib) wherein n1 is 1, n2 is 1, $R^{46}$ is CH$_3$, and $R^{44}$ is CH$_2$C(O)NH$_2$. In another embodiment is a compound of Formula (Ib) wherein n1 is 1, n2 is 1, $R^{46}$ is CH$_3$, and $R^{44}$ is CH$_2$CH$_2$CH$_2$CH$_2$NH$_2$.

In another embodiment of the aforementioned embodiments is a compound of Formula (Ib) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (Ib) wherein each m is 0. In another embodiment of the aforementioned embodiments is a compound of Formula (Ib) wherein $R^{41}$, $R^{41'}$, $R^{42}$, $R^{4'}$, and $R^{4''}$ are each independently H.

In another embodiment of the aforementioned embodiments is a compound of Formula (Ib) wherein n3 is 1 and n8 is 1. In another embodiment of the aforementioned embodiments is a compound of Formula (Ib) wherein n3 is 1, n8 is 1, and $R^2$ and $R^3$ are each hydroxy. In another embodiment of the aforementioned embodiments is a compound of Formula (Ib) wherein n3 is 1, n8 is 1, $R^2$ is hydroxy, and $R^3$ is —OR$^{40}$. In another embodiment of the aforementioned embodiments is a compound of Formula (Ib) wherein n3 is 1, n8 is 1, $R^2$ is hydroxy, $R^3$ is —OR$^{40}$, and $R^{40}$ is —(C$_1$-C$_6$)alkyl. In another embodiment of the aforementioned embodiments is a compound of Formula (Ib) wherein n3 is 1, n8 is 1, $R^2$ is hydroxy, $R^3$ is —OR$^{40}$, and $R^{40}$ is —(C$_1$-C$_6$)alkyl-NR$^{41}$R$^{42}$. In another embodiment of the aforementioned embodiments is a compound of Formula (Ib) wherein n3 is 1, n8 is 1, $R^2$ is —OH, $R^3$ is —OR$^{40}$, and $R^{40}$ is —(C$_1$-C$_6$)alkyl-NH$_2$. In another embodiment of the aforementioned embodiments is a compound of Formula (Ib) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a heterocycloalkyl ring. In another embodiment of the aforementioned embodiments is a compound of Formula (Ib) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a morpholinyl ring.

In another embodiment of the aforementioned embodiments is a compound of Formula (Ib) wherein n3 is 1, n8 is 1, $R^3$ is hydroxy, and $R^2$ is —OR$^{40}$. In another embodiment of the aforementioned embodiments is a compound of Formula (Ib) wherein n3 is 1, n8 is 1, $R^3$ is hydroxy, $R^2$ is —OR$^{40}$, and $R^{40}$ is —(C$_1$-C$_6$)alkyl. In another embodiment of the aforementioned embodiments is a compound of Formula (Ib) wherein n3 is 1, n8 is 1, $R^3$ is hydroxy, $R^2$ is —OR$^{40}$, and $R^{40}$ is —(C$_1$-C$_6$)alkyl-NR$^{41}$R$^{42}$. In another embodiment of the aforementioned embodiments is a compound of Formula (Ib) wherein n3 is 1, n8 is 1, $R^3$ is —OH, $R^2$ is —OR$^{40}$, and $R^{40}$ is —(C$_1$-C$_6$)alkyl-NH$_2$. In another embodiment of the aforementioned embodiments is a compound of Formula (Ib) wherein n3 is 1, n8 is 1, $R^3$ is hydroxy, $R^2$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a heterocycloalkyl ring. In another embodiment of the aforementioned embodiments is a compound of Formula (Ib) wherein n3 is 1, n8 is 1, $R^3$ is hydroxy, $R^2$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a morpholinyl ring.

In another embodiment of the aforementioned embodiments is a compound of Formula (Ib) wherein n3 is 1, n8 is 1, $R^2$ is hydroxy, $R^3$ is —OR$^{40}$, and any carbon atom of $R^3$ is substituted with J. In another embodiment of the aforementioned embodiments is a compound of Formula (Ib) wherein n3 is 1, n8 is 1, $R^2$ is hydroxy, $R^3$ is —OR$^{40}$, $R^{40}$ is —(C$_1$-C$_6$)alkyl, and any carbon atom of $R^3$ is substituted with J. In another embodiment of the aforementioned embodiments is a compound of Formula (Ib) wherein n3 is 1, n8 is 1, $R^2$ is hydroxy, $R^3$ is —OR$^{40}$, $R^{40}$ is —(C$_1$-C$_6$)alkyl, and any carbon atom of $R^3$ is substituted with J wherein J is CO$_2$H. In another embodiment of the aforementioned embodiments is a compound of Formula (Ib) wherein n3 is 1, n8 is 1, $R^2$ is hydroxy, $R^3$ is —O—(C$_1$-C$_6$)alkyl-CO$_2$H. In another embodiment of the aforementioned embodiments is a compound of Formula (Ib) wherein n3 is 1, n8 is 1, $R^2$ is hydroxy, $R^3$ is —OCH$_2$CO$_2$H. In another embodiment of the aforementioned embodiments is a compound of Formula (Ib) wherein n3 is 1, n8 is 1, $R^2$ is —OCH$_2$CH$_2$NH$_2$, $R^3$ is —OCH$_2$CO$_2$H. In another embodiment of the aforementioned embodiments is a compound of Formula (Ib) wherein n3 is 1, n8 is 1, $R^2$ is hydroxy, $R^3$ is —OR$^{40}$, $R^{40}$ is $R^{40}$ is —(C$_1$-C$_6$)alkyl-NR$^{41}$R$^{42}$, and any carbon atom of $R^3$ is substituted with J. In another embodiment of the aforementioned embodiments is a compound of Formula (Ib) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, $R^{41}$ is hydrogen, $R^{42}$ is —$(C_1$-$C_6)$alkyl, and any carbon atom of $R^3$ is substituted with J. In another embodiment of the aforementioned embodiments is a compound of Formula (Ib) wherein n3 is 1, n8 is 1, $R^2$ is hydroxy, $R^3$ is —$OR^{40}$, $R^{40}$ is —$(C_1$-$C_6)$alkyl-$NR^{41}R^{42}$, $R^{41}$ is hydrogen, $R^{42}$ is —$(C_1$-$C_6)$ alkyl, and any carbon atom of $R^3$ is substituted with J wherein J is —$NHCH_3$. In another embodiment of the aforementioned embodiments is a compound of Formula (Ib) wherein n3 is 1, n8 is 1, $R^2$ is hydroxy, $R^3$ is —O—$(C_1$-$C_6)$alkyl-N(H)—$(C_1$-$C_6)$alkyl-N(H)$CH_3$. In another embodiment of the aforementioned embodiments is a compound of Formula (Ib) wherein n3 is 1, n8 is 1, $R^2$ is hydroxy, $R^3$ is —$OCH_2CH_2N(H)CH_2CH_2N(H)CH_3$. In another embodiment of the aforementioned embodiments is a compound of Formula (Ib) wherein n3 is 1, n8 is 1, $R^2$ is hydroxy, $R^3$ is —$OCH_2CH_2N(H)CH_2CH_2CH_2N(H)CH_3$.

In another embodiment of the aforementioned embodiments is a compound of Formula (Ib) wherein n3 is 1, n8 is 1, $R^3$ is hydroxy, $R^2$ is —$OR^{40}$, and any carbon atom of $R^2$ is substituted with J. In another embodiment of the aforementioned embodiments is a compound of Formula (Ib) wherein n3 is 1, n8 is 1, $R^3$ is hydroxy, $R^2$ is —$OR^{40}$, $R^{40}$ is —$(C_1$-$C_6)$alkyl, and any carbon atom of $R^2$ is substituted with J. In another embodiment of the aforementioned embodiments is a compound of Formula (Ib) wherein n3 is 1, n8 is 1, $R^3$ is hydroxy, $R^2$ is —$OR^{40}$, $R^{40}$ is —$(C_1$-$C_6)$ alkyl, and any carbon atom of $R^2$ is substituted with J wherein J is $CO_2H$. In another embodiment of the aforementioned embodiments is a compound of Formula (Ib) wherein n3 is 1, n8 is 1, $R^3$ is hydroxy, $R^2$ is —O—$(C_1$-$C_6)$alkyl-$CO_2H$. In another embodiment of the aforementioned embodiments is a compound of Formula (Ib) wherein n3 is 1, n8 is 1, $R^3$ is hydroxy, $R^2$ is —$OCH_2CO_2H$. In another embodiment of the aforementioned embodiments is a compound of Formula (Ib) wherein n3 is 1, n8 is 1, $R^3$ is —$OCH_2CH_2NH_2$, $R^2$ is —$OCH_2CO_2H$. In another embodiment of the aforementioned embodiments is a compound of Formula (Ib) wherein n3 is 1, n8 is 1, $R^3$ is hydroxy, $R^2$ is —$OR^{40}$, $R^{40}$ is $R^{40}$ is —$(C_1$-$C_6)$alkyl-$NR^{41}R^{42}$, and any carbon atom of $R^2$ is substituted with J. In another embodiment of the aforementioned embodiments is a compound of Formula (Ib) wherein n3 is 1, n8 is 1, $R^3$ is hydroxy, $R^2$ is —$OR^{40}$, $R^{40}$ is —$(C_1$-$C_6)$alkyl-$NR^{41}R^{42}$, $R^{41}$ is hydrogen, $R^{42}$ is —$(C_1$-$C_6)$alkyl, and any carbon atom of $R^2$ is substituted with J. In another embodiment of the aforementioned embodiments is a compound of Formula (Ib) wherein n3 is 1, n8 is 1, $R^3$ is hydroxy, $R^2$ is —$OR^{40}$, $R^{40}$ is —$(C_1$-$C_6)$alkyl-$NR^{41}R^{42}$, $R^{41}$ is hydrogen, $R^{42}$ is —$(C_1$-$C_6)$ alkyl, and any carbon atom of $R^2$ is substituted with J wherein J is —$NHCH_3$. In another embodiment of the aforementioned embodiments is a compound of Formula (Ib) wherein n3 is 1, n8 is 1, $R^3$ is hydroxy, $R^2$ is —O—$(C_1$-$C_6)$alkyl-N(H)—$(C_1$-$C_6)$alkyl-N(H)$CH_3$. In another embodiment of the aforementioned embodiments is a compound of Formula (Ib) wherein n3 is 1, n8 is 1, $R^3$ is hydroxy, $R^2$ is —$OCH_2CH_2N(H)CH_2CH_2N(H)CH_3$. In another embodiment of the aforementioned embodiments is a compound of Formula (Ib) wherein n3 is 1, n8 is 1, $R^3$ is hydroxy, $R^2$ is —$OCH_2CH_2N(H)CH_2CH_2CH_2N(H)CH_3$.

In another embodiment is a compound of Formula (I) having the structure of Formula (Ic):

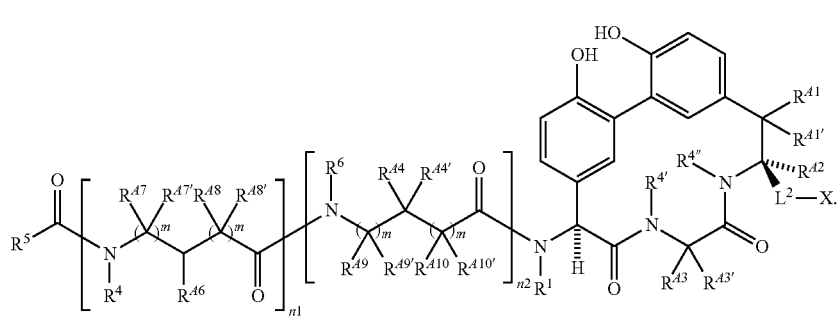

Formula (Ic)

In another embodiment is a compound of Formula (Ic) wherein $L^2$ is a bond. In another embodiment is a compound of Formula (Ic) wherein $L^2$ is optionally substituted $(C_1$-$C_6)$ alkylene. In a further embodiment, $L^2$ is methylene, ethylene, n-propylene, iso-propylene, n-butylene, iso-butylene, or tert-butylene.

In one embodiment is a compound of Formula (Ic) wherein X is —$CH_2OH$, —$CH(OH)CH_3$, —$N(R^4)CH(R^{24})$CN, —$NHCH(R^{24})C(O)CH_3$, —$NHN(R^{24})C(O)CH_3$, —$NHCH(R^{24})CH$=$CHS(O)_2CH_3$, or —$NHCH(R^{24})$CH=$CHS(O)_2NH_2$; and $R^{24}$ is H or $(C_1$-$C_6)$alkyl. In some embodiments is a compound of Formula (Ic) wherein X is —$CH_2OH$. In some embodiments is a compound of Formula (Ic) wherein X is —$CH(OH)CH_3$. In some embodiments is a compound of Formula (Ic) wherein X is —$NHCH(R^{24})C(O)CH_3$. In some embodiments is a compound of Formula (Ic) wherein X is —$NHN(R^{24})C(O)CH_3$. In some embodiments is a compound of Formula (Ic) wherein X is —$NHCH(R^{24})CH$=$CHS(O)_2CH_3$. In some embodiments is a compound of Formula (Ic) wherein X is —$NHCH(R^{24})$CH=$CHS(O)_2NH_2$.

In some embodiments is a compound of Formula (Ic) wherein X is

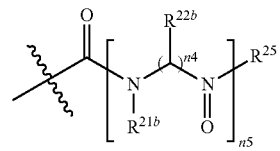

wherein n4 and n5 are each independently 1, 2 or 3; $R^{21b}$ and $R^{22b}$ are independently at each occurrence hydrogen, hydroxy, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 J; and $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1$-$C_6$alkyl), —$CH_2PO_3H$, —$CH_2P(O)(OH)OCH_3$, —$CH_2OC$ (O)CH₃, —CH₂OC(O)R³⁰, —CH₂CO₂R²⁵ᵇ, —CF₂CO₂R²⁵ᵇ, —CH₂CH₂CO₂R²⁵ᵇ, —CH₂CH₂C(O)N(R²⁵ᵇ)₂, —CH₂CH₂C(O)N(H)CH(R²⁶)CO₂R²⁵ᵇ, —CH₂N(H)CH(R²⁶)C(O)N(H)R²⁵ᵇ, —CH₂CH₂R³⁰, —N(H)CH₂(R³⁰), —CH=CHR³⁰, —CH=CHSO₂R²⁵ᵇ,

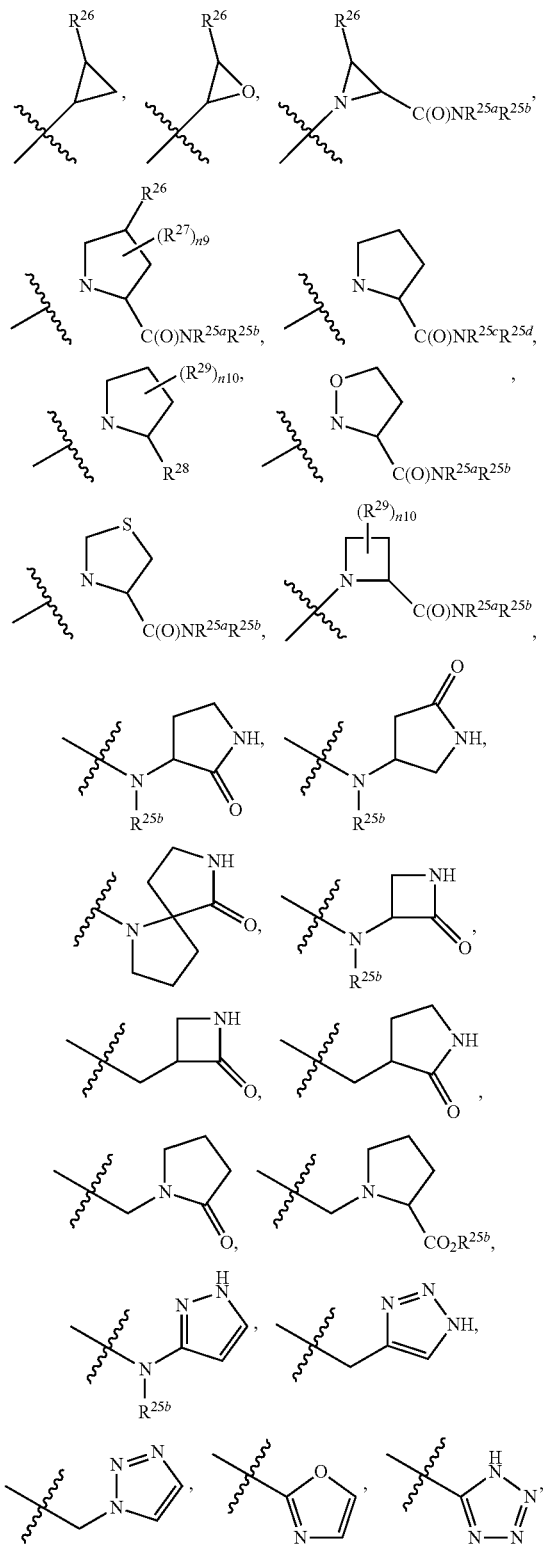

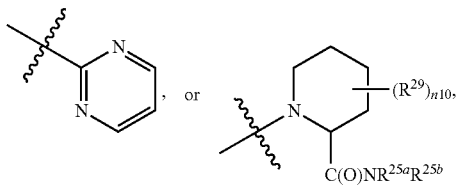

where $R^{25a}$ is H, —OH, —OCH₃, NH₂, SO₂(C₁-C₆)alkyl, or optionally substituted alkyl; each $R^{25b}$ is independently H, or optionally substituted alkyl; $R^{25c}$ is H or optionally substituted alkyl; $R^{25d}$ is —OH, —OCH₃, or NH₂; each $R^{26}$ is independently H, halo or (C₁-C₆)alkyl; each $R^{27}$ is independently —OH, halo, (C₁-C₆)alkyl, or $R^{26}$ and $R^{27}$ are joined to form a cycloalkyl ring; $R^{28}$ is H, —CH₂OH, —CH₂NH₂, —C(O)CH₃, or (C₁-C₆)alkyl; each $R^{29}$ is independently —OH, halo, or (C₁-C₆)alkyl; $R^{30}$ is heterocyclyl, heteroaryl, or aryl; n9 is 1, 2 or 3; and n10 is 0, 1, 2, 3 or 4.

In another embodiment is a compound of Formula (Ic) wherein X is

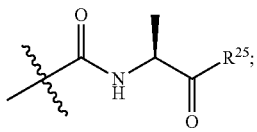

wherein $R^{25}$ is —CH₃, —CH₂Cl, —CH₂OR²⁵ᵇ, —CH₂R³⁰, —C(R²⁶)₂C(O)NH₂, —CH₂SO₂N(R²⁵ᵇ)₂, —CH₂N(R²⁵ᵇ)SO₂(C₁-C₆alkyl), —CH₂PO₃H, —CH₂P(O)(OH)OCH₃, —CH₂OC(O)CH₃, —CH₂OC(O)R³⁰, —CH₂CO₂R²⁵ᵇ, —CF₂CO₂R²⁵ᵇ, —CH₂CH₂CO₂R²⁵ᵇ, —CH₂CH₂C(O)N(R²⁵ᵇ)₂, —CH₂CH₂C(O)N(H)CH(R²⁶)CO₂R²⁵ᵇ, —CH₂N(H)CH(R²⁶)C(O)N(H)R²⁵ᵇ, —CH₂CH₂R³⁰, —N(H)CH₂(R³⁰), —CH=CHR³⁰, —CH=CHSO₂R²⁵ᵇ,

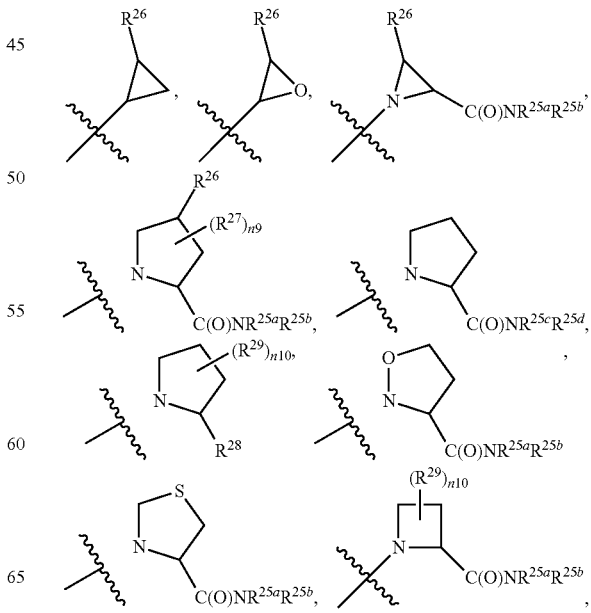

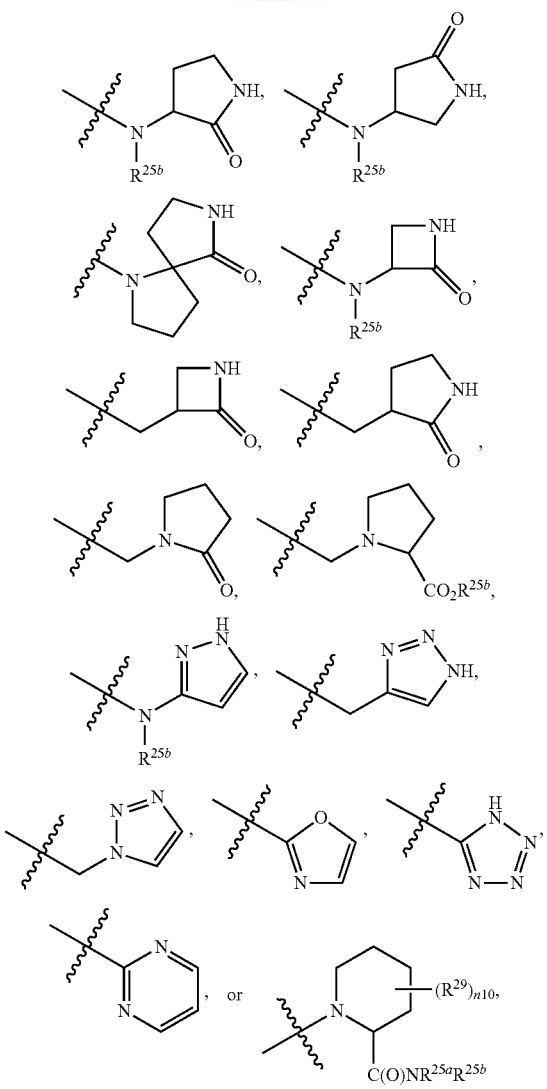

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4. In some embodiments is a compound of Formula (Ic) wherein X is

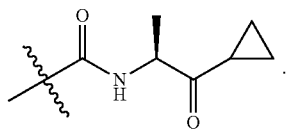 [SMILES: *C(=O)N[C@@H](C)C(=O)C1CC1]

In some embodiments is a compound of Formula (Ic) wherein X is

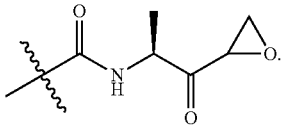 [SMILES: *C(=O)N[C@@H](C)C(=O)C1CO1]

In some embodiments is a compound of Formula (Ic) wherein X is

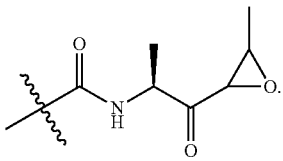 [SMILES: *C(=O)N[C@@H](C)C(=O)C1OC1C]

In some embodiments is a compound of Formula (Ic) wherein X is

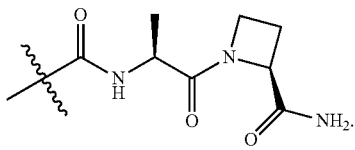 [SMILES: *C(=O)N[C@@H](C)C(=O)N1CC[C@H]1C(N)=O]

In some embodiments is a compound of Formula (Ic) wherein X is

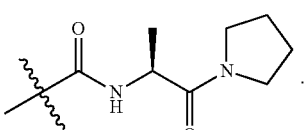

In some embodiments is a compound of Formula (Ic) wherein X is

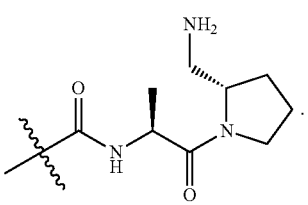

In some embodiments is a compound of Formula (Ic) wherein X is

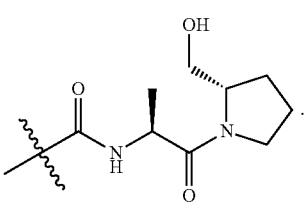 [SMILES: *C(=O)N[C@@H](C)C(=O)N1CCC[C@H]1CO]

In some embodiments is a compound of Formula (Ic) wherein X is

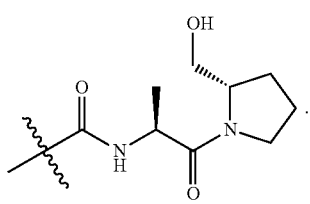 [SMILES: *C(=O)N[C@@H](C)C(=O)N1CCC[C@H]1CO]

In some embodiments is a compound of Formula (Ic) wherein X is

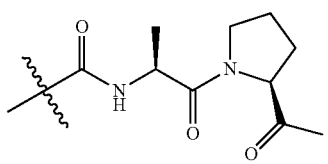

In some embodiments is a compound of Formula (Ic) wherein X is

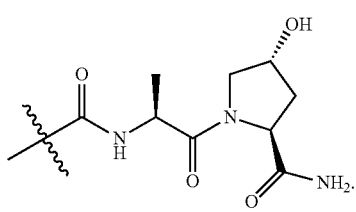 [SMILES: *C(=O)N[C@@H](C)C(=O)N1C[C@H](O)C[C@H]1C(N)=O]

In some embodiments is a compound of Formula (Ic) wherein X is

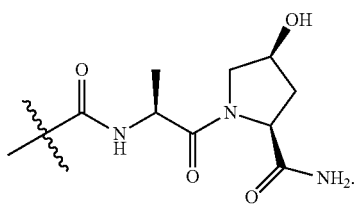 [SMILES: *C(=O)N[C@@H](C)C(=O)N1C[C@@H](O)C[C@H]1C(N)=O]

In some embodiments is a compound of Formula (Ic) wherein X is

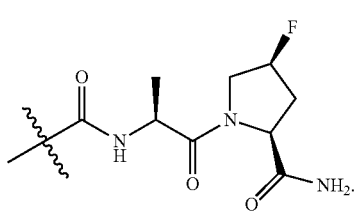 [SMILES: *C(=O)N[C@@H](C)C(=O)N1C[C@@H](F)C[C@H]1C(N)=O]

In some embodiments is a compound of Formula (Ic) wherein X is

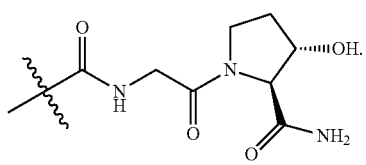 [SMILES: *C(=O)NCC(=O)N1CC[C@H](O)[C@H]1C(N)=O]

In some embodiments is a compound of Formula (Ic) wherein X is

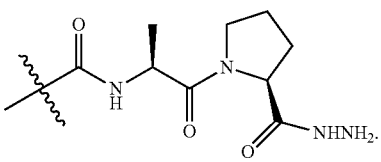 [SMILES: *C(=O)N[C@@H](C)C(=O)N1CCC[C@H]1C(=O)NN]

In some embodiments is a compound of Formula (Ic) wherein X is

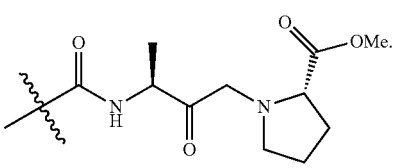 [SMILES: *C(=O)N[C@@H](C)C(=O)CN1CCC[C@H]1C(=O)OC]

In some embodiments is a compound of Formula (Ic) wherein X is

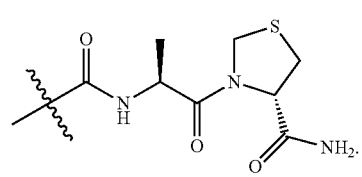 [SMILES: *C(=O)N[C@@H](C)C(=O)N1CSC[C@@H]1C(N)=O]

In some embodiments is a compound of Formula (Ic) wherein X is

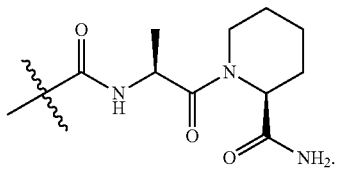 [SMILES: *C(=O)N[C@@H](C)C(=O)N1CCCC[C@H]1C(N)=O]

In some embodiments is a compound of Formula (Ic) wherein X is

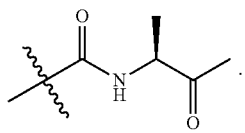 [SMILES: *C(=O)N[C@@H](C)C(C)=O]

In some embodiments is a compound of Formula (Ic) wherein X is

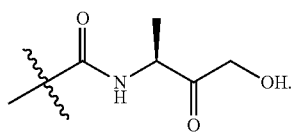 [SMILES: *C(=O)N[C@@H](C)C(=O)CO]

In some embodiments is a compound of Formula (Ic) wherein X is

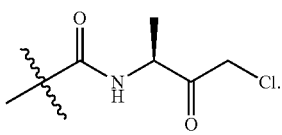 [SMILES: *C(=O)N[C@@H](C)C(=O)CCl]

In some embodiments is a compound of Formula (Ic) wherein X is

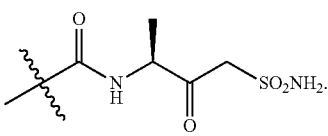 [SMILES: *C(=O)N[C@@H](C)C(=O)CS(N)(=O)=O]

In some embodiments is a compound of Formula (Ic) wherein X is

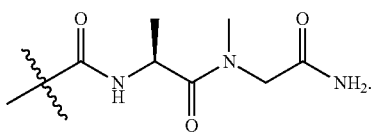 [SMILES: *C(=O)N[C@@H](C)C(=O)N(C)CC(N)=O]

In some embodiments is a compound of Formula (Ic) wherein X is

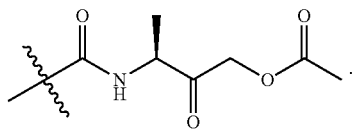 [SMILES: *C(=O)N[C@@H](C)C(=O)COC(C)=O]

In some embodiments is a compound of Formula (Ic) wherein X is

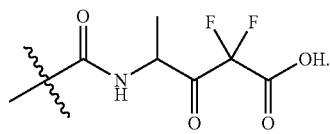 [SMILES: *C(=O)NC(C)C(=O)C(F)(F)C(=O)O]

In some embodiments is a compound of Formula (Ic) wherein X is

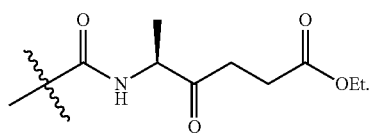 [SMILES: *C(=O)N[C@@H](C)C(=O)CCC(=O)OCC]

In some embodiments is a compound of Formula (Ic) wherein X is

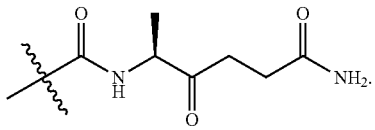 [SMILES: *C(=O)N[C@@H](C)C(=O)CCC(N)=O]

In some embodiments is a compound of Formula (Ic) wherein X is

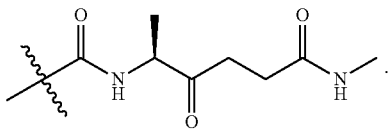 [SMILES: *C(=O)N[C@@H](C)C(=O)CCC(=O)NC]

In some embodiments is a compound of Formula (Ic) wherein X is

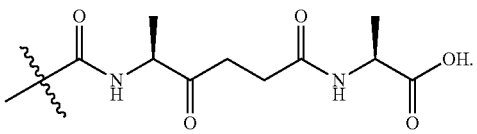 [SMILES: *C(=O)N[C@@H](C)C(=O)CCC(=O)N[C@@H](C)C(=O)O]

In some embodiments is a compound of Formula (Ic) wherein X is

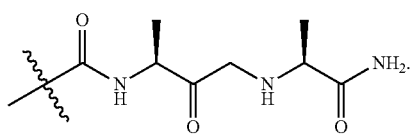 [SMILES: *C(=O)N[C@@H](C)C(=O)CN[C@@H](C)C(N)=O]

In some embodiments is a compound of Formula (Ic) wherein X is

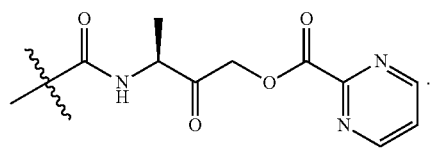 [SMILES: *C(=O)N[C@@H](C)C(=O)COC(=O)c1ncccn1]

In some embodiments is a compound of Formula (Ic) wherein X is

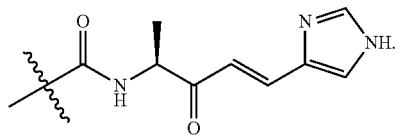 [SMILES: *C(=O)N[C@@H](C)C(=O)/C=C/c1c[nH]cn1]

In some embodiments is a compound of Formula (Ic) wherein X is

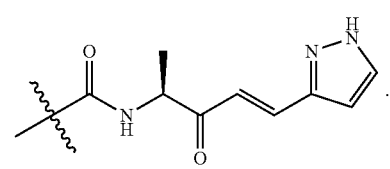 [SMILES: *C(=O)N[C@@H](C)C(=O)/C=C/c1cc[nH]n1]

In some embodiments is a compound of Formula (Ic) wherein X is

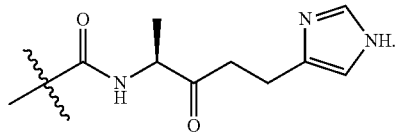 [SMILES: *C(=O)N[C@@H](C)C(=O)CCc1c[nH]cn1]

In some embodiments is a compound of Formula (Ic) wherein X is

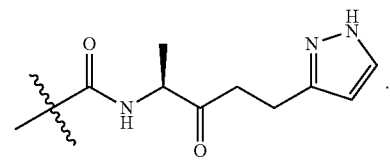 [SMILES: *C(=O)N[C@@H](C)C(=O)CCc1cc[nH]n1]

In some embodiments is a compound of Formula (Ic) wherein X is

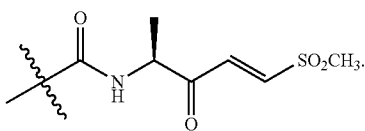 [SMILES: *C(=O)N[C@@H](C)C(=O)/C=C/S(C)(=O)=O]

In some embodiments is a compound of Formula (Ic) wherein X is

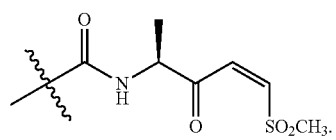 [SMILES: *C(=O)N[C@@H](C)C(=O)/C=C\S(C)(=O)=O]

In some embodiments is a compound of Formula (Ic) wherein X is

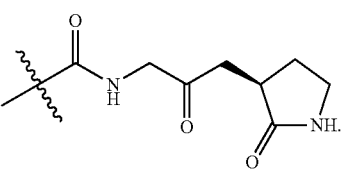 [SMILES: *C(=O)NCC(=O)C[C@H]1CCNC1=O]

In some embodiments is a compound of Formula (Ic) wherein X is

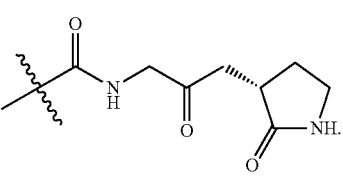 [SMILES: *C(=O)NCC(=O)C[C@@H]1CCNC1=O]

In some embodiments is a compound of Formula (Ic) wherein X is

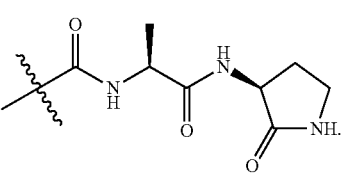 [SMILES: *C(=O)N[C@@H](C)C(=O)N[C@H]1CCNC1=O]

In some embodiments is a compound of Formula (Ic) wherein X is

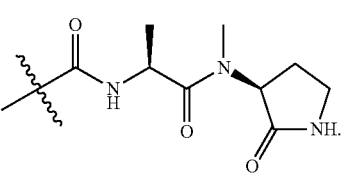 [SMILES: *C(=O)N[C@@H](C)C(=O)N(C)[C@H]1CCNC1=O]

In some embodiments is a compound of Formula (Ic) wherein X is

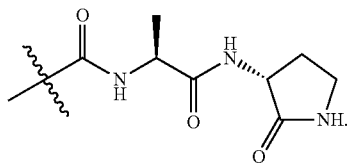 [SMILES: *C(=O)N[C@@H](C)C(=O)N[C@@H]1CCNC1=O]

In some embodiments is a compound of Formula (Ic) wherein X is


In some embodiments is a compound of Formula (Ic) wherein X is

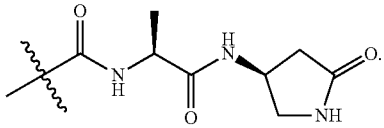 [SMILES: *C(=O)N[C@@H](C)C(=O)N[C@@H]1CNC(=O)C1]

In some embodiments is a compound of Formula (Ic) wherein X is

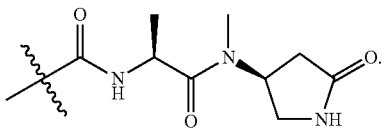 [SMILES: *C(=O)N[C@@H](C)C(=O)N(C)[C@@H]1CNC(=O)C1]

In some embodiments is a compound of Formula (Ic) wherein X is

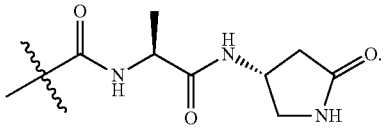 [SMILES: *C(=O)N[C@@H](C)C(=O)N[C@H]1CNC(=O)C1]

In some embodiments is a compound of Formula (Ic) wherein X is

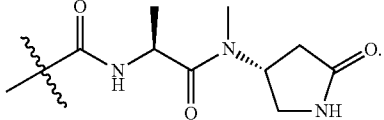 [SMILES: *C(=O)N[C@@H](C)C(=O)N(C)[C@H]1CNC(=O)C1]

In some embodiments is a compound of Formula (Ic) wherein X is

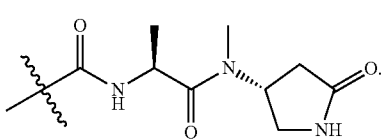

In some embodiments is a compound of Formula (Ic) wherein X is

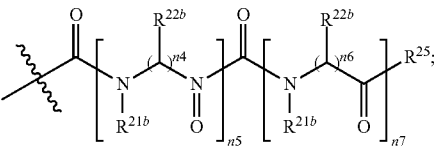

wherein n4 and n5 are each independently 1, 2 or 3; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; and $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1-C_6alkyl)$, —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH(R^{26})CO_2R^{25b}$, —$CH_2N(H)CH(R^{26})C(O)N(H)R^{25b}$, —$CH_2CH_2R^{30}$, —N(H)$CH_2(R^{30})$, —CH=$CHR^{30}$, —CH=$CHSO_2R^{25b}$,

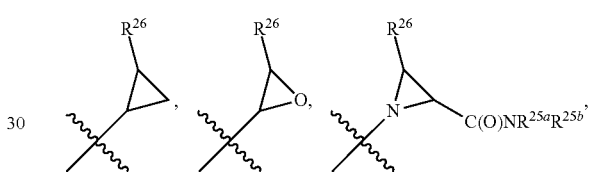

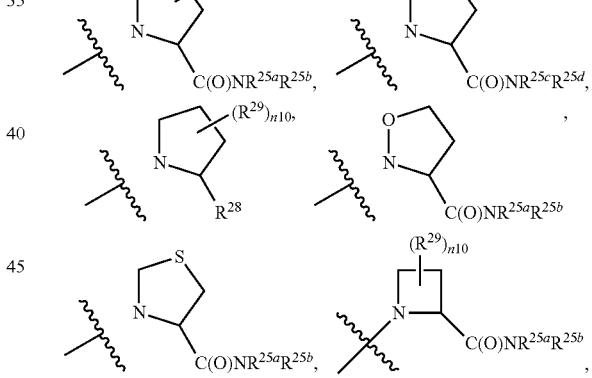

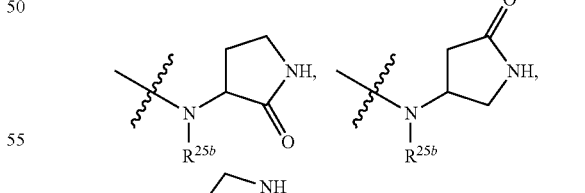

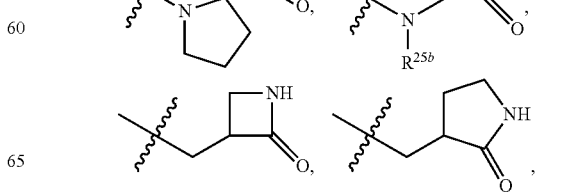

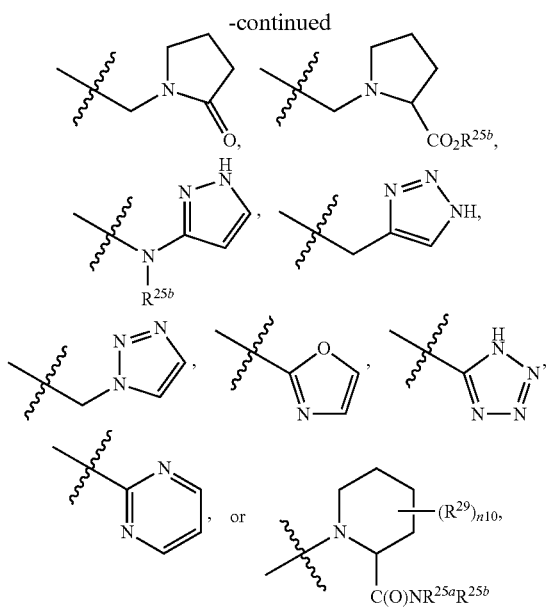

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In some embodiments is a compound of Formula (Ic) wherein R$^5$ is a linear or branched alkyl chain of about 1-22 carbon atoms, wherein R$^5$ is bonded to the carbonyl carbon to which it is attached directly or by an NR$^4$, to provide an amide or urea linkage, respectively; optionally comprising within the chain or at a chain terminus optionally substituted aryl, optionally substituted heteroaryl, or optionally substituted

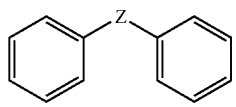

wherein Z is a bond, O, S, NH, CH$_2$ or C≡C. In some embodiments is a compound of Formula (Ic) wherein R$^5$ is a linear or branched alkyl chain of about 1-22 carbon atoms, wherein R$^5$ is bonded to the carbonyl carbon to which it is attached directly to provide an amide linkage, optionally comprising within the chain or at a chain terminus optionally substituted aryl, optionally substituted heteroaryl, or optionally substituted

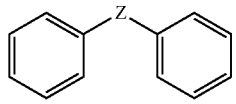

wherein Z is a bond, O, S, NH, CH$_2$ or C≡C. In some embodiments is a compound of Formula (Ic) wherein R$^5$ is a linear alkyl chain of about 1-22 carbon atoms, wherein R$^5$ is bonded to the carbonyl carbon to which it is attached directly to provide an amide linkage, comprising within the chain or at a chain terminus

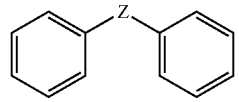

wherein Z is a bond. In some embodiments is a compound of Formula (Ic) wherein R$^5$ is a linear alkyl chain of about 4-22 carbon atoms, wherein R$^5$ is bonded to the carbonyl carbon to which it is attached directly to provide an amide linkage, comprising at a chain terminus

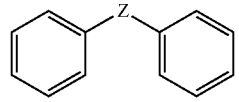

wherein Z is a bond. In some embodiments is a compound of Formula (Ic) wherein R$^5$ is a linear alkyl chain of about 4-22 carbon atoms, wherein R$^5$ is bonded to the carbonyl carbon to which it is attached directly to provide an amide linkage, comprising within the chain

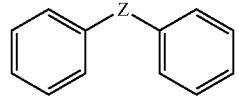

wherein Z is a bond. In some embodiments is a compound of Formula (Ic) wherein R$^5$ is a linear or branched alkyl chain of about 1-22 carbon atoms, wherein R$^5$ is bonded to the carbonyl carbon to which it is attached directly or by an NR$^4$, to provide an amide or urea linkage, respectively; optionally comprising within the chain or at a chain terminus optionally substituted aryl. In some embodiments is a compound of Formula (Ic) wherein R$^5$ is a linear or branched alkyl chain of about 2-22 carbon atoms, wherein R$^5$ is bonded to the carbonyl carbon to which it is attached directly to provide an amide linkage, comprising within the chain or at a chain terminus optionally substituted aryl. In some embodiments is a compound of Formula (Ic) wherein R$^5$ is a linear or branched alkyl chain of about 2-22 carbon atoms, wherein R$^5$ is bonded to the carbonyl carbon to which it is attached directly to provide an amide linkage, comprising at a chain terminus optionally substituted aryl. In some embodiments is a compound of Formula (Ic) wherein R$^5$ is a linear or branched alkyl chain of about 2-22 carbon atoms, wherein R$^5$ is bonded to the carbonyl carbon to which it is attached directly to provide an amide linkage, comprising within the chain optionally substituted aryl. In some embodiments is a compound of Formula (Ic) wherein R$^5$ is a linear or branched alkyl chain of about 1-22 carbon atoms, wherein R$^5$ is bonded to the carbonyl carbon to which it is attached directly to provide an amide or urea linkage. In some embodiments is a compound of Formula (Ic) wherein R$^5$ is a linear or branched alkyl chain of about 4-18 carbon atoms, wherein R$^5$ is bonded to the carbonyl carbon to which it is attached directly to provide an amide or urea linkage. In some embodiments is a compound of Formula (Ic) wherein $R^5$ is a linear or branched alkyl chain of about 6-16 carbon atoms, wherein $R^5$ is bonded to the carbonyl carbon to which it is attached directly to provide an amide or urea linkage. In some embodiments is a compound of Formula (Ic) wherein $R^5$ is

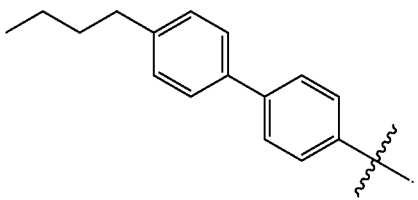

In some embodiments is a compound of Formula (Ic) wherein $R^5$ is

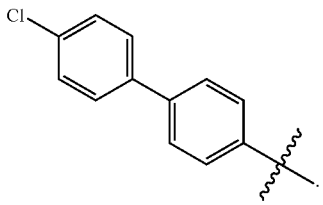

In some embodiments is a compound of Formula (Ic) wherein $R^5$ is a linear or branched alkyl chain of about 1-22 carbon atoms, comprising within the chain at least one —O— or —N($R^4$)—. In some embodiments is a compound of Formula (Ic) wherein $R^5$ is a linear or branched alkyl chain of about 1-22 carbon atoms, comprising within the chain at least one —O—. In some embodiments is a compound of Formula (Ic) wherein $R^5$ is a linear or branched alkyl chain of about 1-22 carbon atoms, comprising within the chain at least one —N($R^4$)—. In some embodiments is a compound of Formula (Ic) wherein $R^5$ is a linear or branched alkyl chain of about 1-22 carbon atoms, comprising within the chain at least one —N(H)—. In some embodiments is a compound of Formula (Ic) wherein $R^5$ is —$CH_2CH_2N(H)(CH_2)_9CH_3$.

In another embodiment is a compound of Formula (Ic) wherein n1 is 0 and n2 is 1. In another embodiment is a compound of Formula (Ic) wherein n1 is 0, n2 is 1, and $R^{44}$ is H. In another embodiment is a compound of Formula (Ic) wherein n1 is 0, n2 is 1, and $R^{44}$ is $(C_1-C_6)$alkyl optionally substituted with 1 to 3 J. In another embodiment is a compound of Formula (Ic) wherein n1 is 0, n2 is 1, and $R^{44}$ is $CH_3$. In another embodiment is a compound of Formula (Ic) wherein n1 is 0, n2 is 1, and $R^{44}$ is $CH_2CH_3$. In another embodiment is a compound of Formula (Ic) wherein n1 is 0, n2 is 1, and $R^{44}$ is $CH_2CH(CH_3)_2$. In another embodiment is a compound of Formula (Ic) wherein n1 is 0, n2 is 1, and $R^{44}$ is $CH_2OH$. In another embodiment is a compound of Formula (Ic) wherein n1 is 0, n2 is 1, and $R^{44}$ is $CH(OH)CH_3$. In another embodiment is a compound of Formula (Ic) wherein n1 is 0, n2 is 1, and $R^{44}$ is $CH_2C(O)NH_2$. In another embodiment is a compound of Formula (Ic) wherein n1 is 0, n2 is 1, and $R^{44}$ is $CH_2CH_2CH_2CH_2NH_2$.

In another embodiment is a compound of Formula (Ic) wherein n1 is 1 and n2 is 1. In another embodiment is a compound of Formula (Ic) wherein n1 is 1, n2 is 1, $R^{46}$ is $CH_3$, and $R^{44}$ is $(C_1-C_6)$alkyl optionally substituted with 1 to 3 J. In another embodiment is a compound of Formula (Ic) wherein n1 is 1, n2 is 1, $R^{46}$ is $CH_3$, and $R^{44}$ is $CH_3$. In another embodiment is a compound of Formula (Ic) wherein n1 is 1, n2 is 1, $R^{46}$ is $CH_3$, and $R^{44}$ is $CH_2CH_3$. In another embodiment is a compound of Formula (Ic) wherein n1 is 1, n2 is 1, $R^{46}$ is $CH_3$, and $R^{44}$ is $CH_2CH(CH_3)_2$. In another embodiment is a compound of Formula (Ic) wherein n1 is 1, n2 is 1, $R^{46}$ is $CH_3$, and $R^{44}$ is $CH_2OH$. In another embodiment is a compound of Formula (Ic) wherein n1 is 1, n2 is 1, $R^{46}$ is $CH_3$, and $R^{44}$ is $CH(OH)CH_3$. In another embodiment is a compound of Formula (Ic) wherein n1 is 1, n2 is 1, $R^{46}$ is $CH_3$, and $R^{44}$ is $CH_2C(O)NH_2$. In another embodiment is a compound of Formula (Ic) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (Ic) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (Ic) wherein each m is 0. In another embodiment of the aforementioned embodiments is a compound of Formula (Ic) wherein $R^{41}$, $R^{41'}$, $R^{42}$, $R^{4'}$, and $R^{4''}$ are each independently H.

In another embodiment of the aforementioned embodiments is a compound of Formula (I) having the structure of Formula (Id):

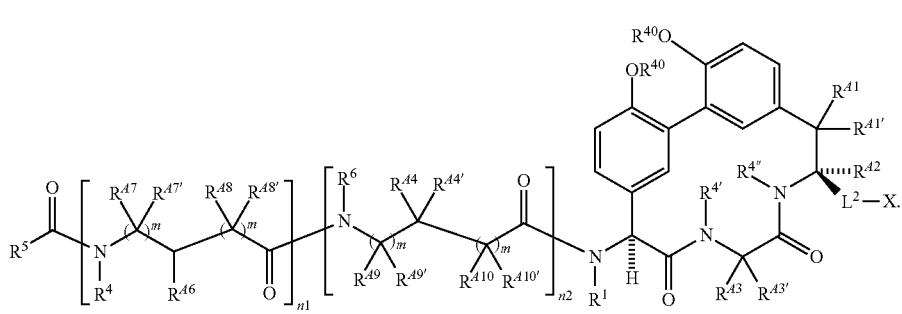

Formula (Id)

In another embodiment described herein are compounds of Formula (II):

Formula (II)

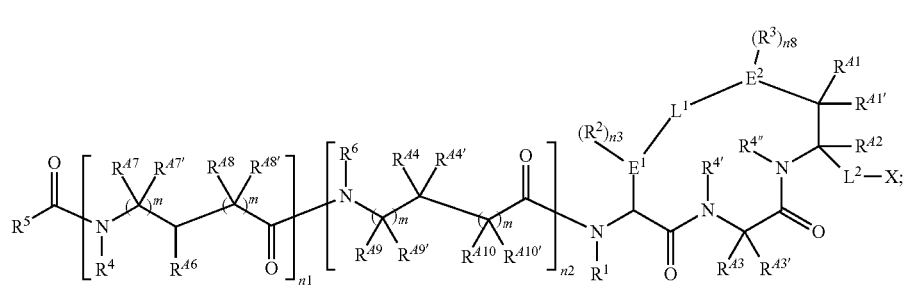

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1-C_4)$alkylene optionally substituted with OH, CN, NO$_2$, halogen, $(C_1-C_6)$alkyl;

$L^2$ is a bond, or optionally substituted $(C_1-C_6)$alkylene;

X is a group of formula

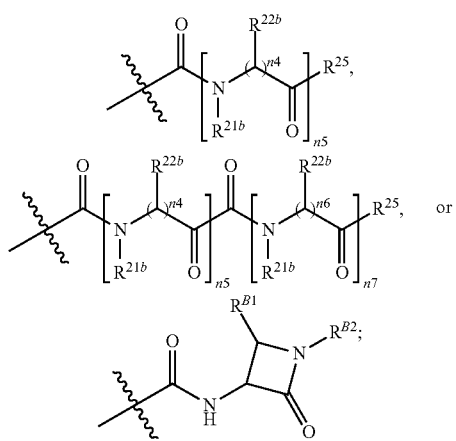

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, OR$^C$,

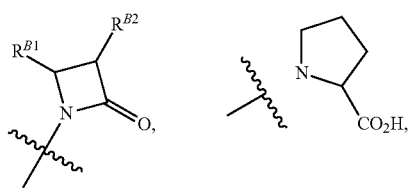

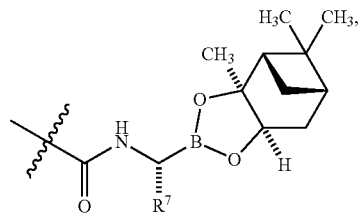

or NR$^{25a}$R$^{25b}$ where $R^{25a}$ and $R^{25b}$ are each independently H, SO$_2$(C$_1$-C$_6$)alkyl, or optionally substituted alkyl; $R^{B1}$ and $R^{B2}$ are each independently H, $(C_1-C_6)$ alkyl, $(C_3-C_6)$ cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, $(C_1-C_6)$alkoxy, $(C_1-C_6)$thioalkoxy, N(R$^C$)$_2$, 5-7 membered heterocyclyl or 5-7 membered heteroaryl, or $(C_6-C_{10})$ aryl; $R^C$ is independently at each occurrence H or $(C_1-C_6)$ alkyl; or X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

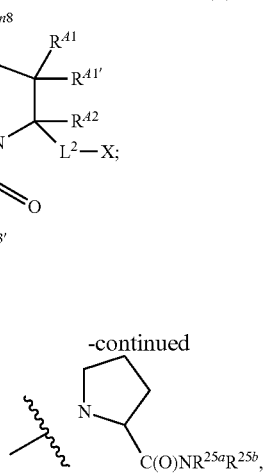

wherein $R^7$ is H, methyl, ethyl, or —CH$_2$OH; or $R^7$ and $R^{B3}$ together with the boron atom form a 5- or 6-membered boron containing ring; $R^{B3}$ and $R^{B4}$ are each independently H, $(C_1-C_6)$alkyl, —CH$_2$CO$_2$H, —CH$_2$CH$_2$CO$_2$H; or $R^{B3}$ and $R^{B4}$ together with the boron atom form an optionally substituted 5- or 6-membered boron containing ring;

$R^5$ is a linear or branched alkyl chain of about 1-22 carbon atoms, comprising within the chain at least one —O— or —N(R$^4$)—;

each $R^2$ and $R^3$ are each independently hydroxy, nitro, halo, cyano, glycosyloxy, amino, $(C_1-C_4)$alkyl, OR$^{40}$, or a group cleavable under physiological conditions to provide a compound of formula (II) wherein $R^2$ or $R^3$ respectively is hydroxy, wherein any carbon atom is optionally substituted with J;

each $R^{40}$ is independently —$(C_1-C_6)$alkyl, or —$(C_1-C_6)$alkyl-NR$^{41}$R$^{42}$;

each $R^{41}$ and $R^{42}$ is hydrogen, —$(C_1-C_6)$alkyl, —$(C_1-C_6)$heteroalkyl, —C(O)(C$_1$-C$_6$)alkyl, —C(O)N(R$^{43}$)$_2$, —SO$_2$N(R$^{43}$)$_2$; or $R^{41}$ and $R^{42}$ and the nitrogen atom to which that are attached form a heterocycloalkyl ring;

each $R^{43}$ is independently hydrogen or —$(C_1-C_6)$alkyl; or two $R^{43}$ and the nitrogen atom to which that are attached form a heterocycloalkyl ring;

n1 and n2 are independently 0 or 1;
n3 and n8 are independently 0, 1, or 2;
each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{A4}$ form a ring;

$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{A6}$ is H, amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

each J is independently halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (II) having the structure of Formula (IIa):

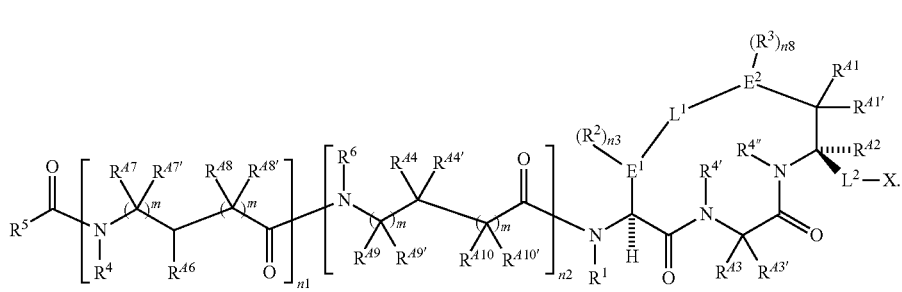

Formula (IIa)

In another embodiment described herein are compounds of Formula (II) having the structure of Formula (IIb):

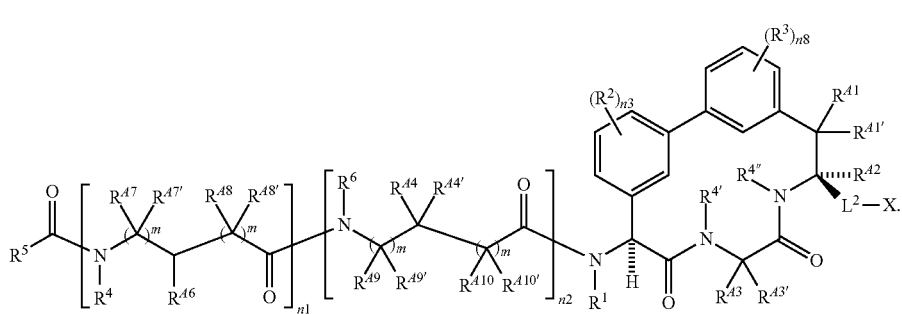

Formula (IIb)

In another embodiment described herein are compounds of Formula (II) having the structure of Formula (IIc):

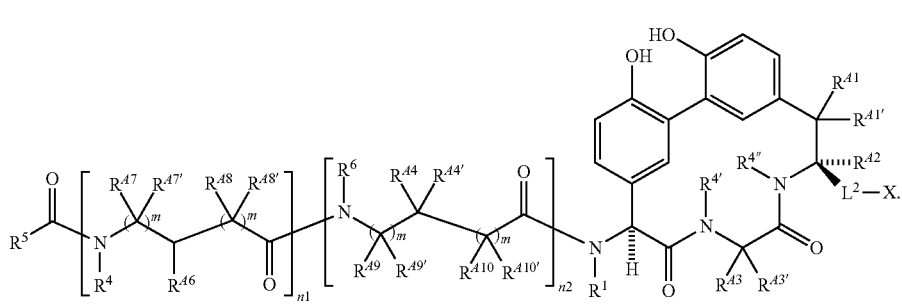

Formula (IIc)

In another embodiment is a compound of Formula (II), (IIa), (IIb), or (IIc) wherein L² is a bond. In another embodiment is a compound of Formula (II), (IIa), (IIb), or (IIc) wherein L² is optionally substituted (C₁-C₆)alkylene. In a further embodiment, L² is methylene, ethylene, n-propylene, iso-propylene, n-butylene, iso-butylene, or tert-butylene.

In one embodiment is a compound of Formula (II), (IIa), (IIb), or (IIc) wherein X is CO₂H, CH₂CO₂H, C(=O)NHCH₂C(=O)H, CH₂C(=O)H, C(=O)N(H)CH(R⁷)B(OR^{B3})(OR^{B4}), or

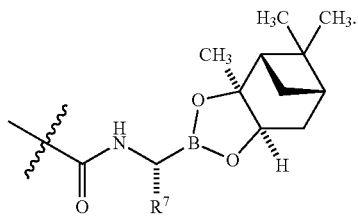

In some embodiments is a compound of Formula (II), (IIa), (IIb), or (IIc) wherein X is CO₂H. In some embodiments is a compound of Formula (II), (IIa), (IIb), or (IIc) wherein X is CH₂CO₂H. In some embodiments is a compound of Formula (II), (IIa), (IIb), or (IIc) wherein X is C(=O)NHCH₂C(=O)H. In some embodiments is a compound of Formula (II), (IIa), (IIb), or (IIc) wherein X is CH₂C(=O)H.

In some embodiments is a compound of Formula (II), (IIa), (IIb), or (IIc) wherein X is C(=O)N(H)CH(R⁷)B(OR^{B3})(OR^{B4}). In further embodiments is a compound of Formula (II), (IIa), (IIb), or (IIc) wherein X is C(=O)N(H)CH₂B(OH)₂. In further embodiments is a compound of Formula (II), (IIa), (IIb), or (IIc) wherein X is C(=O)N(H)CH(CH₃)B(OH)₂. In further embodiments is a compound of Formula (II), (IIa), (IIb), or (IIc) wherein X is C(=O)N(H)CH(CH₂CH₃)B(OH)₂. In further embodiments is a compound of Formula (II), (IIa), (IIb), or (IIc) wherein X is C(=O)N(H)CH(CH₂OH)B(OH)₂. In further embodiments is a compound of Formula (II), (IIa), (IIb), or (IIc) wherein X is C(=O)N(H)CH₂B(OCH₃)₂. In further embodiments is a compound of Formula (II), (IIa), (IIb), or (IIc) wherein X is C(=O)N(H)CH(CH₃)B(OCH₃)₂. In further embodiments is a compound of Formula (II), (IIa), (IIb), or (IIc) wherein X is C(=O)N(H)CH(CH₂CH₃)B(OCH₃)₂. In further embodiments is a compound of Formula (II), (IIa), (IIb), or (IIc) wherein X is C(=O)N(H)CH(CH₂OH)B(OCH₃)₂.

In some embodiments is a compound of Formula (II), (IIa), (IIb), or (IIc) wherein X is C(=O)N(H)CH(R⁷)B(OR^{B3})(OR^{B4}) and R^{B3} and R⁷ together with the boron atom form an optionally substituted 5- or 6-membered boron containing ring. In some embodiments is a compound of Formula (II), (IIa), (IIb), or (IIc) wherein X is

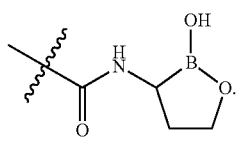 [SMILES: *C(=O)NC1CCOB1O]

In some embodiments is a compound of Formula (II), (IIa), (IIb), or (IIc) wherein X is

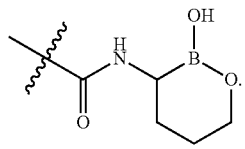 [SMILES: *C(=O)NC1CCCOB1O]

In some embodiments is a compound of Formula (II), (IIa), (IIb), or (IIc) wherein X is C(=O)N(H)CH(R⁷)B(OR^{B3})(OR^{B4}) and R^{B3} and R^{B4} together with the boron atom form an optionally substituted 5- or 6-membered boron containing ring. In some embodiments is a compound of Formula (II), (IIa), (IIb), or (IIc) wherein X is

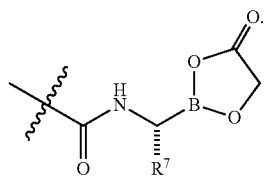

In some embodiments is a compound of Formula (II), (IIa), (IIb), or (IIc) wherein X is

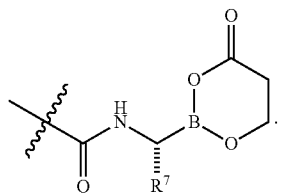

In some embodiments is a compound of Formula (II), (IIa), (IIb), or (IIc) wherein X is C(=O)N(H)CH(R⁷)B(OR^{B3})(OR^{B4}) and R^{B3} and R^{B4} together with the boron atom form an optionally substituted 5- or 6-membered boron containing ring derived from a sugar. In some embodiments is a compound of Formula (II), (IIa), (IIb), or (IIc) wherein X is

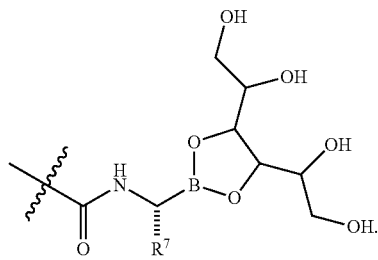

In some embodiments is a compound of Formula (II), (IIa), (IIb), or (IIc) wherein X is

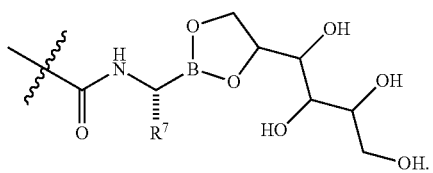

In some embodiments is a compound of Formula (II), (IIa), (IIb), or (IIc) wherein X is

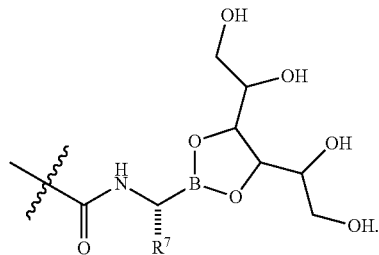

In some embodiments is a compound of Formula (II), (IIa), (IIb), or (IIc) wherein X is

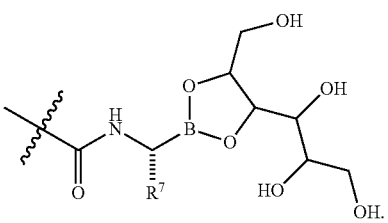

In some embodiments is a compound of Formula (II), (IIa), (IIb), or (IIc) wherein X is

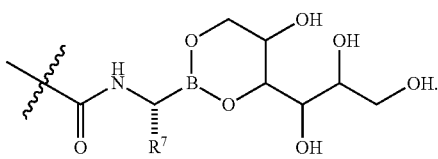

In some embodiments is a compound of Formula (II), (IIa), (IIb), or (IIc) wherein X is

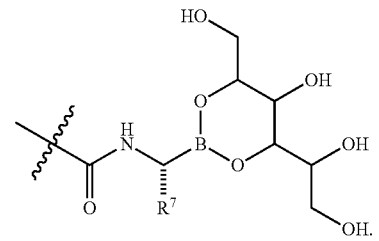

In some embodiments is a compound of Formula (II), (IIa), (IIb), or (IIc) wherein X is

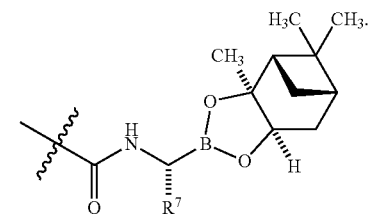

In further embodiments is a compound of Formula (II), (IIa), (IIb), or (IIc) wherein X is

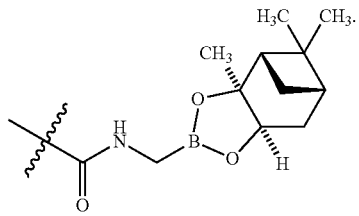 [SMILES: *C(=O)NCB1O[C@@H]2C[C@@H]3C[C@@H](C3(C)C)[C@]2(C)O1]

In further embodiments is a compound of Formula (II), (IIa), (IIb), or (IIc) wherein X is

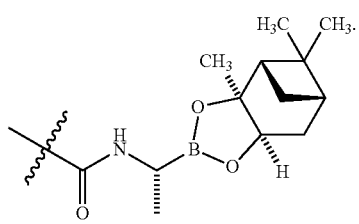 [SMILES: *C(=O)N[C@@H](C)B1O[C@@H]2C[C@@H]3C[C@@H](C3(C)C)[C@]2(C)O1]

In further embodiments is a compound of Formula (II), (IIa), (IIb), or (IIc) wherein X is

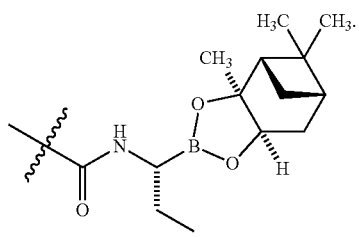 [SMILES: *C(=O)N[C@@H](CC)B1O[C@@H]2C[C@@H]3C[C@@H](C3(C)C)[C@]2(C)O1]

In further embodiments is a compound of Formula (II), (IIa), (IIb), or (IIc) wherein X is

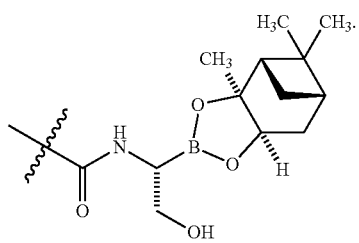 [SMILES: *C(=O)N[C@@H](CO)B1O[C@@H]2C[C@@H]3C[C@@H](C3(C)C)[C@]2(C)O1]

In some embodiments is a compound of Formula (II), (IIa), (IIb), or (IIc) wherein $R^5$ is a linear or branched alkyl chain of about 1-22 carbon atoms, comprising within the chain at least one —O— or —N($R^4$)—. In some embodiments is a compound of Formula (II), (IIa), (IIb), or (IIc) wherein $R^5$ is a linear or branched alkyl chain of about 1-22 carbon atoms, comprising within the chain at least one —O—. In some embodiments is a compound of Formula (II), (IIa), (IIb), or (IIc) wherein $R^5$ is a linear or branched alkyl chain of about 1-22 carbon atoms, comprising within the chain at least one —N($R^4$)—. In some embodiments is a compound of Formula (II), (IIa), (IIb), or (IIc) wherein $R^5$ is a linear or branched alkyl chain of about 1-22 carbon atoms, comprising within the chain at least one —N(H)—. In some embodiments is a compound of Formula (II), (IIa), (IIb), or (IIc) wherein $R^5$ is —CH$_2$CH$_2$N(H)(CH$_2$)$_9$CH$_3$.

In another embodiment is a compound of Formula (II), (IIa), (IIb), or (IIc) wherein n1 is 0 and n2 is 1. In another embodiment is a compound of Formula (II), (IIa), (IIb), or (IIc) wherein n1 is 0, n2 is 1, and $R^{44}$ is H. In another embodiment is a compound of Formula (II), (IIa), (IIb), or (IIc) wherein n1 is 0, n2 is 1, and $R^{44}$ is (C$_1$-C$_6$)alkyl optionally substituted with 1 to 3 J. In another embodiment is a compound of Formula (II), (IIa), (IIb), or (IIc) wherein n1 is 0, n2 is 1, and $R^{44}$ is CH$_3$. In another embodiment is a compound of Formula (II), (IIa), (IIb), or (IIc) wherein n1 is 0, n2 is 1, and $R^{44}$ is CH$_2$CH$_3$. In another embodiment is a compound of Formula (II), (IIa), (IIb), or (IIc) wherein n1 is 0, n2 is 1, and $R^{44}$ is CH$_2$CH(CH$_3$)$_2$. In another embodiment is a compound of Formula (II), (IIa), (IIb), or (IIc) wherein n1 is 0, n2 is 1, and $R^{44}$ is CH$_2$OH. In another embodiment is a compound of Formula (II), (IIa), (IIb), or (IIc) wherein n1 is 0, n2 is 1, and $R^{44}$ is CH(OH)CH$_3$. In another embodiment is a compound of Formula (II), (IIa), (IIb), or (IIc) wherein n1 is 0, n2 is 1, and $R^{44}$ is CH$_2$C(O)NH$_2$. In another embodiment is a compound of Formula (II), (IIa), (IIb), or (IIc) wherein n1 is 0, n2 is 1, and $R^{44}$ is CH$_2$CH$_2$CH$_2$CH$_2$NH$_2$.

In another embodiment is a compound of Formula (II), (IIa), (IIb), or (IIc) wherein n1 is 1 and n2 is 1. In another embodiment is a compound of Formula (II), (IIa), (IIb), or (IIc) wherein n1 is 1, n2 is 1, $R^{46}$ is H, and $R^{44}$ is H. In another embodiment is a compound of Formula (II), (IIa), (IIb), or (IIc) wherein n1 is 1, n2 is 1, $R^{46}$ is H, and $R^{44}$ is (C$_1$-C$_6$)alkyl optionally substituted with 1 to 3 J. In another embodiment is a compound of Formula (II), (IIa), (IIb), or (IIc) wherein n1 is 1, n2 is 1, $R^{46}$ is H, and $R^{44}$ is CH$_3$. In another embodiment is a compound of Formula (II), (IIa), (IIb), or (IIc) wherein n1 is 1, n2 is 1, $R^{46}$ is H, and $R^{44}$ is CH$_2$CH$_3$. In another embodiment is a compound of Formula (II), (IIa), (IIb), or (IIc) wherein n1 is 1, n2 is 1, $R^{46}$ is H, and $R^{44}$ is CH$_2$CH(CH$_3$)$_2$. In another embodiment is a compound of Formula (II), (IIa), (IIb), or (IIc) wherein n1 is 1, n2 is 1, $R^{46}$ is H, and $R^{44}$ is CH$_2$OH. In another embodiment is a compound of Formula (II), (IIa), (IIb), or (IIc) wherein n1 is 1, n2 is 1, $R^{46}$ is H, and $R^{44}$ is CH(OH)CH$_3$. In another embodiment is a compound of Formula (II), (IIa), (IIb), or (IIc) wherein n1 is 1, n2 is 1, $R^{46}$ is H, and $R^{44}$ is CH$_2$C(O)NH$_2$. In another embodiment is a compound of Formula (II), (IIa), (IIb), or (IIc) wherein n1 is 1, n2 is 1, $R^{46}$ is H, and $R^{44}$ is CH$_2$CH$_2$CH$_2$CH$_2$NH$_2$.

In another embodiment of the aforementioned embodiments is a compound of Formula (II), (IIa), (IIb), or (IIc) wherein n3 is 1 and n8 is 1.

In another embodiment of the aforementioned embodiments is a compound of Formula (II), (IIa), or (IIb) wherein n3 is 1, n8 is 1, and $R^2$ and $R^3$ are each hydroxy. In another embodiment of the aforementioned embodiments is a compound of Formula (II), (IIa), or (IIb) wherein n3 is 1, n8 is 1, $R^2$ is hydroxy, and $R^3$ is —OR$^{40}$. In another embodiment of the aforementioned embodiments is a compound of Formula (II), (IIa), or (IIb) wherein n3 is 1, n8 is 1, $R^2$ is hydroxy, $R^3$ is —OR$^{40}$, and $R^{40}$ is —(C$_1$-C$_6$)alkyl. In another embodiment of the aforementioned embodiments is a compound of Formula (II), (IIa), or (IIb) wherein n3 is 1, n8 is 1, $R^2$ is hydroxy, $R^3$ is —OR$^{40}$, and $R^{40}$ is —(C$_1$-C$_6$)alkyl-NR$^{41}$R$^{42}$. In another embodiment of the aforementioned embodiments is a compound of Formula (II), (IIa), or (IIb) wherein n3 is 1, n8 is 1, $R^2$ is —OH, $R^3$ is —OR$^{40}$, and $R^{40}$ is —(C$_1$-C$_6$)alkyl-NH$_2$. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a heterocycloalkyl ring. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a morpholinyl ring.

In another embodiment of the aforementioned embodiments is a compound of Formula (II), (IIa), or (IIb) wherein n3 is 1, n8 is 1, $R^3$ is hydroxy, and $R^2$ is —OR$^{40}$. In another embodiment of the aforementioned embodiments is a compound of Formula (II), (IIa), or (IIb) wherein n3 is 1, n8 is 1, $R^3$ is hydroxy, $R^2$ is —OR$^{40}$, and $R^{40}$ is —(C$_1$-C$_6$)alkyl. In another embodiment of the aforementioned embodiments is a compound of Formula (II), (IIa), or (IIb) wherein n3 is 1, n8 is 1, $R^3$ is hydroxy, $R^2$ is —OR$^{40}$, and $R^{40}$ is —(C$_1$-C$_6$)alkyl-NR$^{41}$R$^{42}$. In another embodiment of the aforementioned embodiments is a compound of Formula (II), (IIa), or (IIb) wherein n3 is 1, n8 is 1, $R^3$ is —OH, $R^2$ is —OR$^{40}$, and $R^{40}$ is —(C$_1$-C$_6$)alkyl-NH$_2$. In another embodiment of the aforementioned embodiments is a compound of Formula (II), (IIa), or (IIb) wherein n3 is 1, n8 is 1, $R^3$ is hydroxy, $R^2$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a heterocycloalkyl ring. In another embodiment of the aforementioned embodiments is a compound of Formula (II), (IIa), or (IIb) wherein n3 is 1, n8 is 1, $R^3$ is hydroxy, $R^2$ is —OR$^{40}$, $R^{40}$ is —(C$_1$-C$_6$)alkyl-NR$^{41}$R$^{42}$, and $R^{41}$ and $R^{42}$ and the nitrogen atom to which that are attached form a morpholinyl ring.

In another embodiment of the aforementioned embodiments is a compound of Formula (II), (IIa), or (IIb) wherein n3 is 1, n8 is 1, $R^2$ is hydroxy, $R^3$ is —OR$^{40}$, and any carbon atom of $R^3$ is substituted with J. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl, and any carbon atom of $R^3$ is substituted with J. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl, and any carbon atom of $R^3$ is substituted with J wherein J is CO$_2$H. In another embodiment of the aforementioned embodiments is a compound of Formula (II), (IIa), or (IIb) wherein n3 is 1, n8 is 1, $R^2$ is hydroxy, $R^3$ is —O—(C$_1$-C$_6$)alkyl-CO$_2$H. In another embodiment of the aforementioned embodiments is a compound of Formula (II), (IIa), or (IIb) wherein n3 is 1, n8 is 1, $R^2$ is hydroxy, $R^3$ is —OCH$_2$CO$_2$H. In another embodiment of the aforementioned embodiments is a compound of Formula (II), (IIa), or (IIb) wherein n3 is 1, n8 is 1, $R^2$ is —OCH$_2$CH$_2$NH$_2$, $R^3$ is —OCH$_2$CO$_2$H. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is $R^{40}$ is —(C$_1$-C$_6$)alkyl-NR$^{41}$R$^{42}$, and any carbon atom of $R^3$ is substituted with J. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, $R^{41}$ is hydrogen, $R^{42}$ is —(C$_1$-C$_6$)alkyl, and any carbon atom of $R^3$ is substituted with J. In another embodiment of the aforementioned embodiments is a compound of Formula (II), (IIa), or (IIb) wherein n3 is 1, n8 is 1, $R^2$ is hydroxy, $R^3$ is —OR$^{40}$, $R^{40}$ is —(C$_1$-C$_6$)alkyl-NR$^{41}$R$^{42}$, $R^{41}$ is hydrogen, $R^{42}$ is —(C$_1$-C$_6$)alkyl, and any carbon atom of $R^3$ is substituted with J wherein J is —NHCH$_3$. In another embodiment of the aforementioned embodiments is a compound of Formula (II), (IIa), or (IIb) wherein n3 is 1, n8 is 1, $R^2$ is hydroxy, $R^3$ is —O—(C$_1$-

$C_6$)alkyl-N(H)—($C_1$-$C_6$)alkyl-N(H)$CH_3$. In another embodiment of the aforementioned embodiments is a compound of Formula (II), (IIa), or (IIb) wherein n3 is 1, n8 is 1, $R^2$ is hydroxy, $R^3$ is —$OCH_2CH_2$N(H)$CH_2CH_2$N(H)$CH_3$. In another embodiment of the aforementioned embodiments is a compound of Formula (II), (IIa), or (IIb) wherein n3 is 1, n8 is 1, $R^2$ is hydroxy, $R^3$ is —$OCH_2CH_2$N(H)$CH_2CH_2CH_2$N(H)$CH_3$.

In another embodiment of the aforementioned embodiments is a compound of Formula (II), (IIa), or (IIb) wherein n3 is 1, n8 is 1, $R^3$ is hydroxy, $R^2$ is —$OR^{40}$, and any carbon atom of $R^2$ is substituted with J. In another embodiment of the aforementioned embodiments is a compound of Formula (II), (IIa), or (IIb) wherein n3 is 1, n8 is 1, $R^3$ is hydroxy, $R^2$ is —$OR^{40}$, $R^{40}$ is —($C_1$-$C_6$)alkyl, and any carbon atom of $R^2$ is substituted with J. In another embodiment of the aforementioned embodiments is a compound of Formula (II), (IIa), or (IIb) wherein n3 is 1, n8 is 1, $R^3$ is hydroxy, $R^2$ is —$OR^{40}$, $R^{40}$ is —($C_1$-$C_6$)alkyl, and any carbon atom of $R^2$ is substituted with J wherein J is $CO_2H$. In another embodiment of the aforementioned embodiments is a compound of Formula (II), (IIa), or (IIb) wherein n3 is 1, n8 is 1, $R^3$ is hydroxy, $R^2$ is —O—($C_1$-$C_6$)alkyl-$CO_2H$. In another embodiment of the aforementioned embodiments is a compound of Formula (II), (IIa), or (IIb) wherein n3 is 1, n8 is 1, $R^3$ is hydroxy, $R^2$ is —$OCH_2CO_2H$. In another embodiment of the aforementioned embodiments is a compound of Formula (II), (IIa), or (IIb) wherein n3 is 1, n8 is 1, $R^3$ is —$OCH_2CH_2NH_2$, $R^2$ is —$OCH_2CO_2H$. In another embodiment of the aforementioned embodiments is a compound of Formula (II), (IIa), or (IIb) wherein n3 is 1, n8 is 1, $R^3$ is hydroxy, $R^2$ is —$OR^{40}$, $R^{40}$ is $R^{40}$ is —($C_1$-$C_6$)alkyl-$NR^{41}R^{42}$, and any carbon atom of $R^2$ is substituted with J.

In another embodiment of the aforementioned embodiments is a compound of Formula (II), (IIa), or (IIb) wherein n3 is 1, n8 is 1, $R^3$ is hydroxy, $R^2$ is —$OR^{40}$, $R^{40}$ is —($C_1$-$C_6$)alkyl-$NR^{41}R^{42}$, $R^{41}$ is hydrogen, $R^{42}$ is —($C_1$-$C_6$)alkyl, and any carbon atom of $R^2$ is substituted with J. In another embodiment of the aforementioned embodiments is a compound of Formula (II), (IIa), or (IIb) wherein n3 is 1, n8 is 1, $R^3$ is hydroxy, $R^2$ is —$OR^{40}$, $R^{40}$ is —($C_1$-$C_6$)alkyl-$NR^{41}R^{42}$, $R^{41}$ is hydrogen, $R^{42}$ is —($C_1$-$C_6$)alkyl, and any carbon atom of $R^2$ is substituted with J wherein J is —$NHCH_3$. In another embodiment of the aforementioned embodiments is a compound of Formula (II), (IIa), or (IIb) wherein n3 is 1, n8 is 1, $R^3$ is hydroxy, $R^2$ is —O—($C_1$-$C_6$)alkyl-N(H)—($C_1$-$C_6$)alkyl-N(H)$CH_3$. In another embodiment of the aforementioned embodiments is a compound of Formula (II), (IIa), or (IIb) wherein n3 is 1, n8 is 1, $R^3$ is hydroxy, $R^2$ is —$OCH_2CH_2$N(H)$CH_2CH_2$N(H)$CH_3$. In another embodiment of the aforementioned embodiments is a compound of Formula (II), (IIa), or (IIb) wherein n3 is 1, n8 is 1, $R^3$ is hydroxy, $R^2$ is —$OCH_2CH_2$N(H)$CH_2CH_2CH_2$N(H)$CH_3$.

In another embodiment of the aforementioned embodiments is a compound of Formula (II), (IIa), (IIb), or (IIc) wherein $R^{A7}$, $R^{A7'}$, $R^{A8}$, $R^{A8'}$, $R^{A9}$, $R^{A9'}$, $R^{A4'}$, $R^{A10}$, and $R^{A10'}$ are each independently H. In another embodiment of the aforementioned embodiments is a compound of Formula (II), (IIa), (IIb), or (IIc) wherein each m is 0. In another embodiment of the aforementioned embodiments is a compound of Formula (II), (IIa), (IIb), or (IIc) wherein $R^{A1}$, $R^{A1'}$, $R^{A2}$, $R^{4'}$, and $R^{4''}$ are each independently H.

In another embodiment of the aforementioned embodiments is a compound of Formula (II) having the structure of Formula (IId):

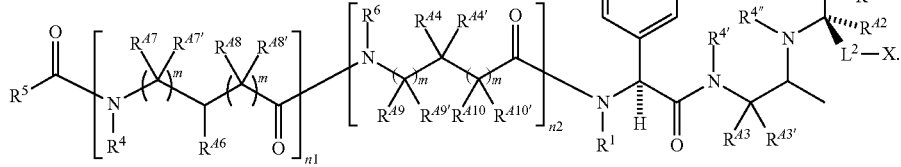

Formula (IId)

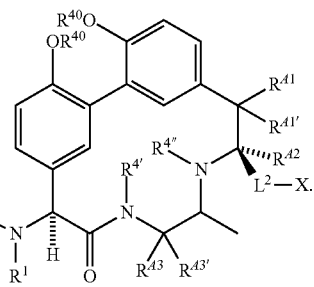

In another embodiment described herein are compounds of Formula (III):

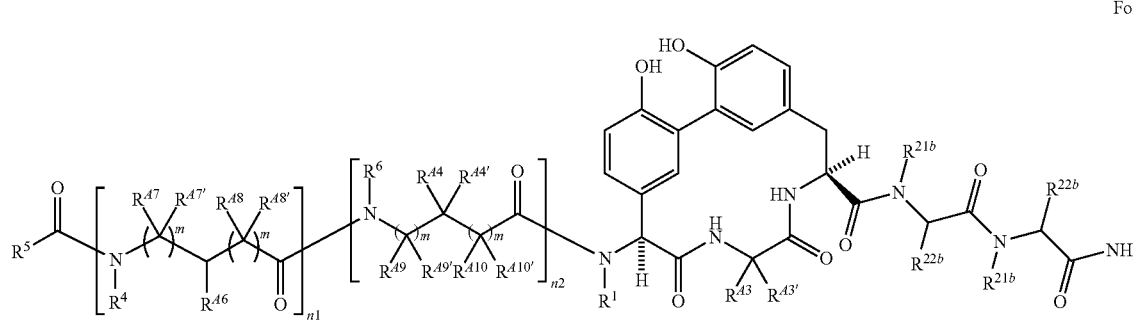

Formula (III)

wherein:

R⁵ is aryl, heteroaryl, or a linear or branched alkyl chain of about 1-22 carbon atoms, wherein R⁵ is bonded to the carbonyl carbon to which it is attached directly or by an O or NR⁴, to provide an amide, carbamate, or urea linkage, respectively; optionally comprising within the chain or at a chain terminus optionally substituted aryl, optionally substituted heteroaryl, or optionally substituted

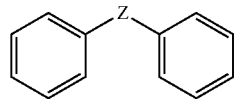

wherein Z is a bond, O, S, NH, CH$_2$ or C≡C;
n1 and n2 are independently 0 or 1;
each m is independently 0 or 1;
R¹ is hydrogen or (C$_1$-C$_6$)alkyl optionally substituted with 1 to 3 J;
each R⁴ is independently hydrogen, or (C$_1$-C$_6$)alkyl optionally substituted with 1 to 3 J;
R⁶ is hydrogen, or (C$_1$-C$_6$)alkyl optionally substituted with 1 to 3 J; or R⁶ together with R$^{44}$ form a ring;
R$^{A3}$, R$^{A3'}$, R$^{A4}$, R$^{A4'}$, R$^{A7}$, R$^{A7'}$, R$^{A8}$, R$^{A8'}$, R$^{A9}$, R$^{A9'}$, R$^{A10}$, and R$^{A10'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
R$^{A6}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;
each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In some embodiments is a compound of Formula (III) wherein R⁵ is a linear or branched alkyl chain of about 1-22 carbon atoms, wherein R⁵ is bonded to the carbonyl carbon to which it is attached directly or by an NR⁴, to provide an amide or urea linkage, respectively; optionally comprising within the chain or at a chain terminus optionally substituted aryl, optionally substituted heteroaryl, or optionally substituted

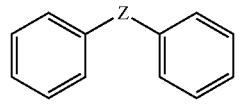

wherein Z is a bond, O, S, NH, CH$_2$ or C≡C. In some embodiments is a compound of Formula (III) wherein R⁵ is a linear or branched alkyl chain of about 1-22 carbon atoms, wherein R⁵ is bonded to the carbonyl carbon to which it is attached directly to provide an amide linkage, optionally comprising within the chain or at a chain terminus optionally substituted aryl, optionally substituted heteroaryl, or optionally substituted

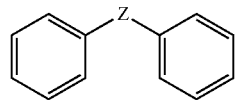

wherein Z is a bond, O, S, NH, CH$_2$ or C≡C. In some embodiments is a compound of Formula (III) wherein R⁵ is a linear alkyl chain of about 1-22 carbon atoms, wherein R⁵ is bonded to the carbonyl carbon to which it is attached directly to provide an amide linkage, comprising within the chain or at a chain terminus

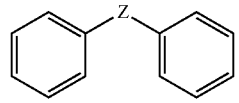

wherein Z is a bond. In some embodiments is a compound of Formula (III) wherein R⁵ is a linear alkyl chain of about 4-22 carbon atoms, wherein R⁵ is bonded to the carbonyl carbon to which it is attached directly to provide an amide linkage, comprising at a chain terminus

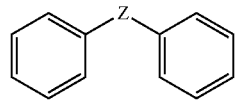

wherein Z is a bond. In some embodiments is a compound of Formula (III) wherein R⁵ is a linear alkyl chain of about 4-22 carbon atoms, wherein R⁵ is bonded to the carbonyl carbon to which it is attached directly to provide an amide linkage, comprising within the chain

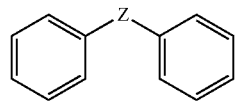

wherein Z is a bond. In some embodiments is a compound of Formula (III) wherein R⁵ is a linear or branched alkyl chain of about 1-22 carbon atoms, wherein R⁵ is bonded to the carbonyl carbon to which it is attached directly or by an NR⁴, to provide an amide or urea linkage, respectively; optionally comprising within the chain or at a chain terminus optionally substituted aryl. In some embodiments is a compound of Formula (III) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (III) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (III) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (III) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (III) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (III) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (III) wherein $R^{44}$ is H. In another embodiment is a compound of Formula (III) wherein $R^{44}$ is $(C_1-C_6)$alkyl optionally substituted with 1 to 3 J. In another embodiment is a compound of Formula (III) wherein $R^{44}$ is $CH_3$. In another embodiment is a compound of Formula (III) wherein $R^{44}$ is $CH_2CH_3$. In another embodiment is a compound of Formula (III) wherein $R^{44}$ is $CH_2CH(CH_3)_2$. In another embodiment is a compound of Formula (III) wherein $R^{44}$ is $CH_2OH$. In another embodiment is a compound of Formula (III) wherein $R^{44}$ is $CH(OH)CH_3$. In another embodiment is a compound of Formula (III) wherein $R^{44}$ is $CH_2C(O)NH_2$. In another embodiment is a compound of Formula (III) wherein $R^{44}$ is $CH_2CH_2CH_2CH_2NH_2$.

In another embodiment is a compound of Formula (III) wherein $R^{48}$ is H, and $R^{44}$ is H. In another embodiment is a compound of Formula (III) wherein $R^{48}$ is H, and $R^{44}$ is $(C_1-C_6)$alkyl optionally substituted with 1 to 3 J. In another embodiment is a compound of Formula (III) wherein $R^{48}$ is H, and $R^{44}$ is $CH_3$. In another embodiment is a compound of Formula (III) wherein $R^{48}$ is H, and $R^{44}$ is $CH_2CH_3$. In another embodiment is a compound of Formula (III) wherein $R^{48}$ is H, and $R^{44}$ is $CH_2CH(CH_3)_2$. In another embodiment is a compound of Formula (III) wherein $R^{48}$ is H, and $R^{44}$ is $CH_2OH$. In another embodiment is a compound of Formula (III) wherein $R^{48}$ is H, and $R^{44}$ is $CH(OH)CH_3$. In another embodiment is a compound of Formula (III) wherein $R^{48}$ is H, and $R^{44}$ is $CH_2C(O)NH_2$. In another embodiment is a compound of Formula (III) wherein $R^{48}$ is H, and $R^{44}$ is $CH_2CH_2CH_2CH_2NH_2$.

In another embodiment of the aforementioned embodiments is a compound of Formula (III) wherein $R^{44'}$, $R^{48'}$, $R^{49}$, $R^{49'}$, $R^{410}$, and $R^{410'}$ are each independently H. In another embodiment of the aforementioned embodiments is a compound of Formula (III) wherein each m is 0.

Some embodiments of compounds of Formula (I), (Ia), (Ib), (Ic), (II), (IIa), (IIb), (IIc), (III), or (IV) include, but are not limited to, compounds selected from the group consisting of:

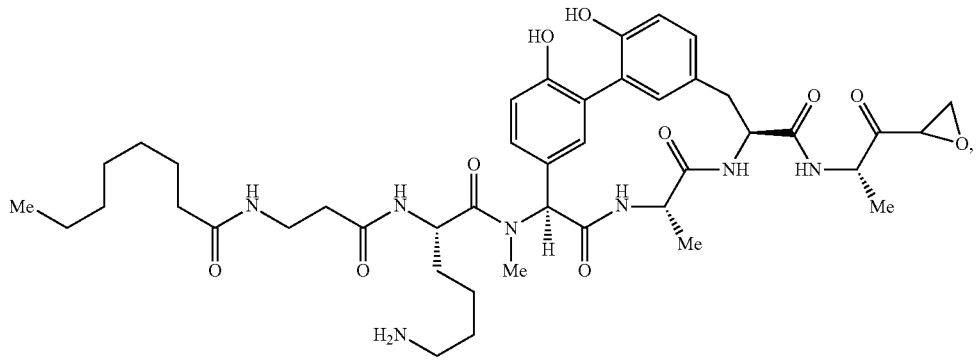

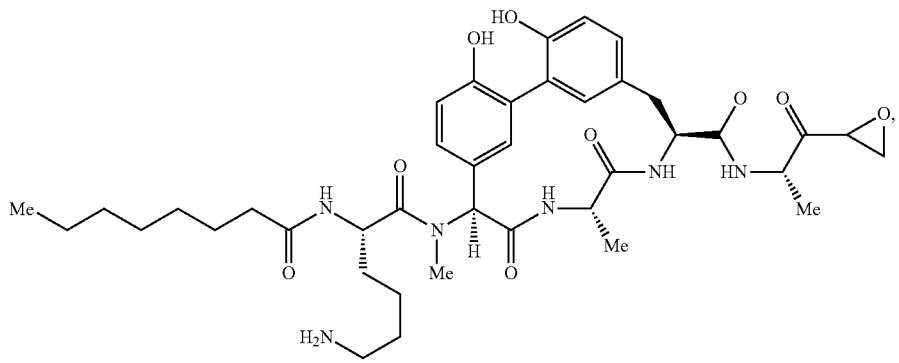

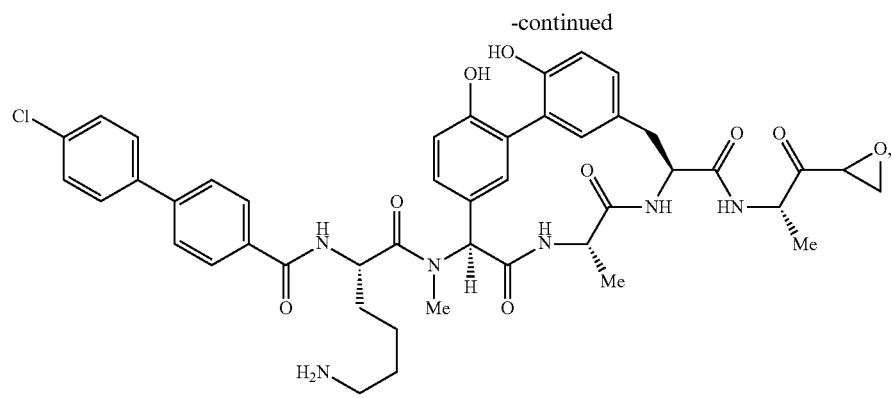
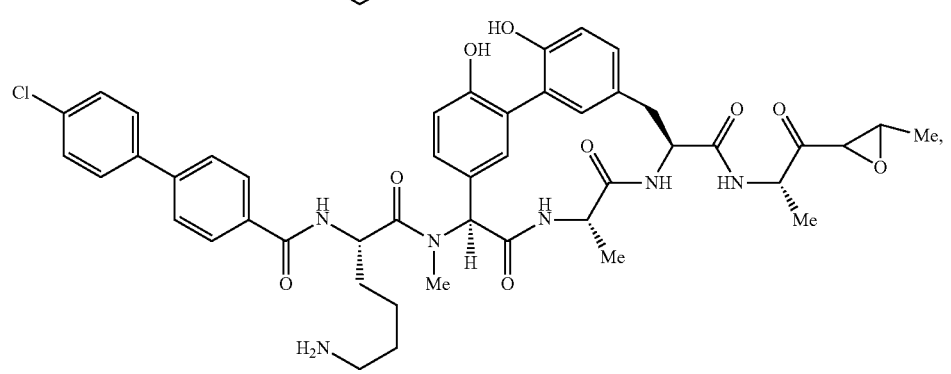
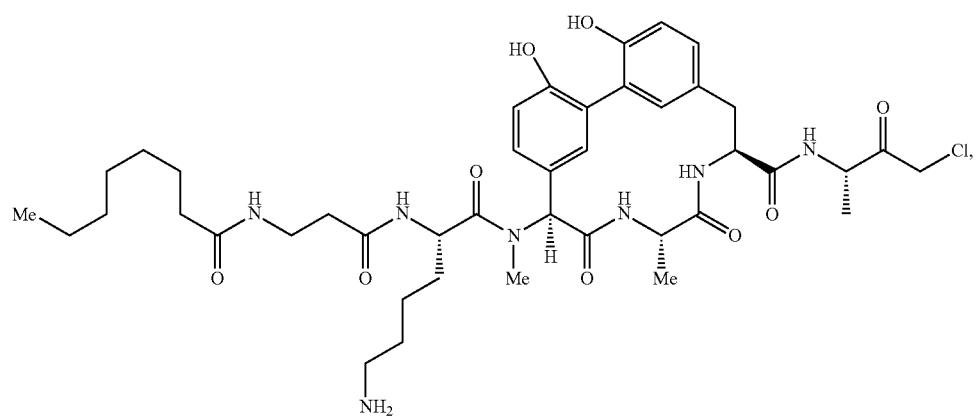
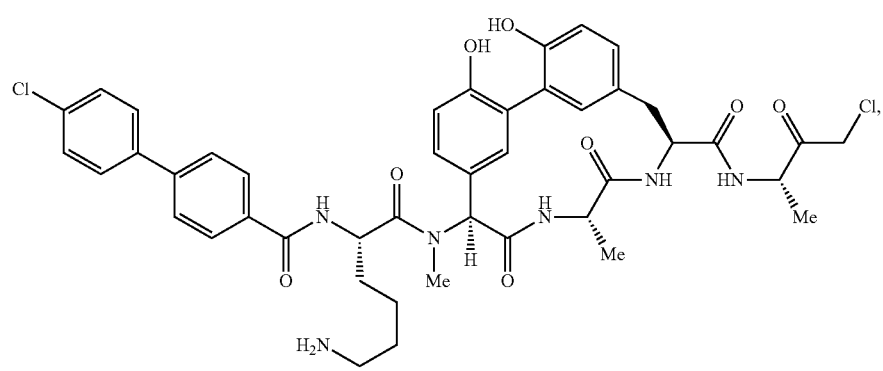

-continued
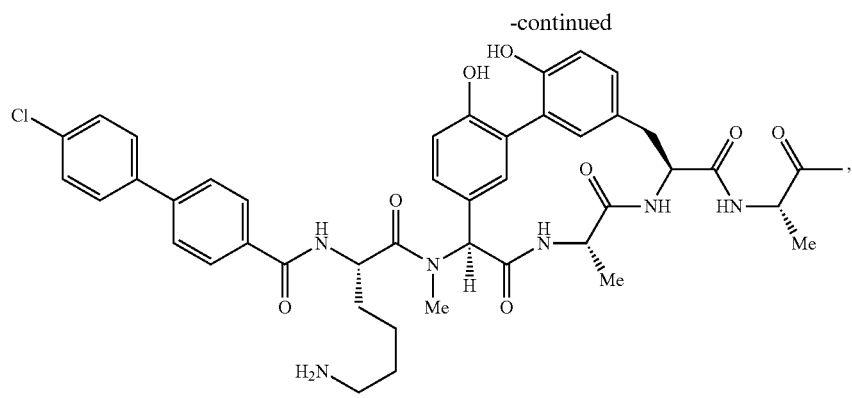
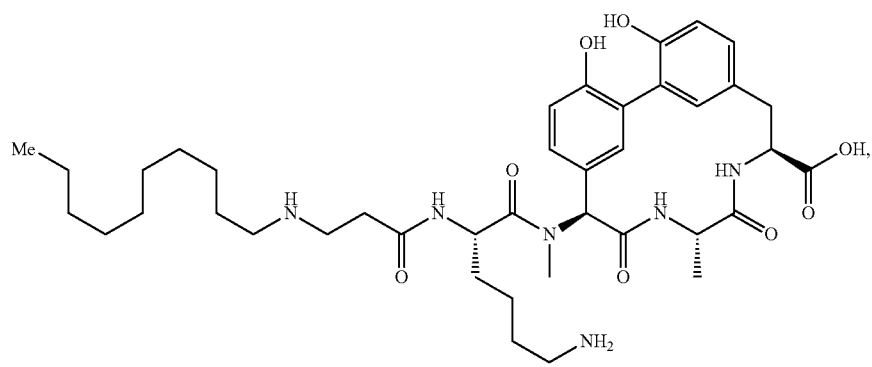
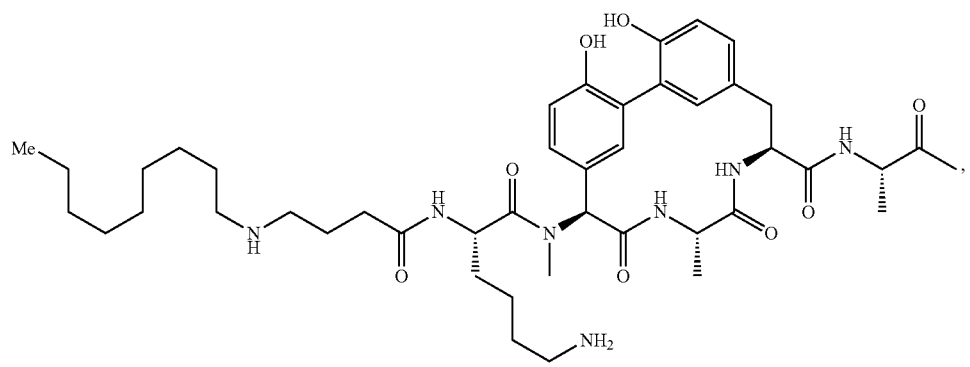
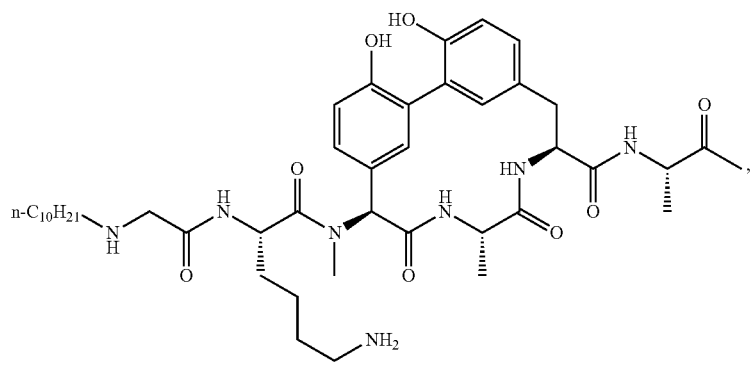

-continued
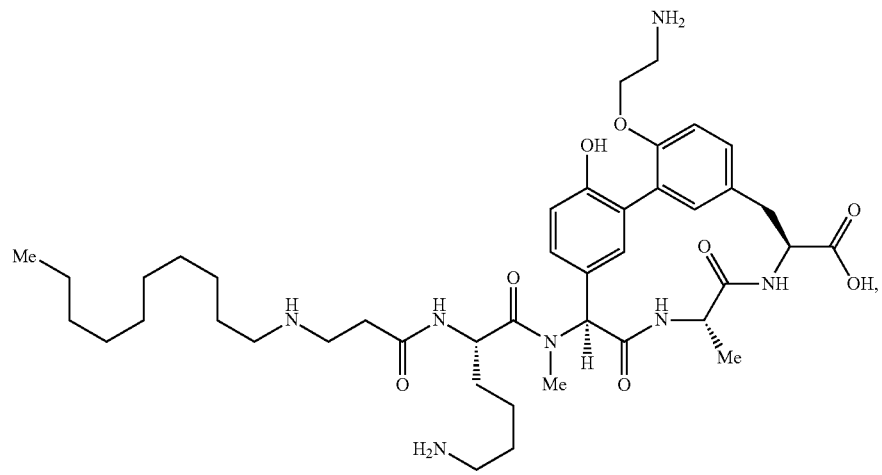
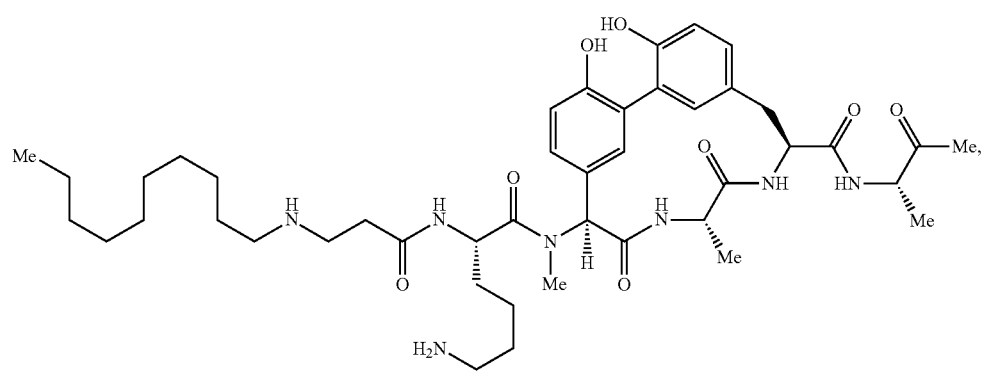
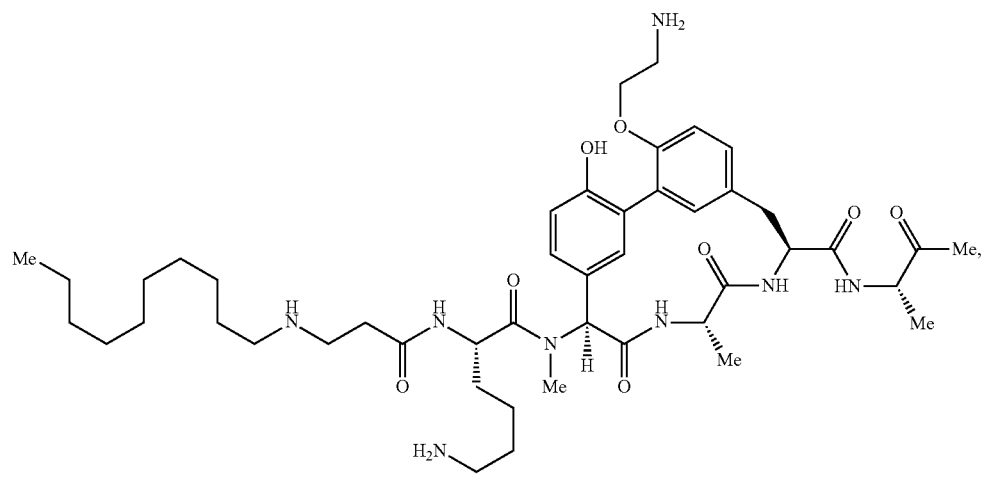

-continued
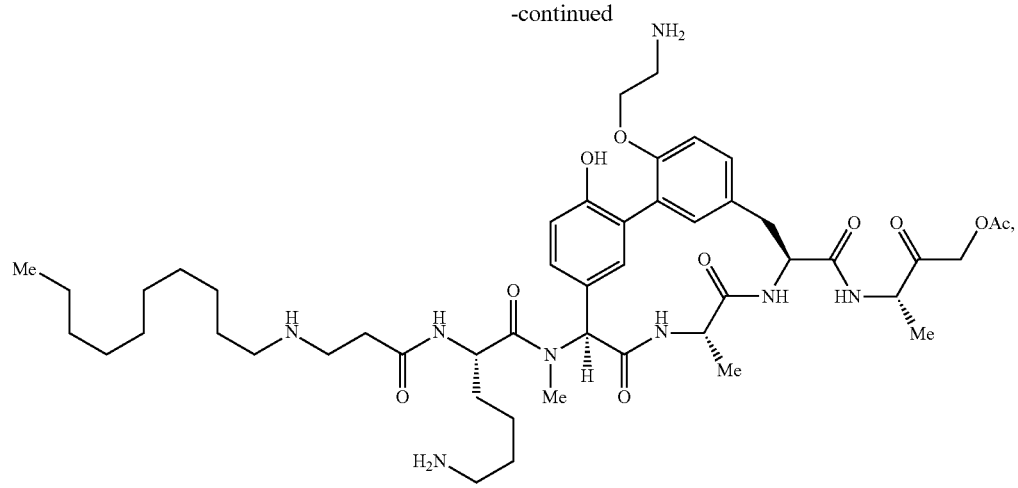
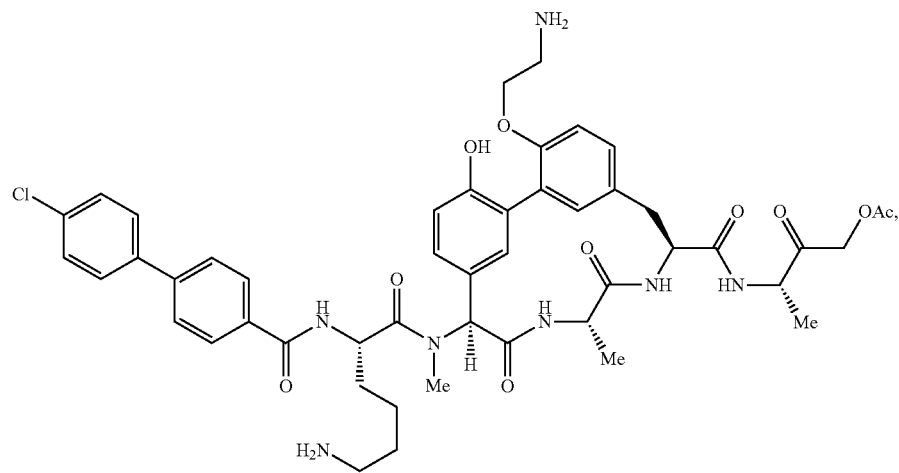
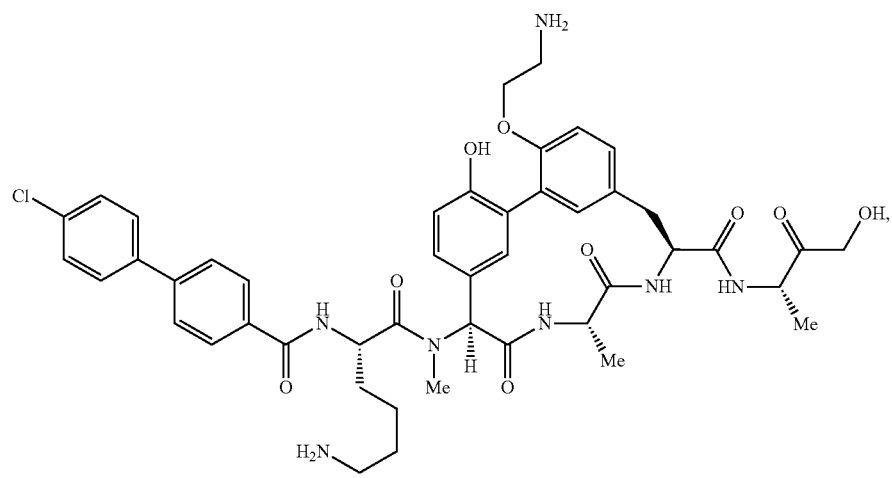

-continued
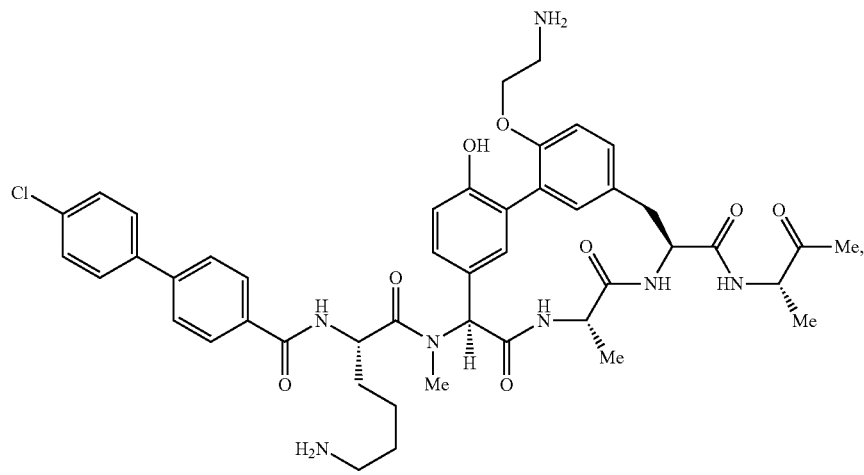
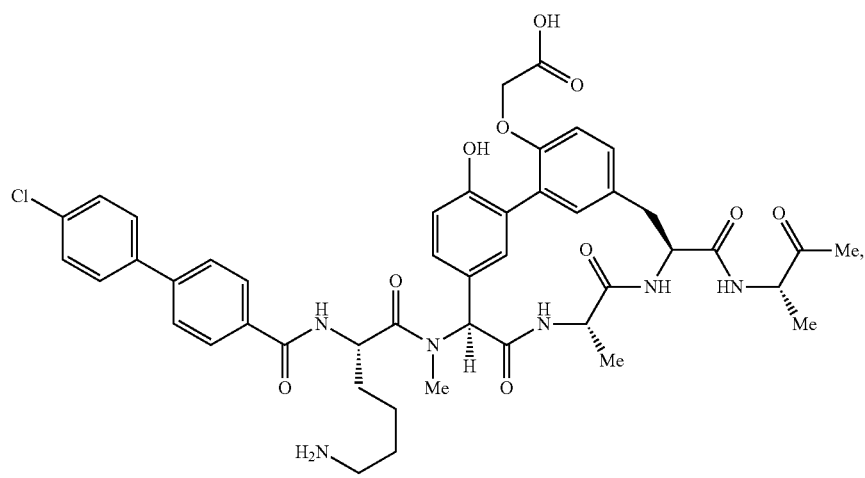
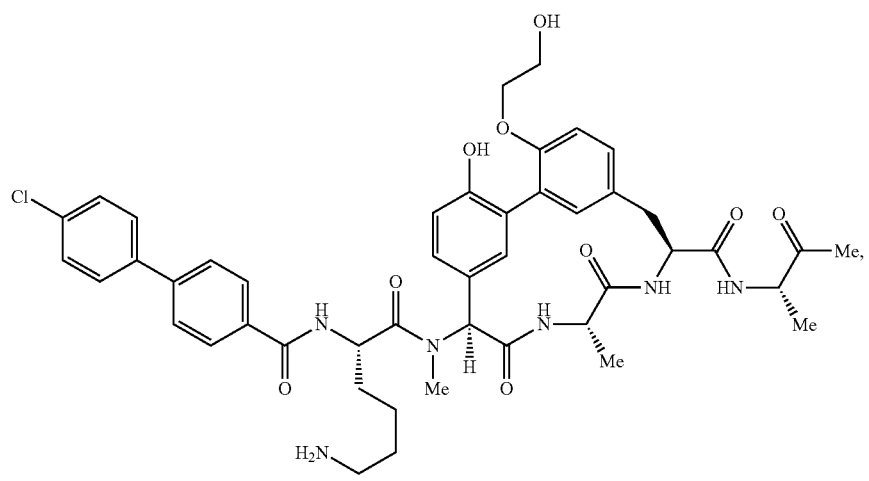

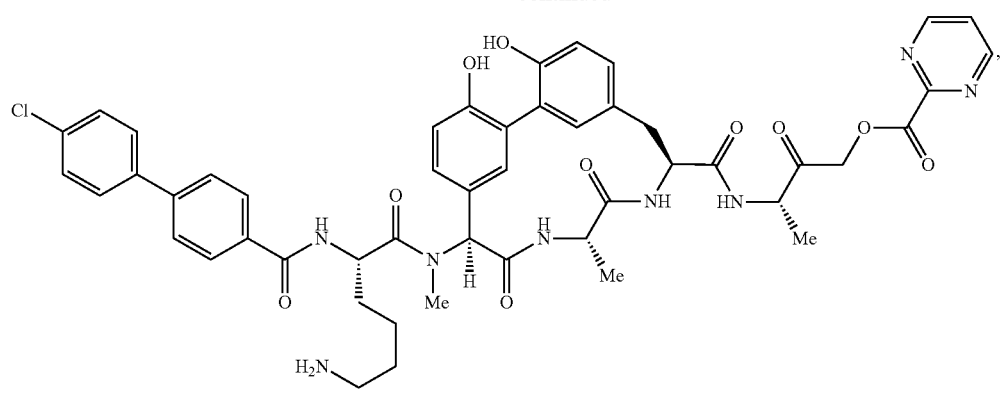
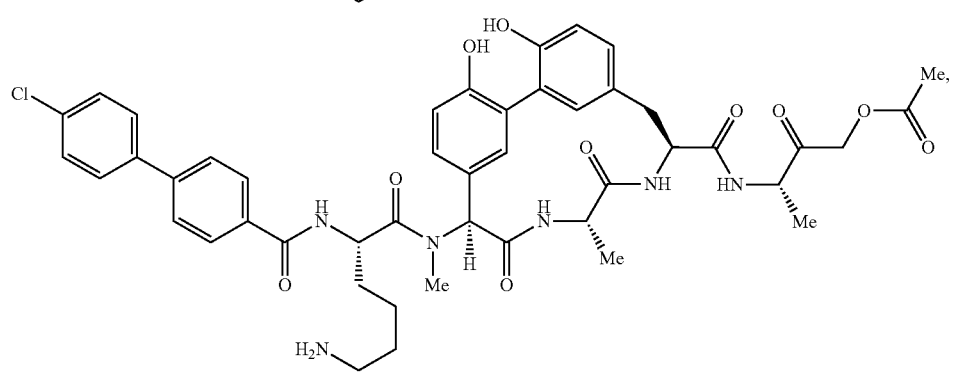
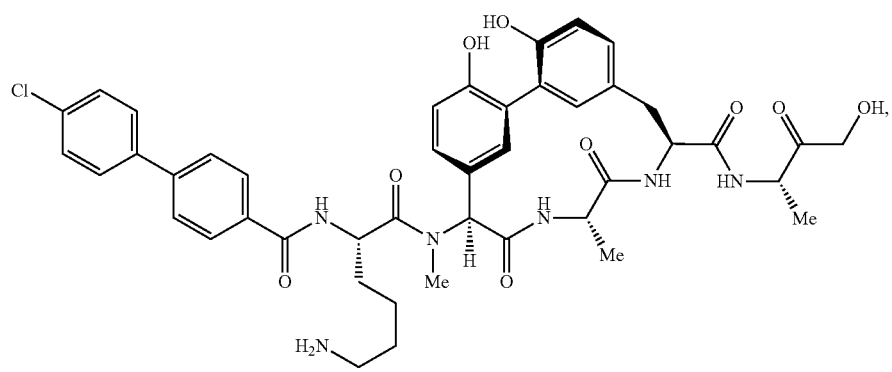
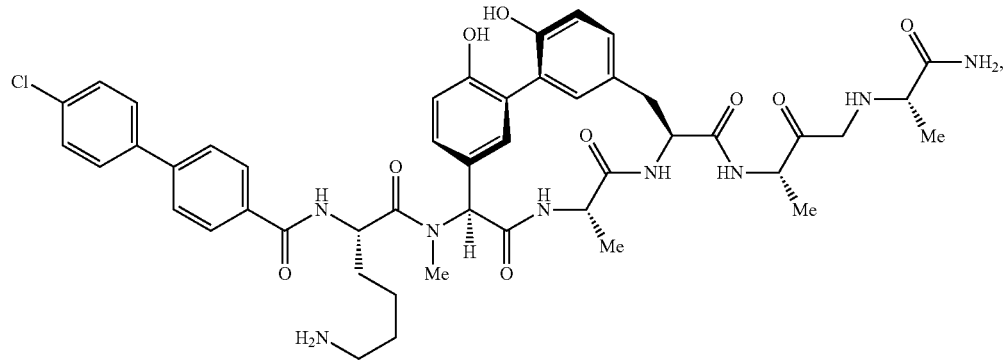

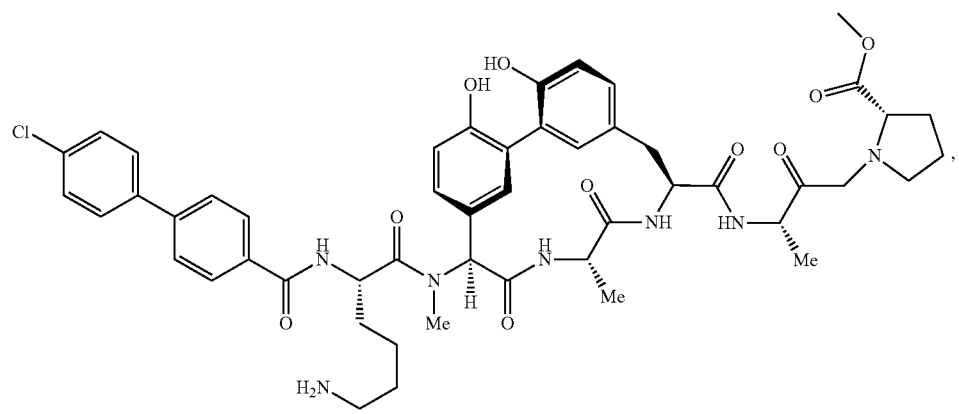
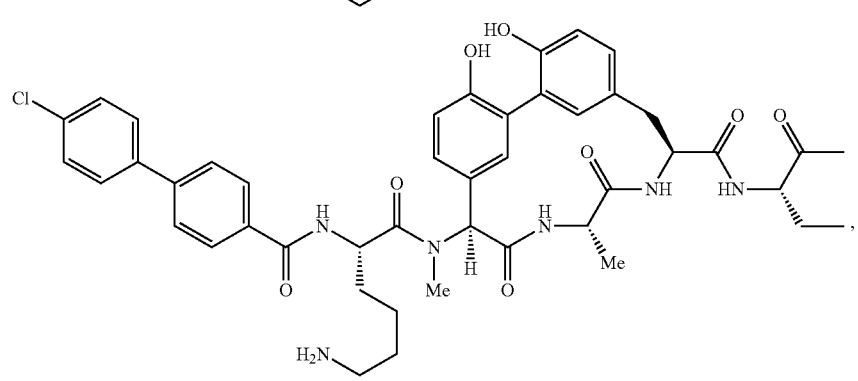
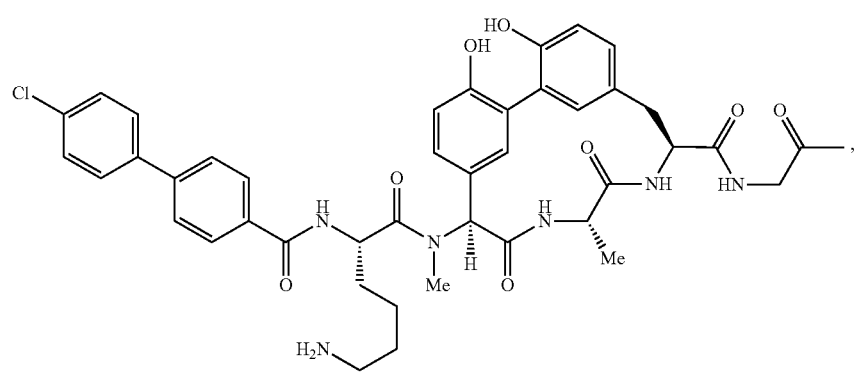
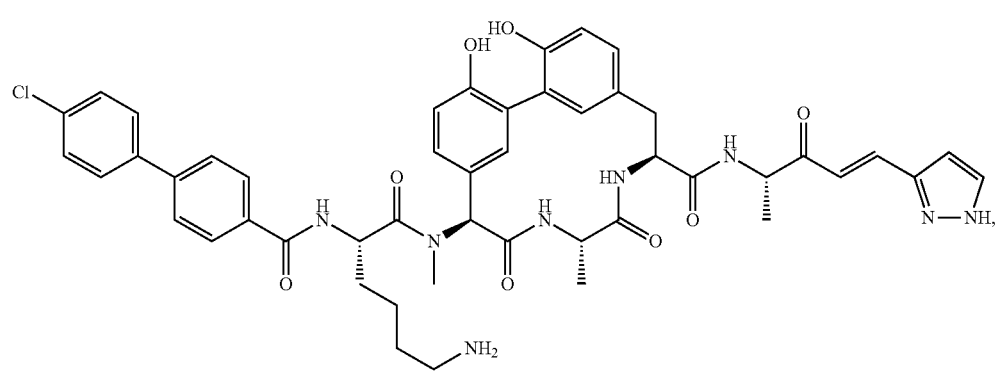

-continued
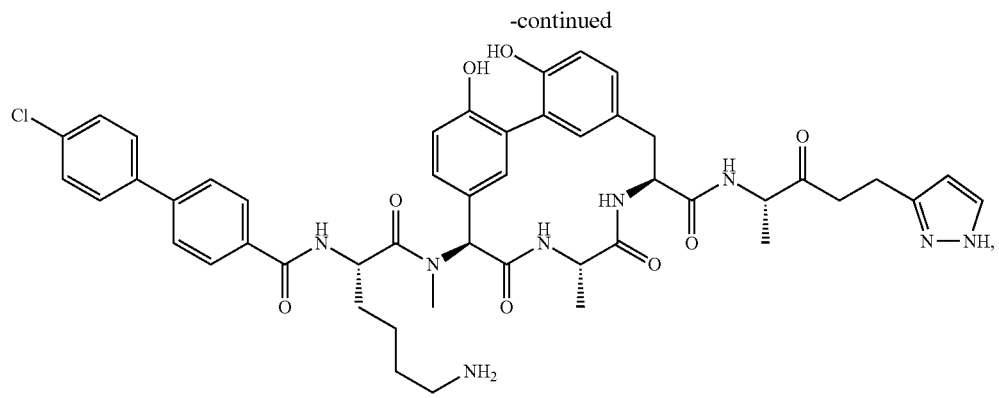
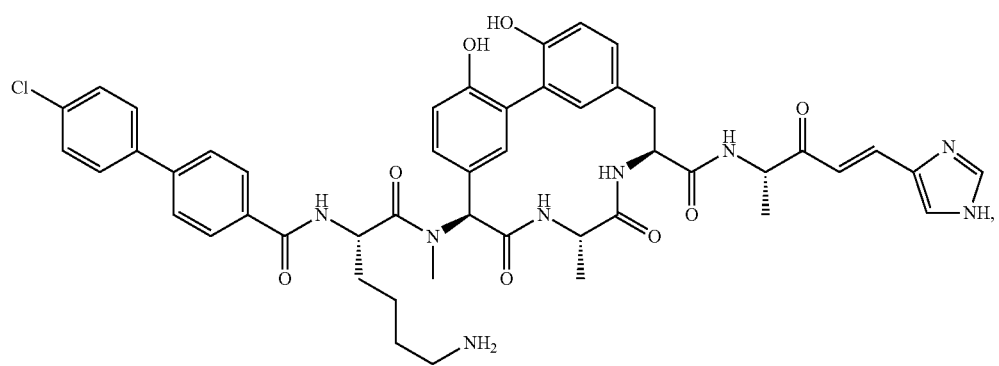
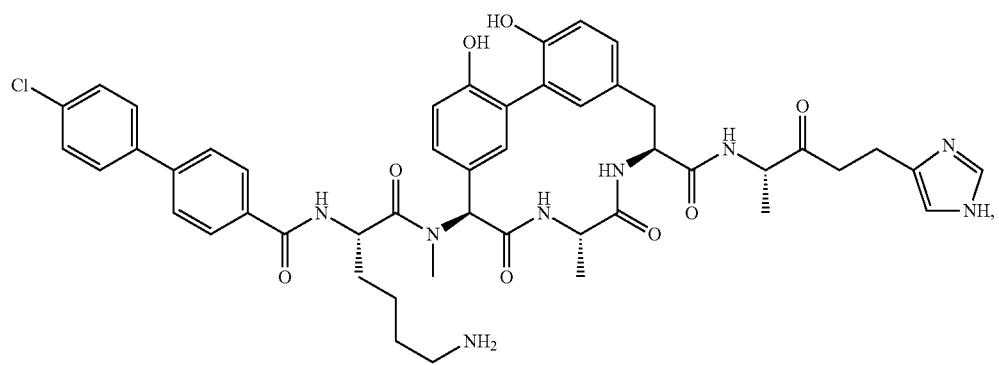
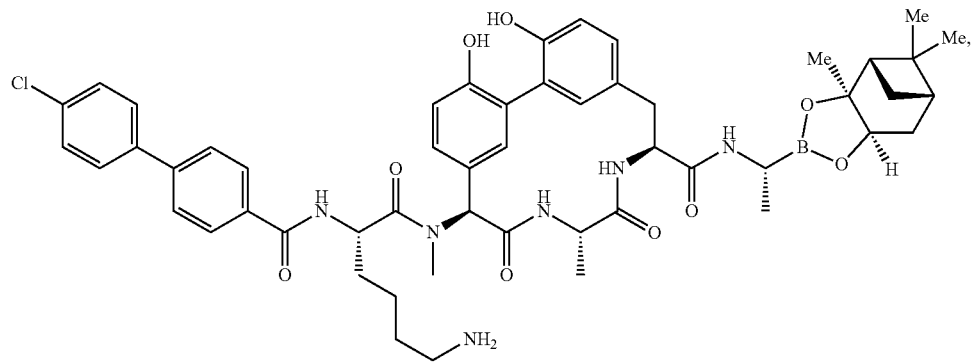

-continued
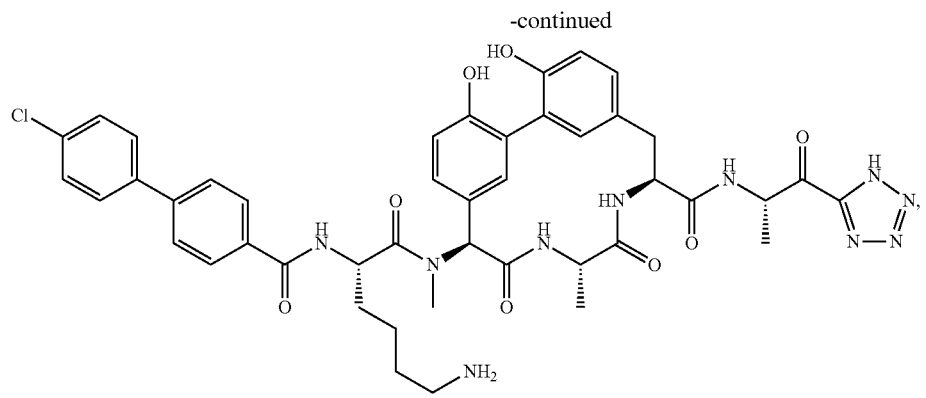
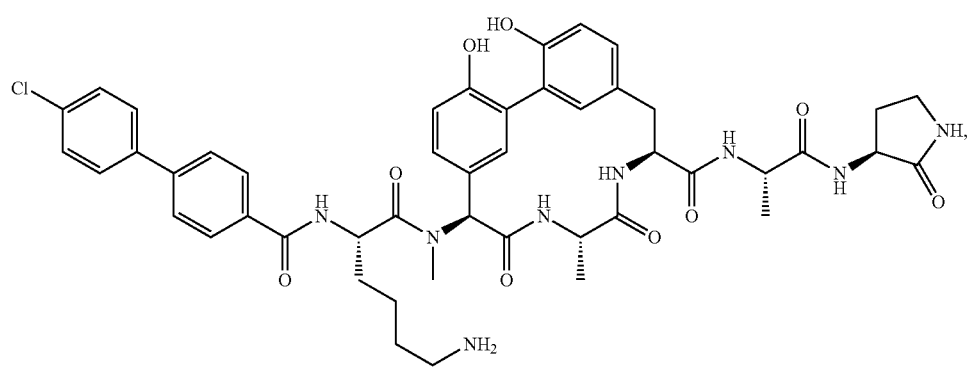
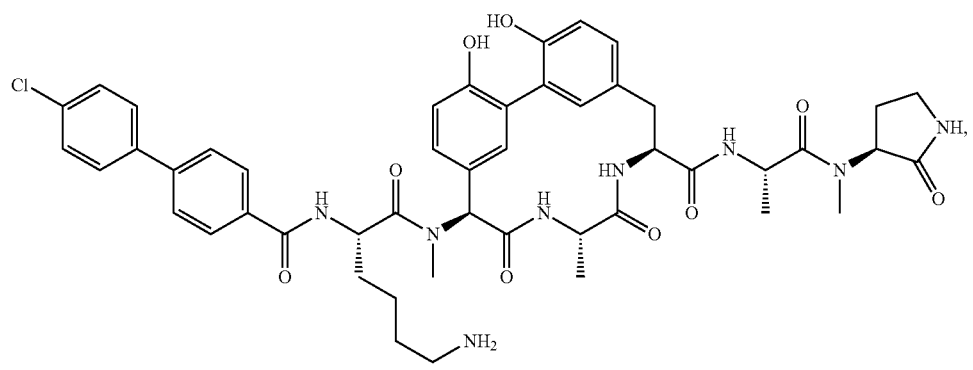
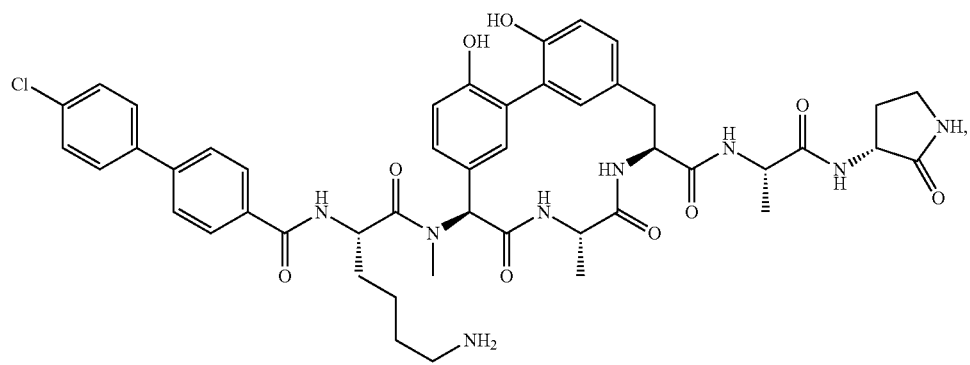

-continued
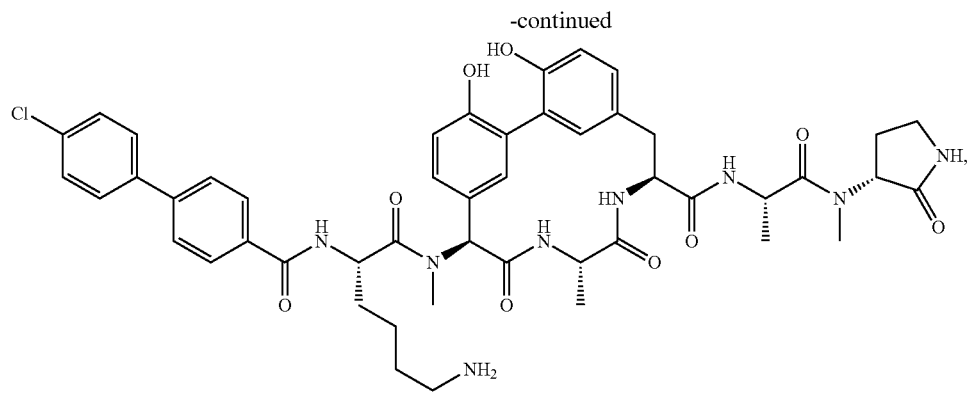
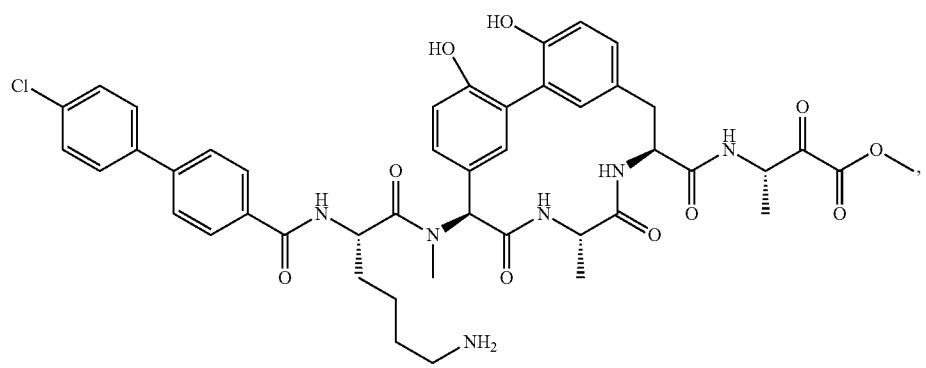
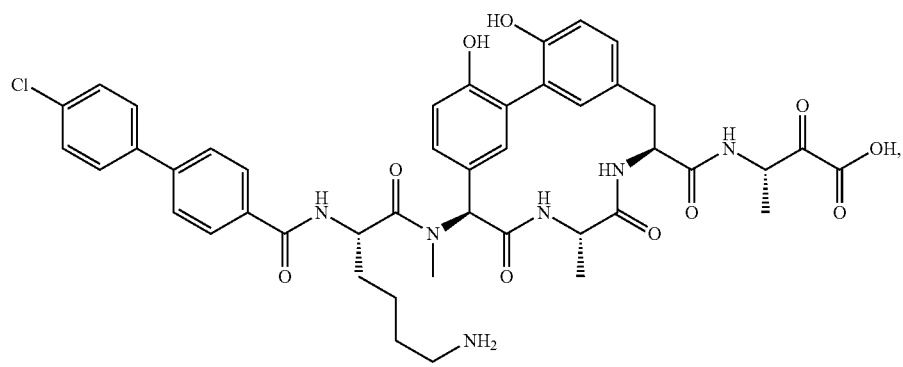
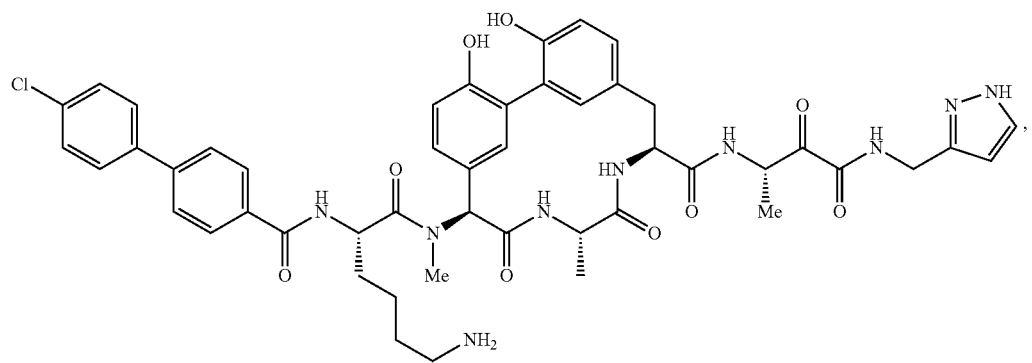

-continued
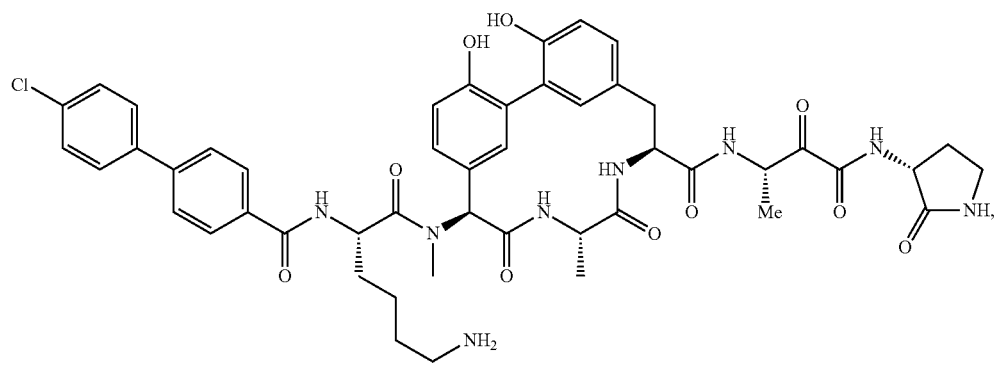
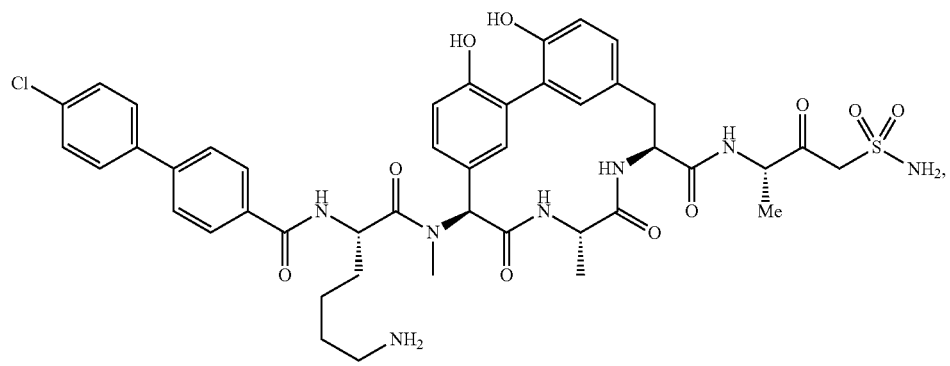
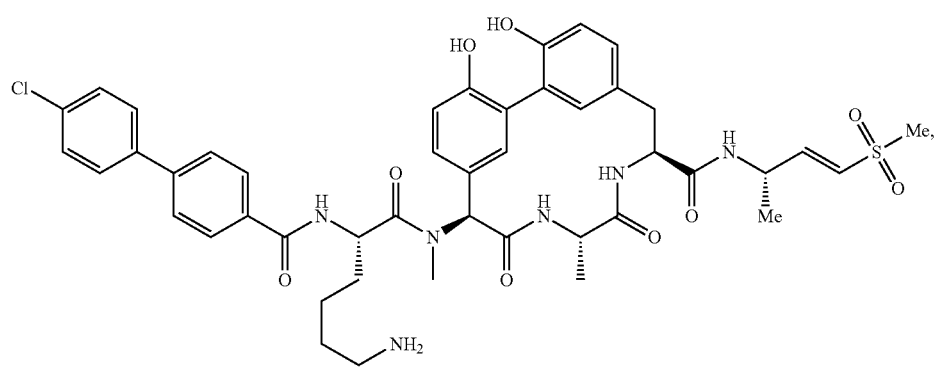
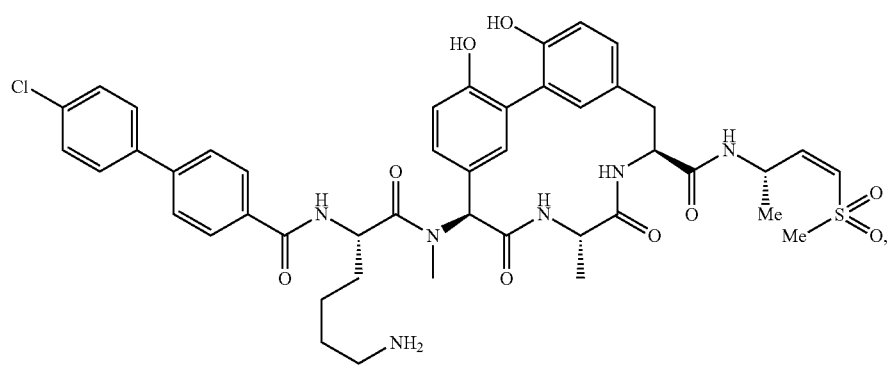

-continued
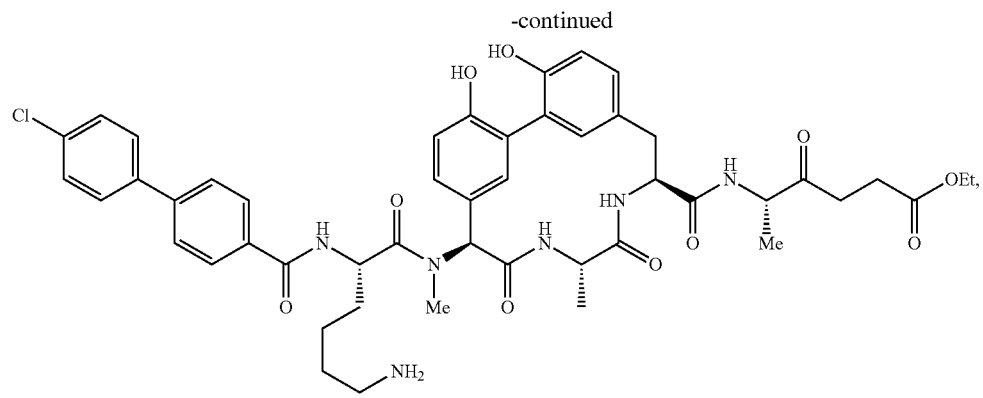
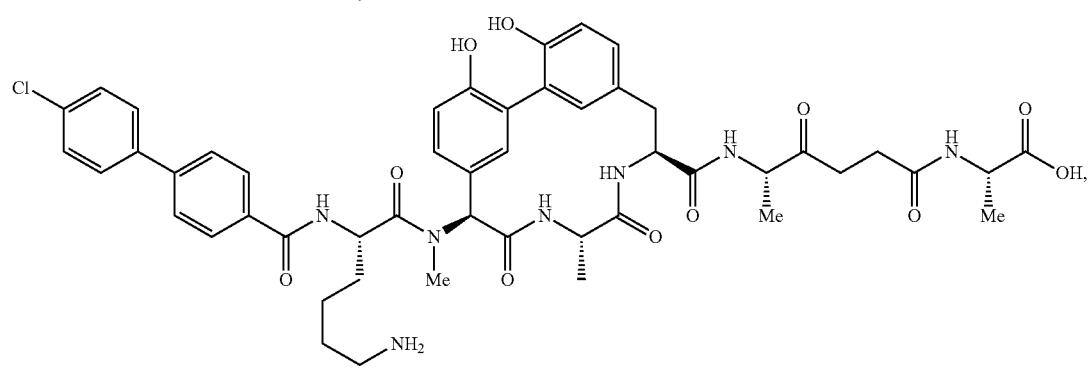
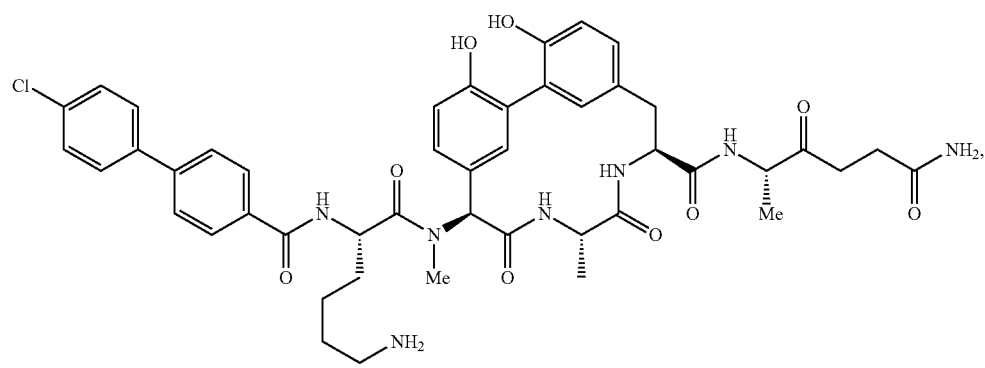
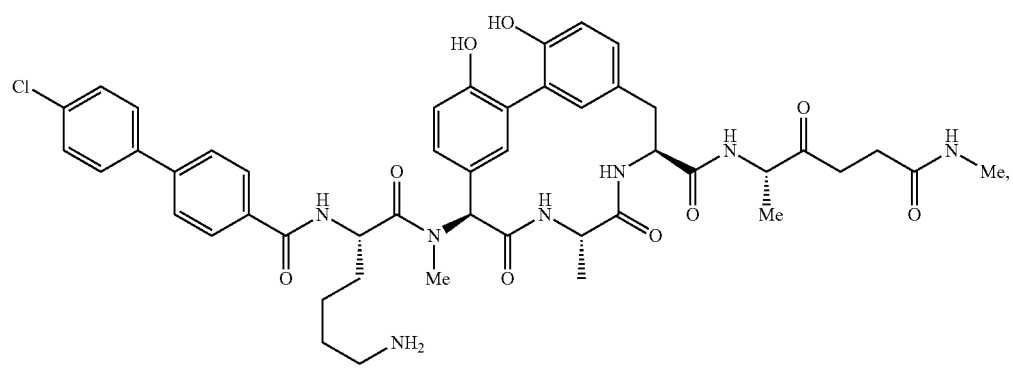

-continued
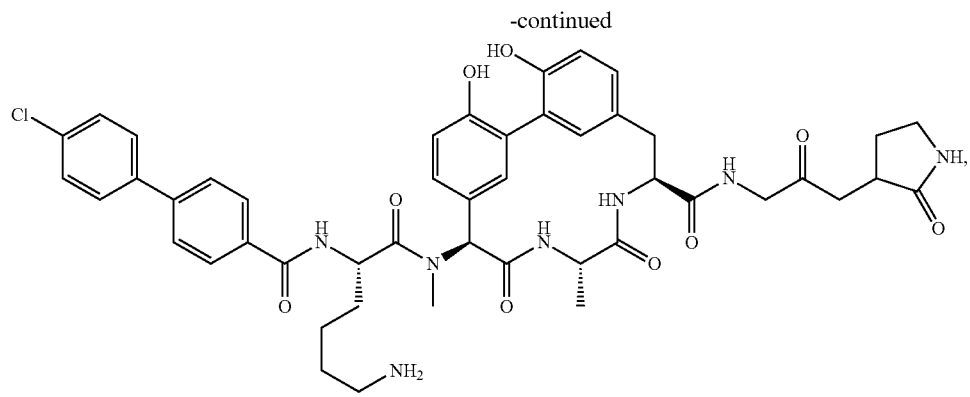
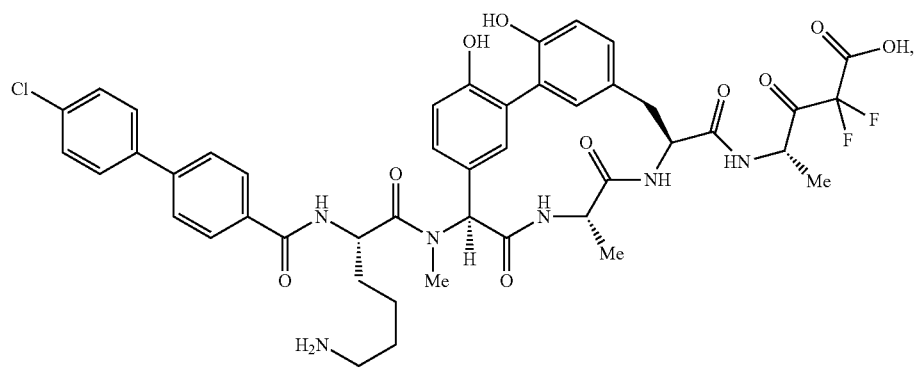
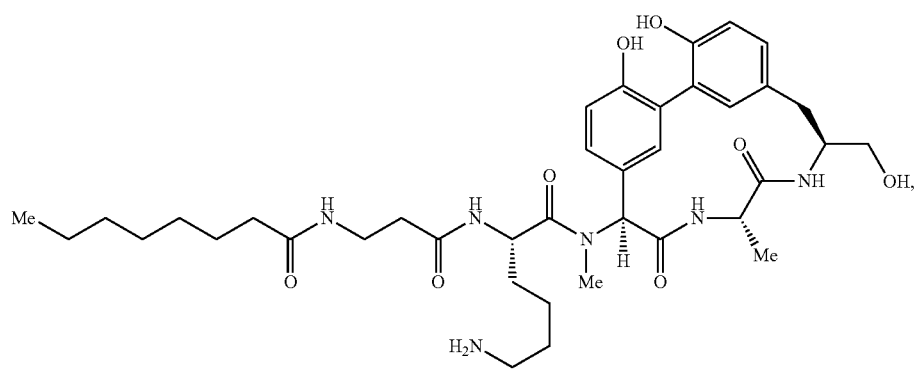
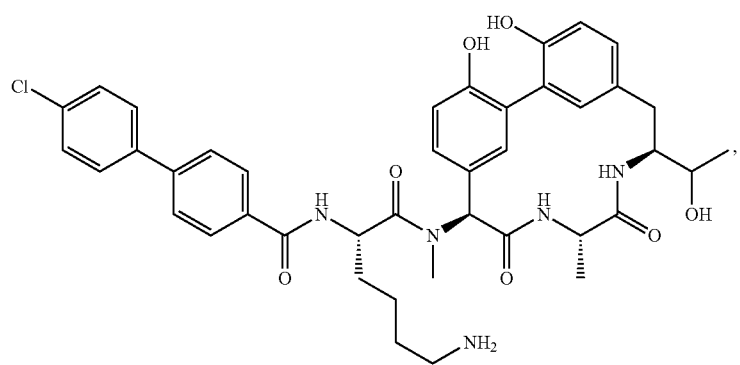

-continued
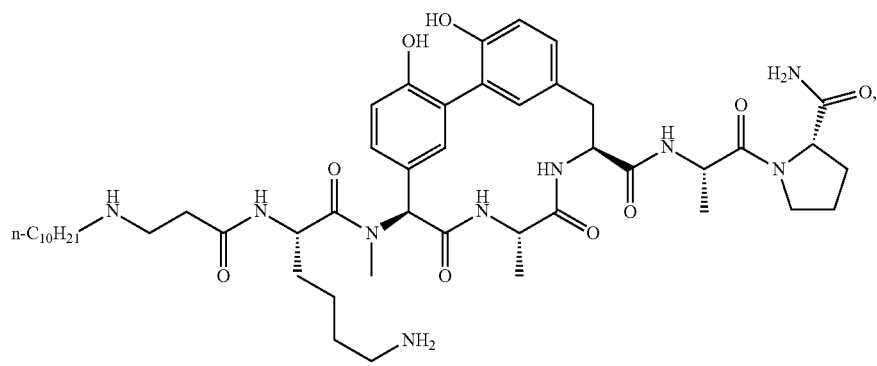
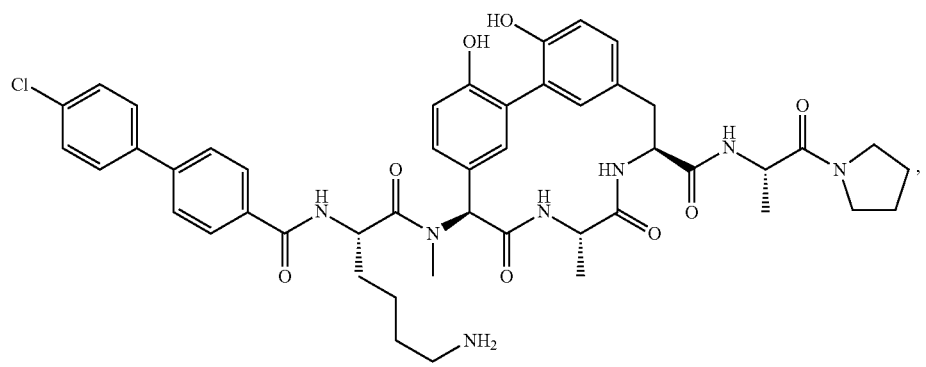
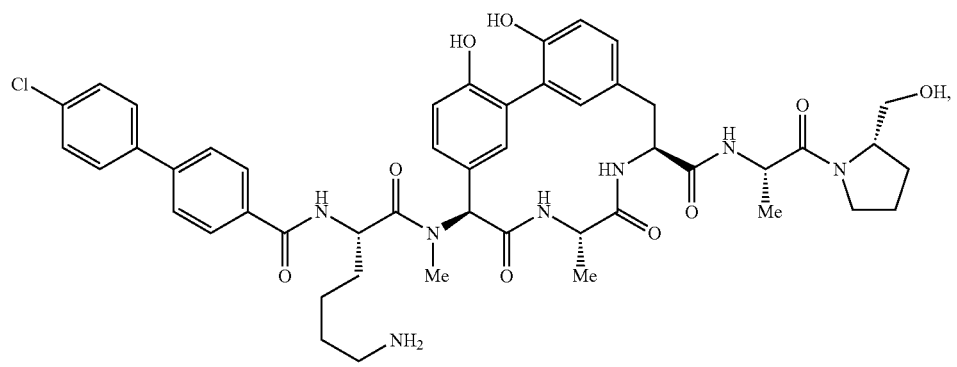
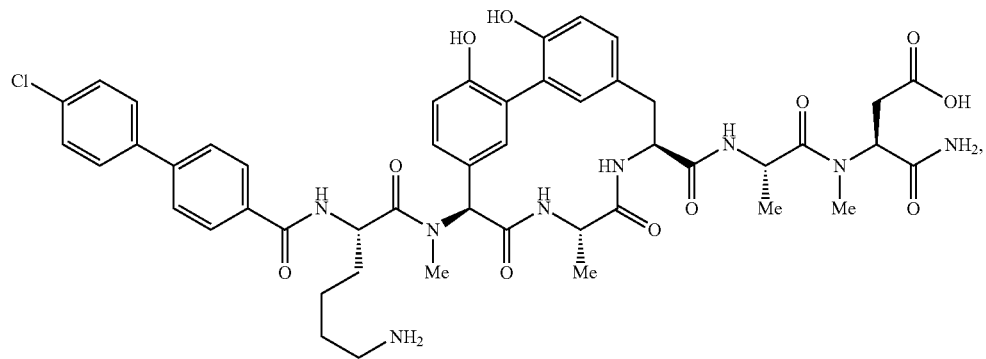

-continued
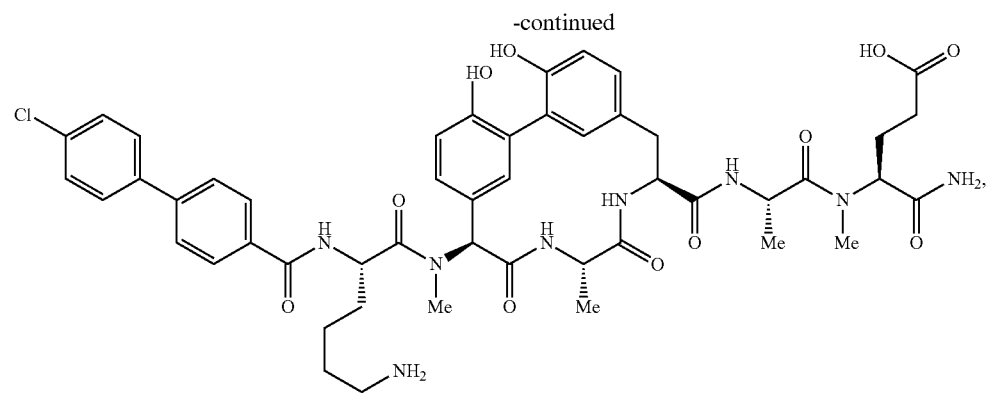
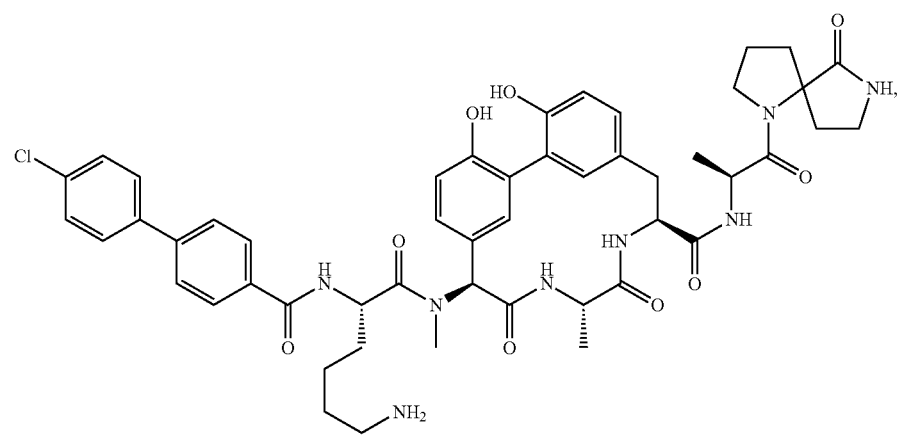
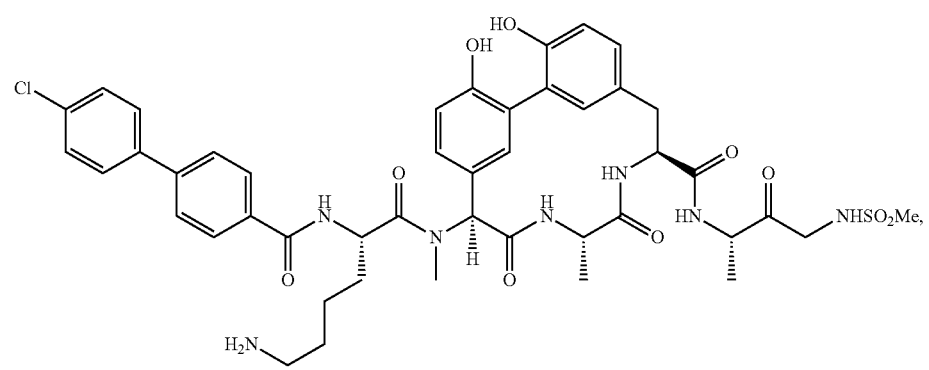
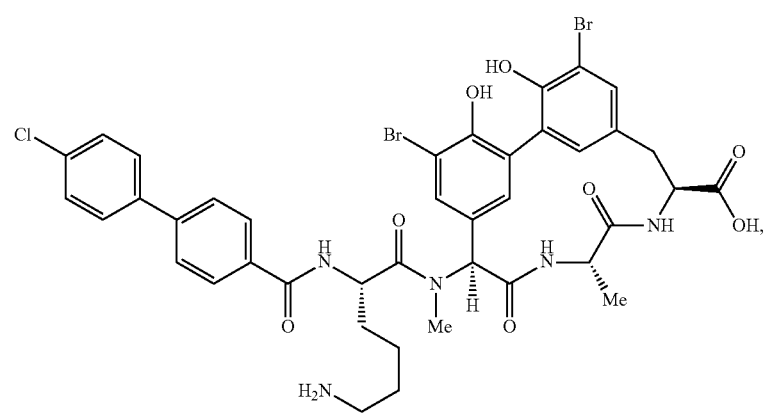

-continued
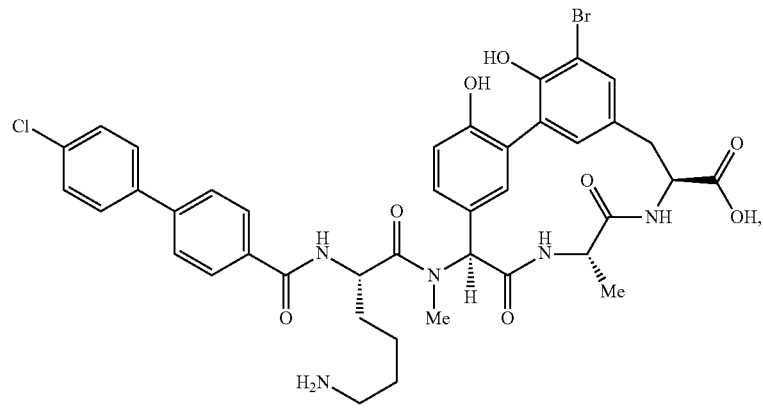
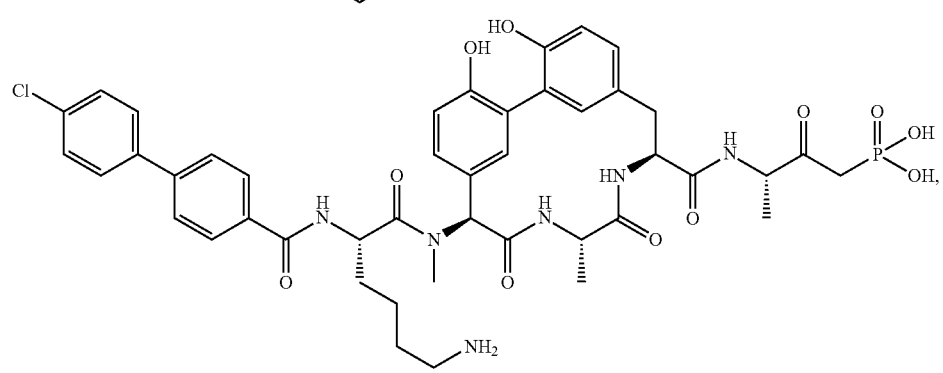
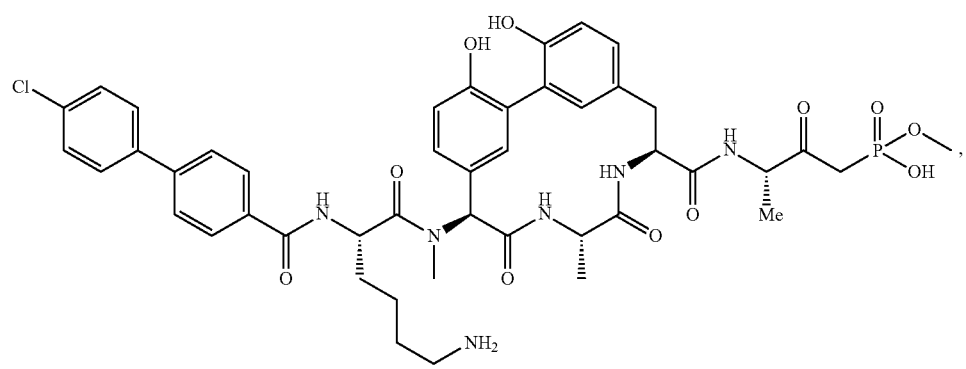
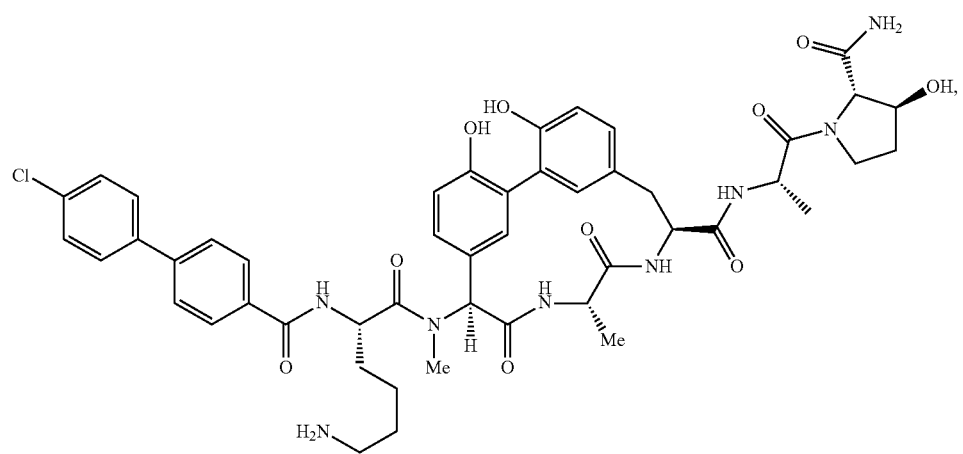

-continued
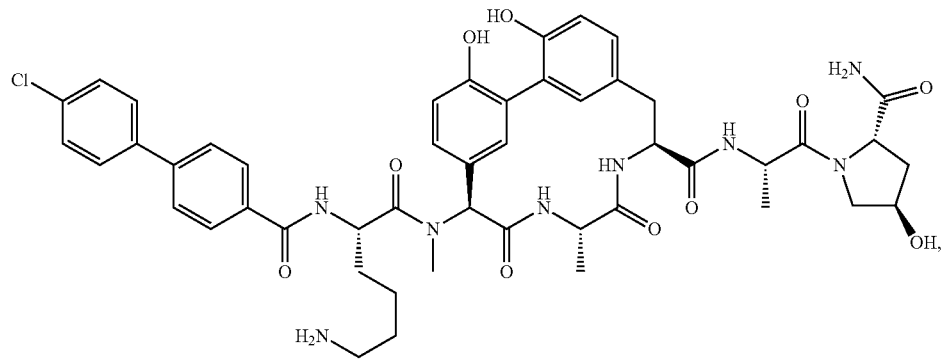
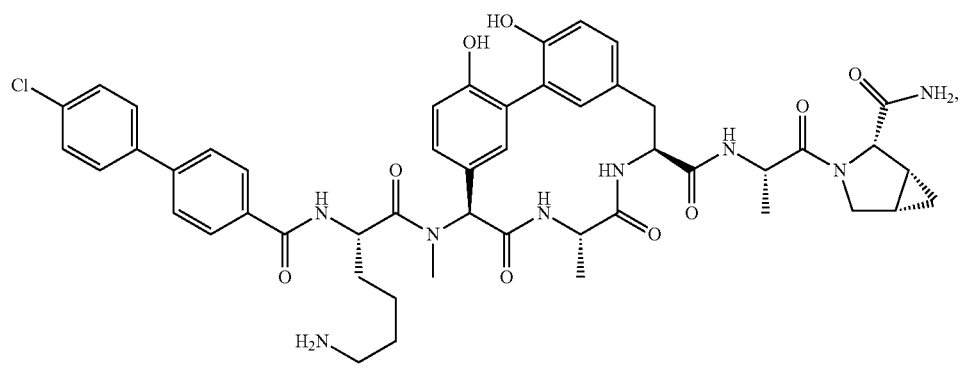
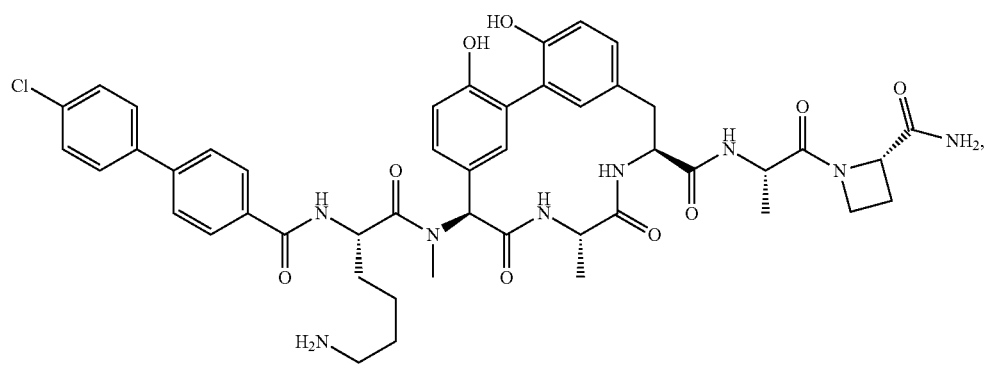
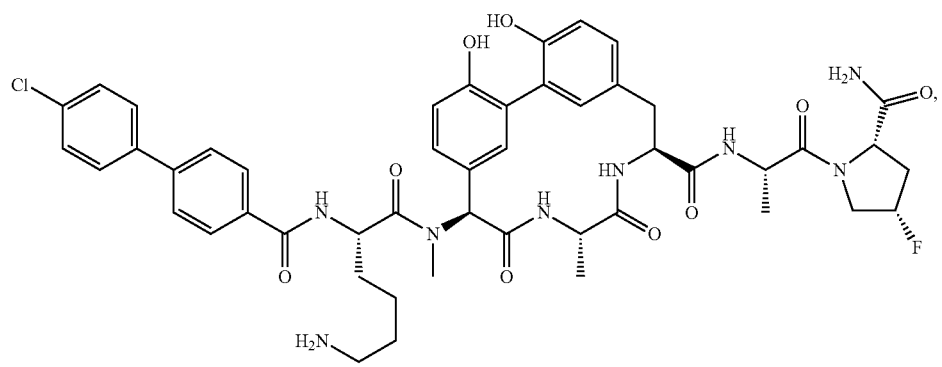

-continued
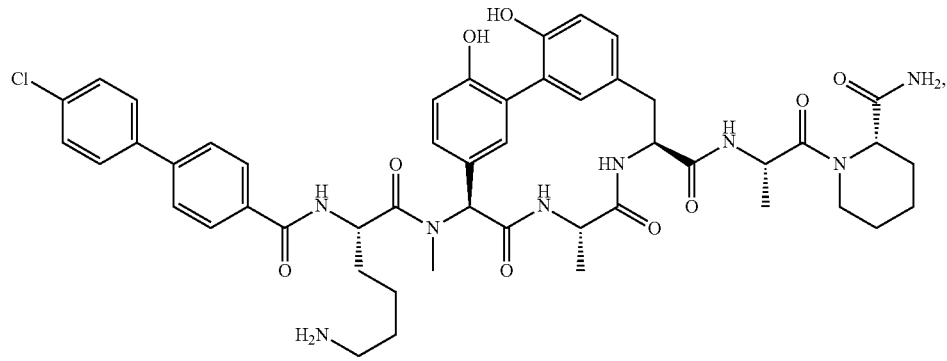
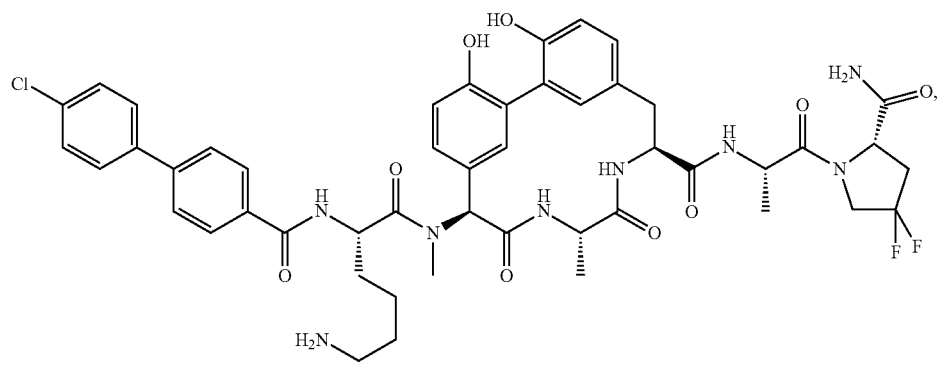
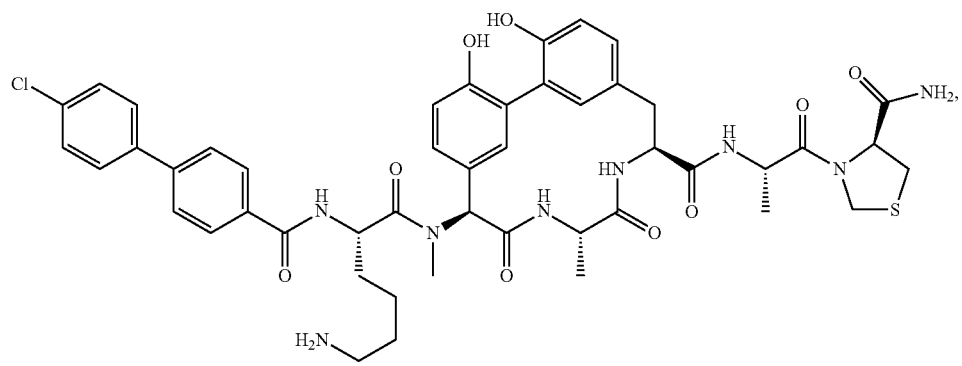
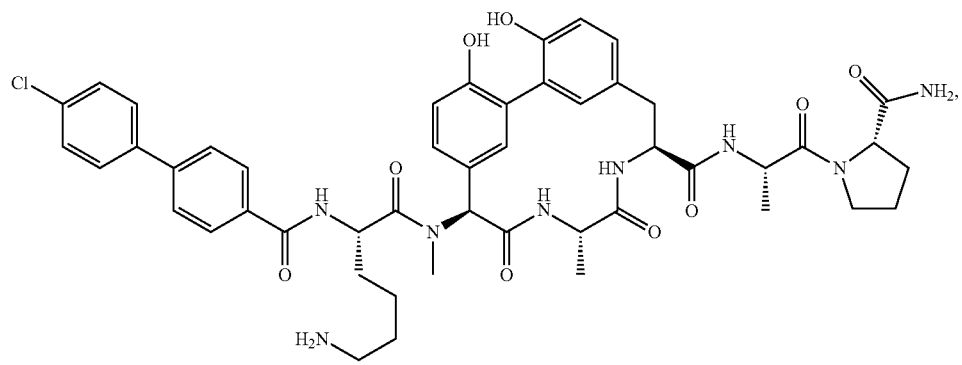

-continued
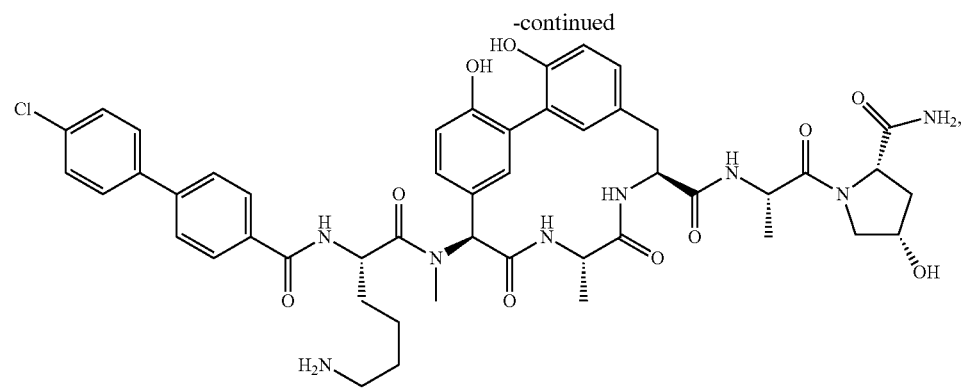
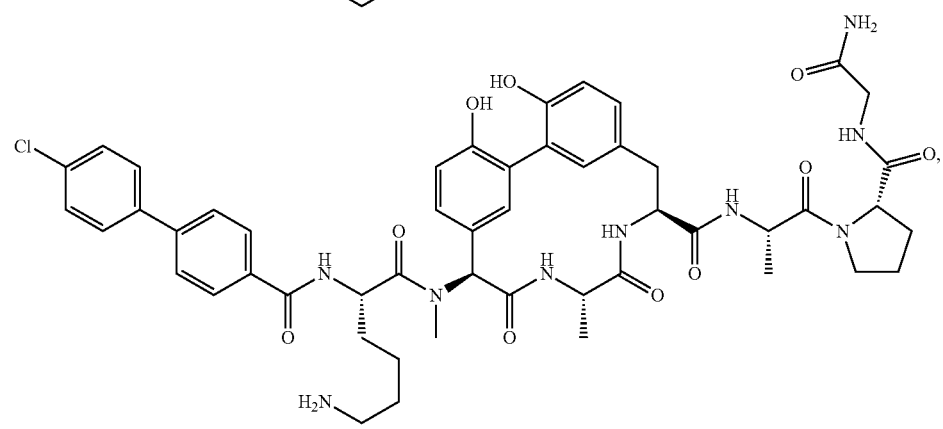
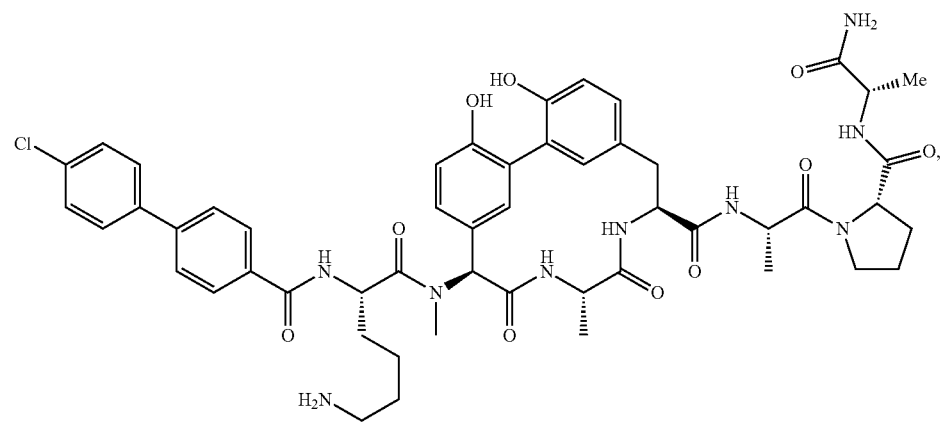
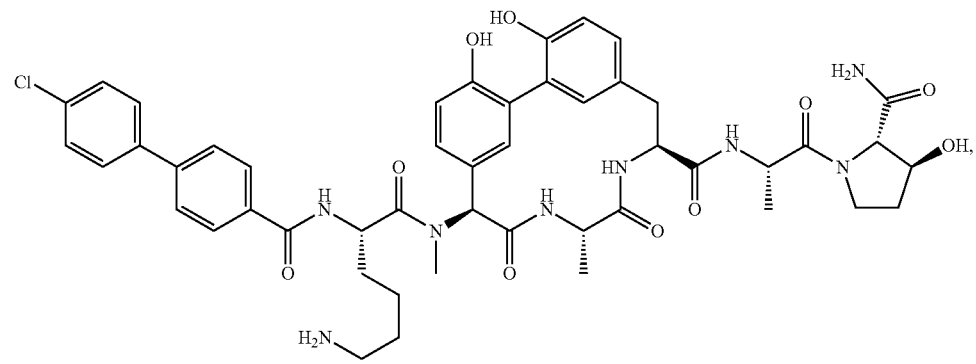

-continued
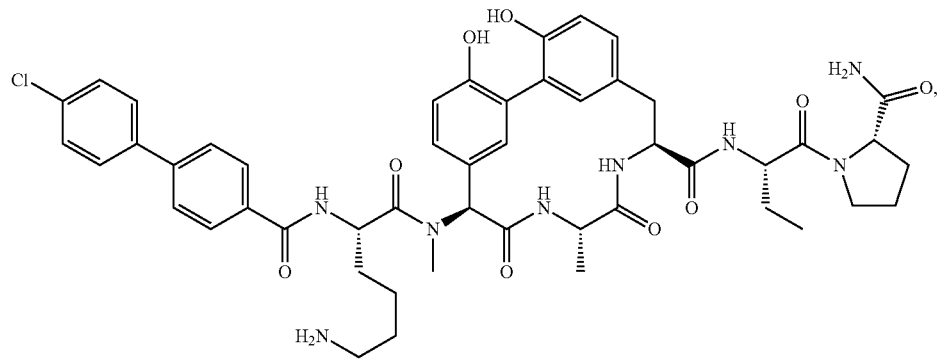
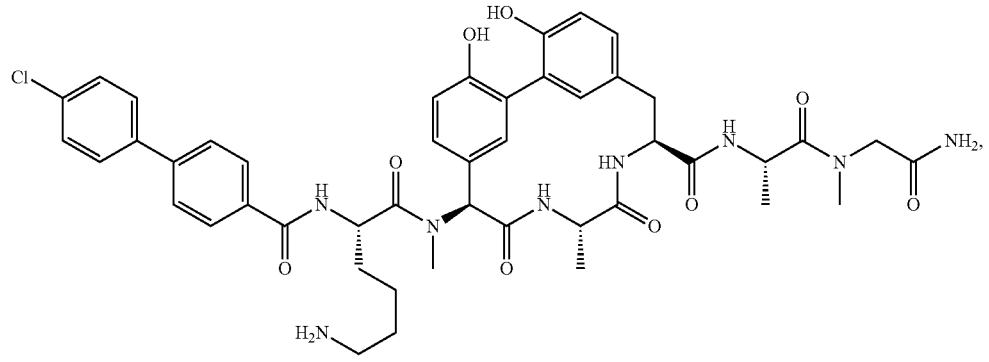
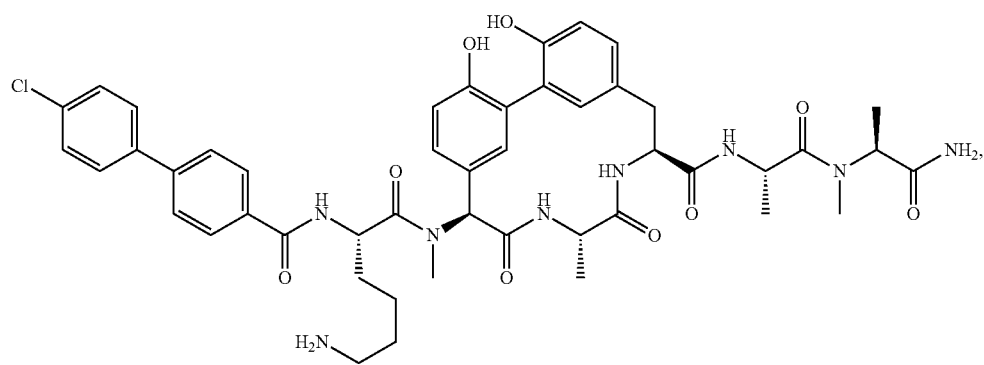
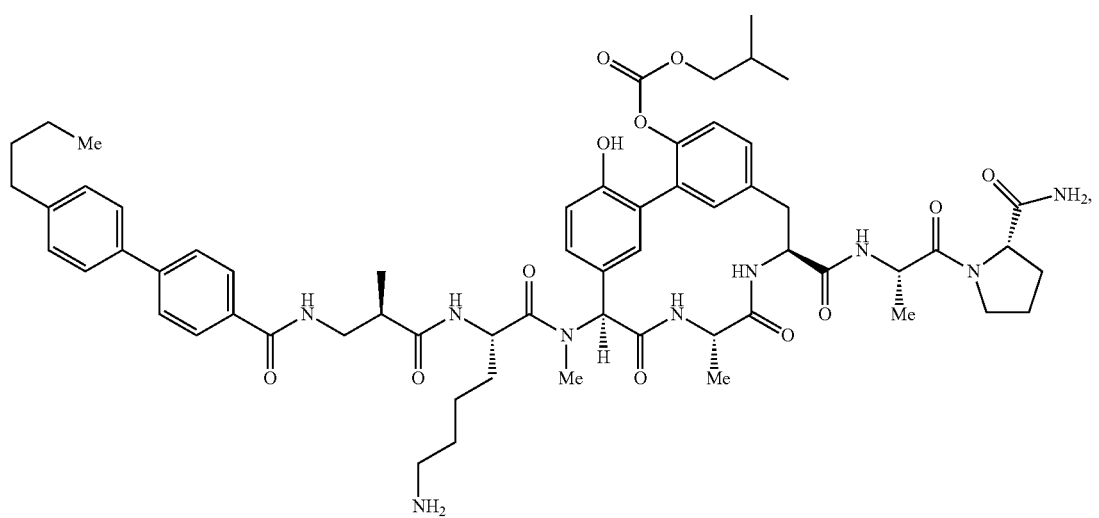

-continued
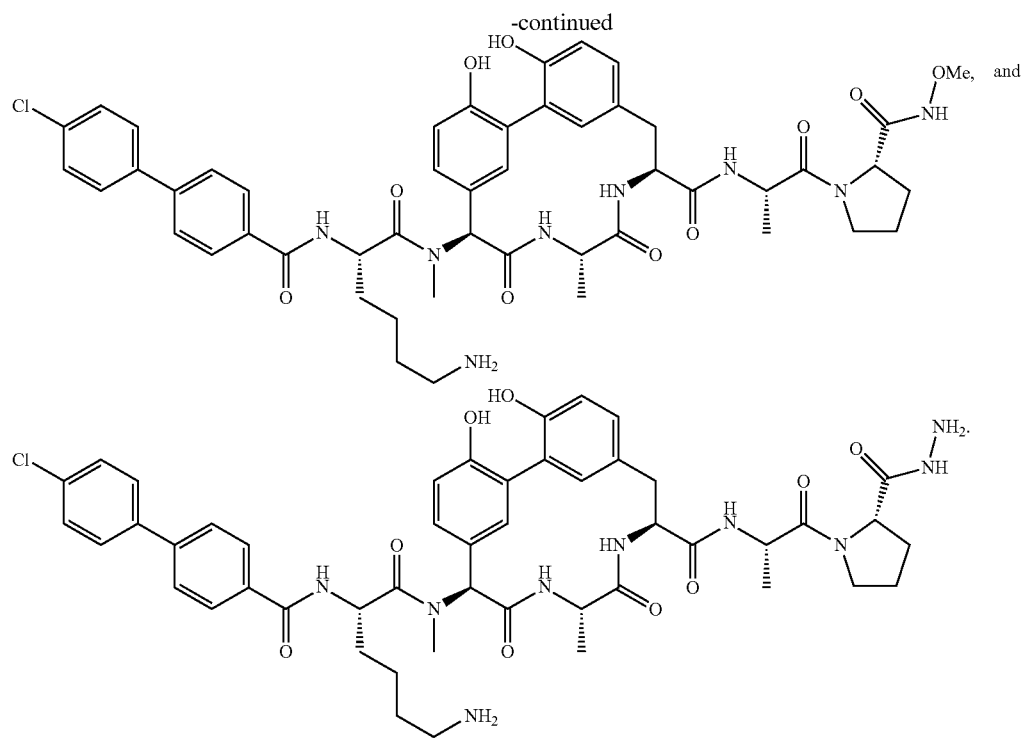
Some embodiments of compounds of Formula (I), (Ia), (Ib), (Ic), (II), (IIa), (IIb), (IIc), (III), or (IV) include, but are not limited to, compounds selected from the group consisting of:
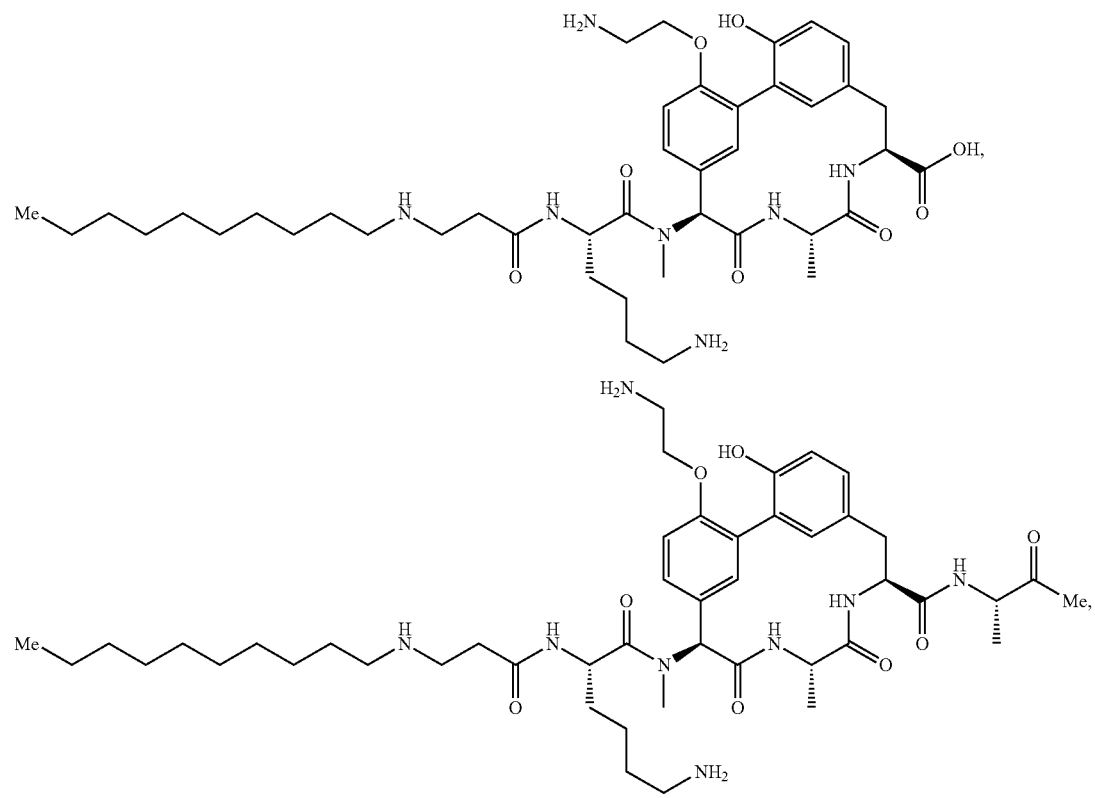

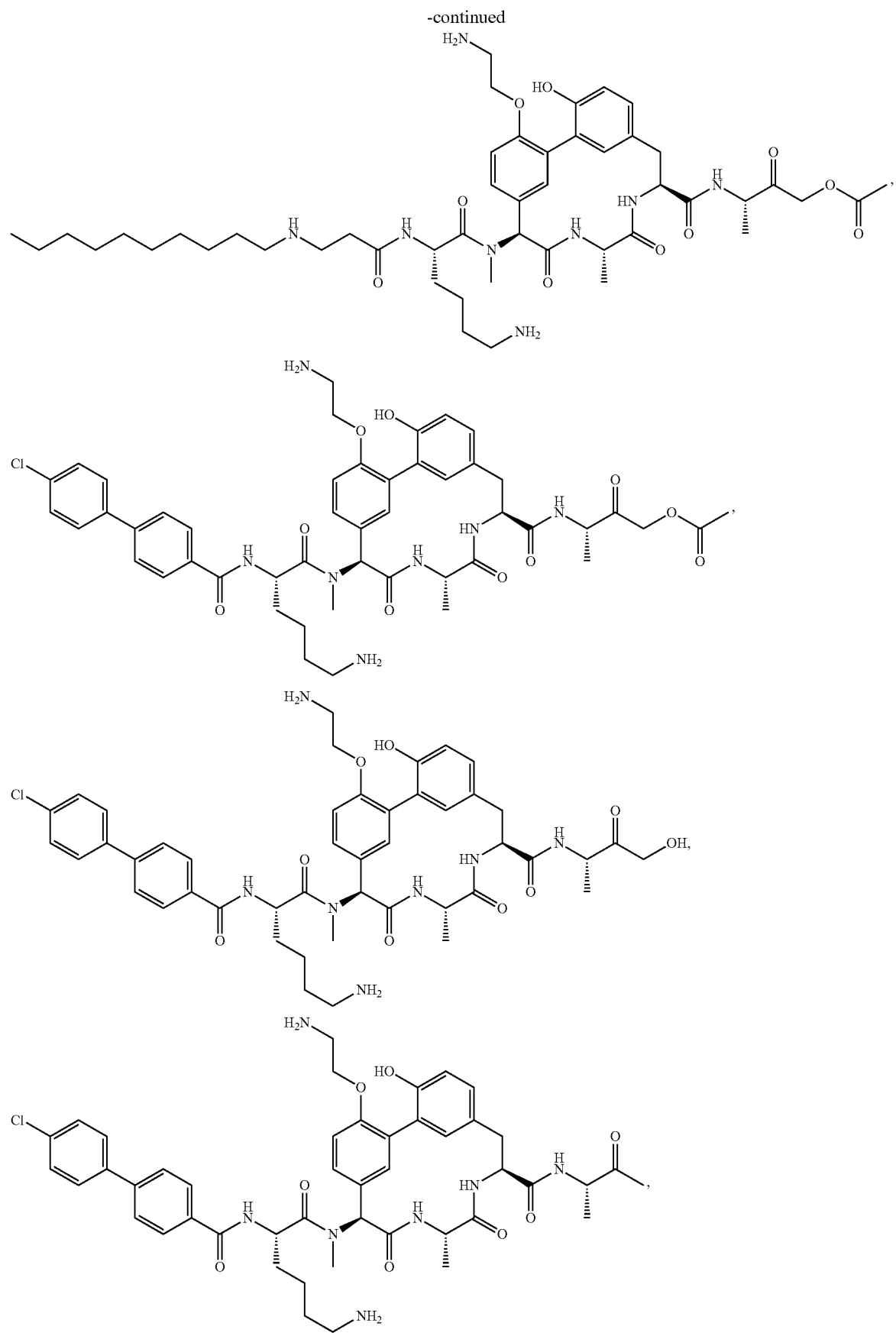

-continued
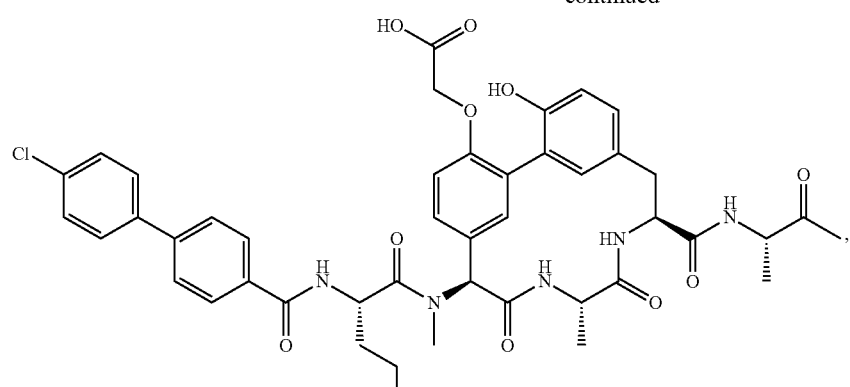
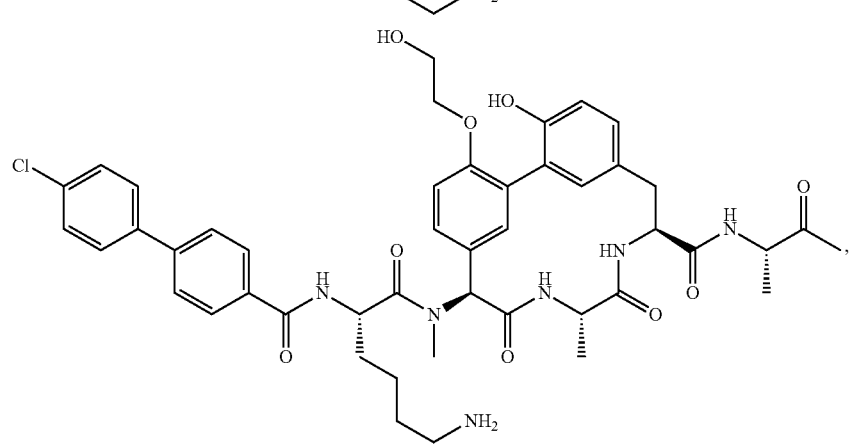
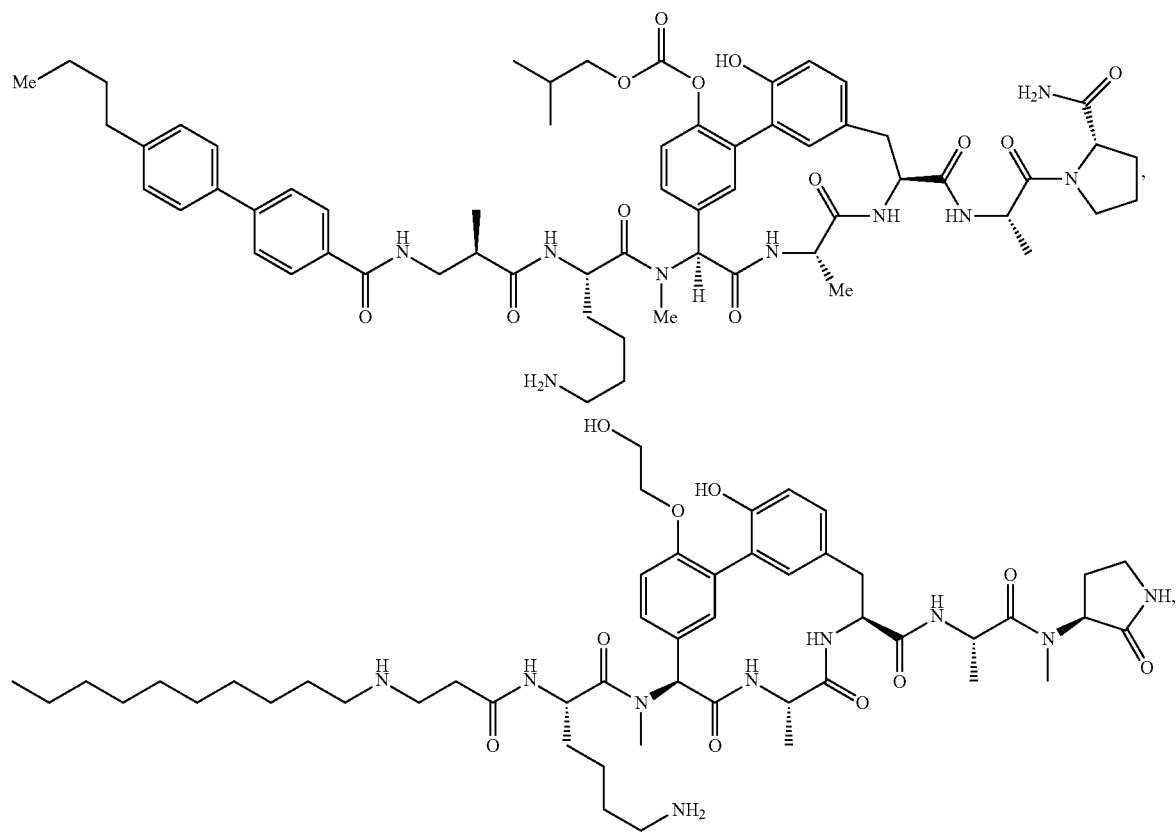

-continued
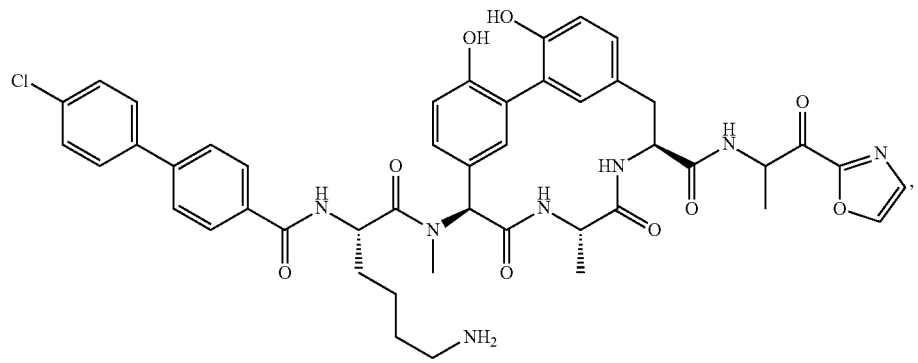
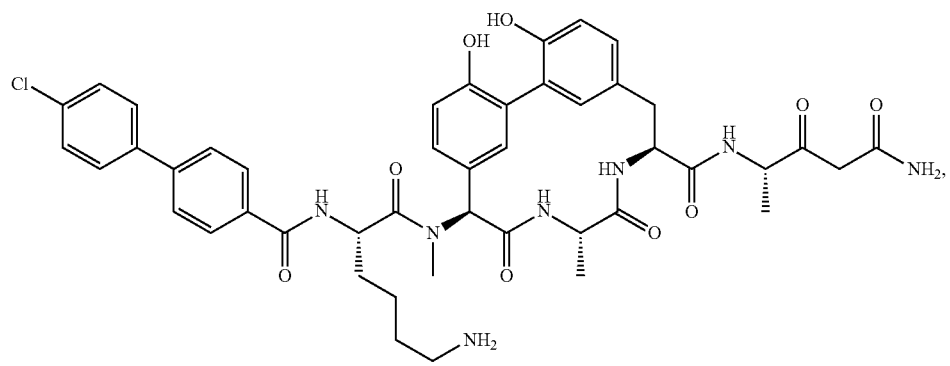
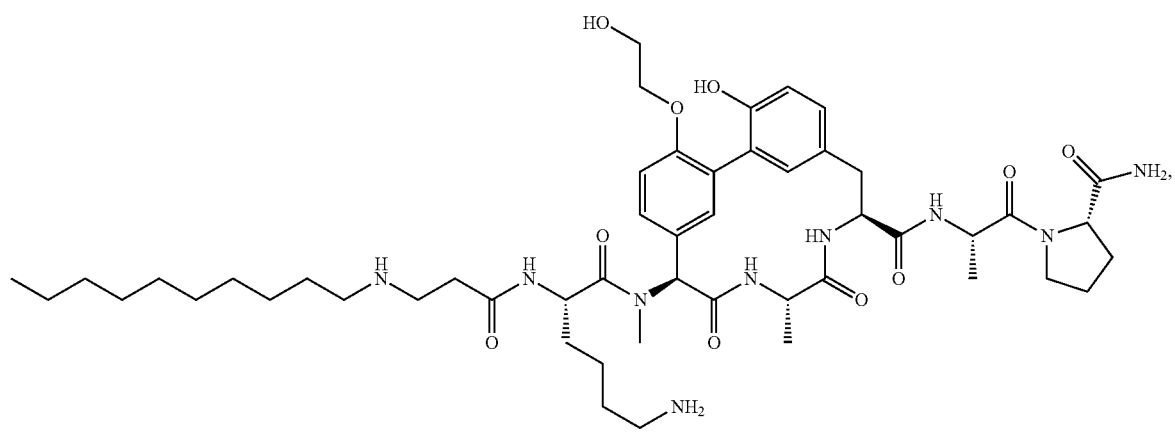
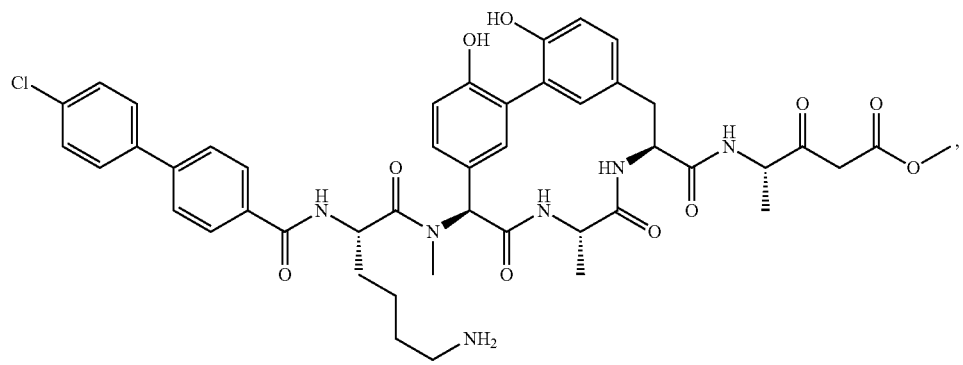

-continued
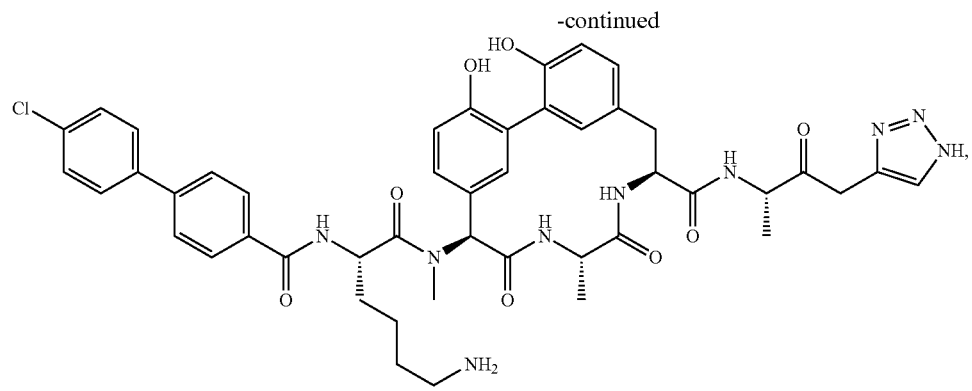
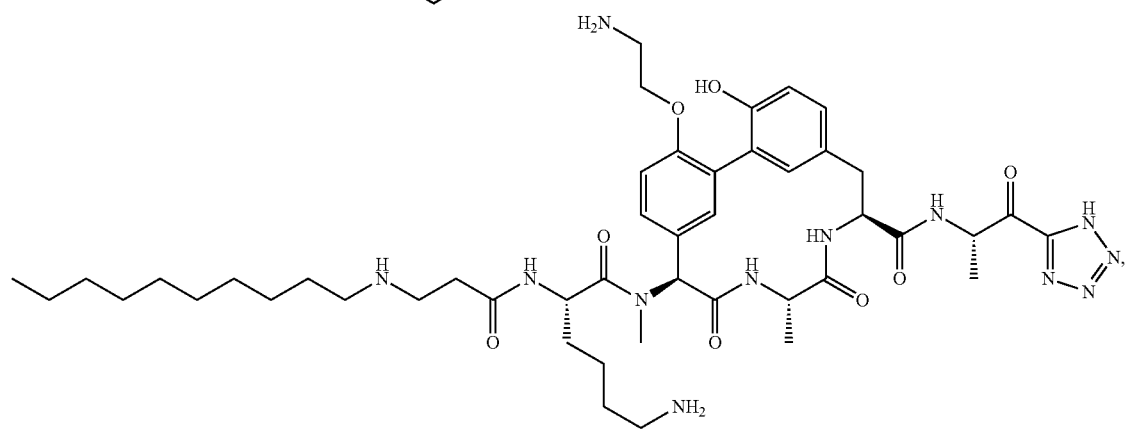
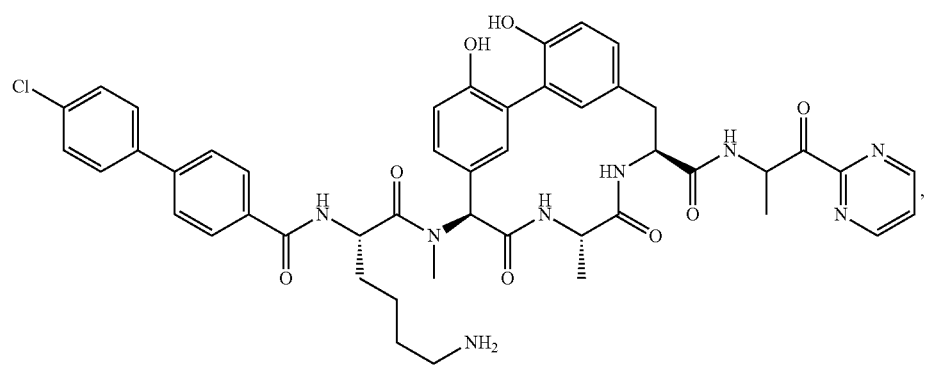
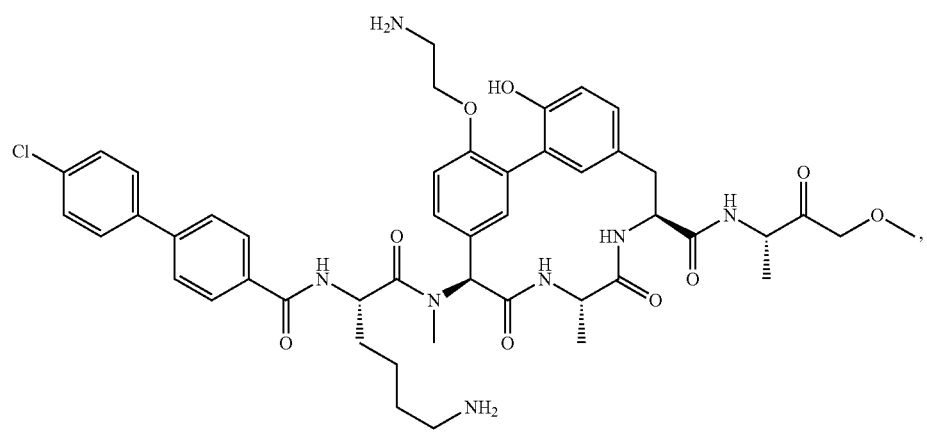

-continued
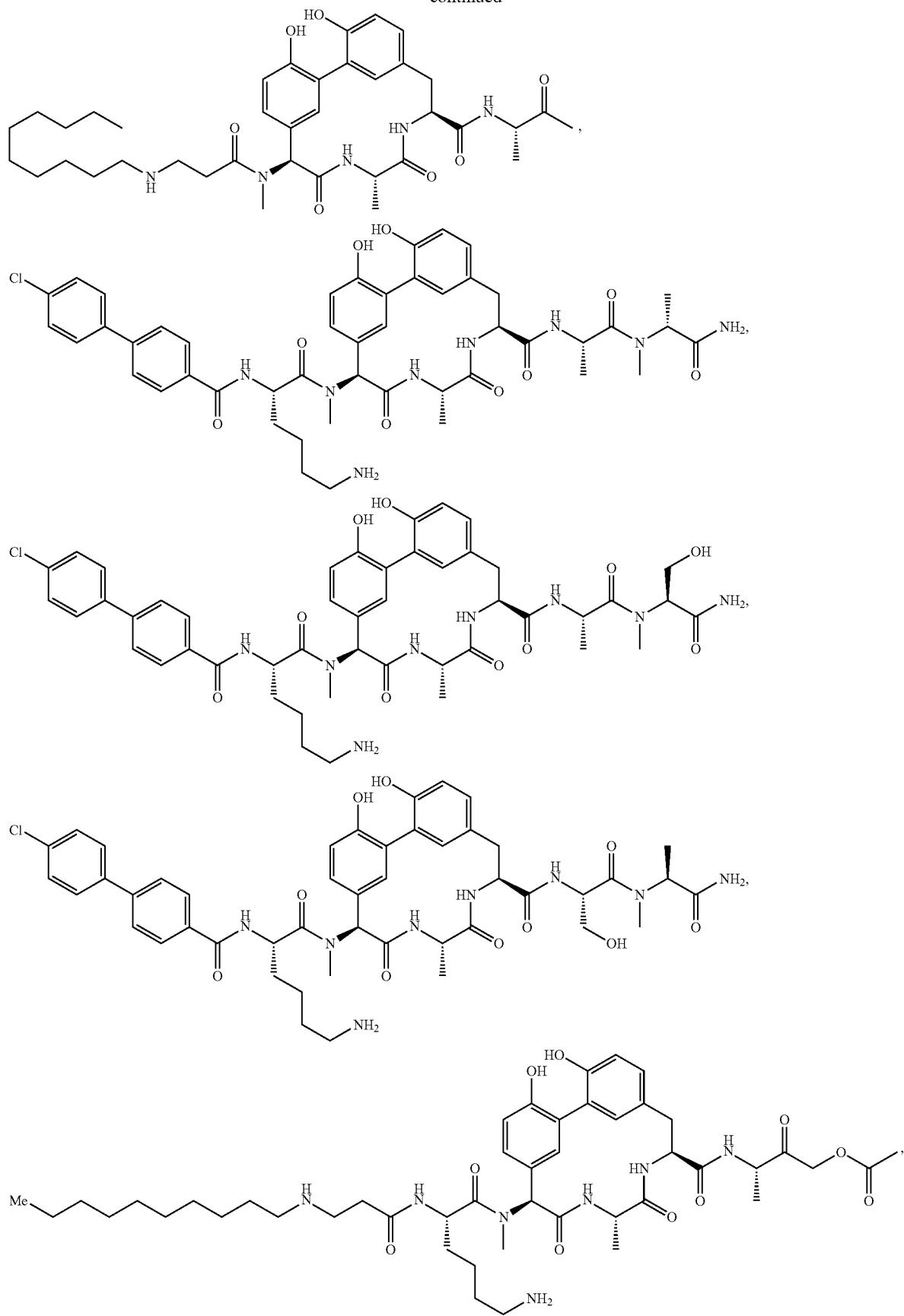

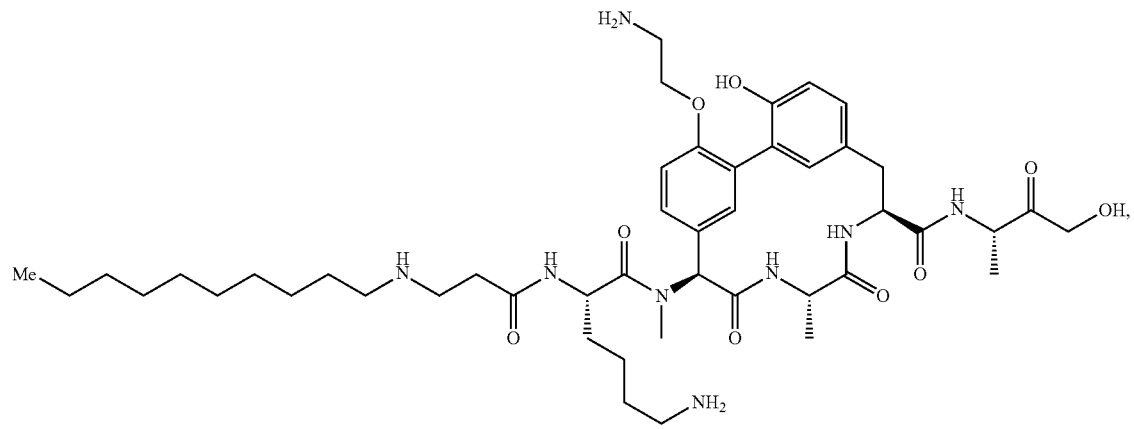
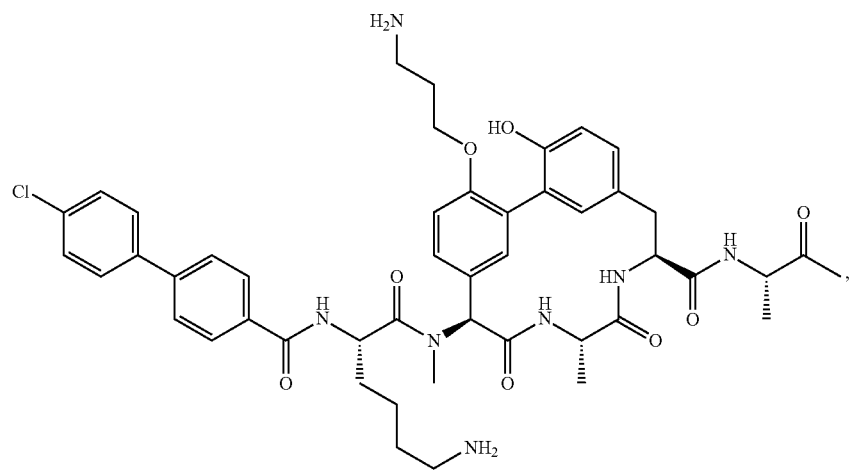
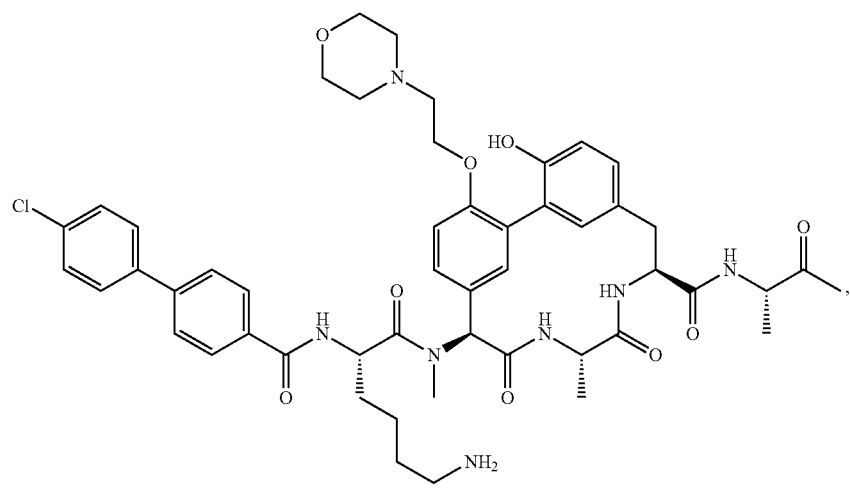

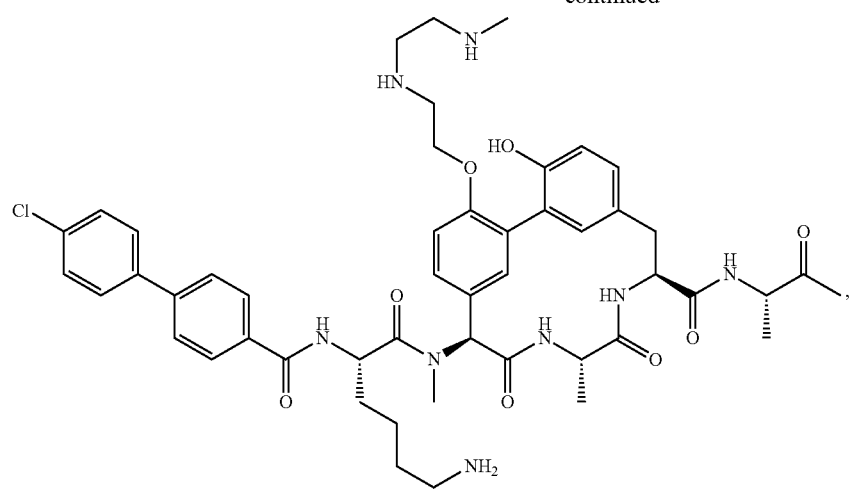
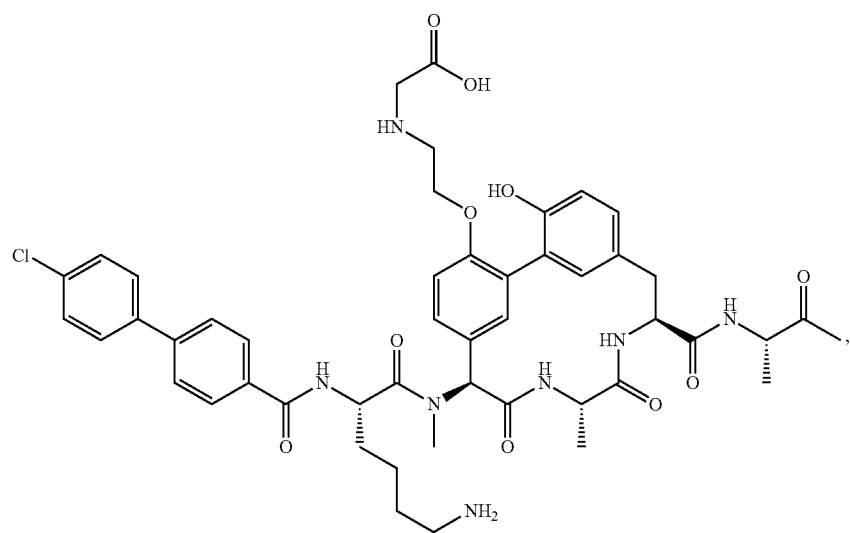
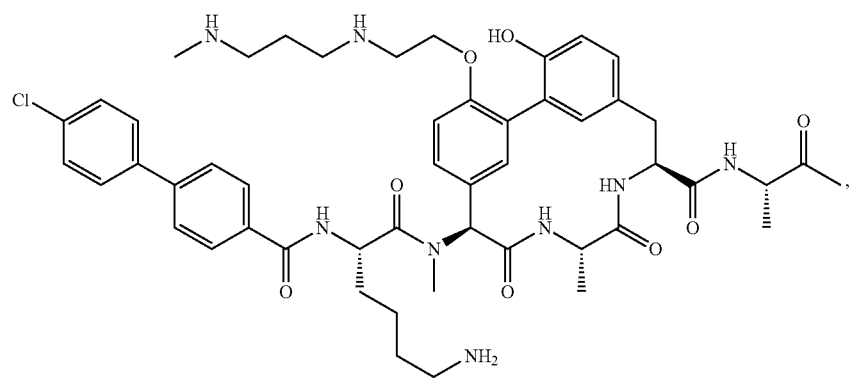

-continued
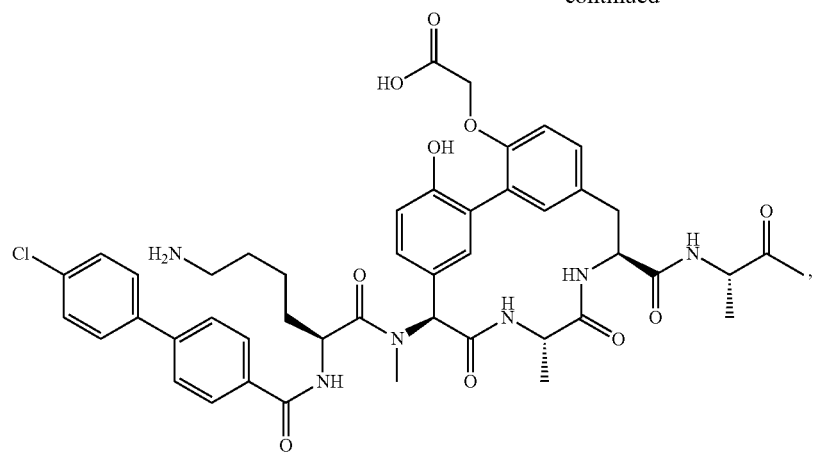
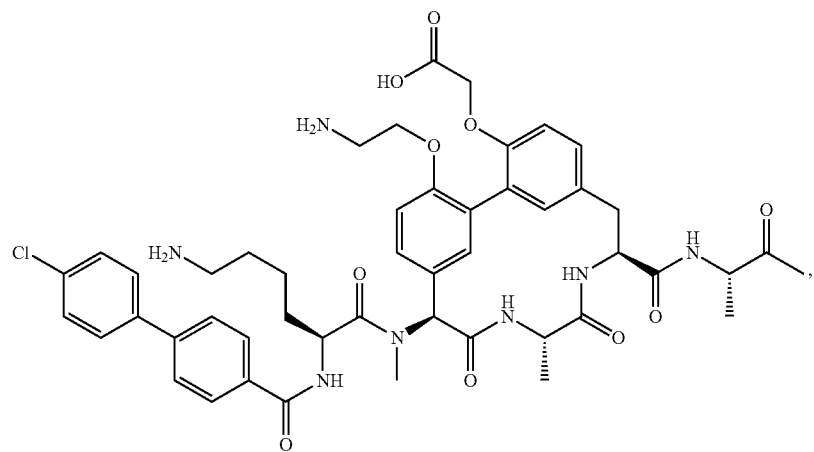
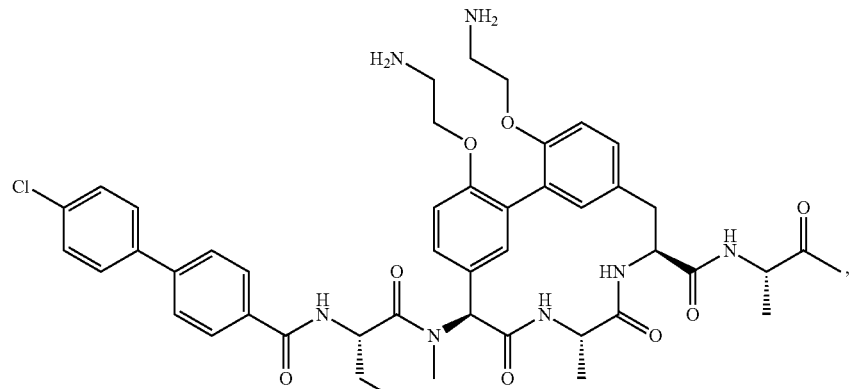
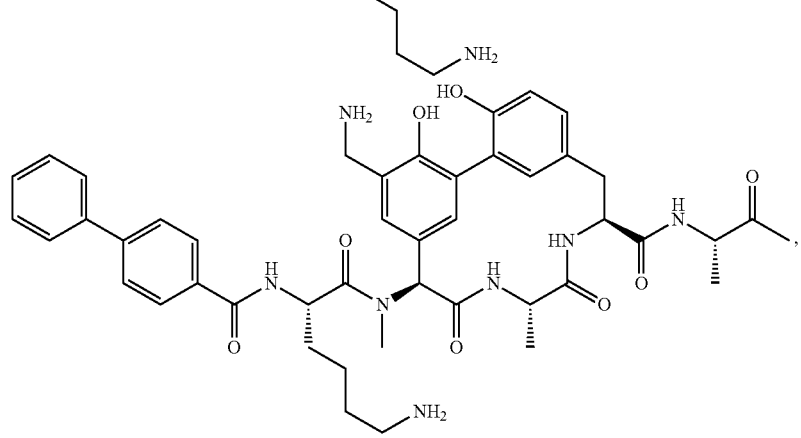

-continued
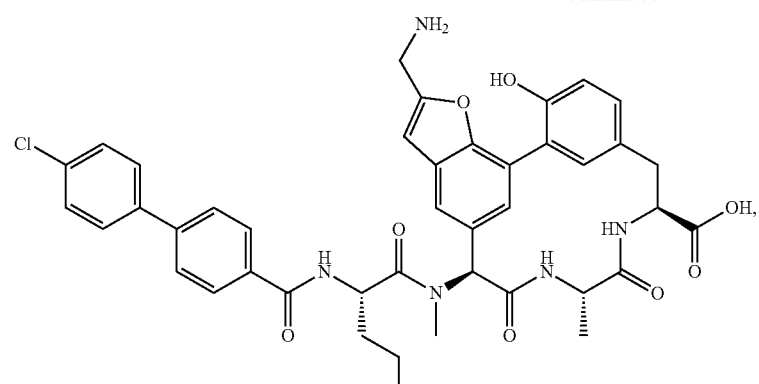
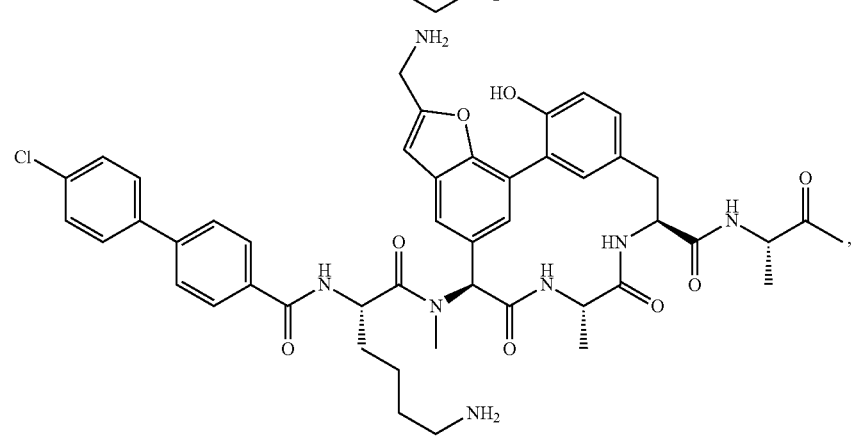
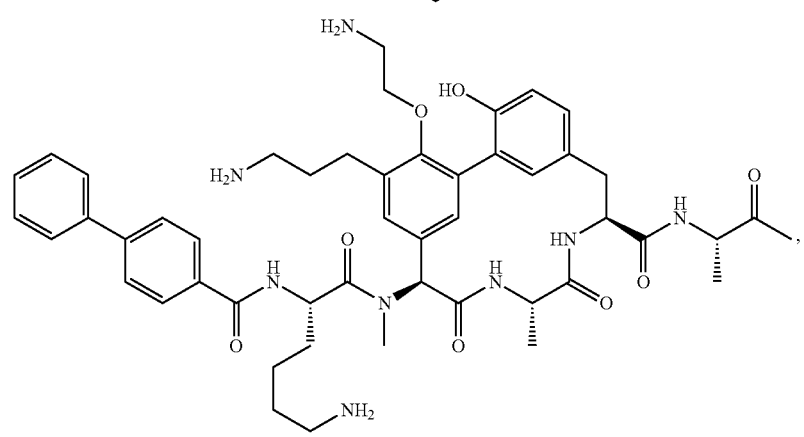
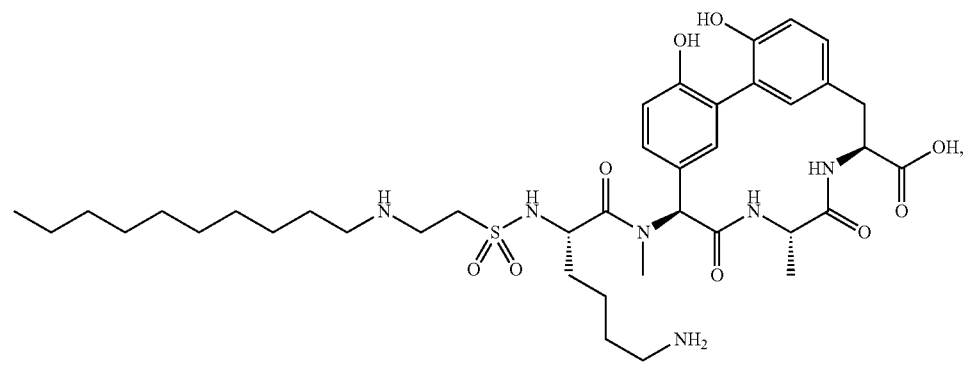

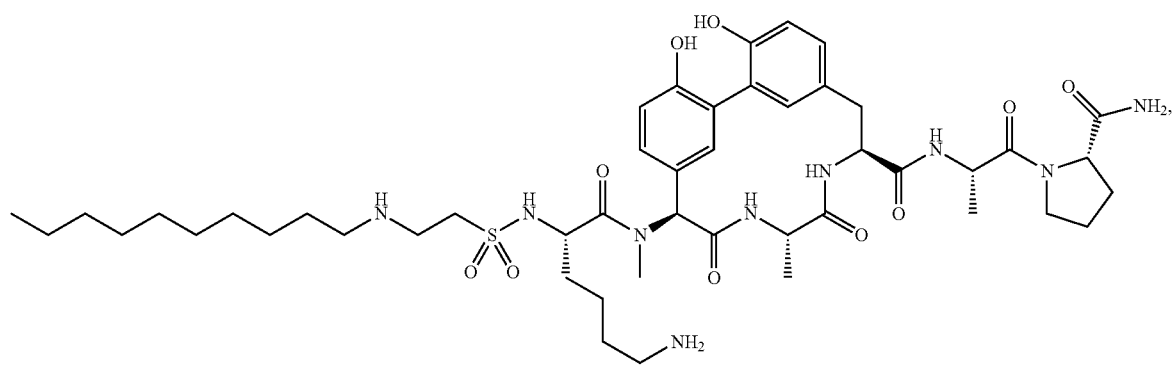
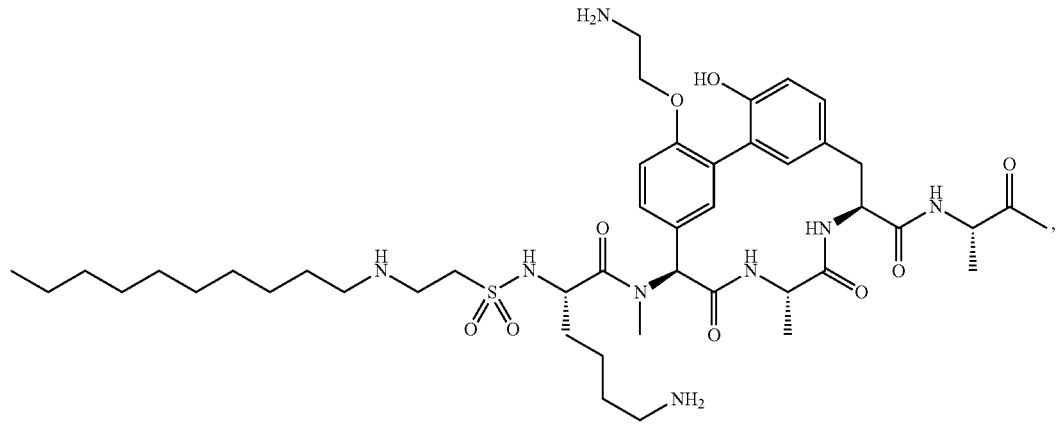
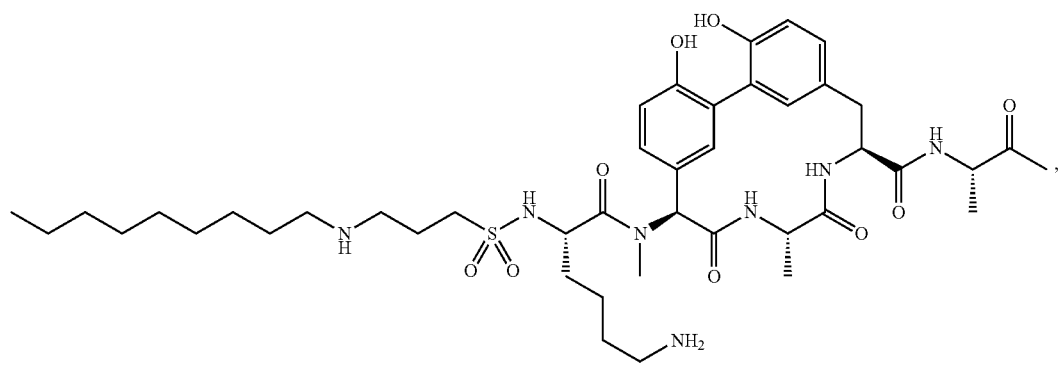
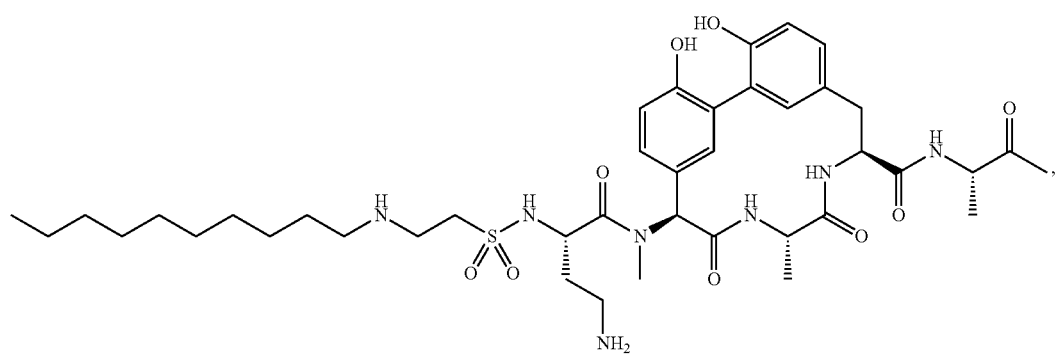

-continued
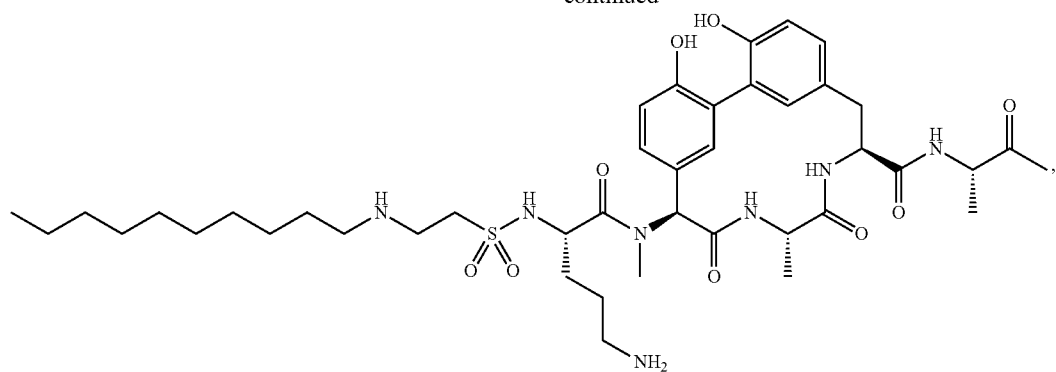
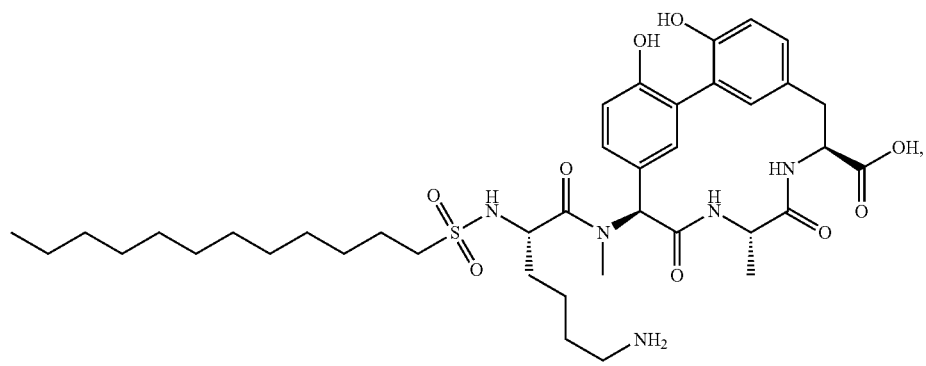
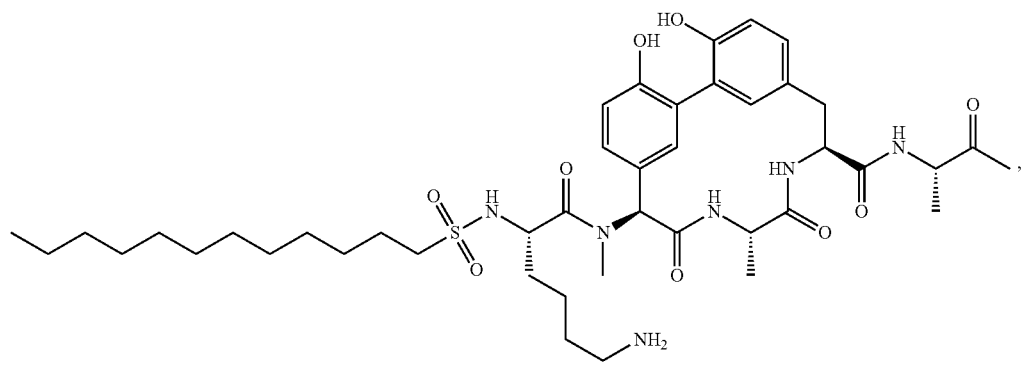
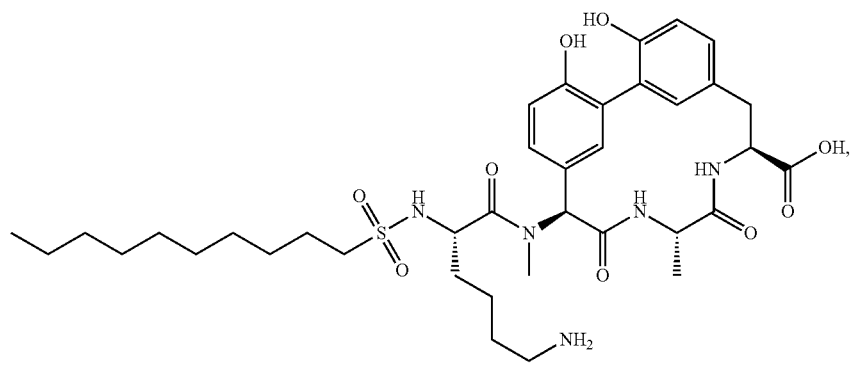

-continued

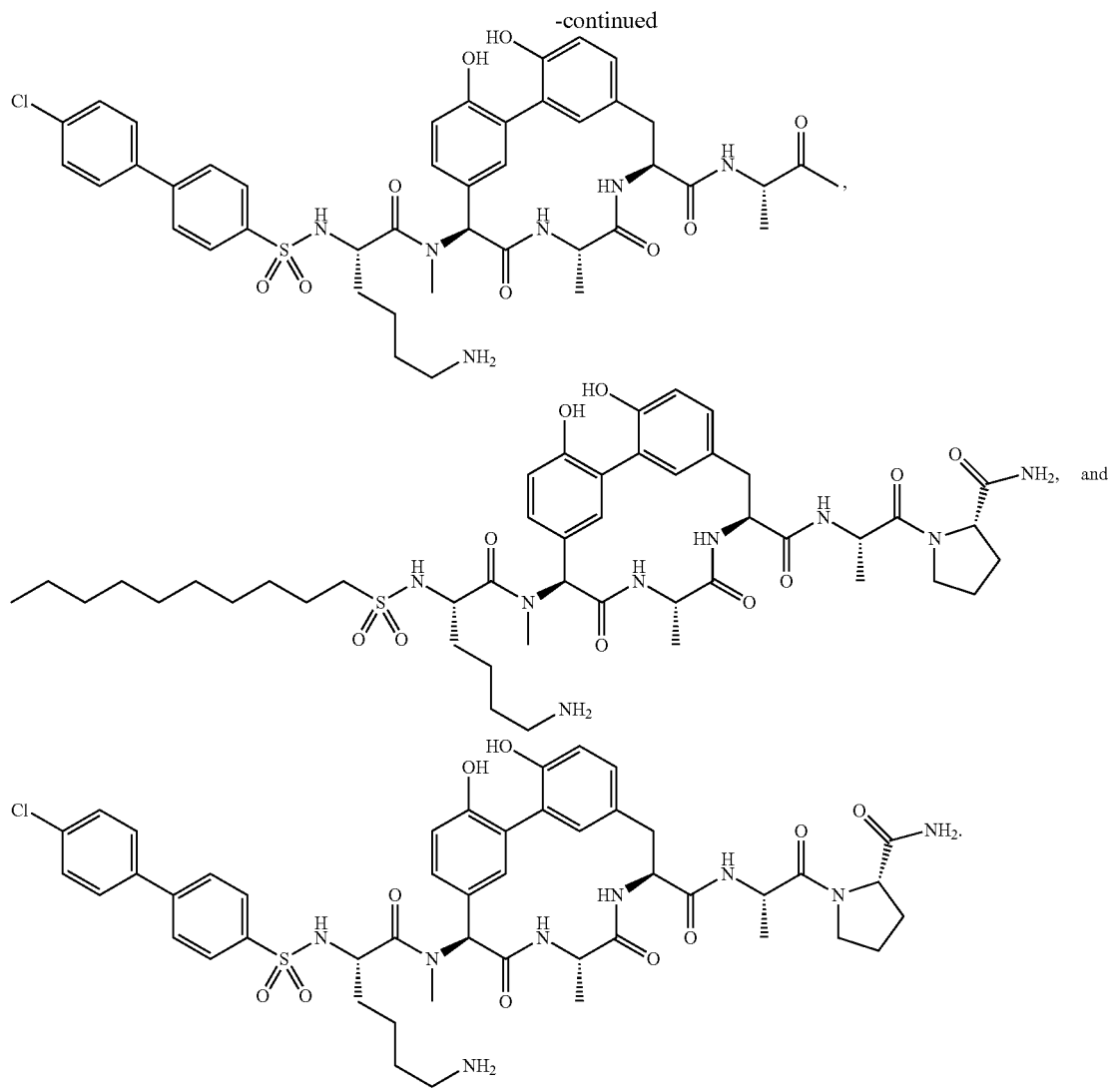

In another aspect described herein are compounds of Formula (IV):

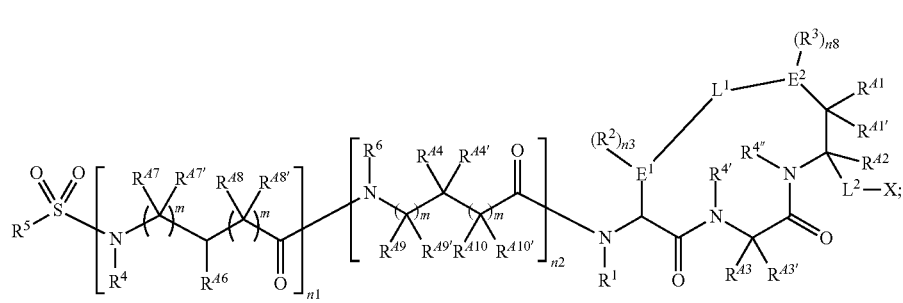

Formula (IV)

wherein:
$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;
$E^2$ is $(C_2-C_7)$alkenyl, $(C_2-C_7)$alkynyl, $(C_3-C_7)$cycloalkyl, heterocyclyl, heteroaryl, or aryl;
$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1-C_4)$alkylene optionally substituted with OH, CN, NO$_2$, halogen, $(C_1-C_6)$alkyl;
$L^2$ is a bond, or optionally substituted $(C_1-C_6)$alkylene;
X is —CO$_2$H, —CH$_2$CO$_2$H, —C(═O)NHCH$_2$C(═O)H, —CH$_2$C(═O)H, —C(═O)N(H)CH(R$^7$)B(OR$^{B3}$)(OR$^{B4}$), —CH$_2$OH, —CH(OH)CH$_3$, —N(R$^4$)CH(R$^{24}$)CN, —NHCH($R^{24}$)C(O)CH$_3$, —NHN($R^{24}$)C(O)CH$_3$, —NHCH($R^{24}$)CH=CHS(O)$_2$CH$_3$, —NHCH($R^{24}$)CH=CHS(O)$_2$NH$_2$,

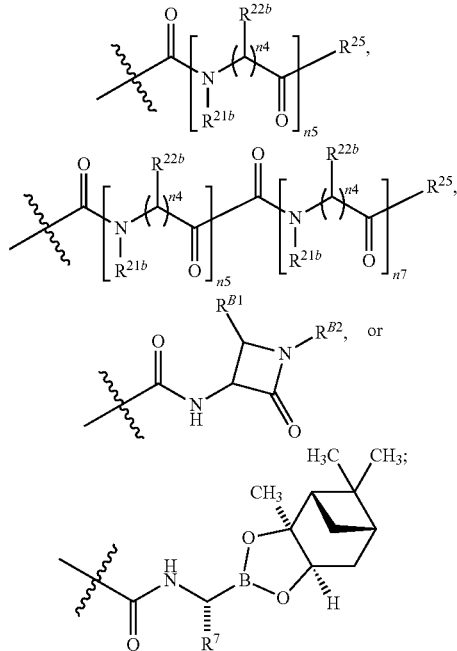

wherein n4, n5, and n6 are each independently 1, 2 or 3; n7 is 0, 1 or 2; $R^7$ is H, methyl, ethyl, or —CH$_2$OH; or $R^7$ and $R^{B3}$ together with the boron atom form a 5- or 6-membered boron containing ring; $R^{B3}$ and $R^{B4}$ are each independently H, (C$_1$–C$_6$)alkyl, —CH$_2$CO$_2$H, —CH$_2$CH$_2$CO$_2$H; or $R^{B3}$ and $R^{B4}$ together with the boron atom form an optionally substituted 5- or 6-membered boron containing ring; $R^{21b}$ and $R^{22b}$ are independently at each occurrence hydrogen, hydroxy, (C$_1$—C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; $R^{24}$ is H or (C$_1$-C$_6$)alkyl; $R^{25}$ is H, OH, OR$^C$, NR$^{25a}$R$^{25b}$, —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

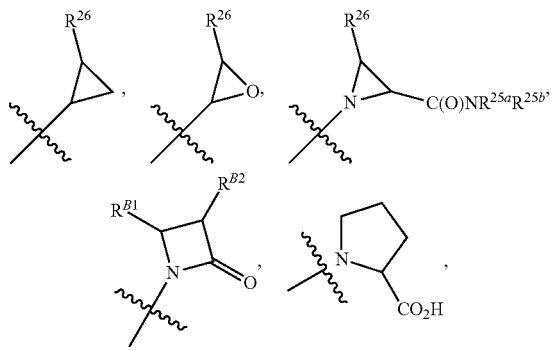

-continued

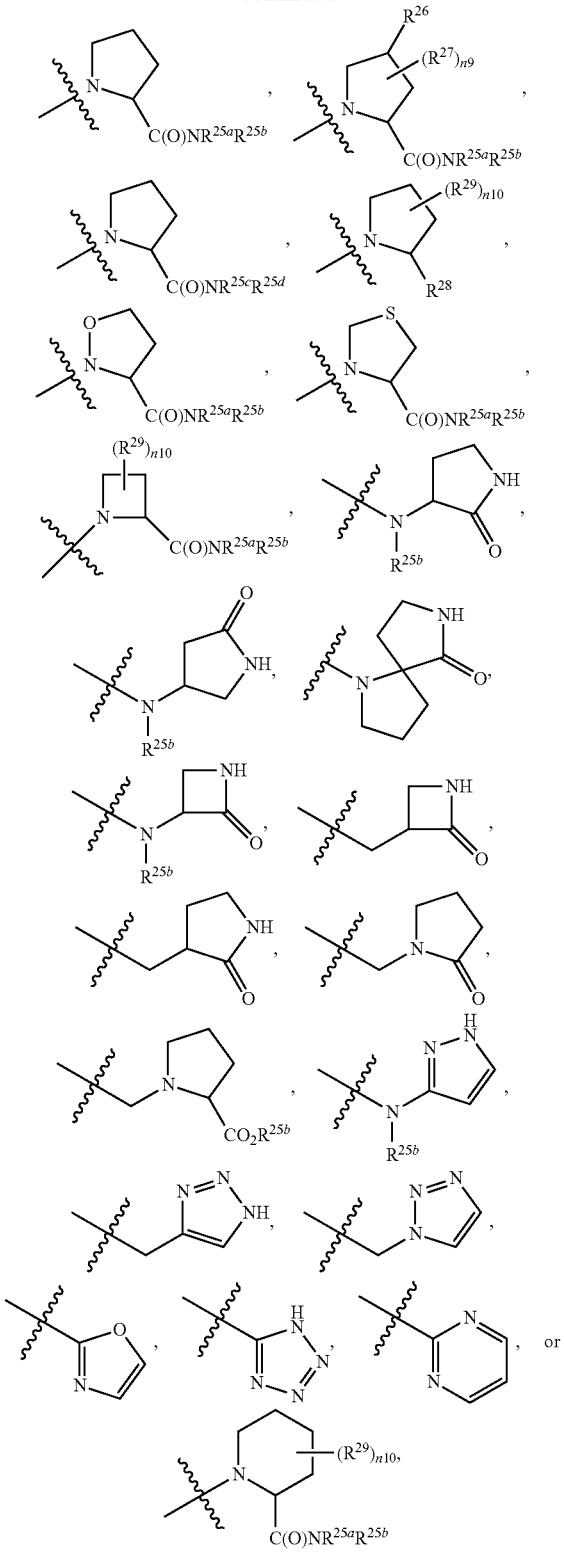

where $R^{B1}$ and $R^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or ($C_1$-$C_6$) alkyl; $R^{25a}$ is H, —OH, —OCH$_3$, NH$_2$, SO$_2$($C_1$-$C_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or ($C_1$-$C_6$)alkyl; each $R^{27}$ is independently —OH, halo, ($C_1$-$C_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or ($C_1$-$C_6$)alkyl; each $R^{29}$ is independently —OH, halo, or ($C_1$-$C_6$)alkyl; $R^{30}$ is heterocyclyl, heteroaryl, or aryl; n9 is 1, 2 or 3; n10 is 0, 1, 2, 3 or 4;

$R^5$ is aryl, heteroaryl, or a linear or branched alkyl chain of about 1-22 carbon atoms optionally comprising within the chain or at a chain terminus optionally substituted aryl, optionally substituted heteroaryl, or optionally substituted

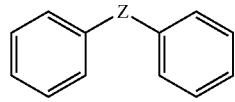

wherein Z is a bond, O, S, NH, CH$_2$ or C≡C; or $R^5$ is a linear or branched alkyl chain of about 1-22 carbon atoms, comprising within the chain at least one —O— or —N($R^4$)—;

each $R^2$ and $R^3$ are each independently hydroxy, nitro, halo, cyano, glycosyloxy, amino, ($C_1$-$C_4$)alkyl, $OR^{40}$, or a group cleavable under physiological conditions to provide a compound of formula (IV) wherein $R^2$ or $R^3$ respectively is hydroxy, wherein any carbon atom is optionally substituted with J;

each $R^{40}$ is independently —($C_1$-$C_6$)alkyl, or —($C_1$-$C_6$)alkyl-$NR^{41}R^{42}$;

each $R^{41}$ and $R^{42}$ is hydrogen, —($C_1$-$C_6$)alkyl, —($C_1$-$C_6$) heteroalkyl, —C(O)($C_1$-$C_6$)alkyl, —C(O)N($R^{43}$)$_2$, —SO$_2$N ($R^{43}$)$_2$; or $R^{41}$ and $R^{42}$ and the nitrogen atom to which that are attached form a heterocycloalkyl ring;

each $R^{43}$ is independently hydrogen or —($C_1$-$C_6$)alkyl; or two $R^{43}$ and the nitrogen atom to which that are attached form a heterocycloalkyl ring;

n1 and n2 are independently 0 or 1;
n3 and n8 are independently 0, 1, or 2;
each m is independently 0 or 1;

$R^1$ is hydrogen or ($C_1$-$C_6$)alkyl optionally substituted with 1 to 3 J; or $R^1$ together with $E^1$ form a ring;

$R^4$, $R^{4'}$, and $R^{4''}$ are each independently at each occurrence hydrogen, or ($C_1$-$C_6$)alkyl optionally substituted with 1 to 3 J;

$R^6$ is hydrogen, or ($C_1$-$C_6$)alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

$R^{46}$ is H, amino, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S (O)$_2$N(R')$_2$, (CH$_2$)$_{0-p}$SO$_3$R', (CH$_2$)$_{0-p}$C(O)R', (CH$_2$)$_{0-p}$C(O) OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R') C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N(($C_1$-$C_4$)alkyl)$_2$-, —NH($C_1$-$C_4$)alkyl, $C_1$-$C_6$alkyl, $C_3$-$C_8$cycloalkyl, or $C_1$-$C_6$heteroalkyl; or a pharmaceutically acceptable salt, solvate, or prodrug thereof.

In one embodiment is a compound of Formula (IV) wherein $E^1$ and $E^2$ are each independently aryl or heteroaryl. In another embodiment is a compound of Formula (IV) wherein $E^1$ and $E^2$ are each independently aryl. In another embodiment is a compound of Formula (IV) wherein $E^1$ and $E^2$ are each phenyl. In another embodiment is a compound of Formula (IV) wherein $E^1$ is aryl and $E^2$ is heteroaryl. In another embodiment is a compound of Formula (IV) wherein $E^1$ and $E^2$ are each heteroaryl.

In another embodiment is a compound of Formula (IV) wherein $L^1$ is a bond, —O—, —OCH$_2$—, or —CH$_2$O—. In some embodiments is a compound of Formula (IV) wherein $L^1$ is a bond. In some embodiments is a compound of Formula (IV) wherein $L^1$ is —O—. In some embodiments is a compound of Formula (IV) wherein $L^1$ is —OCH$_2$—. In some embodiments is a compound of Formula (IV) wherein $L^1$ is —CH$_2$O—.

In another embodiment is a compound of Formula (IV) wherein $E^1$ and $E^2$ are each phenyl and $L^1$ is a bond. In another embodiment is a compound of Formula (IV) wherein $E^1$ and $E^2$ are each phenyl and $L^1$ is —O—. In another embodiment is a compound of Formula (IV) wherein $E^1$ and $E^2$ are each phenyl and $L^1$ is —OCH$_2$—. In another embodiment is a compound of Formula (IV) wherein $E^1$ and $E^2$ are each phenyl and $L^1$ is —CH$_2$O—.

In another embodiment is a compound of Formula (IV) wherein $L^2$ is a bond. In another embodiment is a compound of Formula (IV) wherein $L^2$ is optionally substituted ($C_1$-$C_6$)alkylene. In a further embodiment, $L^2$ is methylene, ethylene, n-propylene, iso-propylene, n-butylene, iso-butylene, or tert-butylene.

In another embodiment is a compound of Formula (IV) wherein X is CO$_2$H, CH$_2$CO$_2$H, C(=O)NHCH$_2$C(=O)H, CH$_2$C(=O)H, C(=O)N(H)CH($R^7$)B($OR^{B3}$)($OR^{B4}$), or

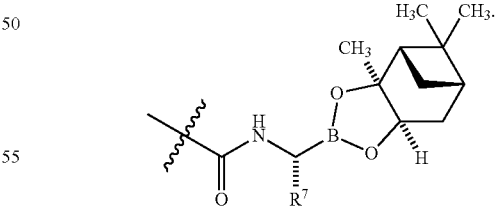

In some embodiments is a compound of Formula (IV) wherein X is CO$_2$H. In some embodiments is a compound of Formula (IV) wherein X is CH$_2$CO$_2$H. In some embodiments is a compound of Formula (IV) wherein X is C(=O) NHCH$_2$C(=O)H. In some embodiments is a compound of Formula (IV) wherein X is CH$_2$C(=O)H.

In some embodiments is a compound of Formula (IV) wherein X is C(=O)N(H)CH($R^7$)B($OR^{B3}$)($OR^{B4}$). In further embodiments is a compound of Formula (IV) wherein X is C(=O)N(H)CH$_2$B(OH)$_2$. In further embodiments is a compound of Formula (IV) wherein X is C(=O)N(H)CH(CH$_3$)B(OH)$_2$. In further embodiments is a compound of Formula (IV) wherein X is C(=O)N(H)CH(CH$_2$CH$_3$)B(OH)$_2$. In further embodiments is a compound of Formula (IV) wherein X is C(=O)N(H)CH(CH$_2$OH)B(OH)$_2$. In further embodiments is a compound of Formula (IV) wherein X is C(=O)N(H)CH$_2$B(OCH$_3$)$_2$. In further embodiments is a compound of Formula (IV) wherein X is C(=O)N(H)CH(CH$_3$)B(OCH$_3$)$_2$. In further embodiments is a compound of Formula (IV) wherein X is C(=O)N(H)CH(CH$_2$CH$_3$)B(OCH$_3$)$_2$. In further embodiments is a compound of Formula (IV) wherein X is C(=O)N(H)CH(CH$_2$OH)B(OCH$_3$)$_2$.

In some embodiments is a compound of Formula (IV) wherein X is C(=O)N(H)CH(R$^7$)B(OR$^{B3}$)(OR$^{B4}$) and R$^{B3}$ and R$^7$ together with the boron atom form an optionally substituted 5- or 6-membered boron containing ring. In some embodiments is a compound of Formula (IV) wherein X is

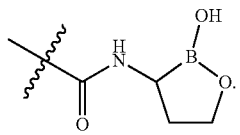 [SMILES: *C(=O)NC1CCOB1O]

In some embodiments is a compound of Formula (IV) wherein X is

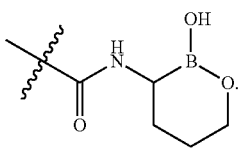 [SMILES: *C(=O)NC1CCCOB1O]

In some embodiments is a compound of Formula (IV) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (IV) wherein X is

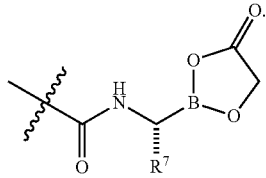

In some embodiments is a compound of Formula (IV) wherein X is

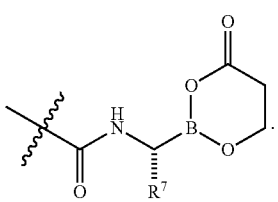

In some embodiments is a compound of Formula (IV) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (IV) wherein X is

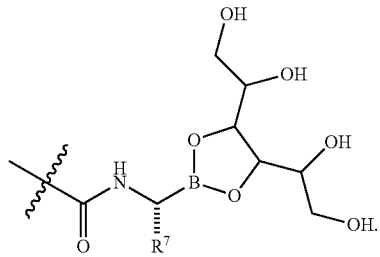

In some embodiments is a compound of Formula (IV) wherein X is

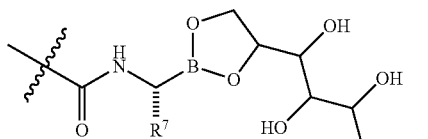

In some embodiments is a compound of Formula (IV) wherein X is

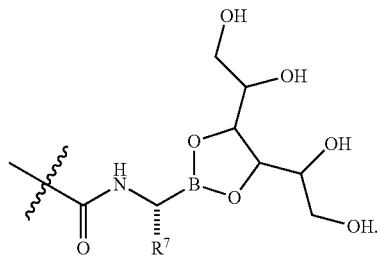

In some embodiments is a compound of Formula (IV) wherein X is

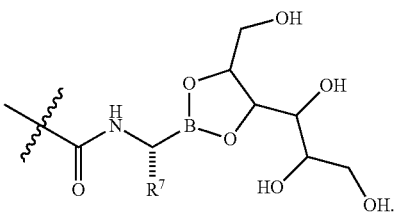

In some embodiments is a compound of Formula (IV) wherein X is

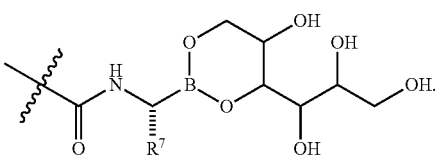

In some embodiments is a compound of Formula (IV) wherein X is

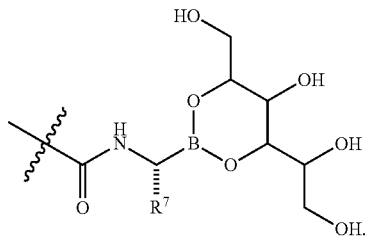

In some embodiments is a compound of Formula (IV) wherein X is

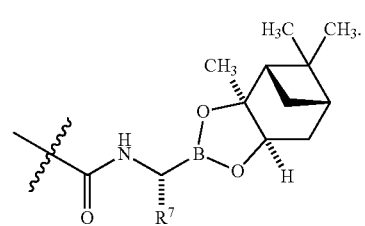

In further embodiments is a compound of Formula (IV) wherein X is

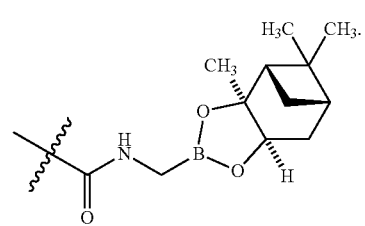 [SMILES: *C(=O)NCB1O[C@@H]2C[C@@H]3C[C@@H](C3(C)C)[C@]2(C)O1]

In further embodiments is a compound of Formula (IV) wherein X is

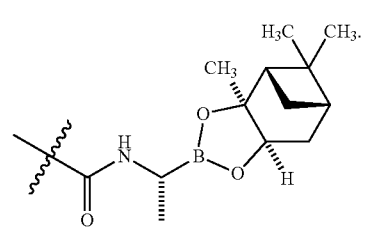

In further embodiments is a compound of Formula (IV) wherein X is

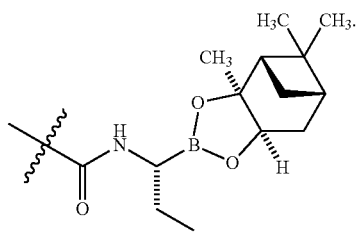 [SMILES: *C(=O)N[C@@H](CC)B1O[C@@H]2C[C@@H]3C[C@@H](C3(C)C)[C@]2(C)O1]

In further embodiments is a compound of Formula (IV) wherein X is

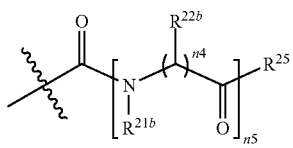

In another embodiment is a compound of Formula (IV) wherein X is —CH$_2$OH, —CH(OH)CH$_3$, —N(R$^4$)CH(R$^{24}$)CN, —NHCH(R$^{24}$)C(O)CH$_3$, —NHN(R$^{24}$)C(O)CH$_3$, —NHCH(R$^{24}$)CH═CHS(O)$_2$CH$_3$, or —NHCH(R$^{24}$)CH═CHS(O)$_2$NH$_2$; and R$^{24}$ is H or (C$_1$-C$_6$)alkyl. In some embodiments is a compound of Formula (IV) wherein X is —CH$_2$OH. In some embodiments is a compound of Formula (IV) wherein X is —CH(OH)CH$_3$. In some embodiments is a compound of Formula (IV) wherein X is —NHCH(R$^{24}$)C(O)CH$_3$. In some embodiments is a compound of Formula (IV) wherein X is —NHN(R$^{24}$)C(O)CH$_3$. In some embodiments is a compound of Formula (IV) wherein X is —NHCH(R$^{24}$)CH═CHS(O)$_2$CH$_3$. In some embodiments is a compound of Formula (IV) wherein X is —NHCH(R$^{24}$)CH═CHS(O)$_2$NH$_2$.

In some embodiments is a compound of Formula (IV) wherein X is wherein n4 and n5 are each independently 1, 2 or 3; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; and R$^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^3$, —N(H)CH$_2$(R$^{30}$), —CH═CHR$^{30}$, —CH═CHSO$_2$R$^{25b}$,

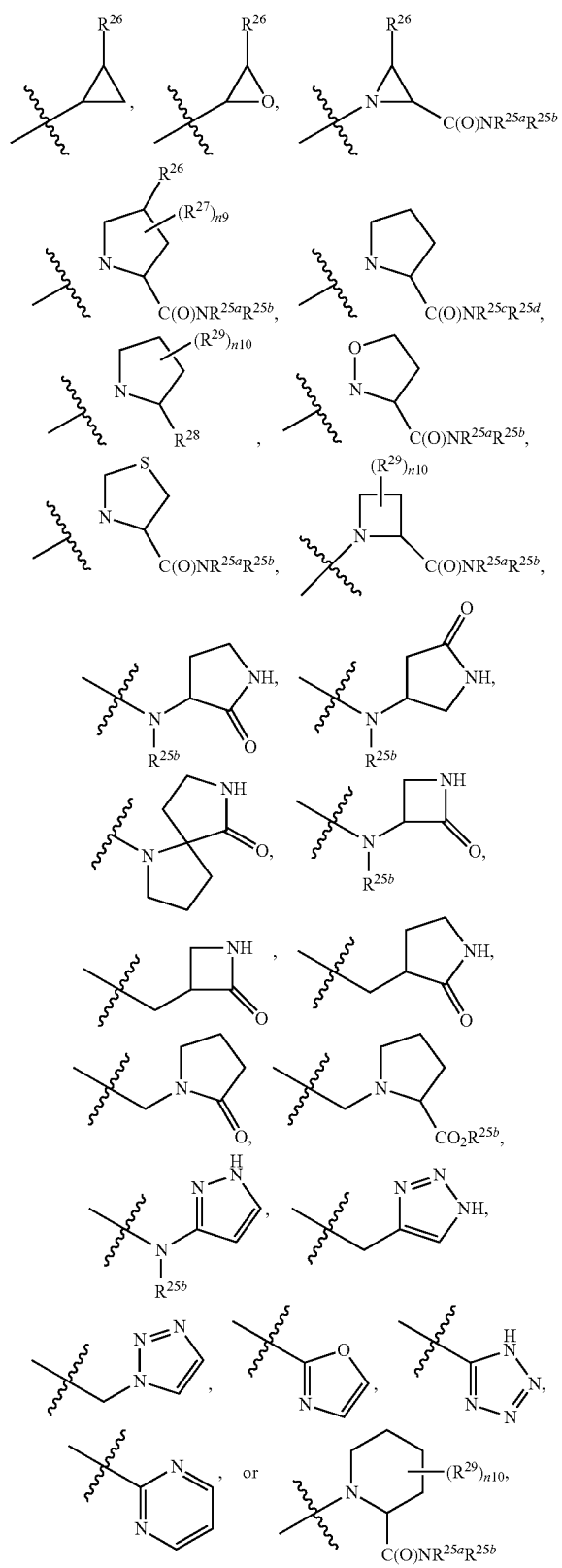

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In another embodiment is a compound of Formula (IV) wherein X is

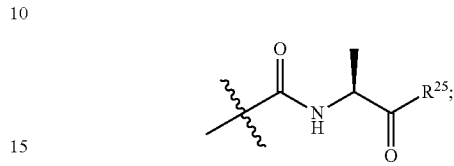

wherein $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

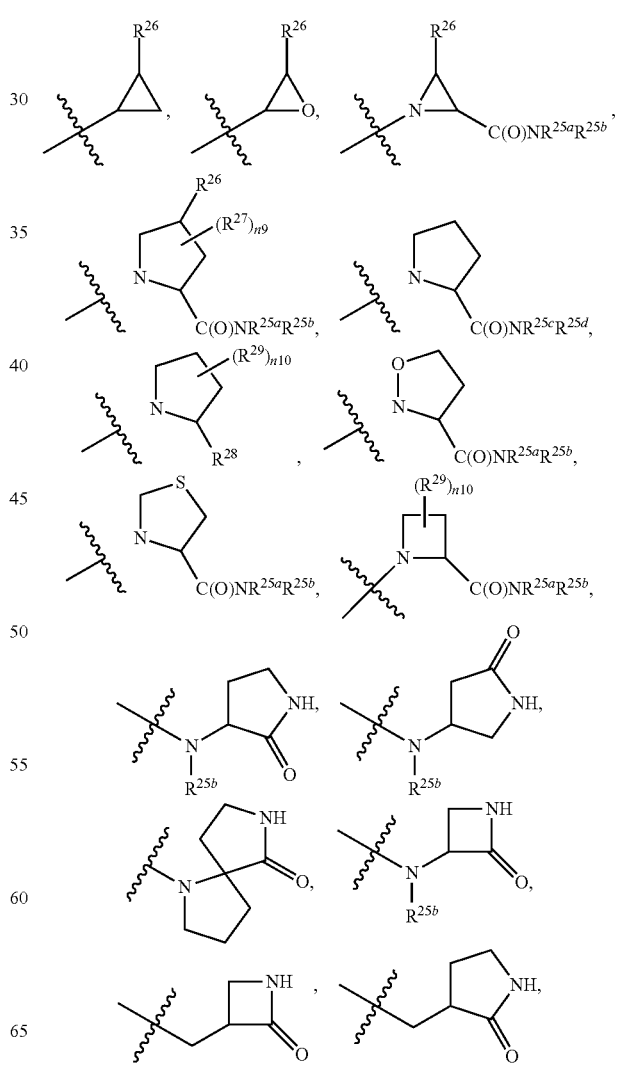

-continued

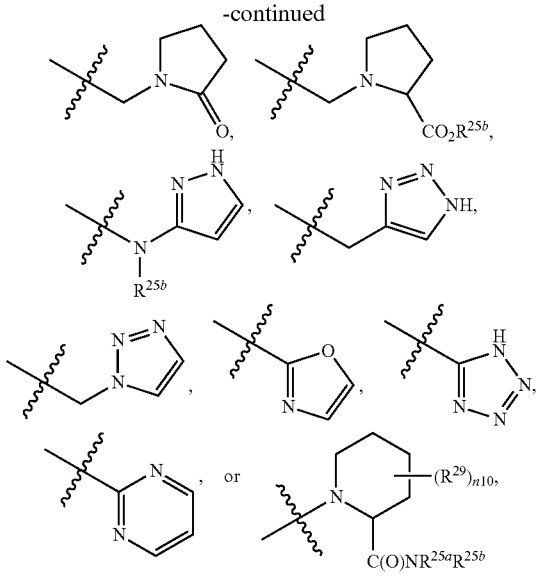

where R$^{25a}$ is H, —OH, —OCH$_3$, NH$_2$, SO$_2$(C$_1$-C$_6$)alkyl, or optionally substituted alkyl; each R$^{25b}$ is independently H, or optionally substituted alkyl; R$^{25c}$ is H or optionally substituted alkyl; R$^{25d}$ is —OH, —OCH$_3$, or NH$_2$; each R$^{26}$ is independently H, halo or (C$_1$-C$_6$)alkyl; each R$^{27}$ is independently —OH, halo, (C$_1$-C$_6$)alkyl, or R$^{26}$ and R$^{27}$ are joined to form a cycloalkyl ring; R$^{28}$ is H, —CH$_2$OH, —CH$_2$NH$_2$, —C(O)CH$_3$, or (C$_1$-C$_6$)alkyl; each R$^{29}$ is independently —OH, halo, or (C$_1$-C$_6$)alkyl; R$^{30}$ is heterocyclyl, heteroaryl, or aryl; n9 is 1, 2 or 3; and n10 is 0, 1, 2, 3 or 4. In some embodiments is a compound of Formula (IV) wherein X is

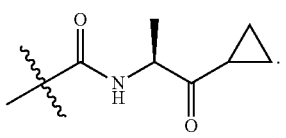 [SMILES: *C(=O)N[C@@H](C)C(=O)C1CC1]

In some embodiments is a compound of Formula (IV) wherein X is

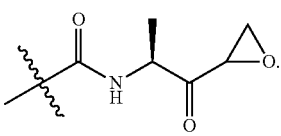 [SMILES: *C(=O)N[C@@H](C)C(=O)C1CO1]

In some embodiments is a compound of Formula (IV) wherein X is

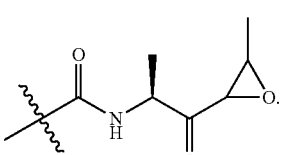

In some embodiments is a compound of Formula (IV) wherein X is

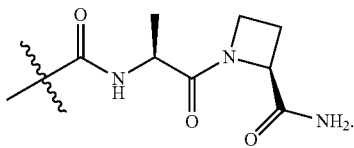 [SMILES: *C(=O)N[C@@H](C)C(=O)N1CC[C@H]1C(N)=O]

In some embodiments is a compound of Formula (IV) wherein X is

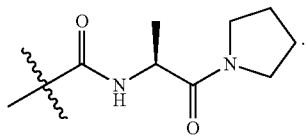 [SMILES: *C(=O)N[C@@H](C)C(=O)N1CCCC1]

In some embodiments is a compound of Formula (IV) wherein X is

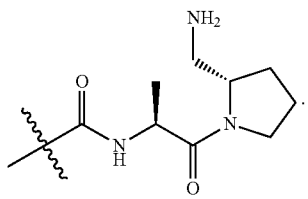

In some embodiments is a compound of Formula (IV) wherein X is

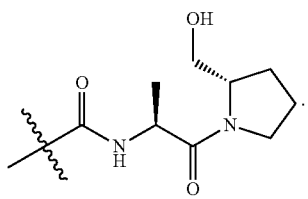

In some embodiments is a compound of Formula (IV) wherein X is

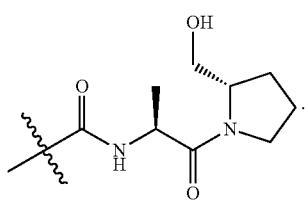

In some embodiments is a compound of Formula (IV) wherein X is

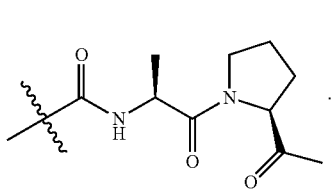

In some embodiments is a compound of Formula (IV) wherein X is

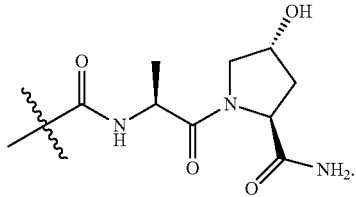 [SMILES: *C(=O)N[C@@H](C)C(=O)N1C[C@H](O)C[C@H]1C(N)=O]

In some embodiments is a compound of Formula (IV) wherein X is

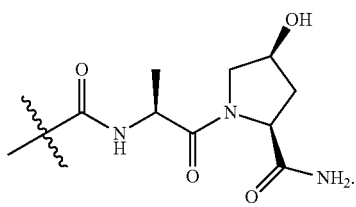 [SMILES: *C(=O)N[C@@H](C)C(=O)N1C[C@@H](O)C[C@H]1C(N)=O]

In some embodiments is a compound of Formula (IV) wherein X is


In some embodiments is a compound of Formula (IV) wherein X is

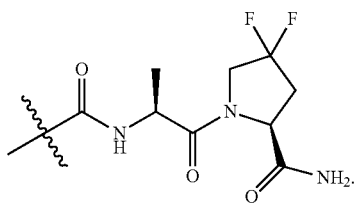 [SMILES: *C(=O)N[C@@H](C)C(=O)N1CC(F)(F)C[C@H]1C(N)=O]

In some embodiments is a compound of Formula (IV) wherein X is

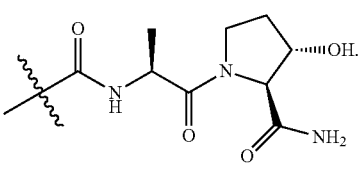 [SMILES: *C(=O)N[C@@H](C)C(=O)N1CC[C@H](O)[C@H]1C(N)=O]

In some embodiments is a compound of Formula (IV) wherein X is

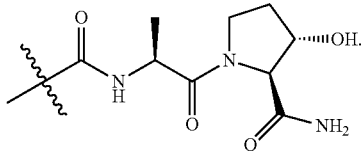 [SMILES: *C(=O)N[C@@H](C)C(=O)N1CC[C@H](O)[C@H]1C(N)=O]

In some embodiments is a compound of Formula (IV) wherein X is

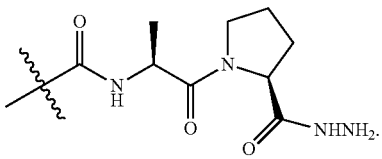 [SMILES: *C(=O)N[C@@H](C)C(=O)N1CCC[C@H]1C(=O)NN]

In some embodiments is a compound of Formula (IV) wherein X is

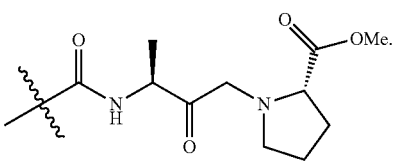 [SMILES: *C(=O)N[C@@H](C)C(=O)CN1CCC[C@H]1C(=O)OC]

In some embodiments is a compound of Formula (IV) wherein X is

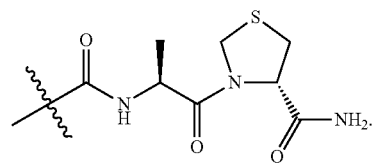 [SMILES: *C(=O)N[C@@H](C)C(=O)N1CSC[C@@H]1C(N)=O]

In some embodiments is a compound of Formula (IV) wherein X is

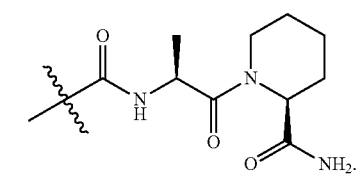 [SMILES: *C(=O)N[C@@H](C)C(=O)N1CCCC[C@H]1C(N)=O]

In some embodiments is a compound of Formula (IV) wherein X is

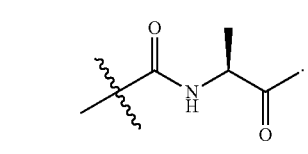

In some embodiments is a compound of Formula (IV) wherein X is

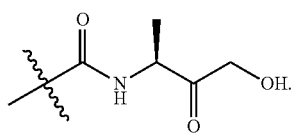 [SMILES: *C(=O)N[C@@H](C)C(=O)CO]

In some embodiments is a compound of Formula (IV) wherein X is

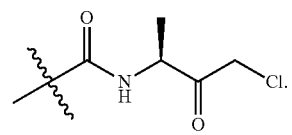 [SMILES: *C(=O)N[C@@H](C)C(=O)CCl]

In some embodiments is a compound of Formula (IV) wherein X is

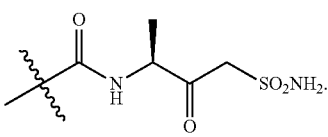 [SMILES: *C(=O)N[C@@H](C)C(=O)CS(N)(=O)=O]

In some embodiments is a compound of Formula (IV) wherein X is

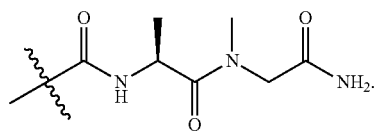 [SMILES: *C(=O)N[C@@H](C)C(=O)N(C)CC(N)=O]

In some embodiments is a compound of Formula (IV) wherein X is

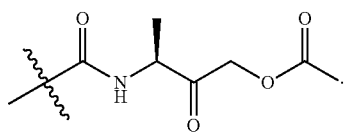

In some embodiments is a compound of Formula (IV) wherein X is

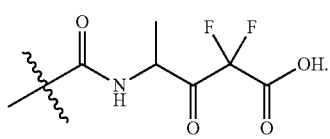 [SMILES: *C(=O)NC(C)C(=O)C(F)(F)C(=O)O]

In some embodiments is a compound of Formula (IV) wherein X is

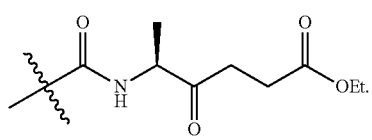 [SMILES: *C(=O)N[C@@H](C)C(=O)CCC(=O)OCC]

In some embodiments is a compound of Formula (IV) wherein X is

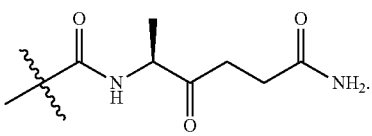 [SMILES: *C(=O)N[C@@H](C)C(=O)CCC(N)=O]

In some embodiments is a compound of Formula (IV) wherein X is

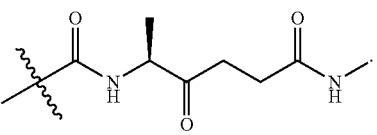

In some embodiments is a compound of Formula (IV) wherein X is

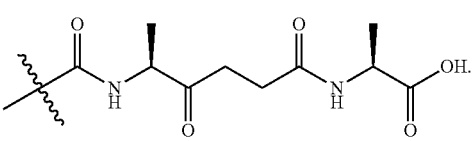 [SMILES: *C(=O)N[C@@H](C)C(=O)CCC(=O)N[C@@H](C)C(=O)O]

In some embodiments is a compound of Formula (IV) wherein X is

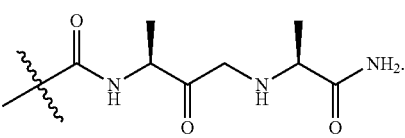 [SMILES: *C(=O)N[C@@H](C)C(=O)CN[C@@H](C)C(N)=O]

In some embodiments is a compound of Formula (IV) wherein X is

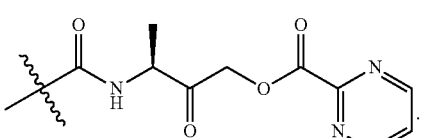

In some embodiments is a compound of Formula (IV) wherein X is

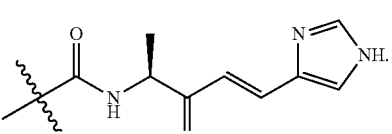

In some embodiments is a compound of Formula (IV) wherein X is

221

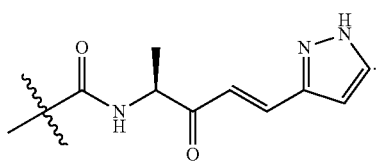 [SMILES: *C(=O)N[C@@H](C)C(=O)/C=C/c1cc[nH]n1]

In some embodiments is a compound of Formula (IV) wherein X is

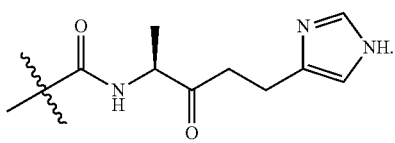 [SMILES: *C(=O)N[C@@H](C)C(=O)CCc1c[nH]cn1]

In some embodiments is a compound of Formula (IV) wherein X is

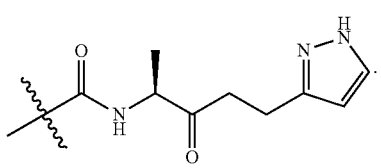 [SMILES: *C(=O)N[C@@H](C)C(=O)CCc1cc[nH]n1]

In some embodiments is a compound of Formula (IV) wherein X is

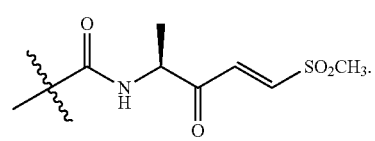 [SMILES: *C(=O)N[C@@H](C)C(=O)/C=C/S(C)(=O)=O]

In some embodiments is a compound of Formula (IV) wherein X is

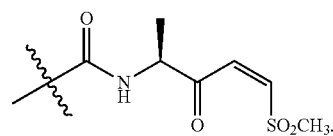 [SMILES: *C(=O)N[C@@H](C)C(=O)/C=C\S(C)(=O)=O]

In some embodiments is a compound of Formula (IV) wherein X is

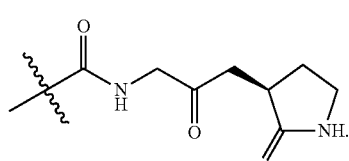

In some embodiments is a compound of Formula (IV) wherein X is

222

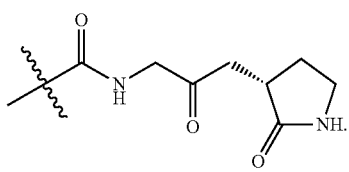 [SMILES: *C(=O)NCC(=O)C[C@@H]1CCNC1=O]

In some embodiments is a compound of Formula (IV) wherein X is

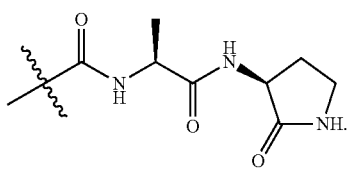 [SMILES: *C(=O)N[C@@H](C)C(=O)N[C@H]1CCNC1=O]

In some embodiments is a compound of Formula (IV) wherein X is

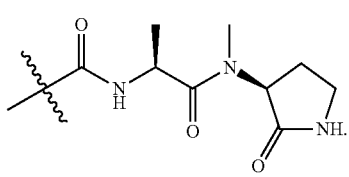 [SMILES: *C(=O)N[C@@H](C)C(=O)N(C)[C@H]1CCNC1=O]

In some embodiments is a compound of Formula (IV) wherein X is

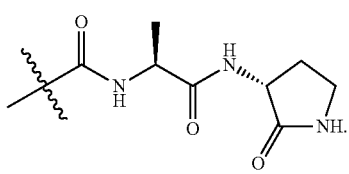 [SMILES: *C(=O)N[C@@H](C)C(=O)N[C@@H]1CCNC1=O]

In some embodiments is a compound of Formula (IV) wherein X is

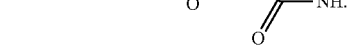

In some embodiments is a compound of Formula (IV) wherein X is

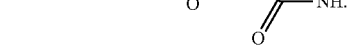

In some embodiments is a compound of Formula (IV) wherein X is

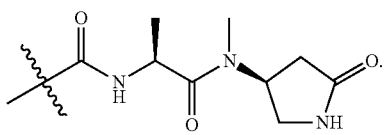 [SMILES: *C(=O)N[C@@H](C)C(=O)N(C)[C@@H]1CNC(=O)C1]

In some embodiments is a compound of Formula (IV) wherein X is

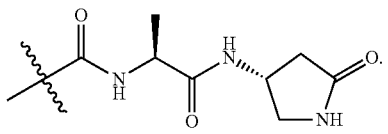

In some embodiments is a compound of Formula (IV) wherein X is

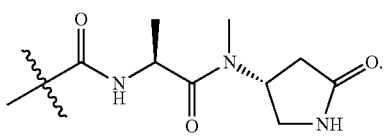 [SMILES: *C(=O)N[C@@H](C)C(=O)N(C)[C@H]1CNC(=O)C1]

In some embodiments is a compound of Formula (IV) wherein X is

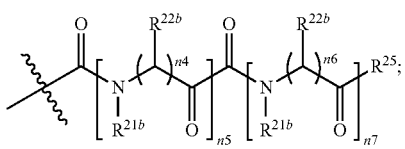

wherein n4 and n5 are each independently 1, 2 or 3; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J; and $R^{25}$ is —CH$_3$, —CH$_2$Cl, —CH$_2$OR$^{25b}$, —CH$_2$R$^{30}$, —C(R$^{26}$)$_2$C(O)NH$_2$, —CH$_2$SO$_2$N(R$^{25b}$)$_2$, —CH$_2$N(R$^{25b}$)SO$_2$(C$_1$-C$_6$alkyl), —CH$_2$PO$_3$H, —CH$_2$P(O)(OH)OCH$_3$, —CH$_2$OC(O)CH$_3$, —CH$_2$OC(O)R$^{30}$, —CH$_2$CO$_2$R$^{25b}$, —CF$_2$CO$_2$R$^{25b}$, —CH$_2$CH$_2$CO$_2$R$^{25b}$, —CH$_2$CH$_2$C(O)N(R$^{25b}$)$_2$, —CH$_2$CH$_2$C(O)N(H)CH(R$^{26}$)CO$_2$R$^{25b}$, —CH$_2$N(H)CH(R$^{26}$)C(O)N(H)R$^{25b}$, —CH$_2$CH$_2$R$^{30}$, —N(H)CH$_2$(R$^{30}$), —CH=CHR$^{30}$, —CH=CHSO$_2$R$^{25b}$,

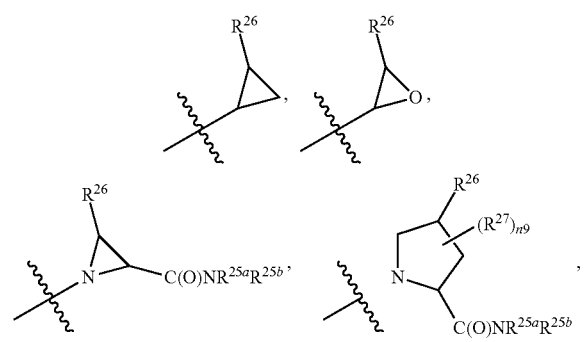

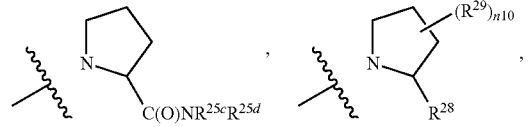

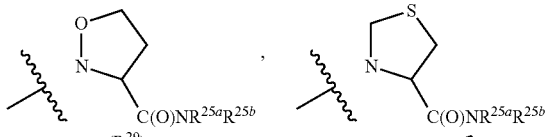

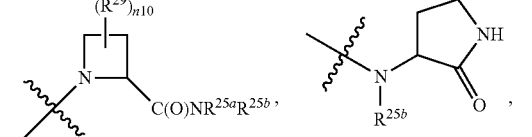

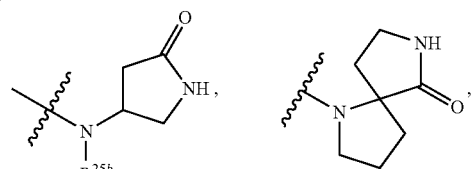

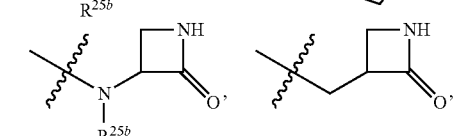

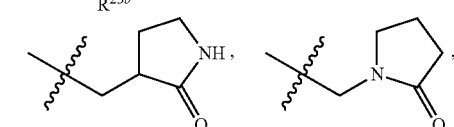

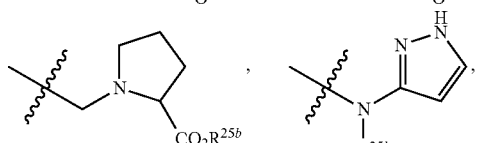

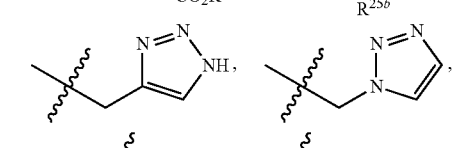

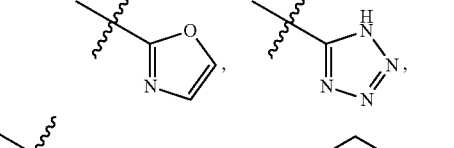

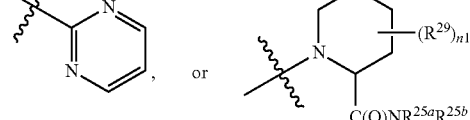

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; and n10 is 0, 1, 2, 3 or 4.

In some embodiments is a compound of Formula (IV) wherein R⁵ is a linear or branched alkyl chain of about 1-22 carbon atoms optionally comprising within the chain or at a chain terminus optionally substituted aryl, optionally substituted heteroaryl, or optionally substituted

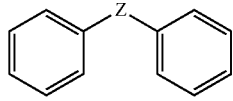

wherein Z is a bond, O, S, NH, CH₂ or C≡C. In some embodiments is a compound of Formula (IV) wherein R⁵ is a linear alkyl chain of about 1-22 carbon atoms comprising within the chain or at a chain terminus

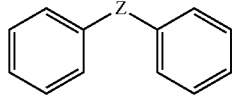

wherein Z is a bond. In some embodiments is a compound of Formula (IV) wherein R⁵ is a linear alkyl chain of about 4-22 carbon atoms comprising at a chain terminus

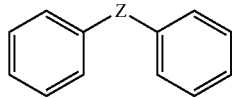

wherein Z is a bond. In some embodiments is a compound of Formula (IV) wherein R⁵ is a linear alkyl chain of about 4-22 carbon atoms comprising within the chain

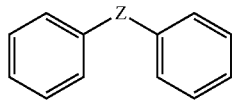

wherein Z is a bond. In some embodiments is a compound of Formula (IV) wherein R⁵ is a linear or branched alkyl chain of about 1-22 carbon atoms optionally comprising within the chain or at a chain terminus optionally substituted aryl. In some embodiments is a compound of Formula (IV) wherein R⁵ is a linear or branched alkyl chain of about 2-22 carbon atoms comprising within the chain or at a chain terminus optionally substituted aryl. In some embodiments is a compound of Formula (IV) wherein R⁵ is a linear or branched alkyl chain of about 2-22 carbon atoms comprising at a chain terminus optionally substituted aryl. In some embodiments is a compound of Formula (IV) wherein R⁵ is a linear or branched alkyl chain of about 2-22 carbon atoms comprising within the chain optionally substituted aryl. In some embodiments is a compound of Formula (IV) wherein R⁵ is a linear or branched alkyl chain of about 1-22 carbon atoms. In some embodiments is a compound of Formula (IV) wherein R⁵ is a linear or branched alkyl chain of about 4-18 carbon atoms. In some embodiments is a compound of Formula (IV) wherein R⁵ is a linear or branched alkyl chain of about 6-16 carbon atoms. In some embodiments is a compound of Formula (IV) wherein R⁵ is

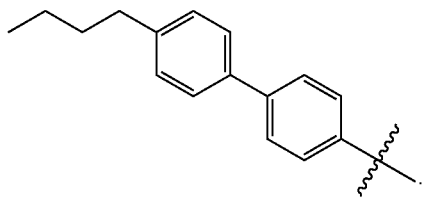 [SMILES: *c1ccc(-c2ccc(CCCC)cc2)cc1]

In some embodiments is a compound of Formula (IV) wherein R⁵ is

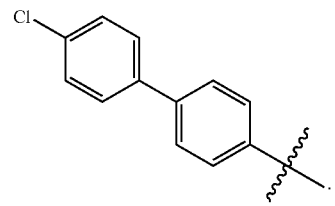 [SMILES: *c1ccc(-c2ccc(Cl)cc2)cc1]

In some embodiments is a compound of Formula (IV) wherein R⁵ is a linear or branched alkyl chain of about 1-22 carbon atoms, comprising within the chain at least one —O— or —N(R⁴)—. In some embodiments is a compound of Formula (IV) wherein R⁵ is a linear or branched alkyl chain of about 1-22 carbon atoms, comprising within the chain at least one —O—. In some embodiments is a compound of Formula (IV) wherein R⁵ is a linear or branched alkyl chain of about 1-22 carbon atoms, comprising within the chain at least one —N(R⁴)—. In some embodiments is a compound of Formula (IV) wherein R⁵ is a linear or branched alkyl chain of about 1-22 carbon atoms, comprising within the chain at least one —N(H)—. In some embodiments is a compound of Formula (IV) wherein R⁵ is —CH₂CH₂N(H)(CH₂)₉CH₃.

In another embodiment is a compound of Formula (IV) wherein n1 is 0 and n2 is 1. In another embodiment is a compound of Formula (IV) wherein n1 is 0, n2 is 1, and R⁴⁴ is H. In another embodiment is a compound of Formula (IV) wherein n1 is 0, n2 is 1, and R⁴⁴ is (C₁-C₆)alkyl optionally substituted with 1 to 3 J. In another embodiment is a compound of Formula (IV) wherein n1 is 0, n2 is 1, and R⁴⁴ is CH₃. In another embodiment is a compound of Formula (IV) wherein n1 is 0, n2 is 1, and R⁴⁴ is CH₂CH₃. In another embodiment is a compound of Formula (IV) wherein n1 is 0, n2 is 1, and R⁴⁴ is CH₂CH(CH₃)₂. In another embodiment is a compound of Formula (IV) wherein n1 is 0, n2 is 1, and R⁴⁴ is CH₂OH. In another embodiment is a compound of Formula (IV) wherein n1 is 0, n2 is 1, and R⁴⁴ is CH(OH)CH₃. In another embodiment is a compound of Formula (IV) wherein n1 is 0, n2 is 1, and R⁴⁴ is CH₂C(O)NH₂. In another embodiment is a compound of Formula (IV) wherein n1 is 0, n2 is 1, and R⁴⁴ is CH₂CH₂CH₂CH₂NH₂.

In another embodiment is a compound of Formula (IV) wherein n1 is 1 and n2 is 1. In another embodiment is a compound of Formula (IV) wherein n1 is 1, n2 is 1, R⁴⁶ is CH₃, and R⁴⁴ is (C₁-C₆)alkyl optionally substituted with 1 to 3 J. In another embodiment is a compound of Formula (IV) wherein n1 is 1, n2 is 1, R⁴⁶ is CH₃, and R⁴⁴ is CH₃. In another embodiment is a compound of Formula (IV) wherein n1 is 1, n2 is 1, R⁴⁶ is CH₃, and R⁴⁴ is CH₂CH₃. In another embodiment is a compound of Formula (IV) wherein n1 is 1, n2 is 1, R⁴⁶ is CH₃, and R⁴⁴ is CH₂CH(CH₃)₂. In another embodiment is a compound of Formula (IV) wherein n1 is 1, n2 is 1, $R^{46}$ is $CH_3$, and $R^{44}$ is $CH_2OH$. In another embodiment is a compound of Formula (IV) wherein n1 is 1, n2 is 1, $R^{46}$ is $CH_3$, and $R^{44}$ is $CH(OH)CH_3$. In another embodiment is a compound of Formula (IV) wherein n1 is 1, n2 is 1, $R^{46}$ is $CH_3$, and $R^{44}$ is $CH_2C(O)NH_2$. In another embodiment is a compound of Formula (IV) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (IV) wherein $R^{47}$, $R^{47'}$, $R^{48}$, $R^{48'}$, $R^{49}$, $R^{49'}$, $R^{44}$, $R^{410}$, and $R^{410'}$ are each independently H. In another embodiment of the aforementioned embodiments is a compound of Formula (IV) wherein each m is 0. In another embodiment of the aforementioned embodiments is a compound of Formula (IV) wherein $R^{41}$, $R^{41'}$, $R^{42}$, $R^{4'}$, and $R^{4''}$ are each independently H.

In another embodiment of the aforementioned embodiments is a compound of Formula (IV) wherein n3 is 1 and n8 is 1. In another embodiment of the aforementioned embodiments is a compound of Formula (IV) wherein n3 is 1, n8 is 1, and $R^2$ and $R^3$ are each hydroxy. In another embodiment of the aforementioned embodiments is a compound of Formula (IV) wherein n3 is 1, n8 is 1, $R^2$ is hydroxy, and $R^3$ is —$OR^{40}$. In another embodiment of the aforementioned embodiments is a compound of Formula (IV) wherein n3 is 1, n8 is 1, $R^2$ is hydroxy, $R^3$ is —$OR^{40}$, and $R^{40}$ is —$(C_1$-$C_6)$alkyl. In another embodiment of the aforementioned embodiments is a compound of Formula (IV) wherein n3 is 1, n8 is 1, $R^2$ is hydroxy, $R^3$ is —$OR^{40}$, and $R^{40}$ is —$(C_1$-$C_6)$alkyl-$NR^{41}R^{42}$. In another embodiment of the aforementioned embodiments is a compound of Formula (IV) wherein n3 is 1, n8 is 1, $R^2$ is —OH, $R^3$ is —$OR^{40}$, and $R^{40}$ is —$(C_1$-$C_6)$alkyl-$NH_2$. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$-$C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$—$C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (IV) wherein n3 is 1, n8 is 1, $R^3$ is hydroxy, and $R^2$ is —$OR^{40}$. In another embodiment of the aforementioned embodiments is a compound of Formula (IV) wherein n3 is 1, n8 is 1, $R^3$ is hydroxy, $R^2$ is —$OR^{40}$, and $R^{40}$ is —$(C_1$-$C_6)$alkyl. In another embodiment of the aforementioned embodiments is a compound of Formula (IV) wherein n3 is 1, n8 is 1, $R^3$ is hydroxy, $R^2$ is —$OR^{40}$, and $R^{40}$ is —$(C_1$-$C_6)$alkyl-$NR^{41}R^{42}$. In another embodiment of the aforementioned embodiments is a compound of Formula (IV) wherein n3 is 1, n8 is 1, $R^3$ is —OH, $R^2$ is —$OR^{40}$, and $R^{40}$ is —$(C_1$-$C_6)$alkyl-$NH_2$. In another embodiment of the aforementioned embodiments is a compound of Formula (IV) wherein n3 is 1, n8 is 1, $R^3$ is hydroxy, $R^2$ is —$OR^{40}$, $R^{40}$ is —$(C_1$-$C_6)$alkyl-$NR^{41}R^{42}$, and $R^{41}$ and $R^{42}$ and the nitrogen atom to which that are attached form a heterocycloalkyl ring. In another embodiment of the aforementioned embodiments is a compound of Formula (IV) wherein n3 is 1, n8 is 1, $R^3$ is hydroxy, $R^2$ is —$OR^{40}$, $R^{40}$ is —$(C_1$-$C_6)$alkyl-$NR^{41}R^{42}$, and $R^{41}$ and $R^{42}$ and the nitrogen atom to which that are attached form a morpholinyl ring.

In another embodiment of the aforementioned embodiments is a compound of Formula (IV) wherein n3 is 1, n8 is 1, $R^2$ is hydroxy, $R^3$ is —$OR^{40}$, and any carbon atom of $R^3$ is substituted with J. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$-$C_6)$alkyl, and any carbon atom of $R^3$ is substituted with J. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$-$C_6)$alkyl, and any carbon atom of $R^3$ is substituted with J wherein J is $CO_2H$. In another embodiment of the aforementioned embodiments is a compound of Formula (IV) wherein n3 is 1, n8 is 1, $R^2$ is hydroxy, $R^3$ is —O—$(C_1$-$C_6)$alkyl-$CO_2H$. In another embodiment of the aforementioned embodiments is a compound of Formula (IV) wherein n3 is 1, n8 is 1, $R^2$ is hydroxy, $R^3$ is —$OCH_2CO_2H$. In another embodiment of the aforementioned embodiments is a compound of Formula (IV) wherein n3 is 1, n8 is 1, $R^2$ is —$OCH_2CH_2NH_2$, $R^3$ is —$OCH_2CO_2H$. In another embodiment of the aforementioned embodiments is a compound of Formula (IV) wherein n3 is 1, n8 is 1, $R^2$ is hydroxy, $R^3$ is —$OR^{40}$, $R^{40}$ is $R^{40}$ is —$(C_1$-$C_6)$alkyl-$NR^{41}R^{42}$, and any carbon atom of $R^3$ is substituted with J. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$-$C_6)$alkyl-$NR^{41}R^{42}$, $R^{41}$ is hydrogen, $R^{42}$ is —$(C_1$-$C_6)$alkyl, and any carbon atom of $R^3$ is substituted with J. In another embodiment of the aforementioned embodiments is a compound of Formula (IV) wherein n3 is 1, n8 is 1, $R^2$ is hydroxy, $R^3$ is —$OR^{40}$, $R^{40}$ is —$(C_1$—$C_6)$alkyl-$NR^{41}R^{42}$, $R^{41}$ is hydrogen, $R^{42}$ is —$(C_1$-$C_6)$alkyl, and any carbon atom of $R^3$ is substituted with J wherein J is —$NHCH_3$. In another embodiment of the aforementioned embodiments is a compound of Formula (IV) wherein n3 is 1, n8 is 1, $R^2$ is hydroxy, $R^3$ is —O—$(C_1$-$C_6)$alkyl-$N(H)$—$(C_1$-$C_6)$alkyl-$N(H)CH_3$. In another embodiment of the aforementioned embodiments is a compound of Formula (IV) wherein n3 is 1, n8 is 1, $R^2$ is hydroxy, $R^3$ is —$OCH_2CH_2N(H)CH_2CH_2N(H)CH_3$. In another embodiment of the aforementioned embodiments is a compound of Formula (IV) wherein n3 is 1, n8 is 1, $R^2$ is hydroxy, $R^3$ is —$OCH_2CH_2N(H)CH_2CH_2CH_2N(H)CH_3$.

In another embodiment of the aforementioned embodiments is a compound of Formula (IV) wherein n3 is 1, n8 is 1, $R^3$ is hydroxy, $R^2$ is —$OR^{40}$, and any carbon atom of $R^2$ is substituted with J. In another embodiment of the aforementioned embodiments is a compound of Formula (IV) wherein n3 is 1, n8 is 1, $R^3$ is hydroxy, $R^2$ is —$OR^{40}$, $R^{40}$ is —$(C_1$-$C_6)$alkyl, and any carbon atom of $R^2$ is substituted with J. In another embodiment of the aforementioned embodiments is a compound of Formula (IV) wherein n3 is 1, n8 is 1, $R^3$ is hydroxy, $R^2$ is —$OR^{40}$, $R^{40}$ is —$(C_1$-$C_6)$alkyl, and any carbon atom of $R^2$ is substituted with J wherein J is $CO_2H$. In another embodiment of the aforementioned embodiments is a compound of Formula (IV) wherein n3 is 1, n8 is 1, $R^3$ is hydroxy, $R^2$ is —O—$(C_1$-$C_6)$alkyl-$CO_2H$. In another embodiment of the aforementioned embodiments is a compound of Formula (IV) wherein n3 is 1, n8 is 1, $R^3$ is hydroxy, $R^2$ is —$OCH_2CO_2H$. In another embodiment of the aforementioned embodiments is a compound of Formula (IV) wherein n3 is 1, n8 is 1, $R^3$ is —$OCH_2CH_2NH_2$, $R^2$ is —$OCH_2CO_2H$. In another embodiment of the aforementioned embodiments is a compound of Formula (IV) wherein n3 is 1, n8 is 1, $R^3$ is hydroxy, $R^2$ is —$OR^{40}$, $R^{40}$ is $R^{40}$ is —$(C_1$-$C_6)$alkyl-$NR^{41}R^{42}$, and any carbon atom of $R^2$ is substituted with J. In another embodiment of the aforementioned embodiments is a compound of Formula (IV) wherein n3 is 1, n8 is 1, $R^3$ is hydroxy, $R^2$ is —OR⁴⁰, R⁴⁰ is —(C₁-C₆)alkyl-NR⁴¹R⁴², R⁴¹ is hydrogen, R⁴² is —(C₁-C₆)alkyl, and any carbon atom of R² is substituted with J. In another embodiment of the aforementioned embodiments is a compound of Formula (IV) wherein n3 is 1, n8 is 1, R³ is hydroxy, R² is —OR⁴⁰, R⁴⁰ is —(C₁-C₆)alkyl-NR⁴¹R⁴², R⁴¹ is hydrogen, R⁴² is —(C₁-C₆)alkyl, and any carbon atom of R² is substituted with J wherein J is —NHCH₃. In another embodiment of the aforementioned embodiments is a compound of Formula (IV) wherein n3 is 1, n8 is 1, R³ is hydroxy, R² is —O—(C₁-C₆)alkyl-N(H)—(C₁-C₆)alkyl-N(H)CH₃. In another embodiment of the aforementioned embodiments is a compound of Formula (IV) wherein n3 is 1, n8 is 1, R³ is hydroxy, R² is —OCH₂CH₂N(H)CH₂CH₂N(H)CH₃. In another embodiment of the aforementioned embodiments is a compound of Formula (IV) wherein n3 is 1, n8 is 1, R³ is hydroxy, R² is —OCH₂CH₂N(H)CH₂CH₂CH₂N(H)CH₃.

In another embodiment of the aforementioned embodiments is a compound of Formula (IV) having the structure of Formula (IVa):

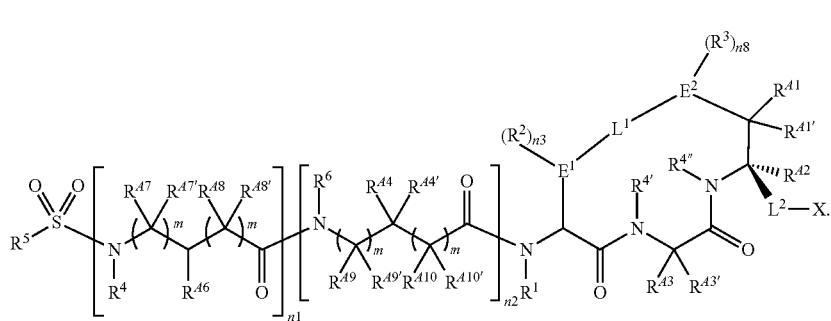

Formula (IVa)

In another embodiment of the aforementioned embodiments is a compound of Formula (IV) having the structure of Formula (IVb):

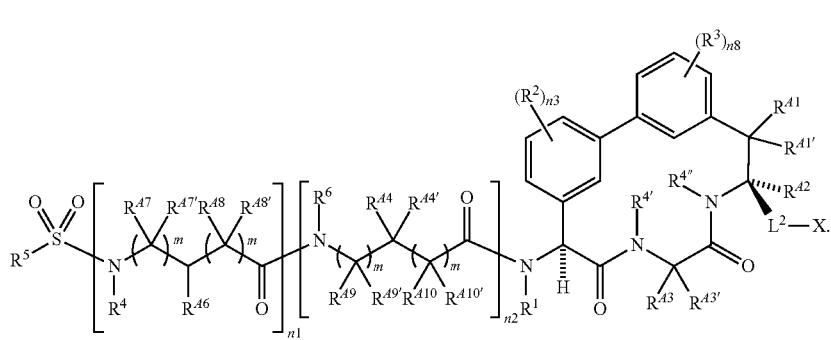

Formula (IVb)

In another embodiment of the aforementioned embodiments is a compound of Formula (IV) having the structure of Formula (IVc):

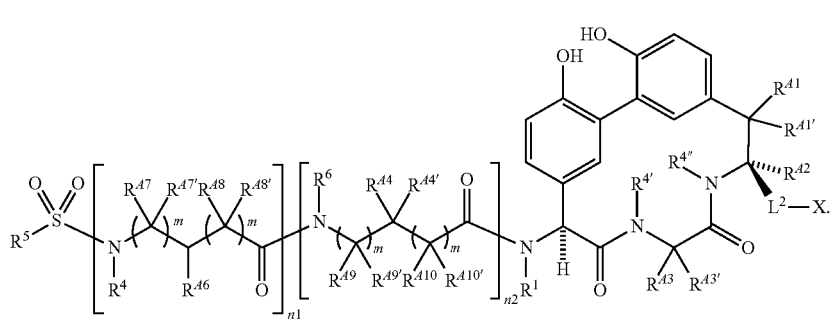

Formula (IVc)

In another embodiment of the aforementioned embodiments is a compound of Formula (IV) having the structure of Formula (IVd):

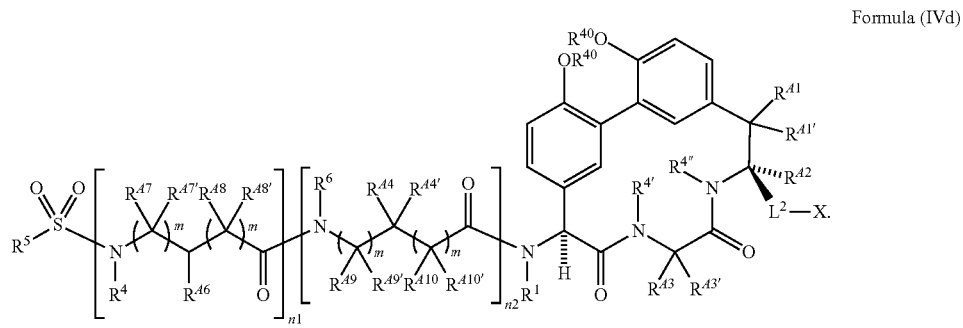

Formula (IVd)

In another embodiment the compound of Formula (IV) is

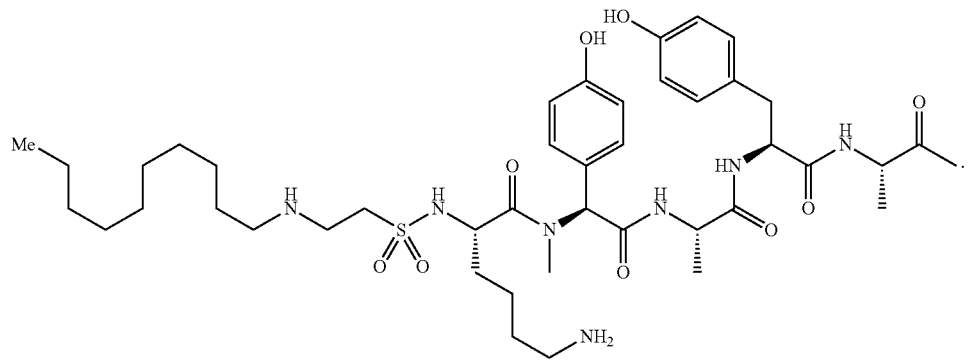 [SMILES: CCCCCCCCCCNCCS(=O)(=O)N[C@@H](CCCCN)C(=O)N(C)[C@H](C(=O)N[C@@H](C)C(=O)N[C@@H](Cc1ccc(O)cc1)C(=O)N[C@@H](C)C(C)=O)c1ccc(O)cc1]

In another aspect described herein are compounds of Formula (V):

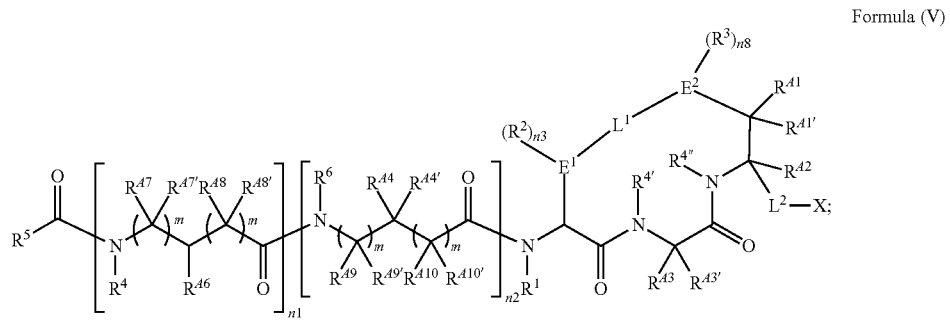

Formula (V)

wherein:
$E^1$ is $(C_1$-$C_6)$alkyl, $(C_2$-$C_7)$alkenyl, $(C_2$-$C_7)$alkynyl, $(C_3$-$C_7)$cycloalkyl, heterocyclyl, heteroaryl, or aryl;
$E^2$ is $(C_2$-$C_7)$alkenyl, $(C_2$-$C_7)$alkynyl, $(C_3$-$C_7)$cycloalkyl, heterocyclyl, heteroaryl, or aryl;
$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1$-$C_4)$alkylene optionally substituted with OH, CN, NO$_2$, halogen, $(C_1$-$C_6)$alkyl;

$L^2$ is a bond, or optionally substituted $(C_1$-$C_6)$alkylene;
X is —NHCH(R$^{24}$)CH=CHS(O)$_2$OCH$_2$CH$_3$, —NHCH(R$^{24}$)CH=CHC(O)OCH$_3$,

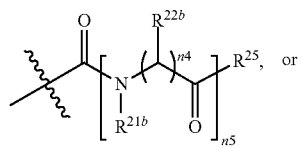

or

-continued

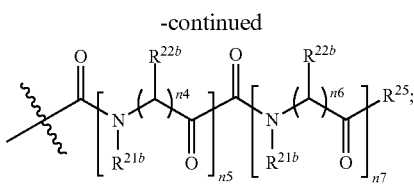

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{24}$ is H or $(C_1-C_6)$alkyl; $R^{25}$ is —$CH_2F$, —$CH_2N_3$, —$CH_2CH_3$, —$CF_2C(O)NH_2$, —$CH_2NHC(O)H$,

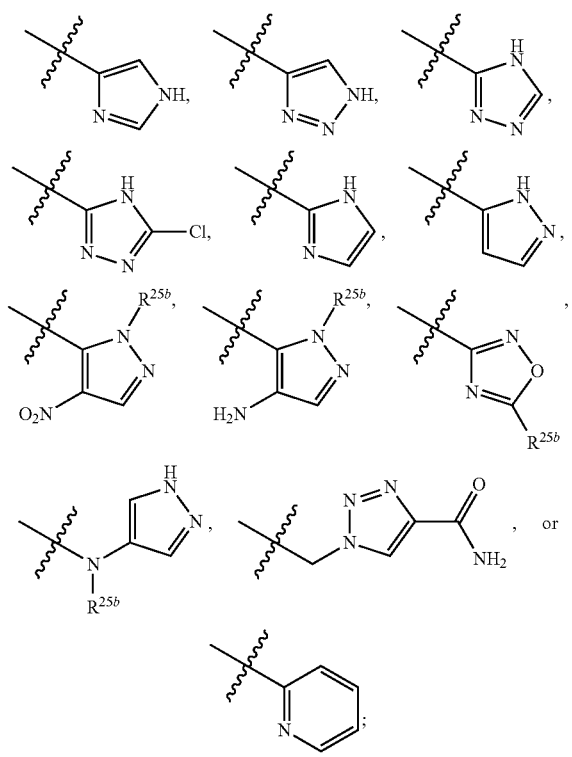

$R^{25b}$ is independently H, or optionally substituted alkyl;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

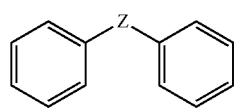

1 wherein Z is a bond, O, S, NH, $CH_2$ or C≡C; or $R^5$ is a linear or branched alkyl chain of about 1-22 carbon atoms, comprising within the chain at least one —O— or —$N(R^4)$—;

each $R^2$ and $R^3$ are each independently hydroxy, nitro, halo, cyano, glycosyloxy, amino, $(C_1-C_4)$alkyl, $OR^{40}$, or a group cleavable under physiological conditions to provide a compound of formula (I) wherein $R^2$ or $R^3$ respectively is hydroxy, wherein any carbon atom is optionally substituted with J;

each $R^{40}$ is independently —$(C_1-C_6)$alkyl, or —$(C_1-C_6)$alkyl-$NR^{41}R^{42}$;

each $R^{41}$ and $R^{42}$ is hydrogen, —$(C_1-C_6)$alkyl, —$(C_1-C_6)$heteroalkyl, —$C(O)(C_1-C_6)$alkyl, —$C(O)N(R^{43})_2$, —$SO_2N(R^{43})_2$; or $R^{41}$ and $R^{42}$ and the nitrogen atom to which that are attached form a heterocycloalkyl ring;

each $R^{43}$ is independently hydrogen or —$(C_1-C_6)$alkyl; or two $R^{43}$ and the nitrogen atom to which that are attached form a heterocycloalkyl ring;

n1 and n2 are independently 0 or 1;

n3 and n8 are independently 0, 1, or 2;

each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{46}$ is H, amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

each J is independently halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)$alkyl$)_2$-, —$NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment is a compound of Formula (V) having the structure of Formula (Va):

Formula (Va)

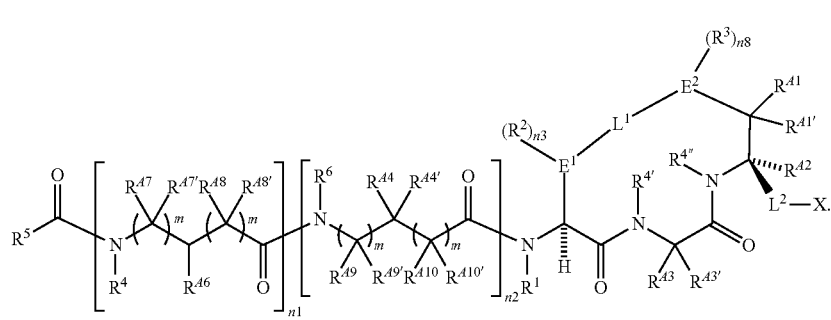

In another embodiment is a compound of Formula (V) having the structure of Formula (Vb):

Formula (Vb)

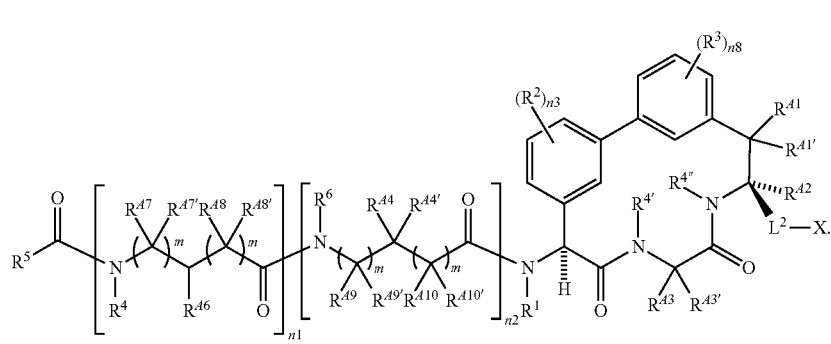

In another embodiment is a compound of Formula (V), (Va), or (Vb) wherein $L^2$ is a bond. In another embodiment is a compound of Formula (V), (Va), or (Vb) wherein $L^2$ is optionally substituted ($C_1$-$C_6$)alkylene. In a further embodiment, $L^2$ is methylene, ethylene, n-propylene, iso-propylene, n-butylene, iso-butylene, or tert-butylene.

In another embodiment is a compound of Formula (V), (Va), or (Vb) wherein X is —NHCH($R^{24}$)CH=CHS(O)$_2$OCH$_2$CH$_3$ or —NHCH($R^{24}$)CH=CHC(O)OCH$_3$; and $R^{24}$ is H or ($C_1$-$C_6$)alkyl. In some embodiments is a compound of Formula (V), (Va), or (Vb) wherein X is —NHCH($R^{24}$)CH=CHS(O)$_2$OCH$_2$CH$_3$. In some embodiments is a compound of Formula (V), (Va), or (Vb) wherein X is —NHCH($R^{24}$)CH=CHC(O)OCH$_3$.

In some embodiments is a compound of Formula (V), (Va), or (Vb) wherein X is

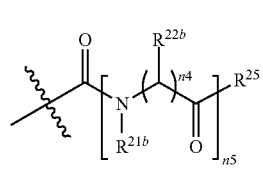

wherein n4, n5, and n6 are each independently 1, 2 or 3; n7 is 0, 1 or 2; $R^{21b}$ and $R^{22b}$ are independently at each occurrence hydrogen, hydroxy, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; $R^{25}$ is —CH$_2$F, —CH$_2$N$_3$, —CH$_2$CH$_3$, —CF$_2$C(O)NH$_2$, —CH$_2$NHC(O)H,

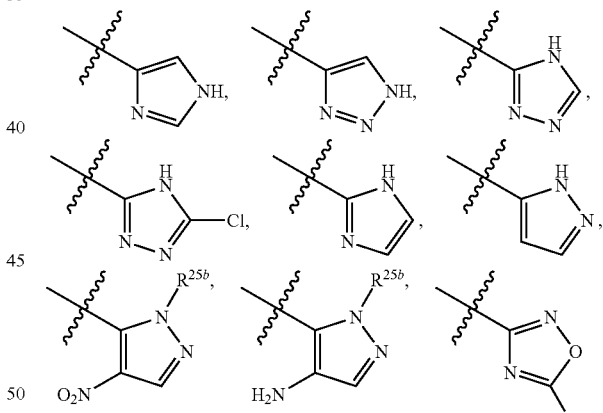

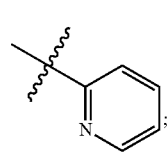

and $R^{25b}$ is independently H, or optionally substituted alkyl.

In another embodiment is a compound of Formula (V), (Va), or (Vb) wherein X is

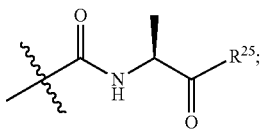

wherein R$^{25}$ is —CH$_2$F, —CH$_2$N$_3$, —CH$_2$CH$_3$, —CF$_2$C(O)NH$_2$, —CH$_2$NHC(O)H,

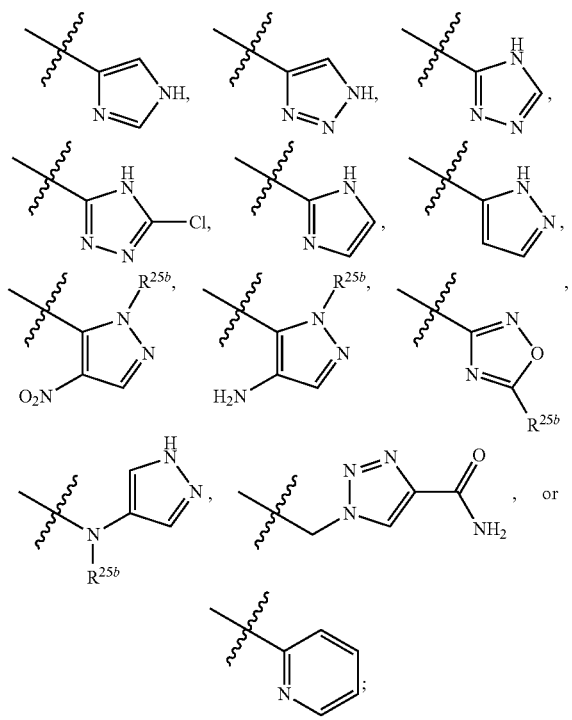

and

R$^{25b}$ is independently H, or optionally substituted alkyl.

In some embodiments is a compound of Formula (V), (Va), or (Vb) wherein R$^5$ is a linear or branched alkyl chain of about 1-22 carbon atoms, wherein R$^5$ is bonded to the carbonyl carbon to which it is attached directly to provide an amide linkage, optionally comprising within the chain or at a chain terminus optionally substituted aryl, optionally substituted heteroaryl, or optionally substituted

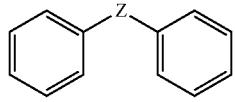

wherein Z is a bond, O, S, NH, CH$_2$ or C≡C. In some embodiments is a compound of Formula (V), (Va), or (Vb) wherein R$^5$ is

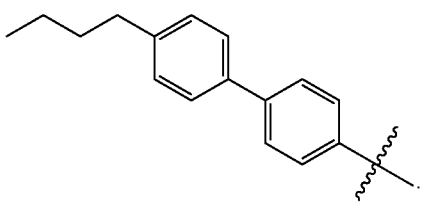 [SMILES: *c1ccc(-c2ccc(CCCC)cc2)cc1]

In some embodiments is a compound of Formula (V), (Va), or (Vb) wherein R$^5$ is

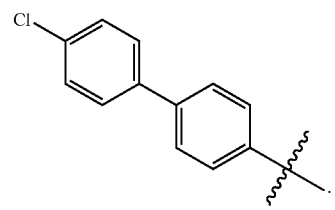 [SMILES: *c1ccc(-c2ccc(Cl)cc2)cc1]

In some embodiments is a compound of Formula (V), (Va), or (Vb) wherein R$^5$ is a linear or branched alkyl chain of about 1-22 carbon atoms, comprising within the chain at least one —O— or —N(R$^4$)—. In some embodiments is a compound of Formula (V), (Va), or (Vb) wherein R$^5$ is a linear or branched alkyl chain of about 1-22 carbon atoms, comprising within the chain at least one —O—. In some embodiments is a compound of Formula (V), (Va), or (Vb) wherein R$^5$ is a linear or branched alkyl chain of about 1-22 carbon atoms, comprising within the chain at least one —N(R$^4$)—. In some embodiments is a compound of Formula (V), (Va), or (Vb) wherein R$^5$ is a linear or branched alkyl chain of about 1-22 carbon atoms, comprising within the chain at least one —N(H)—. In some embodiments is a compound of Formula (V), (Va), or (Vb) wherein R$^5$ is —CH$_2$CH$_2$N(H)(CH$_2$)$_9$CH$_3$.

In another aspect described herein are compounds of Formula (VI):

Formula (VI)

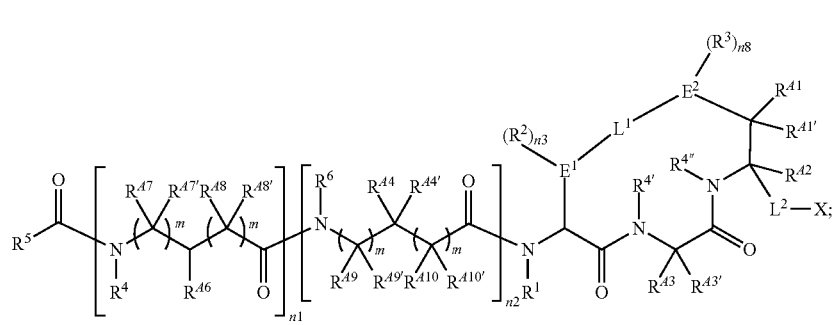

wherein:

E¹ is (C₁-C₆)alkyl, (C₂-C₇)alkenyl, (C₂-C₇)alkynyl, (C₃-C₇)cycloalkyl, heterocyclyl, heteroaryl, or aryl;

E² is (C₂-C₇)alkenyl, (C₂-C₇)alkynyl, (C₃-C₇)cycloalkyl, heterocyclyl, heteroaryl, or aryl;

L¹ is a bond, —O—, —S—, —NR⁴—, —C(O)—, —CH₂O—, —OCH₂—, —CH₂S—, —SCH₂—, —CH₂NR⁴—, —NR⁴CH₂—, —NR⁴C(O)—, —C(O)NR⁴—, —NR⁴S(O)₂—, —S(O)₂NR⁴—, —NR⁴C(O)NR⁴—, —NR⁴C(O)O—, —OC(O)NR⁴—, or (C₁-C₄)alkylene optionally substituted with OH, CN, NO₂, halogen, (C₁-C₆)alkyl;

L² is a bond, or optionally substituted (C₁-C₆)alkylene;

X is —CH₂OH, —CH(OH)CH₃, NHS(O)₂CF₃, —N(R⁴)CH(R²⁴)CN, —NHCH(R²⁴)C(O)CH₃, —NHN(R²⁴)C(O)CH₃, —NHCH(R²⁴)CH=CHS(O)₂CH₃, —NHCH(R²⁴)CH=CHS(O)₂NH₂,

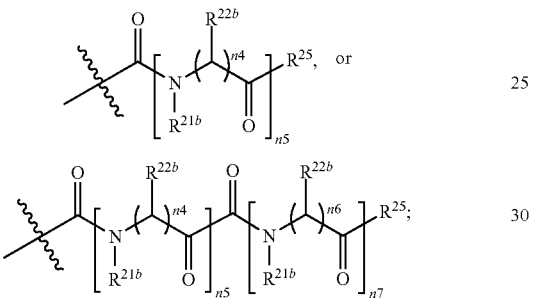

wherein n4, n5, and n6 are each independently 1, 2 or 3; n7 is 0, 1 or 2; R²¹ᵇ and R²²ᵇ are independently at each occurrence hydrogen, hydroxy, (C₁-C₆)alkyl, (C₃-C₇)cycloalkyl, 5- to 7-membered heteroaryl, 5- to 7-membered heterocyclyl, or (C₆-C₁₀) aryl, wherein any alkyl, cycloalkyl, heterocyclyl, aryl or heteroaryl is optionally substituted with 1 to 3 J; R²⁴ is H or (C₁-C₆)alkyl; R²⁵ is —CH₃, —CH₂Cl, —CH₂OR²⁵ᵇ, —CH₂R³⁰, —C(R²⁶)₂C(O)NH₂, —CH₂SO₂N(R²⁵ᵇ)₂, —CH₂N(R²⁵ᵇ)SO₂(C₁-C₆alkyl), —CH₂PO₃H, —CH₂P(O)(OH)OCH₃, —CH₂OC(O)CH₃, —CH₂OC(O)R³⁰, —CH₂CO₂R²⁵ᵇ, —CF₂CO₂R²⁵ᵇ, —CH₂CH₂CO₂R²⁵ᵇ, —CH₂CH₂C(O)N(R²⁵ᵇ)₂, —CH₂CH₂C(O)N(H)CH(R²⁶)CO₂R²⁵ᵇ, —CH₂N(H)CH(R²⁶)C(O)N(H)R²⁵ᵇ, —CH₂CH₂R³⁰, —N(H)CH₂(R³⁰), —CH=CHR³⁰, —CH=CHSO₂R²⁵ᵇ,

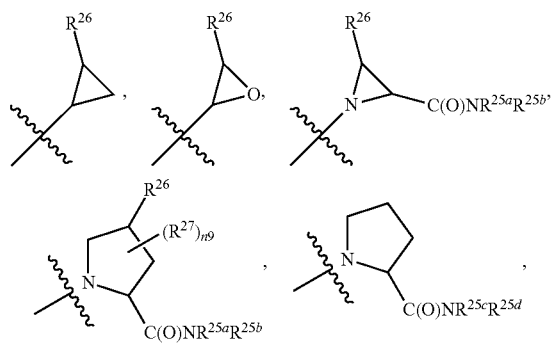

where R²⁵ᵃ is H, —OH, —OCH₃, NH₂, SO₂(C₁-C₆)alkyl, or optionally substituted alkyl; each R²⁵ᵇ is independently H, or optionally substituted alkyl; R²⁵ᶜ is H or optionally substituted alkyl; R²⁵ᵈ is —OH, —OCH₃, or NH₂; each R²⁶ is independently H, halo or (C₁-C₆)alkyl; each R²⁷ is independently —OH, halo, (C₁-C₆)alkyl, or R²⁶ and R²⁷ are joined to form a cycloalkyl ring; R²⁸ is H, —CH₂OH, —CH₂NH₂, —C(O)CH₃, or (C₁-C₆)alkyl; each R²⁹ is independently —OH, halo, or (C₁-C₆)alkyl; R³⁰ is heterocyclyl, heteroaryl, or aryl; n9 is 1, 2 or 3; n10 is 0, 1, 2, 3 or 4; R⁵ is aryl, heteroaryl, or a linear or branched alkyl chain of about 1-22 carbon atoms, wherein R⁵ is bonded to the carbonyl carbon to which it is attached directly or by an O or NR⁴, to provide an amide, carbamate, or urea linkage, respectively; optionally comprising within the chain or at a chain terminus optionally substituted aryl, optionally substituted heteroaryl, or optionally substituted

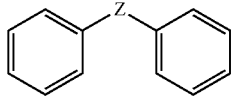

wherein Z is a bond, O, S, NH, $CH_2$ or C≡C; or $R^5$ is a linear or branched alkyl chain of about 1-22 carbon atoms, comprising within the chain at least one —O— or —N($R^4$)—; each $R^2$ and $R^3$ are each independently hydroxy, $OR^{40}$, —C≡C—$CH_2NH_2$, or

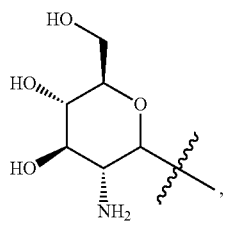

wherein at least one $R^2$ and $R^3$ is —C≡C—$CH_2NH_2$, or

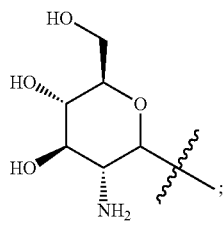 [SMILES: *C1O[C@H](CO)[C@@H](O)[C@H](O)[C@H]1N]

each $R^{40}$ is independently —($C_1$-$C_6$)alkyl, or —($C_1$-$C_6$)alkyl-$NR^{41}R^{42}$;

each $R^{41}$ and $R^{42}$ is hydrogen, —($C_1$-$C_6$)alkyl, —($C_1$-$C_6$)heteroalkyl, —C(O)($C_1$-$C_6$)alkyl, —C(O)N($R^{43}$)$_2$, —$SO_2$N($R^{43}$)$_2$; or $R^{41}$ and $R^{42}$ and the nitrogen atom to which that are attached form a heterocycloalkyl ring;
each $R^{43}$ is independently hydrogen or —($C_1$-$C_6$)alkyl; or two $R^{43}$ and the nitrogen atom to which that are attached form a heterocycloalkyl ring;
n1 and n2 are independently 0 or 1;
n3 and n8 are independently 1 or 2;
each m is independently 0 or 1;
$R^1$ is hydrogen or ($C_1$-$C_6$)alkyl optionally substituted with 1 to 3 J; or $R^1$ together with $E^1$ form a ring;
$R^4$, $R^{4'}$, and $R^{4''}$ are each independently at each occurrence hydrogen, or ($C_1$-$C_6$)alkyl optionally substituted with 1 to 3 J;
$R^6$ is hydrogen, or ($C_1$-$C_6$)alkyl optionally substituted with 1 to 3 J; or $R^6$ together with $R^{44}$ form a ring;
$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;
$R^{A6}$ is H, amino, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;
each J is independently halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;
each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —N(($C_1$-$C_4$)alkyl)$_2$-, —NH($C_1$-$C_4$)alkyl, $C_1$-$C_6$alkyl, $C_3$-$C_8$cycloalkyl, or $C_1$-$C_6$heteroalkyl; or a pharmaceutically acceptable salt, solvate, or prodrug thereof.
In another embodiment is a compound of Formula (VI) having the structure of Formula (VIa):

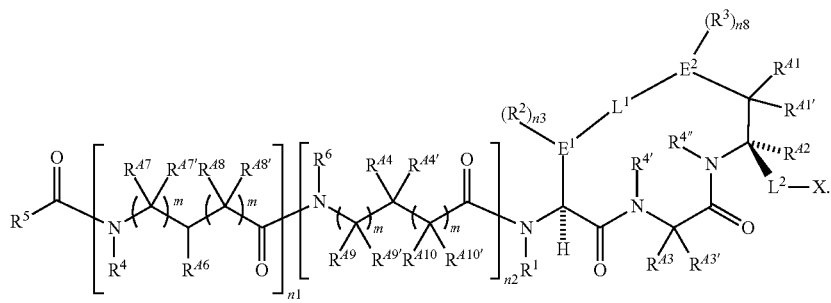

Formula (VIa)

In another embodiment is a compound of Formula (VI) having the structure of Formula (VIb):

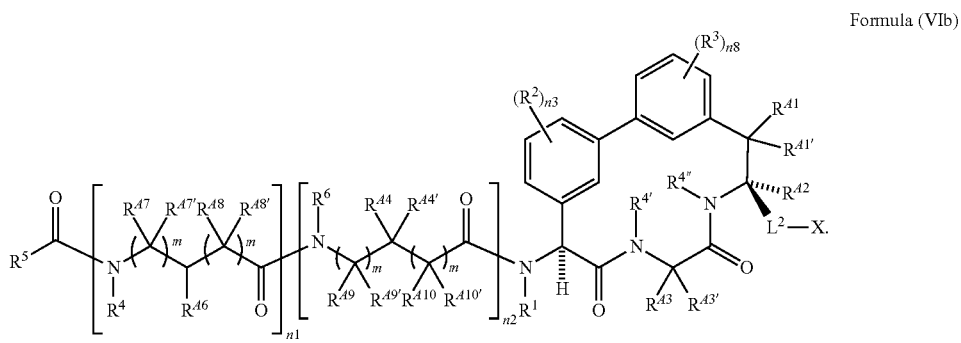

Formula (VIb)

In some embodiments is a compound of Formula (VI), (VIa), or (VIb) wherein n3 is 1 and n8 is 1. In some embodiments is a compound of Formula (VI), (VIa), or (VIb) wherein n3 is 1, n8 is 1, and $R^2$ and $R^3$ are each independently hydroxy, $OR^{40}$, —C≡C—CH$_2$NH$_2$, or


wherein at least one $R^2$ and $R^3$ is —C≡C—CH$_2$NH$_2$, or

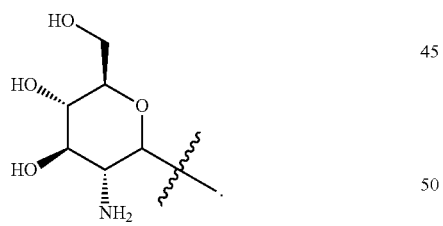

In some embodiments is a compound of Formula (VI), (VIa), or (VIb) wherein n3 is 1, n8 is 1, $R^2$ is

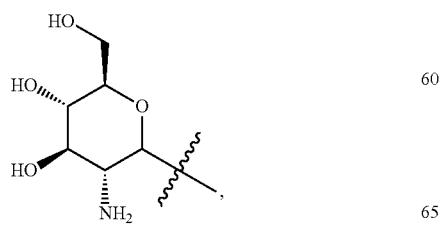

and $R^3$ is hydroxy. In some embodiments is a compound of Formula (VI), (VIa), or (VIb) wherein n3 is 1, n8 is 1, $R^2$ is and $R^3$ is —$OR^{40}$. In some embodiments is a compound of Formula (VI), (VIa), or (VIb) wherein n3 is 1, n8 is 1, $R^2$ is $R^3$ is —$OR^{40}$, and $R^{40}$ is —(C$_1$-C$_6$)alkyl-NR$^{41}$R$^{42}$. In some embodiments is a compound of Formula (VI), (VIa), or (VIb) wherein n3 is 1, n8 is 1, $R^2$ is $R^3$ is —$OR^{40}$, and $R^{40}$ is —(C$_1$-C$_6$)alkyl-NH$_2$. In some embodiments is a compound of Formula (VI), (VIa), or (VIb) wherein n3 is 1, n8 is 1, $R^2$ is hydroxy, $R^3$ is —$OR^{40}$, $R^{40}$ is —(C$_1$-C$_6$)alkyl-NR$^{41}$R$^{42}$, and $R^{41}$ and $R^{42}$ and the nitrogen atom to which that are attached form a heterocycloalkyl ring. In some embodiments is a compound of Formula (VI), (VIa), or (VIb) wherein n3 is 1, n8 is 1, $R^2$ is hydroxy, and $R^3$ is

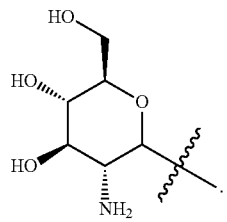 [SMILES: *C1O[C@H](CO)[C@@H](O)[C@H](O)[C@H]1N]

In some embodiments is a compound of Formula (VI), (VIa), or (VIb) wherein n3 is 1, n8 is 1, $R^2$ is

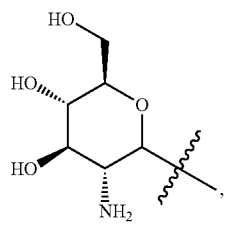 [SMILES: *C1O[C@H](CO)[C@@H](O)[C@H](O)[C@H]1N]

and $R^3$ is

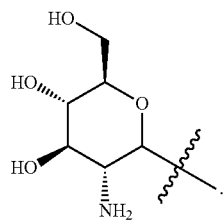 [SMILES: *C1O[C@H](CO)[C@@H](O)[C@H](O)[C@H]1N]

In another aspect described herein are compounds of Formula (VII):

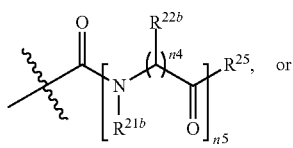

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{24}$ is H or $(C_1-C_6)$alkyl; $R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1-C_6alkyl)$, —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH(R^{26})CO_2R^{25b}$, —$CH_2N(H)CH(R^{26})C(O)N(H)R^{25b}$, —$CH_2CH_2R^{30}$, —$N(H)CH_2(R^{30})$, —CH═$CHR^{30}$, —CH═$CHSO_2R^{25b}$, Formula (VII)

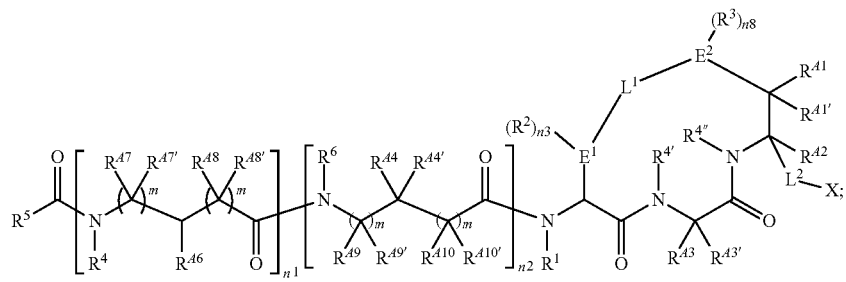

wherein:
$E^1$ is $(C_1-C_6)$alkyl, $(C_2-C_7)$alkenyl, $(C_2-C_7)$alkynyl, $(C_3-C_7)$ cycloalkyl, heterocyclyl, heteroaryl, or aryl;
$E^2$ is $(C_2-C_7)$alkenyl, $(C_2-C_7)$alkynyl, $(C_3-C_7)$cycloalkyl, heterocyclyl, heteroaryl, or aryl;
$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —$C(O)NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;
$L^2$ is a bond, or optionally substituted $(C_1-C_6)$alkylene;
X is —$CH_2OH$, —$CH(OH)CH_3$, $NHS(O)_2CF_3$, —$N(R^4)CH(R^{24})CN$, —$NHCH(R^{24})C(O)CH_3$, —$NHN(R^{24})C(O)CH_3$, —$NHCH(R^{24})CH$═$CHS(O)_2CH_3$, —$NHCH(R^{24})CH$═$CHS(O)_2NH_2$,

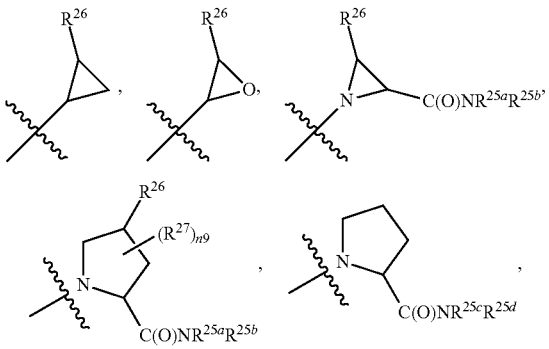

-continued

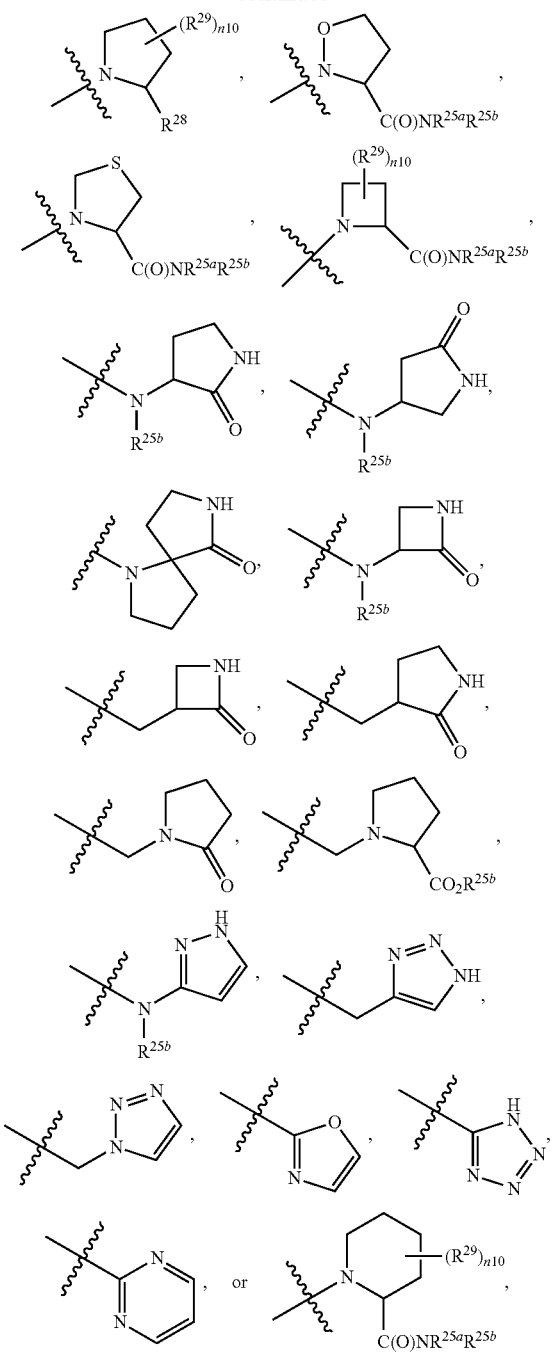

where $R^{25a}$ is H, —OH, —OCH$_3$, NH$_2$, SO$_2$(C$_1$-C$_6$)alkyl, or optionally substituted alkyl; each $R^{25b}$ is independently H, or optionally substituted alkyl; $R^{25c}$ is H or optionally substituted alkyl; $R^{25d}$ is —OH, —OCH$_3$, or NH$_2$; each $R^{26}$ is independently H, halo or (C$_1$-C$_6$)alkyl; each $R^{27}$ is independently —OH, halo, (C$_1$-C$_6$)alkyl, or $R^{26}$ and $R^{27}$ are joined to form a cycloalkyl ring; $R^{28}$ is H, —CH$_2$OH, —CH$_2$NH$_2$, —C(O)CH$_3$, or (C$_1$-C$_6$)alkyl; each $R^{29}$ is independently —OH, halo, or (C$_1$-C$_6$)alkyl; $R^{30}$ is heterocyclyl, heteroaryl, or aryl; n9 is 1, 2 or 3; n10 is 0, 1, 2, 3 or 4;

$R^5$ is

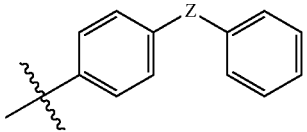

wherein Z is a —C≡C— or phenyl;
each $R^2$ and $R^3$ are each independently hydroxy, nitro, halo, cyano, glycosyloxy, amino, (C$_1$-C$_4$)alkyl, OR$^{40}$, or a group cleavable under physiological conditions to provide a compound of formula (I) wherein $R^2$ or $R^3$ respectively is hydroxy, wherein any carbon atom is optionally substituted with J;
each $R^{40}$ is independently —(C$_1$-C$_6$)alkyl, or —(C$_1$-C$_6$)alkyl-NR$^{41}$R$^{42}$;
each $R^{41}$ and $R^{42}$ is hydrogen, —(C$_1$-C$_6$)alkyl, —(C$_1$-C$_6$) heteroalkyl, —C(O)(C$_1$-C$_6$)alkyl, —C(O)N(R$^{43}$)$_2$, —SO$_2$N (R$^{43}$)$_2$; or $R^{41}$ and $R^{42}$ and the nitrogen atom to which that are attached form a heterocycloalkyl ring;
each $R^{43}$ is independently hydrogen or —(C$_1$-C$_6$)alkyl; or two $R^{43}$ and the nitrogen atom to which that are attached form a heterocycloalkyl ring;
n1 and n2 are independently 0 or 1;
n3 and n8 are independently 0, 1, or 2;
each m is independently 0 or 1;
$R^1$ is hydrogen or (C$_1$-C$_6$)alkyl optionally substituted with 1 to 3 J; or $R^1$ together with $E^1$ form a ring;
$R^4$, $R^{4'}$, and $R^{4''}$ are each independently at each occurrence hydrogen, or (C$_1$-C$_6$)alkyl optionally substituted with 1 to 3 J;
$R^6$ is hydrogen, or (C$_1$-C$_6$)alkyl optionally substituted with 1 to 3 J; or $R^6$ together with $R^{44}$ form a ring;
$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
$R^{46}$ is H, amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
each J is independently halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S (O)$_2$N(R')$_2$, (CH$_2$)$_{0-p}$SO$_3$R', (CH$_2$)$_{0-p}$C(O)R', (CH$_2$)$_{0-p}$C(O) OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R') C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;
each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate, or prodrug thereof.

In another embodiment is a compound of Formula (VII) having the structure of Formula (VIIa):

Formula (VIIa)

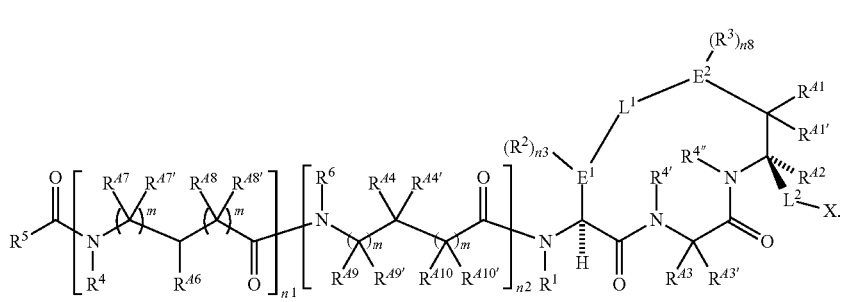

In another embodiment is a compound of Formula (VII) having the structure of Formula (VIIb):

Formula (VIIb)

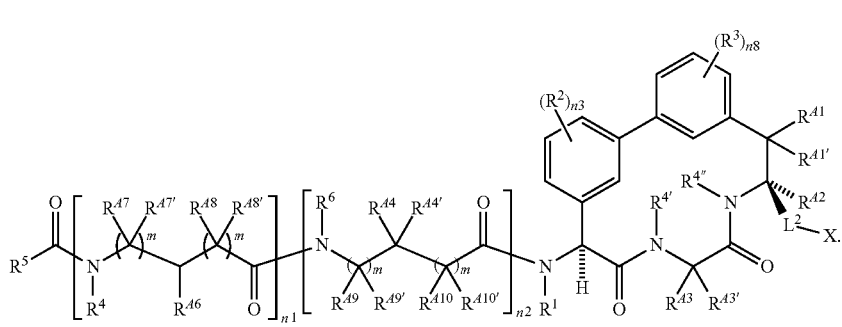

In some embodiments is a compound of Formula (VII), (VIIa), or (VIIb) wherein $R^5$ is

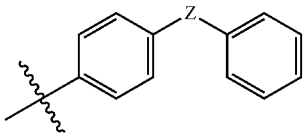

and Z is a —C═C—. In some embodiments is a compound of Formula (VII), (VIIa), or (VIIb) wherein $R^5$ is

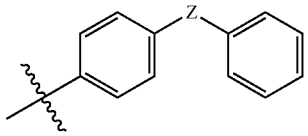

and Z is phenyl.

In some embodiments, compounds of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) have the structure:

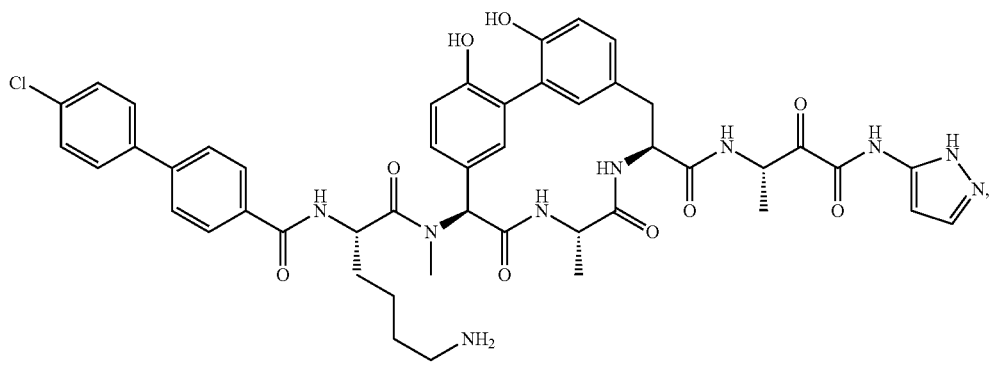

-continued
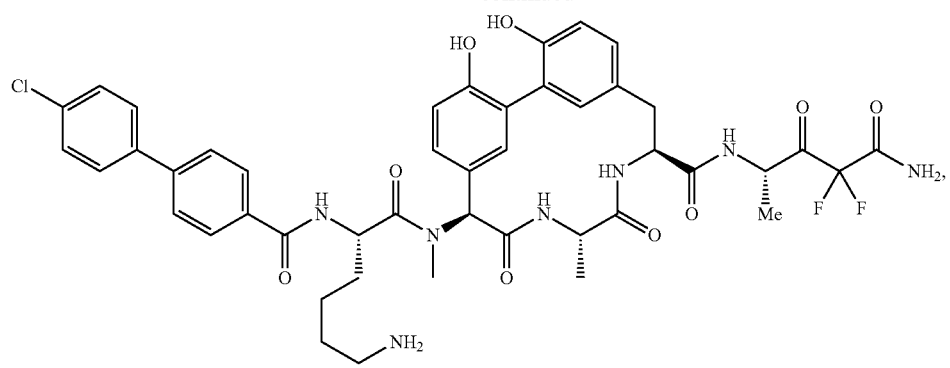
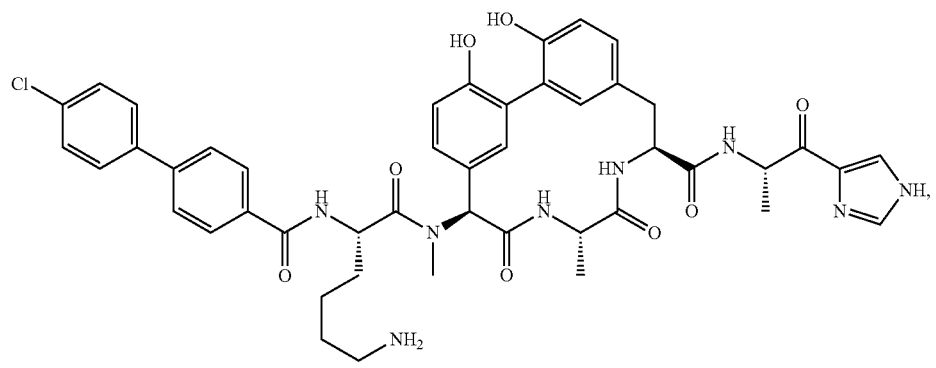
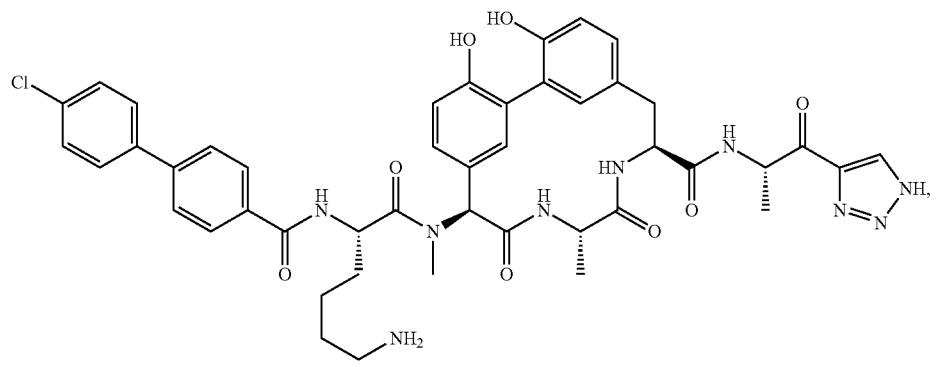
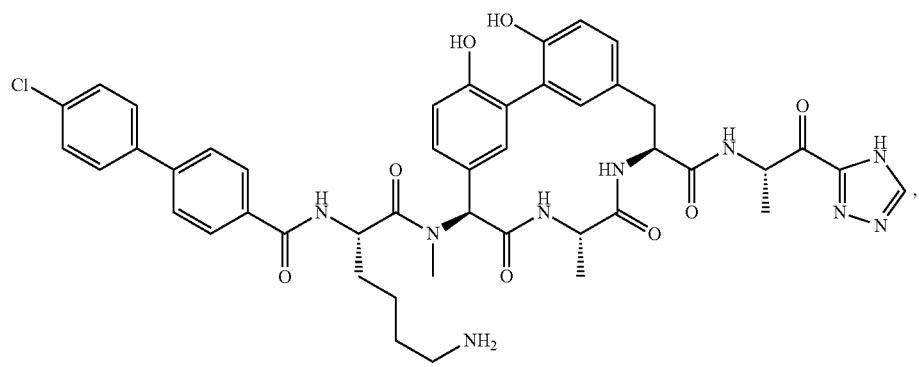

-continued
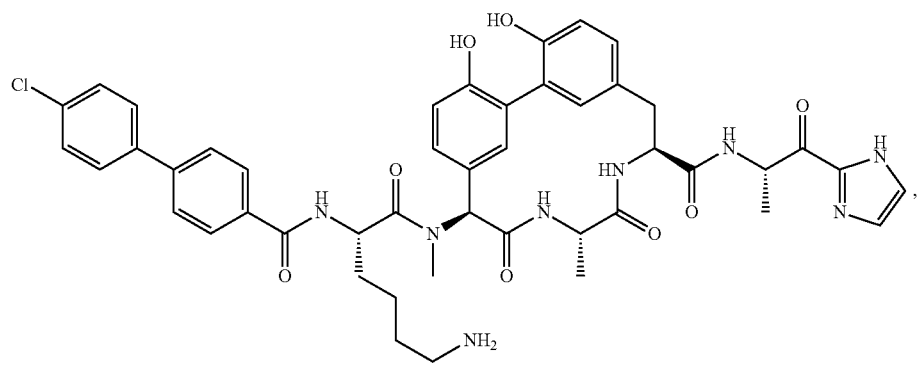
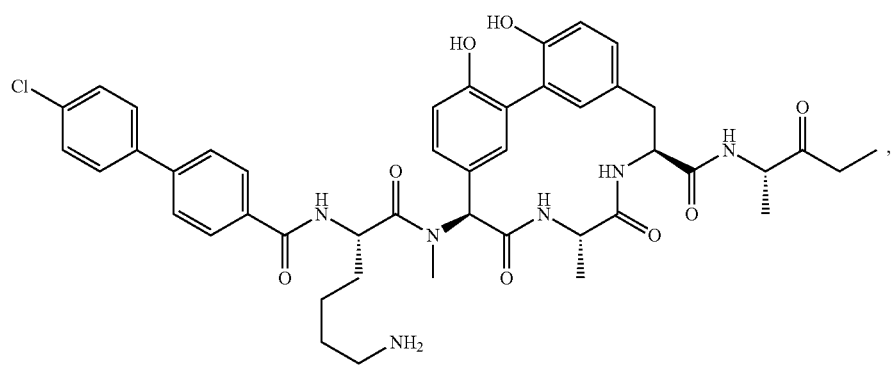
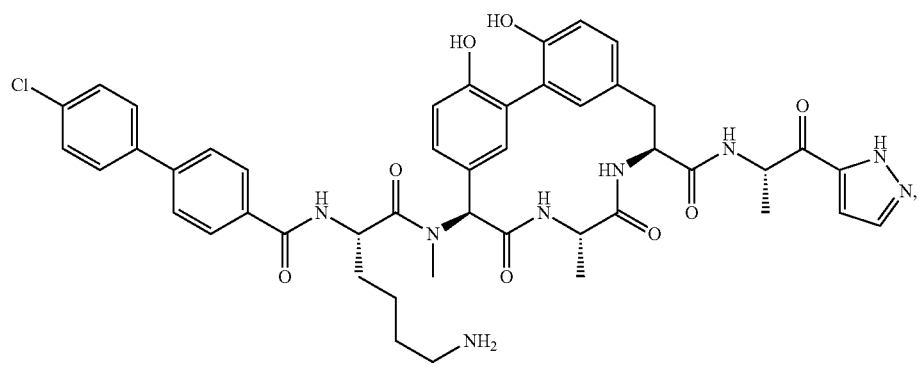
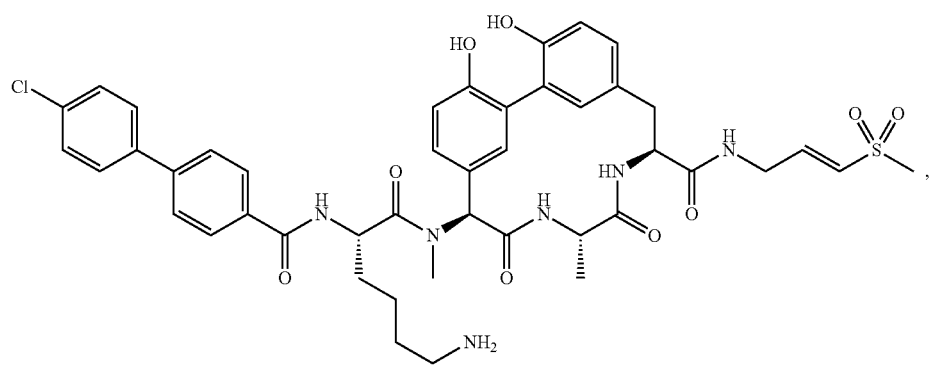

-continued
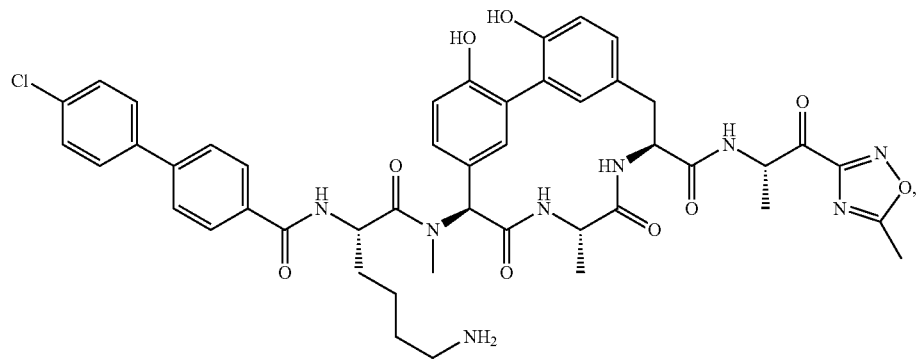
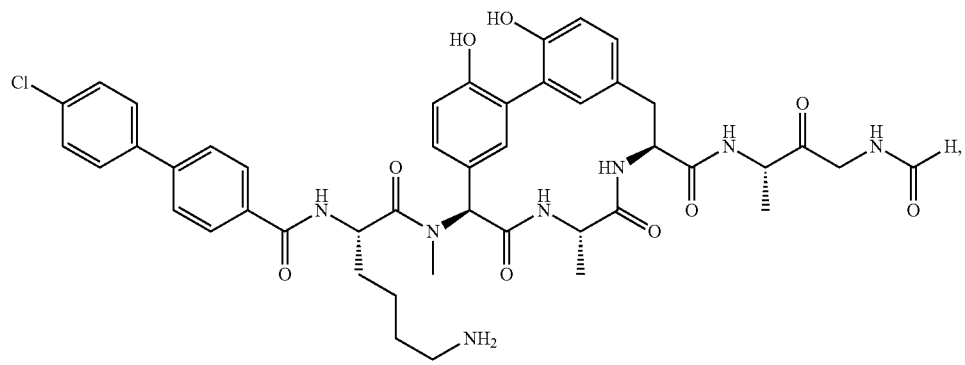
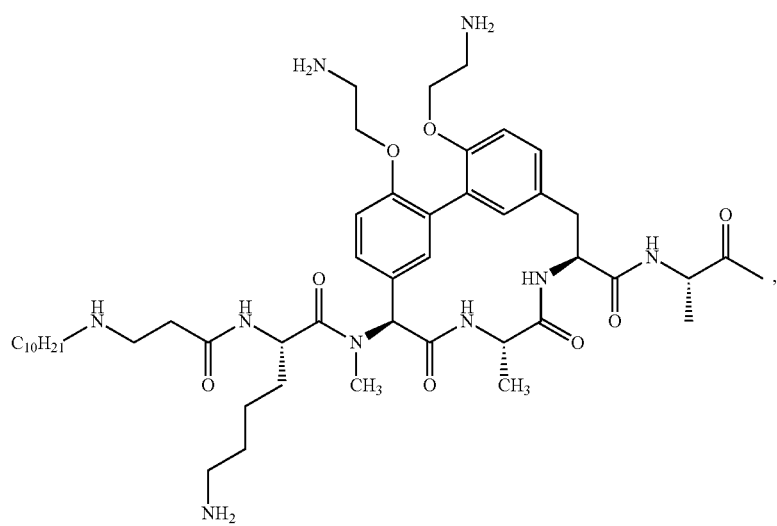
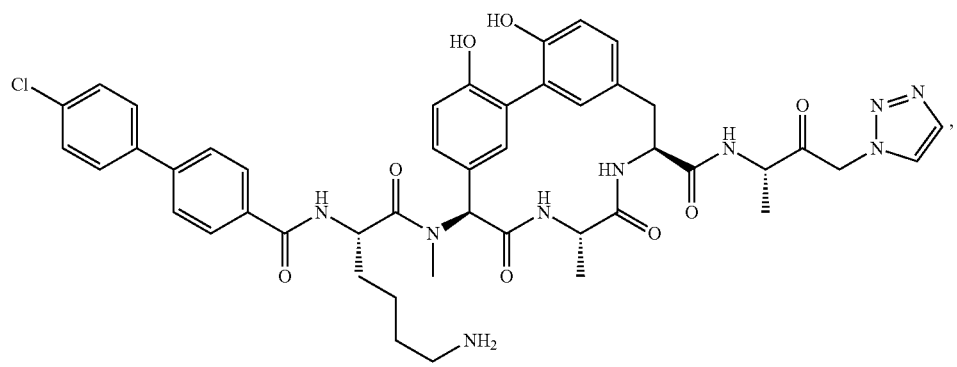

-continued
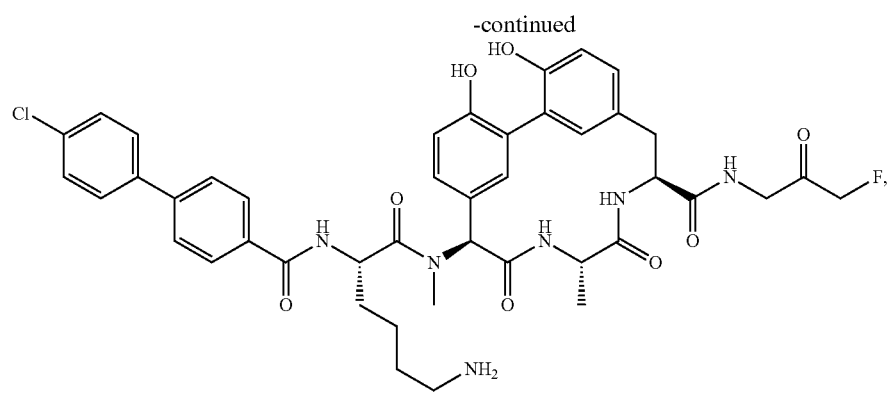
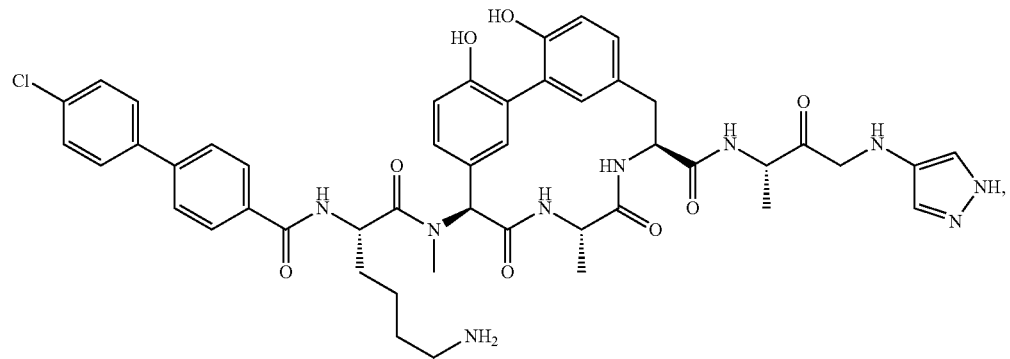
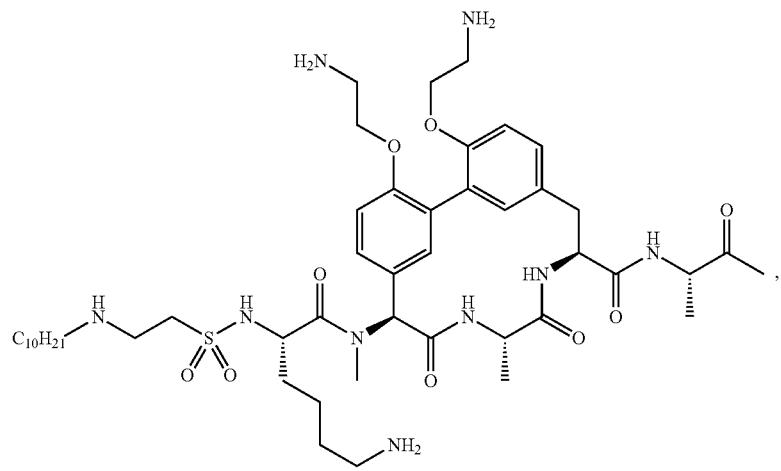
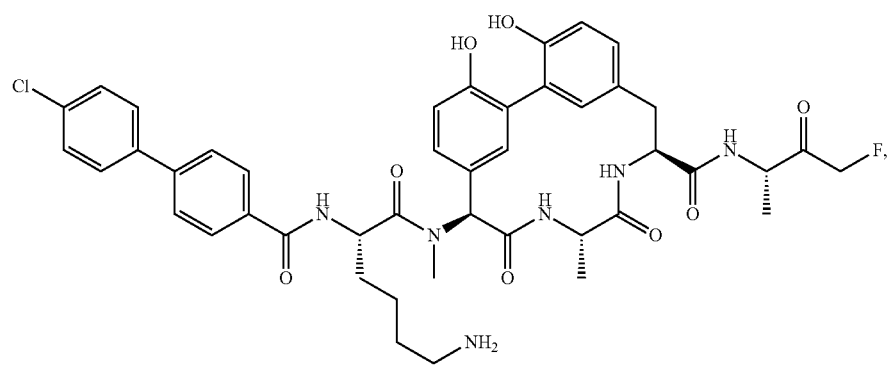

-continued
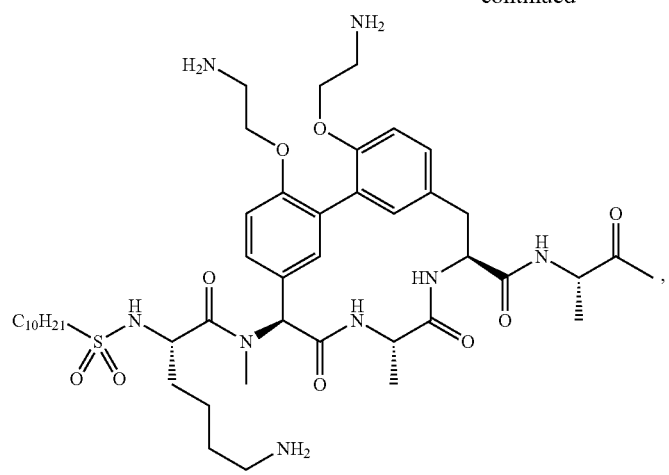
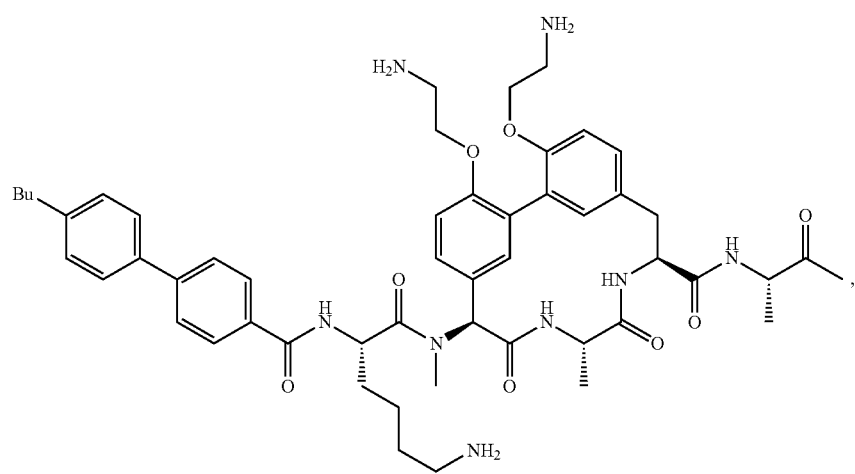
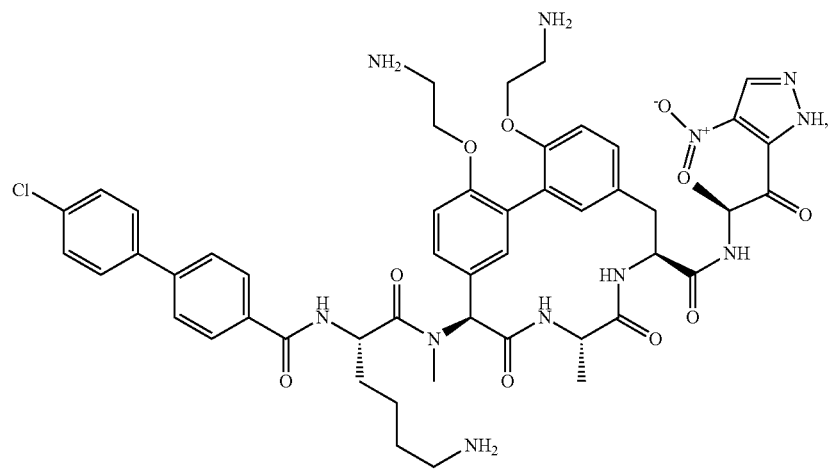

-continued
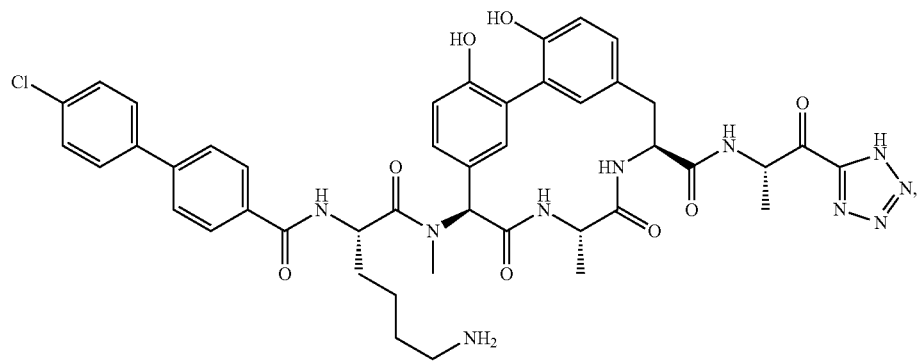
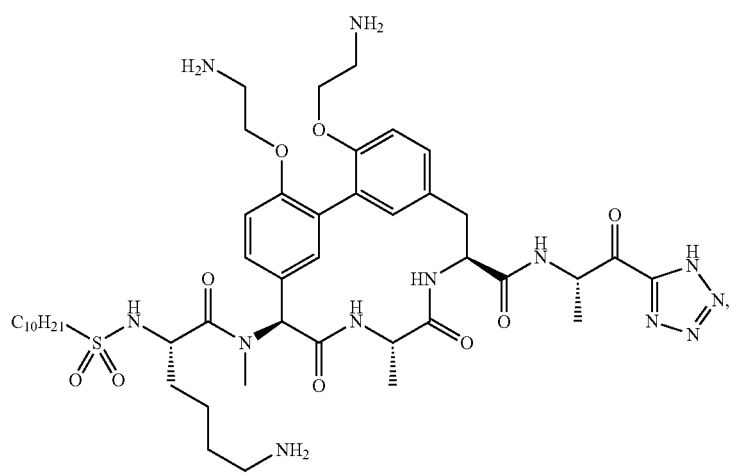
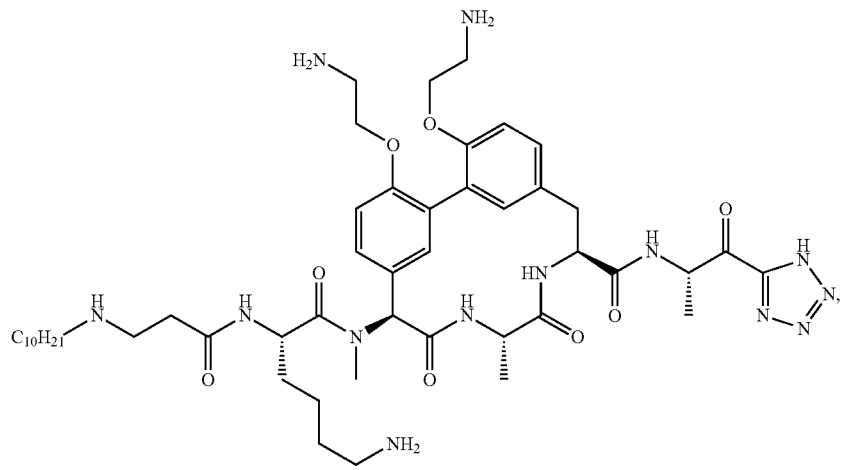

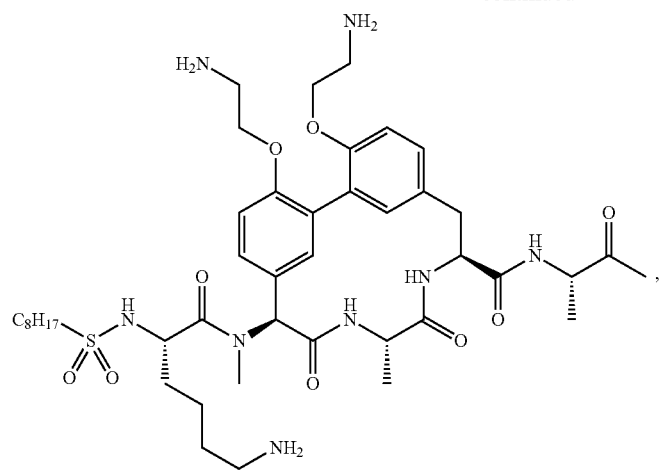
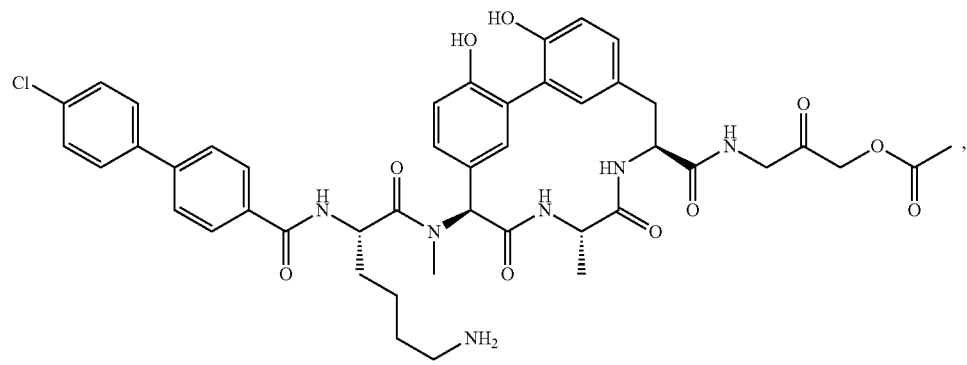
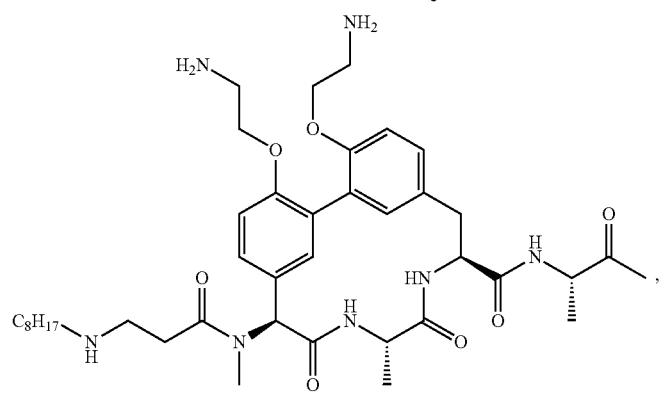
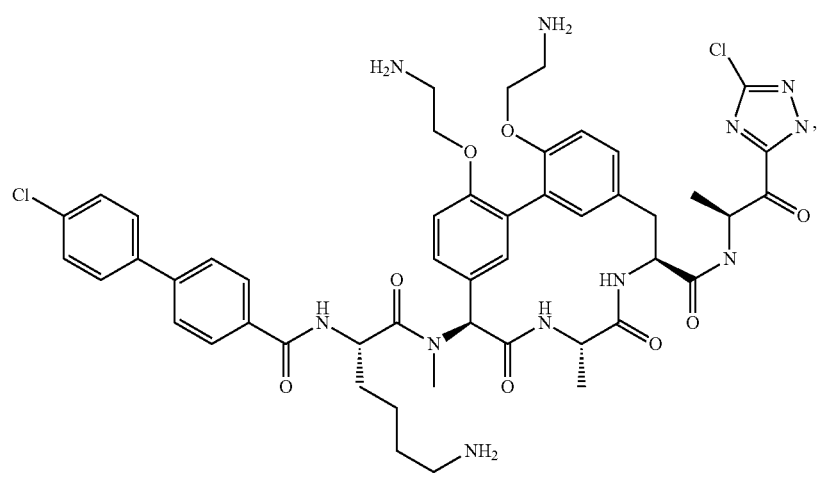

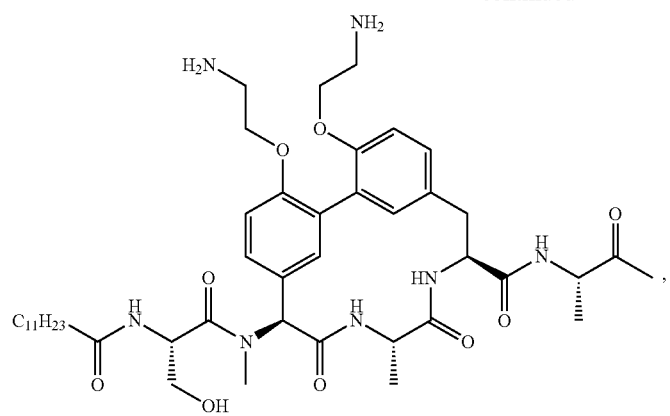
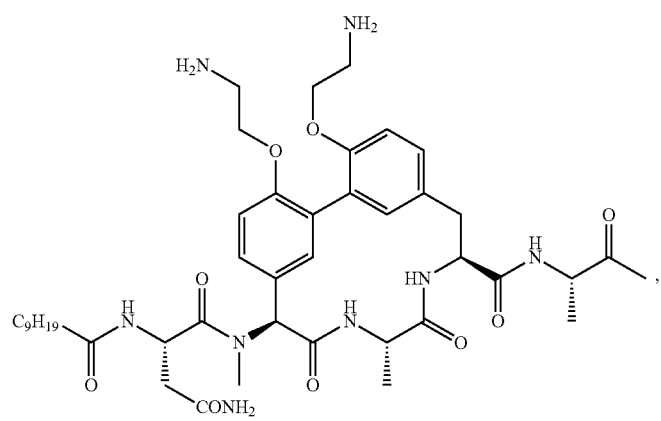
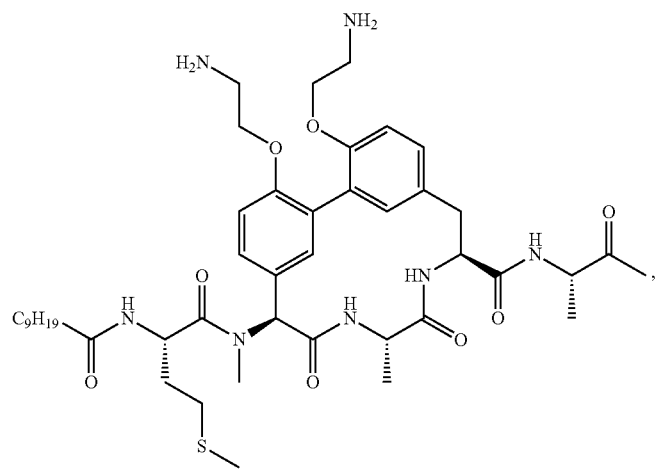

-continued
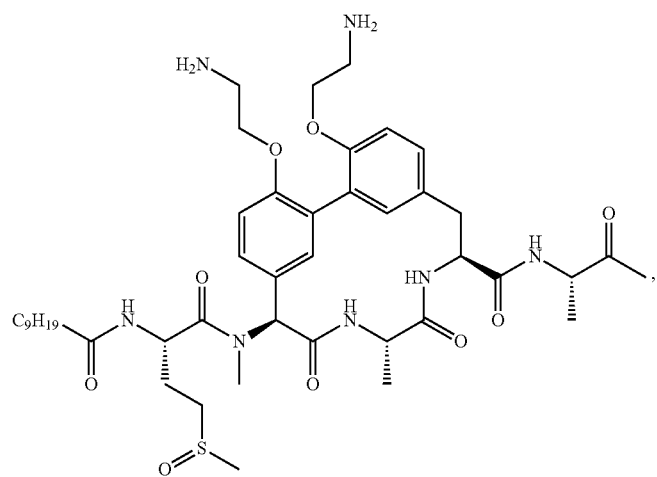
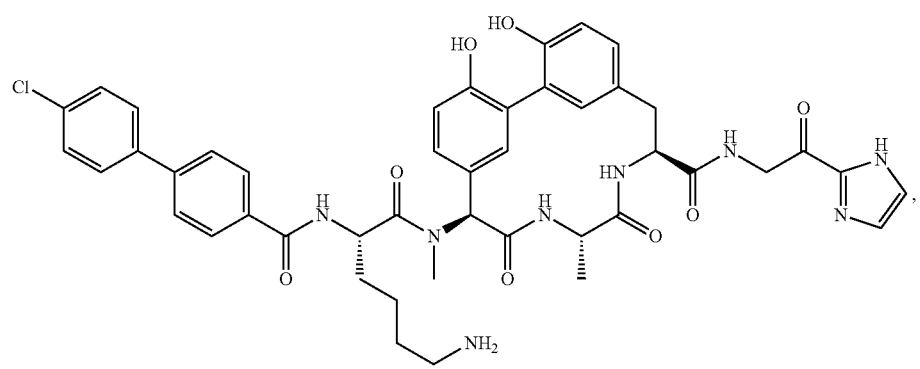
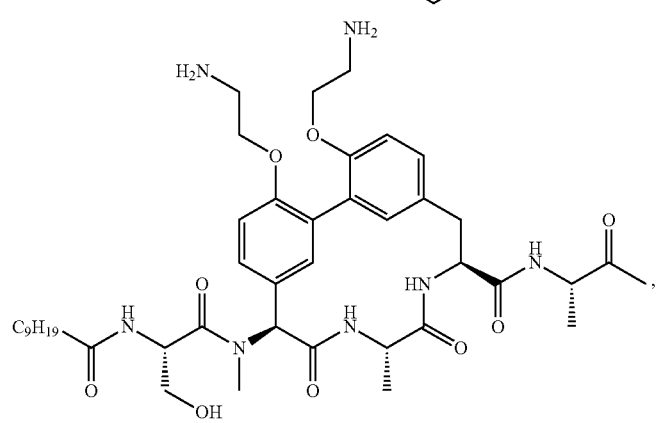
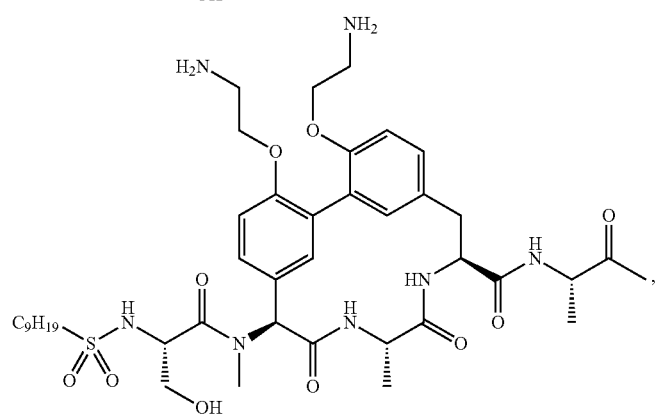

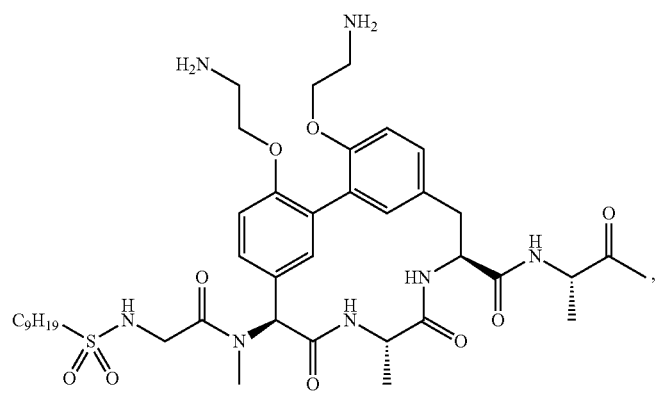
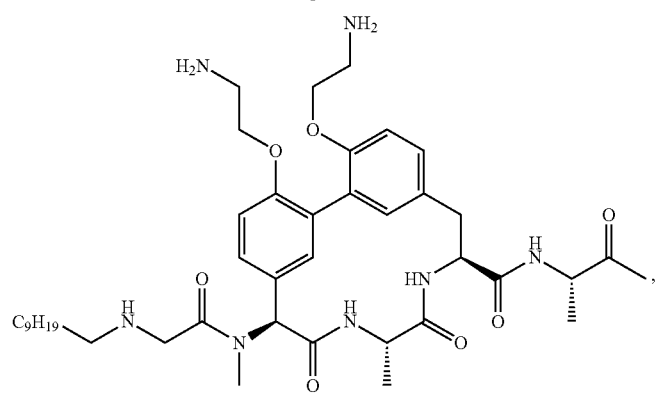
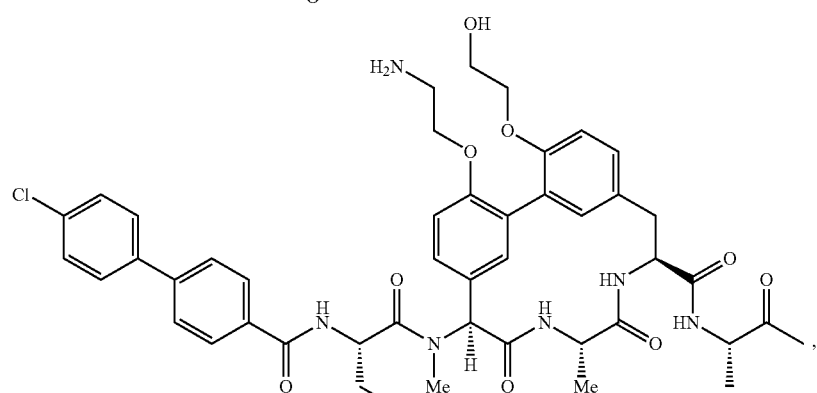
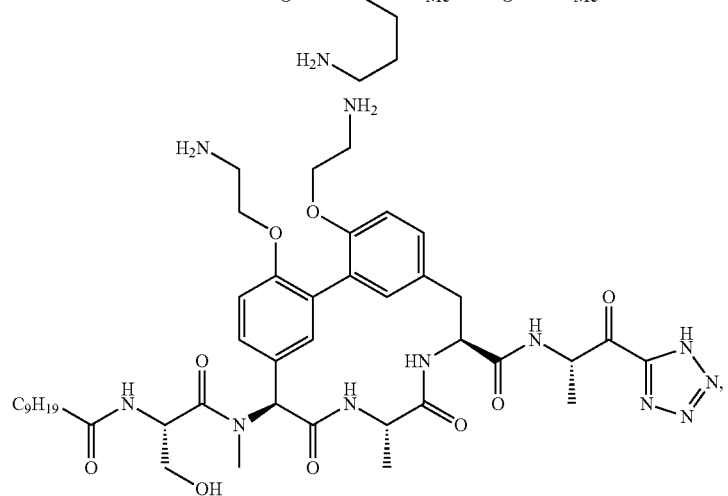

-continued
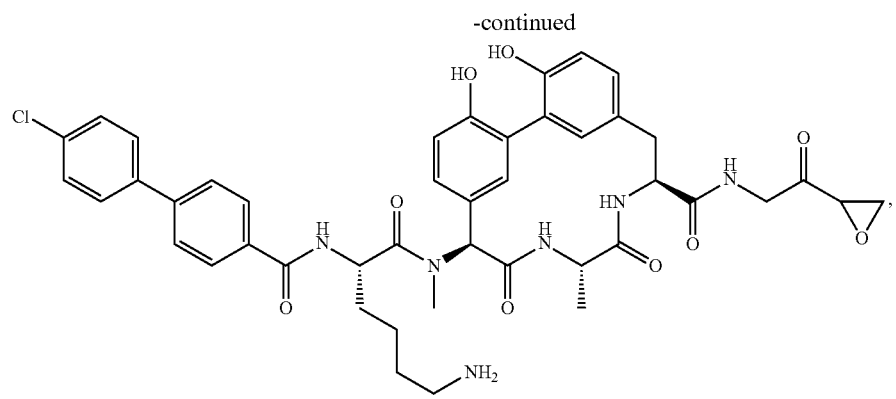
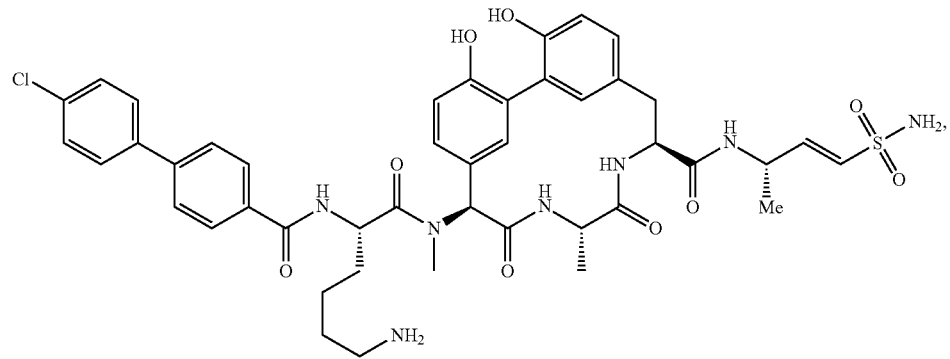
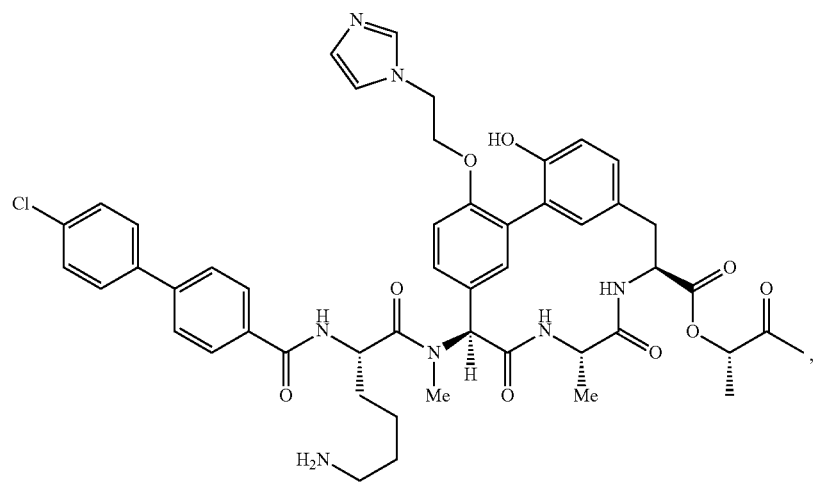
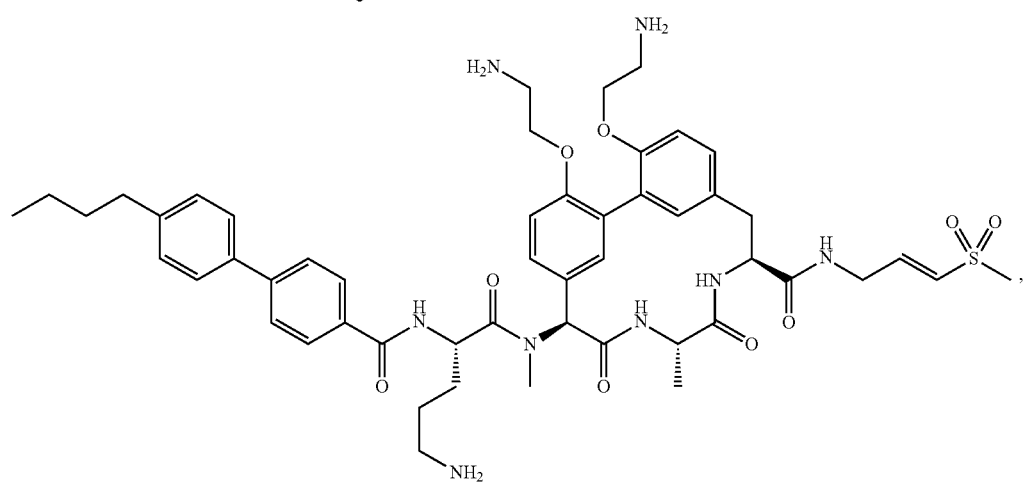

-continued
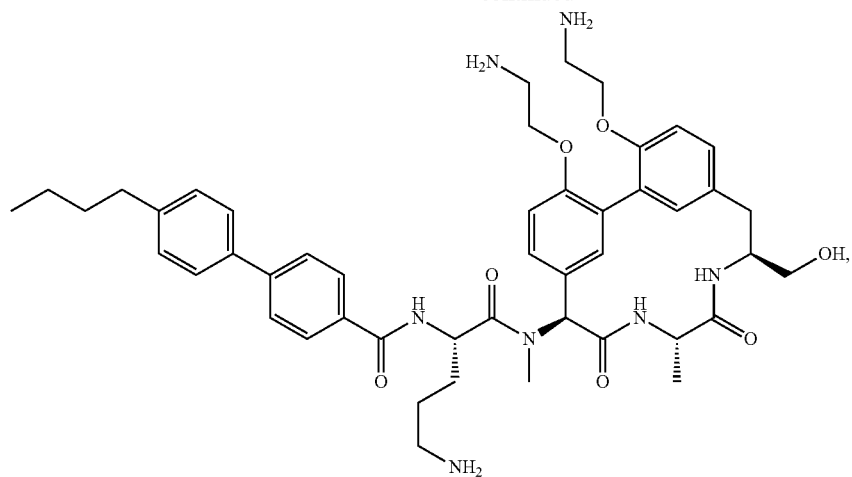
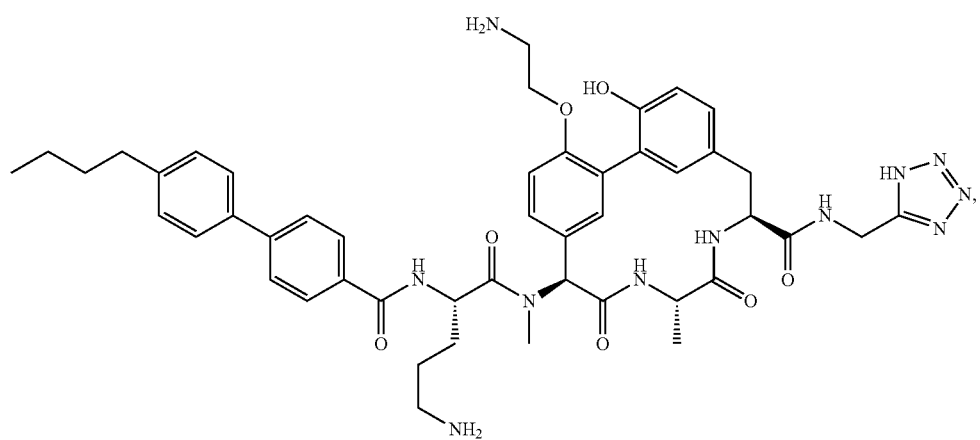
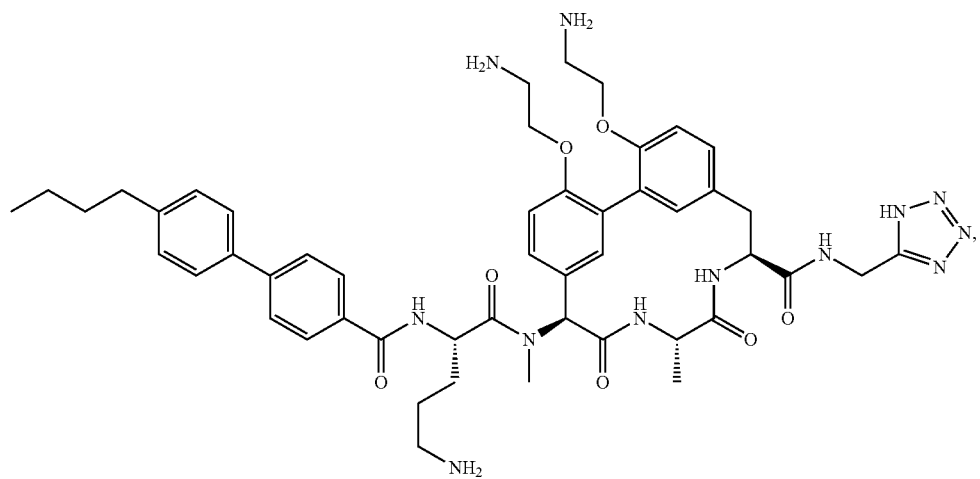

-continued
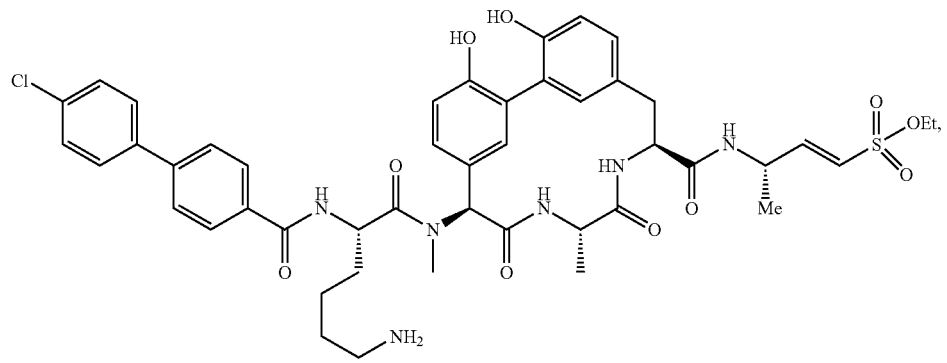
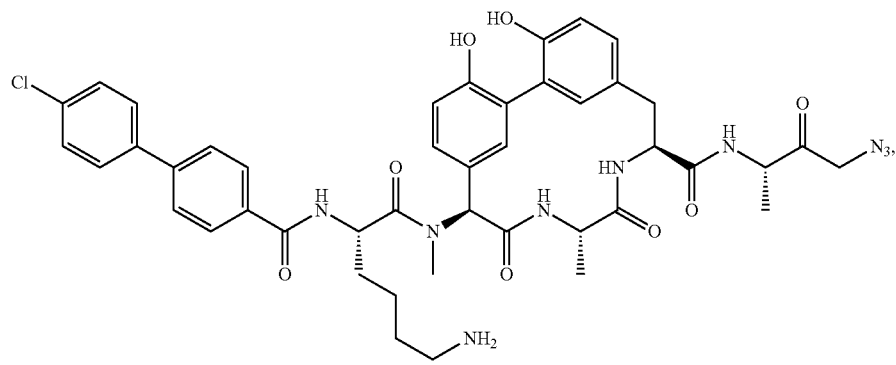
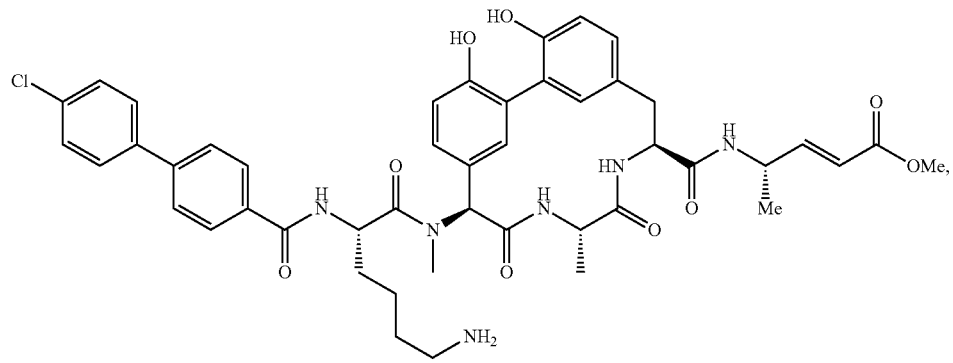
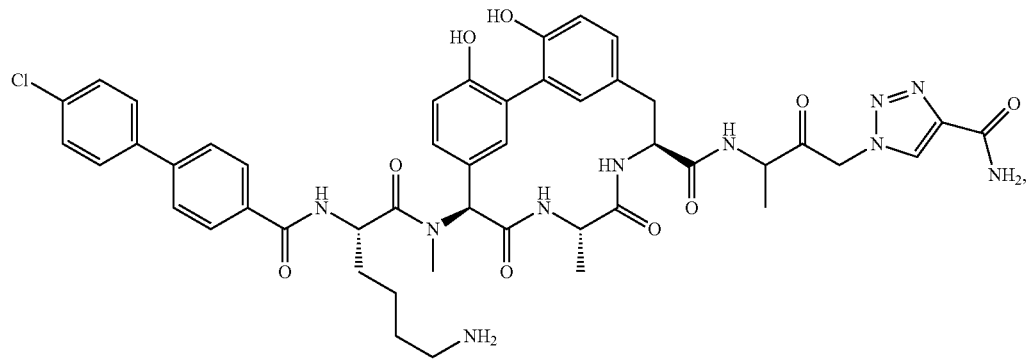

-continued
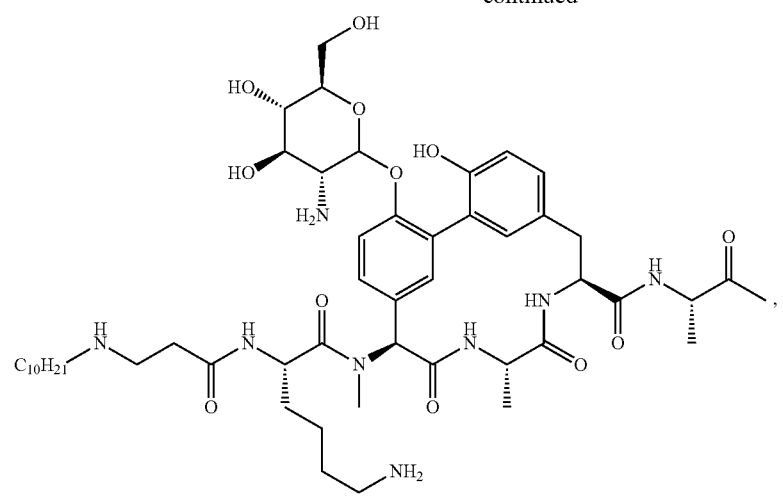
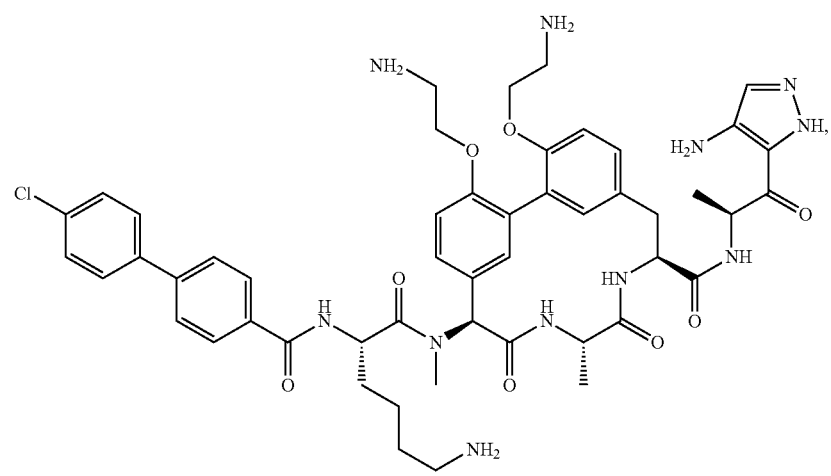
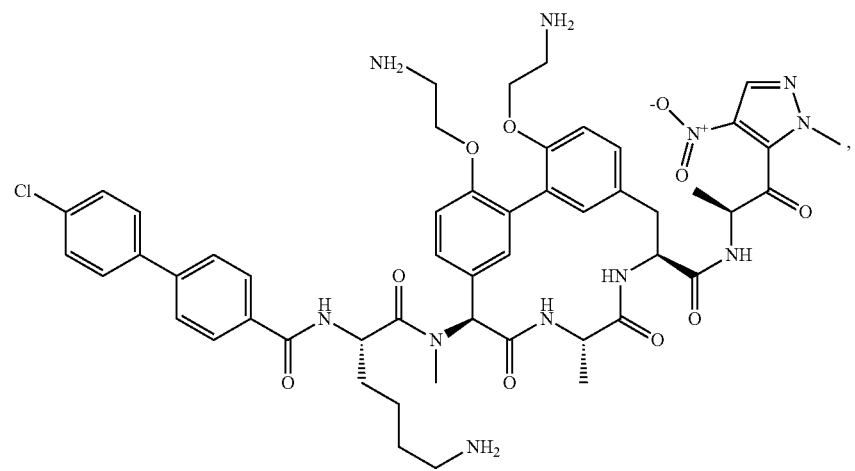

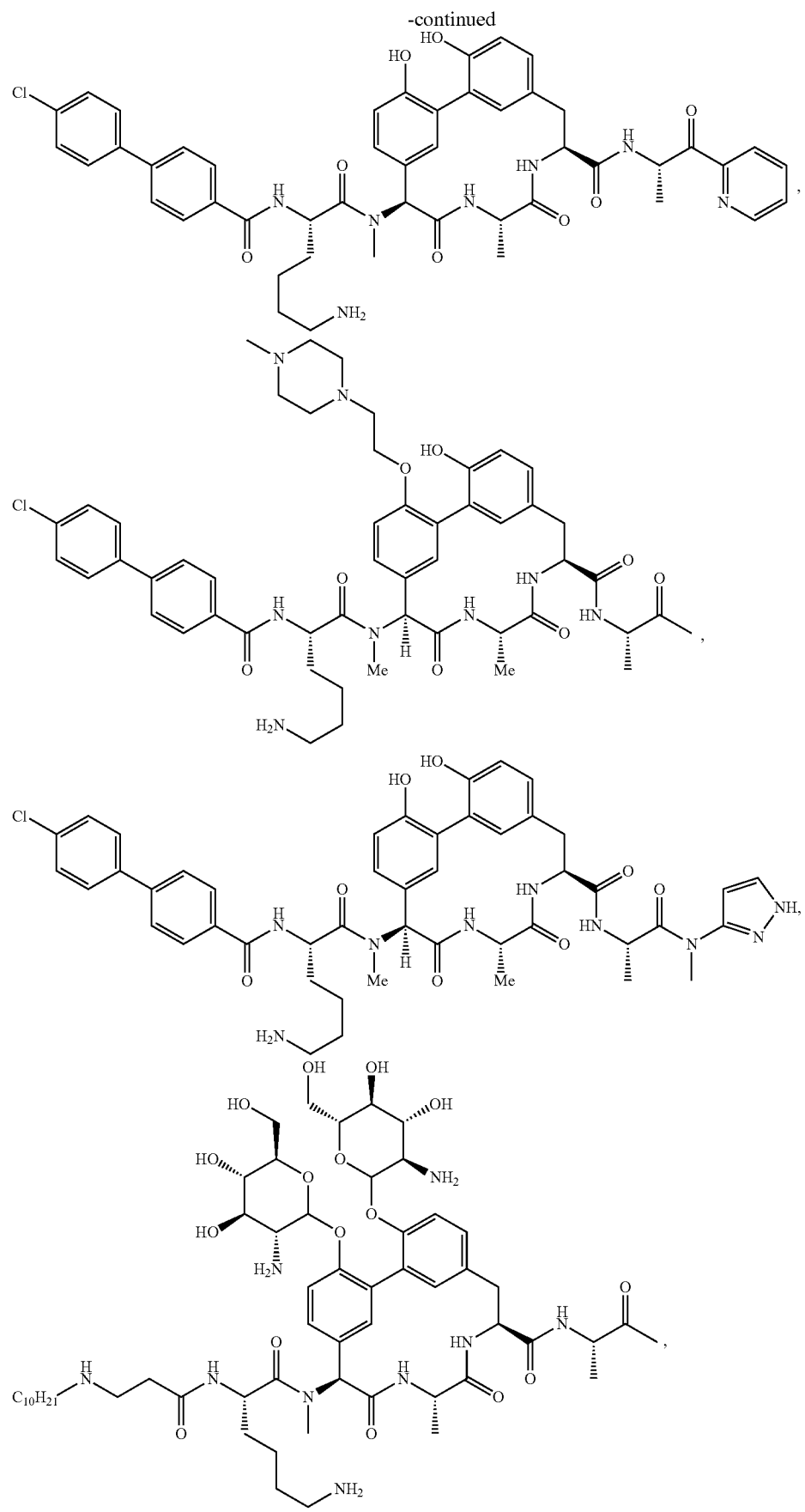

-continued
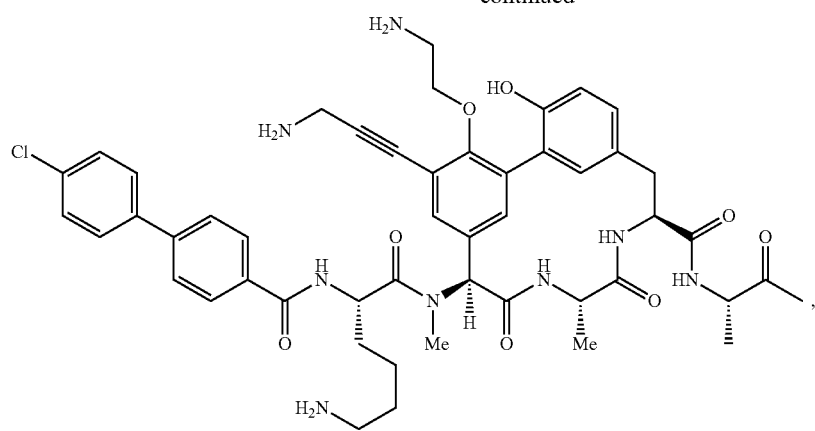
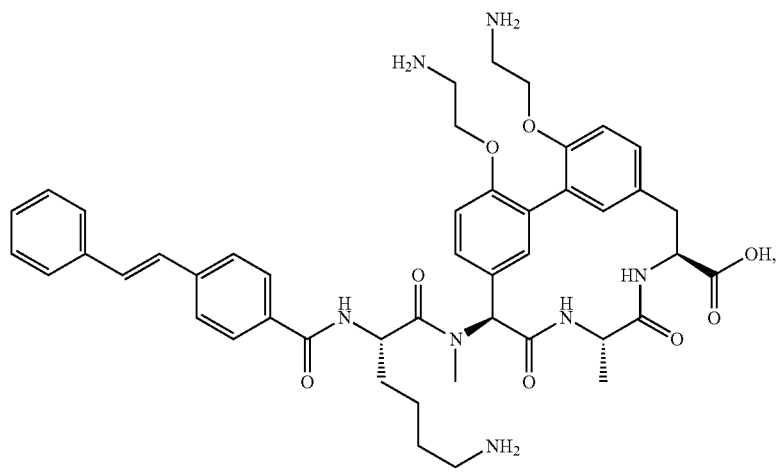
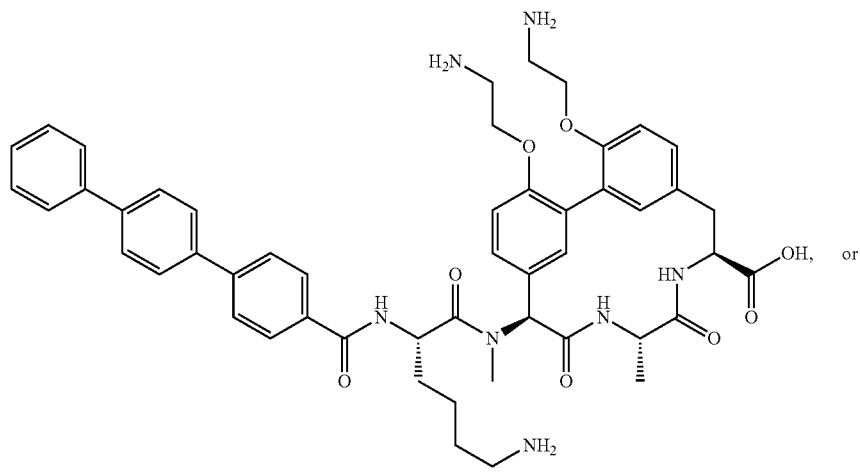

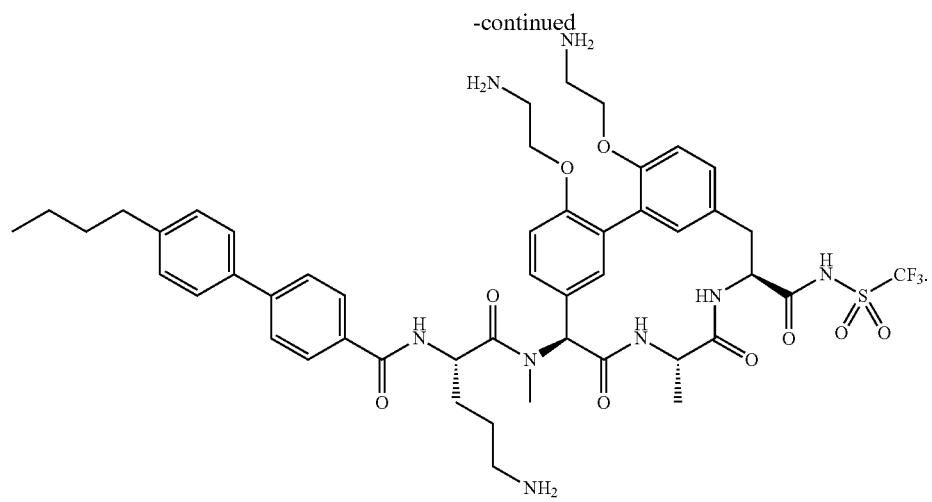
In another aspect is a compound having the structure:
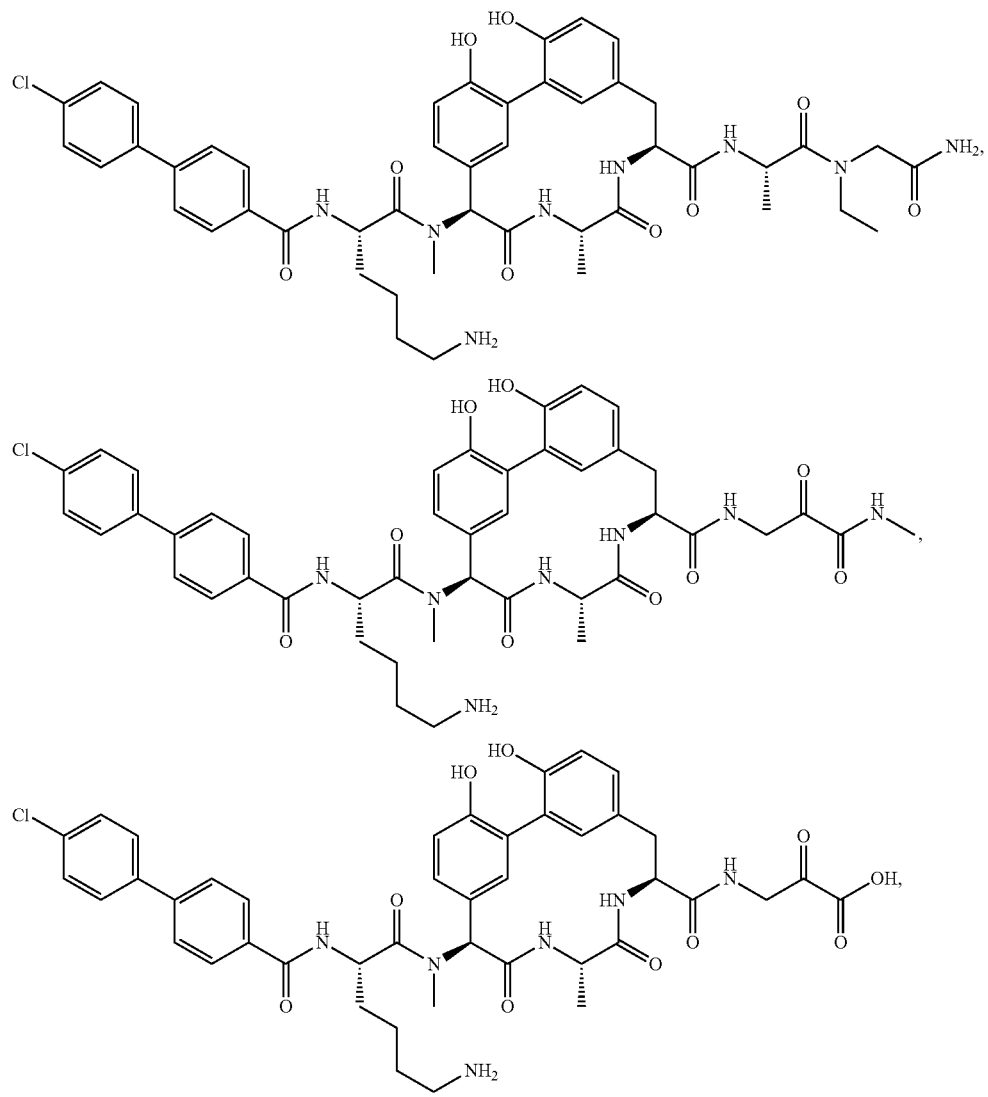

-continued
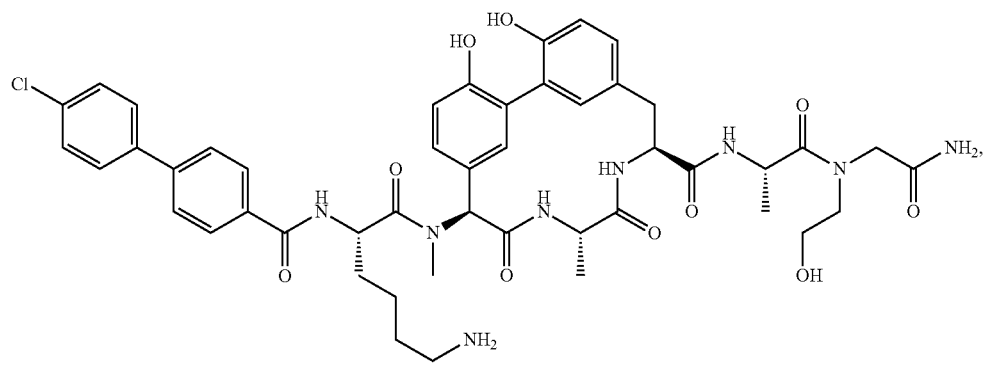
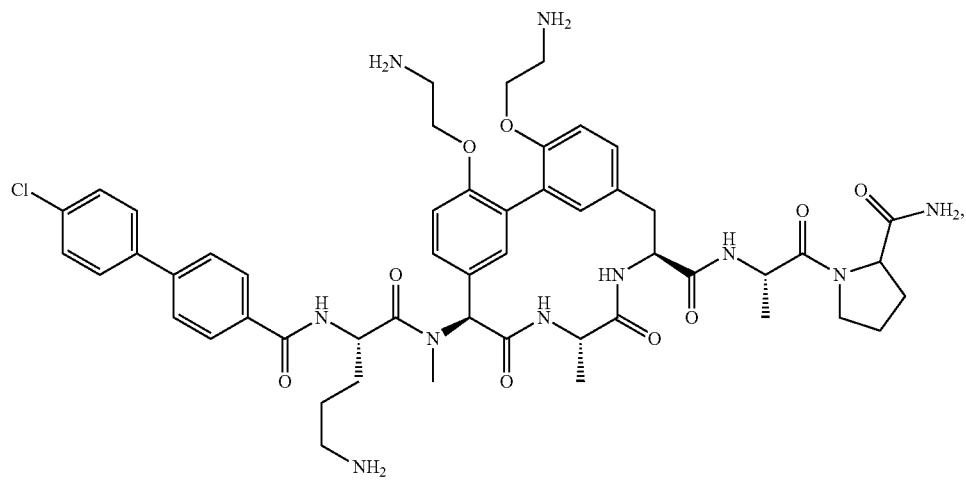
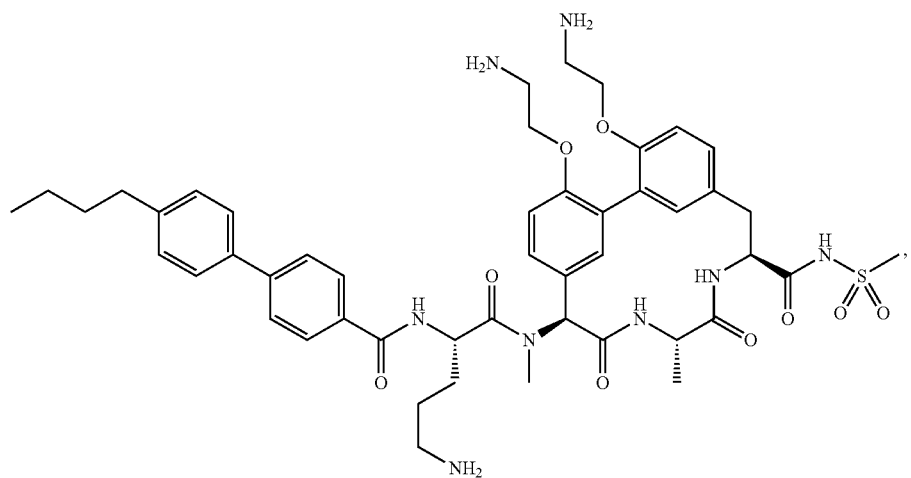

-continued
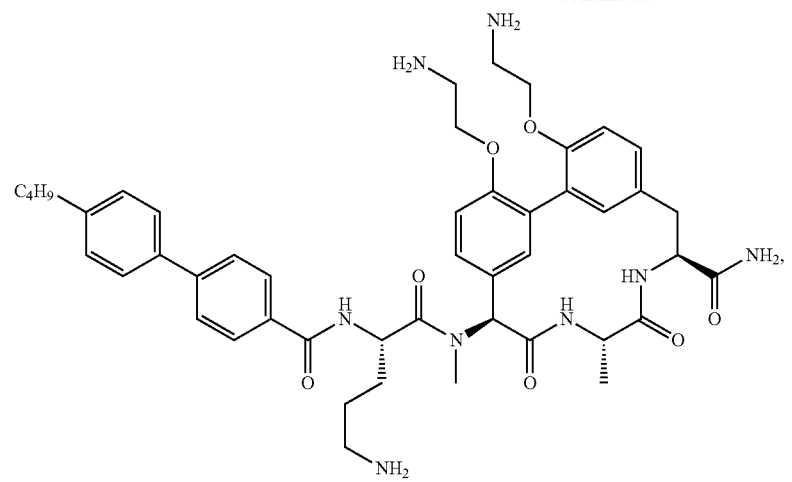
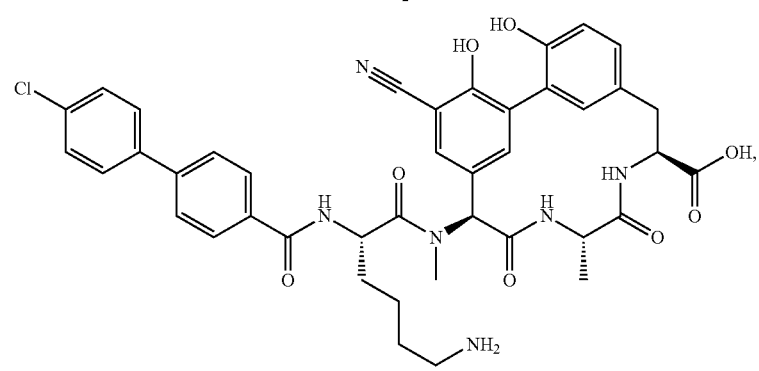
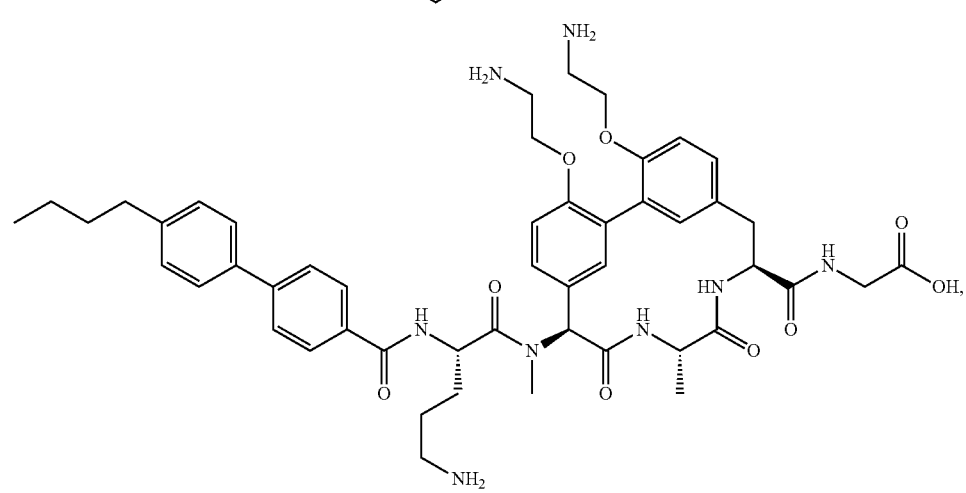
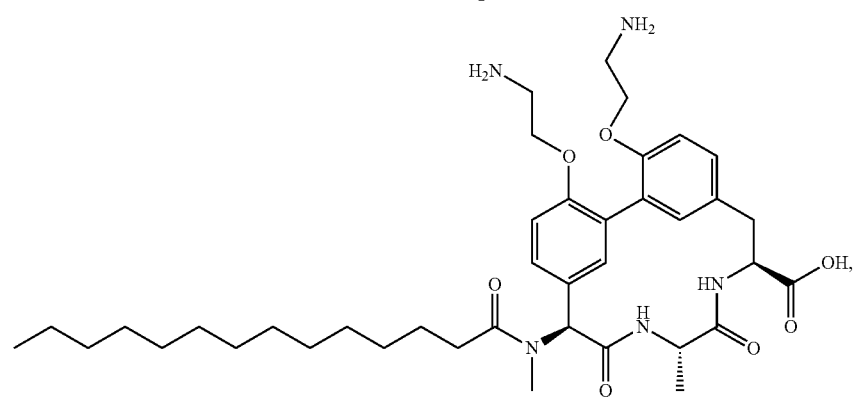

-continued
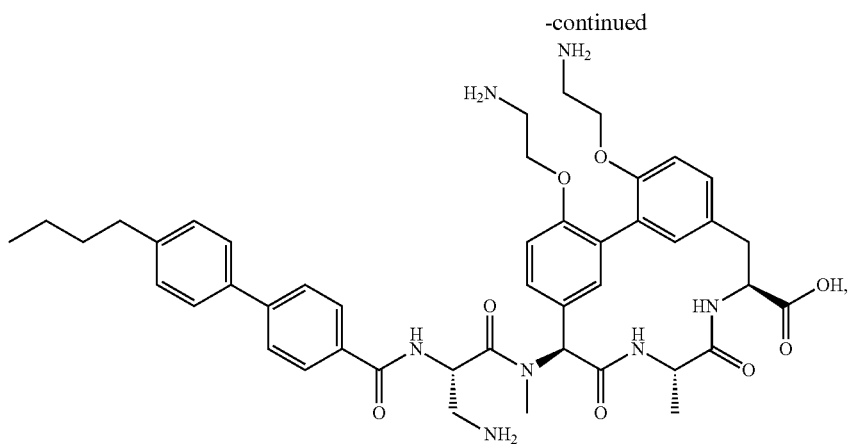
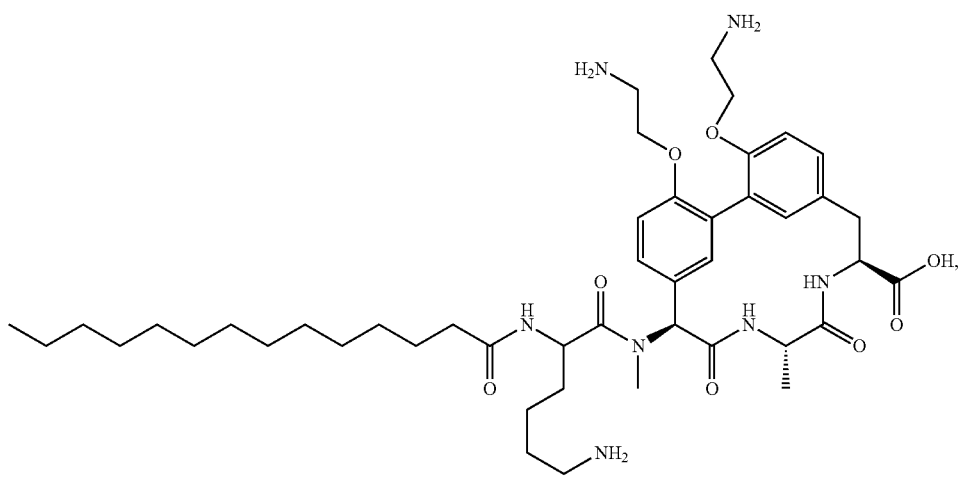
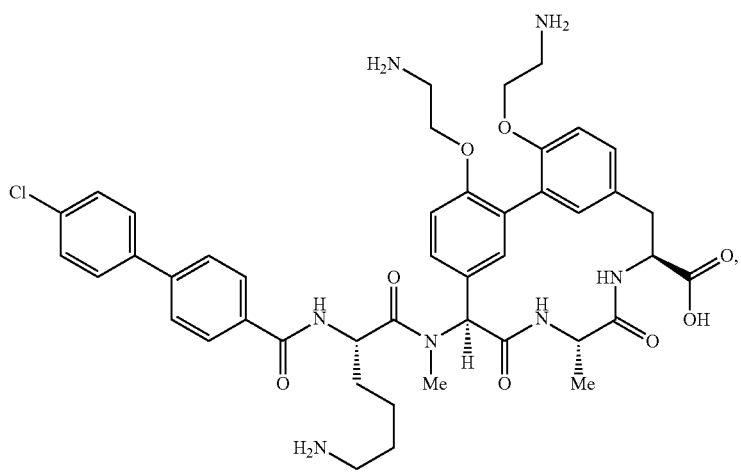

-continued
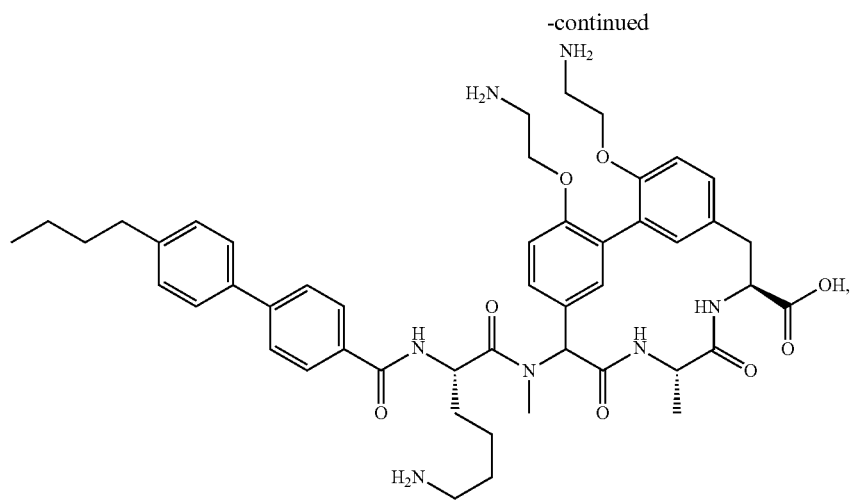
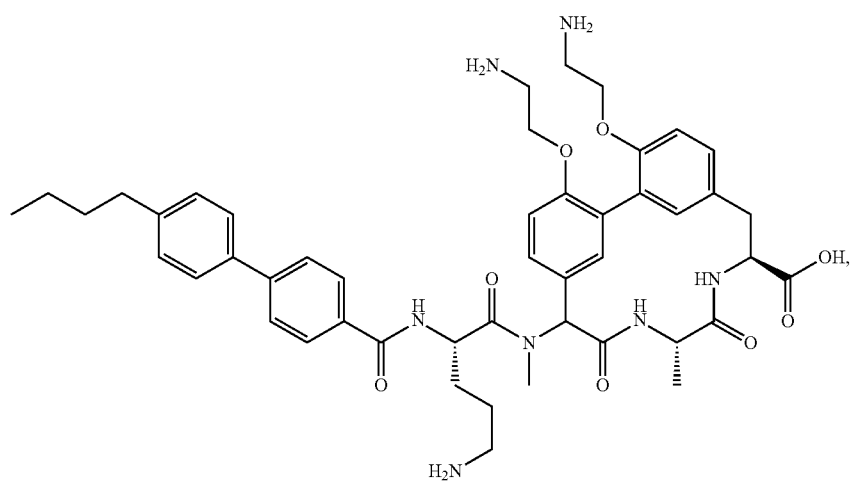
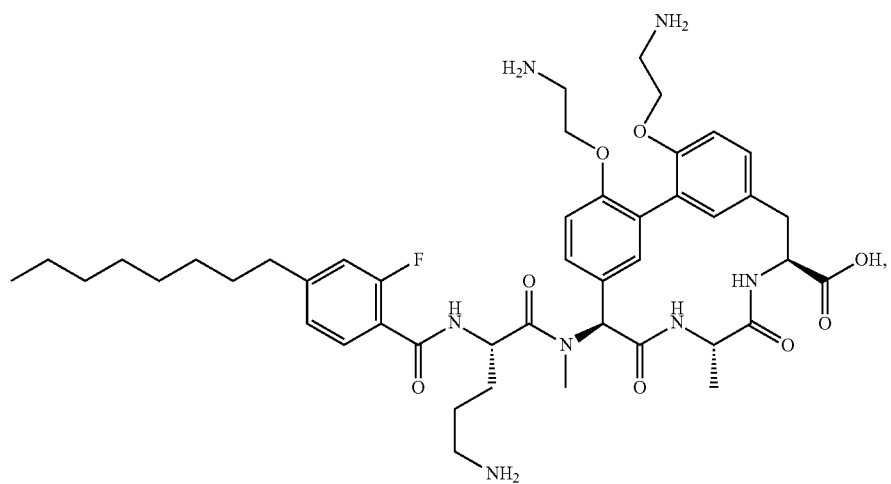

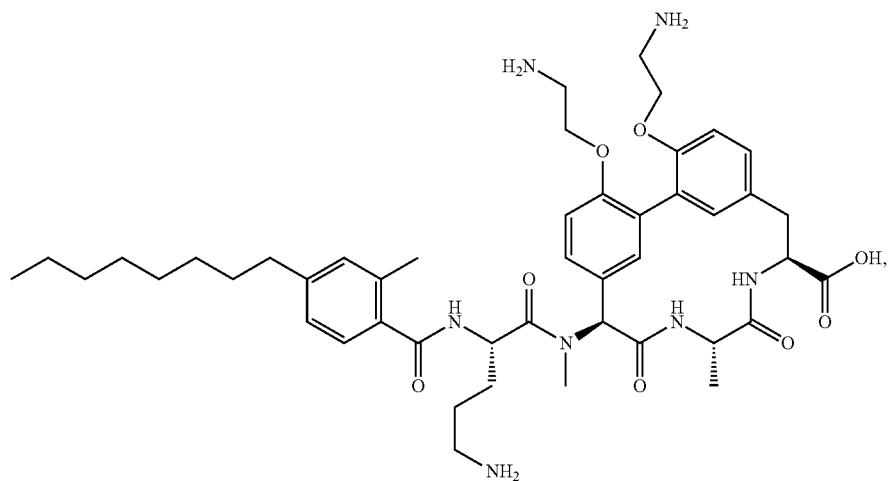
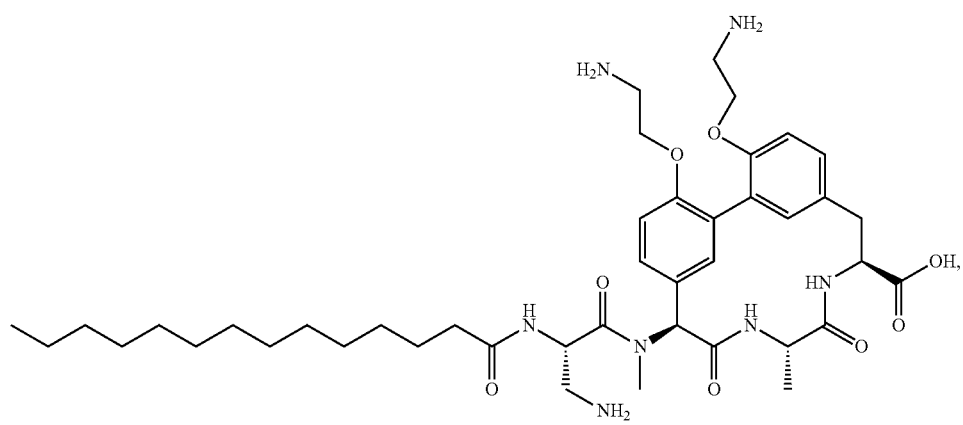
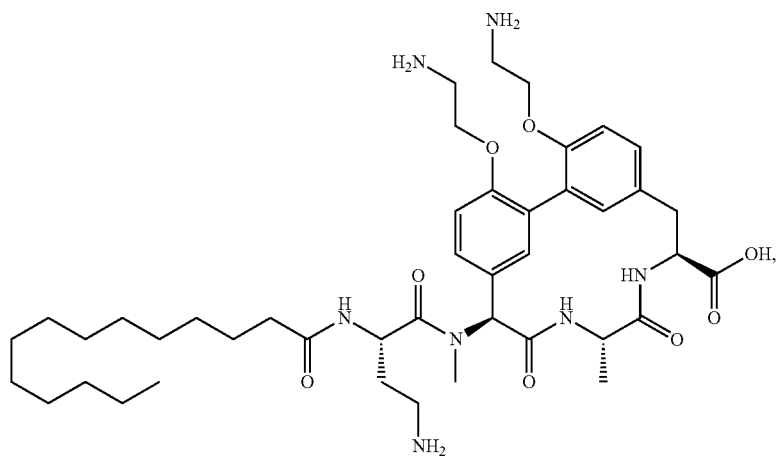

-continued
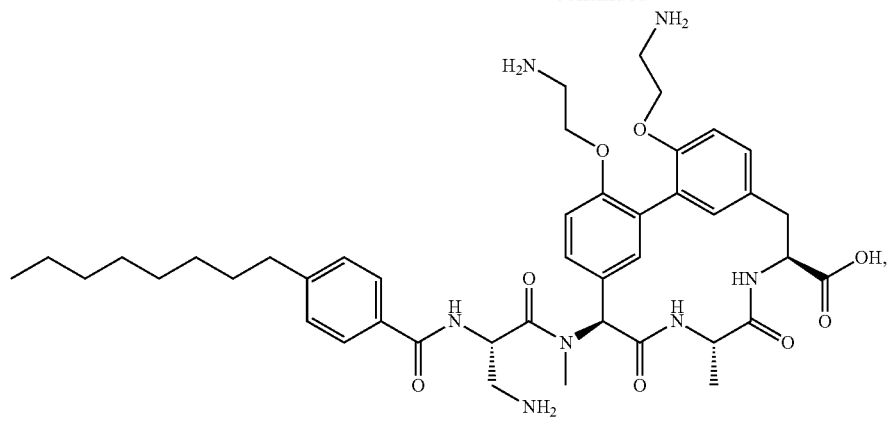
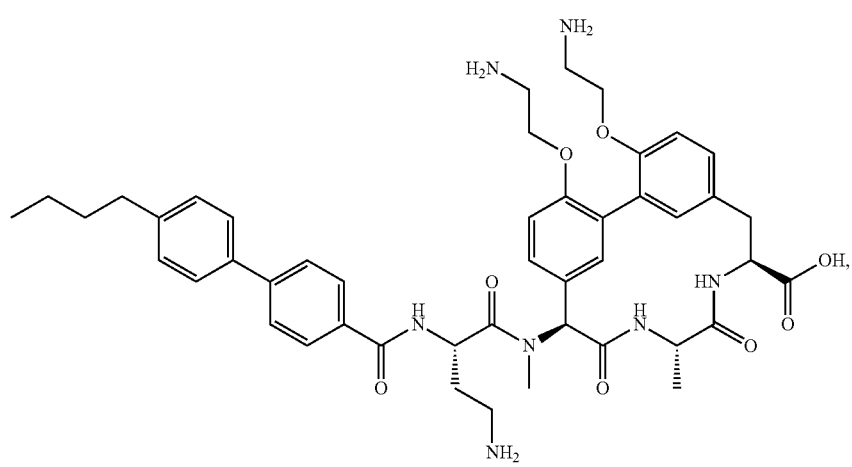
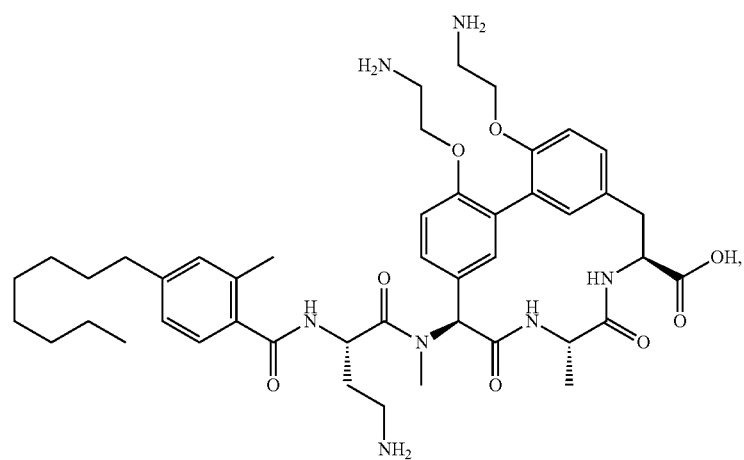

-continued
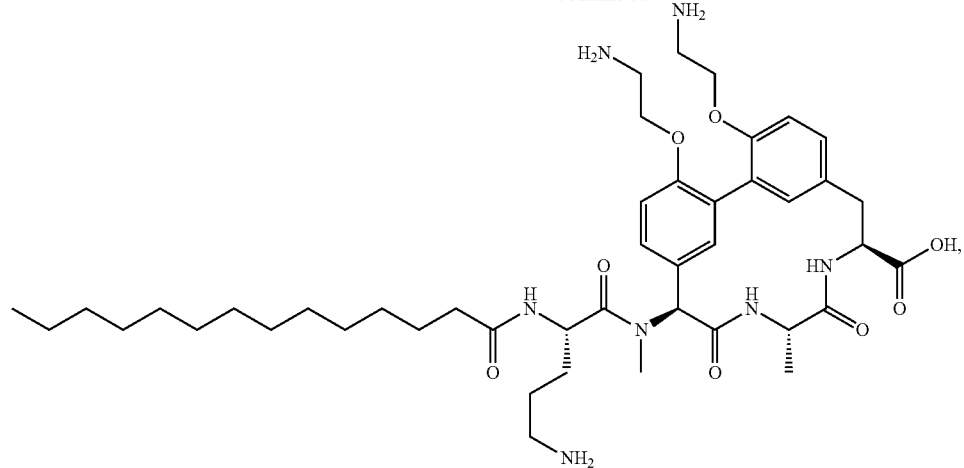
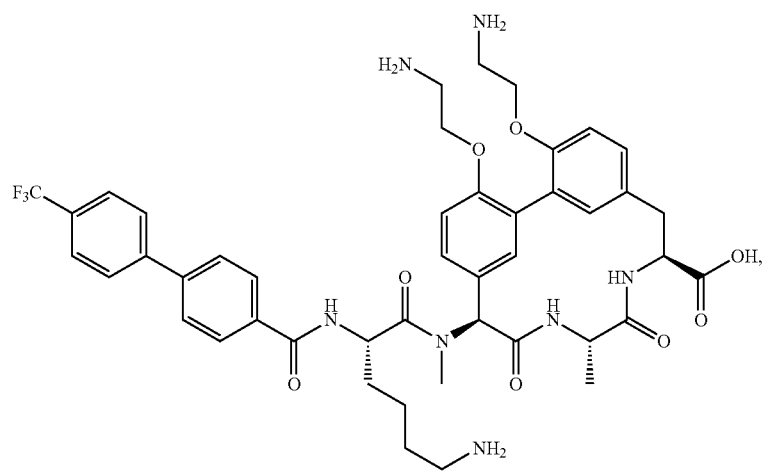
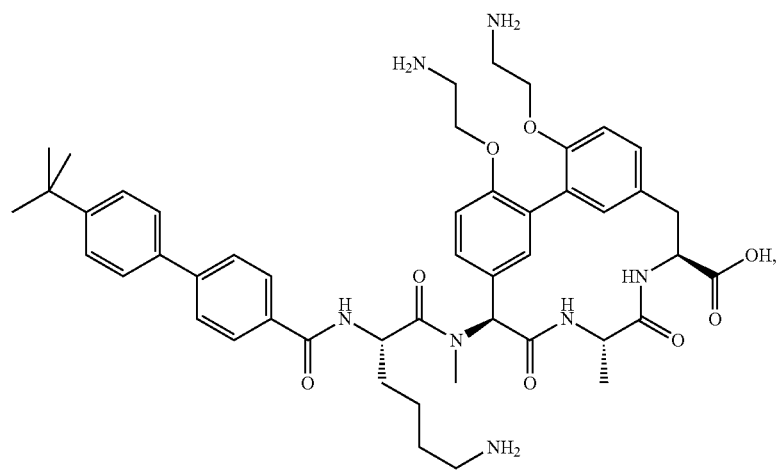

-continued
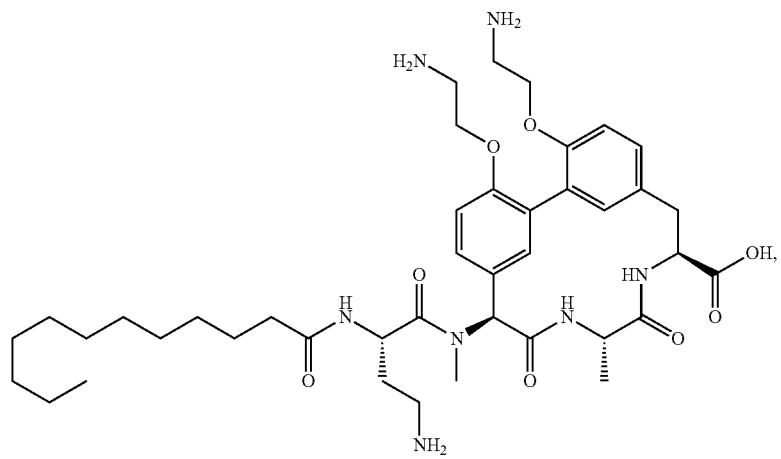
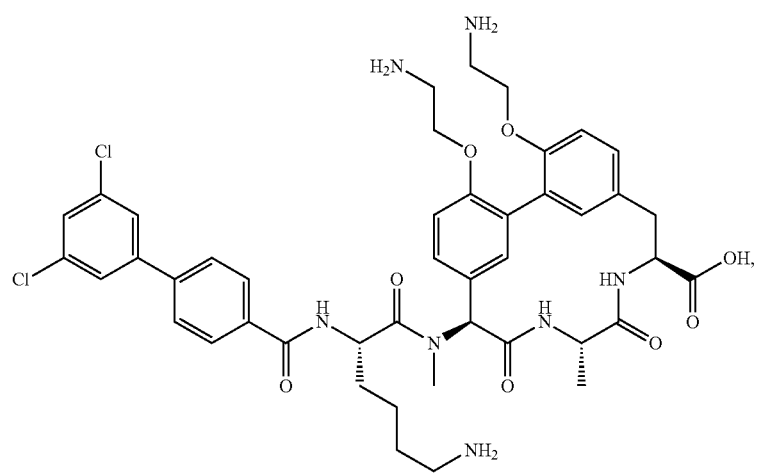
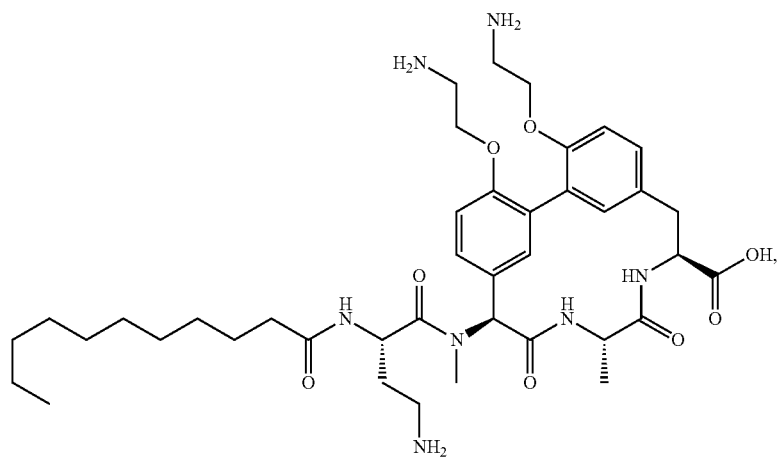

-continued
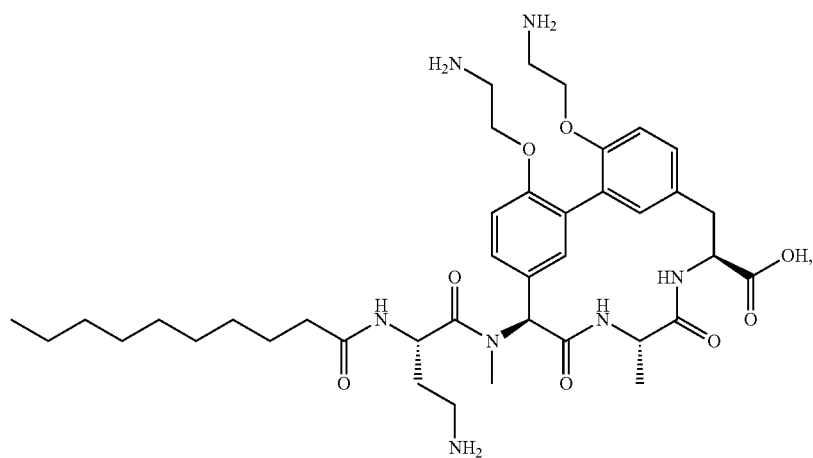
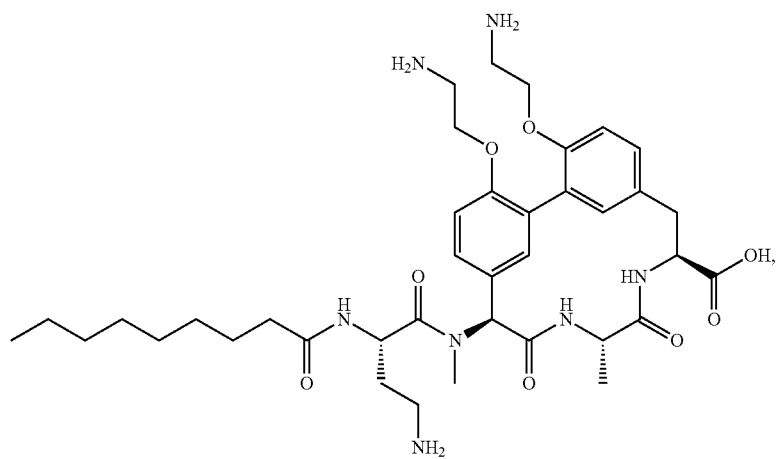
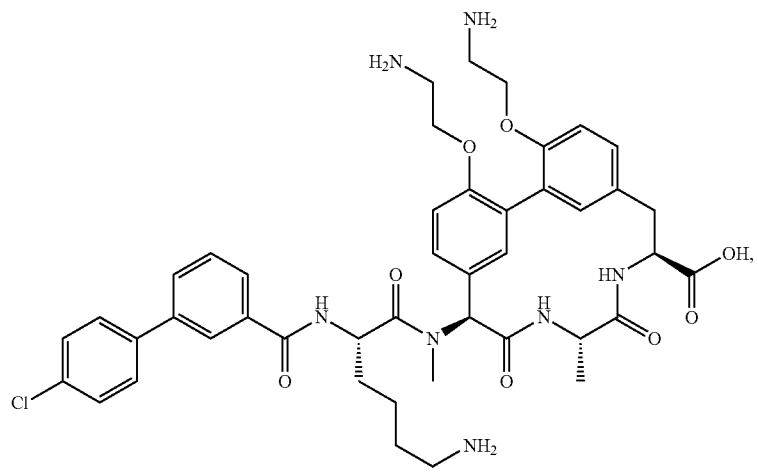

-continued
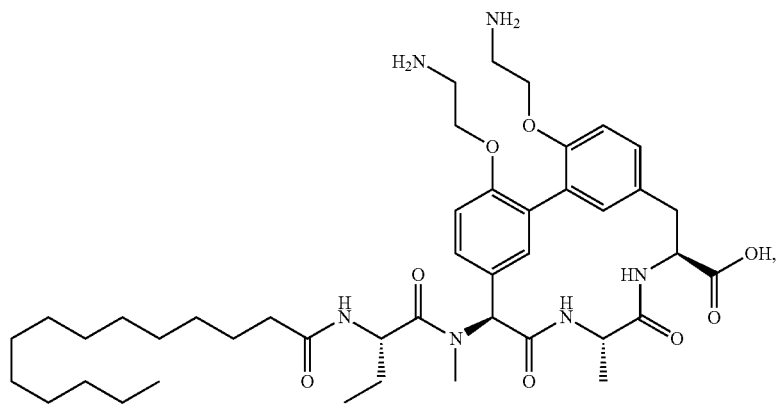
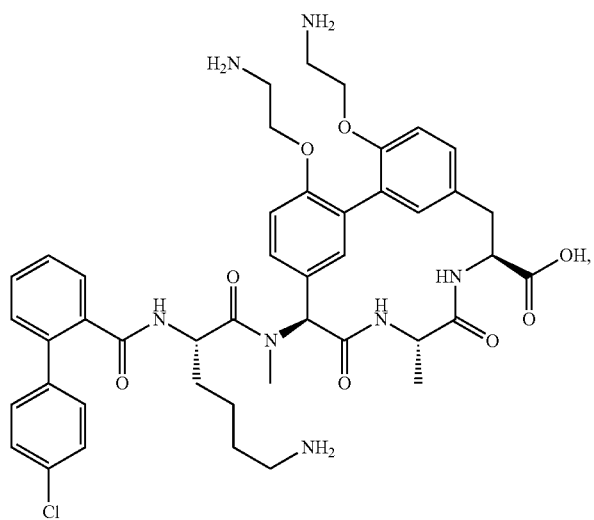
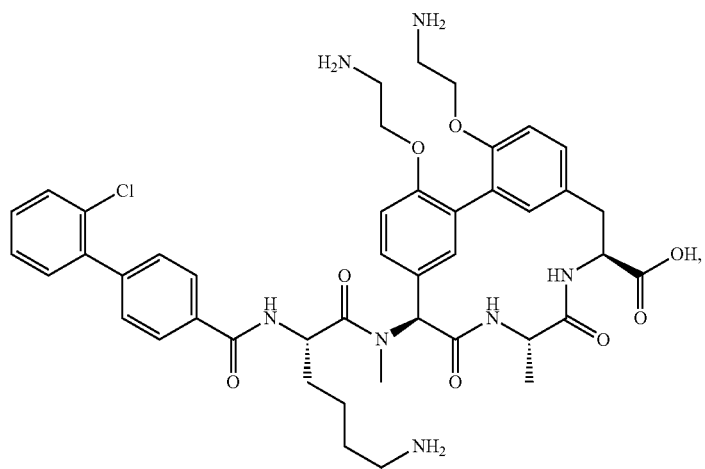

-continued
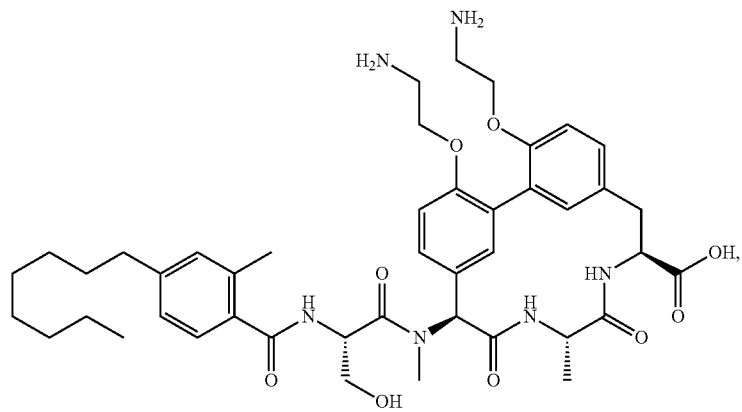
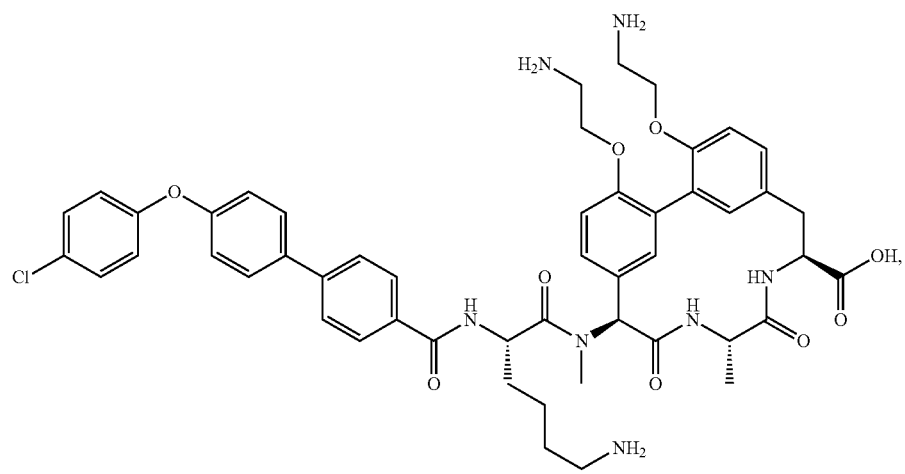
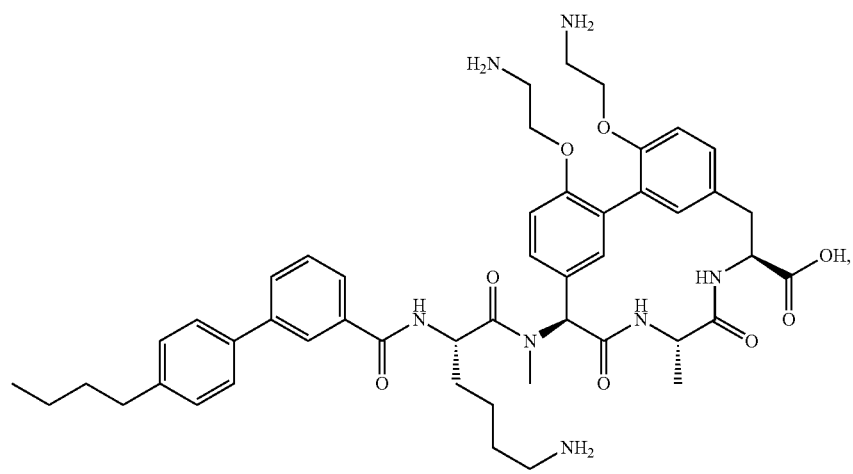

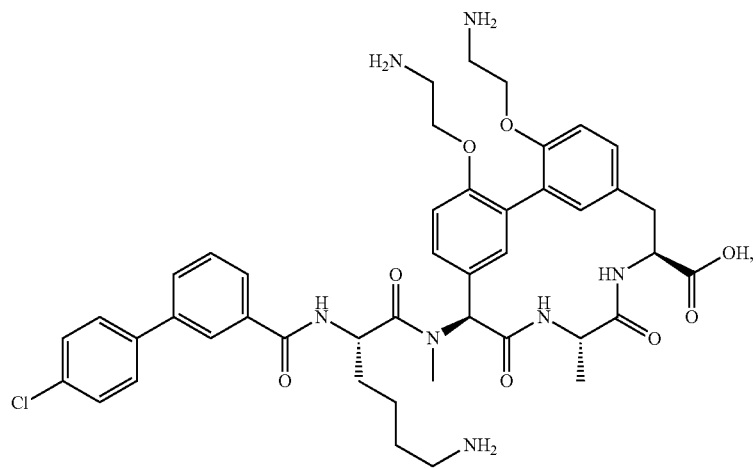
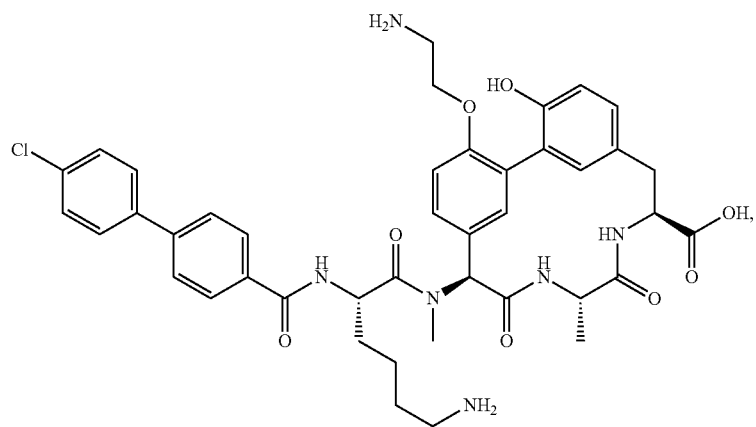
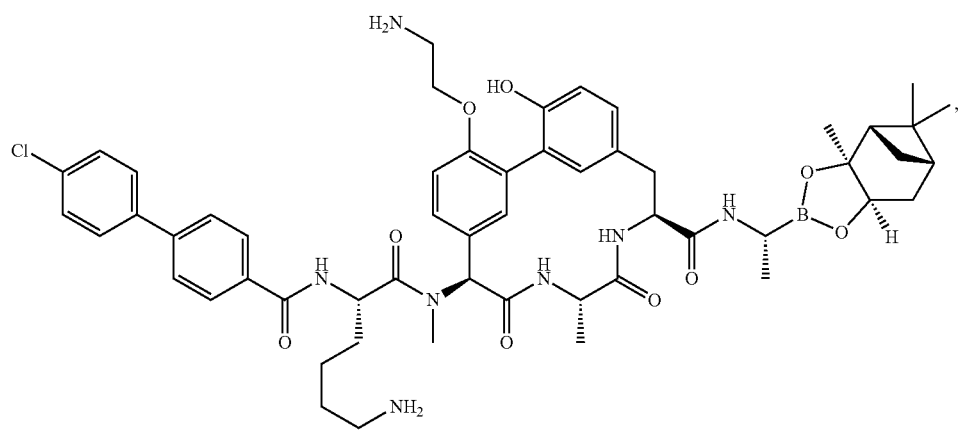

-continued
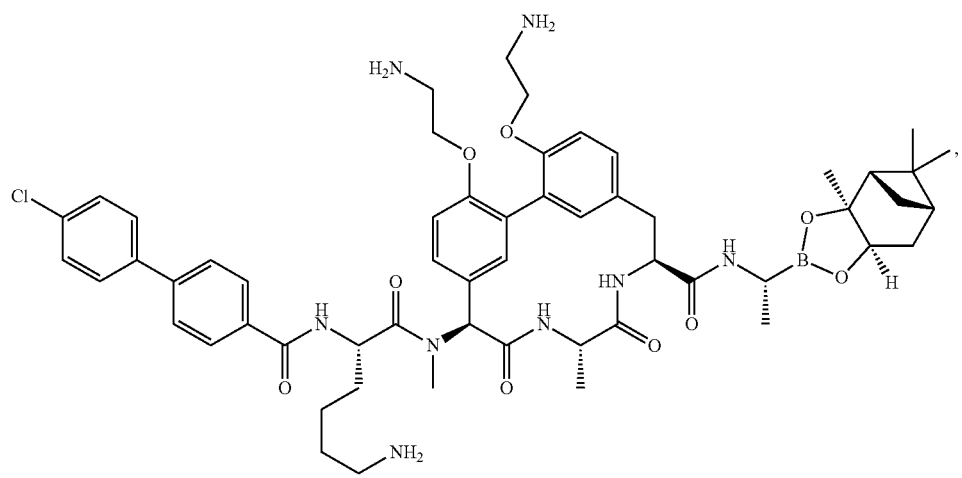
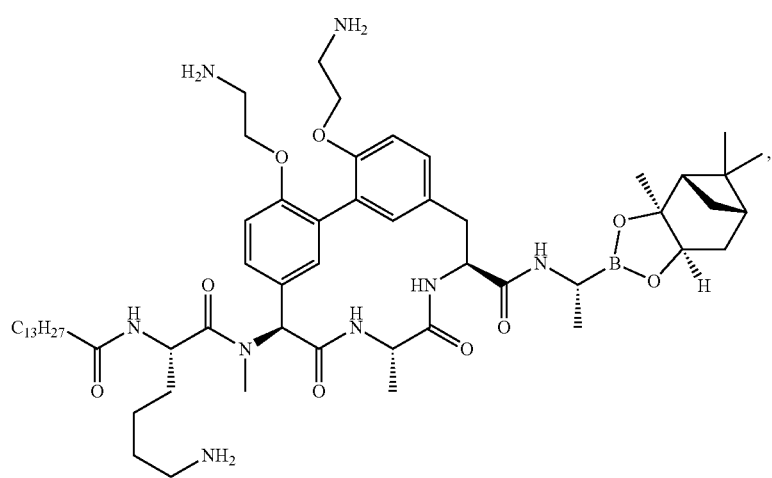
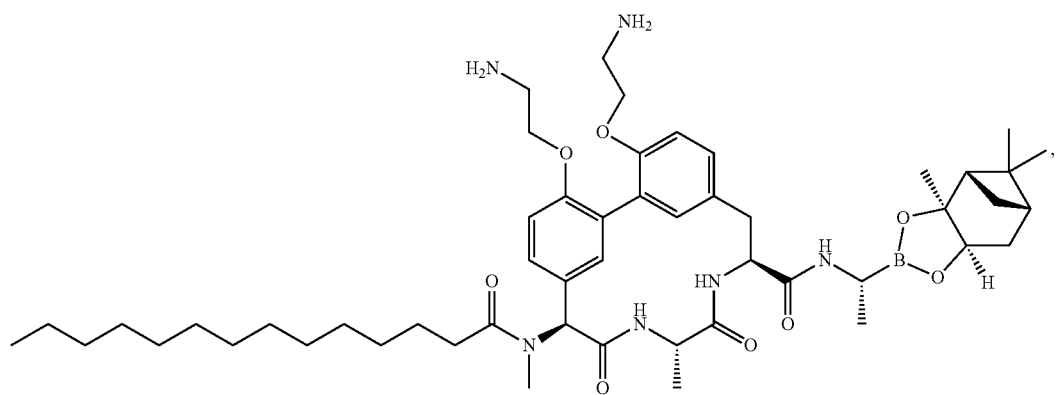

311
312
-continued
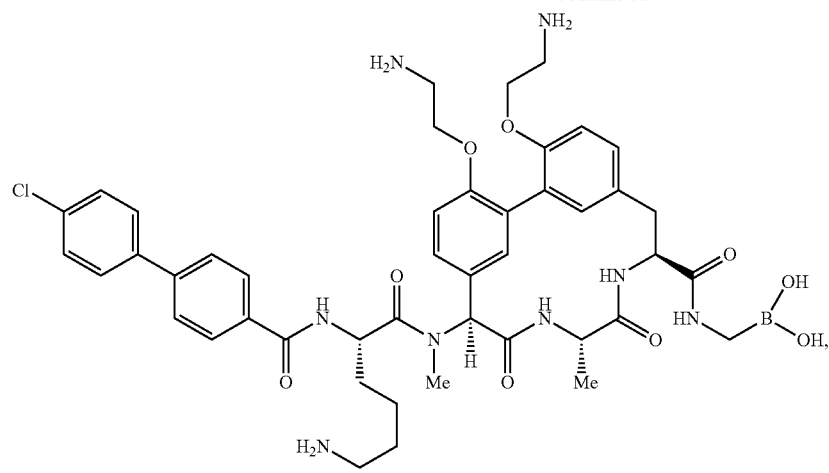
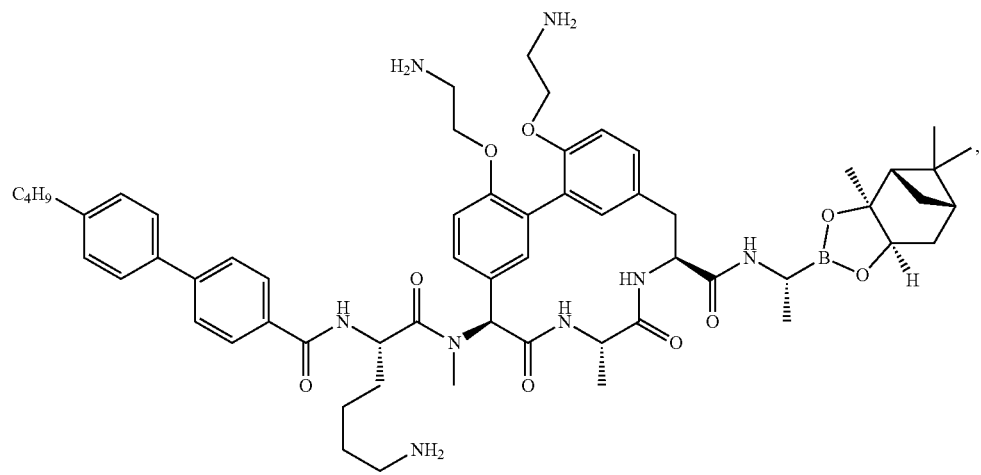
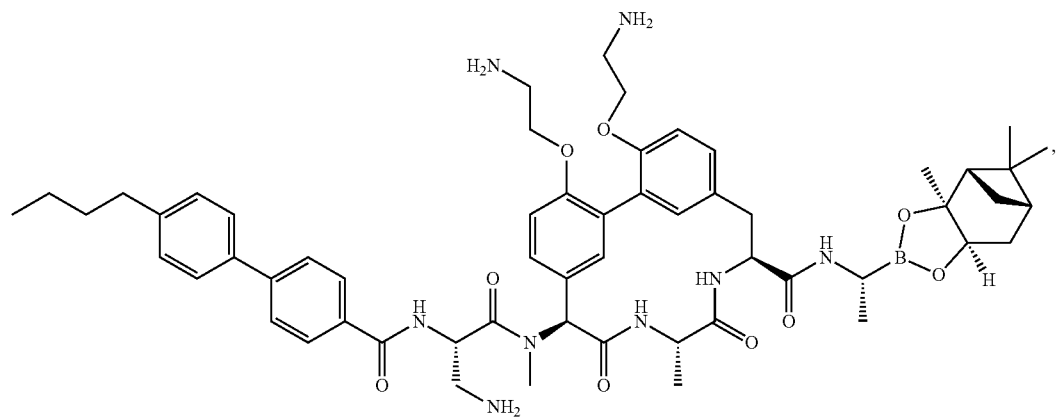

-continued
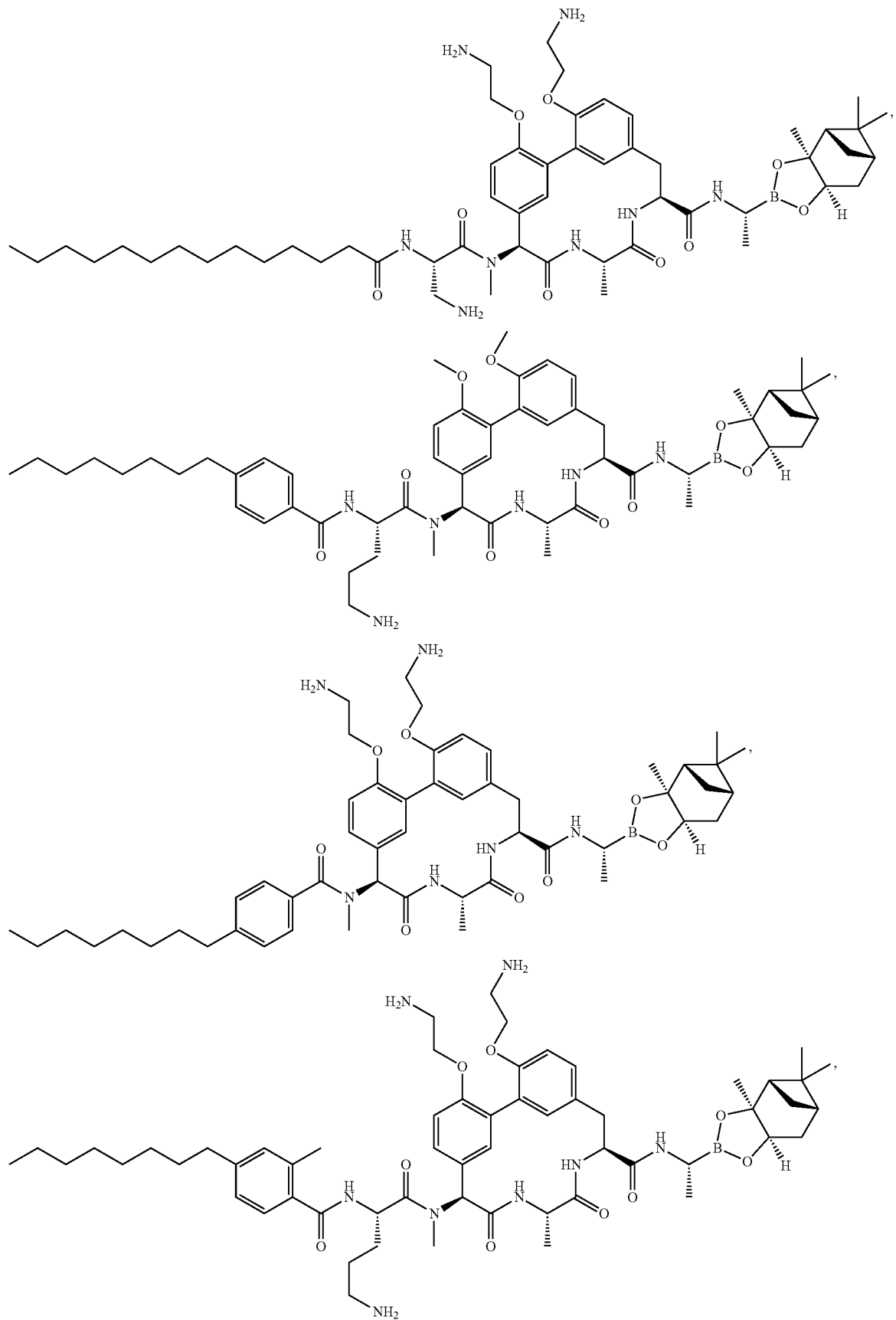

-continued
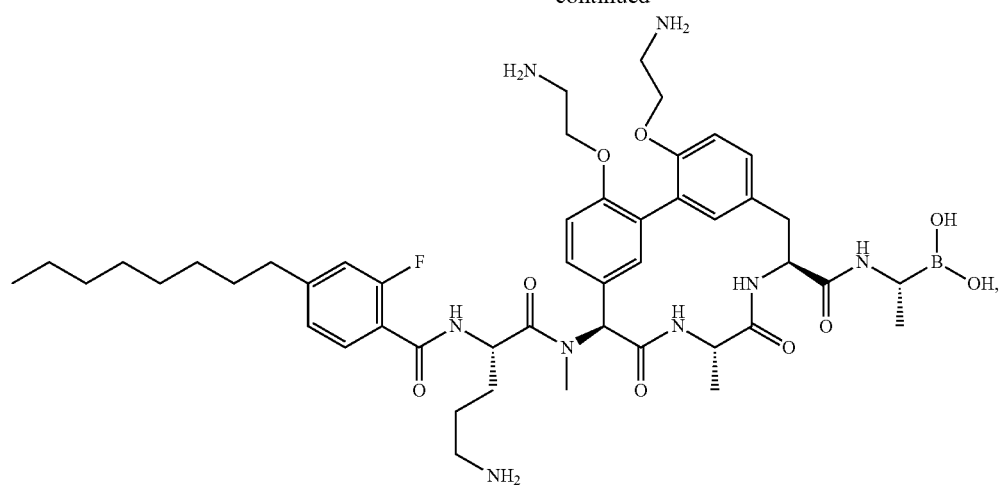
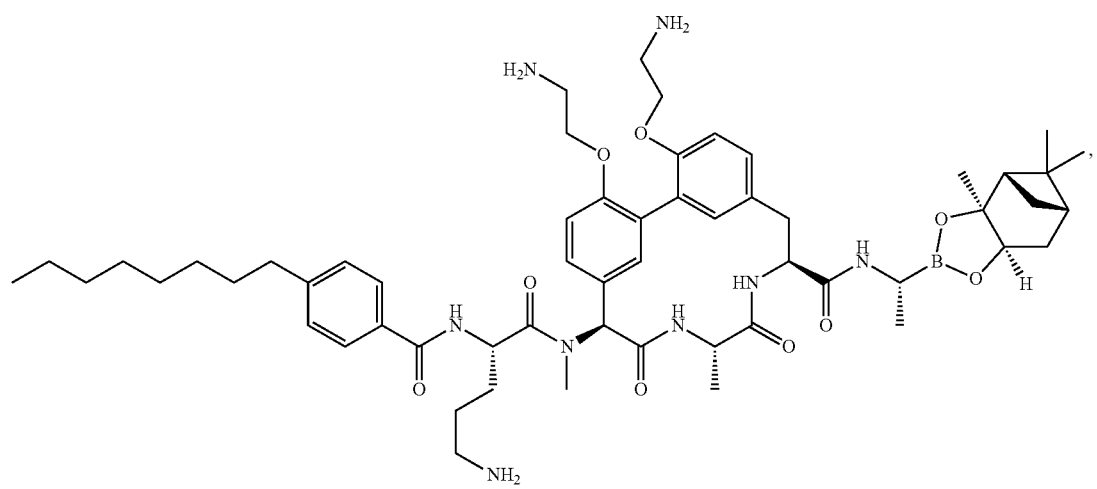
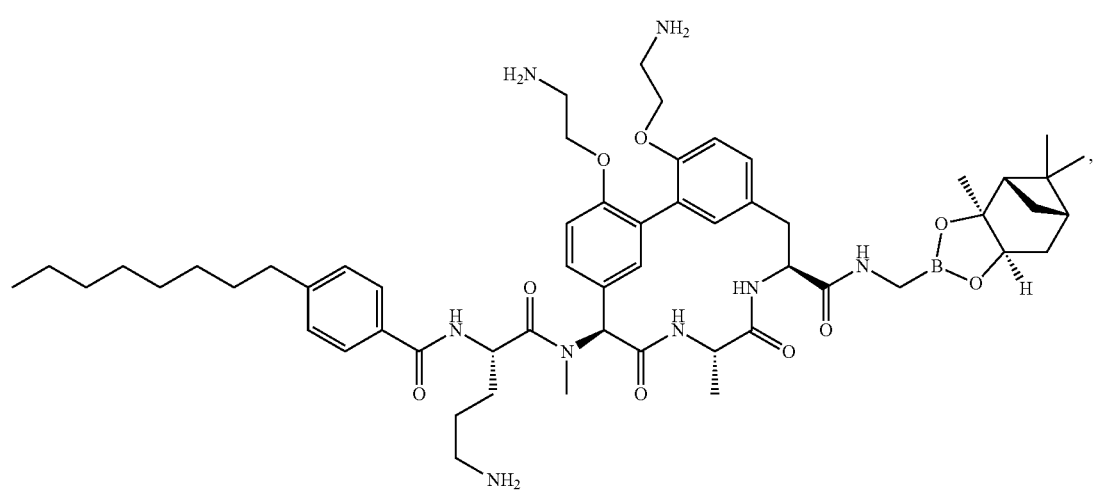

-continued

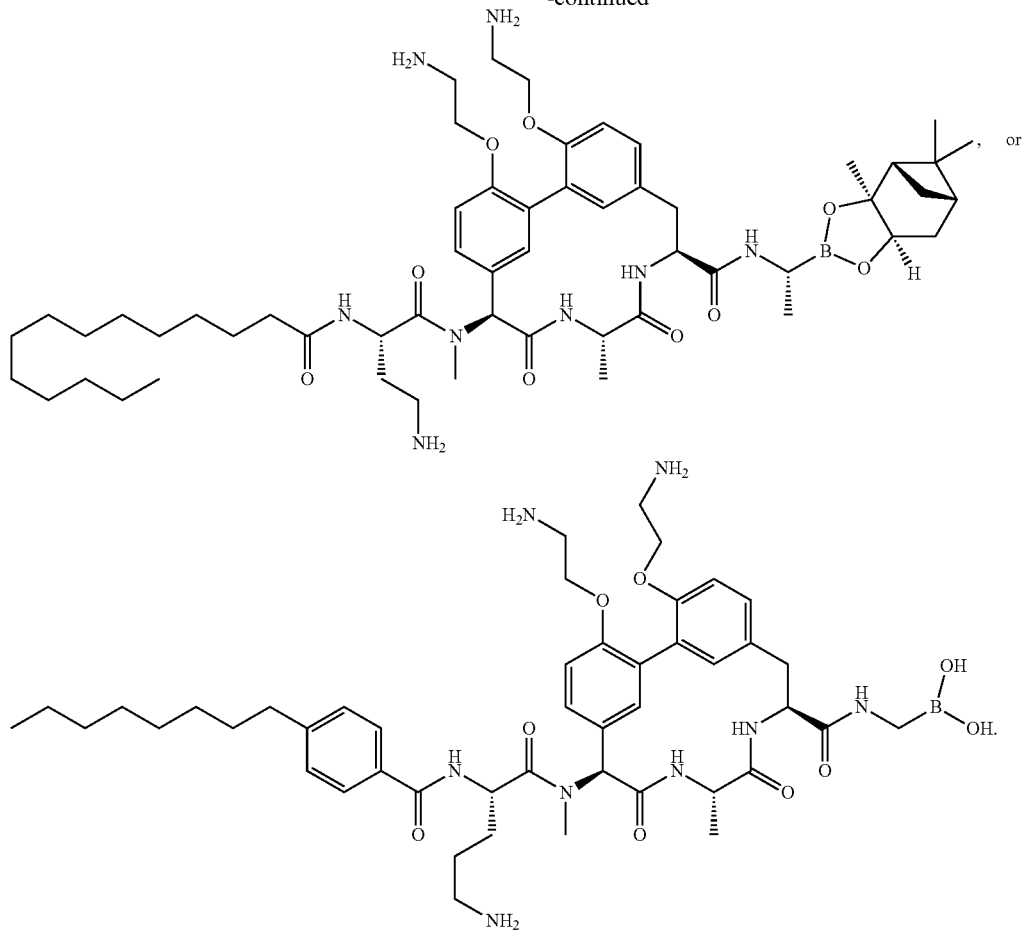

In another aspect are hydrates or metabolites comprising any of the aforementioned compounds.

In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with arylomycin A2. In a further embodiment, the causative bacteria species of the bacteria infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.* In another embodiment the bacterial infection is an infection involving a Gram-negative bacteria. In a further embodiment, the bacterial infection is an infection involving a Gram-positive bacteria.

In a further embodiment are methods of treating a mammal in need of such treatment comprising administering to the mammal a second therapeutic agent to any of the aforementioned methods of treatment. In another embodiment, the second therapeutic agent is a not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

In another aspect is a hydrate or metabolite of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb).

In another aspect is a pharmaceutical composition comprising a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) and a pharmaceutically acceptable excipient thereof.

In another aspect is the use of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, pharmaceutically acceptable solvate, or pharmaceutically acceptable prodrug thereof, for the preparation of a medicament for the treatment of a bacterial infection in a patient.

In some embodiments is a method for treating a bacterial infection in a patient, preferably a human, where the treatment includes administering a therapeutically or pharmacologically effective amount of a combination of 1) a β-lactam antibiotic; and 2) a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), or a pharmaceutically acceptable salt thereof; and 3) a pharmaceutically acceptable carrier. In embodiments where a β-lactam antibiotic is used in combination with a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), the β-lactam antibiotic may be a carbapenem, cephalosporin, cephamycin, monobactam or penicillin. Exemplary carbapenem antibiotics useful in the methods of the invention include ertapenem, imipenem, biapenem, and meropenem. Exemplary cephalosporin antibiotics useful in the methods of the invention include, ceftobiprole, ceftaroline, Cefiprome, Cefozopran, cefepime, Cefotaxime, and ceftriazone. Exemplary penicillin antibiotics useful in the methods of the invention include ampicillin, amoxacillin, piperacillin, oxacillin, cloxacillin, methicillin, and nafcillin. In some embodiments of the invention, the β-lactam may be administered with a β-lactamase inhibitor. In some embodiments of the invention, the carbapenem may be administered with a DHP inhibitor, e.g., cilastatin.

In various embodiments of the invention where a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) and a β-lactam antibiotic are used in combination, the β-lactam antibiotic and compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) can be administered sequentially or concurrently. Preferably, the β-lactam antibiotic and compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) are administered together. When administered concurrently, the β-lactam antibiotic and compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) may be administered in the same formulation or in separate formulations. When administered sequentially, either the β-lactam or compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) may be administered first. After administration of the first compound, the other compound is administered, for example, within from 1 to 60 minutes, e.g., within 1, 2, 3, 4, 5, 10, 15, 30, or 60 minutes. In one aspect of the invention, when a β-lactamase inhibitor is used, it may be administered separately, or in a formulation with the compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) and/or β-lactam antibiotic. In one aspect of the invention, when a DHP inhibitor is used to improve the stability of a carbapenem, it may be administered separately, or in a formulation with the compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) and/or carbapenem.

Further described herein are pharmaceutical compositions comprising a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), a pharmaceutically acceptable carrier, and optionally a β-lactam antibiotic. In embodiments where a combination is used, the β-lactam antibiotic and the compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), are present in such amounts that their combination constitutes a therapeutically effective amount. Due to the potentiating effects of the compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), the amount of β-lactam antibiotic present in a combination may be less that of a β-lactam antibiotic used alone. In certain embodiments, the composition further comprises a β-lactamase antibiotic.

In further embodiments where the β-lactam antibiotic is a carbapenem, is provided a pharmaceutical composition comprising a carbapenem antibiotic, a DHP inhibitor, a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), and a pharmaceutically acceptable carrier. In some embodiments where the β-lactara antibiotic is a carbepenem, the carbapenem antibiotic is preferably selected from the group consisting of ertapenem, imipenem, and meropenem.

In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) for use in treating a bacterial infection. In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), in combination with one or more additional therapeutical agents including a β-lactam antibiotic, for use in treating a bacterial infection. In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) for use as a medicament for treating a bacterial infection. In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), in combination with one or more additional therapeutical agents including a β-lactam antibiotic, for use as a medicament for treating a bacterial infection. In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) for use in the preparation of a medicament for treating a bacterial infection. In some embodiments is a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb), in combination with one or more additional therapeutical agents including a β-lactam antibiotic, for use in the preparation of a medicament for treating a bacterial infection.

In some embodiments described herein, a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) can enhance the activity of a β-lactam antibacterial agent by inducing susceptibility to the antibacterial agent in a drug-resistant strain such as MRSA. In some embodiments, a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) can enhance the activity of a β-lactam antibacterial agent by reducing the dosage of the antibacterial agent need for a therapeutic effect in a drug-sensitive strain. For example, if a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. In some embodiments, compounds of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) can enhance the activity of an antibacterial agent such as a carbapenem to prevent the emergence of a resistant sub-population in a heterogeneous bacterial population with a resistant sub-population.

Potentiators can be used to enhance the activity of antibacterial agents whose clinical efficacy has been limited by the increasing prevalence of resistant strains. In some embodiments described herein, a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) is used as a potentiator wherein a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) can be administered together with a β-lactam antibiotic (either concurrently or sequentially) to allow effective treatment of an infection involving a resistant bacterium, or to reduce the amount of antibacterial agent necessary to treat an infection.

In one embodiment, is a compound described herein which displays antibiotic activity useful in the treatment of bacterial infections, such as by way of example only, various strains of *S. aureus*, *S. pneumoniae*, *E. faecalis*, *E. faecium*, *B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of staph infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing postsurgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA). The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof. In one embodiment, the bacterium is a Gram-positive bacteria. In another embodiment, the Gram-positive bacterium is *S. aureus*. In further embodiment, the *S. aureus* is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant *S. aureus* bacteria. In one embodiment the beta-lactam antibiotic is flucloxacillin. In another embodiment is a method for treating a subject having a dicloxacillin-resistant bacteria comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to dicloxacillin. Also disclosed herein is a method for treating a subject having a methicillin-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to ceftezole.

In one embodiment is a method for treating a subject having a second-generation cephalosporin-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefmenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem, Vancomycin-Intermediate and
Vancomycin-Resistant *Staphylococcus aureus*

Vancomycin-intermediate *Staphylococcus aureus* and vancomycin-resistant *staphylococcus aureus* are specific types of antimicrobial-resistant Staph bacteria that are refractory to vancomycin treatment. *S. aureus* isolates for which vancomycin MICs are 4-8 µg/mL are classified as vancomycin-intermediate and isolates for which vancomycin MICs are ≥16 µg/mL are classified as vancomycin-resistant (Clinical and Laboratory Standards Institute/NC-CLS. Performance Standards for Antimicrobial Susceptibility Testing. Sixteenth informational supplement. M100-S16. Wayne, Pa.: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 µg/mL. In another embodiment, the vancomycin-intermediate *Staphylococcus aureus* bacterium has a MIC of about 4 µg/mL. In yet another embodiment, the vancomycin-intermediate *Staphylococcus aureus* bacterium has a MIC of about 5 µg/mL. In a further embodiment, the vancomycin-intermediate *Staphylococcus aureus* bacterium has a MIC of about 6 µg/mL. In yet a further embodiment, the vancomycin-intermediate *Staphylococcus aureus* bacterium has a MIC of about 7 µg/mL. In one embodiment, the vancomycin-intermediate *Staphylococcus aureus* bacterium has a MIC of about 8 µg/mL.

In another aspect is a method of treating a subject having a bacterial infection comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the bacterial infection comprises a vancomycin-resistant *Staphylococcus aureus* bacterium. In one embodiment, the vancomycin-resistant *Staphylococcus aureus* bacterium has a MIC of between about 16 µg/mL. In another embodiment, the vancomycin-resistant *Staphylococcus aureus* bacterium has a MIC of about ≥16 µg/mL. In yet another embodiment, the vancomycin-resistant *Staphylococcus aureus* bacterium has a MIC of about 20 µg/mL. In a further embodiment, the vancomycin-resistant *Staphylococcus aureus* bacterium has a MIC of about 25 µg/mL.

In one embodiment, conditions treated by the compounds described herein include, but are not limited to, endocarditis, osteomyelitis, neningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fasciitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes endoding proteins that direct peptidoglycan precursors to incorporate D-Ala-D-Lac instead of D-Ala-D-Ala. The six different types of vancomycin resistance shown by *enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized with VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the *enterococcus* has Van-A resistance.

In another embodiment, is a method of treating a subject having a vancomycin-resistant enterococci comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the *enterococcus* has Van-B resistance.

In another embodiment, is a method of treating a subject having a vancomycin-resistant enterococci comprising administering to the subject a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or a pharmaceutically acceptable salt, ester, solvate, alkylated quaternary ammonium salt, stereoisomer, tautomer or prodrug thereof wherein the *enterococcus* has Van-C resistance.

Administration and Pharmaceutical Composition

Pharmaceutical compositions described herein comprise a therapeutically effective amount of a compound described herein (i.e., a compound of any of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb)) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb)) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of a aerosol particles having with a mass medium average diameter predominantly between 1 to 5. Further, the formulation preferably has balanced osmolarity ionic strength and chloride concentration, and the smallest aerosolizable volume able to deliver effective dose of the compounds described herein compound described herein (i.e., a compound of any of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb)) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5 t. Predominantly in this application means that at least 70% but preferably more than 90% of all generated aerosol particles are within 1-5 t range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb)) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound of any of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb)) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data. Some abbreviations used herein are as follows:
DIPEA: diisopropylethylamine
DMAP: 4-dimethylaminopyridine
DMF: dimethylformamide
DCM: dichloromethane
TFA: trifluoroacetic acid
EDC: 1-ethyl-3-(3-dimethylaminopropyl)carbodiimide
HATU: O-(7-azabenzotriazol-1-yl)-N,N,N',N'-tetramethyluronium hexafluorophosphate
HCTU: O-(6-Chlorobenzotriazol-1-yl)-N,N,N',N'-tetramethyluronium hexafluorophosphate
HOBt: hydroxybenzotriazole
pyBOP: (Benzotriazol-1-yloxy)tripyrrolidinophosphonium hexafluorophosphate
DMDO: 3,3-Dimethyldioxirane
DMP: Dess-Martin periodinane (R)-BoroAla-(+)-pinanediol HCl: (R)-1-((3aS,4S,6S,7aR)-3a, 5,5-trimethylhexahydro-4,6-methanobenzo[d][1,3,2]dioxaborol-2-yl)ethanamine hydrochloride (1:1)
BoroGly-(+)-pinanediol HCl: ((3aS,4S,6S,7aR)-3a, 5,5-trimethylhexahydro-4,6-methanobenzo[d][1,3,2]dioxaborol-2-yl)methanamine hydrochloride (1:1)
THF: tetrahydrofuran
MeOH: methanol
EtOAc: ethyl acetate
Trt resin: 2-Chlorotrityl chloride resin
Rink amide resin: Rink amide (aminomethyl)polystyrene
Boc: t-butoxycarbonyl
CBz: benzyloxycarbonyl
Fmoc: [(9H-fluoren-9-yl)methoxy]carbonyl
TLC: thin-layer chromatography General Method 1:

Attachment of an Fmoc-protected amino acid onto a 2-chlorotrityl resin is depicted in Scheme I.

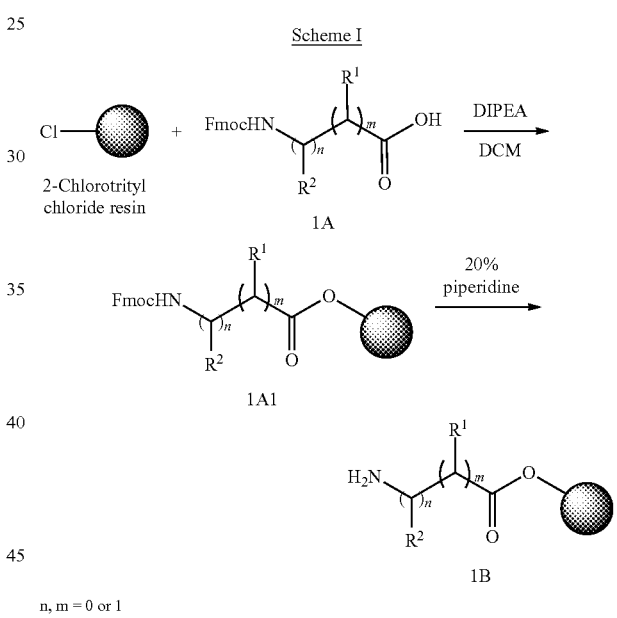

A mixture of 2-chlorotrityl chloride resin (500 mg, 0.5 mmol), diisopropylethylamine (DIPEA) (0.26 g, 2 mmol) in dry DCM (10 mL) was added a solution of an Fmoc-protected amino acid (1A, 1.5 mmol) in dry DCM (10 ml) at 0° C. Then the mixture was shaken for 5 hr at room temperature. The mixture was filtered and the cake was washed with DCM (30 mL×3), DMF (30 mL×3) and MeOH (30 mL×3) to afford Compound 1A1.

To the above resin was added approximately 20% piperidine/DMF (70 mL) to remove the Fmoc group. The mixture was shaken for 10 mins and the cycle was repeated three times. The mixture was washed with DCM (2×30 mL) and DMF (3×30 mL) to give Compound 1B.

General Method 2:

The solid phase peptide and/or amide coupling and cleavage from the resin is depicted in Scheme II.

Scheme II

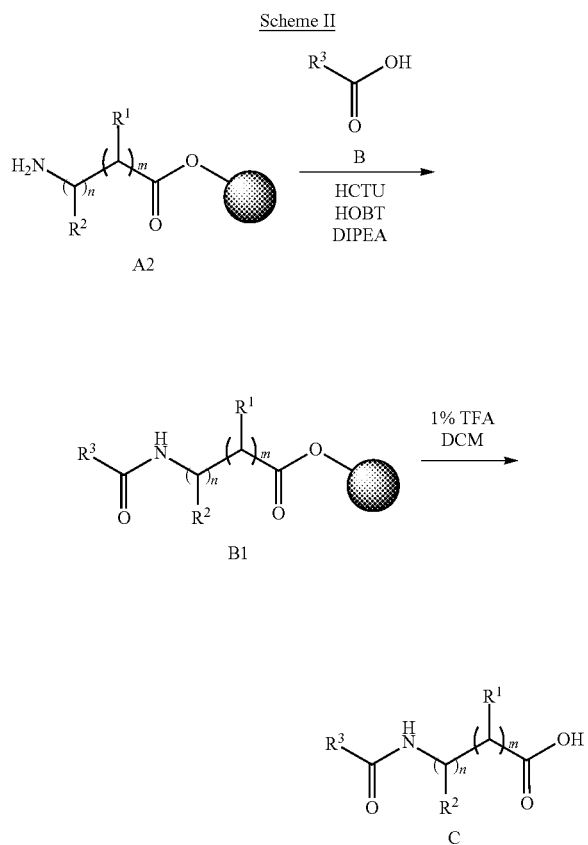

Scheme III

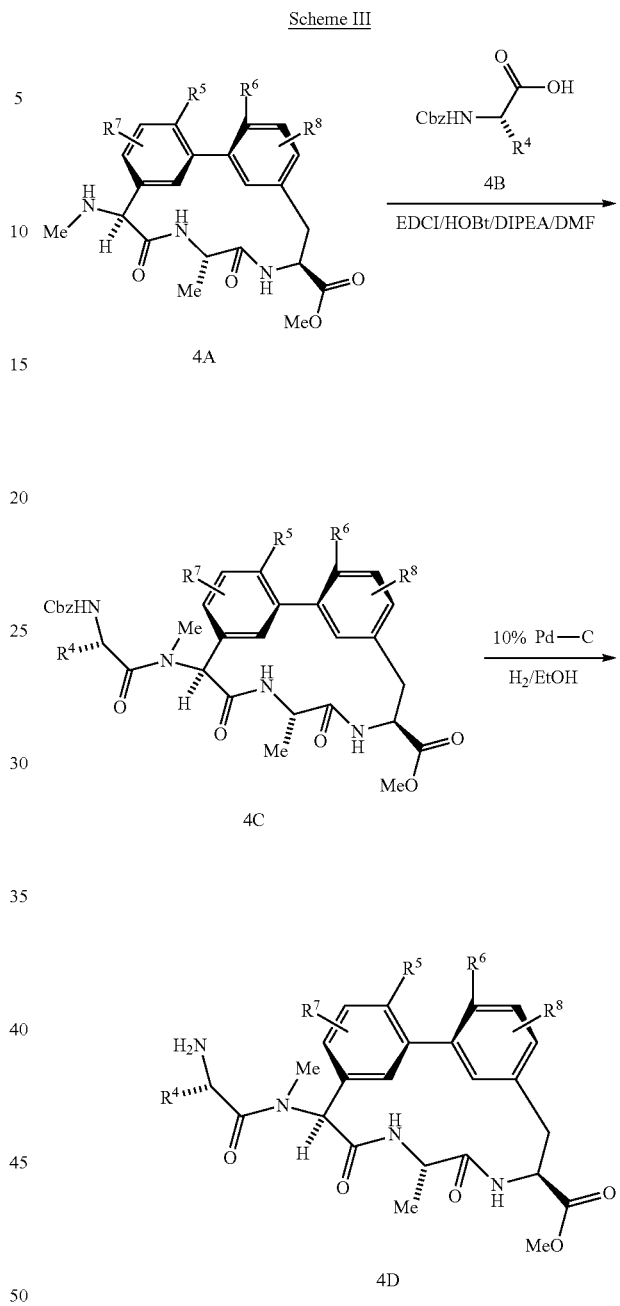

A mixture of B (1.5 eq), HCTU (1.5 eq), HOBT (1.5 eq) and DIPEA (1.5 eq) in dry DMF (6-8 mL/eq) was stirred at 20° C. for 30 mins. The mixture was then added to Compound A2 (1 eq) and shaken at 20° C. for 1.5 hrs. After LCMS showed the reaction was completed, the mixture was filtered and the residue was washed with DMF (3×10 mL/mmol) and DCM (3×10 mL/mmol) to give Compound B1. An analytical portion of resin B1 was treated and mixed in 1% TFA/DCM to cleave the peptide from the resin, and the desired product was detected by MS with confirmation that no starting material remains. In cases where the peptide coupling is slow or does not go to completion, HCTU can be replaced with EDCI. In cases where a protected alpha-amino acid is used, the Fmoc-group is used as the protecting group.

Cleavage of the resin in Compound B1 is accomplished by repeated treatment of the resin with 1% TFA in $CH_2Cl_2$. A mixture of Compound B1 (3 mmol) was treated with 1% TFA/DCM (3-4 mL/mmol) for 5 mins and filtered. This operation was repeated three times. The filtrate was treated with saturated $NaHCO_3$ solution until pH=7~8. The aqueous layer was adjusted to pH=3~4 with citric acid. The mixture was extracted with DCM (6-8 mL/mmol) three times, then the combined organic layers were washed with brine, dried over $Na_2SO_4$ and concentrated to give Compound C. The reported yields are based on the theoretical loading of the chlorotrityl chloride resin.

General Method 3:

The coupling of an N-methyl amino acid to a protected amino acid followed by reductive removal of the CBz protecting group is depicted in Scheme III.

To a solution of N-methyl peptide Compound 4A (1 eq) in DMF (2 mL) was added HOBT (1.5-2.7 eq), DIPEA (1.5-2.7 eq), Compound 4B (1.1 eq) and EDCI (1.5-2.7 eq). The resulting solution was stirred at 20° C. overnight and diluted with water. The precipitate was filtered and the resulting filter cake was washed with water and dried by aspiration to give a crude product, which was recrystallized from PE to give Compound 4C, as a white solid.

General Method 4:

The deprotection of bis-arylmethyl ethers with $AlBr_3$ and EtSH is depicted in Scheme IV. With the methyl ester, concomitant hydrolysis of the ester is observed.

Scheme IV

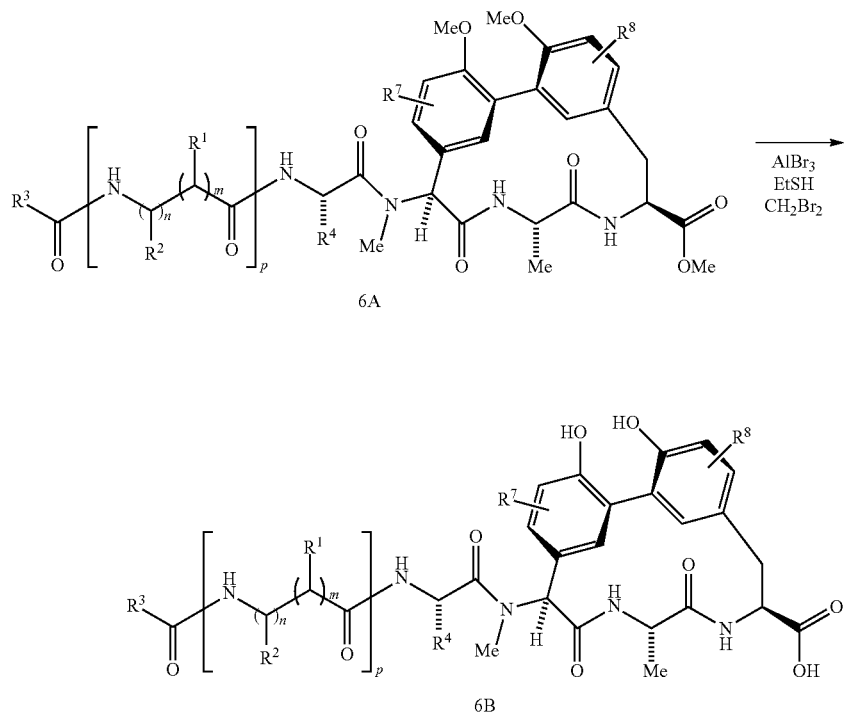

m, n, p independently 0 or 1

To a mixture of the bis-arylmethyl ether 6A (1 eq) in EtSH (50 mL/mmol) and $CH_2Br_2$ was added 1.0 M $AlBr_3$ (25 eq) under Ar. The mixture was heated to 50° C. for 4 hr. After HPLC analysis showed the reaction was complete, the reaction was quenched with MeOH (16 mL/mmol). The solvent was evaporated to give a crude product which was purified by preparative HPLC to afford the desired bis-phenol 6B. In cases where a methyl ester is present, concomitant hydrolysis of the ester to the carboxylic acid is observed.

General Method 5:

TFA hydrolysis of a Boc-protected amino acid.

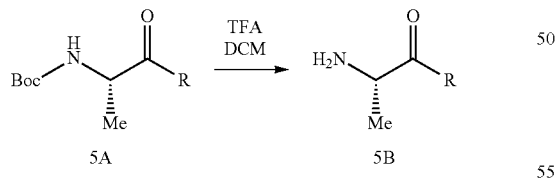

A boc-protected amino acid is dissolved in DCM (0.02-0.2 M) and cooled to 0° C. TFA is added to dropwise to create a 4:1 ratio of DCM:TFA. The solution is stirred for 15 minutes or until LC-MS analysis shows the reaction to be completed. The TFA and DCM are removed under reduced pressure to afford the desired amine, Compound 5B.

General Method 6:

Coupling of an amine to a carboxylic acid using isobutyl chloroformate and N-methyl morpholine using an amino-epoxyketone as an example.

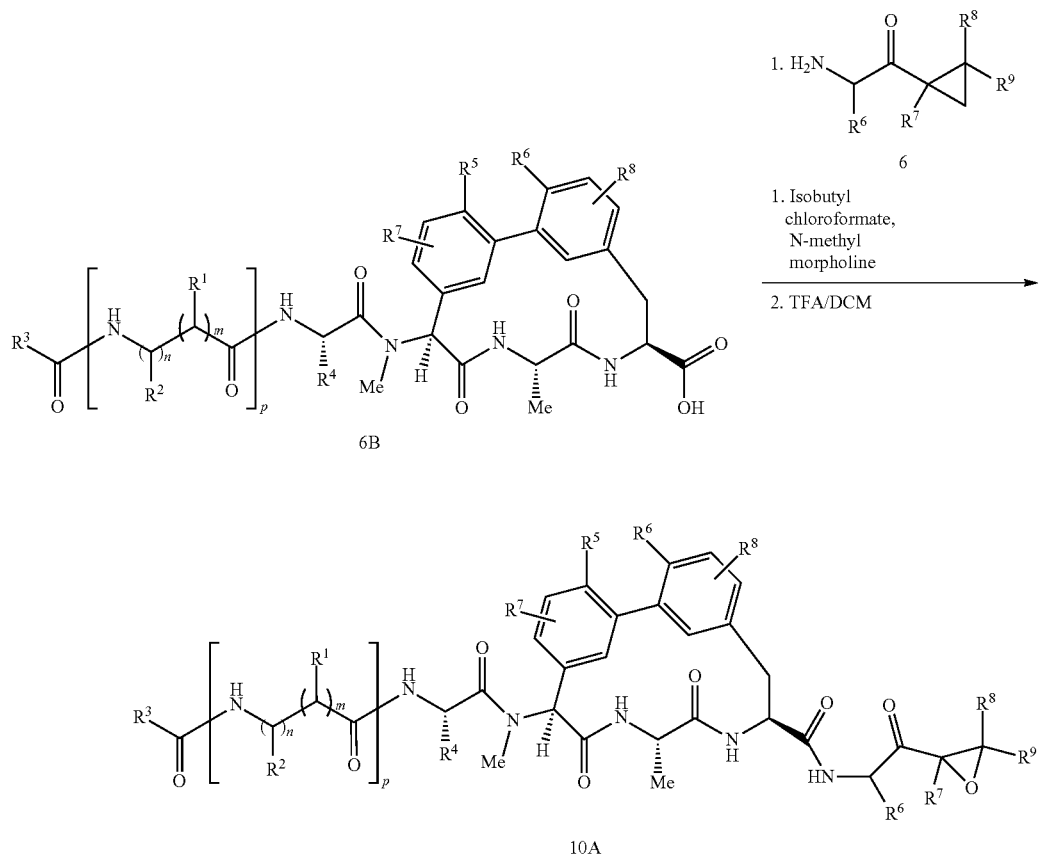

Compound 6B (1 eq) was dissolved in anhydrous THF and cooled to 0° C. in ice bath. Isobutyl chloroformate (1.5 eq) was added followed by N-methyl morpholine (5 eq) under $N_2$ atm. The reaction mixture was stirred for 30 min, and then a solution of the aminoketone 6 in anhydrous THF was added. The reaction mixture was stirred for about 1 to 2 h while allowing the mixture to warm to rt. After completion of the reaction, the reaction mixture was quenched with saturated $NH_4Cl$ solution and diluted with brine (2 mL). The aqueous layer was extracted with EtOAc and the combined organic layers washed with brine, dried over anhydrous $Na_2SO_4$, filtered and the solvent was removed under vacuum. The residue was purified by flash chromatography using 1:4 MeOH-DCM. The residue was dissolved in 1:3 TFA-DCM and stirred at rt for about 1 to 2 h. After completion of the reaction, the solvent was evaporated and dried under high vacuum. The residue was purified by prep HPLC ($CH_3CN$—$H_2O$ containing 0.05% TFA).

General Method 7:

The base-mediated alkylation of a phenol followed by acidic deprotection of the Boc-protecting groups.

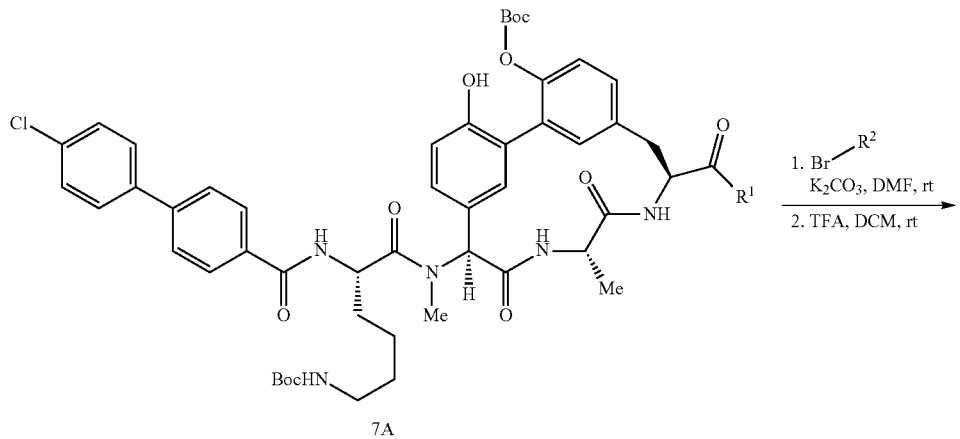

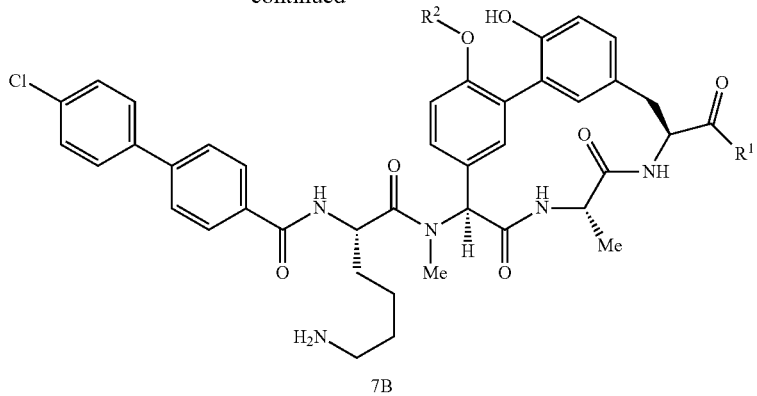

7B

To a stirred solution of Compound 7A (1 eq) in dry DMF was added K$_2$CO$_3$ (1.5 eq) followed by the alkyl halide (1.5 eq). The reaction mixture was stirred at rt overnight. After completion of the reaction, crushed ice was added and the resultant off-white solid was collected by filtration and dried under vacuum. The resultant solid was dissolved in 1:3 TFA-DCM and stirred at rt for about 1 to 2 h. After completion of the reaction, the solvent was evaporated and the residue was dried under high vacuum. The residue was purified by prep HPLC (CH$_3$CN—H$_2$O containing 0.05% TFA) to afford the desired compound 7B.

General Method 8:

Coupling of an amine to a carboxylic acid using HATU and DIPEA using the amine in excess.

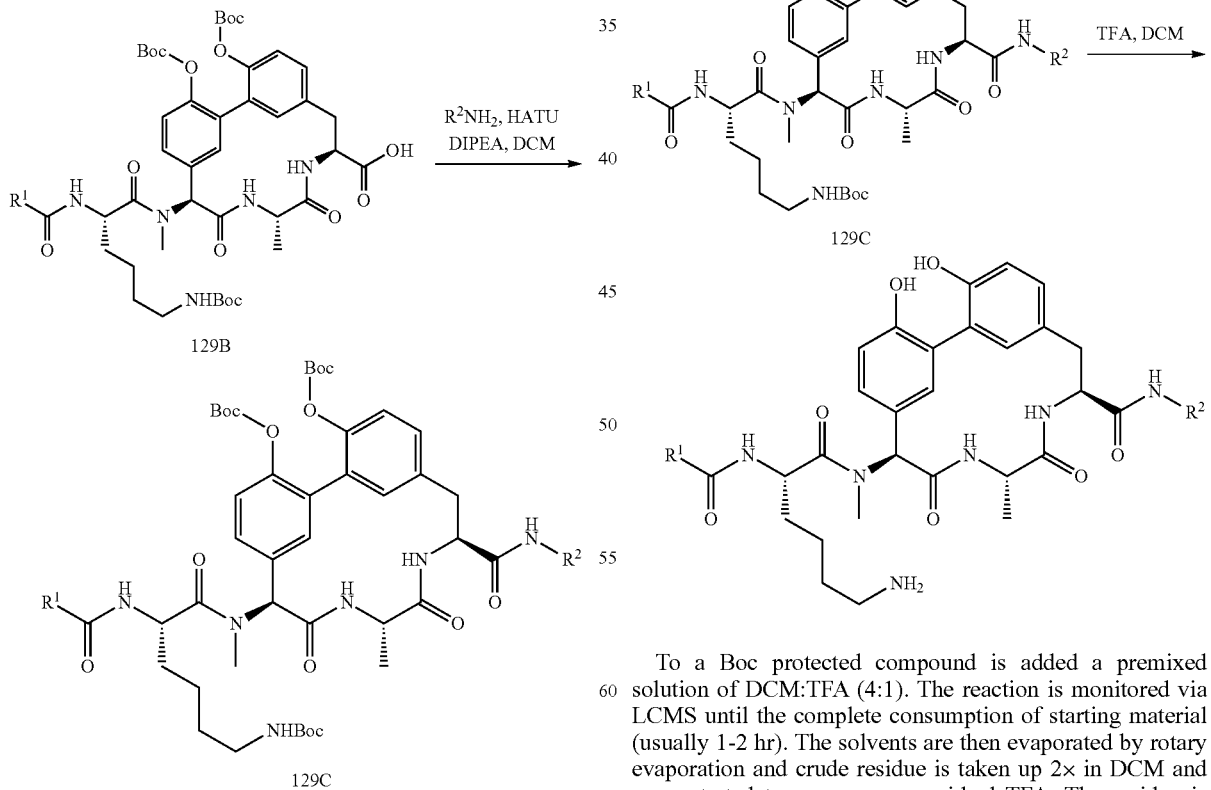

To a solution of a carboxylic acid (1 eq) in DCM/DMF, HATU (2 eq) and an amine (2 eq) were added at 0° C., followed by the addition of DIPEA (3 eq). The mixture was stirred at 15° C. for 2 h. After the reaction was complete, the mixture was partitioned between H$_2$O and DCM and the aqueous layer was further extracted by DCM. The combined organic layers were concentrated to afford the corresponding amide, which can be used directly for the following step.

General Method 9:

TFA deprotection of O-Boc and NH-Boc protecting groups with TFA.

To a Boc protected compound is added a premixed solution of DCM:TFA (4:1). The reaction is monitored via LCMS until the complete consumption of starting material (usually 1-2 hr). The solvents are then evaporated by rotary evaporation and crude residue is taken up 2× in DCM and concentrated to remove any residual TFA. The residue is then put on a vacuum pump to dry further. In instances where purification is required, preparative HPLC is used (MeCN/H$_2$O, 0.1% formic acid or MeCN/H$_2$O, 0.1% TFA).

If formic acid is the mobile phase additive, the product is isolated as the formate salt. If TFA is the additive, the product is isolated as the TFA salt.

General Method 10:

Coupling of an amine to a carboxylic acid using EDCI and HOBt.

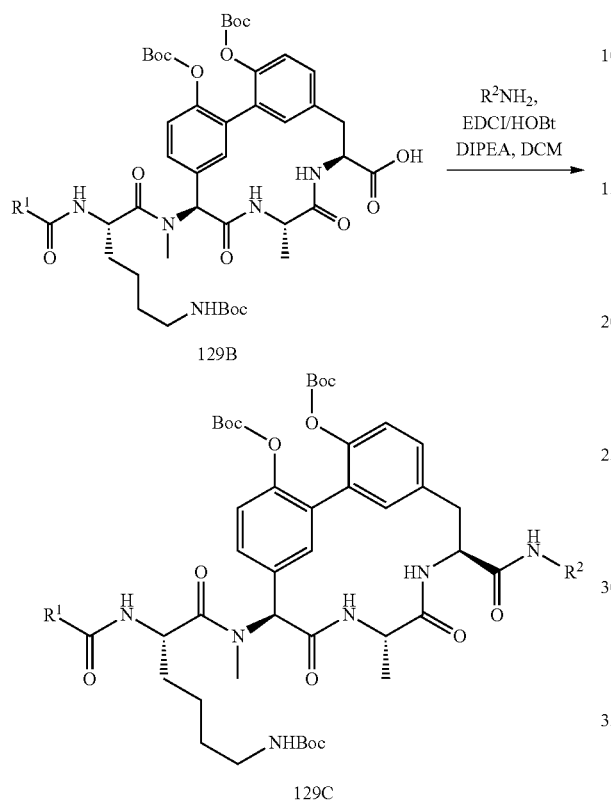

To a solution of Compound 129B (1 eq) in DCM/DMF, $R^2NH_2$ (2 eq) and DIPEA (3 eq) were added at 0° C., followed by the addition of EDCI (2 eq) and HOBt (2 eq). The mixture was stirred at 15° C. for 2 h. After the reaction was complete, the mixture was added in the equal amount of $H_2O$ and DCM and the aqueous layer was further extracted by DCM. The combined organic layers were concentrated to give crude Compound 129C, which can be used directly for the following step.

General Method 11:

Dess-Martin periodinane (DMP) oxidation of an alcohol to a ketone.

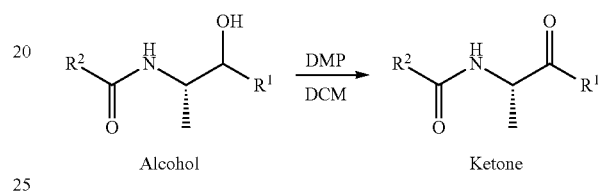

To a solution of the Alcohol (1 eq) in DCM, was added DMP (3 eq) at 0° C. The reaction mixture was stirred at 20° C. for 16 h. After the reaction was complete, the reaction mixture was poured into a saturated solution of $NaHCO_3$/$Na_2S_2O_3$; which was further extracted with DCM. The organic layer was dried over $Na_2SO_4$, evaporated under reduced pressure and the residue was purified by silica gel column to afford the Ketone.

General Method 12:

The general synthesis of ketoamides is shown for Compound KA3.

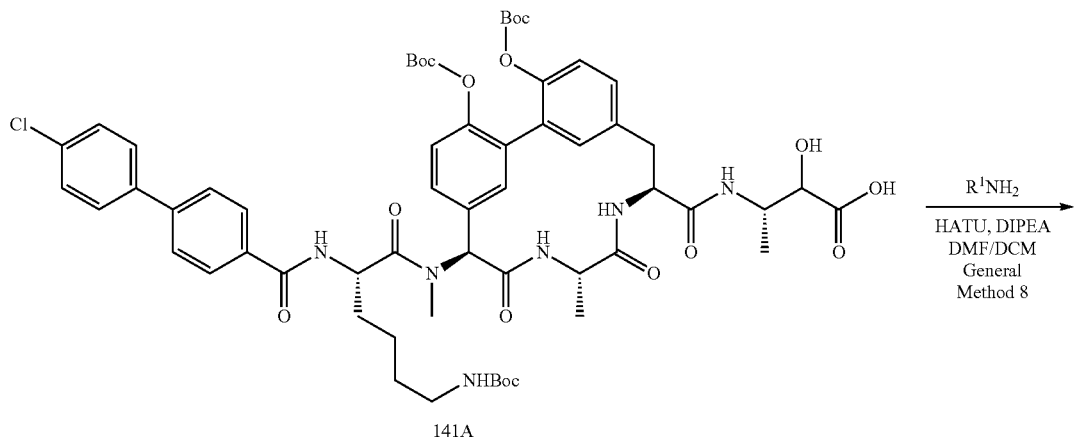

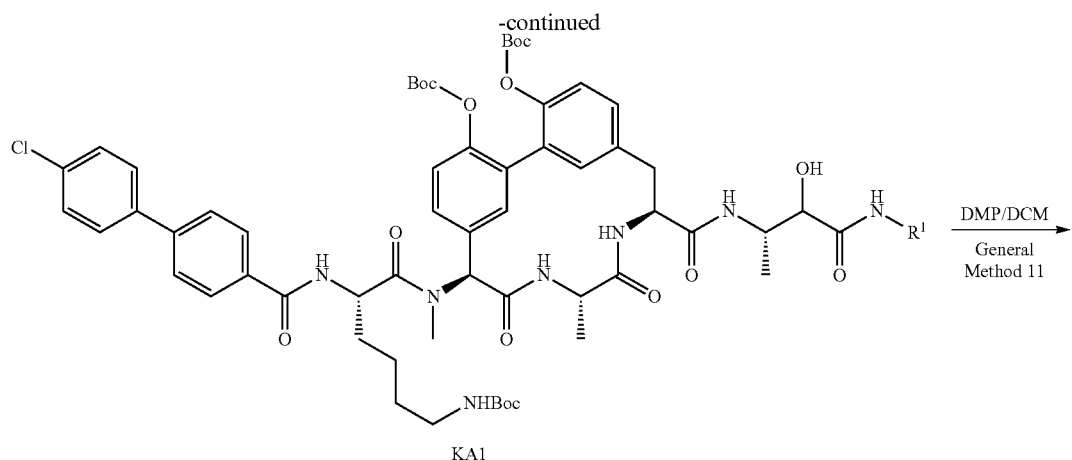
KA1
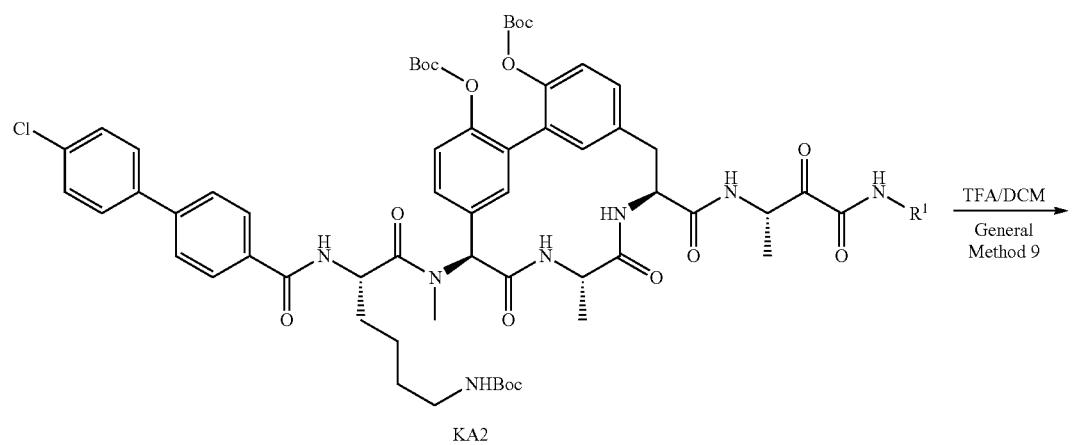
KA2
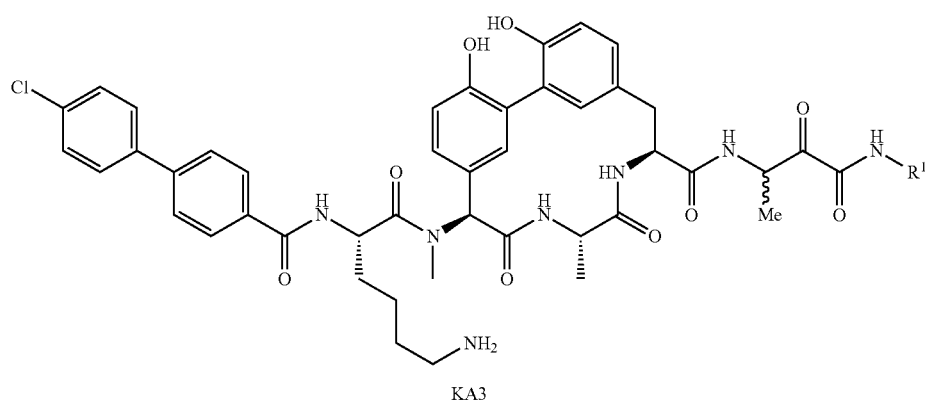
KA3
Compound KA1 was prepared according to General Method 8 from Compound 141A and Compound 139A. Compound KA2 was prepared according to General Method 11 from Compound KA1. Compound KA3 was prepared according to General Method 9 from Compound KA2.

General Method 13:
The synthesis of amide analogs is depicted in Scheme V.
Scheme V
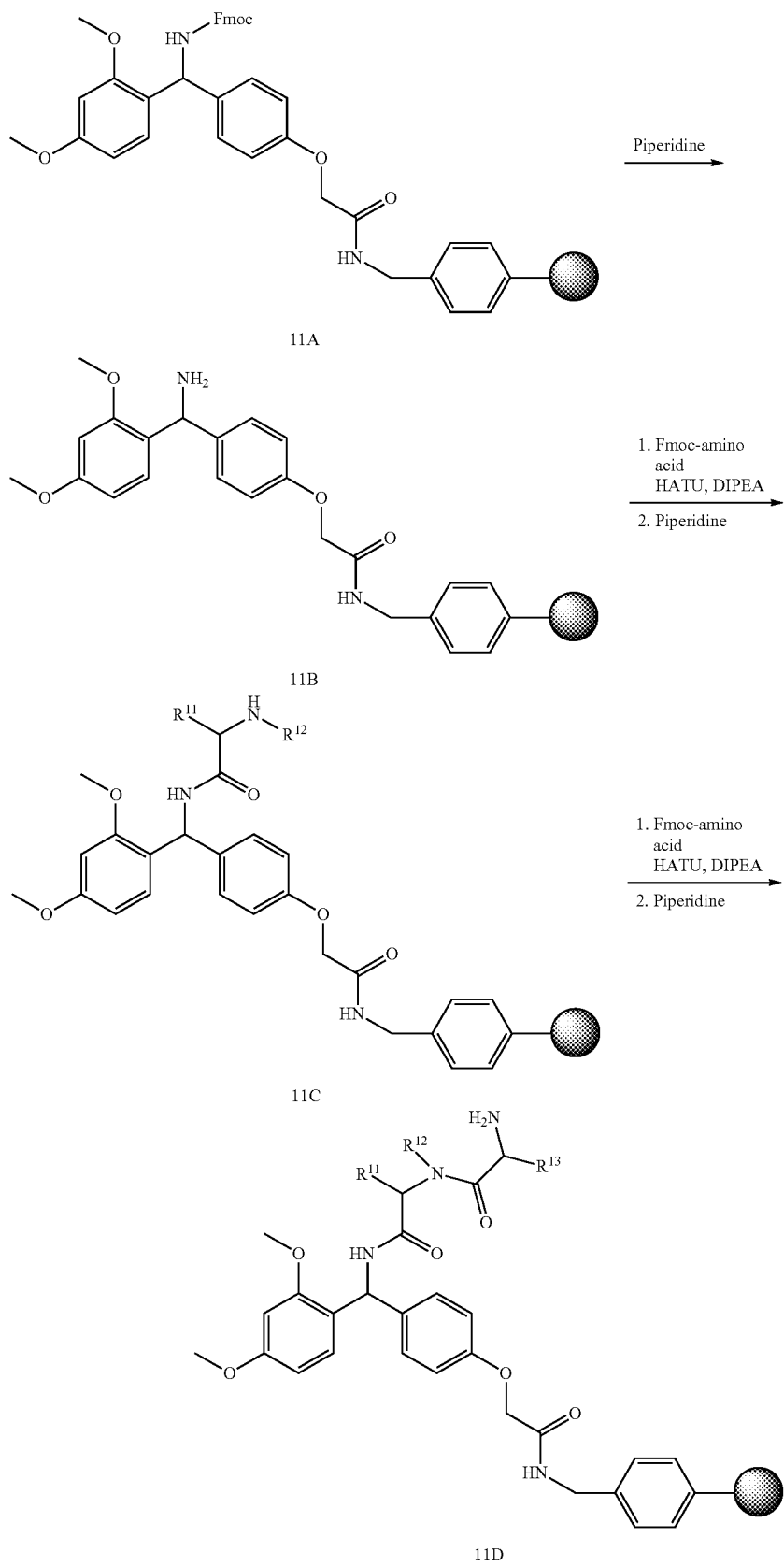

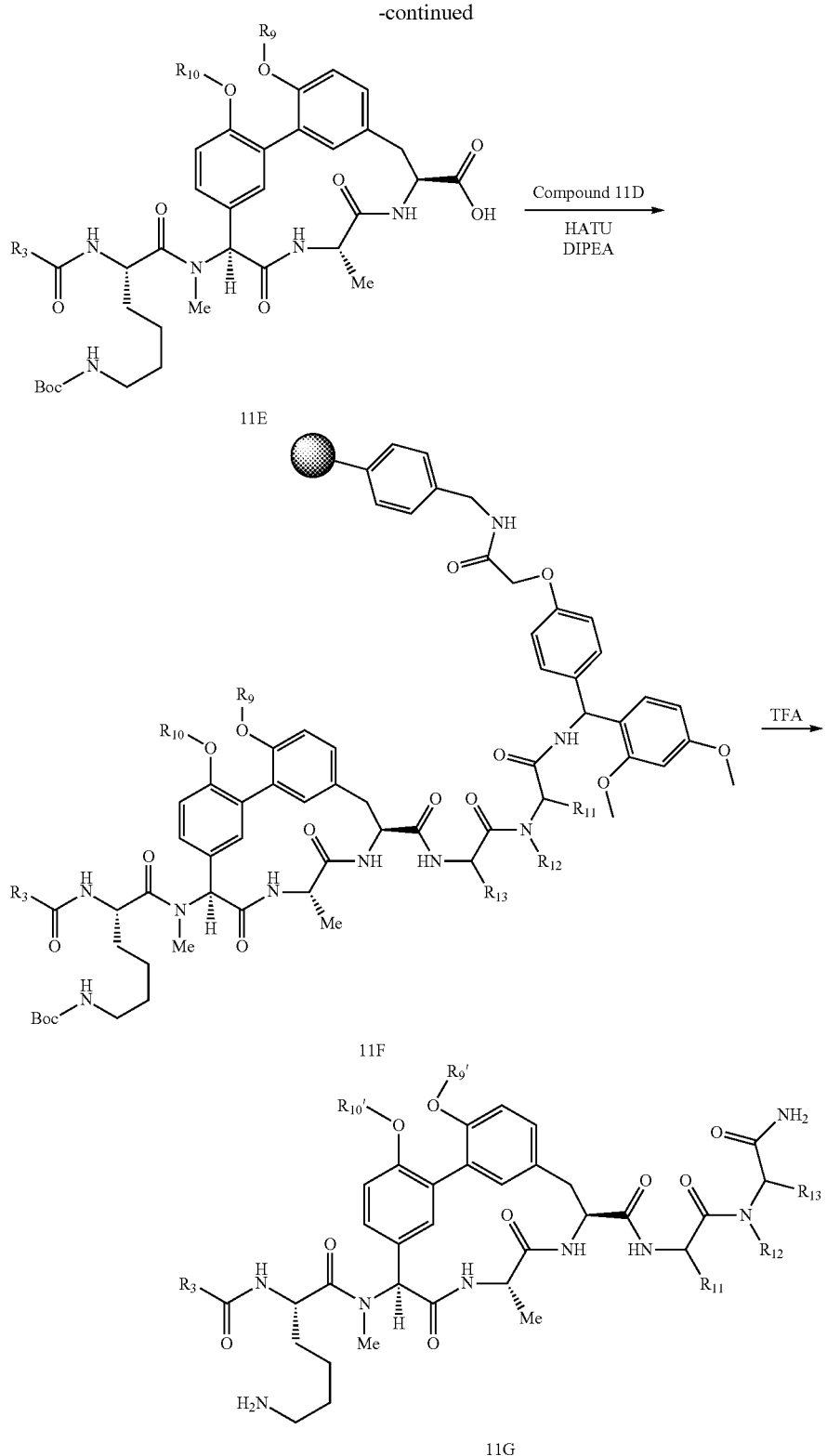

Fmoc-protected Rink amide resin is treated with piperidine to afford the free amine Compound 11B. Coupling with an Fmoc-protected amino acid using HATU and DIPEA, followed by deprotection of the protecting group with piperidine affords Compound 11C. Coupling of Compound 11C to another N-protected amino acid and subsequent Fmoc deprotection with piperidine affords Compound 11D. This method can be used to prepare amide-linked amino acids of varying length terminated with a free amine group. Compound 11D is coupled to Compound 11E under standard peptide coupling conditions using HATU and DIPEA, followed by deprotection of the protecting group with piperidine to afford Compound 11F. Deprotection under acidic conditions, for example TFA in DCM, affords Compound 11G. If the phenol-OH-groups are protected as Boc-groups, the free phenol is isolated. If they are protected with acid-stable functionalities, such as a 2-aminoethyl group, then the phenol OH-group remains substituted.

General Method 14:

The synthesis of phenol substituted analogs is depicted in Scheme VI.

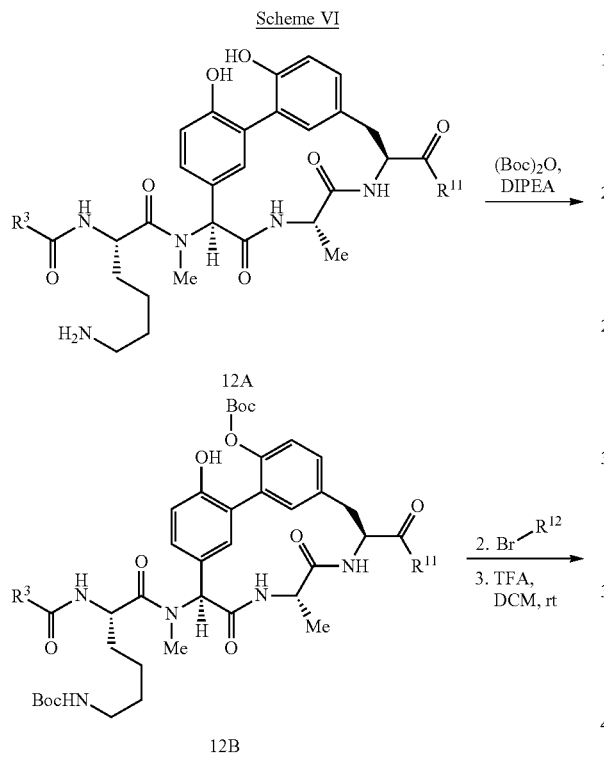

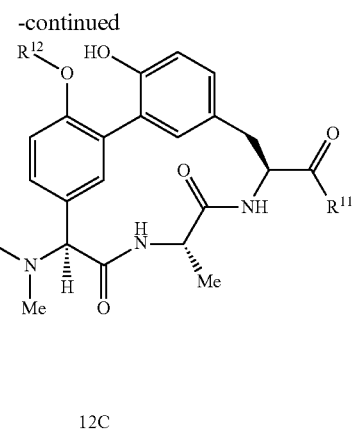

One of the phenol groups can be selectively Boc-protected by treatment with Boc$_2$ and DIPEA. The remaining phenol can be alkylated with, for example, an alkyl bromide, in the presence of a base, for example K$_2$CO$_3$, followed by deprotection of the protecting groups to afford Compound 12C.

Example 1: Synthesis of Compound 101

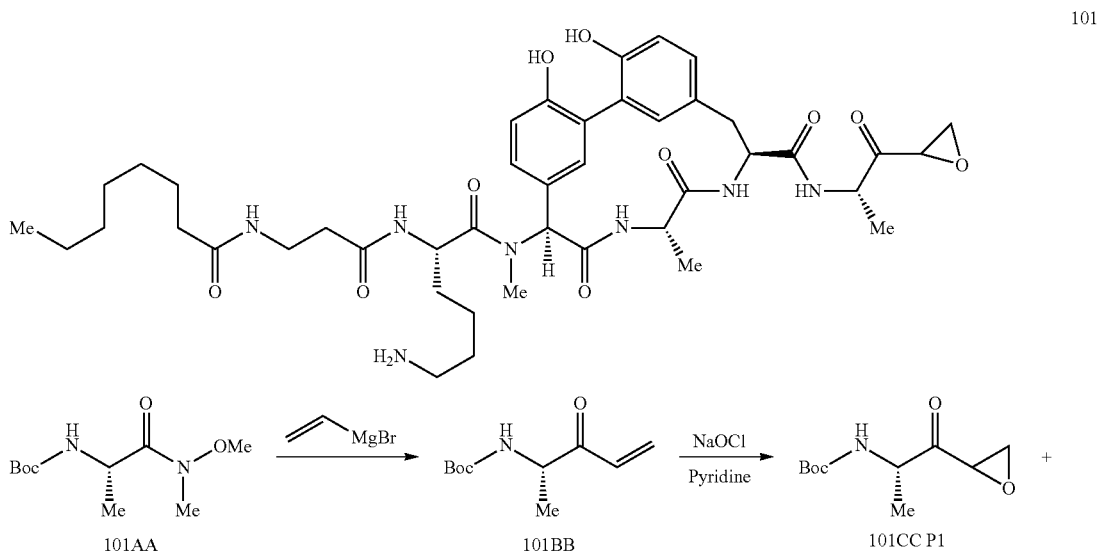

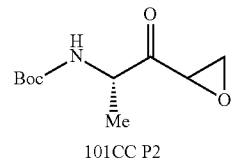

101CC P2

A solution of Compound 101AA (1 g, 4.3 mmol, 1 eq) in anhydrous THF (76 mL) was cooled to −78° C. and a 1 M solution of vinyl magnesium bromide (9.1 mL, 2.1 eq) was added dropwise over 15 mins. The solution was then warmed to 0° C. on an ice bath. After stirring for 2 hrs, TLC indicated complete consumption of starting material and the reaction mixture was poured into stirring 1N HCl (30 mL) at 0° C., the mixture was then diluted with an equivalent amount of water and extracted 3× with EtOAc. The combined organic layers were then washed with brine, dried over $Na_2SO_4$ and concentrated. The crude material was purified via flash chromatography (0 to 50% EtOAc in hexanes) to afford Compound 101BB (706 mg, 82%). $R_f$ 0.6 (25% EtOAc/hexanes). $^1H$ NMR ($CDCl_3$, 500 MHz) δ 6.47 (dd, (J=15 Hz, 10 Hz), 1H) 6.38 (dd, (J=18 Hz, 1.5 Hz), 1H), 5.85 (d, J=10 Hz, 1H), 5.35 (br s, 1H), 4.64-4.61 (m, 1H), 1.44 (s, 9H), 1.34 (d, J=7 Hz, 3H).

To a solution of Compound 101BB (250 mg, 1.3 mmol, 1 eq) in pyridine (5 mL) at −10° C. was added a 10% solution of aqueous NaOCl (1.87 mL, 2 eq) dropwise over 10 mins. The reaction was then warmed to 0° C. and allowed to stir for 2 hrs. The reaction was then diluted with EtOAc at 0° C., the organic layer was washed twice with water and brine, dried over sodium sulfate and concentrated. The crude material was purified via flash chromatography (0 to 50% EtOAc in hexanes) to give two products, Compound 101CC P1 (106 mg, $R_f$ 0.5 (25% EtOAc in hexanes)) and Compound 101CC P2 (63 mg, $R_f$ 0.2 (25% EtOAc in hexanes)) (62% combined yield) as a mixture of diastereomers. Data for Compound 101CC P1: $^1H$ NMR ($CDCl_3$, 500 MHz) δ 5.04 (m, 1H), 4.31-4.29 (m, 1H), 3.54-3.52 (m, 1H), 3.10-3.09 (m, 1H), 3.06-3.04 (m, 1H), 1.42 (s, 9H), 1.31 (d, J=7 Hz, 3H). Data for Compound 101CC P2: $^1H$ NMR ($CDCl_3$, 500 MHz) δ 5.14 (m, 1H), 4.58-4.50 (m, 1H), 3.68 (dd, J=4.5 Hz, 2.5 Hz, 1H), 3.00 (dd, J=6.5 Hz, 4.5 Hz, 1H), 2.91 (dd, J=6.5 Hz, 2.5 Hz), 1.44 (s, 9H), 1.39 (d, J=7 Hz, 3H).

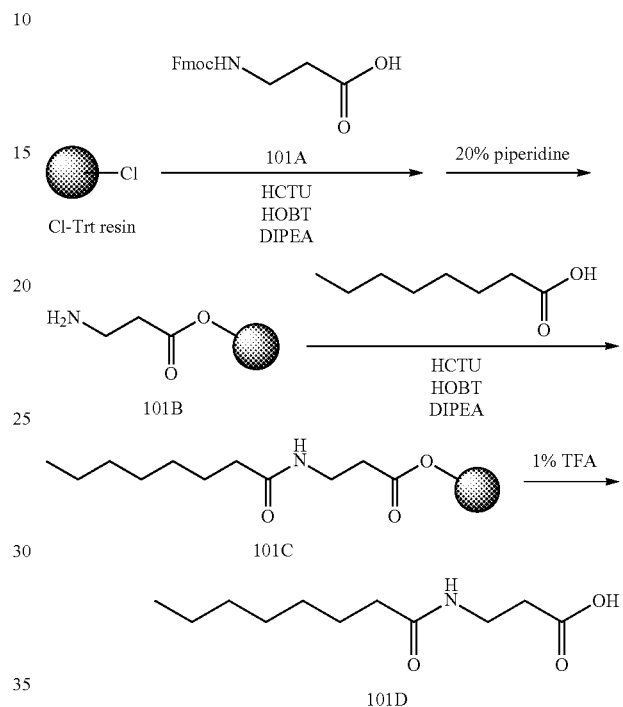

Compound 101D was prepared according to General Methods 1 and 2 from Fmoc-3-aminopropionic acid (622 mg, 2 mmol), octanoic acid (216 mg, 1.5 mmol), and 2-chlorotrityl chloride resin (1 g) to afford 200 mg Compound 101D. MS (ESI) m/z 216.1 (M+H)$^+$.

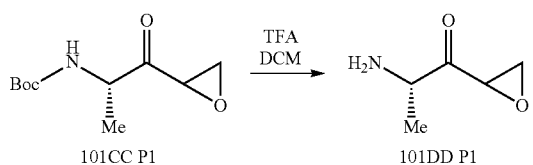

A boc-protected amino acid is dissolved in DCM (0.02-0.2 M) and cooled to 0° C. TFA is added to dropwise to create a 4:1 ratio of DCM:TFA. The solution is stirred for 15 minutes or until LC-MS analysis shows the reaction to be completed. The TFA and DCM are removed under reduced pressure to afford the desired amine.

Compound 101DD P1 was prepared from Compound 101CC P1 according to General Method 5 and was used immediately in the next step.

Compound 101DD P2 was prepared from Compound 101CC P2 according to General Method 5 and was used immediately in the next step.

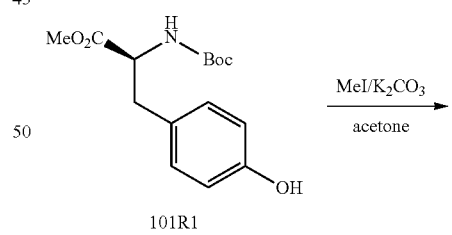

101R1

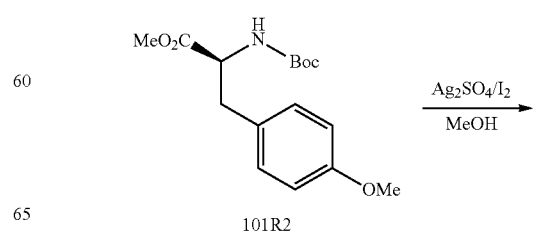

101R2

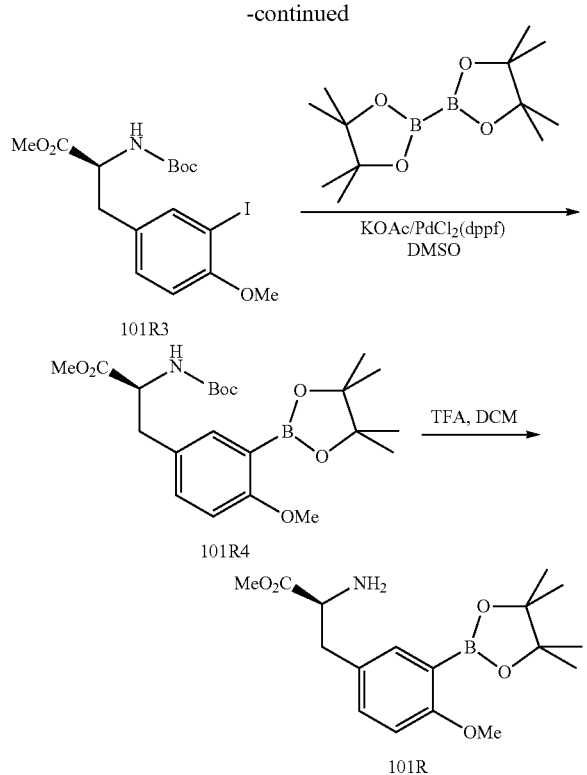

½-added for each batch) and KOAc (103 g, 1.05 mol, ½-added for each batch). This mixture was degassed with argon for twenty minutes then Pd(dppf)Cl₂ (4.6 g, 6 mmol, ½-added for each batch) was added. The mixture was degassed with argon for 5 times, and then kept under argon and heated to 80° C. for 3 hrs. TLC showed that the reaction was complete, and the reaction mixture was cooled to room temperature and filtered. The reaction mixture was dissolved in EA and washed with H₂O. The aqueous layer was extracted ethyl acetate (3×200 mL). The combined organic layers were dried over sodium sulfate, filtered and concentrated to give the crude product. The batches were then combined and purified together by flash column chromatography on silica gel (3% ethyl acetate in hexanes, then 20% to 25% ethyl acetate in hexanes to give Compound 101R4 (70 g, 76%).

Compound 101R4 (22 g, 50.6 mmol) was dissolved in dichloromethane (150 mL) and treated with trifluoroacetic acid (50 mL). The reaction was stirred at room temperature and the reaction was monitored by HPLC. When all of the starting material had been consumed, the solvents were evaporated, DCM was added and Na₂CO₃ was added to neutralize the TFA. The mixture was filtered, and the solution was concentrated. DCM was added to the concentrated oil, and the mixture was cooled at 0° C. for 1 hr, whereupon the solid precipitates that formed were filtered. The filtrate was concentrated to give Compound 101R. The material was used without further purification.

To a solution of Compound 101R1 (100 g, 0.323 mol) in acetone (2.0 L) was added K₂CO₃ (37 g, 0.34 mol). After the addition, MeI (32 mL, 0.97 mol) was added dropwise, and the reaction mixture was stirred at room temperature for 72 h and monitored by TLC. The reaction had not yet gone to completion, so NaOH (0.1 eq) was added to the reaction mixture. And after 2 hrs, the reaction was completed. The solid was filtered and the solvent was removed. The residue was taken up in ethyl acetate and wash with H₂O, extracted with ethyl acetate (300 mL×3). The combined organic layers were washed with brine, dried over Na₂SO₄ and concentrated to give Compound 101R2 (100 g, 95.4%).

To a solution of the Compound 101R2 (80 g, exactly 40 g each×2, run in two separate batches, 259 mmol overall) in methanol (1.5 L in each of the two flasks) was added sequentially Ag₂SO₄ (85 g, 272 mmol, ½-added to each flask) and I₂ (72 g, 283 mmol, ½-added to each flask). The reaction mixture was stirred at room temperature for 2 hrs. The reaction was monitored by LCMS. When all Compound 101R2 had been consumed, then a solution of 10% (w/w) sodium thiosulfate was added until the reaction turned pale yellow. Then the solid was filtered and most of the methanol was evaporated by rotary evaporation. Water and ethyl acetate were added to each batch. The aqueous layer was extracted with ethyl acetate (3×200 mL) then the combined organic layers were washed with brine, dried over sodium sulfate and concentrated. The crude material was combined for the two batches and they were purified together by flash column chromatography on silica gel (25% then 35% then 40% ethyl acetate in hexanes) to give Compound 101R3 (97 g, 89%).

Compound 101R3 (92 g, 46 g each run in two separate batches, 211 mmol) was dissolved in anhydrous DMSO (1.5 L, ½-added for each batch) under argon and to the solution was added bis(pinacolato) diboron (80.5 g, 317 mmol,

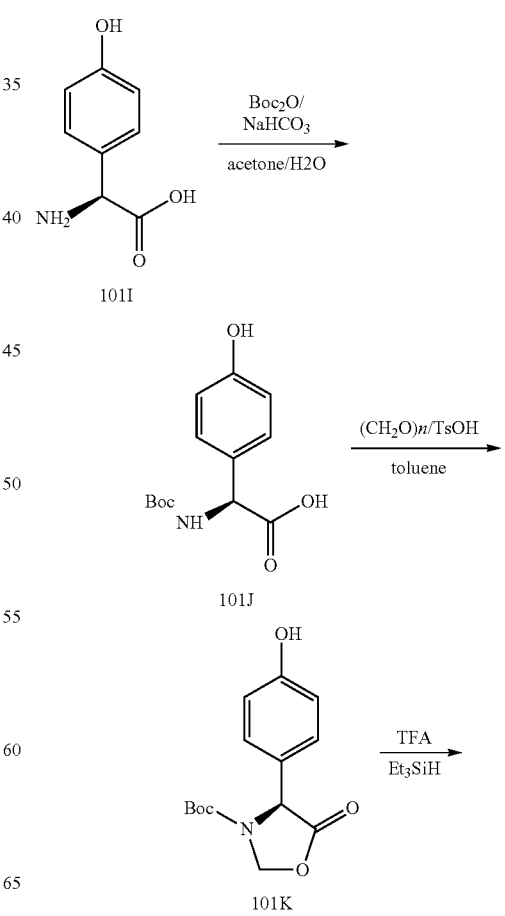

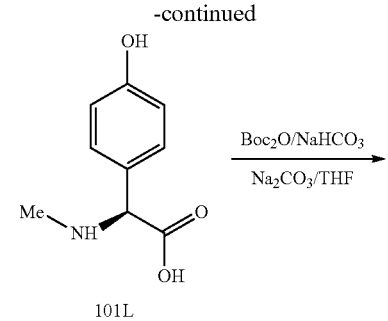

101L

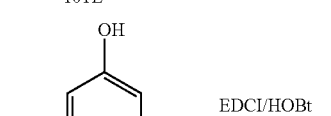

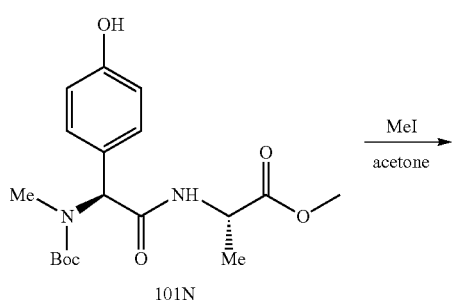

101N

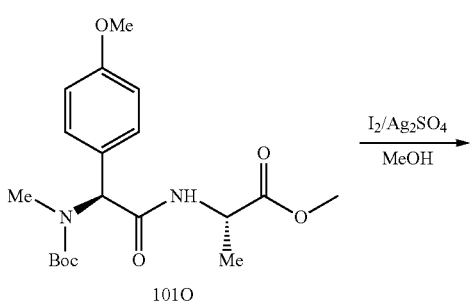

101O

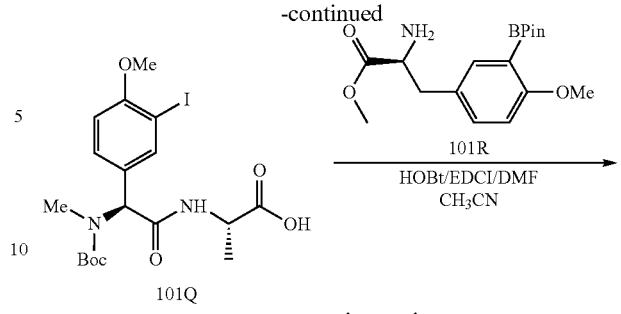

101Q

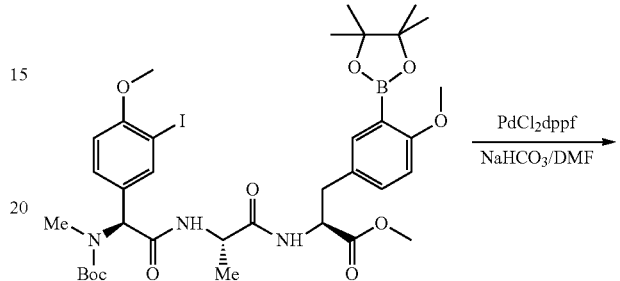

101S

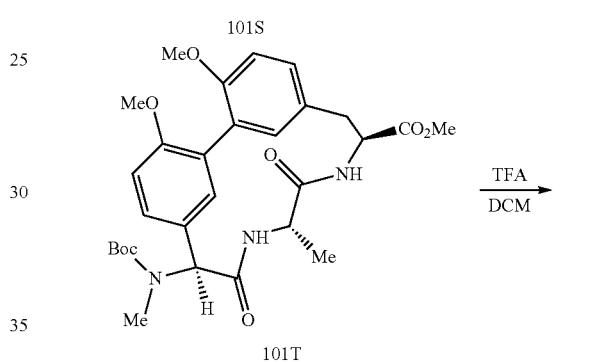

101T

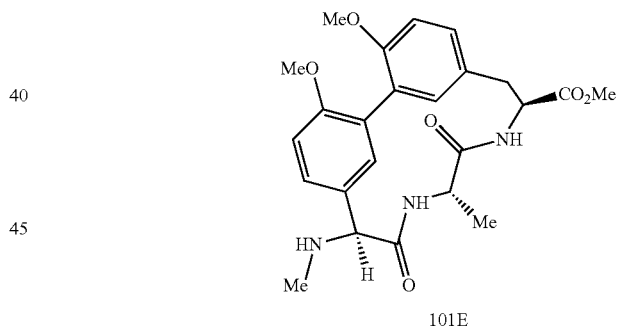

101E

To a stirred mixture of 4-hydroxyphenylglycine (Compound 101I) (100 g, 0.6 mol, 1 eq) in a mixture of acetone (400 mL) and water (400 mL) was added di-tert-butyl dicarbonate (130.5 g, 0.6 mol, 1 eq) and NaHCO₃ (75.4 g, 0.9 mol, 1.5 eq). The mixture was allowed to stir at 25° C. overnight. After HPLC showed the reaction was complete, the mixture was acidified with 5% citric acid (pH~3). The mixture was filtered and the filter cake was washed with water, then dried to give Compound 101J (140 g, 87.5%). The crude product was used directly without further purification.

To a solution of Compound 101J (45 g, 0.17 mol) in dry benzene (500 mL) was added paraformaldehyde (75.6 g, 0.84 mol, 5 eq) and p-toluenesulfonic acid (1.6 g, 8.5 mmol, 0.05 eq). A Dean-Stark apparatus with an attached condenser was then fit to the top of the flask and the mixture was heated at approximately 120° C. until LC-MS showed the reaction was complete. The reaction was then cooled and the benzene was evaporated. The residue was taken up in ethyl acetate, washed with saturated NaHCO₃ (2×150 mL), then dried over sodium sulfate, and filtered. The solvent was removed to give Compound 101K (36 g, 76.5%).

Compound 101K (36 g, 0.13 mol, 1 eq) was dissolved in trifluoroacetic acid (75 mL) at 0° C. then treated with triethylsilane (80 mL, 4 eq). The mixture was stirred at room temperature overnight. After LC-MS showed the reaction was complete, TFA was then evaporated and the residue was dissolved in water (85 mL). To this solution was added solid NaHCO₃ until the pH reached 7. The solution was cooled to 0° C., then Na₂CO₃ was added until pH reached 9. A solution of di-tert-butyldicarbonate (28.3 g, 1.0 eq) in THF (75 mL) was added to the mixture. The mixture was allowed to warm to room temperature then stirred overnight. After HPLC showed the reaction was complete, THF was then evaporated. The aqueous solution was extracted 2× with hexanes and then acidified with citric acid to pH=3-4. The acidified solution was then extracted with ethyl acetate (200 mL×3). The combined organic layers were washed with brine, dried over sodium sulfate, filtered and concentrated to give Compound 101M (35 g, 97% via 2 steps).

To a solution of Compound 101M (35 g, 0.12 mol) in DMF (300 mL) was added triethylamine (18.4 mL, 0.14 mol, 1.1 eq), HOBt (16.2 g, 0.12 mol, 1 eq), Ala-OMe HCl (19.5 g, 0.14 mol, 1.1 eq) and EDC (26.7 g, 0.14 mol, 1.1 eq) and the reaction was stirred overnight. After LC-MS showed the reaction was complete, water and EtOAc were added. The aqueous layer was extracted with EtOAc (3×150 mL), and the combined organic layers were washed with 5% citric acid (pH−3), saturated NaHCO₃ (aq), water and brine. The combined organic layers were then dried over sodium sulfate, filtered and concentrated to give Compound 101N (30 g, 65.8%) as a white foam. The crude product was taken on to the next step directly without further purification.

To a solution of the Compound 101N (30 g, 82 mmol) in acetone (400 mL) was added K₂CO₃ (56.6 g, 0.41 mol, 5 eq) and iodomethane (20.8 mL, 0.41 mol, 5 eq) and the reaction was stirred at reflux overnight. After LC-MS showed the reaction was complete, the reaction was then cooled to room temperature and the mixture was filtered. The filtrate was concentrated and the residue was taken up in water and ethyl acetate. The aqueous phase was extracted with EtOAc (3×150 mL). The combined organic layers were dried over sodium sulfate, filtered and concentrated to give Compound 101O (28 g, 90%), as a white foam.

To a solution of Compound 101O (85 g, 0.22 mol, 1 eq) in methanol (1000 mL) was added sequentially Ag₂SO₄ (72.6 g, 0.23 mol, 1.05 eq) and I₂ (59.6 g, 1.05 eq). After LC-MS showed the reaction was complete, a solution of 10% (w/w) sodium thiosulfate was added until the reaction turned pale yellow. Most of the methanol was evaporated by rotary evaporation and then water and ethyl acetate were added. The aqueous layer was extracted with ethyl acetate (3×300 mL). The combined organic layers were washed with brine, dried over sodium sulfate and concentrated to give Compound 101P (100 g, 88.5%).

To Compound 101P (25 g, 49.4 mmol, 1 eq) in THF (300 mL) was added 0.2 M LiOH (500 mL, 98.8 mmol, 2 eq). The solution was stirred until TLC showed all starting material had been consumed. 5% citric acid (pH−3) was added to pH−3 and then the THF was evaporated by rotary evaporation. The aqueous layer was extracted with EtOAc (3×100 mL). The combined organic layers were washed with brine, dried over sodium sulfate, filtered and concentrated to give Compound 101Q (23 g, 94.6%), which was used directly without further purification.

To a solution of Compound 101R (6.5 g, 19.4 mmol, 1 eq) and Compound 101Q (10 g, 20.3 mmol, 1.05 eq) in acetonitrile:DMF (2.2:1, 168 mL) was added HOBt (6.5 g, 48.5 mmol, 2.5 eq) and EDC (8.1 g, 42.7 mmol, 2.2 eq). The reaction was stirred at room temperature overnight. After LC-MS showed the reaction was complete, diluted citric acid (pH−3) was added and the aqueous was extracted with EtOAc (3×150 mL). The combined organic layers were then washed with saturated NaHCO₃ solution, brine and dried over sodium sulfate. The mixture was filtered and the filtrate was concentrated to give the crude product Compound 101S, which was used directly without further purification.

Compound 101S (16 g, 19.4 mmol, 1 eq) and NaHCO₃ (16.3 g, 0.19 mol) were sealed in a flask with a condenser and put under an atmosphere of argon. DMF (600 mL) in a round bottle flask was purged several times via cycling with vacuum and Ar. PdCl₂(dppf) (3.3 g, 4.5 mmol) was then added to the DMF. The DMF solution was then degassed with Ar for 15 minutes. The solution of PdCl₂(dppf) dissolved in DMF was then transferred via syringe to the flask containing the substrate and NaHCO₃. The resulting mixture was submitted to several more cycles of vacuum and Ar then heated to 120° C. overnight. After LCMS showed the reaction was completed, DMF was evaporated under vacuum. The crude material was subjected to abbreviated column chromatography (40% EA in PE) to remove most of the Pd species and then purified by prep HPLC to give Compound 101T (2.1 g, 19.5% over two steps).

To a stirred solution of Compound 101T (2.1 g, 3.78 mmol) in DCM (25 mL) was added TFA (2 mL). The reaction was monitored via TLC and when starting material was consumed, the solvent was evaporated under vacuum. The residue was then dissolved in EtOAc and the organic layer was washed with saturated NaHCO₃ (10 mL), dried over sodium sulfate and concentrated to give Compound 101E (1.7 g, 98.8%). MS (ESI) m/z 456.2 (M+H)⁺.

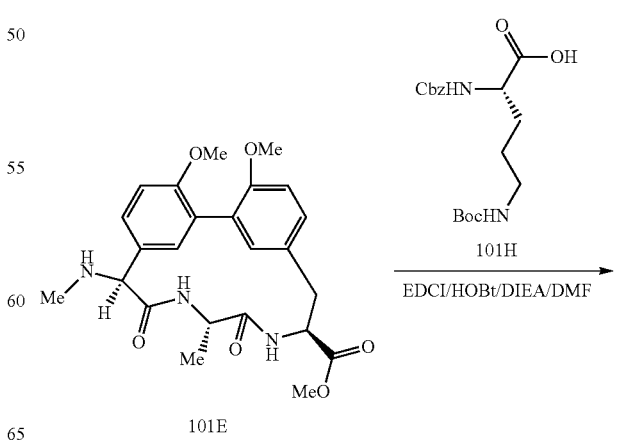

101E

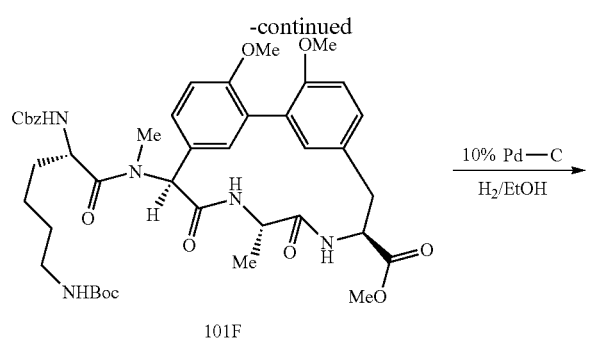

Compound 101F was prepared according to General Method 3 and was performed as follows: To a solution of Compound 101E (275 mg, 0.73 mmol) in DMF (2 mL) were added HOBT (267 mg, 1.98 mmol), DIPEA (255 mg, 1.98 mmol), Compound 101H (300 mg, 0.66 mmol) and EDCI (378 mg, 1.98 mmol). The resulting solution was stirred at 20° C. overnight and diluted with water. The precipitate was filtered and the resulting filter cake was washed with water and dried by aspiration to give a crude product, which was recrystallized from PE to give Compound 101F (0.5 g, 84%) as a white solid.

A suspension of Compound 101F (500 mg, 0.61 mmol) and 10% Pd/C (0.7 g) in EtOH (15 mL) was stirred at 20° C. overnight under a hydrogen atmosphere until LC-MS showed the reaction was completed. The catalyst was removed by filtration and the solvent was evaporated to afford Compound 101G (350 mg, 90%), which was used without further purification.

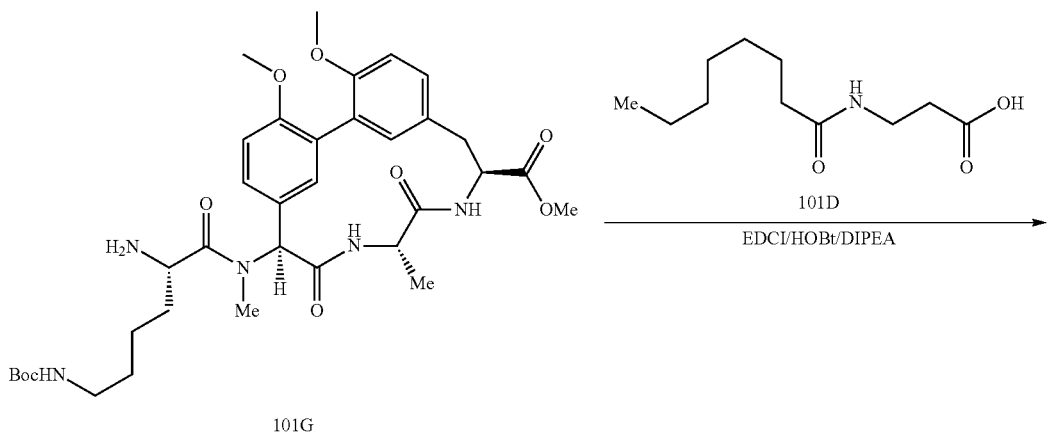

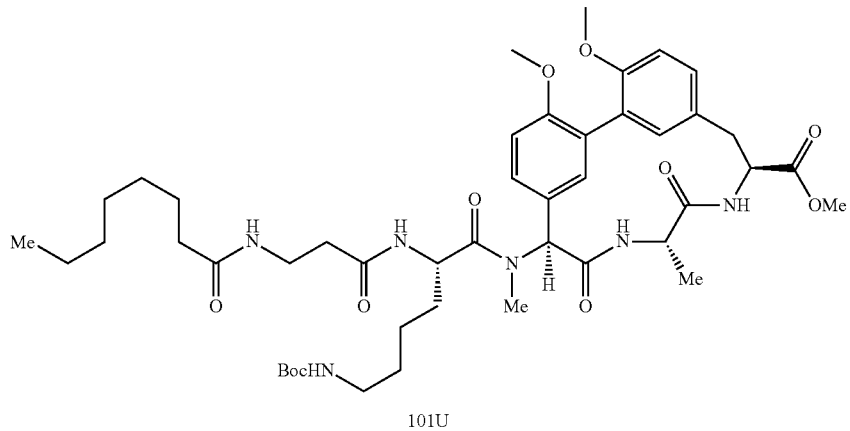

Compound 101U was prepared using General Method 3. To a solution of Compound 101D (157 mg, 0.732 mmol) in DMF (10 mL) were added EDCI (210 mg, 1.10 mmol), DIPEA (142 mg, 1.10 mmol) and HOBT (149 mg, 1.10 mmol). After 30 min, Compound 101G (500 mg, 0.732 mmol) was added, and the solution was stirred overnight. The reaction was diluted with water. The precipitate was filtered and washed sequentially with water and PE to afford 480 mg of Compound 101U. MS (ESI) m/z 881.5 (M+H)$^+$.

The solvent was evaporated to give a crude product, which was purified by preparative HPLC to afford 300 mg of Compound 101V. MS (ESI) m/z 739.2 (M+H)$^+$. $^1$H NMR (400 MHz, CD$_3$OD) δ 0.89 (t, J=6.8 Hz, 3H), 1.3 (s, 9H), 1.37 (d, J=6.4 Hz, 3H), 1.40-1.75 (m, 7H), 1.78-1.90 (m, 2H), 2.15 (t, J=8.0 Hz, 1H), 2.38-2.51 (m, 2H), 2.87 (s, 3H), 2.94 (t, J=7.6 Hz, 2H), 3.08-3.13 (m, 1H), 3.35-3.50 (m, 3H), 6.41 (s, 1H), 6.87 (d, J=8.4 Hz, 1H), 6.96 (d, J=8.4 Hz,

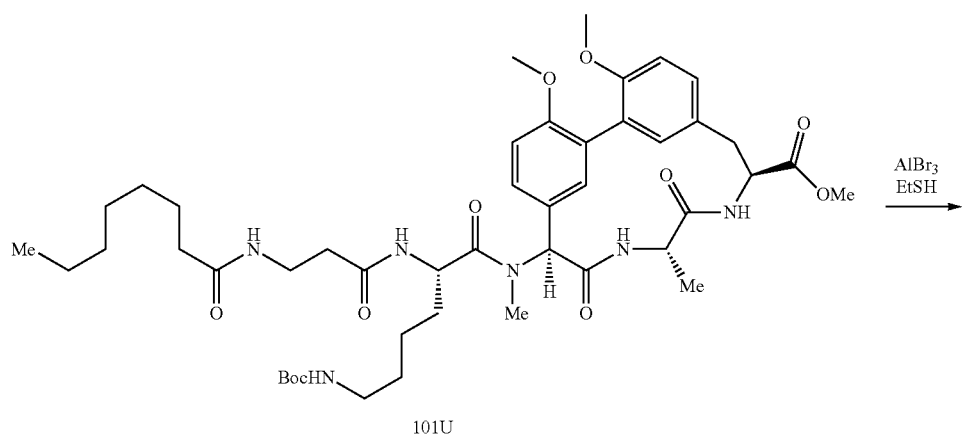

101U

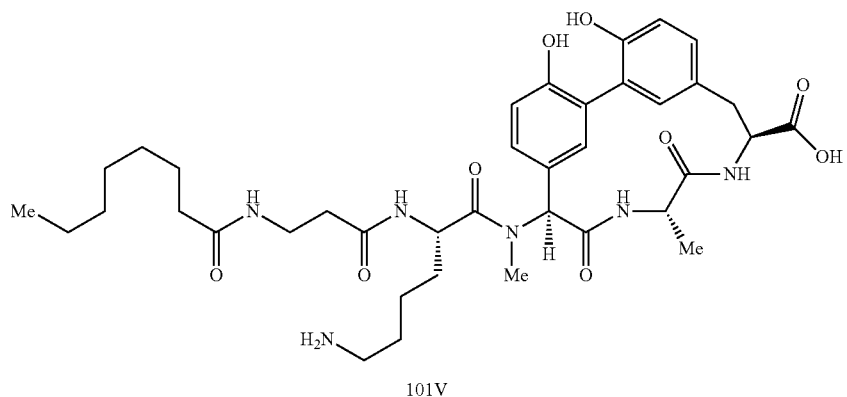

101V

To a mixture of Compound 101U (480 mg) in EtSH (20 mL) and 10 mL CH$_2$Br$_2$ was added 1.0 M AlBr$_3$ in CH$_2$Br$_2$ (13.6 mL, 25 eq) under Ar. The mixture was heated to 50° C. for 4 hr. After HPLC analysis showed the reaction was complete, the reaction was quenched with MeOH (10 mL).

1H), 7.00-7.02 (m, 2H) 7.08-7.14 (m, 2H), 8.29 (d, J=7.2 Hz, 1H), 8.67 (d, J=8.8 Hz, 1H), 8.89 (d, J=7.6 Hz, 1H). MS (ESI) m/z 739.2 (M+H)$^+$. t$_R$ 2.24 min (10% AcCN/H$_2$O, 0.3 min; 10%-80% AcCN/H$_2$O, 5 min; 1 mL/min Luna C18, 2×50 mm).

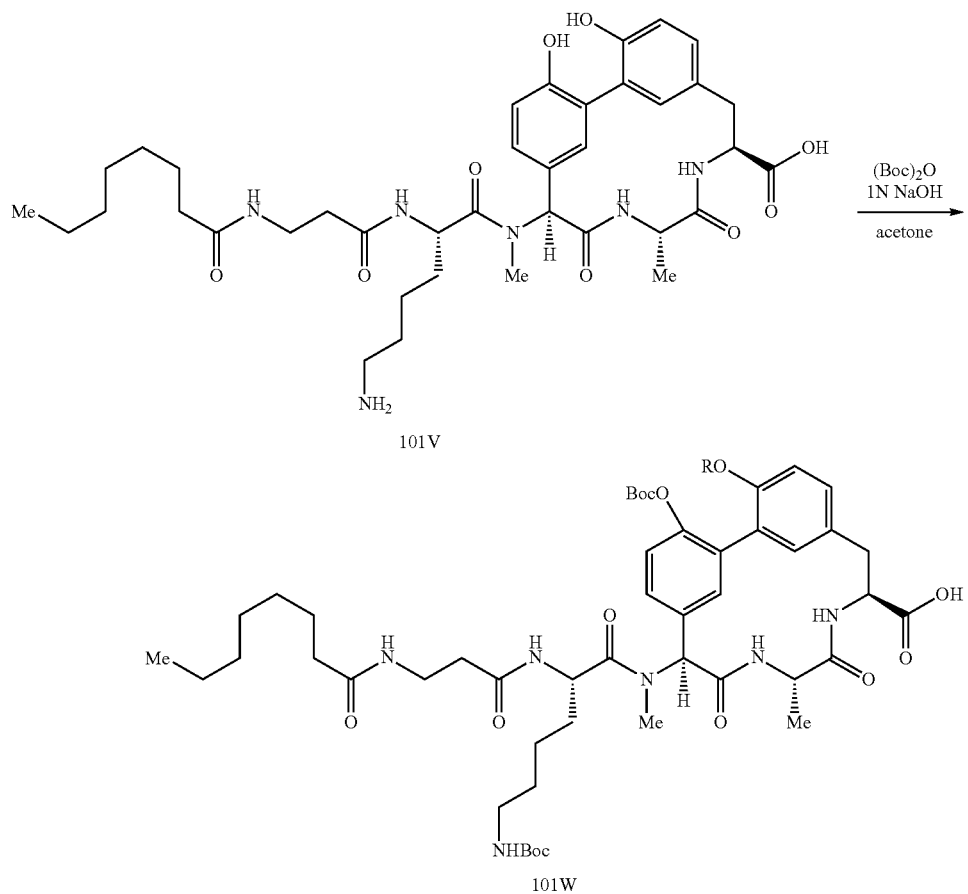

101V

R = Boc, H mixture of compounds

101W

To a solution of Compound 101V (74 mg, 0.1 mmol) in acetone-H₂O (1:1, 1 mL) was added 1M NaOH (0.5 mL, 0.5 mmol) and (Boc)₂O (0.115 mL, 0.5 mmol). The reaction mixture was stirred at room temperature for 2 days. The acetone was removed under vacuum and the reaction mixture was diluted with H₂O (2 mL). The mixture was acidified with 1M HCl and the resultant white precipitate was filtered and dried to afford 92 mg (89%) in which either one of the bis-phenols are either Boc protected, or Boc-protected at both positions, to afford Compound 101W. MS (ESI) for ($C_{48}H_{70}N_6O_{13}$): m/z 939 (M+H)⁺.

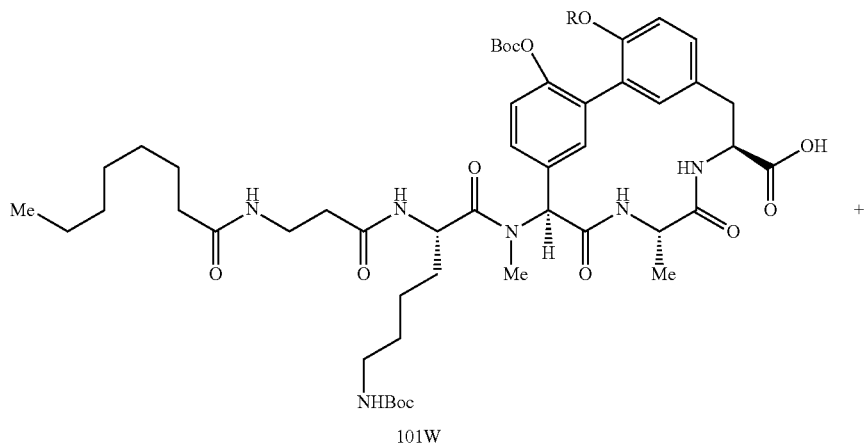

101W

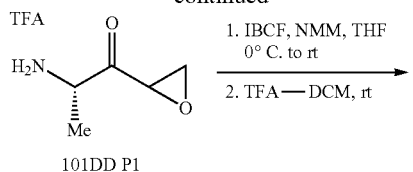
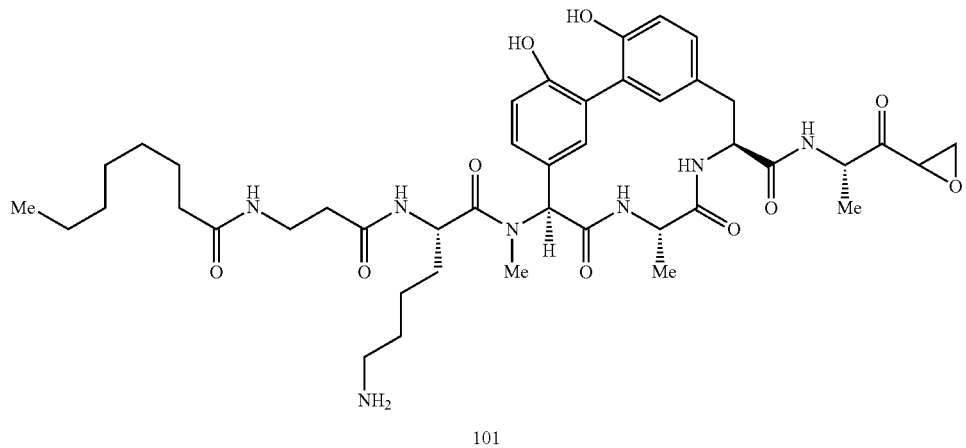
R = Boc, H mixture of compounds
Compound 101 was synthesized from Compound 101W (19 mg, 0.02 mmol) and Compound 101DD P1 (11 mg, 0.05 mmol) using General Method 6. MS (ESI) for ($C_{43}H_{61}N_7O_{10}$): m/z 836.50 (M+H)$^+$.
Example 2: Synthesis of Compound 102
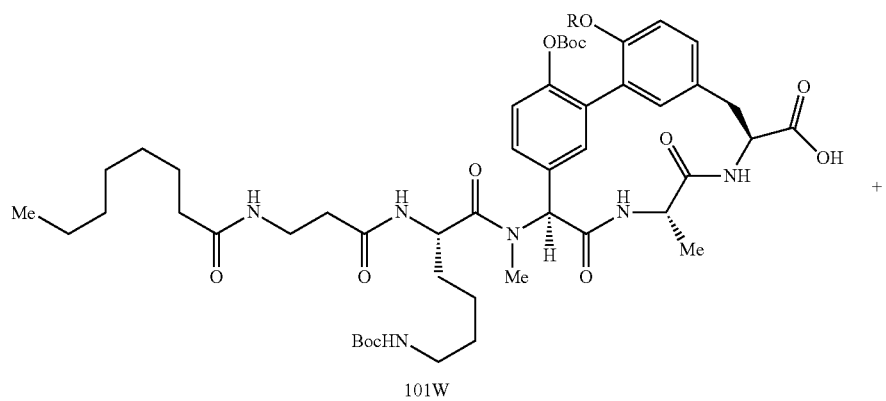
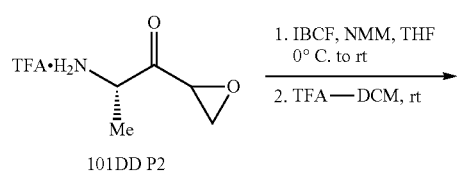

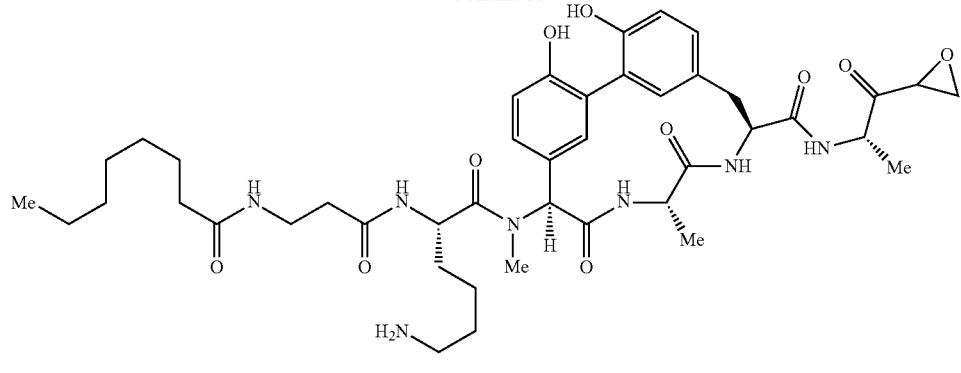
102
R = Boc, H mixture of compounds
Compound 102 was synthesized from Compound 101W (19 mg, 0.02 mmol) and Compound 101DD P2 (11 mg, 0.05 mmol) using General Method 6. MS (ESI) for ($C_{43}H_{61}N_7O_{10}$): m/z 836.30 (M+H)$^+$.
Example 3: Synthesis of Compound 103
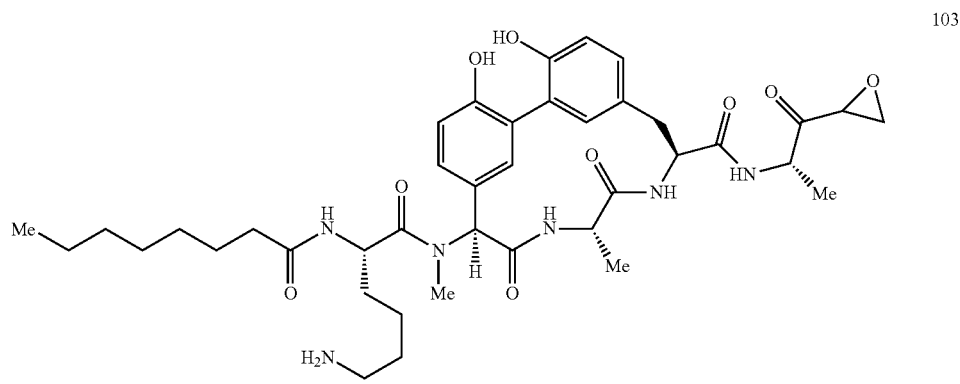
103
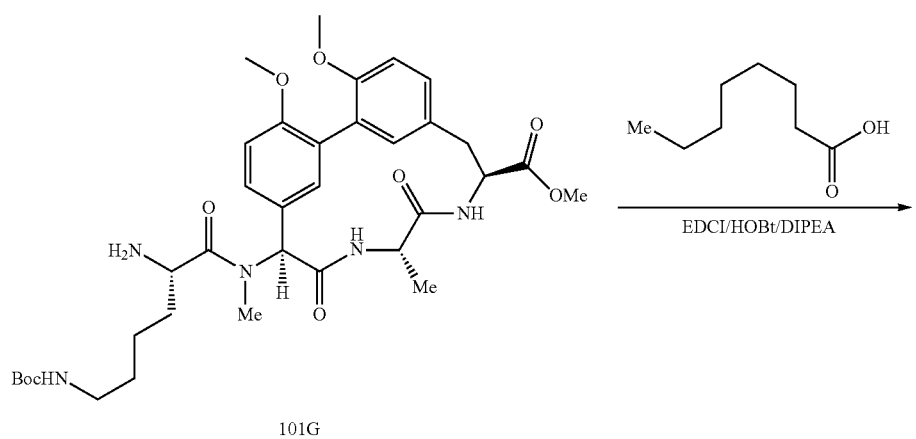
101G

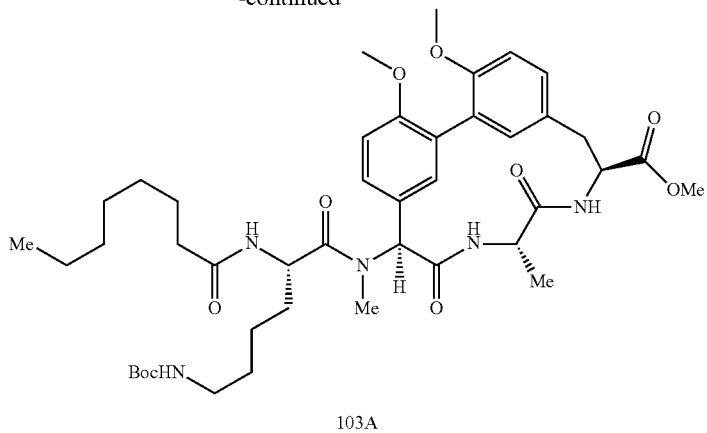

103A

To a solution of octanoic acid (105 mg, 0.732 mmol) in DMF (10 mL) were added EDCI (210 mg, 1.1 mmol), DIPEA (142 mg, 1.1 mmol) and HOBT (149 mg, 1.1 mmol). After 30 min, Compound 101G (500 mg, 0.732 mmol) was added. The reaction solution was stirred overnight. The reaction was diluted with water, and the precipitate was filtered and washed sequentially with water and PE to afford 550 mg (0.68 mmol) of Compound 103A. MS (ESI) m/z 810.4 (M+H)$^+$.

heated to 50° C. for 4 hr. After HPLC analysis showed the reaction was complete, the reaction was quenched with MeOH (30 mL), and then the solvent was evaporated. The residue was purified by preparative HPLC to afford 300 mg of Compound 103B. MS (ESI) m/z 668.1 (M+H)$^+$; $^1$H NMR (400 MHz, CD$_3$OD) δ 0.89 (t, J=6.8 Hz, 3H), 0.91-1.31 (m, 8H), 1.37 (d, J=6.8 Hz, 1H), 1.55-1.58 (m, 4H), 1.65-1.75 (m, 4H), 1.80-1.90 (m, 1H), 2.05-2.45 (m, 2H), 2.89 (s, 3H), 2.93 (t, J=7.6 Hz, 2H), 3.05-3.15 (m, 1H), 3.35-3.45 (m,

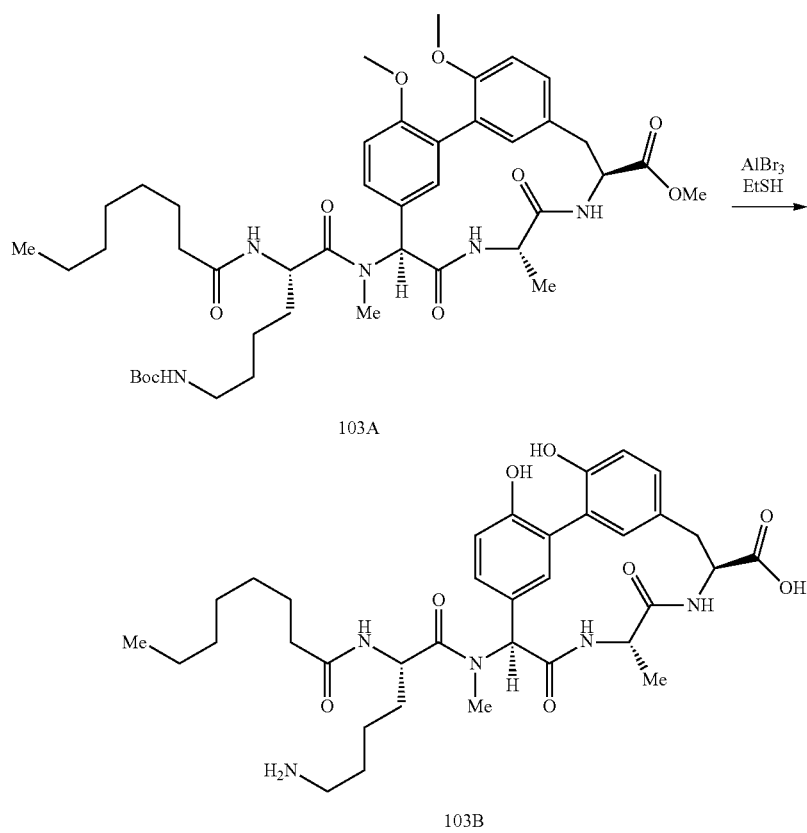

To a mixture of Compound 103A (550 mg, 0.68 mmol) in EtSH (20 mL) and 17 mL CH$_2$Br$_2$ was added 1.0 M AlBr$_3$ in CH$_2$Br$_2$ (4.4 g, 17 mmol) under Ar. The mixture was 1H), 6.5 (s, 1H), 6.88 (d, J=8.0 Hz, 1H), 6.96 (d, J=8.4 Hz, 1H), 7.01-7.00 (m, 2H) 7.01-7.10 (m, 2H), 8.73 (d, J=9.2 Hz, 1H), 8.97 (d, J=8.0 Hz, 1H).

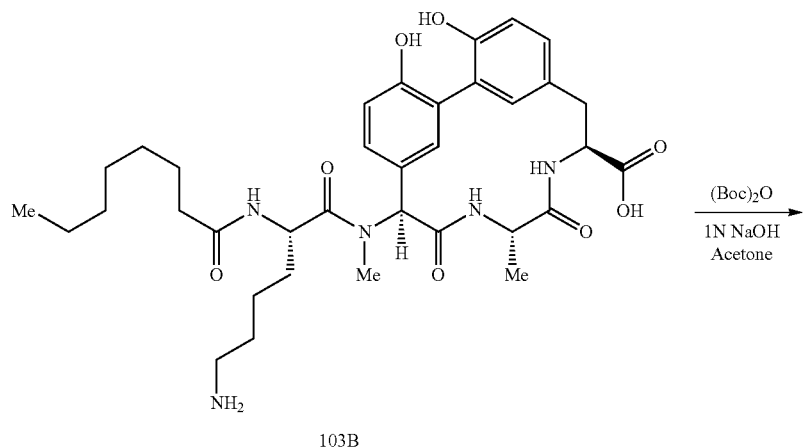

103B

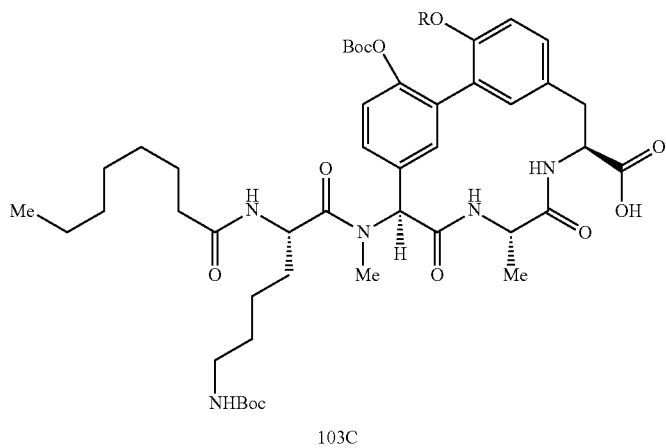

103C

R = Boc, H, mixture of compounds

Compound 103B (67 mg, 0.1 mmol) was dissolved in acetone-H$_2$O (1:1, 1 mL) and 1M NaOH (0.5 mL, 0.5 mmol) and (Boc)$_2$O (0.115 mL, 0.5 mmol) was added and the reaction mixture was stirred at room temperature for 2 days. The acetone was removed under vacuum and the reaction mixture was diluted with H$_2$O (2 mL). The mixture was acidified with 1M HCl and the resultant white precipitate was filtered and dried to afford 60 mg (69%) as 30:70 mixture of tris and bis boc protected Compound 103C. MS (ESI) for tris-boc product (C$_{50}$H$_{73}$N$_5$O$_{14}$); m/z 968 (M+H)$^+$. Bis-boc product (C$_{45}$H$_{65}$N$_5$O$_{12}$): m/z 868 (M+H)$^+$.

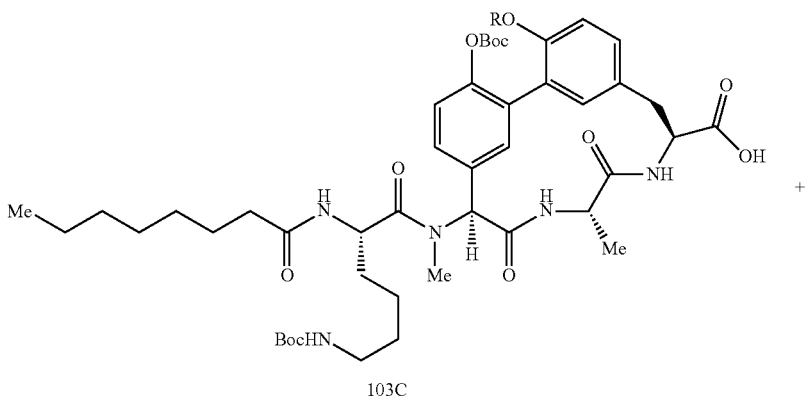

103C

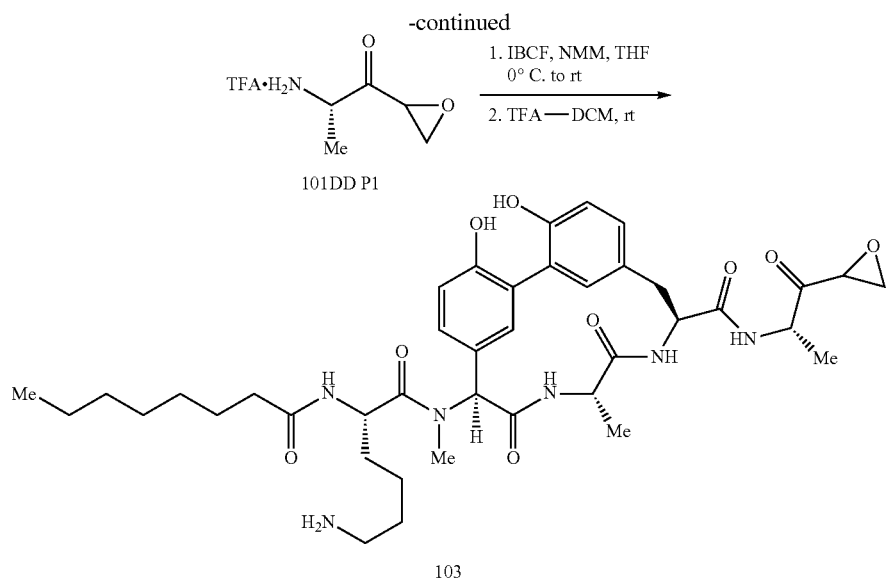

Compound 103 was synthesized from Compound 103C (17 mg, 0.02 mmol) and Compound 101DD P1 (11 mg, 0.05 mmol) using General Method 6. MS (ESI) for ($C_{40}H_{56}N_6O_9$): m/z 764.92 (M+H)$^+$.

Example 4: Synthesis of Compound 104

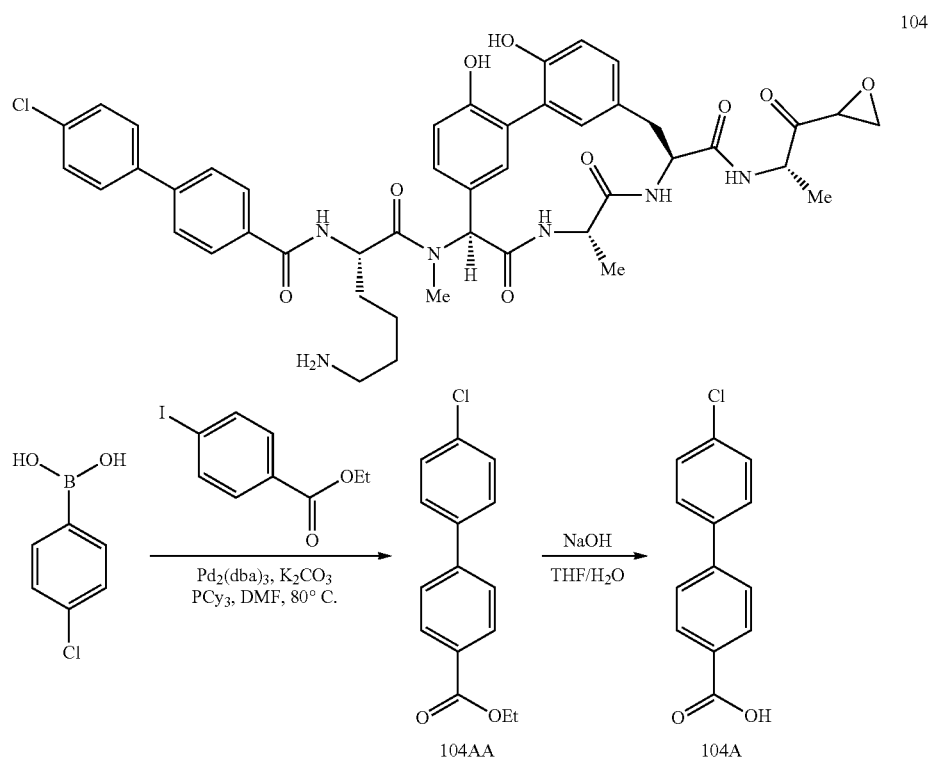

An oven-dried three neck flask (500 mL) was charged with (4-chlorophenyl)boronic acid (12 g, 74.7 mmol), ethyl 4-iodobenzoate (14.1 g 51.2 mmol), Pd$_2$(dba)$_3$ (4.68 g, 5.12 mmol), PCy$_3$ (1.43 g, 5.12 mmol) and K$_2$CO$_3$ (21.21 g, 153.5 mmol). DMF (100 mL) was added and the reaction mixture was purged with N$_2$. The mixture was stirred at 80° C. for 12 h. The reaction mixture was cooled to room temperature and filtered to remove K$_2$CO$_3$. The solvent was removed and the brown residue was purified by column (1% to 5% EtOAc in petroleum ether) to give Compound 104AA (9.52 g, 71.4%).

To a solution of ethyl 4'-chloro-[1,1'-biphenyl]-4-carboxylate (104AA) (9.52 g, 36.6 mmol) in a mixture of THF (150 mL) and $H_2O$ (20 mL) was added NaOH (4N, 5.86 g, 146 mmol). After the mixture was stirred at 70° C. for 10 h, the organic solvent was removed under reduced pressure, and pH was adjusted to 3 with 4M HCl. The product was collected by filtration, washed with water and dried to give Compound 104A (8.5 g, 100%). $^1$H NMR (400 MHz, $CDCl_3$) δ 8.10 (d, J=8.4 Hz, 2H), 7.70 (d, J=8 Hz, 2H), 7.65 (d, J=8.8 Hz, 2H), 7.47 (d, J=8.8 Hz, 2H).

DIPEA (226.8 mg, 1.75 mmol) and Compound 104A (204.1 mg, 0.87 mmol) was added to a solution of Compound 101G (400 mg, 0.58 mmol) in DMF (5 mL) at 0° C. After the mixture was kept at room temperature for 10 min, HATU (445 mg, 1.17 mmol) was added. The mixture was stirred at room temperature for 16 h and then poured into water (40 mL). The precipitate was collected by filtration, washed with water and dried in vacuo. The crude product was purified by silica chromatography (DCM/MeOH=60/1) to give Compound 104B as a white solid (500 mg, 96%).

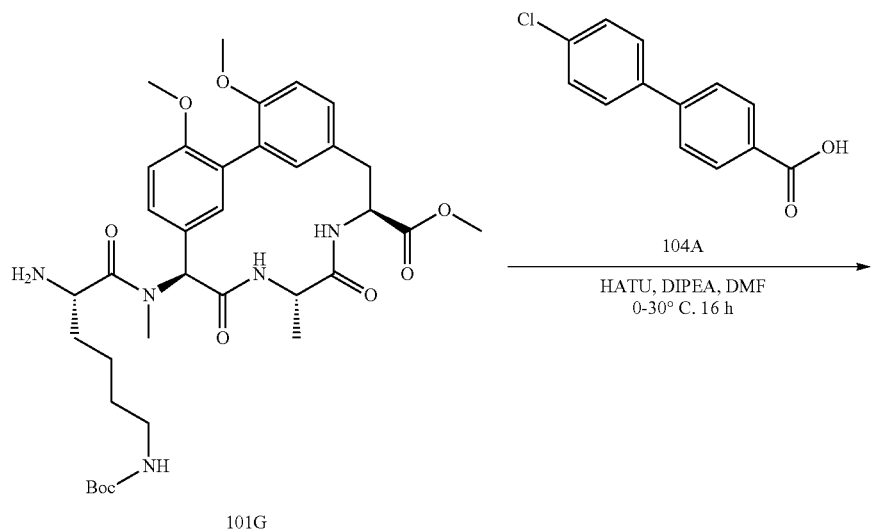

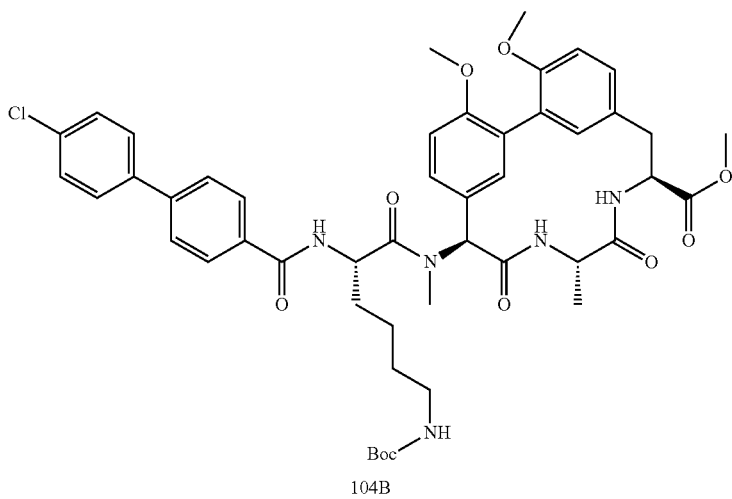

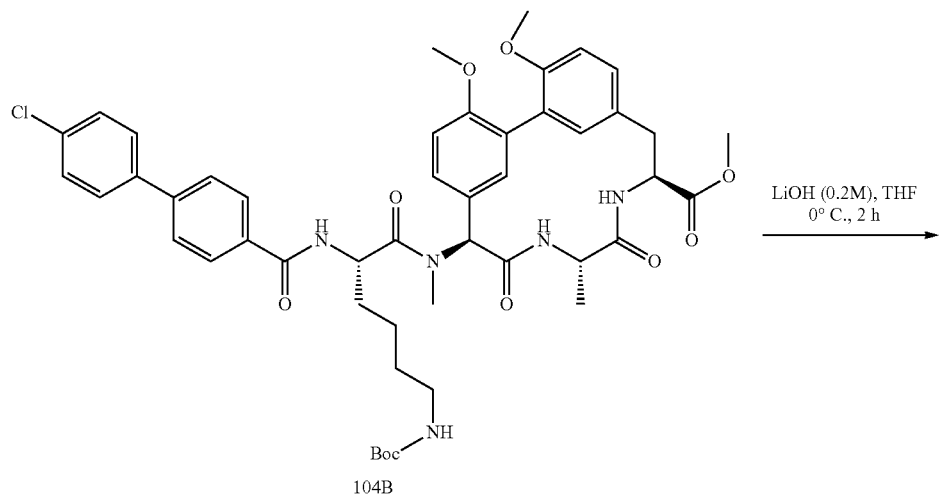

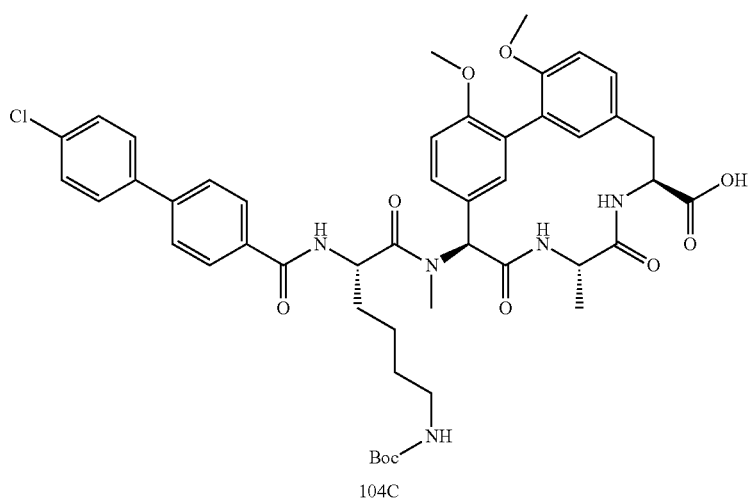

To a solution of Compound 104B (500 mg, 0.556 mmol) in THF (10 mL) was added aqueous LiOH solution (0.2M, 6 mL) at 0° C. After the reaction was stirred at 0° C. for 0.5 h, saturated NH$_4$Cl solution was added until pH reached below 7. The mixture was extracted with DCM (30 mL×3), washed with brine (30 mL×3), dried over Na$_2$SO$_4$, filtered and concentrated to give Compound 104C (480 mg, 96%). $^1$H NMR (400 MHz, DMSO-d$_6$) δ 0.79-0.85 (m, 2H), 1.15 (d, J=6.4 Hz, 2H), 1.21 (s, 1H), 1.29-1.35 (m, 9H), 1.39 (d, J=6.4 Hz, 2H), 1.73 (m, 3H), 2.76 (s, 2H), 2.87-3.01 (m, 3H), 3.30 (d, J=10 Hz, 2H), 3.57 (t, J=6.4 Hz, 1H), 3.65-3.79 (m, 6H), 4.41 (brs, 1H), 4.59-4.67 (m, 1H), 4.60-4.70 (m, 1H), 4.78 (d, J=6.80 Hz, 1H), 6.28 (s, 1H), 6.63-6.79 (m, 3H), 6.90 (d, J=8.60 Hz, 1H), 7.00-7.13 (m, 3H), 7.53 (d, J=8.4, 2 H), 7.74-7.79 (m, 4H), 8.01 (d, J=8.0 Hz, 2H), 8.38 (m, 1H), 8.69 (d, J=7.60 Hz, 1H).

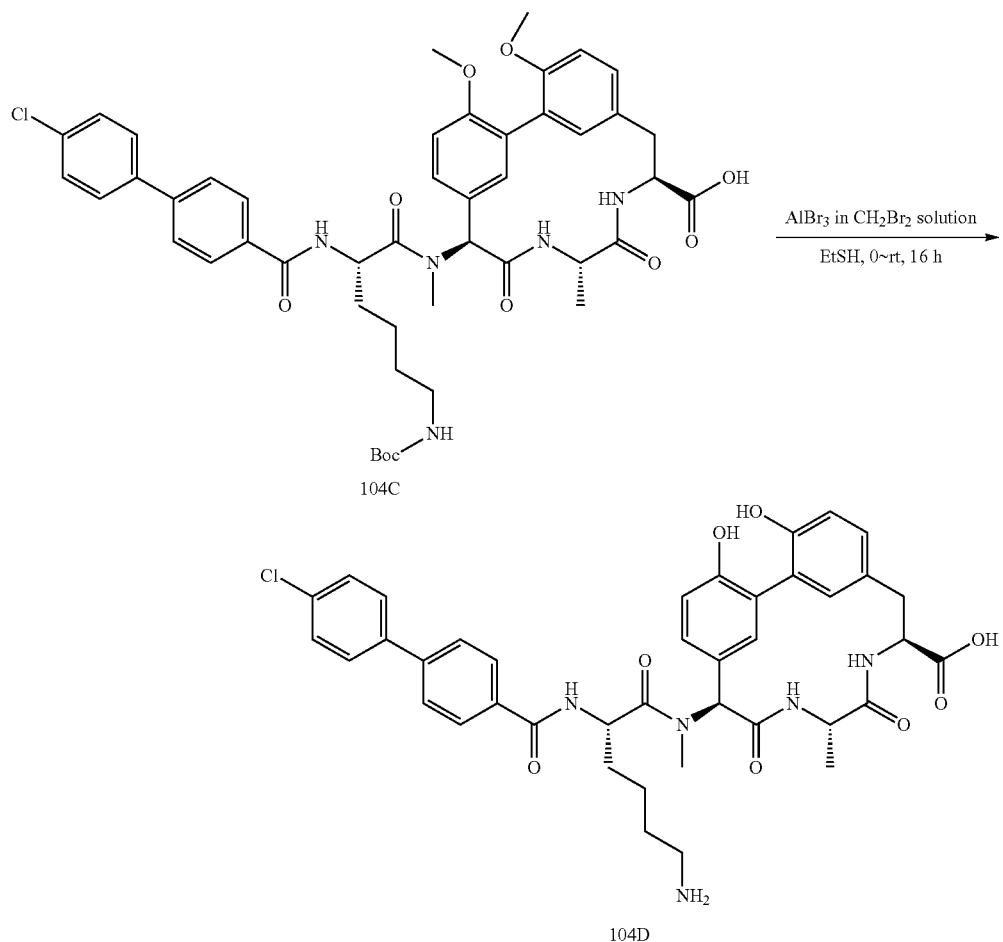

104C

104D

To a solution of Compound 104C (500 mg, 565 umol) in EtSH (5 mL) at 0° C. was added a solution of AlBr$_3$ in dibromomethane (1M, 5.65 mL, 5.65 mmol). The reaction mixture was stirred at room temperature for 16 h and then the solvent was removed under vacuum. The residue was dissolved in DCM (2 mL), quenched with MeOH (0.5 mL) at 0° C., and the mixture was concentrated under reduced pressure. The residue was purified by prep-HPLC (Luna C18, AcCN/Water plus HCOOH) to give (250 mg, 58.5%) of Compound 104D. $^1$H NMR (400 MHz, DMSO-d$_6$) δ 1.09-1.15 (m, 3H), 1.55-1.57 (m, 1H), 2.64-2.76 (m, 5H), 3.23-3.36 (m, 2H), 4.74-4.83 (m, 1H), 6.24 (s, 1H), 6.53-6.57 (m, 1H), 6.58-6.78 (m, 1H), 6.83-6.92 (m, 3H), 7.53 (d, J=8.4 Hz, 2H), 7.75-7.78 (m, 4H), 8.00 (d, J=8.4 Hz, 2H 2H), 8.55 (d, J=8.0 Hz, 1H), 8.70 (d, J=7.2 Hz, 1H). MS (ESI): 756.1 (M+H)$^+$.

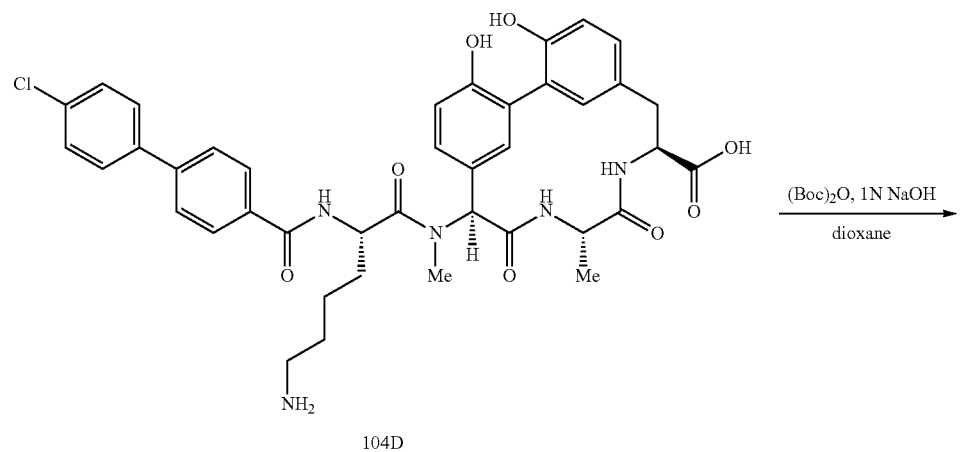

104D

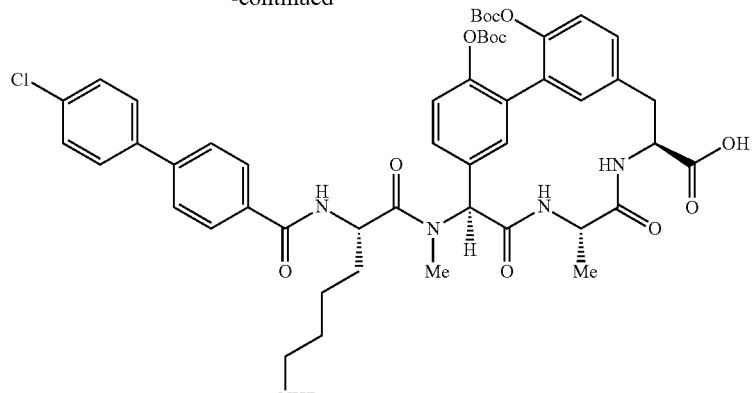

104E

To a solution of Compound 104D (500 mg, 0.5 mmol) in dioxane (20 mL) was added 1M NaOH (10 mL, 10 mmol) and (Boc)₂O (1.2 mL, 5 mmol). The reaction mixture was stirred at room temperature overnight. The dioxane was removed under reduced pressure and the mixture was acidified with 1M HCl. The resultant white pasty material was dried to afford Compound 104E (507 mg, 96%). MS (ESI) for ($C_{55}H_{66}ClN_5O_{14}$): m/z 1056 (M+H)⁺.

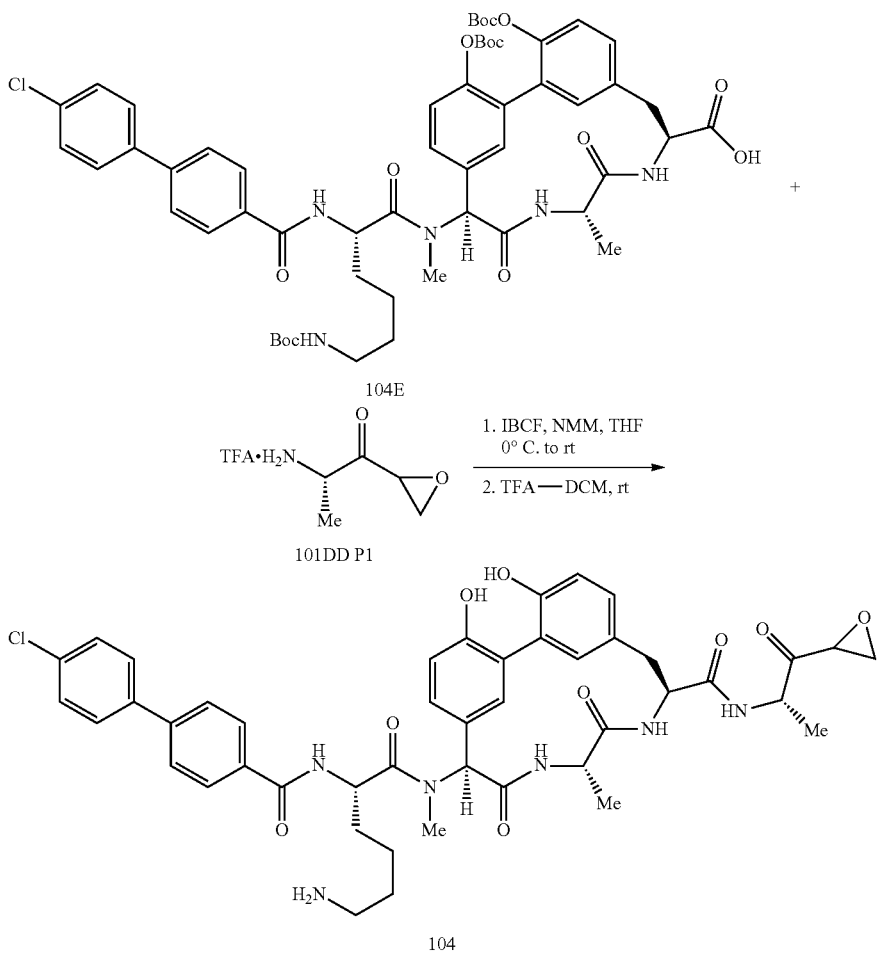

Compound 104 was synthesized from Compound 104E (64 mg, 0.06 mmol) and Intermediate 101DD P1 (25 mg, 0.12 mmol) using the general procedure. MS (ESI) for ($C_{45}H_{49}ClN_6O_9$): m/z 953.37 (M+H)⁺.

Example 5: Synthesis of Compound 105

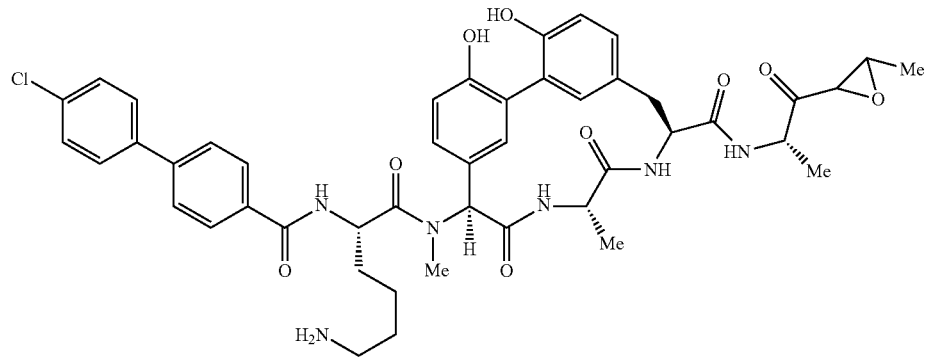

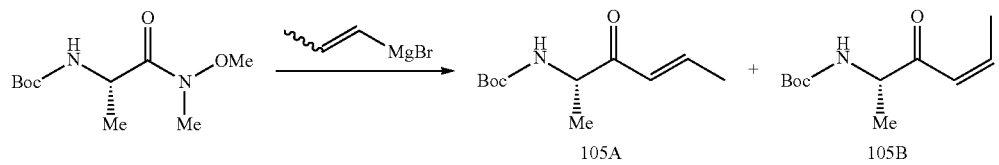

A solution of 1-propenyl magnesium bromide (0.5 M in THF, 45 mL) was added dropwise to Boc-L-Ala-N(OMe)(Me) (1.74 g, 7.5 mmol) in THF (15 mL) at −5 OC. The reaction was stirred at −5° C. for 1.5 h, and then was poured into a cold mixture of ether/0.2N $NaHSO_4$. The mixture was extracted with ether, and the combined organic layers were washed sequentially with saturated $NaHCO_3$ and brine, dried over $Na_2SO_4$, filtered and concentrated. Flash chromatography (10% EtOAc/hexanes-50% EtOAc/hexanes) afforded 0.35 g (22%) of 105B and 0.70 g (44%) of 105A. Data for Compound 105A: $^1$H NMR ($CDCl_3$) δ 7.02 (dq, J=15.5, 7.0, 1H), 6.22 (broad d, J=15.5, 1H), 5.37 (broad s, 1H), 4.5-4.6 (m, 1H), 1.93 (dd, J=7.0, 1.5, 3H), 1.44 (s, 9H), 1.32 (d, J=7.0, 3H). $R_f$ 0.32 (4:1 hexanes:EtOAc). Data for Compound 105B: $^1$H NMR ($CDCl_3$, 500 MHz) δ 6.37 (dq, J=11.5, 7.5, 3H), 6.21 (broad d, J=11.5, 1H), 5.37 (broad s, 1H), 4.3-4.4 (m, 1H), 2.15 (dd, J=7.5, 1.8, 3H), 1.44 (s, 9H), 1.32 (d, J=7.0, 3H). $R_f$ 0.38 (4:1 hexanes:EtOAc).

C. DIPEA (0.39 mL, 2.2 mmol) was added, and the reaction was stirred for 3 h at 0° C., whereupon it was warmed to room temperature and stirred for 30 min. The methanol was evaporated, and the mixture partitioned between ether and 0.2N $NaHSO_4$. The organic layer was washed sequentially with saturated $NaHCO_3$ and brine, dried over $Na_2SO_4$, filtered and concentrated. Flash chromatography (10% EtOAc/hexanes-40% EtOAc/hexanes) afforded 17 mg (24%) of 105C P1 and 12 mg (17%) of 105C P2. Data for Compound 105C P1: $^1$H NMR ($CDCl_3$, 500 MHz) δ 5.0-5.1 (m, 1H), 4.2-4.3 (m, 1H), 3.29-3.36 (m, 1H), 3.28 (broad s, 1H), 1.43 (d, 3H), 1.42 (s, 9H), 1.29 (d, J=7.5, 3H). $R_f$ 0.42 (3:1 hexanes:EtOAc). Data for Compound 105C P2: $^1$H NMR ($CDCl_3$, 500 MHz) δ 5.1-5.2 (broad s, 1H), 4.45-4.55 (m, 1H), 3.43 (d, J=1.5, 1H), 3.1-3.2 (m, 1H), 1.42-1.47 (12H, N-Boc, $CH_3$), 1.38 (d, 3H). $R_f$ 0.25 (3:1 hexanes:EtOAc).

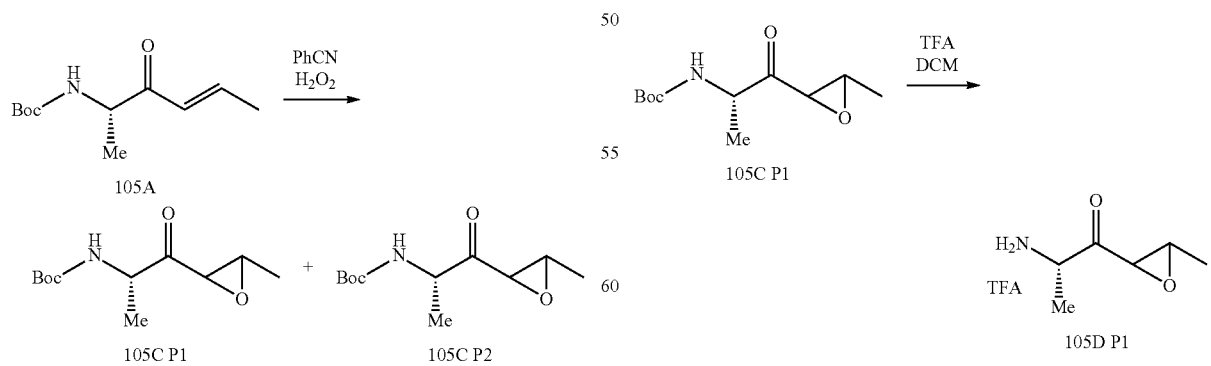

A solution of 50% $H_2O_2$ (0.13 mL, 2.2 mmol) was added to a solution of Compound 105A (64 mg, 0.30 mmol) and benzonitrile (0.23 mL, 2.2 mmol) in methanol (3 mL) at 0°

Compound 105D P1 was prepared from Compound 105C P1 following General Method 5 and was used immediately in the next step.

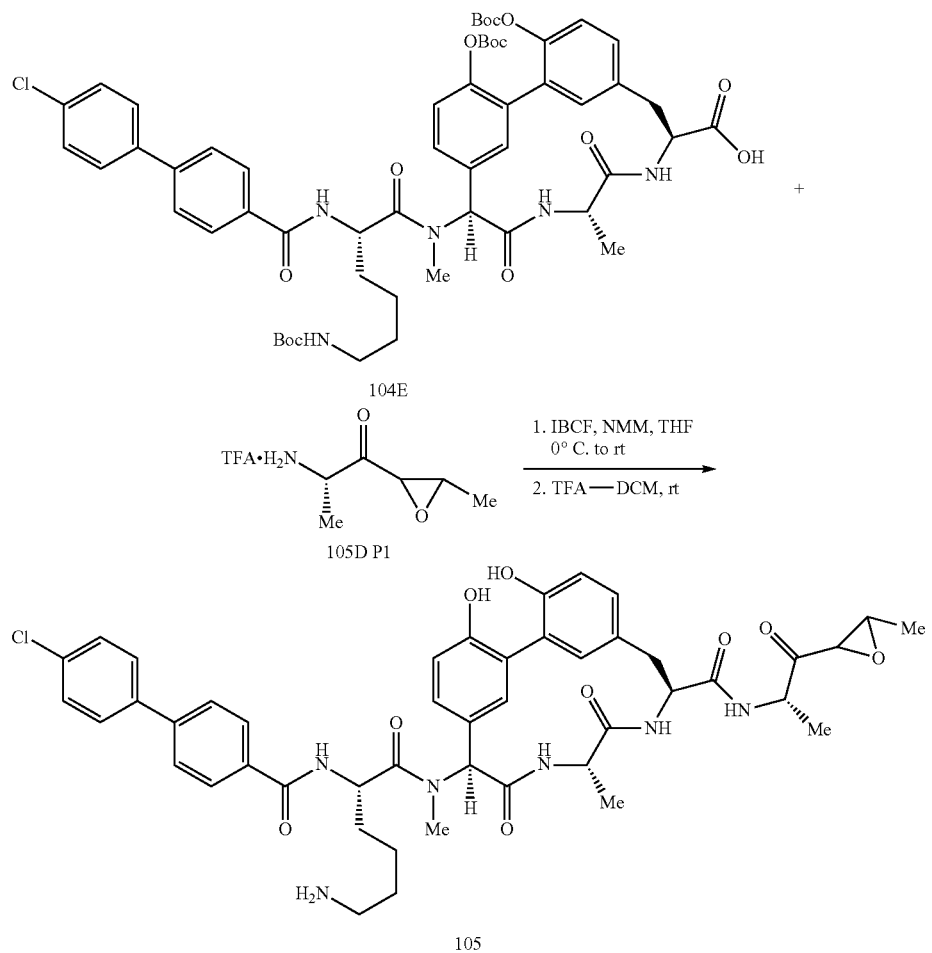
Compound 105 was synthesized from Compound 104E (64 mg, 0.06 mmol) and Compound 105D P1 (27 mg, 0.12 mmol) using General Method 6. MS (ESI) for ($C_{46}H_{51}ClN_6O_9$): m/z 867.30 (M+H)$^+$.
Example 6: Synthesis of Compound 106
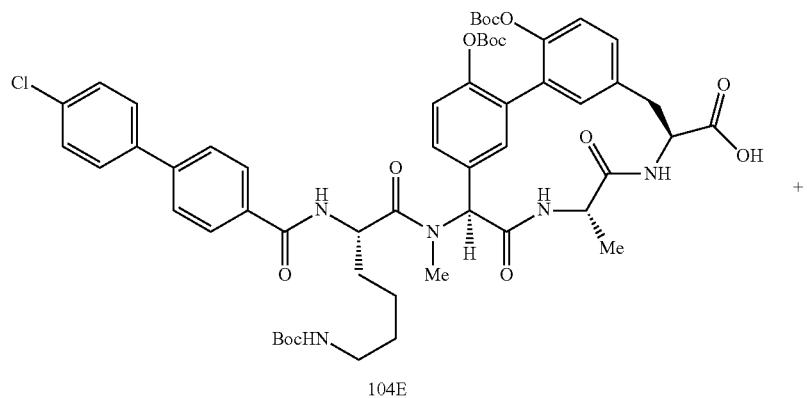

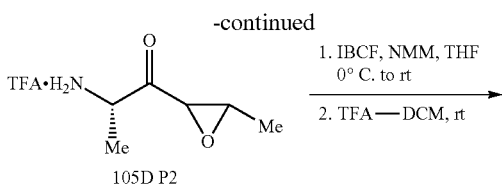

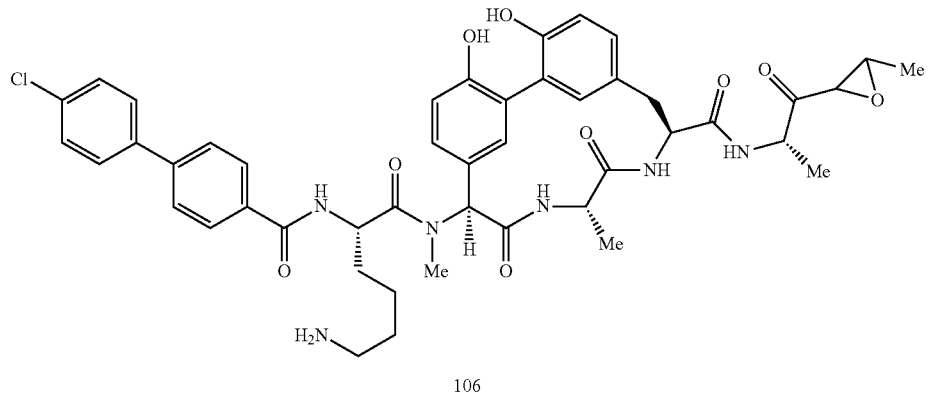

Compound 105D P2 was prepared from Compound 105C P2 according to General Method 5 and was used immediately in the next step.

Compound 106 was synthesized from Compound 104E (64 mg, 0.06 mmol) and Compound 105D P2 (27 mg, 0.12 mmol) using General Method 6. MS (ESI) for ($C_{46}H_{51}ClN_6O_9$): m/z 867.39 (M+H)$^+$.

Example 7: Synthesis of Compound 107

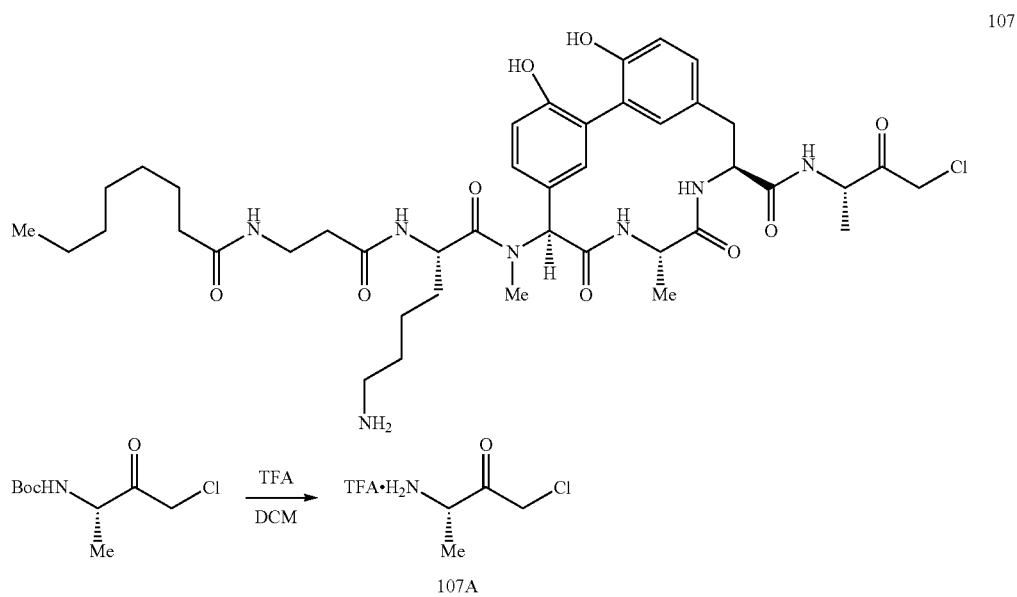

A solution of tert-butyl (S)-(4-chloro-3-oxobutan-2-yl)carbamate (9 mg, 0.05 mmol) in 1:3 TFA-DCM (1 mL) was stirred at rt for about 1 h. After completion of the reaction (monitored by TLC), the solvent was evaporated and the residue was dried under high vacuum to afford Compound 107A.

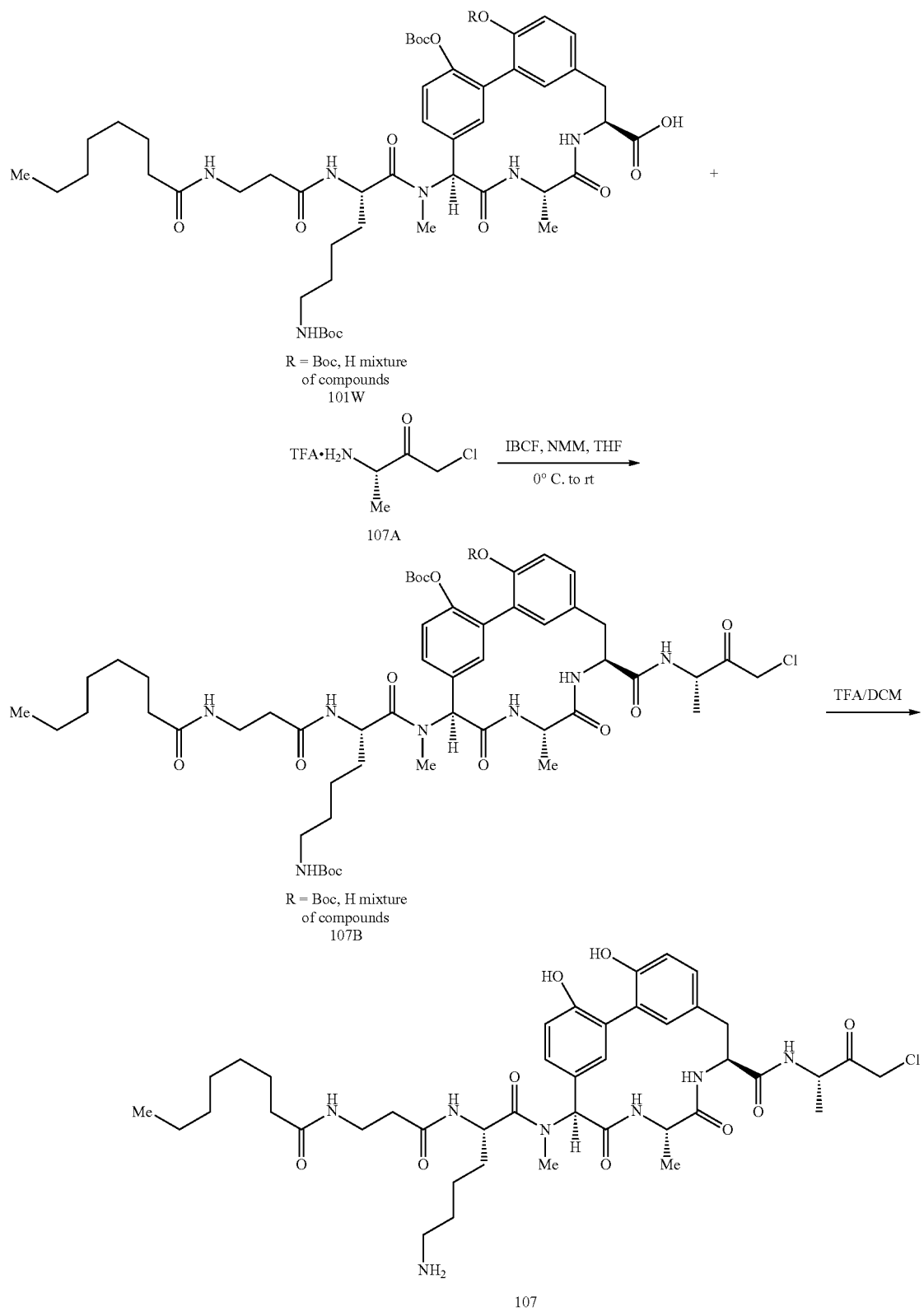

R = Boc, H mixture of compounds
101W

R = Boc, H mixture of compounds
107B

107

To a stirred solution of Compound 101W (24 mg, 0.025 mmol) in dry DMF (1 mL) was added Compound 107A (8 mg, 0.05 mmol) and HATU (20 mg, 0.05 mmol), followed by DIEA (22 μL, 0.125 mmol). The reaction mixture was stirred at rt for about 3 h. After completion of the reaction, crushed ice was added. The mixture was extracted with EtOAc and the combined organic layers washed with brine. The organic layer was dried over anhydrous $Na_2SO_4$, filtered and the solvent was removed under vacuum. The residue was purified by flash chromatography using 1:9 MeOH-DCM to give Compound 107B as a mixture of bis-boc and tris-boc products. MS (ESI) for tris-boc product ($C_{57}H_{84}ClN_7O_{15}$): m/z 1142.7 (M+H)$^+$ and bis-boc product ($C_{52}H_{76}ClN_7O_{13}$): m/z 1042.4 (M+H)$^+$.

The resultant solid was dissolved in 1:3 TFA-DCM (1 mL) and stirred at rt for about 1 to 2 h. After completion of the reaction, the solvent was evaporated and the residue dried under high vacuum. The residue was purified by prep HPLC ($CH_3CN$—$H_2O$ containing 0.05% TFA) to afford Compound 107 as a white solid. MS (ESI) for ($C_{42}H_{60}ClN_7O_9$): m/z 842.2 (M+H)$^+$.

Example 8: Synthesis of Compound 108

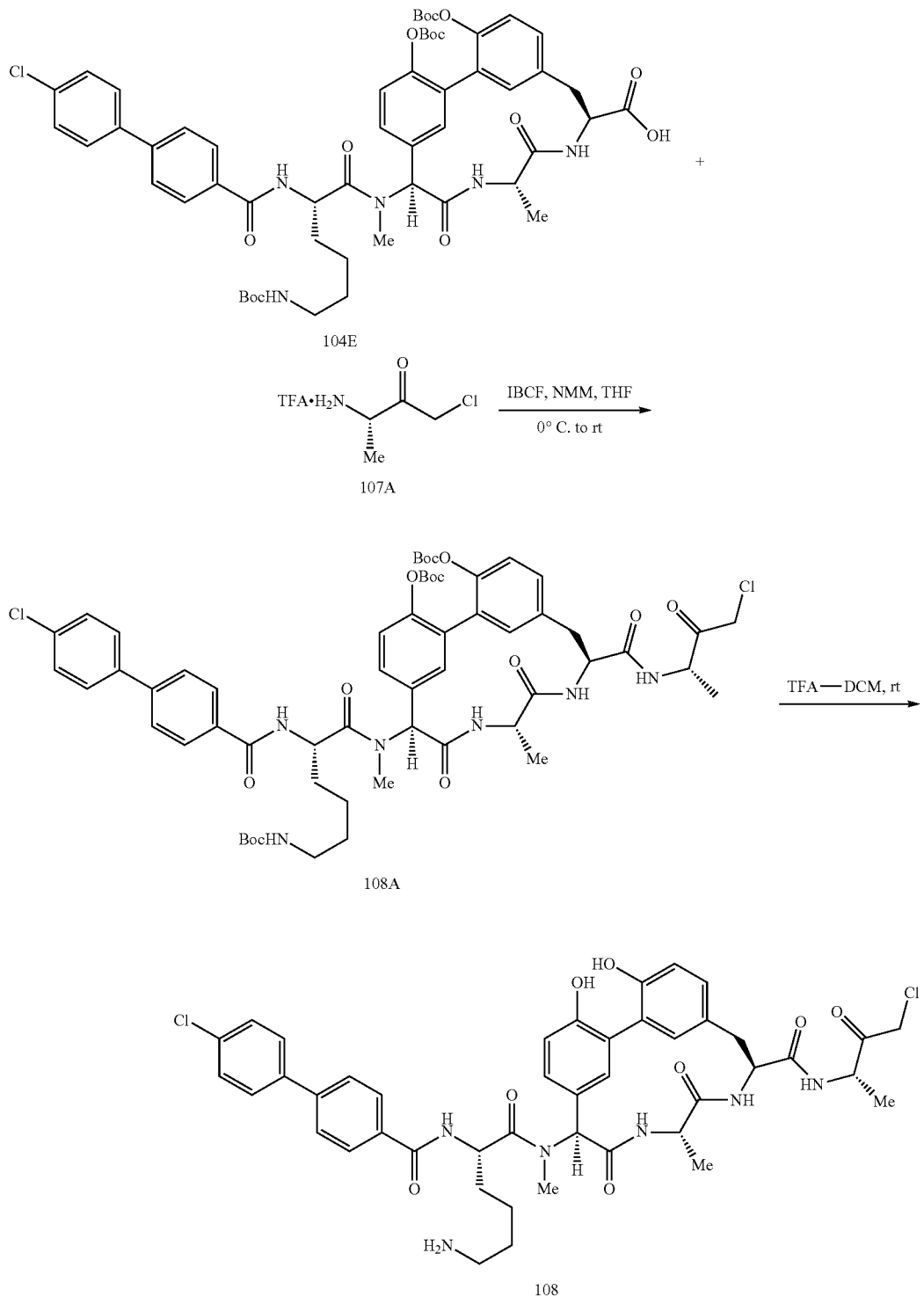

A stirred solution of Compound 104E (105 mg, 0.1 mmol) in anhydrous THF was cooled in an ice bath to 0° C. Isobutyl chloroformate (20.0 μL, 0.15 mmol) was added followed by N-methyl morpholine (56.0 μL, 0.5 mmol) under $N_2$ atm. The reaction mixture was stirred for 30 min, and then a solution of Compound 107A (44 mg, 0.2 mmol) in anhydrous THF was added. The reaction mixture was stirred for about 1 to 2 h while allowing the temp to reach rt. After completion of the reaction, the reaction mixture was quenched with saturated $NH_4Cl$ solution and diluted with brine (2 mL). The reaction mixture was extracted with EtOAc and the combined organic layers washed with brine. The combined organic layers were dried over anhydrous $Na_2SO_4$, filtered and the solvent was removed under vacuum. The residue was purified by flash chromatography using 1:9 MeOH-DCM to afford Compound 108A. MS (ESI) for ($C_{59}H_{72}Cl_2N_6O_{14}$): m/z 1159.2 (M+H)$^+$.

Compound 108A (18 mg, 0.015 mmol) was dissolved in 1:3 TFA-DCM (1 mL) and stirred at rt for about 1 to 2 h. After completion of the reaction, the solvent was evaporated and the residue was dried under high vacuum. The residue was purified by prep HPLC ($CH_3CN$—$H_2O$ containing 0.05% TFA) to afford Compound 108. MS (ESI) for ($C_{44}H_{48}Cl_2N_6O_8$): m/z 859.1 (M+H)$^+$.

Example 9: Synthesis of Compound 109 mmol) at 0° C. After 10 min, N,O-dimethylhydroxylamine (2.0 g, 21.14 mmol) in DMF (5 mL) was added to the above solution. The mixture was stirred at 15° C. for 12 h. The mixture was concentrated. The residue was by silica gel chromatography (EA/PE=3:1) to give Compound 101AA (2.2 g, 89.4%). $^1$H NMR (400 MHz, MeOH-$d_4$) δ 4.56 (brs, 1H), 3.83 (s, 3H), 3.22 (s, 3H), 1.44 (s, 9H), 1.28 (d, J=7.2, 3 H).

To a mixture of Compound 101AA (1 g, 4.31 mmol) in THF (40 mL), MeMgBr (9.2 mL, 12.9 mmol, 1.4M) was added dropwise under $N_2$ at 0° C. The solution was allowed to stir at 0° C. until TLC showed complete conversion of starting material. Water was slowly added to quench the reaction, followed by an aqueous solution of $NH_4Cl$. The aqueous layer was then extracted with EA (30 mL×3), the combined organic layers were then washed with brine, dried over $Na_2SO_4$ and concentrated to give (S)-tert-butyl (3-oxobutan-2-yl)carbamate (800 mg, 99.2%) as a yellow oil, which was used to the next step directly.

To a mixture of (S)-tert-butyl (3-oxobutan-2-yl)carbamate (800 mg, 4.27 mmol) in THF (40 mL) was added 4N HCl/EtOAc (40 mL) at 0° C. TLC showed complete consumption of starting material. The mixture was concentrated

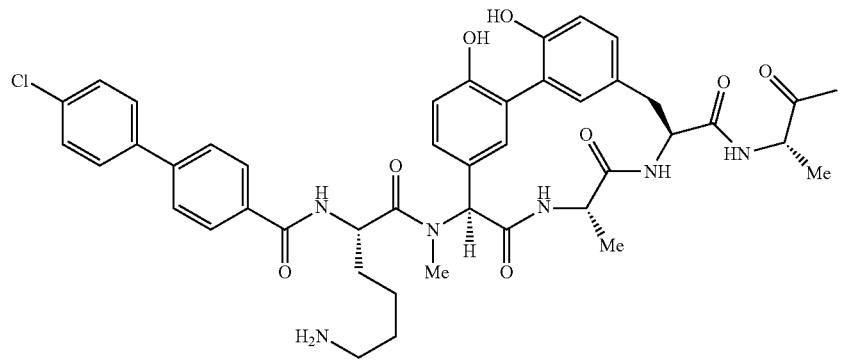

109

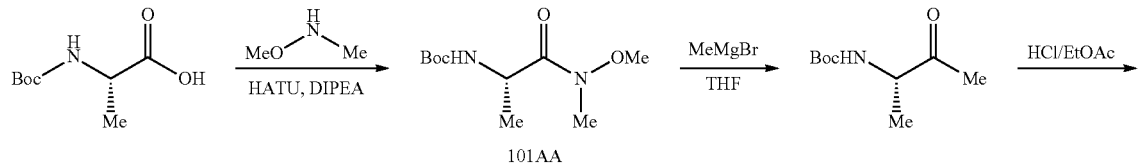

101AA

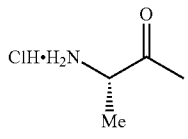

109A

To a mixture of (S)-2-((tert-butoxycarbonyl)amino)propanoic acid (2.0 g, 10.6 mmol) and HATU (8.0 g, 21.1 mmol) in DCM (15 mL) was added DIPEA (4.1 g, 31.7 to give Compound 109A (475 mg, 90%) as a light yellow solid. $^1$H NMR (400 MHz, MeOH-$d_4$) δ 4.17 (m, 1H), 2.27 (s, 3H), 1.52 (d, J=7.2, 3 H).

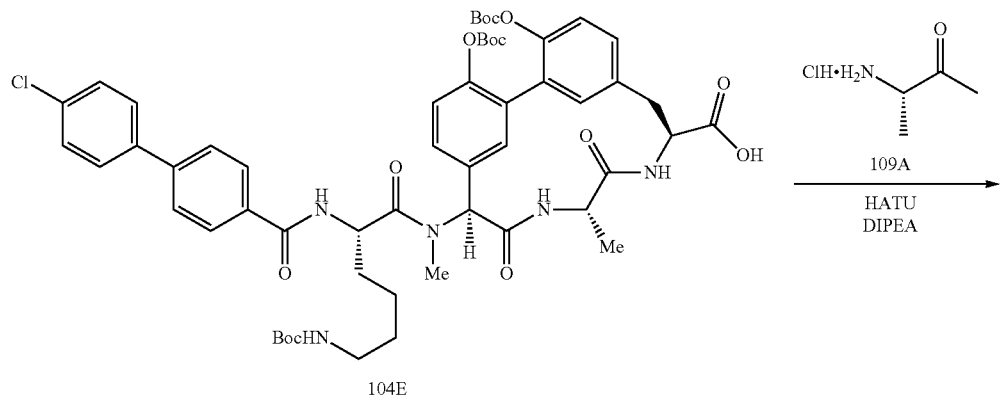
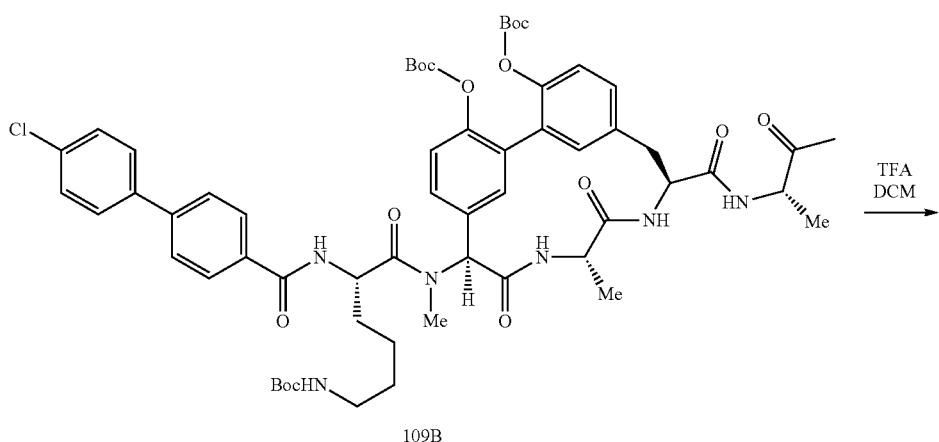
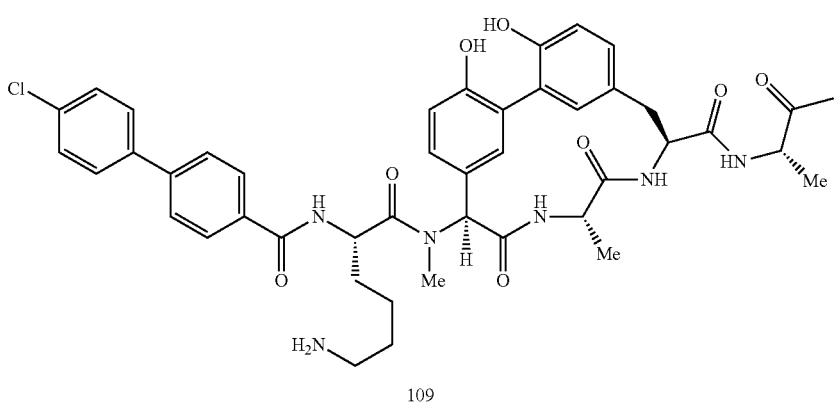
Compound 109 was prepared according to General Methods 8 and 9 from Compound 104E and Compound 109A. $^1$H NMR (400 MHz, MeOH-d$_4$) δ 8.50 (s, 1H), 7.90-7.80 (d, J=8.0 Hz, 2H), 7.70-7.60 (d, J=8.0 Hz, 2H), 7.60-7.50 (d, J=8.0 Hz, 2H), 7.50-7.40 (d, J=8.4 Hz, 2H), 7.20-7.15 (m, 1H), 7.12-7.08 (m, 1H), 7.02-6.95 (d, J=8.8 Hz, 2H), 7.93-7.80 (m, 2H), 7.75-7.65 (m, 1H), 5.10-5.00 (m, 2H), 4.90-4.80 (m, 1H), 4.70-4.55 (m, 1H), 4.50-4.38 (m, 1H), 3.30-3.15 (m, 1H), 3.02-2.88 (m, 5H), 2.25-2.15 (s, 3H), 2.10-1.85 (m, 2H), 1.80-1.70 (m, 2H), 1.68-1.50 (m, 2H), 1.42-1.20 (m, 7H). LCMS (5-95 AB, ESI): RT=0.773, M+H$^+$=825.8.

Example 10: Synthesis of Compound 110

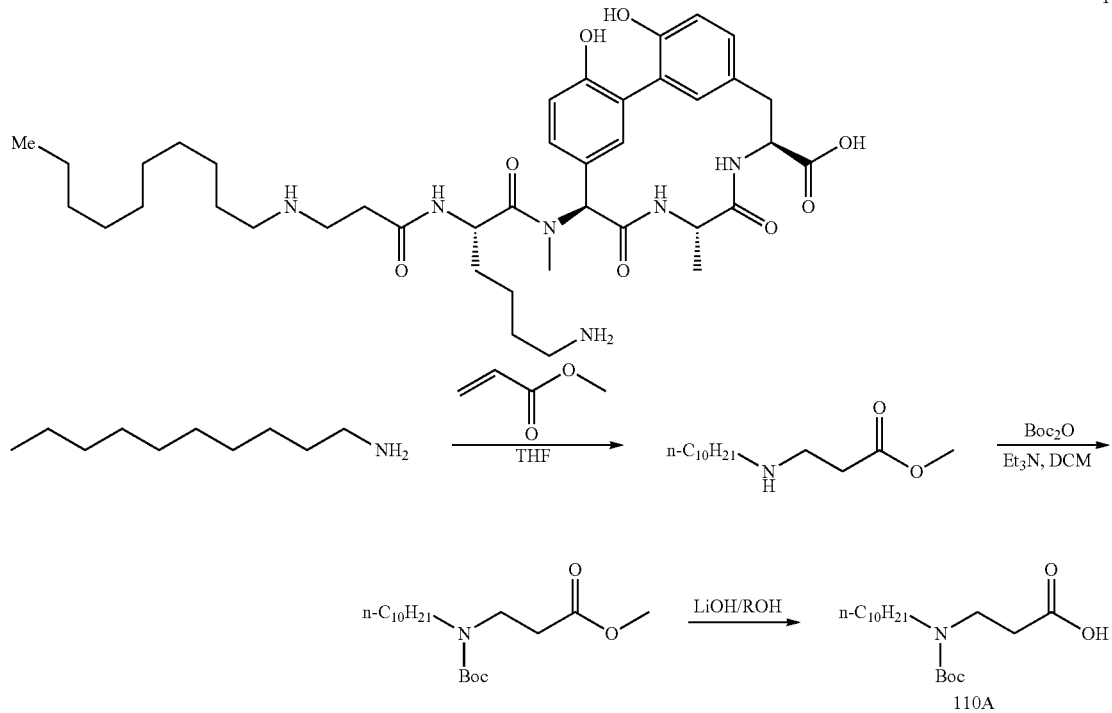

To a solution of methyl acrylate (2.2 g, 26 mmol) in THF (20 mL) was added a solution of decan-1-amine (6 g, 38 mmol) in THF (20 mL) at 0° C. The reaction mixture was stirred at 30° C. for 48 h. The resulting solution was concentrated to obtain methyl 3-(decylamino)propanoate (6.4 g).

To a solution of crude methyl 3-(decylamino)propanoate (6.4 g, 15 mmol) and Et$_3$N (4 g, 40 mmol) in DCM (30 mL) was added dropwise a solution of Boc$_2$O (5.7 g, 26 mmol) in DCM (20 mL) at 0° C. The reaction mixture was then allowed to warm to 30° C. gradually and stirred for 18 h. After the reaction was completed, H$_2$O (50 mL) was added and the resulting aqueous layer was further extracted with DCM (50 mL*2). The combined organic layers were concentrated and the residue was purified by silica gel column (PE/EtOAc=50/1-20/1) to give methyl 3-((tert-butoxycarbonyl)(decyl)amino)propanoate (6.5 g, 73%) as a colorless oil.

To a solution of methyl 3-((tert-butoxycarbonyl)(decyl)amino)propanoate (8.2 g, 23.9 mmol, crude) in EtOH (40 mL) was added a solution of LiOH (1.15 g, 48 mmol) in H$_2$O (20 mL) at 0° C. The reaction mixture was then allowed to warm to 30° C. gradually and stirred for 18 h. After the reaction was complete, EtOH was removed under reduced pressure. The remaining aqueous solution was then adjusted to pH=2-3 with 6N HCl, followed by the extraction with EtOAc (50 mL*3). The combined EtOAc layers were dried over Na$_2$SO$_4$, and concentrated to give Compound 110A (7 g, 88.6%) as a colorless oil. $^1$H NMR (400 MHz, CDCl$_3$) δ 3.47-3.43 (t, J=6.8 Hz, 2H), 3.19-3.15 (t, J=7.2 Hz, 2H), 2.61 (brs, 2H), 1.51-1.39 (m, 11H), 1.24-1.22 (m, 14H), 0.88-0.84 (t, J=6.8 Hz, 3H).

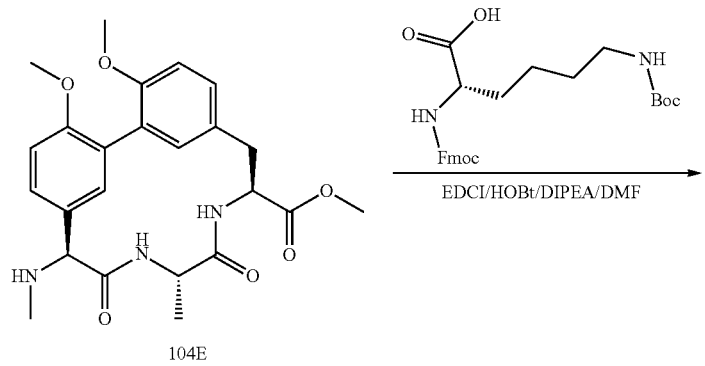

-continued
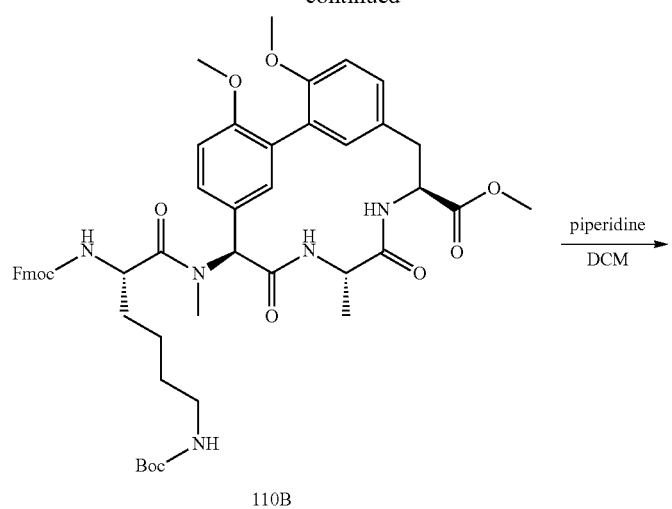
110B
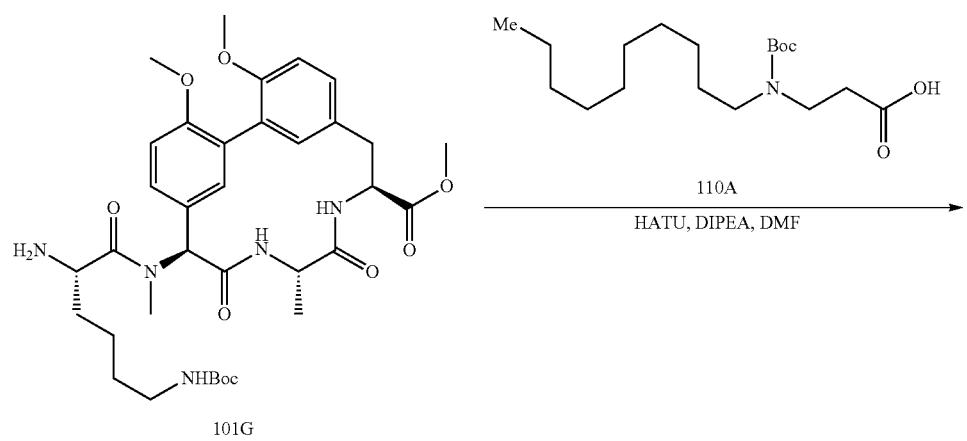
101G
110A
HATU, DIPEA, DMF
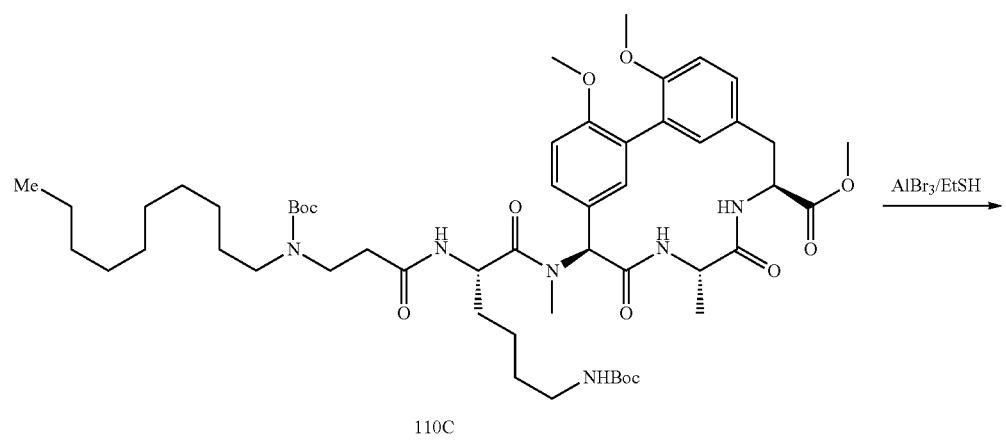
110C
AlBr₃/EtSH

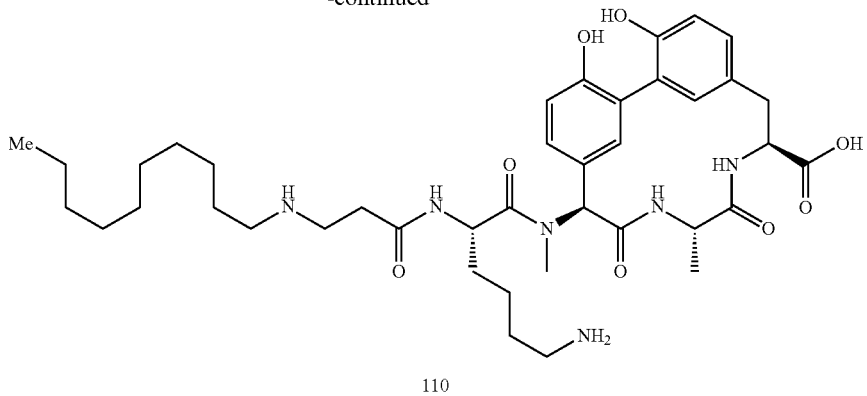

110

To a solution of Compound 104E (1.03 g, 0.61 mmol), (S)-2-((((9H-fluoren-9-yl)methoxy) carbonyl)amino)-6-((tert-butoxycarbonyl)amino)hexanoic acid (1.27 g, 3.04 mmol) and DIPEA (0.87 g, 6.78 mmol) in DMF (20 mL) at 0° C., was added EDCI (1.30 g, 6.78 mmol) and HOBt (0.92 g, 6.78 mmol). The reaction mixture was stirred at 20° C. for 10 hr. After the reaction was complete, water (20 mL) was added to the reaction mixture at 0° C. The precipitate was filtered and then washed with water and dried. The residue was purified by silica gel column (DCM/MeOH=70/1) to give Compound 110B (550 mg, 27%).

To a solution of Compound 110B (550 mg, 0.607 mmol) in DCM (5 mL) was added piperidine (258 mg, 3.03 mmol). The solution was stirred at 25° C. for 3 h. The mixture was concentrated under reduced pressure, and the residue was washed with PE. DCM (40 mL) was added and the solution was washed with saturated NH$_4$Cl (40 mL) and water (40 mL). The organic layer was dried and concentrated to give the residue, which was purified by silica gel column (DCM/MeOH=50/1) to give Compound 101G (380 mg, 92%) as a white solid.

To a solution of Compound 101G (1 g, 1.46 mmol) in DMF (3 mL), was added Compound 110A (0.963 g, 2.92 mmol) and DIPEA (0.37 g, 2.92 mmol). After mixing at 0° C. for 10 mins, HATU (1.11 g, 2.92 mmol) was added and the reaction was stirred at rt for 16 hr. The reaction mixture was suspended in water (30 mL) and DCM (30 mL) and the aqueous layer was further extracted with DCM (20 mL*2). The combined organic layers were concentrated and the residue was purified by silica gel column (DCM/MeOH=80/1-50/1) to give Compound 110C (700 mg, 48.2%) as a yellow solid.

Compound 110 was prepared from Compound 110C according to General Method 4 except the reaction was conducted at room temperature for 16 h to afford Compound 110 as the formic acid salt. $^1$H NMR (400 MHz, DMSO-d$_6$) δ 8.50 (brs, 1H), 8.45 (brs, 1H), 8.29 (brs, 1H), 6.92-6.62 (m, 6H), 6.32 (s, 1H), 4.76 (brs, 1H), 4.62 (brs, 1H), 4.35 (s, 2H), 3.20-3.16 (m, 12H, mixed in water peak), 2.94 (s, 3H), 2.72 (s, 6H), 1.62-1.50 (m, 6H), 1.32-1.17 (m, 16H), 0.82-0.80 (m, 3H). LCMS (5-95 AB, 1.5 min, ELSD): RT=0.743, M+H$^+$=753.3.

Example 11: Synthesis of Compound 111

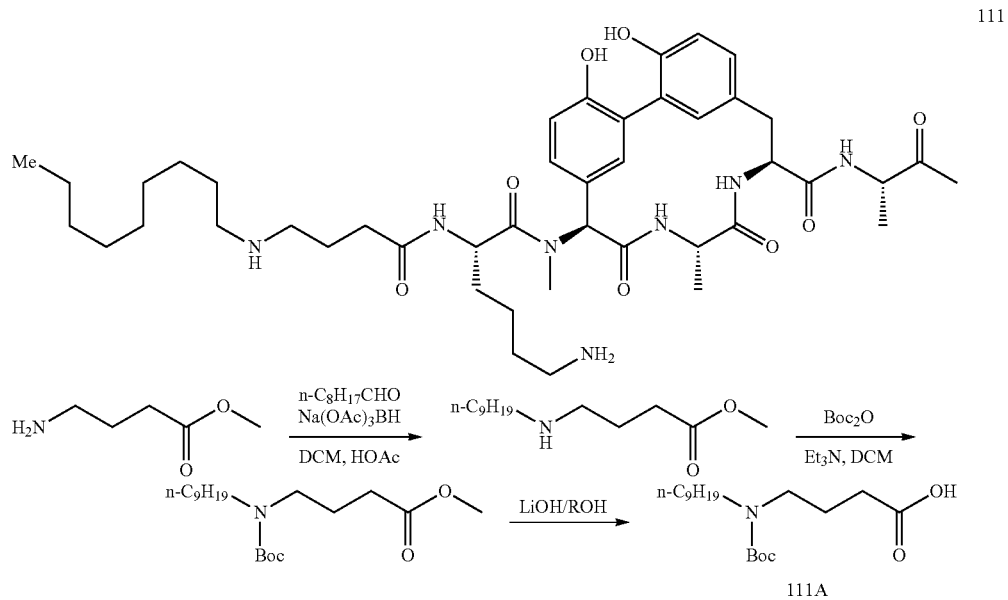

To a solution of nonanal (600 mg, 4.22 mmol) in DCM (25 mL) at 0° C. was added methyl 4-aminobutanoate (988 mg, 8.44 mmol) and HOAc (1 mL), followed by the addition of NaBH$_3$CN (398 mg, 2 mmol). The mixture was stirred at 15° C. for 12 h. After the reaction was complete, H$_2$O (20 mL) was added and the aqueous layer was extracted by DCM (30 mL*2). The combined organic layers were concentrated to obtain methyl 4-(nonylamino) butanoate.

The N-Boc formation and LiOH ester hydrolysis was performed in a manner similar to Example 10 to afford 0.46 g of Compound 111A. ELSD-LC/MS 352.3 [M+Na$^+$].

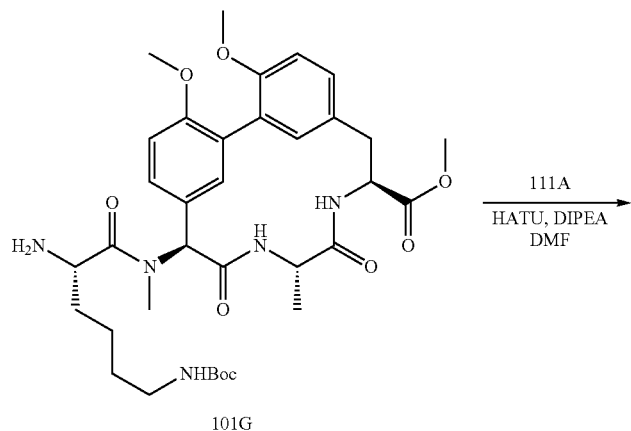

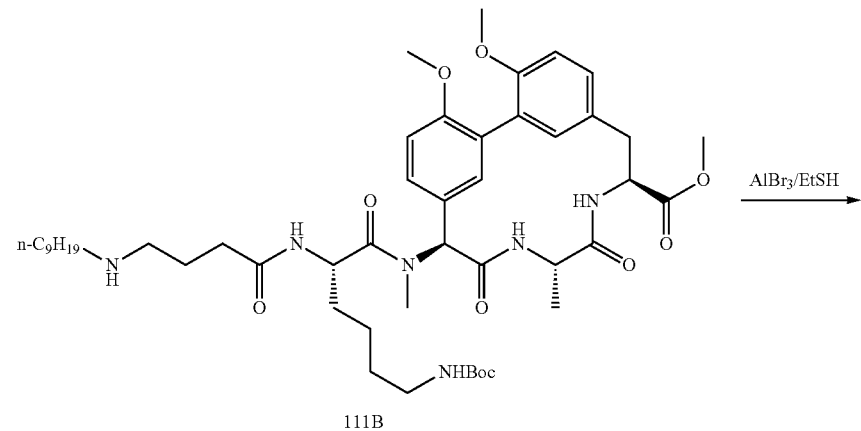

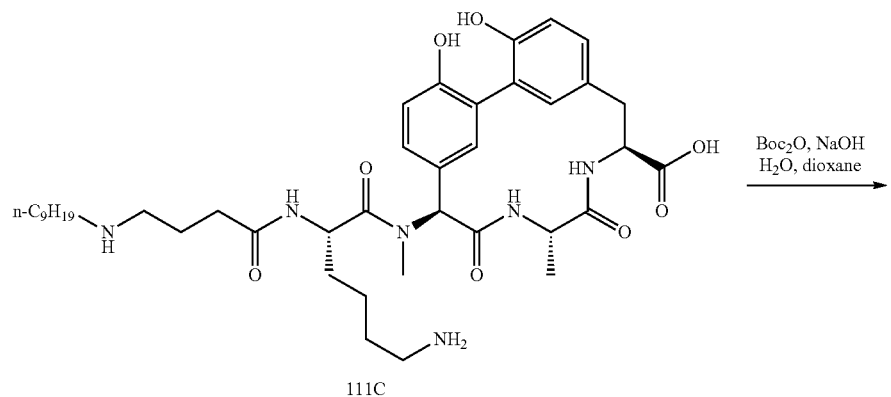

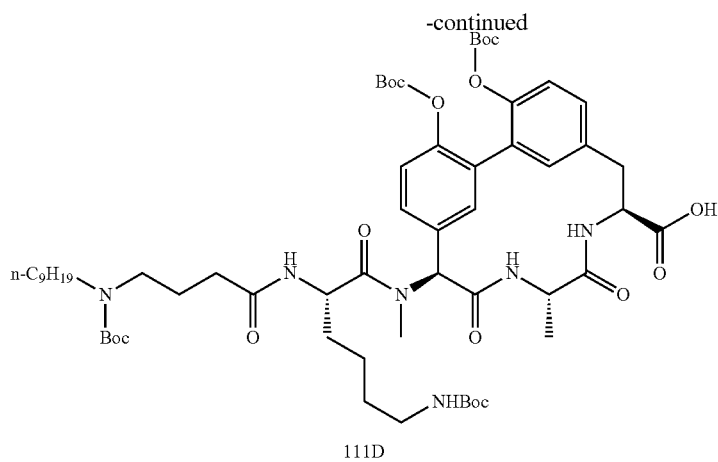

111D

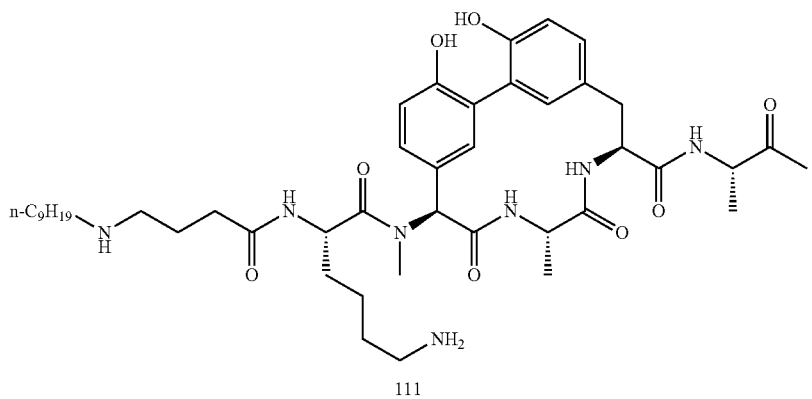

111

To a solution of Compound 111A (88 mg, 0.26 mmol) in DCM (5 mL), was added HATU (167 mg, 0.44 mmol) and Compound 101G (150 mg, 0.22 mmol) at 0° C., followed by the addition of DIPEA (85 mg, 0.66 mmol). The reaction mixture was stirred at 15° C. for 12 h. After the reaction was complete, H$_2$O (20 mL) was added and the mixture was extracted by DCM (20 mL*2). The combined organic layers were concentrated and the residue was purified by Prep-TLC to afford Compound 111B (150 mg, 68.8%) as a light yellow solid.

Compound 111C was prepared from Compound 111B according to General Method 4 except the reaction was conducted at room temperature for 16 h to afford Compound 111C.

To a solution of Compound 111C (50 mg, 0.066 mmol) in dioxane (5 mL) was added 1M NaOH (1.33 mL) at 0° C., followed by the addition of Boc$_2$O (145 mg, 0.664 mmol). The mixture was stirred at 15° C. for 12 h. After the reaction was complete, THF was removed from the resulting mixture under the reduced pressure. The remaining aqueous solution was then adjusted to pH=3 with citric acid, followed by extraction with DCM. The organic layer was dried over Na$_2$SO$_4$ and concentrated to give Compound 111D (50 mg, 65.3%) as a white solid.

Compound 111 was prepared from Compound 111D and Compound 109A using General Methods 8 and 9 to give Compound 111 as a formic acid salt. $^1$H NMR (400 MHz, MeOH-d$_4$) δ 7.20-7.16 (d, J=8.4 Hz, 1H), 7.15-7.10 (d, J=8.4 Hz, 1H), 7.10-7.00 (m, 2H), 7.00-6.95 (d, J=8.0 Hz, 1H), 6.95-6.85 (d, J=8.0 Hz, 1H), 6.52-6.45 (m, 1H), 4.90-4.80 (m, 1H), 4.70-4.55 (m, 2H), 4.50-4.35 (m, 1H), 3.20-3.08 (m, 1H), 3.05-2.92 (m, 6H), 2.91 (s, 3H), 2.43 (s, 2H), 2.22 (s, 3H), 2.00-1.85 (m, 3H), 1.85-1.65 (m, 5H), 1.62-1.48 (m, 2H), 1.45-1.20 (m, 19H), 0.92-0.80 (t, J$_1$=6.4 Hz, J$_2$=7.2 Hz, 3H). LCMS (5-95 AB, ESI): RT=0.743, M+H$^+$=822.8.

Example 12: Synthesis of Compound 112

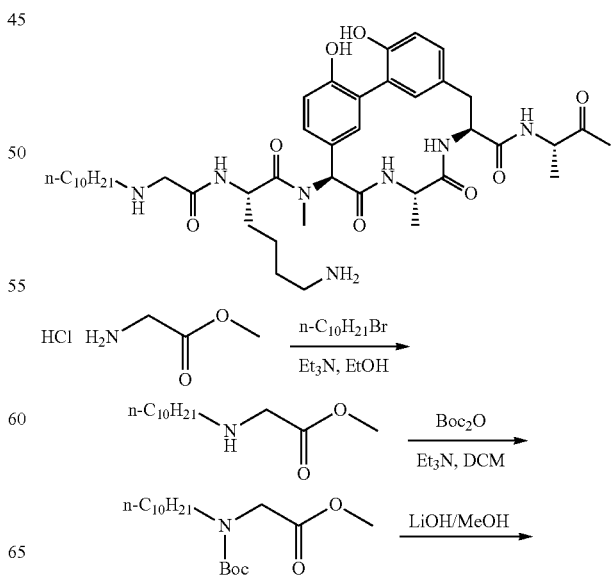

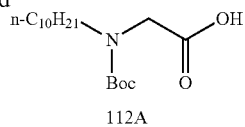

112A

To a solution of decan-1-amine (10.5 g, 66.8 mmol) in anhydrous dichloromethane (250 mL) was added triethylamine (13.5 g, 133.5 mmol) at 0° C. and the reaction mixture was stirred at 0° C. for 30 min. Methyl bromoacetate (10.2 g, 66.8 mmol) was then added dropwise at 0° C., and the reaction mixture was stirred at room temperature for 14 h. The solution containing methyl 2-(decylamino)acetate was used directly for the next step.

The N-Boc formation and LiOH ester hydrolysis was performed in a manner similar to Example 10, to afford 1.1 g of Compound 112A. $^1$H NMR (400 MHz, CDCl$_3$) δ 3.96 (s, 1H), 3.89 (s, 1H), 3.25-3.23 (m, 2H), 1.50-1.41 (m, 11H), 1.25 (m, 14H), 0.88-0.85 (t, J=6.8 Hz, 3H).

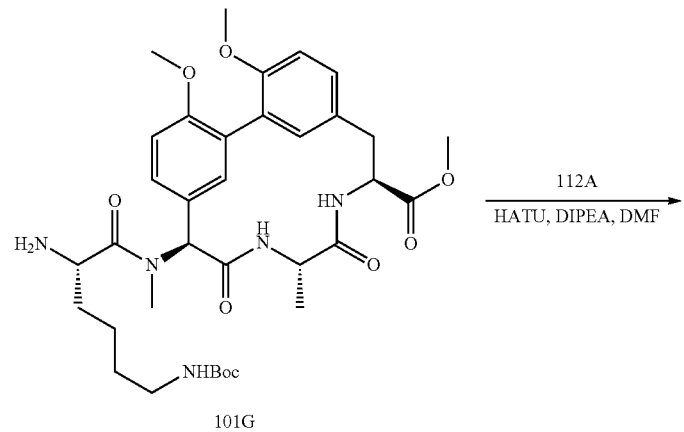

101G

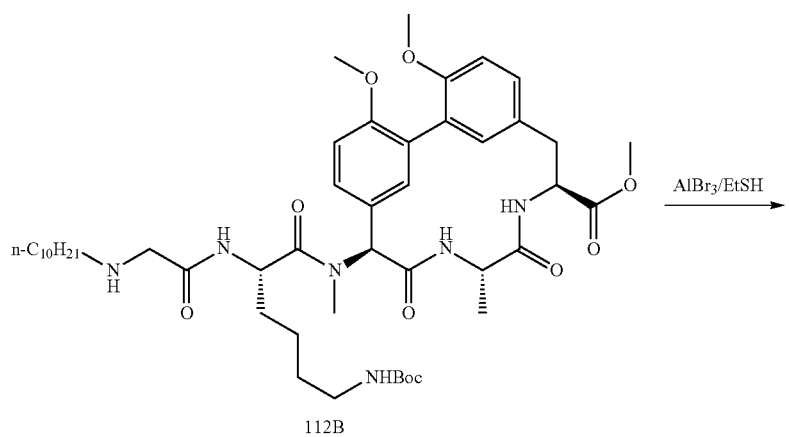

112B

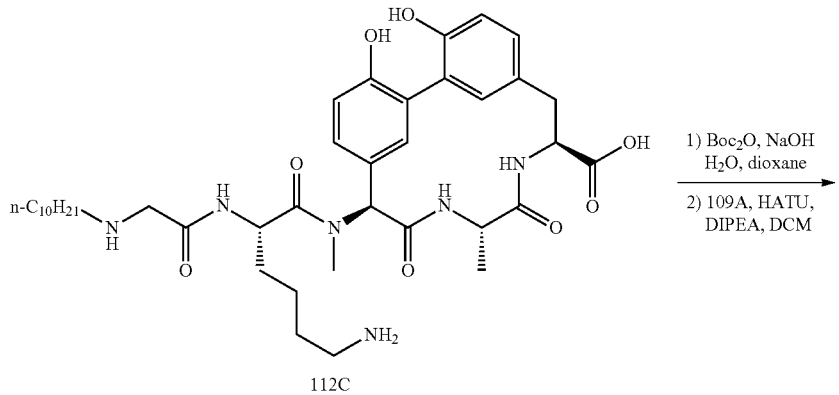

112C

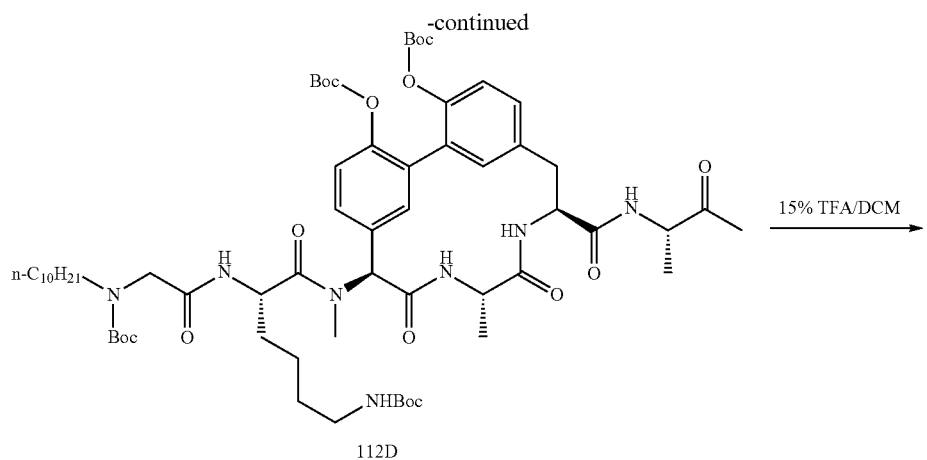
112D
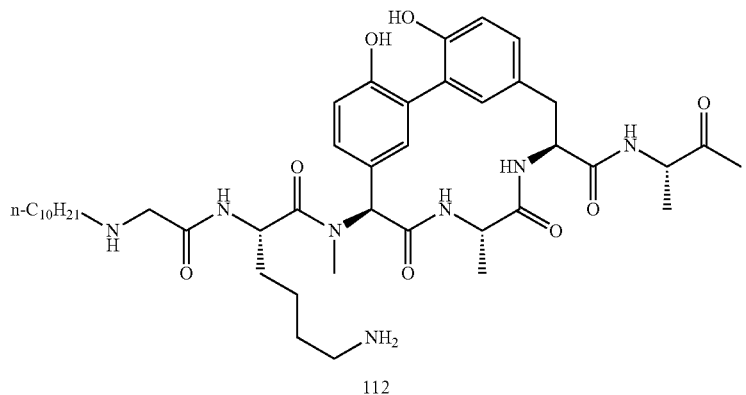
112
Compound 112 was prepared in a manner similar to Compound 111 except that Compound 112A was utilized in the synthesis. $^1$H NMR (400 MHz, MeOH-d$_4$) δ 0.88 (t, J=6.60 Hz, 3H), 1.18-1.46 (m, 21H), 1.52 (br. s., 3H), 1.69 (br. s., 6H), 1.90 (d, J=14.18 Hz, 2H), 2.12-2.23 (m, 3H), 2.88 (s, 3H), 2.93 (t, J=7.46 Hz, 3H), 2.99-3.05 (m, 2H), 3.85 (br. s., 2H), 4.37-4.44 (m, 1H), 6.38 (s, 1H), 6.87 (d, J=8.31 Hz, 1H), 6.93 (d, J=8.31 Hz, 1H), 7.00 (br. s., 2H), 7.06-7.14 (m, 2H). LCMS (5-95 AB, ESI): RT=0.769, M+H$^+$=808.4.
Example 13: Synthesis of Compound 113
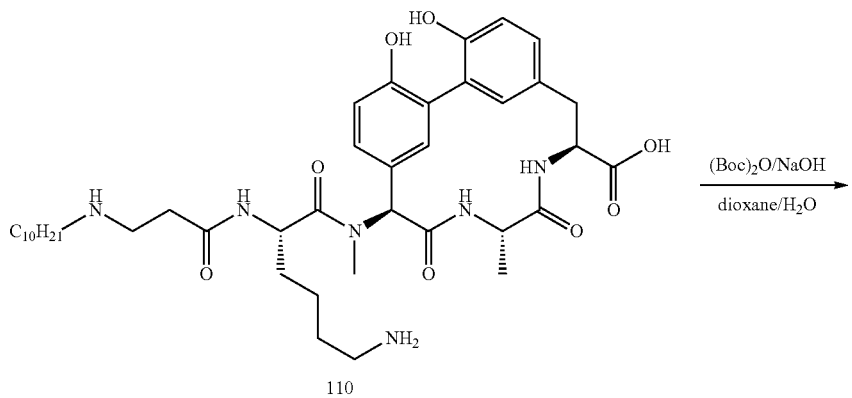
110

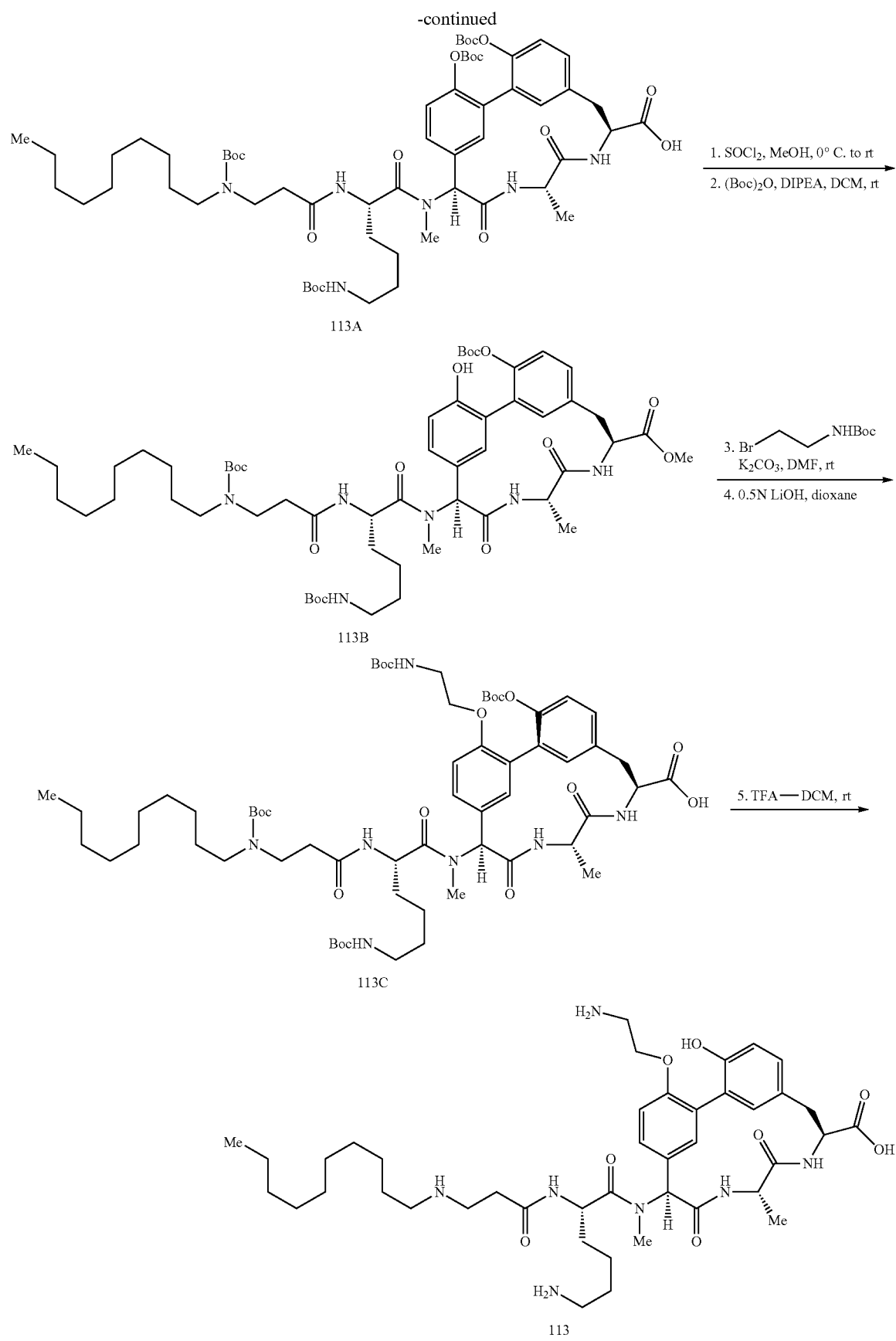

To a solution of Compound 110 (1.5 g, 1.99 mmol) in dioxane (60 mL), (Boc)$_2$O (10.8 g, 49.8 mmol) was added at 0° C., followed by the addition of 1N NaOH (60 mL) at the same temperature. The solution was kept at 35° C. for 72 h. After the reaction was complete, the mixture was concentrated and the residue was purified by HPLC (0.1% TFA) to give Compound 113A (890 mg, 40%) as a white solid. $^1$H NMR (400 MHz, MeOH-d$_4$) δ 8.26 (s, 1H), 7.29-7.22 (m, 3H), 7.09-7.07 (m, 1H), 6.97-6.94 (d, J=12.0 Hz, 2H), 6.43 (s, 1H), 4.92 (m, 1H), 4.78-4.71 (m, 4H), 3.51-3.45 (m, 3H), 3.23-3.18 (m, 3H), 3.03-3.01 (m, 2H), 2.87 (s, 3H), 2.52-2.49 (m, 2H), 1.46 (m, 2H), 1.40-1.39 (m, 2H), 1.35 (s, 15H), 1.33-1.32 (m, 16H), 1.28 (m, 24H), 0.90-0.87 (m, 3H). LCMS (5-95 AB, ESI): RT=1.201, M+Na$^+$=1176.7.

To a stirred solution of Compound 113A (230 mg, 0.2 mmol) in dry MeOH (5 mL) at 0° C., was slowly added SOCl$_2$ (0.2 mL) was added slowly dropwise. The reaction mixture was stirred at rt overnight. The solvent was removed under reduced pressure and the residue was dried under high vacuum and used as it is in the next reaction. LCMS: MS (ESI) for C$_{41}$H$_{63}$N$_6$O$_8$: m/z 767.0 (M+H)$^+$.

The above residue (0.2 mmol) was dissolved in CH$_2$Cl$_2$ (10 mL) and Et$_3$N (167 μL, 1.2 mmol, 6 eq). To this stirred solution was added (Boc)$_2$O (160 μL, 0.7 mmol, 3.5 eq). The reaction mixture was stirred at rt overnight. After the reaction was complete, brine solution was added and the mixture was extracted with ethyl acetate. The combined organic layers were washed with brine, dried over anhydrous Na$_2$SO$_4$, filtered and the solvent was removed under reduced pressure. The residue was purified by flash chromatography (DCM-5% DCM-MeOH) to afford 158 mg (76%, over 2 steps) of Compound 113B as a white solid. MS (ESI) for (C$_{56}$H$_{87}$N$_6$O$_{14}$): m/z 1067.4 (M+H)$^+$.

To a stirred solution of Compound 113B (160 mg, 0.15 mmol) in dry DMF (5 mL) was added K$_2$CO$_3$ (42 mg, 0.3 mmol, 2 eq) followed by tert-butyl (2-bromoethyl)carbamate (100 mg, 0.45 mmol). The reaction mixture was stirred at rt overnight. After completion of the reaction, crushed ice was added and the resultant white cloudy mixture was extracted with EtOAc. The combined organic layers washed with brine, dried over anhydrous Na$_2$SO$_4$, filtered and the solvent was removed under vacuum. The residue was purified by flash chromatography (DCM-5% DCM-MeOH) to afford 152 mg (83%) of the desired compound as a white solid. MS (ESI) for (C$_{63}$H$_{100}$N$_7$O$_{16}$): m/z 1210.5 (M+H)$^+$.

The above material (151 mg, 0.125 mmol) was dissolved in dioxane-H$_2$O (3:1, 2 mL) and 0.5 M LiOH solution (750 μL, 0.375 mmol) was added at 0° C. and the reaction mixture was stirred at rt for 2 h. After completion of the reaction, water (2 mL) was added and the reaction mixture was extracted with ether. The aqueous layer acidified with 0.5 M HCl. The resultant white cloudy mixture was extracted with EtOAc. The combined organic layers washed with brine, dried over anhydrous Na$_2$SO$_4$, filtered and the solvent was removed. The residue was dried under high vacuum to afford 120 mg (80%) of Compound 113C as a white solid. MS (ESI) for (C$_{62}$H$_{97}$N$_7$O$_{16}$): m/z 1196.4 (M+H)$^+$.

A solution of Compound 113C (12 mg, 0.01 mmol) in 1:3 TFA-DCM (1 mL) was stirred at rt for about 1 to 2 h. After completion of the reaction, the solvent was evaporated and the residue dried under high vacuum. The residue was purified by prep HPLC (CH$_3$CN—H$_2$O containing 0.05% TFA) to afford Compound 113 as a white solid. MS (ESI) for (C$_{42}$H$_{65}$N$_7$O$_8$): m/z 796.3 (M+H)$^+$.

Example 14: Synthesis of Compound 114

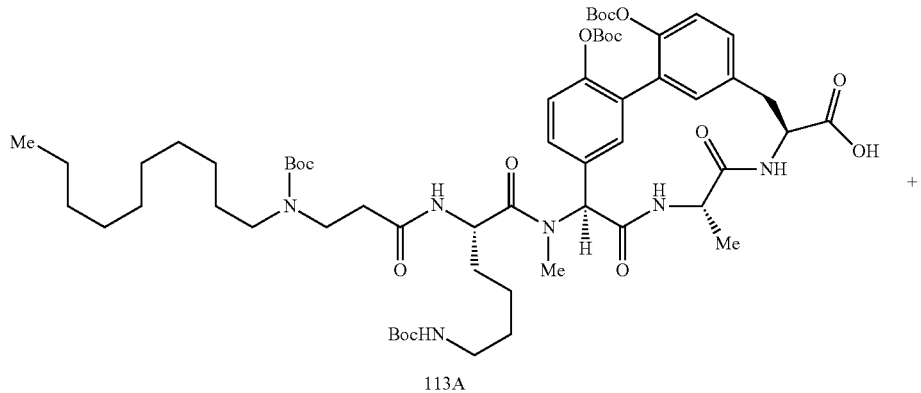

113A

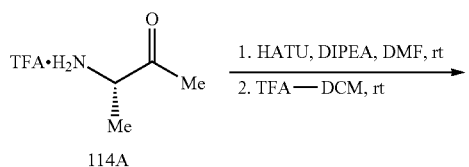

114A

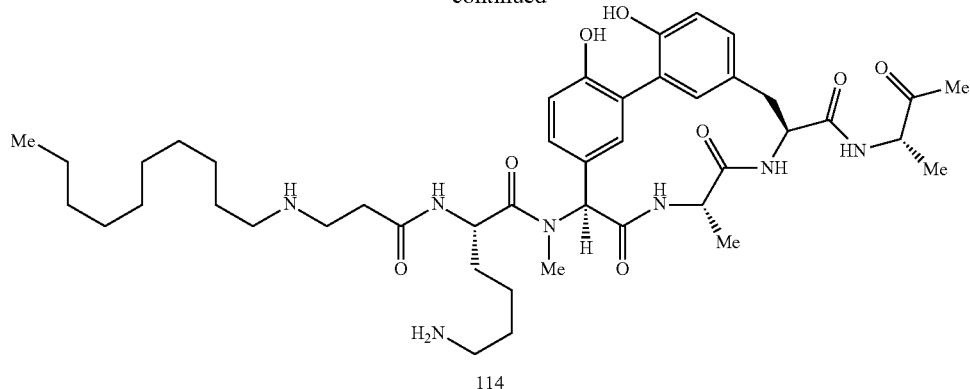

114

To a stirred solution of Compound 113A (30 mg, 0.026 mmol) in dry DMF (1 mL) was added Compound 114A (11 mg, 0.052 mmol), HATU (25 mg, 0.065 mmol) followed by DIPEA (23 μL, 0.13 mmol). The reaction mixture was stirred at rt for about 2 h. After completion of the reaction, crushed ice was added and the resultant white solid was collected by filtration and dried under high vacuum. MS (ESI) for ($C_{64}H_{99}N_7O_{16}$): m/z 1222.5 (M+H)$^+$.

The resultant solid was dissolved in 1:3 TFA-DCM (1 mL) and stirred at rt for about 1 to 2 h. After completion of the reaction, the solvent was evaporated and the residue dried under high vacuum. The residue was purified by prep HPLC ($CH_3CN$—$H_2O$ containing 0.05% TFA) to afford Compound 114 as a white solid. MS (ESI) for ($C_{44}H_{67}N_7O_8$): m/z 822.2 (M+H)$^+$.

Example 15: Synthesis of Compound 115

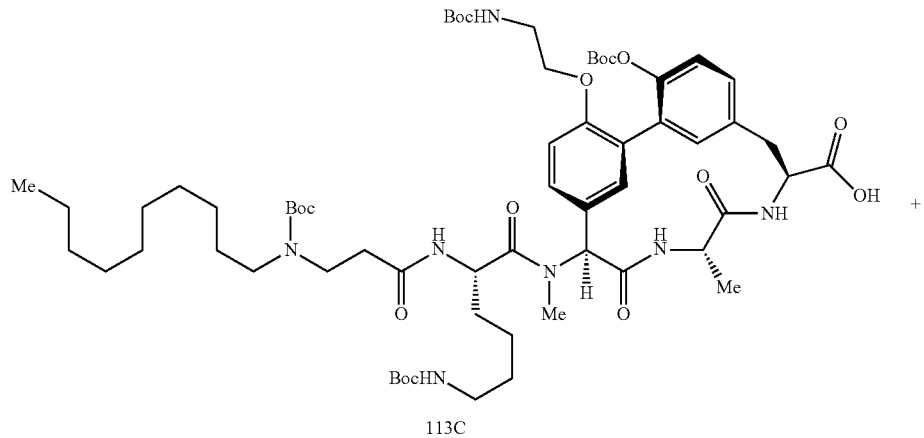

113C

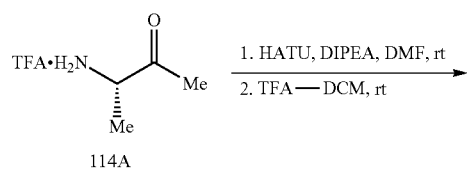

114A

1. HATU, DIPEA, DMF, rt
2. TFA—DCM, rt

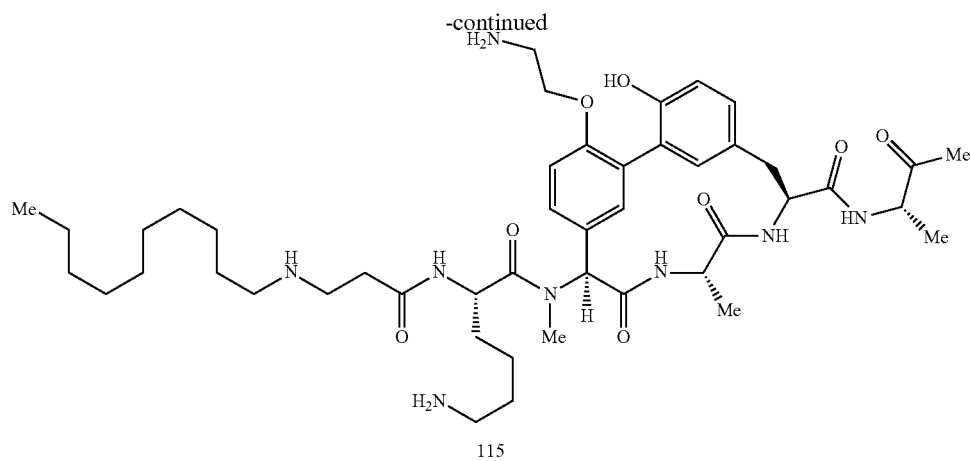

115

To a solution of Compound 113C (32 mg, 0.026 mmol) in dry DMF (1 mL) was added Compound 114D (11 mg, 0.052 mmol) and HATU (25 mg, 0.065 mmol) followed by DIPEA (23 μL, 0.13 mmol). The reaction mixture was stirred at rt for about 2 h. After completion of the reaction, crushed ice was added and the resultant white solid was collected by filtration and dried under high vacuum. MS (ESI) for ($C_{66}H_{104}N_8O_{16}$): m/z 1265.7 (M+H)$^+$.

The resultant solid was dissolved in 1:3 TFA-DCM (1 mL) and stirred at rt for about 1 to 2 h. After completion of the reaction, the solvent was evaporated and the residue dried under high vacuum. The residue was purified by prep HPLC (CH$_3$CN—H$_2$O containing 0.05% TFA) to afford Compound 115 as a white solid. MS (ESI) for ($C_{46}H_{72}N_8O_8$): m/z 865.13 (M+H)$^+$.

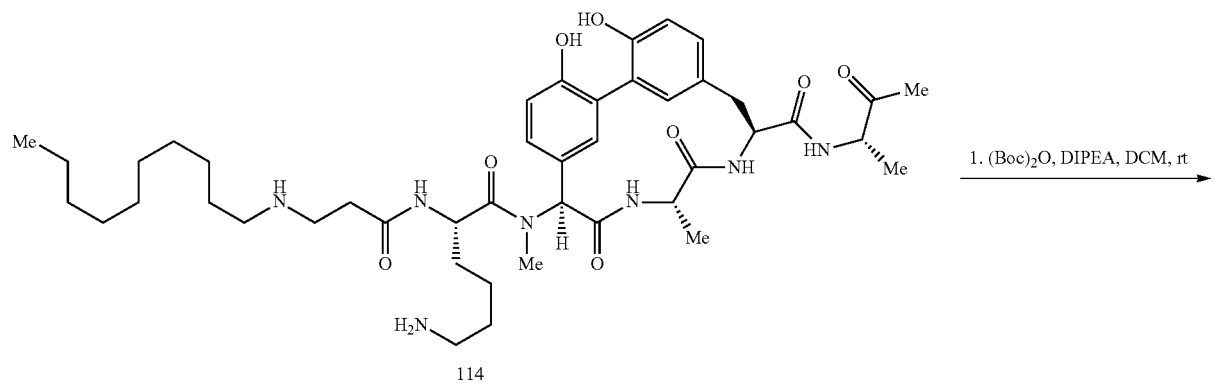

114

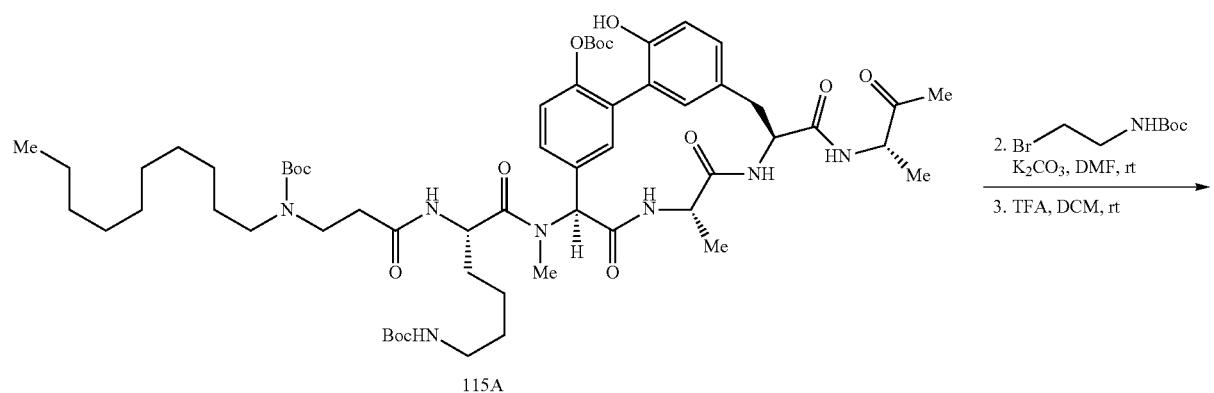

115A

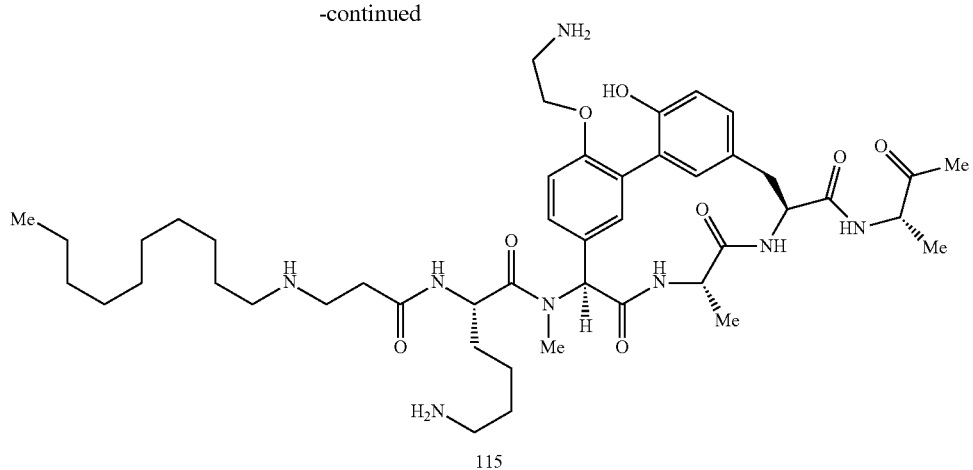

115

Alternate Synthesis

To a stirred solution of Compound 114 (82 mg, 0.1 mmol) dissolved in $CH_2Cl_2$ (5 mL) and $Et_3N$ (84 µL, 0.6 mmol, 6 eq) was added $(Boc)_2O$ (80 µL, 0.35 mmol, 3.5 eq). The reaction mixture was stirred at rt overnight. After the reaction was complete, brine solution was added and the mixture was extracted with ethyl acetate. The combined organic layers were washed with brine, dried over anhydrous $Na_2SO_4$, filtered and the solvent was removed under reduced pressure. The residue was purified by flash chromatography (DCM-5% DCM-MeOH) to afford 86 mg (77%) of Compound 115A as a white solid. MS (ESI) for ($C_{59}H_{91}N_7O_{14}$): m/z 1122.5 (M+H)$^+$.

To a stirred solution of Compound 115A (84 mg, 0.075 mmol) in dry DMF (2 mL) was added $K_2CO_3$ (21 mg, 0.15 mmol) followed by tert-butyl (2-bromoethyl)carbamate (50 mg, 0.225 mmol). The reaction mixture was stirred at rt overnight. After completion of the reaction, crushed ice was added and the resultant off white solid was collected by filtration and dried under vacuum to afford 58 mg (62%) of the desired compound. MS (ESI) for ($C_{66}H_{104}N_8O_{16}$): m/z 1265.5 (M+H)$^+$.

The resultant solid was dissolved in 1:3 TFA-DCM (1 mL) and stirred at rt for about 1 to 2 h. After completion of the reaction, the solvent was evaporated and dried under high vacuum. The residue was purified by prep HPLC ($CH_3CN$—$H_2O$ containing 0.05% TFA) to afford Compound 115 as a white solid. MS (ESI) for ($C_{46}H_{72}N_8O_8$): m/z 865.01 (M+H)$^+$.

Example 16: Synthesis of Compound 116

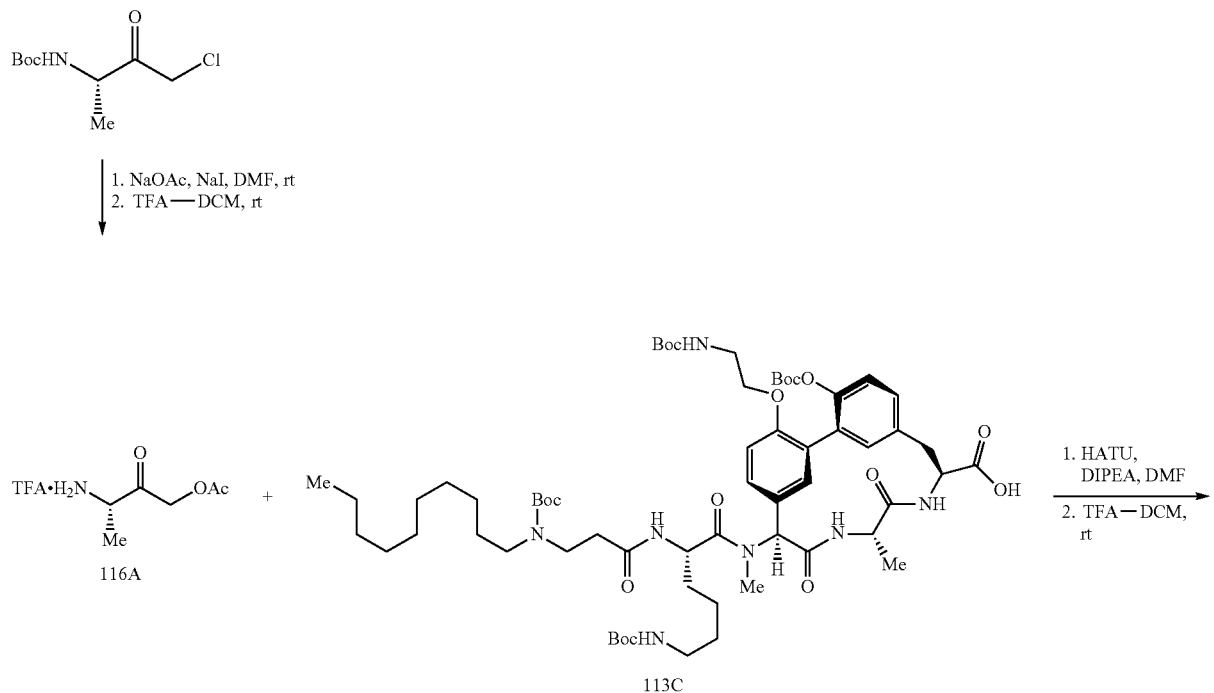

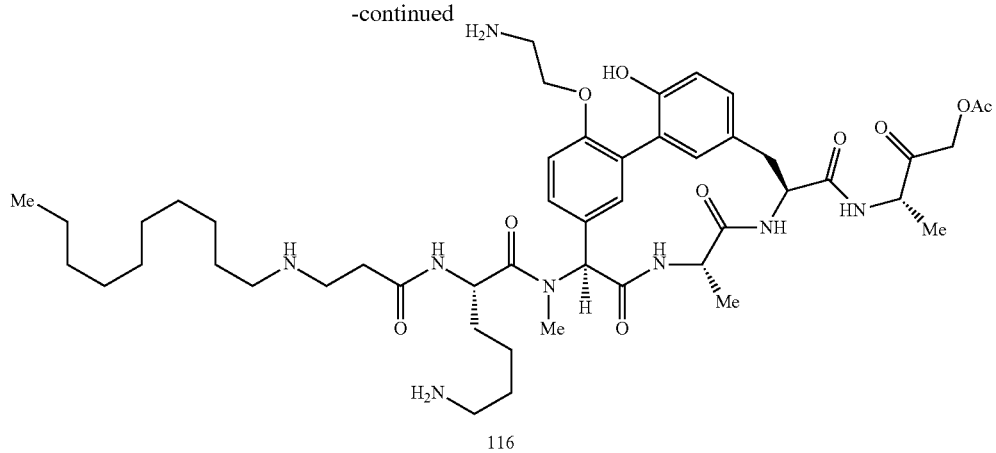

116

To a stirred solution of tert-butyl (S)-(4-chloro-3-oxobutan-2-yl)carbamate (221 mg, 1.0 mmol) in dry DMF (2 mL) was added NaOAc (123 mg, 1.5 mmol) and NaI (180 mg, 1.2 mmol). The reaction mixture was stirred at rt overnight. After completion of the reaction (monitored by TLC), crushed ice was added and the resultant white solid was collected by filtration and dried under vacuum to afford 130 mg (52%) of Compound 116A. MS (ESI) for ($C_6H_{1l}NO_3$): m/z 146.1 (M+H-Boc)$^+$.

To a solution of Compound 113C (24 mg, 0.02 mmol) in dry DMF (1 mL) was added Compound 116A (10 mg, 0.04 mmol) and HATU (20 mg, 0.05 mmol) followed by DIPEA (17 μL, 0.1 mmol). The reaction mixture was stirred at rt for about 5 h. After completion of the reaction, crushed ice was added. The reaction mixture was extracted with EtOAc and the combined organic layers washed with brine. The organic layer dried over anhydrous $Na_2SO_4$, filtered and the solvent was removed under vacuum. The residue was purified by flash chromatography using DCM-5% DCM-MeOH. MS (ESI) for ($C_{68}H_{106}N_8O_{10}$): m/z 1323.6 (M+H)$^+$.

The resultant residue was dissolved in 1:3 TFA-DCM (1 mL) and stirred at rt for about 1 to 2 h. After completion of the reaction, the solvent was evaporated and dried under high vacuum. The residue was purified by prep HPLC ($CH_3CN$—$H_2O$ containing 0.05% TFA) to afford Compound 116 as a white solid. MS (ESI) for ($C_{48}H_{74}N_8O_{10}$): m/z 923.5 (M+H)$^+$.

Example 17: Synthesis of Compound 117

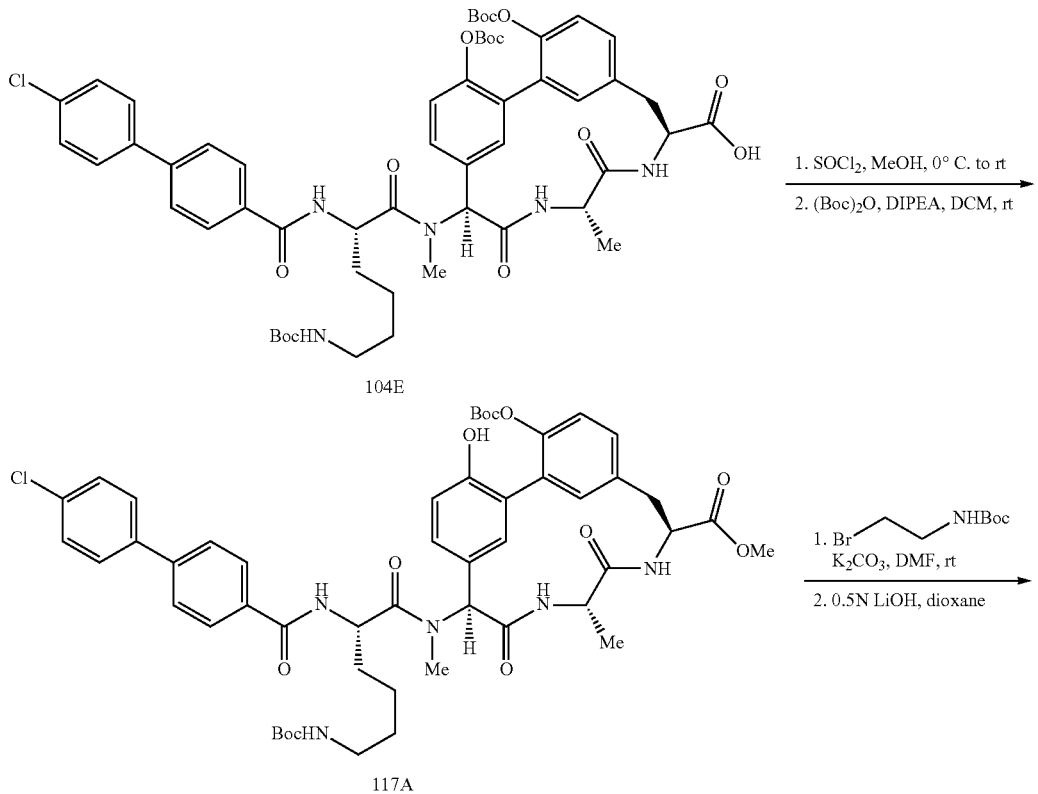

-continued

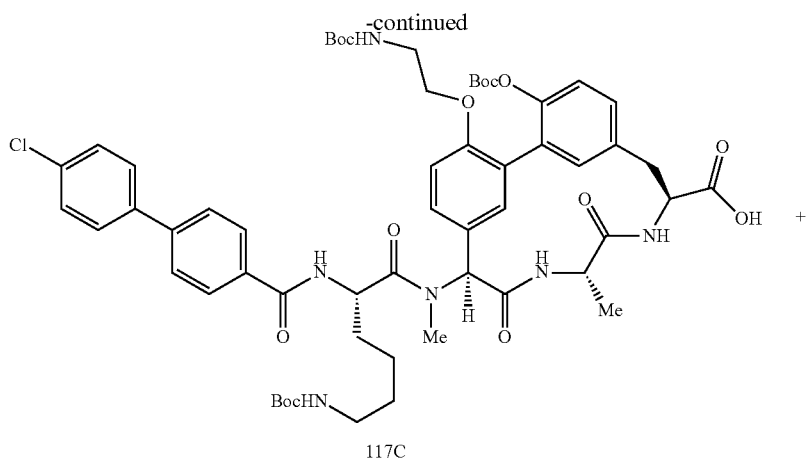

117C

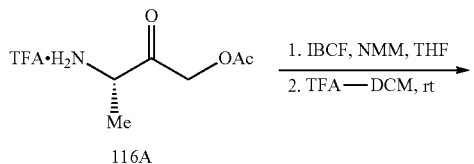

116A

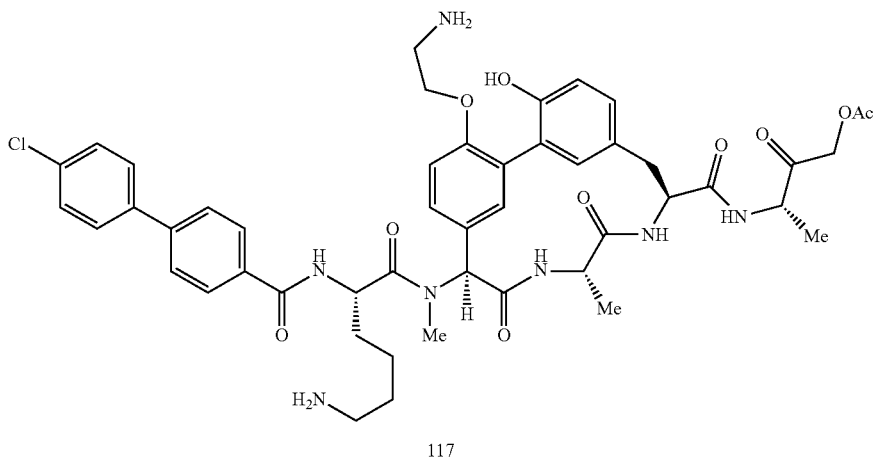 [SMILES: CC(=O)OCC(=O)[C@H](C)NC(=O)[C@@H]1Cc2ccc(O)c(c2)-c2cc(ccc2OCCN)[C@H](N(C)C(=O)[C@H](CCCCN)NC(=O)c2ccc(-c3ccc(Cl)cc3)cc2)C(=O)N[C@@H](C)C(=O)N1]

117

To a stirred solution of Compound 104E (211 mg, 0.2 mmol) in dry MeOH (5 mL) at 0° C., was slowly added $SOCl_2$ (0.2 mL) dropwise. The reaction mixture was stirred at rt overnight. The solvent was removed under reduced pressure and the residue was dried under high vacuum and used directly in the next reaction. LCMS: MS (ESI) for $C_{41}H_{44}ClN_5O_8$: m/z 770.1 (M+H)$^+$.

The above residue (0.3 mmol) was dissolved in $CH_2Cl_2$ (8 mL) and $Et_3N$ (140 μL, 1.0 mmol, 5 eq), to this stirred solution was added $(Boc)_2O$ (106 μL, 0.46 mmol, 2.3 eq). The reaction mixture was stirred at rt overnight. After the reaction was complete, brine solution was added and the mixture was extracted with ethyl acetate. The combined organic layers washed with brine, dried over anhydrous $Na_2SO_4$, filtered and solvent was removed under reduced pressure. The residue was purified by flash chromatography (DCM-5% DCM-MeOH) to afford 152 mg (78%, over 2 steps) of Compound 117A as a white solid. MS (ESI) for $(C_{51}H_{60}ClN_5O_{12})$: m/z 970.2 (M+H)$^+$.

To a stirred solution of Compound 117A (145 mg, 0.15 mmol) in dry DMF (5 mL) was added $K_2CO_3$ (42 mg, 0.3 mmol, 2 eq) followed by tert-butyl (2-bromoethyl)carbamate (100 mg, 0.45 mmol). The reaction mixture was stirred at rt overnight. After completion of the reaction, crushed ice was added and the resultant white cloudy mixture was extracted with EtOAc. The combined organic layers were washed with brine and dried over anhydrous $Na_2SO_4$, filtered and the solvent was removed under vacuum. The residue was purified by flash chromatography (DCM-5% DCM-MeOH) to afford 118 mg (71%) of the desired compound as a white solid. MS (ESI) for $(C_{58}H_{73}ClN_6O_{14})$: m/z 1113.4 (M+H)$^+$.

The above material (77 mg, 0.07 mmol) was dissolved in dioxane-H₂O (3:1, 2 mL) and 0.5 M LiOH solution (42 µL, 0.21 mmol) was added at 0° C. The reaction mixture was stirred at rt for 2 h. After completion of the reaction, water (2 mL) was added and the resultant mixture was extracted with ether. The aqueous layer acidified with 0.5 M HCl. The resultant white cloudy mixture was extracted with EtOAc. The combined organic layers were washed with brine and dried over anhydrous Na₂SO₄, filtered and the solvent was removed. The residue was dried under high vacuum to afford 64 mg (84%) of Compound 117C as a white solid. MS (ESI) for ($C_{57}H_{71}ClN_6O_{14}$): m/z 1099.3 (M+H)⁺.

Compound 117C (22 mg, 0.02 mmol) was dissolved in anhydrous THF and was cooled to 0° C. in ice bath. Isobutyl chloroformate (6.0 µL, 0.04 mmol) followed by N-Methyl morpholine (12.0 µL, 0.1 mmol) was added under N₂ atm. The reaction mixture was stirred for 30 min, and then a solution of Compound 116A (14 mg, 0.05 mmol) in anhydrous THF was added. The reaction mixture was stirred for about 1 to 2 h while allowing the temp to reach to rt. After completion of the reaction, the reaction mixture was quenched with saturated NH₄Cl solution and diluted with brine (2 mL). The mixture was extracted with EtOAc and the combined organic layers washed with brine. The organic layer was dried over anhydrous Na₂SO₄, filtered and the solvent was removed under vacuum. The residue was purified by flash chromatography using 1:9 MeOH-DCM. MS (ESI) for ($C_{63}H_{80}ClN_7O_{16}$): m/z 1226.3 (M+H)⁺.

The residue was dissolved in 1:3 TFA-DCM and stirred at rt for about 1 to 2 h. After completion of the reaction, the solvent was evaporated and the residue dried under high vacuum. The residue was purified by prep HPLC (CH₃CN—H₂O containing 0.05% TFA) to afford Compound 117. MS (ESI) for ($C_{48}H_{56}ClN_7O_{10}$): m/z 926.3 (M+H)⁺.

Example 18: Synthesis of Compound 118

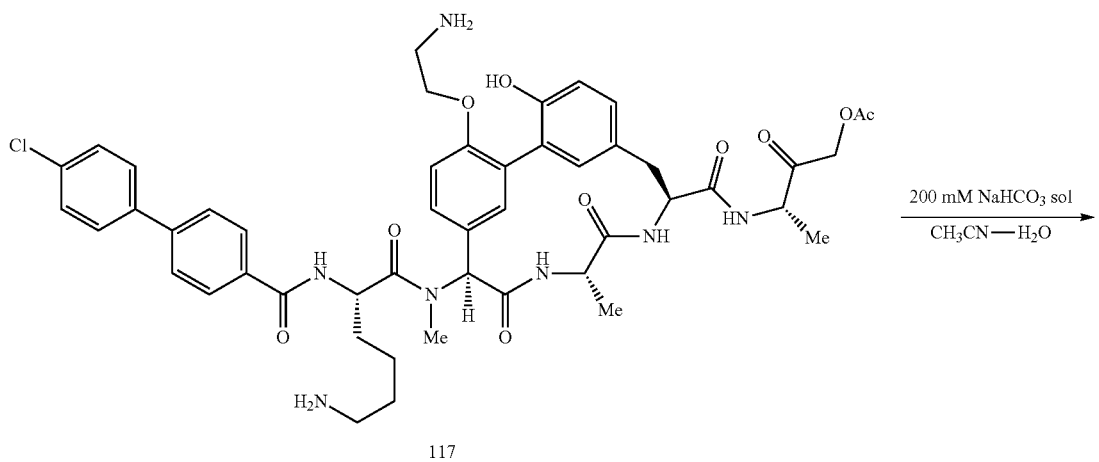

117

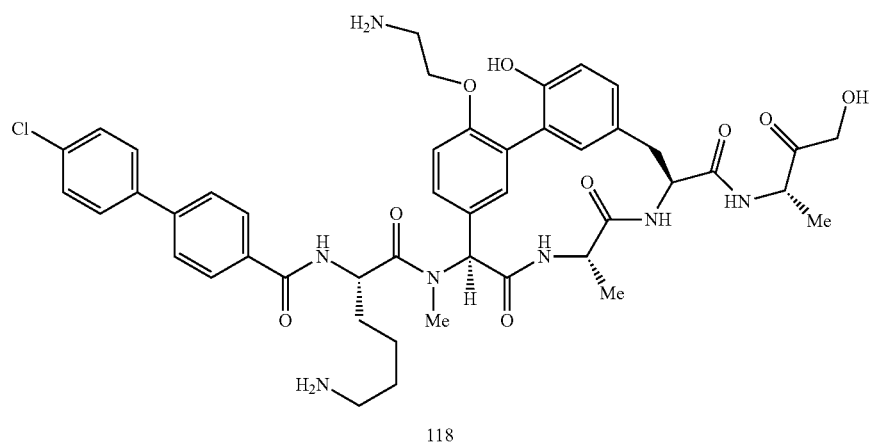

118

To a stirred solution of Compound 117 (10 mg, 0.01 mmol) in THF (1 mL) was added a solution of NaHCO₃ (20 mM solution, 500 µL). The reaction mixture was stirred at rt for about 6 h. After completion of the reaction, the THF was evaporated and the resultant mixture purified by prep HPLC (CH₃CN—H₂O containing 0.05% TFA) to afford Compound 118. MS (ESI) for ($C_{46}H_{54}ClN_7O_9$): m/z 884.4 (M+H)⁺.

Example 19: Synthesis of Compound 119

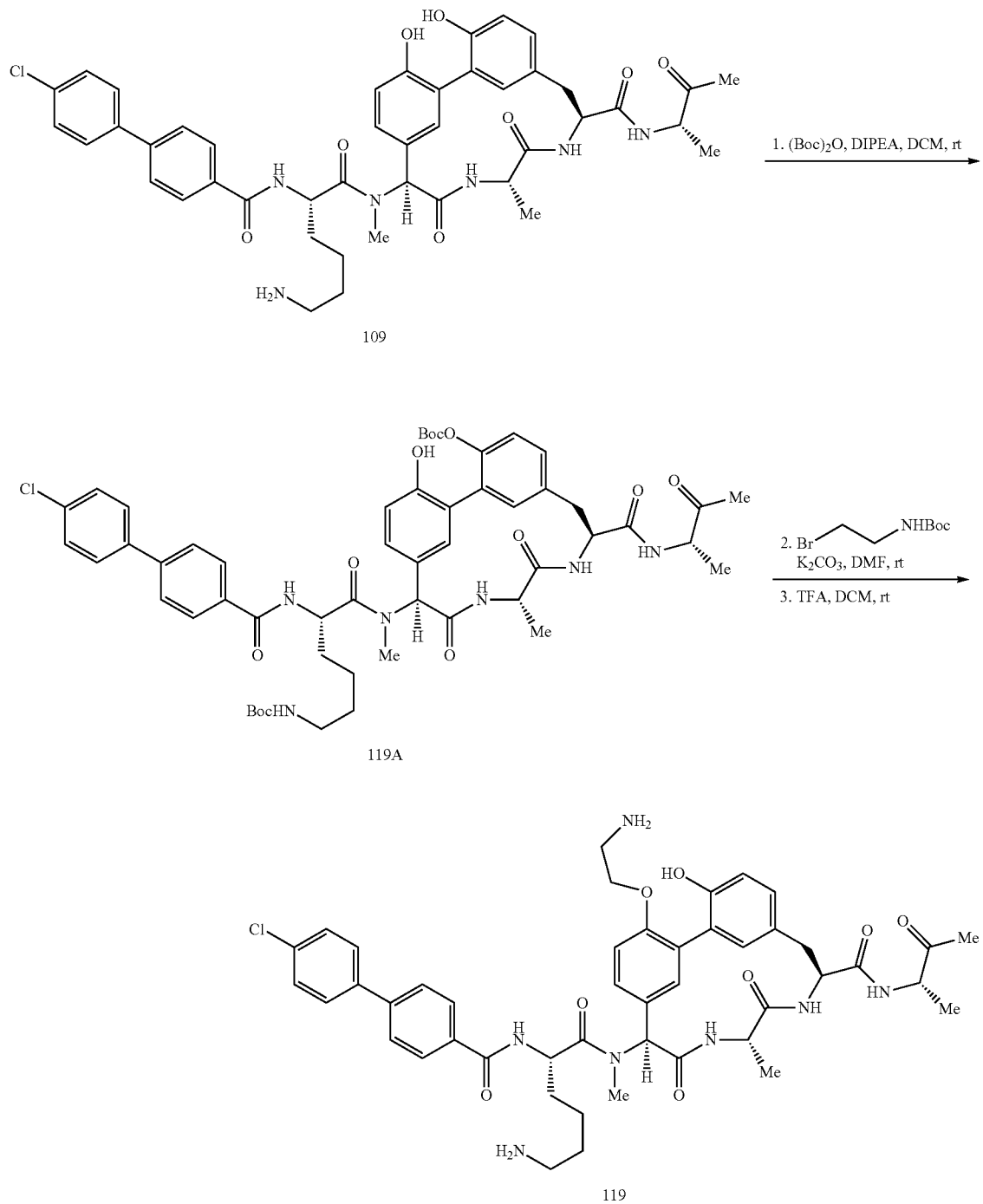

To a stirred solution of Compound 109 (Example 9) (83 mg, 0.1 mmol) in CH$_2$Cl$_2$ (5 mL) and Et$_3$N (70 µL, 0.5 mmol, 5 eq) was added (Boc)$_2$O (53 µL, 0.23 mmol, 2.3 eq). The reaction mixture was stirred at rt overnight. After the reaction was complete, brine solution was added and the mixture was extracted with ethyl acetate. The combined organic layers washed with brine, dried over anhydrous Na$_2$SO$_4$, filtered and solvent was removed under reduced pressure. The residue was purified by flash chromatography (DCM-5% DCM-MeOH) to afford 64 mg (62%) of Compound 119A as white solid. MS (ESI) for (C$_{59}$H$_{73}$ClN$_6$O$_{14}$): m/z 1025.2 (M+H)$^+$.

Compound 119 was synthesized from Compound 119A (42 mg, 0.04 mmol) using K$_2$CO$_3$ (10 mg, 0.06 mmol) and tert-butyl (2-bromoethyl)carbamate (14 mg, 0.06 mmol) following General Method 7. MS (ESI) for (C$_{46}$H$_{54}$ClN$_7$O$_8$): m/z 868.2 (M+H)$^+$.

Example 20: Preparation of Compound 120
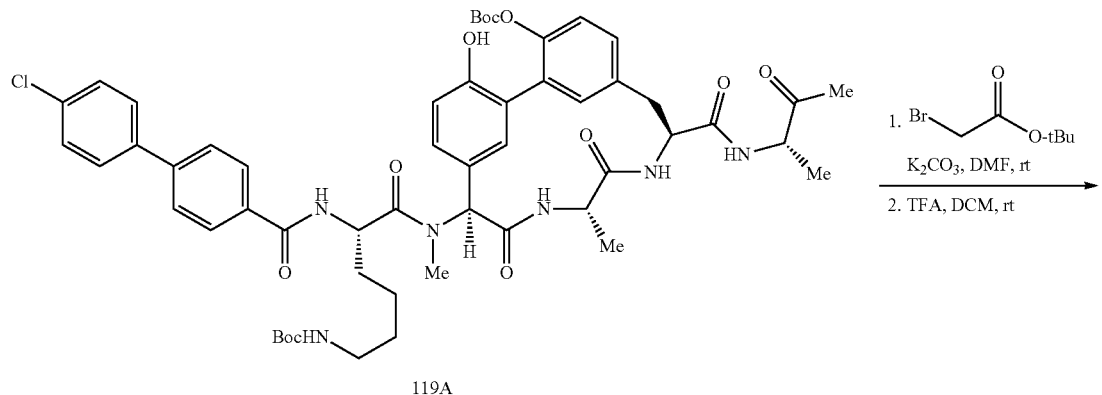
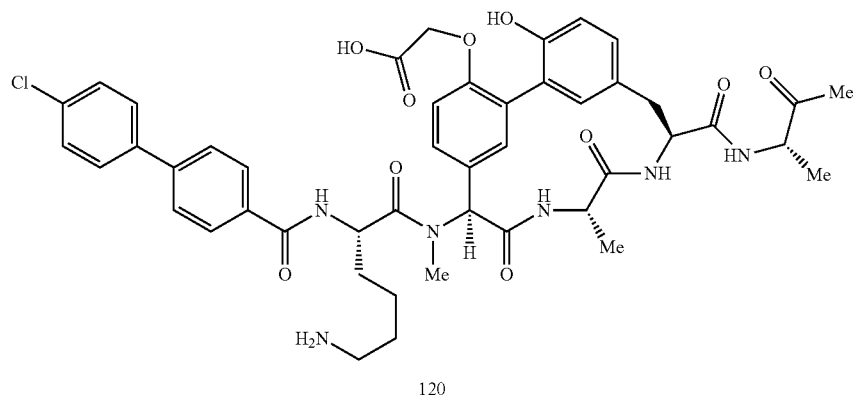
Compound 120 was synthesized from Compound 119A (10 mg, 0.01 mmol) using $K_2CO_3$ (2 mg, 0.015 mmol) and tert-butyl 2-bromoacetate (5 mg, 0.03 mmol) by following General Method 7. MS (ESI) for ($C_{46}H_{51}ClN_6O_{10}$): m/z 883.2 (M+H)$^+$.
Example 21: Preparation of Compound 121
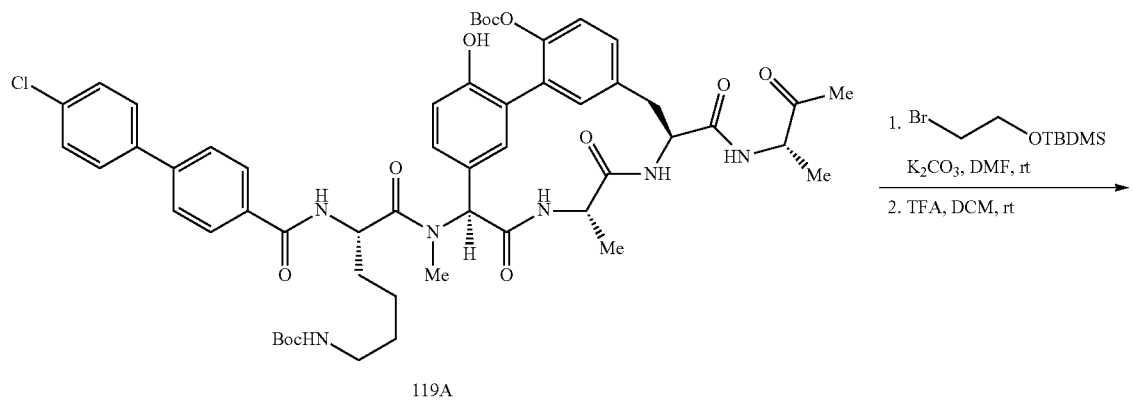

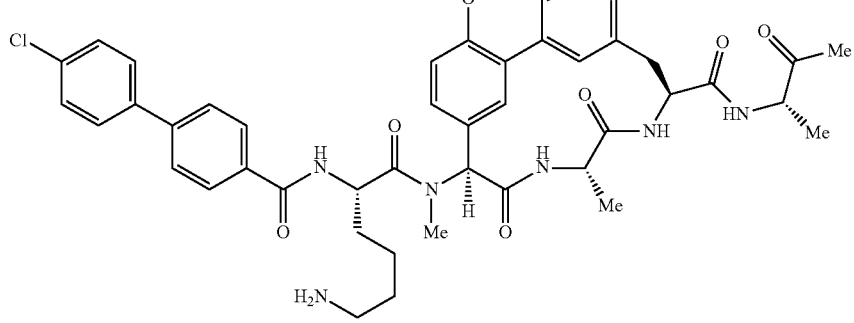
121
Compound 121 was synthesized from Compound 119A (20 mg, 0.02 mmol) using $K_2CO_3$ (5 mg, 0.03 mmol) and (2-bromoethoxy)(tert-butyl)dimethylsilane (13 µL, 0.06 mmol) by following General Method 7. MS (ESI) for ($C_{46}H_{53}ClN_6O_9$): m/z 869.4 (M+H)$^+$.
Example 22: Preparation of Compound 122
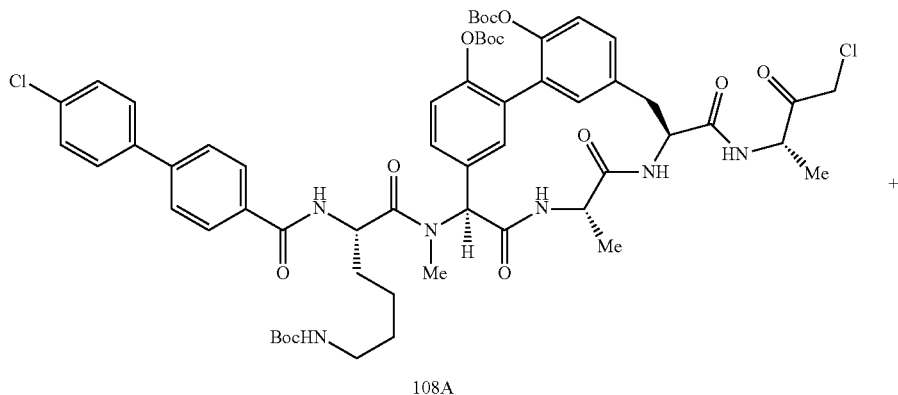
108A
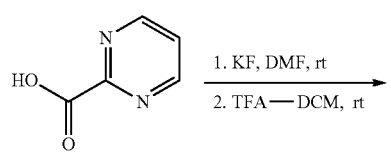

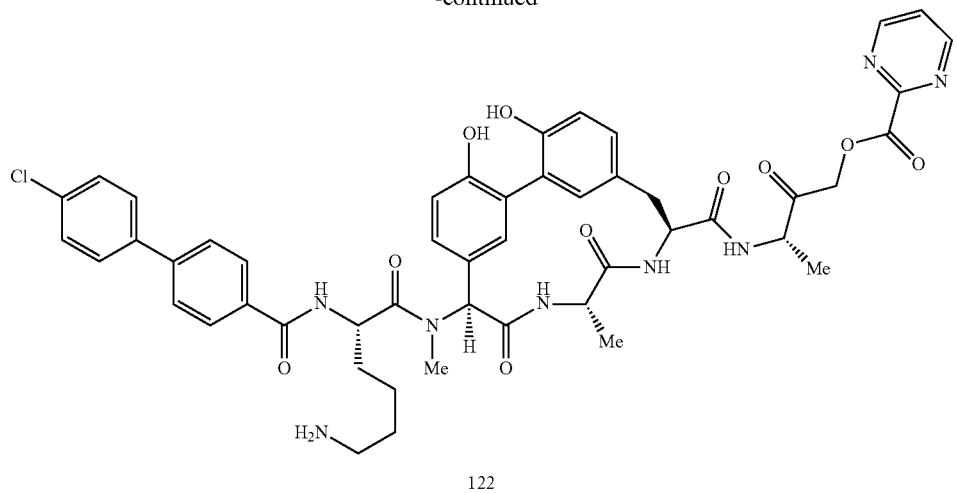

122

To a stirred solution of Compound 108A (23 mg, 0.02 mmol) in dry DMF (1 mL) was added KF (6 mg, 0.1 mmol) and pyrimidine-2-carboxylic acid (13 mg, 0.1 mmol). The reaction mixture was stirred at rt overnight. After completion of the reaction, crushed ice was added and the resultant white cloudy mixture was extracted with EtOAc. The combined organic layers were washed with brine and dried over anhydrous $Na_2SO_4$, filtered and the solvent was removed under vacuum. The residue was purified by flash chromatography (DCM-5% DCM-MeOH) to afford 15 mg (60%) of the desired intermediate as a white solid. MS (ESI) for ($C_{64}H_{75}ClN_8O_{16}$): m/z 1247.5 (M+H).

The resultant material was dissolved in 1:3 TFA-DCM (1 mL) and stirred at rt for about 1 to 2 h. After completion of the reaction, the solvent was evaporated and the residue dried under high vacuum. The residue was purified by prep HPLC ($CH_3CN$—$H_2O$ containing 0.05% TFA) to afford Compound 122. MS (ESI) for ($C_{49}H_{51}ClN_8O_{10}$): m/z 947.3 (M+H)$^+$.

Example 23: Preparation of Compound 123

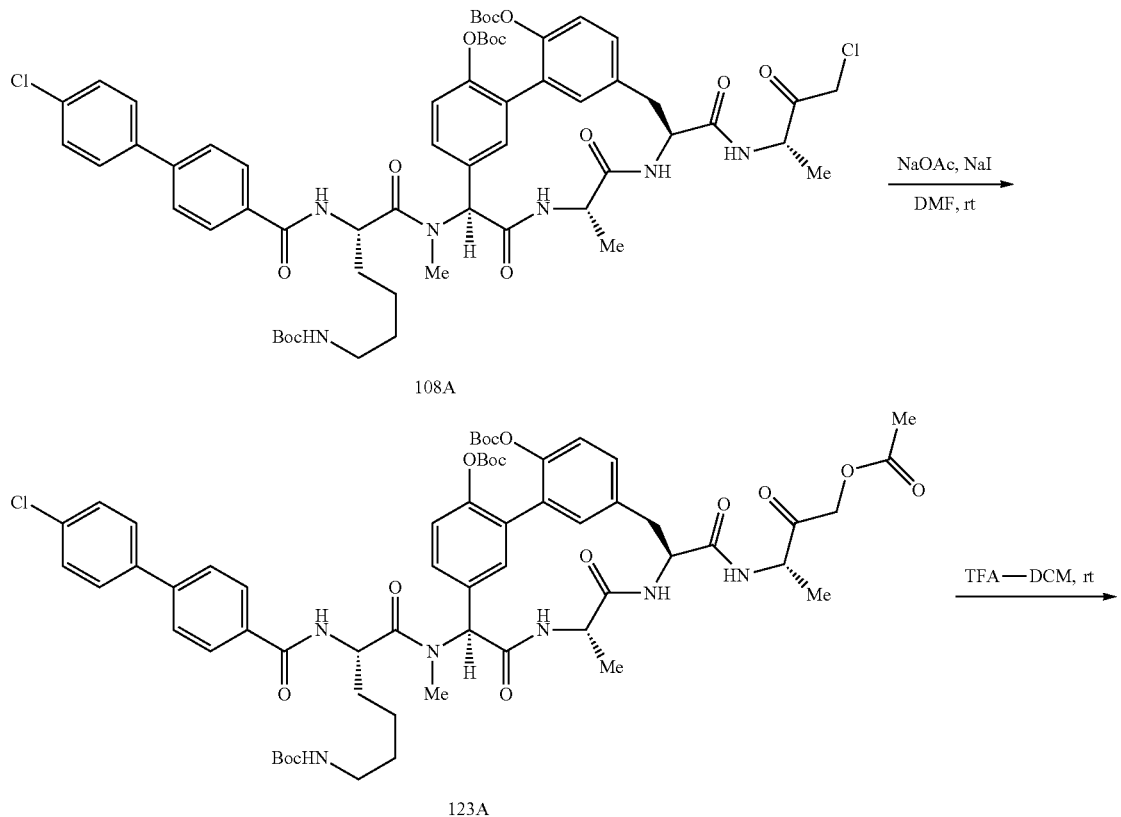

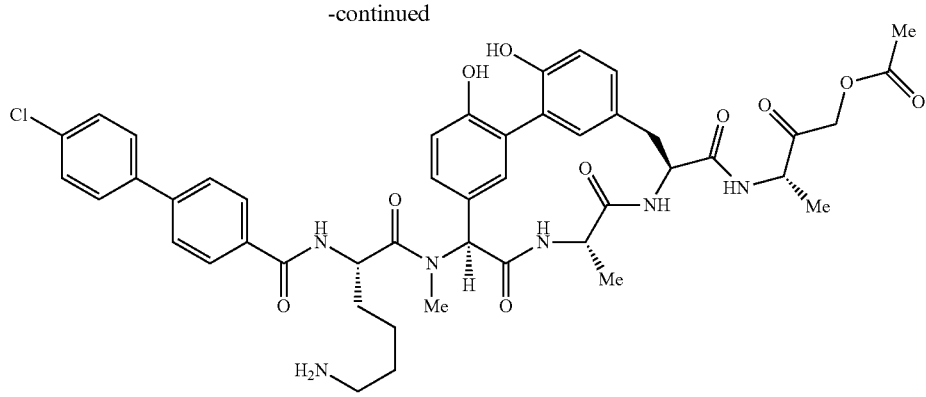

123

To a stirred solution of Compound 108A (23 mg, 0.02 mmol) in dry DMF (1 mL) was added NaOAc (9 mg, 0.1 mmol) and NaI (6 mg, 0.04 mmol). The reaction mixture was stirred at rt overnight. After completion of the reaction, crushed ice was added and the resultant white cloudy mixture was extracted with EtOAc. The combined organic layers washed with brine, dried over anhydrous $Na_2SO_4$, filtered and the solvent was removed under vacuum. The residue was purified by flash chromatography (DCM-5% DCM-MeOH) to afford 18 mg (78%) of Compound 123A as a white solid. MS (ESI) for ($C_{61}H_{75}ClN_6O_{16}$): m/z 1183.1 $(M+H)^+$.

Compound 123A (18 mg, 0.015 mmol) was dissolved in 1:3 TFA-DCM (1 mL) and stirred at rt for about 1 to 2 h. After completion of the reaction, the solvent was evaporated and the residue was dried under high vacuum. The residue was purified by prep HPLC ($CH_3CN$—$H_2O$ containing 0.05% TFA) to afford Compound 123. MS (ESI) for ($C_{46}H_{51}ClN_6O_{10}$): m/z 883.3 $(M+H)^+$.

Example 24: Preparation of Compound 124

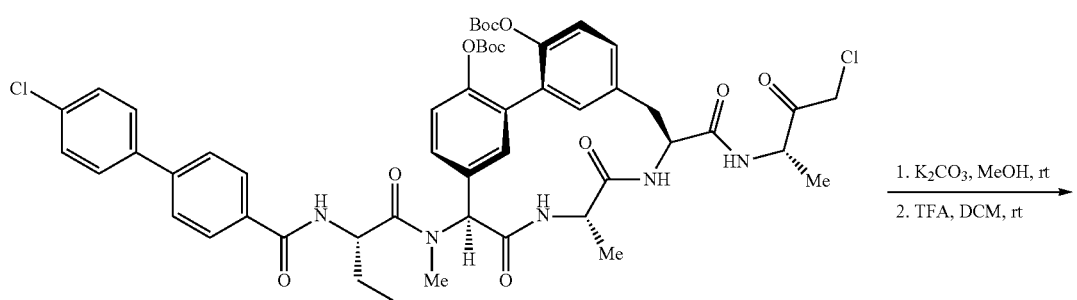

108A

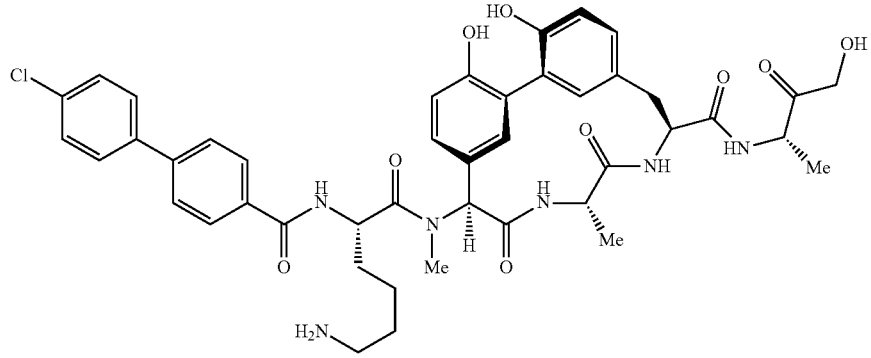

124

To a stirred solution of Compound 108A (23 mg, 0.02 mmol) in MeOH (2 mL) was added $K_2CO_3$ (2 mg, 0.03 mmol) and the reaction mixture was stirred at rt for 3 h. After completion of the reaction, the solvent was removed under vacuum. The residue was dissolved in 1:3 TFA-DCM (1 mL) and stirred at rt for about 1 h. The solvent was evaporated and the residue was dried under high vacuum. The residue was purified by prep HPLC ($CH_3CN$—$H_2O$ containing 0.05% TFA) to afford Compound 124. MS (ESI) for ($C_{44}H_{49}ClN_6O_9$): m/z 841.2 $(M+H)^+$.

Example 25: Preparation of Compound 125

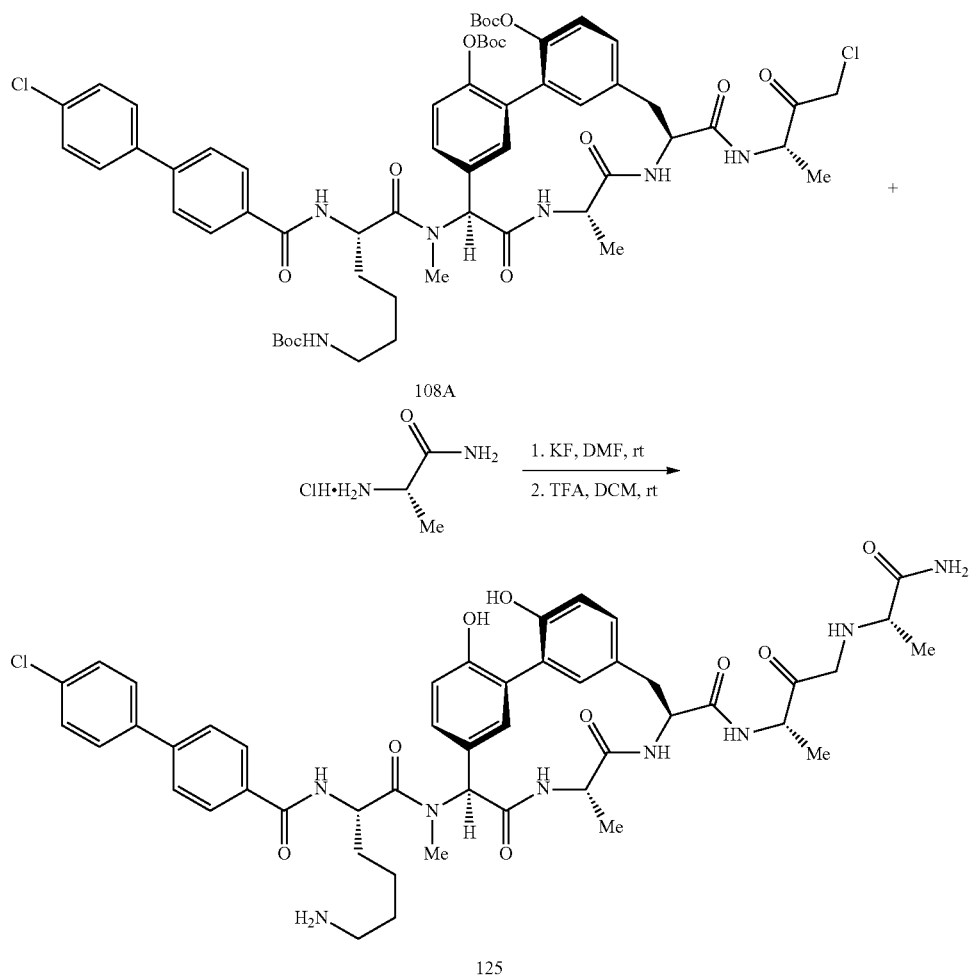

To a stirred solution of Compound 108A (23 mg, 0.02 mmol) in DMF (2 mL) was added (S)-2-aminopropanamide hydrochloride (6 mg, 0.04 mmol), KF (2.5 mg, 0.02 mmol) and the reaction mixture was stirred at rt overnight. After completion of the reaction, crushed ice was added. The resultant off-white precipitate was collected by filtration and dried under vacuum. The residue was dissolved in 1:3 TFA-DCM (1 mL) and stirred at rt for about 1 h. Solvent was evaporated and the residue was dried under high vacuum. The residue was purified by prep HPLC ($CH_3CN$—$H_2O$ containing 0.05% TFA) to afford Compound 125. MS (ESI) for ($C_{47}H_{55}ClN_8O_9$): m/z 911.2 $(M+H)^+$.

Example 26: Preparation of Compound 126
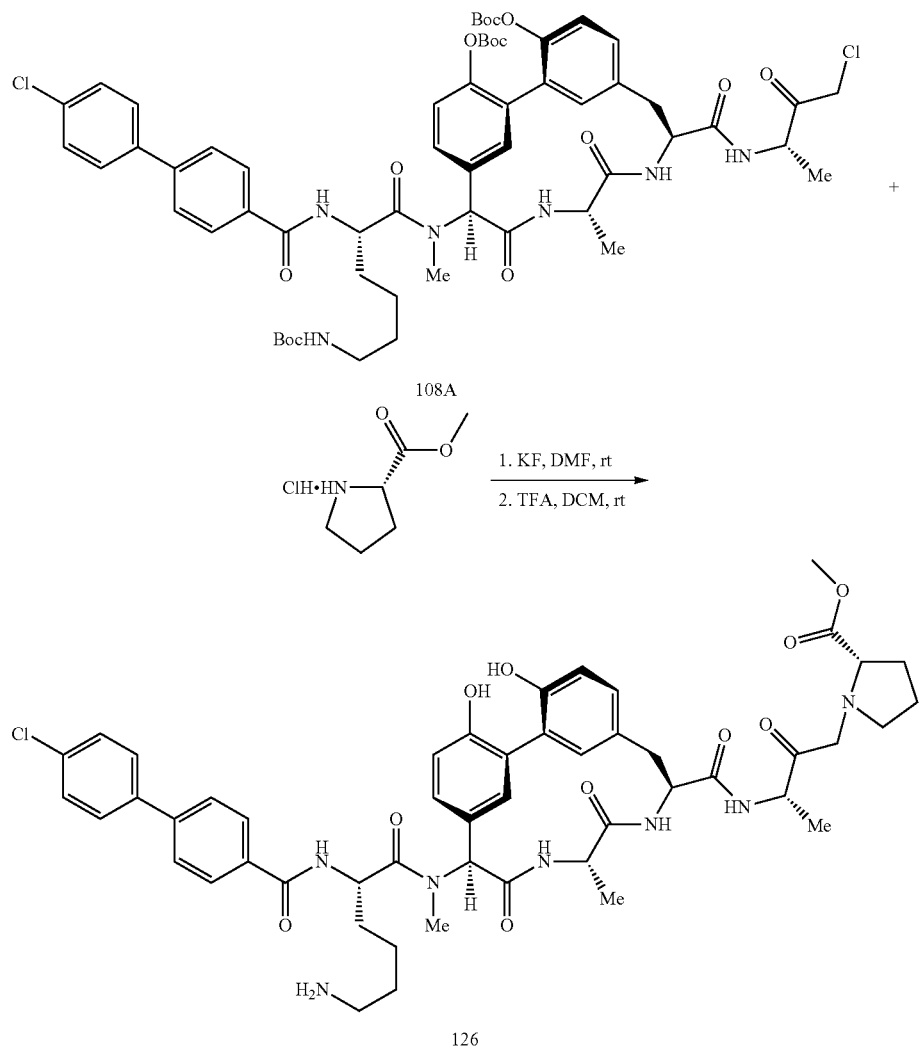
Compound 126 was prepared from Compound 108A (23 mg, 0.02 mmol) and methyl L-prolinate hydrochloride (7 mg, 0.04 mmol) in a manner similar to Example 25, Compound 125. MS (ESI) for ($C_{50}H_{58}ClN_7O_{10}$): m/z 952.2 (M+H)$^+$.
Example 27: Preparation of Compound 127
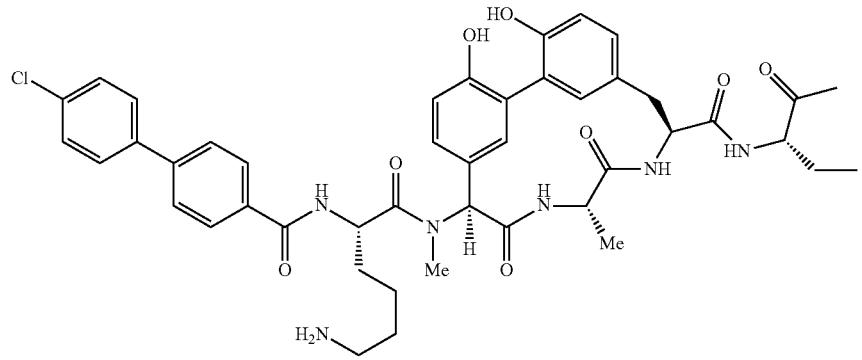

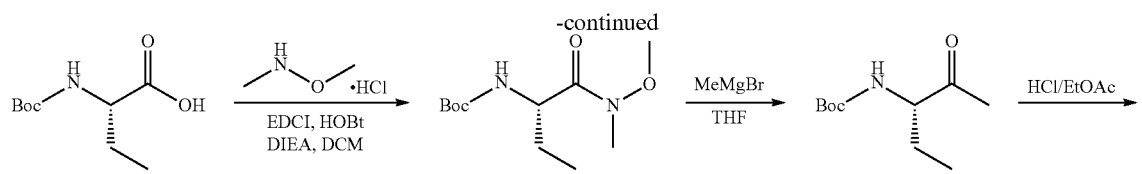
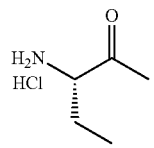

Compound 127A (HCl salt) was prepared in a manner similar to that of Compound 109A using (S)-2-((tert-butoxycarbonyl)amino)butanoic acid as the starting material. $^1$H NMR (400 MHz, CDCl$_3$-d$_4$) δ 5.26-5.22 (s, 1H), 4.26-4.25 (s, 1H), 2.15 (s, 3H), 1.91-1.87 (m, 1H), 1.61-1.54 (m, 1H), 1.45-1.40 (s, 9H), 0.87-0.83 (m, 3H).

Compound 127 was prepared in a similar manner to Compound 109 from Compound 104E and Compound 127A. $^1$H NMR (400 MHz, MeOH-d$_4$) δ 8.51 (s, 1H), 7.94 (s, 1H), 7.76-7.63 (m, 4H), 7.45-7.41 (m, 3H), 7.14 (m, 2H), 6.97 (m, 3H), 6.83 (m, 1H), 6.51 (s, 1H), 4.77 (m, 1H), 4.48-4.15 (m, 2H), 3.12 (m, 2H), 2.99-2.94 (m, 4H), 2.74-2.64 (m, 2H), 2.19-2.15 (m, 3H), 1.93 (m, 3H), 1.71-1.62 (m, 5H), 1.45 (m, 1H), 1.37-1.35 (m, 2H), 0.89 (s, 3H). LCMS (5-95 AB, ESI): RT=0.788, M+H$^+$=839.4

Example 28: Preparation of Compound 128

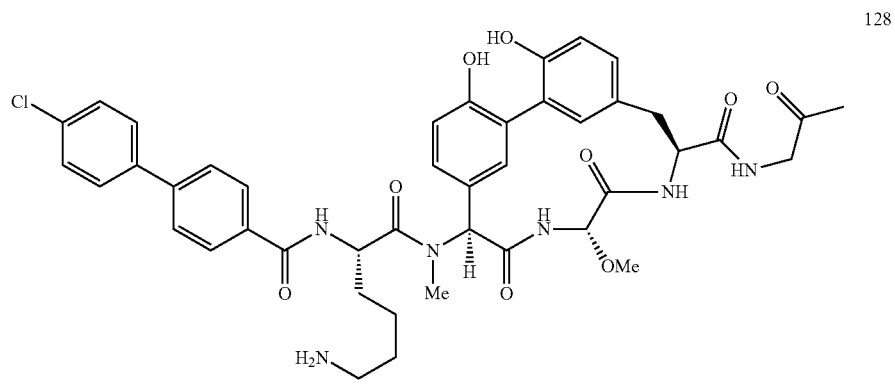 [SMILES: CO[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)NCC(C)=O)NC1=O]

Compound 128 was prepared in a similar manner to Compound 109 (Example 9) from Compound 104E and 1-aminopropan-2-one. $^1$H NMR (400 MHz, MeOH-d$_4$) δ 8.50 (s, 1H), 7.90-7.80 (d, J=8.0 Hz, 2H), 7.70-7.60 (d, J=8.0 Hz, 2H), 7.60-7.50 (d, J=8.0 Hz, 2H), 7.50-7.40 (d, J=8.4 Hz, 2H), 7.20-7.15 (m, 1H), 7.12-7.08 (m, 1H), 7.02-6.95 (d, J=8.8 Hz, 2H), 7.93-7.80 (m, 2H), 7.75-7.65 (m, 1H), 5.10-5.00 (m, 2H), 4.90-4.80 (m, 1H), 4.70-4.55 (m, 1H), 4.50-4.38 (m, 1H), 3.30-3.15 (m, 1H), 3.02-2.88 (m, 5H), 2.25-2.15 (s, 3H), 2.10-1.85 (m, 2H), 1.80-1.70 (m, 2H), 1.68-1.50 (m, 2H), 1.42-1.20 (m, 7H). LCMS (5-95 AB, ESI): RT=0.773, M+H$^+$=825.8.

Example 29: Preparation of Compound 129

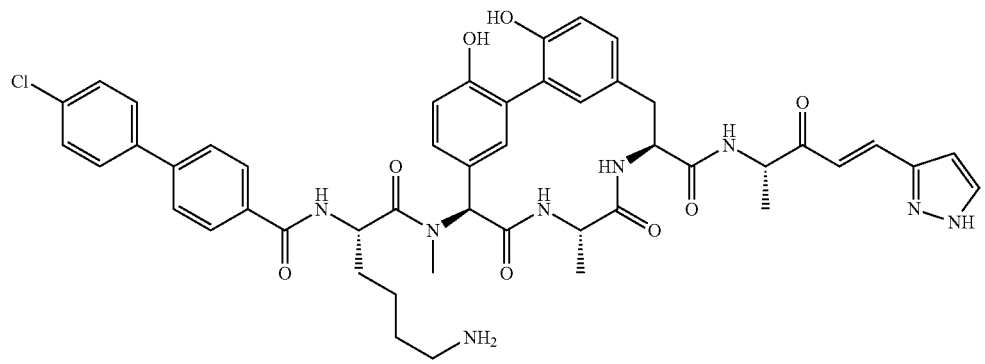

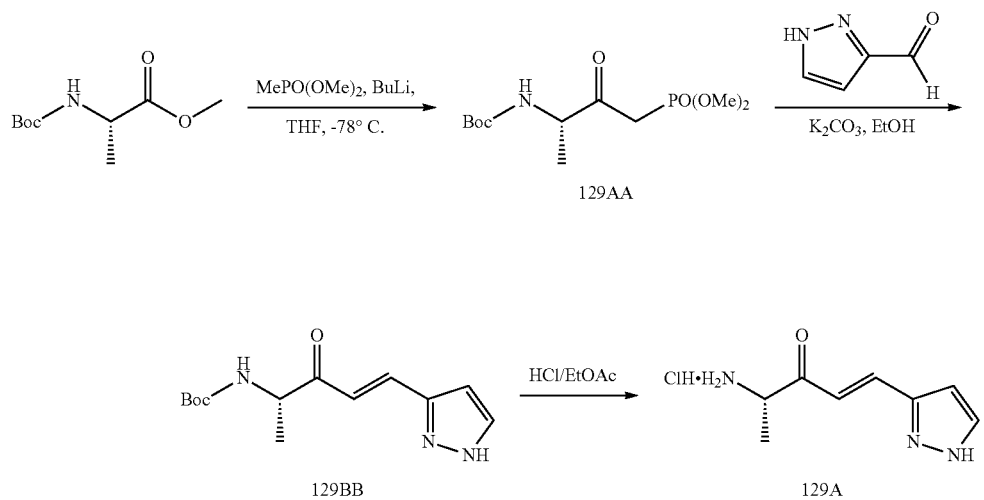

To a mixture of MePO(OMe)$_2$ (45.8 g, 369 mmol) in dry THF (375 mL) at −78° C., was added n-BuLi in n-hexane (2.5 M, 148 mL, 369 mmol) dropwise. After the mixture was stirred at −78° C. for 30 min, a solution of (S)-methyl 2-((tert-butoxycarbonyl)amino)propanoate (25 g, 123 mmol) in dry THF (125 mL) was added dropwise. The resulting mixture was stirred at −78° C. for 2 h and then −30° C. for 1 h. The reaction was quenched by adding 20% citric acid at −30° C. The resulting mixture was extracted with EA (200 mL*3) and the combined EA layers were washed sequentially with saturated NaHCO$_3$ (500 mL), brine (500 mL), dried over MgSO$_4$ and concentrated under reduced pressure. The resulting residue was purified by silica gel column chromatography (PE/EA=1/1) to give the Compound 129AA (34 g, 93.6%) as a light yellow oil.

To a mixture of Compound 129AA (4.4 g, 14.92 mmol) in ethanol (40 mL) was added K$_2$CO$_3$ (1.89 g, 13.68 mmol). The mixture was stirred for 15 min at 15° C. Then 1H-pyrazole-3-carbaldehyde (1.3 g, 13.55 mmol) was added as a solution in ethanol (10 mL) and the mixture was stirred for 8 h. The mixture was filtered and evaporated to dryness. The yellow residue was partitioned between EA (40 mL) and 20% citric acid (40 mL). The organic layer was washed with 20% citric acid (40 mL). The combined aqueous phases were extracted with EA (40 mL). The organic extracts were washed with brine (40 mL), dried over anhydrous Na$_2$SO$_4$ and evaporated to afford a residue, which was purified by silica gel chromatography (EA/PE=1:1) to give Compound 129BB (1.32 g, 37%). $^1$H NMR (400 MHz, CDCl$_3$), δ 10.30 (brs, 1H), 7.92-7.88 (d, J=16.8 Hz, 1H), 7.62-7.61 (d, J=2 Hz, 1H), 6.80-6.76 (d, J=16 Hz, 1H), 6.64-6.63 (d, J=2 Hz, 1H), 5.60-5.58 (d, J=7.2 Hz, 1H), 4.90-4.86 (t, J=6.8 Hz, 1H), 1.45 (s, 9H), 1.42-1.40 (d, J=7.2 Hz, 3H).

To a mixture of Compound 129BB (800 mg, 3.04 mmol) in EtOAc (5 mL) at 0° C. was added 4N HCl/EtOAc (30 mL). The mixture was stirred at 15° C. for 30 min. After the reaction was complete, the mixture was evaporated to give Compound 129A (600 mg, 98%) as a white solid.

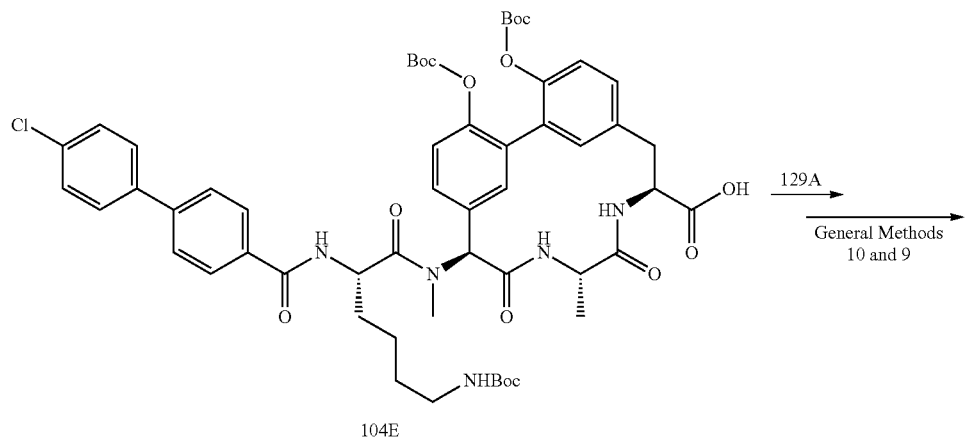
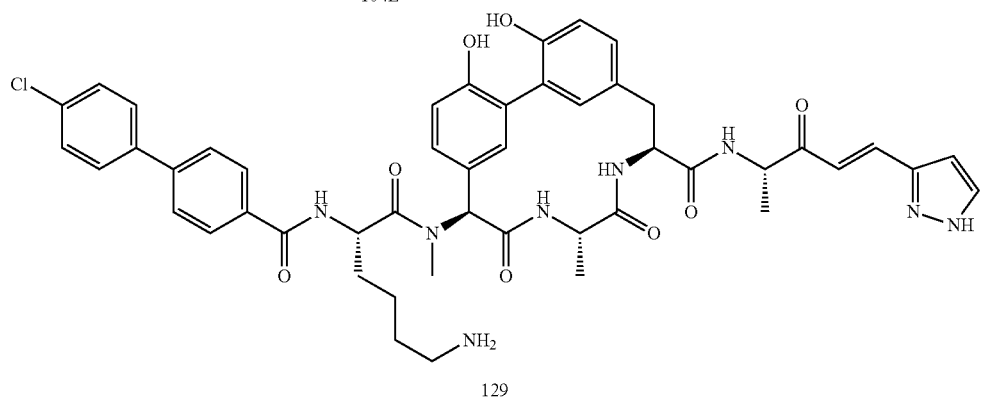
Compound 129 was prepared according to General Methods 10 and 9 from Compound 104E and Compound 129A. $^1$H NMR (400 MHz, MeOH-d$_4$) δ 7.90-7.80 (m, 2H), 7.75-7.60 (m, 3H), 7.60-7.50 (m, 2H), 7.50-7.40 (m, 2H), 7.20-7.10 (m, 1H), 7.08-7.02 (m, 1H), 7.00-6.90 (m, 2H), 7.90-7.85 (m, 2H), 7.83-7.75 (m, 1H), 7.72-7.68 (m, 1H), 7.60-7.50 (m, 1H), 5.10-5.00 (m, 1H), 5.00-4.85 (m, 1H), 4.85-4.65 (m, 2H), 3.30-3.10 (m, 3H), 3.00-2.85 (m, 4H), 2.65-2.60 (m, 1H), 2.10-1.85 (m, 2H), 1.80-1.70 (m, 2H), 1.65-1.50 (m, 2H), 1.42-1.35 (m, 3H), 1.35-1.25 (m, 3H). LCMS (5-95 AB, ESI): RT=0.781, M+H$^+$=903.4.
Example 30: Preparation of Compound 130
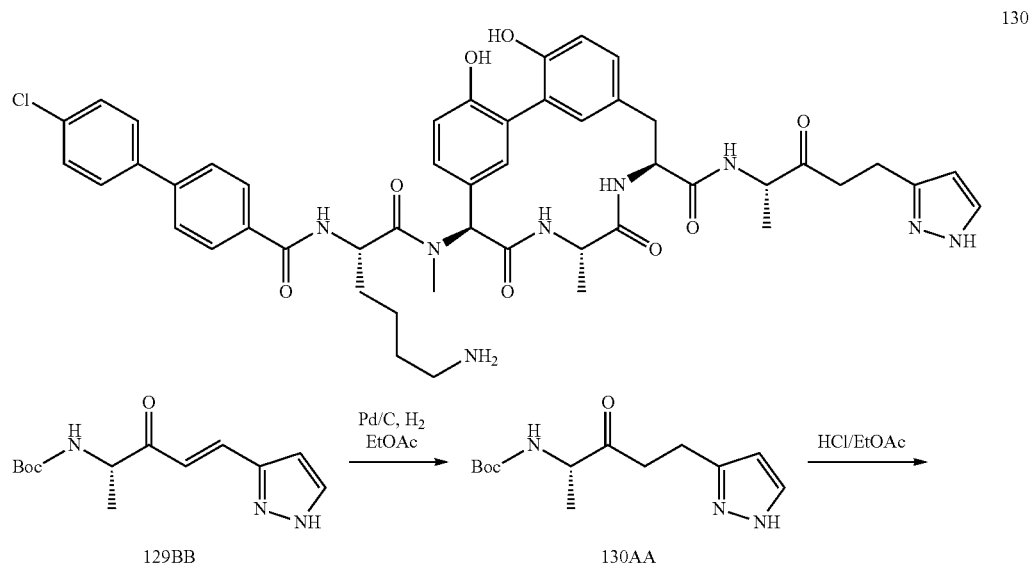

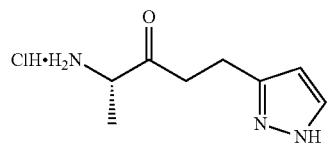

130A

To a mixture of Compound 129BB (600 mg, 2.26 mmol) in EtOAc (30 mL) was added 10% Pd/C (100 mg). The mixture was stirred at 15° C. under H$_2$ balloon for 40 min. The mixture was filtered and evaporated to give Compound 130AA (600 mg, 99.3%) as a white solid. $^1$H NMR (400 MHz, CDCl$_3$), δ 4.47-7.46 (d, J=2 Hz, 1H), 6.08-6.07 (d, J=2 Hz, 1H), 5.25 (brs, 1H), 4.30 (brs, 1H), 2.99-2.97 (d, J=6.4 Hz, 2H), 2.91-2.90 (d, J=6.4 Hz, 2H), 2.90-2.89 (d, J=6.8 Hz, 1H), 1.44 (s, 9H), 1.42-1.40 (d, J=7.6 Hz, 3H).

To a mixture of Compound 130AA (600 mg, 2.24 mmol) in EtOAc (5 mL) was added 4N HCl/EtOAc (20 mL) at 0° C. The mixture was stirred at 15° C. for 30 min. The mixture was evaporated to give Compound 130A (450 mg, 98.4%) as a white solid.

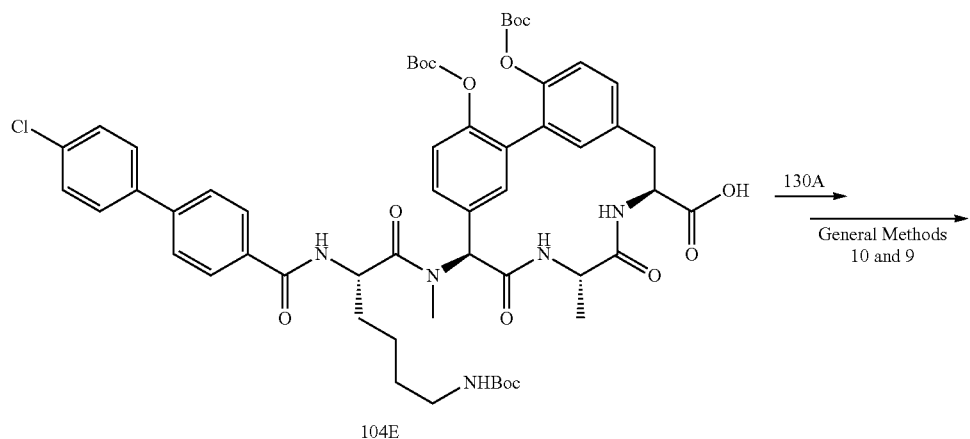

104E

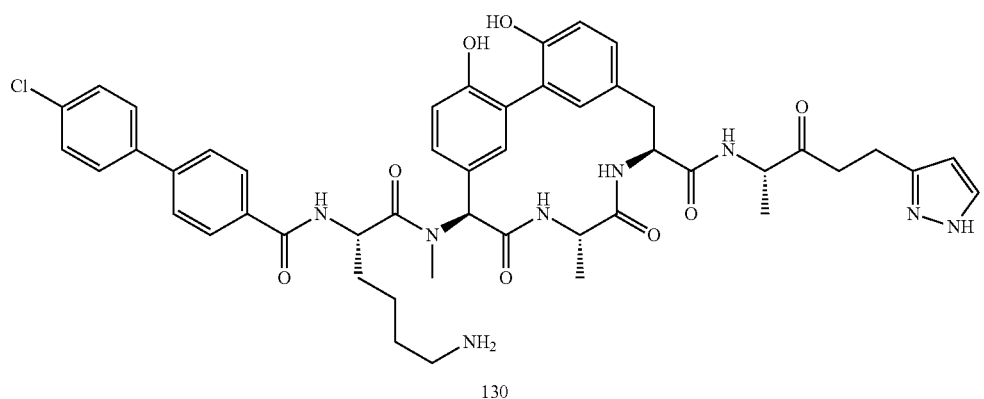

130

Compound 130 was prepared according to General Methods 10 and 9 from Compound 104E and Compound 130A. $^1$H NMR (400 MHz, MeOH-d$_4$) δ 8.15-8.06 (m, 1H), 8.05-7.90 (m, 1H), 7.82-7.70 (m, 2H), 7.65-7.55 (m, 2H), 7.52-7.40 (m, 2H), 7.22-7.18 (m, 1H), 7.15-7.08 (m, 1H), 7.06-7.03 (m, 1H), 7.02-6.95 (m, 2H), 6.92-6.88 (m, 1H), 6.65-6.55 (m, 1H), 6.50-6.45 (m, 1H), 5.10-5.00 (m, 1H), 4.85-4.75 (m, 2H), 4.50-4.40 (m, 1H), 3.35-3.12 (m, 3H), 3.10-3.00 (m, 4H), 3.00-2.95 (m, 2H), 2.95-2.90 (m, 3H), 2.10-1.85 (m, 2H), 1.80-1.70 (m, 2H), 1.65-1.50 (m, 2H), 1.40-1.20 (m, 6H). LCMS (5-95 AB, ESI): RT=0.775, M+H=905.4.

Example 31: Preparation of Compound 131

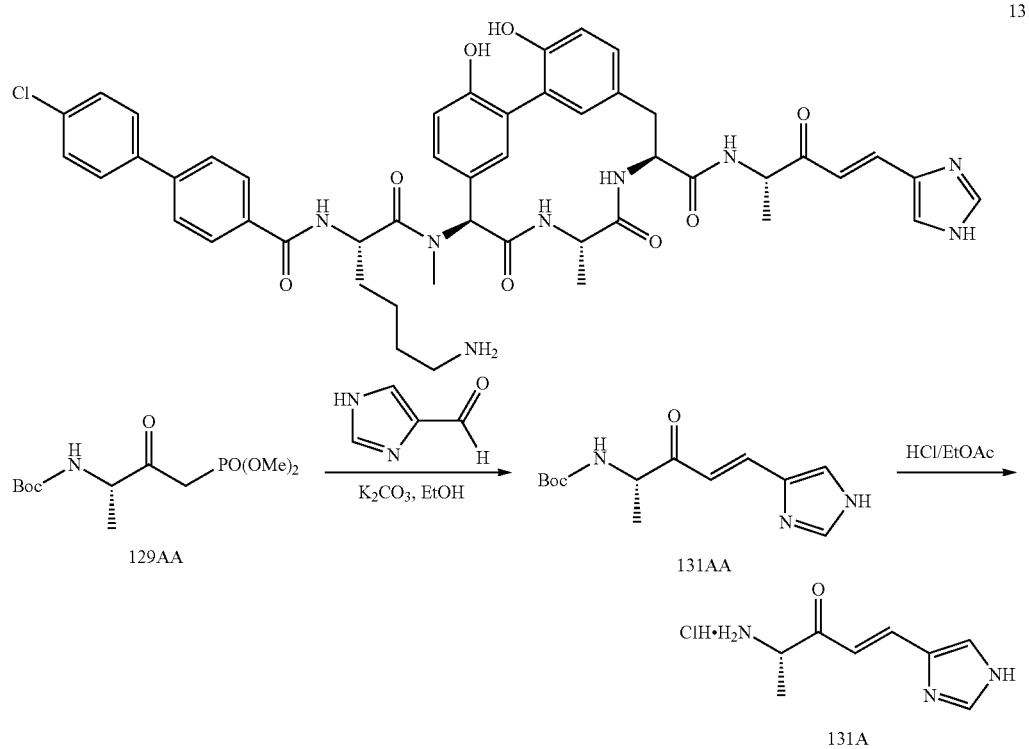

Compound 131AA was prepared in a manner similar to Compound 129BB (Example 29) from Compound 129AA and 1H-imidazole-4-carbaldehyde. $^1$H NMR (400 MHz, CDCl$_3$) δ 9.69 (s, 1H), 7.60-7.56 (d, J=15.6 Hz, 1H), 7.30 (s, 1H), 6.90-6.86 (d, J=15.6 Hz, 1H), 4.55-4.41 (t, J=7.2 Hz, 1H), 1.43 (s, 9H), 1.37-1.35 (d, J=7.6 Hz, 3H).

Compound 131A was prepared in a manner similar to Compound 129A (Example 29) by treatment with 4N HCl/EtOAc in EtOAc to afford Compound 131A which was carried on immediately to the next step.

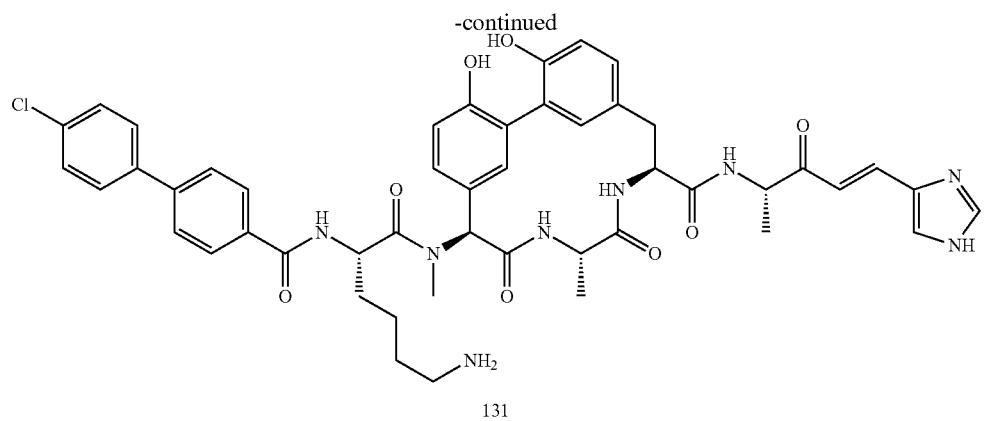

131

Compound 131 was prepared according to General Methods 10 and 9 from Compound 104E and Compound 131A. $^1$H NMR (400 MHz, MeOH-$d_4$) δ 9.05 (s, 1H), 8.76-8.72 (m, 1H), 7.99-7.98 (m, 1H), 7.90-7.85 (m, 2H), 7.71-7.69 (m, 2H), 7.60-7.59 (m, 2H), 7.46-7.44 (m, 2H), 7.25-7.18 (m, 1H), 7.15-7.08 (m, 2H), 7.05-6.92 (m, 2H), 6.90-6.80 (m, 1H), 6.52-6.50 (d, J=9.6 Hz, 3H), 5.03-4.99 (s, 1H), 4.93 (s, 1H), 4.90-4.85 (m, 1H), 4.73-4.63 (m, 1H), 3.15-3.11 (m, 1H), 2.99-2.96 (s, 1H), 2.95-2.93 (s, 3H), 1.92-1.73 (m, 2H), 1.73-1.61 (m, 2H), 1.60-1.59 (m, 2H), 1.40-1.39 (m, 3H), 1.34-1.32 (m, 2H); LCMS (10-80 AB, ESI): RT=1.025, M+1=903.5.

Example 32: Preparation of Compound 132

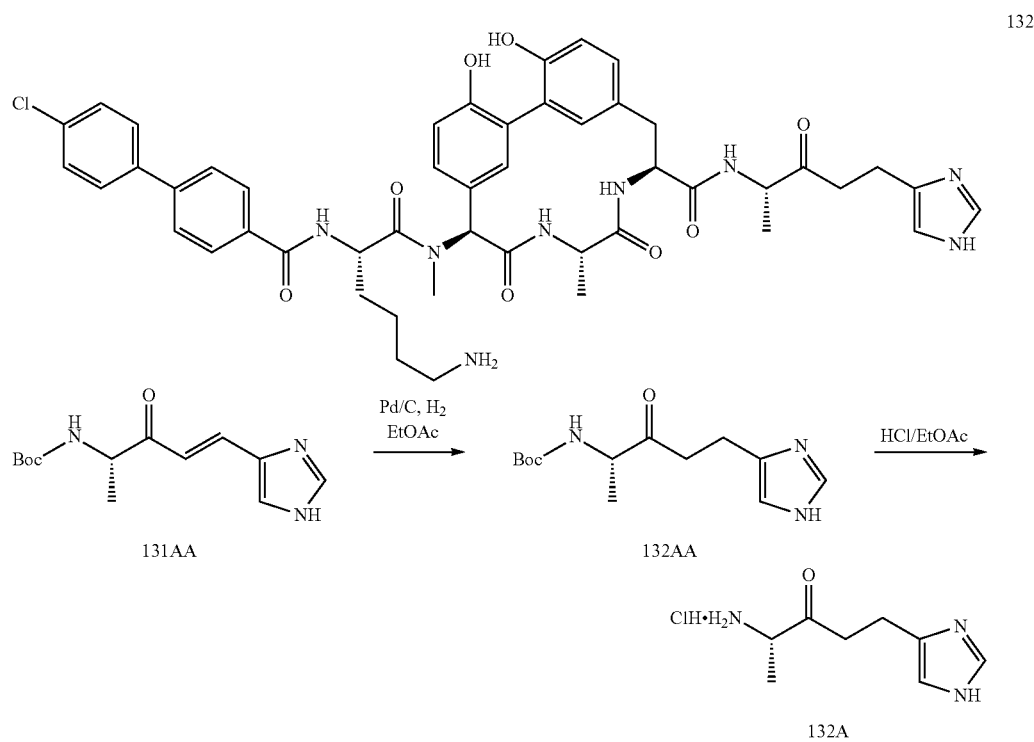

Compound 132AA was prepared in a manner similar to Compound 130AA (Example 30) from Compound 131AA: $^1$H NMR (400 MHz, CDCl$_3$) δ 7.49 (s, 1H), 6.74 (s, 1H), 4.25 (m, 1H), 2.88-2.83 (m, 4H), 1.41 (s, 9H), 1.26-1.25 (d, J=6.8 Hz, 3H).

Compound 132A was prepared in a manner similar to Compound 130A (Example 30) and was used immediately in the next step.

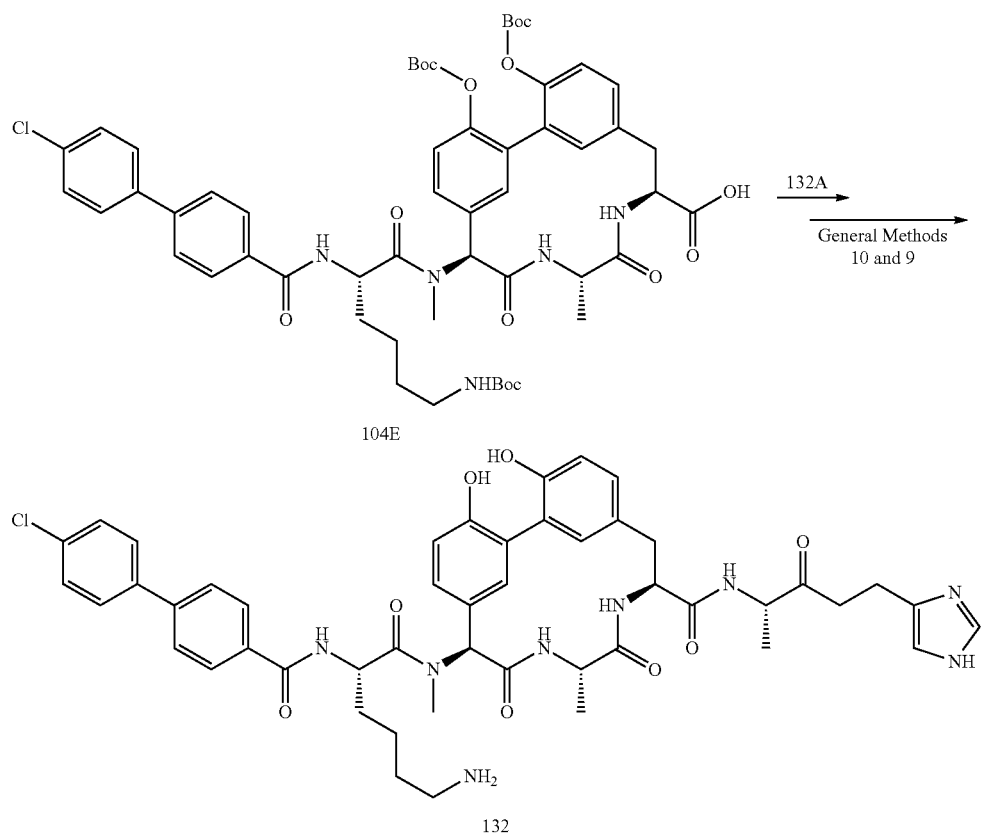
Compound 132 was prepared according to General Methods 10 and 9 from Compound 104E and Compound 132A. $^1$H NMR (400 MHz, MeOH-d$_4$) δ 8.76 (s, 1H), 8.66-8.62 (m, 1H), 7.96-7.94 (m, 2H), 7.75-7.73 (m, 2H), 7.67-7.65 (m, 2H), 7.48-7.46 (m, 2H), 7.30 (s, 1H), 7.16 (s, 1H), 7.10 (s, 1H), 6.98-6.95 (m, 3H), 6.87-6.80 (m, 1H), 6.42 (s, 1H), 6.04-6.01 (m, 1H), 4.80-4.78 (m, 4H), 4.41-4.35 (m, 1H), 3.22-3.14 (m, 2H), 2.98-2.93 (m, 10H), 1.90-1.76 (m, 1H), 1.73-1.71 (m, 2H), 1.34-1.18 (m, 7H). LCMS (5-95 AB, ESI): RT=0.628, M+1=905.4.
Example 33: Preparation of Compound 133
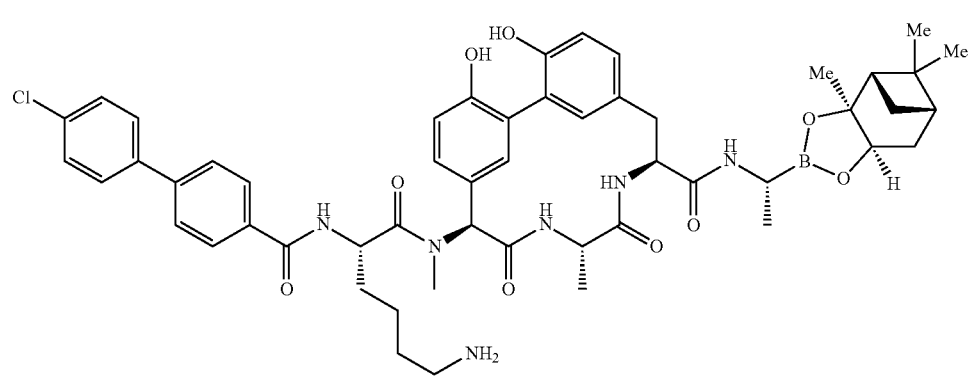

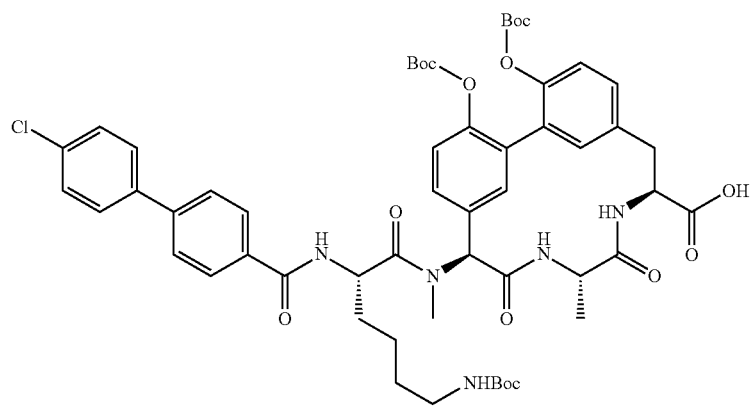
104E
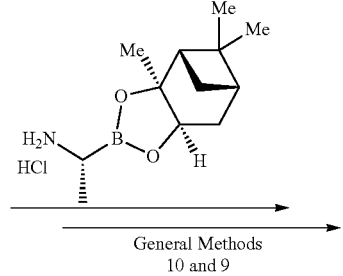
General Methods 10 and 9
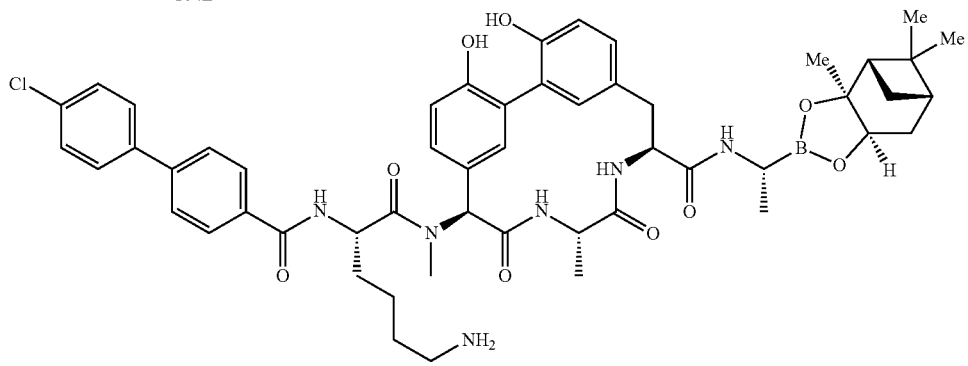
133
Compound 133 was prepared according to General Methods 6 and 9 from Compound 104E and (R)-BoroAla-(+)-pinanediol HCl. $^1$H NMR (400 MHz, MeOH-d$_4$) δ 8.89-8.87 (s, 1H), 8.50 (s, 1H), 7.72-7.71 (m, 2H), 7.60-7.58 (m, 2H), 7.44 (m, 2H), 7.40 (m, 2H), 7.38 (m, 1H), 7.00-6.98 (m, 2H), 6.89 (s, 1H), 6.85-6.83 (d, J=8.0 Hz, 1H), 6.78 (s, 1H), 6.61 (m, 1H), 4.96-4.91 (m, 3H), 4.23-4.21 (d, J=8.0 Hz, 1H), 3.14-3.11 (m, 2H), 2.95 (m, 5H), 2.74-2.73 (m, 1H), 2.71 (s, 1H), 1.98-1.96 (m, 1H), 1.72 (m, 3H), 1.50 (m, 8H), 1.50-1.47 (d, J=12.0 Hz, 1H), 1.39 (s, 3H), 1.38 (s, 1H), 1.29 (s, 3H), 1.16-1.14 (d, J=8.0 Hz, 3H), 0.89 (s, 3H). LCMS (5-95 AB, ESI): RT=0.863 (91%, bornic ester), M+1=961.5; RT=0.766 (9%, boronic acid), M+1: 827.2.
Example 34: Preparation of Compound 134
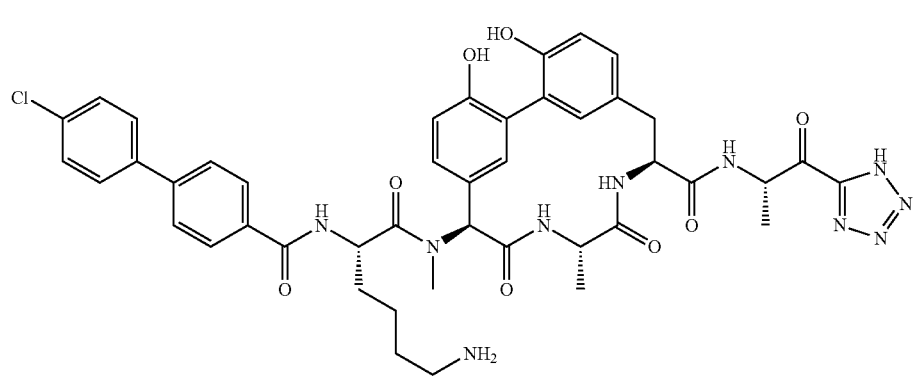
134

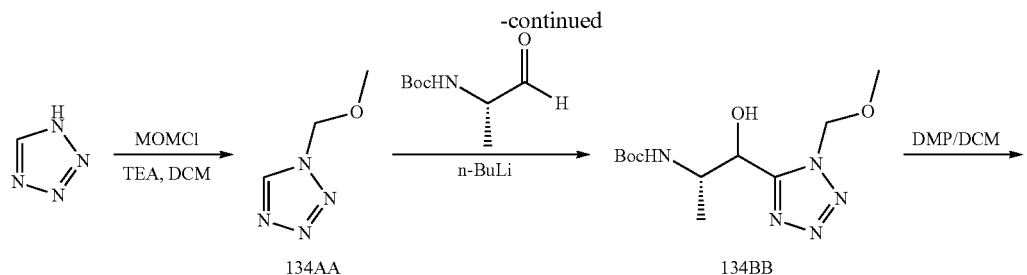

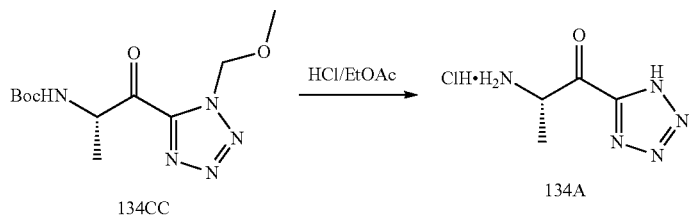

To a solution of 1H-tetrazole (10 g, 142.8 mmol) in tetrahydrofuran (200 mL) was added triethylamine (29.0 g, 186 mmol) under an argon atmosphere, followed by the addition of MOMCl (14.9 g, 186 mmol) after 30 min. The reaction was warmed to room temperature and stirred for 10 hr. THF was removed from the resulting mixture under reduced pressure. The residue was portioned between water and EtOAc and the aqueous layer was further extracted with EtOAc. The combined organic layers were washed with brine, dried over MgSO$_4$ and concentrated in vacuo. The oily residue was purified by silica gel column to give Compound 134AA (5.5 g, 48.2 mmol, 33.8%) as a colorless oil.

To a stirred solution of Compound 134AA in 10 mL THF, n-BuLi (9.24 mL, 2.5 M in THF, 23.1 mmol) was added dropwise at −78° C. After 5 min when the color changed from red to colorless, (S)-tert-butyl (1-oxopropan-2-yl)carbamate (2 g, 11.55 mmol) was added and the mixture was stirred for 15 min. The mixture was then slowly allowed to warm up to room temperature over a period of 12 hr. The reaction was then quenched by saturated NH$_4$Cl solution, followed by the extraction with ethyl acetate (20 mL*2). The combined organic extracts were washed with brine, dried over MgSO$_4$ and concentrated. The residue was purified by silica gel column to give Compound 134BB as an oil (yield 0.45 g, 13.6%).

To a solution of Compound 134BB (200 mg, 0.696 mmol) in DCM (20 mL) was added Dess-Martin reagent (471 mg, 1.11 mmol) at 0° C. The reaction mixture was stirred at 0° C. for 20 min. The reaction mixture was poured into a saturated solution of sodium bicarbonate/sodium thiosulfate (30 mL) and the aqueous phase was extracted with dichloromethane (20 mL×3). The combined organic layers were dried over Na$_2$SO$_4$, and evaporated under reduced pressure. The residue was purified by Prep-TLC to give Compound 134CC (110 mg, 55.4%) as an oily residue. $^1$H NMR (400 MHz, CD$_3$OD) δ 6.01 (s, 2H), 4.99-5.22 (m, 1H), 3.49 (s, 1H), 1.27-1.55 (m, 12H).

To a solution of Compound 134CC (50 mg, 0.175 mmol) in ethyl acetate (2 mL) was added 4N HCl/EtOAc (2 mL) in an ice-water bath and then the reaction was stirred at room temperature for 2 h. After the reaction was complete, the reaction mixture was concentrated to give Compound 134A (30 mg, 96.4% yield) which was used in the next step directly.

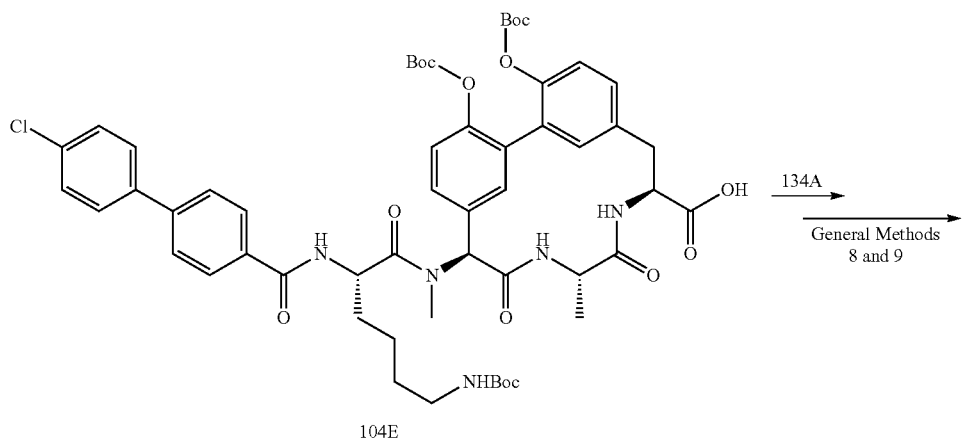

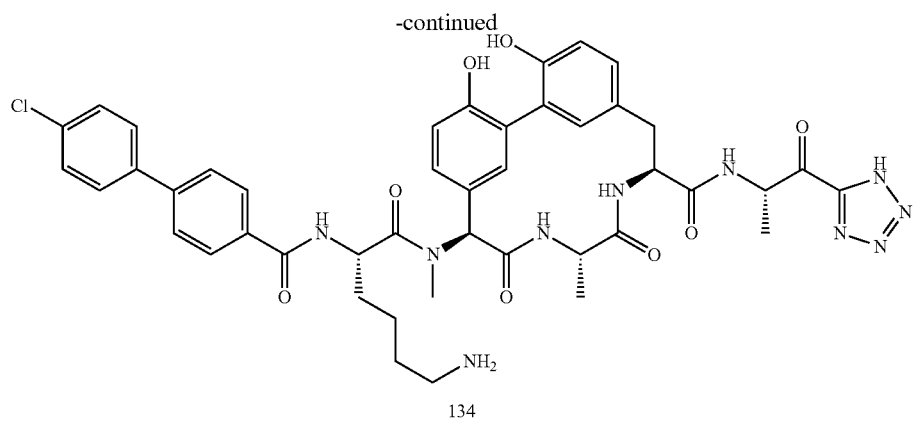
134
Compound 134 was prepared according to General Methods 8 and 9 from Compound 104E and Compound 134A. $^1$H NMR (400 MHz, CD$_3$OD) δ 7.52-7.60 (m, 2H), 7.47 (s, 2H), 7.33-7.38 (m, 1H), 7.30 (s, 1H), 7.13 (s, 1H), 6.99-7.05 (d, J=8.4 Hz, 1H), 6.95 (s, 1H), 6.88 (s, 1H), 6.79-6.84 (d, J=8.4 Hz, 1H), 6.37-6.50 (m, 1H), 5.50-5.58 (m, 1H), 4.60-4.72 (m, 2H), 3.16-3.23 (m, 1H), 2.94-3.12 (m, 7H), 1.97-2.15 (m, 2H), 1.72-1.84 (m, 3H), 1.59-1.68 (m, 1H), 1.51-1.56 (d, J=7.2 Hz, 3H), 1.41-1.49 (d, J=6.8 Hz, 3H). LCMS (5-95 AB, ESI): RT=0.794, M+H$^+$=879.7.
Example 35: Preparation of Compound 135
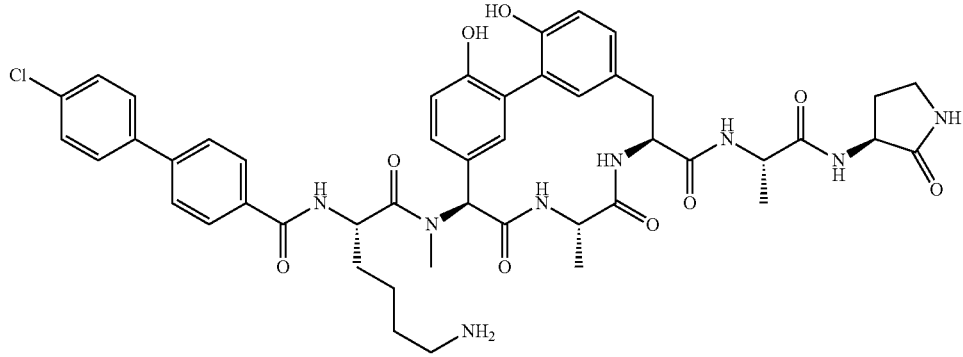
135
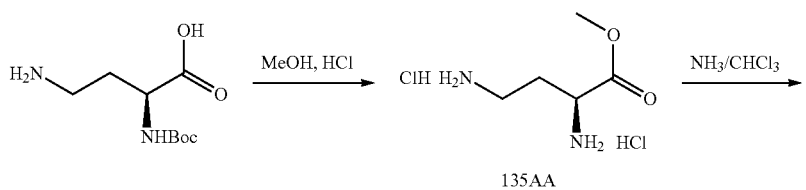
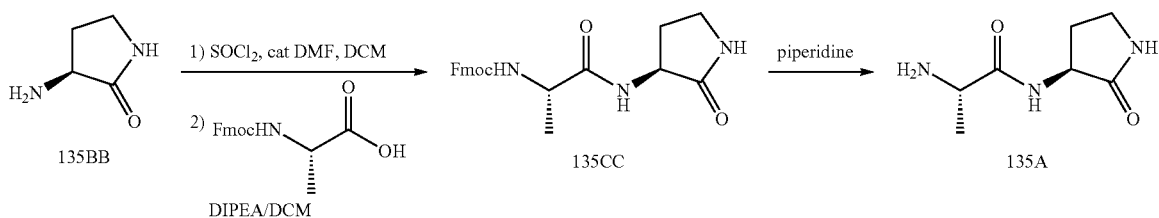

A solution of (S)-4-amino-2-((tert-butoxycarbonyl)amino)butanoic acid (10 g, 45.8 mmol) in 4N HCl/MeOH (150 mL) was heated to reflux and stirred for 16 h. The reaction mixture was concentrated to give Compound 135AA (9.5 g, yield-100%) as a light-brown oil, which was used without further purification.

To a solution of Compound 135AA (9.5 g, 45.8 mmol) in DCM (20 mL) at −30° C. was added 10N NH$_3$/DCM solution (150 mL) at the same temperature. The resulting mixture was stirred and allowed to warm up to room temperature over a period of 16 h. The reaction mixture was concentrated to give Compound 135BB (1.5 g, yield 32%) as an off-white solid which was used without further purification.

white solid. $^1$H NMR (400 MHz, DMSO-d6) δ 8.05-8.03 (d, J=8 Hz, 1H), 7.87-7.85 (d, J=7.6 Hz, 2H), 7.79 (brs, 1H), 7.70-7.68 (d, J=6.4 Hz, 2H), 7.47-7.45 (d, J=7.6 Hz, 1H), 7.41-7.37 (t, J=7.6 Hz, 2H), 7.32-7.28 (t, J=7.6 Hz, 2H), 4.27-4.18 (m, 4H), 4.04-4.00 (t, J=7.2 Hz, 1H), 3.15-3.13 (d, J=8.8 Hz, 2H), 2.25 (brs, 1H), 1.77-1.71 (t, J=11.6 Hz, 1H), 1.21-1.19 (d, J=7.2 Hz, 3H).

To a solution of piperidine/DCM (v/v ¼, 5 mL) at rt was added Compound 135CC (200 mg, 0.1 mmol) and the mixture was stirred for 10 min. The reaction mixture was concentrated under reduced pressure and the residue was lyophilized to give Compound 135A (200 mg, yield ~100%) as a white solid, which was used without further purification.

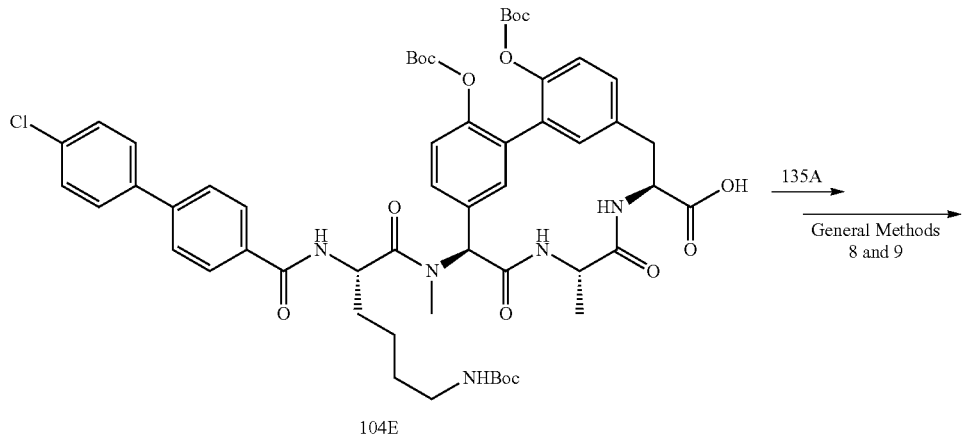

104E

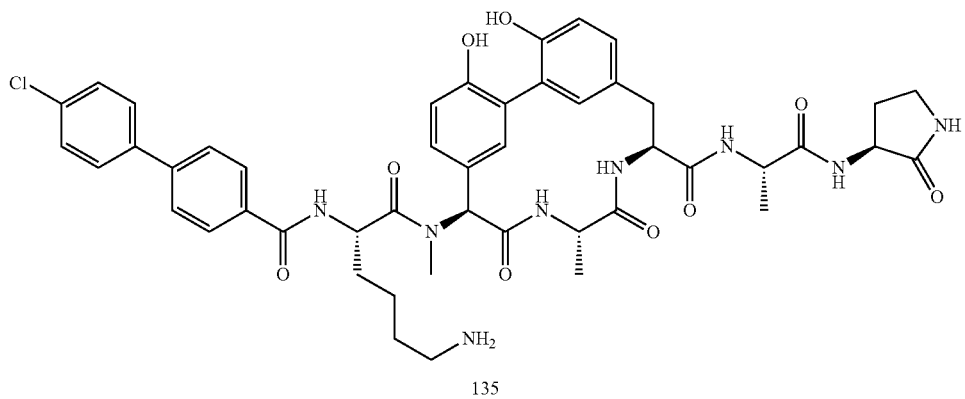

135

To a solution of Compound 135BB (155 mg, 0.5 mmol) in dry DCM (5 mL) was added DMF (cat., 1 drop), followed by the addition of SOCl$_2$ (240 mg, 2 mmol). The resulting mixture was heated at reflux for 3 h. The reaction mixture was cooled and concentrated. The residue was re-dissolved in dry DCM (3 mL), followed by the dropwise addition of a solution of (S)-2-((((9H-fluoren-9-yl)methoxy)carbonyl)amino)propanoic acid (50 mg, 0.5 mmol) and DIEA (130 mg, 1 mmol) in dry DCM (3 mL) at 0° C. The resulting mixture was stirred at 18° C. for 3 h. The reaction mixture was concentrated and the residue was purified by HPLC to obtain Compound 135CC (40 mg, yield 20%) as an off- Compound 135 was prepared according to General Methods 8 and 9 from Compound 104E and Compound 135A. $^1$H NMR (400 MHz, MeOH-d$_4$) δ 8.47 (s, 1H), 7.98-7.96 (d, J=8.4 Hz, 1H), 7.92-7.80 (d, J=8.4 Hz, 1H), 7.76-7.61 (m, 4H), 7.49-7.45 (t, J=8.0 Hz, 2H), 7.25-7.05 (m, 3H), 7.00-6.90 (m, 2H), 6.86-6.84 (d, J=8.0 Hz, 1H), 6.50-6.47 (d, J=13.2 Hz, 1H), 5.05-5.02 (m, 1H), 4.80-4.75 (m, 2H), 4.46-4.38 (m, 2H), 3.36-3.34 (m, 2H), 2.99-2.94 (m, 5H), 2.48 (m, 1H), 2.12-1.91 (m, 5H), 1.73 (m, 2H), 1.59-1.57 (m, 2H), 1.40-1.35 (m, 6H). LCMS (10-80 AB, ESI): RT=1.079, M+H$^+$=909.3.

Example 36: Preparation of Compound 136

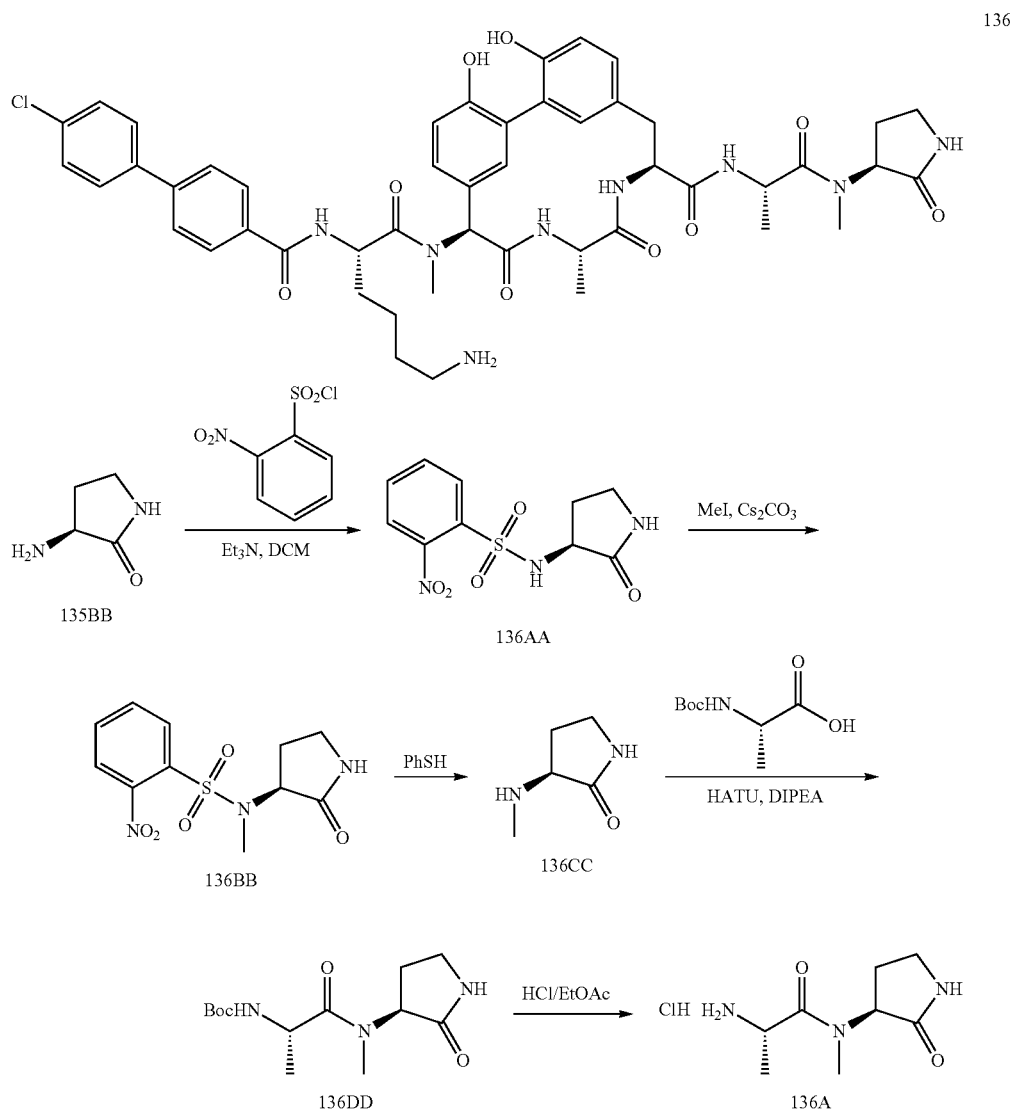

To a mixture of Compound 135BB (200 mg, 2 mmol) in DCM (10 mL) was added Et₃N (606 mg, 6 mmol) at 0° C., followed by the addition of 2-nitrobenzene-1-sulfonyl chloride (443 mg, 2 mmol) in DCM (5 mL). The resulting mixture was stirred at 15° C. for 12 h. The mixture was concentrated and the residue was purified by silica gel column (DCM/MeOH=40/1) to give Compound 136AA (440 mg, 77.2%) as a white solid.

To a mixture of Compound 136AA (440 mg, 1.54 mmol) in DMF (4 mL) was added Cs₂CO₃ (502.5 mg, 1.54 mmol) at 0° C., followed by the addition of CH₃I (492.6 mg, 3.47 mmol). The mixture was stirred at 15° C. for 12 h. The mixture was purified by silica gel column (DCM/MeOH=40/1) to give Compound 136BB (400 mg, 86.7%) as a yellow oil.

To a mixture of Compound 136BB (400 mg, 1.2 mmol) in DMF (5 mL) was added K₂CO₃ (960 mg, 6.8 mmol) at 0° C., followed by the addition of PhSH (620 mg, 5.6 mmol). The mixture was stirred at 15° C. for 5 h. Water (40 mL) was added to the mixture, which was then extracted by DCM (30 mL*2). The aqueous phase that was confirmed to contain the desired product was lyophilized and the residue was re-dissolved in DCM (30 mL). The filtrate was then concentrated to afford Compound 136CC (50 mg, 32.9%) as a light yellow oil. $^1$H NMR (400 MHz, CDCl₃) δ 6.44 (brs, 1H), 3.40-3.28 (m, 3H), 2.47 (s, 3H), 2.39-2.35 (m, 1H), 2.18 (brs, 2H), 1.96-1.91 (dd, $J_1$=8.8 Hz, $J_2$=12.4 Hz, 1H).

To a mixture of (S)-2-((tert-butoxycarbonyl)amino)propanoic acid (85 mg, 0.45 mmol) in DCM (10 mL) was added HATU (342 mg, 0.90 mmol) at 0° C., followed by the addition of Compound 136CC (50 mg, 0.45 mmol) in DCM (2 mL) and DIPEA (174 mg, 1.35 mmol). The mixture was stirred at 15° C. for 2 h. The mixture was purified by HPLC (0.1% HCl) to give Compound 136DD (50 mg, 40%) as a white solid.

To a mixture of Compound 136DD (50 mg, 0.18 mmol) in EtOAc (1 mL) at 0° C. was added 4N HCl/EtOAc (2 mL). The mixture was stirred at 15° C. for 1 h. The mixture was concentrated to give Compound 136A (38 mg, 97.4%), which was used for the next step directly.

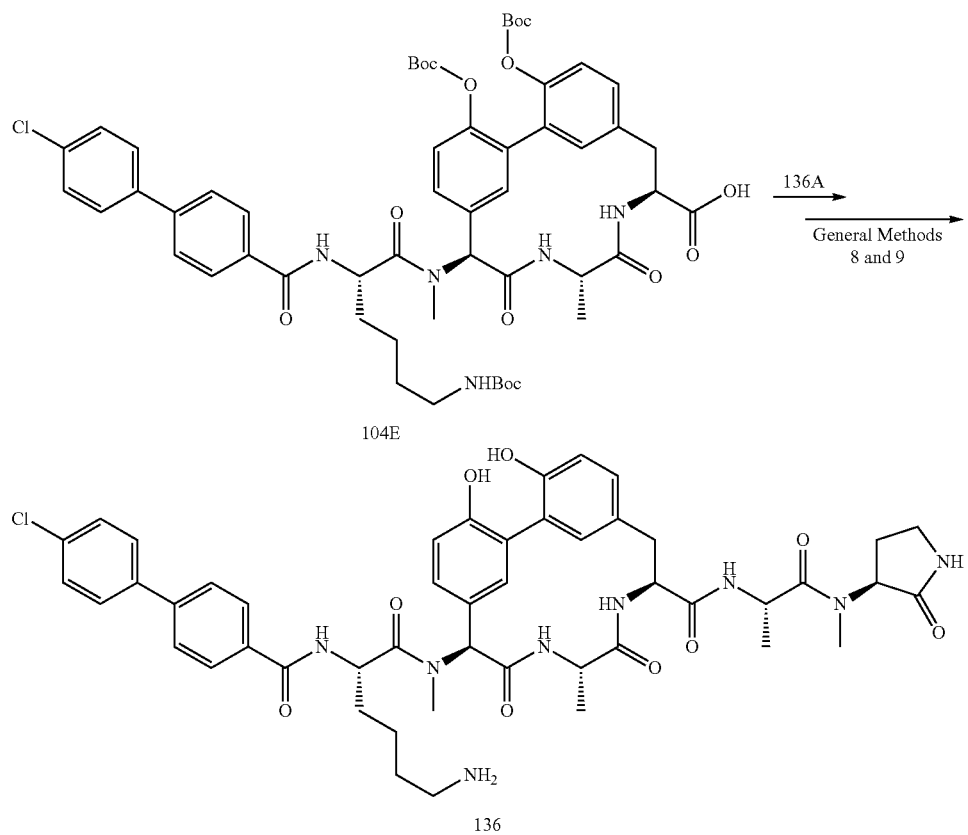
Compound 136 was prepared according to General Methods 8 and 9 from Compound 104E and Compound 136A. $^1$H NMR (400 MHz, MeOH-d$_4$) δ 7.80-7.68 (m, 3H), 7.65-7.60 (m, 2H), 7.58-7.50 (m, 1H), 7.50-7.35 (m, 3H), 7.20-7.10 (m, 1H), 7.02-6.96 (m, 2H), 6.90-6.85 (m, 1H), 6.85-6.79 (m, 1H), 5.10-5.00 (m, 3H), 4.80-4.70 (m, 3H), 3.50-3.35 (m, 2H), 3.20-3.10 (m, 1H), 3.07 (s, 3H), 2.98 (s, 3H), 2.98-2.96 (m, 2H), 2.60-2.50 (m, 1H), 1.45-1.28 (m, 1H), 2.10-1.95 (m, 2H), 1.80-1.68 (m, 3H), 1.65-1.50 (m, 1H), 1.50-1.40 (m, 1H), 1.40-1.30 (m, 1H). LCMS (5-95 AB, ESI): RT=0.781, M+H$^+$=923.2.
Example 37: Preparation of Compound 137
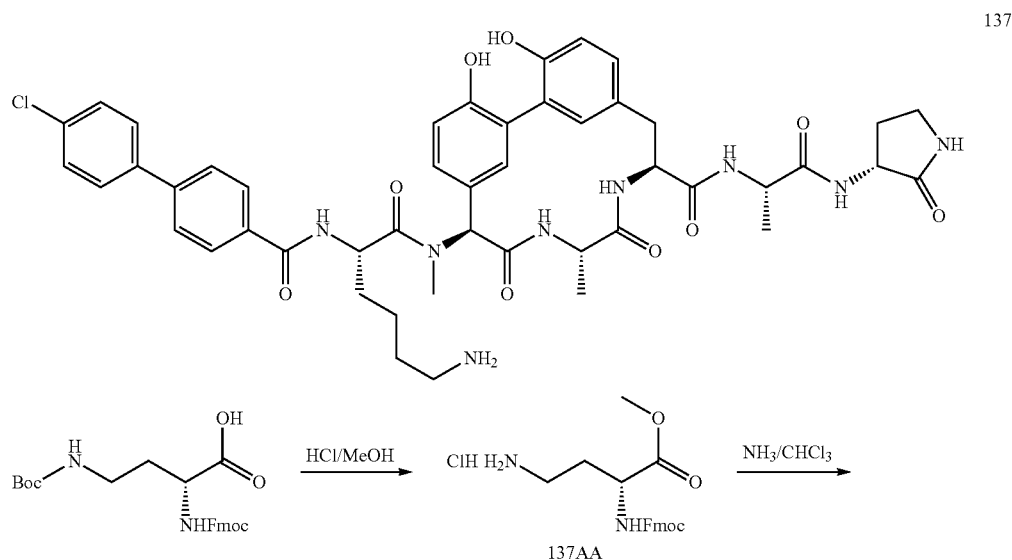

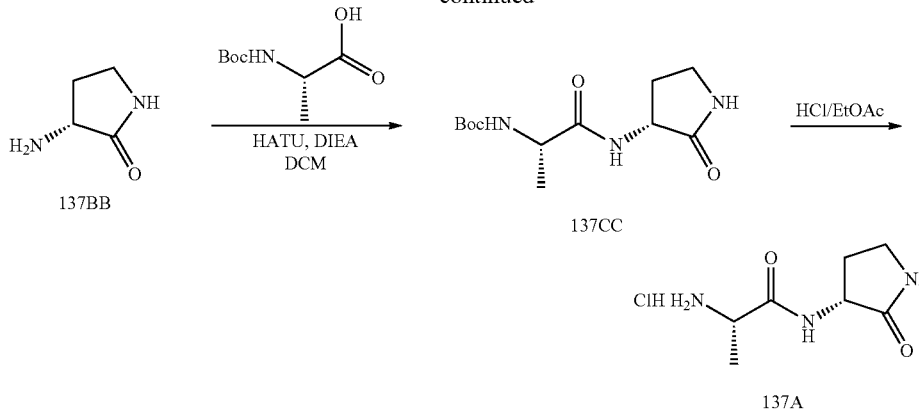

A similar procedure as outlined in the synthesis of 135BB (Example 35) was applied to (R)-2-((((9H-fluoren-9-yl)methoxy)carbonyl)amino)-4-((tert-butoxycarbonyl)amino)butanoic acid to afford Compound 137BB as a yellow solid (2.0 g).

To a solution of Compound 137BB (189 mg, 1.0 mmol) and (S)-2-((tert-butoxycarbonyl)amino) propanoic acid (100 mg, 1.0 mmol) in DCM (10 mL), HATU (569 mg, 1.5 mmol) and DIEA (193 mg, 1.5 mmol) were added. The mixture was stirred for 6 h under room temperature. Water (20 mL) was added to the resulting mixture and the aqueous layer was further extracted by DCM (20 mL*2). The combined DCM layers were concentrated and the residue was purified by HPLC (0.1% NH₃) to give Compound 137CC (80 mg, 30%) as a white solid (LCMS purity: 98%).

To a solution of Compound 137CC (80 mg, 0.3 mmol) in EtOAc (2 mL) was added 4N HCl/EtOAc (2 mL) at 0° C. and the mixture was stirred for 30 minutes at this temperature. After the reaction was complete, the volatiles were removed to give Compound 137A (60 mg, 98%) as a white solid.

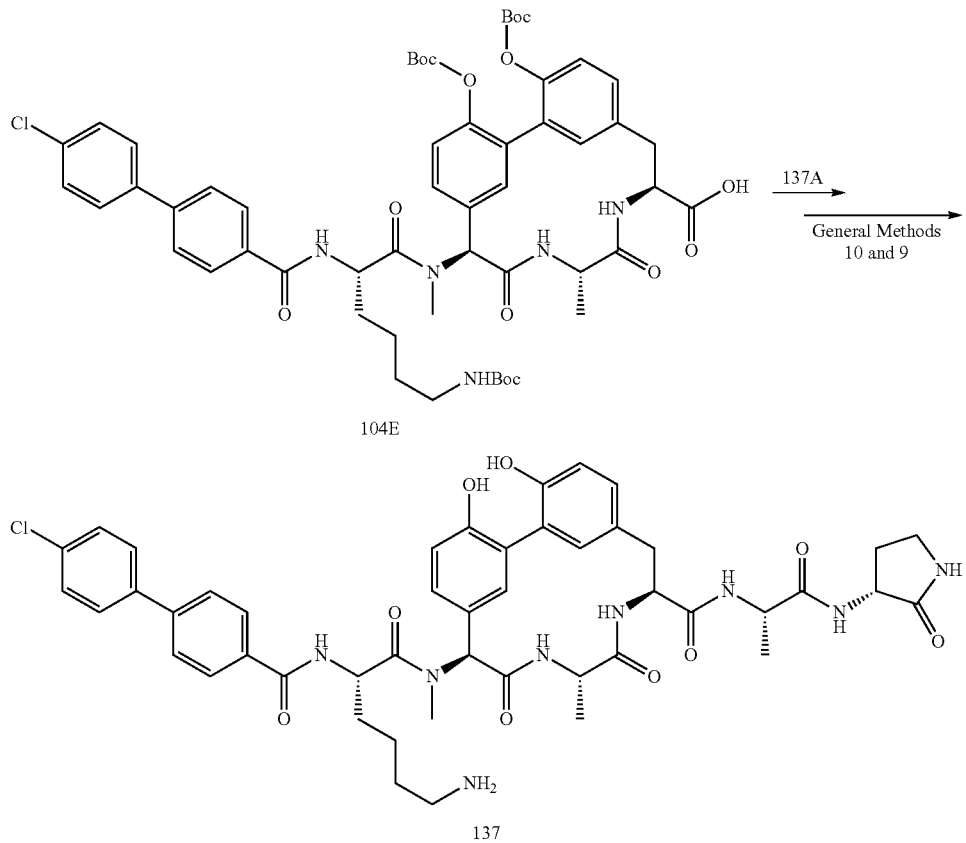

Compound 137 was prepared according to General Method 10 and General Method 9 from Compound 104E and Compound 137A. $^1$H NMR (400 MHz, MeOH-d$_4$) δ 7.83 (d, J=8.0 Hz, 2H), 7.65 (d, J=8.0 Hz, 2H), 7.55 (d, J=8.4 Hz, 2H), 7.43 (d, J=8.4 Hz, 2H), 7.13 (d, J=8.4 Hz, 1H), 7.04 (d, J=8.0 Hz, 1H), 6.99-6.94 (m, 2H), 6.84 (d, J=8.4 Hz, 2H), 6.64-6.60 (m, 1H), 5.01 (dd, J=8.4, 4.8 Hz, 1H), 4.75 (d, J=9.6 Hz, 1H), 4.51-4.43 (m, 2H), 3.36 (d, J=8.4 Hz, 2H), 3.22-3.20 (m, 1H), 3.11-3.05 (m, 1H), 2.95 (s, 3H), 2.46 (d, J=6.4 Hz, 1H), 2.11-1.88 (m, 4H), 1.81-1.67 (m, 3H), 1.66-1.49 (m, 3H), 1.44-1.33 (m, 6H). LCMS (5-95 AB, ESI): RT=0.763, M+H$^+$=909.

Example 38: Synthesis of Compound 138

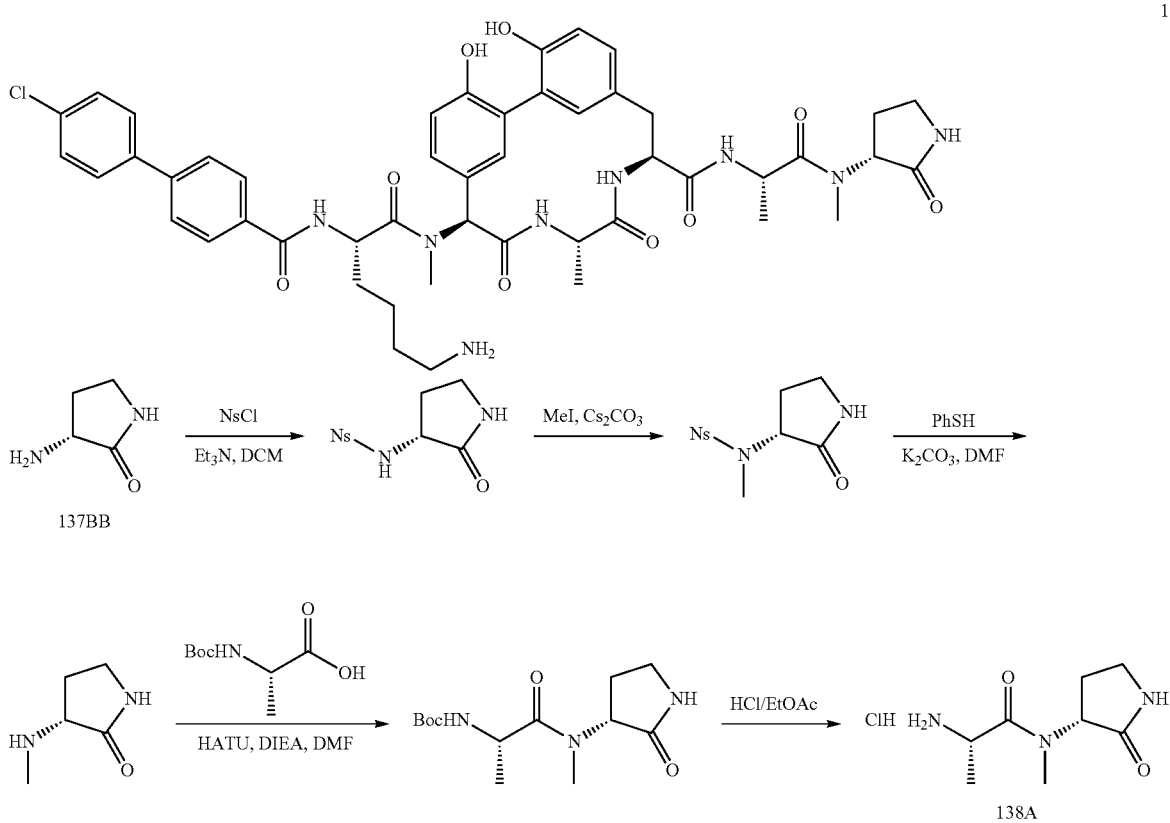

A similar procedure as outlined in the synthesis of 136A (Example 36) was applied to (R)-3-aminopyrrolidin-2-one to afford Compound 138A as a white solid (20 mg).

Compound 138 was prepared according to General Methods 8 and 9 from Compound 104E and Compound 138A. $^1$H NMR (400 MHz, MeOH-d4) δ 1.18-1.49 (m, 6H), 1.58 (br. s., 1H), 1.73 (d, J=7.72 Hz, 3H), 2.00 (br. s., 2H), 2.17-2.26 (m, 1H), 2.36 (br. s., 1H), 2.82 (s, 1H), 2.94 (s, 3H), 2.97-3.02 (m, 1H), 3.05 (d, J=8.60 Hz, 1H), 3.08 (s, 1H), 3.20 (d, J=18.08 Hz, 1H), 3.35-3.45 (m, 2H), 4.59 (br. s., 2H), 4.81 (br. s., 3H), 5.01 (br. s., 3H), 6.75-6.86 (m, 2H), 6.90-6.99 (m, 2H), 7.01 (d, J=6.84 Hz, 1H), 7.11 (br. s., 1H), 7.40-7.49 (m, 2H), 7.51-7.58 (m, 1H), 7.60-7.69 (m, 2H) 7.74 (br. s., 1H) 7.82 (dd, J=15.66, 7.94 Hz, 2H). LCMS (5-95 AB, ESI): RT=0.769, M+H$^+$=923.6.

Example 39: Synthesis of Compound 139

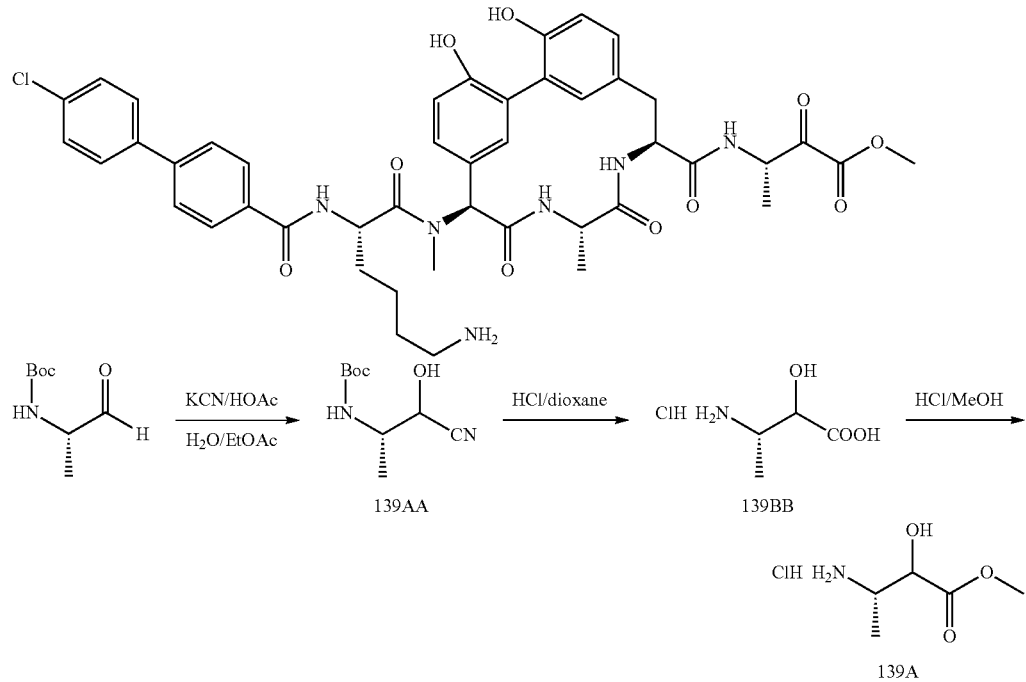

To a mixture of (S)-tert-butyl (1-oxopropan-2-yl)carbamate (10 g, 57.7 mmol) in EtOAc (90 mL) and MeOH (90 mL) at 0° C., was added solid KCN (4.2 g, 63.5 mmol), followed by the addition of AcOH (3.9 g, 63.5 mmol) at the same temperature. The reaction was stirred at 30° C. for 16 hr. After the reaction was complete, volatiles were removed under reduced pressure and the residue was poured into water (50 mL), which was further extracted with EtOAc (50 mL*3). The combined organic layers were dried over Na$_2$SO$_4$, evaporated under reduced pressure and the residue was purified by silica gel column (PE/EtOAc=10/1-6/1) to give Compound 139AA (10.3 g, 89%) as a colorless oil.

To a solution of Compound 139AA (10.3 g, 51.5 mmol) in dioxane (30 mL) was added concentrated HCl (30 mL) at 0° C. The solution was kept at 25° C. for 1 h and then the solution was heated at 100° C. for another 16 h. Volatiles were removed to afford Compound 139BB (7.1 g, 88.9%) as a brown oil.

To a solution of Compound 139BB (7.1 g, crude) in MeOH (3 mL) was added 4N HCl/MeOH (30 ml) at 0° C. The solution was kept at 25° C. for 16 h. Volatiles were removed to afford Compound 139A (7.8 g) as brown oil.

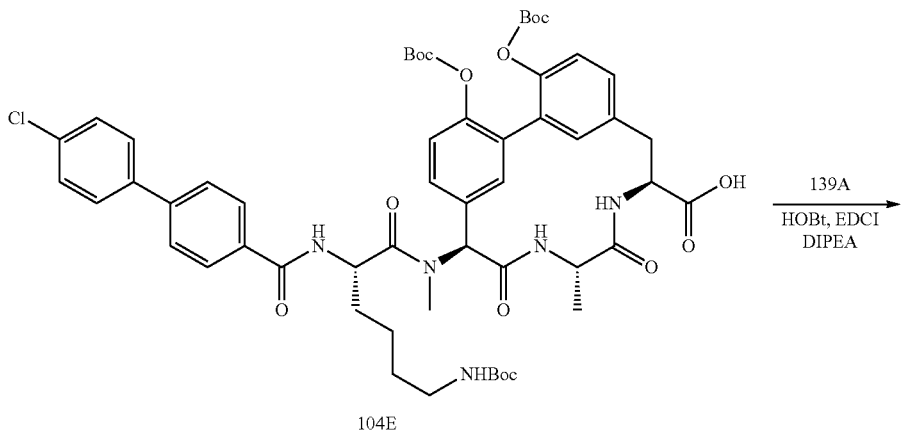

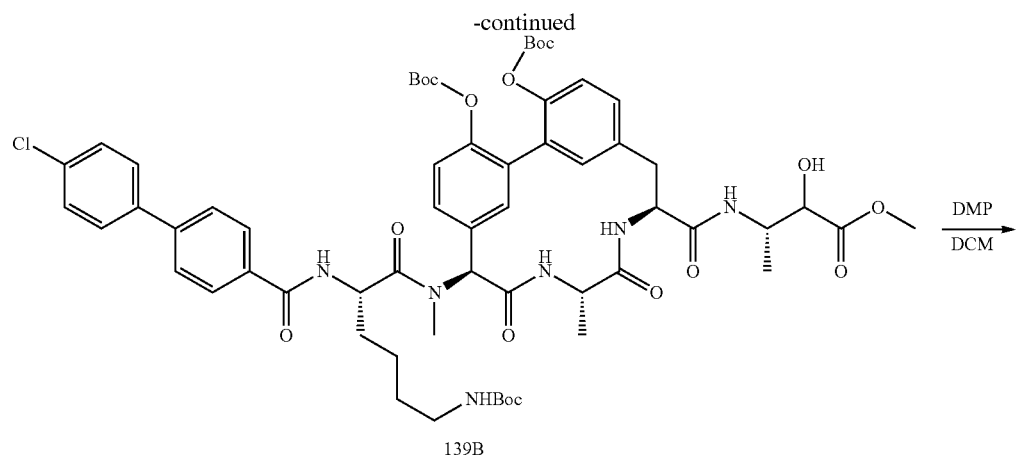
139B
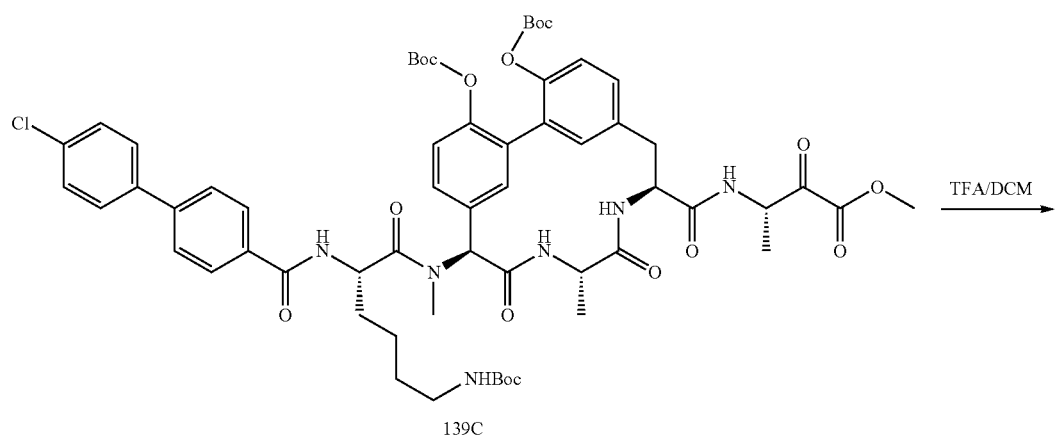
139C
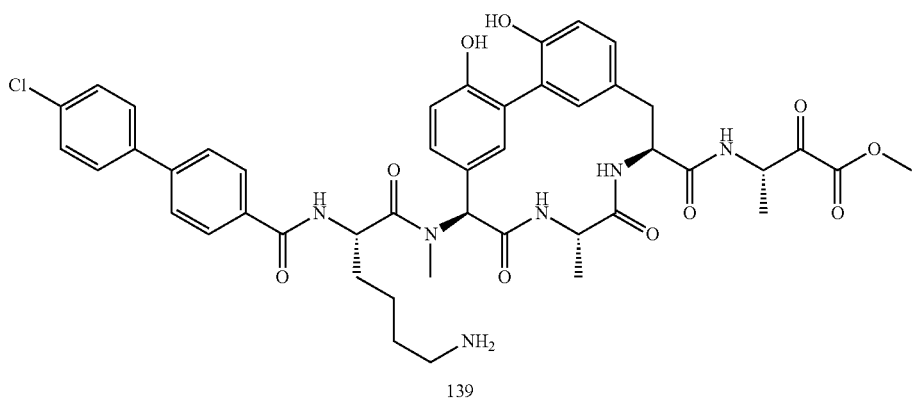
139
Compound 139B was prepared according to General Method 10 from Compound 104E and Compound 139A. Compound 139C was prepared according to General Method 11 from Compound 139B.
Compound 139 (formic acid salt) was prepared according to General Method 9 from Compound 139C. $^1$H NMR (400 MHz, MeOH-d$_4$) δ 9.11-9.07 (m, 1H), 8.84-8.82 (m, 1H), 7.74-7.71 (m, 2H), 7.60-7.58 (m, 2H), 7.46-7.39 (m, 4H), 7.00-6.98 (m, 1H), 7.00-6.98 (m, 2H), 6.82-6.80 (m, 3H), 6.65 (m, 1H), 4.62-4.32 (m, 2H), 4.27-4.25 (m, 1H), 3.79-3.71 (m, 3H), 3.07-2.95 (m, 6H), 1.99-1.93 (m, 3H), 1.74 (s, 5H), 1.40-1.37 (m, 3H), 1.15-1.10 (m, 3H). LCMS (5-95 AB, ESI): RT=0.781, M+Na$^+$=891.2.

Example 40: Synthesis of Compound 140
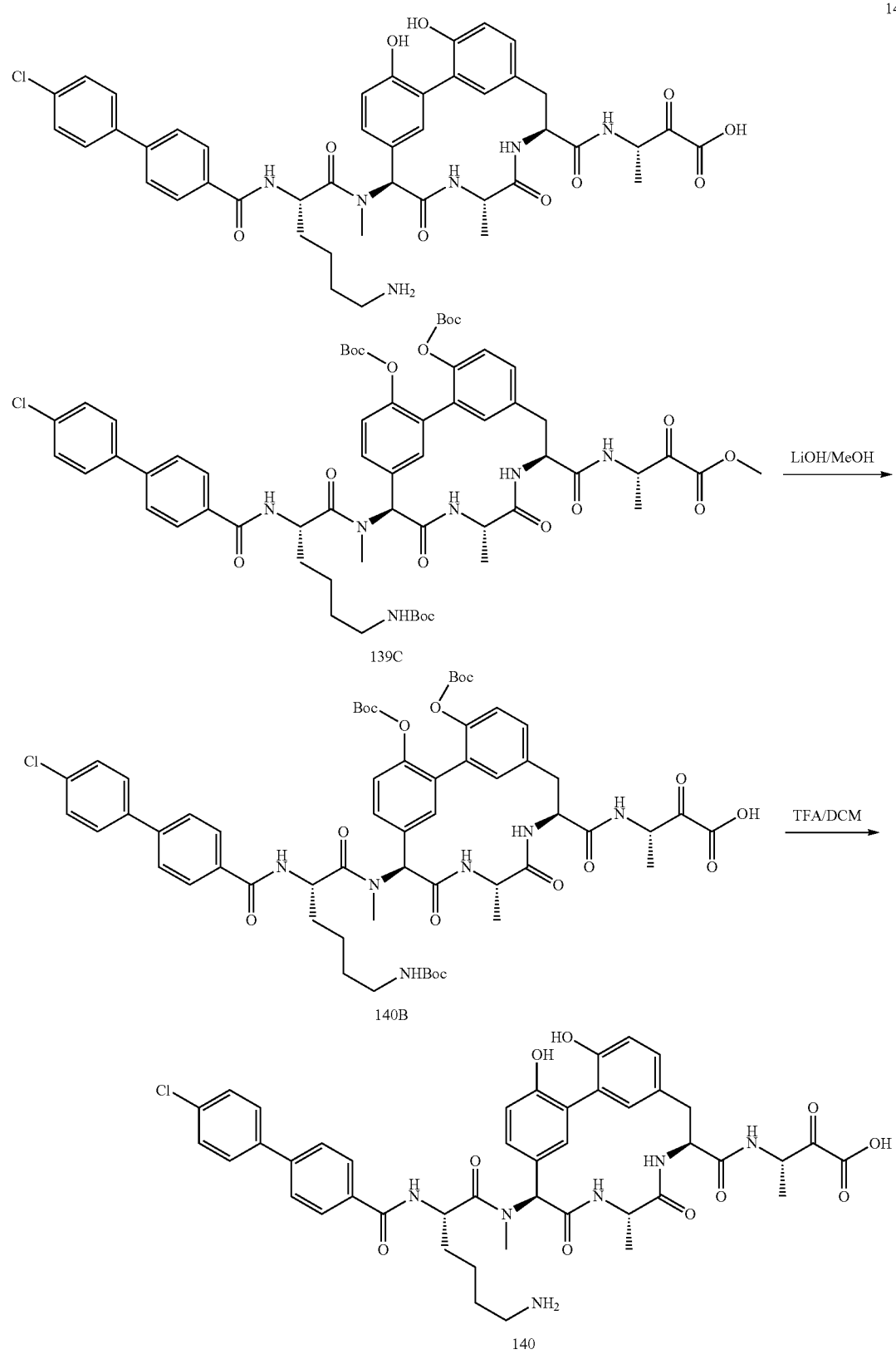

To a solution of Compound 139C (75 mg, 0.064 mmol) in MeOH (3 mL) at 0° C. was added 1N LiOH (0.9 ml) and the solution was kept at the same temperature for 30 mins. After the reaction was complete, volatiles were removed under reduced pressure and the residue was re-dissolved with water (10 mL), whose pH was adjusted to pH=2-3, followed by the extraction of DCM (15 mL*2). The combined DCM layers were dried over Na$_2$SO$_4$ and evaporated to give Compound 140A (70 mg, 90.6%) as a yellow solid.

Compound 140 (formic acid salt) was prepared according to General Method 9 from Compound 140A. $^1$H NMR (400 MHz, MeOH-d$_4$) δ 9.15 (s, 1H), 9.03-8.89 (m, 1H), 7.70 (m, 2H), 7.57 (m, 2H), 7.42-7.39 (m, 4H), 7.12-6.93 (m, 1H), 6.87 (m, 2H), 6.85-6.78 (m, 3H), 6.58 (m, 1H), 4.91 (m, 3H), 4.81 (m, 1H), 4.62 (m, 1H), 4.34-4.29 (m, 1H), 2.98-2.85 (m, 6H), 2.00 (s, 2H), 1.74-1.59 (m, 4H), 1.41-1.37 (m, 3H), 1.17-1.13 (m, 2H). LCMS (5-95 AB, ESI): RT=0.775, M+H$^+$+H$_2$O=873.6.

Example 41: Synthesis of Compound 141

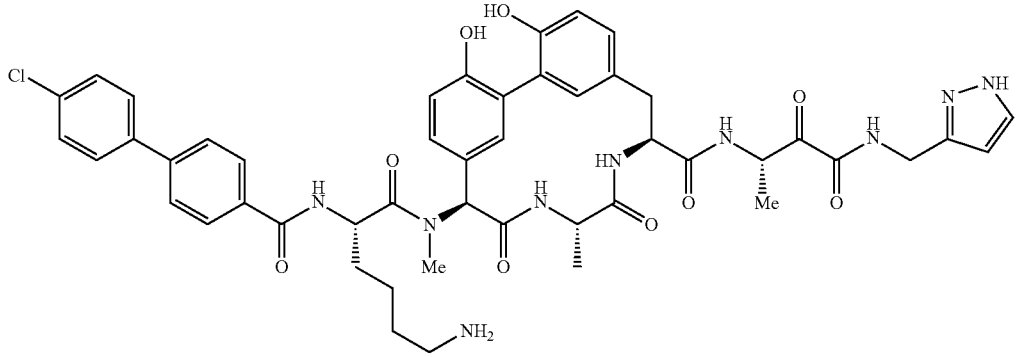

141

Compound 141 was prepared according to General Method 10 from Compound 140B and (1H-pyrazol-3-yl) methanamine. $^1$H NMR (400 MHz, MeOH-d$_4$) δ 7.93-7.90 (m, 1H), 7.87-7.82 (m, 2H), 7.77-7.72 (m, 1H), 7.70-7.65 (m, 2H), 7.58 (d, J=8.80 Hz, 2H), 7.44 (d, J=8.4 Hz, 2H), 7.15 (d, J=8.40 Hz, 2H), 7.00-6.92 (m, 2H), 6.83-6.75 (m, 2H), 6.25 (s, 1H), 5.04-5.02 (m, 1H), 4.59 (s, 1H), 4.46 (d, J=12.0 Hz, 2H), 4.24-4.16 (m, 1H), 2.99-2.96 (m, 1H), 2.94 (s, 3H), 2.05-1.96 (m, 3H), 1.81-1.53 (m, 6H), 1.44-1.34 (m, 4H), 1.32-1.27 (m, 1H), 1.13 (d, J=6.8 Hz, 2H). LCMS (5-95 AB, ESI): RT=0.773, M+H$^+$=935.6.

Example 42: Synthesis of Compound 142

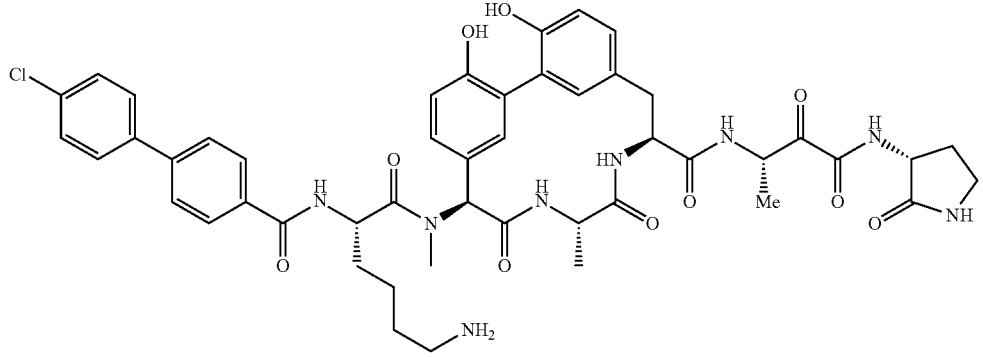

142

Compound 142 was prepared according to General Method 12 from Compound 137BB. ¹H NMR (400 MHz, MeOH-d₄) δ 8.02-7.98 (m 1H), 7.85-7.71 (d, J=8.0 Hz, 2H), 7.70-7.65 (d, J=8.0 Hz, 2H), 7.52-7.40 (m, 2H), 7.22-7.10 (m, 3H), 7.02-6.90 (m, 2H), 6.90-6.80 (m, 1H), 6.52 (s, 1H), 5.15-5.04 (m, 2H), 4.70-4.55 (m, 4H), 3.40-3.35 (m, 2H), 3.05 (s, 3H), 2.97 (s, 3H), 2.50-2.46 (m, 1H), 2.10-1.90 (m, 3H), 1.85-1.78 (m, 3H), 1.71-1.58 (m, 2H), 1.50-1.40 (m, 3H), 1.30-1.10 (m, 3H). LCMS (5-95 AB, ESI): RT=0.783, M+H⁺=937.4.
Example 43: Synthesis of Compound 143
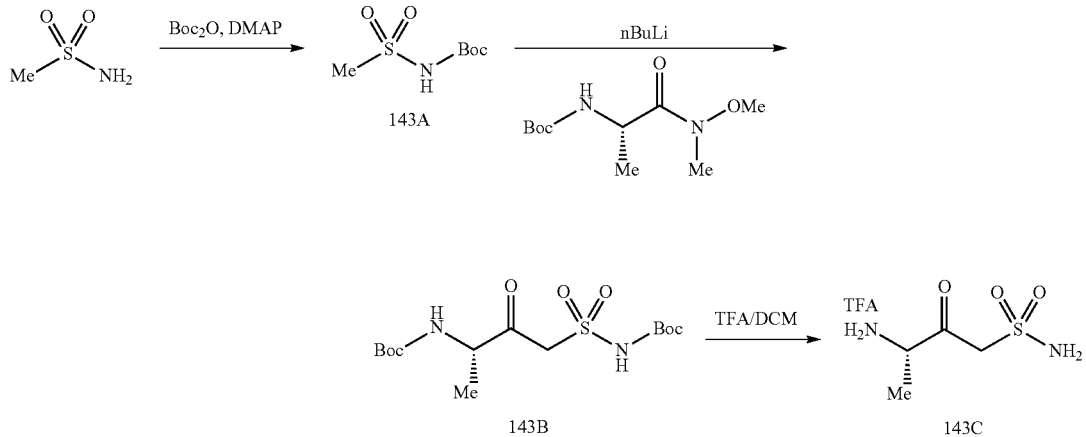
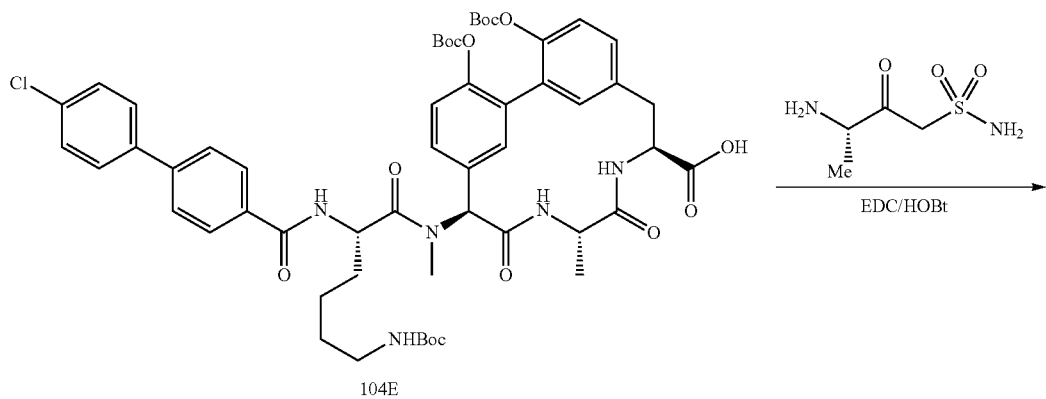
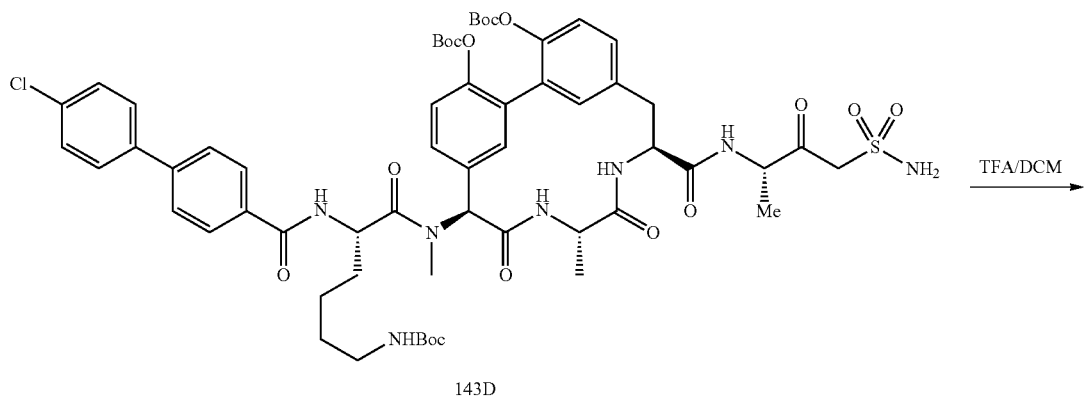

-continued

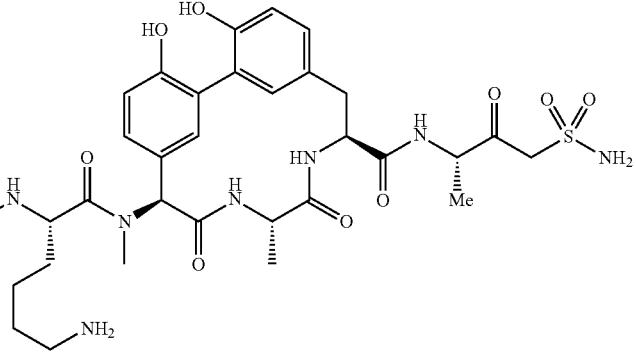

143

Methyl sulfonamide (2 g, 21 mmol, 1 eq) was dissolved in DCM (60 mL) with sonication and cooled to 0° C. The solution was treated with TEA (3.5 mL, 1.2 eq), DMAP (257 mg, 0.1 eq) and Boc$_2$O (4.83 mL, 1.0 eq), then allowed to warm to room temperature with stirring. The reaction was allowed to stir overnight and then the solvents were evaporated. The residue was taken up in EtOAc, washed with 1N HCl and H$_2$O, then dried over sodium sulfate and concentrated. The residue was recrystallized 2× with hexanes and dried under vacuum to afford Compound 143A (3.54 g, 87%). $^1$H NMR (CDCl$_3$, 500 MHz) δ 7.06 (s, 1H), 3.27 (s, 3H), 1.52 (s, 9H).

To a solution of Compound 143A (200 mg, 0.86 mmol, 1 eq) in anhydrous THF (4 mL) under Ar in a flame dried flask at −78° C. was added 2.4 M nBuLi in hexanes (2.5 mL, 7 eq) and the reaction was allowed to stir for 1.5 hrs. In a second flame dried flask under Ar, Boc-L-Ala-N(OMe)(Me) was dissolved in anhydrous THF (4 mL) and this solution was transferred dropwise via syringe to the flask containing compound 143A. The reaction was allowed to stir for an additional 2 hrs at −78° C. then glacial AcOH (~2 mL) was added and the flask was warmed to room temp. The residue was then diluted with water and EtOAc and the aqueous was further extracted 2× with EtOAc. The combined organic layers were washed with H$_2$O and brine, then dried over sodium sulfate and concentrated. The crude material was purified by column chromatography (0 to 6% MeOH in DCM) to give a semi-pure product, containing compound 143B. MS (ESI) for (C$_{14}$H$_{26}$N$_2$O$_7$S): m/z 389.1 (M+Na).

Compound 143B (0.15 mmol, 2.5 eq) was Boc deprotected via General Method 5 to afford Compound 143C.

Compound 143C was dissolved in DCM:DMF (2:1, 3 mL) and treated with HOBt (28 mg, 3 eq), Compound 104E (63 mg, 60 μmol, 1 eq) and EDC (35 mg, 3 eq). The solution was stirred overnight then dilute citric acid and EtOAc were added. The aqueous layer was extracted 3× with EtOAc and the combined organic layers were washed with water (2×), saturated NaHCO$_3$ and brine then dried over sodium sulfate and concentrated. The crude material was purified by column chromatography (0-8% MeOH in DCM) to give Compound 143D (36 mg, 50%). MS (ESI) for (C$_{59}$H$_{74}$ClN$_7$O$_{16}$S): m/z 1204.5 (M+H)$^+$.

Compound 143D (33 mg, 27 μmol) was Boc deprotected via General Method 9 to give Compound 143 as the TFA salt (17.2 mg, 63%). MS (ESI) for (C$_{44}$H$_{50}$ClN$_7$O$_{10}$S): m/z 904.2 (M+H)$^+$. HPLC t$_R$ 2.48 min (30% AcCN/H$_2$O-70% AcCN/H$_2$O, 3.0 min, 1.0 mL/min Kinetix C18, 4.8×50 mm).

Example 44: Synthesis of Compound 144

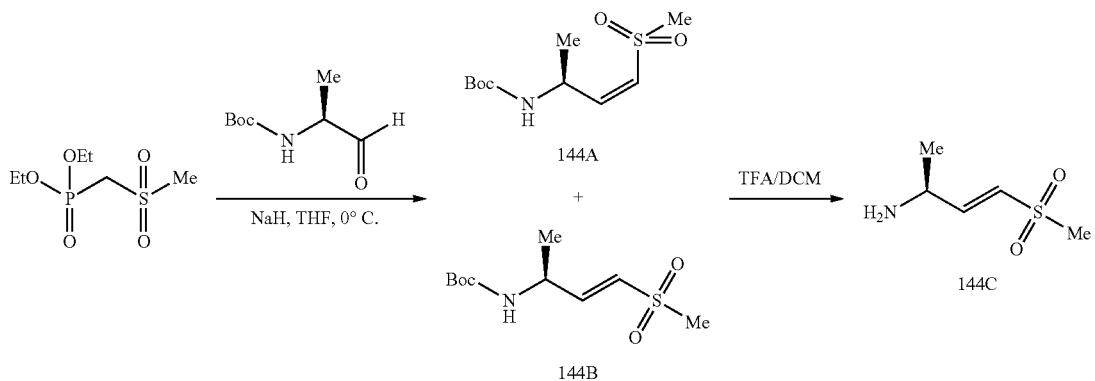

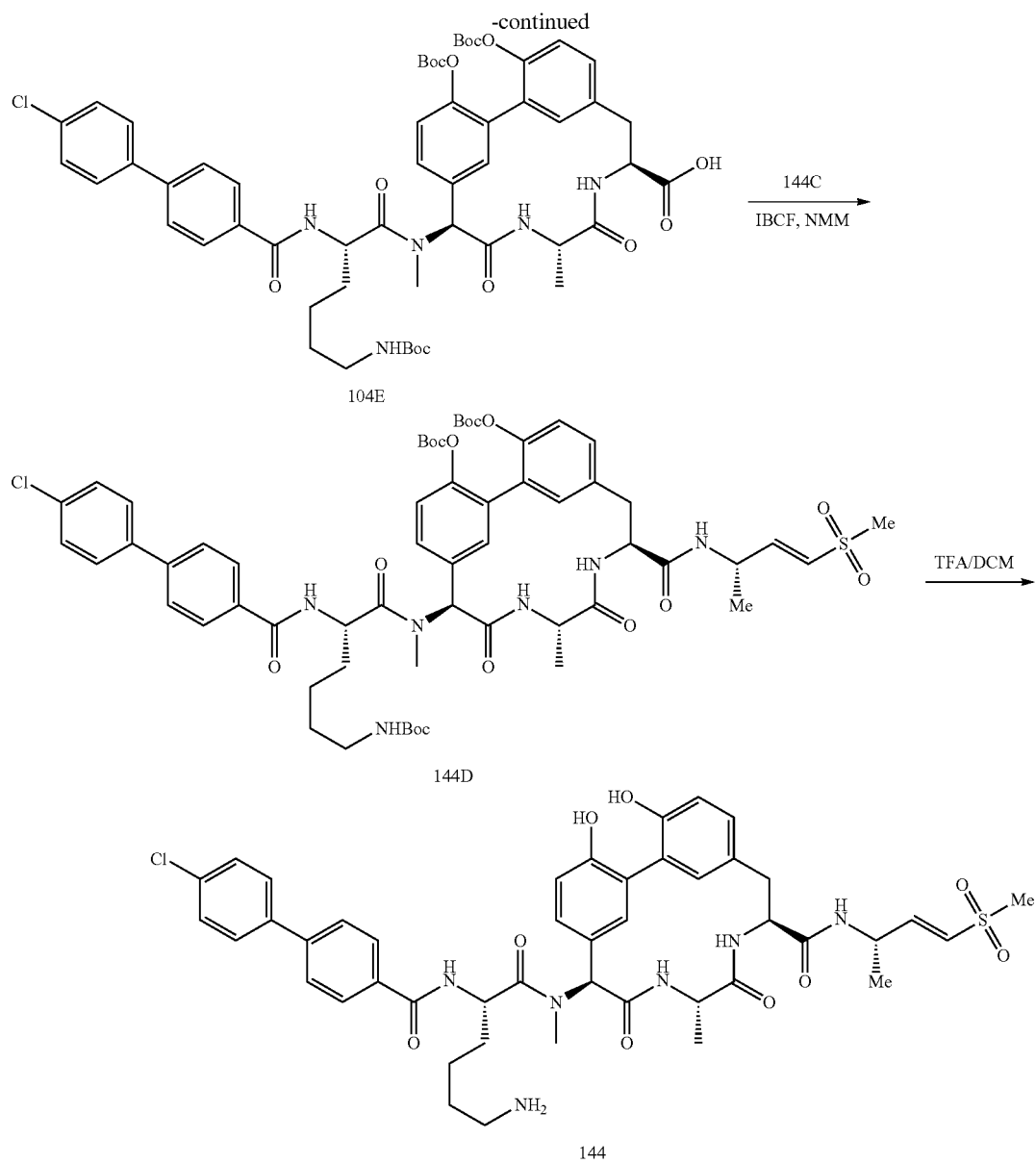

To a solution of diethyl((methylsulfonyl)methyl) phosphonate (200 mg, 0.87 mmol, 1.5 eq) in anhydrous THF (4 mL) under Ar in a flame dried flask at 0° C. was added NaH (35 mg, 1.5 eq, 60% w/w in mineral oil). The reaction was then allowed to stir for 45 mins. In a second flame dried flask under Ar, (S)-Boc-Alanal (100 mg, 1 eq) was dissolved in anhydrous THF (2 mL) and this solution was transferred dropwise via syringe to the flask containing the phosphonate at 0° C. The reaction was allowed to warm to room temp with stirring and monitored by TLC for disappearance of (S)-Boc-Alanal (30% EtOAc in Hex). After 2.5 hr, 0.2N HCl was added and the aqueous layer was extracted 3× with EtOAc. The combined organic layers were washed with 0.2N HCl and brine, and then dried over sodium sulfate and concentrated. The crude material was purified by ISCO column chromatography (0 to 70% EtOAc in Hex) to give Compound 144A as two products (144A (cis) and 144B (trans)). Compound 144A (cis)—(12 mg, 8%), Rf −0.58 (50% EtOAc in Hex), MS (ESI) for ($C_{10}H_{19}NO_4S$): m/z 272.2 (M+H)$^+$. $^1$H NMR (CDCl$_3$, 500 MHz) δ 6.25 (d, (J=11. Hz), 1H) 6.16 (dd, (J=11 Hz, 9.5 Hz), 1H), 5.17-5.12 (m, 1H), 4.63 (br s, 1H), 3.18 (s, 3H), 1.42 (s, 9H), 1.31 (d, J=7 Hz, 3H). Compound 144B (trans)—(88 mg, 61%), Rf −0.38 (50% EtOAc in Hex), MS (ESI) for ($C_{10}H_{19}NO_4S$): m/z 272.1 (M+H)$^+$. $^1$H NMR (CDCl$_3$, 500 MHz) δ 6.85 (dd, (J=15 Hz, 4.5 Hz), 1H), 6.16 (dd, (J=15 Hz, 1.5 Hz), 1H), 4.55 (br s, 1H), 4.46 (br s, 1H), 2.94 (s, 3H), 1.45 (s, 9H), 1.31 (d, J=7 Hz, 3H).

Compound 144B (0.1 mmol, 1.8 eq) was Boc deprotected via General Method 5 to give Compound 144C.

A solution of Compound 104E (60 mg, 57 μmol, 1 eq) in THF (2 mL) at 0° C. was treated with isobutyl chloroformate (13 μL, 1.8 eq) and N-methylmorpholine (31 μL, 5 eq). The reaction was allowed to stir at 0° C. for 1 hr then a solution of Compound 144C (1.8 eq) and N-methylmorpholine (16 μL, 2.5 eq) in THF (1 mL) was added. The solution was stirred at 0° C. for 30 mins then allowed to warm to room temp and stirred for 2 hr. The reaction was diluted with H$_2$O and extracted 3× with EtOAc. The combined organic layers were washed with water, dilute citric acid and brine then dried over sodium sulfate and concentrated to give Compound 144D (92 mg).

A portion of the crude Compound 144D (40 mg) was Boc deprotected using General Procedure 9 to give Compound 144 which was purified via preparative HPLC to give the pure Compound 144 as a TFA salt (11.4 mg, 44%). MS (ESI) for ($C_{45}H_{51}ClN_6O_9S$): m/z 887.2 (M+H). HPLC $t_R$ 2.54 min (30% AcCN/$H_2O$-90% AcCN/$H_2O$, 3.0 min, 1.0 mL/min Kinetix C18, 4.8×50 mm).

Example 45: Synthesis of Compound 145

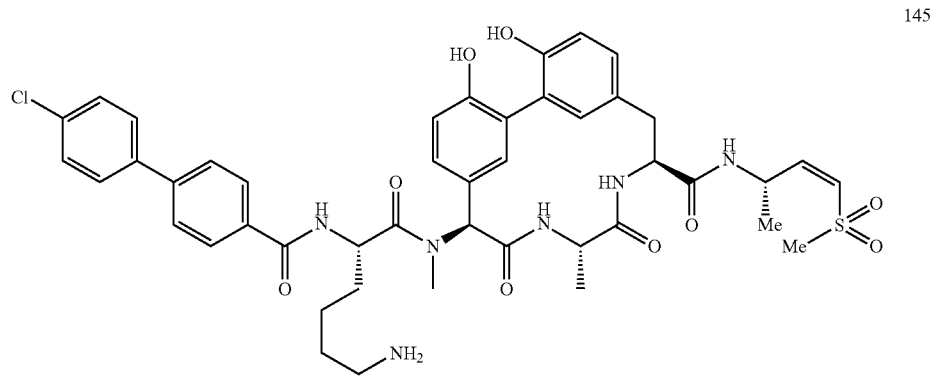 [SMILES: C[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)N[C@@H](C)/C=C\S(C)(=O)=O)NC1=O]

145

Compound 145 was synthesized in a similar manner to Compound 144 (Example 44) from Compound 104E and Compound 144A. MS (ESI) for ($C_{45}H_{51}ClN_6O_9S$): m/z 887.2 (M+H). HPLC $t_R$ 3.39 min (10% AcCN/$H_2O$-90% AcCN/$H_2O$, 3.5 min, 1.0 mL/min Kinetix C18, 4.8×50 mm).

Example 46: Synthesis of Compound 146

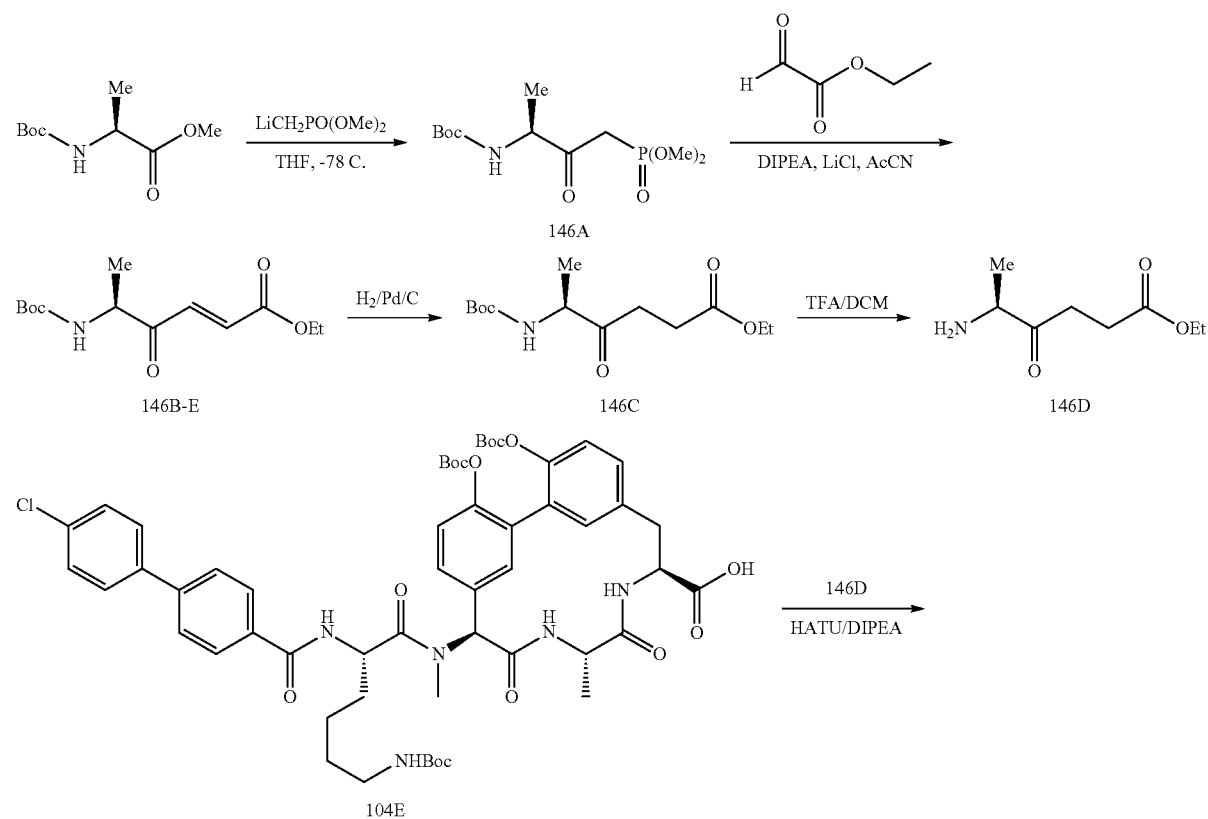

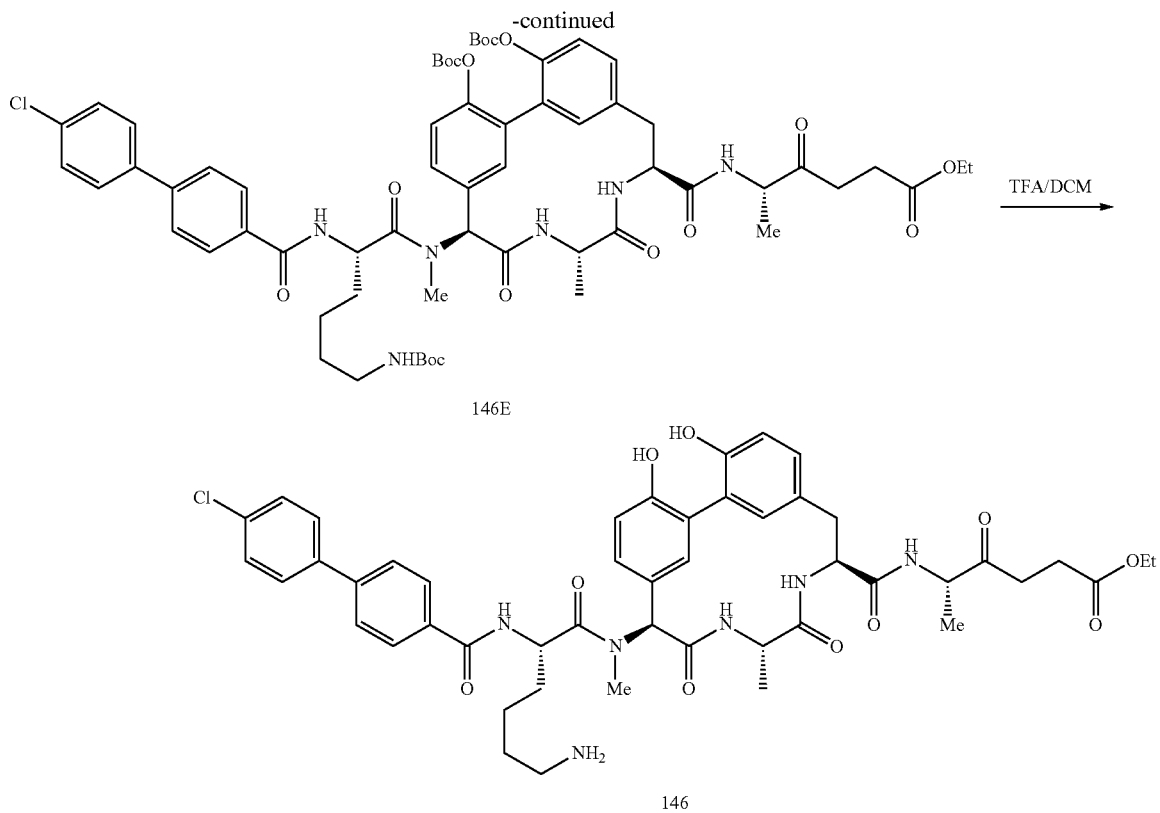

To a solution of dimethyl methyl phosphonate (6.12 mL, 2.5 eq) in anhydrous THF (45 mL) under Ar in a flame dried flask at −78° C. was added 2.0 M nBuLi in cyclohexane (28.9 mL, 2.55 eq). In a second flame dried flask under Ar, Boc-L-Ala-OMe (4.6 g, 22.7 mmol, 1 eq) was dissolved in anhydrous THF (20 mL) and this solution was transferred dropwise via syringe to the flask containing the phosphonate. The reaction was allowed to stir for 1.5 hr at −78° C. Glacial AcOH (~2 mL) was added and the reaction mixture was warmed to room temp. The mixture was poured into saturated NaHCO$_3$ and the aqueous mixture was extracted 3× with EtOAc. The combined organic layers were washed with H$_2$O and brine then dried over sodium sulfate and concentrated. The crude material was purified by ISCO column chromatography (0 to 8% MeOH in DCM) to give Compound 146A (4.52 g, 67%). MS (ESI) for ($C_{11}H_{22}NO_6P$): m/z 318.2 (M+Na).

To a solution of Compound 146A (2 g, 6.8 mmol, 1 eq) in AcCN (65 mL) at 0° C. was added LiCl (302 mg, 1.05 eq) and DIPEA (1.11 mL, 1 eq). Ethyl glyoxylate (50% in toluene, 2.08 mL, 1.5 eq) was dissolved in AcCN (65 mL) and this solution was transferred dropwise via addition funnel to the flask containing Compound 146A at 0° C. over 20 min. The reaction was allowed to stir at 0° C. for 4 hr then 5% citric acid solution was added. The aqueous solution was extracted 3× with EtOAc and the combined organic layers were washed with brine, dried over sodium sulfate and concentrated. The crude material was purified by ISCO column chromatography (0 to 50% EtOAc in Hex) to give Compound 146B as two products (Z and E). Compound 146B-Z (Z-isomer) (239 mg, 13%), lower R$_f$, MS (ESI) for ($C_{13}H_{21}NO_5$): m/z 272.2 (M+H), $^1$H NMR (CDCl$_3$, 500 MHz) δ 6.57 (d, J=12.5 Hz, 1H), 6.11 (d, J=12.5 Hz, 1H), 5.23 (br d, J=5.5 Hz, 1H), 4.51-4.48 (m, 1H), 4.22 (q, J=7 Hz, 2H), 1.44 (s, 9H), 1.40 (d, J=7.5 Hz, 3H), 1.28 (t, J=7 Hz, 3H). Compound 146B-E (E-isomer) (908 mg, 49%), higher Rf, MS (ESI) for ($C_{13}H_{21}NO_5$): m/z 272.0 (M+H), $^1$H NMR (CDCl$_3$, 500 MHz) δ 7.20 (d, J=16 Hz, 1H), 6.82 (d, J=16 Hz, 1H), 5.23 (br d, J=5 Hz, 1H), 4.58-4.53 (m, 1H), 4.27 (q, J=7 Hz, 2H), 1.44 (s, 9H), 1.36 (d, J=7.5 Hz, 3H), 1.32 (t, J=7 Hz, 3H).

To a solution of Compound 146B-E (100 mg, 0.37 mmol, 1 eq) in EtOAc (5 mL) was added 10% Pd/C (33 mg, ⅓ by weight). The reaction was put under an atmosphere of H$_2$. The reaction was monitored periodically by TLC (25% EtOAc in Hex) for disappearance of starting material and after 25 min the mixture was filtered through celite (washed through with EtOAc) and concentrated. The crude material was purified by ISCO column chromatography (0-55% EtOAc in Hex) to give pure Compound 146C (73 mg, 73% yield). MS (ESI) for ($C_{13}H_{23}NO_5$): m/z 274.4 (M+H).

Compound 146C (53 mg, 0.19 mmol, 1.35 eq) was Boc deprotected via General Method 5 to give Compound 146D, and was carried on immediately to the next step.

Compound 146D and Compound 104E (150 mg, 0.14 mmol, 1 eq) were dissolved in DCM:DMF (3:1, 5.3 mL) and treated with HATU (108 mg, 2 eq) and DIPEA (231 uL, 10 eq). The solution was stirred for 2 hr and then diluted with 0.2 M NaHSO$_4$. The aqueous layer was extracted 3× with DCM. The combined organic layers were washed with water (2×), saturated NaHCO$_3$ and brine, and then dried over sodium sulfate and concentrated. The crude material was purified by ISCO column chromatography (0-8% MeOH in DCM) to give Compound 146E (140 mg, 83%). MS (ESI) for ($C_{63}H_{79}ClN_6O_{16}$): m/z 1211.4 (M+H).

Compound 146E (28.2 mg, 23 μmol) was Boc deprotected via General Method 9 to give Compound 146 as the TFA salt (12.3 mg, 52%). MS (ESI) for ($C_{48}H_{55}ClN_6O_{10}$): m/z 911.4 (M+H). HPLC t$_R$ 3.54 min (10% AcCN/H$_2$O-90% AcCN/H$_2$O, 3.5 min, 1.0 mL/min Kinetix C18, 4.8×50 mm).

Example 47: Synthesis of Compound 147
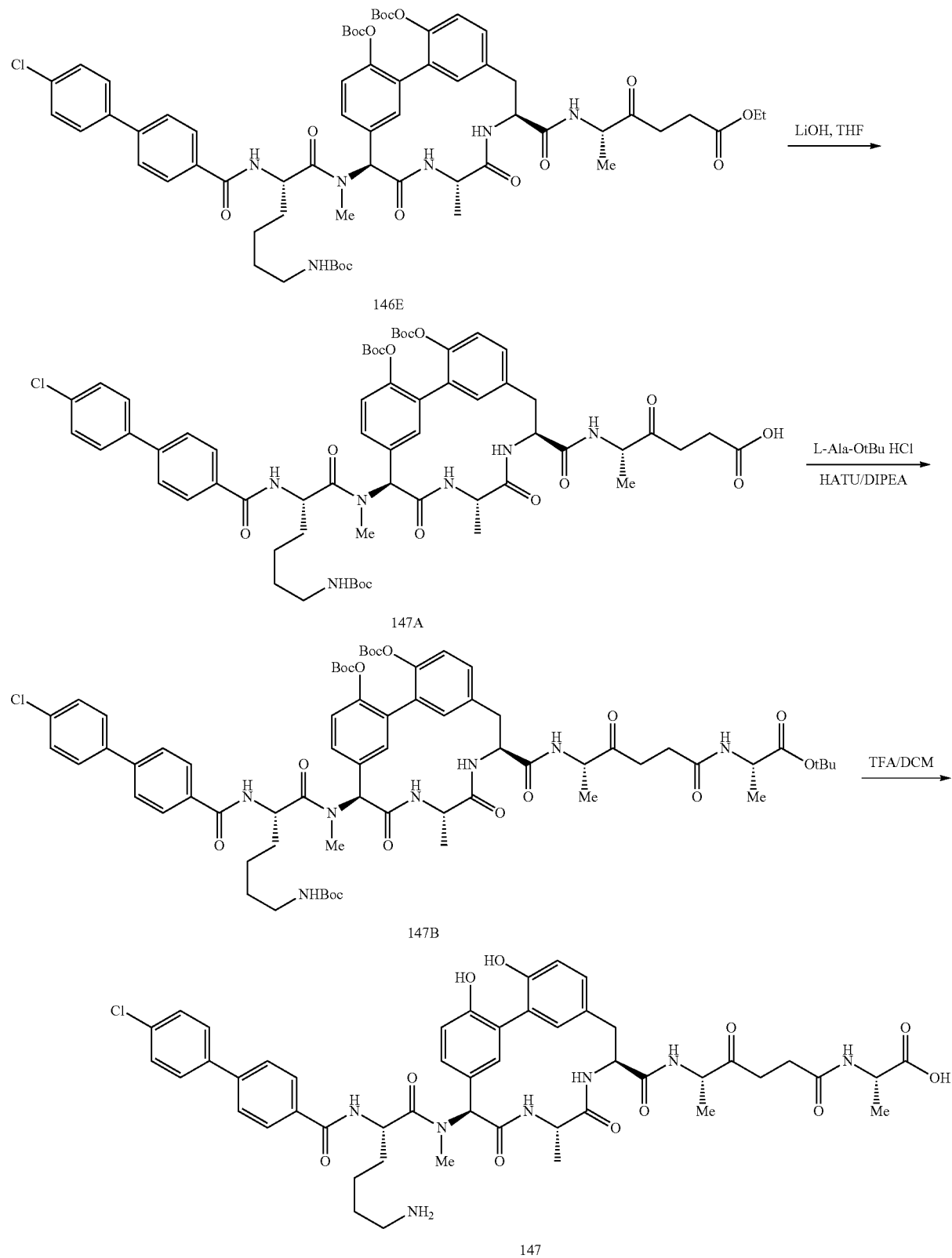

To a solution of Compound 146E (101 mg, 83 umol, 1 eq) in THF (5 mL) was added 0.2N LiOH (834 uL, 2 eq). After 35 min, LCMS indicated the complete consumption of starting material and 1 M NaHSO$_4$ was added. The aqueous layer was extracted 3× with ethyl acetate then the combined organic layers were washed with brine dried over sodium sulfate and concentrated. The obtained Compound 147A (84 mg) was taken forward without further purification. MS (ESI) for ($C_{61}H_{75}ClN_6O_{16}$): m/z 1183.3 (M+H)$^+$.

To a solution of Compound 147A (41 mg, 35 μmol, 1 eq) in DCM:DMF (3:1, 2.0 mL) was added L-Ala-OtBu HCl (13 mg, 2 eq), HATU (33 mg, 2.5 eq) and DIPEA (57 uL, 10 eq). The solution was stirred for 1.25 hr then diluted with 0.2 M NaHSO$_4$. The aqueous layer was extracted 3× with DCM and the combined organic layers were washed with water (2×), saturated NaHCO$_3$ and brine, and then dried over sodium sulfate and concentrated. The obtained Compound 147B was not purified further. MS (ESI) for ($C_{68}H_{88}ClN_7O_{17}$): m/z 1310.3 (M+H).

Compound 147B (35 μmol (assumed), 1 eq) was Boc deprotected via General Method 9 to give Compound 147 as the TFA salt (15.8 mg, 52%). MS (ESI) for ($C_{49}H_{56}ClN_7O_{11}$): m/z 954.1 (M+H). HPLC $t_R$ 3.31 min (10% AcCN/H$_2$O-90% AcCN/H$_2$O, 3.5 min, 1.0 mL/min Kinetix C18, 4.8×50 mm).

Example 48: Synthesis of Compound 148

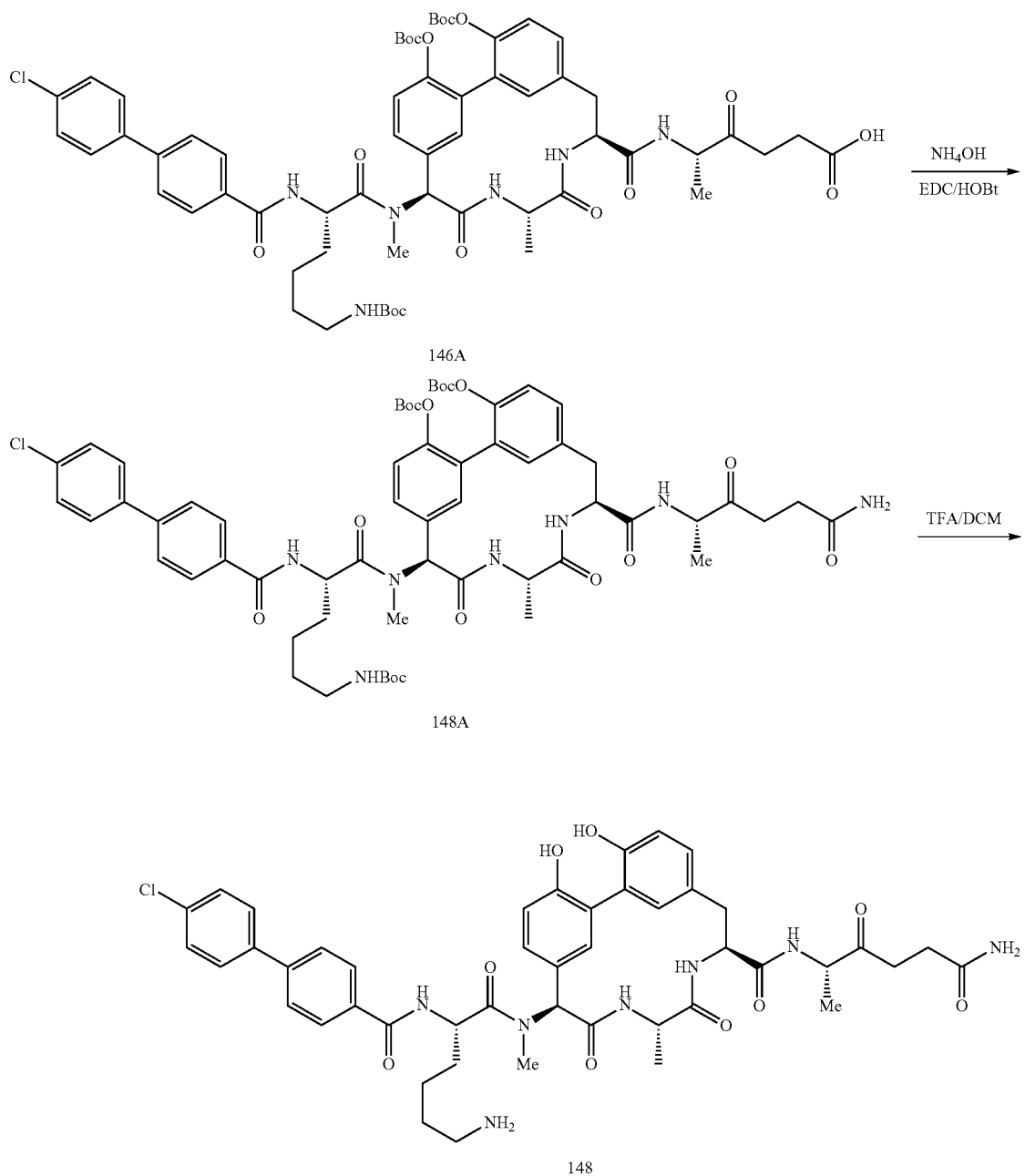

To a solution of Compound 146A (10 mg, 8.5 μmol, 1 eq) in DMF (0.5 mL) was added HOBt (2.7 mg, 2.1 eq), EDC (3.6 mg, 2.2 eq) and NH$_4$OH (14.8 M, 1.2 μL, 2 eq). The solution was stirred overnight and then diluted with H$_2$O. The aqueous layer was extracted 3× with EtOAc and the combined organic layers were washed with brine and then dried over sodium sulfate and concentrated. The obtained Compound 148A was not purified further. MS (ESI) for (C$_{61}$H$_{76}$ClN$_7$O$_{15}$): m/z 1182.3 (M+Na).

Compound 148A (8.5 μmol (assumed), 1 eq) was Boc deprotected via General Method to give Compound 148 as the TFA salt (1.0 mg, 12%). MS (ESI) for (C$_{46}$H$_{52}$ClN$_7$O$_9$): m/z 882.3 (M+H)$^+$. The NMR contained doubled resonances. HPLC t$_R$ 3.28 min (10% AcCN/H$_2$O-90% AcCN/H$_2$O, 3.5 min, 1.0 mL/min Kinetix C18, 4.8×50 mm).

Example 49: Synthesis of Compound 149

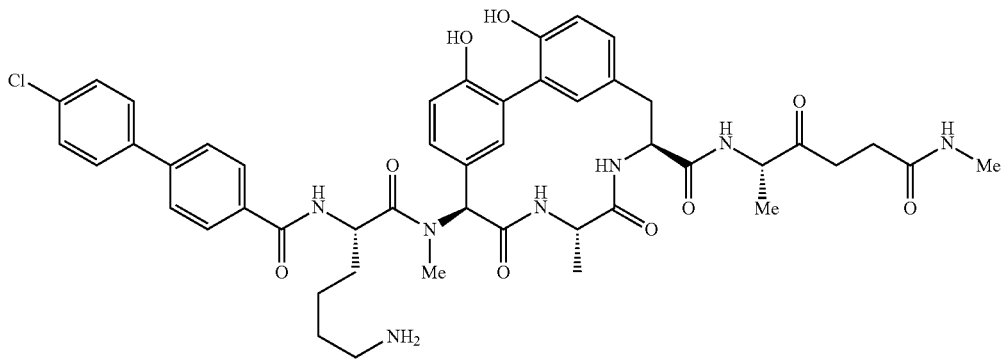

149

Compound 149 was synthesized in a similar manner to Compound 148 (Example 48) from Compound 146E and methylamine. MS (ESI) for (C$_{47}$H$_{54}$ClN$_7$O$_9$): m/z 896.2 (M+H). HPLC t$_R$ 3.25 min (10% AcCN/H$_2$O-90% AcCN/H$_2$O, 3.5 min, 1.0 mL/min Kinetix C18, 4.8×50 mm).

Example 50: Synthesis of Compound 150

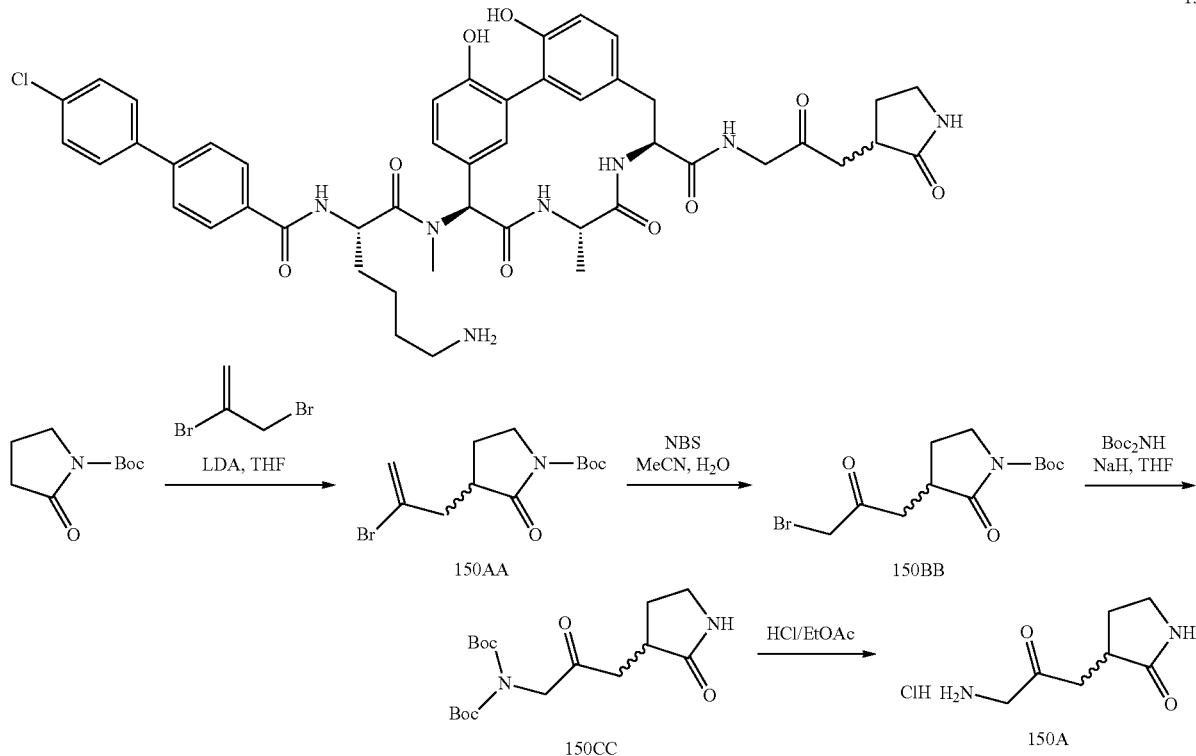

150

To a solution of i-Pr$_2$NH (6.01 g, 59.39 mmol) in anhydrous THF (60 mL) at −78° C., was added n-BuLi (23.8 mL, 59.4 mmol). The reaction mixture was stirred at −78° C. for 2 h and then a solution of tert-butyl 2-oxopyrrolidine-1-carboxylate (10 g, 54.0 mmol) in anhydrous THF (100 mL) was added at −78° C. and stirred for another 1 h. The reaction mixture was added to a solution of 2,3-dibromoprop-1-ene (11.87 g, 59.4 mmol) in anhydrous THF (100 mL) and stirred for another 2 h at −78° C. The reaction was quenched with saturated NH$_4$Cl (100 mL) and extracted with EtOAc (100 mL×3). All the organic layers were combined, dried with Na$_2$SO$_4$, filtered, and concentrated in vacuum. The resulting residue was further purified by silica gel chromatography (PE/EA=20/1) to give Compound 150AA (3.01 g, 18.8%) as a white solid. $^1$H NMR (400 MHz, CDCl$_3$) δ 1.51 (s, 9H), 1.61-1.69 (m, 1H), 2.16-2.24 (m, 1H), 2.38 (1H, dd, J=16.0 Hz, J=12.0 Hz), 2.84-2.92 (m, 1H), 3.08 (1H, dd, J=16.0 Hz, J=12.0 Hz), 3.55-3.61 (m, 1H), 3.75-3.81 (m, 1H), 5.47 (s, 1H), 5.65 (s, 1H).

To a solution of Compound 150AA (1.0 g, 3.28 mmol) in acetonitrile (20 mL) and water (4 mL), NBS (761 mg, 4.27 mmol) was added in portions at 0° C. The mixture was warmed to room temperature slowly and stirred overnight at room temperature. The reaction mixture was diluted with EtOAc (50 mL) and washed with saturated Na$_2$CO$_3$ solution (20 mL). The organic layer was separated and dried with Na$_2$SO$_4$, filtered, and concentrated in vacuum. The resulting residue was further purified by silica gel chromatography (PE/EA=20/1) to give Compound 150BB (712 mg, 64.2%) as a white solid. $^1$H NMR (400 MHz, CDCl$_3$) δ 1.46 (s, 9H), 2.23-2.30 (m, 1H), 2.74-2.76 (m, 1H), 2.93-3.01 (m, 1H), 3.16 (1H, dd, J=15.0 Hz, J=12.0 Hz), 3.51-3.58 (m, 1H), 3.76 (1H, t, J=12.0 Hz), 3.85-3.92 (m, 2H).

To a solution of Boc$_2$NH (522.3 mg, 2.19 mmol) in anhydrous DMF (5 mL) was added NaH (73.5 mg, 3.06 mmol) at room temperature. The reaction mixture was stirred for 1.5 hours. A solution of Compound 150BB (700 mg, 2.19 mmol) in DMF (3 mL) was then added and the reaction mixture stirred for another 2 hours. The reaction mixture was diluted with EtOAc (100 mL) and washed with brine (30 mL×3). The organic layer was separated and dried with Na$_2$SO$_4$, filtered, and concentrated in vacuum. The resulting residue was further purified by silica gel chromatography (PE/EA=20/1) to give Compound 150CC (475 mg, 61.2%) as a white solid. $^1$H NMR (400 MHz, CDCl$_3$) δ 1.46-1.47 (m, 18H), 2.31-2.38 (m, 1H), 2.44-2.51 (m, 1H), 2.96-3.09 (m, 2H), 3.54-3.61 (m, 1H), 3.75-3.80 (m, 1H), 4.33-4.44 (m, 2H).

To a stirred suspension of Compound 150CC (200 mg, 0.56 mmol) in EtOAc (2 mL) at 0° C. was added 4N HCl/EA (5 mL). The reaction mixture was stirred at room temperature for 1 h. After the reaction was complete, the mixture was evaporated to afford Compound 150A, which was used in next step without further purification.

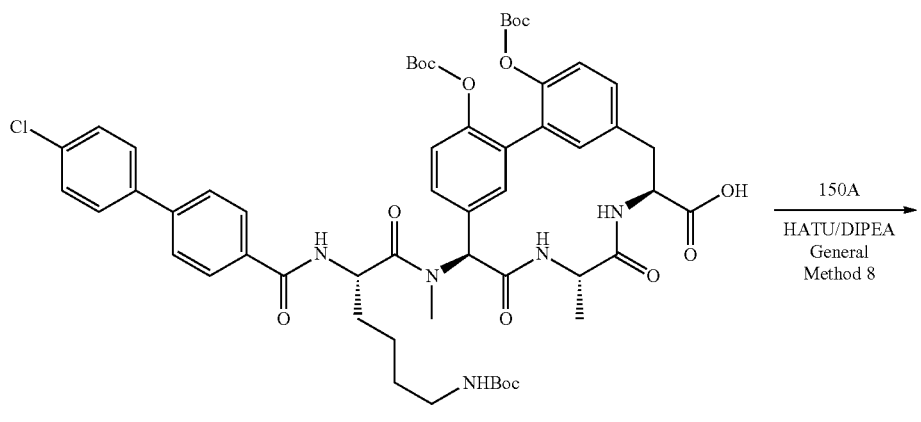

104E

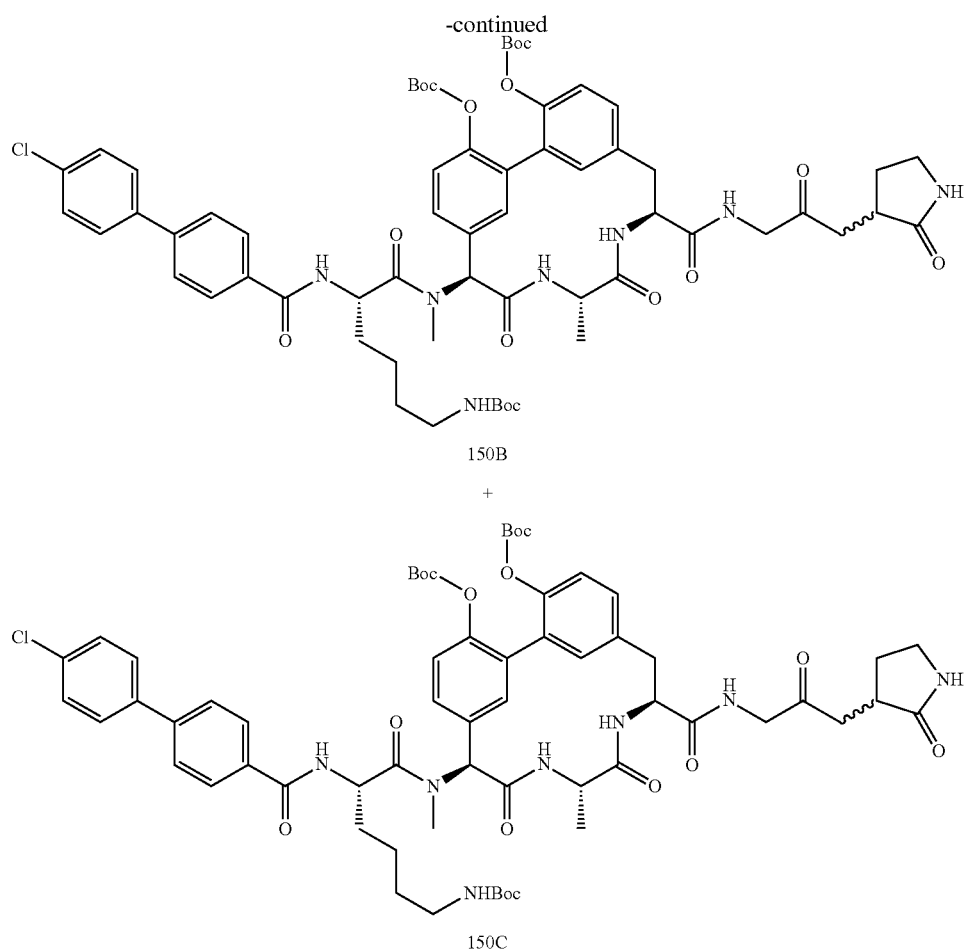
Compound 104E and Compound 150A were subjected to General Method 8 to afford diastereomeric Compounds 150B (peak 1) and 150C (peak 2) which were separated by supercritical fluid chromatography.
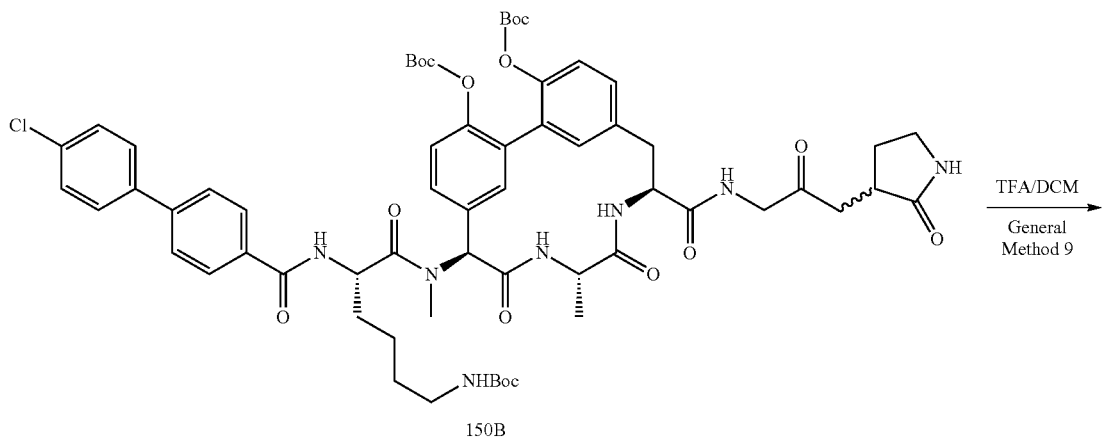

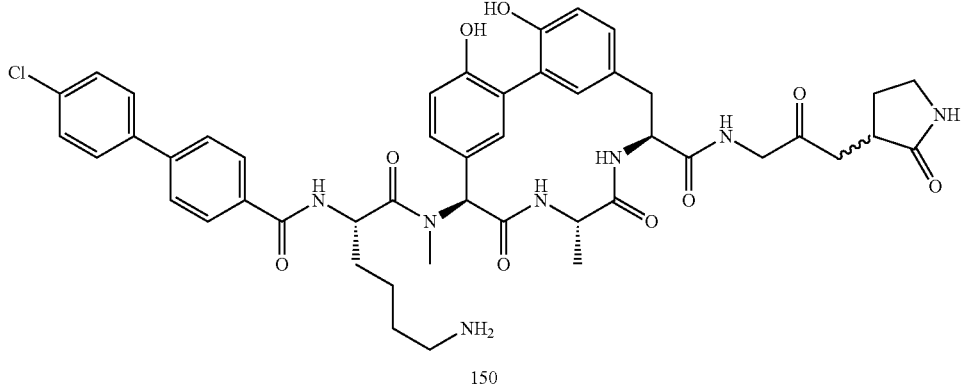
150
Compound 150 was prepared according to General Method 9 from Compound 150B. ¹H NMR (400 MHz, MeOH-d₄) δ 1.39 (d, J=4.0 Hz, 3H), 1.58-1.84 (m, 6H), 1.95-2.01 (m, 2H), 2.33-2.38 (m, 1H), 2.57-2.63 (m, 1H), 2.80-3.13 (m, 9H), 3.20-3.24 (m, 1H), 4.06-4.17 (m, 2H), 4.78-4.81 (m, 2H), 4.98-5.01 (m, 2H), 6.75 (s, 1H), 6.82 (d, J=8.0 Hz, 1H), 6.92-6.97 (m, 2H), 7.02 (d, J=8.0 Hz, 1H), 7.12 (d, J=8.0 Hz, 1H), 7.40 (d, J=8.0 Hz, 1H), 7.48 (d, J=8.0 Hz, 1H), 7.59 (d, J=8.0 Hz, 1H), 7.76 (d, J=8.0 Hz, 1H). LCMS (5-95 AB, ESI): RT=0.773, M+H⁺=894.3.
Example 51: Synthesis of Compound 151
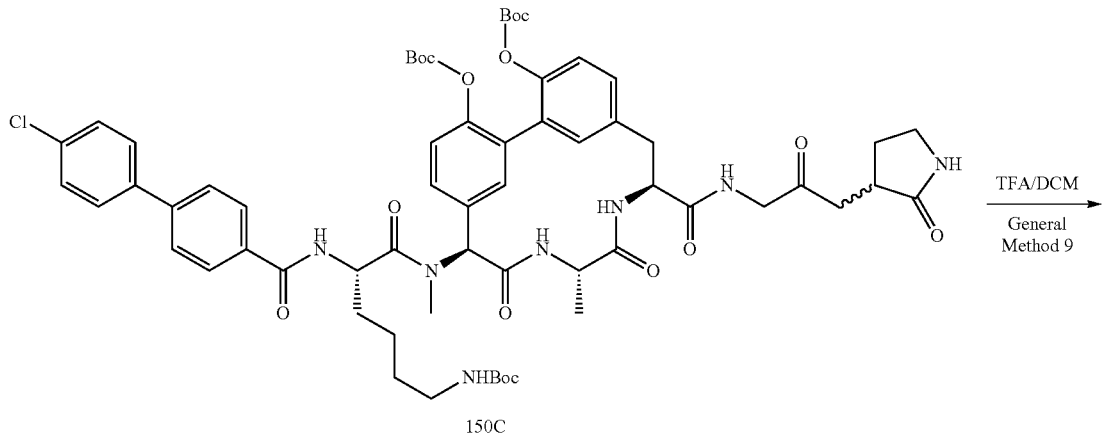
150C
TFA/DCM
General Method 9
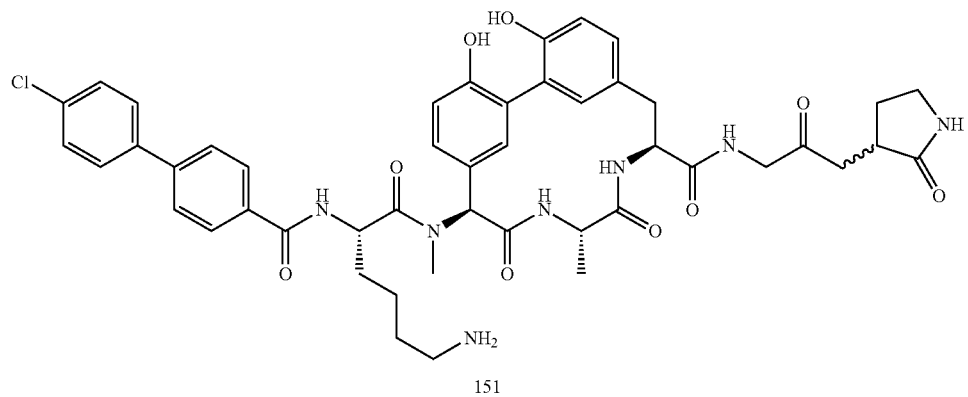
151

Compound 151 (diastereomer of Compound 150) was prepared according to General Method 9 from Compound 150C. $^1$H NMR (400 MHz, MeOH-d$_4$) δ 1.39 (d, J=4.0 Hz, 3H), 1.58-1.84 (m, 6H), 1.95-2.01 (m, 2H), 2.33-2.38 (m, 1H), 2.57-2.63 (m, 1H), 2.80-3.13 (m, 9H), 3.20-3.24 (m, 1H), 4.06-4.17 (m, 2H), 4.78-4.81 (m, 2H), 4.98-5.01 (m, 2H), 6.75 (s, 1H), 6.82 (d, J=8.0 Hz, 1H), 6.92-6.97 (m, 2H), 7.02 (d, J=8.0 Hz, 1H), 7.12 (d, J=8.0 Hz, 1H), 7.40 (d, J=8.0 Hz, 1H), 7.48 (d, J=8.0 Hz, 1H), 7.59 (d, J=8.0 Hz, 1H), 7.76 (d, J=8.0 Hz, 1H). LCMS (5-95 AB, ESI): RT=0.773, M+H$^+$=894.3.

Example 52: Synthesis of Compound 152

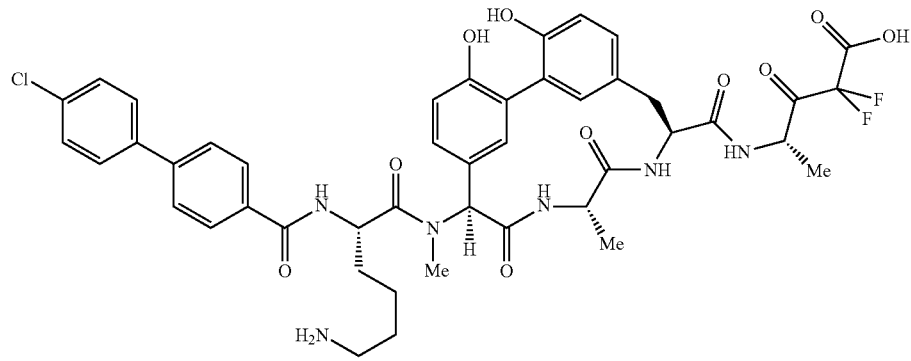

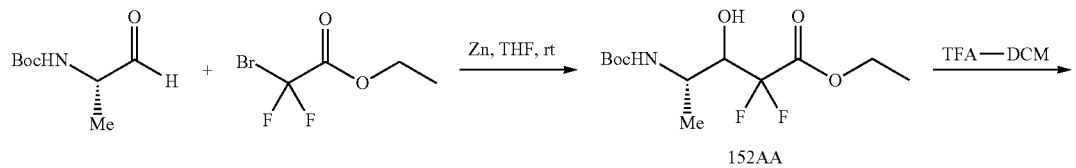

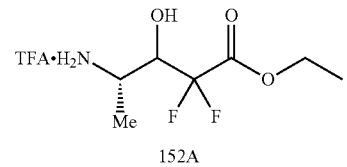

To a suspension of Zn dust (198 mg, 3.0 mmol) was added ethyl 2-bromo-2,2-difluoroacetate (400 µL, 2.5 mmol). The reaction mixture was stirred at rt for about 1 h and heated at 50° C. for about 10 min to initiate the reaction. (S)-tert-butyl (1-oxopropan-2-yl)carbamate (173 mg, 1.0 mmol) was then added and the reaction mixture was stirred at rt for 2 h. After completion of the reaction, the reaction mixture was cooled in ice bath and quenched with saturated NH$_4$Cl solution (10 mL). The mixture was diluted with water and extracted with EtOAc. The combined organic layers washed with brine and dried over anhydrous Na$_2$SO$_4$, filtered and the solvent was removed. The residue was purified by flash chromatography (50% EtOAC-hexanes) to afford 183 mg (61%) of Compound 152AA as viscous oil. MS (ESI) for (C$_{12}$H$_{21}$F$_2$NO$_5$): m/z 198.1 (M+H-Boc, two peaks, 1:1 mixture of P3-hydroxyester isomers).

A solution of Compound 152AA (60 mg, 0.2 mmol) in 1:3 TFA-DCM (2 mL) was stirred at rt for about 1 to 2 h. After completion of the reaction, the solvent was evaporated and the residue was dried under high vacuum to afford Compound 152A.

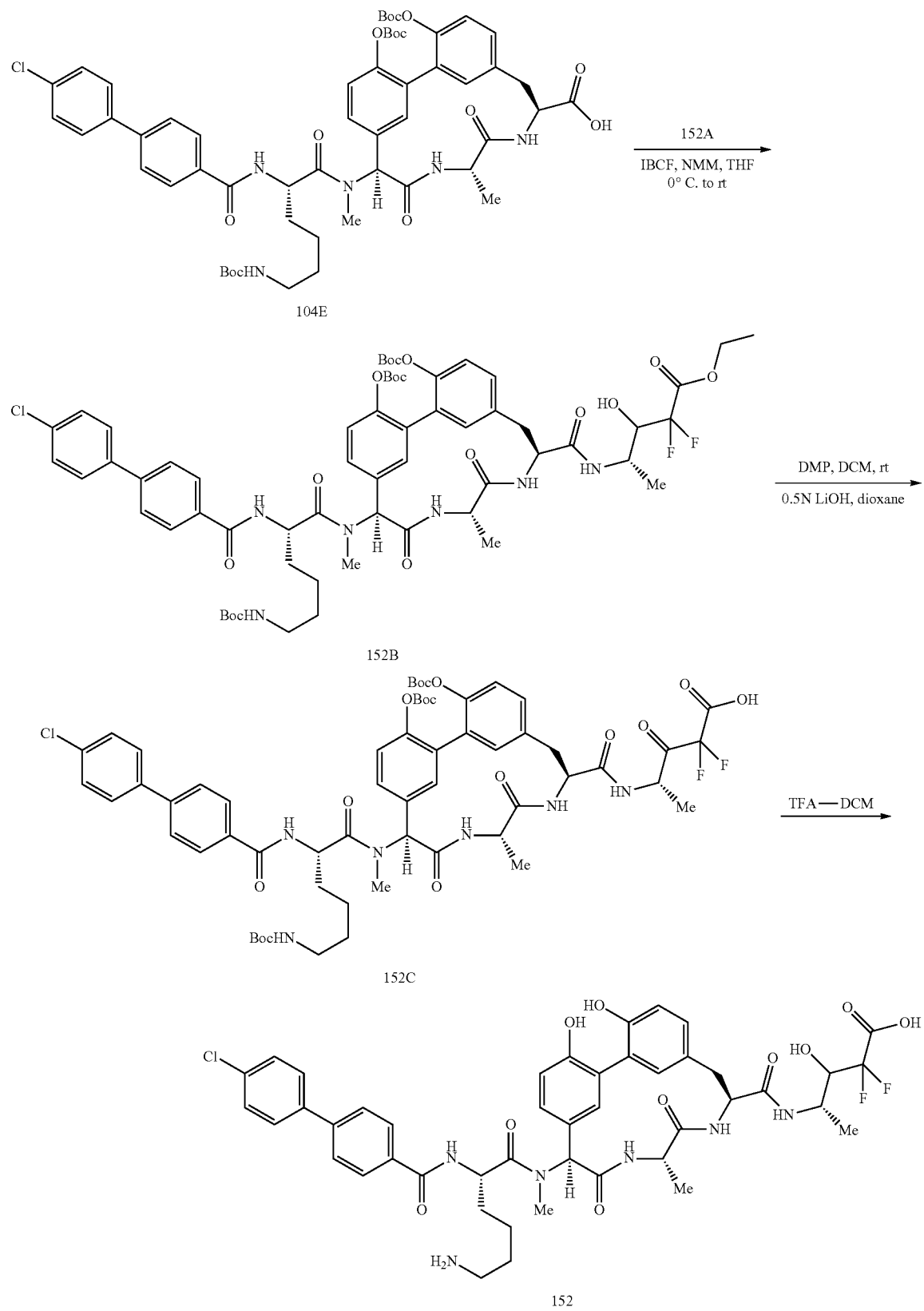

Compound 104E (105 mg, 0.1 mmol) was dissolved in anhydrous THF and cooled to 0° C. in ice bath. Isobutyl chloroformate (20.0 µL, 0.15 mmol) was added followed by N-methyl morpholine (56.0 µL, 0.5 mmol) under $N_2$ atm. The reaction mixture was stirred for 30 min, and then a solution of Compound 152A (60 mg, 0.2 mmol) in anhydrous THF was added. The reaction mixture was stirred for about 1 to 2 h while allowing the reaction mixture to warm to rt. After completion of the reaction, the reaction mixture was quenched with saturated $NH_4Cl$ solution and diluted with brine (2 mL). The mixture was extracted with EtOAc and the combined organic layers washed with brine. The organic layer was dried over anhydrous $Na_2SO_4$, filtered and the solvent was removed under vacuum. The residue was purified by flash chromatography using 1:9 MeOH-DCM to afford 68 mg (55%) of Compound 152B as an off-white solid. MS (ESI) for ($C_{62}H_{77}ClF_2N_6O_{16}$): m/z 1235.2 (M+H, broad peak, mixture of isomers at β-hydroxy ester).

To a stirred solution of Compound 152B (61 mg, 0.05 mmol) in DCM (5 mL) was added Dess-Martin periodinane (106 mg, 0.25 mmol). The resultant heterogeneous reaction mixture was stirred at rt overnight. After completion of the reaction, the reaction mixture was filtered through a pad of celite and the celite bed washed with DCM. The filtrate was washed with saturated $NaHCO_3$ solution and brine. The organic layer was dried over anhydrous $Na_2SO_4$ and solvent was removed under vacuum. The residue was purified by flash chromatography using 5% MeOH-DCM to afford 32 mg (51%) of the desired compound as a white solid. MS (ESI) for ($C_{62}H_{75}ClF_2N_6O_{16}$): m/z 1233.4 (M+H)$^+$.

The resultant solid (13 mg, 0.01 mmol) was dissolved in dioxane-$H_2O$ (3:1, 1 mL) and 0.5 M LiOH solution (30 µL, 0.015 mmol) was added at 0° C. The reaction mixture was stirred at rt for 2 h. After completion of the reaction, water (2 mL) was added and the mixture was acidified with 0.5 M HCl. The resultant white cloudy mixture was extracted with EtOAc. The combined organic layers washed with brine, dried over anhydrous $Na_2SO_4$, filtered, and the solvent was removed. The residue was purified by prep HPLC ($CH_3CN$—$H_2O$ containing 0.05% TFA) to afford 5.8 mg (48%) of Compound 152C as a white solid. MS (ESI) for ($C_{60}H_{71}ClF_2N_6O_{16}$): m/z 1205.2 (M+H).

Compound 152C was dissolved in 1:3 TFA-DCM (1 mL) and stirred at rt for about 1 to 2 h. After completion of the reaction, the solvent was evaporated and the residue was dried under high vacuum to afford Compound 152 as a white solid. MS (ESI) for ($C_{45}H_{47}ClF_2N_6O_{10}$): m/z 905.1 (M+H).

Example 53: Synthesis of Compound 153

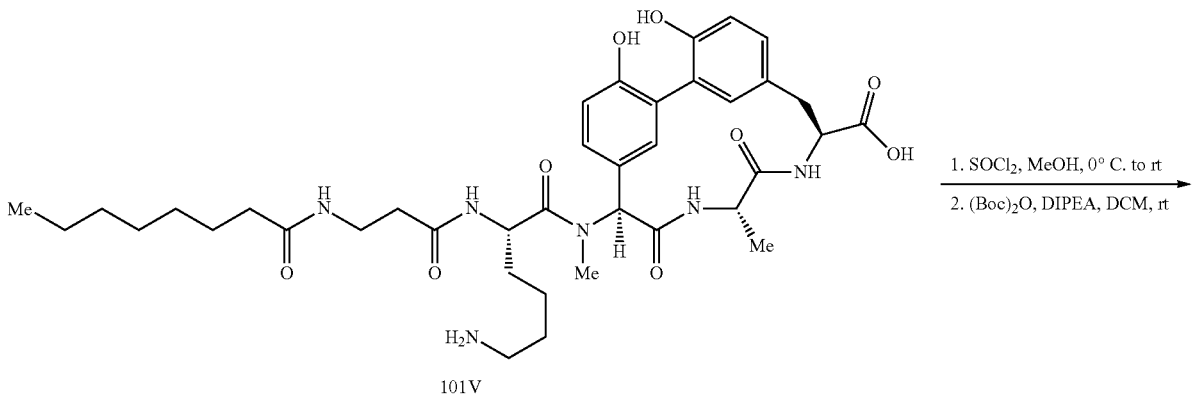

101V

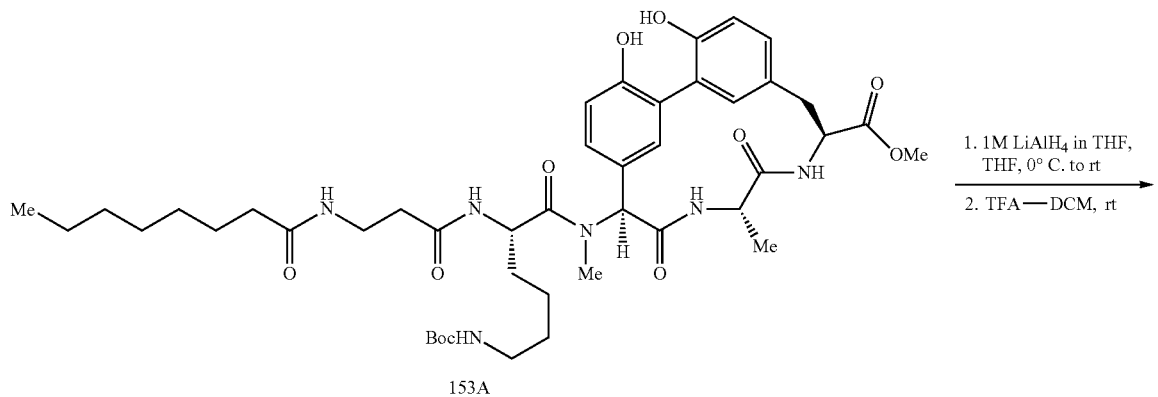

153A

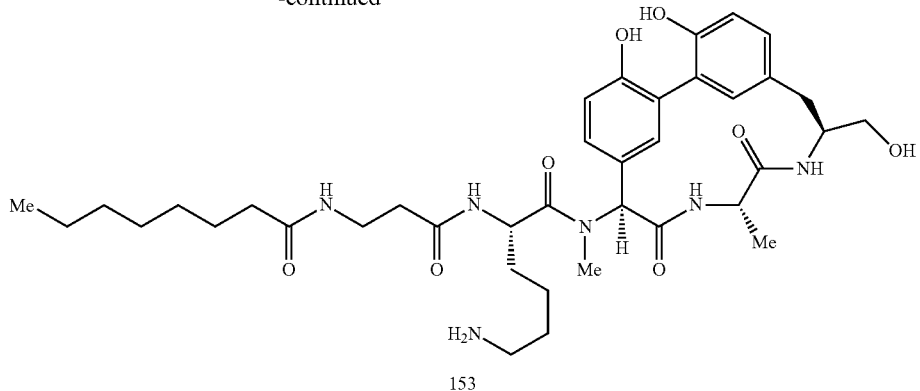

153

To a stirred solution of Compound 101V (52 mg, 0.07 mmol) in dry MeOH (5 mL) at 0° C., was slowly added $SOCl_2$ (0.1 mL) dropwise. The reaction mixture was stirred at rt overnight. The solvent was removed under reduced pressure and the residue was dried under high vacuum and the residue was used directly in the next reaction. LCMS: MS (ESI) for $C_{39}H_{56}N_6O_9$: m/z 753.2 (M+H)$^+$.

The residue (0.07 mmol) was dissolved in $CH_2Cl_2$ (10 mL) and DIPEA (35 µL, 0.21 mmol) and to this stirred solution was added (Boc)$_2$O (20 µL, 0.084 mmol). The reaction mixture was stirred at rt overnight. After the reaction was complete, a brine solution was added and the mixture was extracted with ethyl acetate. The combined organic layers were washed with brine, dried over anhydrous $Na_2SO_4$, filtered and the solvent was removed in vacuum to afford Compound 153A along with 30% of bis-Boc protected product. MS (ESI) for ($C_{44}H_{64}ClN_6O_{11}$): m/z 853.4 (M+H)$^+$ and bis boc product ($C_{49}H_{72}ClN_6O_{13}$): m/z 953.5 (M+H)$^+$.

To a stirred solution of Compound 153A (22 mg, 0.025 mmol) in dry THF (2 mL) was added 1M solution of LiAlH$_4$ (75 µL, 0.075 mmol) slowly dropwise at 0° C. under $N_2$ atm and the reaction mixture was stirred for 2 h. After completion of the reaction, the reaction was quenched with ethyl acetate and crushed ice and the mixture was extracted with EtOAc. The combined organic layers were washed with brine, dried over anhydrous $Na_2SO_4$, filtered and the solvent was removed under reduced pressure. The residue was dissolved in 1:3 TFA-DCM (1 mL) and stirred at rt for about 1 to 2 h. After completion of the reaction, the solvent was evaporated and dried under high vacuum. The residue was purified by prep HPLC (CH$_3$CN—H$_2$O containing 0.05% TFA) to afford Compound 153 as a white solid. MS (ESI) for ($C_{38}H_{56}N_6O_8$): m/z 725.1 (M+H).

Example 54: Synthesis of Compound 154

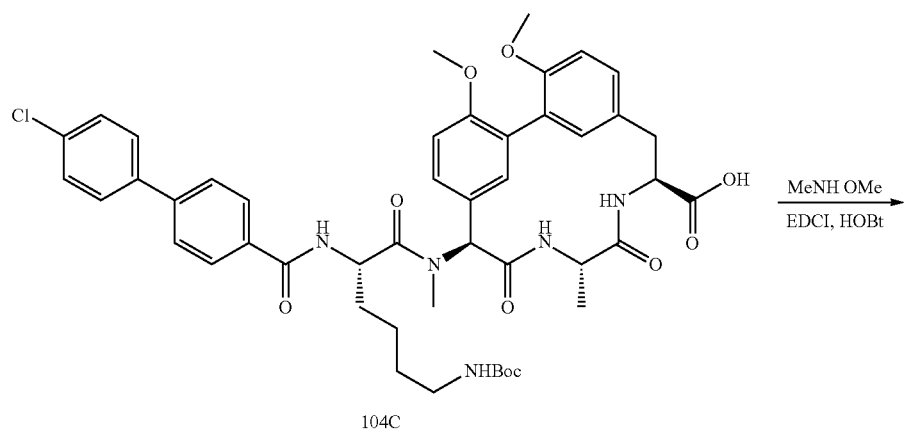

104C

-continued
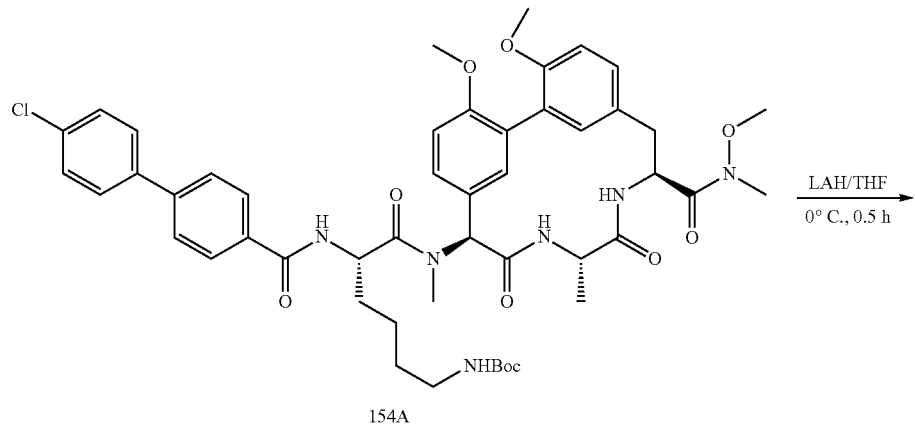
154A
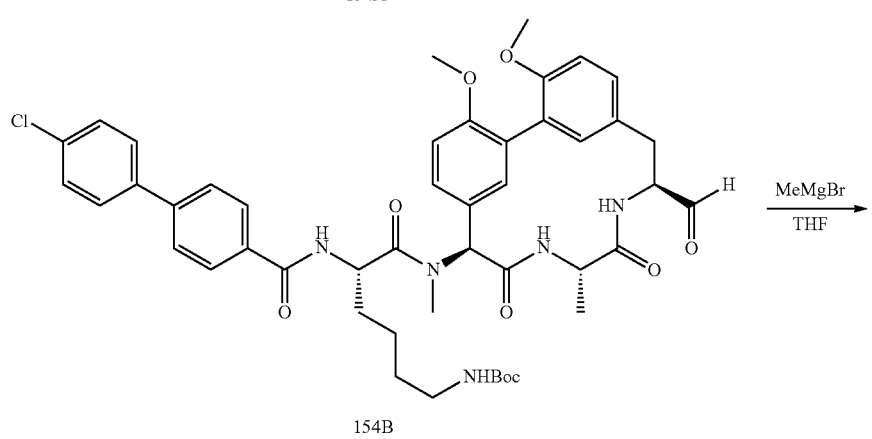
154B
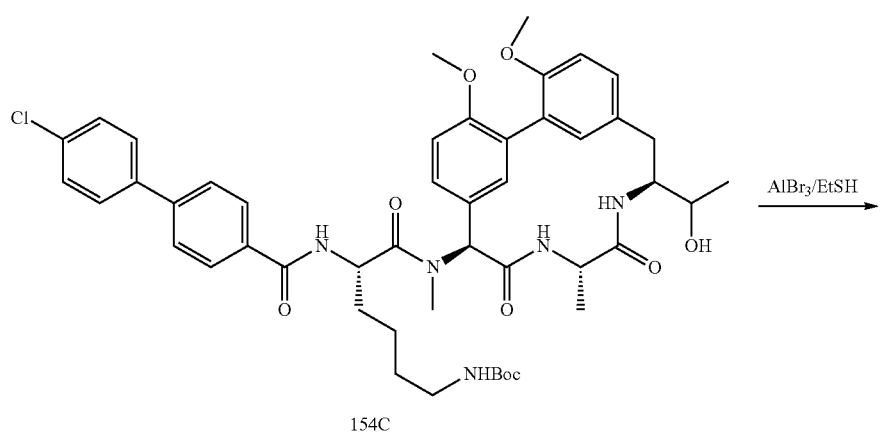
154C
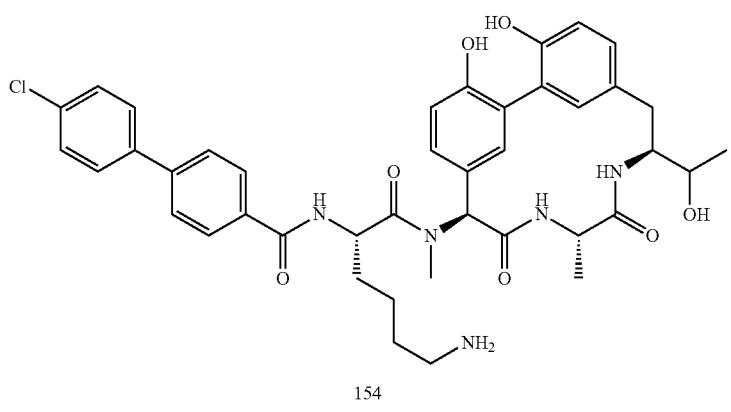
154

Compound 154A was prepared according to General Method 10 from Compound 104C and N,O-dimethylhydroxylamine.

To a solution of Compound 154A (3.5 g, 3.77 mmol) in THF (15 mL) at 0° C. was added LAH (287 mg, 7.54 mmol) and the mixture was stirred at the same temperature for 1 h. After the reaction was complete, the reaction mixture was carefully quenched by NH$_4$Cl solution (50 mL) and extracted with DCM (50 mL*3). The combined DCM layers were washed with brine (50 mL*2), dried over Na$_2$SO$_4$ and concentrated under reduced pressure. The residue was purified by silica gel column (DCM/MeOH=80/1) to give Compound 154B (1.7 g, yield 52%) as a white solid.

To a solution of Compound 154B (500 mg, 0.58 mmol) in THF (10 mL) at −70° C. was added MeMgBr (1.4 M, 2.47 mL, 3.45 mmol) at the same temperature. The reaction mixture was gradually warmed up to room temperature and stirred for 12 h. The reaction mixture was quenched by 0.5N HCl (15 mL), and then extracted with DCM (20 mL*3). The combined DCM layers were dried over Na$_2$SO$_4$ and concentrated under reduced pressure. The resulting residue was purified by prep-TLC to give Compound 154C (130 mg, 25.5% yield) as a white solid.

Compound 154 was prepared according to General Method 4 from Compound 154C. $^1$H NMR (400 MHz, MeOH-d4) δ 8.43 (s, 1H), 7.70 (d, J=7.6 Hz, 2H), 7.50 (d, J=7.6 Hz, 2H), 7.38 (s, 4H), 6.81-7.08 (m, 7H), 5.01-5.05 (m, 1H), 4.80 (m, 3H), 4.20-4.23 (m, 1H), 3.83-3.85 (m, 1H), 2.88-3.06 (m, 8H), 1.97-2.00 (m, 2H), 1.58-1.72 (m, 4H), 1.38-1.41 (m, 3H), 1.11-1.20 (m, 3H). LCMS (5-95 AB, ESI): RT=0.778, M+H$^+$=756.3.

Example 55: Synthesis of Compound 155

To a solution of (S)-pyrrolidine-2-carboxamide (2 g, 17.52 mmol) in DCM (5 mL) was added (S)-2-((tert-butoxycarbonyl)amino)propanoic acid (3.64 g, 19.28 mmol) and DIPEA (4.52 g, 35.04 mmol). The solution was kept at 0° C. for 10 min, then HOBT (4.6 g, 35.04 mmol) and EDCI (6.6 g, 35.04 mmol) was added. The reaction was stirred at rt for 16 hr. The reaction mixture was poured into water (10 mL) and then extracted with DCM (10 mL) three times. The combined organic layers were concentrated and the residue was purified by silica gel column chromatography (DCM/MeOH=80/1-50/1) to give Compound 155AA (3 g, 60%) as a yellow solid. $^1$H NMR (400 MHz, CDCl$_3$-d$_4$) δ 4.57-4.55 (m, 1H), 4.46-4.42 (m, 1H), 3.55-3.48 (m, 2H), 2.31-2.26 (m, 2H), 2.06-2.00 (m, 2H), 1.40 (s, 9H), 1.31-1.29 (m, 3H).

To a solution of Compound 155AA (285 mg, 1 mmol) in EtOAc (1 mL) at 0° C. was added HCl/EtOAc (3 mL). The reaction solution was kept at 0° C. for 30 min and then concentrated to give Compound 155A (200 mg, 90%) as a white solid, which was used directly in the next step.

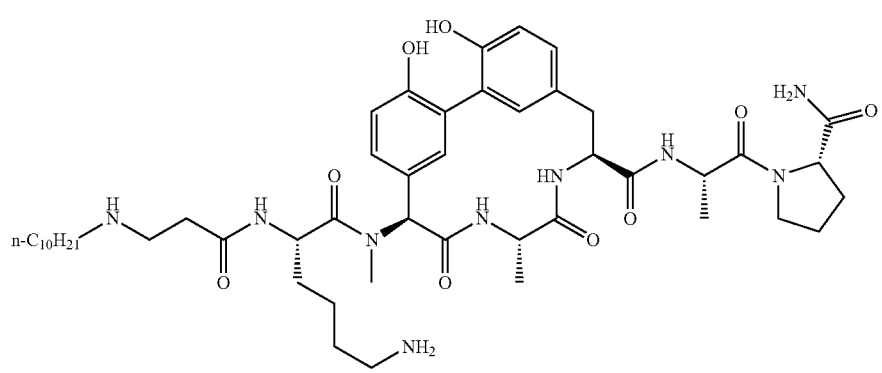

155

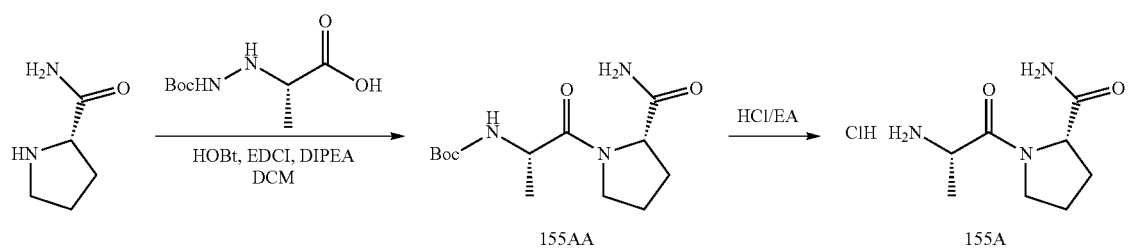

155AA     155A

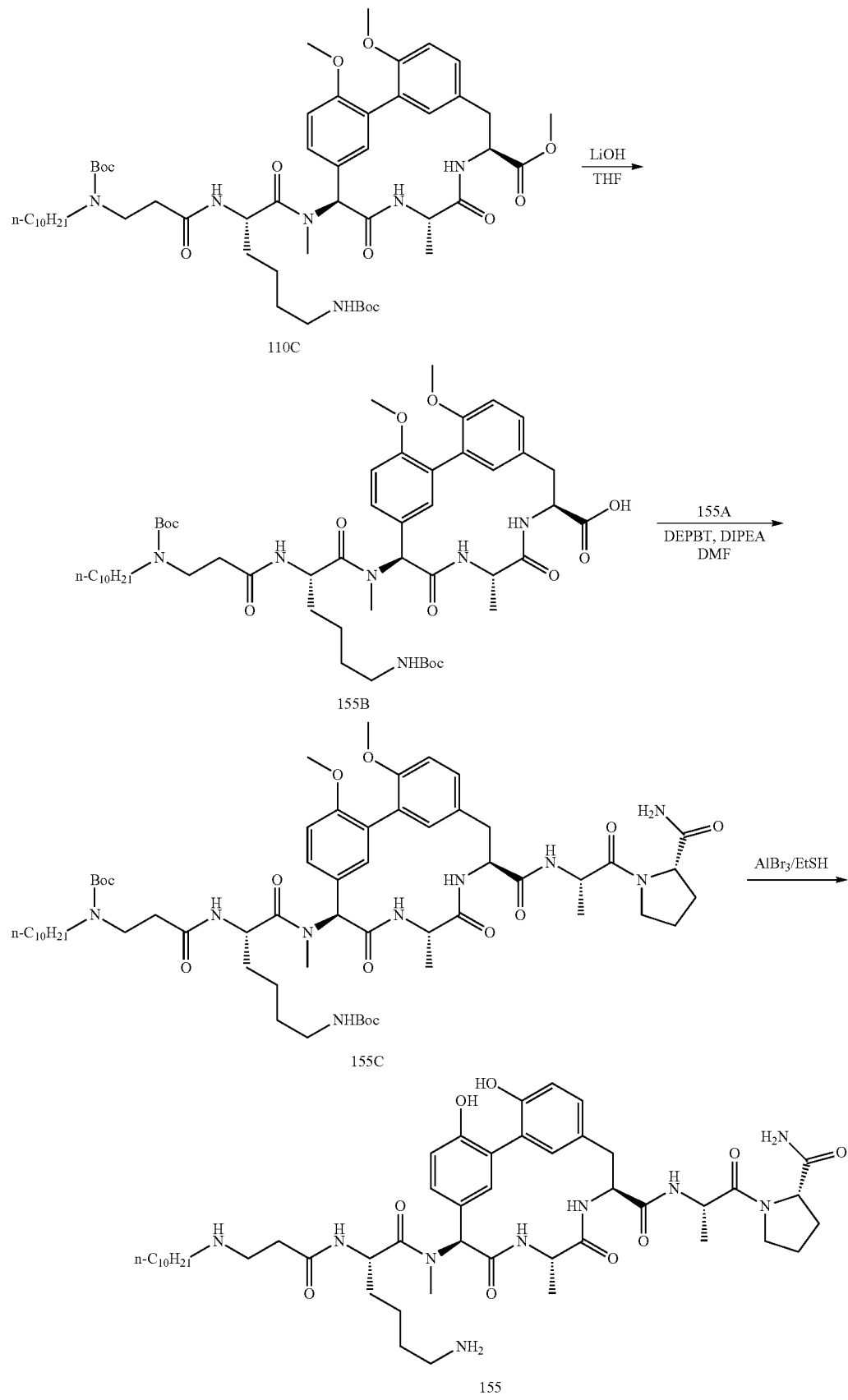

To a solution of Compound 110C (550 mg, 0.452 mmol) in THF (9 mL) at 0° C. was added LiOH (0.9 mmol). The reaction solution was kept at 0° C. for 30 min. THF was removed from the resulting mixture under the reduced pressure. The remaining aqueous solution was then adjusted to pH=2~3 with 6N HCl, followed by the extraction with DCM (20 mL*3). The combined DCM layers were dried over $Na_2SO_4$ and concentrated to give Compound 155B (350 mg, 64.6%) as a yellow solid.

DIPEA (96.75 mg, 0.75 mmol) and Compound 155A (165 mg, 0.75 mmol) was added to a stirred suspension of Compound 155B (150 mg, 0.15 mmol) in THF (2 mL) at 0° C. The mixture was kept at 0° C. for 10 min, and DEPBT (91.5 mg, 0.3 mmol) was then added. The reaction was stirred at 25° C. for 16 hr. After the reaction was complete, THF was removed from the resulting mixture under the reduced pressure. The residue was suspended with water (20 mL) and DCM (20 mL) and the aqueous layer was further extracted by DCM (20 mL). The combined DCM layers were concentrated to give Compound 155C (140 mg, 80%) as a yellow solid.

Compound 155 was prepared according to General Method 4 from Compound 155C and was isolated as the formic acid salt (60 mg, 53%). $^1$H NMR (400 MHz, MeOH-$d_4$) δ 8.49 (s, 1H), 7.08-7.06 (d, J=8.0 Hz, 1H), 6.99-6.97 (m, 3H), 6.90-6.89 (d, J=4.0 Hz, 1H), 6.86-6.84 (d, J=8.0 Hz, 1H), 6.56 (m, 1H), 4.80-4.78 (m, 2H), 4.65-4.63 (m, 1H), 4.43-4.40 (m, 2H), 3.78 (m, 1H), 3.67 (m, 1H), 3.25-3.20 (m, 5H), 3.12-3.09 (m, 6H), 3.07 (m, 2H), 2.94 (s, 1H), 2.92 (m, 2H), 2.88 (m, 1H), 2.22 (m, 2H), 1.97-1.96 (m, 1H), 1.67 (m, 4H), 1.52-1.50 (m, 3H), 1.37-1.29 (m, 18H), 0.89-0.86 (m, 3H); LCMS (5-95 AB, 220 nm): RT=0.732, M+H$^+$=920.7.

Example 56: Synthesis of Compound 156

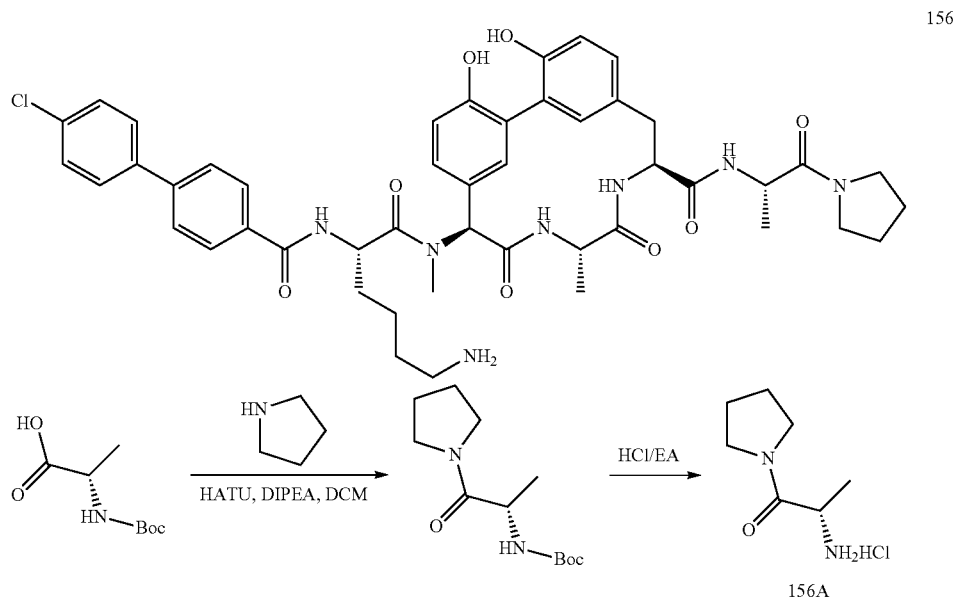

To a solution of 2-((tert-butoxycarbonyl)amino)propanoic acid (2.0 g, 10.6 mmol), pyrrolidine (0.9 g, 12.7 mmol) and HATU (6.0 g, 15.9 mmol) in DCM (15 ml) at 0° C., was added DIPEA (2.0 g, 15.9 mmol) dropwise. The resulting mixture was stirred at 25° C. for 2 h. The mixture was diluted with DCM (40 mL) and the resulting mixture was washed sequentially with water (40 mL) and brine (40 mL). The organic layer was dried over $Na_2SO_4$ and concentrated. The residue was purified by silica gel column chromatography (DCM/MeOH=50:1) to afford (S)-tert-butyl (1-oxo-1-(pyrrolidin-1-yl)propan-2-yl)carbamate (1.0 g, 40%) as a white solid.

(S)-Tert-butyl (1-oxo-1-(pyrrolidin-1-yl)propan-2-yl)carbamate (400 mg, 16.4 mmol) was added to 4N HCl/EtOAc (5 mL) at 0° C. The resulting mixture was stirred at 25° C. for 2 h. The mixture was concentrated to give Compound 156A (280 mg, 99%) as a yellow oil.

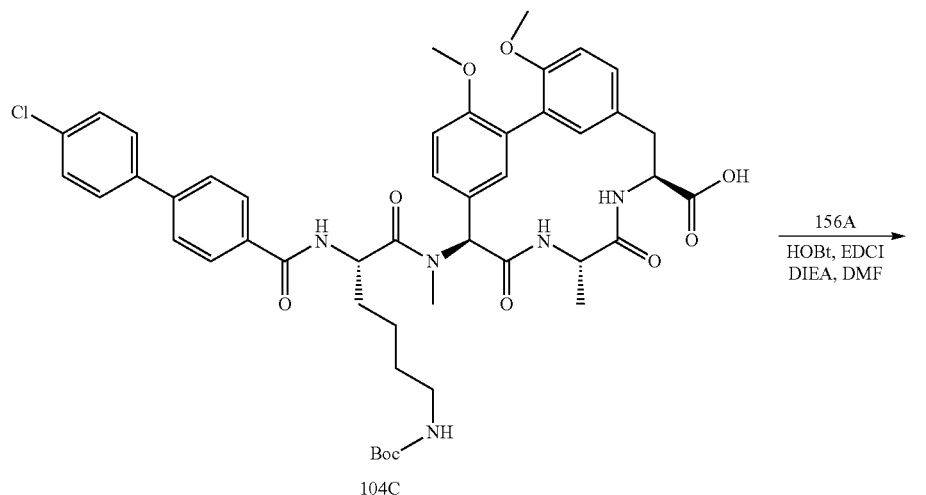
104C
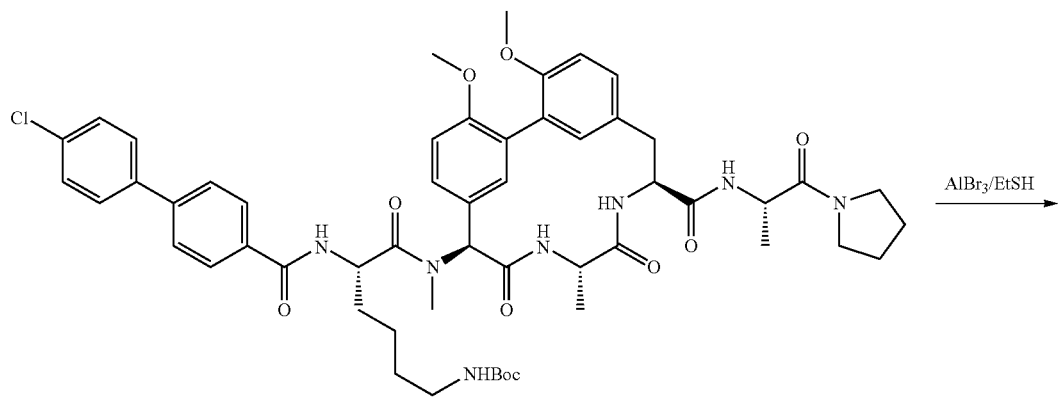
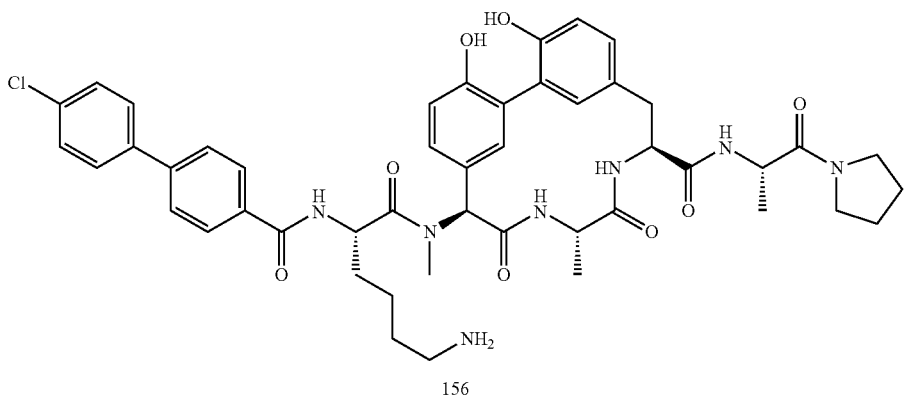
156
Compound 156 was prepared according to General Method 10 and General Method 4 from Compound 104C and Compound 156A to afford the desired compound as a formic acid salt (white solid). $^1$H NMR (400 MHz, MeOH-d4) δ 1.34 (d, J=8.0 Hz, 3H), 1.39 (d, J=4.0 Hz, 3H), 1.62 (br. s., 2H), 1.76 (m, 2H), 1.90-1.97 (m, 3H), 1.99-2.07 (m, 3H), 2.93-3.02 (m, 6H), 3.03-3.14 (m, 1H), 3.20-3.30 (m, 2H), 3.37-3.46 (m, 1H), 3.47-3.58 (m, 2H), 3.68-3.77 (m, 1H), 4.68-4.60 (m, 1H), 5.06 (br. s., 1H), 6.86 (d, J=8.0 Hz, 1H), 6.92 (br. s., 1H), 6.97 (d, J=8.0 Hz, 2H), 7.06 (d, J=8.0 Hz, 1H), 7.15 (d, J=8.0 Hz, 1H), 7.48 (d, J=8.0 Hz, 2H), 7.54-7.64 (m, 2H), 7.65-7.74 (m, 2H), 7.83-7.93 (m, 2H), 8.55 (s, 1H). LCMS (5-95 AB, 220 nm): RT=0.760, M+H$^+$=880.3.

Example 57: Synthesis of Compound 157

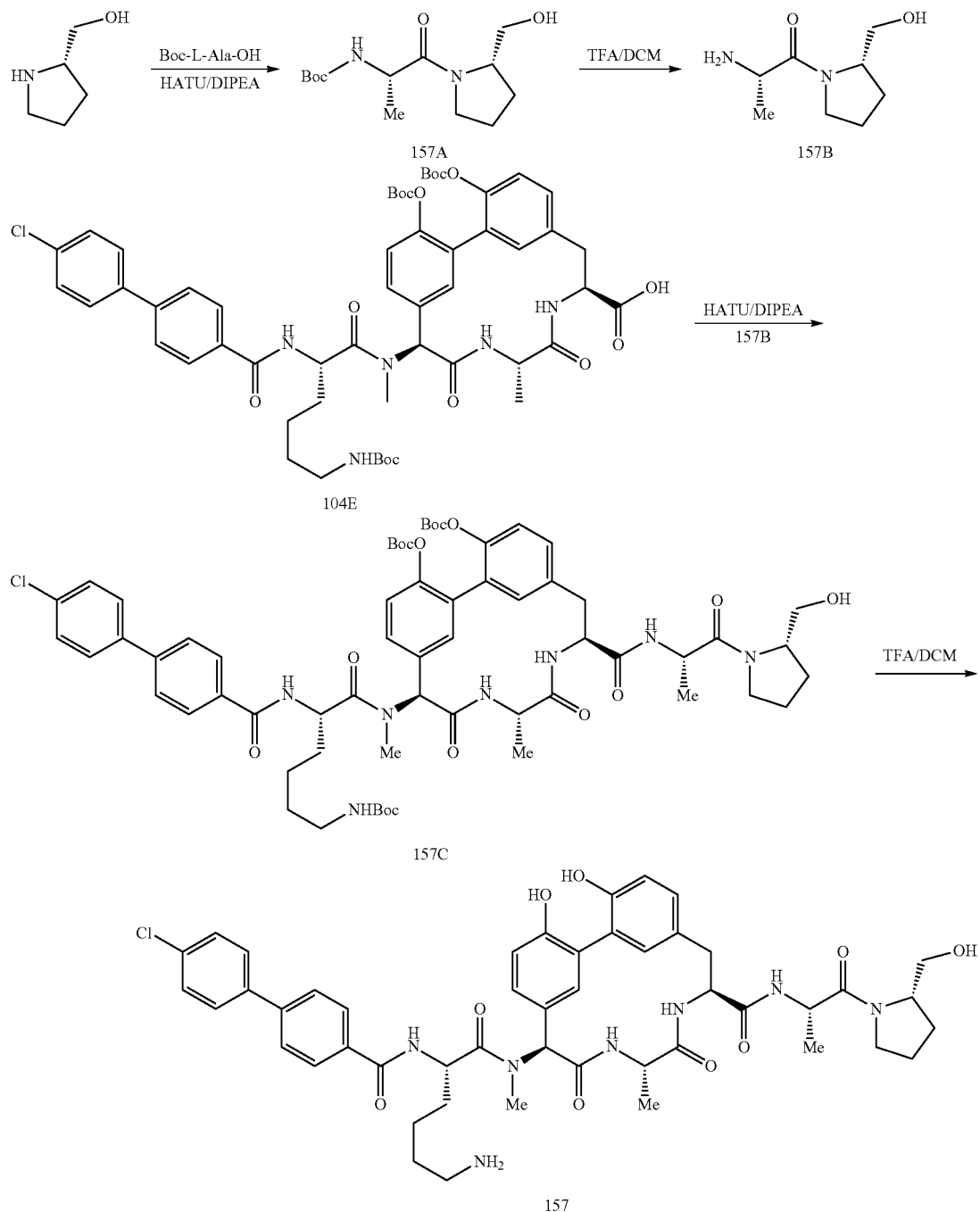

To a solution of L-Prolinol (200 mg, 2.0 mmol, 1 eq) min DCM:DMF (3:1, 6.0 mL) was added Boc-L-Ala-OH (374 mg, 1 eq), HATU (912 mg, 1.2 eq) and DIPEA (3.27 mL, 10 eq). The solution was stirred for 2.5 hrs and then diluted with 0.2 M HCl. The aqueous layer was extracted 3× with DCM and the combined organic layers were washed with water (2×), saturated $NaHCO_3$ and brine. The organic solution was dried over sodium sulfate and concentrated to give Compound 157A which was taken forward without further purification. MS (ESI) for ($C_{13}H_{24}N_2O_4$): m/z 273.1 (M+H).

Compound 157A (74 μmol, 1.3 eq) was Boc deprotected via General Method 5 to afford Compound 157B.

To a solution of Compound 157B in DCM:DMF (3:1, 2.0 mL) was added 104E (60 mg, 57 μmol, 1 eq), HATU (43 mg, 2.0 eq) and DIPEA (111 μL, 12 eq). The solution was stirred for 2 hrs then diluted with 0.2 M HCl. The aqueous layer was extracted 3× with DCM. The combined organic layers were washed with water (2×), saturated $NaHCO_3$ and brine, then dried over sodium sulfate and concentrated. The crude material was purified by silica gel column chromatography (0-10% MeOH in DCM) to give Compound 157C (33 mg, 48%). MS (ESI) for ($C_{63}H_{80}ClN_7O_{15}$): m/z 1210.5 (M+H).
Compound 157C (32 mg, 27 μmol) was Boc deprotected via General Method 9 to give Compound 157 as the TFA salt (8.9 mg, 32%) MS (ESI) for ($C_{48}H_{56}ClN_7O_9$): m/z 910.5 (M+H). $t_R$ 3.26 min (90% AcCN/$H_2O$-70% AcCN/$H_2O$, 3.5 min, 1.0 mL/min Kinetix C18, 4.8×50 mm).
Example 58: Synthesis of Compound 158
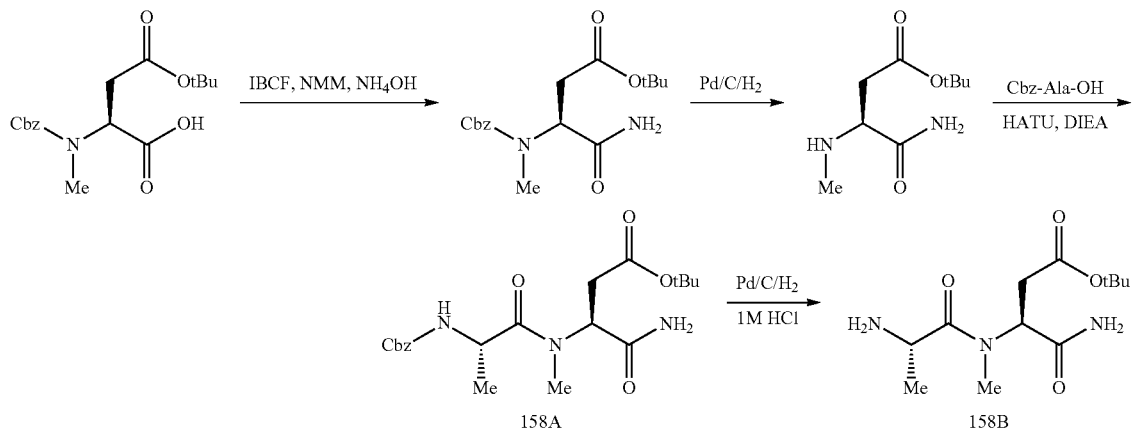
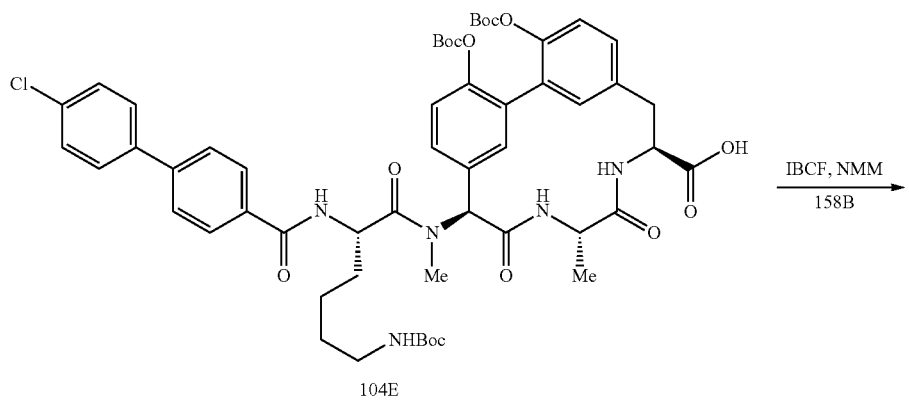
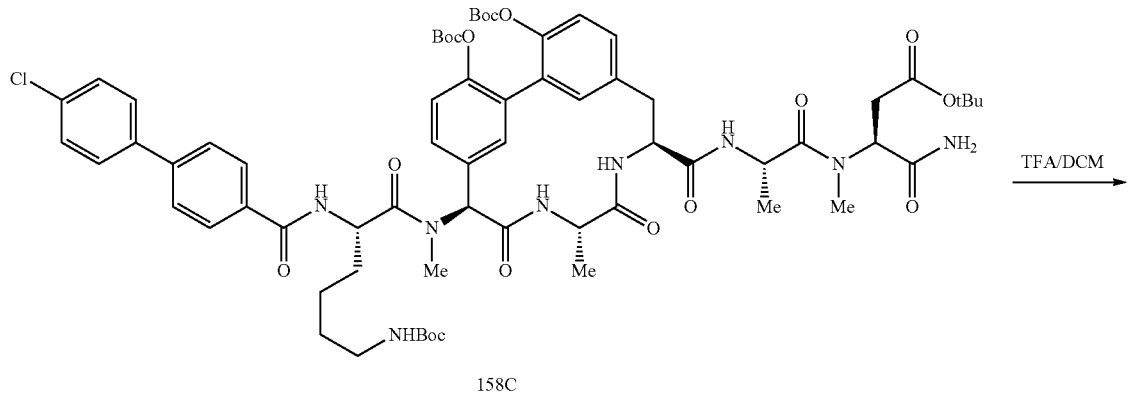

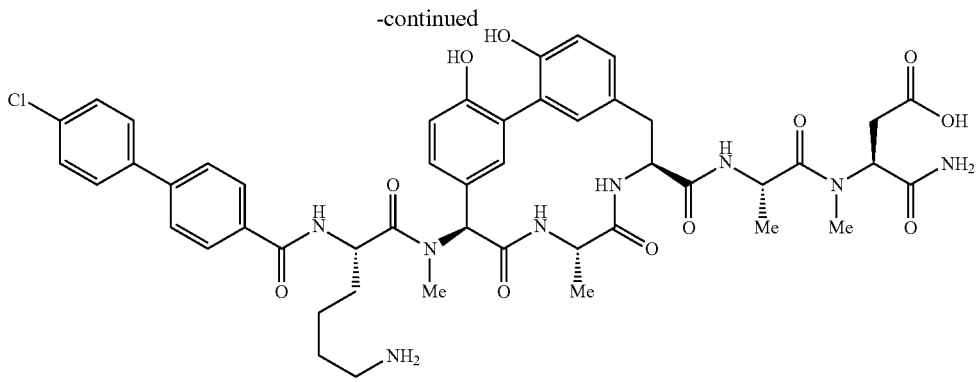

158

To a solution of Cbz-N-Me-L-Asp(OtBu)-OH.DCHA (400 mg, 0.77 mmol, 1 eq) in THF:DMF (5:1, 7 mL) at 0° C. was added isobutyl chloroformate (250 μL, 2.5 eq) dropwise and N-methylmorpholine (253 μL, 3 eq). The reaction was allowed to stir at 0° C. for 1 h then NH$_4$OH (14.8 M, 130 μL, 2.5 eq) and N-methylmorpholine (253 μL, 3 eq) were added. The solution was allowed to warm to room temp and the reaction was stirred for 3.5 h. The reaction was then diluted with half saturated NH$_4$Cl and extracted 3× with EtOAc. The combined organic layers were washed with brine, dried over sodium sulfate and concentrated. The isolated Cbz-N-Me-L-Asp(OtBu)-NH$_2$ (226 mg) was used in the next reaction without further purification. MS (ESI) for (C$_{17}$H$_{24}$N$_2$O$_5$): m/z 359.0 (M+Na).

To a solution of Cbz-N-Me-L-Asp(OtBu)-NH$_2$ (89 mg, 0.26 mmol, 1 eq) in THF (5 mL) was added 10% Pd/C (30 mg, ⅓ by weight). The reaction was put under an atmosphere of H$_2$ and allowed to stir until TLC indicated complete consumption of starting material (~3 hrs). The mixture was then filtered through celite (washed through with EtOAc) and concentrated to give N-Me-L-Asp(OtBu)-NH$_2$. To N-Me-L-Asp(OtBu)-NH$_2$ dissolved in DMF was added Cbz-Ala-OH (64 mg, 1.1 eq), N-methylmorpholine (71 μL, 2.5 eq) and then HATU (99 mg, 1 eq). The solution was allowed to stir overnight then was diluted with 1% citric acid and extracted 3× with EtOAc. The combined organic layers were washed twice with diluted brine and then dried over sodium sulfate and concentrated. The isolated Compound 158A (51.3 mg, 48%) was used in the next reaction without further purification. MS (ESI) for (C$_{20}$H$_{29}$N$_3$O$_6$): m/z 429.8 (M+Na).

To a solution of Compound 158A (15 mg, 34 μmol, 1 eq) in MeOH (3 mL) was added 1N HCl (aq) (41 μL, 1.2 eq) followed by 10% Pd/C (5 mg, ⅓ by weight). The reaction was put under an atmosphere of H$_2$ and allowed to stir overnight. The mixture was then filtered through celite (washed through with EtOAc) and concentrated to give Compound 158B. The isolated material was used in the next reaction without further purification.

To a solution of Compound 104E (36 mg, 34 μmol, 1 eq) in DMF (1 mL) at 0° C. was added a 10% solution of isobutylchloroformate in DMF (53 μL, 1.2 eq) and N-methylmorpholine (9 μL, 2.5 eq). The reaction was allowed to stir at 0° C. for 1 h and then Compound 158B (1 eq) in DMF (1 mL) and N-methylmorpholine (9 μL, 2.5 eq) were added. The solution was stirred at 0° C. for 30 mins then allowed to warm to room temp and stirred for 3.5 h. The reaction was then diluted with 1% citric acid and a small amount of brine and extracted 3× with EtOAc. The combined organic layers were washed with water (2×), saturated NaHCO$_3$ and brine, then dried over sodium sulfate and concentrated. The crude material contained approximately 40% Compound 104E and 60% Compound 158E by LCMS. Compound 158E was Boc deprotected via General Method 9 to give Compound 158 as the TFA salt (6.7 mg, 18% over 3 steps). NMR showed doubled resonances likely due to slow isomerism about the N-Me bond. MS (ESI) for (C$_{47}$H$_{53}$ClN$_8$O$_{11}$): m/z 955.2 (M+H). HPLC t$_R$ 3.24 min (10% AcCN/H$_2$O-90% AcCN/H$_2$O, 3.5 min, 1.0 mL/min Kinetix C18, 4.8×50 mm).

Example 59: Synthesis of Compound 159

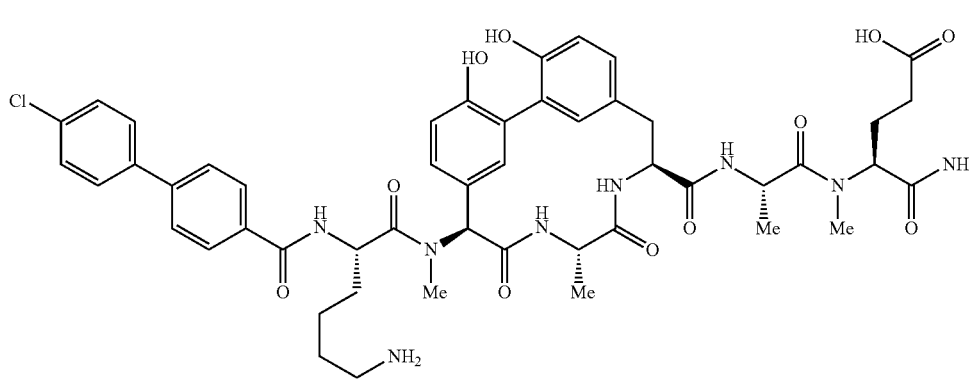

159

Compound 159 was synthesized in a similar manner to Compound 158 from Compound 104E and Cbz-N-Me-L-Glu(OtBu)-OH. MS (ESI) for ($C_{48}H_{55}ClN_8O_{11}$): m/z 969.1 (M+H). The NMR contained doubled resonances. HPLC $t_R$ 3.24 min (10% AcCN/$H_2O$-90% AcCN/$H_2O$, 3.5 min, 1.0 mL/min Kinetix C18, 4.8×50 mm).

Example 60: Synthesis of Compound 160

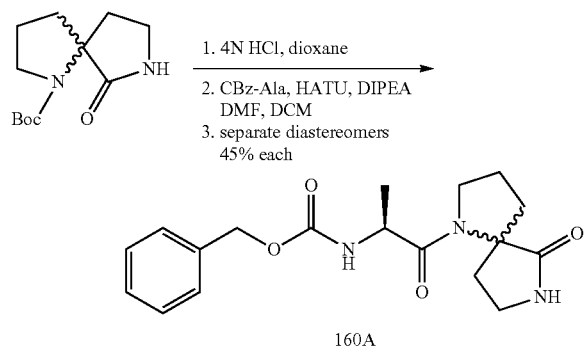

160A
Diastereomer 1

160B
Diastereomer 2

Tert-butyl 9-oxo-4,8-diazaspiro[4.4]nonane-4-carboxylate (526 mg, 2.08 mmol) was weighed into a reaction vial equipped with a stirbar. 4N HCl in 1,4-dioxane (4 mL, 16 mmol) was added in a single portion and the reaction was stirred at room temperature for 1 h. The volatiles were removed under reduced pressure to give 1,7-diazaspiro[4.4]nonan-6-one HCl as a tan solid.

(S)-2-(((benzyloxy)carbonyl)amino)propanoic acid (1.072 g, 4.802 mmol) and HATU (1.829 g, 4.714 mmol) were weighed into a reaction vial equipped with a stirbar. N,N-dimethylformamide (3 mL) was added, then N,N-diisopropylethylamine (1.8 mL, 10 mmol), and the resulting solution was aged 5 minutes. 1,7-diazaspiro[4.4]nonan-6-one HCl (2.08 mmol) was dissolved in DCM (30 mL) with the addition of 1 mL DMF and added to the activated amino acid. The reaction was stirred for 1 h. A clear yellow solution formed. LC/MS showed a new peak with an M+ of 346.

The reaction was poured into 50 mL 1M HCl, extracted 3× with 10 ml DCM, and then the combined organics were washed with 20 mL saturated NaHCO3, dried over MgSO4, filtered and concentrated. The resulting mixture of diastereomers were separated using SFC and were carried on separately without identifying their absolute stereochemistry. Compound 160A yielded 326.4 mg (45.4%) and Compound 160B yielded 328.5 mg (45.7%).

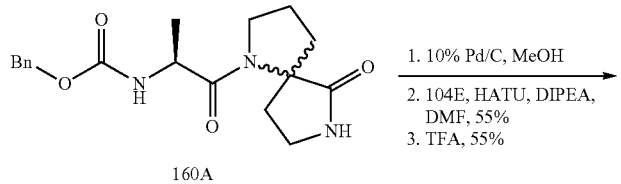

160A

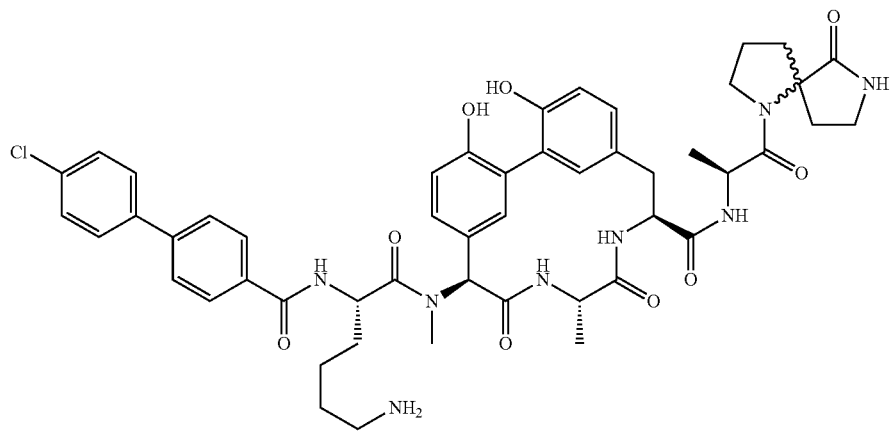

160

Compound 160A (120.6 mg, 0.3492 mmol) was dissolved in methanol (3 mL) and 10% palladium on carbon (51.8 mg, 0.0487 mmol) was added. The reaction flask was evacuated and refilled with nitrogen three times. The atmosphere was then replaced with hydrogen gas and stirred under 1 atmosphere of hydrogen for 4 hours. The reaction was filtered through a plug of Celite and concentrated to a solid.

Compound 104E (0.505 g, 0.478 mmol) and HATU (0.247 g, 0.637 mmol) were weighed into a reaction vial. N,N-dimethylformamide (3 mL) was added, then N,N-diisopropylethylamine (0.20 mL, 1.1 mmol). The solution was aged 5 minutes, and then added to the compound produced in the previous step. The reaction was stirred 2 h at RT. The reaction was poured into 50 mL 1N HCl, then extracted with 10% MeOH in DCM (3×15 mL). The combined organics were washed with saturated NaHCO$_3$, dried with MgSO$_4$, filtered and concentrated. The crude material was concentrated onto silica gel and purified through flash chromatography, using a 25 g cartridge and a gradient of 0-15% MeOH in dichloromethane. The product containing fractions were concentrated to give Compound 160 (diastereomer 1) (0.24 g, 0.19 mmol, 55%) as a light solid. $^1$H NMR (400 MHz, DMSO) δ 9.09-8.96 (m, 1H), 8.73-8.40 (m, 3H), 8.20-7.94 (m, 4H), 7.89-7.73 (m, 5H), 7.61-7.50 (m, 3H), 7.22-6.69 (m, 6H), 6.54-6.35 (m, 3H), 6.26 (d, J=13.5 Hz, 1H), 5.09-4.48 (m, 6H), 3.99-3.85 (m, 1H), 3.68-3.47 (m, 3H), 3.19-2.63 (m, 13H), 2.46-2.28 (m, 3H), 2.04-0.94 (m, 22H).

Example 61: Synthesis of Compound 161

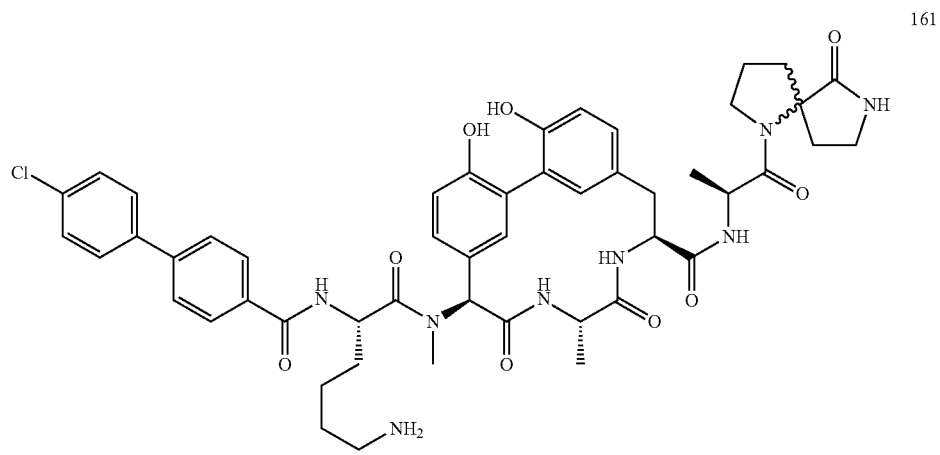

161

Compound 160B was converted to Compound 161 (diastereomer of Compound 160) using the same procedures as described in Example 60. $^1$H NMR (400 MHz, DMSO) δ 8.73-8.56 (m, 2H), 8.22-8.10 (m, 1H), 8.09-7.88 (m, 4H), 7.84-7.74 (m, 5H), 7.60-7.50 (m, 4H), 7.15 (s, 1H), 7.05-7.01 (m, 1H), 6.88-6.66 (m, 3H), 6.51-6.35 (m, 3H), 6.29-6.22 (m, 1H), 5.10-4.41 (m, 6H), 3.92-3.66 (m, 3H), 3.48-3.37 (m, 3H), 3.18-3.06 (m, 3H), 2.88 (s, 2H), 2.83-2.64 (m, 5H), 2.01-1.71 (m, 9H), 1.65-1.34 (m, 6H), 1.35-1.07 (m, 8H).

Example 62: Synthesis of Compound 162

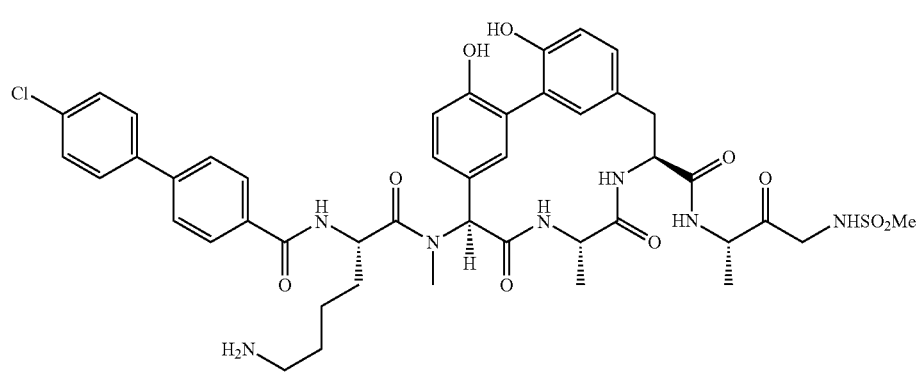

162

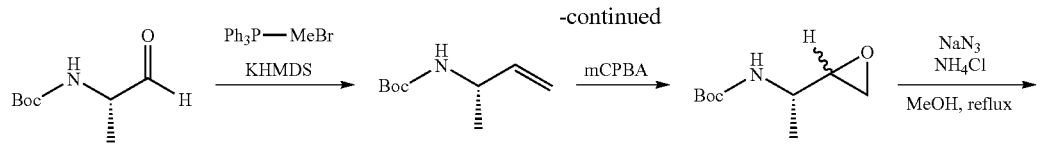

-continued

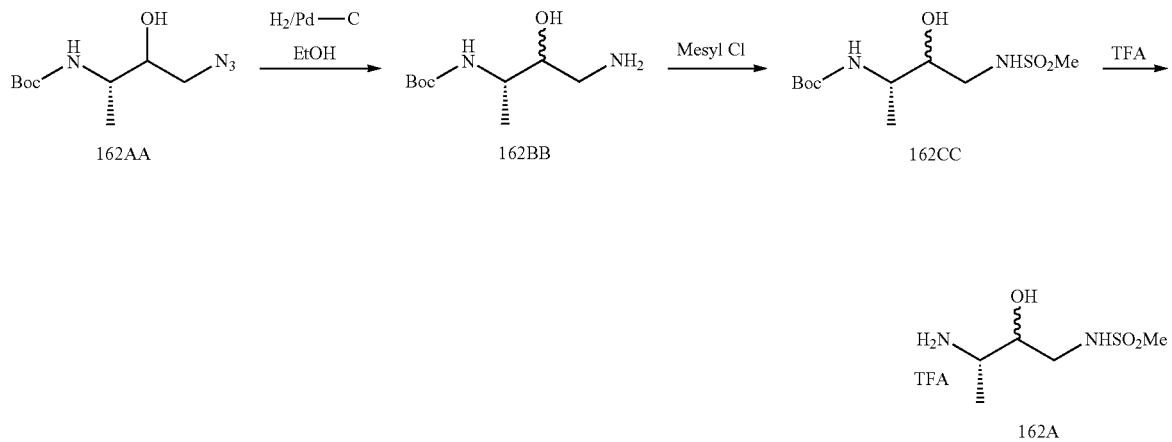

To a solution of methyltriphenylphosphonium bromide (15.0 g, 42 mmol) in THF (80 mL) was added 0.5 M KHMDS in toluene (84 mL, 42 mmol) in a cool water bath. The deep yellow suspension was stirred at rt for 1 h, and then the reaction mixture was cooled to −78° C. A solution of (S)-tert-butyl 1-oxopropan-2-ylcarbamate (3.46 g, 20.0 mmol) in THF (20 mL) was added dropwise, and the reaction mixture was allowed to warm to rt. After stirring at rt for 30 min, the reaction mixture was quenched with methanol (20 mL). The mixture was partitioned between ether and Rochelle's salt. The aqueous layer was extracted twice with ether, and the combined organic layers were washed with brine, dried over $Na_2SO_4$, and filtered. The residue was cooled, and solids were filtered and rinsed with hexanes. The filtrate was concentrated to an oil, and purified by silica gel chromatography (3% ethyl acetate/hexanes to 50% ethyl acetate/hexanes) to afford (S)-t-butyl but-3-en-2-ylcarbamate (2.60 g, 76%) as a white solid. Rf 0.34 (9:1 hexanes:ethyl acetate).

mCPBA (70-75%) (3.81 g, 16 mmol) was added to a suspension of (S)-t-butyl but-3-en-2-ylcarbamate (1.37 g, 8.0 mmol), $NaHCO_3$ (1.34 g, 16 mmol) in DCM (24 mL) at 0° C. The reaction mixture was allowed to warm to rt. After 2 h, additional mCPBA (1.90 g, 8.0 mmol) and $NaHCO_3$ (0.670 g, 8.0 mmol) were added and the suspension was stirred for an additional 2 h. The mixture was partitioned between ether and water, and the aqueous layer was extracted with ether. The combined ether layers were washed sequentially with saturated sodium thiosulfate and brine, dried over $Na_2SO_4$, filtered and concentrated. The residue was purified by silica gel chromatography (5% ethyl actetate/hexanes to 75% ethyl acetate/hexanes) to afford tert-butyl ((1S)-1-(oxiran-2-yl)ethyl)carbamate (0.76 g, 51%) as a colorless oil and a mixture of isomers. Rf 0.44 (7:3 hexanes:ethyl acetate).

A suspension of t-butyl ((1S)-1-(oxiran-2-yl)ethyl)carbamate (0.64 g, 3.4 mmol), $NH_4Cl$ (0.32 g, 6.0 mmol), $NaN_3$ (0.57 g, 8.8 mmol) in MeOH (18 mL) was heated at reflux for 16 h. The solvent was removed under reduced pressure, and the residue was partitioned between ether and water. The aqueous layer was extracted with ether, and the combined organic layers were washed with brine, dried over $Na_2SO_4$, filtered, and concentrated. The residue was purified by silica gel chromatography (10% ethyl acetate/hexanes to 70% ethyl acetate/hexanes) to afford Compound 162AA (0.49 g, 62%) as a colorless oil. Rf 0.38 (7:3 hexanes:ethyl acetate).

10% Palladium on carbon (20.6 mg) was added to a solution of Compound 162AA (0.26 g, 1.1 mmol) in ethanol (11 mL). The suspension was placed under an atmosphere of $H_2$ and stirred for 16 h. The mixture was filtered through Celite and rinsed with ethyl acetate. The filtrate was concentrated to afford Compound 162BB (0.22 g, 96%) as an oil.

To a solution of Compound 162BB (31.4 mg, 0.15 mmol) in DCM (1.5 mL) at 0° C. was added triethylamine (23.4 mg, 0.23 mmol) and methanesulfonyl chloride (21.1 mg, 0.18 mmol). After 3 h, the mixture was partitioned between EA:saturated $NaHCO_3$, and the aqueous layer was extracted with EtOAc. The combined organic layers were washed with brine, dried over $Na_2SO_4$, filtered, and concentrated under reduced pressure. Silica gel chromatography (1% MeOH/DCM to 16% MeOH/DCM) afforded 16 mg (37%) of Compound 162CC.

To a solution of Compound 162CC (14 mg, 0.0495 mmol) in 0.8 mL DCM was added 0.2 mL TFA. After 40 min, the solvent was evaporated under reduced pressure to give Compound 162A as an oil which was used immediately.

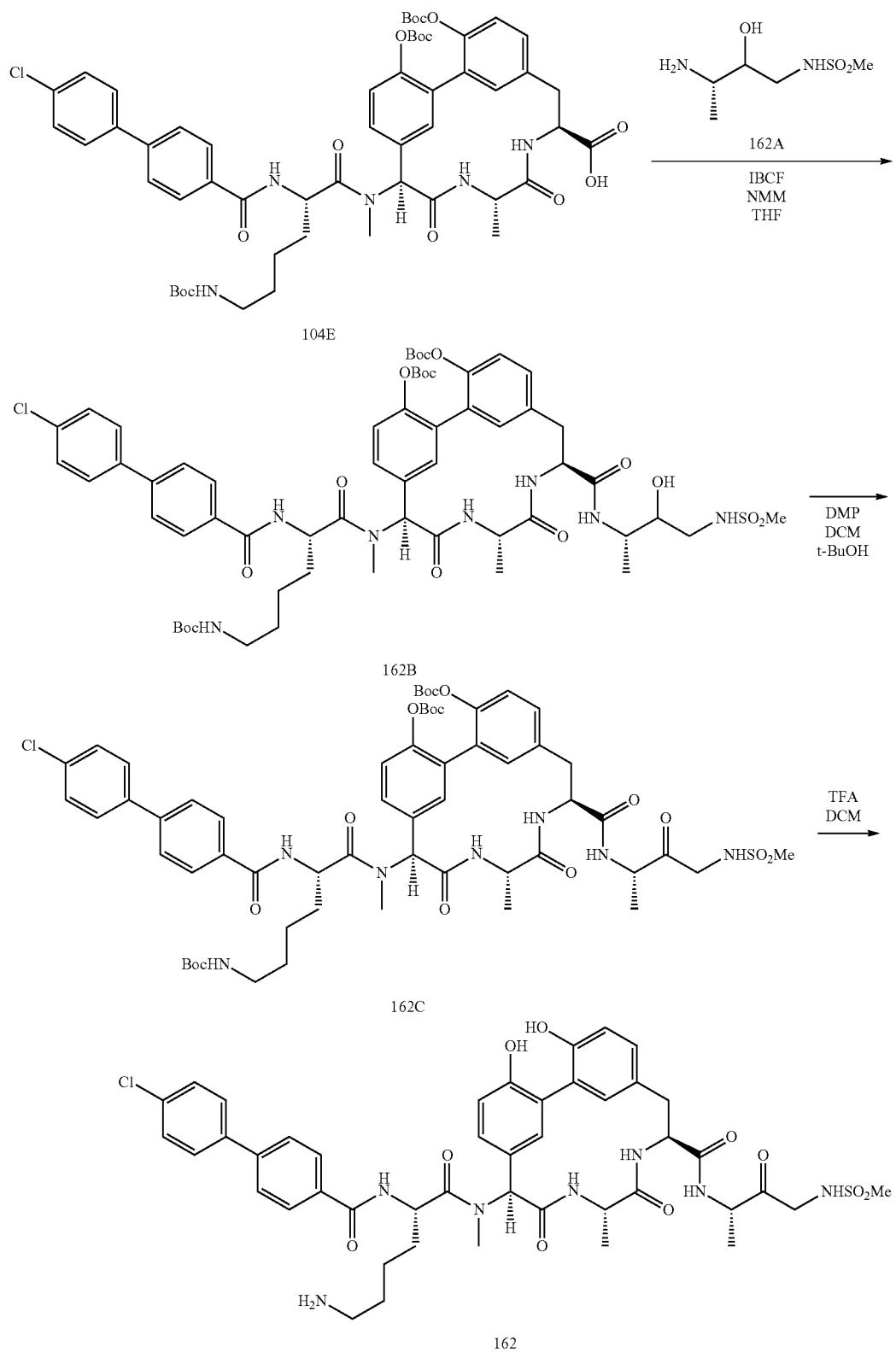
To a solution of Compound 104E (26.4 mmol, 0.25 mol) in 0.8 mL THF at 0° C. was added isobutyl chloroformate (5.2 mg, 0.038 mmol), then N-methylmorpholine (7.5 mg, 0.074 mmol). After 45 min, a solution of Compound 162A (14 mg, 0.047 mmol) in 0.8 mL THF was added. The mixture was allowed to warm to rt. After 1 h, the mixture was quenched with brine, and the mixture extracted with EtOAc (2×). The combined organic layers washed with brine, dried over Na$_2$SO$_4$, filtered, and concentrated under reduced pressure to give Compound 162B which was carried on without further purification. MS (ESI): m/z 1120.6 (M+H)$^+$; HPLC t$_R$ 3.48 min (50% AcCN/H$_2$O-95% AcCN/H$_2$O, 3.0 min, 1.0 mL/min Kinetix C18, 4.8×50 mm).

To Compound 162B in DCM (2.4 mL) was added Dess-Martin periodinane (52 mg, 0.12 mmol). The reaction was stirred overnight but did not go to completion. The mixture was diluted with a 1:1 mixture of EtOAc:DCM, washed sequentially with sat'd NaHCO$_3$ and brine, dried over Na$_2$SO$_4$, filtered, and concentrated under reduced pressure to a solid. The compound was dissolved in DCM (2.4 mL) and Dess-Martin periodinane (78 mg, 0.18 mmol) was added. Approximately 0.1 mL t-butanol was added, and the reaction stirred overnight. After the reaction was shown to be complete, it was subjected to the same workup to afford a solid. Silica gel chromatography (100% DCM to 16% MeOH/DCM) afforded Compound 162C (14.7 mg, 49%) as a white solid. MS (ESI): m/z 1118.3 (M-Boc+H)$^+$; HPLC t$_R$ 3.60 min (50% AcCN/H$_2$O-95% AcCN/H$_2$O, 3.0 min, 1.0 mL/min Kinetix C18, 4.8×50 mm).

To a solution of Compound 162C in DCM (1.2 mL) was added TFA (0.3 mL). After 2 h, the solvents were evaporated and the resultant residue purified by prep HPLC (CH$_3$CN—H$_2$O containing 0.05% TFA) to afford 2.7 mg (23%) of Compound 162, as a white solid. MS (ESI): m/z 918.4 (M+H)$^+$; HPLC t$_R$ 4.15 min (10% AcCN/H2O-95% AcCN/H$_2$O, 6.0 min, 1.0 mL/min Kinetix C18, 4.8×50 mm).

concentrated and the residue was purified by silica gel column (PE/EA=5/1) to afford isopropyl ethanesulfonate (19.5 g, 84.7%) as a colorless oil. $^1$H NMR (400 MHz, CDCl$_3$) δ 0.81 (d, J=4.2 Hz, 6H), 4.74-4.83 (m, 1H), 6.05 (1H, d, J=10.0 Hz), 6.38 (1H, d, J=12.4 Hz), 6.54 (1H, dd, J=12.4 Hz, J=10.0 Hz).

To a solution of n-C$_{10}$H$_{21}$NH$_2$ (19.0 g, 121 mmol) in MeOH (200 mL) at 0° C. was added isopropyl ethanesulfonate (18.2 g, 121 mmol) dropwise. The mixture was warmed to room temperature slowly and stirred for two days at room temperature. The reaction mixture was then concentrated and the residue was purified by silica gel chromatography (PE/EA=20/1 to 3/1) to afford isopropyl 2-(decylamino)ethanesulfonate (20.2 g, 54.4%) as a colorless oil. $^1$H NMR (400 MHz, CDCl$_3$) δ 0.81 (3H, t, J=6.8 Hz), 1.36-1.40 (m, 2H), 2.54 (2H, t, J=7.2 Hz), 3.03 (2H, t, J=7.2 Hz), 3.20 (2H, t, J=4.5 Hz), 4.87-4.95 (m, 1H).

To a solution of isopropyl 2-(decylamino)ethanesulfonate (20.0 g, 65 mmol) and Et$_3$N (13.2 g, 130 mmol) in DCM (200 mL) at 0° C. was added CbzCl (12.2 g, 71.6 mmol) dropwise. The mixture was warmed to room temperature slowly and stirred for two days at room temperature. The reaction was washed sequentially with 1N HCl (200 mL) and saturated NaHCO$_3$ (100 mL). The aqueous layer was further extracted by DCM (200 mL*2). The combined DCM layers were concentrated and the residue was purified by silica gel column (PE/EA=10/1) to afford Compound 163AA (28.0 g, 96.6%) as a colorless oil. $^1$H NMR (400 MHz, CDCl$_3$) δ 0.81 (3H, t, J=6.8 Hz), 1.17-1.20 (m, 16H), 1.14-1.15 (m, 2H), 3.15-3.33 (m, 4H), 3.59-3.62 (m, 2H), 4.85-4.89 (m, 1H), 5.06 (s, 2H), 7.21-7.30 (m, 5H).

Example 63: Synthesis of Compound 163

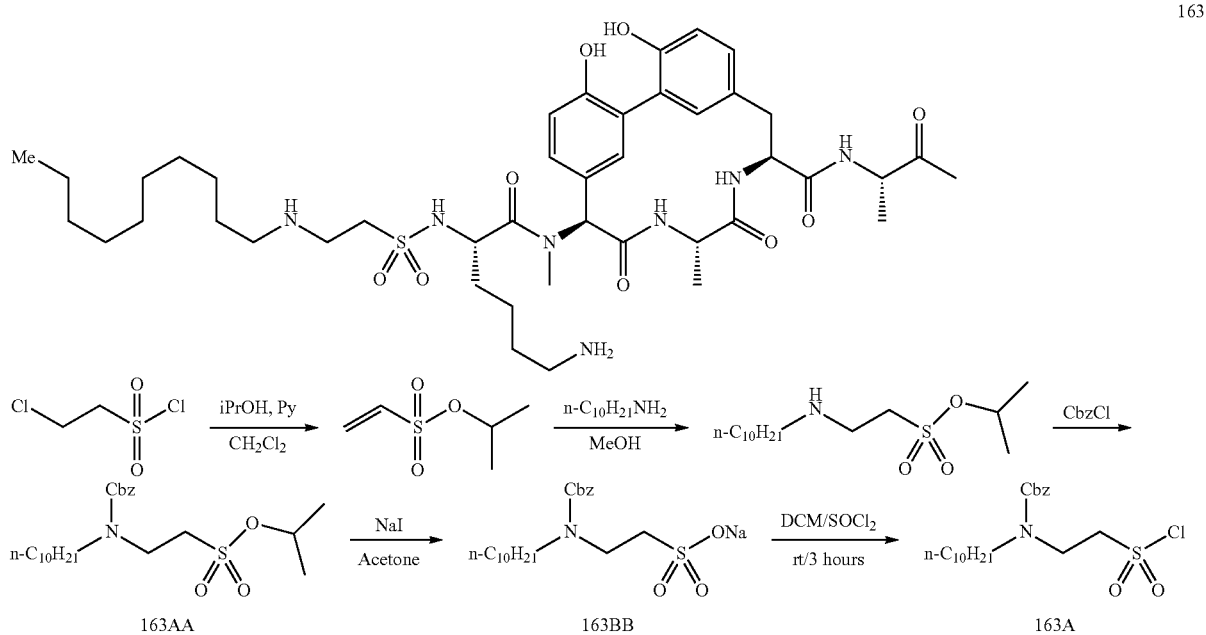

To a solution of 2-chloroethanesulfonyl chloride (25.0 g, 153 mmol) and pyridine (24.3 g, 307 mmol) in DCM (200 mL) was added i-PrOH (27.6 g, 460 mmol) at 0° C. The mixture was warmed to room temperature and stirred for another 3 h at the same temperature. The reaction was washed sequentially with 1N HCl (200 mL) and saturated NaHCO$_3$ (100 mL). The aqueous layer was further extracted by DCM (200 mL*2). The combined DCM layers were To a solution of Compound 163AA (28.0 g, 63.4 mmol) in acetone (300 mL) was added NaI (11.4 g, 76.1 mmol) in one portion. The reaction mixture was heated to reflux overnight. The reaction mixture was cooled to room temperature and the resulting solid was filtered and dried in vacuum to give Compound 163BB (26.1 g, 97.8%) as a white solid. $^1$H NMR (400 MHz, DMSO) δ 0.82 (3H, t, J=6.8 Hz), 1.20 (br, 14H), 1.39-1.43 (m, 2H), 2.58-2.64 (m, 2H), 3.14-3.18 (m, 2H), 5.03 (s, 2H), 7.27-7.35 (m, 5H).
To a mixture of Compound 163BB (7.0 g, 25.0 mmol) in DCM (100 mL) and DMF (0.1 mL) at 0° C. was added SOCl₂ (29.7 g, 250 mmol). The mixture was slowly warmed to room temperature and stirred for 3 h at room temperature. The reaction mixture was concentrated in vacuum to afford Compound 163A, which was used directly without further purification.
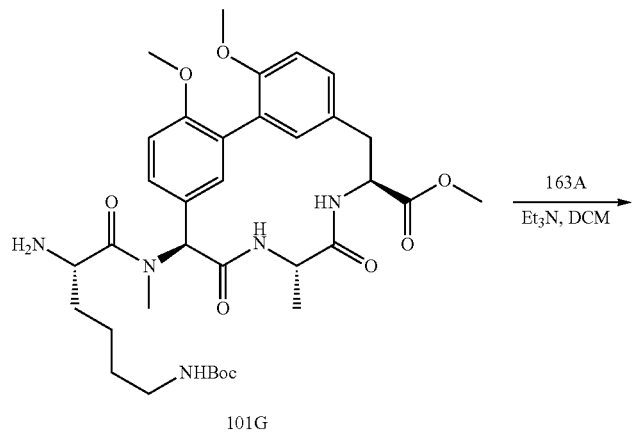
101G
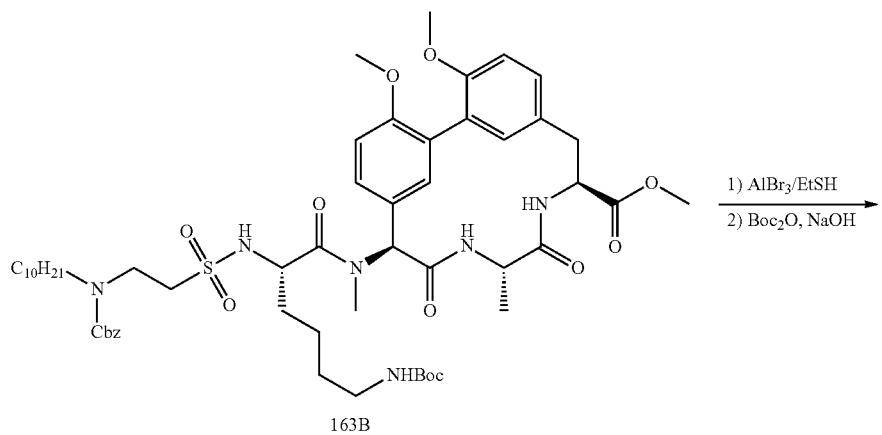
163B
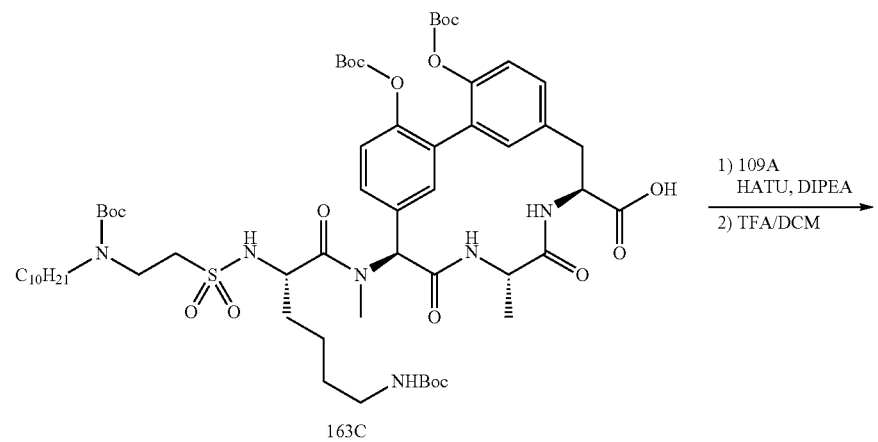
163C

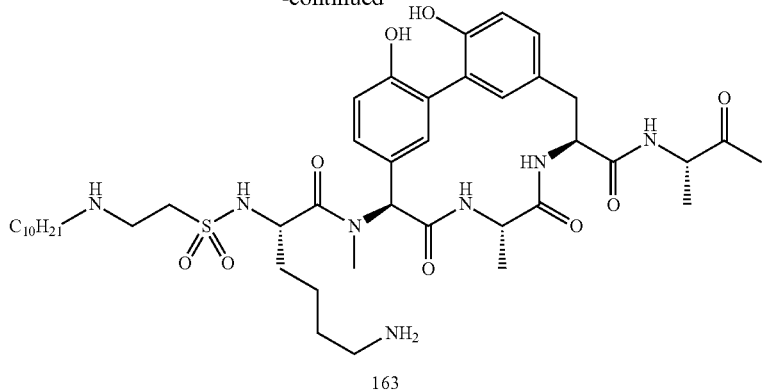

163

To a solution of Compound 101G (300 mg, 0.44 mmol) and TEA (177.3 mg, 1.75 mmol) in DCM (5 mL) was added a solution of Compound 163A (366 mg, 1.75 mmol) in DCM (5 mL). The reaction mixture was stirred overnight at room temperature. The reaction mixture was concentrated, the residue was washed with 1N HCl (10 mL) and the aqueous layer was further extracted with EA (20 mL*2). The combined EA layers were concentrated and the residue was purified by silica gel chromatography (DCM/MeOH=20/1) to afford Compound 163B (147 mg, 31.5%) a colorless oil.

Compound 163 was synthesized in a manner similar to Compound 111 (Example 11) except the use of Compound 163B is used instead of Compound 111A to afford Compound 163 (22 mg) as a white solid. $^1$H NMR (400 MHz, MeOH-$d_4$) δ 0.85-0.90 (m, 3H), 1.29-1.41 (m, 19H), 1.59-1.92 (m, 10H), 2.14-2.18 (m, 3H), 2.68 (s, 1H), 2.84 (s, 2H), 2.92-3.15 (m, 6H), 3.14-3.39 (m, 3H), 4.26-4.46 (m, 3H) 6.87 (d, J=8.0 Hz, 1H), 6.88-6.99 (m, 3H), 7.10-7.12 (m, 2H). LCMS (5-95 AB, ESI): RT=0.770, M+H$^+$=859.1.

Example 64: Synthesis of Compound 164

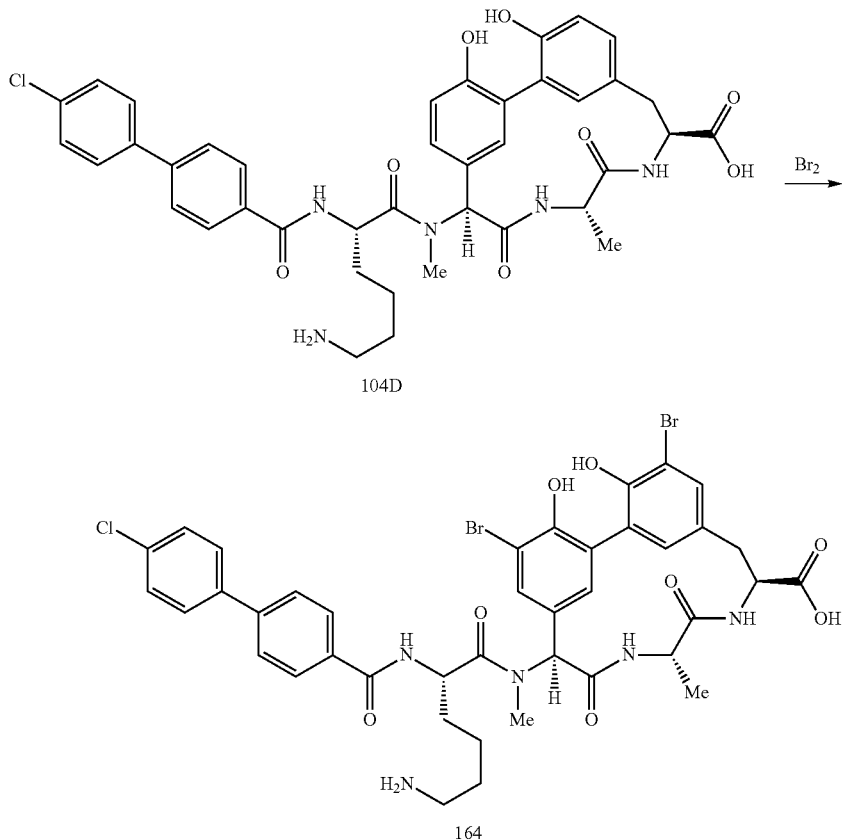

Bromine (14.3 mg, 0.09 mmol) was added to a solution of Compound 104D (65 mg, 0.07 mmol) in dichloromethane (3 mL) and the reaction was stirred at room temperature for 16 h. The solution was then concentrated and the residue was purified by reverse phase HPLC to give Compound 164 (11.6 mg) as a white solid. LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=5.03 min, m+H=912.1.

Example 65: Synthesis of Compound 165

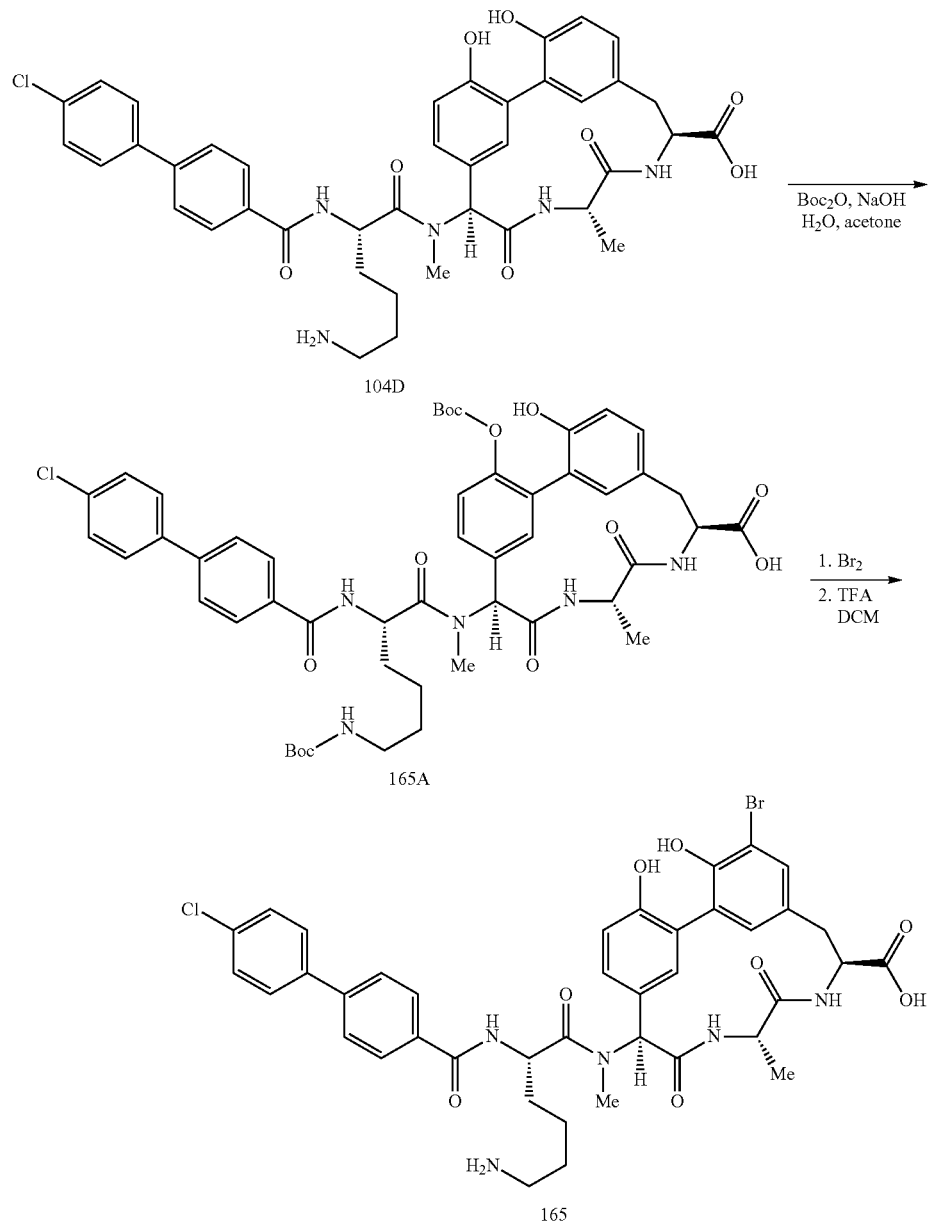

pH~6 by addition of 1N HCl. The resulting white solid was collected by filtration and washed with water. The solid was purified by flash chromatography (100% DCM to 20% MeOH/DCM, 24 g column) to give 120 mg of Compound 165A as a white solid. LCMS (3% AcCN/H$_2$O, 0.3 min; 3% AcCN-95% AcCN/H$_2$O with 0.05% TFA, 6.5 min, 0.4 mL/min, Agilent SB C18, 2.1×30 mm, ESI, ESI): RT=3.0 min, M+H=957.7.

Bromine (12.5 mg, 0.08 mmol), dissolved in dichloromethane (1 mL) was slowly added to a solution of Compound 165A (75 mg, 0.08 mmol) in dichloromethane (3 mL) at 0° C. The reaction was allowed to warm up to room temperature and stirred for 6 h. Water was added, the phases were separated, and the aqueous phase was extracted with 2×20 mL of dichloromethane. The combined organic phases were dried with MgSO$_4$, filtered and concentrated. The A mixture of Compound 104D (380 mg, 0.50 mmol) and di-tert-butyl dicarbonate (439 mg, 2.01 mmol) in 5 mL of a 1N solution of sodium hydroxide and 5 mL of acetone (5 mL, 68 mmol, 4000 mg) was stirred at room temperature for 5 h. The mixture was then poured on ice and brought to residue was purified by flash chromatography (10% to 25% MeOH/DCM, 24 g column) to give 65 mg of a white solid.

Trifluoroacetic acid (0.24 mL, 3.14 mmol) was added to a solution of the solid in dichloromethane (3 mL) and the mixture was stirred at room temperature for 30 min. The reaction was then concentrated and the residue was purified by reverse phase HPLC to give Compound 165 (3.6 mg) as a white solid. LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.62 min, m+H=834.2 $^1$H NMR (400 MHz, DMSO-d6) δ 8.68 (d, J=7.9 Hz, 1H), 8.53 (d, J=9.1 Hz, 1H), 8.09-7.94 (m, 2H), 7.85-7.72 (m, 4H), 7.56 (dd, J=8.5, 3.9 Hz, 2H), 7.09 (d, J=2.4 Hz, 1H), 6.90 (d, J=15.3 Hz, 2H), 6.83-6.70 (m, 1H), 6.52 (d, J=8.3 Hz, 1H), 6.25 (s, 1H), 4.91-4.73 (m, 2H), 4.54-4.36 (m, 2H), 2.98-2.86 (m, 2H), 2.84-2.73 (m, 3H), 2.73-2.63 (m, 1H), 1.79 (s, 2H), 1.66-1.36 (m, 4H), 1.17 (d, J=6.7 Hz, 3H), 1.12 (d, J=7.3 Hz, 1H).

Example 66: Synthesis of Compounds 166 and 167

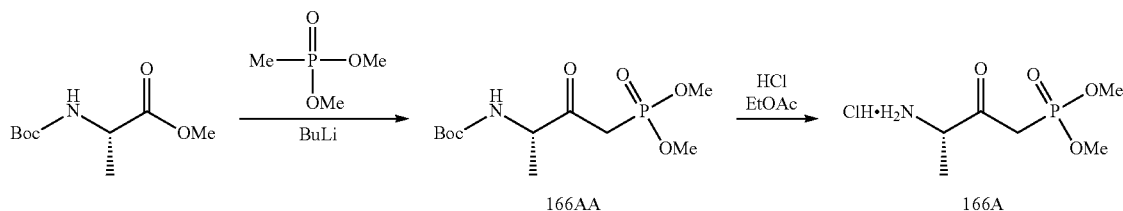

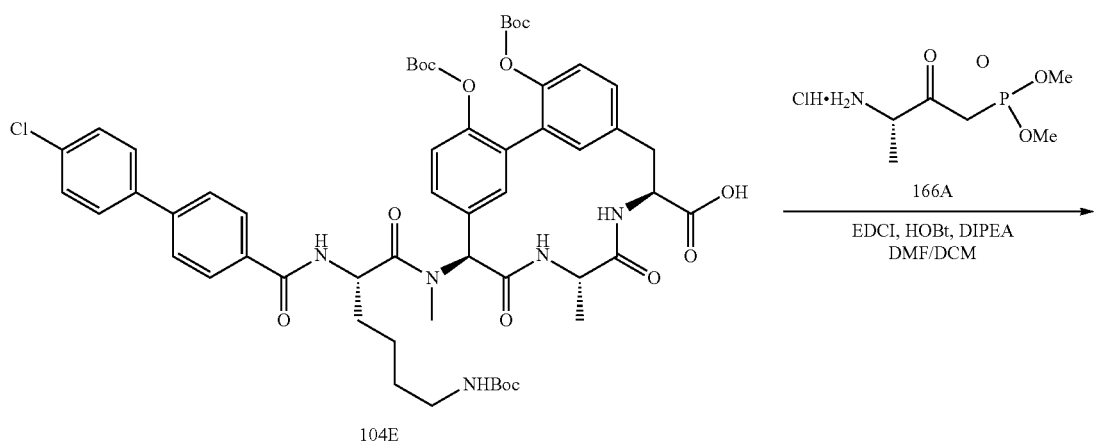

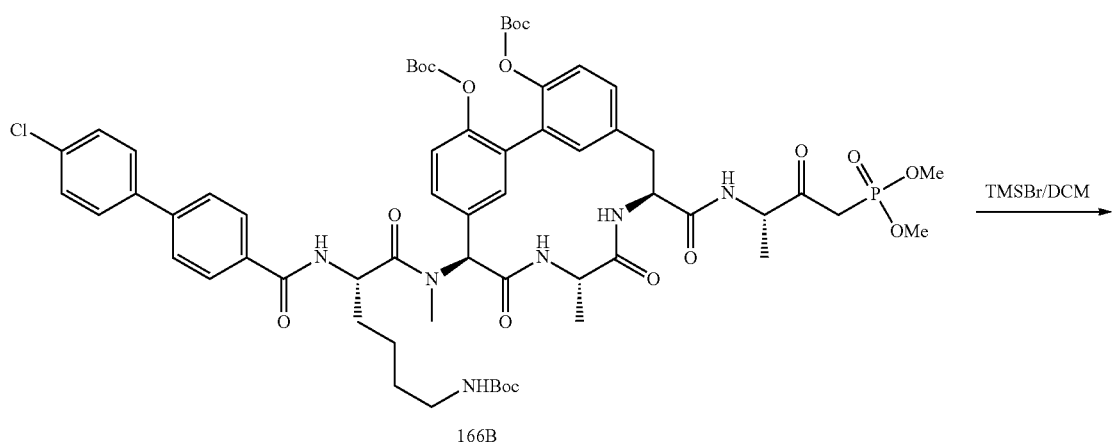

-continued

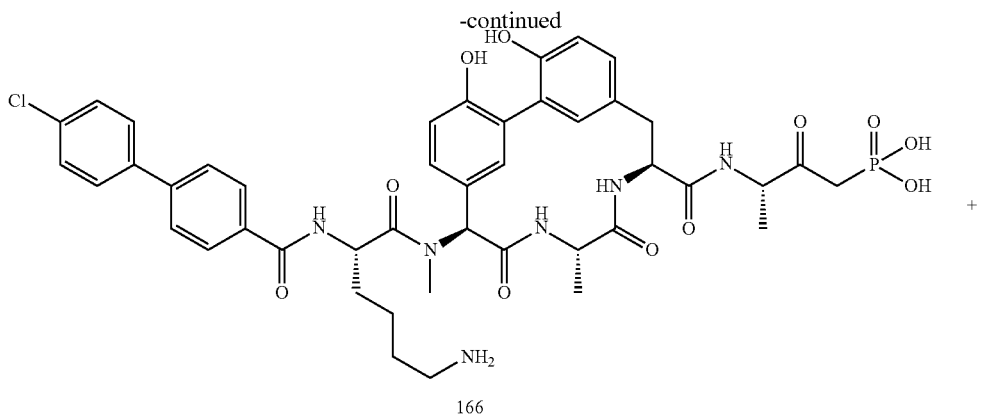

166

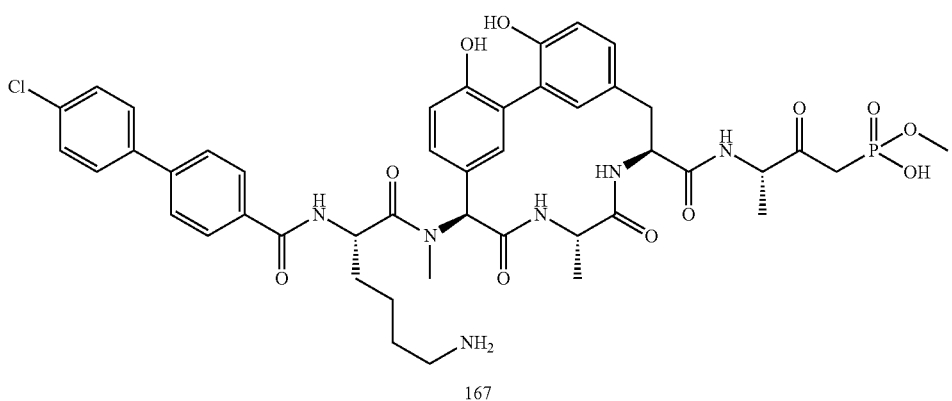 [SMILES: COP(=O)(O)CC(=O)[C@H](C)NC(=O)[C@@H]1Cc2ccc(O)c(c2)-c2cc(ccc2O)[C@H](N(C)C(=O)[C@H](CCCCN)NC(=O)c2ccc(-c3ccc(Cl)cc3)cc2)C(=O)N[C@@H](C)C(=O)N1]

167

To a mixture of MePO(OMe)$_2$ (45.8 g, 369 mmol) in dry THF (375 mL) at −78° C., n-BuLi in n-hexane (2.5 M; 148 mL, 369 mmol) was added dropwise. After the mixture was stirred at −78° C. for 30 min, a solution of (S)-methyl 2-((tert-butoxycarbonyl)amino)propanoate (25 g, 123 mmol) in dry THF (125 mL) was added dropwise. The resulting mixture was stirred at −78° C. for 2 h and then −30° C. for 1 h. The reaction was quenched by adding 20% citric acid at −30° C. The resulting mixture was extracted with EA (200 mL*3) and the combined EtOAc layers were washed sequentially with saturated NaHCO$_3$ (500 mL), brine (500 mL), dried over MgSO$_4$ and concentrated under reduced pressure. The resulting residue was purified by silica gel column chromatography (PE/EA=1/1) to give the Compound 166AA (34 g, 93.6%) as light yellow oil.

To a solution of Compound 166AA (100 mg, 0.34 mmol) in EtOAc (2 mL) was added 4N HCl/EtOAc (2 mL) at 0° C. The mixture was stirred at 15° C. for 1 h. After the reaction was complete, the mixture was concentrated to afford Compound 166A as a white solid (75 mg, 95.6%).

Compound 166B was prepared according to General Method 10 from Compound 104E and Compound 166A to afford 80 mg of a white solid.

To a solution of Compound 166B (60 mg, 0.048 mmol) in DCM (2 mL) was added TMSBr (29.4 mg, 0.192 mmol) at 15° C. The mixture was stirred at 15° C. for 3 h. The mixture was quenched with MeOH (0.1 mL) and the resulting solution was stirred at 15° C. for another 1 h. Volatiles were removed under reduced pressure and the residue was purified by prep-HPLC separation (0.1% NH$_4$OH) to give Compound 166 (6.2 mg, 14.3%) and Compound 167 (10.0 mg, 23.1%) as white solids. Data for Compound 166: $^1$H NMR (400 MHz, MeOH-d$_4$) δ 7.56-7.46 (d, J=8.4 Hz, 2H), 7.45-7.41 (d, J=8.0 Hz, 2H), 7.40-7.30 (d, J=8.0 Hz, 2H), 7.30-7.20 (m, 3H), 7.02-7.00 (d, J=6.4 Hz, 1H), 6.98-6.90 (m, 2H), 6.90-6.85 (m, 2H), 7.82-6.78 (d, J=6.4 Hz, 1H), 4.70-4.50 (m, 4H), 3.28-3.10 (m, 3H), 2.98 (s, 3H), 2.97-2.86 (m, 3H), 2.16-2.06 (m, 1H), 2.05-1.96 (m, 1H), 1.82-1.72 (m, 3H), 1.71-1.58 (m, 1H), 1.50-1.45 (m, 3H), 1.45-1.30 (m, 3H). LCMS (5-95 AB, ESI): RT=1.384, M−H=903.3. Data for Compound 167: $^1$H NMR (400 MHz, MeOH-d$_4$) δ 7.50-7.46 (d, J=8.4 Hz, 2H), 7.45-7.39 (d, J=8.0 Hz, 2H), 7.35-7.30 (d, J=8.0 Hz, 2H), 7.28-7.18 (m, 3H), 7.15-7.10 (d, J=6.4 Hz, 1H), 7.09-7.00 (m, 1H), 6.95-6.82 (m, 1H), 6.81-6.75 (m, 2H), 6.30 (s, 1H), 5.00-4.95 (m, 1H), 4.85-4.75 (m, 1H), 4.65-4.56 (m, 2H), 3.66-3.58 (m, 3H), 3.50-3.40 (m, 2H), 3.25-3.15 (m, 1H), 3.03 (s, 3H), 2.98-2.88 (m, 3H), 2.20-2.06 (m, 1H), 2.04-1.96 (m, 1H), 1.82-1.75 (m, 3H), 1.70-1.55 (m, 1H), 1.50-1.45 (m, 3H), 1.44-1.30 (m, 3H). LCMS (5-95 AB, ESI): RT=1.553, M−H=917.3.

Example 67: Synthesis of Compound 168

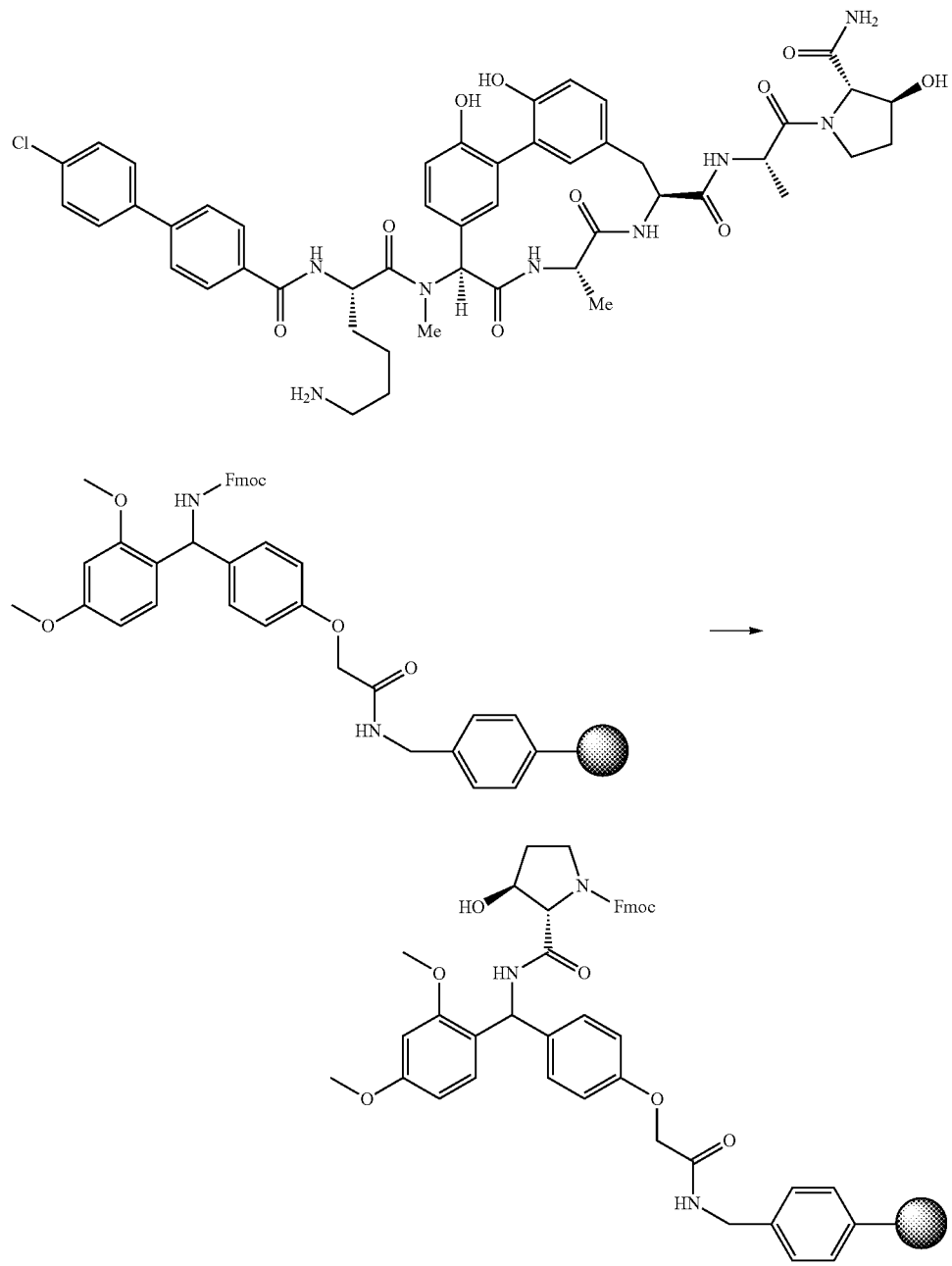

A fritted bottomed flask, equipped with a 3 way valve was charged with rink amide resin (1.0 g, 0.66 mmol). Piperidine (20% solution in DMF) (3 mL, 6.07 mmol, 2580 mg) was added. The mixture was stirred by bubbling nitrogen through the fritted glass for 45 min. Vacuum was applied to remove solvent. Then 3 mL of DMF was added and nitrogen was bubbled through for 5 min. The solvent was removed by filtration and the process was repeated. Then 3 mL of DCM were added and nitrogen was bubbled through for 5 min. The solvent was removed by filtration and the process was repeated. 3 mL of DMF was added to the resin and nitrogen was bubbled through. Then, a solution of Fmoc-Hyp-OH (Fmoc-Peptide I) (710 mg, 2.0 mmol) and HATU (750 mg, 2.0 mmol) in 3 mL of DMF and 1 mL of DCM was added. N,N-Diisopropylethylamine (0.35 mL, 2.0 mmol) was then added slowly and nitrogen was bubbled through the solution for 4 h. The solvent was then removed by vacuum. Then 3 mL of DMF were added and nitrogen was bubbled through for 5 min. The solvent was removed by filtration and repeated the process. Then 3 mL of DCM were added and nitrogen was bubbled through for 5 min. Removed solvent by filtration and the process was repeated. The dried beads were used for next step. Yield was assumed to be 100%.

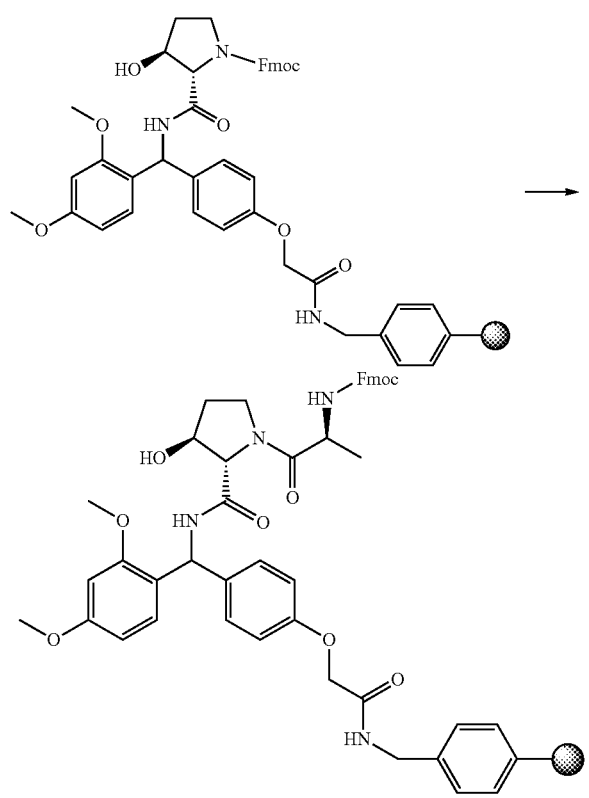

A fritted bottomed flask, equipped with a 3 way valve was charged with resin supported 9H-fluoren-9-ylmethyl (2S, 4R)-2-[[(2,4-dimethoxyphenyl)-[4-[2-oxo-2-(p-tolylmethylamino)ethoxy]phenyl]methyl]carbamoyl]-4-hydroxy-pyrrolidine-1-carboxylate (1.0 g, 0.66 mmol). Piperidine (20% solution in DMF) (3 mL, 6.07 mmol, 2580 mg) was added. The mixture was stirred by bubbling nitrogen through the fritted glass for 45 min. Vacuum was applied to remove solvent. Then 3 mL of DMF were added and nitrogen was bubbled through for 5 min. The solvent was removed by filtration and the process was repeated. Then 3 mL of DCM were added and nitrogen was bubbled through for 5 min. The solvent was removed by filtration and the process was repeated. 3 mL of DMF was added to the resin and nitrogen was bubbled through. Then, a solution of Fmoc-Ala-OH (Fmoc-Peptide II) (620 mg, 2.0 mmol) and HATU (750 mg, 2.0 mmol) in 3 mL of DMF and 1 mL of DCM was added. N,N-Diisopropylethylamine (0.35 mL, 2.0 mmol) was then added slowly and nitrogen was bubbled through the solution for 4 h. The solvent was then removed by vacuum. Then 3 mL of DMF were added and nitrogen was bubbled through for 5 min. The solvent was removed by filtration and the process was repeated. Then 3 mL of DCM were added and nitrogen was bubbled through for 5 min. The solvent was removed by filtration and the process was repeated. The dried beads were used for next step. Yield was assumed to be 100%.

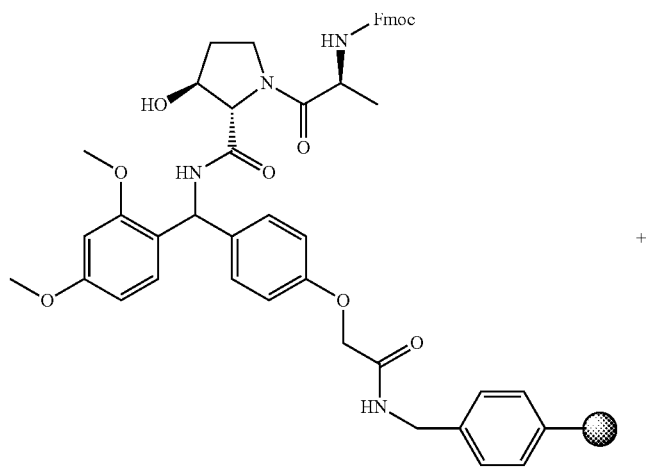

+

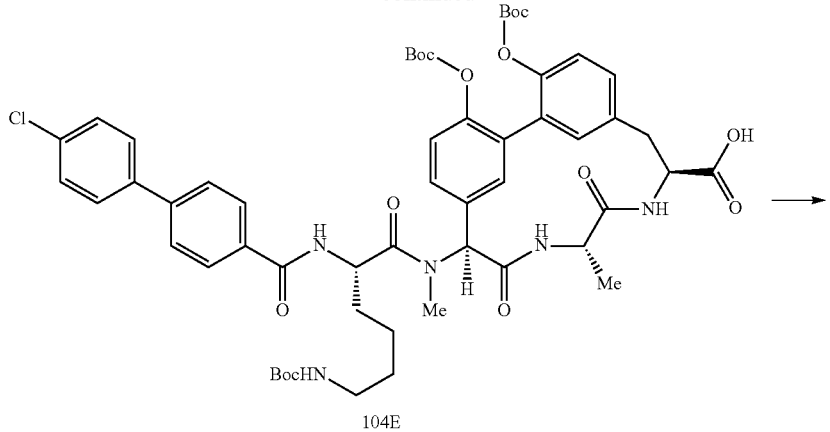

104E

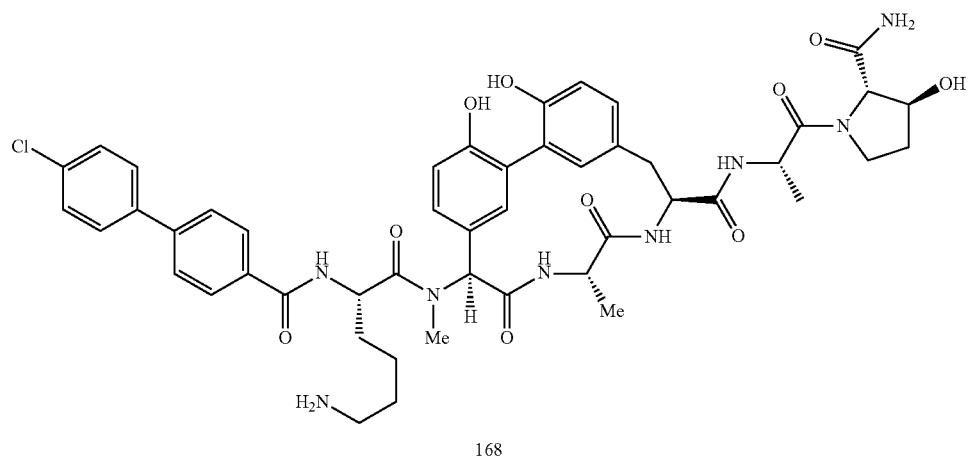

168

A fritted bottomed flask, equipped with a 3 way valve was charged with resin supported 9H-fluoren-9-ylmethyl N-[(1 S)-2-[(2S,3 S)-2-[[(2,4-dimethoxyphenyl)-[4-[2-oxo-2-(p-tolylmethylamino)ethoxy]phenyl]methyl]carbamoyl]-3-hydroxy-pyrrolidin-1-yl]-1-methyl-2-oxo-ethyl]carbamate (500 mg, 0.33 mmol). Piperidine (20% solution in DMF) (3 mL, 6.07 mmol, 2580 mg) was added. The mixture was stirred by bubbling nitrogen through the fritted glass for 45 min. Vacuum was applied to remove solvent. Then 3 mL of DMF were added and nitrogen was bubbled through for 5 min. The solvent was removed by filtration and the process was repeated. Then 3 mL of DCM were added and nitrogen was bubbled through for 5 min. The solvent was removed by filtration and the process was repeated. 3 mL of DMF was added to the resin and nitrogen was bubbled through. Then, a solution of Compound 104E (700 mg, 0.66 mmol) and HATU (250 mg, 0.66 mmol) in 3 mL of DMF and 1 mL of DCM was added. N,N-Diisopropylethylamine (0.09 mL, 2.0 mmol) was then added slowly and nitrogen was bubbled through the solution for 4 h. The solvent was then removed by vacuum. Then 3 mL of DMF were added and nitrogen was bubbled through for 5 min. The solvent was removed by filtration and the process was repeated. Then 3 mL of DCM were added and nitrogen was bubbled through for 5 min. Removed solvent by filtration and repeated the process. 3 mL of DCM were then added, followed by trifluoroacetic acid (5.0 mL, 66.1 mmol) and nitrogen was bubbled through for 1 h. The beads were then filtered and washed 3 times with 10 mL of a 5% solution of MeOH in DCM. The filtrate was concentrated and the residue was purified by reverse phase HPLC to give 15.4 mg of Compound 168 as a white solid. LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=5.27 min, M+H=939.4 $^1$H NMR (400 MHz, DMSO) δ 8.99 (d, J=7.9 Hz, 1H), 8.75-8.63 (m, 1H), 8.10-7.93 (m, 3H), 7.87-7.72 (m, 3H), 7.60-7.50 (m, 2H), 7.26 (s, 1H), 6.96 (s, 1H), 6.78 (d, J=35.2 Hz, 2H), 6.43 (dd, J=8.7, 7.0 Hz, 2H), 6.31-6.19 (m, 1H), 5.23 (s, 1H), 4.85 (s, 2H), 4.58 (d, J=28.7 Hz, 2H), 4.12 (s, 2H), 3.67 (s, 2H), 2.82-2.70 (m, 3H), 2.01 (s, 1H), 1.79 (d, J=17.3 Hz, 3H), 1.65-1.28 (m, 5H), 1.27-1.15 (m, 4H).

Example 68: Synthesis of Compound 169

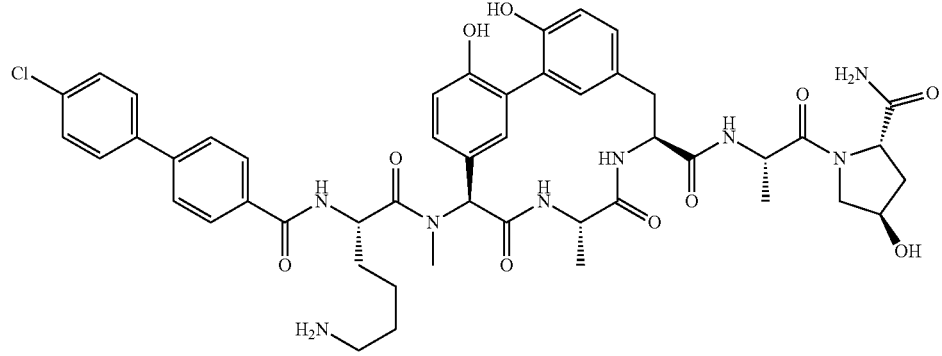

169

Compound 169 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.19 min, M+H=939.4.

Example 69: Synthesis of Compound 170

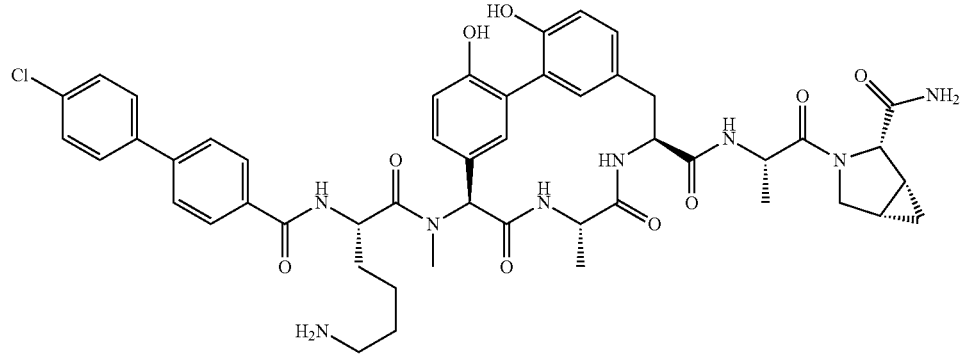

170

Compound 170 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.31 min, M+H=935.5.

Example 70: Synthesis of Compound 171

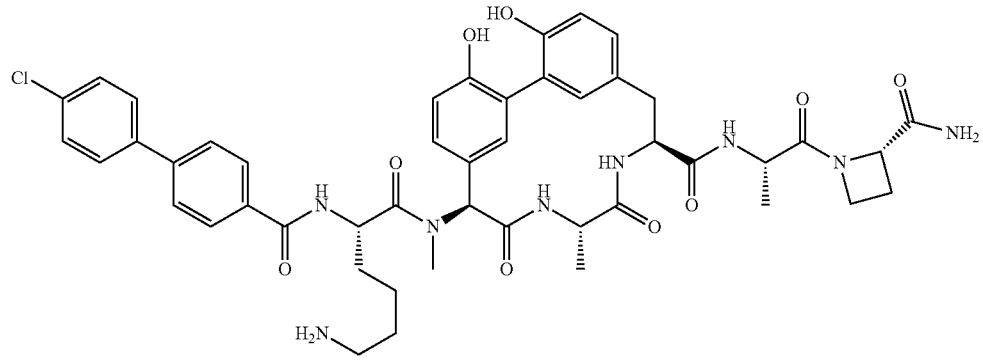

171

Compound 171 was synthesized in a similar manner to Compound 168 (Example 67). MS (ESI) M+H=909.36. $^1$H NMR (400 MHz, DMSO) δ 9.77 (s, 3H), 8.30 (s, 4H), 7.75 (s, 4H), 6.43 (s, 3H), 3.98 (t, J=8.0 Hz, 3H), 3.87 (td, J=7.9, 5.6 Hz, 3H), 3.82-3.68 (m, 6H), 3.53-3.43 (m, 3H), 3.27-3.18 (m, 6H), 2.23-2.00 (m, 10H), 1.92 (s, 4H), 1.02-0.88 (m, 3H).

Example 71: Synthesis of Compound 172

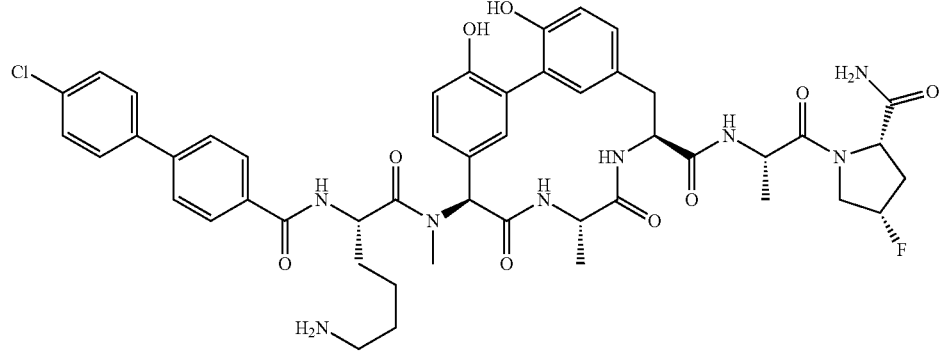

172

Compound 172 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=5.37 min, M+H=941.37. $^1$H NMR (400 MHz, DMSO) δ 9.75 (s, 2H), 8.31 (s, 2H), 8.01 (s, 2H), 7.77 (s, 3H), 6.50 (s, 3H), 4.62 (d, J=13.0 Hz, 2H), 3.98 (t, J=8.0 Hz, 2H), 3.86 (td, J=7.9, 5.5 Hz, 2H), 3.77 (dt, J=8.1, 7.1 Hz, 2H), 3.69 (dd, J=8.1, 7.1 Hz, 2H), 3.26-3.17 (m, 2H), 3.08 (d, J=6.5 Hz, 4H), 2.84 (t, J=12.3 Hz, 4H), 2.22-1.98 (m, 6H), 1.73 (d, J=13.0 Hz, 4H), 1.55 (d, J=10.8 Hz, 2H), 1.35 (q, J=7.1 Hz, 4H), 1.15-0.99 (m, 4H), 0.94 (d, J=6.7 Hz, 3H).

Example 72: Synthesis of Compound 173

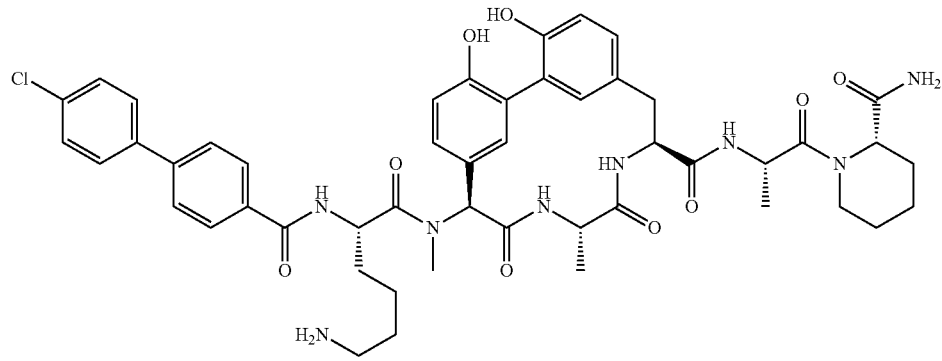

173

Compound 173 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.41 min, M+H=937.4.

Example 73: Synthesis of Compound 174

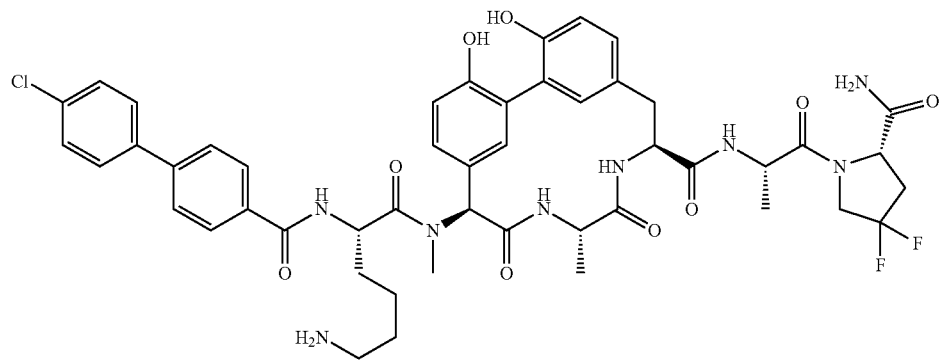

174

Compound 174 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.39 min, M+H=959.4.

Example 74: Synthesis of Compound 175

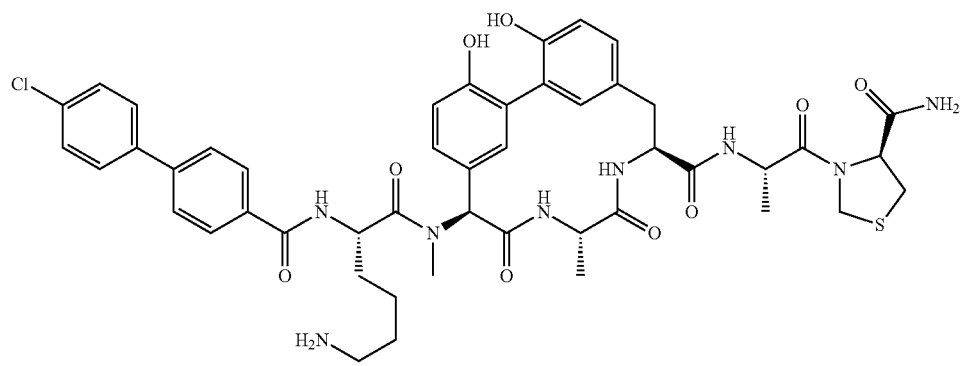

175

Compound 175 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.31 min, M+H=941.4.

Example 75: Synthesis of Compound 176

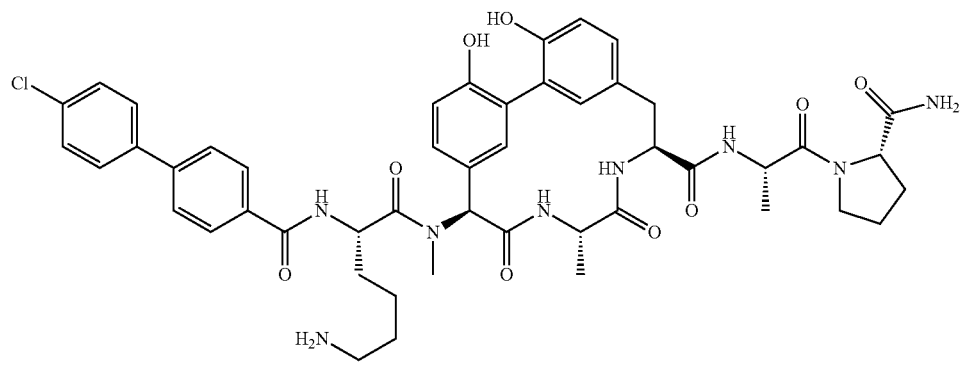

176

Compound 176 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=3.95 min, M+H=909.37. $^1$H NMR (400 MHz, DMSO) δ 9.13 (d, J=7.8 Hz, 1H), 8.66 (d, J=7.9 Hz, 1H), 8.11-7.96 (m, 2H), 7.87-7.70 (m, 4H), 7.64-7.49 (m, 2H), 7.27 (s, 1H), 6.93 (s, 1H), 6.83 (d, J=2.8 Hz, 1H), 6.73 (t, J=8.3 Hz, 2H), 6.56-6.36 (m, 2H), 6.31-6.19 (m, 1H), 4.86 (s, 2H), 4.61 (s, 1H), 4.22 (d, J=8.5 Hz, 1H), 3.93 (d, J=20.4 Hz, 3H), 3.44 (s, 3H), 2.77 (s, 3H), 2.67 (d, J=1.8 Hz, 1H), 2.33 (t, J=1.9 Hz, 1H), 2.09-1.90 (m, 1H), 1.89-1.73 (m, 4H), 1.64-1.33 (m, 4H), 1.28-1.11 (m, 3H).

Example 76: Synthesis of Compound 177

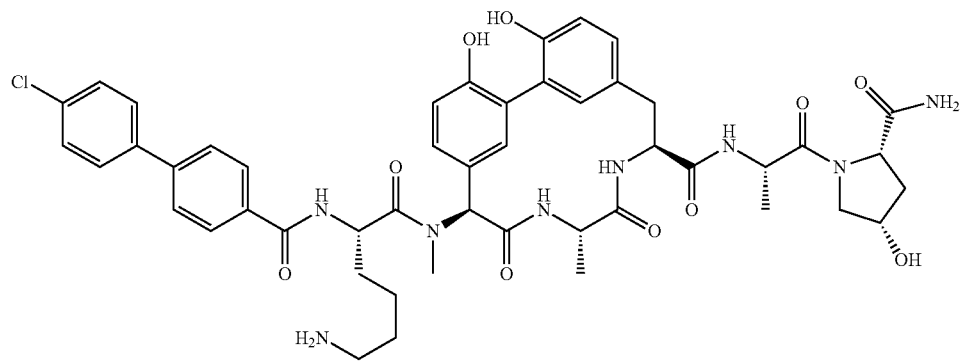

Compound 177 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.17 min, M+H=939.4.

Example 77: Synthesis of Compound 178

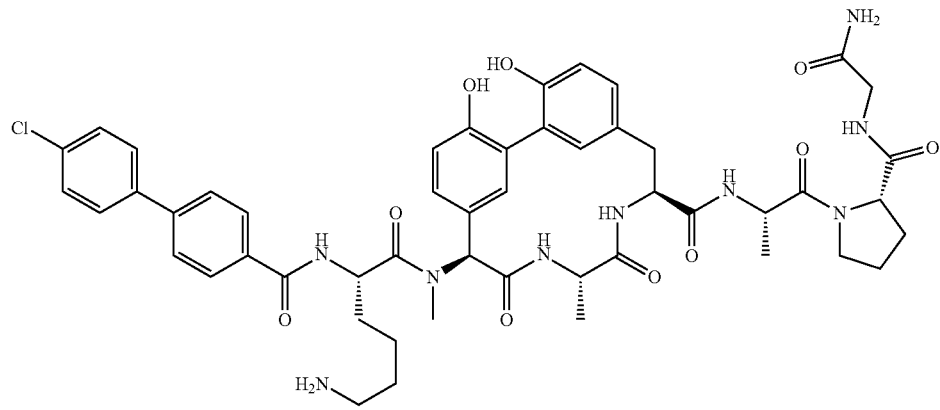

Compound 178 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=3.91 min, M+H=980.1. $^1$H NMR (400 MHz, DMSO) δ 8.95 (d, J=8.0 Hz, 1H), 8.67 (d, J=7.8 Hz, 1H), 8.41 (d, J=9.7 Hz, 1H), 8.18-7.94 (m, 3H), 7.86-7.72 (m, 3H), 7.60-7.47 (m, 2H), 7.07 (d, J=6.5 Hz, 2H), 6.96 (s, 1H), 6.83 (s, 1H), 6.73 (s, 1H), 6.54-6.35 (m, 2H), 4.85 (t, J=7.4 Hz, 2H), 4.72-4.43 (m, 2H), 4.28 (dd, J=8.5, 4.6 Hz, 1H), 2.76 (d, J=5.9 Hz, 3H), 2.07 (s, 1H), 1.90 (s, 3H), 1.56 (s, 4H), 1.25-1.14 (m, 3H).

Example 78: Synthesis of Compound 179

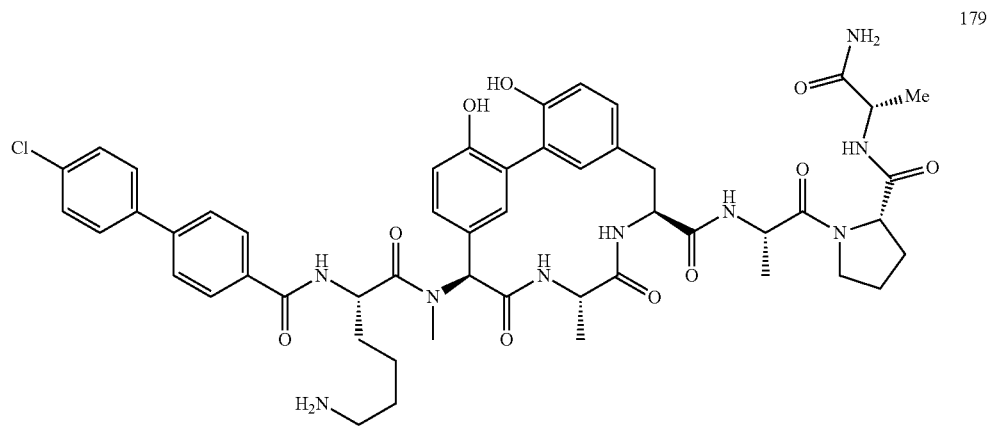 [SMILES: C[C@H](NC(=O)[C@@H]1CCCN1C(=O)[C@H](C)NC(=O)[C@@H]1Cc2ccc(O)c(c2)-c2cc(ccc2O)[C@H](N(C)C(=O)[C@H](CCCCN)NC(=O)c2ccc(-c3ccc(Cl)cc3)cc2)C(=O)N[C@@H](C)C(=O)N1)C(N)=O]

Compound 179 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=3.9. min, M+H=994.42.

Example 79: Synthesis of Compound 180

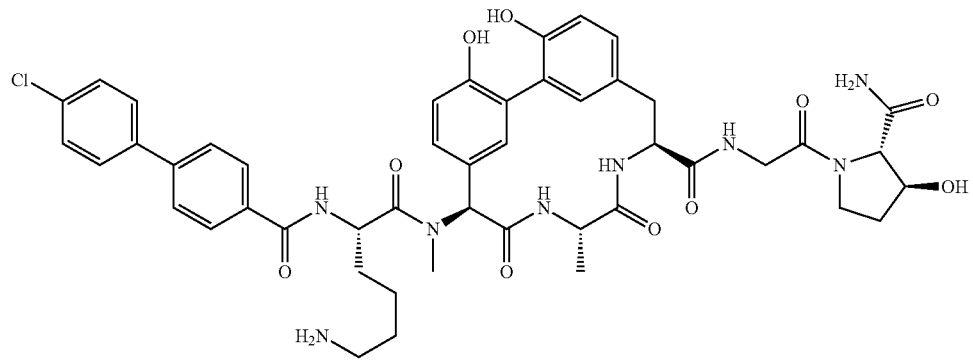

Compound 180 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.08 min, M+H=925.36.

Example 80: Synthesis of Compound 181

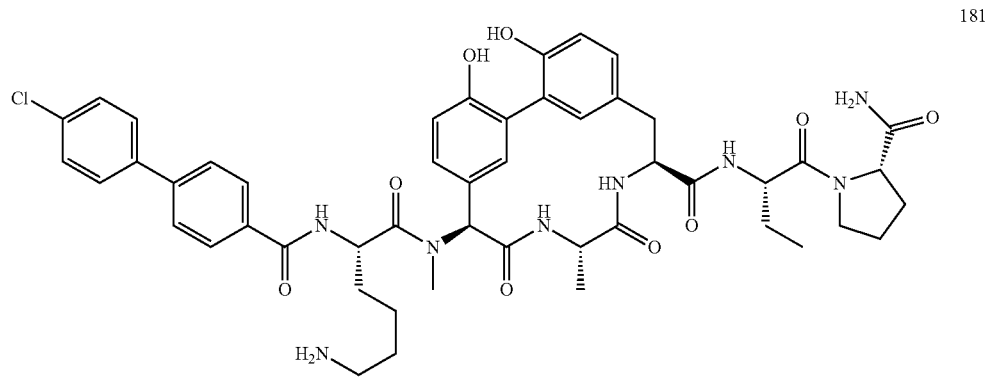 [SMILES: CC[C@H](NC(=O)[C@@H]1Cc2ccc(O)c(c2)-c2cc(ccc2O)[C@H](N(C)C(=O)[C@H](CCCCN)NC(=O)c2ccc(-c3ccc(Cl)cc3)cc2)C(=O)N[C@@H](C)C(=O)N1)C(=O)N1CCC[C@H]1C(N)=O]

Compound 181 was synthesized in a similar manner to Compound 168 (Example 67). LCMS (3% AcCN/H2O, 0.3 min; 3% AcCN-95% AcCN/H2O with 0.05% TFA, 6.5 min, 0.4 mL/min, Agilent SB C18, 2.1×30 mm, ESI): RT=4.40 min, M+H=938.42.

Example 81: Synthesis of Compound 182

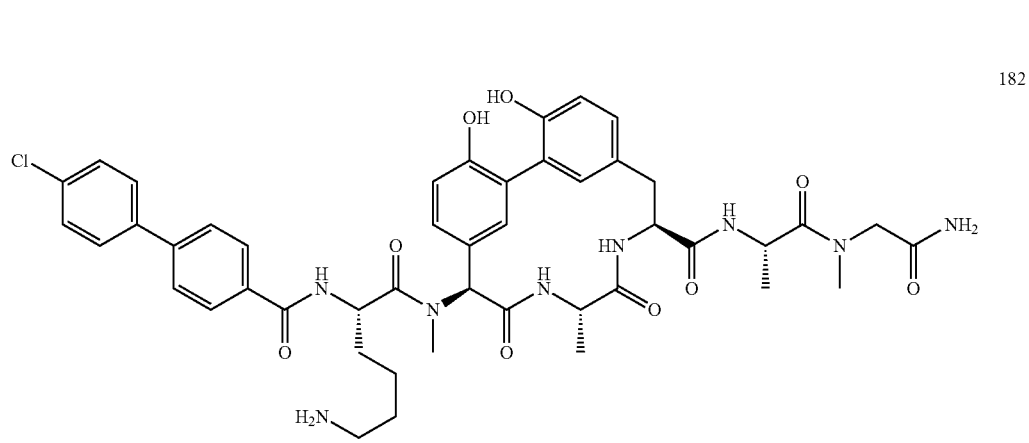 [SMILES: C[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)N[C@@H](C)C(=O)N(C)CC(N)=O)NC1=O]

182

Compound 182 was synthesized in a similar manner to Compound 168 (Example 67). LCMS (Method Waters, ESI): RT=4.26. min, M+H=897.4. $^1$H NMR (400 MHz, DMSO) δ 8.66 (d, J=7.7 Hz, 1H), 8.42 (s, 1H), 8.16-7.89 (m, 2H), 7.87-7.68 (m, 3H), 7.62-7.37 (m, 2H), 7.20 (s, 1H), 6.99 (d, J=30.5 Hz, 2H), 6.89-6.66 (m, 1H), 6.60-6.35 (m, 2H), 6.32-6.15 (m, 1H), 4.85 (s, 4H), 4.03-3.69 (m, 2H), 3.13-2.92 (m, 3H), 2.88-2.59 (m, 5H), 1.78 (s, 2H), 1.56 (s, 4H), 1.27-1.00 (m, 4H).

Example 82: Synthesis of Compound 183

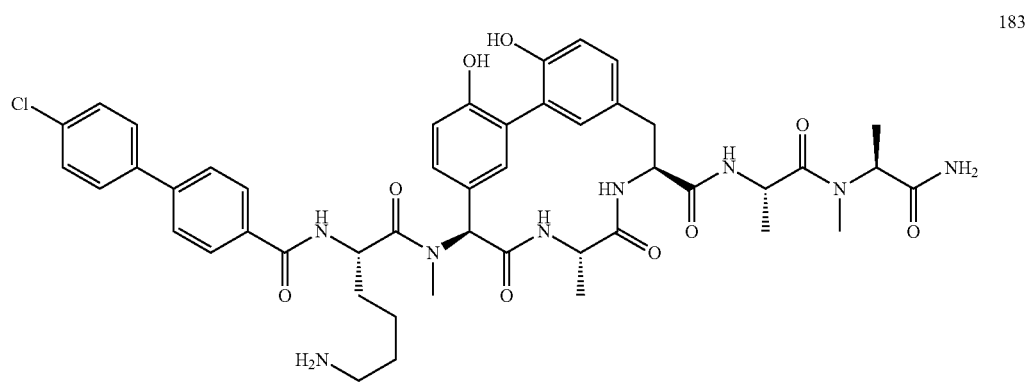 [SMILES: C[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)N[C@@H](C)C(=O)N(C)[C@@H](C)C(N)=O)NC1=O]

183

Compound 183 was synthesized in a similar manner to Compound 168 (Example 67). LCMS (Method Waters, ESI): RT=4.30. min, M+H=911.4. $^1$H NMR (400 MHz, DMSO) δ 8.65 (d, J=7.7 Hz, 1H), 8.37 (s, 1H), 8.14-7.94 (m, 3H), 7.85-7.73 (m, 4H), 7.61-7.51 (m, 2H), 7.17 (s, 1H), 6.97 (s, 2H), 6.83 (s, 1H), 6.79-6.67 (m, 2H), 6.52-6.34 (m, 2H), 6.30-6.20 (m, 1H), 4.95-4.60 (m, 5H), 3.00-2.83 (m, 4H), 2.81-2.63 (m, 5H), 1.78 (d, J=6.9 Hz, 2H), 1.50 (d, J=38.0 Hz, 5H), 1.35-1.05 (m, 9H).

Example 83: Synthesis of Compound 184

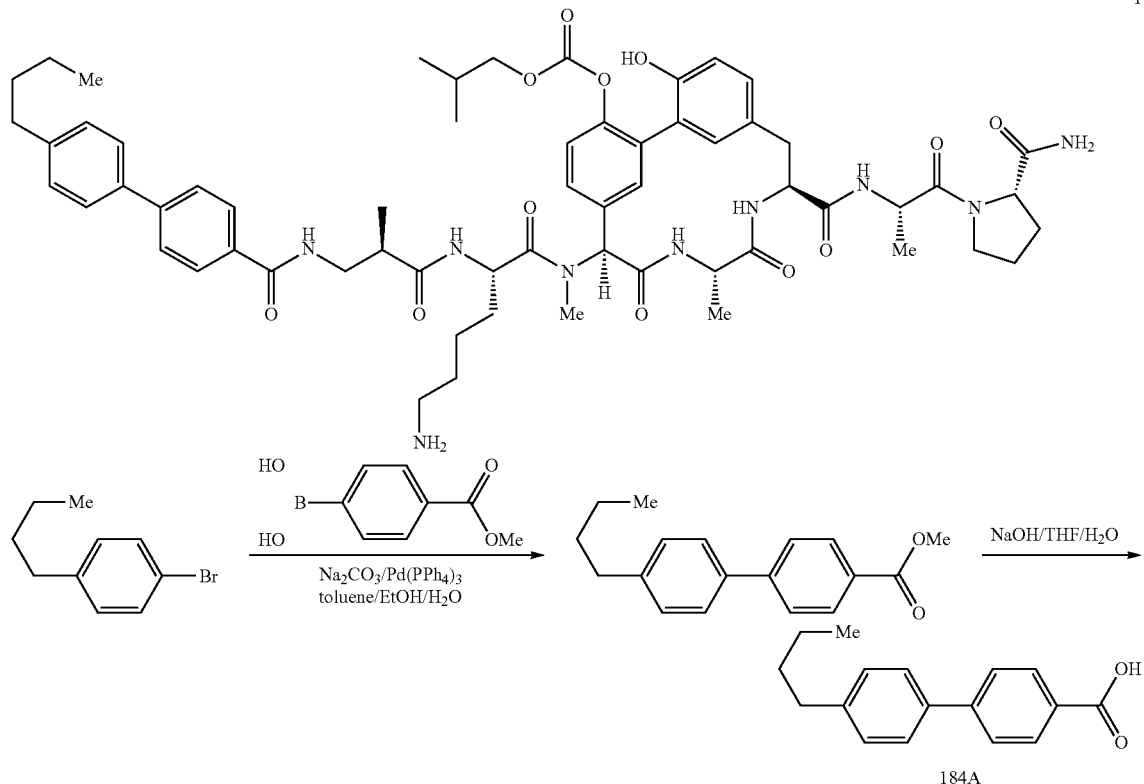

A solution of 1-bromo-4-n-butylbenzene (100 g, 0.472 mol), 4-(methoxycarbonyl)benzeneboronic acid (82.0 g, 0.456 mol), 2 M $Na_2CO_3$ (150 g, 1.42 mol) in toluene/EtOH (900 mL/300 mL) was degassed with $N_2$ three times, then $Pd(PPh_3)_4$ (27.2 g, 23.6 mmol) was added. The resulting mixture was degassed with $N_2$ three times and then heated to reflux for 5 h. After TLC showed the reaction was complete, toluene and EtOH was removed under vacuum. The residue was extracted with EA (3×). The combined organic layers were washed with brine and dried with $Na_2SO_4$. The solvent was removed to give the crude product. The crude product was purified by column chromatography on silica gel eluted with PE: EA (150:1). The solvent was removed to give methyl 4'-butyl-[1,1'-biphenyl]-4-carboxylate (105 g, 86.0%) as a white solid.

A mixture of methyl 4'-butyl-[1,1'-biphenyl]-4-carboxylate (89.0 g, 0.332 mol), NaOH (26.6 g, 0.664 mol) in $THF/H_2O$ (500 mL/100 mL) was heated to reflux overnight. After TLC showed the reaction was complete, THF was removed. The residue was adjusted pH=3-4 with 2N HCl solution. The resulting mixture was filtered and the cake was washed with water, and dried to give Compound 184A (60.0 g, 71.1%) as a white solid.

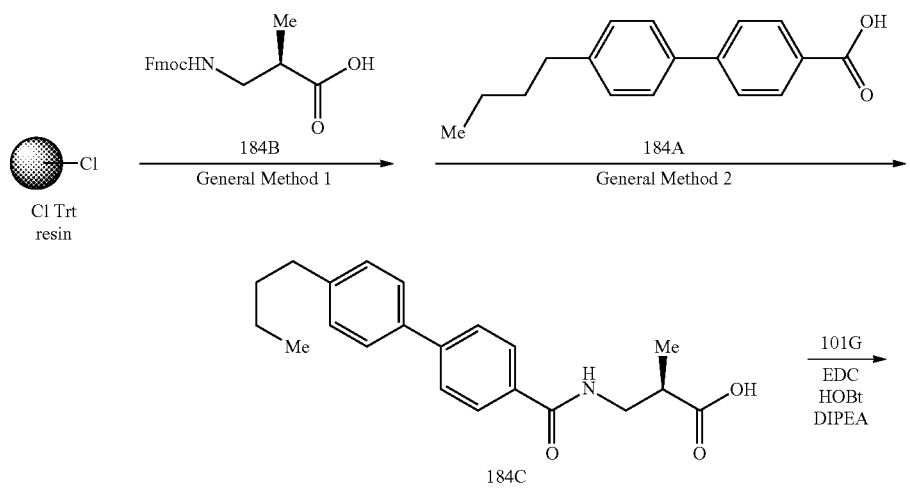

-continued
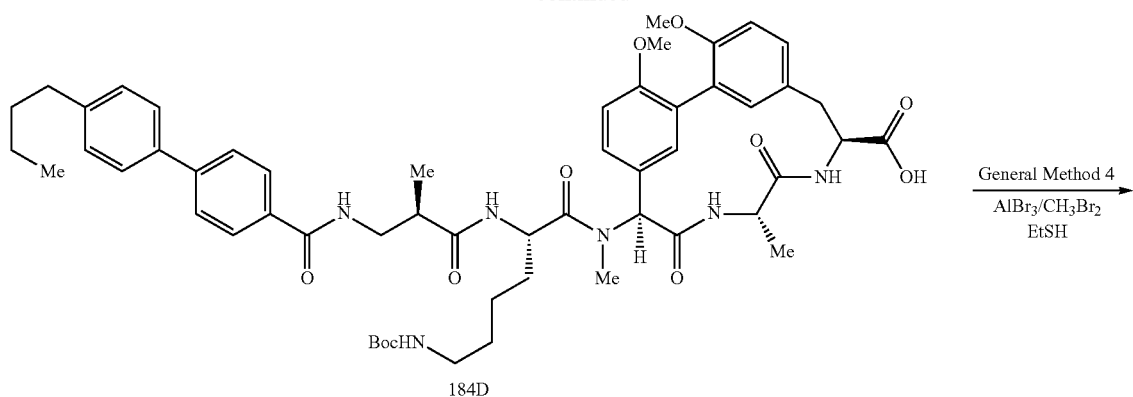
184D
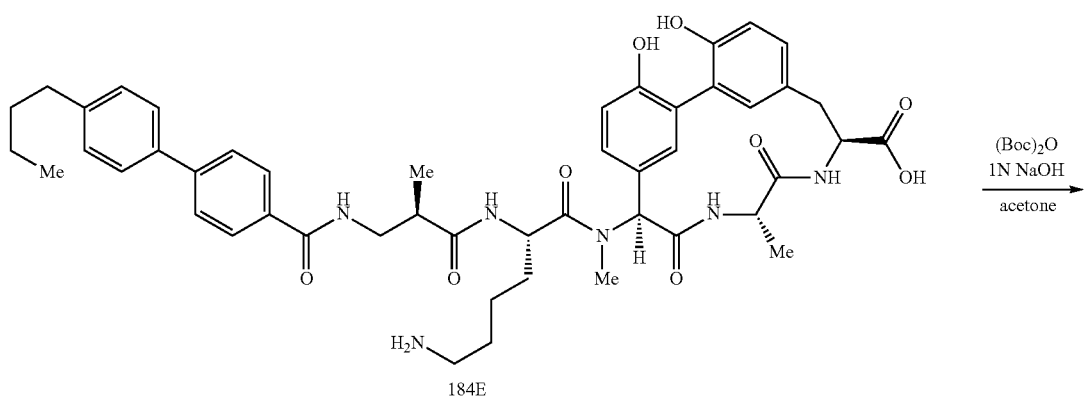
184E
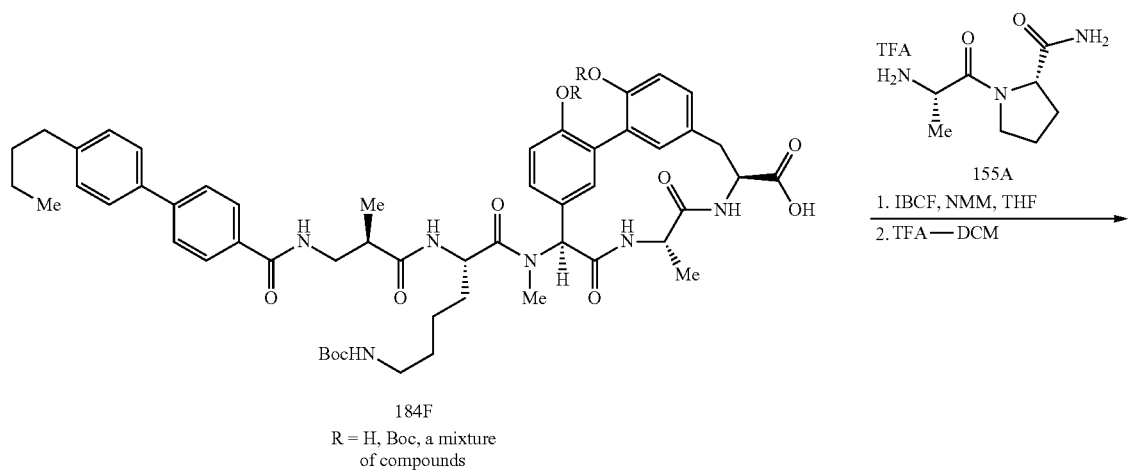
184F
R = H, Boc, a mixture of compounds -continued

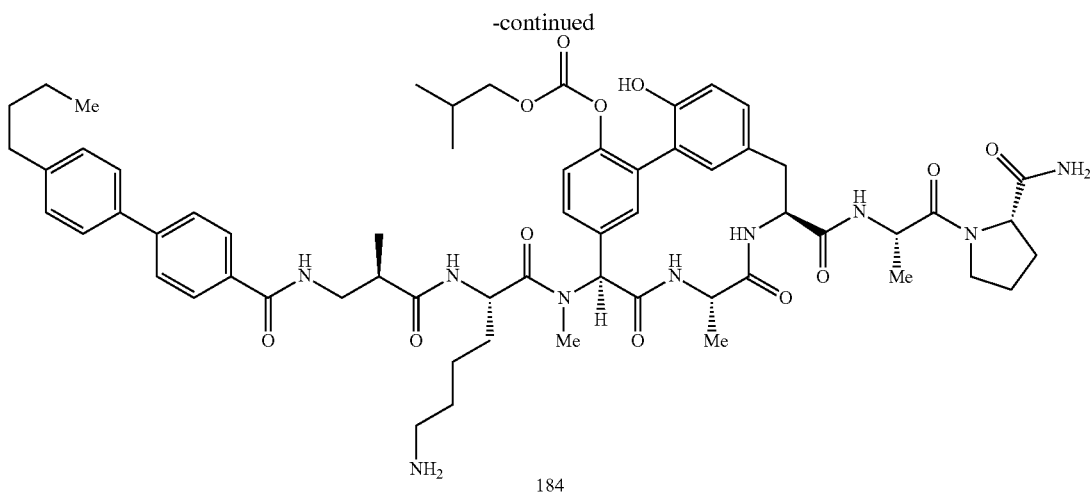

184

+

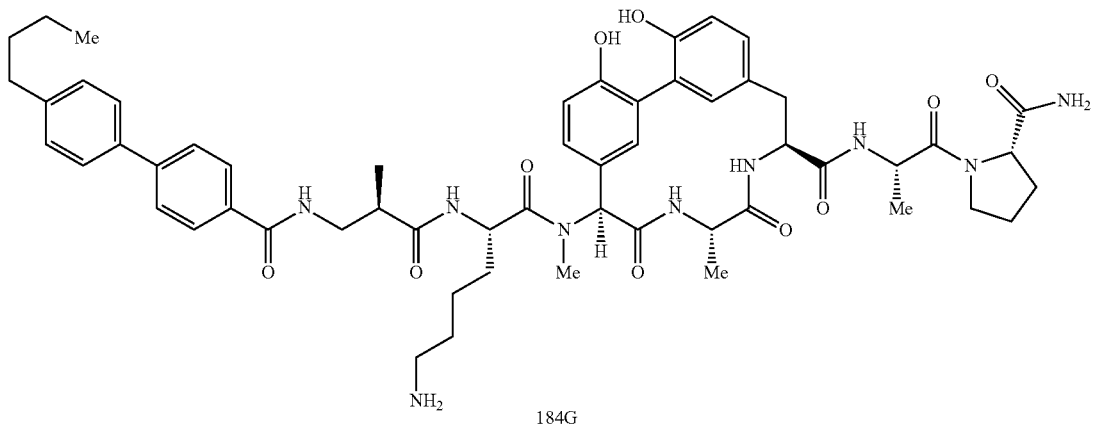

184G

Compound 184C was prepared according to General Methods 1 and 2 from Compound 184A and Compound 184B.

A solution of Compound 184C (508.5 mg, 1.5 mmol) in anhydrous DMF (3 mL) was treated with EDCI (380 mg, 0.2 mmol) and HOBt (270 mg, 2 mmol) followed by DIPEA (260 mg, 2 mmol) and Compound 101G (683 mg, 1 mmol). The resulting solution was stirred at 20° C. overnight and diluted with water. The precipitate was filtered and the resulting cake was washed with water and dried to give Compound 184D (900 mg, 90%).

Compound 184E was prepared according to General Method 4 from Compound 184D (450 mg, 58%). MS (ESI) m/z 863.6 (M+H)$^+$.

To a solution of Compound 184E (65 mg, 0.075 mmol) in acetone-H$_2$O (1:1, 1 mL) was added 1M NaOH (0.36 mL, 0.36 mmol) and (Boc)$_2$O (86 μL, 0.36 mmol). The reaction mixture was stirred at room temperature overnight. The acetone was removed and the mixture acidified with 1M HCl. The resultant white solid was filtered and dried to afford Compound 184F (74 mg, 92%) as a mixture of bis-Boc protected [mixture with either one of the phenols protected predominantly on the (4-hydroxyphenyl)glycine] along with a small amount of mono-Boc protected. MS (ESI) for bis-Boc (C$_{58}$H$_{74}$N$_6$O$_{13}$): m/z 1063 (M+H)$^+$; mono-Boc for (C$_{53}$H$_{66}$N$_6$O$_{11}$): m/z 963 (M+H)$^+$.

Compound 184 and Compound 184G were prepared from Compound 184F (21 mg, 0.02 mmol) in anhydrous THF (1 mL), isobutyl chloroformate (4.0 μL, 0.03 mmol), N-methyl morpholine (11 μL, 0.1 mmol) and Compound 155A (12 mg, 0.04 mmol) following the procedure described for Compound 158 (Example 58) and subsequent TFA hydrolysis. Data for Compound 184: MS (ESI) for (C$_{61}$H$_{79}$N$_9$O$_{12}$): m/z 1130.3 (M+H)$^+$.

Example 84: Synthesis of Compound 185

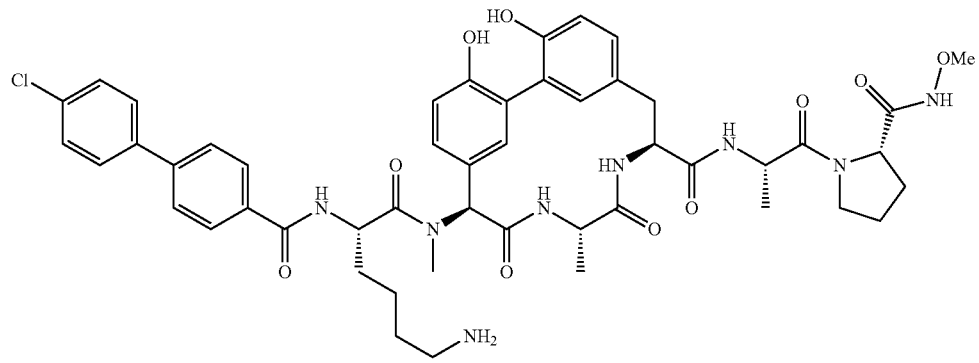

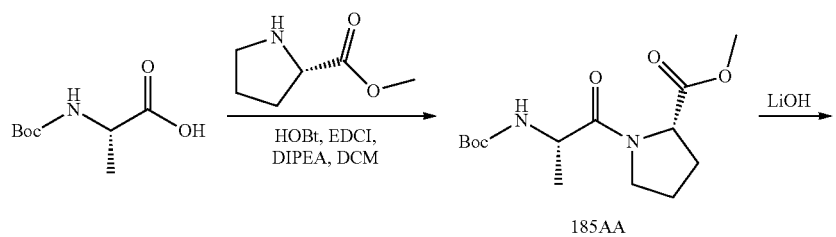

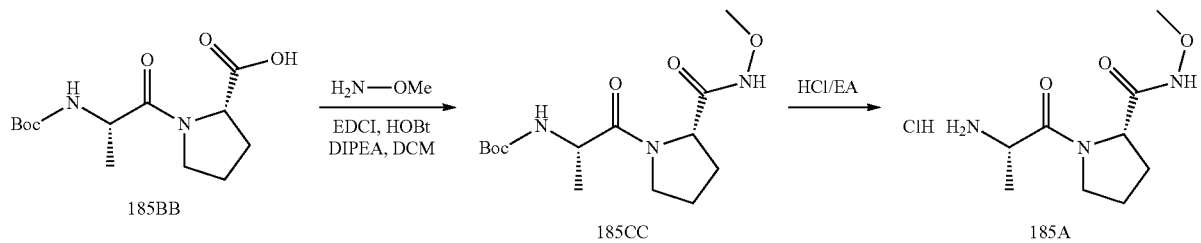

To a solution of (S)-2-((tert-butoxycarbonyl)amino)propanoic acid (10 g, 52.8 mmol) in DCM (50 mL) at 0° C., DIEA (14.3 g, 106 mmol), HOBT (20.5 g, 106 mmol) and EDCI (20.3 g, 106 mmol) was added, and the mixture was stirred at 0° C. for 20 mins. (S)-methyl pyrrolidine-2-carboxylate (10.5 g, 63.4 mmol) was then added and the reaction mixture was stirred at 20° C. for another 16 h. Water (50 mL) was added to the resulting mixture and the aqueous layer was further extracted by DCM (50 mL*2). The combined DCM layers were purified by silica gel column (PE/EA=30/1-20/1) to give Compound 185AA (12.0 g, 75.6%) as a yellow oil.

To a solution of Compound 185AA (3.5 g, 11.6 mmol) in EtOH (20 mL) at 0° C. was added 1N LiOH (15 ml). The solution was kept at the same temperature for 30 mins. After the reaction was complete, volatiles were removed under reduced pressure and the residue was re-dissolved with water (30 mL), whose pH was adjusted to pH=2-3 by HCl, followed by the extraction of DCM (30 mL*3). The combined DCM layers were dried over $Na_2SO_4$ and evaporated to give Compound 185BB (3.3 g, 92%) as a white solid.

To a solution of Compound 185BB (500 mg, 1.75 mmol) in DCM (50 mL) 0° C. was added DIPEA (677 mg, 5.24 mmol), HOBt (471 mg, 3.49 mmol) and EDCI (669 mg, 3.49 mmol). The reaction mixture was stirred at the same temperature for 20 mins, followed by the addition of O-methylhydroxylamine (291 mg, 3.49 mmol). The reaction mixture was stirred at 20° C. for 16 h. Water (30 mL) was added to the resulting mixture and the aqueous layer was further extracted by DCM (30 mL*2). The combined DCM layers were purified HPLC (0.1% HCl) to give Compound 185CC (140 mg, 25.5%) as white solid (LCMS purity: 98%).

To a solution of Compound 185CC (120 mg, 0.38 mmol) in EtOAc (1 mL) at 0° C. was added 4N HCl/EtOAc (3 ml). The solution was kept at the same temperature for 30 mins. After the reaction was complete, volatiles were removed to afford Compound 185A (80 mg, 99%) as a white solid.

Compound 185 was prepared according to General Methods 8 and 9 from Compound 104E and Compound 185A. $^1H$ NMR (400 MHz, MeOH-$d_4$) δ 8.51 (s, 1H), 7.79-7.77 (m, 2H), 7.62-7.60 (m, 2H), 7.51-7.50 (m, 2H), 7.43-7.41 (m, 2H), 7.05 (s, 1H), 6.93-6.89 (m, 2H), 6.80-6.78 (m, 3H), 4.99-4.97 (m, 2H), 4.66-4.64 (m, 1H), 4.25 (m, H), 3.76 (s, 1H), 3.70-3.65 (m, 4H), 3.05-3.02 (m, 2H), 2.98-2.93 (m, 5H), 2.20-2.10 (m, 3H), 1.96 (m, 4H), 1.37-1.69 (m, 5H), 1.34 (s, 6H). LCMS (5-95 AB, ESI): RT=0.779, $M+H^+$=953.4.

Example 85: Synthesis of Compound 186

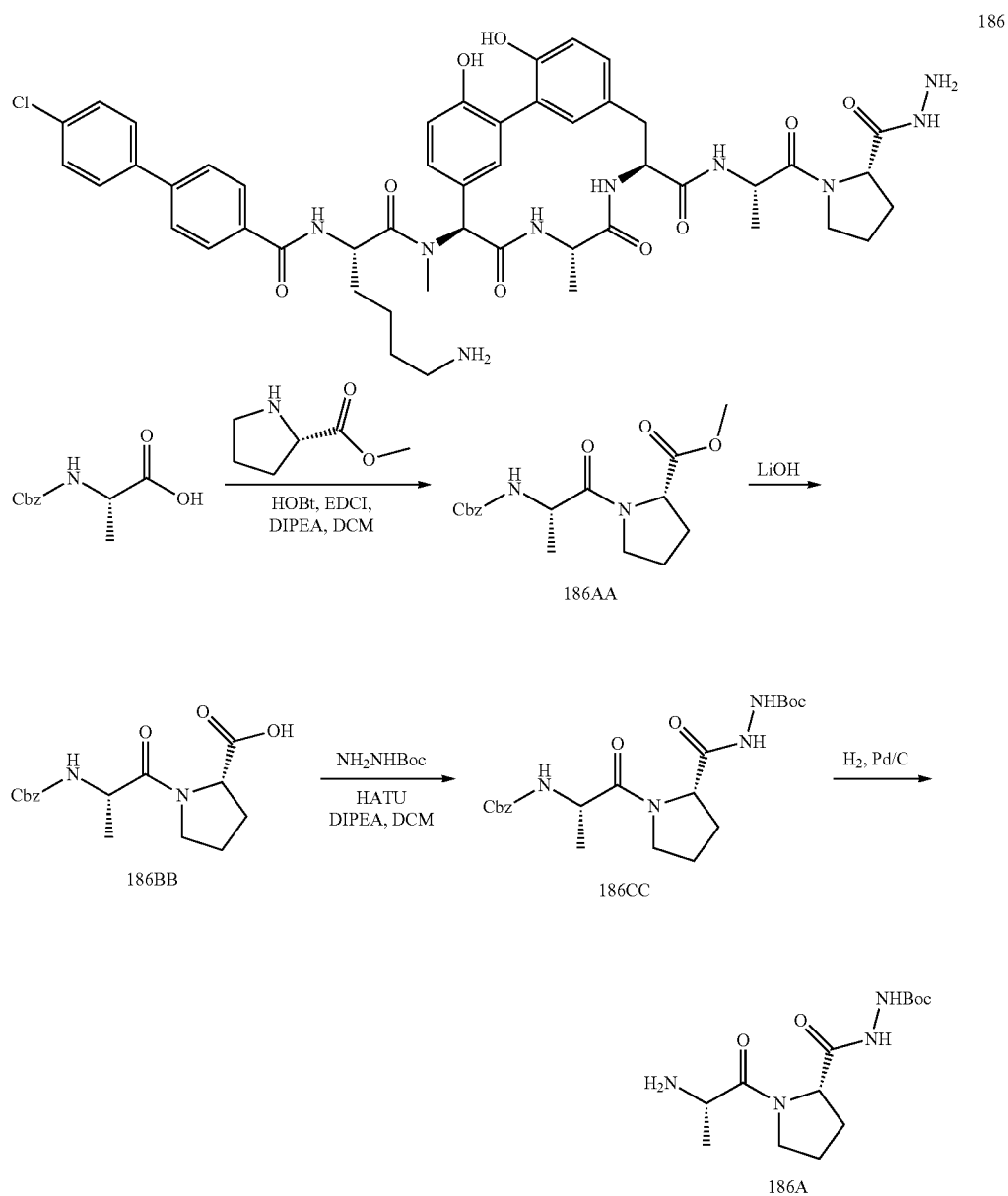

Compound 186BB was prepared in a manner similar to that of Compound 185BB except CBz-L-Ala-OH was used as the starting material.

To a solution of Compound 186BB (0.64 g, 2 mmol) and H$_2$NH$_2$Boc (264 mg, 2 mmol) in DCM (20 mL) at 0° C. were added HATU (1.52 g, 4 mmol) and DIEA (0.52 g, 4 mmol). The mixture was stirred for 6 h under room temperature. Water (20 mL) was added to the resulting mixture and the aqueous layer was further extracted by DCM (20 mL*2). The combined organic layers were dried and concentrated to afford Compound 186CC (0.3 g, 34.6%) as a yellow oil which was used directly in the next step without any further purification.

To a solution of Compound 186CC (0.3 g, 0.7 mmol) in MeOH (10 mL) was added 10% Pd/C (0.1 g). The mixture was stirred for 6 h under room temperature. After filtration, volatiles were removed to give the residue, which was purified by HPLC (0.1% FA) to give Compound 186A (100 mg, 47.6%) as a white solid (LCMS purity: 98%).

Compound 186 was prepared according to General Methods 8 and 9 from Compound 104E and Compound 186A. $^1$H NMR (400 MHz, MeOH-d$_4$+D$_2$O) δ 8.48 (s, 1H), 7.89-7.87 (m, 1H), 7.74-7.63 (m, 4H), 7.49-7.48 (m, 2H), 7.07-7.05 (m, 2H), 6.98-6.85 (m, 4H), 4.88-4.86 (m, 5H), 4.40-4.35 (m, 1H), 3.82-3.67 (m, 2H), 3.18-3.01 (m, 2H), 2.98-2.93 (m, 5H), 2.20-2.01 (m, 2H), 2.01-1.97 (m, 5H), 1.73-1.72 (m, 2H), 1.72-1.58 (m, 2H), 1.38-1.27 (m, 9H); LCMS (5-95 AB, ESI): RT=0.773, M+H$^+$=938.5.

Example 86: Synthesis of Compound 187

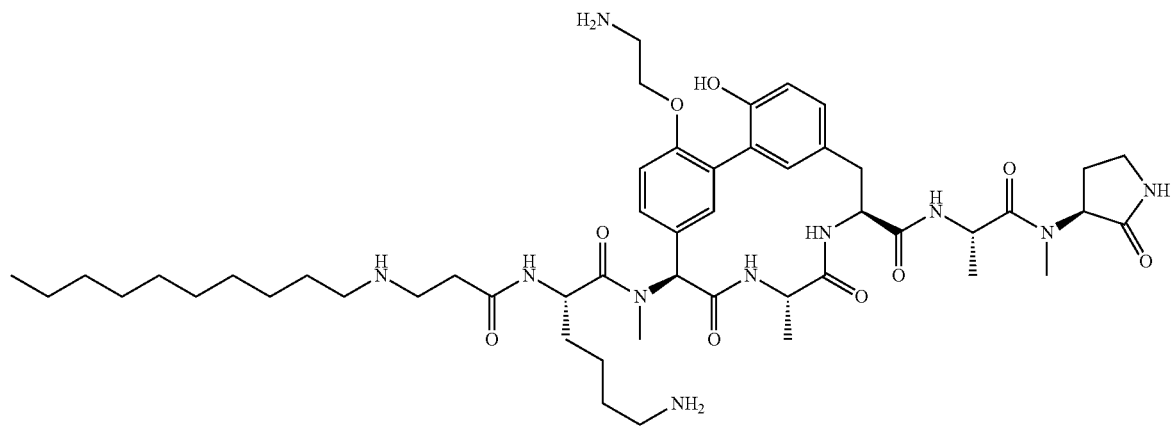

187

Compound 187 was synthesized using similar procedures as described above from Compound 113C and Compound 136A and was isolated as the formic acid salt. LCMS (5-95 AB, ESI): $t_R$=0.714, (M+H)$^+$=963.8.

Example 87: Synthesis of Compound 188

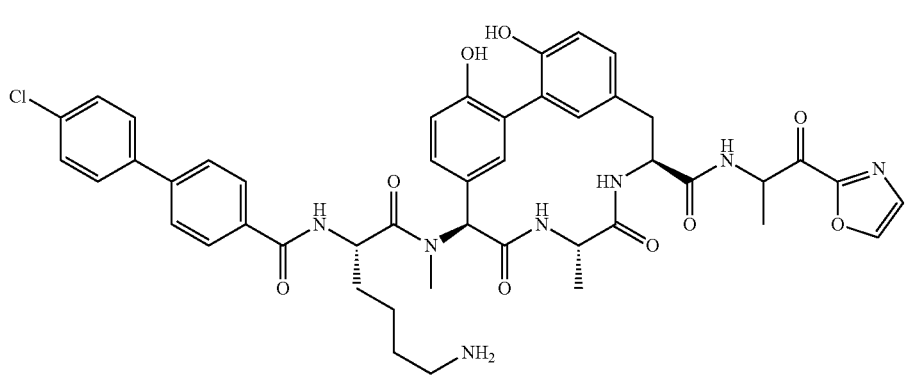

188

Compound 188 was synthesized using similar procedures as described above from Compound 104E and (S)-2-amino-1-(oxazol-2-yl)propan-1-one and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.794 min, (M+H)$^+$=878.4.

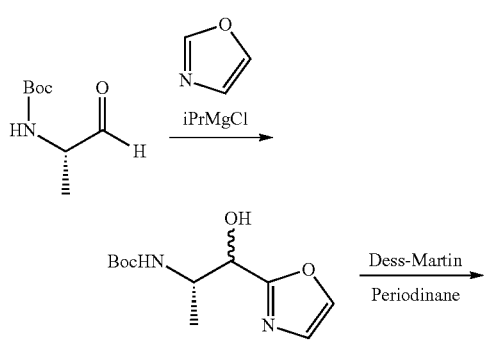

-continued

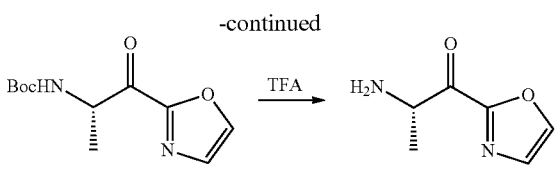

Synthesis of (S)-2-amino-1-(oxazol-2-yl)propan-1-one: To a solution of oxazole (329 mg, 4.76 mmol) in toluene (5 mL), isopropyl magnesium chloride (2M in THF solution, 2.38 mL, 4.76 mmol) was added at 0° C. and stirred for 1 h. The resulting mixture was added to a solution of (S)-tert-butyl (1-oxopropan-2-yl) carbamate (750 mg, 4.33 mmol) in THF (10 mL) at 0° C. and stirred for 1 hour then at room temperature for 3 hours. The reaction mixture was quenched with 5% sodium carbonate (10 mL), extracted by ethyl acetate (30 mL×3). The combined organic layer was washed with brine (10 mL×3), dried over Na$_2$SO$_4$ and then the mixture was filtered. The filtrate was concentrated under reduced pressure to afford the crude product, which was purified by silica gel column (eluting with 5% methanol in dichloromethane) to afford (S)-tert-butyl 1-hydroxy-1-(oxazol-2-yl)propan-2-ylcarbamate (672 mg, 64%) as a yellow oil. $^1$H NMR (400 MHz, CDCl$_3$) δ 1.10 (1.5H, d, J=6.8 Hz), 1.12 (1.5H, d, J=6.8 Hz), 1.41 (6H, s), 1.45 (6H, s), 4.75 (0.5H, d, J=3.2 Hz), 4.87 (1H, br), 5.01 (0.5H, d, J=3.2 Hz), 7.90 (1H, d, J=12.4 Hz), 7.67 (s, 1H).

To a solution (S)-tert-butyl 1-hydroxy-1-(oxazol-2-yl)propan-2-ylcarbamate (672 mg, 2.77 mmol) in anhydrous dichloromethane (5 mL), Dess-Martin reagent (2.35 g, 5.55 mmol) was added at 0° C. The reaction was stirred at 0° C. for 1 hour and then room temperature overnight. The reaction mixture was diluted with ethyl acetate (100 mL), washed with NaOH (1M, 10 mL×3), brine (20 mL×3) and dried over Na$_2$SO$_4$. Crude product was obtained after filtration and concentration, which was further purified by silica gel chromatography (eluting with 5% methanol in dichloromethane) to afford (S)-tert-butyl 1-(oxazol-2-yl)-1-oxopropan-2-ylcarbamate (555.7 mg, 83.4%) as a white solid. $^1$H NMR (400 MHz, CDCl$_3$) δ:1.44 (s, 9H), 1.52 (3H, d, J=6.8 Hz), 4.12 (1H, q, J=6.8 Hz), 7.38 (s, 1H), 7.86 (s, 1H).

To a solution of (S)-tert-butyl 1-(oxazol-2-yl)-1-oxopropan-2-ylcarbamate (212 mg, 0.88 mmol) in dichloromethane (6 mL), was added TFA (2 mL). The reaction mixture was stirred at room temperature for 3 hours and concentrated under reduced pressure to afford the crude product (S)-2-amino-1-(oxazol-2-yl)propan-1-one, which was used in next step without further purification.

Example 88: Synthesis of Compound 189

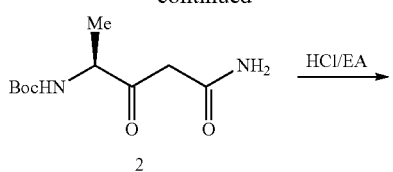

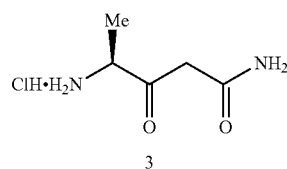

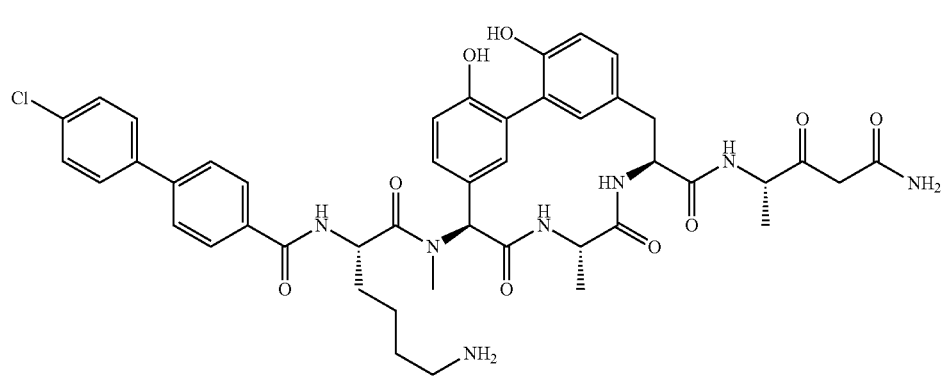

Compound 189 was synthesized using similar procedures as described above from Compound 104E and (S)-4-amino-3-oxopentanamide hydrochloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.787 min, (M+H)$^+$=868.3.

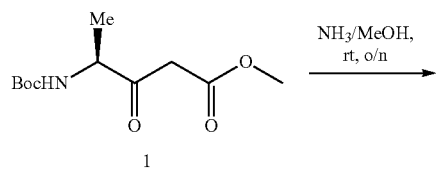

Synthesis of (S)-4-amino-3-oxopentanamide hydrochloride: To a solution of(S)-methyl 4-((tert-butoxycarbonyl)amino)-3-oxopentanoate (1.0 g, 4.1 mmol) in MeOH (30 mL) was saturated with ammonia in sealed tube at 0° C. and the mixture was stirred at room temperature for 12 h. The volatiles were removed to afford (S)-tert-butyl (5-amino-3,5-dioxopentan-2-yl)carbamate (0.45 g, 48% yield) as a white solid.

(S)-tert-butyl (5-amino-3,5-dioxopentan-2-yl)carbamate (100 mg, 0.43 mmol) was treated with HCl in EtOAc at rt and evaporated under reduced pressure to afford (S)-4-amino-3-oxopentanamide hydrochloride (73 mg, quantitative yield) as a yellow solid.

Example 89: Synthesis of Compound 190

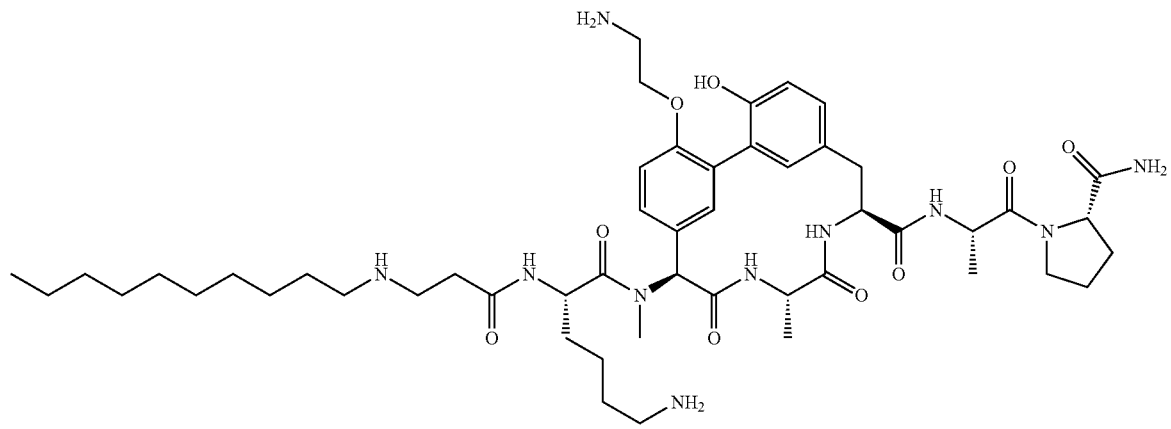

190

Compound 190 was synthesized using similar procedures as described above from Compound 113C and Compound 155A and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.714 min, (M+H)$^+$=963.8.

Example 90: Synthesis of Compound 191

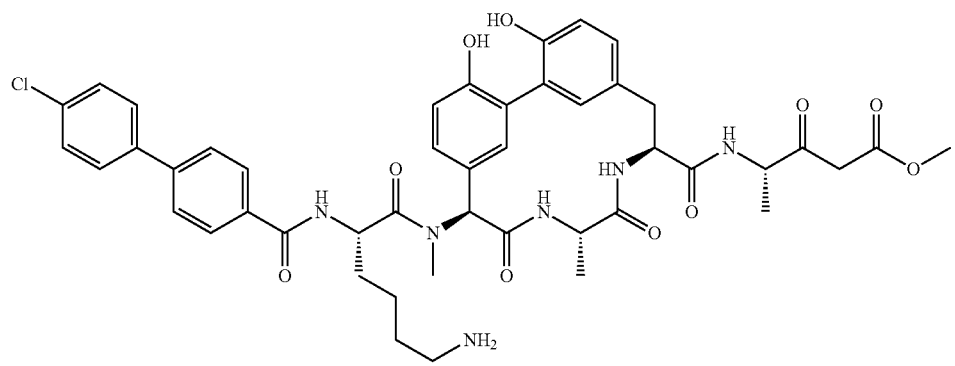

191

Compound 191 was synthesized using similar procedures as described above from Compound 104E and (S)-methyl 4-amino-3-oxopentanoate hydrochloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.798 min, (M+H)$^+$=883.6.

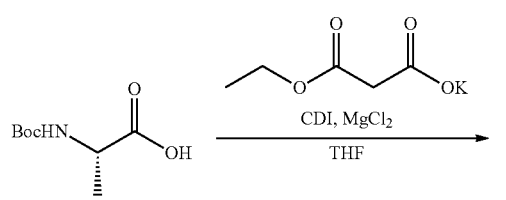

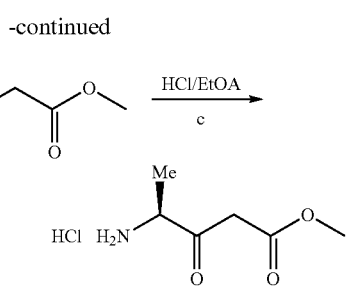

Synthesis of (S)-methyl 4-amino-3-oxopentanoate hydrochloride: 1,1'-Carbonyldiimidazole (5.7 g, 34.9 mmol) was added to a solution of (S)-2-((tert-butoxycarbonyl)amino)propanoic acid (6.0 g, 31.7 mmol) in THF (50 ml) and the mixture was stirred at 25° C. for 2 h. To the above mixture was added MgCl₂ (3.0 g, 31.7 mmol) and potassium 3-ethoxy-3-oxopropanoate (5.7 g, 33.7 mmol) and the resulting mixture was heated and stirred at 60° C. for 3 h. The volatiles were removed to dryness, which was re-dissolved in EtOAc (100 mL), followed by the wash with 1M HCl solution, saturated NaHCO₃ solution and brine (each 50 mL). The organic layer was dried over Na₂SO₄ and concentrated to afford (S)-methyl 4-((tert-butoxycarbonyl)amino)-3-oxopentanoate (5.6 g, 68.1% yield) as a white solid. ¹H NMR (DMSO-d₆, 400 MHz) δ 7.33 (d, J=7.2 Hz, 1H), 3.98-4.05 (m, 1H), 3.58-3.59 (m, 5H), 1.37 (s, 9H), 1.13-1.14 (m, 3H).

(S)-Methyl 4-((tert-butoxycarbonyl)amino)-3-oxopentanoate (455 mg, 1.9 mmol) was treated with HCl in EtOAc at rt and evaporated under reduced pressure to afford (S)-methyl 4-amino-3-oxopentanoate hydrochloride (337 mg, quantitative yield) as a yellow solid.

Example 91: Synthesis of Compound 192

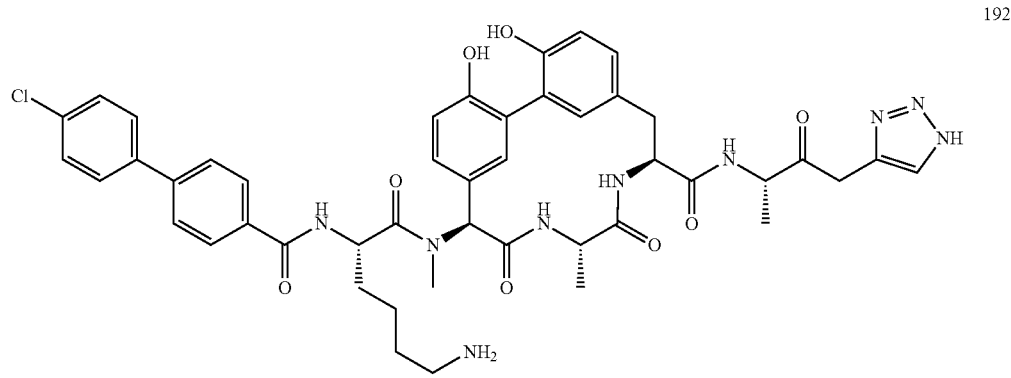 [SMILES: C[C@H](NC(=O)[C@@H]1Cc2ccc(O)c(c2)-c2cc(ccc2O)[C@H](N(C)C(=O)[C@H](CCCCN)NC(=O)c2ccc(-c3ccc(Cl)cc3)cc2)C(=O)N[C@@H](C)C(=O)N1)C(=O)Cc1c[nH]nn1]

192

Compound 192 was synthesized using similar procedures as described above from Compound 104E and (S)-3-amino-1-(1H-1,2,3-triazol-4-yl)butan-2-one and was isolated as the formic acid salt. LCMS (ESI): (5% AcCN/H₂O, 0.7 min; then 95% AcCN/H₂O, 0.4 min; 1.5 mL/min, Merck RP-18e, 2×25 mm) t_R=0.794 min, (M+H)⁺=892.6.

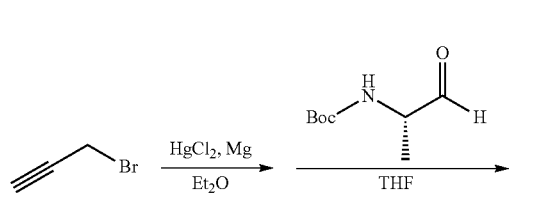

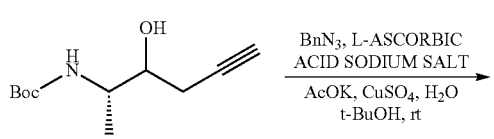

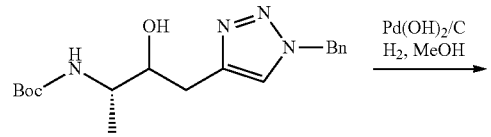

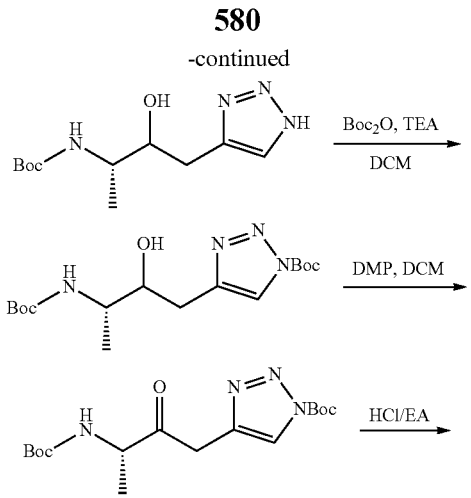

-continued

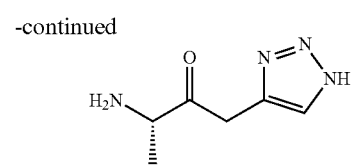

Synthesis of (S)-3-amino-1-(1H-1,2,3-triazol-4-yl)butan-2-one: Under N₂ atmosphere, magnesium turnings (2.4 g, 101 mmol) and mercury chloride (1.14 g, 4.2 mmol) were mixed in dry THF (200 mL) in a 250 mL round-bottom flask. To the above solution was added 3-bromoprop-1-yne (10.0 g, 84.1 mmol) dropwise at 60° C. over 1 h. The resulting mixture was kept at the same temperature until the yellow solution turned cloudy. The resultant solution was added dropwise to a solution of (S)-tert-butyl (1-oxopropan-2-yl)carbamate (5.0 g, 28.9 mmol) in THF (200 mL) under N₂ at −78° C. The mixture was warmed and stirred at room temperature for 16 h. The reaction was quenched with saturated NH₄Cl solution (200 mL), which was extracted with EtOAc (3×100 mL). The combined organic layers were dried over Na₂SO₄, and concentrated. The residue was by silica gel chromatography to afford tert-butyl ((2S)-3-hydroxyhex-5-yn-2-yl)carbamate (3.1 g, 50.3% yield) as colorless oil. ¹H NMR (400 MHz, CDCl₃): δ 3.72-3.76 (m, 3H), 2.31-2.36 (m, 2H), 1.98-2.00 (m, 1H), 1.41 (s, 9H), 1.0-1.37 (m, 3H).

To a mixture of tert-butyl ((2S)-3-hydroxyhex-5-yn-2-yl)carbamate (2.0 g, 9.4 mmol), L-ascorbic acid sodium salt (372 mg, 1.88 mmol) and Cu (OAc)$_2$ (170 mg, 0.94 mmol) in t-BuOH/H$_2$O (20 mL, v/v=1/1) was added BnN$_3$ (1.25 mg, 9.4 mmol) at 0° C. The reaction mixture was warmed and stirred at room temperature for 16 h. The reaction was then added brine (50 mL), which was extracted with EtOAc (3×50 mL). The combined organic layers were further washed with brine (100 mL), dried over Na$_2$SO$_4$, and concentrated. The residue was purified by flash chromatography on silica gel (eluting with CH$_2$Cl$_2$/MeOH=20/1) to afford tert-butyl ((2S)-4-(1-benzyl-1H-1,2,3-triazol-4-yl)-3-hydroxybutan-2-yl)carbamate (3.0 g, 92.3%) as a colorless oil. $^1$H NMR (400 MHz, CDCl$_3$) δ 7.19-7.33 (m, 5H), 5.43-5.49 (m, 2H), 4.76-4.86 (m, 1H), 2.68-2.75 (m, 2H), 1.35-1.40 (m, 9H), 1.14-1.20 (m, 3H).

To a solution of tert-butyl ((2S)-4-(1-benzyl-1H-1,2,3-triazol-4-yl)-3-hydroxybutan-2-yl)carbamate (3.0 g, 8.66 mmol) in MeOH (100 mL) was added 10% Pd(OH)$_2$ on carbon (600 mg) at room temperature and the mixture was stirred under H$_2$ (50 psi) at the same temperature for 16 h. The reaction mixture was filtered and the filtrate was concentrated to afford tert-butyl ((2S)-3-hydroxy-4-(1H-1,2,3-triazol-4-yl)butan-2-yl)carbamate (2.2 g, quantitative yield) as colorless oil.

tert-Butyl ((2S)-3-hydroxy-4-(1H-1,2,3-triazol-4-yl)butan-2-yl)carbamate was treated with HCl in EtOAc at rt and evaporated under reduced pressure to afford to afford (S)-3-amino-1-(1H-1,2,3-triazol-4-yl)butan-2-one.

Example 92: Synthesis of Compound 193

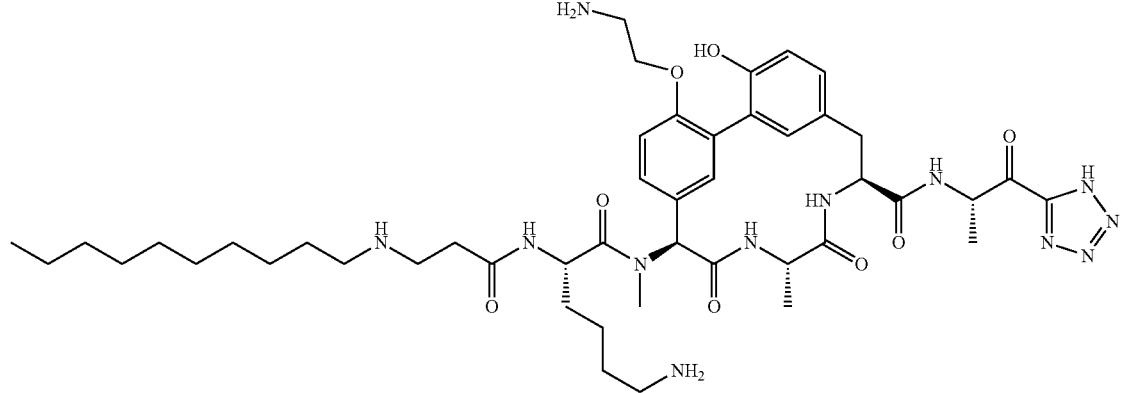

193

Compound 193 was synthesized using similar procedures as described above and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.837 min, M/2+H$^+$=460.5.

Example 93: Synthesis of Compound 194

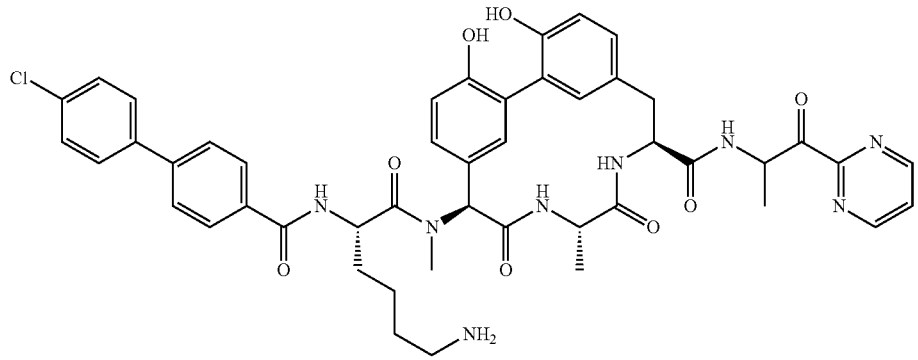

194

Compound 194 was synthesized from Compound 104E and (2S)-2-amino-1-(pyrimidin-2-yl)propan-1-ol using the amide coupling, oxidation, and TFA Boc-deprotection as described for Compound 139 and was isolated as the formic acid salt. LCMS (ESI): (5% AcCN/H₂O, 0.7 min; then 95% AcCN/H₂O, 0.4 min; 1.5 mL/min, Merck RP-18e, 2×25 mm) $t_R$=0.794 min, (M+H)⁺=889.6.

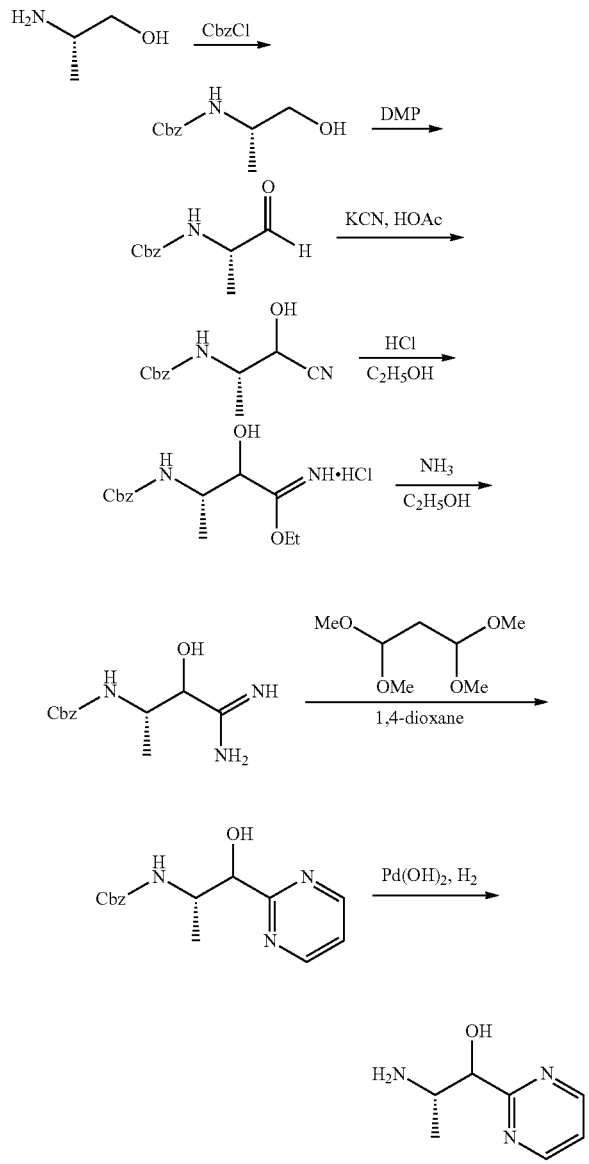

Synthesis of (2S)-2-amino-1-(pyrimidin-2-yl)propan-1-ol: To a solution of (S)-2-aminopropan-1-ol (10 g, 133 mmol) and DIPEA (34.4 g, 266 mmol) in DCM (300 mL) was added CbzCl (22.7 g, 133 mmol) in DCM (100 mL) dropwise at 0° C., then the reaction mixture was stirred at 30° C. for 2 h. After TLC showed that the reaction was completed, the reaction mixture was washed with water (500 mL) and brine (500 mL). The organic layer was dried and concentrated under reduced pressure; and the residue was purified by silica gel column (PE:EtOAc=20/1-10/1) to afford (S)-benzyl (1-hydroxypropan-2-yl)carbamate as a white solid (19.8 g, 71%).

To a mixture of (S)-benzyl (1-hydroxypropan-2-yl)carbamate (22 g, 105 mmol) in DMF (50 mL) was added solid NaHCO₃ (177 g, 2.1 mol); and then DMP (67 g, 158 mmol) was added to the solution at 0° C. The reaction was stirred at 30° C. for 2 h. After TLC showed that the reaction was completed, the reaction mixture was poured into a saturated solution of NaHCO₃/NaS₂O₃. The aqueous phase was extracted with DCM (500 mL×3). The combined organic layers were dried over Na₂SO₄ and concentrated under reduced pressure; and the residue was purified by silica gel column (PE:EtOAc=20/1-15/1) to afford (S)-benzyl (1-oxopropan-2-yl)carbamate as a colorless oil (21.7 g, 93%).

To a mixture of (S)-benzyl (1-oxopropan-2-yl)carbamate (16 g, 77.2 mmol) in EA (90 mL)/MeOH (90 mL) was added solid KCN (5.7 g, 87 mmol), followed by the addition AcOH (4.6 g, 87 mmol) at 0° C. The reaction was stirred at 30° C. for 16 h. After TLC showed that the reaction was completed, reaction volatiles were removed under reduced pressure and the residue was poured into water (100 mL), which was extracted with EA (100 mL×3). The combined organic layers were dried over Na₂SO₄ and concentrated under reduced pressure; and the residue was purified by silica gel column (PE:EtOAc=10/1-6/1) to afford benzyl ((2S)-1-cyano-1-hydroxypropan-2-yl)carbamate as colorless oil (14 g, 61.4%).

A mixture of benzyl ((2S)-1-cyano-1-hydroxypropan-2-yl)carbamate (14 g, 59.7 mmol) in C₂H₅OH (30 mL) was stirred at −40° C. for 5 min. HCl gas was then passed into the solution for 12 min. The reaction was stirred at 0° C. for another 50 min. After that, reaction volatiles were removed under reduced pressure to obtain (3S)-ethyl 3-(((benzyloxy)carbonyl)amino)-2-hydroxybutanimidate hydrochloride without further purification. The crude was re-dissolved in C₂H₅OH (40 mL) and the mixture was stirred at −40° C. for 5 min. NH₃ gas was then passed into the solution for 12 min. The reaction mixture was stirred at 30° C. for 16 h. After that, reaction volatiles were removed under reduced pressure to obtain benzyl ((2S)-4-amino-3-hydroxy-4-iminobutan-2-yl)carbamate (15.0 g) without further purification.

A mixture of 1,1,3,3-tetramethoxypropane (9.79 g, 59.7 mmol) in 1,4-dioxane (20 mL) was added EtOAc/HCl (5 mL) at 30° C. for 30 min. Et₃N (10 mL) was then added dropwise at 0° C. for 15 min, followed by the addition of benzyl ((2S)-4-amino-3-hydroxy-4-iminobutan-2-yl)carbamate (15.0 g, 59.7 mmol). The reaction mixture was stirred at 80° C. for 16 h. After TLC showed that the reaction was completed, reaction volatiles were removed under reduced pressure and the residue was poured into water (100 mL), which was extracted with DCM (100 mL×3). The combined organic layers were dried over Na₂SO₄ and concentrated under reduced pressure; and the residue was purified by silica gel column (PE:EtOAc=6/1-3/1) to afford benzyl ((2S)-1-hydroxy-1-(pyrimidin-2-yl)propan-2-yl)carbamate as colorless oil (700 mg, 4%).

To a mixture of benzyl ((2S)-1-hydroxy-1-(pyrimidin-2-yl)propan-2-yl)carbamate (220 mg, 0.76 mmol) in MeOH (20 mL) was added Pd(OH)₂ (70 mg), and the solution was stirred at 30° C. under H₂ for 5 min. After that, the reaction mixture was filtered and the filtrate was removed under reduced pressure to obtain (2S)-2-amino-1-(pyrimidin-2-yl)propan-1-ol (106 mg) and used without further purification.

Example 94: Synthesis of Compound 195

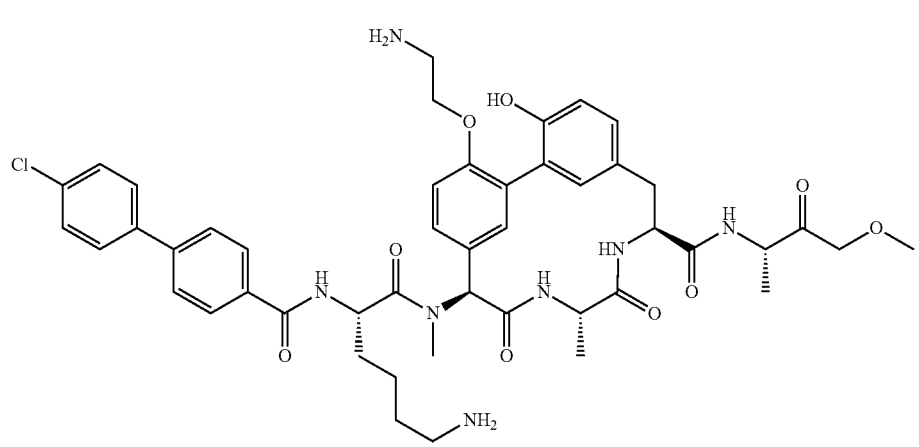

Compound was synthesized using the coupling method, DM oxidation, and Boc-group hydrolysis as described for Compound 139 from Compound 117C and (3S)-3-amino-1-methoxybutan-2-ol. MS (ESI) for ($C_{47}H_{56}ClN_7O_9$): m/z 898.4 (M+H)$^+$. HPLC: $t_R$ 2.81 min (10% AcCN/H$_2$O-90% AcCN/H$_2$O (with 0.05% TFA), 3.0 min, 1.0 mL/min Kinetix C18, 4.8×50 mm). $^1$H NMR (400 MHz, MeOH-d4) δ 7.91 (d, J=7.0 Hz, 2H), 7.71 (d, J=7.0 Hz, 2H), 7.66 (d, J=7.0 Hz, 2H), 7.47 (d, J=7.0 Hz, 2H), 7.28 (t, J=8.0 Hz, 1H), 7.26 (d, J=4.0 Hz, 1H), 7.14 (d, J=8.0 Hz, 1H), 6.01 (s, 1H), 6.94 (d, J=8.0 Hz, 1H), 6.85 (d, J=8.0 Hz, 1H), 6.51 (s, 1H), 5.06 (dd, J=4.0, 2.0 Hz, 1H), 4.89-4.83 (m, 2H), 4.57-455 (m, 2H), 4.27-4.21 (m, 2H), 3.41 (s, 3H), 3.39-3.31 (m, 2H), 3.30-3.23 (m, 1H), 3.13-3.03 (m, 1H), 2.99-2.96 (m, 2H), 2.95 (s, 3H), 2.02 (m, 1H), 2.11 (m, 1H), 1.76-1.72 (m, 2H), 1.61-1.46 (m, 2H), 1.32 (d, J=8.0 Hz, 3H), 1.28 (d, J=8.0 Hz, 3H).

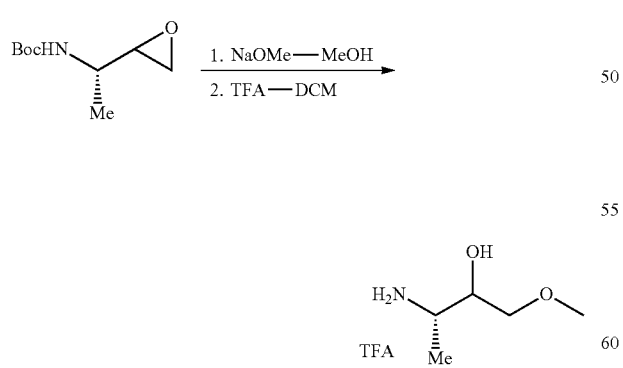

The synthesis of (3S)-3-amino-1-methoxybutan-2-ol: To a stirred solution of tert-butyl ((1S)-1-(oxiran-2-yl)ethyl) carbamate (Example 62) (57 mg, 0.3 mmol) in dry MeOH (2.0 mL) was added 25% NaOMe solution in MeOH (0.32 mL, 1.5 mmol) at 0° C. under argon atmosphere. The reaction mixture was stirred at rt for overnight. The reaction progress was monitored by TLC (1:1EtOAc-hexanes Rf 0.3) and after completion of the reaction neutralized with 1M HCl. The mixture was extracted with ethyl acetate and the combined organic layers washed with brine, dried over anhydrous Na$_2$SO$_4$, filtered and solvent was removed in vacuum. The residue was purified by flash chromatography (hexanes-EtOAc) to afford 38 mg (58%) of oily compound which was subjected for Boc removal using TFA-DCM (General Method 5) to afford (3S)-3-amino-1-methoxybutan-2-ol as the TFA salt.

Example 95: Synthesis of Compound 196

Compound 196 was synthesized using similar procedures as described above from Compound 101E and Compound 110A and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.686 min, (M+H)$^+$=694.4.

Example 96: Synthesis of Compound 197

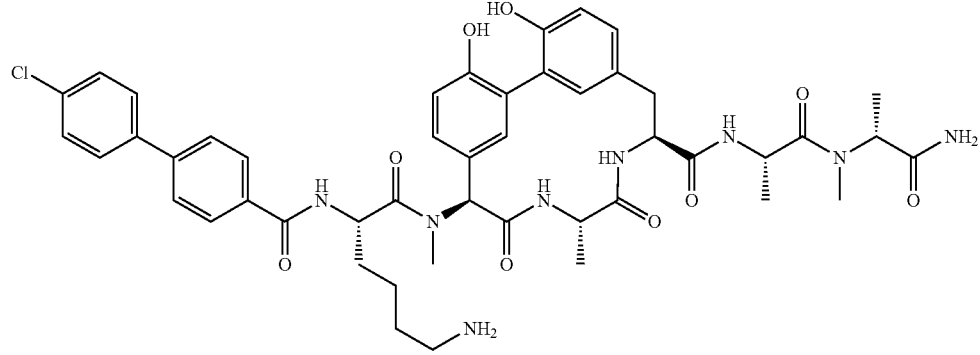

197

Compound 197 was synthesized using similar procedures as described above from Compound 104E and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.634 min, (M+H)$^+$=911.3.

Example 97: Synthesis of Compound 198

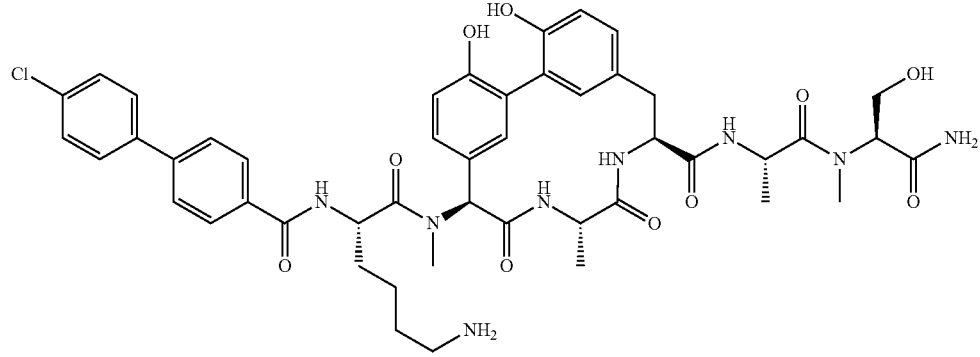

198

Compound 198 was synthesized using similar procedures as described above from Compound 104E and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.772 min, (M+H)$^+$=927.3.

Example 98: Synthesis of Compound 199

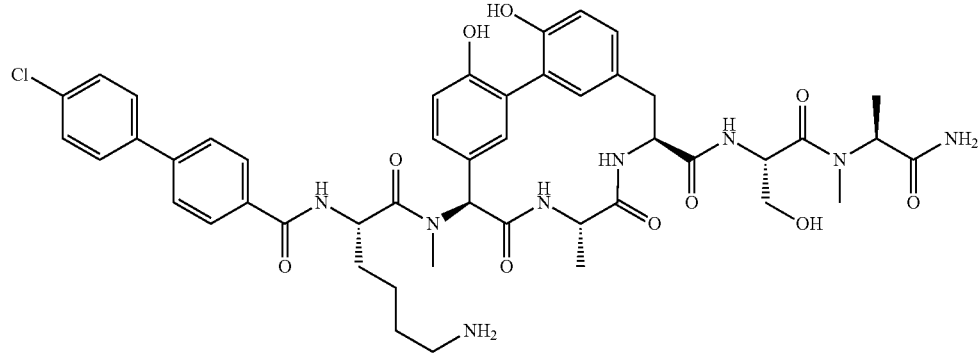

199

Compound 199 was synthesized using similar procedures as described above from Compound 104E and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.772 min, (M+H)$^+$=927.4.

Example 99: Synthesis of Compound 200

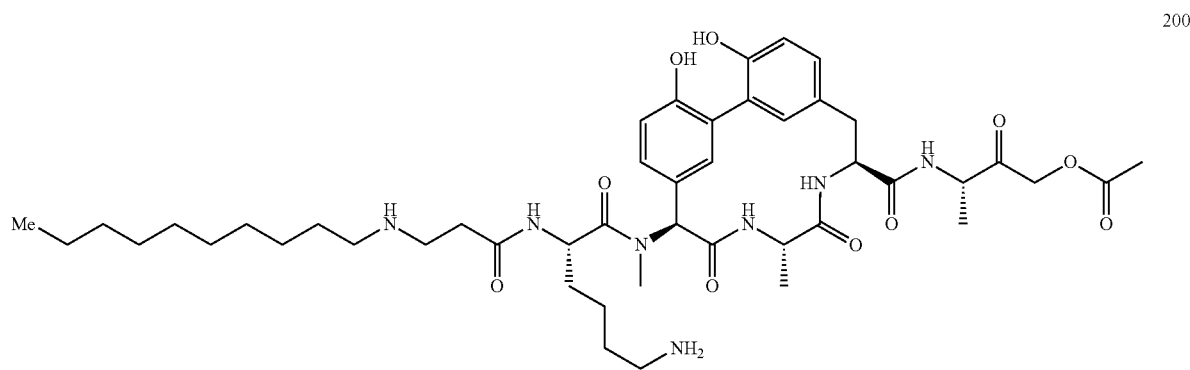 [SMILES: CCCCCCCCCCNCCC(=O)N[C@@H](CCCCN)C(=O)N(C)[C@@H]1C(=O)N[C@@H](C)C(=O)N[C@H](C(=O)N[C@@H](C)C(=O)COC(C)=O)Cc2ccc(O)c(c2)-c2cc1ccc2O]

Compound 200 was synthesized using similar procedures as described for Compound 116 from Compound 113A and Compound 116A. LCMS (ESI): (10% AcCN/H$_2$O-90% AcCN/H$_2$O for 3 min; then 95% AcCN/H$_2$O for 1 min; 1.0 mL/min, Kinetex-5u-C18, 4.6×50 mm) t$_R$=3.08 min, (M+H)$^+$=881.21.

Example 100: Synthesis of Compound 201

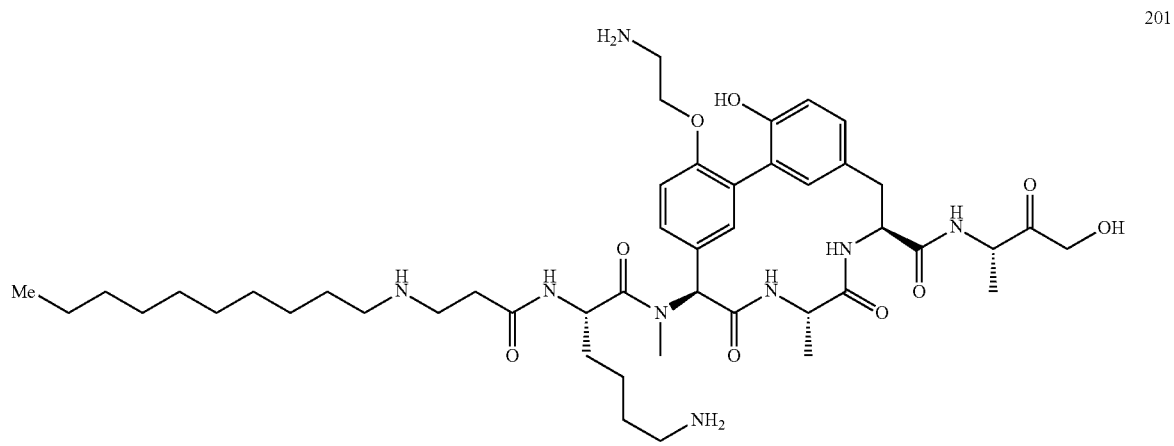 [SMILES: CCCCCCCCCCNCCC(=O)N[C@@H](CCCCN)C(=O)N(C)[C@@H]1C(=O)N[C@@H](C)C(=O)N[C@H](C(=O)N[C@@H](C)C(=O)CO)Cc2ccc(O)c(c2)-c2cc1ccc2OCCN]

Compound 201 was synthesized using similar procedures as described for Compound 118 from Compound 116. LCMS (ESI): (10% AcCN/H$_2$O-90% AcCN/H$_2$O for 3 min; then 95% AcCN/H$_2$O for 1 min; 1.0 mL/min, Kinetex-5u-C18, 4.6×50 mm) t$_R$=2.73 min, M+2H$^+$=882.19.

Example 101: Synthesis of Compound 202

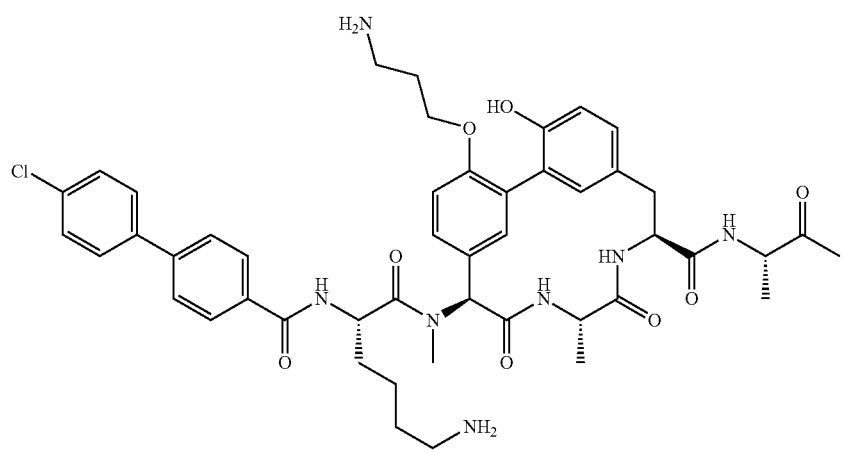

Compound 202 was synthesized using similar procedures as described above from Compound 202A and was isolated as the formic acid salt. LCMS (ESI): (5% AcCN/H₂O, 0.7 min; then 95% AcCN/H₂O, 0.4 min; 1.5 mL/min, Merck RP-18e, 2×25 mm) $t_R$=0.749 min, (M+H)⁺=882.8.

The synthesis of Compound 202A: To a solution of Compound 117A (197 mg, 0.2 mmol), tert-butyl (3-hydroxypropyl)carbamate (88 mg, 0.5 mmol) and Ph₃P (131 mg, 0.5 mmol) in dry THF (5 mL) was added DIAD (100 µL, 0.5 mmol) at 0° C. and the mixture was warmed and

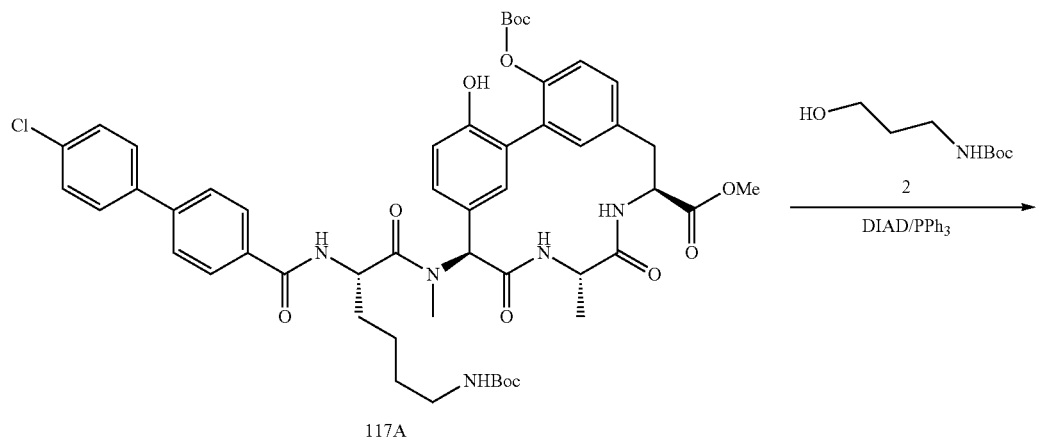

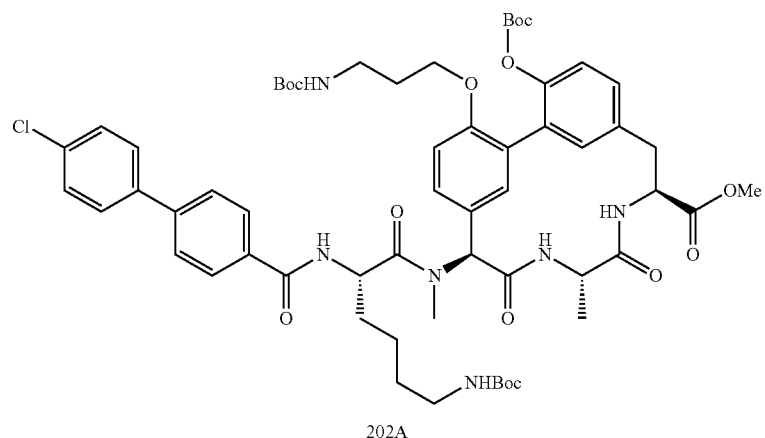

stirred at room temperature for 4 h. The reaction mixture was then purified by HPLC to afford Compound 202A as a white solid (75 mg, 34% yield).

Example 102: Synthesis of Compound 203

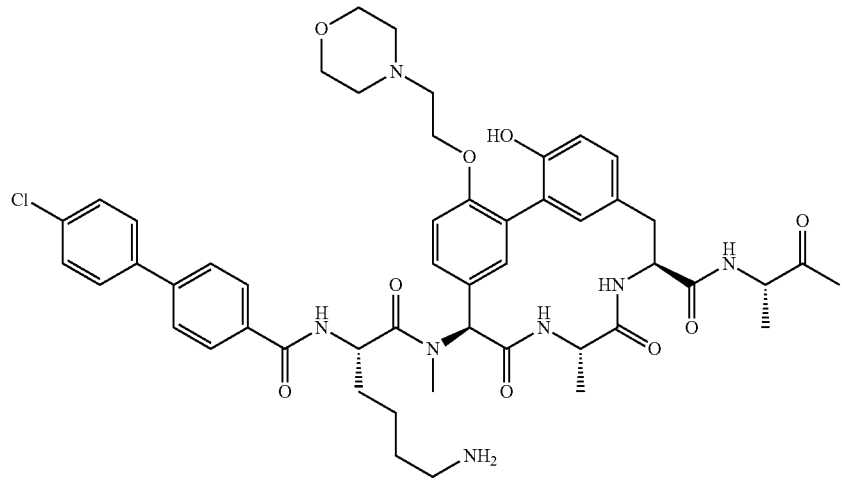

203

Compound 203 was synthesized in a manner similar to Compound 202 starting from Compound 117A and 2-morpholinoethanol and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.616 min, (M+H)$^+$=937.

Example 103: Synthesis of Compound 204

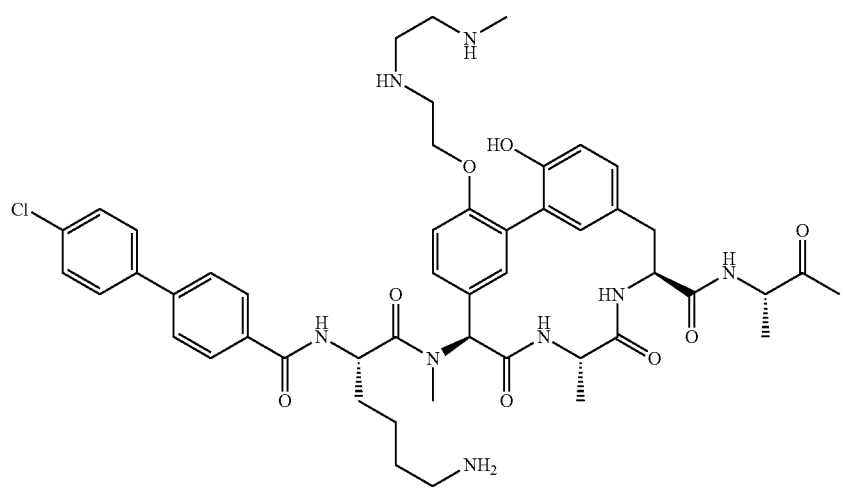

204

Compound 204 was synthesized in a manner similar to Compound 115 from Compound 204A and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.720 min, (M+H)$^+$=925.2.

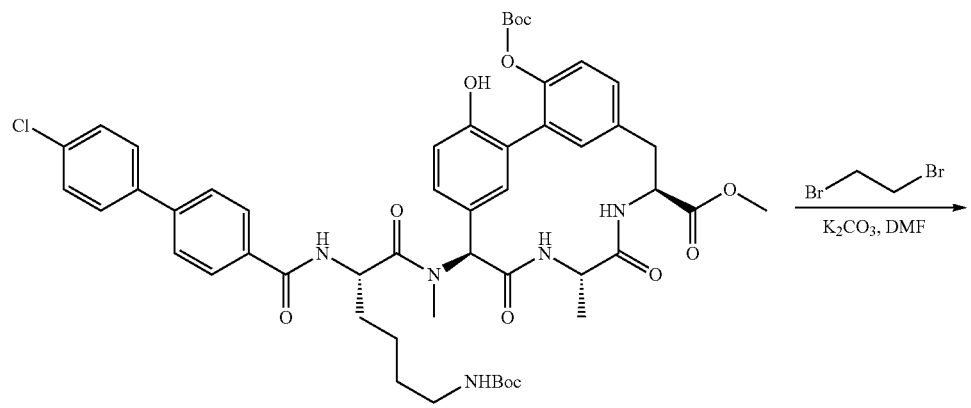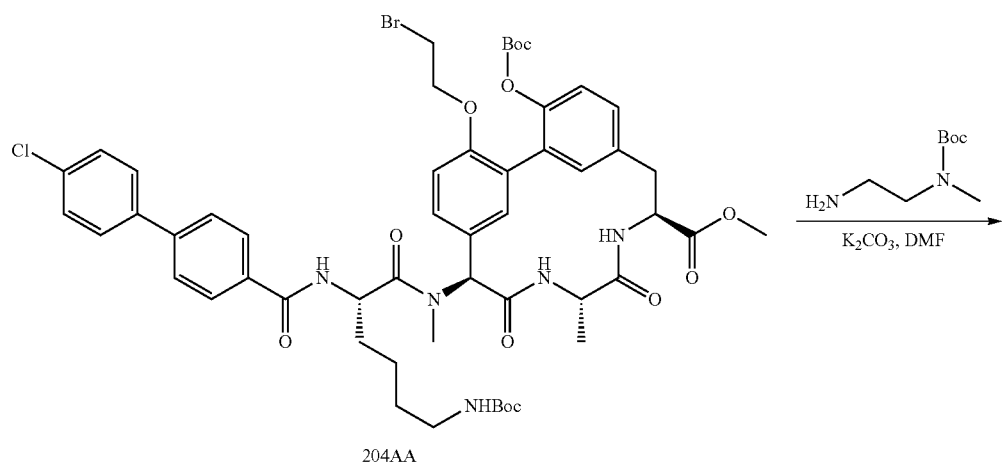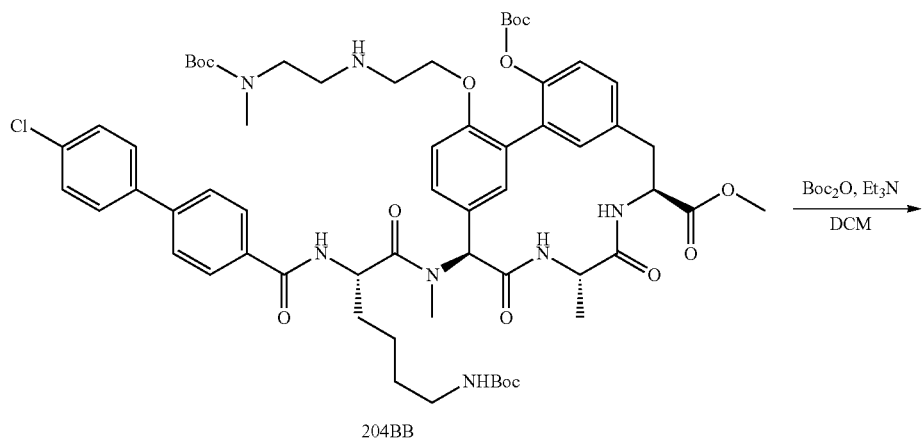

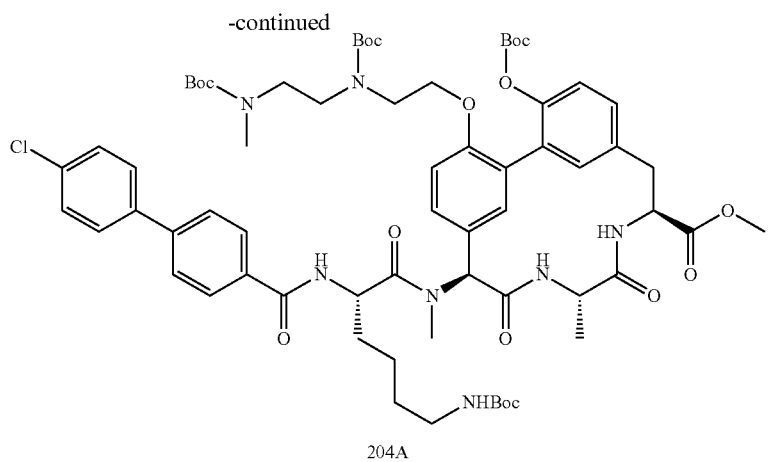

204A

The synthesis of Compound 204A: To a solution of Compound 117A (2.0 g, 2.1 mmol) in anhydrous DMF (10 mL) was added 1,2-dibromoethane (7.7 g, 41.2 mmol) and K$_2$CO$_3$ (5.7 g, 41.2 mmol) at 0° C. and the mixture was stirred at room temperature for 16 h. The reaction was then added with brine (100 mL), which was extracted with EtOAc (3×100 mL). The combined organic layers were dried over Na$_2$SO$_4$ and concentrated to afford Compound 204AA (1.9 g, 85.6%) as a white solid.

To a solution of Compound 204AA (100 mg, 0.093 mmol) and tert-butyl (2-aminoethyl)(methyl)carbamate (81 mg, 0.46 mmol) in DMF (2 mL) was added K$_2$CO$_3$ (128 mg, 0.93 mmol) and the mixture was stirred at room temperature for 16 h. The reaction was then taken up in EtOAc (50 ml), which was washed with brine (2×50 mL). The organic layer was dried over Na$_2$SO$_4$, and concentrated. The residue was purified by flash column chromatography (eluting 5-10% DCM in MeOH) to afford Compound 204BB (70 mg, 65%) as a white solid. Compound 204BB was subjected to the standard Boc-conditions as described for the synthesis of Compound 110A to afford Compound 204A.

Example 104: Synthesis of Compound 205

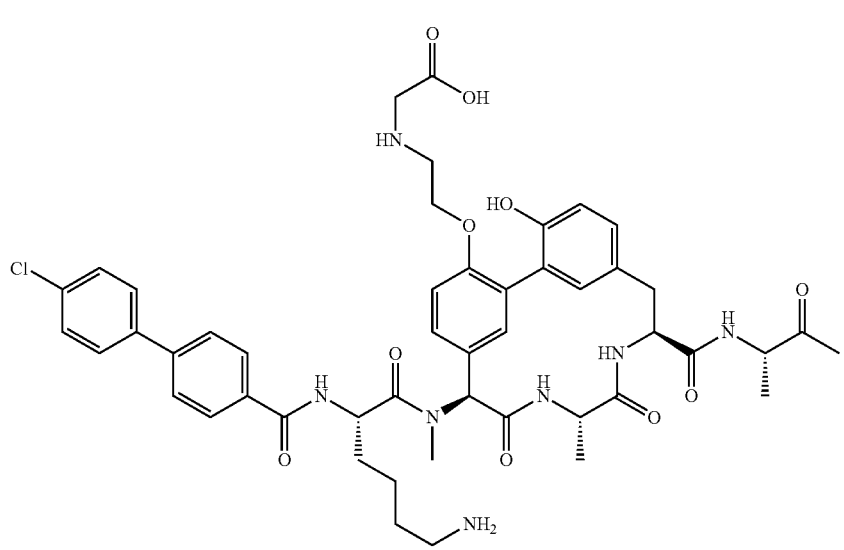

205

Compound 205 was synthesized in a manner similar to Compound 204 from Compound 204AA and tert-butyl 2-aminoacetate hydrochloride and was isolated as the formic acid salt. LCMS (ESI): (5% AcCN/H₂O, 0.7 min; then 95% AcCN/H₂O, 0.4 min; 1.5 mL/min, Merck RP-18e, 2×25 mm) $t_R$=0.764 min, (M+H)⁺=926.1.

Example 105: Synthesis of Compound 206

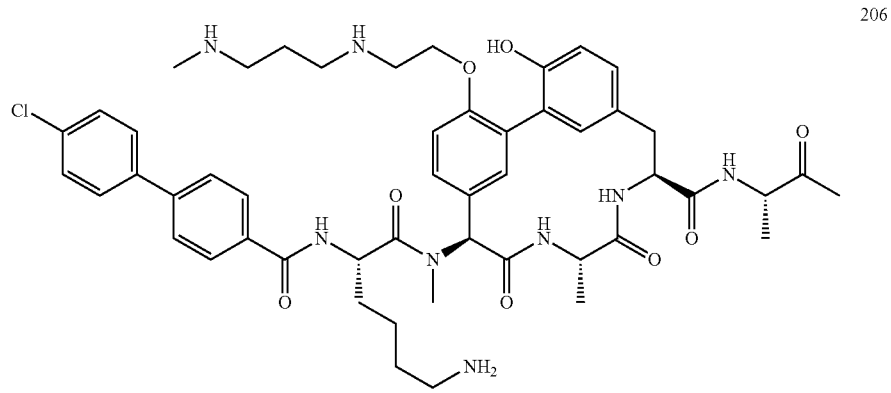 [SMILES: CNCCCNCCOc1ccc2cc1-c1cc(ccc1O)C[C@@H](C(=O)N[C@@H](C)C(C)=O)NC(=O)[C@H](C)NC(=O)[C@H]2N(C)C(=O)[C@H](CCCCN)NC(=O)c1ccc(-c2ccc(Cl)cc2)cc1]

Compound 206 was synthesized in a manner similar to Compound 115 from Compound 206A and was isolated as the formic acid salt. LCMS (ESI): (5% AcCN/H₂O, 0.7 min; then 95% AcCN/H₂O, 0.4 min; 1.5 mL/min, Merck RP-18e, 2×25 mm) $t_R$=0.717 min, (M+H)⁺=939.3.

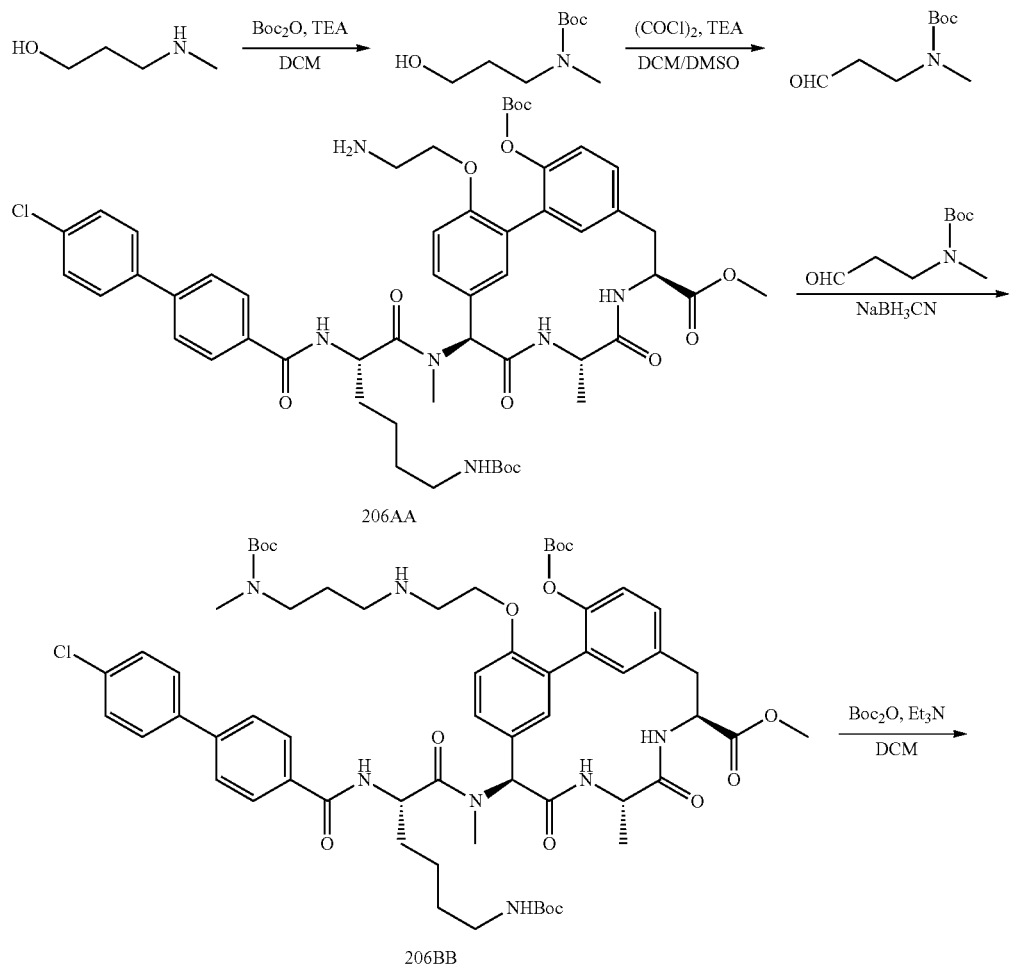

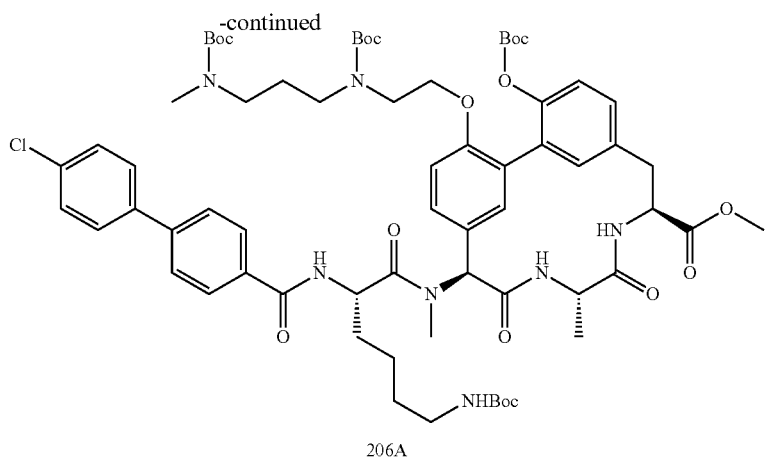

206A

The synthesis of Compound 206A: Starting from 3-(methylamino)propan-1-ol (2.0 g, 22.4 mmol), standard Boc addition was used as in the preparation of Compound 110A to afford tert-butyl (3-hydroxypropyl)(methyl)carbamate. Tert-butyl (3-hydroxypropyl)(methyl)carbamate was subject to standard Swern oxidation conditions. To a solution of oxalyl chloride (2 eq) in DCM (0.1M was added DMSO (3 eq) at −75° C. over 10 min. After 15 min, tert-butyl (3-hydroxypropyl)(methyl)carbamate (1 eq) in 0.03M DCM was then added to the above mixture at −75° C. over 15 min and the mixture was stirred for 1 h, followed by the addition of Et$_3$N (5 eq) over 15 min. The reaction warmed and stirred at 0° C. for 15 min. The mixture was then added with saturated NH$_4$Cl (50 mL) and the aqueous layer was further extracted with DCM (2×25 mL). The combined organic layers were washed with brine (100 mL), dried over anhydrous Na$_2$SO$_4$ and concentrated to afford tert-butyl methyl(3-oxopropyl)carbamate (1.2 g) as colorless oil after silica column chromatography. $^1$H NMR (400 MHz, CDCl$_3$) δ 9.79 (s, 1H), 3.52 (br s, 2H), 2.87 (s, 3H), 2.66 (br s, 2H), 1.43 (s, 9H).

To a solution of Compound 206AA (Example 17) (57 mg, 0.06 mmol) in MeOH (2 mL) was added tert-butyl methyl (3-oxopropyl)carbamate (21 mg, 0.11 mmol) and NaBH$_3$CN (63 mg, 0.13 mmol), and the mixture was stirred at room temperature for 16 h. The reaction mixture was quenched with saturated NaHCO$_3$ (10 mL), which was extracted with DCM (3×15 mL). The combined organic layers were dried over MgSO$_4$, and concentrated. The residue was purified by flash column chromatography (eluting with DCM/MeOH=20:1) to afford Compound 206BB (37 mg, 55.6% yield) as a white solid. Compound 206BB was subject to the standard Boc-addition as described for Compound 110A to afford Compound 206A.

Example 106: Synthesis of Compound 207

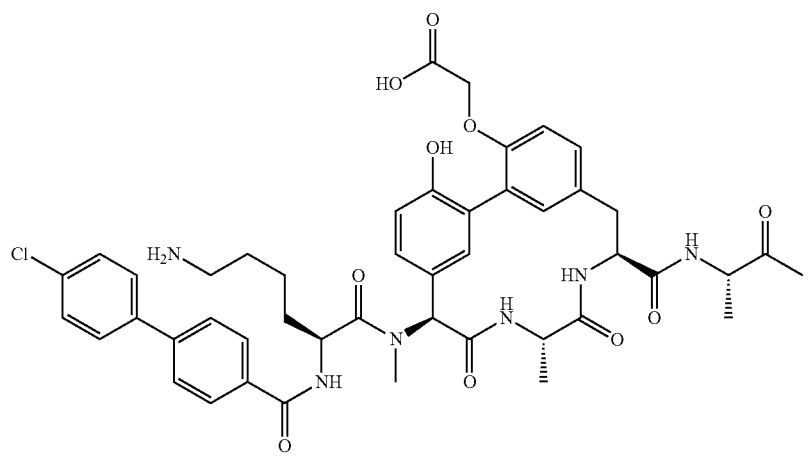

207

Compound 207 was synthesized from Compound 109, which is subject to the mono-Boc conditions as described for Compound 209 and then treated with tert-butyl 2-bromoacetate using the conditions for Compound 120. LCMS (ESI): (10% AcCN/H$_2$O-90% AcCN/H$_2$O for 3 min; then 95% AcCN/H$_2$O for 1 min; 1.0 mL/min, Kinetex-5u-C18, 4.6×50 mm) t$_R$=3.09 min, (M+H)$^+$=884.01.

Example 107: Synthesis of Compound 208

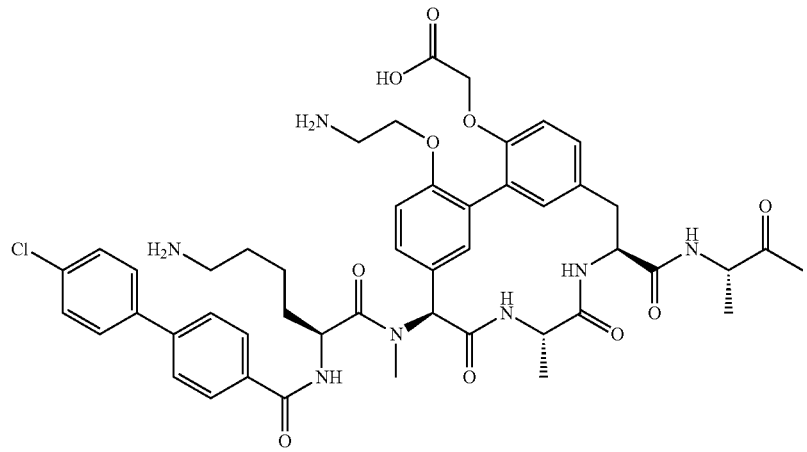

208

Compound 208 was synthesized in a manner similar to Compound 207 from the intermediates used in the preparation of Compound 119 under the conditions used for Compound 120. LCMS (ESI): (10% AcCN/H$_2$O-90% AcCN/H$_2$O for 3 min; then 95% AcCN/H$_2$O for 1 min; 1.0 mL/min, Kinetex-5u-C18, 4.6×50 mm) t$_R$=2.88 min, (M+H)$^+$=927.21.

Example 108: Synthesis of Compound 209

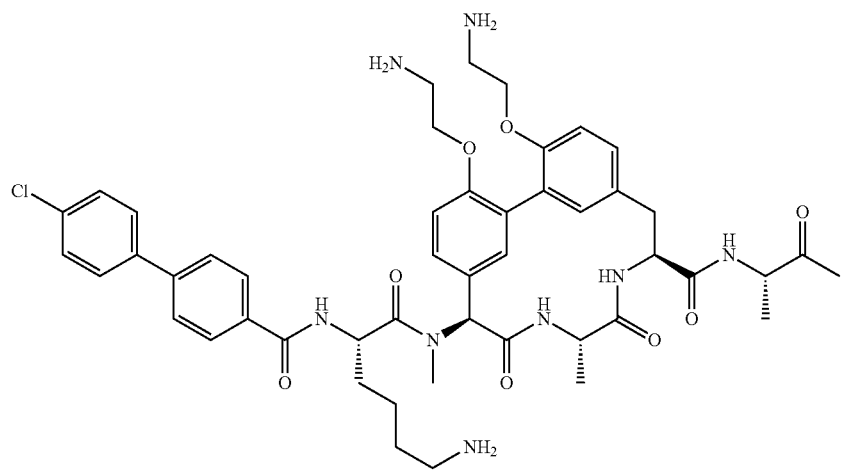

209

Compound 209 was synthesized in a manner similar to Compound 114 from Compound 209A. LCMS (ESI): (10% AcCN/H$_2$O-90% AcCN/H$_2$O for 3 min; then 95% AcCN/H$_2$O for 1 min; 1.0 mL/min, Kinetex-5u-C18, 4.6×50 mm) t$_R$=2.67 min, (M+H)+=912.0.

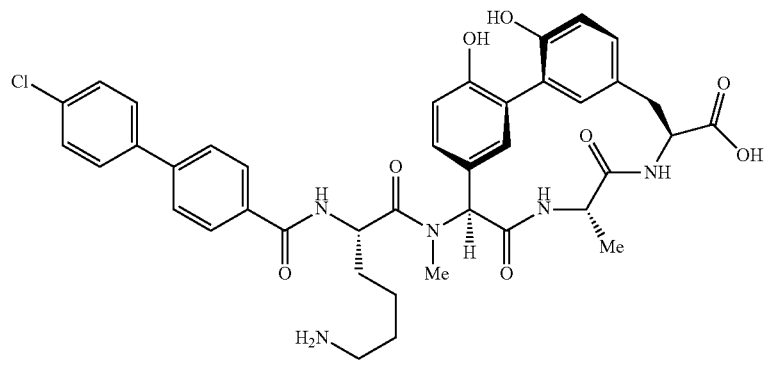
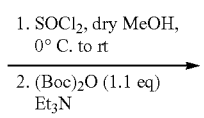

104D

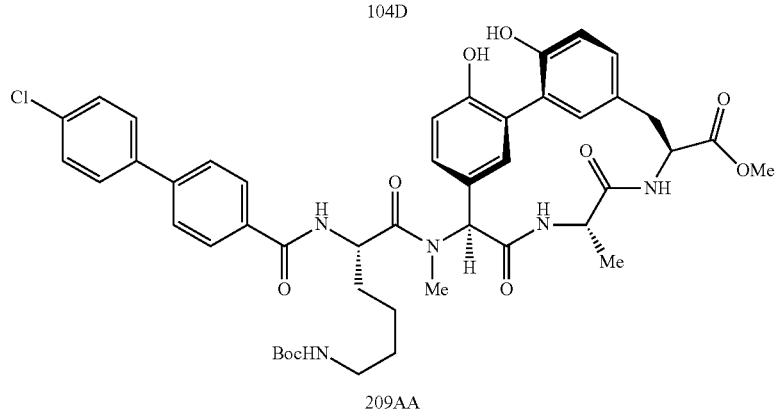
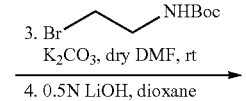

209AA

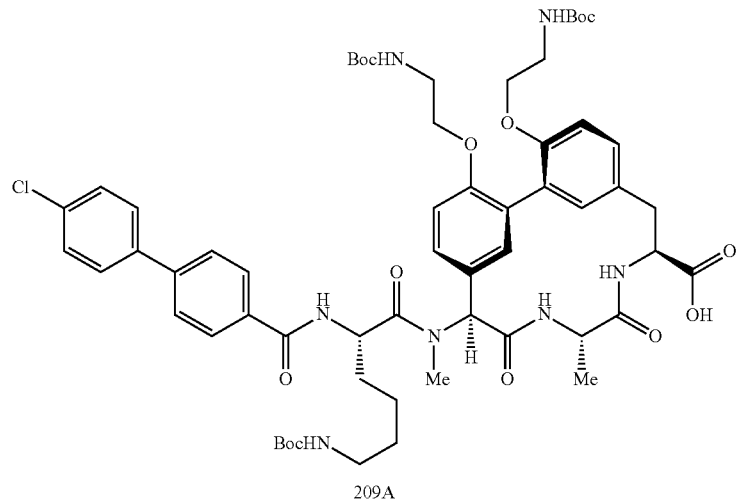

209A

The synthesis of Compound 209A: Compound 104D was subject to the standard methyl ester formation conditions. To a solution of Compound 104D (317 mg, 0.3 mmol) in dry MeOH (5 mL) at 0° C., $SOCl_2$ (0.3 mL) was added slowly drop wise. The reaction mixture was stirred at rt for about 10 h. The solvent was removed in vacuum and the residue was dried under high vacuum and used as it is in the next reaction. LCMS: MS (ESI) for $C_{41}H_{44}ClN_5O_8$: m/z 770.14 $(M+H)^+$. HPLC: $t_R$ 3.22 min (10% AcCN/$H_2$O-90% AcCN/$H_2$O (with 0.05% TFA), 3.0 min, 1.0 mL/min Kinetix C18, 4.8×50 mm).

The above residue was subject to the standard mono-Boc forming reaction conditions. The above residue (0.3 mmol) was dissolved in $CH_2Cl_2$ (10 mL) and $Et_3N$ (208 μL, 1.5 mmol, 5 eq), to this stirred solution $(Boc)_2O$ (76 μL, 0.33 mmol, 1.1 eq) was added. The reaction mixture was stirred at rt for about 1 h while monitoring the reaction progress by LCMS. After the reaction was complete brine solution was added and the mixture was extracted with ethylacetate. Combined organic layers washed with Brine, dried over anhydrous $Na_2SO_4$, filtered and solvent was removed in vacuum. The residue was purified by flash chromatography (DCM-5% DCM-MeOH) to afford 140 mg (54%, over 2 steps) of Compound 209AA as a white solid. MS (ESI) for $(C_{46}H_{52}ClN_5O_{10})$: m/z 871.64 (M+2H). HPLC: $t_R$ 4.05 min (10% AcCN/$H_2$O-90% AcCN/$H_2$O (with 0.05% TFA), 3.0 min, 1.0 mL/min Kinetix C18, 4.8×50 mm).

To a stirred solution of Compound 209AA (70 mg, 0.08 mmol) in dry DMF (2 mL) was added $K_2CO_3$ (33 mg, 0.24 mmol, 3 eq) followed by tert-butyl (2-bromoethyl)carbamate (89 mg, 0.4 mmol, 5 eq). The reaction mixture was stirred at rt for 3 d. After completion of the reaction (monitored by LCMS) crushed ice was added and the resultant white cloudy mixture was extracted with EtOAc. The combined organic layers washed with brine and dried over anhydrous $Na_2SO_4$. Filtered and solvent was removed under vacuum. The residue was purified by flash chromatography (DCM-5% DCM-MeOH) to afford 85 mg (92%) as a white solid. MS (ESI) for ($C_{60}H_{78}ClN_7O_{14}$): m/z 1157.36 (M+2H). HPLC: $t_R$ 4.07 min (50% AcCN/$H_2O$-90% AcCN/$H_2O$ (with 0.05% TFA), 3.0 min, 1.0 mL/min Kinetix C18, 4.8×50 mm).

The white solid was dissolved in dioxane-$H_2O$ (3:1, 2 mL), and a 0.5 M LiOH solution (3 eq) was added at 0° C. and the reaction mixture was stirred at rt for 2 h. After completion of the reaction (monitored by LCMS) water (2 mL) was added and extracted with ether. The aqueous layer acidified with 0.5 M HCl. The resultant white cloudy mixture was extracted with EtOAc. The combined organic layers washed with brine and dried over anhydrous $Na_2SO_4$. Filtered and solvent was removed and dried under high vacuum to afford 72 mg (87%) of Compound 209A as a white solid. MS (ESI) for ($C_{59}H_{76}ClN_7O_{14}$): m/z 1143.4 (M+2H). HPLC: $t_R$ 2.62 min (50% AcCN/$H_2O$-90% AcCN/$H_2O$ (with 0.05% TFA), 3.0 min, 1.0 mL/min Kinetix C18, 4.8×50 mm).

Example 109: Synthesis of Compound 210

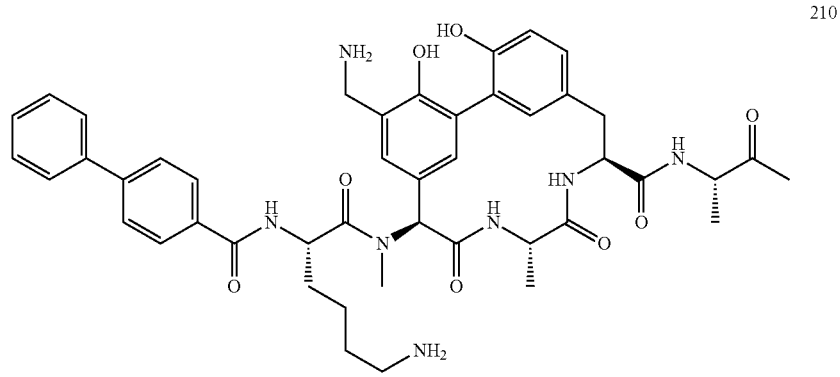 [SMILES: CC(=O)[C@H](C)NC(=O)[C@@H]1Cc2ccc(O)c(c2)-c2cc(cc(CN)c2O)[C@H](N(C)C(=O)[C@H](CCCCN)NC(=O)c2ccc(-c3ccccc3)cc2)C(=O)N[C@@H](C)C(=O)N1]

Compound 210 was synthesized in a similar manner to Compound 115 using the LiOH hydrolysis, HATU coupling, and TFA Boc-deprotection conditions starting from Compound 210A. MS (ESI) for ($C_{45}H_{53}ClN_7O_8$): m/z 820.4 (M+H)$^+$.

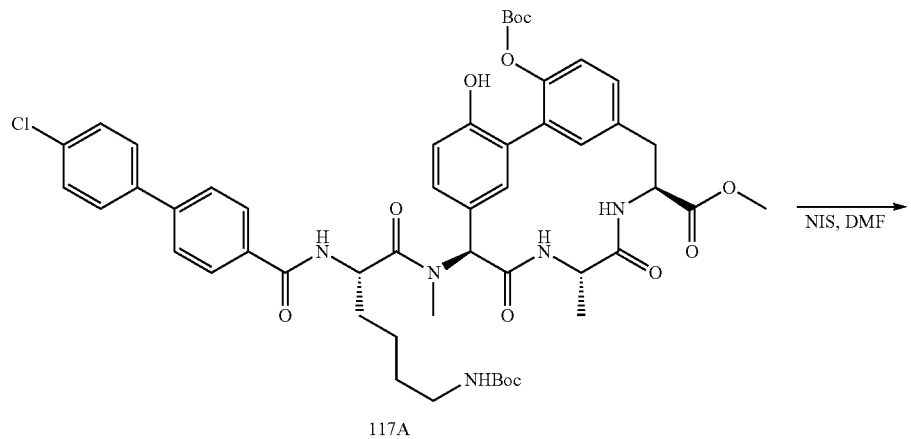

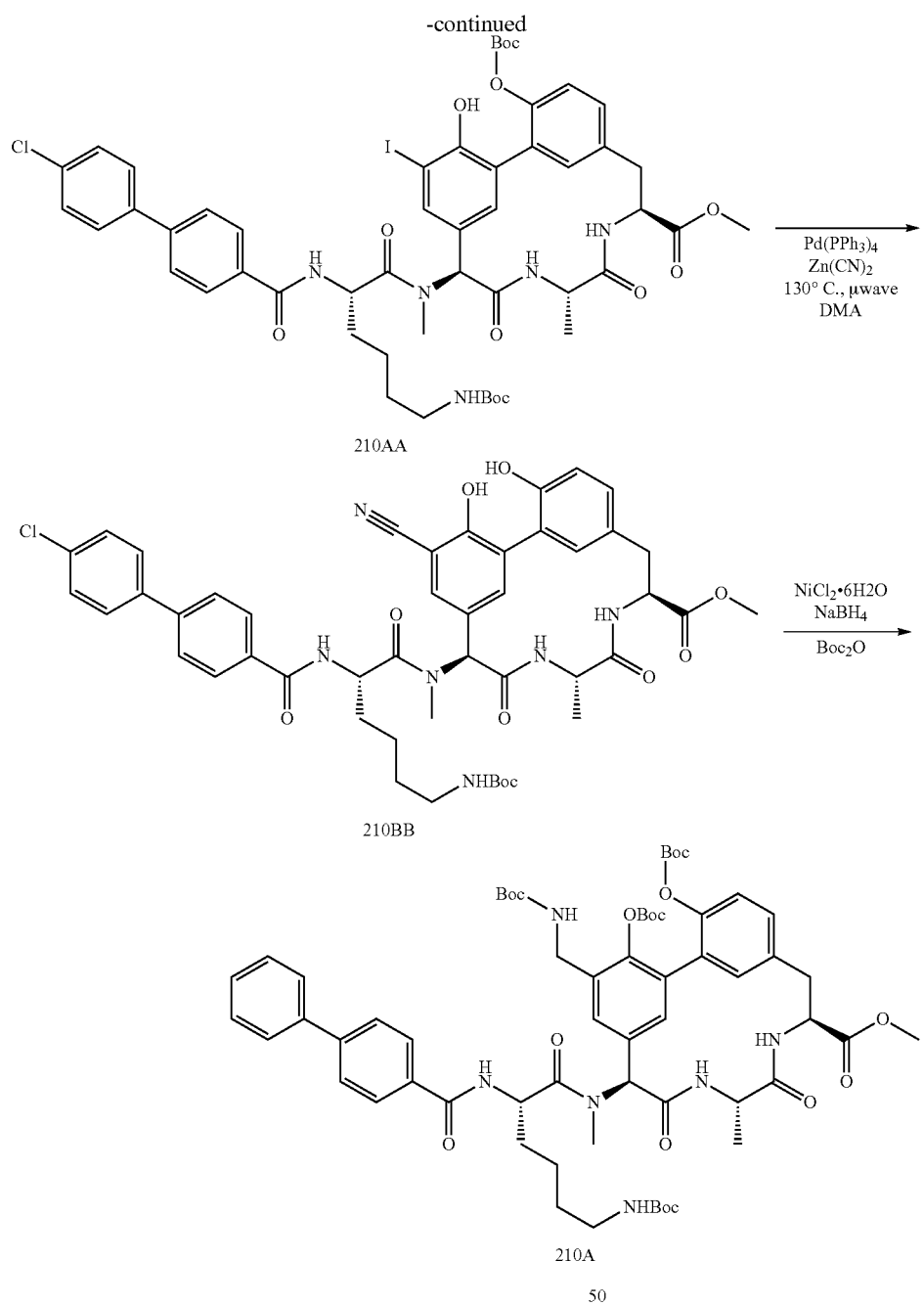

The synthesis of Compound 210A: To a solution of Compound 117A (1.275 mmol, 1110.0 mg) in N,N-dimethylformamide (15 mL) at 0° C. was added a solution of N-iodosuccinimide (NIS, 4.463 mmol, 1025 mg) in N,N-dimethylformamide (5 mL) dropwise. The reaction mixture was then kept in dark and stirred at room temperature for 18 hours. The reaction mixture was quenched by addition of saturated aqueous $Na_2S_2O_3$, diluted with brine, and extracted with EtOAc. The organic layer was washed with water (3×), dried with $Na_2SO_4$, concentrated, and the residue was purified on silica eluted with 0 to 100% EtOAc in DCM to afford Compound 210AA as an off-white solid (967 mg, 76%).

A mixture of Compound 210AA (0.106 mmol, 105 mg), zinc cyanide (0.135 mmol, 16.2 mg, 0.00876 mL), and tetrakis(triphenylphosphine)palladium(0) (0.0212 mmol, 24.4 mg) in N,N-dimethylacetamide (3 mL) was purged with nitrogen, sealed, and heated at 130° C. under microwave irradiation for 40 min. The reaction mixture was diluted with EtOAc, washed 3× with water, dried with $Na_2SO_4$, and concentrated. The residue was purified on silica eluted with 0 to 10% MeOH in DCM to afford Compound 210BB (46.7 mg, 49%).

A solution of Compound 210BB (0.0922 mmol, 82.6 mg), di-t-butyl dicarbonate (0.277 mmol, 62.3 mg) and dichloronickel hexahydrate (0.0922 mmol, 21.9 mg) in methanol (5 mL) was cooled to 0° C. Then sodium borohydride (0.646 mmol, 24.4 mg) was added slowly in small portions. The reaction mixture was then stirred at rt for 1 hr. More $NaBH_4$ and $Boc_2O$ were added, continue stirring overnight. The reaction mixture was concentrated. The residue was was purified on silica eluted with 0 to 100% EtOAc in DCM to afford Compound 210A (46.5 mg, 43%).

Example 110: Synthesis of Compound 211

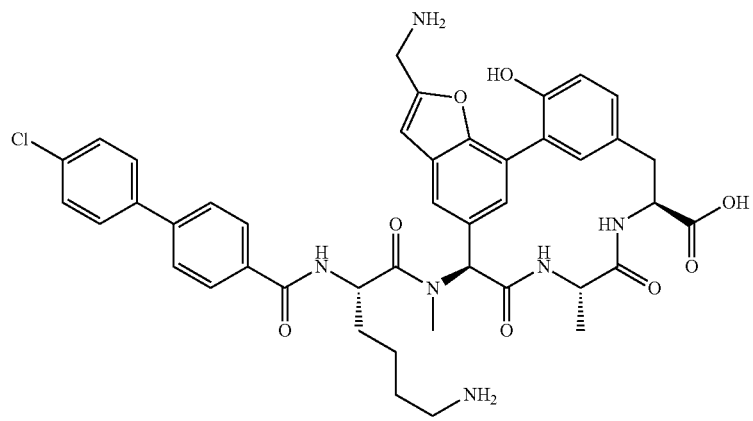

Compound 211 was synthesized from Compound 211A using the LiOH ester hydrolysis and TFA Boc-deprotection as described for Compound 117. MS (ESI) for ($C_{43}H_{45}ClN_6O_8$): m/z 809.4 (M+H)$^+$.

The synthesis of Compound 211A: To a mixture of Compound 210AA (0.324 mmol, 50.4 mg) in acetonitrile (5 mL) under argon was added diisopropylamine (1.62 mmol, 164 mg), bis(triphenylphosphine)palladium(II) dichloride (0.01623 mmol, 11.39 mg), and cuprous iodide (0.03245 mmol, 6.180 mg). The reaction vial was sealed and stirred at room temperature for 18 hours. The mixture was concentrated and the residue was purified on silica eluted with 0 to 100% EtOAc in DCM to afford Compound 211A (154 mg, 86%).

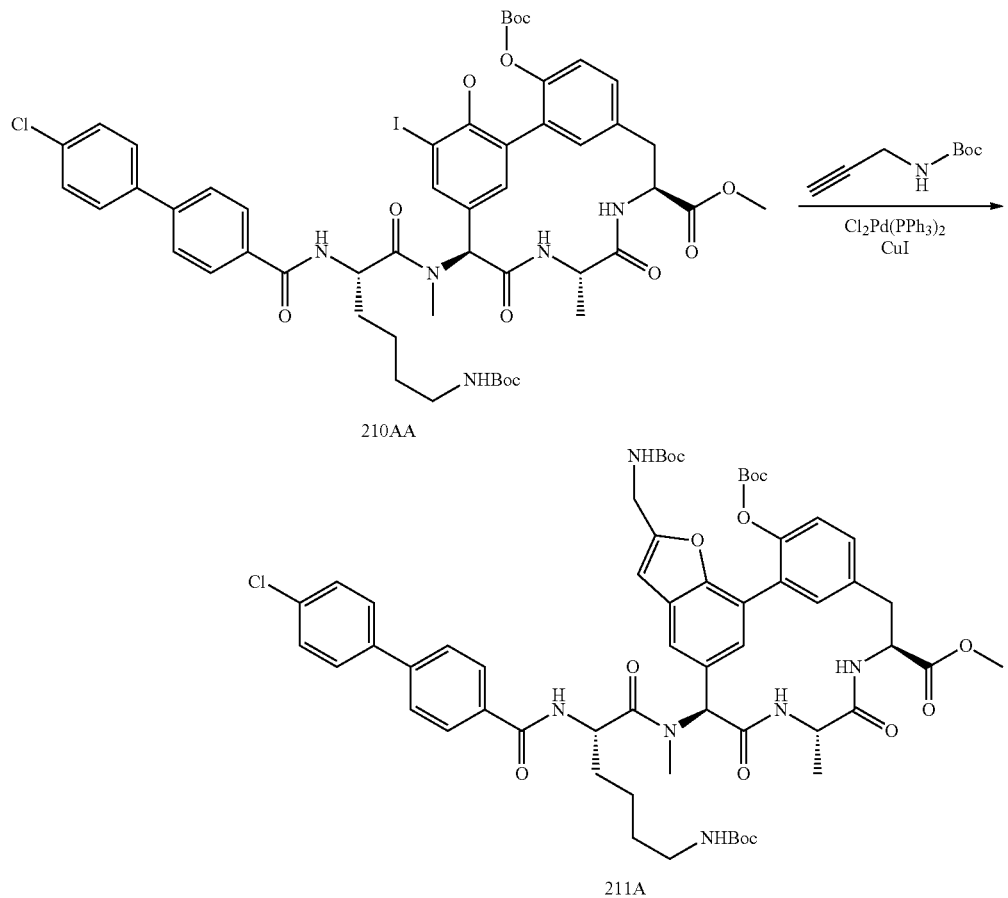

Example 111: Synthesis of Compound 212

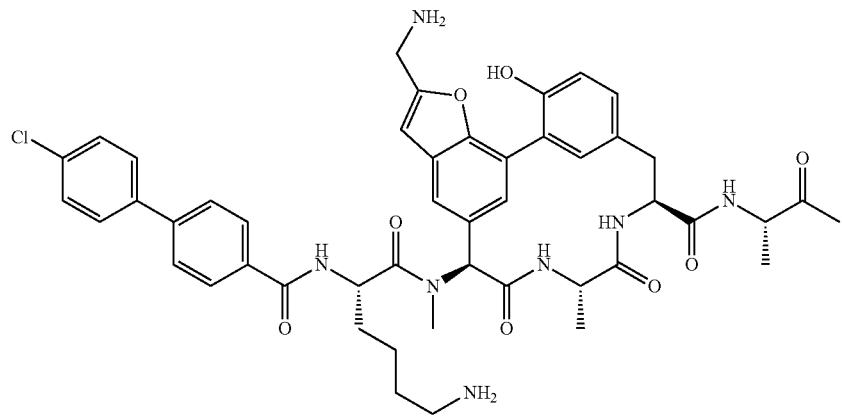

212

Compound 212 was synthesized from Compound 211A using the LiOH ester hydrolysis, HATU coupling of Compound 109A and TFA Boc-deprotection as described for Compound 117. MS (ESI) for ($C_{47}H_{52}ClN_7O_8$): m/z 878.4 (M+H)$^+$.

Example 112: Synthesis of Compound 213

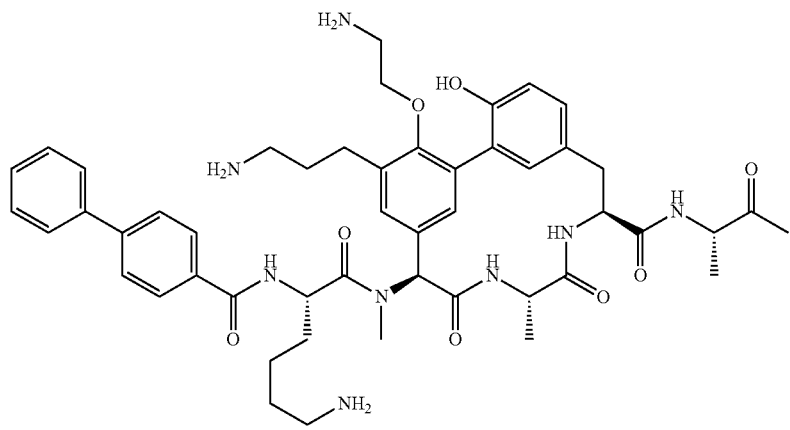

213

Compound 213 was synthesized by treatment of Compound 226 (0.0629 mmol, 58 mg) in MeOH was hydrogenated on H-cube Pro, 10% Pd/C 70 mm cat. cartridge, at 5 bar, 25° C. The reaction mixture was concentrated, and the residue was purified by reverse phase HPLC to afford 10 mg (18%) of the final compound. MS (ESI) for ($C_{49}H_{62}N_8O_8$): m/z 891.2 (M+H)$^+$.

Example 113: Synthesis of Compound 214

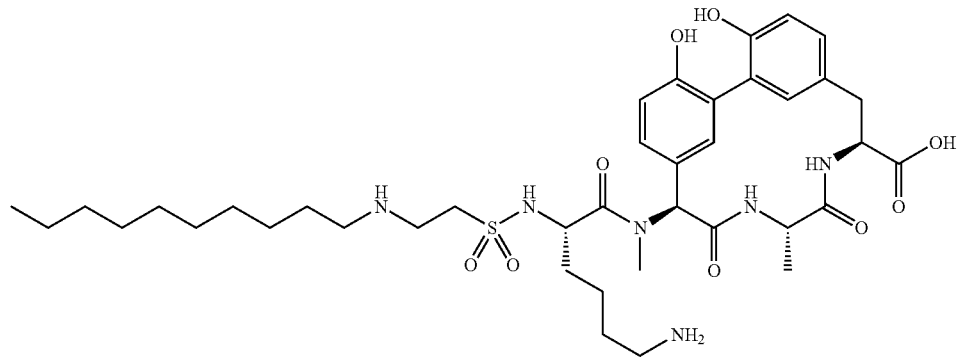

214

Compound 214 was synthesized using similar procedures as described above from Compound 163C and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.761 min, (M+H)$^+$=789.5.

Example 114: Synthesis of Compound 215

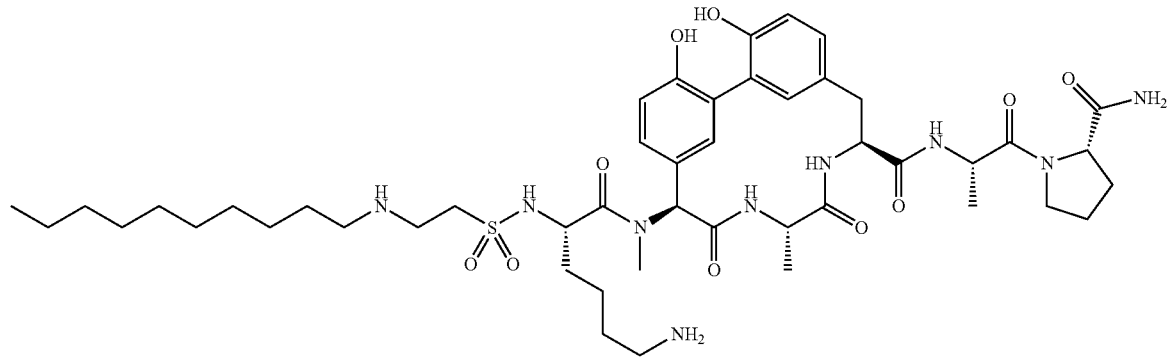

215

Compound 215 was synthesized using similar procedures as described above from Compound 163C and Compound 155A and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.763 min, (M+H)$^+$=956.6.

Example 115: Synthesis of Compound 216

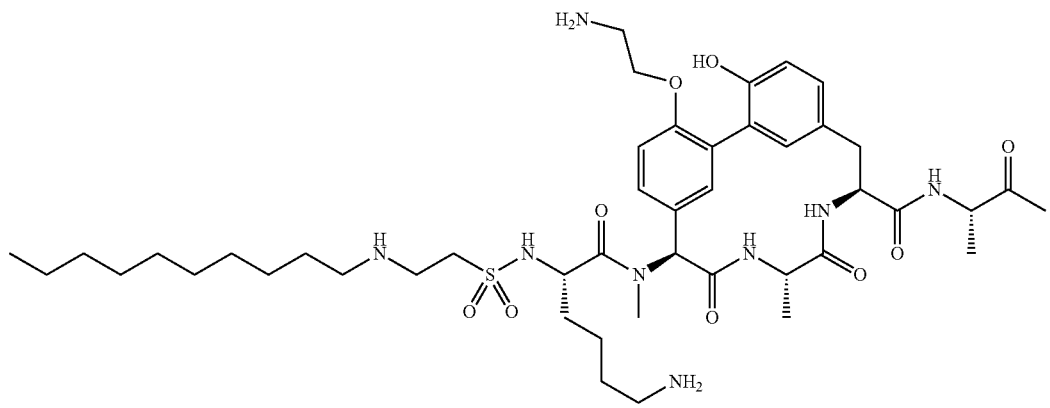

216

Compound 216 was synthesized from Compound 216A using the LiOH hydrolysis, HATU coupling conditions, and TFA Boc-deprotection similar to Compound 115 and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.735 min, (M+H)$^+$=901.6.
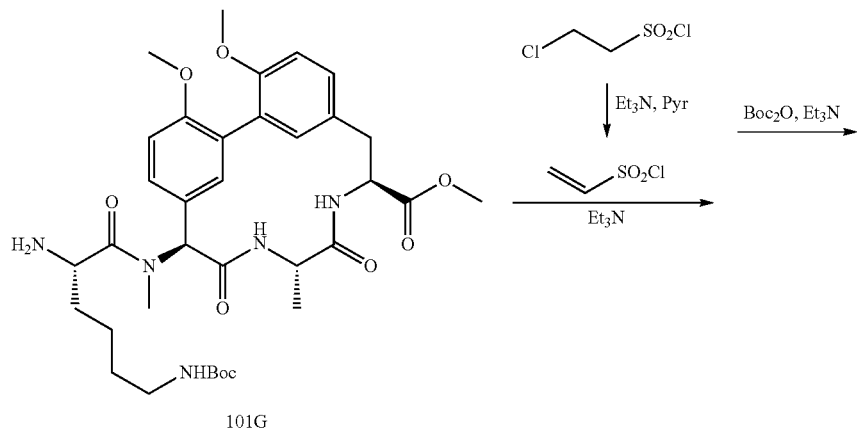
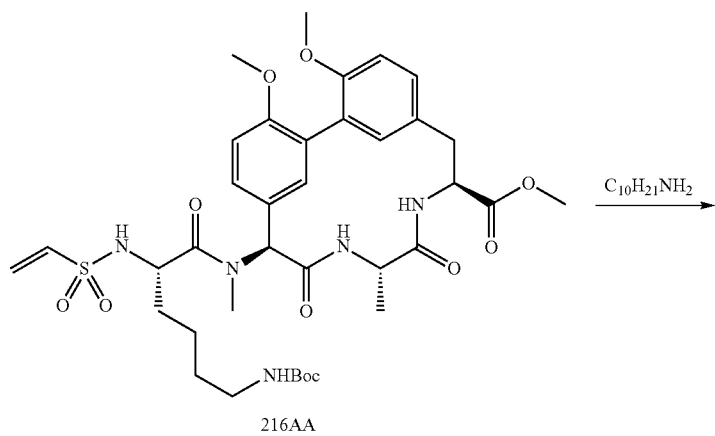
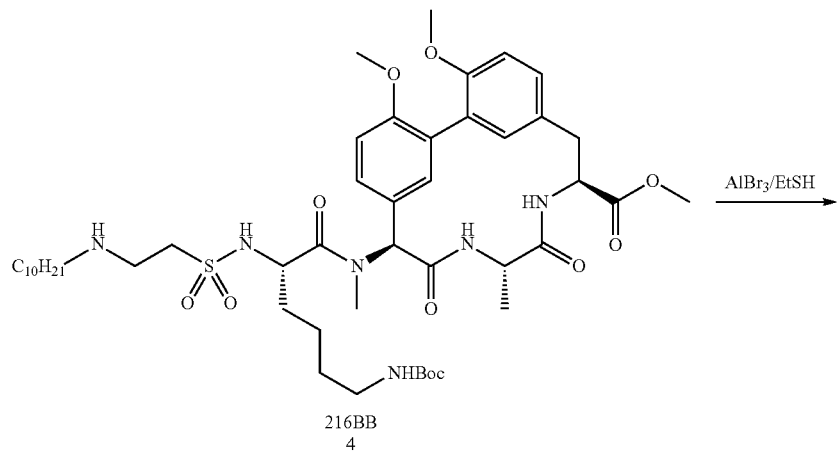

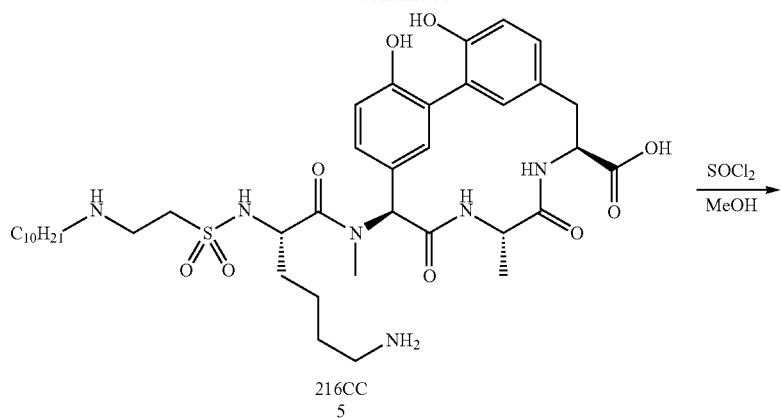
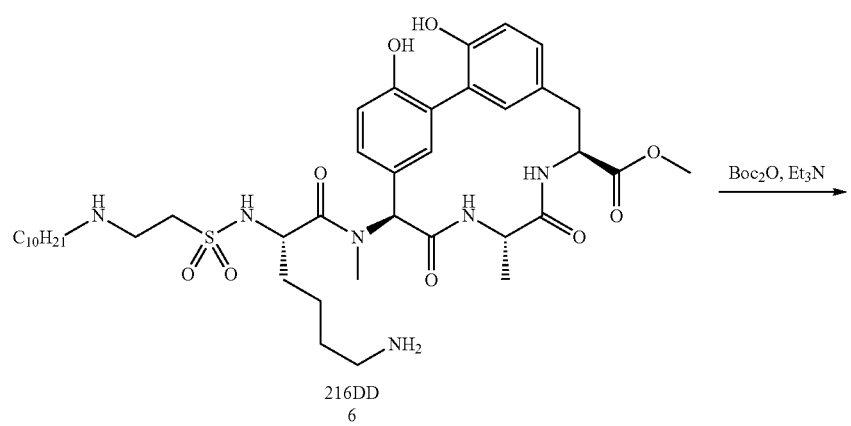
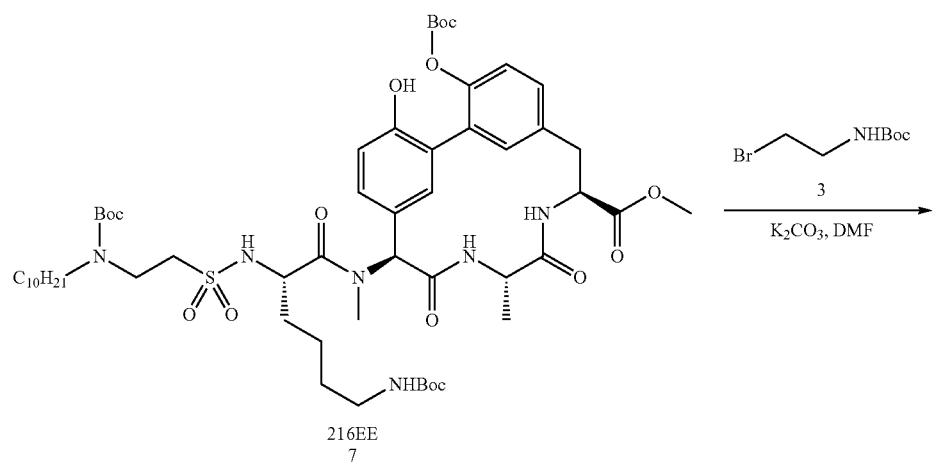

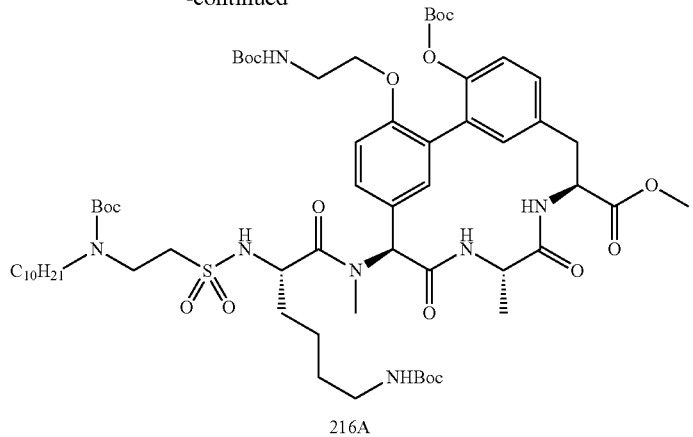

216A

Synthesis of Compound 216A: To a solution of 2-chlorosulfonyl chloride (3.2 mL, 30.7 mmol) in DCM (100 mL) was added pyridine (4.85 g, 61.3 mmol), the mixture was stirred for 1 h at −78° C. The mixture was then warmed to 0° C. and stirred for another 20 mins. The volatiles were removed to afford ethenesulfonyl chloride, which was used directly in next step.

To a solution of Compound 101G (3.0 g, 4.4 mmol) and Et$_3$N (1.83 mL, 13.2 mmol) in DCM (50 mL), was added ethenesulfonyl chloride (1.1 g, 8.8 mmol) at 0° C. and the mixture was stirred at the same temperature for 1 h. The reaction mixture was diluted with DCM (100 mL), which sequentially washed by 2N HCl, saturated NaHCO$_3$ solution and brine (each 100 mL). The organic layer was then dried over Na$_2$SO$_4$, and concentrated. The residue was purified by flash column chromatography to afford Compound 216AA (2.5 g, 73.6% yield) as a yellow solid.

To a solution of Compound 216AA (2.5 g, 3.23 mmol) in MeOH (30 mL) was added 1-aminodecane (0.61 g, 3.88 mmol) at 0° C. and the mixture was warmed and stirred at room temperature for 16 h. The volatiles were removed and the residue was purified by flash column chromatography to afford Compound 216BB (2.4 g, 79.8% yield) as a yellow oil.

Compound 216BB was treated according to General Method 4 (AlBr$_3$ deprotection) to afford Compound 216CC (800 mg, 39% yield) as a white solid after HPLC purification.

To a solution of Compound 216CC (800 mg, 1.01 mmol) in MeOH (15 mL) was added thionyl chloride (241 mg, 2.03 mmol) at 0° C., and the mixture was stirred at 75° C. for 1.5 h. The volatiles were removed to afford Compound 216DD (810 mg, 99.5% yield) as a white solid.

To a solution of Compound 216DD (200 mg, 0.25 mmol) in dioxane (10 mL) was added Et$_3$N (126 mg, 1.25 mmol) and Boc$_2$O (163 g, 0.75 mmol) sequentially at 0° C. and the mixture was warmed and stirred at room temperature for 16 h. The volatiles were removed and the residue was added with H$_2$O (30 mL), which was extracted by EtOAc (2×30 mL). The combined organic layers were washed with brine (50 mL), dried over Na$_2$SO$_4$, and concentrated. The residue was purified by HPLC to afford Compound 216EE (75 mg, 27.8% yield) as a white solid.

To a solution of Compound 216EE (70 mg, 0.063 mmol) in DMF (0.5 mL) was added K$_2$CO$_3$ (26 mg, 0.19 mmol) and tert-butyl (2-bromoethyl)carbamate (43 mg, 0.19 mmol) and the mixture was stirred at room temperature for 16 h. The reaction was added with iced water (20 mL), which was extracted with EtOAc (2×20 mL). The combined organic layers were washed with brine, dried over Na$_2$SO$_4$, concentrated. The residue was purified by flash chromatograph to afford Compound 216A as a white solid (44 mg, 55.6% yield). LCMS (5-95 AB, ESI): RT=1.227, M+Na$^+$=1268.5.

Example 116: Synthesis of Compound 217

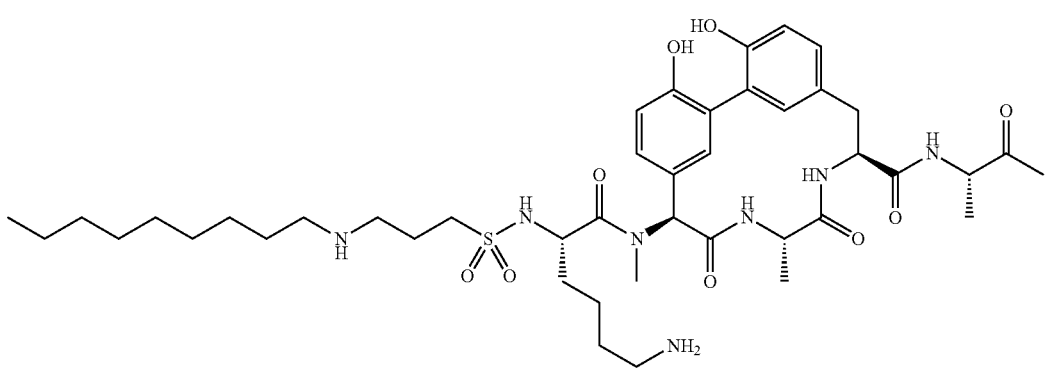

217

Compound 217 was synthesized in a manner similar to Compound 163C from Compound 101G and benzyl (3-(chlorosulfonyl)propyl)(nonyl)carbamate and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.768 min, (M+H)$^+$=858.4.

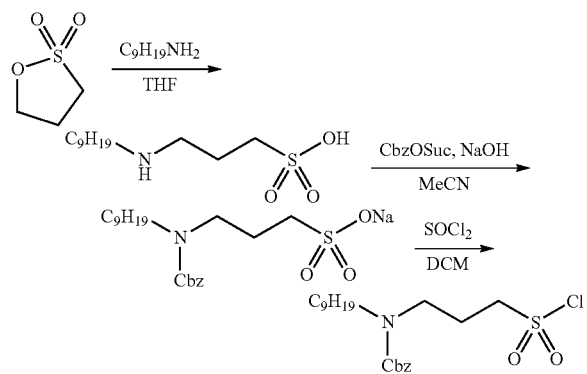

The synthesis of benzyl (3-(chlorosulfonyl)propyl)(nonyl)carbamate: To a solution of 1,2-oxathiolane 2,2-dioxide (4.0 g, 32.8 mmol) in THF (25 ml) was added nonylamine (4.9 g, 34.4 mmol) and the mixture was stirred at refluxed temperature for 2 h. The reaction was then cooled to room temperature and the resulting solid was collected, which was washed with acetone/EtOH (50 mL, 1:1) and dried in vacuum, to afford 3-(nonylamino)propane-1-sulfonic acid (3.7 g, 37% yield).

To a solution of 3-(nonylamino)propane-1-sulfonic acid (500 mg, 1.9 mmol) in water (4 mL) was added sodium hydroxide (83 mg, 2.1 mmol) and CbzOSuc (516 mg, 2.1 mmol) and the mixture was stirred at room temperature for 4 h. The volatiles were removed and the residue was added with acetone (10 mL), which was heated under reflux temperature for 20 min. The mixture was then cooled to room temperature and the solid was collected, which was washed with acetone and dried overnight in the vacuum, to afford sodium 3-(((benzyloxy)carbonyl)(nonyl)amino)propane-1-sulfonate (550 mg, 73% yield) as a white solid.

To a solution of sodium 3-(((benzyloxy)carbonyl)(nonyl)amino)propane-1-sulfonate (500 mg, 1.9 mmol) in DCM (10 mL) was added a drop of DMF and SOCl$_2$ (83 mg, 2.1 mmol) and the mixture was stirred at 50° C. for 2 h. The volatiles were removed and the residue was purified by silica chromatography to afford benzyl (3-(chlorosulfonyl)propyl)(nonyl)carbamate (200 mg, 35%) as a colorless oil.

Example 117: Synthesis of Compound 218

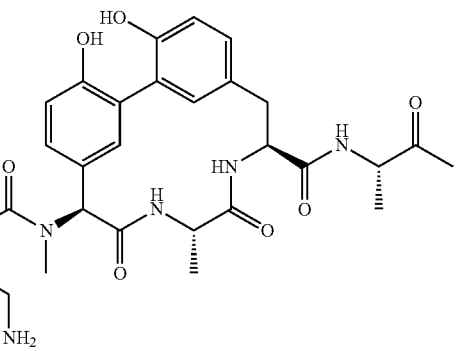

Compound 218 was synthesized using similar procedures as described for Compound 163 and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.773 min, (M+H)$^+$=830.4.

Example 118: Synthesis of Compound 219

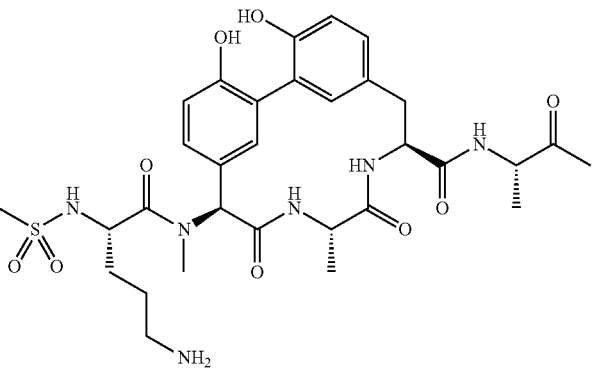

Compound 219 was synthesized using similar procedures as described for Compound 163C and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.771 min, (M+H)$^+$=844.5.

Example 119: Synthesis of Compound 220

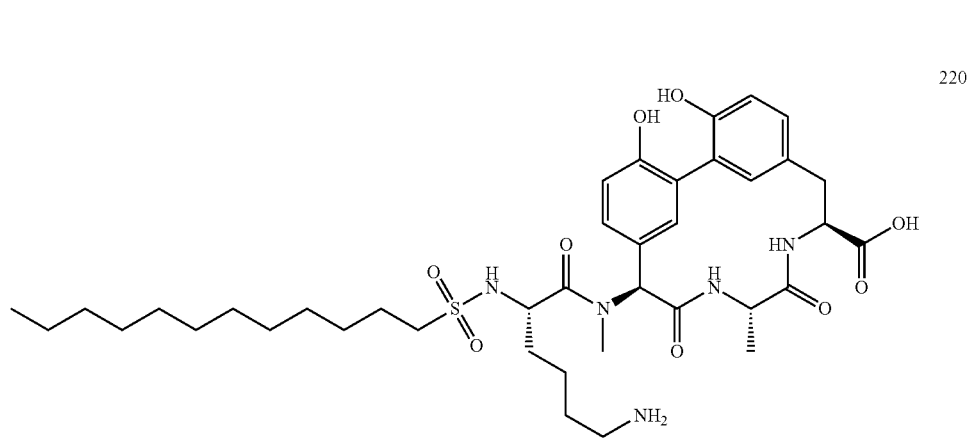 [SMILES: CCCCCCCCCCCCS(=O)(=O)N[C@@H](CCCCN)C(=O)N(C)[C@@H]1C(=O)N[C@@H](C)C(=O)N[C@H](C(=O)O)Cc2ccc(O)c(c2)-c2cc1ccc2O]

Compound 220 was synthesized using similar procedures as described above from dodecane-1-sulfonyl chloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.878 min, (M+H)$^+$=774.6.

Example 120: Synthesis of Compound 221

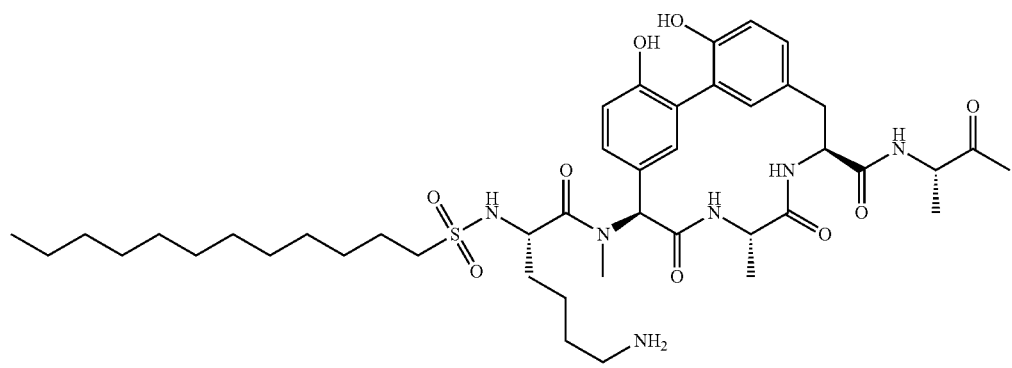

Compound 221 was synthesized in a manner similar to Compound 163 from dodecane-1-sulfonyl chloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.866 min, (M+H)$^+$=843.5.

Example 121: Synthesis of Compound 222

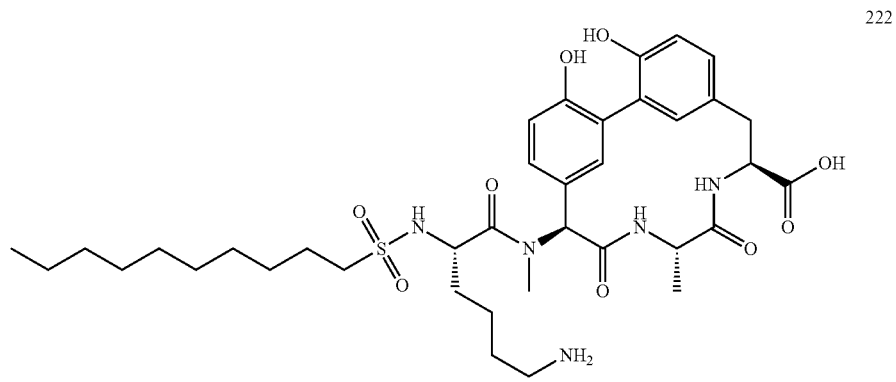 [SMILES: CCCCCCCCCCS(=O)(=O)N[C@@H](CCCCN)C(=O)N(C)[C@@H]1C(=O)N[C@@H](C)C(=O)N[C@H](C(=O)O)Cc2ccc(O)c(c2)-c2cc1ccc2O]

Compound 222 was synthesized using similar procedures as described above from decane-1-sulfonyl chloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.827 min, (M+H)$^+$=746.4.

Example 122: Synthesis of Compound 223

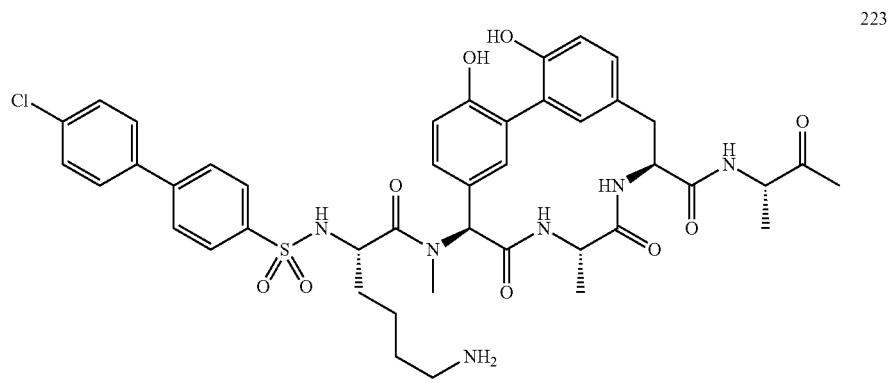 [SMILES: CC(=O)[C@H](C)NC(=O)[C@@H]1Cc2ccc(O)c(c2)-c2cc(ccc2O)[C@H](N(C)C(=O)[C@H](CCCCN)NS(=O)(=O)c2ccc(-c3ccc(Cl)cc3)cc2)C(=O)N[C@@H](C)C(=O)N1]

Compound 223 was synthesized using similar procedures as described above from Compound 101G and 4'-chloro-[1,1'-biphenyl]-4-sulfonyl chloride and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.795 min, (M+H)$^+$=861.3.

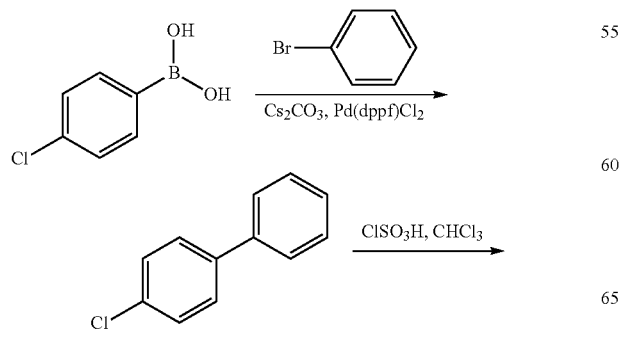

-continued

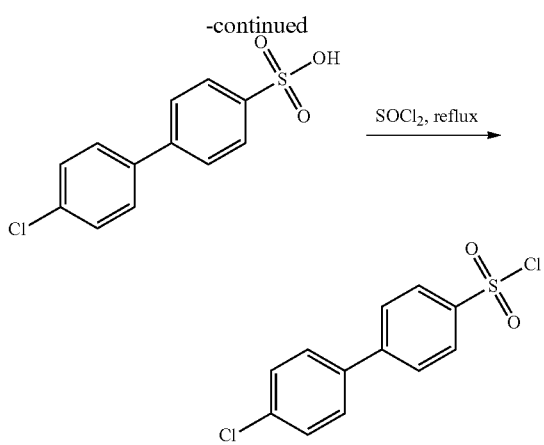

The synthesis of 4'-chloro-[1,1'-biphenyl]-4-sulfonyl chloride: A mixture of (4-chlorophenyl)boronic acid (13 g, 84 mmol) and bromobenzene (11 g, 70 mmol), Cs$_2$CO$_3$ (45 g, 140 mmol), Pd(dppf)Cl$_2$ (5.1 g, 7 mmol) in 1,4-dioxane/H$_2$O (165 mL, v/v=10/1) was stirred at 90° C. under N$_2$ for 16 h. The mixture was added with water (150 mL), which was extracted by EtOAc (3×200 mL). The combined organic layers were washed with brine (300 mL), dried over Na$_2$SO$_4$, and concentrated. The residue was purified by silica gel column chromatography to afford 4-chloro-1,1'-biphenyl (13 g, 98.5% yield) as a yellow solid.

To a solution of 4-chloro-1,1'-biphenyl (10.5 g, 55.5 mmol) in chloroform (250 mL) was added ClSO$_3$H (9.72 g, 83.3 mmoL) dropwise and the mixture was stirred at room temperature for 4 h. The resulting precipitate was collected, which was oven-dried at 40° C. to a constant weight to afford 4'-chloro-[1,1'-biphenyl]-4-sulfonic acid (8.95 g, 60% yield) as a pale green solid, which was used directly in the next step.

To a solution of (8.95 g, 33.3 mmol) in thionyl chloride (100 ml) was added DMF (0.5 mL) and the mixture was stirred at refluxed temperature for 4 h. The reaction was then cooled to room temperature and the volatiles were removed. The resulting residue was re-crystallized from hexane/EtOAc to afford 4'-chloro-[1,1'-biphenyl]-4-sulfonyl chloride (6.8 g, 71.4% yield) as a pale green solid.

Example 123: Synthesis of Compound 224

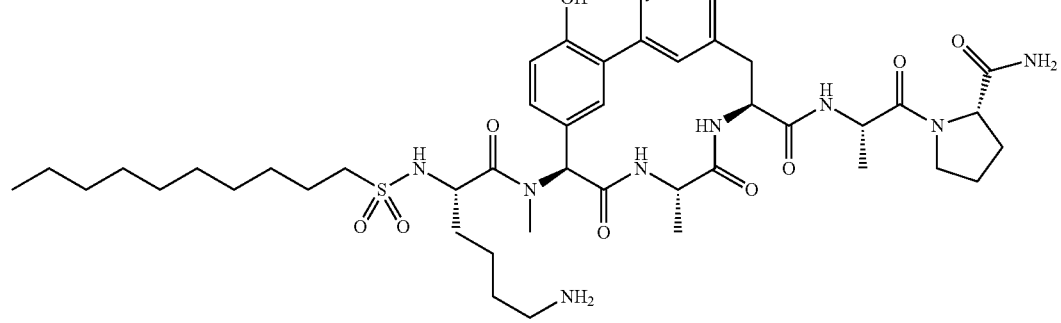

224

Compound 224 was synthesized using similar procedures as described above and isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) $t_R$=0.805 min, (M+H)$^+$=913.5.

Example 124: Synthesis of Compound 225

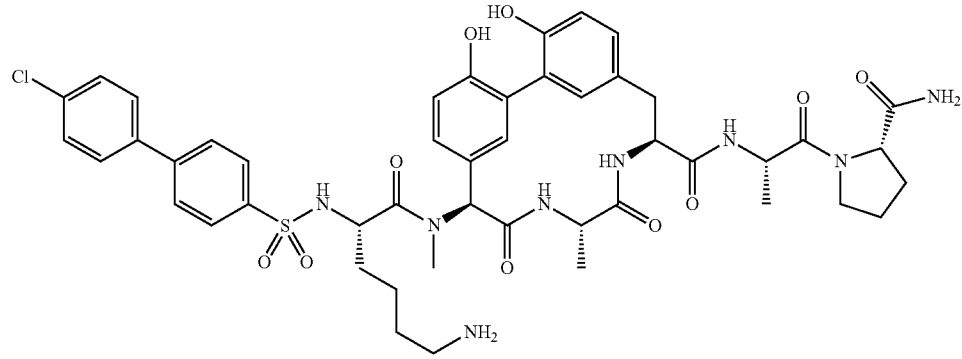

225

Compound 225 was synthesized using similar procedures as described for Compound 223 and was isolated as the formic acid salt. LCMS (ESI): (5% AcCN/H$_2$O, 0.7 min; then 95% AcCN/H$_2$O, 0.4 min; 1.5 mL/min, Merck RP-18e, 2×25 mm) t$_R$=0.769 min, (M+H)$^+$=959.1.

Example 125: Synthesis of Compound 226

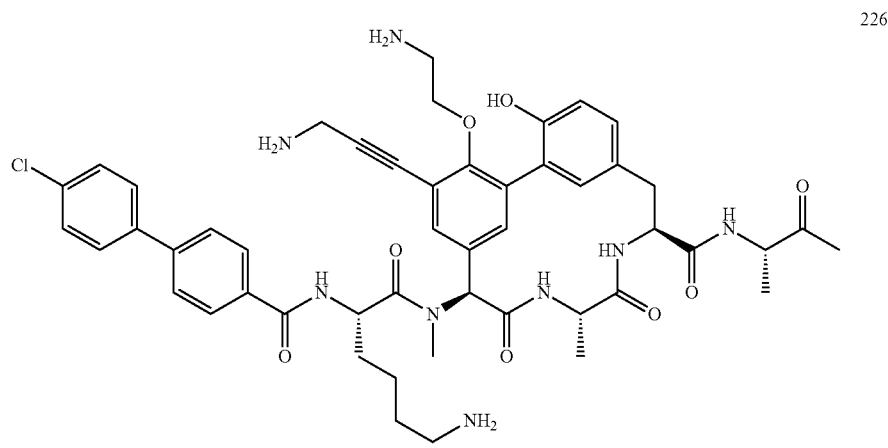 [SMILES: CC(=O)[C@H](C)NC(=O)[C@@H]1Cc2ccc(O)c(c2)-c2cc(cc(C#CCN)c2OCCN)[C@H](N(C)C(=O)[C@H](CCCCN)NC(=O)c2ccc(-c3ccc(Cl)cc3)cc2)C(=O)N[C@@H](C)C(=O)N1]

Compound 226 was synthesized in a similar manner to Compound 115 using the LiOH hydrolysis, HATU coupling, and TFA Boc-deprotection conditions starting from Compound 226A. MS+ 921.1

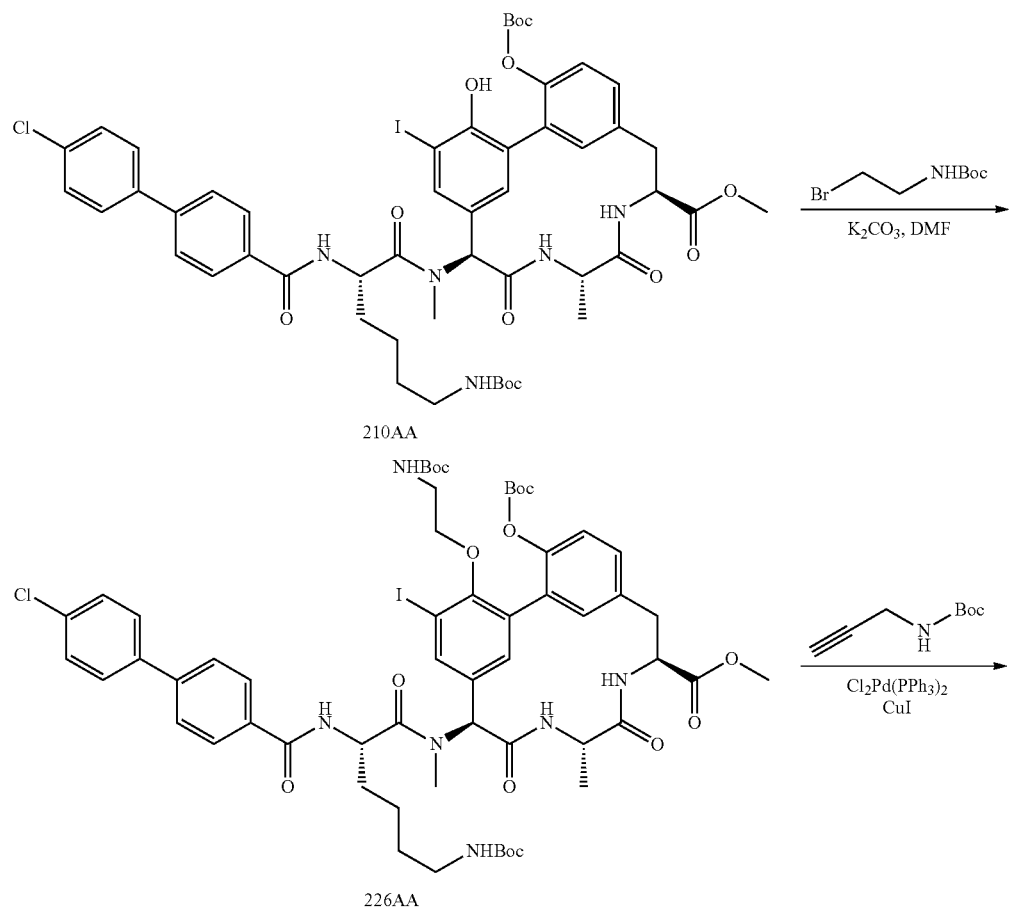

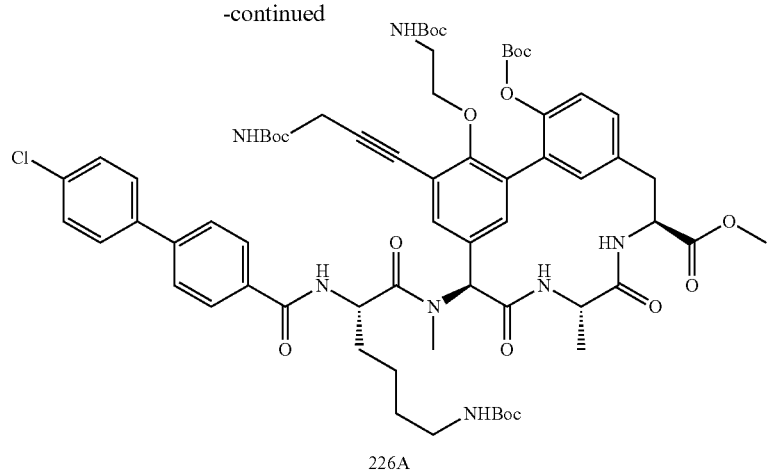

226A

The synthesis of Compound 226AA: To a solution of Compound 210AA (0.178 mmol, 195 mg) in DMF (5 mL) was added potassium carbonate (0.356 mmol, 49.2 mg) and t-butyl N-(2-bromoethyl)carbamate (0.534 mmol, 121 mg). The reaction mixture was stirred at room temperature for 4 days. The reaction mixture was diluted with EtOAc, and washed with brine (3×). The organic layer was dried and concentrated. The residue was purified on silica eluted with 0 to 100% EtOAc in DCM to afford Compound 226AA (172 mg, 78%).

To a mixture of Compound 226AA (0.138 mmol, 172 mg) and tert-butyl N-prop-2-ynylcarbamate (0.277 mmol, 43.0 mg) in DMF (5 mL) under argon was added diisopropylamine (1.38 mmol, 140 mg, 0.195 mL), bis(triphenylphosphine)palladium(II) dichloride (0.0138 mmol, 9.72 mg), and cuprous iodide (0.0277 mmol, 5.28 mg). The reaction vial was sealed and heated at room temperature for 18 hours. The reaction mixture was dilute, with EtOAc and washed with water (3×). The organic layer was concentrated and the residue was purified on silica eluted with 0 to 100% EtOAc in DCM to afford Compound 226A (175 mg, 99%).

Example 126: Synthesis of Compound 227

Compound 227 was prepared using the coupling method, DMP oxidation, and Boc-group hydrolysis as described for Compound 139 from Compound 104E and tert-butyl 5-((3S)-3-amino-2-hydroxybutanamido)-1H-pyrazole-1-carboxylate and was isolated as the formic acid salt.

Method LCMS (5-95 AB, ESI) refers to the following LC-MS conditions for analysis: Using acetonitrile (0.02% TFA) and H$_2$O (0.04% TFA), the HPLC gradient is 5% AcCN/H$_2$O-95% AcCN/H$_2$O, 0.7 min, then 95% AcCN/H$_2$O, 0.4 min; 1.5 mL/min, MERCK RP-18e, 2×25 mm). Data for Compound 227: LCMS (5-95 AB, ESI): t$_R$=0.780, (M+H)$^+$=920.6.

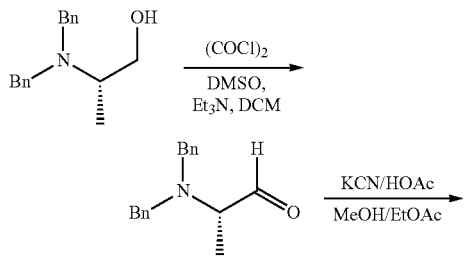

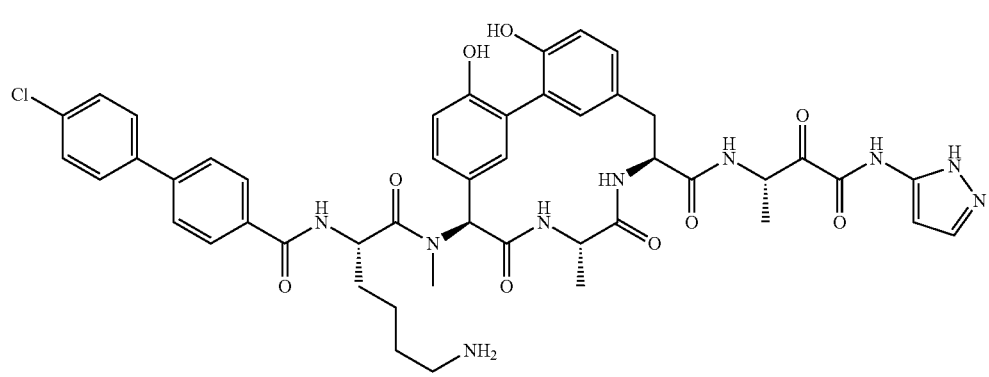

227

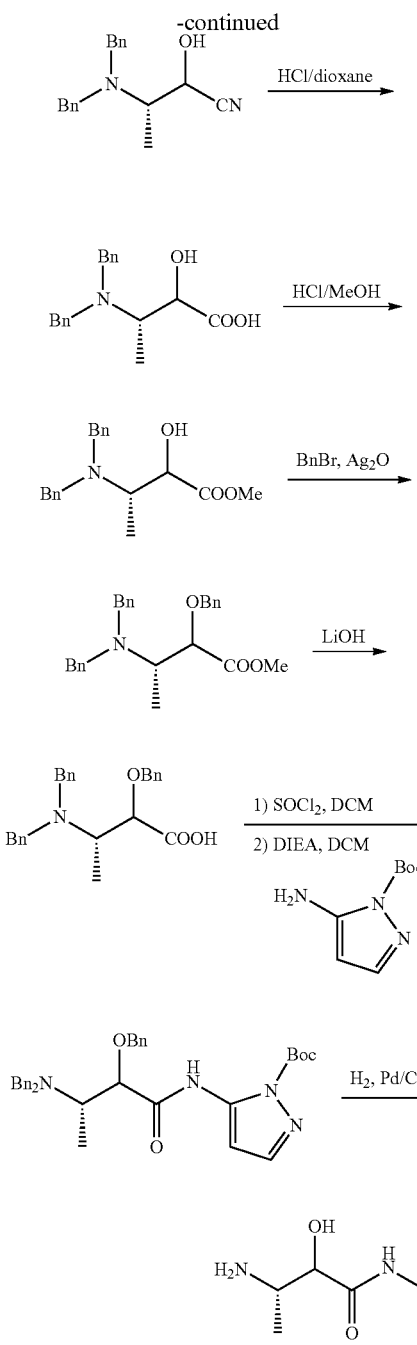

Synthesis of tert-butyl 5-((3 S)-3-amino-2-hydroxybutanamido)-1H-pyrazole-1-carboxylate: (S)-2-(dibenzylamino)propan-1-ol (20 g, 79 mmol) was subject to Standard Swern oxidation procedure as described for tert-butyl methyl(3-oxopropyl)carbamate (Example 105) to afford (S)-2-(dibenzylamino)propanal (20 g, quantitative yield) as colorless oil, which was used directly in the next step.

To a solution of (S)-2-(dibenzylamino)propanal (15 g, 59 mmol) and KCN (4.4 g, 65 mmol) in MeOH/EtOAc (100 mL, v/v=1/1) was added AcOH (14.3 g, 71 mmol) and the mixture was stirred at room temperature for 2.5 h. The volatiles were removed and the residue was re-dissolved with DCM (200 mL), which was washed with brine (2×150 mL). The organic layer was dried over $Na_2SO_4$ and concentrated to give (3S)-3-(dibenzylamino)-2-hydroxybutanenitrile (16 g, 96%) as a white solid, which was used directly in the next step.

To a solution of (3S)-3-(dibenzylamino)-2-hydroxybutanenitrile (14 g, 50 mmol) in dioxane (50 mL) was added concentrated HCl (50 mL) at room temperature and the reaction was stirred at 100° C. for 6 h. The volatiles were removed to give (3S)-3-(dibenzylamino)-2-hydroxybutanoic acid (16.8 g, quantitative yield) as a pale solid, which was used directly in the next step.

A mixture of (3S)-3-(dibenzylamino)-2-hydroxybutanoic acid (16.8 g, 50 mmol) in 4N HCl/MeOH (80 mL) was stirred at room temperature for 16 h. The volatiles were removed and the residue was re-dissolved with EtOAc (300 mL), which was washed with the saturated $NaHCO_3$ and brine (each 200 mL). The organic layer was dried over $Na_2SO_4$, and concentrated. The residue was purified by silica column chromatography to give (3S)-methyl 3-(dibenzylamino)-2-hydroxybutanoate (12 g, 69% yield) as colorless oil.

To a solution of (3S)-methyl 3-(dibenzylamino)-2-hydroxybutanoate (8.0 g, 25.5 mmol) and BnBr (5.2 g, 30.6 mmol) in DMF (20 mL) was added anhydrous $Na_2SO_4$ (8.0 g) and TBAI (1.65 g, 5.11 mmol) at 0° C. and the mixture was stirred at the same temperature for 10 min. $Ag_2O$ (11.8 g, 51.1 mmol) was then added to the above mixture at 40° C. for 16 h. The mixture was filtered and the filtrate was diluted with water (200 mL), which was extracted with EtOAc (3×200 mL). The combined organic layers were washed with brine (500 mL), dried over $Na_2SO_4$, and concentrated. The residue was purified by HPLC to afford (3S)-methyl 2-(benzyloxy)-3-(dibenzylamino)butanoate (6.2 g, 60% yield) as a white solid. $^1$H NMR (400 MHz, $CDCl_3$) δ 7.49-7.21 (m, 15H), 4.59 (d, J=11.2 Hz, 1H), 4.39 (d, J=11.2 Hz, 1H), 4.07 (d, J=7.6 Hz, 1H), 3.62 (d, J=13.6 Hz, 2H), 3.58 (s, 3H), 3.45 (d, J=13.6 Hz, 2H), 3.22-3.17 (s, 1H), 1.16 (d, J=6.8 Hz, 3H).

Standard ester hydrolysis (LiOH) was applied to (3S)-methyl 2-(benzyloxy)-3-(dibenzylamino)butanoate (1 g, 2.5 mmol) to afford (3S)-2-(benzyloxy)-3-(dibenzylamino)butanoic acid (0.94 g, 98% yield) as a white solid.

To a solution of (3S)-2-(benzyloxy)-3-(dibenzylamino) butanoic acid (400 mg, 1 mmol) in DCM (10 mL) was added $SOCl_2$ (364 mg, 4 mmol) and DMF (20 μL) at 0° C. and the mixture was kept at 50° C. for 2 h. The volatiles were removed to dryness, which was added to a solution of tert-butyl 5-amino-1H-pyrazole-1-carboxylate (94 mg, 0.51 mmol) and DIPEA (99 mg, 0.76 mmol) in DCM (5 mL) at 0° C. The resulting mixture was stirred at room temperature for 1 h. The volatiles were removed and the residue was purified by prep-TLC to afford tert-butyl 5-((3S)-2-(benzyloxy)-3-(dibenzylamino)butanamido)-1H-pyrazole-1-carboxylate (100 mg, 52% yield) as a white solid.

Standard hydrogenation condition (Pd/C, 1 atm of $H_2$) was applied to tert-butyl 5-((3S)-2-(benzyloxy)-3-(dibenzylamino)butanamido)-1H-pyrazole-1-carboxylate to afford tert-butyl 5-((3 S)-3-amino-2-hydroxybutanamido)-1H-pyrazole-1-carboxylate, which was used directly in the next step.

Example 127: Synthesis of Compound 228

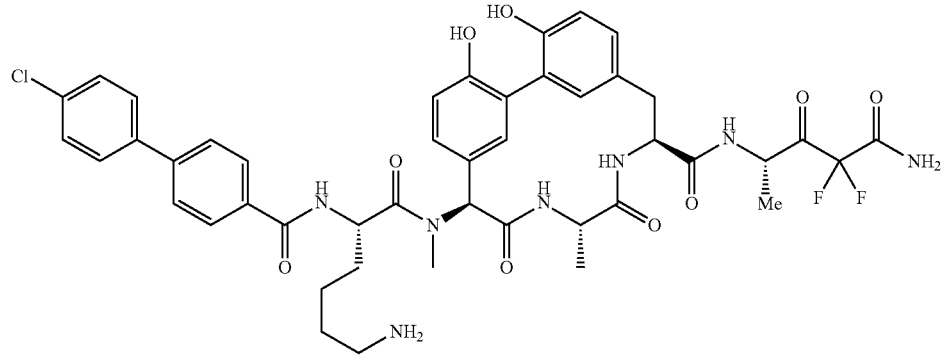

228

Compound 228 was prepared using the DMP oxidation, and Boc-group hydrolysis as described for Compound 139 from Compound 228A to afford the TFA salt after prep-HPLC (8.3 mg). MS (ESI): m/z 922.1 (M+H); HPLC $t_R$ 3.25 min (10% AcCN/H$_2$O-90% AcCN/H$_2$O, 3.0 min, 1.0 mL/min Kinetix C18, 4.8×50 mm).

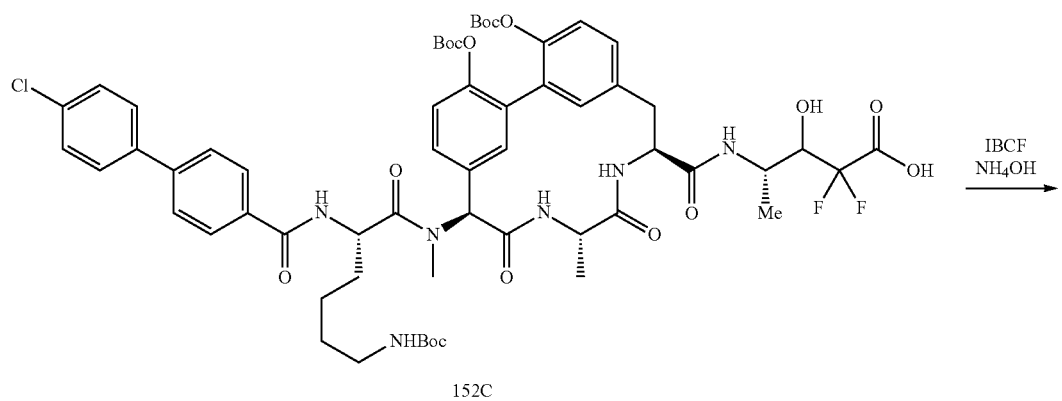

152C

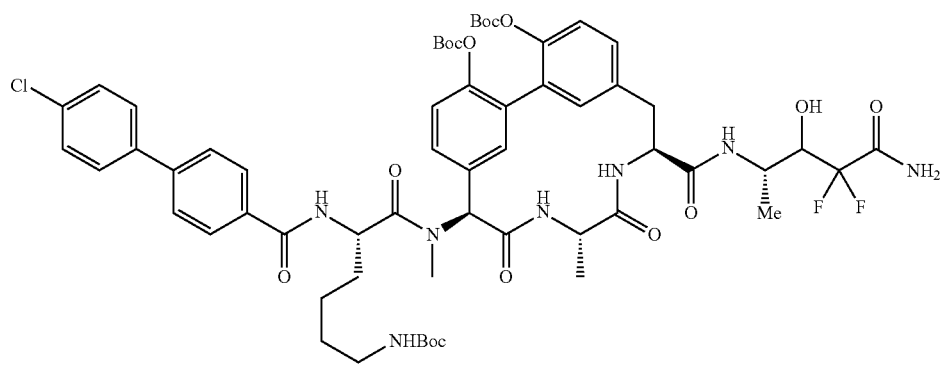

228A

The synthesis of Compound 228A: To a solution of Compound 152C (93 mg, 1 eq, 77 umol) in THF (2.5 mL) at 0° C. was added IBCF (20 uL, 2 eq) and NMM (42 uL, 5 eq) and the solution was allowed to stir for 1 h. A solution of 1.4M NH$_4$OH in THF (14.8 M aqueous solution diluted in THF, 52 uL, 2.5 eq) was added and the solution was allowed to warm to room temperature and stirred for 4 h. The reaction was quenched by the addition of 2% citric acid and the aqueous layer was extracted 3× with EtOAc. The combined organic layers were washed with half saturated NaHCO$_3$ solution then dried over sodium sulfate and concentrated. The crude material was purified via ISCO column chromatography (0-11% MeOH in DCM) to give Compound 228A (33.7 mg, 36%). MS (ESI): m/z 1206.3 (M+H)$^+$.

Example 128: Synthesis of Compound 229

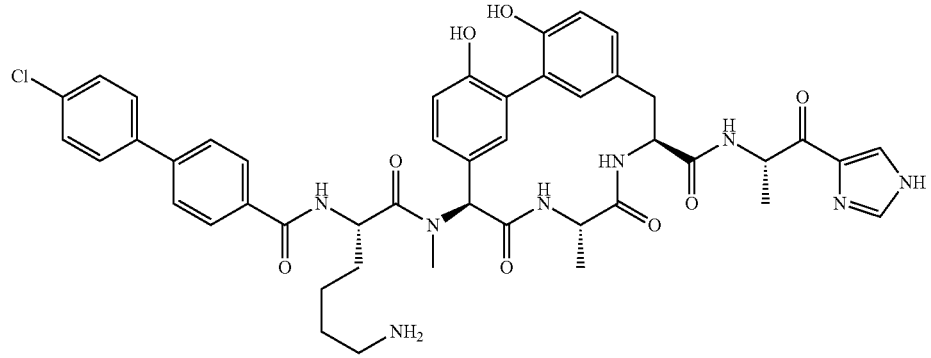

Compound 229 was prepared using the Boc-group hydrolysis (General Method 9) as described for Compound 115 from Compound 229A. MS (ESI): m/z 878.1 (M+H)$^+$; HPLC $t_R$ 3.17 min (10% AcCN/H$_2$O-90% AcCN/H$_2$O, 3.0 min, 1.0 mL/min Kinetix C18, 4.8×50 mm). $^1$H NMR (DMSO, 500 MHz) doubling of resonances indicates isomerization δ 8.97 (d, J=6 Hz, 1H), 8.70 (d, J=8 Hz, 1H), 8.46 (d, J=7.5 Hz, 1H), 8.22 (s, 1H), 7.99 (m, 3H), 7.79 (m, 4H), 7.56 (m, 2H), 6.96 (m, 1H), 6.85 (m, 1H), 6.60 (m, 2H), 6.28 (s, 1H), 5.28 (br s, 1H), 4.85 (m, 1H), 4.71 (m, 1H), 3.09 (br s, 1H), 2.91 (m, 2H), 2.77 (m, 4H), 1.78 (q, J=7H, 2H), 1.59 (m, 2H), 1.46 (m, 1H), 1.33 (d, J=7.5H, 3H), 1.24 (s, 1H), 1.19 (m, 2H), 1.11 (br d, J=6.5H, 1H).

The synthesis of Compound 229A: To a solution of Cbz-Ala-OH (1.5 g, 6.7 mmol, 1.05 eq) in DMF (20 mL) was added sequentially HOBt (1.23 g, 1.2 eq), EDC (615 mg, 1.5 eq), DIEA (4.43 mL, 4 eq) and N,O-dimethylhydroxylamine hydrochloride (615 mg, 1 eq) and the reaction was allowed to stir overnight. After adding 0.5N HCl, the mixture was extracted with EtOAc (3×) then the combined layers were washed with water (2×), saturated NaHCO$_3$ and brine, dried over Na$_2$SO$_4$ and concentrated. The residue was then taken up in DCM, washed 2× with water, dried over Na$_2$SO$_4$ and concentrated to afford (S)-benzyl (1-(methoxy

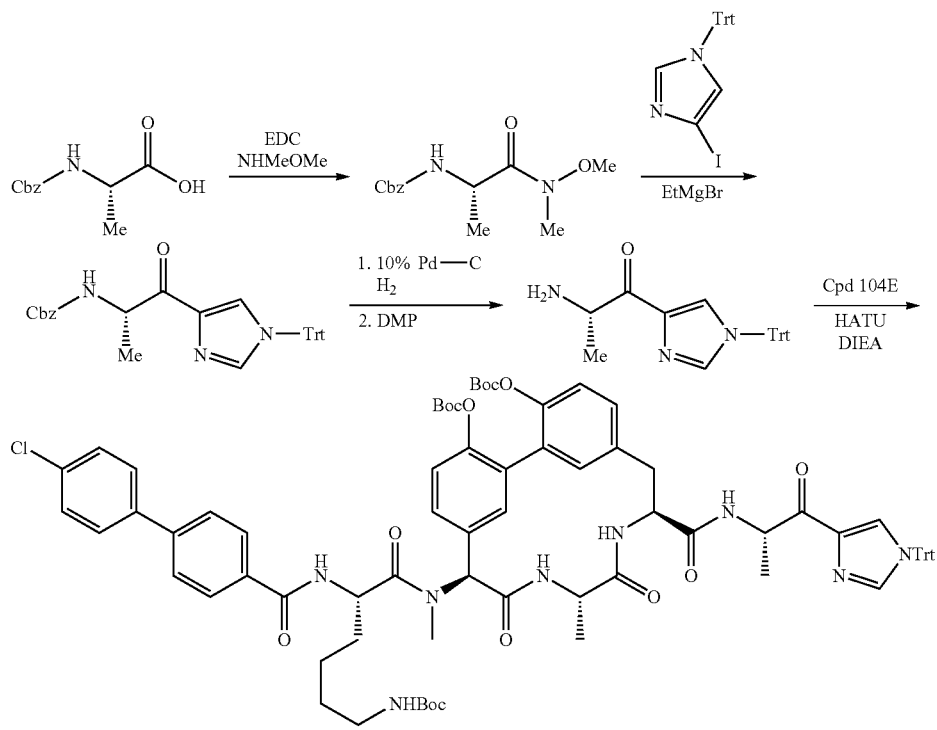

(methyl)amino)-1-oxopropan-2-yl)carbamate, which was used without further purification. MS (ESI): m/z 265.0 (M+H)+.

To a solution of (S)-benzyl (1-(methoxy(methyl)amino)-1-oxopropan-2-yl)carbamate (50 mg, 0.19 mmol, 1 eq) in anhydrous DCM (2 mL) under N₂ in a flame dried flask at −20° C. was added 14% iPrMgBr in THF (197 uL, 1 eq) dropwise. In a second flame dried flask under N₂, 4-iodo-1-tritylimidazole (164 mg, 2 eq), was dissolved in anhydrous DCM (2.5 mL). This solution was treated with EtMgBr (253 uL, 4 eq) at room temperature, stirred for 20 min then transferred dropwise via syringe to the flask containing compound 12 at −20° C. After allowing the reaction to warm to room temperature and stir overnight, it was quenched at −78° C. by adding saturated NH₄Cl. Additional water was added and the aqueous layers were extracted 3× with DCM, and the combined organic layers were dried over Na₂SO₄ and concentrated. The crude material was purified by ISCO column chromatography (0 to 50% EtOAc in Hex) to give (S)-benzyl (1-oxo-1-(1-trityl-1H-imidazol-4-yl)propan-2-yl)carbamate (62.6 mg, 64%). MS (ESI): m/z 516.6 (M+H)+.

To a solution of (S)-benzyl (1-oxo-1-(1-trityl-1H-imidazol-4-yl)propan-2-yl)carbamate (40 mg, 78 umol, 1 eq) in EtOAc (5 mL) was added 10% Pd/C (13 mg, ⅓ by weight) and the mixture was put under an atmosphere of H₂. When the starting material was consumed as judged by TLC, the mixture was filtered through Celite and the filtrate was concentrated to afford (S)-2-amino-1-(1-trityl-1H-imidazol-4-yl)propan-1-one, which was used without further purification. The crude compound was taken up in NMP (1.5 mL) then added to a solution of Compound 104E (54 mg, 52 μmol, 1 eq), HATU (29 mg, 1.5 eq) and DIEA (43 μL, 5 eq) in NMP (1.5 mL). The reaction was allowed to stir overnight then 2% citric acid was added and the aqueous was extracted 3× with EtOAc. The combined organic layers were washed with water (2×), and brine then dried over sodium sulfate and concentrated. The residue was then taken up in DCM, washed with water (3×) and brine, dried over Na₂SO₄ and concentrated to give crude Compound 229A, which was used without further purification. MS (ESI): m/z 1420.6 (M+H)+.

Example 129: Synthesis of Compound 230

879.0 (M+H)+; HPLC tR 3.14 min (10% AcCN/H₂O-90% AcCN/H₂O, 3.0 min, 1.0 mL/min Kinetix C18, 4.8×50 mm).

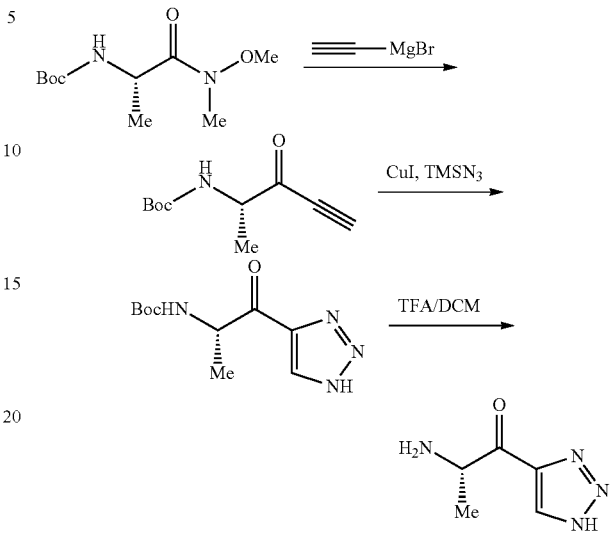

The synthesis of (S)-2-amino-1-(1H-1,2,3-triazol-4-yl)propan-1-one: To a solution of (S)-tert-butyl (1-(methoxy(methyl)amino)-1-oxopropan-2-yl)carbamate (200 mg, 0.87 mmol, 1 eq) in anhydrous THF (7 mL) under N₂ in a flame dried flask at −78° C. was added 0.5 M ethynyl magnesium bromide in THF (6.9 mL, 4 eq) dropwise. The reaction was allowed to stirred for 2.5 hrs at −78° C. then allowed to warm to room temperature and stirred overnight. After quenching by adding saturated 5% citric acid, water was added and the mixture was extracted 2× with EtOAc. The combined organic layers were washed with 5% citric acid, saturated NaHCO₃ and brine, dried over sodium sulfate and concentrated. The crude material was purified by ISCO column chromatography to give (S)-tert-butyl (3-oxopent-4-yn-2-yl)carbamate (120 mg, 70%). MS (ESI): m/z 198.3 (M+H)+.

To a solution of (S)-tert-butyl (3-oxopent-4-yn-2-yl)carbamate (30 mg, 0.15 mmol, 1 eq) in DMF:MeOH (9:1, 1 mL) under N₂ was added CuI (1.5 mg, 5 mol %), and trimethylsilyl azide (30 uL, 1.5 eq). The reaction vial was sealed and heated to 100° C. After stirring overnight the reaction was cooled to room temperature and a dilute brine solution was added. The mixture was extracted 3× with

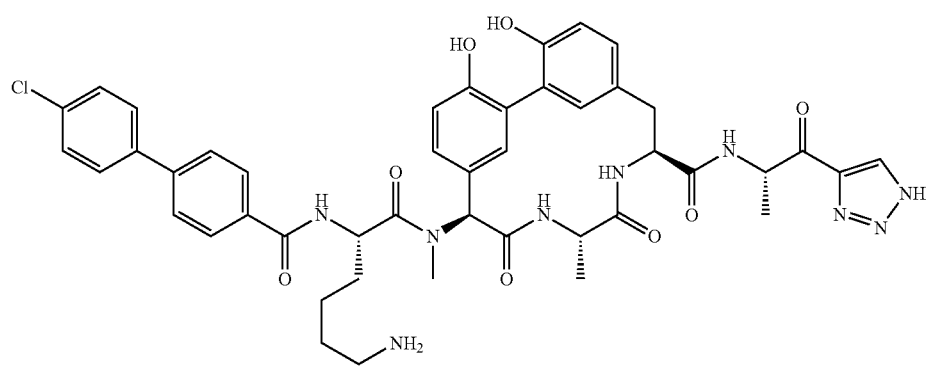

230

Compound 230 was prepared using the amide coupling and Boc-group hydrolysis (General Methods 8 and 9) as described for Compound 115 from (S)-2-amino-1-(1H-1,2,3-triazol-4-yl)propan-1-one in 32% yield. MS (ESI): m/z EtOAc, then the combined organic layers were washed with water (3×) and brine, dried over Na₂SO₄ and concentrated. The crude material was purified by ISCO column chromatography (0 to 70% EtOAc in Hex) to give (S)-tert-butyl (1-oxo-1-(1H-1,2,3-triazol-4-yl)propan-2-yl)carbamate (28 mg, 70%). MS (ESI): m/z 268.6 (M+Na)⁺; ¹H NMR (CDCl₃, 500 MHz) δ 8.22 (d, J=2.5 Hz, 1H), 5.77 (br d, J=7 Hz, 1H), 5.55 (m, 1H), 1.50 (m, 13H).

(S)-tert-butyl (1-oxo-1-(1H-1,2,3-triazol-4-yl)propan-2-yl)carbamate (27 mg, 0.12 mmol) was Boc deprotected with TFA/DCM via General Method 5 to give (S)-2-amino-1-(1H-1,2,3-triazol-4-yl)propan-1-one.

Example 130: Synthesis of Compound 231

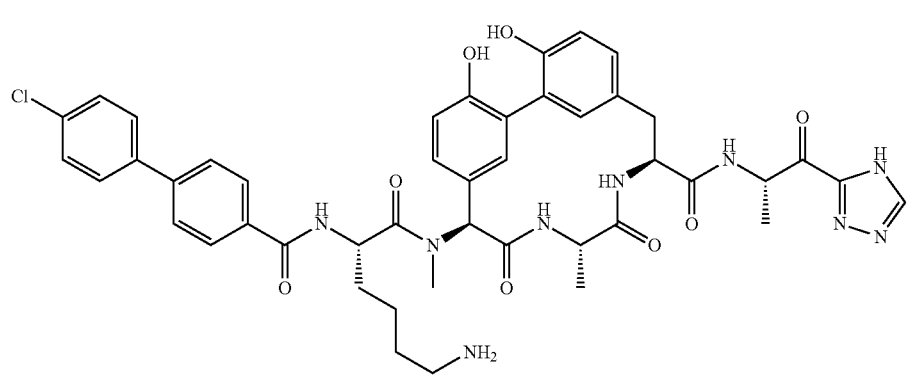

231

Compound 231 was prepared as the formic acid salt using the coupling method, DMP oxidation, and Boc-group hydrolysis as described for Compound 139 from Compound 104E and (2S)-2-amino-1-(4H-1,2,4-triazol-3-yl)propan-1-ol hydrochloride. LCMS (5-95 AB, ESI): t$_R$=0.643, (M+H)⁺=878.6.

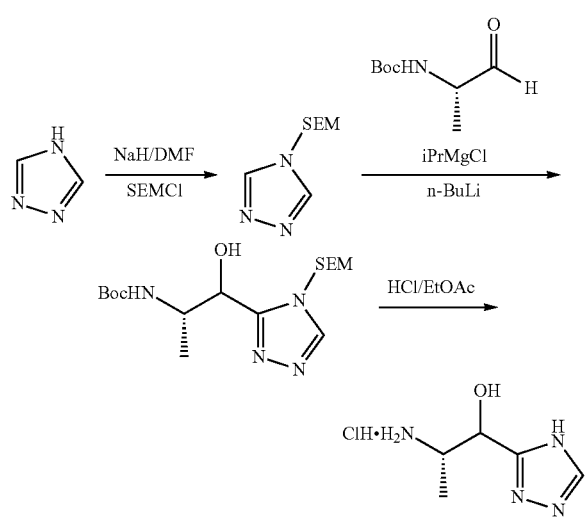

Synthesis of (2S)-2-amino-1-(4H-1,2,4-triazol-3-yl)propan-1-ol hydrochloride: 4H-1,2,4-triazole was subjected to standard SEM-protection conditions. To a solution of 4H-1,2,4-triazole (5.0 g, 72.4 mmol) in DMF (25 mL) was added 60% NaH (4.3 g, 109 mmol) slowly at 0° C. and the mixture was stirred at the same temperature for 1 h. SEM-Cl (14.5 g, 86.9 mmol) was then added to the above mixture dropwise at 0° C. The resulting mixture was warmed and stirred at room temperature for 12 h. The mixture was quenched by saturated NH₄Cl (100 mL), which was extracted with EtOAc (3×100 mL). The combined organic layers were washed with brine (2×300 mL), dried over Na₂SO₄, and concentrated. The residue was purified by silica column chromatography (eluting 5-10% EtOAc in petroleum ether) to give 4-((2-(trimethylsilyl)ethoxy)methyl)-4H-1,2,4-triazole (10 g, 69.4% yield) as colorless oil. LCMS (5-95 AB, ESI): t$_R$=0.895, (M+H)⁺=373.1.

To a solution of 4-((2-(trimethylsilyl)ethoxy)methyl)-4H-1,2,4-triazole (1.73 g, 8.66 mmol) in THF (50 mL) at −75° C. under N₂ was added 2.5M n-BuLi in hexane (2.31 mL, 5.77 mmol). The mixture was stirred at −75° C. for 1.5 h. In a second flask, to a solution of (S)-tert-butyl (1-oxopropan-2-yl)carbamate (1.0 g, 5.77 mmol) in THF (10 mL) at −15° C. under N₂ was added 2M i-PrMgCl in THF (2.89 mL, 5.77 mmol) and the mixture was stirred at −15° C. for 20 min. The second flask mixture was then added to the first flask at −75° C. and the resulting mixture was allowed to warm to room temperature and stirred for 12 h. The reaction was quenched with saturated NH₄Cl (100 mL), which was extracted with EtOAc (3×100 mL). The combined organic layers were washed with brine (200 mL), dried over Na₂SO₄, and concentrated. The residue was purified by silica gel column (eluting with 12% to 20% ethyl acetate in petroleum ether) to afford tert-butyl ((2S)-1-hydroxy-1-(4-((2-(trimethylsilyl)ethoxy)methyl)-4H-1,2,4-triazol-3-yl)propan-2-yl)carbamate (350 mg, 16.3% yield) as colorless oil.

A standard SEM/Boc deprotection conditions were used and is described as follows. To a solution of tert-butyl ((2S)-1-hydroxy-1-(4-((2-(trimethylsilyl)ethoxy)methyl)-4H-1,2,4-triazol-3-yl)propan-2-yl)carbamate (200 mg, 0.54 mmol) in EtOAc (2.5 mL) was added 4M HCl in EtOAc (2.68 mL) at 0° C. and the mixture was stirred at the same temperature for 1.5 h. The volatiles were removed to afford (2S)-2-amino-1-(4H-1,2,4-triazol-3-yl)propan-1-ol hydrochloride (95 mg, 99.1% yield) as a red-pink solid, which was used directly in the next step.

Example 131: Synthesis of Compound 232

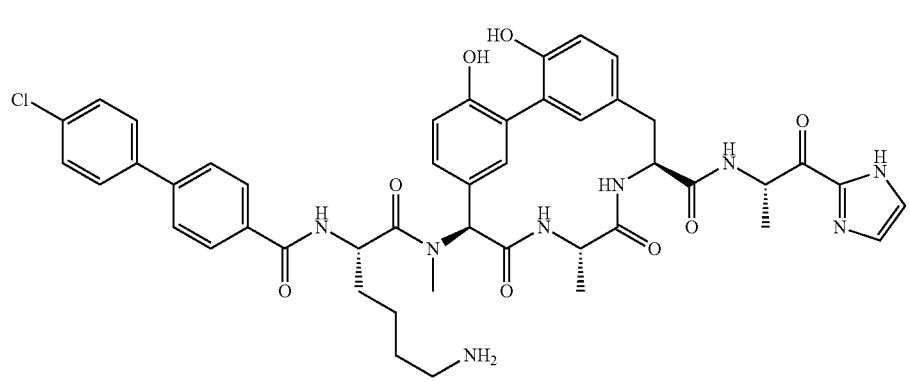

Compound 232 was prepared as the formic acid salt according to General Methods 8 and 9 as described for Compound 115 from Compound 104E and (S)-2-amino-1-(1H-imidazol-2-yl)propan-1-one hydrochloride. LCMS (5-95 AB, ESI): $t_R$=0.643, (M+H)$^+$=877.4.

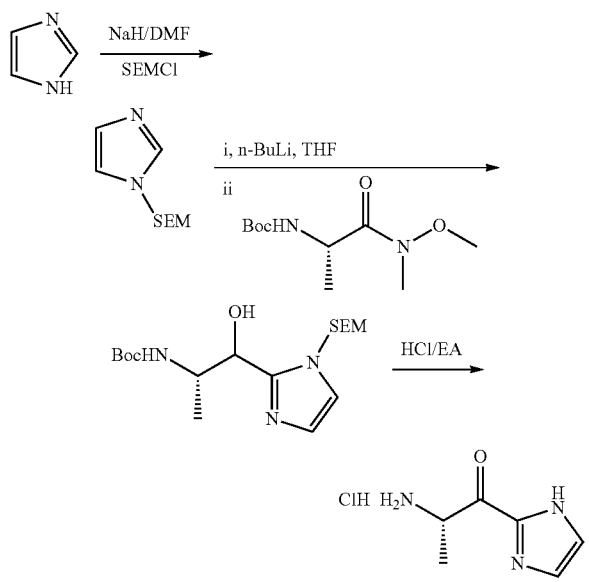

Synthesis of (S)-2-amino-1-(1H-imidazol-2-yl)propan-1-one hydrochloride: Standard SEM protection conditions (Example 130) was applied to 1H-imidazole (2.0 g, 29.4 mmol) to afford 1-((2-(trimethylsilyl)ethoxy)methyl)-1H-imidazole (5.6 g, 96% yield).

To a solution of 1-((2-(trimethylsilyl)ethoxy)methyl)-1H-imidazole (2.13 g, 10.2 mmol) in THF (20 mL) at −78° C. under N$_2$ was added n-BuLi (0.94 mL, 2.15 mmol). The mixture was stirred at −78° C. for 1 h. In a second flask, to a solution of (S)-tert-butyl (1-(methoxy(methyl)amino)-1-oxopropan-2-yl)carbamate (0.5 g, 2.15 mmol) in THF (20 mL) at −15° C. under N$_2$ was added 2M i-PrMgCl in THF (1.1 mL, 2.2 mmol), and the was stirred at −15° C. for 20 min. The contents of the second flask was then added to the first at −78° C., and the resulting mixture was stirred for 3 h. The reaction was quenched with saturated NH$_4$Cl (100 mL), which was extracted with DCM (3×100 mL). The combined organic layers were washed with brine (2×200 mL), dried over Na$_2$SO$_4$, and concentrated. The residue was purified by silica gel column (eluting with 5% to 8% EtOAc in petroleum ether) to give (S)-tert-butyl (1-oxo-1-(1-((2-(trimethylsilyl)ethoxy)methyl)-1H-imidazol-2-yl)propan-2-yl)carbamate (200 mg, 25.2% yield) as a white solid.

Standard Boc/SEM removal condition (Example 130) was applied to (S)-tert-butyl (1-oxo-1-(1-((2-(trimethylsilyl)ethoxy)methyl)-1H-imidazol-2-yl)propan-2-yl)carbamate (150 mg, 0.41 mmol) to afford (S)-2-amino-1-(1H-imidazol-2-yl)propan-1-one hydrochloride (70 mg, 98% yield), which was used directly in the next step.

Example 132: Synthesis of Compound 233

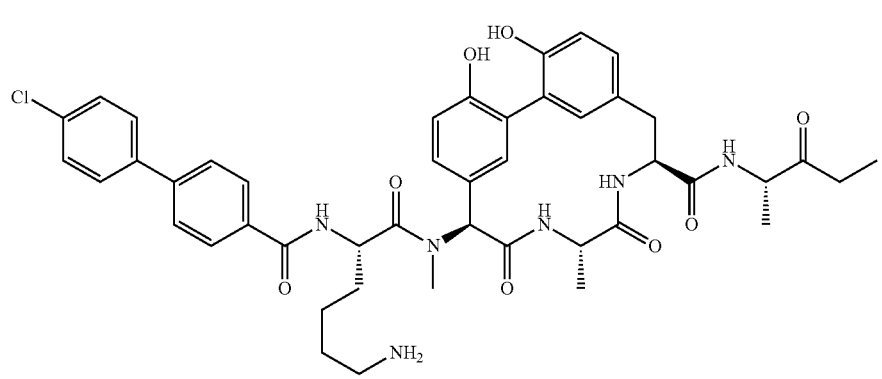

Compound 233 was prepared as the formic acid salt using the same methods as those used to prepare Compound 109. MS (ESI): m/z 840.0 (M+H)+; HPLC $t_R$ 3.44 min (10% AcCN/H$_2$O-90% AcCN/H$_2$O, 3.0 min, 1.0 mL/min Kinetix C18, 4.8×50 mm).

Example 133: Synthesis of Compound 234

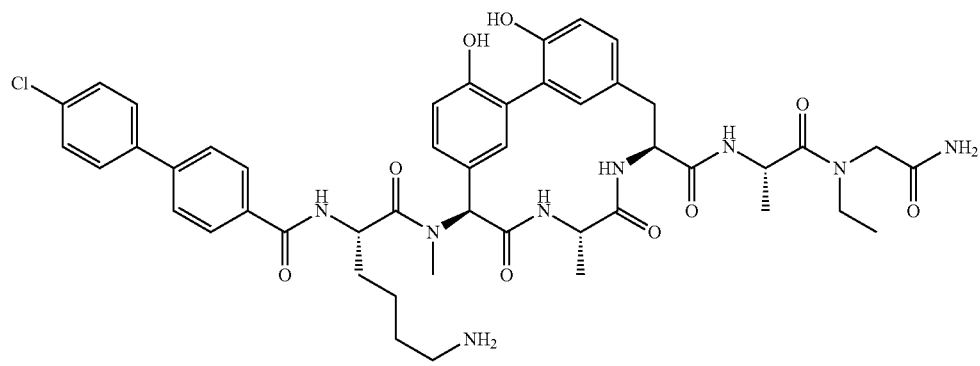

234

Compound 234 was prepared as the formic acid salt using the same solid phase methods as those used to prepare Compound 168. LCMS (5-95 AB, ESI): $t_R$=0.782, (M+H)+=911.4.

Example 134: Synthesis of Compound 235

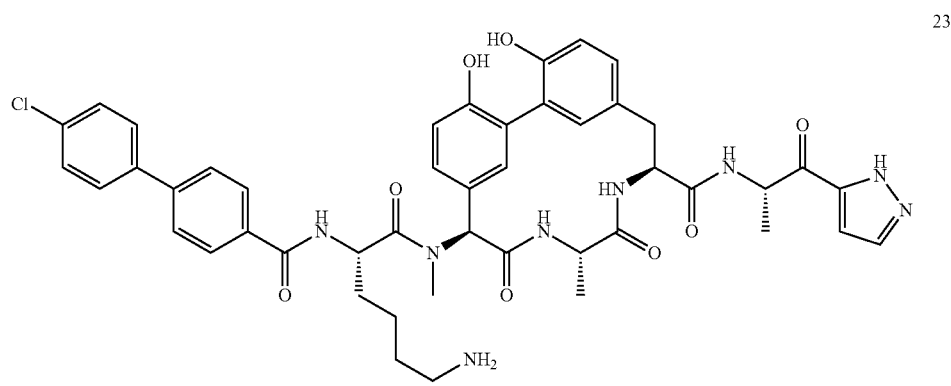 [SMILES: C[C@@H]1NC(=O)[C@@H](N(C)C(=O)[C@H](CCCCN)NC(=O)c2ccc(-c3ccc(Cl)cc3)cc2)c2ccc(O)c(c2)-c2cc(ccc2O)C[C@@H](C(=O)N[C@@H](C)C(=O)c2nnc[nH]2)NC1=O]

235

Compound 235 was prepared as the formic acid salt using the coupling method, DMP oxidation, and Boc-group hydrolysis as described for Compound 139 from Compound 104E and (2S)-2-amino-1-(1H-pyrazol-5-yl)propan-1-ol hydrochloride. LCMS (5-95 AB, ESI): $t_R$=0.800, (M+H)+=877.5.

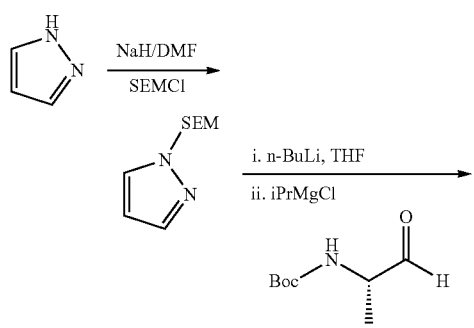

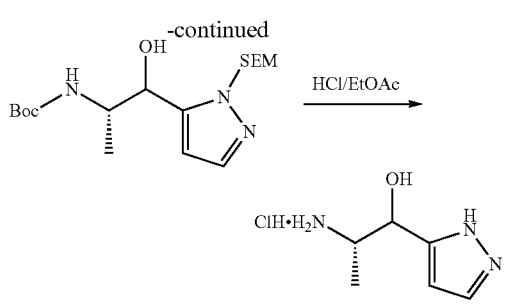

Synthesis of (2S)-2-amino-1-(1H-pyrazol-5-yl)propan-1-ol hydrochloride: To a solution of 60% NaH (2.94 g, 73.4 mmol) in DMF (20 mL), 1H-pyrazole (5.0 g, 73.4 mmol) in DMF (10 mL) was added at 0° C., stirred at the same temperature for 30 min; after that, SEM-Cl (1.22 g, 73.4 mmol) was added slowly to the solution and the mixture was warmed up to room temperature and stirred for 1.5 h. The reaction mixture was then equilibrated between water (200 mL) and EtOAc (200 mL) and the aqueous layer was further extracted by EtOAc (2×150 mL). The combined organic layers were dried over anhydrous sodium sulfate, and concentrated. The residue was purified by chromatography on silica (solvent gradient: 0-2% EtOAc in petroleum ether) to afford 1-((2-(trimethylsilyl)ethoxy)methyl)-1H-pyrazole (6.0 g, 41.2% yield) as colorless oil.

To a solution of 1-((2-(trimethylsilyl)ethoxy)methyl)-1H-pyrazole (2.4 g, 12.1 mmol) in THF (50 mL) at −75° C. under $N_2$ was added 2.5 M BuLi (4.85 mL, 12.1 mmol) in THF, the mixture was stirred at −75° C. for 1.5 h (mixture A). To a solution of (S)-tert-butyl (1-oxopropan-2-yl)carbamate (1.5 g, 8.66 mmol) in THF (10 mL) at −15° C. under $N_2$ was added 2M i-PrMgCl (4.33 mL, 8.66 mmol) in THF, the mixture was stirred at −15° C. for 0.5 h (mixture B). Mixture B was added dropwisely to Mixture A at −75° C. and the resulting mixture was stirred for 12 hr. The mixture was quenched with saturated $NH_4Cl$ (100 mL) and the aqueous layer was extracted with EtOAc (3×100 mL). The combined organic layers were washed with brine, dried over $Na_2SO_4$, and concentrated. The residue was purified by silica gel column (solvent gradient: 0-10% EtOAc in petroleum ether) to give tert-butyl ((2S)-1-hydroxy-1-(1-((2-(trimethylsilyl)ethoxy)methyl)-1H-pyrazol-5-yl)propan-2-yl)carbamate (350 mg, 10.9% yield) as colorless oil.

General Boc removal condition using HCl/EtOAc was followed to afford (2S)-2-amino-1-(1H-pyrazol-5-yl)propan-1-ol hydrochloride.

Example 135: Synthesis of Compound 236

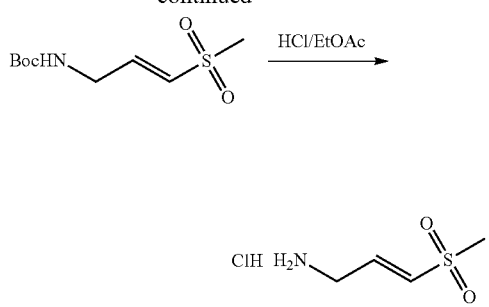

The synthesis of (E)-3-(methylsulfonyl)prop-2-en-1-amine hydrochloride: Under $N_2$ flow and at 0° C., DMP (7.89 g, 18.6 mmol) was added in one portion to a solution of tert-butyl (2-hydroxyethyl)carbamate (2.0 g, 12.4 mmol) in DCM (35 mL). The reaction mixture was stirred for 1.5 h; then quenched with sat. $NaHCO_3/Na_2S_2O_3$ (1:1, 60 mL) and stirred at room temperature for another 0.5 h. The aqueous layer were further extracted with DCM (3×50 mL) and the combined organic layers were washed with brine, dried over $MgSO_4$, and concentrated. The residue was purified on silica gel column (eluting with 5% to 10% ethyl acetate in petroleum ether) to afford tert-butyl (2-oxoethyl)carbamate (1.5 g, 9.4 mmol, 76% yield) as colorless oil.

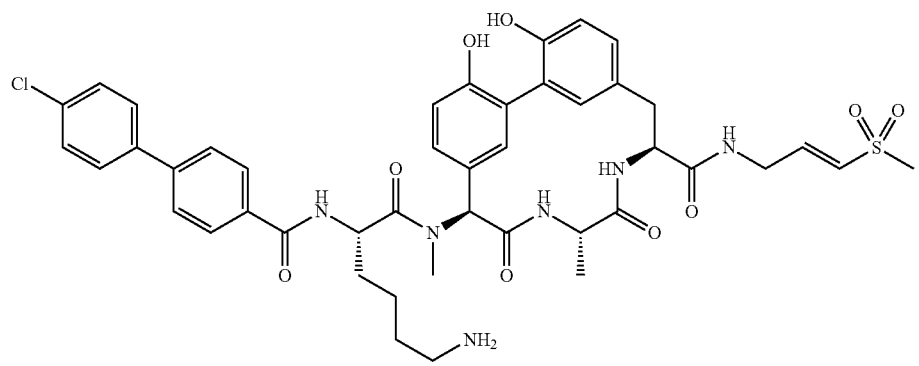

236

Compound 236 was prepared as the formic acid salt using the amide coupling and Boc-group hydrolysis (General Methods 8 and 9) as described for Compound 115 from Compound 104E and (E)-3-(methylsulfonyl)prop-2-en-1-amine hydrochloride. LCMS (5-95 AB, ESI): $t_R$=0.789, $(M+H)^+$=873.3.

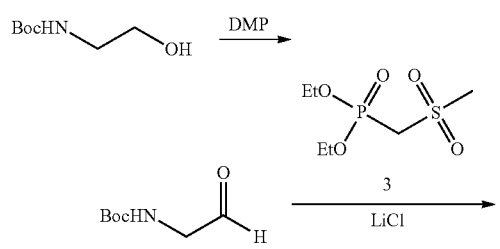

To a solution of diethyl ((methylsulfonyl)methyl)phosphonate (677 mg, 2.94 mmol) in anhydrous MeCN (20 mL) under $N_2$ was added LiCl (166 mg, 3.92 mmol), DIPEA (422 mg, 3.27 mmol) and tert-butyl (2-oxoethyl)carbamate (520 mg, 3.27 mmol) sequentially. The mixture was stirred at room temperature for 1 h. After that, dilute citric acid was added to the reaction and the aqueous layer was extracted by EtOAc (3×30 mL). The combined organics were washed with brine, dried over $Na_2SO_4$, and concentrated. The residue was purified by ISCO column chromatography (0-85% EtOAc in Hex) to give (E)-tert-butyl (3-(methylsulfonyl) allyl)carbamate (300 mg, 1.28 mmol, 39% yield) as a light yellow solid. 1H NMR (400 MHz, $CDCl_3$) δ 6.80 (d, J=15 Hz, 1H), 6.50 (d, J=15 Hz, 1H), 4.85 (brs, 1H, NH), 4.04-3.92 (m, 2H), 2.95 (s, 3H), 1.40 (s, 9H).

General Boc removal condition (HCl/EtOAc) was applied to (E)-tert-butyl (3-(methylsulfonyl)allyl)carbamate to afford (E)-3-(methylsulfonyl)prop-2-en-1-amine hydrochloride.

Example 136: Synthesis of Compound 237

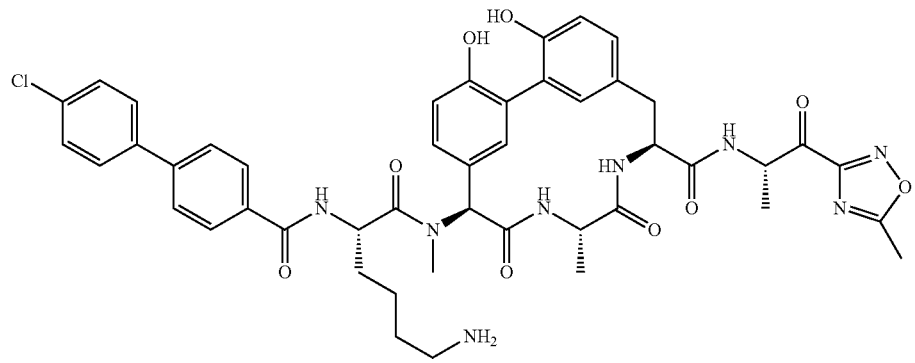

Compound 237 was prepared as the formic acid salt using the coupling method, DMP oxidation, and Boc-group hydrolysis as described for Compound 139 from Compound 104E and (2S)-2-amino-1-(5-methyl-1,2,4-oxadiazol-3-yl)propan-1-ol.

Method LCMS (10-80CD_3MIN) refers to these LC-MS conditions for analysis: Acetonitrile and $H_2O$ (0.05% $NH_3$/$H_2O$) as the mobile phase using a gradient of 10% ACN/$H_2O$—80% ACN/$H_2O$, 2 min, then 80% ACN/$H_2O$, 0.48 min, then 100% $H_2O$, 0.58 min. (flow rate: 1.0 mL/min; Waters Xbridge, 2.1×50 mm).

Data for Compound 237: LCMS (10-80CD_3MIN): $t_R$=1.465, $(M+H)^+$=893.2.

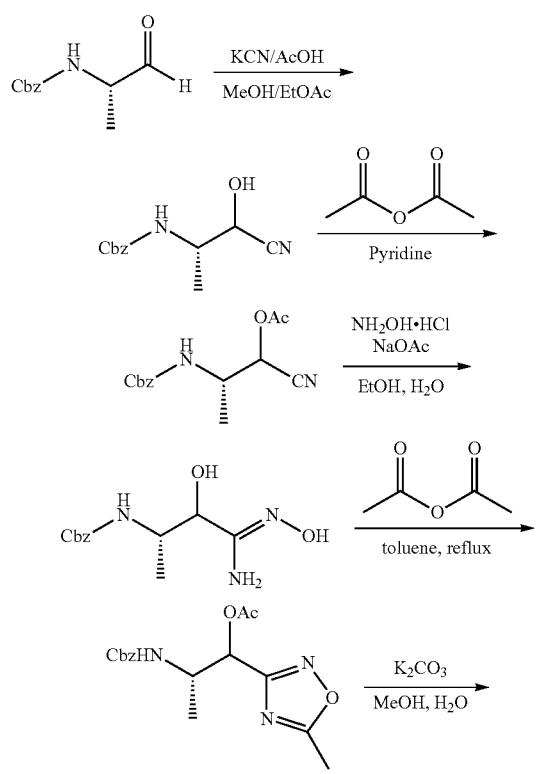

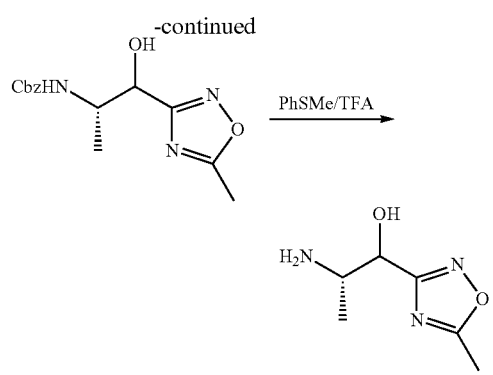

The synthesis of (2S)-2-amino-1-(5-methyl-1,2,4-oxadiazol-3-yl)propan-1-ol: To a solution of (S)-benzyl (1-oxopropan-2-yl)carbamate (7.5 g, 36.2 mmol) in MeOH/EtOAc (120 mL, v/v=1/1) was added KCN (2.7 g, 42.23 mmol) and HOAc (1.72 mL, 43.4 mmol) sequentially and the mixture was stirred at 0° C. for 2.5 h. The volatiles were removed and the residue was re-dissolved with DCM (200 mL), which was washed with brine (2×200 mL). The DCM layer was dried over $Na_2SO_4$, and concentrated. The residue was purified by silica gel column (eluting with 30% to 45% ethyl acetate in petroleum ether) to give benzyl ((2S)-1-cyano-1-hydroxypropan-2-yl)carbamate (7.5 g, 88.5% yield) as a colorless oil.

To a solution of benzyl ((2S)-1-cyano-1-hydroxypropan-2-yl)carbamate (6.7 g, 28.6 mmol) in pyridine (4.0 mL) was added $Ac_2O$ (6.0 mL). The reaction was stirred at room temperature for 3 h. The mixture was diluted with EtOAc (200 mL), which was washed sequentially with the saturated citric acid (150 mL) and brine (150 mL). The EtOAc layer was dried $Na_2SO_4$ and concentrated to give (2S)-2-(((benzyloxy)carbonyl)amino)-1-cyanopropyl acetate (7.9 g, 100% yield) as a colorless oil, which was used directly in the next step.

To a solution of (2S)-2-(((benzyloxy)carbonyl)amino)-1-cyanopropyl acetate (7.9 g, 28.59 mmol) in EtOH/$H_2O$ (60 mL, v/v=5/1) was added hydroxyamine hydrochloride (2.78 g, 40.0 mmol) and sodium acetate (5.86 g, 71.5 mmol) and the mixture was heated at 40° C. for 3 h. The volatiles were removed and the residue was re-dissolved in EtOAc (100 mL), which was washed with brine (2×100 mL). The organic layer was dried over $Na_2SO_4$ and concentrated to give (3

S)-1-amino-3-(((benzyloxy)carbonyl)amino)-1-(hydroxyimino)butan-2-yl acetate (8.8 g, 100% yield) as a yellow oil, which was used directly in the next step.

To a solution of (3 S)-1-amino-3-(((benzyloxy)carbonyl)amino)-1-(hydroxyimino)butan-2-yl acetate (8.8 g, 28.6 mmol) in toluene (20 mL) was added Ac₂O (8.8 g, 85.8 mmol) and the reaction was stirred at 110° C. for 15 h. The volatiles were concentrated to give a residue, which was purified on silica gel column (eluting with 25% to 45% ethyl acetate in petroleum) to afford (2 S)-2-(((benzyloxy)carbonyl)amino)-1-(5-methyl-1,2,4-oxadiazol-3-yl)propyl acetate (3 g, 31.5% yield) as a yellow oil. LCMS (5-95AB), $t_R$=0.808, (M+H)⁺=333.9.

To a solution of (2S)-2-(((benzyloxy)carbonyl)amino)-1-(5-methyl-1,2,4-oxadiazol-3-yl)propyl acetate (600 mg, 1.8 mmol) in MeOH (9 mL) was added a solution of K₂CO₃ (373 mg, 2.7 mmol) in H₂O (3 mL) and the mixture was stirred at room temperature for 1 h. The volatiles were removed to give the residue, which was equilibrated between EtOAc (100 mL) and H₂O (100 mL). The organic layer was washed with brine (100 mL), dried over Na₂SO₄ and concentrated to afford benzyl ((2S)-1-hydroxy-1-(5-methyl-1,2,4-oxadiazol-3-yl)propan-2-yl)carbamate (500 mg, 95.4% yield) as a colorless oil, which was used directly in the next step.

To a solution of benzyl ((2S)-1-hydroxy-1-(5-methyl-1,2,4-oxadiazol-3-yl)propan-2-yl)carbamate (160 mg, 0.55 mmol) in TFA (2 mL) was added thioanisole (100 mg, 0.81 mmol) under N₂ at 0° C. The mixture was stirred at the same temperature for 1 h; then warmed to 26° C. for 15 h. The volatiles were removed to afford (2S)-2-amino-1-(5-methyl-1,2,4-oxadiazol-3-yl)propan-1-ol (148 mg, 99.4% yield) as a red-pink oil, which was used directly in the next step.

Example 137: Synthesis of Compound 238

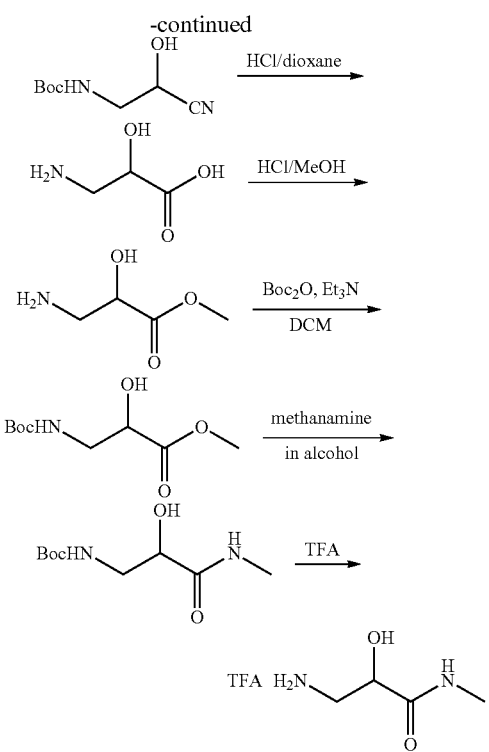

The synthesis of 3-amino-2-hydroxy-N-methylpropanamide 2,2,2-trifluoroacetic acid salt: Tert-butyl (2-oxoethyl)carbamate (5.0 g, 31.4 mmol) was added to a solution of MeOH and EtOAc (1:1, 100 mL) in an ice bath. KCN (6.1 g, 94.2 mmol) and HOAc (1.89 g, 31.4 mmol) was then added to the mixture and stirred at room temperature for 3

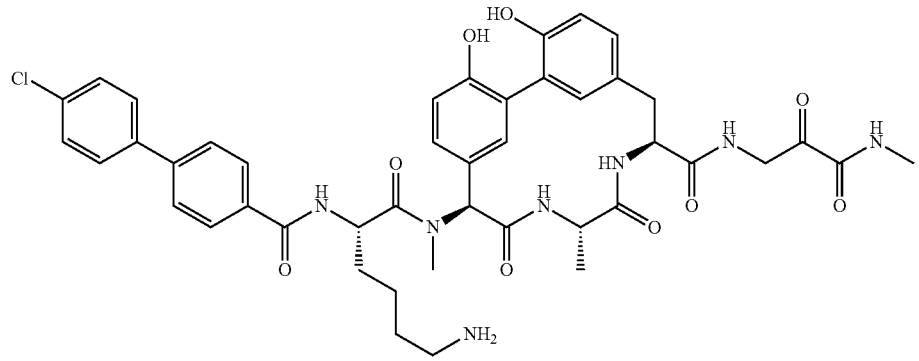

238

Compound 238 was prepared as the formic acid salt using the coupling method, DMP oxidation, and Boc-group hydrolysis as described for Compound 139 from Compound 104E and 3-amino-2-hydroxy-N-methylpropanamide 2,2,2-trifluoroacetic acid salt. LCMS (5-95 AB, ESI): $t_R$=0.632, (M+H)⁺=854.4.

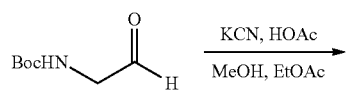

h. The mixture was partitioned between water (200 mL) and EtOAc (200 mL) and the organic layer was separated, dried over MgSO₄, and concentrated. The residue was purified by flash column chromatography eluting 15% EtOAc in petroleum ether to afford tert-butyl (2-cyano-2-hydroxyethyl)carbamate (2.0 g, 10.7 mmol, 34.2% yield) as colorless oil.

To a solution of tert-butyl (2-cyano-2-hydroxyethyl)carbamate (1.0 g, 5.4 mmol) in 1,4-dioxane (10 mL) was added 12M HCl in water (10 ml) at 0° C. The mixture was stirred at 25° C. for 1 h, then at 100° C. for another 16 h. The volatiles were concentrated to afford 3-amino-2-hydroxypropanoic acid (500 mg, 66.7% yield) as a brown solid.

4M HCl in MeOH (10 mL) was added to a solution of 3-amino-2-hydroxypropanoic acid in MeOH (10 mL) under ice bath. The mixture was stirred at room temperature for 16 h. The volatiles were concentrated to afford methyl 3-amino-2-hydroxypropanoate (500 mg, 90.9% yield) as brown oil.

To a solution of methyl 3-amino-2-hydroxypropanoate (400 mg, 2.6 mmol) and Et$_3$N (659 mg, 6.5 mmol) in DCM (10 mL) was added Boc$_2$O (853 mg, 3.91 mmol). The mixture was stirred at 25° C. for 3 h. The mixture was equilibrated between DCM (30 mL) and 10% citric acid (30 mL) and the aqueous layer was further extracted with DCM (2×20 mL). The combined organic layers were then washed with brine, dried over MgSO$_4$, and concentrated. The residue was purified by flash column chromatography eluting 30% EtOAc in petroleum ether to afford methyl 3-((tert-butoxycarbonyl)amino)-2-hydroxypropanoate (500 mg, 87.6% yield) as yellow oil. $^1$H NMR (400 MHz, CDCl$_3$) δ 5.16 (brs, 1H), 4.24 (t, J=4.4 Hz, 1H), 3.72 (s, 3H), 3.46 (d, J=4.4 Hz, 2H), 1.38 (s, 9H).

To a solution of methylamine in alcohol (9.5 M, 4.8 mL, 45.6 mmol) was added methyl 3-((tert-butoxycarbonyl)amino)-2-hydroxypropanoate (50 mg, 0.23 mmol) in ice bath. The mixture was stirred at room temperature for 1 h. The reaction was concentrated to dryness to afford tert-butyl (2-hydroxy-3-(methylamino)-3-oxopropyl)carbamate (42 mg, 84.4% yield) as a yellow solid.

General Boc removal conditions using TFA/DCM (General Method 5) was followed to afford 3-amino-2-hydroxy-N-methylpropanamide 2,2,2-trifluoroacetic acid salt.

Example 138: Synthesis of Compound 239

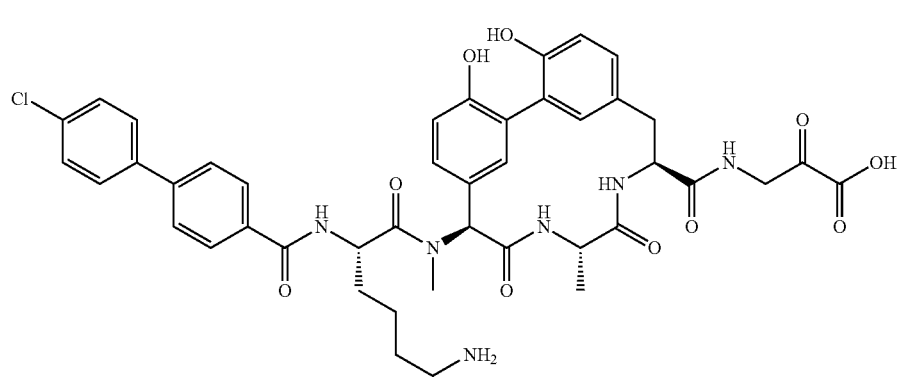

Compound 239 was prepared as the formic acid salt using the coupling method, DMP oxidation, LiOH ester hydrolysis and Boc-group hydrolysis as described for Compound 140 from Compound 104E and methyl 3-amino-2-hydroxypropanoate. HRMS found (M+H)$^+$: 841.3084; theoretical mass: 841.2964.

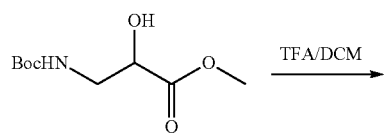

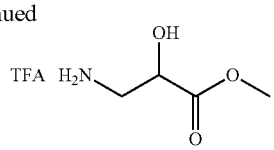

-continued

The synthesis of methyl 3-amino-2-hydroxypropanoate: Standard Boc removal condition with TFA/DCM (General Method 5) was applied to methyl 3-((tert-butoxycarbonyl)amino)-2-hydroxypropanoate (Example 137) (80 mg, 0.36 mmol) to afford methyl 3-amino-2-hydroxypropanoate (70 mg, 82.3% yield) as yellow oil, which was used directly in the next step.

Example 139: Synthesis of Compound 240

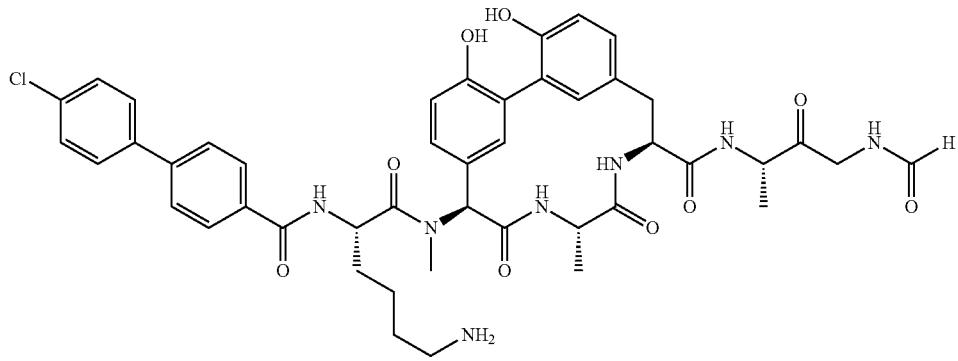

Compound 240 was prepared as a formic acid salt using the coupling method, DMP oxidation, and Boc-group hydrolysis as described for Compound 139 from Compound 104E and N-((3S)-3-amino-2-hydroxybutyl)formamide. LCMS (5-95 AB, ESI): $t_R$=0.779, M+H$^+$=868.6.

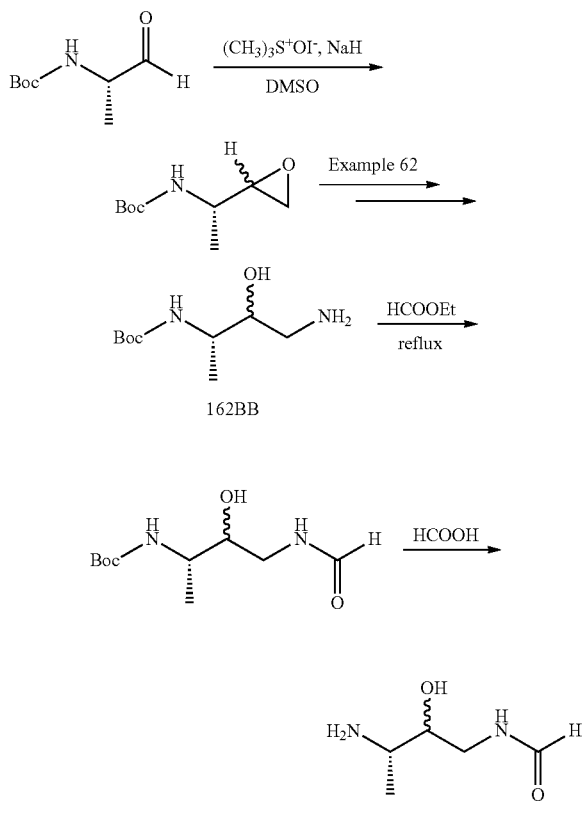

The synthesis of N-((3S)-3-amino-2-hydroxybutyl)formamide: A sulfur ylide epoxidation protocol was used to form the epoxide from the aldehyde. To a suspension of 60% NaH (4.6 g, 11.56 mmol) in DMSO (20 mL), (CH$_3$)$_3$S$^+$OI$^-$ (2.5 g, 11.6 mmol) was added and the mixture was stirred for 0.5 h at room temperature. After that, (S)-tert-butyl (1-oxopropan-2-yl)carbamate (1.0 g, 5.8 mmol) was added to the above mixture and the resulting mixture was stirred at the same temperature for another 3 h. The reaction mixture was taken up in EtOAc (200 ml) and washed with brine (3×200 mL). The organic layer was dried over Na$_2$SO$_4$, and concentrated. The residue was purified by flash column chromatography eluting 5-20% EtOAc in petroleum ether to afford tert-butyl ((1S)-1-(oxiran-2-yl)ethyl)carbamate (660 mg, 61.1% yield) as a colorless oil. $^1$H NMR (400 MHz, CDCl3) δ 4.50-4.32 (m, 1H), 3.95-3.60 (m, 1H), 2.93-2.86 (m, 1H), 2.72-2.16 (m, 1H), 2.54-2.53 (m, 1H), 1.38-1.36 (m, 9H), 1.20-1.07 (m, 3H).

Tert-butyl ((1 S)-1-(oxiran-2-yl)ethyl)carbamate was treated using the same methods as reported previously (Example 162) to afford Compound 162BB.

A solution of tert-butyl ((2S)-4-amino-3-hydroxybutan-2-yl)carbamate (Compound 162BB) (200 mg, 0.98 mmol) in HCOOEt (5 mL) was stirred at 70° C. for 24 h. The resulting mixture was concentrated to afford tert-butyl ((2S)-4-formamido-3-hydroxybutan-2-yl)carbamate (200 mg, 87.9% yield) as a colorless oil. $^1$H NMR (400 MHz, MeOH-d4) δ 8.10 (s, 1H), 3.68-3.50 (m, 2H), 3.37 (s, 1H), 3.27 (s, 1H), 1.46 (s, 9H), 1.17-1.16 (m, 3H).

Tert-butyl ((2S)-4-formamido-3-hydroxybutan-2-yl)carbamate was treated with neat formic acid. When the hydrolysis of the Boc-group is complete, the formic acid is removed by lyophilization to afford N-((3 S)-3-amino-2-hydroxybutyl)formamide.

Example 140: Synthesis of Compound 241

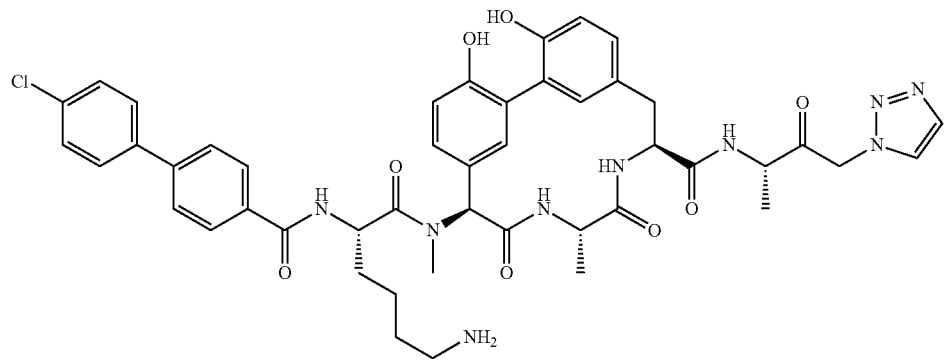

241

Compound 241 was prepared as the formic acid salt using the coupling method, DMP oxidation, and Boc-group hydrolysis as described for Compound 139 from Compound 104E and (3S)-3-amino-1-(1H-1,2,3-triazol-1-yl)butan-2-ol. LCMS (5-95 AB, ESI) $t_R$=0.780, M+H$^+$=892.5.

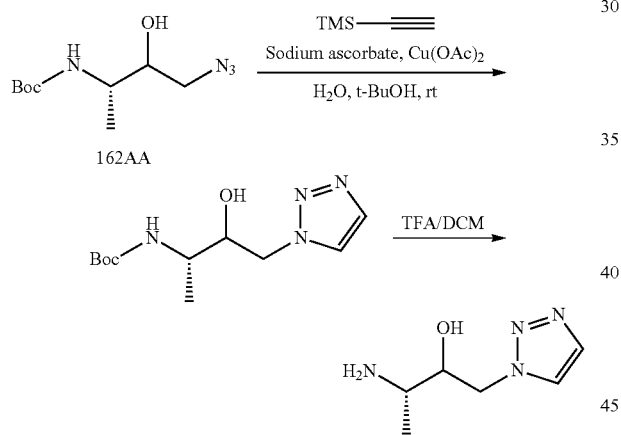

The synthesis of (3S)-3-amino-1-(1H-1,2,3-triazol-1-yl)butan-2-ol: To a solution of tert-butyl ((2S)-4-azido-3-hydroxybutan-2-yl)carbamate (400 mg, 1.74 mmol) and ethynyltrimethylsilane (170 mg, 1.74 mmol) in H$_2$O/t-BuOH (10 mL, v/v=1/1), Cu(OAc)$_2$ (32 mg, 0.17 mmol) and sodium ascorbate (69 mg, 0.35 mmol) was added at 0° C. The reaction mixture was warmed and stirred at room temperature for 16 h. The reaction mixture was added with brine (10 mL) and extracted with EtOAc (3×20 mL). The combined organic layers were dried over MgSO$_4$, and concentrated. The residue was purified by pre-HPLC to obtain tert-butyl ((2S)-3-hydroxy-4-(1H-1,2,3-triazol-1-yl)butan-2-yl)carbamate (88 mg, 19.8% yield). LCMS (5-95AB/1.5 min): $t_R$=0.795 min, (M+H)$^+$329.1.

General Boc removal condition using TFA/DCM (General Method 5) was followed to afford (3 S)-3-amino-1-(1H-1,2,3-triazol-1-yl)butan-2-ol.

Example 141: Synthesis of Compound 242

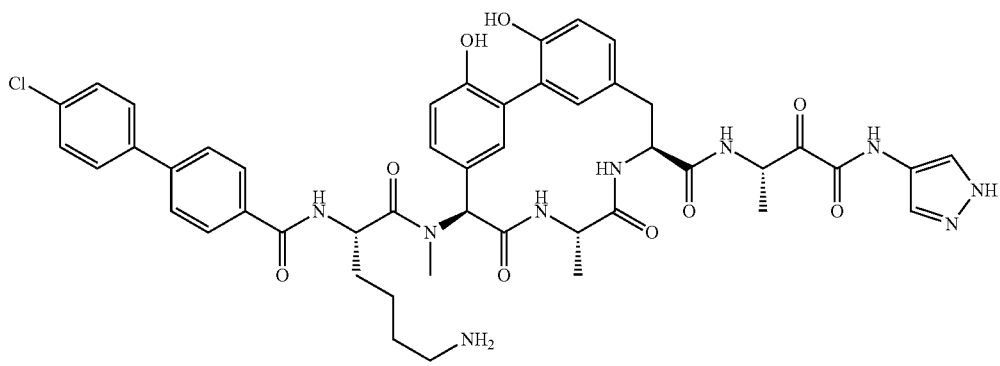

242

Compound 242 was prepared as the formic acid salt using the coupling method, DMP oxidation, and Boc-group hydrolysis as described for Compound 139 from Compound 104E and (3S)-3-amino-2-hydroxy-N-(1-((2-(trimethylsilyl)ethoxy)methyl)-1H-pyrazol-4-yl)butanamide. LCMS (5-95 AB, ESI) $t_R$=0.783, M+H$^+$=920.3.

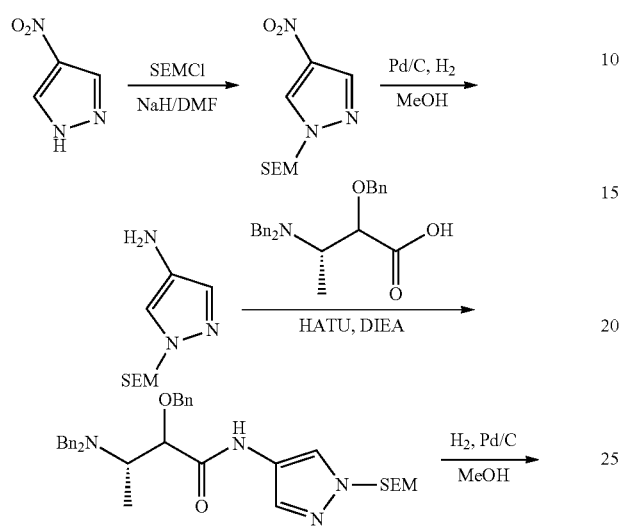

The synthesis of (3 S)-3-amino-2-hydroxy-N-(1-((2-(trimethylsilyl)ethoxy)methyl)-1H-pyrazol-4-yl)butanamide: A solution of 4-nitro-1H-pyrazole (3.0 g, 26.5 mmol) in DMF (40 mL) was added to 60% NaH (1.6 g, 39.8 mmol) slowly and the mixture was stirred at ice-bath for 10 min. SEM-Cl (4.86 g, 29.2 mmol) was then added slowly to the above mixture at 0° C. The resulting mixture was warmed and stirred for 1 h at room temperature. The mixture was quenched by saturated NH$_4$Cl (100 mL) and extracted with EtOAc (3×100 mL). The combined organic layers were washed with brine, dried over Na$_2$SO$_4$, and concentrated. The residue was purified by column (eluting 3-5% EtOAc in petroleum ether) to give 4-nitro-1-((2-(trimethylsilyl)ethoxy)methyl)-1H-pyrazole (5.4 g, 83.6% yield) as a yellow oil.

Standard hydrogenation (Pd/C, 1 atm of H$_2$) condition was applied to 4-nitro-1-((2-(trimethylsilyl)ethoxy)methyl)-1H-pyrazole (500 mg, 1.24 mmol) to afford 1-((2-(trimethylsilyl)ethoxy)methyl)-1H-pyrazol-4-amine (450 mg, 93.2% yield) as a white solid.

Standard HATU coupling conditions (General Method 8) was applied to 1-((2-(trimethylsilyl)ethoxy)methyl)-1H-pyrazol-4-amine (350 mg, 0.90 mmol) and (3S)-2-(benzyloxy)-3-(dibenzylamino)butanoic acid to afford (3S)-2-(benzyloxy)-3-(dibenzylamino)-N-(1-((2-(trimethylsilyl)ethoxy)methyl)-1H-pyrazol-4-yl)butanamide (400 mg, 76.1 yield) as a yellow oil. LCMS (5-95 AB, ESI) $t_R$=0.814, M+H$^+$=585.3.

Standard hydrogenation (Pd/C, 1 atm of H$_2$) condition was applied to (3S)-2-(benzyloxy)-3-(dibenzylamino)-N-(1-((2-(trimethylsilyl)ethoxy)methyl)-1H-pyrazol-4-yl)butanamide (200 mg, 0.34 mmol) to afford (3S)-3-amino-2-hydroxy-N-(1-((2-(trimethylsilyl)ethoxy)methyl)-1H-pyrazol-4-yl)butanamide (106 mg, 98.6% yield) as a yellow oil.

Example 142: Synthesis of Compound 243

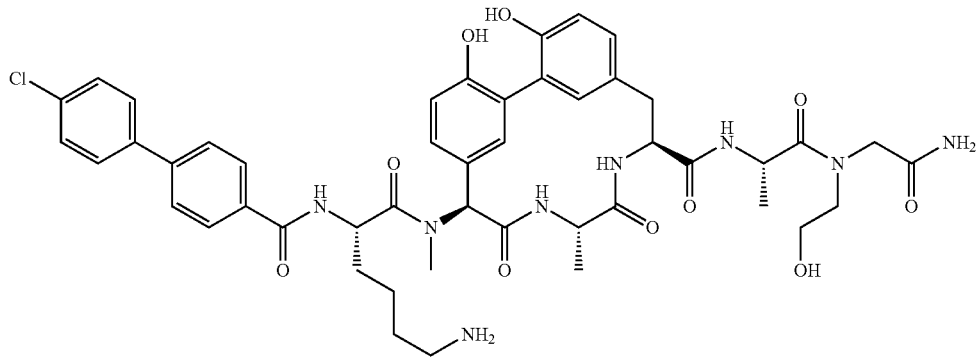

243

Compound 243 was prepared as the formic acid salt using the solid phase coupling methods as described for Compound 168 from Compound 104E and 2-((((9H-fluoren-9-yl)methoxy)carbonyl)(2-(tert-butoxy)ethyl)amino)acetic acid. LCMS (5-95 AB, ESI): $t_R$=0.763, (M+H)$^+$=927.8.

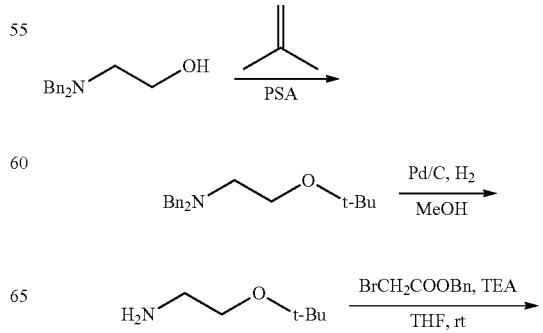

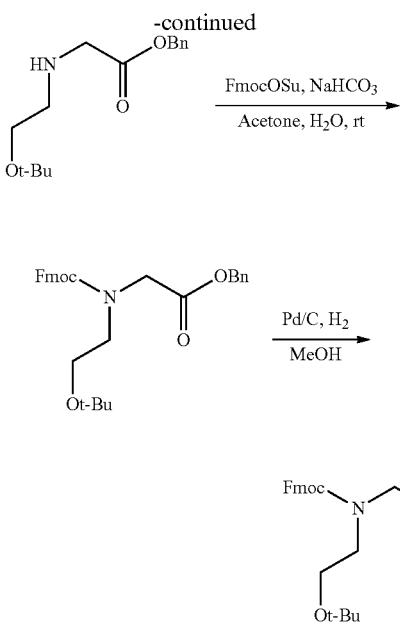

benzyl 2-((2-(tert-butoxy)ethyl)amino)acetate (400 mg, 70.7% yield) as a colorless oil.

To a solution of benzyl 2-((2-(tert-butoxy)ethyl)amino) acetate (250 mg, 0.94 mmol) and NaHCO$_3$ (158 mg, 1.88 mmol) in Acetone/H$_2$O (6 mL, v/v=5/1) was added 9H-fluoren-9-ylmethyl 2,5-dioxopyrrolidine-1-carboxylate (606 mg, 1.88 mmol) at room temperature and the mixture was stirred at the same temperature for 16 h. The volatiles were removed and the residue was extracted with EtOAc (2×25 mL). The combined organic layers were washed with brine (50 mL), dried over Na$_2$SO$_4$ and purified by silica column chromatography (10% EtOAc in petroleum ether) to give benzyl 2-((((9H-fluoren-9-yl)methoxy)carbonyl)(2-(tert-butoxy)ethyl)amino)acetate (400 mg, 87.1% yield) as a yellow oil.

Standard hydrogenation (Pd/C, H$_2$) condition was applied to benzyl 2-((((9H-fluoren-9-yl)methoxy)carbonyl)(2-(tert-butoxy)ethyl)amino)acetate (240 mg, 0.49 mmol) to give 2-((((9H-fluoren-9-yl)methoxy)carbonyl)(2-(tert-butoxy) ethyl)amino)acetic acid (40 mg, 20.4% yield) as a colorless oil after HPLC purification.

Example 143: Synthesis of Compound 244

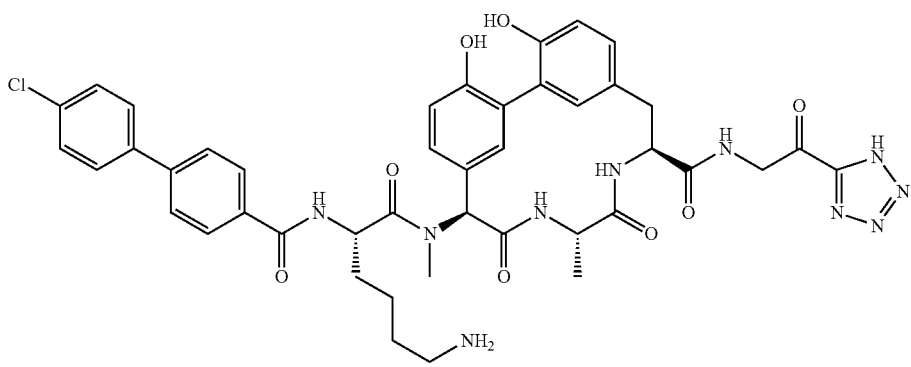

244

The synthesis of 2-((((9H-fluoren-9-yl)methoxy)carbonyl)(2-(tert-butoxy)ethyl)amino)acetic acid: To a solution of 2-(dibenzylamino)ethanol (5.0 g, 20.7 mmol) and TsOH (7.1 g, 41.4 mmol) in DCM (100 mL) was saturated with isobutylene at −78° C. and the mixture was stirred at room temperature for 16 h. The mixture was washed sequentially with saturated NaHCO$_3$ and brine (each 100 mL). The organic layer was concentrated and purified by silica column chromatography (10% EtOAc in petroleum ether) to give N,N-dibenzyl-2-(tert-butoxy)ethanamine (8 g, quantitative yield) as a yellow oil.

Standard hydrogenation (Pd/C, H$_2$) condition was applied to N,N-dibenzyl-2-(tert-butoxy)ethanamine (2.0 g, 6.7 mmol) to give 2-(tert-butoxy)ethanamine (500 mg, 63.5% yield) as colorless oil.

To a solution of 2-(tert-butoxy)ethanamine (250 mg, 2.1 mmol) and Et$_3$N (259 mg, 2.6 mmol) in DMF (5 mL) was added benzyl bromoacetate (342 mg, 1.5 mmol) dropwise at 0° C. and the mixture was stirred at room temperature for 16 h. The reaction mixture was then purified by HPLC to give Compound 244 was prepared as the formic acid salt using the coupling method, DMP oxidation, and Boc-group hydrolysis as described for Compound 139 from Compound 104E and 2-amino-1-(2-((2-(trimethylsilyl)ethoxy)methyl)-2H-tetrazol-5-yl)ethanol. LCMS (5-95 AB, ESI): $t_R$=0.784 min, (M+H)$^+$=865.7.

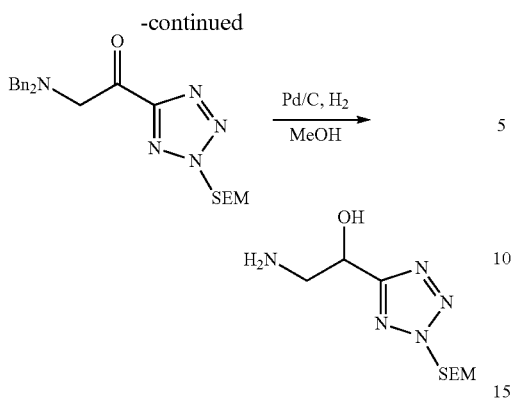

The synthesis of 2-amino-1-(2-((2-(trimethylsilyl)ethoxy)methyl)-2H-tetrazol-5-yl)ethanol: To a stirred solution of 2-((2-(trimethylsilyl)ethoxy)methyl)-2H-tetrazole (1.6 g, 8.0 mmol) in THF (10 mL) was added 2.5M n-BuLi in hexane (4.0 mL) dropwise at −78° C. The mixture was stirred at the same temperature for 30 min. To a stirred solution of 2-(dibenzylamino)-N-methoxy-N-methylacetamide (2.0 g, 6.7 mmol) in 10 mL THF was added to the above-mentioned solution at −78° C., and the resulting mixture was slowly allowed to reach room temperature over a period of 2 h. The mixture was then quenched by addition of saturated NH$_4$Cl solution (100 mL), which was extracted with EtOAc (3×100 mL). The combined organic extracts were washed with brine, dried over MgSO$_4$, and concentrated. The residue was purified by flash column (0-25% EtOAc in petroleum ether) to afford 2-(dibenzylamino)-1-(2-((2-(trimethylsilyl)ethoxy)methyl)-2H-tetrazol-5-yl)ethanone (1.8 g, 61.4% yield) as a light yellow oil.

Standard hydrogenation condition (Pd/C, 1 atm H$_2$) was applied to 2-(dibenzylamino)-1-(2-((2-(trimethylsilyl)ethoxy)methyl)-2H-tetrazol-5-yl)ethanone (1.8 g, 4.1 mmol) to afford 2-amino-1-(2-((2-(trimethylsilyl)ethoxy)methyl)-2H-tetrazol-5-yl)ethanol (120 mg, 11.2% yield) as colorless oil after HPLC purification.

Example 144: Synthesis of Compound 245

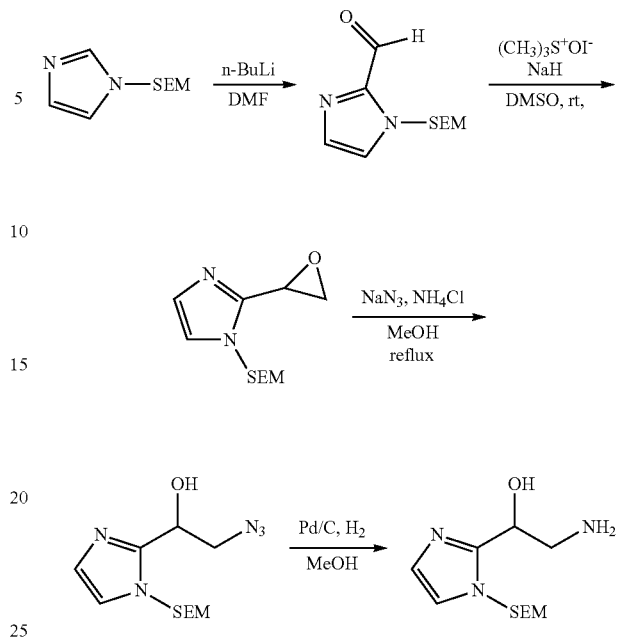

Synthesis of 2-amino-1-(1-((2-(trimethylsilyl)ethoxy)methyl)-1H-imidazol-2-yl)ethanol: To a solution of 1-((2-(trimethylsilyl)ethoxy)methyl)-1H-imidazole (5.0 g, 25.2 mmol) in THF (50 mL) at −75° C., 2.5M n-BuLi in hexane (13 mL) was added to the mixture dropwise, which was stirred at the same temperature for 1 h. DMF (3.7 g, 50.4 mmol) was added to the above mixture slowly at −75° C. The reaction was monitored by TLC (eluting 30% EtOAc in petroleum ether, Rf=0.52). The reaction was quenched by 10% NH$_4$Cl solution (100 mL) and extracted with EtOAc (3×100 mL). The combined organic layers were washed with brine (200 mL), dried over Na$_2$SO$_4$, and concentrated. The residue was purified by flash column chromatography (eluting 10-25% EtOAc in petroleum ether) to afford 1-((2-(trimethylsilyl)ethoxy)methyl)-1H-imidazole-2-carbaldehyde (5 g, 87.6% yield) as a yellow oil.

245

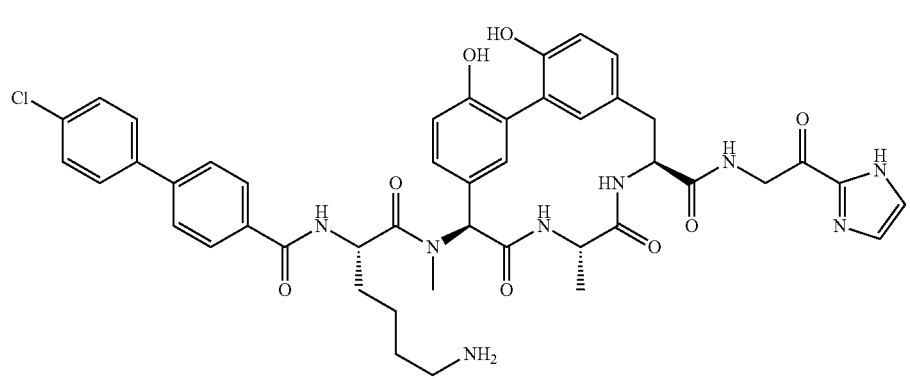

Compound 245 was prepared as the formic acid salt using the coupling method, DMP oxidation, and Boc-group hydrolysis as described for Compound 139 from Compound 104E and 2-amino-1-(1-((2-(trimethylsilyl)ethoxy)methyl)-1H-imidazol-2-yl)ethanol. LCMS (10-80CD_3MIN): t$_R$=1.493, M+1=863.1.

1-((2-(Trimethylsilyl)ethoxy)methyl)-1H-imidazole-2-carbaldehyde was treated under the epoxidation, azide epoxide ring-opening, and reduction as was used in Examples 62 and 139 to afford 2-amino-1-(1-((2-(trimethylsilyl)ethoxy)methyl)-1H-imidazol-2-yl)ethanol as a yellow oil in 15% yield over the three steps.

Example 145: Synthesis of Compound 246

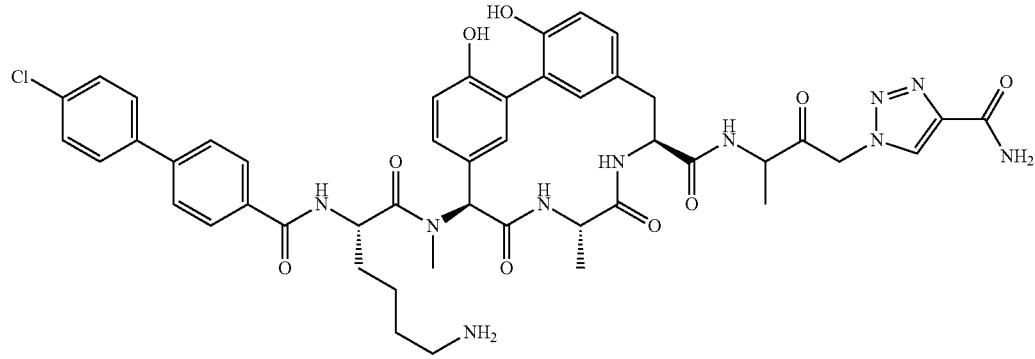

Compound 246 was synthesized using similar procedures as described above from Compound 104E and (S)-tert-butyl (4-(4-carbamoyl-1H-1,2,3-triazol-1-yl)-3-oxobutan-2-yl) carbamate. LCMS (5-95 AB, ESI): $t_R$=0.794 min, $(M+H)^+$=935.4

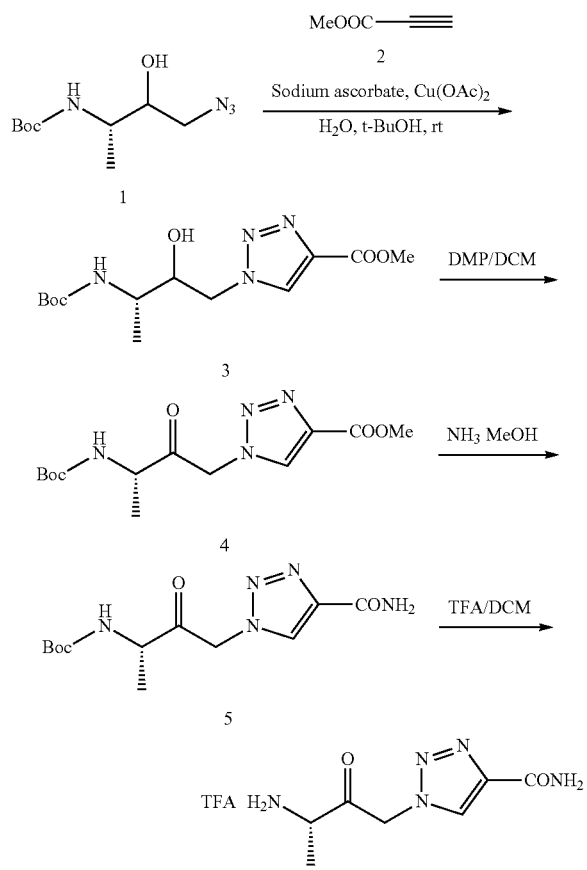

Synthesis of (S)-1-(3-amino-2-oxobutyl)-1H-1,2,3-triazole-4-carboxamide: To a solution of tert-butyl ((2S)-4-azido-3-hydroxybutan-2-yl)carbamate (Compound 162AA) (750 mg, 3.3 mmol), copper diacetate (59 mg, 0.33 mmol), t-BuOH (0.31 mL) and sodium ascorbate (129 mg, 0.65 mmol) in H$_2$O (5 mL) was added methyl propiolate (274 mg, 3.3 mmol) at 0° C. The reaction was warmed and stirred at room temperature for 5 h. The volatiles were removed and the residue was re-dissolved in EtOAc (100 ml), which was washed with brine (2×50 mL). The organic layer was dried over MgSO$_4$ and concentrated to obtain methyl 1-((3S)-3-((tert-butoxycarbonyl)amino)-2-hydroxybutyl)-1H-1,2,3-triazole-4-carboxylate (800 mg, 78.1% yield) as a colorless oil. LCMS (5-95AB/1.5 min): $t_R$=0.718 min, $(M+H)^+$=337.0.

To a solution of methyl 1-((3S)-3-((tert-butoxycarbonyl)amino)-2-hydroxybutyl)-1H-1,2,3-triazole-4-carboxylate (800 mg, 2.5 mmol) in DCM (30 mL), DMP (1.1 g, 2.55 mmol) was added and the mixture was stirred at room temperature for 2 h. The volatiles were removed and the residue was re-dissolved in EtOAc (100 ml), which was washed with saturated Na$_2$S$_2$O$_3$ solution (40 mL) and brine (50 mL). The organic layer was dried over MgSO$_4$, and concentrated. The residue was purified by HPLC to obtain (S)-methyl 1-(3-((tert-butoxycarbonyl)amino)-2-oxobutyl)-1H-1,2,3-triazole-4-carboxylate (110 mg, 27.7% yield) as a white solid. LCMS (5-95 AB, ESI): $t_R$=0.74 min, $(M+H)^+$=313.0.

To a solution of (S)-methyl 1-(3-((tert-butoxycarbonyl)amino)-2-oxobutyl)-1H-1,2,3-triazole-4-carboxylate (39 mg, 0.12 mmol) in MeOH (2 mL) was saturated with ammonia and the mixture was stirred at room temperature for 16 h. The volatiles were concentrated to give (S)-tert-butyl (4-(4-carbamoyl-1H-1,2,3-triazol-1-yl)-3-oxobutan-2-yl)carbamate (37 mg, 99.6% yield) as a white solid, which was used directly in the next step.

Standard Boc removal (TFA/DCM) condition was applied to (S)-tert-butyl (4-(4-carbamoyl-1H-1,2,3-triazol-1-yl)-3-oxobutan-2-yl)carbamate to afford (S)-1-(3-amino-2-oxobutyl)-1H-1,2,3-triazole-4-carboxamide in quantitative yield.

Example 146: Synthesis of Compound 247

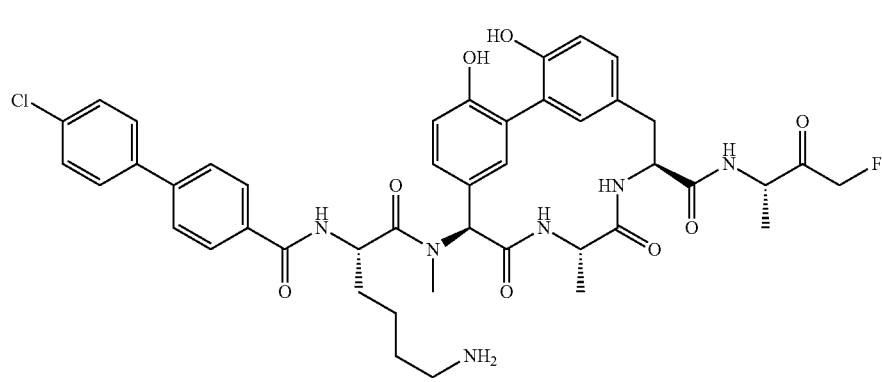

247

Compound 247 was prepared as the formic acid salt using the coupling method, DMP oxidation, and Boc-group hydrolysis as described for Compound 139 from Compound 104E and tert-butyl ((2S)-4-fluoro-3-hydroxybutan-2-yl)carbamate. LCMS (5-95AB_1.5 min): $t_R$=0.795, (M+H)$^+$=843.3.

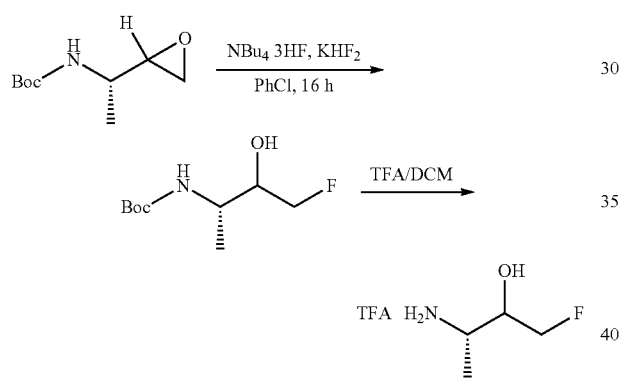

The synthesis of tert-butyl ((2S)-4-fluoro-3-hydroxybutan-2-yl)carbamate: To a solution tert-butyl ((1S)-1-(oxiran-2-yl)ethyl)carbamate (Example 62) (1.0 g, 5.34 mmol) in chlorobenzene (20 mL) was added KHF$_2$ (834 mg, 10.7 mmol) and NBu$_4$·3HF (81.0 mg, 0.27 mmol) at room temperature. The reaction mixture was then stirred at 120° C. for 16 h. The volatiles were removed and the residue was purified by flash column chromatography (eluting with 5-20% EtOAc with petroleum ether) to afford tert-butyl ((2S)-4-fluoro-3-hydroxybutan-2-yl)carbamate (220 mg, 19.9% yield, a mixture of diastereomers) as colorless oil. $^1$H NMR (400 MHz, CDCl$_3$) δ 4.76 (s, 1H), 4.50-4.56 (m, 0.5H), 4.38-4.44 (m, 1H), 4.28-4.32 (m, 0.5H), 3.77-3.83 (m, 1.5H), 2.90-3.00 (m, 0.5H), 1.44 (s, 9H), 1.24-1.27 (m, 3H).

Standard Boc removal condition with TFA/DCM (General Method 5) was applied to tert-butyl ((2S)-4-fluoro-3-hydroxybutan-2-yl)carbamate (100 mg, 0.48 mmol) to afford (3S)-3-amino-1-fluorobutan-2-ol as the TFA salt (100 mg, 93.7% yield) as colorless oil, which was used directly in the next step.

Example 147: Synthesis of Compound 248

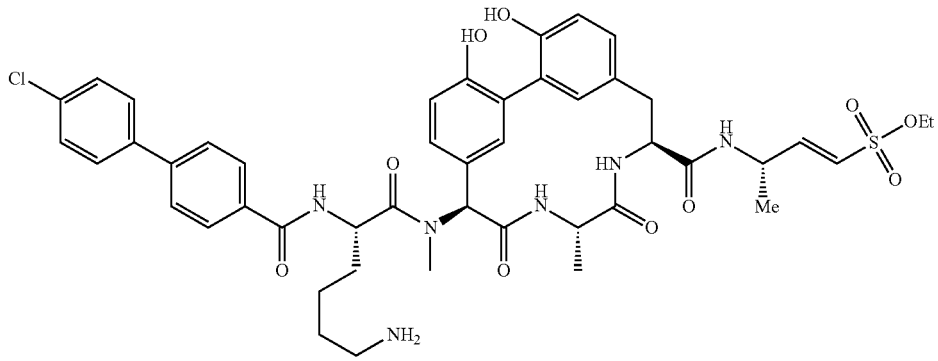

248

Compound 248 was prepared as the TFA acid salt using the amide coupling and Boc-group hydrolysis (General Methods 8 and 9) as described for Compound 115 from Compound 104E and (S,E)-ethyl 3-aminobut-1-ene-1-sulfonate, which is isolated as a 9:1 mixture of the product and the sulfonic acid in 32% yield. MS (ESI): m/z 917.7

(M+H)+; HPLC $t_R$ 3.59 min (10% AcCN/H$_2$O-90% AcCN/H$_2$O, 3.0 min, 1.0 mL/min Kinetix C18, 4.8×50 mm).

The synthesis of (S,E)-ethyl 3-((tert-butoxycarbonyl)amino)but-1-ene-1-sulfonate: To a solution of ethyl methanesulfonate (0.68 mL, 6.2 mmol, 1.8 eq) in anhydrous THF (15 mL) under Ar in a flame dried flask at −78° C. was added 2.5 M nBuLi in THF (2.8 mL, 2 eq). The solution was stirred for 40 min then diethyl chlorophosphate (0.5 mL, 1 eq) was added dropwise and the solution was stirred for 35 min at −78° C. After warming to −40° C. the solution was stirred for an hour, quenched with saturated NH$_4$Cl, warmed to rt and the volatiles were evaporated. Water was added to the remaining crude mixture and the aqueous layer was extracted 3× with DCM. The combined organics were washed with brine then dried over sodium sulfate and concentrated to afford 1.15 g of ethyl (diethoxyphosphoryl)methanesulfonate, a clear oil, which was taken forward without further purification. MS (ESI): m/z 261.0 (M+H)+.

To a solution of ethyl (diethoxyphosphoryl)methanesulfonate (943 mg, 2.35 mmol, 1 eq) in anhydrous THF (15 mL) under Ar in a flame dried flask at −78° C. was added 2.5 M nBuLi in THF (1.3 mL, 2 eq) dropwise. The reaction was then allowed to stir for 30 min. In a second flame dried flask under Ar, (S)-tert-butyl (1-oxopropan-2-yl)carbamate (746 mg, 1 eq) was dissolved in anhydrous THF (3 mL) and this solution was transferred dropwise via syringe to the flask containing compound 2 at −78° C. After 1.5 h, phosphate buffer (pH−7.4) was added and the mixture was allowed to warm to room temp with stirring. The aqueous layer was extracted 3× with Et$_2$O and the combined organic layers were dried over sodium sulfate and concentrated. The crude material was purified by ISCO column chromatography (0 to 55% EtOAc in Hex) to afford (S,E)-ethyl 3-((tert-butoxycarbonyl)amino)but-1-ene-1-sulfonate (729 mg, 91%) MS (ESI): m/z 179.8 (M-Boc+H)+; $^1$H NMR (CDCl$_3$, 500 MHz) δ 6.81 (dd, J=15 Hz, J=5 Hz, 1H) 6.81 (dd, J=15 Hz, 1.5 Hz, 1H), 4.42 (br s, 1H), 4.30 (q, J=7 Hz, 1H), 4.61 (q, J=7 Hz, 2H), 1.43 (s, 9H), 1.36 (t, J=7 Hz, 3H), 1.30 (d, J=7 Hz, 3H).

(S,E)-Ethyl 3-((tert-butoxycarbonyl)amino)but-1-ene-1-sulfonate was Boc deprotected using TFA/DCM (General Method 5) to afford (S,E)-ethyl 3-aminobut-1-ene-1-sulfonate.

Example 148: Synthesis of Compound 249

889.1 (M+H)+; HPLC $t_R$ 3.34 min (10% AcCN/H$_2$O-90% AcCN/H$_2$O, 3.0 min, 1.0 mL/min Kinetix C18, 4.8×50 mm).

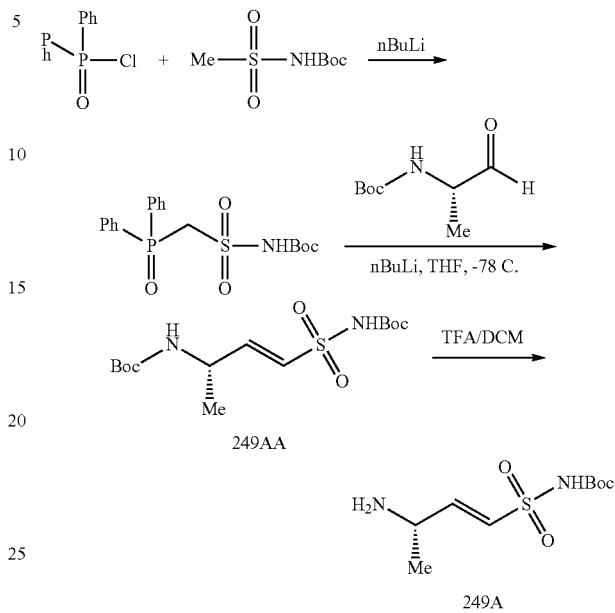

The synthesis of Compound 249A: To a solution diethylamine (842 uL, 3.1 eq) in anhydrous THF (12 mL) under Ar in a flame dried flask at −78° C. was added 2.5 M nBuLi in Hex (3.12 mL, 3 eq). The solution was then warmed to 0° C. on an ice bath then cooled again to −78° C. A solution of tert-butyl methylsulfonylcarbamate (0.5 g, 2.6 mmol, 1 eq) under Ar in a flame dried flask was then added dropwise to the LDA at −78° C. After 10 min, diphenylphosphinic chloride (0.5 mL, 1 eq) was added dropwise and the solution was stirred for 1.5 hrs at −78° C. The reaction was quenched by adding H$_2$O (~200 mL), then the aqueous mixture was washed with EtOAc. The aqueous layer was acidified with 1N HCl, and the precipitate was filtered through a Buchner funnel to afford tert-butyl ((diphenylphosphoryl)methyl)sulfonylcarbamate as a white powder (100 mg). The filtrate was extracted 2× with EtOAc and the combined organic layers

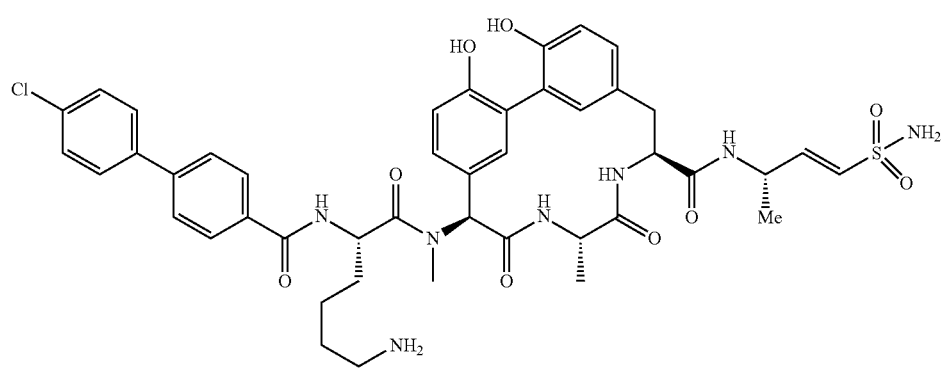

249

Compound 249 was prepared as the TFA acid salt using the amide coupling and Boc-group hydrolysis (General Methods 8 and 9) as described for Compound 115 from Compound 104E and Compound 249A. MS (ESI): m/z were washed with brine and concentrated. The crude product was taken up in a small amount of EtOAc, and again filtered through a Buchner funnel to afford a second batch of product as a white powder. The two batches were combined to afford 598 mg (58%). MS (ESI): m/z 395.9 (M+H)⁺; ¹H NMR (MeOD, 500 MHz) δ 7.84 (m, 4H) 7.64 (m, 2H), 7.57 (m, 4H), 4.84 (s, 1H), 4.84 (s, 9H).

To a solution of tert-butyl ((diphenylphosphoryl)methyl)sulfonylcarbamate (100 mg, 0.25 mmol, 1 eq) and TMEDA (1 mL) in anhydrous THF (2.5 mL) under Ar in a flame dried flask at −78° C. was added 2.5 M nBuLi in THF (220 uL, 2.2 eq) dropwise. The reaction was then allowed to stir for 1 h. In a second flame dried flask under Ar, (S)-tert-butyl (1-oxo-propan-2-yl)carbamate (44 mg, 1 eq) was dissolved in anhydrous THF (2.5 mL) and this solution was transferred dropwise via syringe to the first flask at −78° C. After 1 h, the reaction was warmed to room temperature then allowed to stir overnight. A dilute brine solution was added and the mixture was extracted 2× with EtOAc. The combined organic layers were washed with water and brine, dried over sodium sulfate and concentrated. The crude material was purified by ISCO column chromatography (0 to 60% EtOAc in Hex) to afford Compound 249AA (31.4 mg, 36%). ¹H NMR (CDCl₃, 500 MHz) δ 6.89 (dd, J=15 Hz, J=5 Hz, 1H) 6.56 (d, J=15 Hz, 1H), 4.59 (br s, 1H), 4.49 (br s, 1H), 1.48 (s, 9H), 1.44 (s, 9H), 1.31 (d, J=7 Hz, 3H). Compound 249AA (29 mg, 83 umol) was Boc deprotected under standard TFA/DCM deprotection conditions (General Method 5) to afford Compound 249A.

Example 149: Synthesis of Compound 250

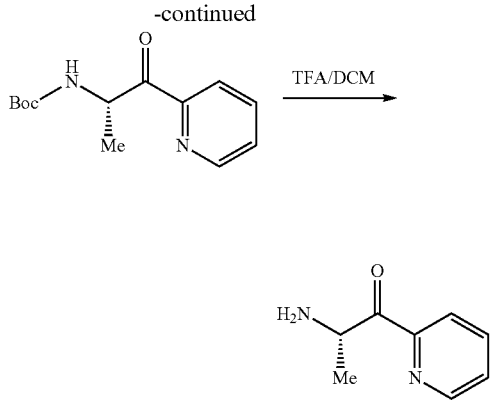

The synthesis of (S)-2-amino-1-(pyridin-2-yl)propan-1-one: To a solution of 2-bromopyridine (205 uL, 5 eq) in anhydrous THF (4 mL) under N₂ in a flame dried flask at −78° C. was added 2.5 M nBuLi in THF (860 uL, 5 eq) dropwise. The reaction was then allowed to stir for 40 min. In a second flame dried flask under N₂, (S)-tert-butyl (1-(methoxy(methyl)amino)-1-oxopropan-2-yl)carbamate (100 mg, 0.43 mmol, 1 eq) was dissolved in anhydrous THF (2.5

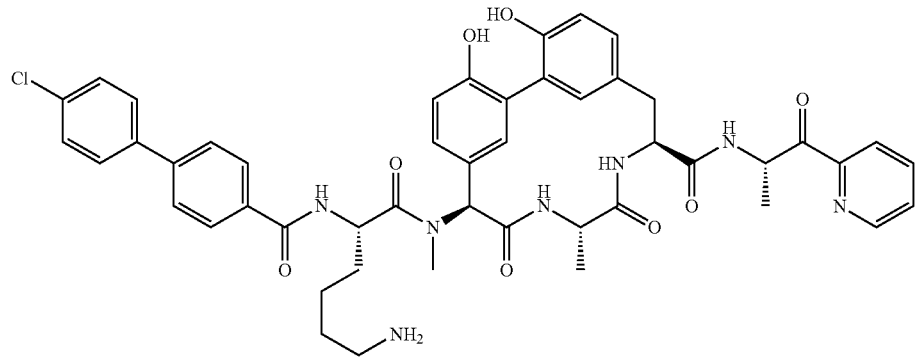

250

Compound 250 was prepared as the TFA acid salt using the amide coupling and Boc-group hydrolysis (General Methods 8 and 9) as described for Compound 115 from Compound 104E and (S)-2-amino-1-(pyridin-2-yl)propan-1-one. MS (ESI): m/z 889.9 (M+H)⁺; HPLC t_R 3.51 min (10% AcCN/H₂O-90% AcCN/H₂O, 3.0 min, 1.0 mL/min Kinetix C18, 4.8×50 mm).

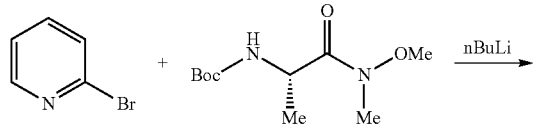

mL) and this solution was transferred dropwise via syringe to the flask containing 2-bromopyridine at −78° C. After 1 h, the reaction was quenched at −78° C. by adding saturated NH₄Cl and allowed to warm to room temperature. Water was added and the mixture was extracted 3× with EtOAc. The combined organic layers were washed with brine, dried over sodium sulfate and concentrated. The crude material was purified by ISCO column chromatography (0 to 4% MeOH in DCM) to afford(S)-tert-butyl (1-oxo-1-(pyridin-2-yl)propan-2-yl)carbamate (71.1 mg, 66%). MS (ESI): m/z 251.0 (M+H)⁺.

(S)-Tert-butyl (1-oxo-1-(pyridin-2-yl)propan-2-yl)carbamate (31 mg, 0.12 mmol) was Boc deprotected with TFA/DCM (General Method 5) to afford (S)-2-amino-1-(pyridin-2-yl)propan-1-one.

Example 150: Synthesis of Compound 251

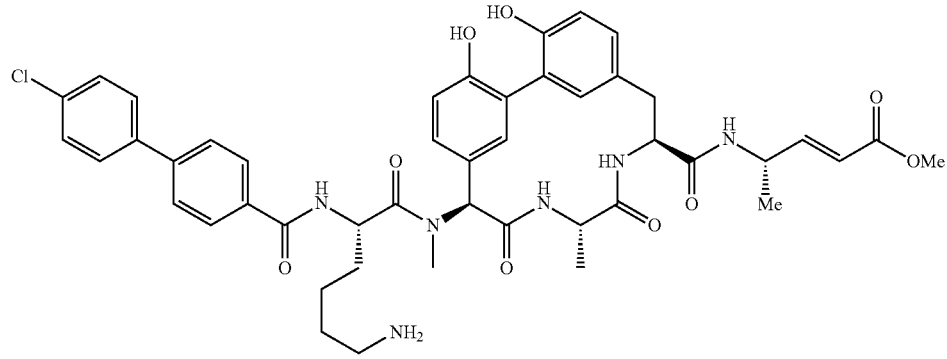

Compound 251 was prepared as the formate acid salt using the amide coupling and Boc-group hydrolysis (General Methods 8 and 9) in 59% yield as described for Compound 115 from Compound 104E and (S,E)-methyl 4-aminopent-2-enoate. MS (ESI): m/z 868.0 (M+H)$^+$; HPLC $t_R$ 3.48 min (10% AcCN/H$_2$O-90% AcCN/H$_2$O, 3.0 min, 1.0 mL/min Kinetix C18, 4.8×50 mm).

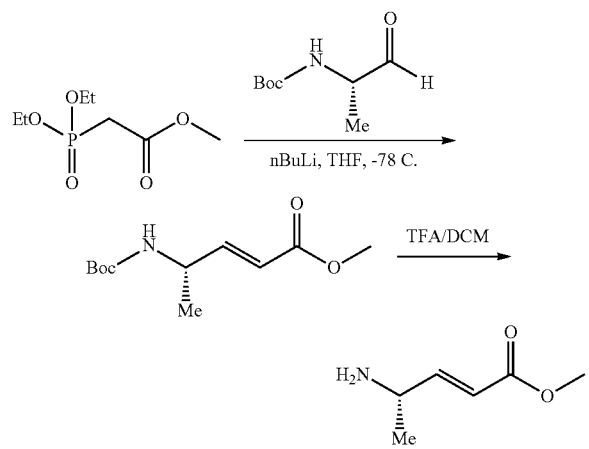

The synthesis of (S,E)-methyl 4-aminopent-2-enoate: To a solution of methyldiethyl phosphonoacetate (161 mg, 1.5 eq) in anhydrous THF (8 mL) under Ar in a flame dried flask at 0° C. was added NaH (60% by weight in mineral oil, 35 mg, 1.5 eq). The reaction was then allowed to stir for 50 min. In a second flame dried flask under Ar, (S)-tert-butyl (1-oxopropan-2-yl)carbamate (100 mg, 0.58 mmol, 1 eq) was dissolved in anhydrous THF (1.5 mL) and this solution was transferred dropwise via syringe to the flask containing methyldiethyl phosphonoacetate at 0° C. After warming to room temperature and stirring overnight, 1N HCl and EtOAc were added. The organic layer was extracted 2× with 1N HCl and brine then dried over sodium sulfate and concentrated. The crude material was purified by ISCO column chromatography (0 to 35% EtOAc in Hex) to afford (S,E)-methyl 4-((tert-butoxycarbonyl)amino)pent-2-enoate (85 mg, 91%). MS (ESI): m/z 130.6 (M-Boc+H)$^+$; $^1$H NMR (CDCl$_3$, 500 MHz) δ 6.88 (dd, J=16 Hz, J=5 Hz, 1H) 6.81 (dd, J=16 Hz, 1 Hz, 1H), 4.51 (br s, 1H), 4.39 (br s, 1H), 3.73 (q, J=7 Hz, 2H), 1.44 (s, 9H), 1.26 (d, J=7 Hz, 3H). (S,E)-methyl 4-((tert-butoxycarbonyl)amino)pent-2-enoate (85 mg, 37 umol, 3 eq) was Boc deprotected with TFA/DCM (General Method 5) to afford (S,E)-methyl 4-aminopent-2-enoate.

Example 151: Synthesis of Compound 252

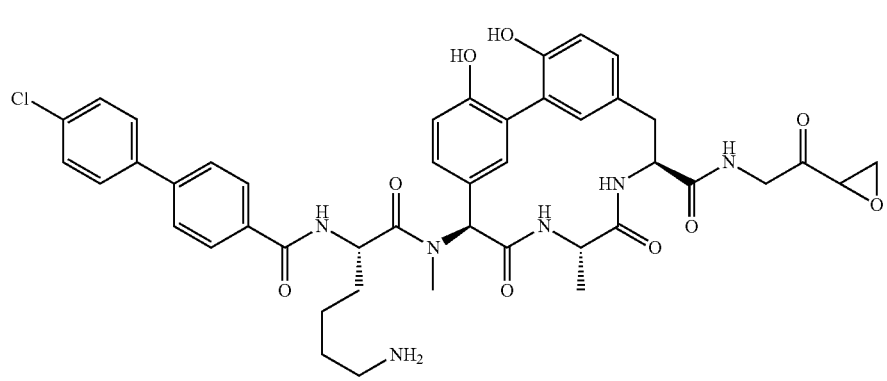

Compound 252 was prepared as the TFA salt using the amide coupling and Boc-group hydrolysis (General Methods 8 and 9) as described for Compound 115 from Compound 104E and 2-amino-1-(oxiran-2-yl)ethanone. Compound 252 was present in 85% purity with 15% of the ring-opened diol. MS (ESI): m/z 839.8 (M+H)+; HPLC $t_R$ 4.16 min (10% AcCN/H$_2$O-95% AcCN/H$_2$O, 6.0 min, 1.0 mL/min Kinetix C18, 4.8×50 mm).

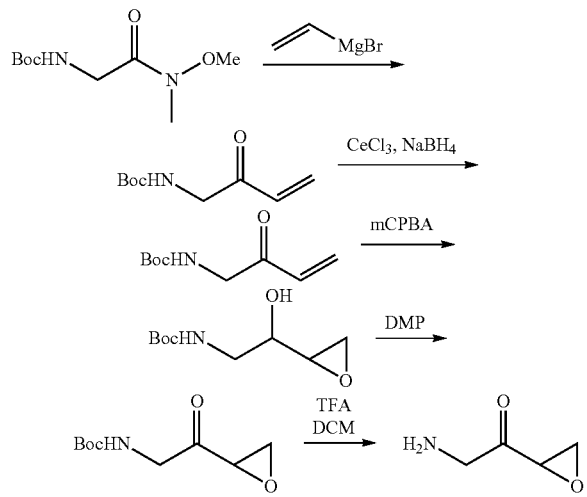

The synthesis of 2-amino-1-(oxiran-2-yl)ethanone: To a solution of tert-butyl (2-(methoxy(methyl)amino)-2-oxoethyl)carbamate (2.18 g, 10.0 mmol) in 40 mL anhydrous THF was added dropwise vinylmagnesium bromide (0.7 M THF, 50 mL, 35.0 mmol) at 0° C. After 1.5 h at 0° C., the mixture was quenched with ether followed by careful addition of 0.3N NaHSO$_4$ solution (110 mL). The aqueous layer was extracted with ether, and the combined organic layers were washed sequentially with saturated NaHCO$_3$ and brine, dried over Na$_2$SO$_4$, and concentrated under reduced pressure. The residue was purified by silica gel gradient elution chromatography (10% EtOAc/Hexanes to 60% EtOAc/hexanes) to afford 0.94 g (46%) of tert-butyl (2-oxobut-3-en-1-yl)carbamate.

A suspension of tert-butyl (2-oxobut-3-en-1-yl)carbamate (700 mg, 3.77 mmol) and cerium trichloride heptahydrate (1.55 g, 4.16 mol) in 10 mL MeOH was placed in a cool water bath (approximately 5 to 10° C.), and NaBH$_4$ (150 mg, 3.95 mmol) was added in one portion. The mixture bubbled vigorously and turned cloudy white. The mixture was stirred at rt for 1 hr, then the mixture was partitioned between ether and 0.2 M NaHSO$_4$. The aqueous layer was extracted with ether, and the combined organic layers were washed sequentially with saturated NaHCO$_3$ and brine, dried over Na$_2$SO$_4$, and concentrated under reduced pressure. The residue was purified by silica gel gradient elution chromatography (20% EtOAc/Hexanes to 60% EtOAc/hexanes) to afford 0.49 g (70%) of tert-butyl (2-hydroxybut-3-en-1-yl)carbamate.

To a suspension of tert-butyl (2-hydroxybut-3-en-1-yl)carbamate (118 mg, 0.630 mmol) and NaHCO$_3$ (159 mg, 3 mmol) was added mCPBA (77%, 212 mg, 0.945 mmol) was added. After 2 hr, additional mCPBA (212 mg, 0.945 mmol) was added, and the mixture was stirred overnight. The solution was partitioned between ether and aqueous Na$_2$S$_2$O$_3$, and the aqueous layer was extracted with ether. The combined organic layers were washed sequentially with saturated NaHCO$_3$ and brine, dried over Na$_2$SO$_4$, and concentrated under reduced pressure. The residue was purified by silica gel gradient elution chromatography (30% EtOAc/hexanes to 80% EtOAc/hexanes) to afford 61 mg (48%) of tert-butyl (2-hydroxy-2-(oxiran-2-yl)ethyl)carbamate. DMP oxidation and Boc-hydrolysis with TFA/DCM afforded 2-amino-1-(oxiran-2-yl)ethanone as the TFA salt.

Example 152: Synthesis of Compound 253

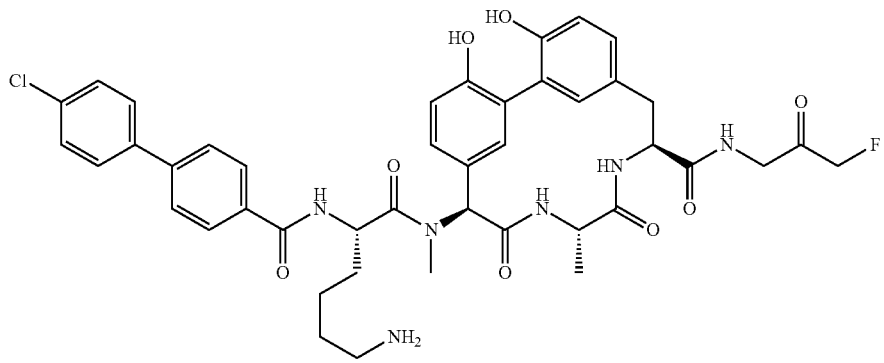

Compound 253 was prepared as the TFA salt using the coupling method, DMP oxidation, and Boc-group hydrolysis as described for Compound 139 from Compound 104E and 1-amino-3-fluoropropan-2-ol. MS (ESI): m/z 829.8 (M+H)+; HPLC $t_R$ 4.23 min (10% AcCN/H$_2$O-95% AcCN/H$_2$O, 6.0 min, 1.0 mL/min Kinetix C18, 4.8×50 mm).

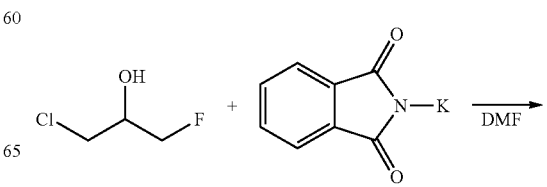

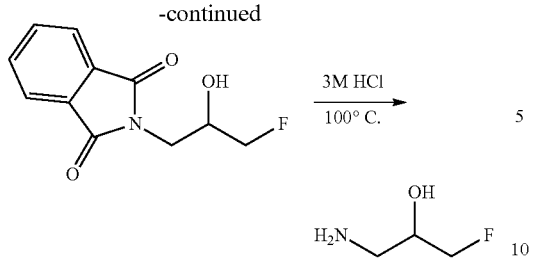

The synthesis of 1-amino-3-fluoropropan-2-ol: A suspension of 1-chloro-3-fluoropropan-2-ol (816 mg, 7.25 mmol) and potassium 1,3-dioxoisoindolin-2-ide (1.48 g, 7.98 mmol) in 12 mL DMF was heated at 80° C. for 4 hr. Then the mixture was partitioned between ether and water. The aqueous layer was extracted with ether (3×), and the combined organic layers were washed sequentially with brine, dried over $Na_2SO_4$, and concentrated under reduced pressure. Silica gel gradient elution chromatography (30% EtOAc/hexanes to 80% EtOAc/hexanes) afforded 911 mg (56%) of 2-(3-fluoro-2-hydroxypropyl)isoindoline-1,3-dione, a white powder. 2-(3-Fluoro-2-hydroxypropyl)isoindoline-1,3-dione (223 mg, 1.00 mmol) in 2 mL 3M HCl was heated at 100° C. for 22 hr. A white precipitate formed in the reaction. Water was added to the mixture, and the solid was filtered off. The filtrate was extracted with EtOAc (3×), and the product aqueous layer was lyophilized to 1-amino-3-fluoropropan-2-ol, an oil (44 mg, 34%).

Example 153: Synthesis of Compound 254

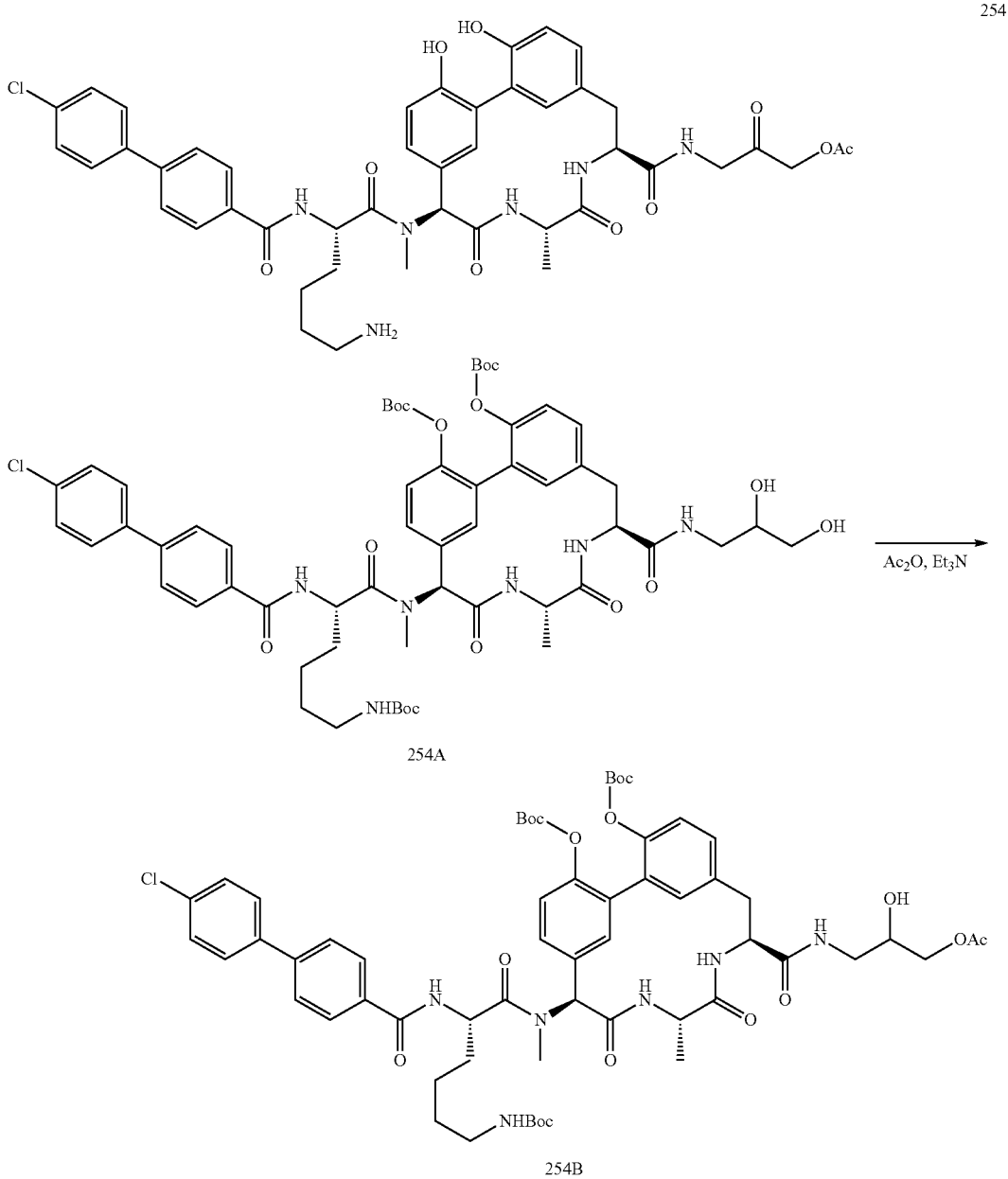

Compound 254A was prepared according to the standard HATU/DIEA coupling method (General Method 8) from Compound 104E and 3-aminopropane-1,2-diol. m/z 1029.8 (M-Boc+H)$^+$; HPLC $t_R$ 3.28 min (50% AcCN/H$_2$O-95% AcCN/H$_2$O, 3.0 min, hold at 95% AcCN, 1.0 mL/min Kinetix C18, 4.8×50 mm).

To a solution of Compound 254A and triethylamine (14.8 mg, 0.146 mmol) in 1 mL DCM was added 0.102 mL of a 1M Ac$_2$O solution (in DCM, 0.102 mmol). After 24 h, the solvents are removed under reduced pressure. Silica gel gradient elution chromatography (100% DCM to 8% MeOH/DCM) afforded Compound 254B (27 mg, 31%). m/z 1171.5 (M+H)$^+$; HPLC $t_R$ 3.49 min (50% AcCN/H$_2$O-95% AcCN/H$_2$O, 3.0 min, hold at 95% AcCN, 1.0 mL/min Kinetix C18, 4.8×50 mm).

Compound 254 was prepared as the TFA salt using the DMP oxidation, and Boc-group hydrolysis as described for Compound 139; m/z 869.6 (M+H)$^+$; HPLC $t_R$ 4.96 min (10% AcCN/H$_2$O-95% AcCN/H$_2$O, 8.0 min, 1.0 mL/min Kinetix C18, 4.8×50 mm).

Example 154: Synthesis of Compound 255

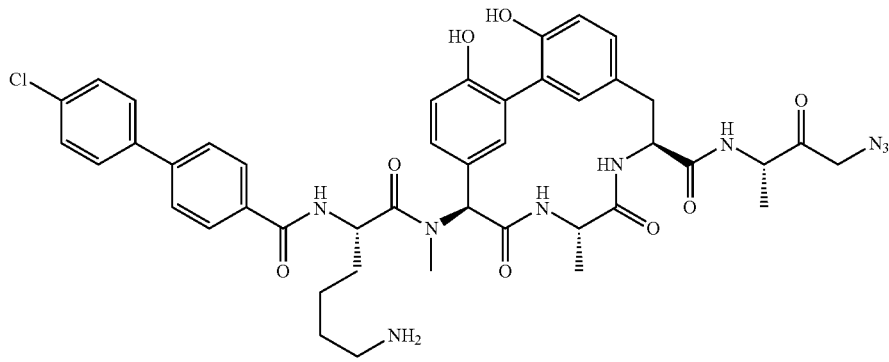

255

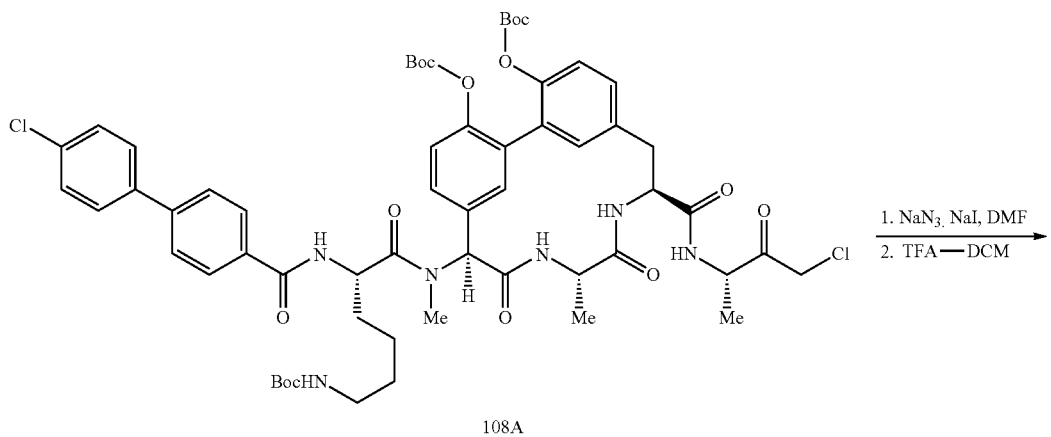

108A

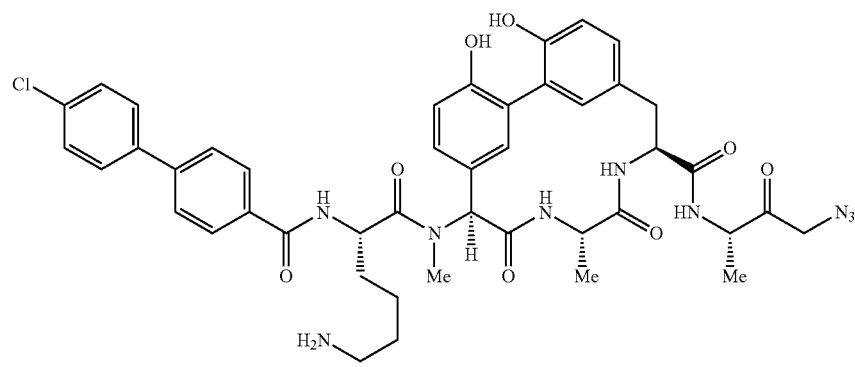

G02945232

Compound 255 was synthesized in two steps from Compound 108A (58 mg, 0.05 mmol) and NaN₃ (10 mg, 0.15 mmol) using the similar procedure described for the synthesis Compound 123. LCMS: MS (ESI) for C₄₄H₄₈ClN₉O₈: m/z 866.4 (M+H). HPLC: $t_R$ 3.27 min (10% AcCN/H₂O-90% AcCN/H₂O (with 0.05% TFA), 3.0 min, 1.0 mL/min Kinetix C18, 4.8×50 mm).

Example 155: Synthesis of Compound 256

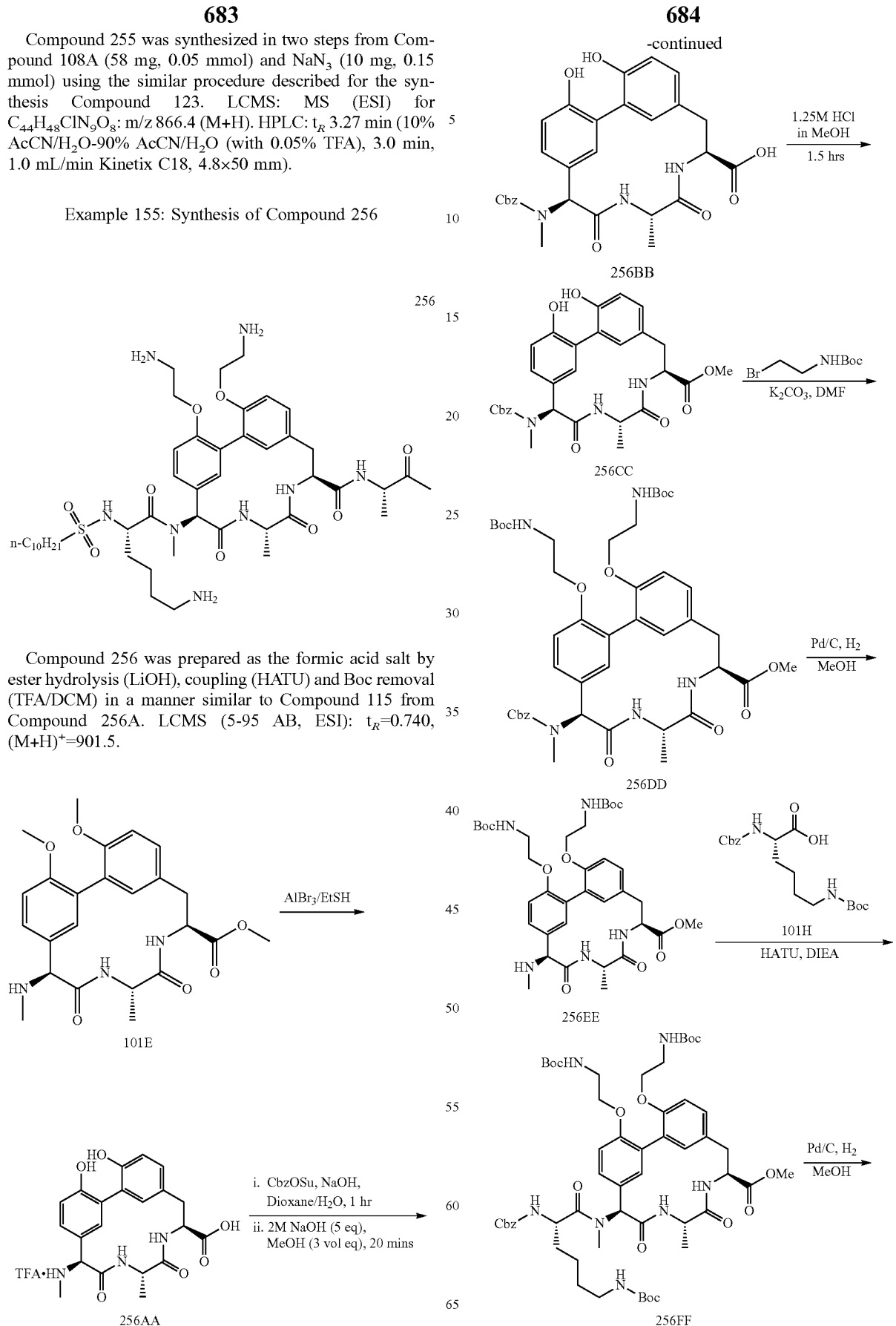

Compound 256 was prepared as the formic acid salt by ester hydrolysis (LiOH), coupling (HATU) and Boc removal (TFA/DCM) in a manner similar to Compound 115 from Compound 256A. LCMS (5-95 AB, ESI): $t_R$=0.740, (M+H)⁺=901.5.

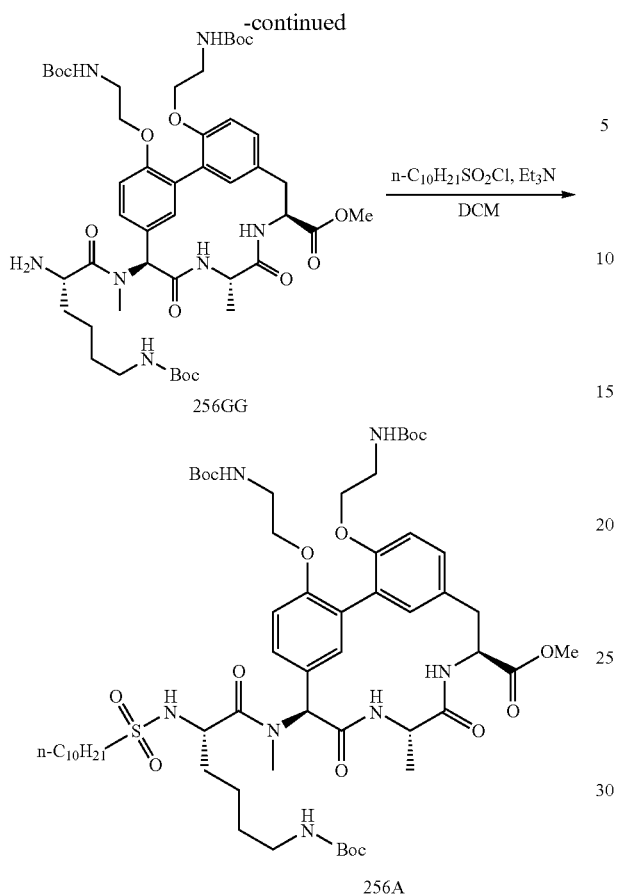

Compound 101E (5.0 g, 11 mmol) was treated according to General Method 4 (Example 1) to afford Compound 256AA (4.5 g, 80% yield) as a white solid after HPLC purification.

To a solution of Compound 256AA (4.7 g, 8.9 mmol) in 1,4-Dioxane/H₂O (9:1, 165 mL) was added 1N NaOH dropwise until pH~11. A solution of Cbz-OSu (6.66 g, 26.7 mmol) dissolved in 1,4-Dioxane (50 mL) was then added. After stirring for 1 h, NaOH (1.07 g, 26.7 mmol) was then added to the reaction followed by MeOH (60 mL). This resulting mixture was allowed to stir for 20 mins. To the reaction was then added dilute citric acid (10% v/v, 50 mL), the aqueous layer was extracted with EtOAc (3×150 mL) and the combined organic layers were washed with brine (3×100 mL), dried over Na₂SO₄ and concentrated to give the crude product. The residue was diluted with DCM (50 mL) and the suspension was filtered to give desired compound (3.2 g). The DCM phase was concentrated and the residue was purified by silica gel column (eluting 10-20% methanol in EtOAc) to give the desired compound (1.0 g). The combined batches gave Compound 256BB (4.2 g, 86.1% yield) as a white solid.

To Compound 256BB (4.3 g, 7.85 mmol) was added a solution of 1.25M HCl in MeOH (128 mL) and the reaction was stirred at 0° C. The volatiles were removed to afford Compound 256CC (4.15 g, 94.1% yield) as a white solid, which was used directly in the next step.

To a solution of Compound 256CC (3.9 g, 6.94 mmol) and K₂CO₃ (14.4 g, 104 mmol) in DMF (50 mL) was added tert-butyl 2-bromoethylcarbamate (15.6 g, 69.5 mmol) at 0° C. The mixture was stirred at room temperature for 48 h. The mixture was filtered and the filtrate was diluted with EtOAc (500 mL). The EtOAc layer was washed with brine (2×400 mL), dried over Na₂SO₄, concentrated and purified by chromatography on silica (solvent gradient: 0-60% EtOAc in petroleum ether) to afford Compound 256DD (4.8 g, 81.5% yield) as a white solid.

Standard hydrogenation (Pd/C), amide coupling (General Method 8) and hydrogenation (Pd/C) conditions were followed to afford Compound 256GG as a white solid. Sulfonyl chloride N-alkylation: To a solution of Compound 256GG (390 mg, 0.41 mmol) and decane-1-sulfonyl chloride (299 mg, 1.24 mmol) in DCM (30 mL) was added Et₃N (209 mg, 2.07 mmol) at 0° C. and the mixture was stirred at 0° C. for 1 h. The reaction mixture was then adjusted pH=3 by citric acid, which was taken up by DCM (20 ml). The DCM layer was washed by brine (50 mL), dried over MgSO₄, concentrated and purified by flash column chromatography (eluting 3.3% MeOH in DCM) to afford Compound 256A (410 mg, 86.4% yield) as a yellow solid.

Example 156: Synthesis of Compound 257

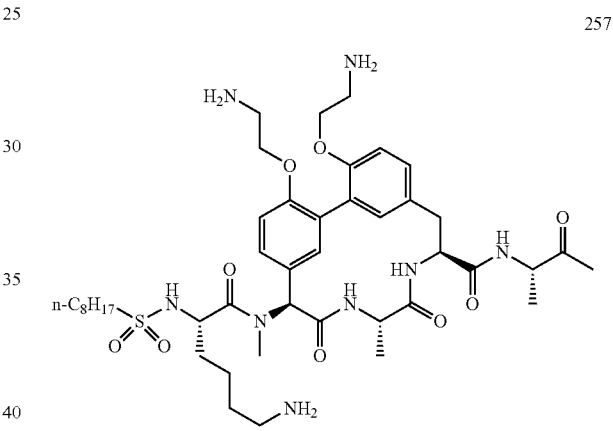

Compound 257 was prepared as the formic acid salt in a manner similar to Compound 256 from Compound 256GG and octane-1-sulfonyl chloride. LCMS (5-95 AB, ESI): $t_R$=0.709 min, (M+H)⁺=873.5.

Example 157: Synthesis of Compound 258

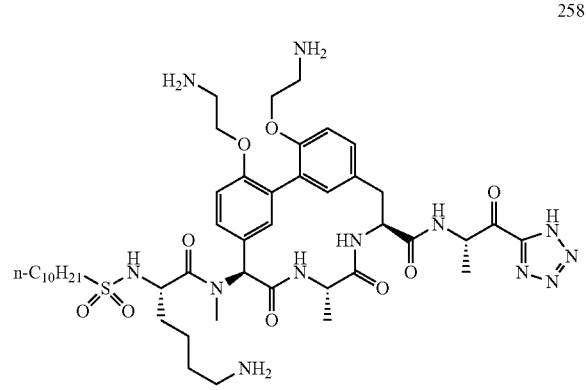

Compound 258 was prepared as the formic acid salt in a manner similar to Compound 256 from Compound 256GG and Compound 134A. LCMS (5-95 AB, ESI): $t_R$=0.743 min, $(M+H)^+$=955.3.

Example 158: Synthesis of Compound 259

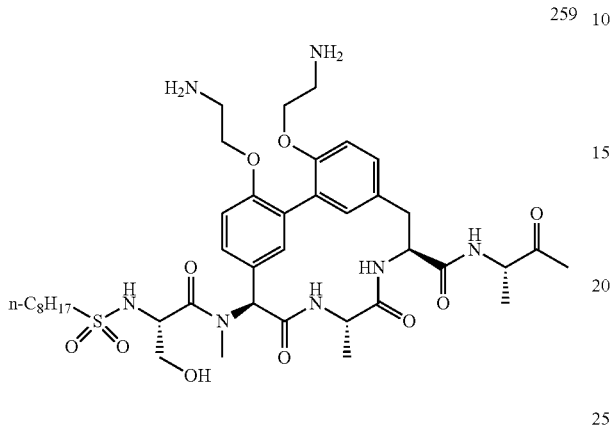

Compound 259 was prepared as the formic acid salt in a manner similar to Compound 256 from Compound 256EE. LCMS (5-95AB_30MIN, with 30 minute gradient): $t_R$=11.23, $(M+H)^+$=832.4.

Example 159: Synthesis of Compound 260

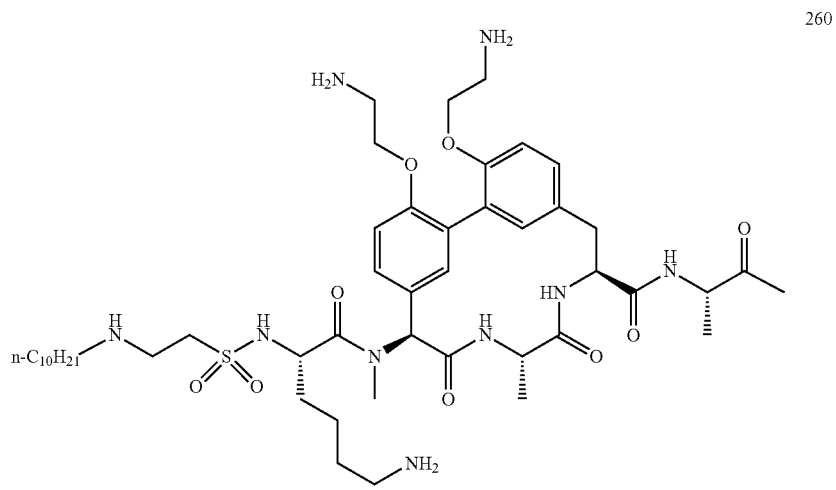

Compound 260 was prepared as the formic acid salt similar manner to Compound 115 using the LiOH hydrolysis, HATU coupling, and TFA Boc-deprotection from Compound 260A. LCMS (5-95 AB, ESI): $t_R$=0.724, $(M+H)^+$=946.1.

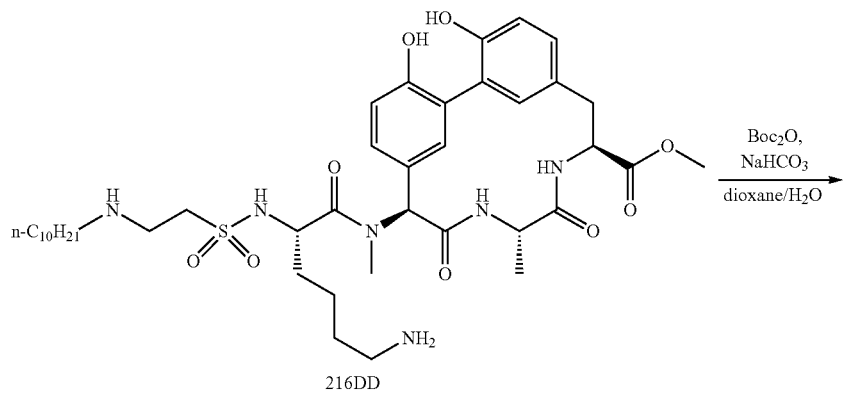

216DD

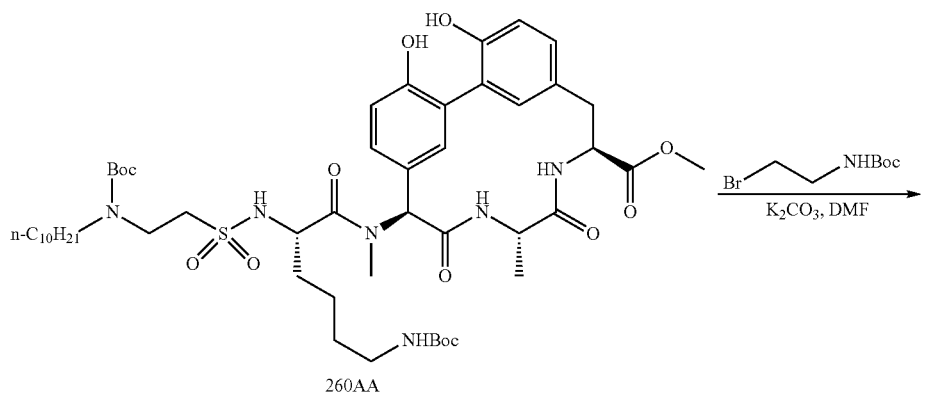

260AA

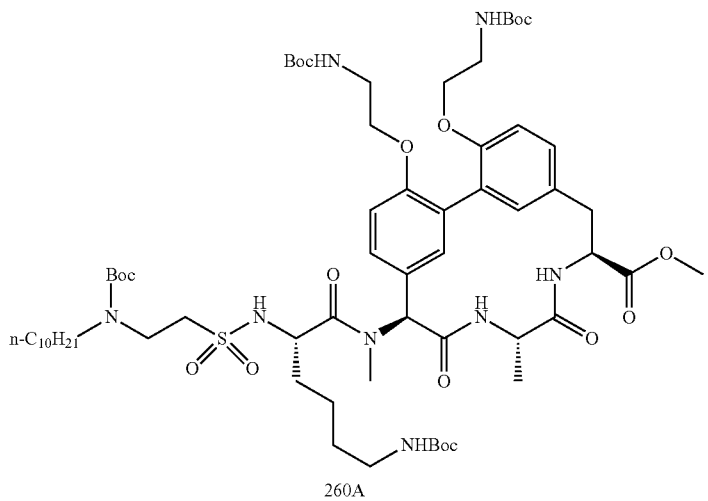

260A

To a solution of 216DD (790 mg, 0.98 mmol) and NaHCO$_3$ (413 mg, 4.92 mmol) in MeOH (20 mL) was added Boc$_2$O (429 mg, 1.97 mmol) in three portions at 0° C. The mixture was stirred at 25° C. for 12 h. The volatiles were removed and the residue was re-dissolved with DCM (100 mL), which was washed by brine (2×100 mL). The organic layer was then dried over Na$_2$SO$_4$, concentrated and purified by HPLC to afford Compound 260AA (220 mg, 22.3% yield) as a white solid.

Compound 260A was prepared from Compound 260AA (220 mg, 0.22 mmol) and tert-butyl 2-bromoethylcarbamate (983 mg, 4.39 mmol) according to General Method 7 to afford 20 mg (7.1%) of a white solid after HPLC purification.

Example 160: Synthesis of Compound 261
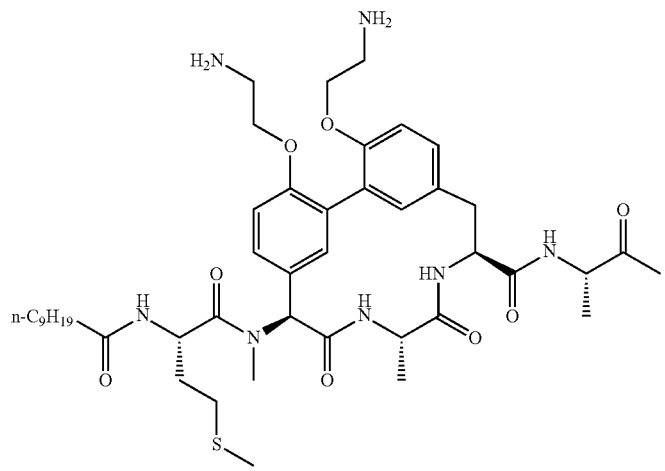
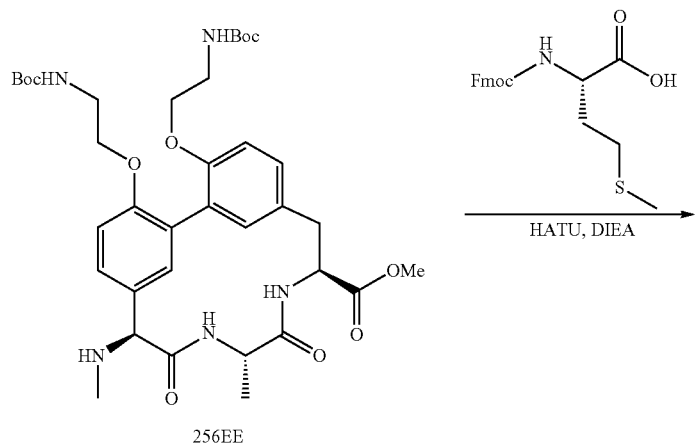
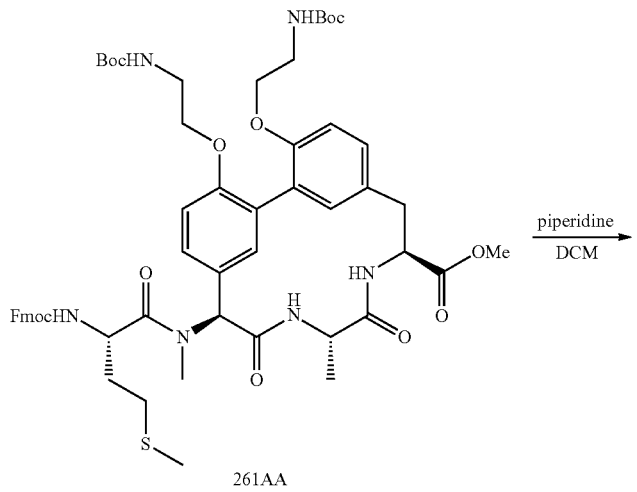

-continued
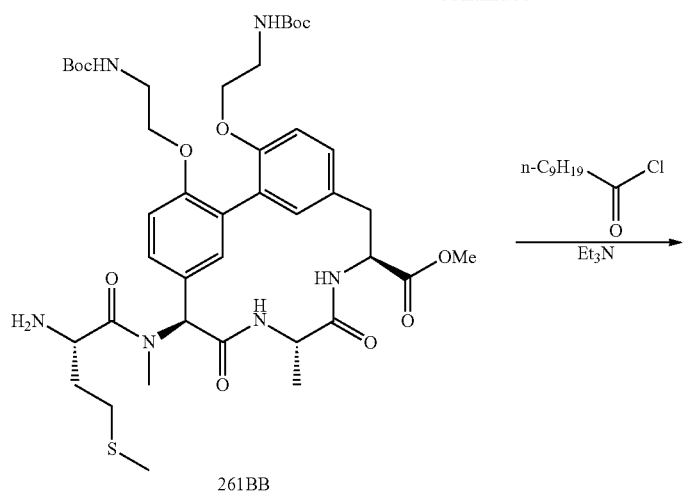
261BB
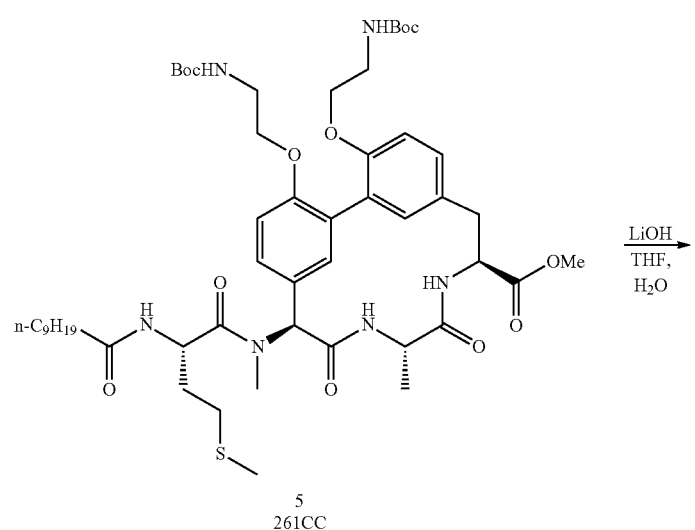
5
261CC
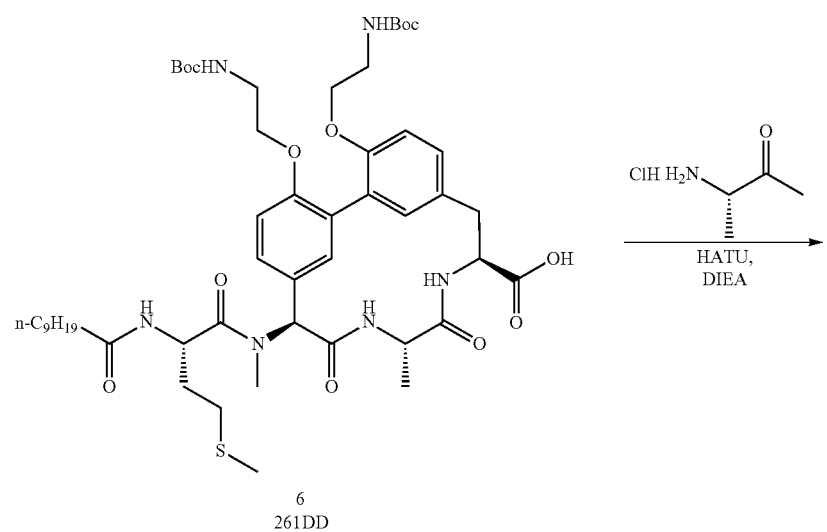
6
261DD

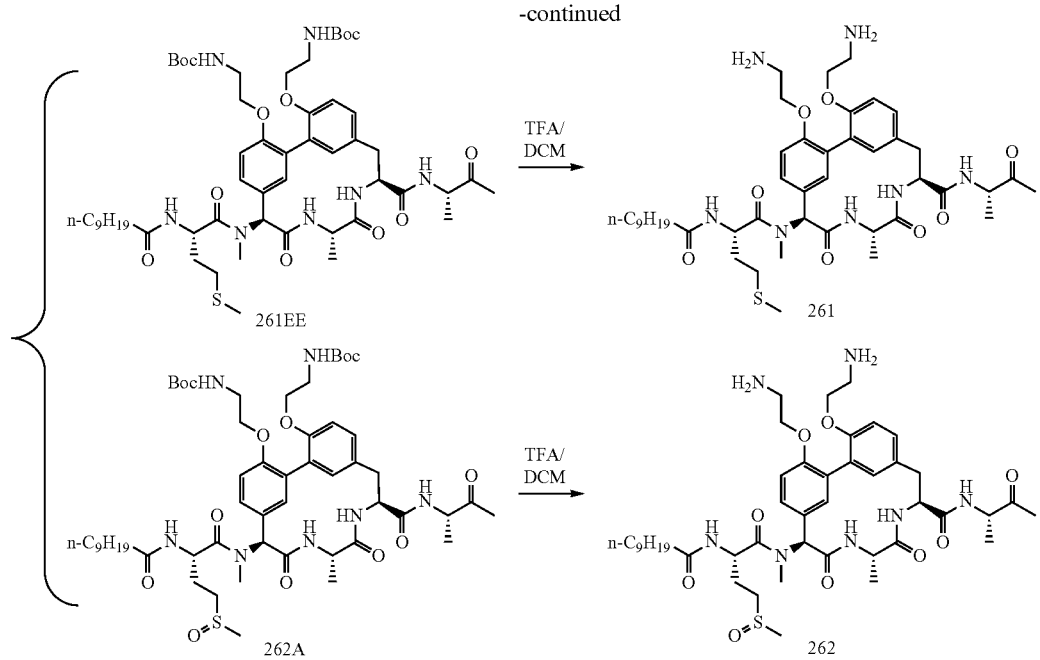

The synthesis of Compound 261: Compound 261AA was prepared according to General Method 8 (Example 9) from Compound 256EE (104 mg, 0.28 mmol) and Fmoc-L-methionine to afford Compound 261AA (100 mg, 66.9%) as a light yellow solid after silica column chromatography.

Compound 261AA was subject to the standard Fmoc-deprotection conditions. To a solution of Compound 261AA (100 mg, 0.18 mmol) in DCM (4 mL) was added piperidine (1.0 mL) at 0° C. and the mixture was stirred at room temperature under $N_2$ for 2 h. The volatiles were concentrated and the residue was re-dissolved in EtOAc (30 ml), which was washed by brine (2×30 mL). The organic layer was dried over $MgSO_4$, concentrated and purified by prep-TLC (eluting 3% MeOH in DCM) to give Compound 261BB (50 mg, 63.1% yield) as a yellow solid.

Compound 261CC was prepared in a manner similar to Compound 256A from Compound 261BB and decanoyl chloride using trimethylamine as a base in DCM.

Compound 261 was prepared as the formic acid salt by ester hydrolysis (LiOH), coupling (HATU) and Boc-removal (TFA/DCM) in a manner similar to Compound 115 from Compound 261CC. LCMS (5-95 AB, ESI): $t_R$=0.788, $(M+H)^+$=854.4.

Example 161: Synthesis of Compound 262

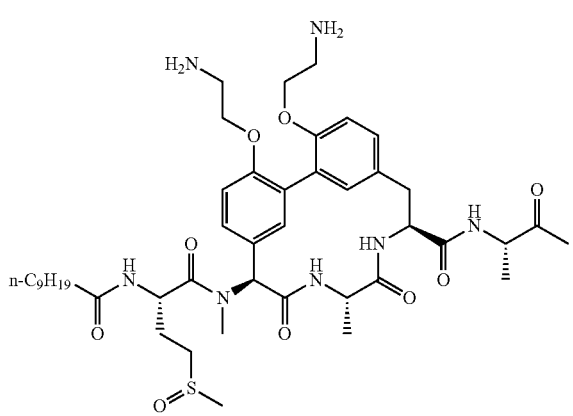

During the coupling of Compound 261D, thiol oxidation to the sulfoxide was observed and provided a mixture of Compound 261EE and Compound 262A, which was separated by column chromatography. Compound 262A was subject to the Boc removal with TFA/DCM (General Method 9) to afford Compound 262. LCMS (5-95 AB, ESI): $t_R$=0.767, $(M+H)^+$=870.5.

Example 162: Synthesis of Compound 263

Compound 263 was prepared as the formic acid salt using similar procedures as described for Compound 261 from Compound 256EE. LCMS (5-95 AB, ESI): $t_R$=0.789 min, (M+H)$^+$=838.5.

Example 163: Synthesis of Compound 264

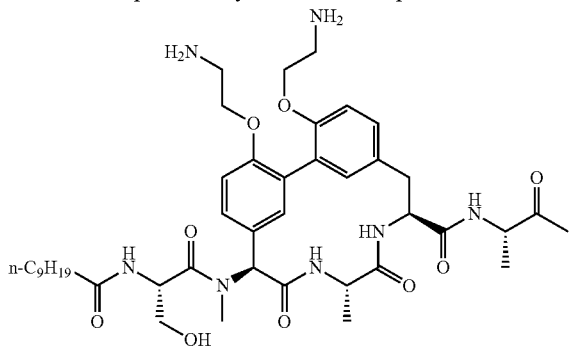

Compound 264 was prepared as the formic acid salt using similar procedures as described for Compound 261 from Compound 256EE LCMS (5-95 AB, ESI): $t_R$=0.624 min, (M+H)=810.3.

Example 164: Synthesis of Compound 265

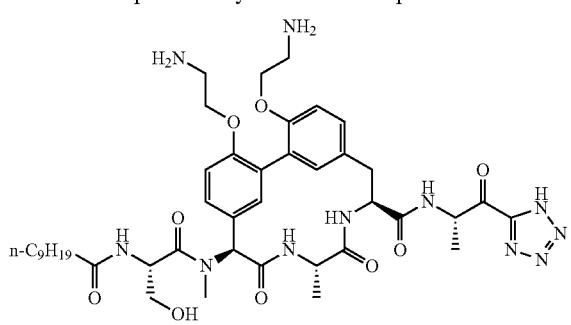

Compound 265 was prepared as the formic acid salt using similar procedures as described for Compound 261 from Compound 256EE and Compound 134A. LCMS (5-95 AB, ESI): $t_R$=0.616, (M+H)$^+$=864.2.

Example 165: Synthesis of Compound 266

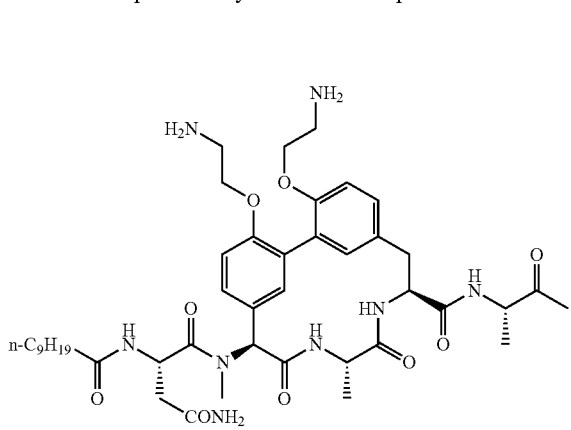

Compound 266 was prepared as the formic acid salt using similar procedures as described for Compound 261 from Compound 256EE. LCMS (5-95 AB, ESI): $t_R$=0.745 min, (M+H)$^+$=837.5.

Example 166: Synthesis of Compound 267

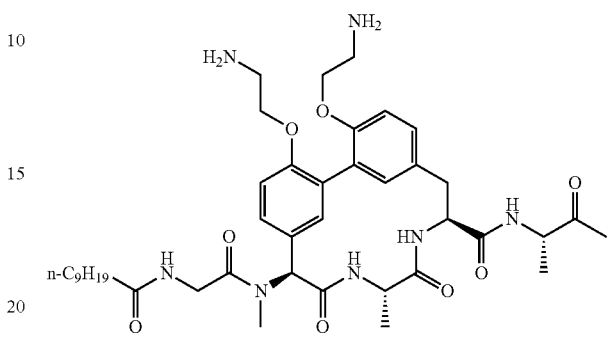

Compound 267 was prepared as the formic acid salt using similar procedures as described for Compound 261 from Compound 256EE. LCMS (5-95 AB, ESI): $t_R$=0.634, (M+H)$^+$=780.3.

Example 167: Synthesis of Compound 268

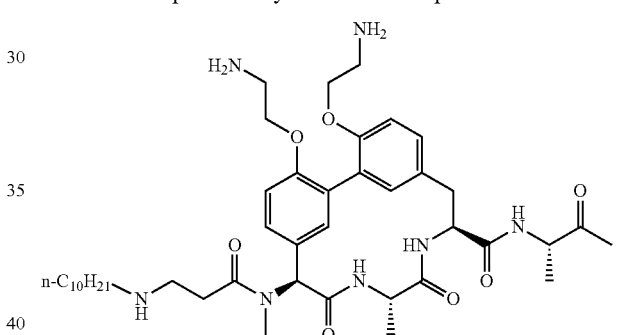

Compound 268 was prepared as the formic acid salt using similar procedures as described for Compound 261 from Compound 256EE and Compound 110A. LCMS (5-95 AB, ESI): $t_R$=0.735 min, (M+H)$^+$=780.5.

Example 168: Synthesis of Compound 269

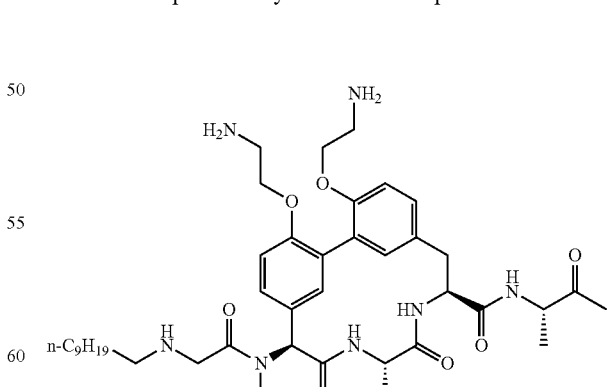

Compound 269 was prepared as the formic acid salt using similar procedures as described for Compound 261 from Compound 256EE and Compound 112A. LCMS (5-95 AB, ESI): $t_R$=0.639, (M+H)$^+$=766.3.

Example 169: Synthesis of Compound 270
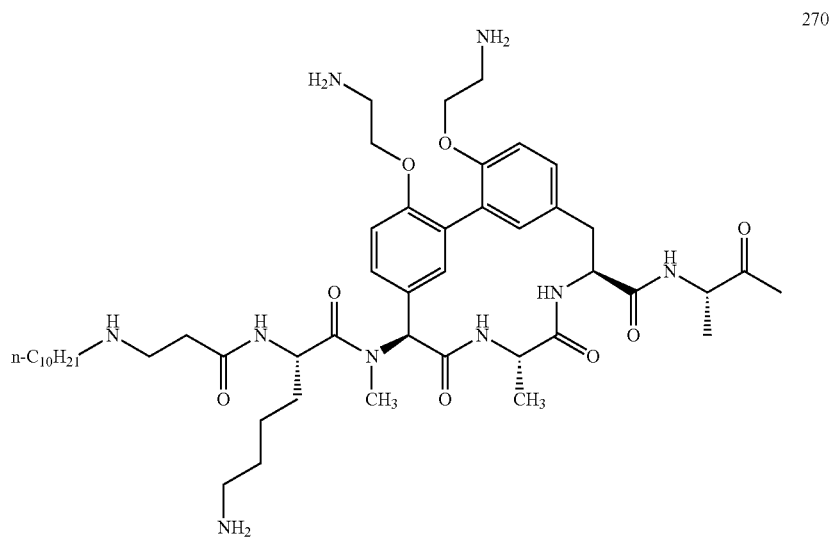
270
Compound 270 was prepared as the formic acid salt in a manner similar to Compound 114 from Compound 256GG, Compound 110A and Compound 109A. LCMS (5-95 AB, ESI): $t_R$=0.688, $(M+H)^+$=908.6.
Example 170: Synthesis of Compound 271
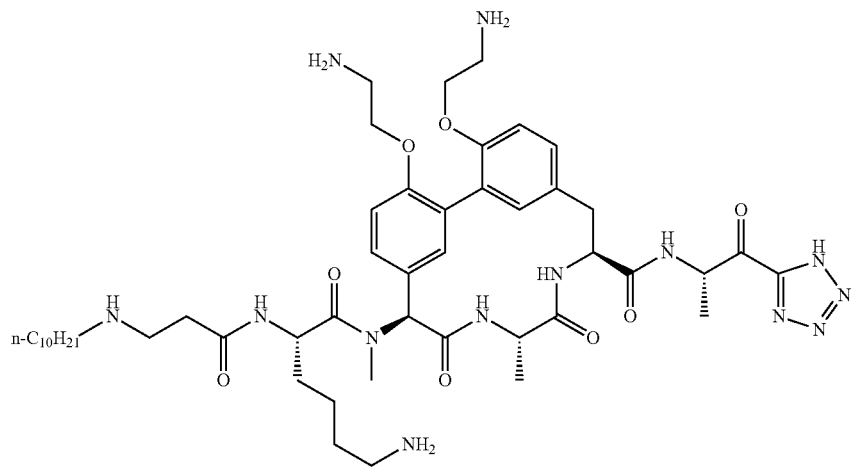
Compound 271 was prepared as the formic acid salt in a manner similar to Compound 270 from Compound 256GG, Compound 110A, and Compound 134A. LCMS (5-95 AB, ESI): $t_R$=0.591 min, $(M+H)^+$=962.5.

Example 171: Synthesis of Compound 272

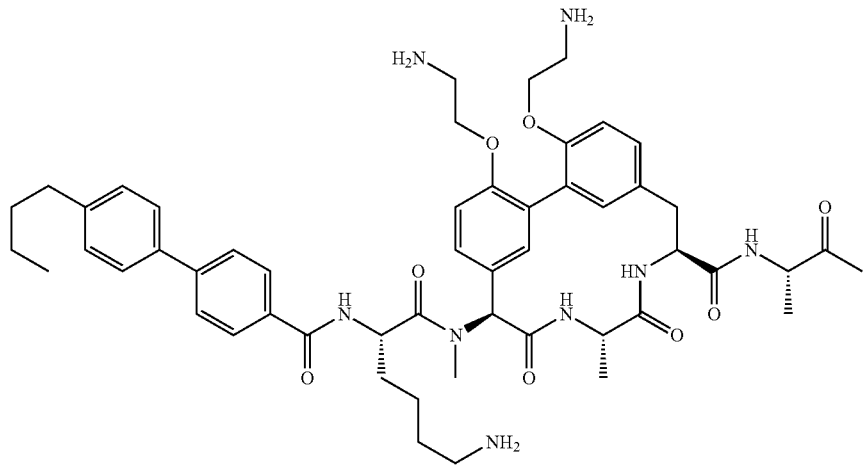

272

Compound 272 was prepared as the formic acid salt in a manner similar to Compound 114 from Compound 256GG and 4'-butyl-[1,1'-biphenyl]-4-carboxylic acid (Compound 184A). LCMS (5-95 AB, ESI): $t_R$=0.754, (M+H)$^+$=933.4.

Example 172: Synthesis of Compound 273

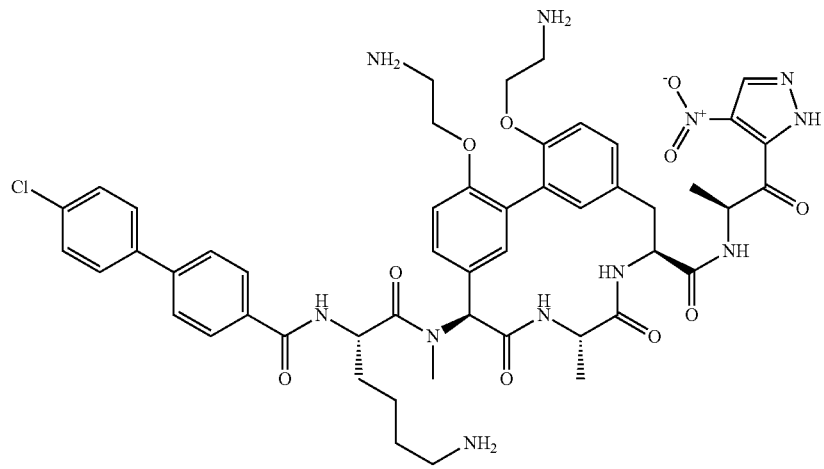

273

Compound 273 was prepared using the coupling method, DMP oxidation, and Boc-group hydrolysis as described for Compound 139 from Compound 209A and (2S)-2-amino-1-(4-nitro-1-((2-(trimethylsilyl)ethoxy)methyl)-1H-pyrazol-5-yl)propan-1-ol, except that 4N HCl in dioxane was used in the final Boc-deprotection step. MS+ 1008.9.

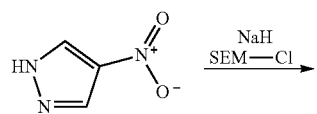

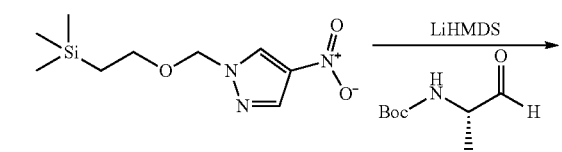

-continued

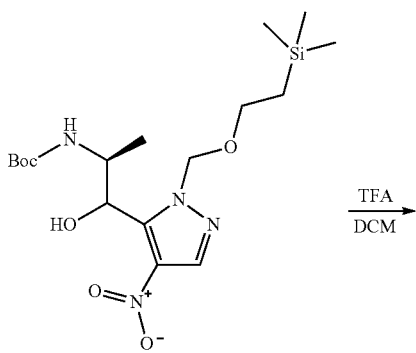

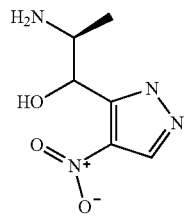

The synthesis of (2S)-2-amino-1-(4-nitro-1-((2-(trimethylsilyl)ethoxy)methyl)-1H-pyrazol-5-yl)propan-1-ol: To a solution of 4-nitro-1H-pyrazole (26.6 mmol, 3006 mg) in THF (30 mL) at 0° C. was added sodium hydride (60 mass %) in mineral oil (39.9 mmol, 1595 mg) in portions. The mixture was stirred at room temperature for 15 minutes. 2-(trimethylsilyl)ethoxymethyl chloride (42.5 mmol, 7464 mg, 7.92 mL) was added dropwise. The reaction mixture was stirred at room temperature for 2 hours. The reaction mixture was quenched carefully with 30 mL of water, extracted with EtOAc (2×50 mL). The organic layer was washed with brine, dried with MgSO₄, concentrated, and the residue was purified on silica eluted with 0 to 10% EtOAc in heptane to afford 4-nitro-1-((2-(trimethylsilyl)ethoxy)methyl)-1H-pyrazole (6.05 g, 94%).

A solution of 4-nitro-1-((2-(trimethylsilyl)ethoxy)methyl)-1H-pyrazole (1.423 mmol, 346.3 mg) in THF (10 mL) was cooled to −78° C. Lithium bis(trimethylsilyl)amide (1 mol/L) in THF (1.708 mmol, 1500 mg, 1.708 mL) was added drop-wise, and the mixture was stirred at −78° C. for 30 minutes. tert-butyl N-[(1S)-1-methyl-2-oxo-ethyl]carbamate (1.779 mmol, 308.1 mg) in THF (3 mL) was then added dropwise. The reaction mixture was stirred at −78° C. for 2 hours, allowed to warm to room temperature, quenched slowly with saturated NH₄Cl. The layers were separated. The aqueous layer was extracted with EtOAc (2×5 ml). The combined organic layers were dried with MgSO₄, concentrated, and the residue was purified on silica eluted with 0 to 10% EtOAc in heptane to afford tert-butyl ((2S)-1-hydroxy-1-(4-nitro-1-((2-(trimethylsilyl)ethoxy)methyl)-1H-pyrazol-5-yl)propan-2-yl)carbamate (155 mg, 26%).

A modified TFA deprotection using 1,1,1,3,3,3-hexafluoro-2-propanol was utilized. A mixture of tert-butyl N-[(1S)-2-hydroxy-1-methyl-2-[4-nitro-2-(2-trimethylsilylethoxymethyl)pyrazol-3-yl]ethyl]carbamate (0.3681 mmol, 153.3 mg) in premixed trifluoroacetic acid (0.5 mL) and 1,1,1,3,3,3-hexafluoro-2-propanol (9.5 mL) was stirred at room temperature for 1 hour. The mixture was then concentrated. The residue was dissolved in acetonitrile, neutralized with solid NaHCO₃, filtered, and the filtrated was concentrated and dried on high vac to afford crude (2S)-2-amino-1-(4-nitro-1-((2-(trimethylsilyl)ethoxy)methyl)-1H-pyrazol-5-yl)propan-1-ol, which was used as is.

Example 173: Synthesis of Compound 274

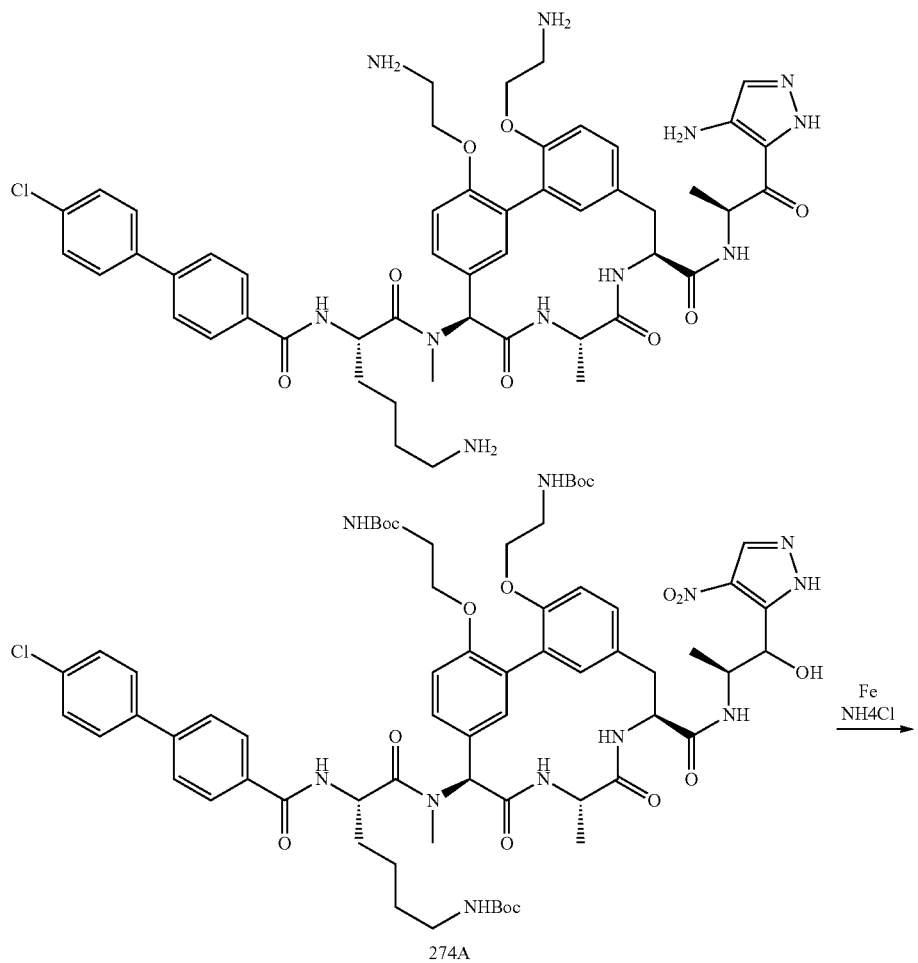

-continued

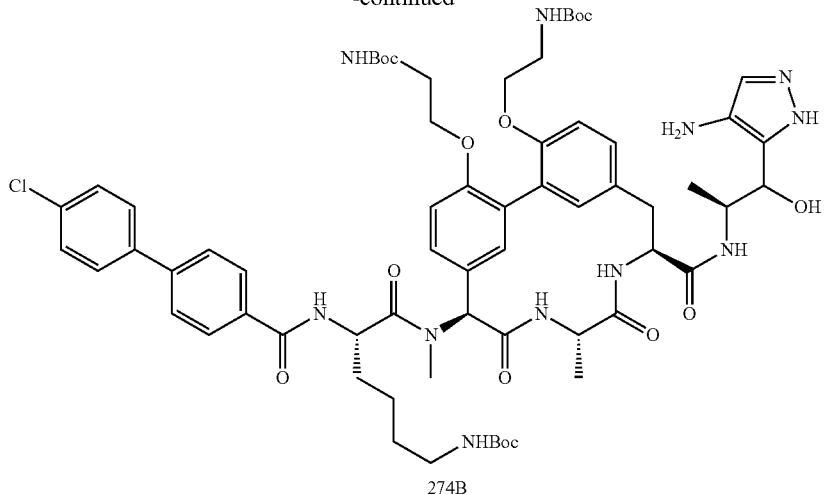

274B

To Compound 274A (0.09344 mmol, 122.3 mg) in ethanol (50 mL) was added water (10 mL), ammonium chloride (0.934 mmol, 50.0 mg), and iron (3.74 mmol, 210 mg). The reaction mixture was stirred at 65° C. for 4 hours then stirred at room temperature overnight. The mixture was filtered through Celite®. The filtrate was concentrated and the residue was purified on silica eluted with 0 to 10% MeOH in DCM to afford Compound 274B (78.2 mg, 33%).

Compound 274 was prepared from Compound 274B using TFA/DCM Boc-deprotection (General Method 9) to afford Compound 274 in 31% yield. MS+ 978.2

Example 174: Synthesis of Compound 275

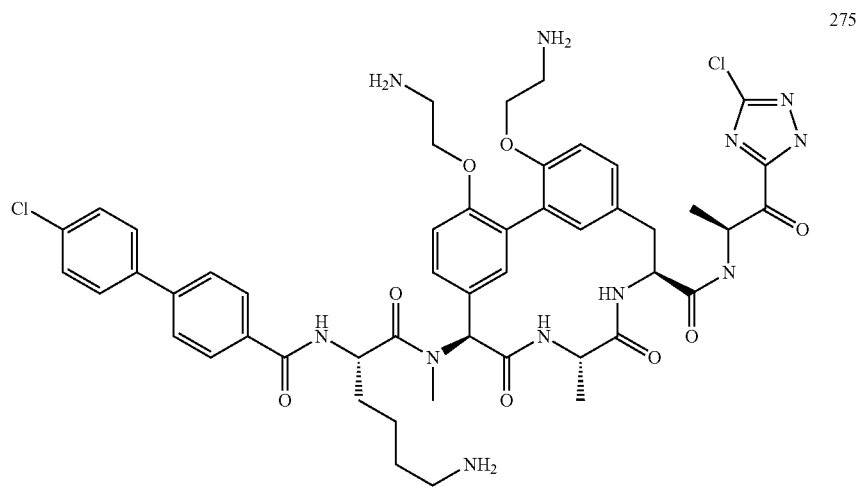 [SMILES: C[C@@H]1NC(=O)[C@@H](N(C)C(=O)[C@H](CCCCN)NC(=O)c2ccc(-c3ccc(Cl)cc3)cc2)c2ccc(OCCN)c(c2)-c2cc(ccc2OCCN)C[C@@H](C(=O)N[C@@H](C)C(=O)c2nc(Cl)n[nH]2)NC1=O]

275

Compound 275 was prepared using the coupling method, DMP oxidation, and Boc-group hydrolysis as described for Compound 139 from Compound 209A and (2S)-2-amino-1-(5-chloro-4H-1,2,4-triazol-3-yl)propan-1-ol. MS+ 998.7.

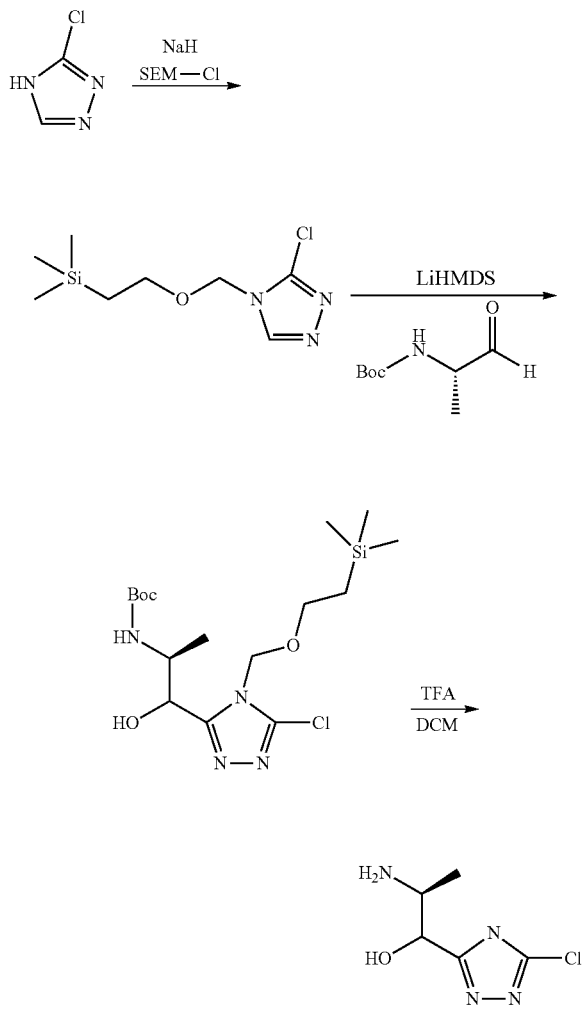

The synthesis of (2S)-2-amino-1-(5-chloro-4H-1,2,4-triazol-3-yl)propan-1-ol: To a solution of 3-chloro-4H-1,2,4-triazole (11.28 mmol, 1229.1 mg) in THF (50 mL) was added sodium hydride (60 mass %) in mineral oil (22.561 mmol, 902.34 mg) in portions. The mixture was stirred at room temperature for 30 minutes and then 2-(trimethylsilyl)ethoxymethyl chloride (22.56 mmol, 3959 mg, 4.20 mL) was added dropwise. The reaction mixture was stirred at room temperature for 18 hours. The reaction mixture was quenched carefully with 20 mL of water, extracted with EtOAc (2×50 mL). The organic layer was washed with brine, dried with MgSO$_4$, concentrated, and the residue was purified on silica eluted with 0 to 50% EtOAc in heptane to afford 3-chloro-4-((2-(trimethylsilyl)ethoxy)methyl)-4H-1,2,4-triazole (2.28 g, 86%).

A solution of 3-chloro-4-((2-(trimethylsilyl)ethoxy)methyl)-4H-1,2,4-triazole (2.678 mmol, 626.0 mg) in THF (20 mL) was cooled to −78° C. N-Butyllithium (2.5 mol/L) in hexane (2.812 mmol, 1.1 mL) was added drop-wise, and the mixture was stirred at −78° C. for 30 minutes and then tert-butyl N-[(1S)-1-methyl-2-oxo-ethyl]carbamate (2.946 mmol, 510.2 mg) in THF (3 mL) was added drop-wise. The reaction mixture was stirred at −78° C. for 2 hours, then allowed to warm to room temperature and stirred overnight. The reaction was quenched slowly with saturated NH$_4$Cl. The layers were separated. The aqueous layer was extracted with EtOAc (2×20 ml). The combined organic layers were dried with MgSO$_4$, concentrated, and the residue was purified on silica eluted with 0 to 100% EtOAc in heptane to afford tert-butyl ((2S)-1-(5-chloro-4-((2-(trimethylsilyl)ethoxy)methyl)-4H-1,2,4-triazol-3-yl)-1-hydroxypropan-2-yl)carbamate (189 mg, 17%).

A mixture of tert-butyl ((2S)-1-(5-chloro-4-((2-(trimethylsilyl)ethoxy)methyl)-4H-1,2,4-triazol-3-yl)-1-hydroxypropan-2-yl)carbamate (0.464 mmol, 189 mg) in premixed trifluoroacetic acid (2 mL) and DCM (2 mL) was stirred at room temperature for 2 hours. The mixture was concentrated to afford crude (2S)-2-amino-1-(5-chloro-4H-1,2,4-triazol-3-yl)propan-1-ol, which was used as is.

Example 175: Synthesis of Compound 276

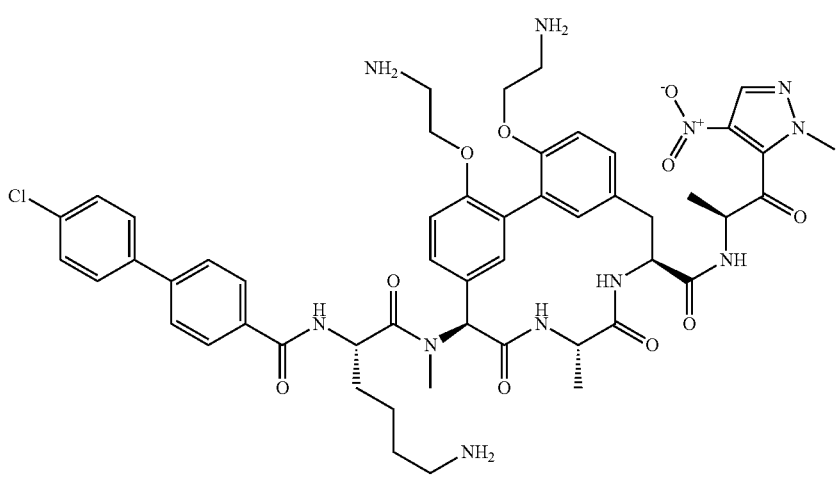

276

Compound 276 was prepared using the coupling method, DMP oxidation, and Boc-group hydrolysis as described for Compound 139 from Compound 209A and (2S)-2-amino-1-(1-methyl-4-nitro-1H-pyrazol-5-yl)propan-1-ol. MS+ 1023.4.

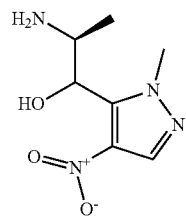

The synthesis of (2S)-2-amino-1-(1-methyl-4-nitro-1H-pyrazol-5-yl)propan-1-ol: (2S)-2-Amino-1-(1-methyl-4-nitro-1H-pyrazol-5-yl)propan-1-ol was prepared from 1-methyl-4-nitro-pyrazole using the same methods that were used for (2S)-2-amino-1-(4-nitro-1-((2-(trimethylsilyl)ethoxy)methyl)-1H-pyrazol-5-yl)propan-1-ol (Example 172).

Example 176: Synthesis of Compound 277

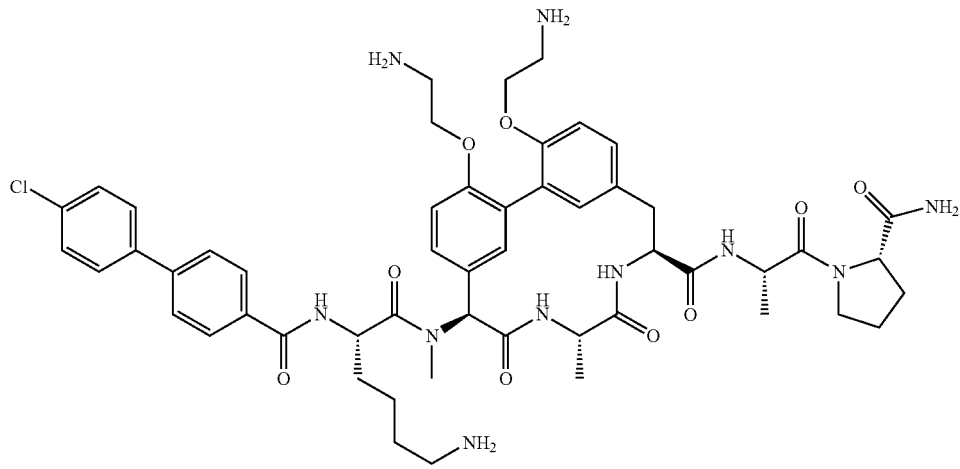 [SMILES: C[C@@H]1NC(=O)[C@@H](N(C)C(=O)[C@H](CCCCN)NC(=O)c2ccc(-c3ccc(Cl)cc3)cc2)c2ccc(OCCN)c(c2)-c2cc(ccc2OCCN)C[C@@H](C(=O)N[C@@H](C)C(=O)N2CCC[C@H]2C(N)=O)NC1=O]

Compound 277 was prepared using the coupling method and Boc-group hydrolysis as described for Compound 115 from Compound 209A and Compound 155A. LCMS (ESI) m/z 1009.6 (M+H)+.

Example 177: Synthesis of Compound 278

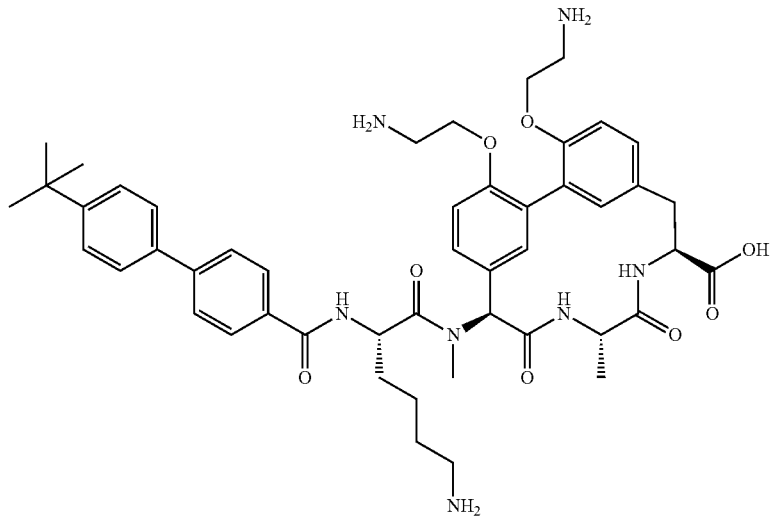

711

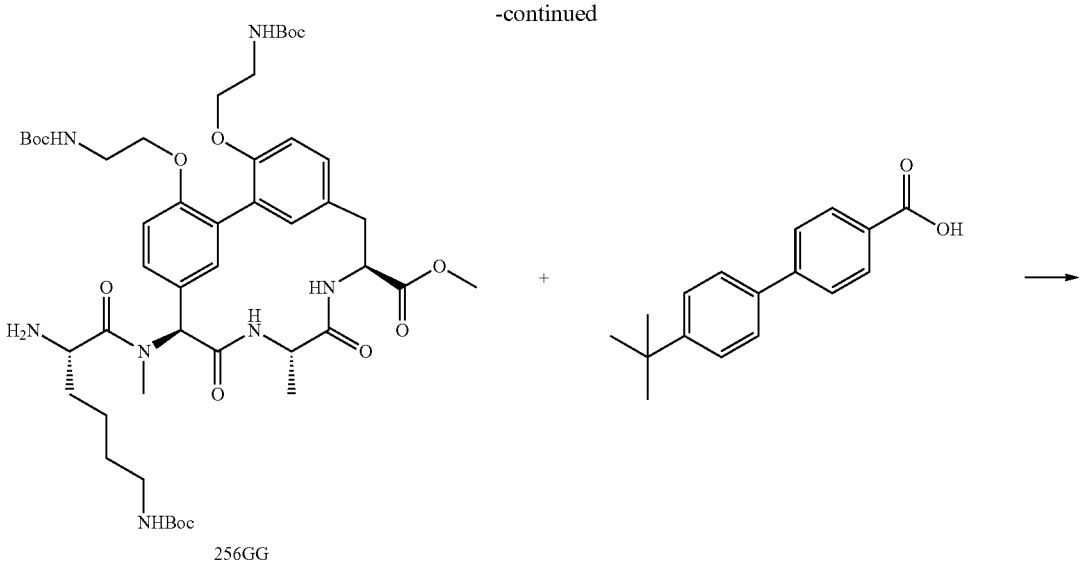

256GG

712

-continued

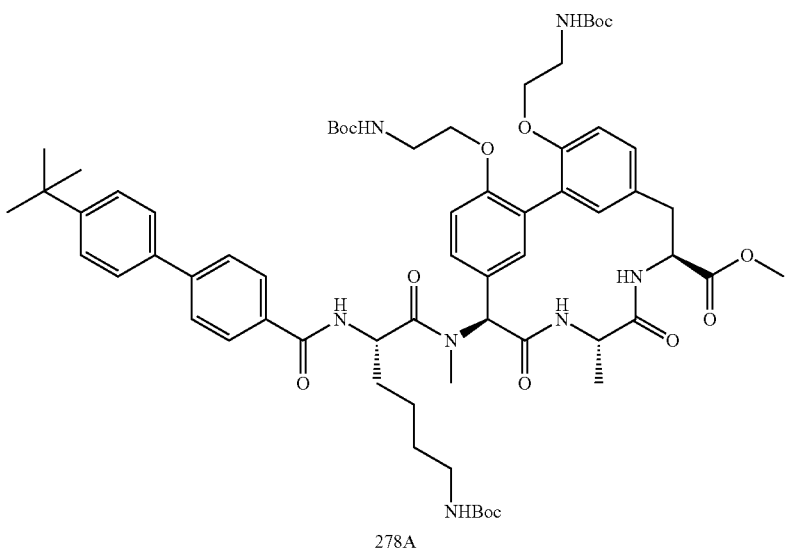

278A

To a mixture of Compound 256GG (100 mg, 0.11 mmol), 4-(4-tert-butylphenyl)benzoic acid (40.49 mg, 0.16 mmol), EDC (40.70 mg, 0.21 mmol), and HOBt (29.27 mg, 0.21 mmol) in DMF (1 mL) was added DIPEA (0.055 ml, 0.32 mmol), stirred at room temperature overnight. The mixture was diluted with 10% citric acid, extracted with EtOAc (2×10 mL), washed the combined EtOAc with sat. NaHCO$_3$, brine, dried over MgSO$_4$, filtered, purified by ISCO, 12 g column, eluded with 20-100% EtOAc/heptane to afford 102 mg (81%) of Compound 278A as a white solid. LC-MS: m/z=1179 (M+H)$^+$.

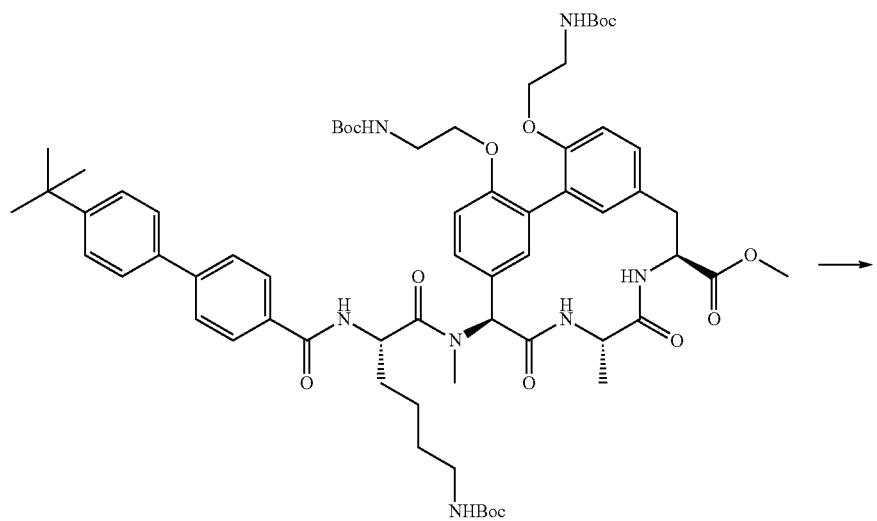
278A
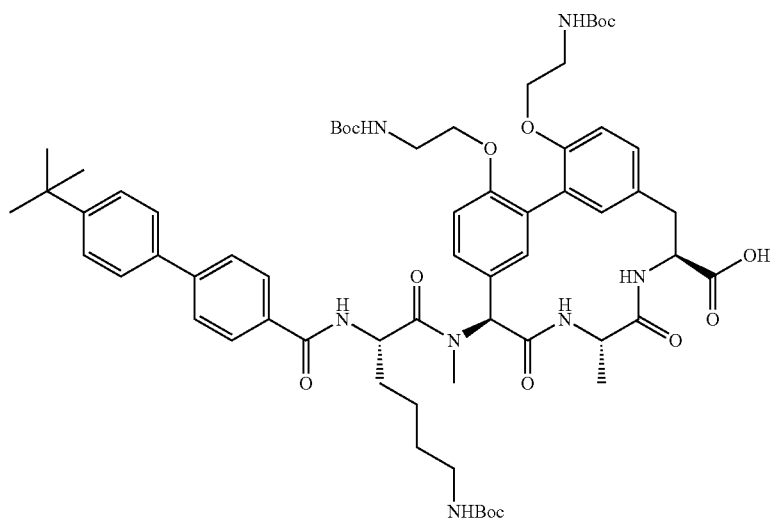
278B
To a solution of Compound 278A (102 mg, 0.086 mmol) in 1,4-dioxane (2 mL) and water (0.5 ml) was added LiOH (6.54 mg, 0.26 mmol) stirred at room temperature for 3 h. The mixture was concentrated in vacuo, dried under high vacuum to afford Compound 278B as off white solid. It was carried on without further purification. LC-MS: m/z=1165 (M+H)$^+$.

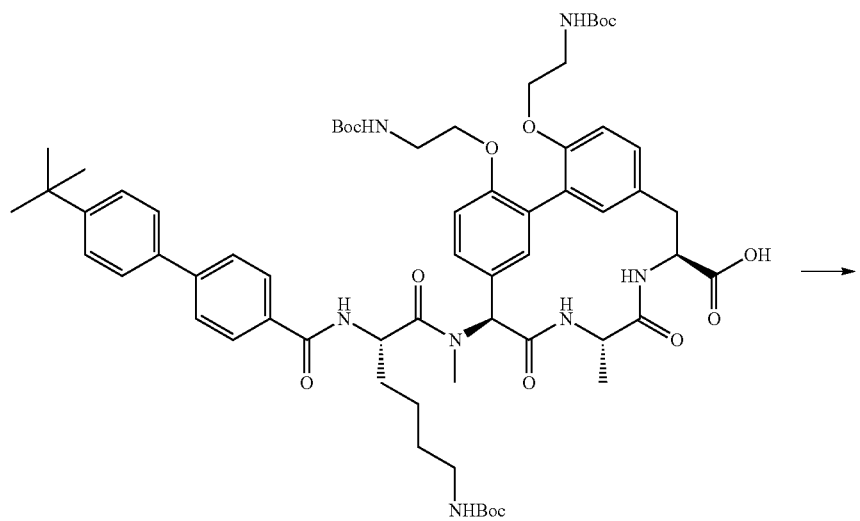

278B

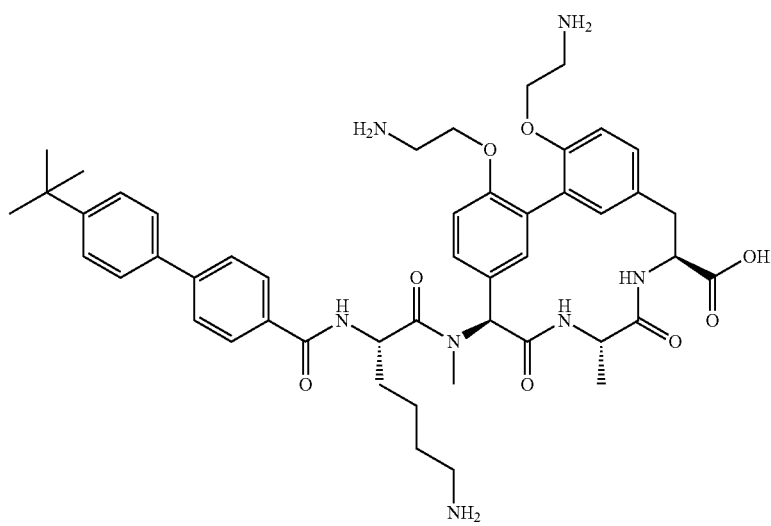

278

Compound 278B (30 mg, 0.026 mmol) was treated with 5% TFA/HFIP (1.5 ml) at room temperature for 1 h. The mixture was concentrated in vacuo, azeotroped with ether 2×, dried under high vacuum. The residue was purified by RP-HPLC to afford 13.3 mg (60%) of Compound 278 as an off white solid. LC-MS: m/z=865 (M+H)$^+$. $^1$H NMR (400 MHz, DMSO-d$_6$) δ 8.58 (d, J=7.7 Hz, 1H), 8.36-8.29 (m, 1H), 8.01 (d, J=8.3 Hz, 2H), 7.85 (d, J=6.1 Hz, 1H), 7.78-7.72 (m, 2H), 7.68-7.64 (m, 2H), 7.53-7.49 (m, 2H), 7.14-7.05 (m, 3H), 6.90 (d, J=8.4 Hz, 1H), 6.78 (dd, J=6.5, 2.3 Hz, 2H), 6.32 (s, 1H), 4.89 (q, J=7.2 Hz, 1H), 4.66 (q, J=7.4 Hz, 1H), 4.20 (q, J=6.0 Hz, 1H), 3.99 (qd, J=9.1, 7.5, 2.6 Hz, 4H), 3.36-3.28 (m, 1H), 3.04 (dd, J=14.9, 7.2 Hz, 1H), 2.86 (d, J=7.9 Hz, 7H), 2.79-2.72 (m, 2H), 1.80 (q, J=7.5 Hz, 2H), 1.60 (q, J=7.4 Hz, 2H), 1.52-1.43 (m, 2H), 1.33 (d, J=4.6 Hz, 12H), 1.18 (d, J=6.7 Hz, 3H).

Example 178: Synthesis of Compound 279

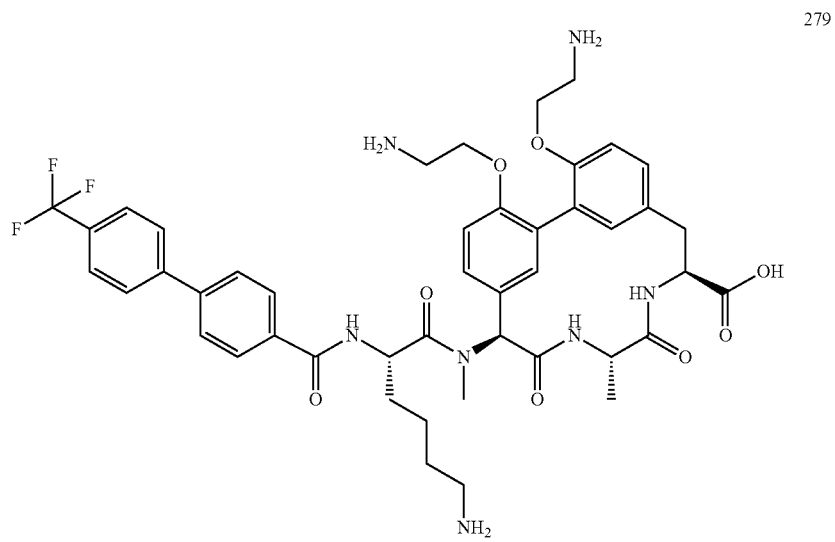 [SMILES: C[C@@H]1NC(=O)[C@@H](N(C)C(=O)[C@H](CCCCN)NC(=O)c2ccc(-c3ccc(C(F)(F)F)cc3)cc2)c2ccc(OCCN)c(c2)-c2cc(ccc2OCCN)C[C@@H](C(=O)O)NC1=O]

279

Compound 279 was prepared as an off-white solid using the same methods described for Compound 278. LC-MS: m/z=877 (M+H)$^+$. $^1$H NMR (400 MHz, DMSO-d$_6$) δ 8.66 (d, J=7.7 Hz, 1H), 8.37-8.29 (m, 1H), 8.09-8.05 (m, 2H), 7.98-7.93 (m, 2H), 7.89-7.80 (m, 5H), 7.14-7.05 (m, 4H), 6.91 (d, J=8.4 Hz, 1H), 6.78 (dd, J=6.2, 2.2 Hz, 2H), 6.33 (s, 1H), 4.89 (q, J=7.2 Hz, 1H), 4.71-4.62 (m, 1H), 4.21 (d, J=5.9 Hz, 1H), 4.00 (tq, J=8.8, 4.6 Hz, 5H), 3.32 (d, J=15.1 Hz, 1H), 3.04 (dd, J=14.9, 7.2 Hz, 1H), 2.86 (d, J=7.5 Hz, 7H), 2.79-2.72 (m, 2H), 1.84-1.76 (m, 2H), 1.60 (q, J=7.4 Hz, 2H), 1.53-1.42 (m, 2H), 1.18 (d, J=6.7 Hz, 3H).

Example 179: Synthesis of Compound 280

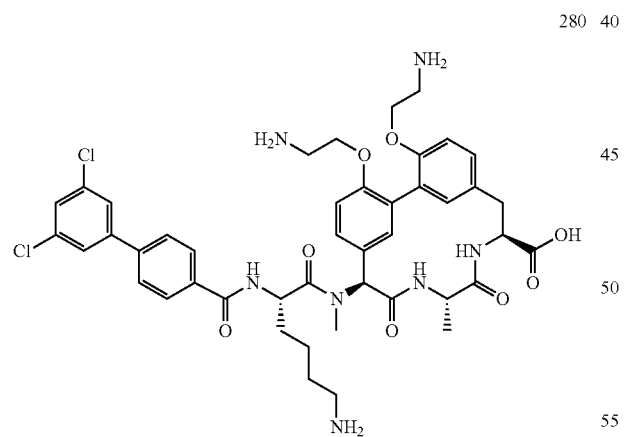

280

Compound 280 was prepared as a greenish solid using the same methods described for Compound 278. LC-MS: m/z=878 (M+H)$^+$. $^1$H NMR (400 MHz, DMSO-d$_6$) δ 8.68 (d, J=7.7 Hz, 1H), 8.35 (d, J=8.9 Hz, 1H), 8.02 (t, J=10.4 Hz, 3H), 7.89-7.84 (m, 2H), 7.80 (d, J=1.9 Hz, 2H), 7.63 (t, J=1.9 Hz, 1H), 7.10 (d, J=7.0 Hz, 3H), 6.93 (d, J=8.2 Hz, 1H), 6.77 (d, J=6.4 Hz, 2H), 6.34 (s, 1H), 4.93-4.83 (m, 1H), 4.71-4.59 (m, 1H), 4.28 (s, 1H), 4.02 (s, 4H), 3.33 (d, J=15.5 Hz, 1H), 3.04 (s, 1H), 2.81 (d, J=26.5 Hz, 9H), 1.84-1.76 (m, 2H), 1.60 (d, J=7.2 Hz, 3H), 1.52-1.41 (m, 1H), 1.18 (d, J=6.7 Hz, 3H).

Example 180: Synthesis of Compound 281

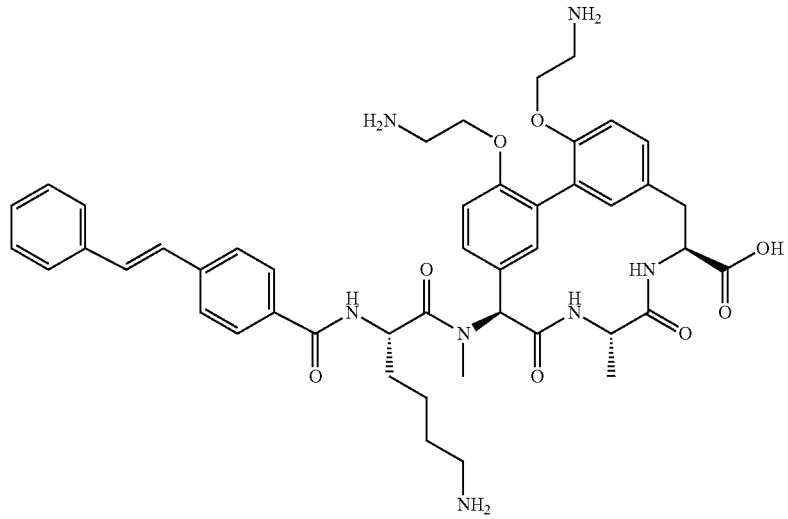
281

Compound 281 was prepared as an off-white solid using the same methods described for Compound 278. LC-MS: m/z=835 (M+H)+. ¹H NMR (400 MHz, DMSO-$d_6$) δ 8.55 (d, J=7.7 Hz, 1H), 8.34 (d, J=9.0 Hz, 1H), 7.98-7.87 (m, 3H), 7.73-7.68 (m, 2H), 7.64 (dt, J=6.4, 1.3 Hz, 2H), 7.44-7.34 (m, 3H), 7.34-7.27 (m, 2H), 7.09 (t, J=7.0 Hz, 3H), 6.92 (d, J=8.3 Hz, 1H), 6.78 (dd, J=7.8, 2.3 Hz, 2H), 6.33 (s, 1H), 4.92-4.83 (m, 1H), 4.67 (t, J=7.8 Hz, 1H), 4.26 (s, 1H), 4.03 (s, 4H), 3.33 (d, J=15.3 Hz, 1H), 3.04 (dd, J=14.8, 7.6 Hz, 1H), 2.87 (d, J=22.1 Hz, 7H), 2.77 (t, J=7.5 Hz, 2H), 1.79 (q, J=7.5 Hz, 2H), 1.60 (q, J=7.3 Hz, 2H), 1.53-1.40 (m, 2H), 1.18 (d, J=6.7 Hz, 3H).

Example 181: Synthesis of Compound 282

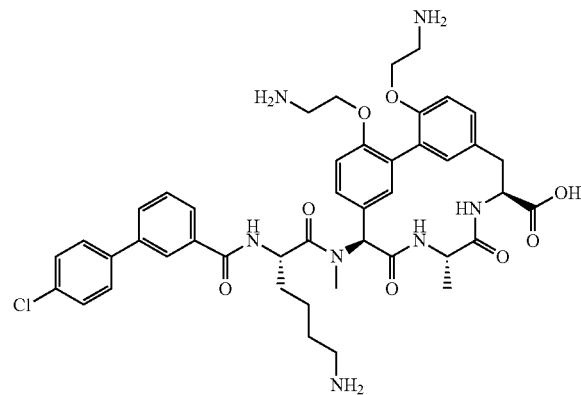
282

Compound 282 was prepared as an off-white solid using the same methods described for Compound 278. LC-MS: m/z=843 (M+H)+. ¹H NMR (400 MHz, DMSO-$d_6$) δ 8.77 (d, J=7.9 Hz, 1H), 8.37 (d, J=8.9 Hz, 1H), 8.25-8.19 (m, 2H), 7.92 (d, J=8.1 Hz, 1H), 7.87-7.78 (m, 3H), 7.62-7.54 (m, 3H), 7.10 (dd, J=19.4, 8.7 Hz, 2H), 6.99 (d, J=8.5 Hz, 1H), 6.91 (d, J=8.4 Hz, 1H), 6.76 (d, J=2.9 Hz, 2H), 6.33 (s, 1H), 4.92 (d, J=6.6 Hz, 1H), 4.70-4.62 (m, 1H), 4.23 (s, 1H), 4.03-3.93 (m, 4H), 3.31 (d, J=15.3 Hz, 1H), 3.04 (dd, J=15.0, 7.3 Hz, 1H), 2.84 (d, J=15.2 Hz, 7H), 2.77 (t, J=7.4 Hz, 2H), 1.82 (s, 2H), 1.60 (q, J=7.1 Hz, 2H), 1.46 (d, J=8.2 Hz, 2H), 1.18 (d, J=6.7 Hz, 3H).

Example 182: Synthesis of Compound 283

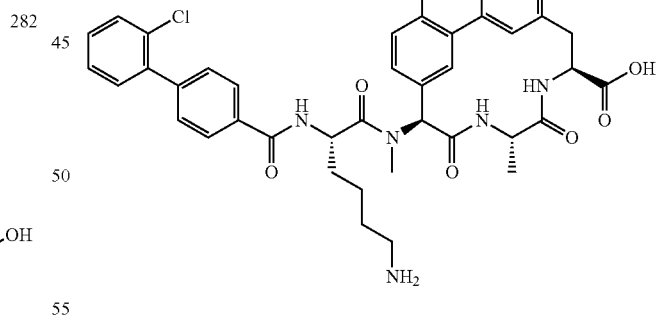
283

Compound 283 was prepared as a white solid using the same methods described for Compound 278. LC-MS: m/z=843 (M+H)+. ¹H NMR (400 MHz, DMSO-$d_6$) δ 8.64 (d, J=7.7 Hz, 1H), 8.35 (d, J=9.0 Hz, 1H), 8.09 (s, 1H), 8.04-7.99 (m, 2H), 7.62-7.51 (m, 3H), 7.48-7.42 (m, 3H), 7.15-7.08 (m, 3H), 6.95 (d, J=8.4 Hz, 1H), 6.77 (d, J=5.5 Hz, 2H), 6.34 (s, 1H), 4.89 (d, J=7.3 Hz, 1H), 4.70-4.63 (m, 1H), 4.33 (s, 1H), 4.06-4.00 (m, 4H), 3.32 (d, J=16.2 Hz, 1H), 3.04 (dd, J=15.5, 8.0 Hz, 1H), 2.91 (t, J=5.6 Hz, 4H), 2.85 (s, 3H), 2.78 (t, J=7.4 Hz, 2H), 1.80 (d, J=7.4 Hz, 2H), 1.61 (q, J=7.5 Hz, 2H), 1.47 (d, J=11.3 Hz, 2H), 1.19 (d, J=6.7 Hz, 3H).

Example 183: Synthesis of Compound 284

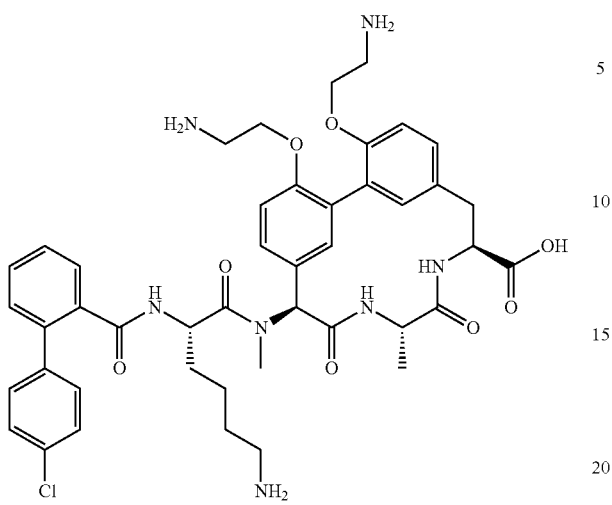

284

Compound 284 was prepared as a white solid using the same methods described for Compound 278. LC-MS: m/z=843 (M+H)⁺. ¹H NMR (500 MHz, DMSO-d₆) δ 8.81 (d, J=7.3 Hz, 1H), 8.51 (d, J=9.0 Hz, 1H), 8.13 (d, J=7.1 Hz, 1H), 7.55 (td, J=7.3, 1.8 Hz, 1H), 7.51-7.40 (m, 7H), 7.12 (dd, J=8.7, 2.2 Hz, 1H), 7.03-6.91 (m, 3H), 6.82-6.78 (m, 1H), 6.74 (d, J=2.4 Hz, 1H), 6.43 (s, 1H), 4.68 (dd, J=9.0, 6.6 Hz, 1H), 4.58 (td, J=8.2, 5.4 Hz, 1H), 4.33 (q, J=6.5 Hz, 1H), 4.13-4.07 (m, 4H), 3.37-3.31 (m, 1H), 3.00 (dt, J=19.2, 5.7 Hz, 5H), 2.76 (s, 5H), 1.66-1.51 (m, 4H), 1.37-1.28 (m, 2H), 1.18 (d, J=6.6 Hz, 3H).

Example 184: Synthesis of Compound 285

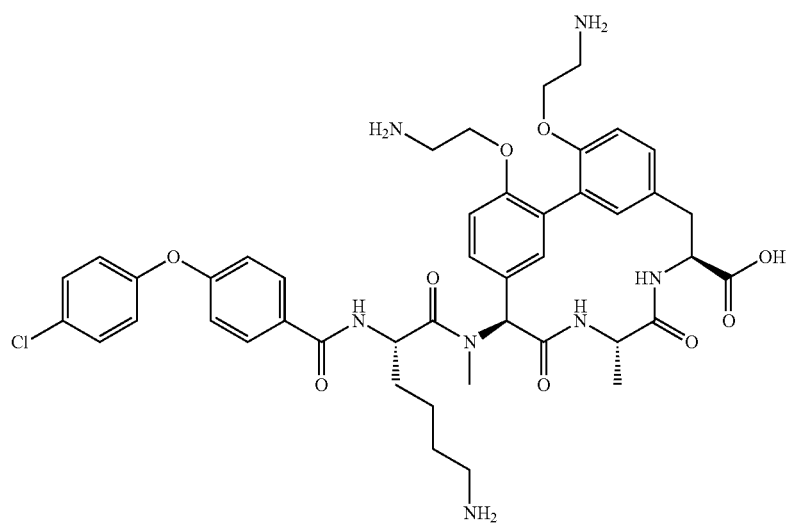

285

Compound 285 was prepared as a white solid using the same methods described for Compound 278. LC-MS: m/z=859 (M+H)⁺. ¹H NMR (400 MHz, DMSO-d₆) δ 8.51 (d, J=7.7 Hz, 1H), 8.35 (d, J=8.9 Hz, 1H), 8.00-7.95 (m, 2H), 7.87 (d, J=5.9 Hz, 1H), 7.50-7.44 (m, 2H), 7.13-7.03 (m, 7H), 6.90 (d, J=8.3 Hz, 1H), 6.76 (d, J=5.2 Hz, 2H), 6.31 (s, 1H), 4.86 (d, J=7.1 Hz, 1H), 4.69-4.62 (m, 1H), 4.18 (s, 1H), 4.02-3.95 (m, 5H), 3.31 (d, J=14.9 Hz, 1H), 3.04 (dd, J=15.1, 7.2 Hz, 1H), 2.85 (dd, J=11.1, 5.2 Hz, 8H), 2.75 (t, J=7.4 Hz, 2H), 1.77 (d, J=7.6 Hz, 2H), 1.58 (q, J=7.3 Hz, 2H), 1.50-1.41 (m, 2H), 1.17 (d, J=6.7 Hz, 3H).

Example 185: Synthesis of Compound 286

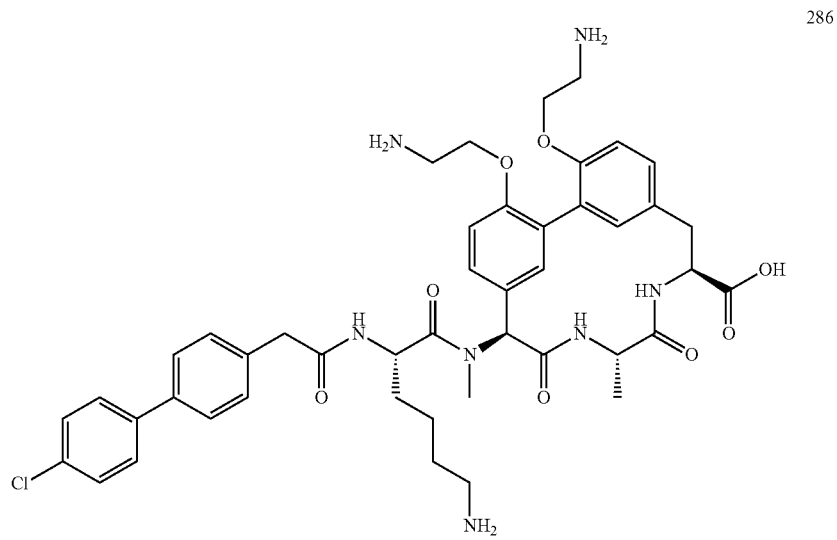

286

Compound 286 was prepared as a white solid using the same methods described for Compound 278. LC-MS: m/z=857 (M+H)+. 1H NMR (400 MHz, DMSO-d6) δ 8.52 (d, J=8.0 Hz, 1H), 8.47 (d, J=8.9 Hz, 1H), 7.88 (s, 1H), 7.73-7.68 (m, 2H), 7.66-7.61 (m, 2H), 7.55-7.51 (m, 2H), 7.39 (d, J=8.1 Hz, 2H), 7.06 (d, J=8.1 Hz, 1H), 6.96 (s, 2H), 6.90 (d, J=8.3 Hz, 1H), 6.73 (d, J=14.8 Hz, 2H), 6.27 (s, 1H), 4.64 (d, J=16.1 Hz, 1H), 4.13 (s, 1H), 4.04-3.88 (m, 5H), 3.54 (s, 2H), 3.03 (d, J=7.2 Hz, 1H), 2.84 (s, 5H), 2.72 (d, J=7.0 Hz, 5H), 1.68 (s, 1H), 1.54 (s, 3H), 1.34 (s, 2H), 1.16 (d, J=6.9 Hz, 3H).

Example 186: Synthesis of Compound 287

Compound 287 was prepared as a white solid using the same methods described for Compound 278. LC-MS: m/z=885 (M+H)+. 1H NMR (400 MHz, DMSO-d6) δ 8.79 (d, J=7.5 Hz, 1H), 8.52 (d, J=9.0 Hz, 1H), 8.06 (d, J=8.2 Hz, 2H), 7.90-7.79 (m, 5H), 7.77-7.73 (m, 2H), 7.51 (t, J=7.6 Hz, 3H), 7.44-7.37 (m, 1H), 7.12 (d, J=1.8 Hz, 2H), 7.07 (d, J=9.4 Hz, 2H), 6.92 (d, J=8.4 Hz, 1H), 6.79-6.75 (m, 2H), 6.33 (s, 1H), 4.86 (d, J=7.2 Hz, 1H), 4.66 (t, J=7.9 Hz, 1H), 4.14 (d, J=5.7 Hz, 1H), 4.01 (dt, J=12.4, 5.6 Hz, 4H), 3.07-2.98 (m, 1H), 2.86 (d, J=15.1 Hz, 7H), 2.78 (d, J=8.0 Hz, 3H), 1.78 (q, J=6.6, 3.9 Hz, 2H), 1.65-1.42 (m, 4H), 1.17 (d, J=6.7 Hz, 3H).

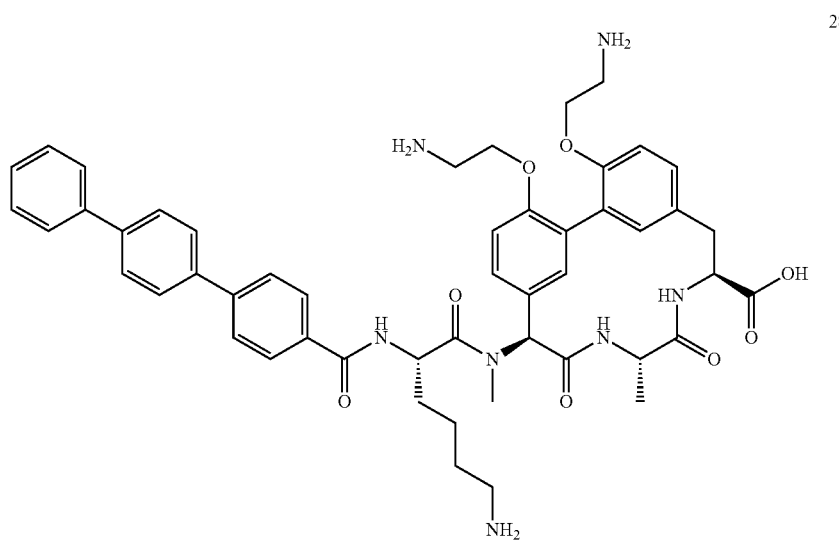

287

Example 187: Synthesis of Compound 288

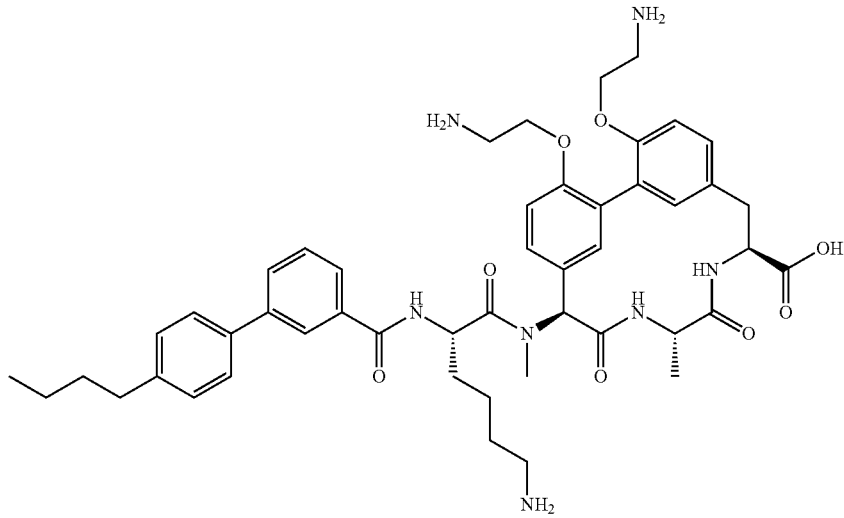

288

Compound 288 was prepared as a white solid using the same methods described for Compound 278. LC-MS: m/z=865 (M+H)+. $^1$H NMR (400 MHz, DMSO-d$_6$) δ 8.73 (d, J=7.9 Hz, 1H), 8.37 (d, J=9.1 Hz, 1H), 8.19 (t, J=1.7 Hz, 1H), 7.88 (d, J=7.9 Hz, 1H), 7.81 (dt, J=7.6, 1.5 Hz, 2H), 7.70-7.66 (m, 2H), 7.55 (t, J=7.7 Hz, 1H), 7.34 (d, J=8.0 Hz, 2H), 7.12 (d, J=8.4 Hz, 1H), 7.05 (d, J=8.6 Hz, 1H), 6.98 (d, J=8.5 Hz, 1H), 6.88 (d, J=8.4 Hz, 1H), 6.76 (d, J=2.4 Hz, 2H), 6.31 (s, 1H), 4.92 (t, J=7.2 Hz, 1H), 4.65 (t, J=7.7 Hz, 1H), 4.13 (s, 1H), 3.94 (d, J=8.1 Hz, 4H), 3.31 (d, J=16.2 Hz, 1H), 3.04 (dd, J=14.9, 6.7 Hz, 1H), 2.82 (d, J=8.3 Hz, 7H), 2.74 (t, J=7.2 Hz, 2H), 2.69-2.62 (m, 2H), 1.86-1.75 (m, 2H), 1.65-1.55 (m, 4H), 1.46 (d, J=7.9 Hz, 2H), 1.36 (dt, J=14.8, 7.4 Hz, 2H), 1.18 (d, J=6.7 Hz, 3H), 0.92 (t, J=7.3 Hz, 3H).

Example 188: Synthesis of Compound 289

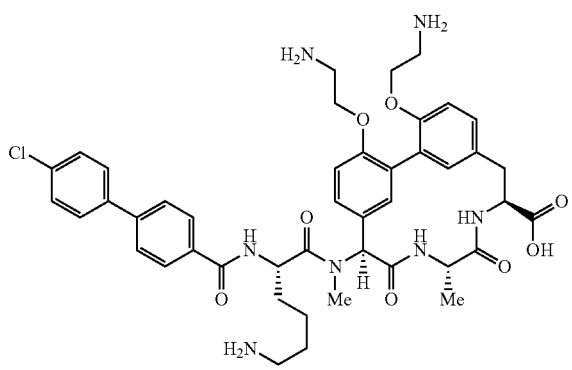

289

Compound 289 was prepared as a formic acid salt from Compound 209A from the Boc-deprotection using TFA/DCM (General Method 9). MS (ESI) for (C$_{44}$H$_{52}$ClN$_7$O$_8$): m/z 842.3 (M+H). HPLC tR 2.62 min (10% AcCN/H$_2$O-90% AcCN/H$_2$O (with 0.05% TFA), 3.0 min, 1.0 mL/min Kinetix C18, 4.8×50 mm). $^1$H NMR (400 MHz, MeOH-d4)$^δ$ 7.81 (d, J=6.0 Hz, 2H), 7.59 (d, J=8.0 Hz, 2H), 7.39 (m, 4H), 7.26 (t, J=6.0 Hz, 2H), 7.12 (d, J=12.0 Hz, 1H), 7.05 (d, J=12.0 Hz, 1H), 7.96 (s, 1H), 6.67 (s, 1H), 6.75 (s, 1H), 5.06 (t, J=6.0 Hz, 1H), 4.83-4.78 (m, 1H), 4.65 (dd, J=6.0, 3.0 Hz, 1H), 4.22 (m, 1H), 4.15 (m, 1H), 4.09 (m, 1H), 3.98 (m, 1H), 1.29 (dd, J=6.8, 2.4 Hz, 1H), 3.17 (m, 2H), 3.16 (m, 1H), 3.3 (s, 3H), 2.93-2.83 (m, 4H), 2.03-1.98 (m, 2H), 1.76-1.70 (m, 2H), 1.62-1.59 (m, 2H), 1.37 (d, J=6.0 Hz, 3H).

Example 189: Synthesis of Compound 290

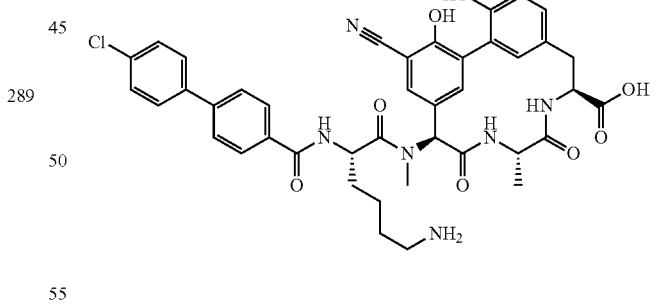

290

Compound 290 was prepared from Compound 210BB by LiOH ester hydrolysis followed by TFA boc-deprotection as described for Compound 113. MS+ 781.4 $^1$H NMR (500 MHz, DMSO-d$_6$) δ 8.78 (t, J=6.9 Hz, 1H), 8.65-8.57 (m, 1H), 8.37 (bs, 1H), 8.07-7.96 (m, 2H), 7.78 (m, 4H), 7.59-7.51 (m, 2H), 7.04 (d, J=2.5 Hz, 1H), 7.01-6.94 (m, 2H), 6.83 (m, 1H), 6.50 (d, J=8.7 Hz, 1H), 6.23 (s, 1H), 4.86-4.70 (m, 2H), 4.31-4.23 (m, 1H), 3.23-3.12 (m, 2H), 2.94-2.84 (m, 1H), 2.83-2.66 (m, 4H), 1.81-1.71 (m, 2H), 1.69-1.39 (m, 4H), 1.20-1.06 (m, 3H).

Example 190: Synthesis of Compound 291
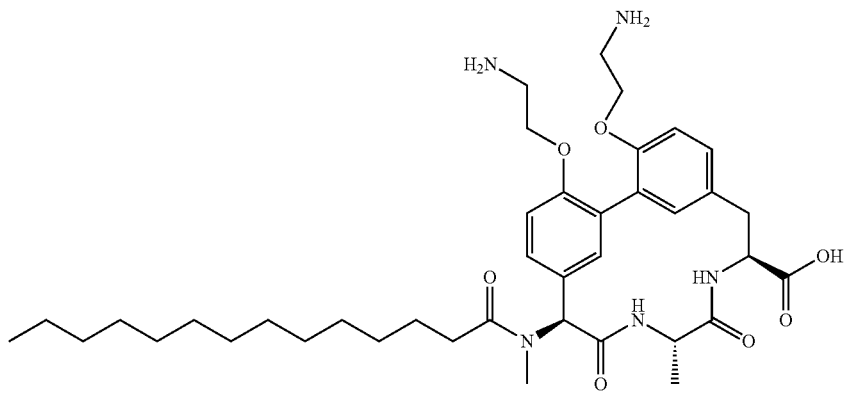
Compound 291 was prepared using methods described above. ¹H NMR (400 MHz, CD₃OD) δ 7.31-7.11 (m, 4H), 6.85-6.82 (m, 2H), 6.32 (s, 1H), 4.87-4.76 (m, 2H), 4.33-4.26 (m, 4H), 3.51-3.46 (m, 2H), 3.16-3.10 (m, 2H), 2.80 (s, 3H), 2.47 (t, J=7.6 Hz, 2H), 1.66-1.64 (m, 3H), 1.38-1.29 (m, 21H), 0.90 (t, J=6.4 Hz, 3H). LCMS (5-95AB_1.5 min): $t_R$=0.834 min, [M+H]⁺ 710.4.
Example 191: Synthesis of Compound 292
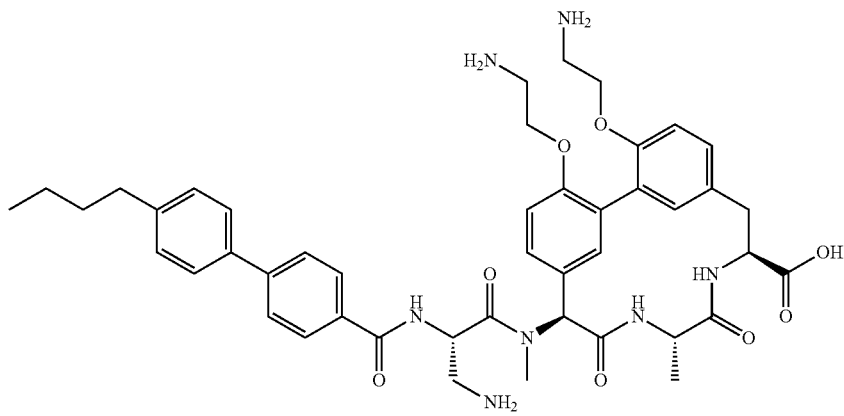
Compound 292 was prepared using methods described above. ¹H NMR (400 MHz, CD₃OD) δ 7.99 (d, J=8.4 Hz, 2H), 7.77 (d, J=8.4 Hz, 2H), 7.61 (d, J=8.0 Hz, 2H), 7.38-7.18 (m, 6H), 6.84-6.79 (m, 2H), 6.26 (s, 1H), 5.32-5.308 (m, 1H), 4.80-4.74 (m, 2H), 4.34-4.23 (m, 4H), 3.55-3.41 (m, 3H), 3.29-3.21 (m, 4H), 2.80 (s, 3H), 2.70-2.61 (m, 2H), 1.67-1.62 (m, 3H), 1.51-1.37 (m, 5H), 0.97 (d, J=7.6 Hz, 3H). LCMS (5-95AB_1.5 min): $t_R$=0.739 min, [M+H]⁺ 822.5.

Example 192: Synthesis of Compound 293

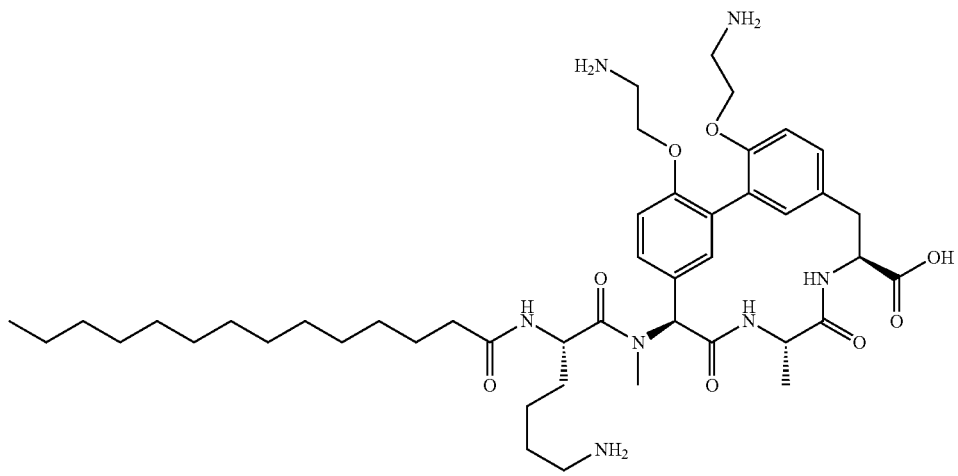

293

Compound 293 was prepared using methods described above. $^1$H NMR (400 MHz, CD$_3$OD) δ 8.82-8.80 (d, J=8 Hz, 1H), 8.39-8.37 (d, J=8 Hz, 1H), 7.29-7.21 (m, 2H), 7.18-7.15 (d, J=12 Hz, 1H), 7.12-7.10 (d, J=8 Hz, 1H), 6.85-6.84 (m, 2H), 6.36 (s, 1H), 4.75-4.35 (m, 4H), 4.35-4.20 (m, 4H), 3.55-3.45 (m, 1H), 3.27-3.19 (m, 2H), 3.17-3.05 (m, 2H), 3.00-2.83 (m, 5H), 2.29-2.22 (m, 2H), 1.89-1.79 (m, 1H), 1.74-1.22 (m, 28H), 0.93-0.84 (m, 3H). LCMS (5-95AB_1.5 min): $t_R$=0.789 min, [M+H]$^+$ 838.7.

Example 193: Synthesis of Compound 294

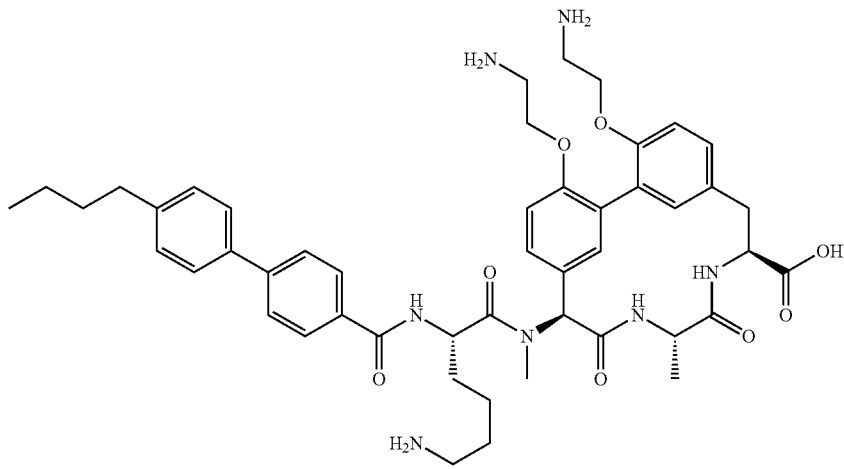

294

Compound 294 was prepared using methods described above. $^1$H NMR (400 MHz, CD$_3$OD) δ 7.95 (d, J=8.4 Hz, 2H), 7.74 (d, J=8.4 Hz, 2H), 7.58 (d, J=8.0 Hz, 2H), 7.32-7.08 (m, 6H), 6.87-6.84 (m, 2H), 6.44 (s, 1H), 5.08-5.04 (m, 1H), 5.01-4.88 (m, 1H), 4.81-4.78 (m, 1H), 4.32-4.27 (m, 4H), 3.47-3.40 (m, 1H), 3.28-3.21 (m, 4H), 3.19-3.01 (m, 1H), 3.00-2.85 (m, 5H), 2.68 (t, J=8.0 Hz, 2H), 2.05-1.78 (m, 2H), 1.75-1.69 (m, 2H), 1.68-1.51 (m, 4H), 1.49-1.33 (m, 5H), 0.97 (t, J=7.2 Hz, 3H). LCMS (5-95AB_1.5 min): $t_R$=0.743 min, [M+H]$^+$ 864.5.

Example 194: Synthesis of Compound 295
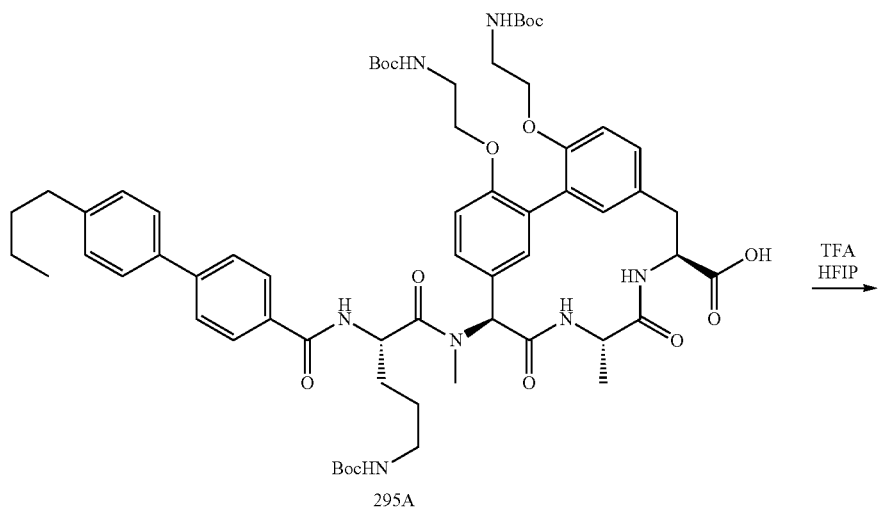
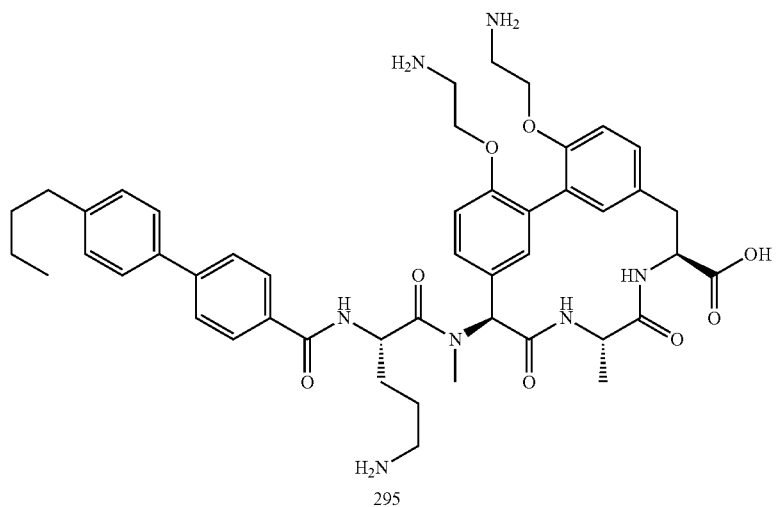
Compound 295 was prepared in a manner similar to Compound 104E. Compound 295 was prepared from Compound 295A using the standard TFA/HFIP hydrolysis method. $^1$H NMR (400 MHz, CD$_3$OD) δ 7.95 (d, J=8.4 Hz, 2H), 7.74 (d, J=8.4 Hz, 2H), 7.59 (d, J=8.0 Hz, 2H), 7.32-7.08 (m, 6H), 6.85 (s, 2H), 6.40 (s, 1H), 5.12-5.08 (m, 1H), 4.89-4.82 (m, 1H), 4.80-4.77 (m, 1H), 4.31-4.27 (m, 4H), 3.51-3.41 (m, 1H), 3.30-3.20 (m, 4H), 3.19-3.15 (m, 1H), 3.14-2.98 (m, 2H), 2.93 (s, 2H), 2.68 (t, J=8.0 Hz, 2H), 2.11-1.75 (m, 4H), 1.94-1.63 (m, 2H), 1.49-1.33 (m, 5H), 0.97 (t, J=7.2 Hz, 3H). LCMS (5-95AB_1.5 min): t$_R$=0.743 min, [M+H]$^+$ 851.8.

Example 195: Synthesis of Compound 296

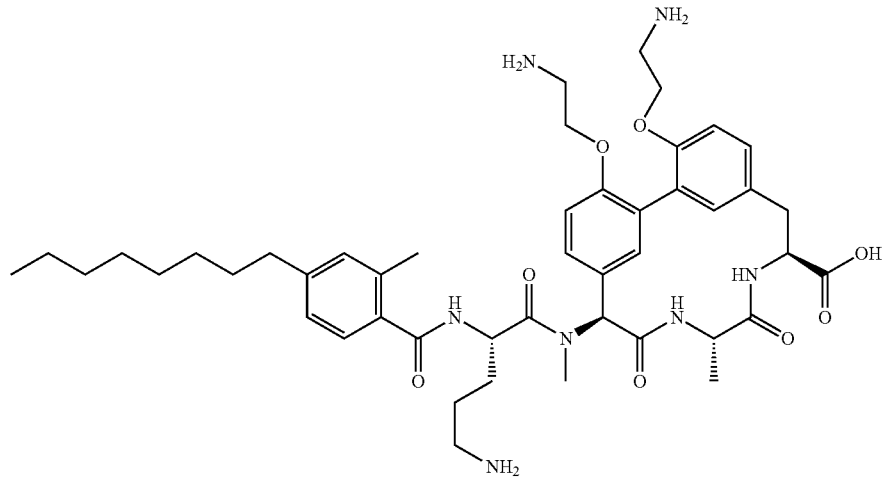

Compound 296 was prepared using methods described above from 2-methyl-4-octylbenzoic acid. $^1$H NMR (400 MHz, CD$_3$OD) δ 7.35-7.29 (m, 2H), 7.28-7.23 (m, 1H), 7.22-7.17 (m, 1H), 7.12-7.08 (m, 3H), 6.89-6.84 (m, 2H), 6.42 (s, 1H), 5.05-4.98 (m, 1H), 4.81-4.72 (m, 2H), 4.33-4.22 (m, 4H), 3.51-3.43 (m, 1H), 3.28-3.22 (m, 2H), 3.15-3.08 (m, 1H), 3.02-3.94 (m, 4H), 2.63-2.52 (m, 2H), 2.42-2.38 (m, 3H), 2.00-1.77 (m, 5H), 1.63-1.57 (m, 2H), 1.34-1.25 (m, 12H), 0.89-0.86 (m, 3H). LCMS (5-95AB_1.5 min): t$_R$=0.761 min, [M+H]$^+$ 844.6.

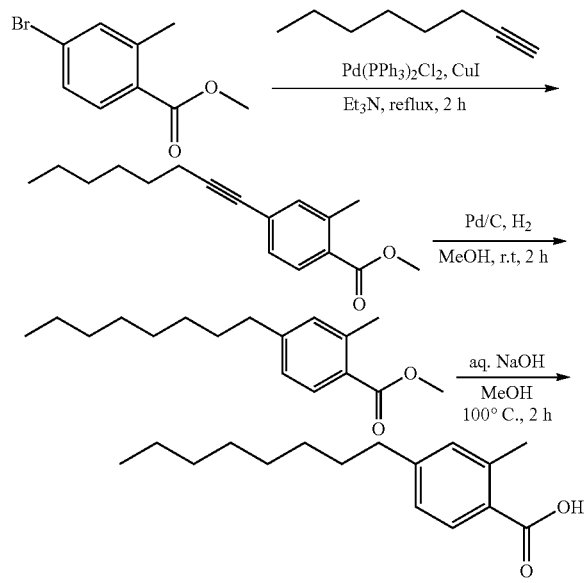

The synthesis of 2-methyl-4-octylbenzoic acid: 2-methyl-4-octylbenzoic acid was synthesized using a Sonogashira coupling method. A mixture of methyl 4-bromo-2-methylbenzoate (1.0 g, 4.39 mmol), oct-1-yne (0.44 g, 3.99 mmol), Pd(PPh$_3$)$_2$Cl$_2$ (140 mg, 0.20 mmol) and CuI (38 mg, 0.20 mmol) in triethylamine (20 mL) was stirred at 100° C. for 2 h under nitrogen atmosphere. The reaction was quenched with water (30 mL). The mixture was extracted with dichloromethane (3×50 mL). The combined extracts were washed with brine (2×50 mL), dried over anhydrous Na$_2$SO$_4$ and concentrated. The residue was purified by column chromatography on silica gel (eluting with petroleum ether/ethyl acetate from 100:1 to 10:1) to afford methyl 2-methyl-4-(oct-1-yn-1-yl)benzoate (1.13 g, 100%) as a yellow oil.

A mixture of methyl 2-methyl-4-(oct-1-yn-1-yl)benzoate (1.13 g, 4.37 mmol) and Pd/C (0.2 g) in methanol (20 mL) was stirred at 25° C. for 16 h under hydrogen atmosphere. The catalyst was filtered off and the solvent was evaporated. The residue was purified by column chromatography on silica gel (eluting with petroleum ether/ethyl acetate from 100:1 to 10:1) to afford methyl 2-methyl-4-octylbenzoate (0.97 g, 84%) as a yellow oil.

To a solution of methyl 2-methyl-4-octylbenzoate (0.97 g, 3.70 mmol) in methanol (10 mL) was added aqueous sodium hydroxide (10 mL, 50 mmol, 5.0 M). The reaction mixture was stirred at 100° C. for 2 h. The reaction was cooled at 20° C. and hydrochloric acid (1.0 M) was added until pH=3-4. The mixture was extracted with ethyl acetate (3×50 mL). The combined extracts were washed with brine (2×50 mL), dried over sodium sulfate and filtered. The filtrate was concentrated to give 2-methyl-4-octylbenzoic acid (890 mg, 97%) as a yellow oil. $^1$H NMR (400 MHz, CDCl$_3$): δ 7.98 (d, J=8.8 Hz, 1H), 7.10-7.08 (m, 2H), 2.64-2.60 (m, 5H), 1.35-1.20 (m, 12H), 0.89 (t, J=6.8 Hz, 3H).

Example 196: Synthesis of Compound 297

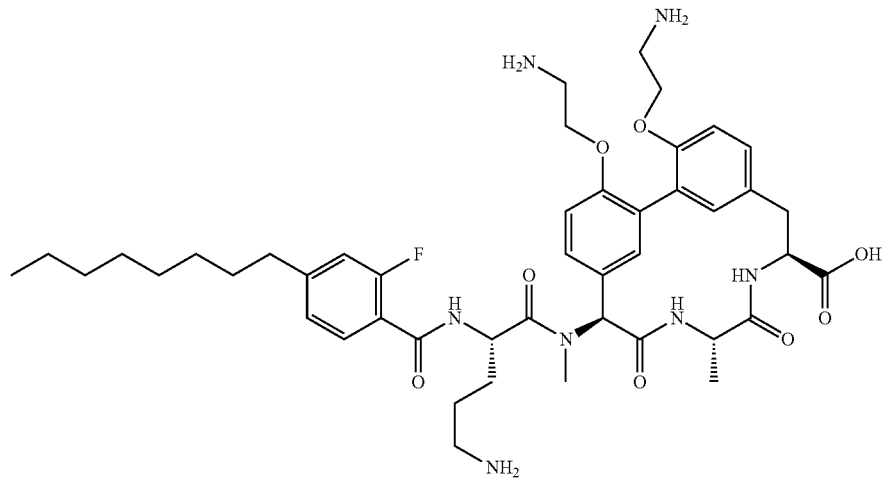

297

Compound 297 was prepared using methods as described or Compound 296 using the Sonogashira coupling method in the preparation of the 2-fluoro-4-octylbenzoic acid. $^1$H NMR (400 MHz, CD$_3$OD) δ 7.35-7.29 (m, 2H), 7.28-7.23 (m, 1H), 7.22-7.17 (m, 1H), 7.12-7.08 (m, 3H), 6.89-6.84 (m, 2H), 6.42 (s, 1H), 5.05-4.98 (m, 1H), 4.81-4.72 (m, 2H), 4.33-4.22 (m, 4H), 3.51-3.43 (m, 1H), 3.28-3.22 (m, 2H), 3.15-3.08 (m, 1H), 3.02-3.94 (m, 4H), 2.63-2.52 (m, 2H), 2.42-2.38 (m, 3H), 2.00-1.77 (m, 5H), 1.63-1.57 (m, 2H), 1.34-1.25 (m, 12H), 0.89-0.86 (m, 3H). LCMS (5-95AB_1.5 min): $t_R$=0.752 min, [M+H]$^+$ 848.6.

Example 197: Synthesis of Compound 298

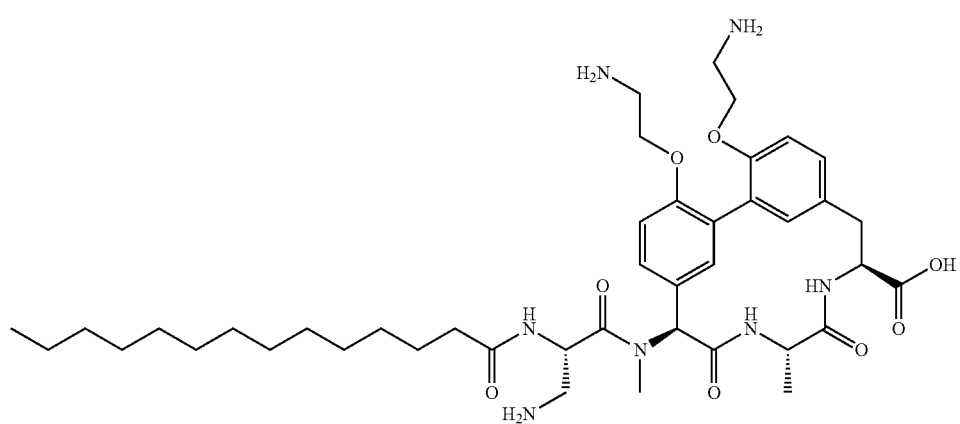

298

Compound 298 was prepared using methods described above. $^1$H NMR (400 MHz, CD$_3$OD) δ 7.26-7.23 (m, 1H), 7.21-7.16 (m, 1H), 7.15-7.10 (m, 1H), 7.12-6.98 (m, 1H), 6.97-6.95 (m, 1H), 6.84-6.81 (m, 1H), 6.22 (s, 1H), 5.10-5.05 (m, 1H), 4.82-4.75 (m, 2H), 4.52-4.46 (m, 1H), 4.25-4.04 (m, 5H), 3.46-3.38 (m, 1H), 3.19-3.02 (m, 6H), 2.81 (s, 2H), 2.30-2.23 (m, 2H), 1.99 (s, 1H), 1.65-1.56 (m, 2H), 1.37-1.20 (m, 22H), 0.92-0.85 (m, 3H). LCMS (5-95AB_1.5 min): $t_R$=0.775 min, [M+H]$^+$ 796.6.

Example 198: Synthesis of Compound 299

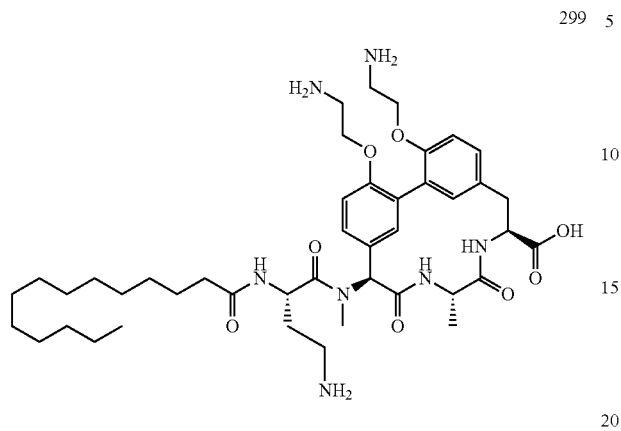

299

Compound 299 was prepared using methods described above. $^1$H NMR (400 MHz, CD$_3$OD) δ 8.46 (s, 2H), 7.28-7.13 (m, 3H), 7.05-7.00 (m, 1H), 6.98-6.95 (m, 1H), 6.87-6.86 (m, 1H), 6.31 (s, 1H), 5.00-4.95 (m, 2H), 4.81-4.76 (m, 1H), 4.55-4.50 (m, 1H), 4.30-4.18 (m, 4H), 3.45-3.37 (m, 1H), 3.27-3.20 (m, 3H), 3.15-2.98 (m, 3H), 2.86 (s, 2H), 2.32-2.10 (m, 4H), 2.05-1.95 (m, 1H), 1.67-1.58 (m, 2H), 1.41-1.25 (m, 23H), 0.95-0.86 (m, 3H). LCMS (5-95AB_1.5 min): $t_R$=0.765 min, [M+H]$^+$ 811.0.

Example 199: Synthesis of Compound 300

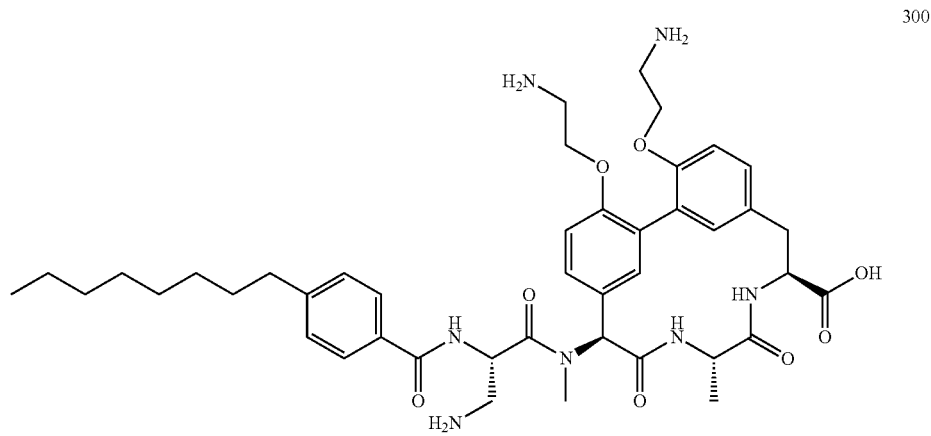 [SMILES: CCCCCCCCc1ccc(C(=O)N[C@@H](CN)C(=O)N(C)[C@@H]2C(=O)N[C@@H](C)C(=O)N[C@H](C(=O)O)Cc3ccc(OCCN)c(c3)-c3cc2ccc3OCCN)cc1]

300

Compound 300 was prepared using methods described above. $^1$H NMR (400 MHz, CD$_3$OD) δ 8.41 (s, 2H), 7.89-7.78 (m, 2H), 7.35-7.27 (m, 3H), 7.22-7.10 (m, 2H), 7.03-6.95 (m, 2H), 6.85-6.82 (m, 1H), 6.26 (s, 1H), 5.32-5.27 (m, 1H), 4.83-4.78 (m, 2H), 4.56-4.51 (m, 1H), 4.25-4.13 (m, 4H), 3.50-3.40 (m, 2H), 3.26-3.09 (m, 6H), 2.83 (br s, 2H), 2.72-2.64 (m, 3H), 1.68-1.60 (m, 2H), 1.38-1.25 (m, 14H), 0.93-0.86 (m, 3H). LCMS (5-95AB_1.5 min): $t_R$=0.761 min, [M+H]$^+$ 802.5.

Example 200: Synthesis of Compound 301

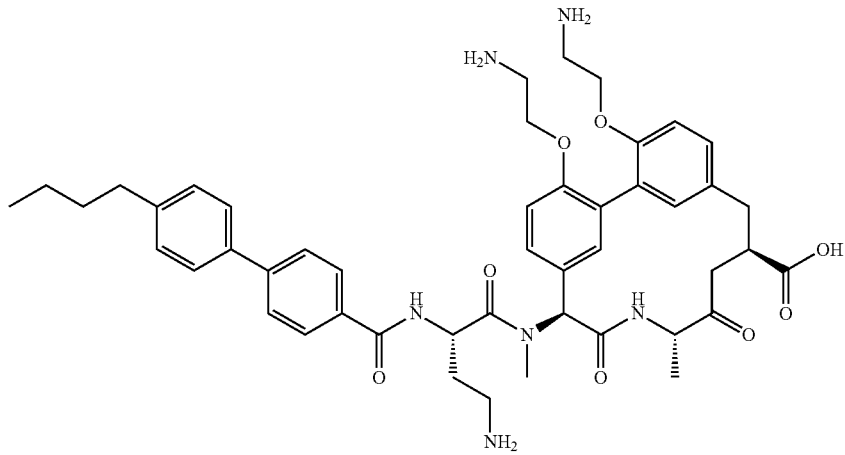

301

Compound 301 was prepared using methods described above. $^1$H NMR (400 MHz, CD$_3$OD) δ 8.31 (s, 2H), 8.01-7.90 (m, 2H), 7.79-7.69 (m, 2H), 7.62-7.54 (m, 2H), 7.35-7.26 (m, 3H), 7.24-7.12 (m, 2H), 7.07-6.95 (m, 2H), 6.89-6.84 (m, 1H), 6.36 (s, 1H), 5.22-5.16 (m, 1H), 4.85-4.77 (m, 1H), 4.61-4.55 (m, 1H), 4.28-4.15 (m, 4H), 3.50-3.41 (m, 1H), 3.27-3.08 (m, 6H), 2.92-2.88 (m, 2H), 2.74-2.65 (m, 2H), 2.37-2.15 (m, 2H), 1.70-1.65 (m, 9H), 1.01-0.98 (m, 3H). LCMS (5-95AB_1.5 min): t$_R$=0.748 min, [M+H]$^+$ 836.5.

Example 201: Synthesis of Compound 302

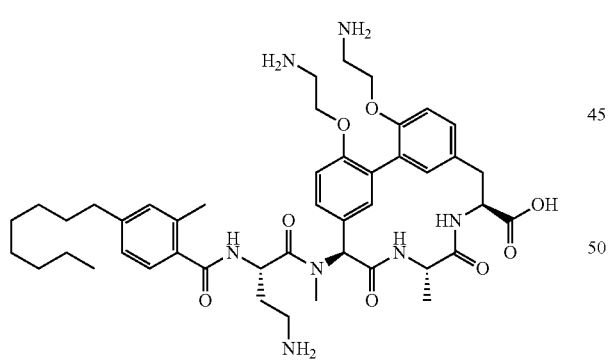

302

Compound 302 was prepared using methods described above. $^1$H NMR (400 MHz, CD$_3$OD) δ 8.41 (d, J=9.2 Hz, 1H), 7.40-7.30 (m, 2H), 7.30-7.20 (m, 2H), 7.20-7.05 (m, 3H), 6.90-6.80 (m, 2H), 6.34 (s, 1H), 5.20-5.10 (m, 1H), 4.85-4.75 (m, 1H), 4.40-4.20 (m, 5H), 3.55-3.45 (m, 1H) 3.20-3.05 (m, 3H), 2.93 (s, 3H), 2.65-2.55 (m, 2H), 2.50-2.05 (m, 7H), 1.65-1.55 (m, 3H), 1.40-1.20 (m, 14H), 0.95-0.85 (m, 3H). LCMS (5-95AB_1.5 min): t$_R$=0.772 min, [M+H]$^+$ 830.4.

Example 202: Synthesis of Compound 303

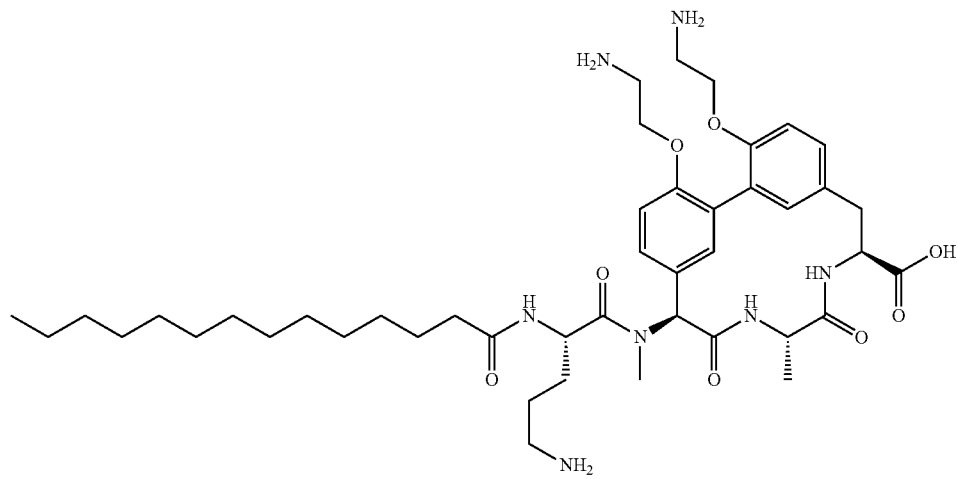

Compound 303 was prepared using methods described above. ¹H NMR (400 MHz, CD$_3$OD) δ 8.36 (s, 2H), 7.29-7.11 (m, 3H), 7.07-7.01 (m, 1H), 6.99-6.93 (m, 1H), 6.90-6.83 (m, 1H), 6.37 (s, 1H), 4.86-4.74 (m, 2H), 4.58-4.53 (m, 1H), 4.32-4.18 (m, 4H), 3.48-3.39 (m, 1H), 3.28-3.22 (m, 4H), 3.17-3.09 (m, 1H), 2.99-2.88 (m, 5H), 2.30-2.22 (m, 2H), 1.95-1.60 (m, 7H), 1.39-1.25 (m, 22H), 0.94-0.86 (m, 3H). LCMS (5-95AB_1.5 min): t$_R$=0.782 min, [M+H]$^+$ 824.6.

Example 203: Synthesis of Compound 304

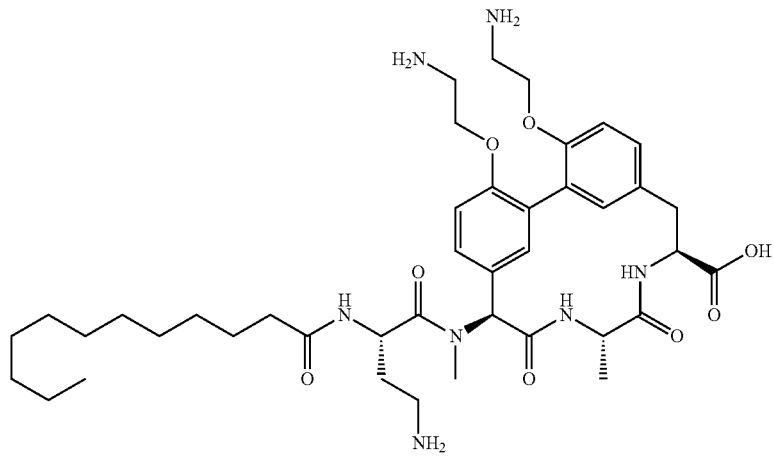

Compound 304 was prepared using methods described above. ¹H NMR (400 MHz, CD$_3$OD) δ 8.47 (s, 2H), 7.30-7.25 (m, 1H), 7.25-7.18 (m, 1H), 7.15 (d, J=7.6 Hz, 1H), 7.02 (d, J=8.4 Hz, 1H), 6.98 (s, 1H), 6.85 (s, 1H), 6.31 (s, 1H), 4.85-4.75 (m, 1H), 4.55-4.45 (m, 1H), 4.30-4.10 (m, 5H), 3.50-3.40 (m, 1H), 3.25-3.15 (m, 3H), 3.15-3.05 (m, 1H), 3.05-2.95 (m, 2H), 2.86 (s, 3H), 2.70-2.65 (m, 1H), 2.35-2.25 (m, 2H), 2.20-2.13 (m, 1H), 2.10-1.95 (m, 1H), 1.70-1.55 (m, 2H), 1.40-1.20 (m, 19H), 0.95-0.85 (m, 3H). LCMS (5-95AB_1.5 min): t$_R$=0.741 min, [M+H]$^+$ 782.4.

Example 204: Synthesis of Compound 305

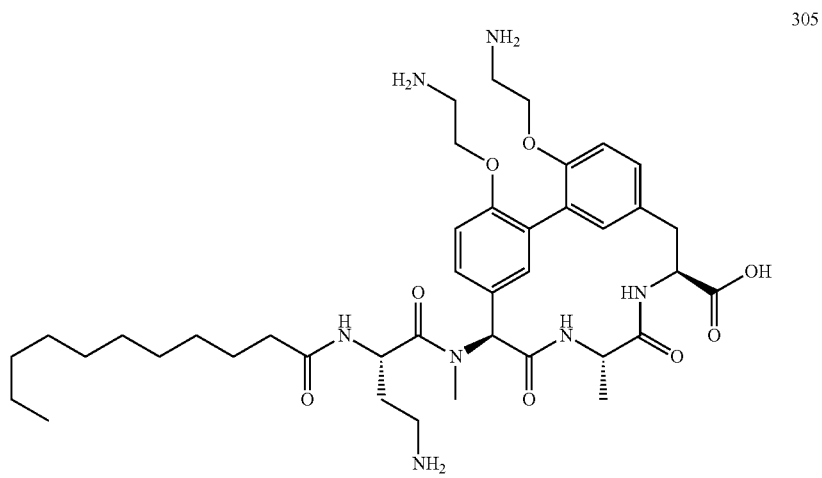 [SMILES: CCCCCCCCCCC(=O)N[C@@H](CCN)C(=O)N(C)[C@@H]1C(=O)N[C@@H](C)C(=O)N[C@H](C(=O)O)Cc2ccc(OCCN)c(c2)-c2cc1ccc2OCCN]

305

Compound 305 was prepared using methods described above. $^1$H NMR (400 MHz, CD$_3$OD) δ 8.45 (s, 2H), 7.30-7.27 (m, 1H), 7.27-7.23 (m, 1H), 7.23-7.10 (d, J=8.4 Hz, 1H), 7.05-6.95 (m, 2H), 6.85 (s, 1H), 6.81 (s, 1H), 6.30 (s, 1H), 4.85-4.75 (m, 1H), 4.55-4.45 (m, 1H), 4.30-4.10 (m, 5H), 3.50-3.40 (m, 1H), 3.25-3.05 (m, 5H), 3.05-2.95 (m, 2H), 2.87 (s, 3H), 2.35-2.25 (m, 2H), 2.20-2.10 (m, 1H), 2.05-1.95 (m, 1H), 1.70-1.55 (m, 2H), 1.40-1.20 (m, 17H), 0.95-0.85 (m, 3H). LCMS (5-95AB_1.5 min): t$_R$=0.717 min, [M+H]$^+$ 768.3.

Example 205: Synthesis of Compound 306

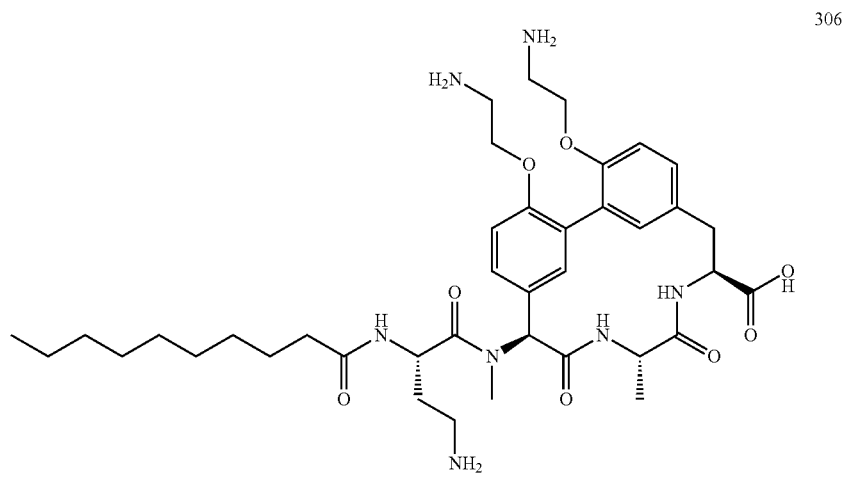 [SMILES: CCCCCCCCCC(=O)N[C@@H](CCN)C(=O)N(C)[C@@H]1C(=O)N[C@@H](C)C(=O)N[C@H](C(=O)O)Cc2ccc(OCCN)c(c2)-c2cc1ccc2OCCN]

306

Compound 306 was prepared using methods described above. $^1$H NMR (400 MHz, CD$_3$OD) δ 8.47 (s, 2H), 7.25 (d, J=8.4 Hz, 1H), 7.20 (d, J=7.6 Hz, 1H), 7.15 (d, J=8.4 Hz, 1H), 7.02 (d, J=8.4 Hz, 1H), 6.97 (s, 1H), 6.85 (s, 1H), 6.30 (s, 1H), 5.0-4.90 (m, 1H), 4.80-4.70 (m, 1H), 4.51 (s, 1H), 4.30-4.10 (m, 4H), 3.50-3.35 (m, 1H), 3.25-3.05 (m, 5H), 3.05-2.90 (m, 2H), 2.86 (s, 3H), 2.27 (t, J=7.6 Hz, 2H), 2.25-2.10 (m, 1H), 2.10-1.90 (m, 1H), 1.70-1.50 (m, 2H), 1.50-1.20 (m, 15H), 0.95-0.85 (s, 3H). LCMS (5-95AB_1.5 min): t$_R$=0.706 min, [M+H]$^+$ 754.3.

Example 206: Synthesis of Compound 307

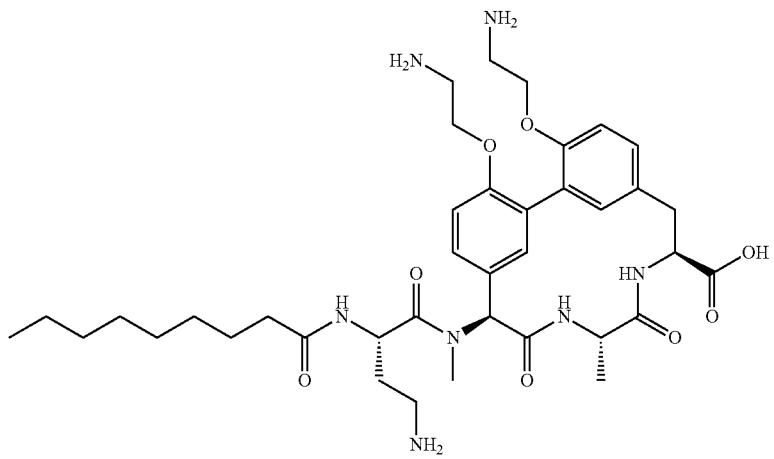

307

Compound 307 was prepared using methods described above. $^1$H NMR (400 MHz, CD$_3$OD) δ 8.48 (s, 2H), 7.30-7.25 (m, 1H), 7.19 (d, J=8.0 Hz, 1H), 7.15 (d, J=8.8 Hz, 1H), 7.02 (d, J=8.8 Hz, 1H), 6.97 (s, 1H), 6.84 (s, 1H), 6.30 (s, 1H), 5.0-4.90 (m, 1H), 4.80-4.70 (m, 1H), 4.55-4.45 (m, 1H), 4.30-4.10 (m, 4H), 3.45-3.35 (m, 1H), 3.25-3.05 (m, 5H), 3.05-2.90 (m, 2H), 2.86 (s, 3H), 2.27 (t, J=7.6 Hz, 2H), 2.25-2.10 (m, 1H), 2.10-1.90 (m, 1H), 1.70-1.50 (m, 2H), 1.50-1.20 (m, 15H), 0.95-0.85 (s, 3H). LCMS (0-30AB_7 min): $t_R$=3.523 min, [M+H]$^+$ 740.2.

Example 207 Synthesis of Compound 308

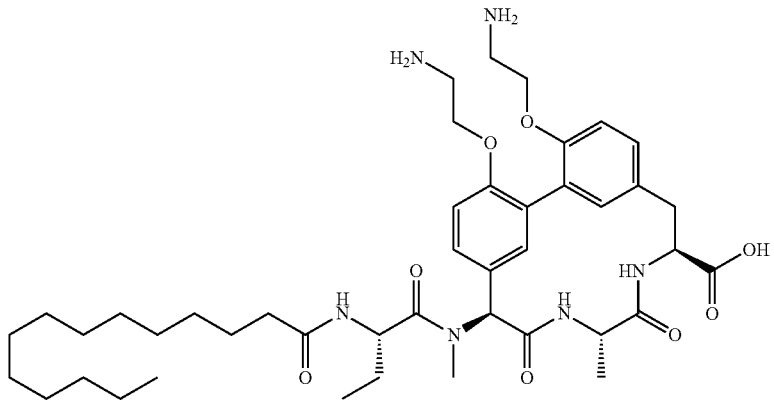

308

Compound 308 was prepared using methods described above. $^1$H NMR (400 MHz, CD$_3$OD) δ 8.82 (d, J=8.0 Hz, 1H), 8.33 (d, J=8.8 Hz, 1H), 7.30-7.22 (m, 2H), 7.17 (d, J=8.8 Hz, 1H), 7.11 (d, J=8.4 Hz, 1H), 6.84 (s, 2H), 6.37 (s, 1H), 4.79-4.72 (m, 2H), 4.70-4.64 (m, 1H), 4.35-4.24 (m, 4H), 3.52-3.44 (m, 2H), 3.25-3.21 (m, 2H), 3.18-3.11 (m, 2H), 2.89 (s, 3H), 2.31-2.21 (m, 3H), 1.91-1.76 (m, 1H), 1.68-1.58 (m, 4H), 1.42-1.25 (m, 21H), 1.01 (t, J=7.2 Hz, 3H), 0.90 (t, J=6.8 Hz, 3H). LCMS (5-95AB_1.5 min): $t_R$=0.844 min, [M+H]$^+$ 795.5.

Example 208: Synthesis of Compound 309

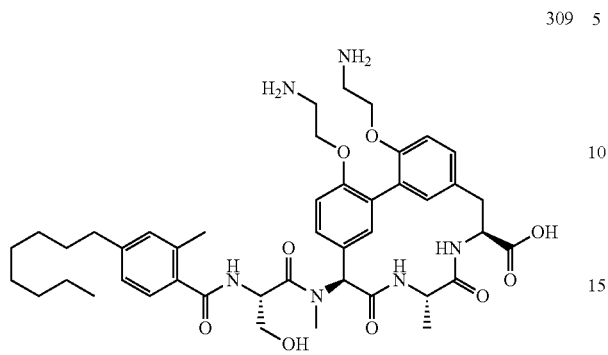

309

Compound 309 was prepared using methods described above. $^1$H NMR (400 MHz, CD$_3$OD) δ 8.46 (s, 1H), 7.38 (d, J=8.0 Hz, 1H), 7.15 (d, J=8.0 Hz, 1H), 7.09-7.03 (m, 2H), 7.03-6.97 (m, 3H), 6.87 (s, 1H), 6.86 (s, 1H), 6.43 (s, 1H), 5.10-5.08 (m, 1H), 4.79-4.77 (m, 1H), 4.51 (m, 1H), 4.26-4.19 (m, 4H), 3.97-3.94 (m, 1H), 3.84-3.82 (m, 1H), 3.45-3.32 (m, 1H), 3.25-3.01 (m, 6H), 3.03 (s, 2H), 2.61 (t, J=7.6 Hz, 2H), 2.43-2.39 (m, 3H), 1.62-1.61 (m, 2H), 1.34-1.29 (m, 13H), 0.92-0.88 (m, 3H). LCMS (5-95AB_1.5 min): $t_R$=0.815 min, [M+H]$^+$ 817.4.

Example 209: Synthesis of Compound 310

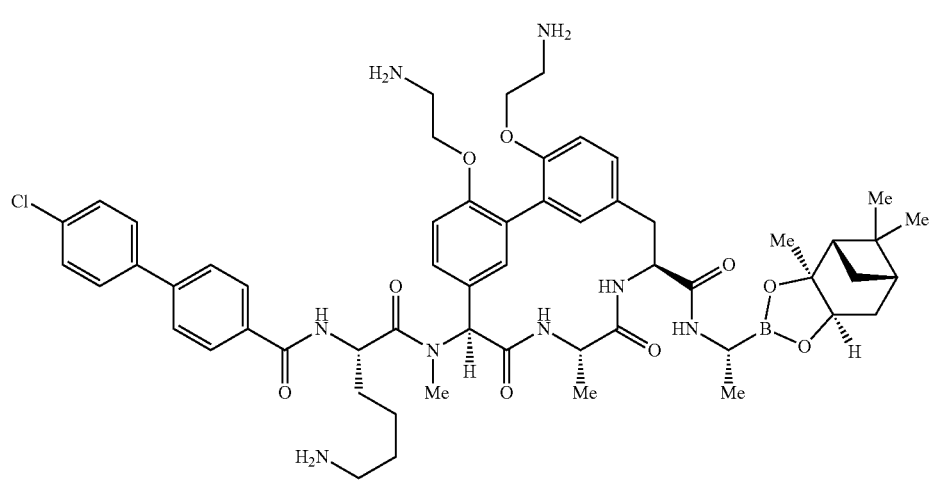

310

Compound 310 was prepared according to IBCF coupling method followed by TFA hydrolysis (General Method 6) from Compound 209A and (R)-BoroAla-(+)-pinanediol HCl, as a mixture of boronic acid and pinanediol protected material. MS (ESI) for (C$_{56}$H$_{72}$BClN$_8$O$_9$): m/z 1048.3 (M+2H; 65% boronic ester); for (C$_{46}$H$_{58}$BClN$_8$O$_9$): m/z 914.3 (M+2H; 34% boronic acid). HPLC $t_R$ 2.63 min (34% boronic acid) and $t_R$ 3.01 (65% boronic ester) (10% AcCN/H$_2$O-90% AcCN/H$_2$O (with 0.05% TFA), 3.0 min, 1.0 mL/min Kinetix C18, 4.8×50 mm).

Example 210: Synthesis of Compound 311

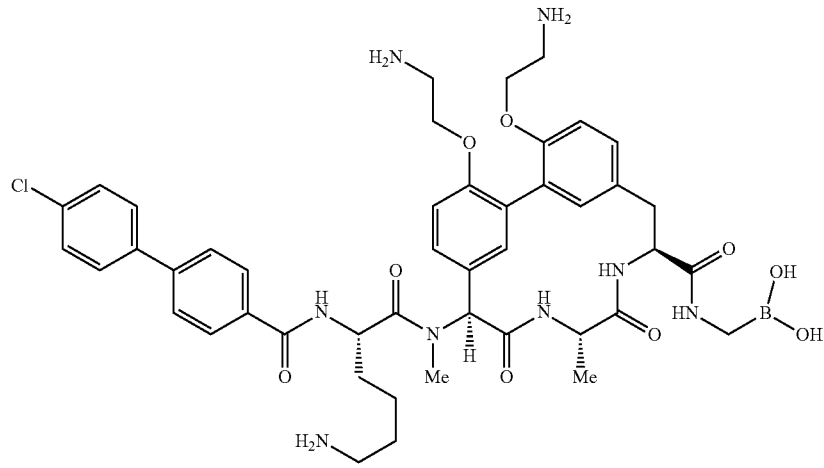

311

Compound 311 was prepared according to General Method 6 from Compound 209A and BoroGly-(+)-pinanediol HCl. MS (ESI) for ($C_{45}H_{56}BClN_8O_9$): m/z 899.2 (M+H); 34% boronic acid). HPLC tR 2.63 min, (10% AcCN/H$_2$O-90% AcCN/H$_2$O (with 0.05% TFA), 3.0 min, 1.0 mL/min Kinetix C18, 4.8×50 mm). $^1$H NMR (400 MHz, MeOH-d4) δ 7.99 (d, J=6.0 Hz, 2H), 7.74 (d, J=6.0 Hz, 2H), 7.65 (d, J=6.0 Hz, 2H), 7.47 (d, J=6.0 Hz, 2H), 7.31 (d, J=4.0 Hz, 1H), 7.25 (d, J=4.0 Hz, 1H), 7.316 (d, J=8.0 Hz, 1H), 7.13 (d, J=8.0 Hz, 1H), 6.86 (s, 1H), 6.77 (s, 1H), 6.52 (s, 1H), 5.05 (dd, J=6.0, 4.0 Hz, 1H), 5.01 (d, J=8.0 Hz, 1H), 4.77 (d, J=8.0 Hz, 1H), 4.25-4.18 (m, 4H), 3.36 (m, 1H), 3.18 (t, J=4.0 Hz, 2H), 3.17-3.12 (m, 3H), 2.96 (s, 3H), 2.94-2.92 (m, 2H), 2.47 (ABq, J=12, 4 Hz, 2H), 2.03 (m, 1H), 1.93 (m, 1H), 1.76-1.70 (m, 2H), 1.60-1.56 (m, 2H), 1.38 (d, J=6.0 Hz, 3H).

Example 211: Synthesis of Compound 312

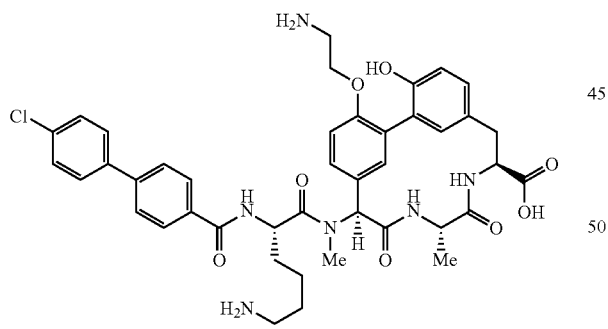

312

Compound 312 was prepared as the formic acid salt from Compound 117C from the Boc-deprotection using TFA/DCM (General Method 9). MS (ESI) for ($C_{42}H_{47}ClN_6O_8$): m/z 799.95 (M+2H). HPLC tR 2.82 min (10% AcCN/H$_2$O-90% AcCN/H$_2$O (with 0.05% TFA), 3.0 min, 1.0 mL/min Kinetix C18, 4.8×50 mm). $^1$H NMR (400 MHz, MeOH-d4) δ 7.74 (d, J=6.0 Hz, 2H), 7.59 (d, J=6.0 Hz, 2H), 7.51 (d, J=6.0 Hz, 2H), 7.37 (d, J=6.0 Hz, 2H), 7.18 (t, J=8.0 Hz, 3H), 6.91 (t, J=8.0 Hz, 3H), 6.79 (s, 1H), 5.00 (d, J=6.0 Hz, 1H), 4.83-4.77 (m, 2H), 4.11 (m, 1H), 3.99 (m, 1H), 3.50-3.44 (m, 2H), 3.12-3.07 (m, 2H), 297 (s, 3H), 2.91-2.85 (m, 2H), 2.08-1.99 (m, 2H), 1.76-1.74 (m, 2H), 1.66-1.58 (m, 2H), 1.37 (d, J=8.0 Hz, 3H).

Example 212: Synthesis of Compound 313

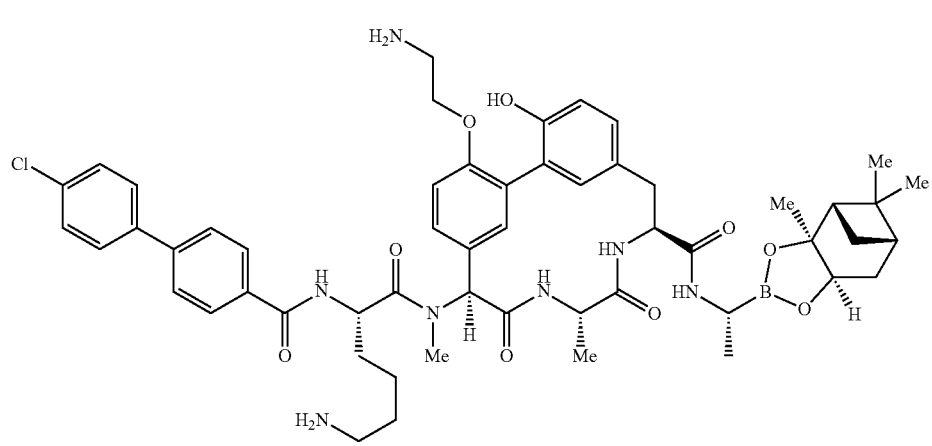

313

Compound 313 was prepared according to General Method 6 from Compound 117C and (R)-BoroAla-(+)-pinanediol HCl. MS (ESI) for ($C_{54}H_{67}BClN_7O_9$): m/z 1004.2 (M+H); HPLC tR 3.25 min, (10% AcCN/$H_2O$-90% AcCN/$H_2O$ (with 0.05% TFA), 3.0 min, 1.0 mL/min Kinetix C18, 4.8×50 mm).

Example 213: Synthesis of Compound 314

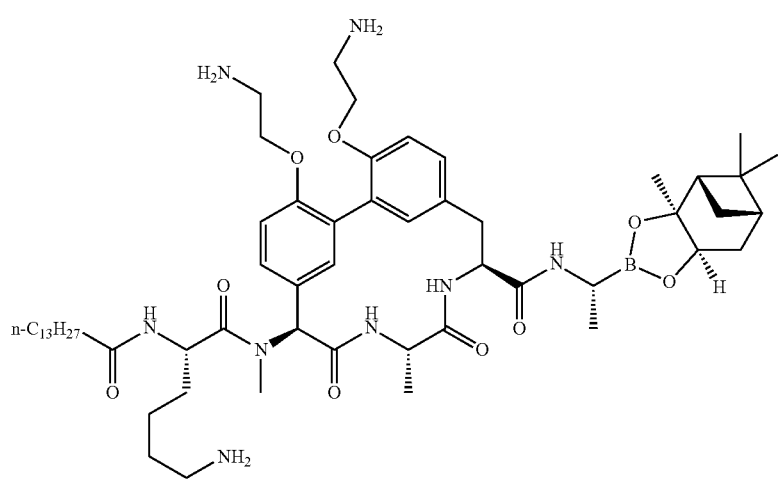

314

Compound 314 was prepared using methods described above. LCMS (5-95AB_1.5 min_220&254_1500): $t_R$=0.835 min, [M+H]$^+$ 1043.9. $^1$H NMR (400 MHz, CD$_3$OD): δ 7.29-7.27 (m, 2H), 7.19 (d, J=8.8 Hz, 1H), 7.14 (d, J=8.4 Hz, 1H), 6.82-6.80 (m, 2H), 6.35 (s, 1H), 5.11-5.06 (m, 1H), 5.85-5.65 (m, 2H), 4.35-4.10 (m, 5H), 3.35-3.30 (m, 1H), 3.20-3.10 (m, 1H), 2.95-2.90 (m, 1H), 2.89-2.80 (m, 3H), 2.78-2.72 (m, 1H), 2.50-1.55 (m, 27H), 1.50-1.27 (m, 23H), 1.23-1.08 (m, 3H), 0.95-0.81 (m, 6H).

Example 214: Synthesis of Compound 315

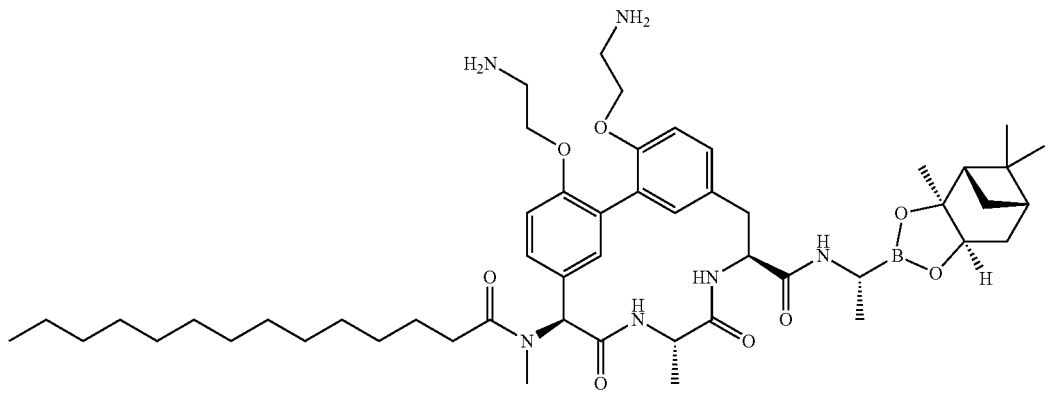

315

Compound 315 was prepared using methods described above. $^1$H NMR (400 MHz, CD$_3$OD) δ 7.31-7.12 (m, 4H), 6.85-6.78 (m, 2H), 6.31 (s, 1H), 5.10-5.01 (m, 2H), 4.80-4.74 (m, 2H), 4.34-4.30 (m, 4H), 4.22 (d, J=8.4 Hz, 2H), 3.25-3.17 (m, 2H), 2.7 (s, 3H), 2.49-2.47 (m, 2H), 2.47-2.46 (m, 2H), 2.46-2.44 (m, 3H), 1.98-1.66 (m, 5H), 1.42-1.39 (m, 3H), 1.38-1.30 (m, 27H) 1.16 (d, J=7.2 Hz, 3H), 0.90-0.85 (m, 6H). LCMS (5-95AB_1.5 min): $t_R$=0.902 min, [M+H]$^+$ 915.6.

Example 215: Synthesis of Compound 316

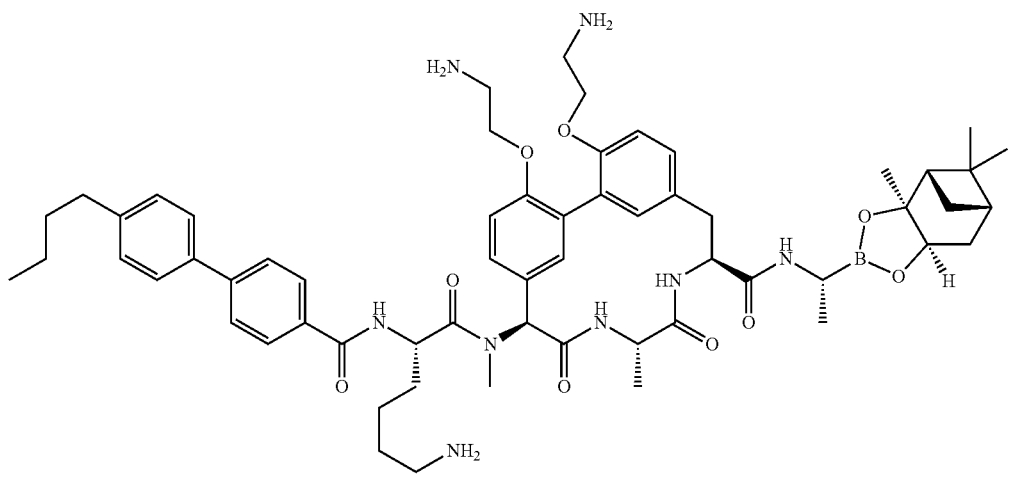

316

Compound 316 was prepared using methods described above. $^1$H NMR (400 MHz, CD$_3$OD): δ 7.94 (d, J=8.4 Hz, 2H), 7.74 (d, J=8.0 Hz, 2H), 7.58 (d, J=8.0 Hz, 2H), 7.35-7.29 (m, 4H), 7.21-7.13 (m, 2H), 6.84-6.79 (m, 2H), 6.44 (s, 1H), 5.07-5.03 (m, 2H), 4.79-4.76 (m, 2H), 4.33-4.21 (m, 5H), 3.25-3.14 (m, 2H), 2.98-2.81 (m, 4H), 2.71-2.63 (m, 4H), 2.47-2.29 (m, 2H), 2.25-2.15 (m, 2H), 2.11-1.51 (m, 13H), 1.50-1.32 (m, 7H), 1.31-1.25 (m, 4H), 1.16 (d, J=6.8 Hz, 3H), 0.97-0.89 (m, 6H). LCMS (Method 5-95AB): $t_R$=0.813 min/1.5 min, [M/2+H]$^+$=535.9.

Example 216: Synthesis of Compound 317

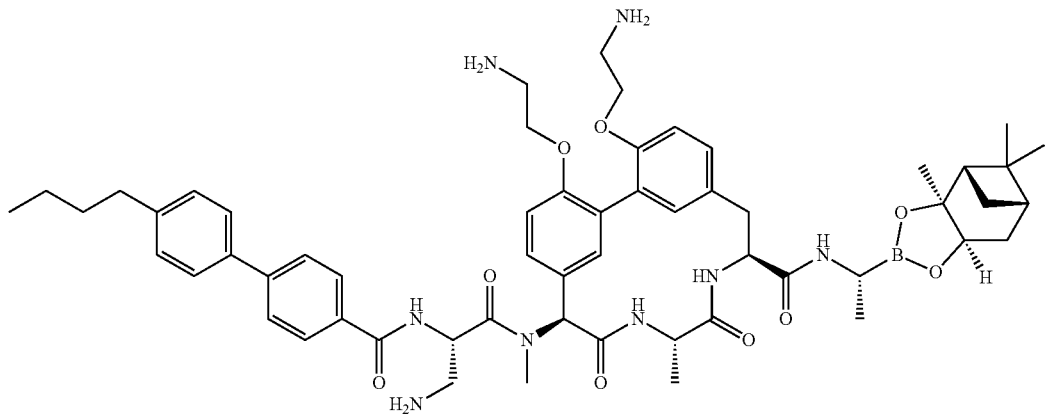

317

Compound 317 was prepared using methods described above. $^1$H NMR (400 MHz, CD$_3$OD) δ 7.99 (d, J=8.4 Hz, 2H), 7.77 (d, J=8.4 Hz, 2H), 7.61 (d, J=8.4 Hz, 2H), 7.35-7.28 (m, 4H), 7.21-7.10 (m, 2H), 6.83-6.78 (m, 2H), 6.25 (s, 1H), 5.32-5.30 (m, 1H), 5.09-4.90 (m, 1H), 4.81-4.77 (m, 2H), 4.35-4.22 (m, 5H), 3.52-3.46 (m, 1H), 3.30-3.23 (m, 2H), 2.81-2.66 (m, 5H), 2.48-2.25 (m, 2H), 2.25-2.21 (m, 2H), 2.00-1.50 (m, 8H), 1.50-1.25 (m, 12H), 1.25-1.00 (m, 3H), 0.99-0.87 (m, 6H). LCMS (5-95AB_1.5 min): t$_R$=0.831 min, [M+H]$^+$ 1027.8.

Example 217: Synthesis of Compound 318

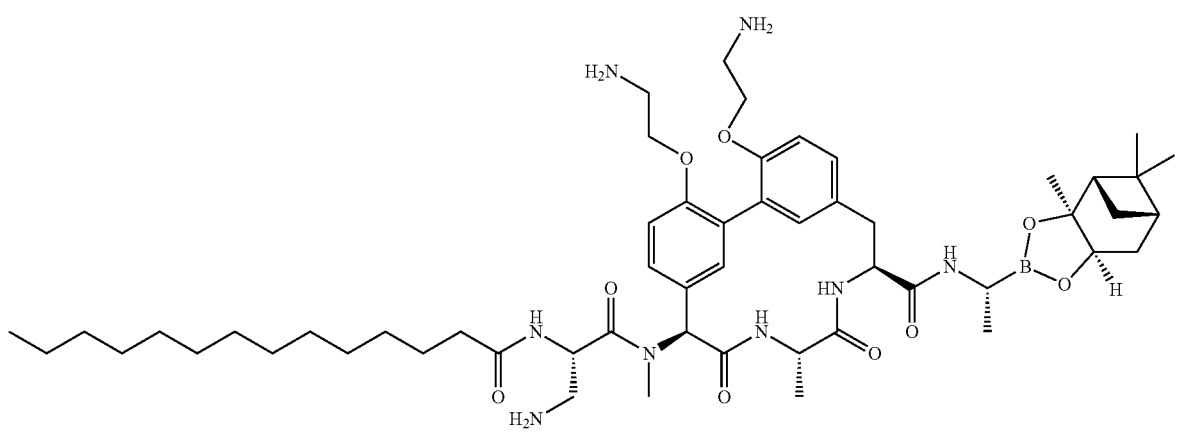

318

Compound 318 was prepared using methods described above. $^1$H NMR (400 MHz, CD$_3$OD) δ 7.34-7.25 (m, 2H), 7.22-7.17 (m, 1H), 7.16-7.12 (m, 1H), 6.85-6.76 (m, 2H), 6.19 (s, 1H), 5.15-5.05 (m, 2H), 4.81-4.72 (m, 2H), 4.37-4.19 (m, 5H), 3.98-3.94 (m, 1H), 3.23-3.08 (m, 3H), 2.80-2.67 (m, 5H), 2.46-2.12 (m, 8H), 2.00-1.57 (m, 10H), 1.48-1.12 (m, 26H), 1.03-0.83 (m, 6H). LCMS (5-95AB_1.5 min): t$_R$=0.839 min, [M+H]$^+$ 1001.7.

Example 218: Synthesis of Compound 319
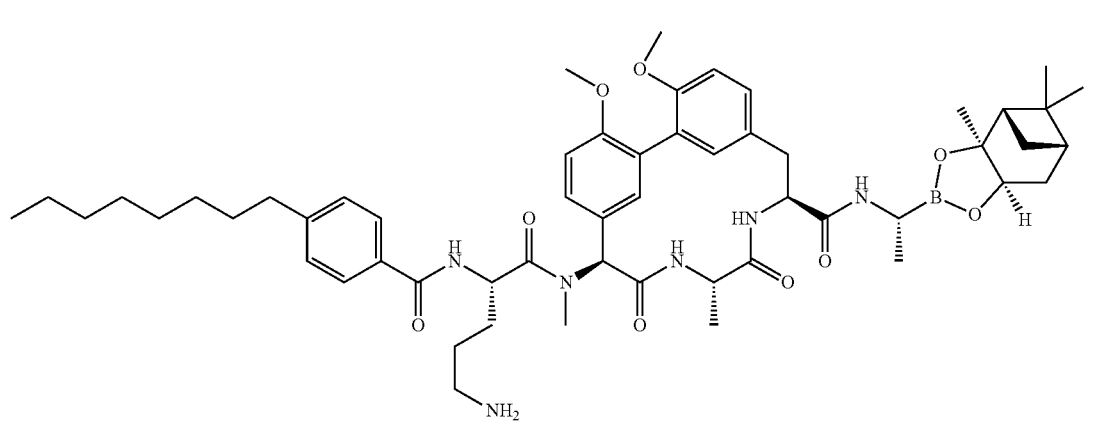
319
Compound 319 was prepared using methods described above. $^1$H NMR (400 MHz, CD$_3$OD) δ 8.55 (s, 1H), 7.59-7.57 (m, 2H), 7.23-7.17 (m, 3H), 7.15-7.00 (m, 2H), 6.75-6.70 (m, 2H), 6.55 (s, 1H), 5.07-5.06 (m, 1H), 4.78-4.77 (m, 2H), 3.84-3.82 (m, 2H), 3.81-3.79 (m, 5H), 3.30-3.26 (m, 1H), 2.95-2.92 (m, 4H), 2.79-2.60 (m, 2H), 2.52-2.50 (m, 2H), 2.40-2.30 (m, 2H), 1.96-1.75 (m, 10H), 1.37-1.10 (m, 24H), 0.92-0.86 (m, 6H). LCMS (5-95AB_1.5 min): $t_R$=0.988 min, [M+H]$^+$ 977.7.
Example 219: Synthesis of Compound 320
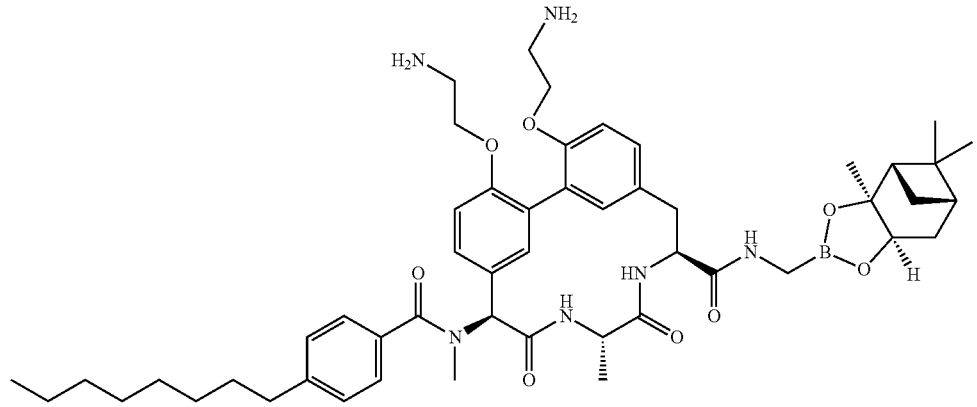
320
Compound 320 was prepared using methods described above. $^1$H NMR (400 MHz, CD$_3$OD) δ 7.50-7.11 (m, 8H), 6.89-6.81 (m, 2H), 6.39 (s, 2H), 5.07-5.03 (m, 2H), 4.34-4.27 (m, 5H), 4.33-4.21 (m, 5H), 4.01-3.91 (m, 1H), 3.18-3.10 (m, 2H), 2.83-2.71 (m, 3H), 2.71-2.53 (m, 4H), 2.47-2.29 (m, 2H), 2.25-2.15 (m, 2H), 2.01-1.74 (m, 5H), 1.69-1.50 (m, 3H), 1.49-1.21 (m, 18H), 1.07-0.85 (m, 6H). LCMS (5-95AB_1.5 min): $t_R$=0.766 min, [M+H]$^+$ 907.7.

Example 220: Synthesis of Compound 321
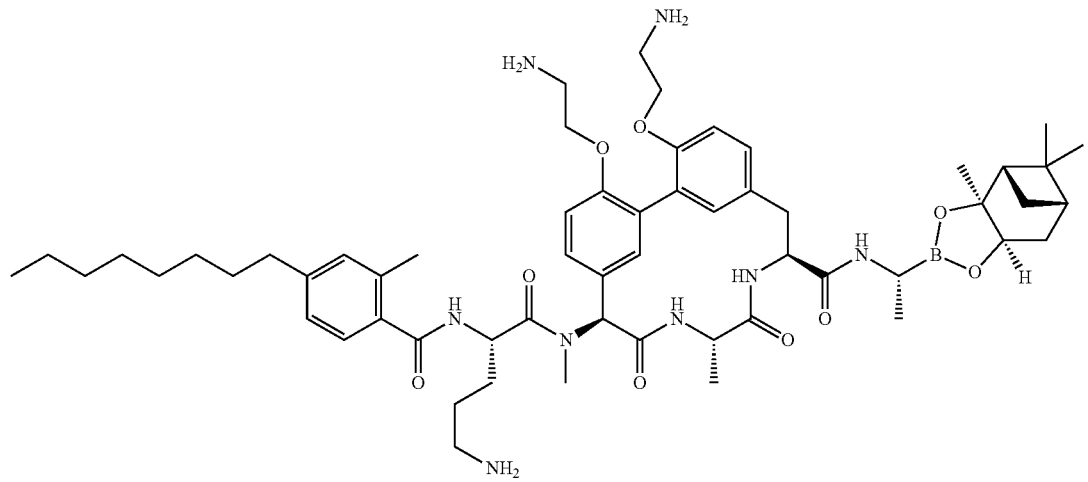
321
Compound 321 was prepared using methods described above. $^1$H NMR (400 MHz, CD$_3$OD) δ 7.35-7.29 (m, 2H), 7.28-7.23 (m, 1H), 7.22-7.17 (m, 1H), 7.12-7.08 (m, 3H), 6.89-6.84 (m, 2H), 6.42 (s, 1H), 5.05-4.98 (m, 1H), 4.81-4.72 (m, 2H), 4.33-4.22 (m, 4H), 3.51-3.43 (m, 1H), 3.28-3.22 (m, 2H), 3.15-3.08 (m, 1H), 3.02-3.94 (m, 4H), 2.63-2.52 (m, 2H), 2.42-2. (m, 3H), 2.00-1.77 (m, 5H), 1.63-1.57 (m, 2H), 1.34-1.25 (m, 12H), 0.89-0.86 (m, 3H). LCMS (5-95AB_1.5 min): t$_R$=0.807 min, [M+H]$^+$ 1049.8.
Example 221: Synthesis of Compound 322
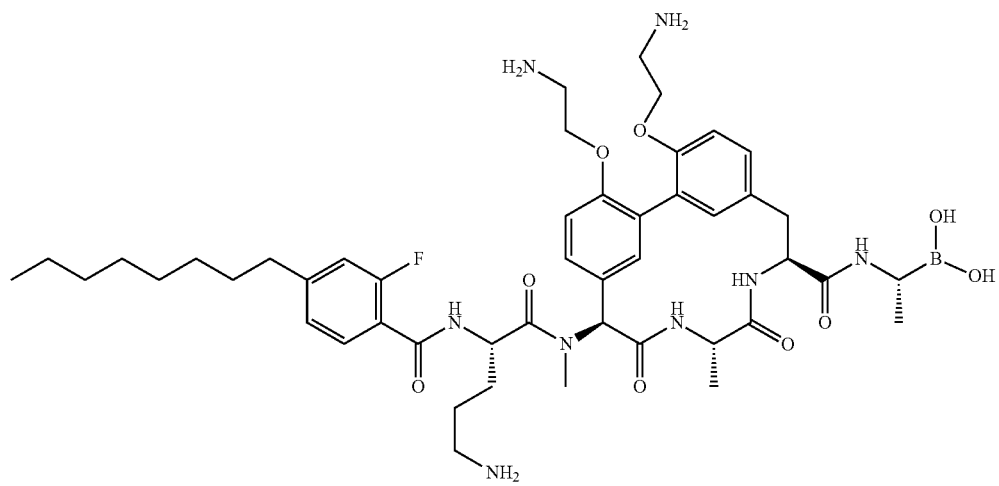
322
Compound 322 was prepared using methods described above. $^1$H NMR (400 MHz, CD$_3$OD) δ 7.74-7.66 (m, 1H), 7.34-7.24 (m, 2H), 7.22-7.05 (m, 4H), 6.86-6.76 (m, 2H), 6.35 (s, 1H), 5.14-5.05 (m, 2H), 4.81-4.70 (m, 3H), 4.34-4.24 (m, 4H), 3.25-3.16 (m, 2H), 3.02-2.88 (m, 5H), 2.79-2.64 (m, 4H), 2.05-1.74 (m, 7H), 1.68-1.58 (m, 2H), 1.37-1.24 (m, 11H), 1.13-1.06 (m, 3H), 0.92-0.85 (m, 3H). LCMS (5-95AB_1.5 min): t$_R$=0.769 min, [M−18+H]$^+$901.8.

Example 222: Synthesis of Compound 323
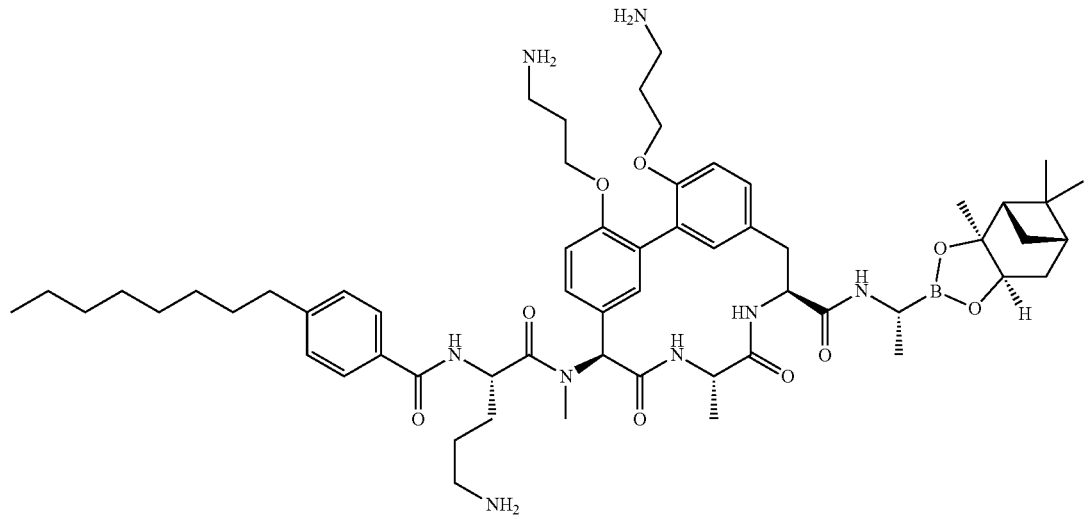
323
Compound 323 was prepared using methods described above. $^1$H NMR (400 MHz, CD$_3$OD) δ 7.84-7.77 (m, 2H), 7.32-7.07 (m, 6H), 6.77-6.69 (m, 2H), 6.38 (s, 1H), 5.06-5.00 (m, 2H), 4.79-4.75 (m, 1H), 4.30-3.95 (m, 5H), 3.21-3.00 (m, 1H), 3.00-2.75 (m, 7H), 2.74-2.64 (m, 3H), 2.50-2.25 (m, 2H), 2.22-1.65 (m, 13H), 1.60-1.51 (m, 2H), 1.49-1.25 (m, 22H), 1.18-1.14 (m, 3H), 0.97-0.85 (m, 7H). LCMS (5-95AB_1.5 min): t$_R$=0.809 min, [M+H]$^+$ 1063.7.
Example 223: Synthesis of Compound 324
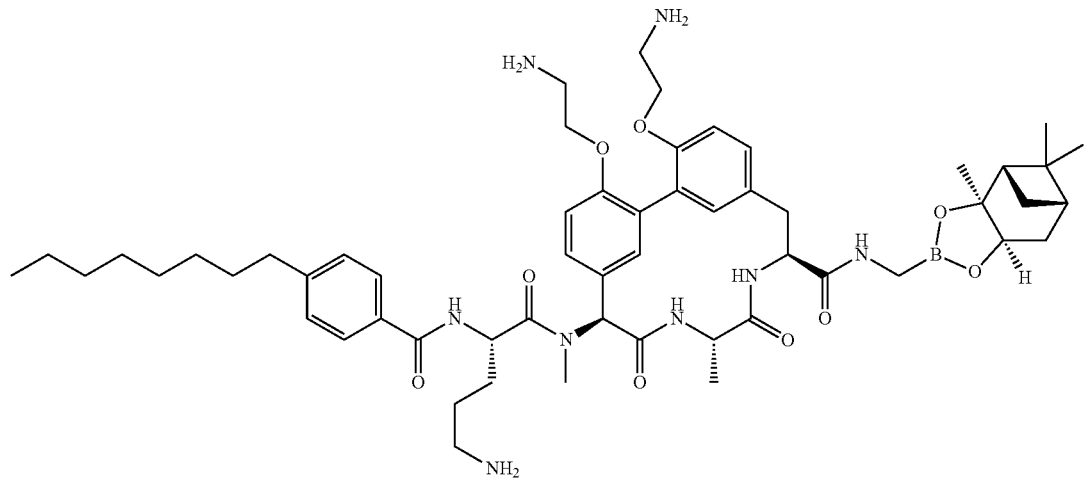
324
Compound 324 was prepared using methods described above. $^1$H NMR (400 MHz, CD$_3$OD) δ 7.80 (d, J=8.0 Hz, 2H), 7.34-7.12 (m, 6H), 6.84-6.79 (m, 2H), 6.37 (m, 1H), 5.06-5.02 (m, 2H), 4.79-4.75 (m, 1H), 4.32-4.25 (m, 4H), 3.97-3.94 (m, 2H), 3.02-2.95 (m, 1H), 2.92 (s, 3H), 2.71-2.65 (m, 2H), 2.60-2.50 (m, 1H), 2.49-2.25 (m, 3H), 2.21-2.14 (m, 2H), 2.00-1.65 (m, 8H), 1.60-1.51 (m, 2H), 1.45-1.25 (m, 20H), 0.97-0.85 (m, 9H). LCMS (5-95AB_1.5 min): t$_R$=0.805 min, [M+Na]$^+$ 1044.5.

Example 224: Synthesis of Compound 325

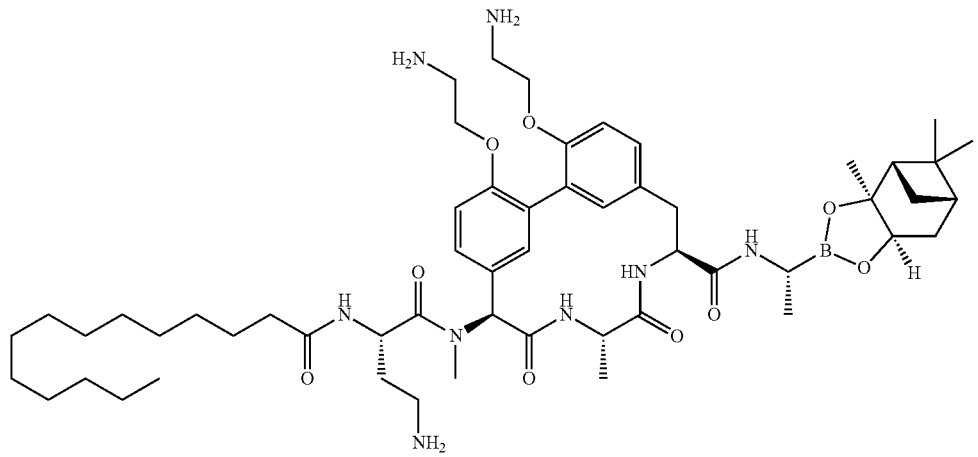

325

Compound 325 was prepared using methods described above. $^1$H NMR (400 MHz, CD$_3$OD) δ 7.32-7.27 (m, 2H), 7.20 (d, J=8.4 Hz, 1H), 7.14 (d, J=8.8 Hz, 1H), 6.83-6.76 (m, 2H), 6.27 (s, 1H), 5.13-5.08 (m, 1H), 4.98-4.92 (m, 1H), 4.76-4.74 (m, 2H), 4.34-4.17 (m, 6H), 3.39-3.34 (m, 1H), 3.25-3.20 (m, 2H), 3.04-3.02 (m, 2H), 2.82-2.76 (m, 5H), 2.41-1.15 (m, 54H), 0.92-0.89 (m, 6H). LCMS (5-95AB_1.5 min): $t_R$=0.810 min, [M+H]$^+$ 1015.6.

Example 225: Synthesis of Compound 326

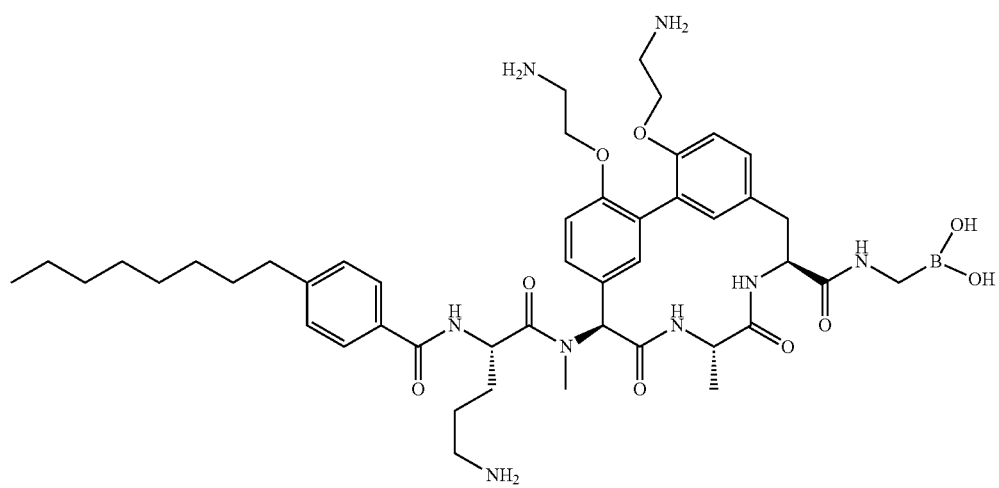

326

Compound 326 was prepared using methods described above. $^1$H NMR (400 MHz, CD$_3$OD) δ 7.80 (d, J=8.0 Hz, 2H), 7.34-7.12 (m, 6H), 6.84-6.79 (m, 2H), 6.36 (m, 1H), 5.07-5.02 (m, 2H), 4.79-4.75 (m, 1H), 4.32-4.25 (m, 4H), 3.41-3.36 (m, 2H), 3.25-3.19 (m, 3H), 3.10-2.95 (m, 2H), 2.92 (s, 2H), 2.71-2.65 (m, 3H), 2.60-2.50 (m, 2H), 2.20-1.65 (m, 5H), 1.60-1.54 (m, 3H), 1.45-1.25 (m, 12H), 0.92-0.86 (m, 3H). LCMS (5-95AB_1.5 min): $t_R$=0.898 min, [M/2+H]$^+$ 444.4.

Example 226: Synthesis of Compound 327

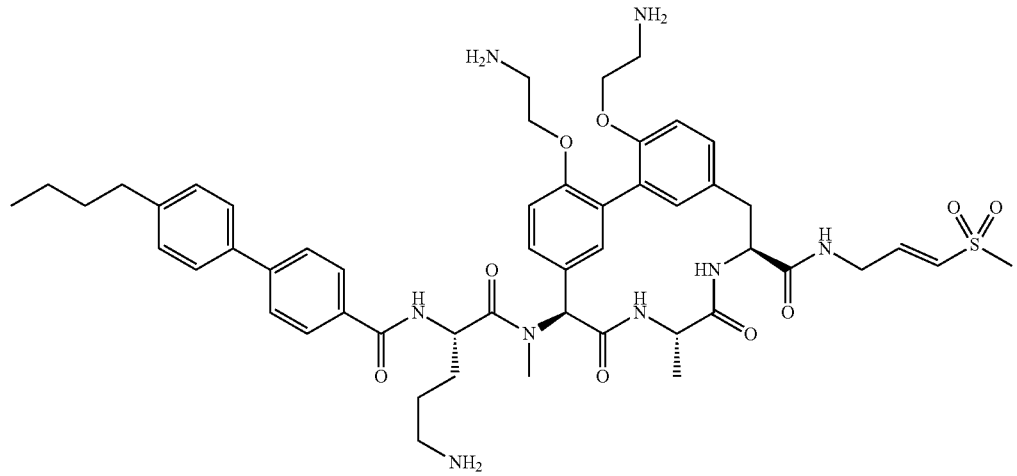

327

Compound 327 was prepared using the methods described previously from (E)-3-(methylsulfonyl)prop-2-en-1-amine hydrochloride (Example 135). $^1$H NMR (400 MHz, CD$_3$OD) δ 8.52 (s, 2H), 7.93 (d, J=7.6 Hz, 2H), 7.73 (d, J=8.0 Hz, 2H), 7.56 (d, J=7.2 Hz, 2H), 7.40-7.20 (m, 4H), 7.20-7.15 (m, 1H), 7.15-7.05 (m, 1H), 6.95-6.75 (m, 3H), 6.70-6.60 (m, 4H), 6.46 (s, 1H), 5.15-5.05 (m, 1H), 4.83-4.70 (m, 2H), 4.22 (s, 4H), 4.08 (s, 2H), 3.40-3.35 (m, 1H), 3.25-3.10 (m, 5H), 3.10-2.80 (m, 8H), 2.68 (t, J=7.4 Hz, 2H), 2.10-1.75 (m, 4H), 1.75-1.50 (m, 2H), 1.45-1.35 (m, 3H), 1.35-1.15 (m, 2H), 0.97 (t, J=6.8 Hz, 3H). LCMS (0-60AB_7 min, ESI): RT=3.446 min, [M/2+H]$^+$484.6.

Example 227: Synthesis of Compound 328

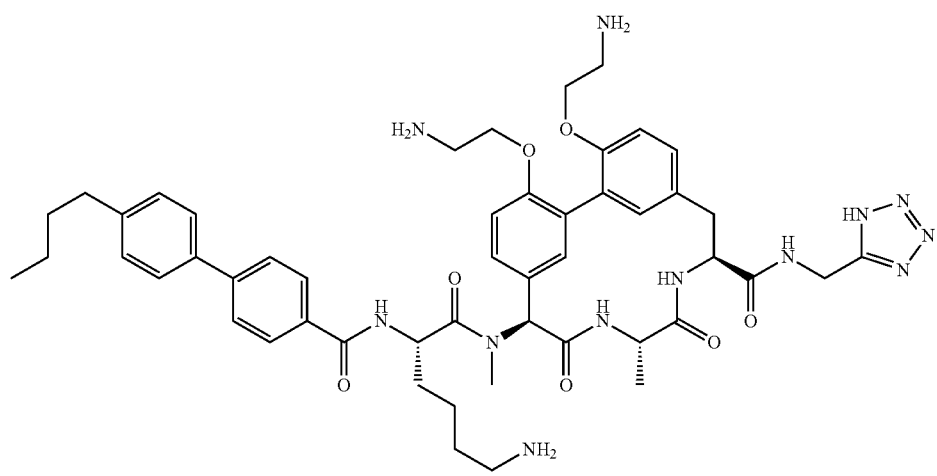

328

Compound 328 was prepared from (1H-tetrazol-5-ylmethyl)amine hydrobromide by HATU coupling (General Method 8) and Boc-deprotection with the modified TFA/HFIP method as a white solid. LC-MS: m/z=946 (M+H)$^+$. $^1$H NMR (400 MHz, DMSO-d6) δ 8.81 (d, J=8.4 Hz, 1H), 8.72 (d, J=7.7 Hz, 1H), 8.36 (d, J=9.8 Hz, 1H), 8.05-7.98 (m, 2H), 7.80-7.75 (m, 2H), 7.69-7.64 (m, 2H), 7.33 (d, J=8.1 Hz, 3H), 7.19-7.09 (m, 3H), 7.01 (d, J=8.5 Hz, 1H), 6.73 (s, 1H), 6.67 (d, J=2.0 Hz, 1H), 6.35 (s, 1H), 4.85 (d, J=7.3 Hz, 1H), 4.76-4.65 (m, 1H), 4.36 (d, J=5.2 Hz, 2H), 3.99 (d, J=19.3 Hz, 5H), 3.00-2.73 (m, 10H), 2.65-2.60 (m, 2H), 1.78 (d, J=8.0 Hz, 2H), 1.63-1.55 (m, 4H), 1.47 (s, 2H), 1.39-1.28 (m, 2H), 1.21 (d, J=6.7 Hz, 3H), 0.94-0.90 (m, 3H).

Example 228: Synthesis of Compound 329
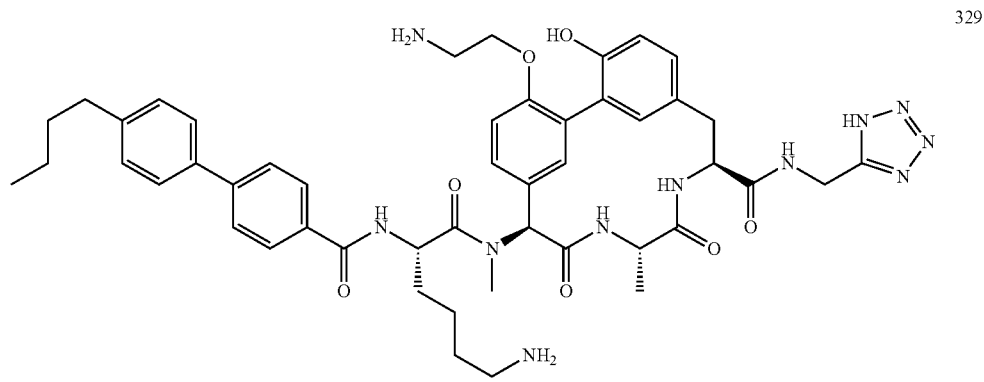 [SMILES: CCCCc1ccc(-c2ccc(C(=O)N[C@@H](CCCCN)C(=O)N(C)[C@@H]3C(=O)N[C@@H](C)C(=O)N[C@H](C(=O)NCc4nnn[nH]4)Cc4ccc(O)c(c4)-c4cc3ccc4OCCN)cc2)cc1]
Compound 329 was prepared using the methods described above as a white solid. LC-MS: m/z=903 (M+H)$^+$.
Example 229: Synthesis of Compound 330
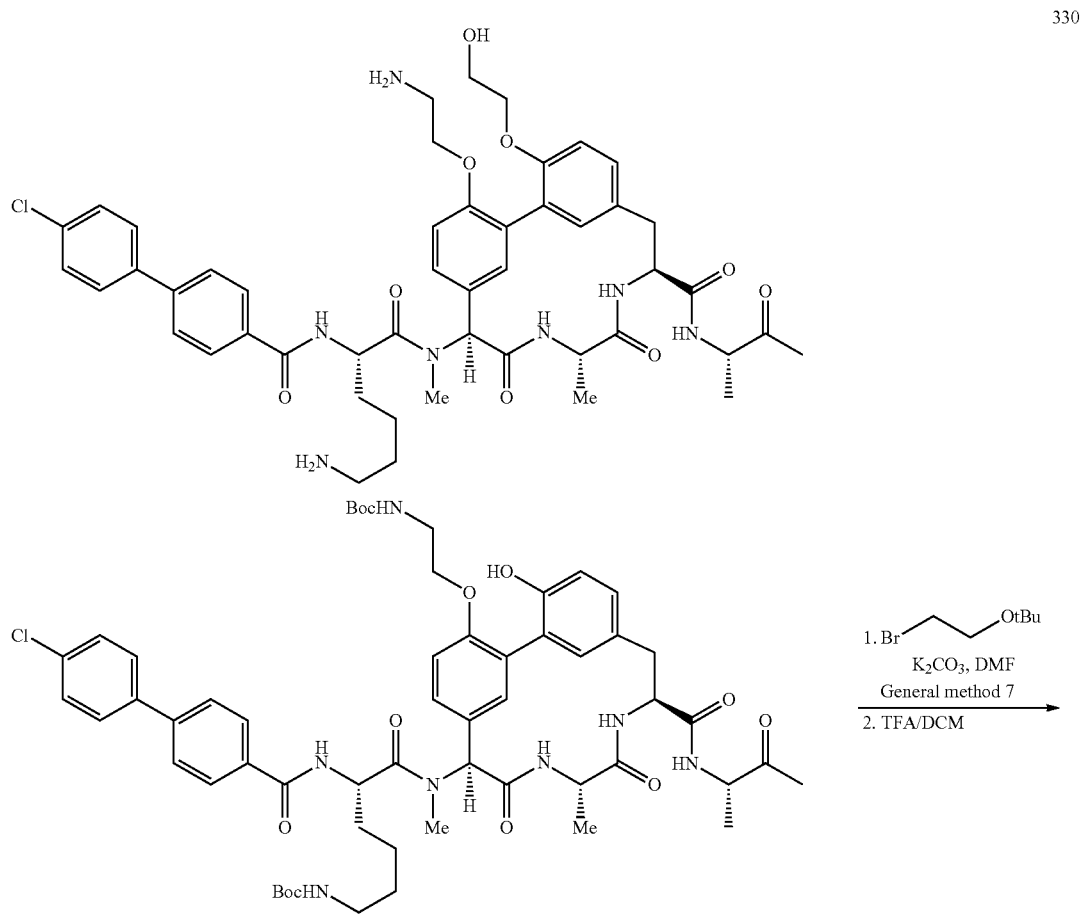

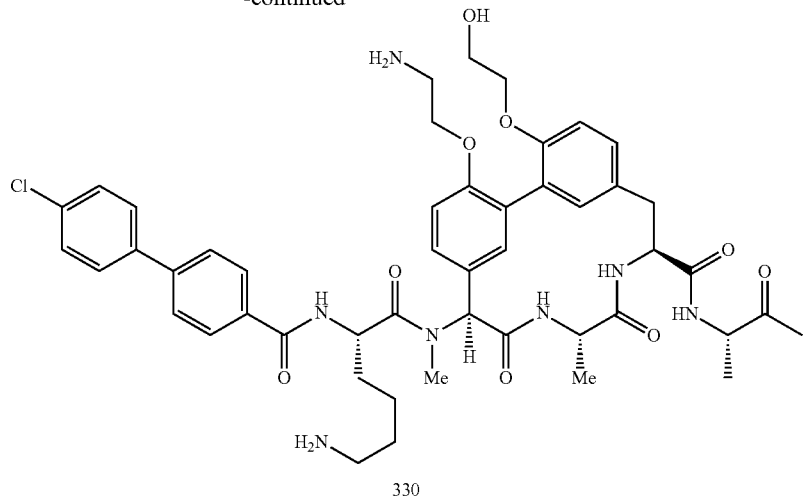

330

Compound 330A is an intermediate prepared during the synthesis of Compound 119. MS (ESI) for ($C_{56}H_{70}ClN_7O_{12}$): m/z 1069.4 (M+2H)$^+$. HPLC: tR 3.27 min (50% AcCN/H$_2$O-90% AcCN/H$_2$O (with 0.05% TFA), 3.0 min, 1.0 mL/min Kinetix C18, 4.8×50 mm). Compound 330 was prepared in two steps. From Compound 330A by phenol alkylation using the General Method 7. MS (ESI) for ($C_{64}H_{88}ClN_7O_{13}Si$): m/z 1227.4 (M+2H)$^+$. HPLC: tR 4.54 min (50% AcCN/H$_2$O-90% AcCN/H$_2$O (with 0.05% TFA), 3.0 min, 1.0 mL/min Kinetix C18, 4.8×50 mm). The above material was Boc deprotected using TFA/DCM (General Method 9) to give Compound 330 as a formate salt. MS (ESI) for ($C_{48}H_{58}ClN_7O_9$): m/z 912.84 (M+2H). HPLC tR 2.88 min (10% AcCN/H$_2$O-90% AcCN/H$_2$O (with 0.05% TFA), 3.0 min, 1.0 mL/min Kinetix C18, 4.8×50 mm). $^1$H NMR (400 MHz, MeOH-d4) δ 7.96 (d, J=6.0 Hz, 2H), 7.75 (d, J=6.0 Hz, 2H), 7.66 (d, J=6.0 Hz, 2H), 7.48 (d, J=6.0 Hz, 2H), 7.28 (d, J=8.0 Hz, 1H), 7.20 (t, J=4.0 Hz, 1H), 7.11 (d, J=8.0 Hz, 1H), 7.05 (d, J=8.0 Hz, 1H), 6.86 (s, 1H), 6.82 (s, 1H), 6.44 (s, 1H), 5.04 (dd, J=4.0, 2.0 Hz, 1H), 4.90 (dd, J=8.0, 2.0 Hz, 1H), 4.85 (d, J=8.0 Hz, 1H), 4.47 (m, 1H), 4.45-4.39 (m, 2H), 4.31-4.15 (m, 2H), 3.92-3.90 (m, 2H), 3.45-3.30 (m, 2H), 3.16-3.08 (m, 2H), 2.96 (s, 3H), 2.94 (m, 2H), 2.20 (s, 3H), 2.02-2.01 (m, 1H), 1.91-1.69 (m, 1H), 1.75-1.72 (m, 2H), 1.62-1.57 (m, 2H), 1.37 (d, J=8.0 Hz, 3H), 1.31 (d, J=8.0 Hz, 3H).

Example 230: Synthesis of Compound 331

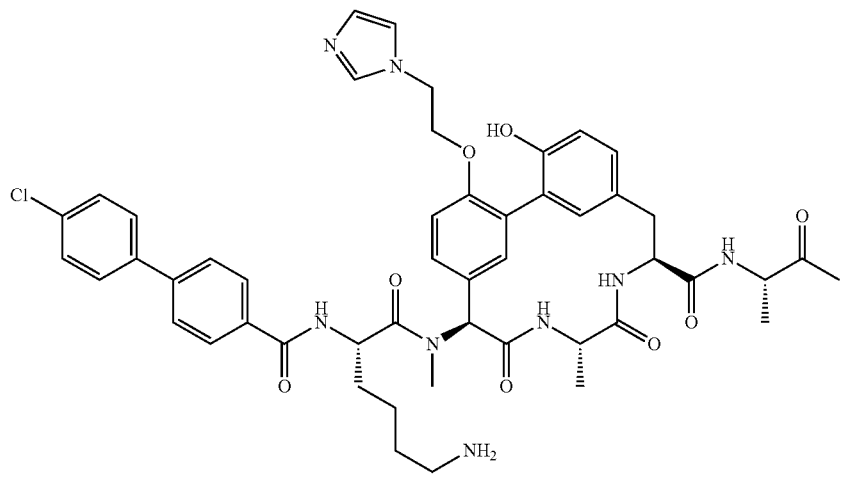

331

Compound 331 was prepared as a formic acid salt from Compound 117A and 1-(2-bromoethyl)-1H-imidazole using the alkytion methods described above. LCMS (5-95 AB, ESI): RT=0.604, M+H$^+$=719.5.

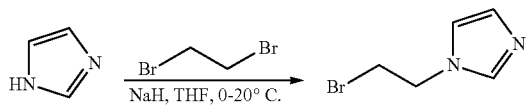

The synthesis of 1-(2-bromoethyl)-1H-imidazole: To a solution of imidazole (1.33 g, 19.5 mmol) in THF (50 mL) was added 60% NaH (0.94 g, 23.4 mmol) slowly at 0° C. and the mixture was stirred at the same temperature for 10 min. 1,2-dibromoethane (5.0 mL, 58.6 mmol) was then added to the above mixture dropwise. The resulting mixture was stirred at room temperature for 12 h. The reaction was then added with H$_2$O (80 ml), which was extracted with DCM (2×30 mL). The combined organic layers were dried over Na$_2$SO$_4$ and concentrated to afford 1-(2-bromoethyl)-1H-imidazole (0.6 g, 17.6%) as a pale yellow oil, which was used directly in the next step.

Example 231: Synthesis of Compound 332

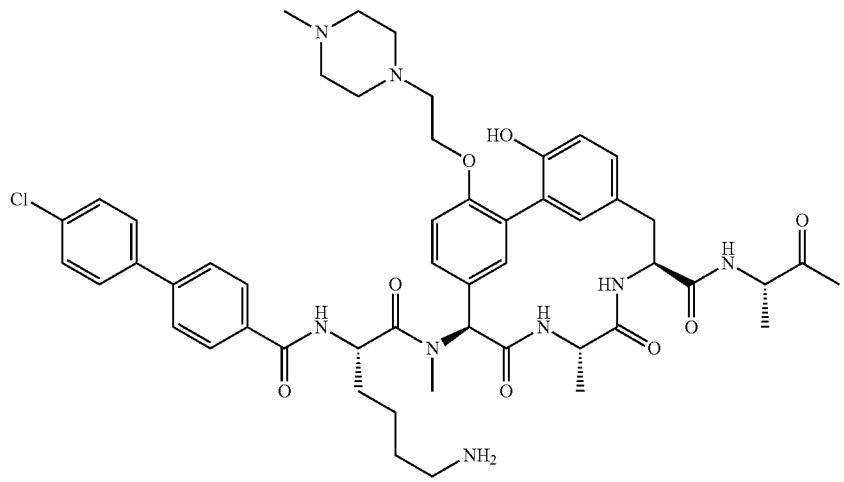

332

Compound 332 was prepared as the formic acid salt from Compound 204AA and N-Me piperazine using the methods described above. LCMS (5-95 AB, ESI): RT=0.744, M+H$^+$=951.5.

Example 232: Synthesis of Compound 333

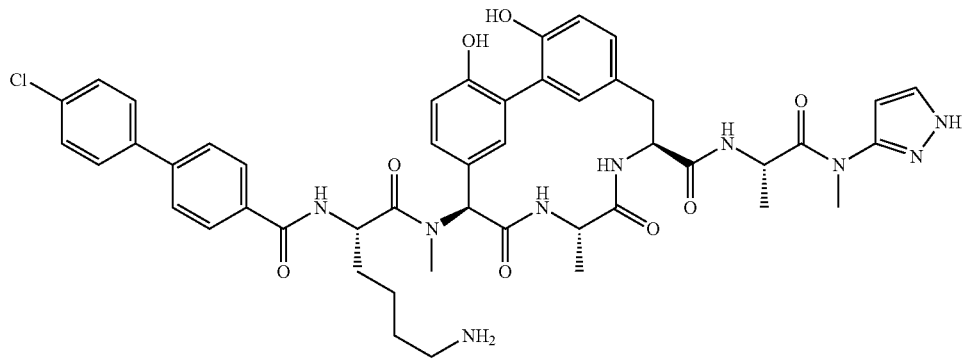

333

Compound 333 was prepared as a formic acid salt using the amide coupling and Boc-group hydrolysis (General Methods 8 and 9) as described for Compound 115 from Compound 104E and (S)-tert-butyl 3-(2-amino-N-methyl-propanamido)-1H-pyrazole-1-carboxylate. LCMS (5-95 AB, ESI): RT=0.799, M+1=906.3.

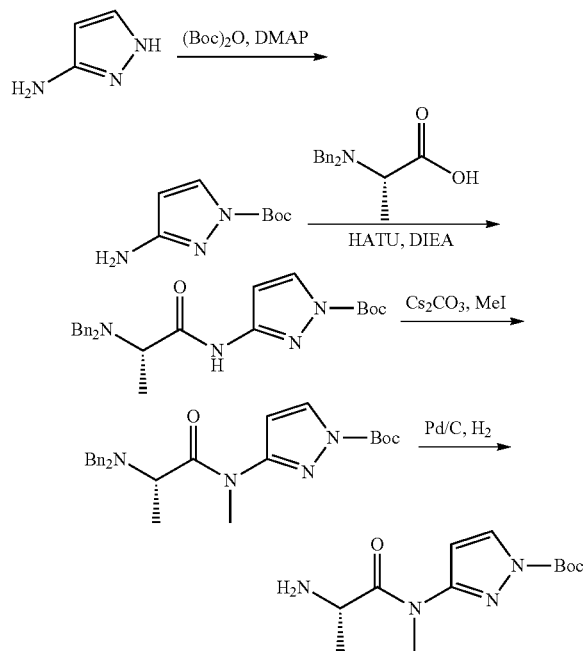

The synthesis of 3-(2-amino-N-methylpropanamido)-1H-pyrazole-1-carboxylate: To a mixture of 1H-pyrazol-3-amine (250 mg, 3.0 mmol), Et$_3$N (300 mg, 3.0 mmol) and DMAP (25 mg, 0.2 mmol) in dioxane (10 mL) was added with Boc$_2$O (750 mg, 3.45 mmol) dropwise at room temperature and the mixture was stirred at the same temperature for 18 h. The volatiles were removed and the residue was re-dissolved with EtOAc (30 mL), which was washed with brine (2×30 mL). The organic layer was dried over MgSO$_4$, concentrated and the residue was purified by silica-gel column chromatography to afford tert-butyl 3-amino-1H-pyrazole-1-carboxylate (220 mg, yield: 40%) as a white solid.

Standard amide coupling condition (HATU/DIEA, General Method 8) was applied to tert-butyl 3-amino-1H-pyrazole-1-carboxylate (1.0 g, 5.5 mmol) and (S)-2-(dibenzylamino)propanoic acid to afford (S)-tert-butyl 3-(2-(dibenzylamino)propanamido)-1H-pyrazole-1-carboxylate (900 mg, 38% yield) as a pale-yellow solid.

To a mixture of (S)-tert-butyl 3-(2-(dibenzylamino)propanamido)-1H-pyrazole-1-carboxylate (900 mg, 2.1 mmol) and Cs$_2$CO$_3$ (675 mg, 2.1 mmol) in DMF (5 mL) was added MeI (294 mg, 2.1 mmol) at 0° C. and the mixture was warmed up and stirred at room temperature for 16 h. The volatiles were removed and the residue was re-dissolved in EtOAc (30 mL), which was washed with brine (2×30 mL). The organic layer was dried over MgSO4 and concentrated to afford (S)-tert-butyl 3-(2-(dibenzylamino)-N-methylpropanamido)-1H-pyrazole-1-carboxylate (900 mg, 96.8% yield) as a yellow oil, which was used directly in the next step.

Standard hydrogenation condition (Pd/C, 1 atm H$_2$) was applied to (S)-tert-butyl 3-(2-(dibenzylamino)-N-methylpropanamido)-1H-pyrazole-1-carboxylate (900 mg, 2.0 mmol) to afford (S)-tert-butyl 3-(2-amino-N-methylpropanamido)-1H-pyrazole-1-carboxylate (450 mg, 84% yield) as a white solid. $^1$H NMR (400 MHz, CDCl$_3$): δ ppm 7.56 (d, J=4 Hz, 1H), 6.22 (s, 1H), 5.48 (d, J=4 Hz, 1H), 4.59 (m, 1H), 3.27 (s, 3H), 1.42 (s, 9H), 1.22 (d, J=8 Hz, 3H).

Example 233: Synthesis of Compound 334

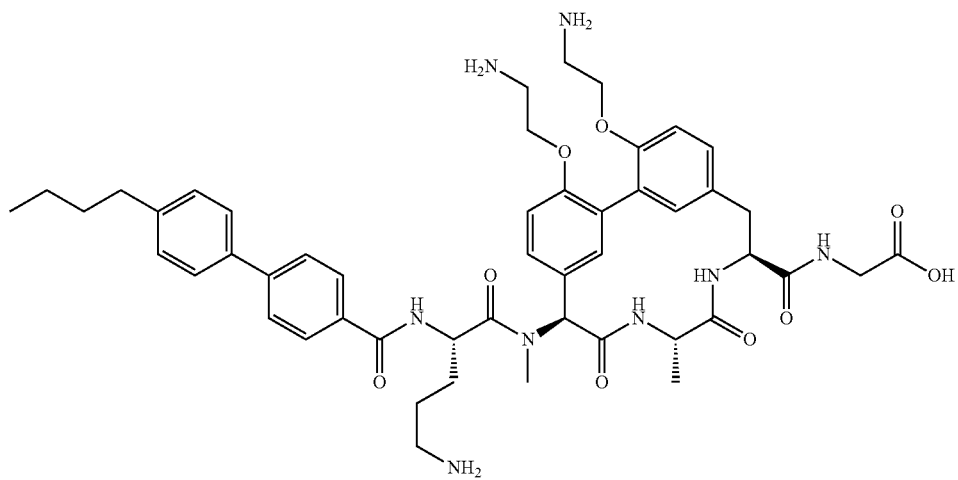

334

Compound 334 is prepared using HATU amide coupling (General Method 8) using methyl aminoacetate hydrochloride followed by LiOH ester hydrolysis and TFA deprotection (General Method 9). $^1$H NMR (400 MHz, CD$_3$OD): δ 8.46 (s, 1H), 7.66 (d, J=6.8 Hz, 2H), 7.49 (d, J=7.6 Hz, 2H), 7.27-7.13 (m, 6H), 7.11-6.86 (m, 2H), 6.61 (s, 1H), 5.13-5.09 (m, 1H), 4.78-4.71 (m, 2H), 4.26-4.18 (m, 4H), 3.73-3.70 (m, 2H), 3.31-3.30 (m, 1H), 3.15-3.01 (m, 3H), 3.00-2.79 (m, 7H), 2.65 (t, J=7.4 Hz, 2H), 2.11-1.75 (m, 5H), 1.69-1.51 (m, 2H), 1.49-1.33 (m, 4H), 0.97 (t, J=7.6 Hz, 3H). LCMS (Method 5-95AB): $t_R$=0.641 min/1.5 min, [M+H]$^+$=907.4.
Example 234: Synthesis of Compound 335
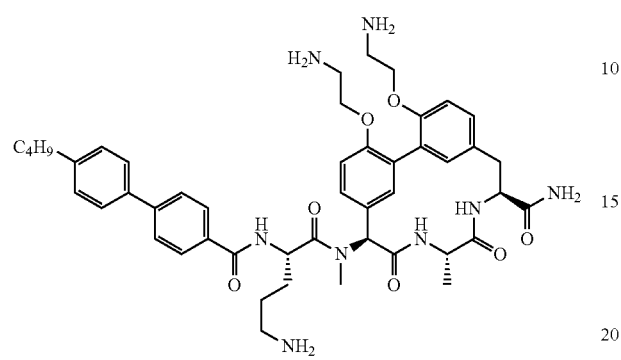
Compound 335 was prepared using the IBCF coupling conditions with ammonium hydroxide follow by TFA deprotection (General Method 6). LCMS (5-95AB_1.5 min_220&254_1500): $t_R$=0.744 min, [M+H]$^+$ 849.5. $^1$H NMR (400 MHz, CD$_3$OD): δ 8.48 (s, 1H), 8.01-7.92 (m, 2H), 7.79-7.69 (m, 2H), 7.64-7.54 (m, 2H), 7.34-7.21 (m, 4H), 7.18-7.06 (m, 4H), 6.91-6.81 (m, 2H), 6.40 (s, 1H), 5.14-5.07 (m, 1H), 4.84-4.75 (m, 3H), 4.25-4.13 (m, 3H), 3.50-3.40 (m, 2H), 3.25-3.21 (m, 1H), 3.19-3.09 (m, 4H), 3.04-2.91 (m, 4H), 2.74-2.64 (m, 2H), 2.08-2.00 (m, 1H), 1.96-1.78 (m, 3H), 1.70-1.60 (m, 2H), 1.47-1.28 (m, 5H), 1.01-0.92 (m, 3H).
Example 235: Synthesis of Compound 336
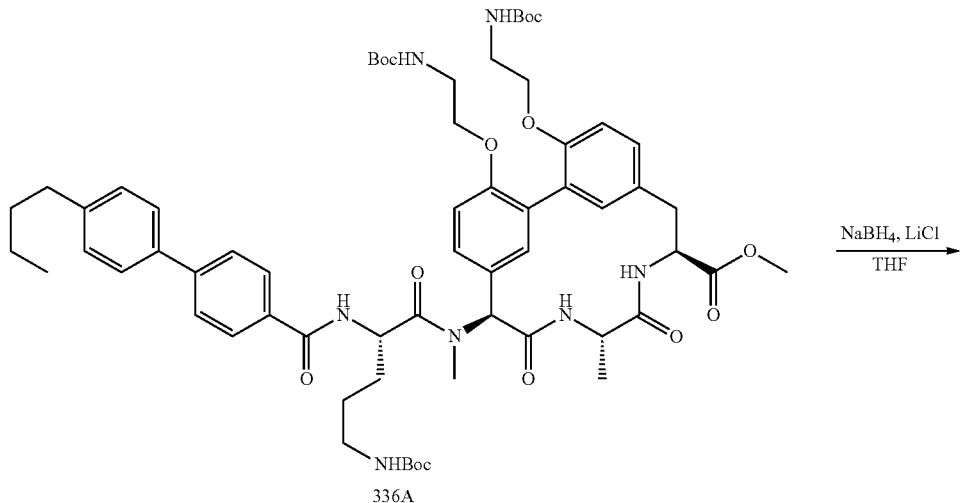
336A
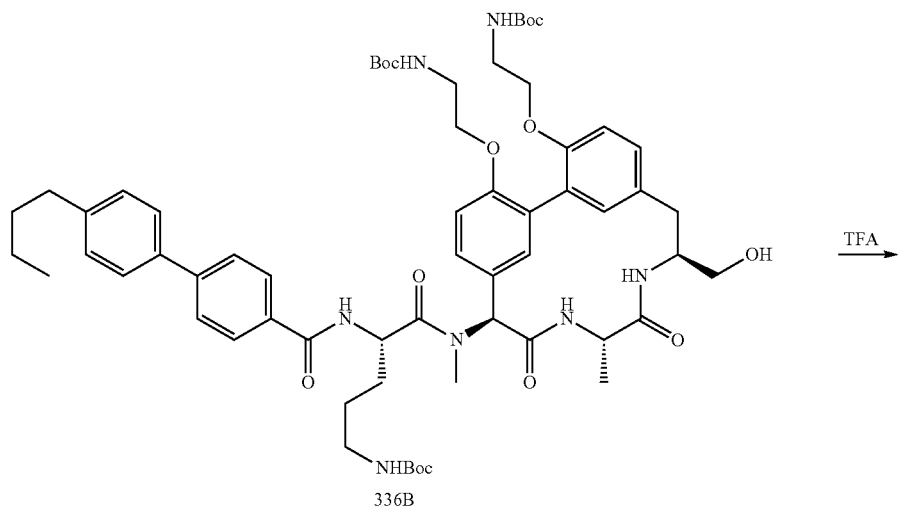
336B -continued

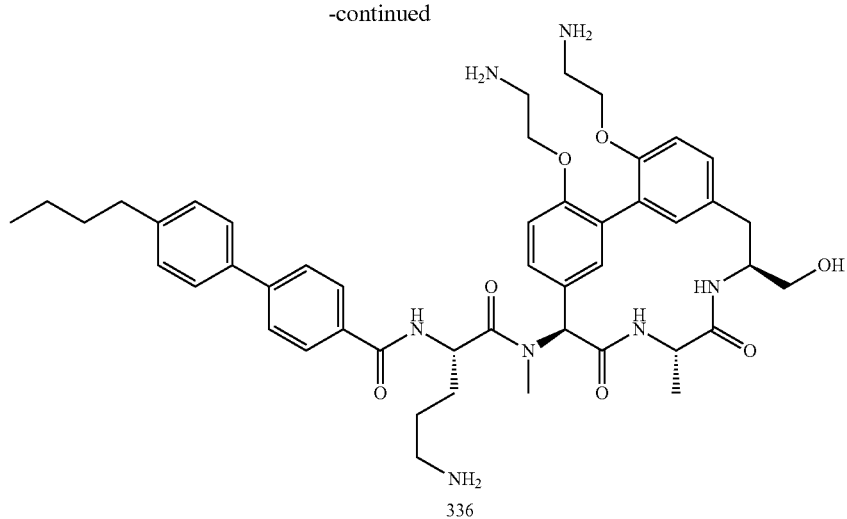

336

To a solution of Compound 336A (450 mg, 0.39 mmol) in tetrahydrofuran (20 mL) was added sodium borohydride (146.21 mg, 3.87 mmol) and lithium chloride (163.84 mg, 3.87 mmol). The reaction mixture was stirred at 15° C. for 1 h, quenched with saturated aqueous ammonium chloride (20 mL) and water (20 mL), and extracted with ethyl acetate (30 mL×3). The organics were washed with water (50 mL×2) and brine (50 mL), dried (sodium sulfate) and concentrated to give Compound 336A (400 mg, yield 91%) as a white solid. LCMS (5-95AB/1.5 min): $t_R$=1.107 min, [M-Boc+H]$^+$1037.0.

A mixture of Compound 336A (50 mg, 0.04 mmol), trifluoroacetic acid (0.2 mL, 2.63 mmol) and 1,1,1,3,3,3-hexafluoro-2-propanol (3.8 mL, 36.18 mmol) was stirred at 15° C. for 1 h. The mixture was concentrated and the residue was purified by prep-HPLC (acetonitrile 10-40%/0.225% FA in water) to obtain Compound 336 (7.8 mg, 0.0091 mmol, 20.8% yield) as a white solid. $^1$H NMR (400 MHz, CD$_3$OD): δ 7.92 (d, J=7.6 Hz, 2H), 7.71 (d, J=8.0 Hz, 2H), 7.52 (d, J=7.6 Hz, 2H), 7.29-7.12 (m, 6H), 6.91-6.85 (m, 2H), 6.52 (s, 1H), 5.10-5.09 (m, 1H), 4.76-4.71 (m, 1H), 4.35-4.21 (m, 5H), 3.56-3.54 (m, 3H), 3.31-2.92 (m, 10H), 2.72-2.65 (m, 2H), 1.94-1.80 (m, 5H), 1.66-1.62 (m, 2H), 1.42-1.32 (m, 4H), 0.98-0.94 (t, J=8.0 Hz, 3H). LCMS (Method 5-95AB): $t_R$=0.671 min/1.5 min, [M+H]$^+$=836.5.

Example 236: Synthesis of Compound 337

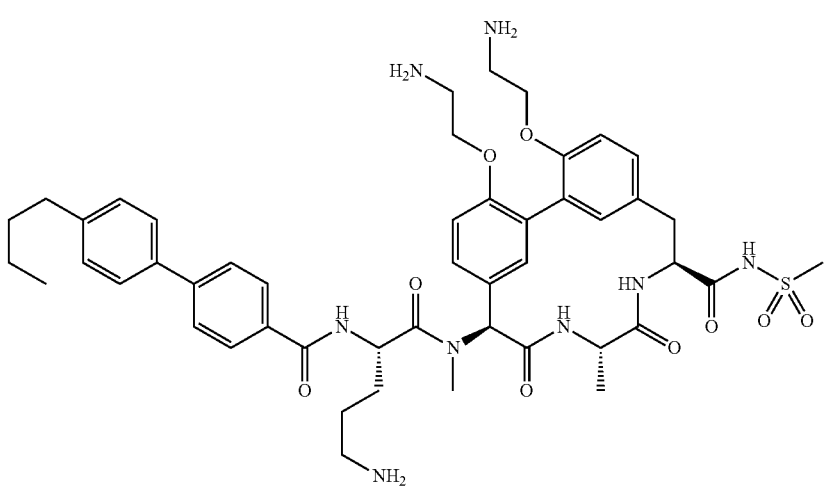

337

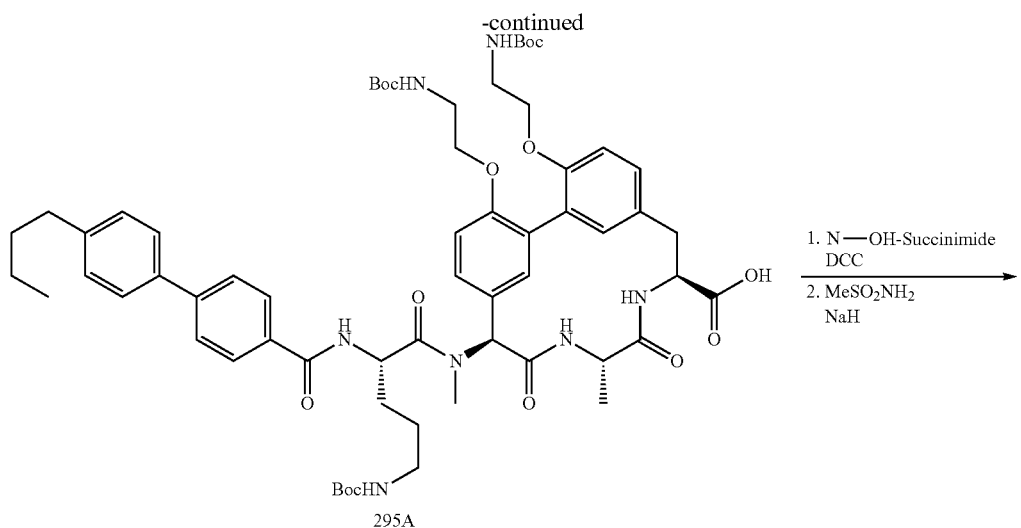

295A

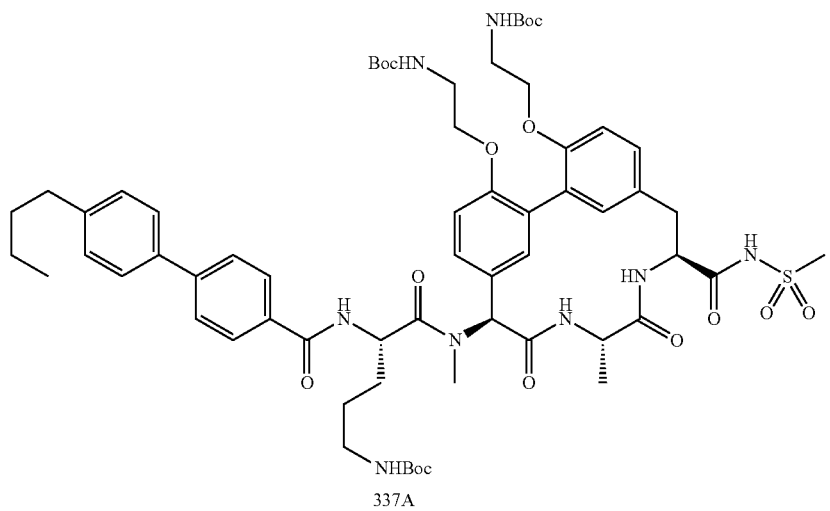

337A

A mixture of Compound 295A (1 eq) and N-hydroxysuccinimide (1.1 eq) in tetrahydrofuran (0.03 M) was treated with N,N'-dicyclohexylcarbodiimide (1.1 eq). The resulting mixture was stirred at 15° C. for 1 h under nitrogen and filtered. The filtrate was used in the next step without purification.

To a solution of methanesulfonamide (1.2 eq) in tetrahydrofuran (0.03 mL) was added sodium hydride (1.2 eq) at 0° C., and the mixture was stirred at 0° C. for 1 h. Then to the mixture was added the solution of step 1, and the reaction mixture was stirred at 0° C. for 1 h. The mixture was quenched with saturated aqueous ammonium chloride), and the mixture was extracted with ethyl acetate (3×). The organics were dried over sodium sulfate and concentrated. The residue was purified by prep-TLC (10% methanol in dichloromethane) to give Compound 337A.

Compound 337A was subject to Boc-hydrolysis conditions (TFA/HFIP) to afford Compound 337. $^1$H NMR (400 MHz, CD$_3$OD) δ 8.57-8.46 (m, 1H), 7.94-7.82 (m, 2H), 7.74-7.61 (m, 2H), 7.48-7.38 (m, 2H), 7.33-7.20 (m, 4H), 7.15-7.02 (m, 2H), 6.99-6.84 (m, 1H), 6.62 (s, 1H), 5.14-5.07 (m, 1H), 4.82-4.77 (m, 1H), 4.66-4.60 (m, 1H), 4.27-3.98 (m, 4H), 3.50-3.41 (m, 2H), 3.22-2.91 (m, 12H), 2.75-2.64 (m, 2H), 2.11-1.75 (m, 4H), 1.70-1.58 (m, 2H), 1.47-1.28 (m, 5H), 1.01-0.92 (m, 3H). LCMS (5-95AB_1.5 min): $t_R$=0.748 min, [M/2+H]$^+$464.6.

Example 237: Synthesis of Compound 338
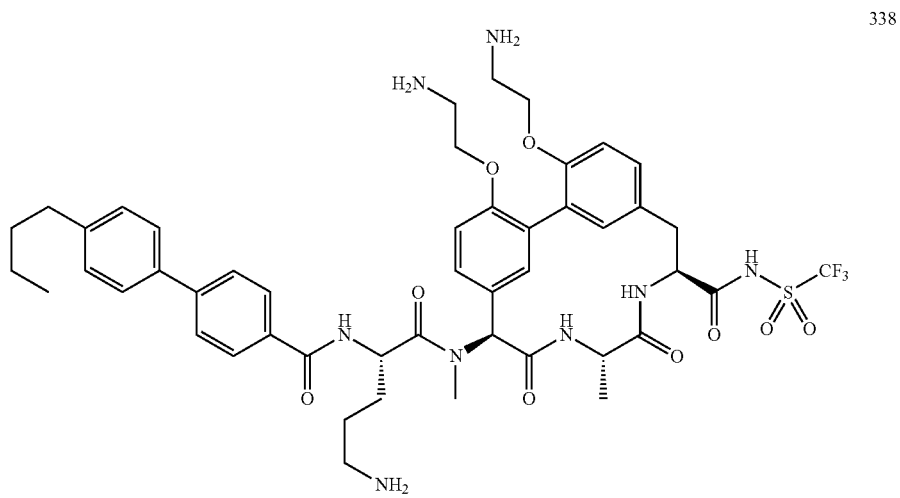 [SMILES: CCCCc1ccc(-c2ccc(C(=O)N[C@@H](CCCN)C(=O)N(C)[C@@H]3C(=O)N[C@@H](C)C(=O)N[C@H](C(=O)NS(=O)(=O)C(F)(F)F)Cc4ccc(OCCN)c(c4)-c4cc3ccc4OCCN)cc2)cc1]
Compound 338 was prepared by HATU coupling and TFA deprotection (General Methods 8 and 9). LCMS (5-95_AB): $t_R$=0.773 min, [M+H]$^+$ 981.5.
Example 238: Synthesis of Compound 339
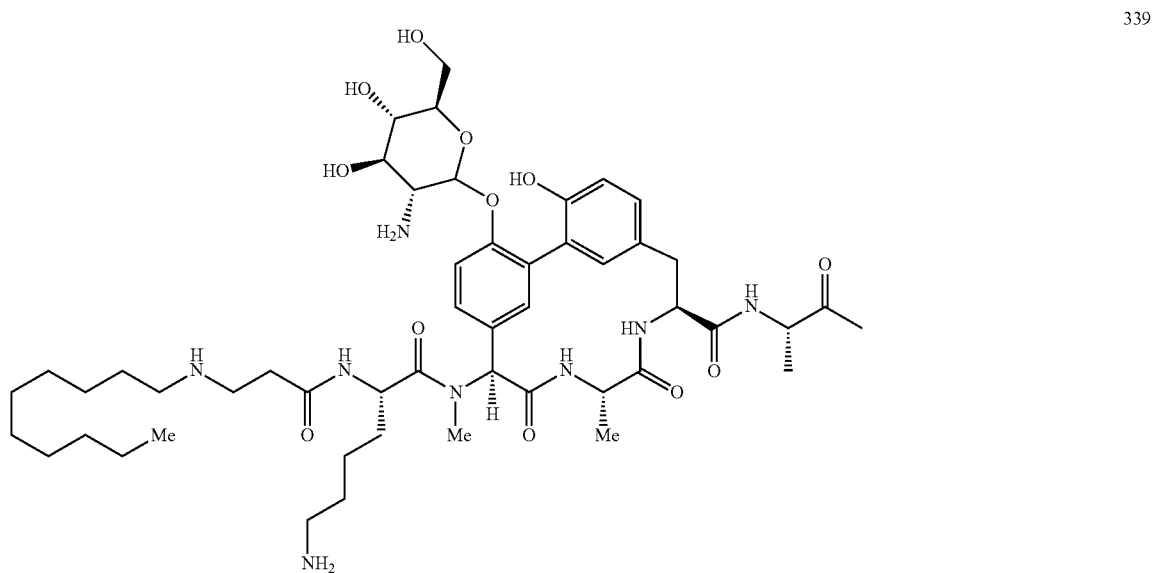

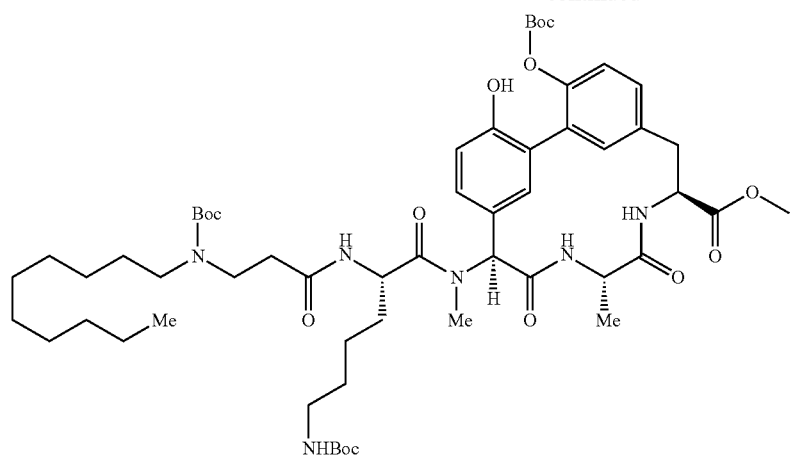
113B
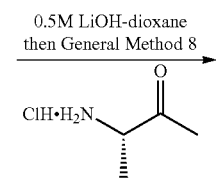
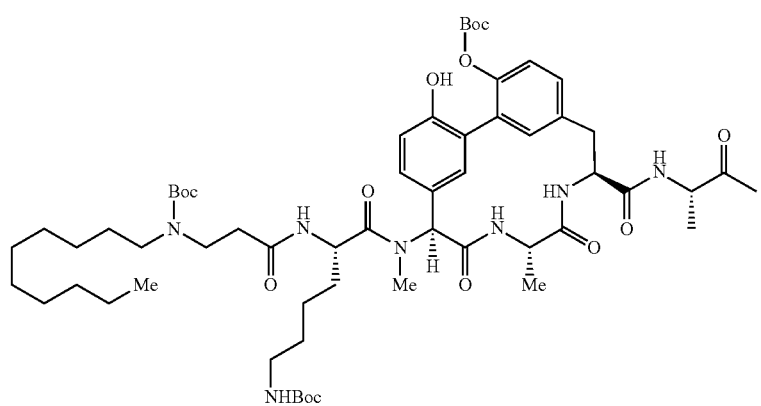
339A
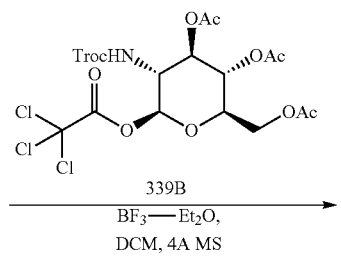
339B
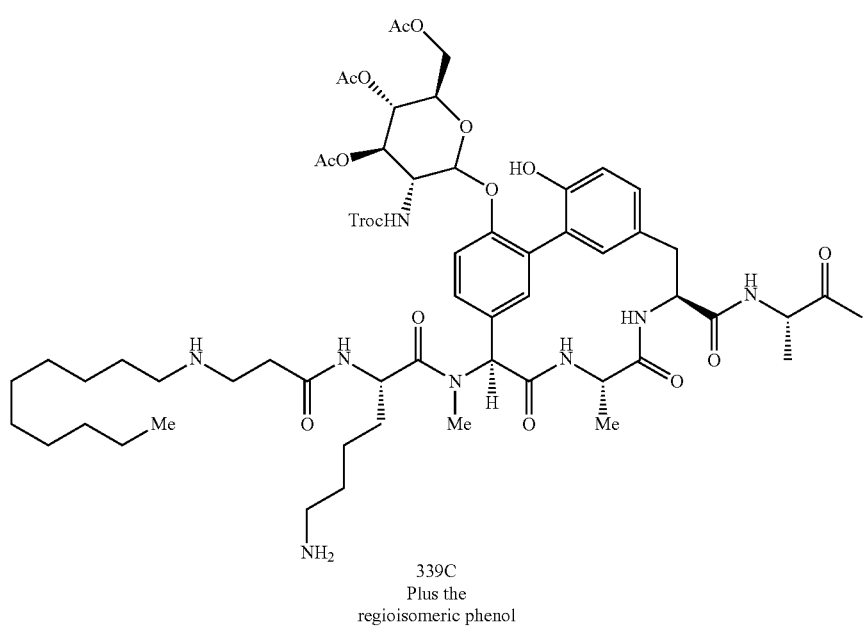
339C
Plus the regioisomeric phenol

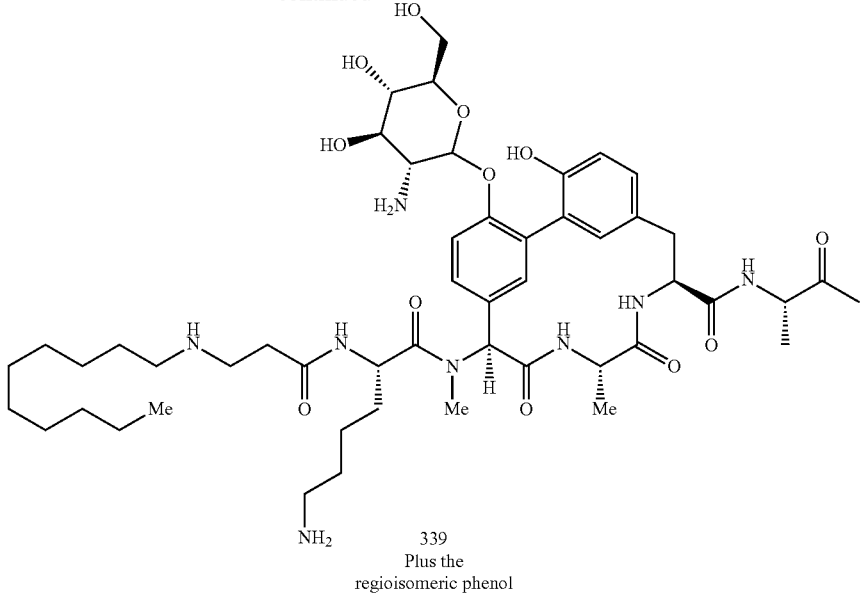

339
Plus the
regioisomeric phenol

Synthesis of Compound 339B

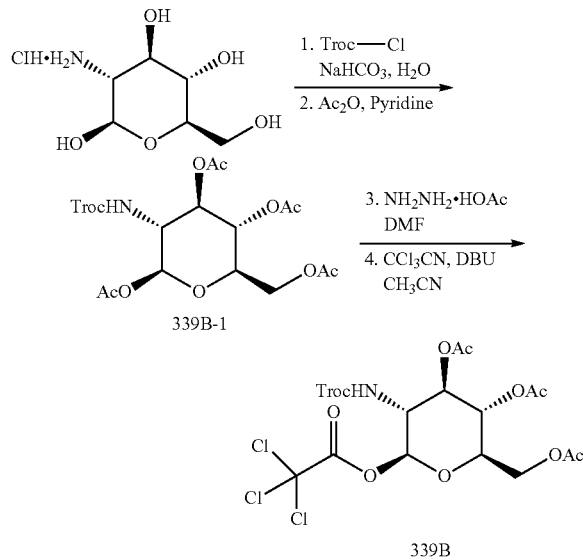

β-D-glucosamine (10.7 g, 50 mmol) and solid NaHCO$_3$ (12.6 g, 150 mmol) was taken in H$_2$O (100 mL) and stirred at rt for 30 min and then 2,2,2-trichloroethyl chloroformate (8.38 g, 60 mmol) was added slowly drop wise. The reaction mixture was stirred at rt for overnight and the resultant white precipitate was filtered and dried. MS (ESI) for (C$_9$H$_{14}$Cl$_3$NO$_7$): m/z 270.4 (M−83)). HPLC: t$_R$ 2.26 min (10% AcCN/H$_2$O-90% AcCN/H$_2$O (with 0.05% TFA), 3.0 min, 1.0 mL/min Kinetix C18, 4.8×50 mm). The resultant white solid (10.5 g, 30 mol) was dissolved in pyridine (30 mL) and then cooled to 0° C., followed by drop wise addition of acetic anhydride (28.4 mL, 60 mmol). The mixture was stirred at rt for overnight and quenched with EtOH (15 mL) 0° C. The mixture was stirred for another 6 h at rt and was concentrated. The resultant residue was diluted with Ethyl acetate (200 mL) and then washed with saturated NaHCO$_3$ solution, 10% HCl solution and with brine. Organic layer dried over Na$_2$SO$_4$, filtered and the solvent was removed under vacuum. The residue was purified by flash chromatography using EtOAc-hexanes to afford 8.2 g (54%) of Compound 339B-1 as a white solid. MS (ESI) for (C$_{17}$H$_{22}$Cl$_3$NO$_{11}$): m/z 344.3 (M−177). HPLC: t$_R$ 3.64 min (10% AcCN/H$_2$O-90% AcCN/H$_2$O (with 0.05% TFA), 3.0 min, 1.0 mL/min Kinetix C18, 4.8×50 mm).

To a solution of Compound 339B-1 (1.5 g, 3 mmol) in DMF (5 mL) was added hydrazine acetate (303 mg, 3.3 mmol) and the mixture was stirred at rt for overnight. The mixture was diluted with EtOAc (200 mL) and washed with saturated NaHCO$_3$ solution, 10% HCl solution and with brine. Organic layer dried over any Na$_2$SO$_4$, filtered and the solvent was removed under vacuum. The residue was purified by flash chromatography using EtOAc-hexanes to afford 870 mg (62%) of desired product as a white solid. MS (ESI) for (C15H$_{20}$Cl$_3$NO$_{10}$): m/z 502.3 (M+Na). HPLC: (two peaks with same mass; t$_R$ 3.24 min (30%) and 3.37 min (70%) (10% AcCN/H$_2$O-90% AcCN/H$_2$O (with 0.05% TFA), 3.0 min, 1.0 mL/min Kinetix C18, 4.8×50 mm). The resultant solid (700 mg, 1.4 mmol) was dissolved in DCM (3 mL) and cooled to 0° C. To this solution was added trichloroacetonitrile (2.8 mL, 28 mmol) followed by DBU (42 μL, 0.28 mmol) and stirring was continued for 2 h. The mixture was concentrated and the residue was purified by flash chromatography using EtOAc-hexanes to afford 764 mg (88%) of Compound 339B as white solid. MS (ESI) for (C$_{15}$H$_{20}$Cl$_3$NO$_{10}$): m/z 344.3 (M−277). HPLC: (two peaks with same mass; t$_R$ 3.21 min (30%) and 3.54 min (70%) (10% AcCN/H$_2$O-90% AcCN/H$_2$O (with 0.05% TFA), 3.0 min, 1.0 mL/min Kinetix C18, 4.8×50 mm). $^1$H NMR (400 MHz, CDCl$_3$)$^δ$ 8.80 (s, 1H), 6.42 (d, J=3.0 Hz, 1H), 5.35 (t, J=8.0 Hz, 1H), 5.25 (t, J=8.0 Hz, 1H), 5.18 (d, J=8.0 Hz, 1H), 4.71 (ABq, J=10.0, 3.0 Hz, 1H), 4.29-4.26 (m, 2H), 2.08 (s, 3H), 2.05 (s, 3H), 2.03 (s, 3H).

The synthesis of Compound 339: Compound 113B (106 mg, 0.01 mmol) was hydrolyzed to the corresponding acid by using dioxane (2.0 mL) and 0.5 M LiOH (600 μL, 0.03 mmol. MS (ESI) for ($C_{55}H_{84}N_6O_{14}$): m/z 1054.3 (M+2H). HPLC: $t_R$ 4.28 min (50% AcCN/$H_2O$-90% AcCN/$H_2O$ (with 0.05% TFA), 3.0 min, 1.0 mL/min Kinetix C18, 4.8×50 mm).

Compound 339A was prepared by using the acid (105 mg, 0.1 mmol) and (S)-3-aminobutan-2-one hydrochloride (19 mg, 0.15 mmol) following the General Method 8 in 75% (84 mg) yield. MS (ESI) for ($C_{59}H_{91}N_7O_{14}$): m/z 1123.4 (M+2H). HPLC: $t_R$ 4.36 min (50% AcCN/$H_2O$-90% AcCN/$H_2O$ (with 0.05% TFA), 3.0 min, 1.0 mL/min Kinetix C18, 4.8×50 mm).

To a mixture of Compound 339A (33 mg, 0.03 mmol), Compound 339B (93 mg, 0.15 mmol) and 4 Å MS (flame dried) in dry DCM (2.0 mL) was added $BF_3$-$Et_2O$ (38 μL, 0.3 mmol) dropwise at 0° C. Stirring was continued for an additional 1 h at the same temperature, and then the reaction was warmed up to rt and stirred for additional 1 h. The reaction mixture was diluted with DCM and filtered through celite and filtrate concentrated under reduced pressure to afford about 70% of Compound 339C as regioisomeric mixture (glycosidation on either one of the phenol resulting from the Boc deprotection during the reaction) along with unreacted starting material with complete Boc deprotection. MS (ESI): ($C_{59}H_{85}Cl_3N_8O_{17}$): m/z 1284.2 (M+2H); Unreacted starting material with Boc deprotection ($C_{44}H_{67}N_7O_8$): m/z 822.3 (M+H). HPLC: $t_R$ 1.83 min and 1.2 min (50% AcCN/$H_2O$-90% AcCN/$H_2O$ (with 0.05% TFA), 3.0 min, 1.0 mL/min Kinetix C18, 4.8×50 mm).

The resultant mixture of Compound 339C was dissolved in 1:1 MeOH—AcOH (2.0 mL) and cooled to 0° C., then Zn dust (50 mg, 20 eq) was added and the reaction mixture was stirred at rt for 3 h. The mixture was filtered through celite bed and thoroughly washed the celite bed with MeOH. The filtrate was concentrated under reduced pressure. MS (ESI): ($C_{56}H_{84}N_8O_{15}$): m/z 1109.3 (M+H); and ($C44H_{67}N_7O_8$): m/z 822.3 (M+H). HPLC: $t_R$ 3.01 min (10% AcCN/$H_2O$-90% AcCN/$H_2O$ (with 0.05% TFA), 3.0 min, 1.0 mL/min Kinetix C18, 4.8×50 mm). The residue was dissolved in MeOH (2.0 mL) and $K_2CO_3$ (21 mg, 5 eq) was added. The mixture was stirred at rt for overnight. The reaction mixture was acidified with 1:1 AcOH—$H_2O$ and concentrated under reduced pressure. The residue was purified by preparative HPLC (10% AcCN/$H_2O$-60% AcCN/$H_2O$ (with 0.05% $HCO_2H$) to afford 6.5 mg (22%) of Compound 339 as a mixture of regioisomers. MS (ESI): ($C_{50}H_{78}N_8O_{12}$): m/z 983.3 (M+H); HPLC: $t_R$ 2.84 min (10% AcCN/$H_2O$-90% AcCN/$H_2O$ (with 0.05% TFA), 3.0 min, 1.0 mL/min Kinetix C18, 4.8×50 mm).

Example 239: Synthesis of Compound 340

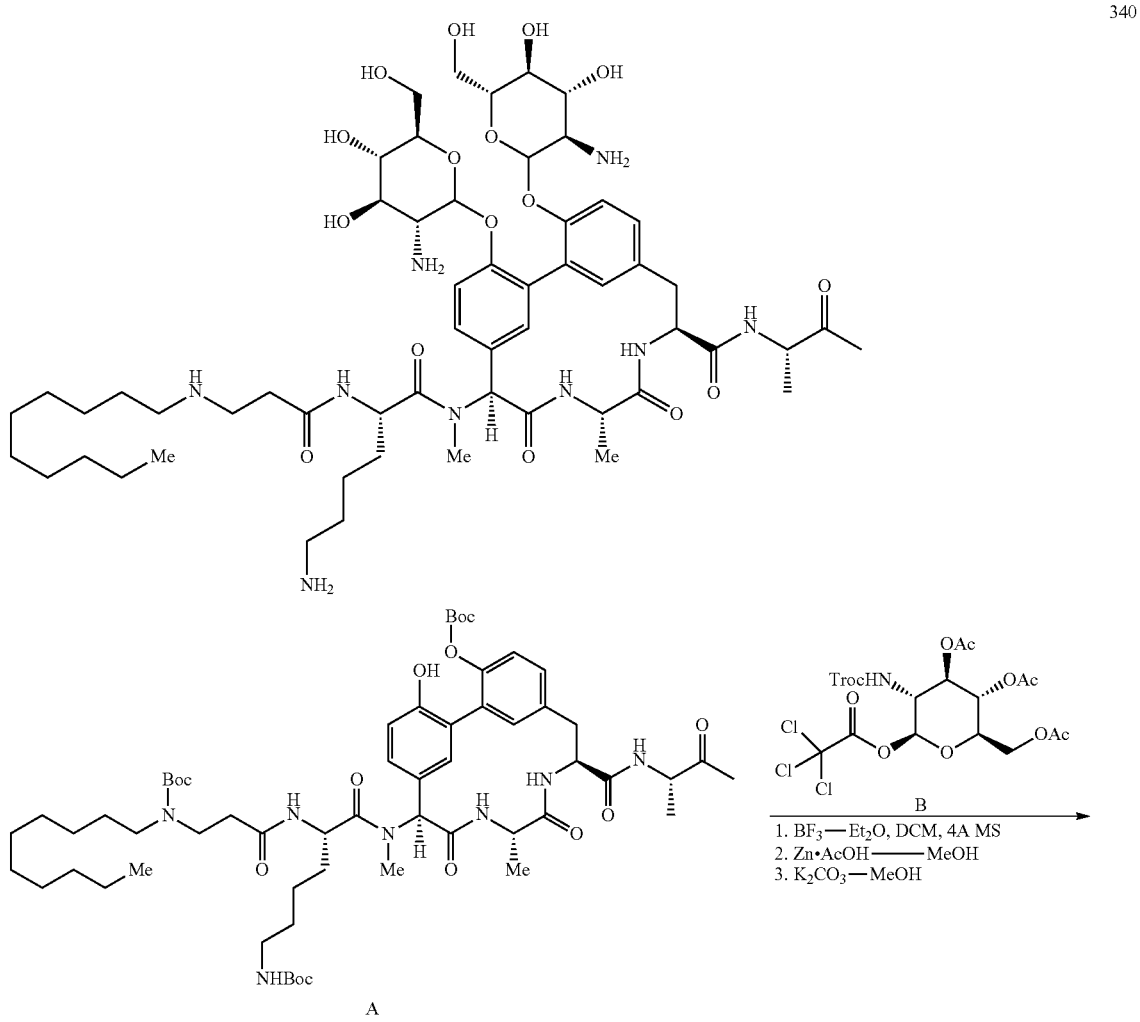

-continued

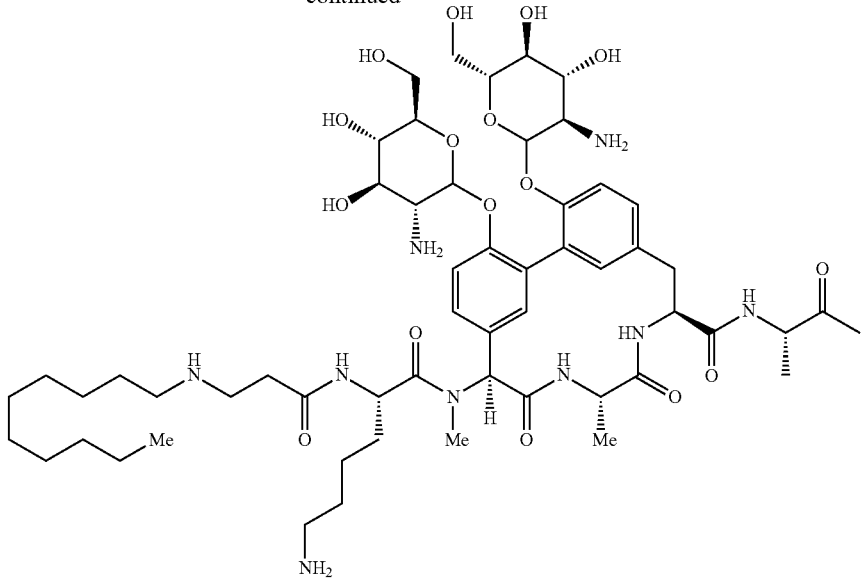

B

To a mixture of Compound 339A (80 mg, 0.07 mmol), Compound 339B (435 mg, 0.7 mmol) and 4 Å MS (flame dried) in dry DCM (2.0 mL) was added BF$_3$-Et$_2$O (88 µL, 0.7 mmol) dropwise at 0° C. Stirring was continued for an additional 8 h at the same temperature, and then the reaction was left at 0° C. (in the refrigerator) for 3 days. The reaction mixture solution was diluted with DCM and filtered through celite and filtrate concentrated under reduced pressure to afford about 70% of the glycosyl adduct as mixture of mono and bis glycosylation along with unreacted starting material with complete Boc deprotection. MS (ESI): For monoglycoside (C$_{59}$H$_{85}$Cl$_3$N$_8$O$_{17}$): m/z 1284.2 (M+2H); For bisglycoside (C$_{74}$H$_{103}$Cl$_6$N$_9$O$_{26}$): m/z 1745.4 (M+2H); Un reacted starting material with Boc deprotection (C$_{44}$H$_{67}$N$_7$O$_8$): m/z 822.3 (M+H). HPLC: t$_R$ 3.0-3.3 min (broad) (10% AcCN/H$_2$O-90% AcCN/H$_2$O (with 0.05% TFA), 3.0 min, 1.0 mL/min Kinetix C18, 4.8×50 mm). The mixture was used as it is for the removal of protecting groups by following the procedures described for the Compound 339 using Zn—AcOH and K$_2$CO$_3$-MeOH and isolated Compound 340 by preparative HPLC (10% AcCN/H$_2$O-60% AcCN/H$_2$O (with 0.05% HCO$_2$H) as formate salt. MS (ESI): (C$_{56}$H$_{89}$N$_9$O$_{16}$): m/z 1144.7 (M+H); HPLC: t$_R$ 2.65 min (10% AcCN/H$_2$O-90% AcCN/H$_2$O (with 0.05% TFA), 3.0 min, 1.0 mL/min Kinetix C18, 4.8×50 mm).

Biological Assays

Example 240: Determination of Minimum Inhibitory Concentration

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, Pa.: Clinical and Laboratory Standards; 2009). Antibacterial activity was measured against three strains of bacteria: a Methicillin Resistant *Staphylococcus aureus* strain USA300 (NRS384); a MRSA COL (NRS100), another Methicillin Resistant *Staphylococcus aureus* strain; and a strain of *Escherichia coli* MC4100 harboring the IMP4213, which results in increased outer-membrane permeability (B Martin and Silhavy T. Imp/OstA is required for cell envelope biogenesis in *Escherichia coli*. (2002) Molecular Microbiology, 45(5), 1289-1302). Cells were inoculated onto plates of Trypticase Soy Agar or Luria Agar respectively and grown at 35° C. for 20 hours. Inocula suspensions were prepared by scraping cells into 1 ml of testing media (cation adjusted Mueller Hinton Broth supplemented with 0.002% v/v Tween-80) and diluting to a final OD$_{600\ nm}$ of 0.01.

Test compounds were prepared in DMSO at a concentration of 10 mg/ml. These compound stocks were diluted into testing media at a concentration of 64 µg/ml and serial 2-fold dilutions were made in the same media, in 96-well U bottom microtiter dishes, for a total of 10 compound concentrations (Table 1). In modified protocols (Table 2), compound stocks were diluted into testing media at a concentration of 4 µg/mL and serial 2-fold dilutions were made in the same media, in 96-well U bottom microtiter dishes, for a total of 10 compound concentrations. Inocula suspensions were added to the 2-fold serial dilutions of test compounds to a final density of OD OD$_{600\ nm}$ of 0.0005 and incubated at 35° C. for 22 hours. After incubation the plates were examined visually and the lowest concentration of test compound that completely prevented bacterial growth were recorded as the MICs. The results from the protocol starting from a concentration of 64 g/mL are listed in Table 1 and the results from the modified protocol are shown in Table 2.

TABLE 1

| Compound | MIC (µg/mL) E. coli | MIC (µg/mL) S. aureus | MIC (µg/mL) (COL) | Compound | MIC (µg/mL) E. coli | MIC (µg/mL) S. aureus | MIC (µg/mL) (COL) |
| --- | --- | --- | --- | --- | --- | --- | --- |
| 101 | >64 | 64 | nt | 102 | >64 | 64 | nt |
| 103 | 23 | 45 | nt | 104 | 2 | 2.8 | 2 |
| 105 | 8 | 4 | nt | 106 | 11 | 5.7 | nt |
| 107 | >64 | 64 | nt | 108 | 8 | 4 | nt |
| 109 | 64 | 4 | 1 | 110 | 64 | 29 | 8 |
| 111 | >64 | 23 | 4 | 112 | 64 | 2.8 | 0.5 |
| 113 | 25 | 9.5 | 2 | 114 | 32 | >64 | 1 |
| 115 | 19 | 0.63 | 0.13 | 116 | 13 | 0.35 | 0.063 |
| 117 | 1.6 | 0.71 | 0.22 | 118 | 2 | 1 | 0.63 |
| 119 | 5.3 | 1 | 0.5 | 120 | 64 | 51 | 13 |
| 121 | 32 | 8 | 3 | 122 | 32 | 1.4 | nt |
| 123 | 32 | 3.2 | nt | 124 | 16 | 1 | 0.5 |
| 125 | nt | 32 | 8 | 126 | >64 | 32 | nt |
| 127 | 64 | >64 | nt | 128 | 64 | 45 | 16 |
| 129 | >64 | 16 | 4 | 130 | >64 | 16 | 8 |
| 131 | >64 | >64 | nt | 132 | >64 | 32 | 8 |
| 133 | 2 | 2.5 | 1.5 | 134 | 45 | 2.8 | 0.75 |
| 135 | 64 | >64 | 32 | 136 | 16 | 8 | 2 |
| 137 | 32 | 32 | 8 | 138 | 64 | 32 | 17 |
| 139 | 8 | 11 | 4 | 140 | 8 | 23 | 8 |
| 141 | 32 | 8 | 4 | 142 | 16 | 64 | 16 |
| 143 | 51 | 6.3 | nt | 144 | 32 | 8 | 2 |
| 145 | >64 | >64 | 64 | 146 | nt | 16 | 8 |
| 147 | >64 | >64 | >64 | 148 | nt | 64 | 32 |
| 149 | 64 | >64 | 64 | 150 | 8 | >64 | nt |
| 151 | 32 | >64 | nt | 152 | 16 | 10 | 4 |
| 153 | nt | 130 | nt | 154 | 64 | 64 | nt |
| 155 | 64 | 2.8 | 1.3 | 156 | 51 | >64 | nt |
| 157 | 45 | >64 | nt | 158 | 64 | 23 | 8 |
| 159 | 32 | 23 | 8 | 160 | 64 | >64 | >64 |
| 161 | 64 | 64 | 32 | 162 | 32 | 8 | 2 |
| 163 | 16 | 0.13 | 0.11 | 164 | 8 | 32 | nt |
| 165 | 11 | 45 | nt | 166 | >64 | 32 | 8 |
| 167 | >64 | 16 | 4 | 168 | 32 | 5.7 | nt |
| 169 | 64 | 45 | nt | 170 | 64 | 45 | nt |
| 171 | 64 | 20 | nt | 172 | 64 | 16 | nt |
| 173 | 32 | 64 | nt | 174 | 64 | 9.5 | nt |
| 175 | 32 | >64 | 32 | 176 | 64 | 64 | nt |
| 177 | 64 | 16 | 4 | 178 | nt | 32 | 16 |
| 179 | 64 | 32 | 16 | 180 | 64 | 64 | nt |
| 181 | 64 | 23 | nt | 182 | 64 | 10 | 2 |
| 183 | 32 | 8 | 2.4 | 184 | nt | 2 | nt |
| 185 | 64 | 45 | nt | 186 | >64 | 45 | 12 |
| 187 | 23 | 3.7 | 0.5 | 188 | 11 | 16 | 4 |
| 189 | 32 | 5.7 | 2 | 190 | 32 | 1.7 | 0.25 |
| 191 | >64 | 32 | 8 | 192 | 64 | 11 | 2 |
| 193 | 8 | 0.5 | 0.13 | 194 | 8 | 8 | 4 |
| 195 | 2 | 2.8 | 0.38 | 196 | >64 | 4 | 1 |
| 197 | 32 | 20 | 3.9 | 198 | 16 | 13 | 2 |
| 199 | 64 | 10 | 2 | 200 | 64 | 2 | 0.5 |
| 201 | 8 | 0.35 | 0.063 | 202 | 8 | 2.8 | 0.5 |
| 203 | nt | 23 | 8 | 204 | 8 | 11 | 1 |
| 205 | 32 | 32 | 6 | 206 | 4 | 4 | 0.19 |
| 207 | 32 | 32 | 6 | 208 | 16 | 23 | 6 |
| 209 | 4 | 0.5 | 0.13 | 210 | 32 | 32 | 4 |
| 211 | 2 | 11 | 2 | 212 | 5.7 | 2.5 | 0.5 |
| 213 | 4 | 16 | 2 | 214 | 64 | 2.8 | 0.75 |
| 215 | >64 | 0.5 | 0.25 | 216 | 64 | 0.13 | 0.063 |
| 217 | >64 | 2 | 0.75 | 218 | >64 | 0.35 | 0.13 |
| 219 | >64 | 0.35 | 0.13 | 220 | 16 | 2 | 0.33 |
| 221 | 45 | 0.5 | 0.13 | 222 | >64 | 16 | 3 |
| 223 | 32 | 0.71 | 2 | 224 | 64 | 16 | 0.13 |
| 225 | >64 | 23 | 6 | 226 | 4 | 4 | 0.25 |
| 227 | >64 | 12 | 2 | 228 | 15 | 5.3 | 2 |
| 229 | 24 | 4 | 1 | 230 | >64 | 64 | 8 |
| 231 | 8 | 6 | 1 | 232 | 8 | 4 | 1 |
| 233 | 32 | 24 | 4 | 234 | 64 | 64 | 8 |
| 235 | 32 | 4 | 2 | 236 | >64 | 48 | 8 |
| 237 | 8 | 12 | 4 | 238 | 64 | 32 | 8 |
| 239 | >4 | >4 | 4 | 240 | 48 | 4 | 2 |
| 241 | 16 | 4 | 1.5 | 248 | >64 | 21 | 4 |
| 249 | 48 | 32 | 16 | 250 | 64 | 64 | 11 |
| 251 | >64 | 64 | 16 | 255 | >64 | 12 | 3 |
| 270 | 8 | 0.25 | 0.063 | 277 | 2 | 0.75 | 0.25 |
| 289 | 0.5 | 2 | 0.5 | 290 | 32 | 64 | 32 |
| 291 | 8 | 8 | 4 | 292 | 0.063 | nt | nt |

TABLE 1-continued

| Compound | MIC (µg/mL) E. coli | MIC (µg/mL) S. aureus | MIC (µg/mL) (COL) | Compound | MIC (µg/mL) E. coli | MIC (µg/mL) S. aureus | MIC (µg/mL) (COL) |
|---|---|---|---|---|---|---|---|
| 293 | 0.063 | 0.063 | 0.063 | 294 | 0.063 | 0.15 | 0.063 |
| 295 | 0.063 | 0.19 | 0.063 | 296 | 0.063 | 0.063 | 0.063 |
| 297 | 0.063 | 0.38 | 0.063 | 310 | 0.19 | 0.5 | 0.094 |
| 311 | 0.19 | 1.5 | 0.13 | 312 | 3 | 24 | 3 |
| 313 | 1 | 2 | 0.38 | 314 | 0.094 | 0.063 | 0.012 |
| 315 | 1 | 1 | 0.5 | 316 | 0.094 | 0.13 | 0.031 |
| 317 | 0.13 | 0.13 | 0.063 | 318 | 0.063 | nt | nt |
| 319 | 0.75 | 2 | 1 | 320 | 4 | 6 | 2 |
| 321 | 0.063 | 0.094 | 0.063 | 322 | 0.13 | 0.13 | 0.063 |
| 331 | 8 | 16 | 2 | 332 | 64 | 64 | 8 |
| 333 | 32 | 64 | 16 | | | | | nt = not tested

TABLE 2

| Compound | MIC (µg/mL) E. coli | MIC (µg/mL) S. aureus | MIC (µg/mL) (COL) | Compound | MIC (µg/mL) E. coli | MIC (µg/mL) S. aureus | MIC (µg/mL) (COL) |
|---|---|---|---|---|---|---|---|
| 242 | >4 | >4 | 4 | 243 | >4 | >4 | >4 |
| 244 | >4 | >4 | 4 | 245 | >4 | 4 | 2 |
| 246 | >4 | 4 | 3 | 247 | >4 | 2 | 1 |
| 252 | >4 | >4 | >4 | 253 | >4 | >4 | 4 |
| 254 | >4 | 4 | 2 | 256 | >4 | 0.063 | 0.016 |
| 257 | >4 | 0.5 | 0.094 | 258 | 4 | 0.047 | 0.012 |
| 259 | >4 | 0.75 | 0.38 | 260 | >4 | 0.047 | 0.016 |
| 261 | >4 | 1.5 | 0.38 | 262 | >4 | >4 | 2 |
| 263 | 1 | 0.25 | 0.13 | 264 | >4 | 2 | 0.75 |
| 265 | 4 | 1 | 0.25 | 266 | >4 | 4 | 1.5 |
| 267 | >4 | 1.5 | 0.5 | 268 | 2.5 | 2.1 | 1 |
| 269 | >4 | 0.38 | 0.13 | 271 | 4 | 0.047 | 0.016 |
| 272 | 0.25 | 0.13 | 0.063 | 273 | 4 | 0.75 | 0.38 |
| 274 | 4 | >4 | 1.5 | 275 | 2 | 1 | 0.13 |
| 276 | 4 | 4 | 1.5 | 278 | 0.031 | 0.25 | 0.094 |
| 279 | 0.25 | 2 | 0.5 | 280 | 0.25 | 0.75 | 0.38 |
| 281 | 0.25 | 3 | 1 | 282 | 1 | >4 | 2 |
| 283 | 1 | 4 | 1.5 | 284 | >4 | >4 | >4 |
| 285 | 0.25 | 2 | 0.5 | 286 | 4 | 4 | 1.5 |
| 287 | 0.047 | 0.25 | 0.094 | 288 | 0.13 | 0.5 | 0.25 |
| 298 | 0.031 | 0.38 | 0.063 | 299 | 0.016 | 0.19 | 0.031 |
| 300 | 0.023 | 0.5 | 0.13 | 301 | 0.012 | 0.38 | 0.094 |
| 302 | 0.0088 | 0.11 | 0.039 | 303 | 0.023 | 0.13 | 0.023 |
| 304 | 0.047 | 0.5 | 0.13 | 305 | 0.13 | 1 | 0.38 |
| 306 | 0.25 | 3 | 1 | 307 | 1 | 4 | 3 |
| 308 | 0.094 | 1 | 0.38 | 309 | 0.031 | 0.5 | 0.25 |
| 323 | 0.063 | 0.13 | 0.031 | 324 | 0.13 | 0.25 | 0.13 |
| 325 | 0.13 | 0.13 | 0.023 | 326 | 0.19 | 0.25 | 0.13 |
| 327 | 0.5 | 0.5 | 0.13 | 328 | 0.25 | 2 | 0.5 |
| 329 | 0.38 | >4 | 2 | 330 | >4 | 3 | 1 |
| 334 | 0.13 | 1 | 0.38 | 335 | 0.13 | 0.19 | 0.063 |
| 336 | 0.25 | 0.5 | 0.13 | 337 | 0.047 | 2 | 0.75 |
| 338 | 0.63 | 3 | 2.5 | 339 | >4 | 2 | 1 |
| 340 | >4 | >4 | 2 | | | | |

Example 241: Checkerboard Synergy Assays

2D MIC assay or "checkerboard assays" are the most common method used to quantify synergistic or antagonistic interactions between two antibiotics with respect to potency (Hallander, H. O., et al., Antimicrob. Agents Chemother. 1982 22:743-752). In this assay in each axis of a 96-well plate contains a 2-fold dilution of a given agent, such that each well contains a unique combination of the agents being tested.

To create a checkerboard dilution scheme, imipenem was diluted in Mueller Hinton II Broth+0.002% Tween-80 to twice the final desired concentration, and six 2-fold serial dilutions were performed in the same media yielding seven imipenem concentrations. Dilutions of Compound 155 were prepared similarly except that ten dilutions were performed for a total of eleven concentrations. For each concentration of imipenem, 50 uL aliquots were transferred to columns 1-12 of a given row of a 96-well clear polypropylene assay plate. For each concentration of Compound 155, 50 uL were transferred to rows A-H of a given column of the same plate. The resulting plate contained imipenem serially diluted on the Y-axis and Compound 155 serially diluted along the X-axis.

MRSA strain USA300 was grown overnight at 35° C. on Mueller Hinton Agar plates, and colonies were suspended in Mueller Hinton II Broth+0.002% Tween-80 to a final density of $1*10^7$ cfu/ml. To each well of the above plate, 5 ul of this suspension were added, resulting in an initial density of $5*10^5$ cfu/ml. The plate was incubated at 35° C. for 22 hours after which growth was determined via visual inspection. For each sub-MIC concentration of imipenem, the concentration of Compound 155 required to prevent visible growth was recorded, and the fractional inhibitor concentration (FIC) of each agent was calculated by dividing the concentration of each agent by MIC of the agent alone. FICs are plotted in FIG. 1 generating an isobologram, and synergy is defined as any point where the sum of the FICs is ≤0.5. Examination of FIG. 1 reveals significant synergy between Compound 155 and imipenem as evidenced by many points where the sum of the FICs is <0.5.

Example 242: Time-Kill Assays

Figure 2:
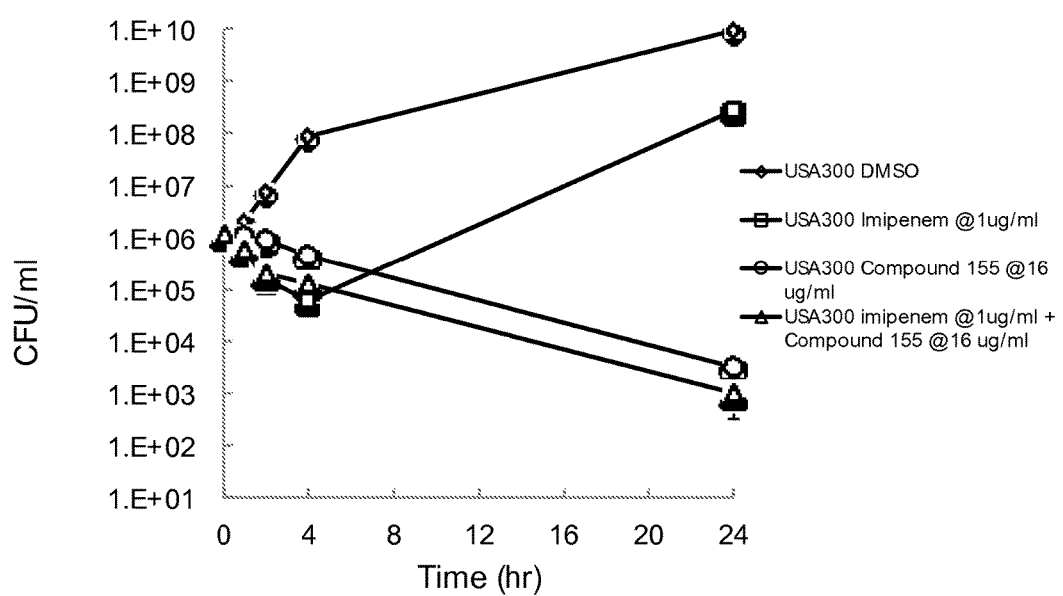
FIG. 2 shows the results for Compound 155 in the time-kill assay.

Time-kill experiments enable quantification of rate of bacterial growth or death in the presence of a fixed concentration of one or more antibiotics (Arhin. F., et. al., Current Protocols in Microbiology 17.1.1-17.1.22, February 2010). Time-kill experiments were performed in 96-well incubation plates using Mueller Hinton II Broth+0.002% Tween-80 as the growth media. Individual wells contained imipenem alone, Compound 155 alone, or a combination of both agents at various concentrations. MRSA strain USA300 was grown overnight at 35° C. on Mueller Hinton Agar plates, and colonies were suspended in Mueller Hinton II Broth+ 0.002% Tween-80 to a final density of $2*10^8$ cfu/mL. To each well of the incubation plates, 5 uL of this suspension were added, resulting in an initial density of $1*10^7$ cfu/mL. Plates were incubated at 35° C., and at various time points 30 ul samples were removed, mixed 1:1 with 25 mg/ml activated carbon, serially diluted in sterile phosphate buffered saline supplemented with 0.05% Tween 20, and spotted onto Mueller Hinton Agar plates to enable cfu quantification. Colonies were counted and the cfu/ml at each time point calculated by based on the dilution factor and volume spotted. FIG. 2 shows the results from a representative time-kill assay. As seen from these results, the combination of 1 ug/mL imipenem plus 16 ug/mL Compound 155 is synergistic by time-kill assay, resulting in a faster and more extensive reduction of viable cells than either agent alone.

Example 243: Synergy of SPase Inhibitors with Partner β-Lactam Antibiotics

Many compounds in the Examples, including Compound 155, synergize with a wide range of beta-lactam antibiotics as quantified by SIC determination, where the SIC is measured and defined in a manner identical to the MIC, with the exception that the testing media contains a partner beta-lactam at a concentration equal to ¼× its MIC against the bacterial strain being tested. When the SIC of a compound is less than or equal to ¼ its MIC, the sum of the FICs for the compound and the partner beta-lactams is ≤0.5 indicating synergy (Hallander, H. O., et al., Antimicrob. Agents Chemother. 1982 22:743-752).

TABLE 3

| | MRSA strain USA$_{300}$ | |
|---|---|---|
| | Compound 155 MIC (µg/ml) | Fold reduction in Compound 155 MIC |
| None | 4 | NA |

| Partner beta-lactam | Compound 155 SIC (µg/ml) | Fold reduction in Compound 155 MIC |
|---|---|---|
| Azlocillin | 1 | 4 |
| Amoxicillin/Clav | 0.25 | 16 |

TABLE 3-continued

| Ampicillin | 1 | 4 |
|---|---|---|
| Doripenem | 0.125 | 32 |
| Meropenem | 0.25 | 16 |
| Biapenem | 0.0625 | 64 |
| Cefamandole | 0.25 | 16 |
| Imipenem | 0.125 | 32 |
| Mezlocillin | 0.5 | 8 |
| Cefmetazole | 0.5 | 8 |
| Cefprozil | 0.25 | 16 |
| Piperacillin/tazobactam | 0.5 | 8 |
| Carbenicillin | 0.5 | 8 |
| Cefaclor | 0.25 | 16 |
| Cephalothin | 0.0625 | 64 |
| Ertapenem | 0.25 | 16 |
| Cefazolin | 0.125 | 32 |
| Cefepime | 0.125 | 32 |
| Cefonicid | 0.25 | 16 |
| Cefoxitin | 0.25 | 16 |
| Ceftazidime | 0.5 | 8 |
| Oxacillin | 0.125 | 32 |
| Cefdinir | ≤0.0156 | >256 |
| Cefixime | 0.25 | 16 |
| Cefotaxime | 0.125 | 32 |
| Cefotetan | 0.5 | 8 |
| Cefpodoxime | 0.125 | 32 |
| Ceftizoxime | 0.25 | 16 |
| Ceftriaxone | 0.0625 | 64 |
| Faropenem | ≤0.0156 | >256 |
| Mecillinam | 1 | 4 |
| Methicillin | 0.25 | 16 |
| Moxalactam | 0.125 | 32 |
| Ticarcillin | 0.125 | 32 |

The data in Table 3 demonstrate that Example compounds synergize with Azlocillin, Amoxicillin, Ampicillin, Doripenem, Meropenem, Biapenem, Cefamandole, Imipenem, Mezlocillin, Cefmetazole, Cefprozil, Piperacillin/tazobactam, Carbenicillin, Cefaclor, Cephalothin, Ertapenem, Cefazolin, Cefepime, Cefonicid, Cefoxitin, Ceftazidime, Oxacillin, Cefdinir, Cefixime, Cefotaxime, Cefotetan, Cefpodoxime, Ceftizoxime, Ceftriaxone, Faropenem, Mecillinam, Methicillin, Moxalactam, and Ticarcillin.

Example 244: SpsB Inhibitor/Imipenem Intraperitoneal Delivery in Neutropenic Thigh Infection Model CD-1 mice are induced neutropenia (100 cells/mm$^3$) by injecting 150 mg/kg and 100 mg/kg cyclophosphamide at day −5 and day −2 respectively. At day 0, mice are infected in the thigh muscle with MRSA strain COL 4×10$^5$ CFU/50 µL. At 2 hours post infection, the SpsB inhibitor at 40 mg/kg is delivered intraperitoneally. At the same time, 10 mg/kg of imipenem/cilastatin is administered subcutaneously into the same mouse. At 8, 12, or 24 hours post infection, bacterial burden in the thigh muscle is determined by plating the tissue homogenate in series dilutions on blood agar plates. Other beta-lactam antibiotics may be used in place of Imipenem in this model.

Example 245: SpsB Inhibitor/Imipenem Intravenous Infusion in Neutropenic Thigh Infection Model Jugular vein cannulated CD-1 mice were subjected to induced neutropenia (<100 cells/mm$^3$) by injecting 150 mg/kg and 100 mg/kg cyclophosphamide at day −5 and day −2 respectively. At day −1, saline was infused at 20 L/hour for 12 hours using Harvard Apparatus PHD 2000 Infusion pumps. At day 0, mice were infected in the thigh muscle with MRSA strain COL 4×10$^5$ CFU/50 μL. Four test groups and one vehicle group began dosing at 1 hour post infection:

Group 1 was the vehicle control (3% HP-beta-cyclodextrin in PBS)

Group 2 was the imipenem (Imp) group dosed at a concentration of 0.21 mg/mL solution, infused at 80 μL/hour for 23 hours, with a target steady-state concentration (Css) of 0.3 μg/mL.

Group 3 was the SpsB inhibitor Compound 115 group dosed at a concentration of 2.14 mg/mL solution, infused at 80 μL/hour for 23 hours to achieve a steady state concentration (Css) of 6.4 ug/mL.

Group 4 was the SpsB inhibitor Compound 115 group dosed at 0.67 mg/mL solution (Css 2 ug/mL) co-dosed with imipenem at a concentration of 0.21 mg/mL (Css of 0.3 μg/mL) infused at 80 μL/hour for 23 hours.

Group 5 was the SpsB inhibitor Compound 115 group dosed at 2.14 mg/mL solution (Css 6.4 ug/mL) co-dosed with imipenem at a concentration of 0.21 mg/mL (Css of 0.3 μg/mL) infused at 80 μL/hour for 23 hours.

Figure 3:
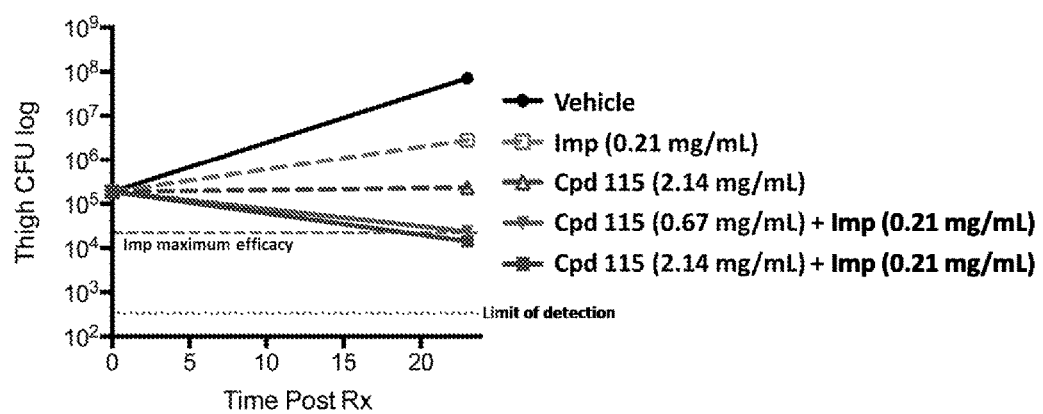
FIG. 3 shows the efficacy of Compound 115, imipenem, and a combination of Compound 115 and imipenem in the neutropenic thigh infection model.

At 24 hours post infection, bacterial burden in the thigh muscle was determined by plating the tissue homogenate in series dilutions on blood agar plates. As shown in FIG. 3, Compound 115 in combination with imipenem exhibits a greater reduction in bacterial burden than is observed when either imipenem or Compound 115 is dosed as a single agent, demonstrating its synergistic activity. Other beta-lactam antibiotics may be used in place of Imipenem in this model.

Example 246: Clinical Trial of the Safety and Efficacy of Compounds of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) in Patients with C. Difficile-Associated Diarrhea Purpose:

This study aims to determine the safety and efficacy of compounds presented herein for the treatment of symptoms of C. difficile-associated diarrhea and lowering the risk of repeat episodes of diarrhea. The compounds are evaluated in comparison to current standard antibiotic treatment, so all patients will receive active medication. All study-related care is provided including doctor visits, physical exams, laboratory tests and study medication. Total length of participation is approximately 10 weeks.

Patients:

Eligible subjects will be men and women 18 years and older.

Criteria:

Inclusion Criteria:

Be at least 18 years old;

Have active mild to moderate C. difficile-Associated Diarrhea (CDAD);

Be able to tolerate oral medication;

Not be pregnant or breast-feeding; and

Sign and date an informed consent form.

Study Design:

This is a randomized, double-blind, active control study of the efficacy, safety, and tolerability of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) in patients with C. difficile-associated diarrhea.

Example 247: Clinical Trial Comparing a Compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) with Vancomycin for the Treatment of MRSA Osteomyleitis Purpose:

This study aims to determine the efficacy of compounds presented herein as compared to vancomycin for the treatment of methicillin-resistant *Staphylococcus aureus* (MRSA) osteomyelitis.

Patients:

Eligible subjects will be men and women 18 years and older.

Criteria:

Inclusion Criteria:

Culture-proven MRSA, obtained in operating room or sterile biopsy procedure from bone site. The infection and sampling site is either within the bone or a deep soft-tissue site that is contiguous with bone; OR radiographic abnormality consistent with osteomyelitis in conjunction with a positive blood culture for MRSA;

Surgical debridement of infection site, as needed;

Subject is capable of providing written informed consent; and

Subject capable of receiving outpatient parenteral therapy for 12 weeks.

Exclusion Criteria:

Hypersensitivity to a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or vancomycin;

*S. aureus* resistant to a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) or vancomycin;

Osteomyelitis that develops directly from a chronic, open wound;

Polymicrobial culture (the only exception is if coagulase-negative *staphylococcus* is present in the culture and the clinical assessment is that it is a contaminant);

Subject has a positive pregnancy test at study enrollment;

Baseline renal or hepatic insufficiency that would preclude administration of study drugs;

Active injection drug use without safe conditions to administer intravenous antibiotics for 3 months; and Anticipated use of antibiotics for greater than 14 days for an infection other than osteomyelitis.

Study Design:

This is a randomized, open-label, active control, efficacy trial comparing vancomycin with a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) for the treatment of MRSA Osteomyelitis.

Example 248: Clinical Trial Evaluating a Compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) in Selected Serious Infections Caused by Vancomycin-Resistant *Enterococcus* (VRE)

Purpose:

This study aims to determine the safety and efficacy of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) in the treatment of selected serious infections caused by VRE.

Patients:

Eligible subjects will be men and women 18 years and older.

Criteria:

Inclusion Criteria:

Isolation of one of the following multi-antibiotic resistant bacteria: vancomycin-resistant *Enterococcus faecium*, vancomycin-resistant *Enterococcus faecalis* alone or as part of a polymicrobial infection; and Have a confirmed diagnosis of a serious infection (eg, bacteremia [unless due to an excluded infection], complicated intra-abdominal infection, complicated skin and skin structure infection, or pneumonia) requiring administration of intravenous (IV) antibiotic therapy.

Exclusion Criteria:

Subjects with any concomitant condition or taking any concomitant medication that, in the opinion of the investigator, could preclude an evaluation of a response or make it unlikely that the contemplated course of therapy or follow-up assessment will be completed or that will substantially increase the risk associated with the subject's participation in this study.

Anticipated length of antibiotic therapy less than 7 days

Study Design:

This is a randomized, double-blind, safety and efficacy study of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) in the treatment of selected serious infections caused by VRE.

Pharmaceutical Compositions

I. Parenteral Composition

To prepare a parenteral pharmaceutical composition suitable for administration by injection, 100 mg of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) | 1 g |
| Anhydrous Sodium Carbonate | 0.1 g |
| Ethanol (200 proof), USP | 10 mL |
| Purified Water, USP | 90 mL |
| Aspartame | 0.003 g |

Topical Gel Composition

To prepare a pharmaceutical topical gel composition, 100 mg of a compound of Formula (I), (Ia), (Ib), (Ic), (Id), (II), (IIa), (IIb), (IIc), (IId), (III), (IV), (IVa), (IVb), (IVc), (IVd), (V), (Va), (Vb), (VI), (VIa), (VIb), (VII), (VIIa), or (VIIb) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A compound of Formula (I):

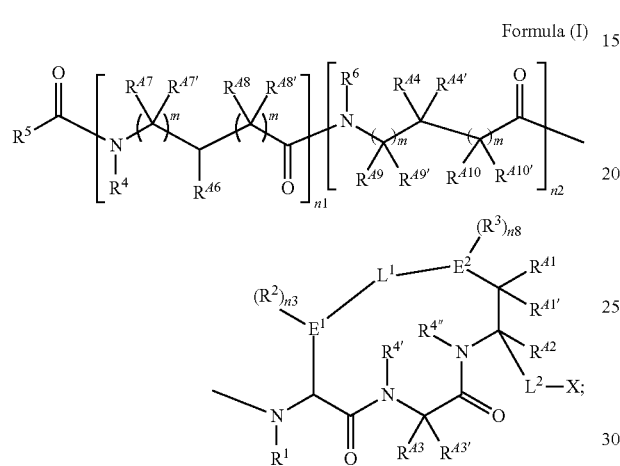

Formula (I)

wherein:
$E^1$ is phenyl
$E^2$ is phenyl;
$L^1$ is a bond;
$L^2$ is a bond;
X is —$CH_2OH$, —$CH(OH)CH_3$, —$N(R^4)CH(R^{24})CN$, —$NHCH(R^{24})C(O)CH_3$, —$NHN(R^{24})C(O)CH_3$, —$NHCH(R^{24})CH=CHS(O)_2CH_3$, —$NHCH(R^{24})CH=CHS(O)_2NH_2$,

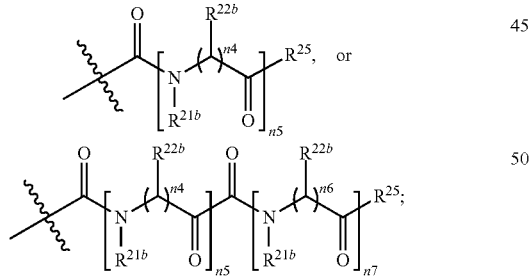

n4, n5, and n6 are each independently 1 or 2;
n7 is 0, 1 or 2;
$R^{21b}$ and $R^{22b}$ are independently at each occurrence hydrogen or $(C_1-C_6)$alkyl;
$R^{24}$ is H or $(C_1-C_6)$alkyl;
$R^{25}$ is —$CH_3$, —$CH_2Cl$, —$CH_2OR^{25b}$, —$CH_2R^{30}$, —$C(R^{26})_2C(O)NH_2$, —$CH_2SO_2N(R^{25b})_2$, —$CH_2N(R^{25b})SO_2(C_1-C_6alkyl)$, —$CH_2PO_3H$, —$CH_2P(O)(OH)OCH_3$, —$CH_2OC(O)CH_3$, —$CH_2OC(O)R^{30}$, —$CH_2CO_2R^{25b}$, —$CF_2CO_2R^{25b}$, —$CH_2CH_2CO_2R^{25b}$, —$CH_2CH_2C(O)N(R^{25b})_2$, —$CH_2CH_2C(O)N(H)CH$ $(R^{26})CO_2R^{25b}$, —$CH_2N(H)CH(R^{26})C(O)N(H)R^{25b}$, —$CH_2CH_2R^{30}$, —$N(H)CH_2(R^{30})$, —$CH=CHR^{30}$, —$CH=CHSO_2R^{25b}$,

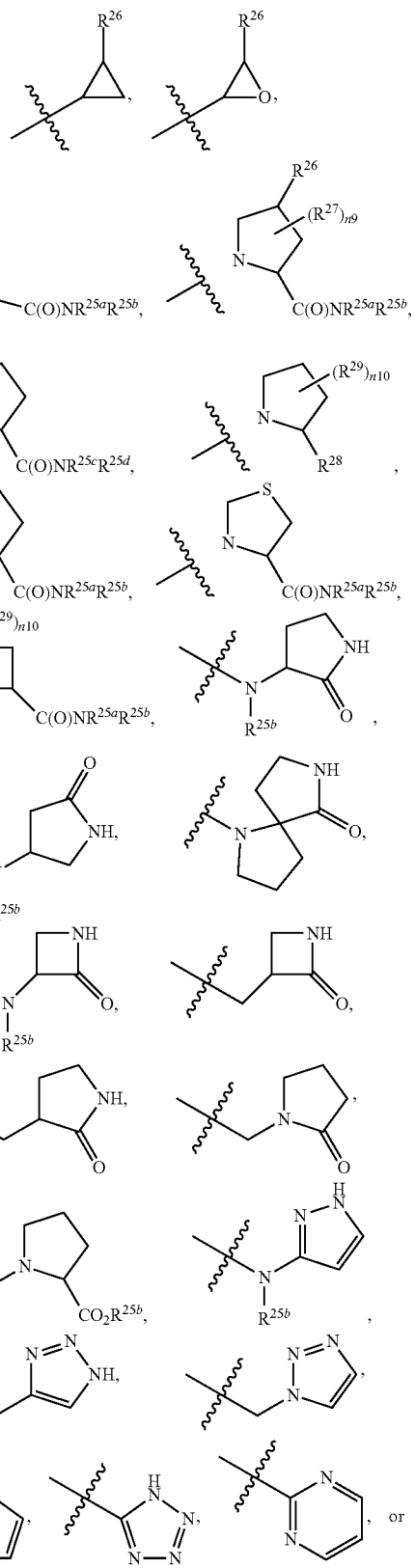

-continued

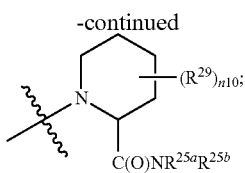

$R^{25a}$ is H, —OH, —OCH$_3$, NH$_2$, SO$_2$(C$_1$-C$_6$)alkyl, or (C$_1$-C$_6$)alkyl;
each $R^{25b}$ is independently H or (C$_1$-C$_6$)alkyl;
$R^{25c}$ is H or (C$_1$-C$_6$)alkyl;
$R^{25d}$ is —OH, —OCH$_3$, or NH$_2$;
each $R^{26}$ is independently H, halo or (C$_1$-C$_6$)alkyl;
each $R^{27}$ is independently —OH, halo, (C$_1$-C$_6$)alkyl, or $R^{26}$ and $R^{27}$ are joined to form a cycloalkyl ring;
$R^{28}$ is H, —CH$_2$OH, —CH$_2$NH$_2$, —C(O)CH$_3$, or (C$_1$-C$_6$)alkyl;
each $R^{29}$ is independently —OH, halo, or (C$_1$-C$_6$)alkyl;
$R^{30}$ is heterocyclyl, heteroaryl, or aryl;
n9 is 1, 2 or 3;
n10 is 0, 1, 2, 3 or 4;
$R^5$ is aryl, heteroaryl, or a linear or branched alkyl chain of about 1-22 carbon atoms, wherein $R^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

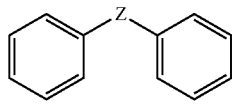

wherein Z is a bond, O, S, NH, CH$_2$ or C≡C; or $R^5$ is a linear or branched alkyl chain of about 1-22 carbon atoms, comprising within the chain at least one —O— or —N(R$^4$)—;
each $R^2$ and $R^3$ are each independently hydroxy or OR$^{40}$;
each $R^{40}$ is independently —(C$_1$-C$_6$)alkyl; or —(C$_1$-C$_6$)alkyl-NR$^{41}$R$^{42}$;
each $R^{41}$ and $R^{42}$ is hydrogen or —(C$_1$-C$_6$)alkyl;
n1 and n2 are independently 0 or 1;
n3 and n8 are 1;
each m is independently 0 or 1;
$R^1$ is hydrogen or (C$_1$-C$_6$)alkyl;
$R^4$, $R^{4'}$, and $R^{4''}$ are each independently at each occurrence hydrogen or (C$_1$-C$_6$)alkyl;
$R^6$ is hydrogen or (C$_1$-C$_6$)alkyl;
$R^{41}$, $R^{41'}$, $R^{42}$, $R^{43}$, $R^{43'}$ are each independently hydrogen or (C$_1$-C$_6$)alkyl;
$R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen or (C$_1$-C$_6$)alkyl optionally substituted with 1 to 3 J;
$R^{46}$ is H, amino, or (C$_1$-C$_6$)alkyl optionally substituted with 1 to 3 J;
each J is independently OR', (CH$_2$)$_{0-p}$N(R')$_2$, (CH$_2$)$_{0-p}$SR', (CH$_2$)$_{0-p}$S(O)$_2$N(R')$_2$, (CH$_2$)$_{0-p}$C(O)OR', or (CH$_2$)$_{0-p}$C(O)N(R')$_2$,
wherein p is 4;
each R' is independently at each occurrence hydrogen or (C$_1$-C$_6$)-alkyl;
or a pharmaceutically acceptable salt or solvate thereof.

2. The compound of claim 1 wherein $R^{41}$, $R^{41'}$, $R^{4'}$, and $R^{4''}$ are H.

3. The compound of claim 2 wherein $R^1$ is CH$_3$.

4. The compound of claim 3 wherein n1 is 1 and n2 is 1.

5. The compound of claim 4 wherein $R^{46}$ is (C$_1$-C$_6$)alkyl optionally substituted with 1 to 3 J.

6. The compound of claim 3 wherein n1 is 0 and n2 is 1.

7. The compound of claim 6 wherein $R^4$ is hydrogen.

8. The compound of claim 3 wherein n1 is 0 and n2 is 0.

9. The compound of claim 8 wherein X is

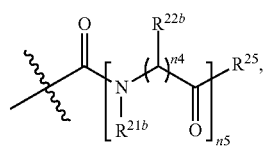

$R^{25}$ is

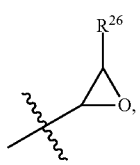

and $R^{26}$ is hydrogen or —CH$_3$.

10. The compound of claim 8 wherein X is

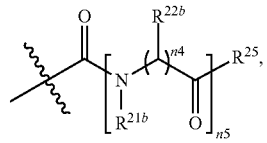

and $R^{25}$ is

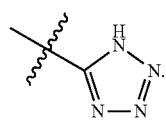

11. The compound of claim 8 wherein X is

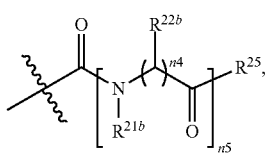

and $R^{25}$ is —CH$_3$.

12. The compound of claim 8 wherein X is

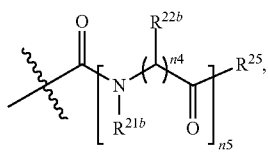

and $R^{25}$ is

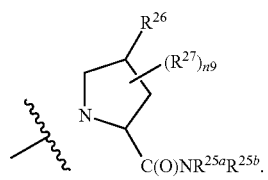

13. The compound of claim 11 wherein X is

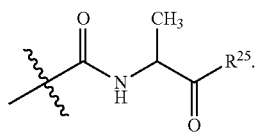

14. A compound of Formula (IV):

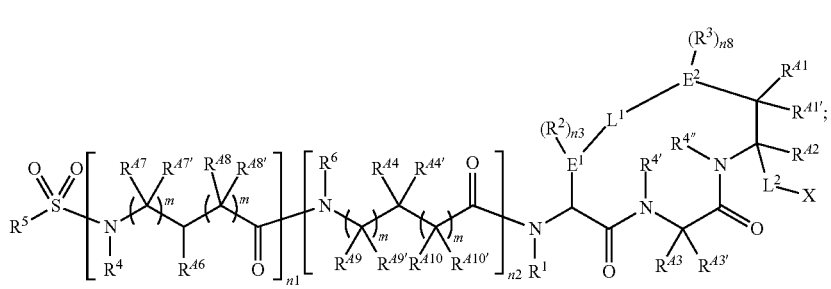

Formula (IV)

wherein:
$E^1$ is phenyl;
$E^2$ is phenyl;
$L^1$ is a bond;
$L^2$ is a bond;
X is —$CO_2H$, —$CH_2CO_2H$, —C(=O)NH$CH_2$C(=O)H, —$CH_2$C(=O)H, —C(=O)N(H)CH($R^7$)B(O$R^{B3}$)(O$R^{B4}$), —$CH_2$OH, —CH(OH)$CH_3$, —N($R^4$)CH($R^{24}$)CN, —NHCH($R^{24}$)C(O)$CH_3$, —NHN($R^{24}$)C(O)$CH_3$, —NHCH($R^{24}$)CH=CHS(O)$_2CH_3$, —NHCH($R^{24}$)CH=CHS(O)$_2NH_2$,

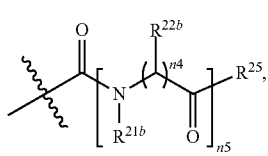

-continued

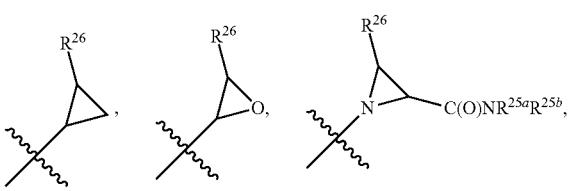

n4, n5, and n6 are each independently 1 or 2;
n7 is 0, 1 or 2;
$R^7$ is H, methyl, ethyl, or —$CH_2$OH;
$R^{B3}$ and $R^{B4}$ are each independently H, ($C_1$-$C_6$)alkyl, —$CH_2CO_2H$, —$CH_2CH_2CO_2H$;
$R^{21b}$ and $R^{22b}$ are independently at each occurrence hydrogen or ($C_1$-$C_6$)alkyl;
$R^{24}$ is H or ($C_1$-$C_6$)alkyl;

$R^{25}$ is H, OH, O$R^C$, N$R^{25a}R^{25b}$, —$CH_3$, —$CH_2$Cl, —$CH_2$O$R^{25b}$, —$CH_2R^{30}$, —C($R^{26}$)$_2$C(O)$NH_2$, —$CH_2SO_2$N($R^{25b}$)$_2$, —$CH_2$N($R^{25b}$)$S_2$($C_1$-$C_6$alkyl), —$CH_2PO_3H$, —$CH_2$P(O)(OH)O$CH_3$, —$CH_2$OC(O)$CH_3$, —$CH_2$OC(O)$R^{30}$, —$CH_2CO_2R^{25b}$, —$CF_2CO_2R^{25b}$, —$CH_2CH_2CO_2R^{25b}$, —$CH_2CH_2$C(O)N($R^{25b}$)$_2$, —$CH_2CH_2$C(O)N(H)CH($R^{26}$)$CO_2R^{25b}$, —$CH_2$N(H)CH($R^{26}$)C(O)N(H)$R^{25b}$, —$CH_2CH_2R^{30}$, —N(H)$CH_2$($R^{30}$), —CH=CH$R^{30}$, —CH=CHS$O_2R^{25b}$,

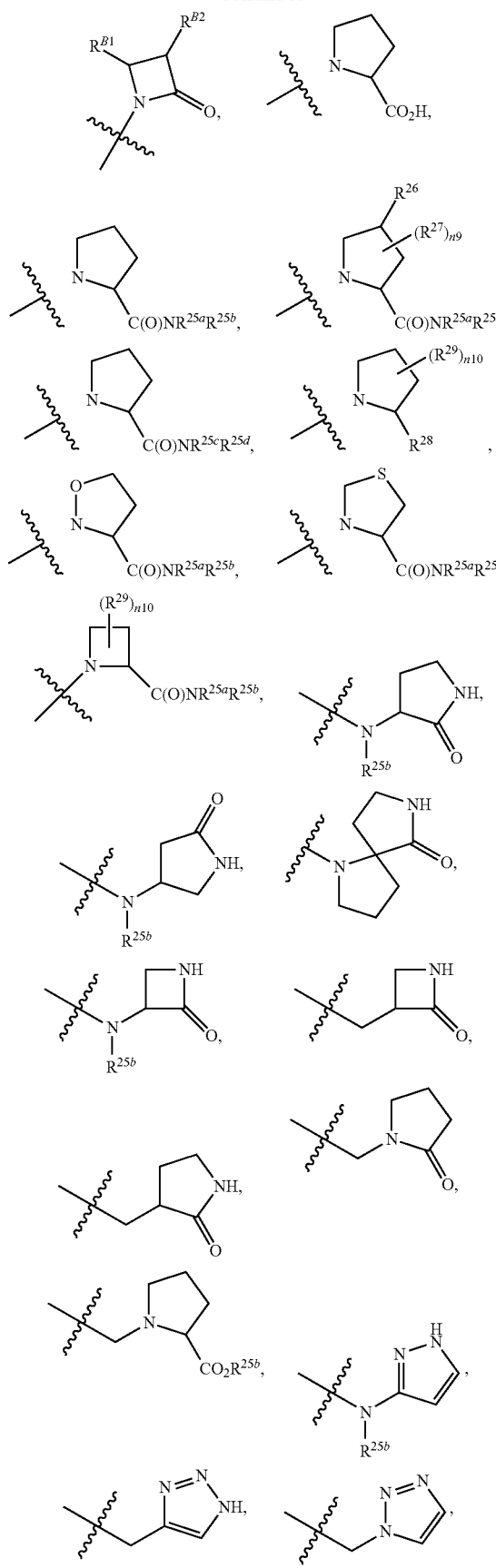
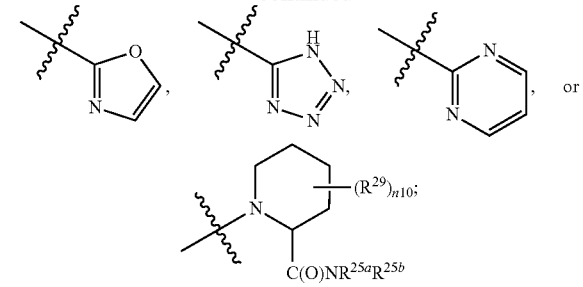
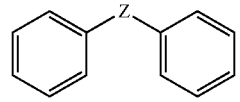

$R^{B1}$ and $R^{B2}$ are each independently H, ($C_1$-$C_6$) alkyl, ($C_3$-$C_6$) cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, ($C_1$-$C_6$)alkoxy, ($C_1$-$C_6$)thioalkoxy, $N(R^C)_2$, 5-7 membered heterocyclyl or 5-7 membered heteroaryl, or ($C_6$-$C_{10}$) aryl;

$R^C$ is independently at each occurrence H or ($C_1$-$C_6$) alkyl;

$R^{25a}$ is H, —OH, —OCH$_3$, NH$_2$, SO$_2$($C_1$-$C_6$)alkyl, or optionally substituted alkyl;

each $R^{25b}$ is independently H, or optionally substituted alkyl;

$R^{25}$ is H or optionally substituted alkyl;

$R^{25d}$ is —OH, —OCH$_3$, or NH$_2$;

each $R^{26}$ is independently H, halo or ($C_1$-$C_6$)alkyl;

each $R^{27}$ is independently —OH, halo, ($C_1$-$C_6$)alkyl, or $R^{26}$ and $R^{27}$ are joined to form a cycloalkyl ring;

$R^{28}$ is H, —CH$_2$OH, —CH$_2$NH$_2$, —C(O)CH$_3$, or ($C_1$-$C_6$)alkyl;

each $R^{29}$ is independently —OH, halo, or ($C_1$-$C_6$)alkyl;

$R^{30}$ is heterocyclyl, heteroaryl, or aryl; n9 is 1, 2 or 3; n10 is 0, 1, 2, 3 or 4;

$R^5$ is aryl, heteroaryl, or a linear or branched alkyl chain of about 1-22 carbon atoms optionally comprising within the chain or at a chain terminus optionally substituted aryl, optionally substituted heteroaryl, or optionally substituted wherein Z is a bond, O, S, NH, CH$_2$ or C≡C; or $R^5$ is a linear or branched alkyl chain of about 1-22 carbon atoms, comprising within the chain at least one —O— or —N($R^4$)—;

each $R^2$ and $R^3$ are each independently hydroxy or $OR^{40}$;

each $R^{40}$ is independently —($C_1$-$C_6$)alkyl; or —($C_1$-$C_6$)alkyl-$NR^{41}R^{42}$;

each $R^{41}$ and $R^{42}$ is hydrogen; or —($C_1$-$C_6$)alkyl;

n1 and n2 are independently 0 or 1;

n3 and n8 are 1;

each m is independently 0 or 1;

$R^1$ is hydrogen or ($C_1$-$C_6$)alkyl;

$R^4$, $R^{4'}$, and $R^{4''}$ are each independently at each occurrence hydrogen or ($C_1$-$C_6$)alkyl;

$R^6$ is hydrogen or ($C_1$-$C_6$)alkyl;

$R^{A1}$, $R^{A1'}$, $R^{A2}$, $R^{A3}$, $R^{A3'}$ are each independently hydrogen or ($C_1$-$C_6$)alkyl;

$R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen or ($C_1$-$C_6$)alkyl optionally substituted with 1 to 3 J;

$R^{46}$ is H, amino, or $(C_1$-$C_6)$alkyl optionally substituted with 1 to 3 J;

each J is independently OR', $(CH_2)_{0-p}N(R')_2$, $(CH_2)_{0-p}SR'$, $(CH_2)_{0-p}S(O)_2N(R')_2$, $(CH_2)_{0-p}C(O)OR'$, or $(CH_2)_{0-p}C(O)N(R')_2$, wherein p is 4;

each R' is independently at each occurrence hydrogen or $(C_1$-$C_6)$-alkyl; or a pharmaceutically acceptable salt or solvate thereof.

15. A pharmaceutical composition comprising the compound of claim 1, or a pharmaceutically acceptable salt or solvate thereof, and a pharmaceutically acceptable excipient.

16. A method of treatment of a bacterial infection in a mammal, comprising administering to the mammal an effective amount of a compound of claim 1, or a pharmaceutically acceptable salt or solvate thereof, to the animal at a frequency and for a duration sufficient to provide a beneficial effect to the mammal.

17. The method of claim 16, wherein the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

18. The method of claim 16, wherein the bacterial infection is an infection involving a Gram-negative bacteria.

19. The method of claim 16, wherein administering comprises topical administration.

* * * * *